US010640563B2

(12) United States Patent
Benatuil et al.

(10) Patent No.: US 10,640,563 B2
(45) Date of Patent: May 5, 2020

(54) ANTI-B7-H3 ANTIBODIES AND ANTIBODY DRUG CONJUGATES

(71) Applicant: AbbVie Inc., North Chicago, IL (US)

(72) Inventors: Lorenzo Benatuil, Northborough, MA (US); Debra Chao, Fremont, CA (US); Kamel Izeradjene, Gurnee, IL (US); Andrew S. Judd, Grayslake, IL (US); Andrew C. Phillips, Libertyville, IL (US); Andrew J. Souers, Libertyville, IL (US); Archana Thakur, Pleasanton, CA (US)

(73) Assignee: AbbVie Inc., North Chicago, IL (US)

( * ) Notice: Subject to any disclaimer, the term of this patent is extended or adjusted under 35 U.S.C. 154(b) by 85 days.

(21) Appl. No.: 15/616,901

(22) Filed: Jun. 7, 2017

(65) Prior Publication Data

US 2017/0355769 A1    Dec. 14, 2017

Related U.S. Application Data

(60) Provisional application No. 62/366,511, filed on Jul. 25, 2016, provisional application No. 62/347,476, filed on Jun. 8, 2016.

(51) Int. Cl.
| *C07K 16/00* | (2006.01) |
| *C07K 16/28* | (2006.01) |
| *A61K 47/68* | (2017.01) |
| *A61K 31/437* | (2006.01) |
| *A61K 31/498* | (2006.01) |
| *A61K 31/519* | (2006.01) |
| *A61K 39/00* | (2006.01) |

(52) U.S. Cl.
CPC ........ *C07K 16/2827* (2013.01); *A61K 31/437* (2013.01); *A61K 31/498* (2013.01); *A61K 31/519* (2013.01); *A61K 47/6803* (2017.08); *A61K 47/6849* (2017.08); *A61K 47/6877* (2017.08); *A61K 47/6889* (2017.08); *A61K 2039/505* (2013.01); *C07K 2317/14* (2013.01); *C07K 2317/24* (2013.01); *C07K 2317/33* (2013.01); *C07K 2317/34* (2013.01); *C07K 2317/51* (2013.01); *C07K 2317/515* (2013.01); *C07K 2317/52* (2013.01); *C07K 2317/56* (2013.01); *C07K 2317/565* (2013.01); *C07K 2317/76* (2013.01); *C07K 2317/92* (2013.01); *C07K 2319/55* (2013.01)

(58) Field of Classification Search
None
See application file for complete search history.

(56) References Cited

U.S. PATENT DOCUMENTS

| 4,399,216 A | 8/1983 | Axel et al. |
| 4,444,887 A | 4/1984 | Hoffmann |
| 4,486,414 A | 12/1984 | Pettit |
| 4,510,245 A | 4/1985 | Cousens et al. |
| 4,526,938 A | 7/1985 | Churchill et al. |
| 4,634,665 A | 1/1987 | Axel et al. |
| 4,676,980 A | 6/1987 | Segal et al. |
| 4,716,111 A | 12/1987 | Osband et al. |
| 4,814,470 A | 3/1989 | Colin et al. |
| 4,816,397 A | 3/1989 | Boss et al. |
| 4,816,444 A | 3/1989 | Pettit et al. |
| 4,816,567 A | 3/1989 | Cabilly et al. |
| 4,879,278 A | 11/1989 | Pettit et al. |
| 4,880,078 A | 11/1989 | Inoue et al. |
| 4,880,935 A | 11/1989 | Thorpe |
| 4,942,184 A | 7/1990 | Haugwitz et al. |
| 4,960,790 A | 10/1990 | Stella et al. |
| 4,968,615 A | 11/1990 | Koszinowski et al. |
| 4,978,744 A | 12/1990 | Pettit et al. |
| 4,980,286 A | 12/1990 | Morgan et al. |
| 4,986,988 A | 1/1991 | Pettit et al. |
| 5,076,973 A | 12/1991 | Pettit et al. |
| 5,122,368 A | 6/1992 | Greenfield et al. |
| 5,124,471 A | 6/1992 | Gansow et al. |
| 5,128,326 A | 7/1992 | Balazs et al. |
| 5,138,036 A | 8/1992 | Pettit et al. |
| 5,157,049 A | 10/1992 | Haugwitz et al. |
| 5,168,062 A | 12/1992 | Stinski |
| 5,179,017 A | 1/1993 | Axel et al. |
| 5,208,020 A | 5/1993 | Chari et al. |
| 5,225,539 A | 7/1993 | Winter |
| 5,278,324 A | 1/1994 | Kingston et al. |
| 5,286,850 A | 2/1994 | Gansoh et al. |
| 5,290,540 A | 3/1994 | Prince et al. |
| 5,362,831 A | 11/1994 | Mongelli et al. |
| 5,380,751 A | 1/1995 | Chen et al. |
| 5,399,363 A | 3/1995 | Liversidge et al. |

(Continued)

FOREIGN PATENT DOCUMENTS

| EP | 0077671 B1 | 6/1986 |
| EP | 0229246 B1 | 8/1993 |

(Continued)

OTHER PUBLICATIONS

Atalay G., et al., "Novel Therapeutic Strategies Targeting the Epidermal Growth Factor Receptor (EGFR) Family and its Downstream Effectors in Breast Cancer," Annals of Oncology, Sep. 2003, vol. 14 (9), pp. 1346-1363.

(Continued)

*Primary Examiner* — Maher M Haddad

(74) *Attorney, Agent, or Firm* — Laura E. Johannes

(57) ABSTRACT

The invention relates to B7 homology 3 protein (B7-H3) antibodies and antibody drug conjugates (ADCs), including compositions and methods of using said antibodies and ADCs.

3 Claims, 5 Drawing Sheets

Specification includes a Sequence Listing.

(56) References Cited

U.S. PATENT DOCUMENTS

| | | | |
|---|---|---|---|
| 5,403,858 A | 4/1995 | Bastard et al. |
| 5,407,683 A | 4/1995 | Shively |
| 5,410,024 A | 4/1995 | Pettit et al. |
| 5,413,923 A | 5/1995 | Kucherlapati et al. |
| 5,415,869 A | 5/1995 | Straubinger et al. |
| 5,424,073 A | 6/1995 | Rahman et al. |
| 5,433,364 A | 7/1995 | Hill et al. |
| 5,434,287 A | 7/1995 | Gansow et al. |
| 5,438,072 A | 8/1995 | Bobee et al. |
| 5,504,191 A | 4/1996 | Pettit et al. |
| 5,521,284 A | 5/1996 | Pettit et al. |
| 5,530,097 A | 6/1996 | Pettit et al. |
| 5,530,101 A | 6/1996 | Queen et al. |
| 5,545,806 A | 8/1996 | Lonberg et al. |
| 5,554,725 A | 9/1996 | Pettit |
| 5,565,332 A | 10/1996 | Hoogenboom et al. |
| 5,569,825 A | 10/1996 | Lonberg et al. |
| 5,585,089 A | 12/1996 | Queen et al. |
| 5,599,902 A | 2/1997 | Pettit et al. |
| 5,622,929 A | 4/1997 | Willner et al. |
| 5,624,821 A | 4/1997 | Winter et al. |
| 5,625,126 A | 4/1997 | Lonberg et al. |
| 5,633,425 A | 5/1997 | Lonberg et al. |
| 5,635,483 A | 6/1997 | Pettit et al. |
| 5,641,803 A | 6/1997 | Carretta et al. |
| 5,648,260 A | 7/1997 | Winter et al. |
| 5,658,570 A | 8/1997 | Newman et al. |
| 5,661,016 A | 8/1997 | Lonberg et al. |
| 5,663,149 A | 9/1997 | Pettit et al. |
| 5,665,671 A | 9/1997 | Zanin |
| 5,665,860 A | 9/1997 | Pettit et al. |
| 5,679,377 A | 10/1997 | Bernstein et al. |
| 5,681,722 A | 10/1997 | Newman et al. |
| 5,693,761 A | 12/1997 | Queen et al. |
| 5,693,762 A | 12/1997 | Queen et al. |
| 5,693,780 A | 12/1997 | Newman et al. |
| 5,705,503 A | 1/1998 | Goodall et al. |
| 5,712,374 A | 1/1998 | Kuntsmann et al. |
| 5,714,350 A | 2/1998 | Co et al. |
| 5,714,352 A | 2/1998 | Jakobovits et al. |
| 5,714,586 A | 2/1998 | Kunstmann et al. |
| 5,723,323 A | 3/1998 | Kauffman et al. |
| 5,728,687 A | 3/1998 | Bissery |
| 5,739,116 A | 4/1998 | Hamann et al. |
| 5,750,106 A | 5/1998 | Ostberg |
| 5,763,192 A | 6/1998 | Kauffman et al. |
| 5,766,886 A | 6/1998 | Studnicka et al. |
| 5,767,285 A | 6/1998 | Hamann et al. |
| 5,770,701 A | 6/1998 | McGahren et al. |
| 5,770,710 A | 6/1998 | McGahren et al. |
| 5,773,001 A | 6/1998 | Hamann et al. |
| 5,773,464 A | 6/1998 | Walker et al. |
| 5,780,588 A | 7/1998 | Pettit et al. |
| 5,807,715 A | 9/1998 | Morrison et al. |
| 5,814,318 A | 9/1998 | Lonberg et al. |
| 5,814,476 A | 9/1998 | Kauffman et al. |
| 5,817,483 A | 10/1998 | Kauffman et al. |
| 5,821,263 A | 10/1998 | Scola et al. |
| 5,824,514 A | 10/1998 | Kauffman et al. |
| 5,824,805 A | 10/1998 | King et al. |
| 5,840,929 A | 11/1998 | Chen |
| 5,855,913 A | 1/1999 | Hanes et al. |
| 5,869,680 A | 2/1999 | Mas et al. |
| 5,874,064 A | 2/1999 | Edwards et al. |
| 5,877,296 A | 3/1999 | Hamann et al. |
| 5,885,793 A | 3/1999 | Griffiths et al. |
| 5,912,015 A | 6/1999 | Bernstein et al. |
| 5,916,597 A | 6/1999 | Lee et al. |
| 5,916,771 A | 6/1999 | Hori et al. |
| 5,934,272 A | 8/1999 | Lloyd et al. |
| 5,939,598 A | 8/1999 | Kucherlapati et al. |
| 5,969,108 A | 10/1999 | McCafferty et al. |
| 5,976,862 A | 11/1999 | Kauffman et al. |
| 5,985,309 A | 11/1999 | Edwards et al. |
| 5,985,320 A | 11/1999 | Edwards et al. |
| 5,989,463 A | 11/1999 | Tracy et al. |
| 6,019,968 A | 2/2000 | Platz et al. |
| 6,034,065 A | 3/2000 | Pettit et al. |
| 6,090,382 A | 7/2000 | Salfeld et al. |
| 6,114,598 A | 9/2000 | Kucherlapati et al. |
| 6,180,370 B1 | 1/2001 | Queen et al. |
| 6,204,023 B1 | 3/2001 | Robinson et al. |
| 6,207,418 B1 | 3/2001 | Hori et al. |
| 6,214,345 B1 | 4/2001 | Firestone et al. |
| 6,235,883 B1 | 5/2001 | Jakobovits et al. |
| 6,239,104 B1 | 5/2001 | Pettit et al. |
| 6,323,315 B1 | 11/2001 | Pettit et al. |
| 6,350,861 B1 | 2/2002 | Co et al. |
| 6,410,319 B1 | 6/2002 | Raubitschek et al. |
| 6,441,163 B1 | 8/2002 | Chari et al. |
| 6,660,843 B1 | 12/2003 | Feige et al. |
| 6,913,748 B2 | 7/2005 | Widdison |
| 7,223,837 B2 | 5/2007 | De Groot et al. |
| 7,227,002 B1 | 6/2007 | Kufer et al. |
| 7,598,028 B2 | 10/2009 | Macoska |
| 7,612,181 B2 | 11/2009 | Wu et al. |
| 7,723,270 B1 | 5/2010 | McCafferty et al. |
| 7,741,319 B2 | 6/2010 | Howard et al. |
| 7,989,434 B2 | 8/2011 | Feng |
| 7,994,135 B2 | 8/2011 | Doronina et al. |
| 8,039,273 B2 | 10/2011 | Jeffrey et al. |
| 8,142,784 B2 | 3/2012 | Ebens, Jr. et al. |
| 8,236,319 B2 | 8/2012 | Chari et al. |
| 8,309,093 B2 | 11/2012 | Gudas et al. |
| 8,349,308 B2 | 1/2013 | Yurkovetskiy et al. |
| 8,389,282 B2 | 3/2013 | Sadelain et al. |
| 8,399,512 B2 | 3/2013 | Akullian et al. |
| 8,524,214 B2 | 9/2013 | Yurkovetskiy et al. |
| 8,535,678 B2 | 9/2013 | Law et al. |
| 8,568,728 B2 | 10/2013 | Jeffrey |
| 8,809,051 B2 | 8/2014 | Jakobovits et al. |
| 8,809,151 B2 | 8/2014 | Flachowsky et al. |
| 8,822,647 B2 | 9/2014 | Jensen |
| 8,906,682 B2 | 12/2014 | June et al. |
| 8,911,993 B2 | 12/2014 | June et al. |
| 8,916,381 B1 | 12/2014 | June et al. |
| 8,975,071 B1 | 3/2015 | June et al. |
| 9,493,568 B2 | 11/2016 | Reilly et al. |
| 2002/0137134 A1 | 9/2002 | Gerngross |
| 2003/0083263 A1 | 5/2003 | Doronina et al. |
| 2004/0018590 A1 | 1/2004 | Gerngross et al. |
| 2004/0028687 A1 | 2/2004 | Waelti |
| 2005/0009751 A1 | 1/2005 | Senter et al. |
| 2005/0042664 A1 | 2/2005 | Wu et al. |
| 2005/0238649 A1 | 10/2005 | Doronina et al. |
| 2005/0271615 A1 | 12/2005 | Shabat et al. |
| 2006/0024317 A1 | 2/2006 | Boyd et al. |
| 2006/0074008 A1 | 4/2006 | Senter et al. |
| 2006/0104968 A1 | 5/2006 | Bookbinder et al. |
| 2006/0116422 A1 | 6/2006 | De Groot et al. |
| 2006/0134709 A1 | 6/2006 | Stavenhagen et al. |
| 2007/0173497 A1 | 7/2007 | Howard et al. |
| 2009/0285757 A1 | 11/2009 | Khaw |
| 2009/0318668 A1 | 12/2009 | Beusker et al. |
| 2010/0129314 A1 | 5/2010 | Singh et al. |
| 2010/0152725 A1 | 6/2010 | Pearson et al. |
| 2011/0076232 A1 | 3/2011 | Old et al. |
| 2011/0217363 A1 | 9/2011 | Chen |
| 2012/0107332 A1 | 5/2012 | Jeffrey |
| 2012/0183471 A1 | 7/2012 | Old et al. |
| 2012/0294796 A1 | 11/2012 | Johnson et al. |
| 2013/0028917 A1 | 1/2013 | Howard et al. |
| 2013/0028919 A1 | 1/2013 | Howard et al. |
| 2013/0117871 A1 | 5/2013 | Kucherlapati et al. |
| 2013/0118921 A1 | 5/2013 | Harding et al. |
| 2013/0189218 A1 | 7/2013 | Akullian et al. |
| 2013/0224228 A1 | 8/2013 | Jackson et al. |
| 2013/0303509 A1 | 11/2013 | Hansen et al. |
| 2013/0309256 A1 | 11/2013 | Lyon et al. |
| 2014/0017265 A1 | 1/2014 | Yurkovetskiy et al. |
| 2014/0286968 A1 | 9/2014 | Leanna et al. |
| 2014/0322275 A1 | 10/2014 | Brogdon et al. |
| 2014/0328750 A1 | 11/2014 | Johnson et al. |
| 2016/0158377 A1 | 6/2016 | Ackler et al. |

(56) References Cited

U.S. PATENT DOCUMENTS

| | | |
|---|---|---|
| 2016/0339117 A1 | 11/2016 | Ackler et al. |
| 2019/0153107 A1 | 5/2019 | Boghaert et al. |
| 2019/0153108 A1 | 5/2019 | Boghaert et al. |

FOREIGN PATENT DOCUMENTS

| | | |
|---|---|---|
| EP | 0239400 B1 | 8/1994 |
| EP | 0618978 A1 | 10/1994 |
| EP | 1176195 A1 | 1/2002 |
| EP | 0592106 B1 | 11/2004 |
| EP | 0519596 B1 | 2/2005 |
| EP | 1800695 A1 | 6/2007 |
| EP | 1176195 B1 | 5/2013 |
| GB | 9201755 | 4/1993 |
| WO | WO-8912624 A2 | 12/1989 |
| WO | WO-9005144 A1 | 5/1990 |
| WO | WO-9014424 A1 | 11/1990 |
| WO | WO-9014430 A1 | 11/1990 |
| WO | WO-9014443 A1 | 11/1990 |
| WO | WO-9105548 A1 | 5/1991 |
| WO | WO-9109967 A1 | 7/1991 |
| WO | WO-9203461 A1 | 3/1992 |
| WO | WO-9211272 A1 | 7/1992 |
| WO | WO-9219244 A2 | 11/1992 |
| WO | WO-9222332 A2 | 12/1992 |
| WO | WO-9306213 A1 | 4/1993 |
| WO | WO-9321232 A1 | 10/1993 |
| WO | WO-9416729 A1 | 8/1994 |
| WO | WO-9418219 A1 | 8/1994 |
| WO | WO-9515770 A1 | 6/1995 |
| WO | WO-9620698 A2 | 7/1996 |
| WO | WO-9720032 A1 | 6/1997 |
| WO | WO-9729131 A1 | 8/1997 |
| WO | WO-9731655 A2 | 9/1997 |
| WO | WO-9732572 A2 | 9/1997 |
| WO | WO-9744013 A1 | 11/1997 |
| WO | WO-9822451 A1 | 5/1998 |
| WO | WO-9828288 A1 | 7/1998 |
| WO | WO-9831346 A1 | 7/1998 |
| WO | WO-9835704 A1 | 8/1998 |
| WO | WO-9906834 A2 | 2/1999 |
| WO | WO-9909021 A1 | 2/1999 |
| WO | WO-9914209 A1 | 3/1999 |
| WO | WO-9915154 A1 | 4/1999 |
| WO | WO-9918113 A1 | 4/1999 |
| WO | WO-9919500 A1 | 4/1999 |
| WO | WO-9920253 A1 | 4/1999 |
| WO | WO-9925044 A1 | 5/1999 |
| WO | WO-9954342 A1 | 10/1999 |
| WO | WO-9966903 A2 | 12/1999 |
| WO | WO-0109785 A1 | 2/2001 |
| WO | WO-0190198 A1 | 11/2001 |
| WO | WO-02088172 A2 | 11/2002 |
| WO | WO-03016466 A2 | 2/2003 |
| WO | WO-03035835 A2 | 5/2003 |
| WO | WO-03093793 A2 | 11/2003 |
| WO | WO-2004010957 A2 | 2/2004 |
| WO | WO-2004050016 A2 | 6/2004 |
| WO | WO-2004078140 A2 | 9/2004 |
| WO | WO-2005081898 A2 | 9/2005 |
| WO | WO-2005100584 A2 | 10/2005 |
| WO | WO-2006042146 A2 | 4/2006 |
| WO | WO-2006083562 A2 | 8/2006 |
| WO | WO-2006089668 A1 | 8/2006 |
| WO | WO-2006111759 A1 | 10/2006 |
| WO | WO-2007150020 A1 | 12/2007 |
| WO | WO-2008017828 A2 | 2/2008 |
| WO | WO-2008097866 A2 | 8/2008 |
| WO | WO-2008097870 A2 | 8/2008 |
| WO | WO-2008100624 A2 | 8/2008 |
| WO | WO-2008103947 A2 | 8/2008 |
| WO | WO-2008103953 A2 | 8/2008 |
| WO | WO-2008135237 A1 | 11/2008 |
| WO | WO-2009134776 A2 | 11/2009 |
| WO | WO-2009134952 A2 | 11/2009 |
| WO | WO-2009134976 A1 | 11/2009 |
| WO | WO-2010080503 A1 | 7/2010 |
| WO | WO-2010111198 A1 | 9/2010 |
| WO | WO-2011000370 A1 | 1/2011 |
| WO | WO-2011057216 A1 | 5/2011 |
| WO | WO-2011058321 A1 | 5/2011 |
| WO | WO-2011109400 A2 | 9/2011 |
| WO | WO-2011130598 A1 | 10/2011 |
| WO | WO-2012027494 A1 | 3/2012 |
| WO | WO-2013055897 A1 | 4/2013 |
| WO | WO-2013078377 A1 | 5/2013 |
| WO | WO-2013173337 A2 | 11/2013 |
| WO | WO-2014093379 A1 | 6/2014 |
| WO | WO-2014093394 A1 | 6/2014 |
| WO | WO-2014093640 A1 | 6/2014 |
| WO | WO-2014093786 A1 | 6/2014 |
| WO | WO-2014100762 A1 | 6/2014 |
| WO | WO-2015143382 A1 | 9/2015 |
| WO | WO-2015146132 A1 | 10/2015 |
| WO | WO-2016064749 A2 | 4/2016 |
| WO | WO-2016094505 A1 | 6/2016 |
| WO | WO-2016094509 A1 | 6/2016 |
| WO | WO-2016094517 A1 | 6/2016 |
| WO | WO-2017214233 A1 | 12/2017 |
| WO | WO-2017214282 A1 | 12/2017 |
| WO | WO-2017214301 A1 | 12/2017 |
| WO | WO-2017214322 A1 | 12/2017 |
| WO | WO-2017214339 A1 | 12/2017 |
| WO | WO-2017214456 A1 | 12/2017 |
| WO | WO-2017214458 A2 | 12/2017 |
| WO | WO-2017214462 A2 | 12/2017 |

OTHER PUBLICATIONS

Baldwin R.W., et al., Eds., Monoclonal Antibodies for Cancer Detection and Therapy, London Academic Press, 1985, pp. 159-179.

Batra S.K., et al., "Epidermal Growth Factor Ligand-Independent, Unregulated, Cell-Transforming Potential of a Naturally Occurring Human Mutant EGFRvIII Gene," Cell Growth and Differentiation, 1995, vol. 6 (10), pp. 1251-1259.

Cai S., et al., "CD98 Modulates Integrin Beta1 Function in Polarized Epithelial Cell," Journal of Cell Science, Mar. 2005, vol. 118 (Pt 5), pp. 889-899.

Cantor J.M., et al., "CD98 at the Crossroads of Adaptive Immunity and Cancers," Journal of Cell Science, Mar. 2012, vol. 125 (Pt 6), pp. 1373-1382.

Cochran J.R., et al., "Domain-Level Antibody Epitope Mapping through Yeast Surface Display of Epidermal Growth Factor Receptor Fragments," Journal of Immunological Methods, 2004, vol. 287 (1-2), pp. 147-158.

Estrach S., et al., "CD98hc (SLC3a2) Loss Protects Against Ras-driven Tumorigenesis by Modulating Integrin-mediated Mechanotransduction," Cancer Research, Dec. 2014, vol. 74 (23), pp. 6878-6889.

Garcia De Palazzo IE., et al., "Expression of Mutated Epidermal Growth Factor Receptor by Non-small Cell Lung Carcinomas," Cancer Research, Jul. 1993, vol. 53 (14), pp. 3217-3220.

Ge H., et al., "Evidence of High Incidence of EGFRvIII Expression and Coexpression With EGFR in Human Invasive Breast Cancer by Laser Capture Microdissection and Immunohistochemical Analysis," International Journal of Cancer, Mar. 2002, vol. 98 (3), pp. 357-361.

Hayes G.M., et al., "Antitumor Activity of an Anti-CD98 Antibody," International Journal of Cancer, Aug. 1, 2015, vol. 137 (3), pp. 710-720.

Haynes B. F. et al., "Characterization of a Monoclonal Antibody (4F2) that Binds to Human Monocytes and to a Subset of Activated Lymphocytes," Journal of Immunology, Apr. 1981, vol. 126 (4), pp. 1409-1414.

Herbst R.S., et al., "Monoclonal Antibodies to Target Epidermal Growth Factor Receptor-Positive Tumors: A New Paradigm for Cancer Therapy.," Cancer, 2002, vol. 94 (5), pp. 1593-1611.

Jonsson U., et al., "Introducing a Biosensor Based Technology for Real-Time Biospecific Interaction Analysis," Annales de Biologie Clinique, 1993, vol. 51 (1), pp. 19-26.

(56) References Cited

OTHER PUBLICATIONS

Kabat E.A., et al., in: Sequence of Proteins of Immunological Interest, 4th Edition, 1987, Table of Contents.
Kaira K., et al., "CD98 Expression is Associated with Poor Prognosis in Resected Non-small-cell Lung Cancer with Lymph Node Metastases," Annals of Surgical Oncology, Dec. 2009, vol. 16 (12), pp. 3473-3481.
Kaira K., et al., "I-type Amino Acid Transporter 1 and CD98 Expression in Primary and Metastatic Sites of Human Neoplasms," Cancer Science, Dec. 2008, vol. 99 (12), pp. 2380-2386.
Kaira K., et al., "Prognostic Significance of L-type Amino Acid Transporter 1 (Lat1) and 4F2 Heavy Chain (CD98) Expression in Stage I Pulmonary Adenocarcinoma," Lung Cancer, Oct. 2009, vol. 66 (1), pp. 120-126.
Kamala T., "Hock Immunization: A Humane Alternative to Mouse Footpad Injections," Journal of Immunological Methods, Dec. 2007, vol. 328 (1-2), pp. 204-214.
Kipriyanov S.M., et al., "Single-Chain Antibody Streptavidin Fusions: Tetrameric Bifunctional scFv-Complexes with Biotin Binding Activity and Enhanced Affinity to Antigen," Human Antibodies and Hybridomas, 1995, vol. 6 (3), pp. 93-101.
Kipriyanov S.M., et al., "Recombinant Single-Chain Fv Fragments Carrying C-Terminal Cysteine Residues: Production of Bivalent and Biotinylated Miniantibodies," Molecular Immunology, 1994, vol. 31 (14), pp. 1047-1058.
Kontermann R., et al., eds., Antibody Engineering, Springer-Verlag Berlin Heidelberg, 2001, Table of Contents.
Kuan C.T., et al., "EGF Mutant Receptor vIII as a Molecular Target in Cancer Therapy," Endocrine-Related Cancer, 2001, vol. 8 (2), pp. 83-96.
Langer, et al., Eds., Medical Applications of Controlled Release, 1984, CRC Press, Boca Raton, Fla.
Lessene G., et al., "Structure-guided Design of a Selective Bcl-x(L) Inhibitor," Nature Chemical Biology, 2013, vol. 9 (6), pp. 390-397.
Lindsten T., et al., "Regulation of 4F2 Heavy-chain Gene Expression During Normal Human T-cell Activation can be Mediated by Multiple Distinct Molecular Mechanisms," Molecular and Cellular Biology, Sep. 1988, vol. 8 (9), pp. 3820-3826.
Mason K.D., et al, "Programmed anuclear cell death delimits platelet life span," Cell, 2007, vol. 128 (6), pp. 1173-1186.
Modjtahedi H., et al., "Phase I Trial and Tumour Localisation of the Anti-EGFR Monoclonal Antibody ICR62 in Head and Neck or Lung Cancer," British Journal of Cancer, 1996, vol. 73 (2), pp. 228-235.
Moscatello D.K., et al., "Frequent Expression of a Mutant Epidermal Growth Factor Receptor in Multiple Human Tumors," Cancer Research, Dec. 1995, vol. 55 (23), pp. 5536-5539.
Mulligan R.C., "The Basic Science of Gene Therapy," Science, May 1993, vol. 260 (5110), pp. 926-932.
Nagane M., et al., "A Common Mutant Epidermal Growth Factor Receptor Confers Enhanced Tumorigenicity on Human Glioblastoma Cells by Increasing Proliferation and Reducing Apoptosis," Cancer Research, 1996, vol. 56 (21), pp. 5079-5086.
Neuberger M.S., et al., "Recombinant Antibodies Possessing Novel Effector Functions," Nature, Dec. 1984, vol. 312 (5995), pp. 604-608.
Ning S., et al., "Intratumoral Radioimmunotherapy of a Human Colon Cancer Xenograft using a Sustained-release Gel," Radiotherapy and Oncology, 1996, vol. 39 (2), pp. 179-189.
Nishikawa R., et al., "A Mutant Epidermal Growth Factor Receptor Common in Human Glioma Confers Enhanced Tumorigenicity," Proceedings of the National Academy of Sciences, 1994, vol. 91 (16), pp. 7727-7731.
Olapade-Olaopa E.O., et al., "Evidence for the Differential Expression of a Variant EGF Receptor Protein in Human Prostate Cancer," British Journal of Cancer, 2000, vol. 82 (1), pp. 186-194.
Padlan E.A., "A Possible Procedure for Reducing the Immunogenicity of Antibody Variable Domains While Preserving Their Ligand-Binding Properties," Molecular Immunology, 1991, vol. 28 (4-5), pp. 489-498.
Parmacek M.S., et al., "Structure, Expression and Regulation of the Murine 4F2 Heavy Chain," Nucleic acids research, Mar. 1989, vol. 17 (5), pp. 1915-1931.
Pauff S.M., et al., "A Trifluoroacetic Acid-labile Sulfonate Protecting Group and its use in the Synthesis of a Near-IR Fluorophore," The Journal of Organic Chemistry, Jan. 2013, vol. 78 (2), pp. 711-716.
Robinson M.J., "Coating of Pharmaceutical Dosage Forms," Remington's Pharmaceutical Sciences, 1980, pp. 1585-1593, A. Osol, ed., Mack Publishing Co., Easton, Pa., (16th edition).
Roguska M.A., et al., "Humanization of Murine Monoclonal Antibodies through Variable Domain Resurfacing," Proceedings of the National Academy of Sciences, 1994, vol. 91 (3), pp. 969-973.
Sefton M.V., et al., "Implantable Pumps," Critical Reviews in Biomedical Engineering, 1987, vol. 14 (3), pp. 201-240.
Smolen V.F., et al., eds., Controlled Drug Bioavailability: Drug Product Design and Performance, vol. 1, John Wiley & Sons, 1984, Table of Contents.
Studnicka G.M., et al., "Human-Engineered Monoclonal Antibodies Retain Full Specific Binding Activity by Preserving Non-CDR Complementarity-Modulating Residues," Protein Engineering, 1994, vol. 7 (6), pp. 805-814.
Sugawa N., et al., "Identical Splicing of Aberrant Epidermal Growth Factor Receptor Transcripts from Amplified Rearranged Genes in Human Glioblastomas," Proceedings of the National Academy of Sciences USA, 1990, vol. 87, pp. 8602-8606.
Takeda S., et al., "Construction of Chimaeric Processed Immunoglobulin Genes Containing Mouse Variable and Human Constant Region Sequences," Nature, Apr. 1985, vol. 314 (6010), pp. 452-454.
Teixeira S., et al., "Post-transcriptional Regulation of the Transferrin Receptor and 4F2 Antigen Heavy Chain mRNA During Growth Activation of Spleen Cells," European Journal of Biochemistry, Dec. 1991, vol. 202 (3), pp. 819-826.
Tsao and Herbst "Factors That Determine Response to EGFR Inhibitors," Signal : The Journal of EGFR-targeted cancer therapy, 2003, vol. 4(4), pp. 4-9.
Verhoeyen M., et al., "Reshaping Human Antibodies: Grafting an Antilysozyme Activity," Science, May 1988, vol. 239 (4847), pp. 1534-1536.
Ward E.S., et al., "Binding Activities of a Repertoire of Single Immunoglobulin Variable Domains Secreted from *Escherichia Coli*," Nature, Oct. 1989, vol. 341 (6242), pp. 544-546.
Wikstrand C.J., et al., "Cell Surface Localization and Density of the Tumor-Associated Variant of the Epidermal Growth Factor Receptor, EGFRvIII," Cancer Research, 1997, vol. 57, pp. 4130-4140.
Wikstrand C.J., et al., "Monoclonal Antibodies against EGFRvIII are Tumor Specific and React with Breast and Lung Carcinomas and Malignant Gliomas," Cancer Research, 1995, vol. 55 (14), pp. 3140-3148.
Wikstrand C.J., et al., "The Class III Variant of the Epidermal Growth Factor Receptor (EGFRvIII): Characterization and Utilization as an Immunotherapeutic Target," Journal of Neurovirology, 1998, vol. 4 (2), pp. 148-158.
Winnaker E.L., From Genes to Clones: Introduction to Gene Technology, VCH Publishers, 1987, Table of Contents.
Wong A.J., et al., "Structural Alterations of the Epidermal Growth Factor Receptor Gene in Human Gliomas," Proceedings of the National Academy of Sciences USA, 1992, vol. 89, pp. 2965-2969.
Woodward J.R. Basic biotechnology; Edited by P Prave. U Faust, W Sittig and D A Sukatsch, VCH Verlagsgesellschaft, Weinheim, W Germany. 1987, pp. 344. ISBN 3-527-26678-X.
Wu G.Y., et al., "Delivery Systems for Gene Therapy," Biotherapy, 1991, vol. 3 (1), pp. 87-95.
Yamazaki H., et al., "A Deletion Mutation within the Ligand Binding Domain is Responsible for Activation of Epidermal Growth Factor Receptor Gene in Human Brain Tumors," Japanese Journal of Cancer, 1990, vol. 81, pp. 773-779.
Yamazaki H., et al., "Amplification of the Structurally and Functionally Altered Epidermal Growth Factor Receptor Gene (c-erbB) in Human Brain Tumors," Molecular and Cellular Biology, 1988, vol. 8 (4), pp. 1816-1820.

(56) References Cited

OTHER PUBLICATIONS

Yanagida O., et al., "Human L-type Amino Acid Transporter 1 (LAT1): Characterization of Function and Expression in Tumor Cell Lines," Biochimica et Biophysica Acta, Oct. 2001, vol. 1514 (2), pp. 291-302.
Ahmed M., et al., "Humanized Affinity-matured Monoclonal Antibody 8h9 Has Potent Antitumor Activity and Binds to Fg Loop of Tumor Antigen B7-H3," The Journal of Biological Chemistry, Dec. 11, 2015, vol. 290 (50), pp. 30018-30029.
Ausubel F.M., et al., eds., Current Protocols in Molecular Biology, vol. 1, Green Publishing Associates, Inc., and John Wiley & Sons, Inc., 1993, pp. 6.3.1-6.3.6 and 2.10.3.
Bostrom J., et al., "Variants of the Antibody Herceptin That Interact with HER2 and VEGF at the Antigen Binding Site," Science, 2009, vol. 323 (5921), pp. 1610-1614.
Canfield S.M., et al., "The Binding Affinity of Human IgG for its High Affinity Fc Receptor is Determined by Multiple Amino Acids in the CH2 Domain and is Modulated by the Hinge Region," The Journal of Experimental Medicine, 1991, vol. 173 (6), pp. 1483-1491.
Danial N.N., et al., "Cell Death: Critical Control Points," Cell, 2004, vol. 116 (2), pp. 205-219.
Datta R., et al., "Overexpression of Bcl-xl by Cytotoxic Drug Exposure Confers Resistance to Ionizing Radiation-induced Internucleosomal Dna Fragmentation," Cell Growth & Differentiation, 1995, vol. 6 (4), pp. 363-370.
Drobyski W.R., et al., "Phase I Study of Safety and Pharmacokinetics of a Human Anticytomegalovirus Monoclonal Antibody in Allogeneic Bone Marrow Transplant Recipients," Transplantation, 1991, vol. 51 (6), pp. 1190-1196.
Fisher., Laboratory Techniques in Biochemistry and Molecular Biology, Elsevier, 1980.
Flanagan., et al.,Monoclonal Antibodies: Methods and Protocols, in: Methods in Molecular Biology, vol. 378.
Gerber H.P., et al., "Antibody Drug-conjugates Targeting the Tumor Vasculature: Current and Future Developments," Mabs, May-Jun. 2009, vol. 1 (3), pp. 247-253.
Gerstenberger B.S., et al., "Tert-buyldiphenylsilylethyl ("TBDPSE"): A Practical Protecting Group for Phenols," The Journal of Organic Chemistry, 2005, vol. 70 (4), pp. 1467-1470.
Goeddel., "Gene Expression Technology" in: Methods in Enzymology, Academic Press, San Diego, CA, 185, 1990.
Haura E.B., et al., "Antiapoptotic Signaling Pathways in Non-small-cell Lung Cancer: Biology and Therapeutic Strategies," Clinical Lung Cancer, 2004, vol. 6 (2), pp. 113-122.
International Search Report and Written Opinion for Application No. PCT/US2015/064686, dated Apr. 4, 2016, 9 pages.
International Search Report and Written Opinion for Application No. PCT/US2015/064693, dated May 10, 2016, 22 pages.
International Search Report and Written Opinion for Application No. PCT/US2015/064706, dated May 27, 2016, 19 pages.
International Search Report and Written Opinion for Application No. PCT/US2017/036288, dated Sep. 7, 2017, 12 pages.
International Search Report and Written Opinion for Application No. PCT/US2017/036368, dated Aug. 22, 2017, 14 pages.
International Search Report and Written Opinion for Application No. PCT/US2017/036399, dated Sep. 7, 2017, 12 pages.
International Search Report and Written Opinion for Application No. PCT/US2017/036428, dated Oct. 4, 2017, 23 pages.
International Search Report and Written Opinion for Application No. PCT/US2017/036449, dated Oct. 2, 2017, 24 pages.
International Search Report and Written Opinion for Application No. PCT/US2017/036639, dated Nov. 15, 2017, 22 pages.
International Search Report and Written Opinion for Application No. PCT/US2017/036645, dated Jan. 11, 2018, 22 pages.
International Search Report and Written Opinion for Application No. PCT/US2017/036650, dated Dec. 11, 2017, 23 pages.
Itoh K., et al., "Phage Display Cloning and Characterization of Monoclonal Antibody Genes and Recombinant Fab Fragment Against the Cd98 Oncoprotein," Japanese Journal of Cancer Research, Dec. 2001, vol. 92 (12), pp. 1313-1321.
Janeway et al., "The Immune System in Health and Disease," in: Immunobiology, 5th Edition., Garland Science, 2001, pp. 94-105.
Jeffrey S.C. et al., "Expanded Utility of the β-Glucuronide Linker: ADCs That Deliver Phenolic Cytotoxic Agents." ACS Medical Chemistry Letters, 2010, vol. 1(6), pp. 277-280.
Jespers L.S., et al., "Guiding the Selection of Human Antibodies from Phage Display Repertoires to a Single Epitope of an Antigen," Bio/Technology, 1994, vol. 12 (9), pp. 899-903.
Leverson J.D., et al., "Exploiting Selective BCL-2 Family Inhibitors to Dissect Cell Survival Dependencies and Define Improved Strategies for Cancer Therapy," Science Translational Medicine, 2015, vol. 7 (279), 279ra40, pp. 1-12.
Loo D., et al., "Abstract 1201: Anti-B7-H3 antibody-drug conjugates as potential therapeutics for solid cancer," Experimental and Molecular Therapeutics, American Association for Cancer Research, New Orleans. USA Cancer Research, Proceedings: AACR 107th Annual Meeting, Apr. 16-20, Apr. 20, 2016, New Orleans, LA, 4 pages.
Loo D., et al., "Development of an Fc-enhanced Anti-B7-H3 Monoclonal Antibody with Potent Antitumor Activity," Clinical Cancer Research, Jul. 15, 2012, vol. 18 (14), pp. 3834-3845.
Lund J., et al., "Human Fc Gamma RI and Fc Gamma RII Interact with Distinct but Overlapping Sites on Human IgG," Journal of Immunology, 1991, vol. 147 (8), pp. 2657-2662.
MacroGenics, Corporate Fact Sheet, Jan. 30, 2018, 2 pages.
Mullard A., et al., "Pioneering Apoptosis-targeted Cancer Drug Poised for FDA Approval," Nature Reviews Drug Discovery, Mar. 2016, vol. 15 (3), pp. 147-149.
Nagase-Zembutsu A., et al., "Development of DS-5573a: A Novel Afucosylated mAb Directed at B7-H3 With Potent Antitumor Activity," Cancer Science, May 2016, vol. 107 (5), pp. 674-681.
Ogitani Y. et al., "Wide application of a novel topoisomerase I inhibitor-based drug conjugation technology." Bioorganic & Medicinal Chemistry Letters, 2016, vol. 26, pp. 5069-5072.
Park D., et al., "Novel Small-molecule Inhibitors of BCL-XL to Treat Lung Cancer," Cancer Research, 2013, vol. 73 (17), pp. 5485-5496.
Peters C., et al., "Antibody-drug Conjugates as Novel Anti-cancer Chemotherapeutics," Bioscience Reports (2015) 35, e00225, doi:10.1042/BSR20150089.
Picarda E., et al., "Molecular Pathways: Targeting B7-H3 (CD276) for Human Cancer Immunotherapy," Clinical Cancer Research, Jul. 15, 2016, vol. 22 (14), pp. 3425-3431.
Riechmann L., et al., "Single Domain Antibodies: Comparison of Camel Vh and Camelised Human Vh Domains," Journal of Immunological Methods, 1999, vol. 231 (1-2), pp. 25-38.
Sambrook J., et al., "Molecular Cloning," A Laboratory Manual, Second Edition, Cold Spring Harbor Laboratory Press,1989, Table of Contents.
MacroGenics Presents Data from Five Preclinical Programs at AACR Annual Meeting 2016, Rockville Maryland Apr. 19, 2016. Available at https://www.globenewswire.com/news-release/2016/04/19/830245/0/en/MacroGenics-Presents-Data-from-Five-Preclinical-Programs-at-AACR-Annual-Meeting-2016.html.
Perez.H.L. et al., "Antibody-Drug Conjugates: Current Status and Future Directions, " Journal of Drug Discovery Today, Jul. 2014, vol. 19 (7), pp. 869-881.
Stewart, J.M., et al., Solid Phase Peptide Synthesis, 2nd Edition, The Pierce Chemical Co., Rockford, IL, 1984.
Toki B.E.., et al., "Protease-Mediated Fragmentation of p-Amidobenzyl Ethers: a New Strategy for the Activation of Anticancer Prodrugs," The Journal of Organic Chemistry, Mar. 2002, vol. 67 (6), pp. 1866-1872.
Wahl R.L., et al., "Improved Radioimaging and Tumor Localization with Monoclonal F(Ab')2," Journal of Nuclear Medicine: Official Publication, Society of Nuclear Medicine, 1983, vol. 24 (4), pp. 316-325.
Wang, Z. X., "An Exact Mathematical Expression for Describing Competitive Binding of Two Different Ligands to a Protein Molecule," FEBS Letters, 1995, vol. 360 (2), pp. 111-114.

(56) References Cited

OTHER PUBLICATIONS

Wolfson W., et al., "Amber Codon Flashing Ambrx Augments Proteins with Unnatural Amino Acids," Chemistry & Biology, 2006, vol. 13 (10), pp. 1011-1012.
Alley S.C., et al., "Contribution of Linker Stability to the Activities of Anticancer Immunoconjugates," Bioconjugate Chemistry, Mar. 2008, vol. 19 (3), pp. 759-765.
Amir R.J., et al., "Self-Immolative Dendrimers," Angewandte Chemie (International Ed. In English), 2003, vol. 42 (37), pp. 4494-4499.
Amsberry K.L., et al., "The Lactonization of 2'-hydroxyhydrocinnamic Acid Amides: a Potential Prodrug for Amines," The Journal of Organic Chemistry, Nov. 1990, vol. 55 (23), pp. 5867-5877.
Amundson S.A., et al., "An Informatics Approach Identifying Markers of Chemosensitivity in Human Cancer Cell Lines," Cancer Research, 2000, vol. 60 (21), pp. 6101-6110.
Arnon R., et al., "Monoclonal Antibodies for Immunotargeting of Drugs in Cancer Therapy," Monoclonal Antibodies and Cancer Therapy, Alan R. Liss, Inc., 1985, pp. 243-256.
Ausubel et al., Current Protocols in Molecular Biology, John Wiley &Sons, NY, 1993, Table of Contents.
Axup J.Y., et al., "Synthesis of Site-Specific Antibody-Drug Conjugates Using Unnatural Amino Acids," Proceedings of the National Academy of Sciences of the United States of America, 2012, vol. 109 (40), pp. 16101-16106.
Badescu G., et al., "Bridging Disulfides for Stable and Defined Antibody Drug Conjugates," Bioconjugate Chemistry, 2014, vol. 25 (6), pp. 1124-1136.
Bird R.E., et al., "Single-Chain Antigen-Binding Proteins," Science, Oct. 1988, vol. 242 (4877), pp. 423-426.
Boger D.L., et al., "CC-1065 and the Duocarmycins: Unraveling the Keys to a New Class of Naturally Derived DNA Alkylating Agents," Proceedings of the National Academy of Sciences of the United States of America, 1995, vol. 92 (9), pp. 3642-3649.
Boger D.L., et al., "Design, Synthesis, and Evaluation of DNA Minor Groove Binding Agents," Pure and Applied Chemistry, Jan. 1993, vol. 65 (6), pp. 1123-1132.
Bouchier-Hayes L., et al., "Measuring Apoptosis at the Single Cell Level," Methods, Mar. 2008, vol. 44 (3), pp. 222-228.
Brown H.C., et al., "Hydroboration. XVIII. The Reaction of Diisopinocampheylborane with Representative cis-Acyclic, Cyclic, and Bicyclic Olefins. A Convenient Systhesis of Optically Active Alcohols and Olefins of High Optical Purity and Established Configuration," Journal of the American Chemical Society, 1964, vol. 86 (3), pp. 397-403.
Buchwald H., et al., "Long-term, Continuous Intravenous Heparin Administration by an Implantable Infusion Pump in Ambulatory Patients with Recurrent Venous Thrombosis," Surgery, 1980, vol. 88 (4), pp. 507-516.
Burke P.J., et al., "Design, Synthesis, and Biological Evaluation of Antibody-Drug Conjugates Comprised of Potent Camptothecin Analogues," Bioconjugate Chemistry, 2009, vol. 20 (6), pp. 1242-1250.
Campos C.B., et al., "Method for Monitoring of Mitochondrial Cytochrome C Release During Cell Death: Immunodetection of Cytochrome C by Flow Cytometry After Selective Permeabilization of the Plasma Membrane," Cytometry, 2006, vol. 69 (6), pp. 515-523.
Carter P., et al., "Humanization of an Anti-p185 HER2 Antibody for Human Cancer Therapy," Proceedings of the National Academy of Sciences, 1992, vol. 89 (10), pp. 4285-4289.
Chapoval A.I., et al., "B7-H3: a Costimulatory Molecule for T Cell Activation and IFN-gamma Production," Nature Immunology, Mar. 2001, vol. 2 (3), pp. 269-274.
Chari R.V., et al., "Immunoconjugates Containing Novel Maytansinoids: Promising Anticancer Drugs," Cancer Research, 1992, vol. 52 (1), pp. 127-131.
Chari R.V., et al., "Targeted Cancer Therapy: Conferring Specificity to Cytotoxic Drugs," Accounts of Chemical Research, 2008, vol. 41 (1), pp. 98-107.

Chothia C., et al., "Canonical Structures for the Hypervariable Regions of Immunoglobulins," Journal of Molecular Biology, 1987, vol. 196 (4), pp. 901-917.
Chothia C., et al., "Conformations of Immunoglobulin Hypervariable Regions," Nature, 1989, vol. 342 (6252), pp. 877-883.
Cleek R.L., et al., "Biodegradable Polymeric Carriers for a bFGF Antibody for Cardiovascular Application," Proc. Intl. Symp. Control. Rel. Bioact. Mater., 1997, vol. 24, pp. 853-854.
Co M.S., et al., "Genetically Engineered Deglycosylation of the Variable Domain Increases the Affinity of an Anti-CD33 Monoclonal Antibody," Molecular Immunology, 1993, vol. 30 (15), pp. 1361-1367.
Controlled Drug Bioavailability, Drug Product Design and Performance, Smolen and Ball (eds.), Wiley, New York (1984).
Crooke S.T., "Molecular Mechanisms of Action of Antisense Drugs," Biochimica et Biophysica Acta, Dec. 1999, vol. 1489 (1), pp. 31-44.
Damle N.K., et al., "Antibody-targeted Chemotherapy with Immunoconjugates of Calicheamicin," Current Opinion in Pharmacology, Aug. 2003, vol. 3 (4), pp. 386-390.
De Groot F.M., et al., "'Cascade-Release Dendrimers' Liberate All End Groups Upon a Single Triggering Event in the Dendritic Core," Angewandte Chemie (International Ed. In English), 2003, vol. 42 (37), pp. 4490-4494.
Dick L.W., et al., "Determination of the Origin of the N-terminal Pyro-glutamate Variation in Monoclonal Antibodies Using Model Peptides," Biotechnology and Bioengineering, Jun. 2007, vol. 97 (3), pp. 544-553.
Dick L.W. Jr., et al., "C-Terminal Lysine Variants in Fully Human Monoclonal Antibodies: Investigation of Test Methods and Possible Causes," Biotechnology and Bioengineering, 2008, vol. 100 (6), pp. 1132-1143.
Doronina S.O., et al., "Development of Potent Monoclonal Antibody Auristatin Conjugates for Cancer Therapy," Nature Biotechnology, Jul. 2003, vol. 21 (7), pp. 778-784.
Dorr R.T., et al., "Interactions of Mitomycin C with Mammalian DMA Detected by Alkaline Elution," Cancer Research, Aug. 1985, vol. 45, pp. 3510-3516.
Dubowchik G.M., et al., "Cathepsin B-Sensitive Dipeptide Prodrugs. 1. a Model Study of Structural Requirements for Efficient Release of Doxorubicin," Bioorganic & Medicinal Chemistry Letters, 1998, vol. 8 (23), pp. 3341-3346.
Dubowchik G.M., et al., "Receptor-mediated and Enzyme-dependent Targeting of Cytotoxic Anticancer Drugs," Pharmacology & Therapeutics, Sep. 1999, vol. 83 (2), pp. 67-123.
Ducry L., et al., "Antibody-Drug Conjugates: Linking Cytotoxic Payloads to Monoclonal Antibodies," Bioconjugate Chemistry, 2010, vol. 21 (1), pp. 5-13.
During M. J., et al., "Controlled Release of Dopamine from a Polymeric Brain Implant: In Vivo Characterization," Annals of Neurology, 1989, vol. 25 (4), pp. 351-356.
Fire A., et al., "Potent and Specific Genetic Interference by Double-Stranded RNA in Caenorhabditis Elegans," Nature, 1998, vol. 391 (6669), pp. 806-811.
Francisco J.A., et al., "cAC10-vcMMAE, an Anti-Cd30-Monomethyl Auristatin E Conjugate with Potent and Selective Antitumor Activity," Blood, 2003, vol. 102 (4), pp. 1458-1465.
Gelboin H.V., et al., "Polyinosinic-polycytidylic Acid Inhibits Chemically Induced Tumorigenesis in Mouse Skin.," Science, Jan. 1970, vol. 167 (3915), pp. 205-207.
Gillies S.D., et al., "High-Level Expression of Chimeric Antibodies Using Adapted cDNA Variable Region Cassettes," Journal of Immunological Methods, Dec. 1989, vol. 125 (1-2), pp. 191-202.
Goldberg D. M. (ed.), Cancer Therapy with Radiolabeled Antibodies, CRC Press, 1995, 6 pages.
Goldspiel B.R., et al., "Human Gene Therapy," Clinical Pharmacy, 1993, vol. 12 (7), pp. 488-505.
Goldstein J.C., et al., "Cytochrome C is Released in a Single Step During Apoptosis," Cell Death and Differentiation, 2005, vol. 12 (5), pp. 453-462..
Goodson J.M., "Dental Applications" in: Medical Applications of Controlled Release, vol. 2, Chapter 6, Langer R.S., et al., eds., CRC Press, 1984, pp. 115-138.

(56) References Cited

OTHER PUBLICATIONS

Hamblett K.J., et al., "Effects of Drug Loading on the Antitumor Activity of a Monoclonal Antibody Drug Conjugate," Clinical Cancer Research, 2004, vol. 10 (20), pp. 7063-7070.
Harlow E., et al., "Antibody: A Laboratory Manual," Cold Spring Harbor Laboratory Press, Cold Spring Harbor, NY, 1998.
Hashiguchi M., et al., "Triggering Receptor Expressed on Myeloid Cell-like Transcript 2 (TLT-2) is a Counter-receptor for B7-H3 and Enhances T Cell Responses," Proceedings of the National Academy of Sciences of the United States of America, Jul. 2008, vol. 105 (30), pp. 10495-10500.
Hay M.P., et al., "A 2-nitroimidazole Carbamate Prodrug of 5-amimo-1-(Chloromethyl)-3-[(5,6,7-trimethoxyindol-2-yl)carbony L]-1,2-dihydro-3h--benz[E]indole (Amino-seco-CBI-TMI) for use with ADEPT and GDEPT," Bioorganic & Medicinal Chemistry Letters, Aug. 1999, vol. 9 (15), pp. 2237-2242.
Hellstrom et al., "Antibodies for Drug Delivery," in: Controlled Drug Delivery, 2nd Edition, 1987, Marcel Dekker, Inc.
Hinman L.M., et al., "Preparation and Characterization of Monoclonal Antibody Conjugates of the Calicheamicins: a Novel and Potent Family of Antitumor Antibiotics," Cancer Research, 1993, vol. 53 (14), pp. 3336-3342.
Hollander I., et al., "Selection of Reaction Additives Used in the Preparation of Monomeric Antibody-Calicheamicin Conjugates," Bioconjugate Chemistry, 2008, vol. 19 (1), pp. 358-361.
Holliger P., et al., ""Diabodies": Small Bivalent and Bispecific Antibody Fragments," Proceedings of the National Academy of Sciences, 1993, vol. 90 (14), pp. 6444-6448.
Howard M.A., et al., "Intracerebral Drug Delivery in Rats with Lesion-Induced Memory Deficits," Journal of Neurosurgery, 1989, vol. 71 (1), pp. 105-112.
Hubbell H.R., et al., "Cyclic AMP Mediates the Direct Antiproliferative Action of Mismatched Double-stranded RNA," Proceedings of the National Academy of Sciences of the United States of America, Feb. 1991, vol. 88 (3), pp. 906-910.
Huston J.S., et al., "Protein Engineering of Antibody Binding Sites: Recovery of Specific Activity in an Anti-Digoxin Single-Chain Fv Analogue Produced in *Escherichia coli*," Proceedings of the National Academy of Sciences, 1988, vol. 85 (16), pp. 5879-5883.
Jefferis R., "Glycosylation of Recombinant Antibody Therapeutics," Biotechnology Program, 2005, vol. 21 (1), pp. 11-16.
Jeffrey S.C., et al., "Development and Properties of Beta-Glucuronide Linkers for Monoclonal Antibody-Drug Conjugates," Bioconjugate Chemistry, 2006, vol. 17 (3), pp. 831-840.
Jeffrey S.C., et al., "Minor Groove Binder Antibody Conjugates Employing a Water Soluble Beta-Glucuronide Linker," Bioorganic & Medicinal Chemistry Letters, 2007, vol. 17 (8), pp. 2278-2280.
Jiang X., et al., "Synthesis and Complete Stereochemical Assignment of Psymberin/Irciniastatin A," Journal of the American Chemical Society, 2005, vol. 127 (32), pp. 11254-11255.
Johnson D.A., et al., "Anti-tumor Activity of CC49-doxorubicin Immunoconjugates," Anticancer Research Jul. 1995, vol. 15 (4), pp. 1387-1393.
Johnsson B., et al., "Comparison of Methods for Immobilization to Carboxymethyl Dextran Sensor Surfaces by Analysis of the Specific Activity of Monoclonal Antibodies," Journal of Molecular Recognition, 1995, vol. 8 (1-2), pp. 125-131.
Johnsson B., et al., "Immobilization of Proteins to a Carboxymethyldextran-Modified Gold Surface for Biospecific Interaction Analysis in Surface Plasmon Resonance Sensors," Analytical Biochemistry, 1991, vol. 198 (2), pp. 268-277.
Joliot A., et al., "Antennapedia Homeobox Peptide Regulates Neural Morphogenesis," Proceedings of the National Academy of Sciences, 1991, vol. 88 (5), pp. 1864-1868.
Jones P.T., et al., "Replacing the Complementarity-determining Regions in a Human Antibody with those from a Mouse," Nature, May 1986, vol. 321 (6069), pp. 522-525.
Jonsson U., et al., "Real-Time Biospecific Interaction Analysis Using Surface Plasmon Resonance and a Sensor Chip Technology," Biotechniques, 1991, vol. 11 (5), pp. 620-627.
Junutula J.R., et al., "Site-specific Conjugation of a Cytotoxic Drug to an Antibody Improves the Therapeutic Index," Nature Biotechnology, 2008, vol. 26 (8), pp. 925-932.
Kabat E.A., et al., "Accession No. PS91-192898, Sequences of Proteins of Immunological Interest," 5th Edition, National Institutes of Health Publication No. 91/3242, 1991, Table of Contents.
Kabat E.A., et al., "Attempts to Locate Complementarity-Determining Residues in the Variable Positions of Light and Heavy Chains," Annals New York Academy of Sciences, 1971, vol. 190, pp. 382-391.
Kabat., et al., "Sequences of Proteins of Immunological Interest," National Institutes of Health, Bethesda, Md. 1987 and 1991.
Kalia J., et al., "Catalysis of Imido Group Hydrolysis in a Maleimide Conjugate," Bioorganic & Medicinal Chemistry Letters, Nov. 2007, vol. 17 (22), pp. 6286-6289.
Kamijo S., et al., "Photochemically Induced Radical Transformation of C(Sp3)-h Bonds to C(Sp3)-cn Bonds," Organic Letters, 2011, vol. 13 (21), pp. 5928-5931.
Kaneko T., et al., "New Hydrazone Derivatives of Adriamycin and their Immunoconjugates-a Correlation Between Acid Stability and Cytotoxicity," Bioconjugate Chemistry, May-Jun. 1991, vol. 2 (3), pp. 133-141.
Kaufman R.J., et al., "Amplification and Expression of Sequences Cotransfected with a Modular Dihydrofolate Reductase Complementary DNA Gene," Journal of Molecular Biology, 1982, vol. 159 (4), pp. 601-621.
Kennedy K.A., et al., "pH Dependence of Mitomycin C-induced Cross-linking Activity in EMT6 Tumor Cells," Cancer Research, Aug. 1985, vol. 45 (8), pp. 3541-3547.
King H.D., et al., "Facile Synthesis of Maleimide Bifunctional Linkers," Tetrahedron Letters, Mar. 2002, vol. 43 (11), pp. 1987-1990.
King H.D., et al., "Monoclonal Antibody Conjugates of Doxorubicin Prepared with Branched Peptide Linkers: Inhibition of Aggregation by Methoxytriethyleneglycol Chains," Journal of Medicinal Chemistry, 2002, vol. 45 (19), pp. 4336-4343.
Kingsbury W.D., et al., "A Novel Peptide Delivery System Involving Peptidase Activated Prodrugs as Antimicrobial Agents. Synthesis and Biological Activity of Peptidyl Derivatives of 5-fluorouracil," Journal of Medicinal Chemistry, Nov. 1984, vol. 27 (11), pp. 1447-1451.
Kirkin V., et al., "The Role of Bcl-2 Family Members in Tumorigenesis," Biochimica et Biophysica Acta, 2004, vol. 1644 (2-3), pp. 229-249.
Kitson S.L., et al., "Antibody-Drug Conjugates (ADCs)—Biotherapeutic Bullets," Chemistry Today, 2013, vol. 31 (4), pp. 30-36.
Kohler G., et al., "Continuous Cultures of Fused Cells Secreting Antibody of Predefined Specificity," Nature, Aug. 1975, vol. 256 (5517), pp. 495-497.
Kriegler M., Gene Transfer and Expression: A Laboratory Manual, Stockton Press, 1990, Table of Contents.
Kung Sutherland M.S., et al., "Sgn-CD33A: a Novel CD33-Targeting Antibody-Drug Conjugate Using a Pyrrolobenzodiazepine Dimer Is Active in Models of Drug-Resistant Aml," Blood, 2013, vol. 122 (8), pp. 1455-1463.
Kupchan S.M., et al., "Maytansine, a Novel Antileukemic Ansa Macrolide From Maytenus Ovatus," Journal of the American Chemical Society, Feb. 1972, vol. 94 (4), pp. 1354-1356.
Kupchan S.M., et al., "Structural Requirements for Antileukemic Activity among the Naturally Occurring and Semisynthetic Maytansinoids," Journal of Medicinal Chemistry, Jan. 1978, vol. 21 (1), pp. 31-37.
Lam X.M., et al., "Microencapsulation of Recombinant Humanized Monoclonal Antibody for Local Delivery," Proceedings of the 24th International Symposium on Controlled Release of Bioactive Materials, 1997, vol. 24, pp. 759-760.
Langer R., et al., "Chemical and Physical Structure of Polymers as Carriers for Controlled Release of Bioactive Agents: A Review," Journal of Macromolecular Science—Reviews in Macromolecular Chemistry & Physics, 1983, vol. C23 (1), pp. 61-126.
Langer R., "New Methods of Drug Delivery," Science, 1990, vol. 249 (4976), pp. 1527-1533.

(56) References Cited

OTHER PUBLICATIONS

Larrick J.W., et al., "Therapeutic Human Antibodies Derived from PCR Amplification of B-Cell Variable Regions," Immunological Reviews, 1992, vol. 130, pp. 69-85.
Lau A., et al., "Conjugation of Doxorubicin to Monoclonal Anti-carcinoembryonic Antigen Antibody via Novel Thiol-directed Cross-linking Reagents," Bioorganic & Medicinal Chemistry, Oct. 1995, vol. 3 (10), pp. 1299-1304.
Lau A., et al., "Novel Doxorubicin-monoclonal Anti-carcinoembryonic Antigen Antibody Immunoconjugate Activity in Vitro," Bioorganic & Medicinal Chemistry, Oct. 1995, vol. 3 (10), pp. 1305-1312.
Lebel H., et al., "Boc-protected Amines via a Mild and Efficient One-pot Curtius Rearrangement," Organic Letters, 2005, vol. 7 (19), pp. 4107-4110.
Lee S., et al., "Cytokines in Cancer Immunotherapy," Cancers, Oct. 2011, vol. 3 (4), pp. 3856-3893.
Levy H.B., et al., "Inhibition of Tumor Growth by Polyinosinic-polycytidylic Acid," Proceedings of the National Academy of Sciences of the United States of America, Feb. 1969, vol. 62 (2), pp. 357-361.
Levy R.D., et al., "Inhibition of Calcification of Bioprosthetic Heart Valves by Local Controlled-Release Diphosphonate," Science, 1985, vol. 228 (4696), pp. 190-192.
Liu Y.D., et al., "N-terminal Glutamate to Pyroglutamate Conversion in Vivo for Human IgG2 Antibodies," The Journal of Biological Chemistry, Apr. 2011, vol. 286 (13), pp. 11211-11217.
Lode H.N., et al., "Targeted Therapy with a Novel Enediyene Antibiotic Calicheamicin Theta(I)1 Effectively Suppresses Growth and Dissemination of Liver Metastases in a Syngeneic Model of Murine Neuroblastoma," Cancer Research, 1998, vol. 58 (14), pp. 2925-2928.
Loos M., et al., "Expression of the Costimulatory Molecule B7-H3 is Associated with Prolonged Survival in Human Pancreatic Cancer," BMC Cancer, Dec. 2009, vol. 9, p. 463.
Lyon R.P., et al., "Self-Hydrolyzing Maleimides Improve the Stability and Pharmacological Properties of Antibody-Drug Conjugates," Nature Biotechnology, 2014, vol. 32 (10), pp. 1059-1062.
MacCallum R.M., et al., "Antibody-Antigen Interactions: Contact Analysis and Binding Site Topography," Journal of Molecular Biology, 1996, vol. 262 (5), pp. 732-745.
Medical Applications of Controlled Release, Langer and Wise (eds.), CRC Pres., Boca Raton, Fla. (1974).
Morgan R.A., et al., "Human Gene Therapy," Annual Review of Biochemistry , 1993, vol. 62, 191-217.
Morrison S.L., et al., "Chimeric Human Antibody Molecules: Mouse Antigen-Binding Domains with Human Constant Region Domains," Proceedings of National Academy of Sciences, 1984, vol. 81 (21), pp. 6851-6855.
Morrison S.L., "Transfectomas Provide Novel Chimeric Antibodies," Science, 1985, vol. 229 (4719), pp. 1202-1207.
Mulligan R.C., "The Basic Science of Gene Therapy," Science, 1993, vol. 260 (5110), pp. 926-932.
Nagamura, Chemistry of Heterocyclic Compounds, 1998, vol. 34, No. 12.
Neuberger M.S., et al., "Recombinant Antibodies Possessing Novel Effector Functions," Nature, 1984, vol. 312 (5995), pp. 604-608.
Neville D.M., et al., "Enhancement of Immunotoxin Efficacy by Acid-cleavable Cross-linking Agents Utilizing Diphtheria Toxin and Toxin Mutants," Journal of Biological Chemistry, Sep. 1989, vol. 264 (25), pp. 14653-14661.
Ning S., et al., "Intratumoral Radioimmunotherapy of a Human Colon Cancer Xenograft Using a Sustained-Release Gel," Radiotherapy & Oncology: The Journal of the European Society for Therapeutic Radiology and Oncology, 1996, vol. 39 (2), pp. 179-189.
Nolting B., et al., "Linker Technologies for Antibody-Drug Conjugates," Methods in Molecular Biology (Clifton, N.J.), 2013, vol. 1045, pp. 71-100.
Nygren M.K., et al., "B7-H3 and its Relevance in Cancer; Immunological and Non-immunological Perspectives," Frontiers in Bioscience, Jun. 2011, vol. 3, pp. 989-993.
Oi V.T., et al., "Chimeric Antibodies," BioTechniques, 1986, vol. 4 (3), pp. 214-221.
Order S.E., "Analysis, Results, and Future Prospective of the Therapeutic Use of Radiolabeled Antibody in Cancer Therapy," in: Monoclonal Antibodies for Cancer Detection and Therapy, Baldwin., et al., Eds., Academic Press, 1985.
Padlan E.A., et al., "Identification of Specificity-determining Residues in Antibodies," FASEB Journal, 1995, vol. 9 (1), pp. 133-139.
Pettit G.R., et al., "Structure of an Antineoplastic Agent from Streptomyces Griseoluteus," Journal of the American Chemical Society, Oct. 1976, vol. 98 (21), pp. 6742-6743.
Pettit G.R., "The Dolastatins," Progress in the Chemistry of Organic Natural Products, 1997, vol. 70, pp. 1-79.
Poljak R.J., "Production and Structure of Diabodies," Structure, 1994, vol. 2 (12), pp. 1121-1123.
Powell., et al., "Additional New Maytansinoids from Trewia nudiflora: 10-Epitrewiasine and Nortrewiasine," Journal of Natural Products, 1983, vol. 46 (5), pp. 660-666.
Prasad D.V., et al., "Murine B7-H3 is a Negative Regulator of T Cells," Journal of Immunology, Aug. 2004, vol. 173 (4), pp. 2500-2506.
Presta L.G., et al., "Humanization of an Antibody Directed against IgE," Journal of Immunology, Sep. 1993, vol. 151 (5), pp. 2623-2632.
Reers M., et al., "J-aggregate Formation of a Carbocyanine as a Quantitative Fluorescent Indicator of Membrane Potential," Biochemistry, May 1991, vol. 30 (18), pp. 4480-4486.
Remillard S., et al., "Antimitotic Activity of the Potent Tumor Inhibitor Maytansine," Science, 1975, vol. 189 (4207), pp. 1002-1005.
Riechmann L., et al., "Reshaping Human Antibodies for Therapy," Nature, 1988, vol. 332 (6162), pp. 323-327.
Roberts D.D., et al., "Solvolysis Reactions: Relative Abilities of Cyclopentyl/Phenyl Groups to Stabilize an Electron-Deficient Carbon," The Journal of Organic Chemistry, 1994, vol. 59, pp. 6464-6469.
Robinson C., "Gene Therapy—Proceeding from Laboratory to Clinic," Trends in Biotechnology, 1993, vol. 11 (5), pp. 155-215.
Robinson J.R., Sustained and Controlled Release Drug Delivery Systems, Marcel Dekker, Inc., 1978, Table of Contents.
Rodrigues M.L., et al., "Synthesis and Beta-lactamase-mediated Activation of a Cephalosporin-taxol Prodrug," Chemistry Biology, Apr. 1995, vol. 2 (4), pp. 223-227.
Roth T.J., et al., "B7-H3 Ligand Expression by Prostate Cancer: a Novel Marker of Prognosis and Potential Target for Therapy," Cancer Research, Aug. 2007, vol. 67 (16), pp. 7893-7900.
Ruvkun G., "Molecular Biology. Glimpses of a Tiny RNA World," Science, Oct. 2001, vol. 294 (5543), pp. 797-799.
Sakai K., et al., "Antitumor Principles in Mosses: the First Isolation and Identification of Maytansinoids, Including a Novel 15-methoxyansamitocin P-3," Journal of Natural Products, Sep.-Oct. 1988, vol. 51 (5), pp. 845-850.
Saudek C.D., et al., "A Preliminary Trial of the Programmable Implantable Medication System for Insulin Delivery," The New England Journal of Medicine, 1989, vol. 321 (9), pp. 574-579.
Sellei C., et al., "Clinical and Pharmacologic Experience with Dibromodulcitol (NSC-104800), a New Antitumor Agent," Cancer Chemotherapy Reports, Dec. 1969, vol. 53 (6), pp. 377-384.
Shamis M., et al., "Bioactivation of Self-Immolative Dendritic Prodrugs by Catalytic Antibody 38C2," Journal of the American Chemical Society, 2004, vol. 126 (6), pp. 1726-1731.
Shields R.L., et al., "Lack of Fucose on Human IgG1 N-linked Oligosaccharide Improves Binding to Human Fcgamma RIII and Antibody-dependent Cellular Toxicity," The Journal of Biological Chemistry, Jul. 2002, vol. 277 (30), pp. 26733-26740.
Sims M.J., et al., "A Humanized CD18 Antibody can Block Function without Cell Destruction," Journal of Immunology, Aug. 1993, vol. 151 (4), pp. 2296-2308.
Smiley S.T., et al., "Intracellular Heterogeneity in Mitochondrial Membrane Potentials Revealed by a J-aggregate-forming Lipophilic

(56) References Cited

OTHER PUBLICATIONS

Cation JC-1," Proceedings of the National Academy of Sciences of the United States of America, May 1991, vol. 88 (9), pp. 3671-3675.
Song Y.K., et al., "Antibody Mediated Lung Targeting of Long-circulating Emulsions," PDA Journal of Pharmaceutical Science and Technology, Nov.-Dec. 1996, vol. 50 (6), pp. 372-397.
Padlan E.A., "A Possible Procedure for Reducing the Immunogenicity of Antibody Variable Domains While Preserving Their Ligand-binding Properties," Molecular Immunology, Apr.-May 1991, vol. 28 (4-5), pp. 489-498.
Roguska M.A., et al., "Humanization of Murine Monoclonal Antibodies Through Variable Domain Resurfacing," Proceedings of the National Academy of Sciences of the United States of America, Feb. 1994, vol. 91 (3), pp. 969-973.
Studnicka G.M., et al., "Human-engineered Monoclonal Antibodies Retain Full Specific Binding Activity by Preserving Non-CDR Complementarity-modulating Residues," Protein Engineering, Jun. 1994, vol. 7(6), pp. 805-814.
Laurent Ducry., "Antibody-Drug Conjugates," Springer Science & Business Media, LLC, 2013.
Steinberger P., et al., "Molecular Characterization of Human 41g-B7-H3, a Member of the B7 Family with Four Ig-like Domains," Journal of Immunology, Feb. 2004, vol. 172 (4), pp. 2352-2359.
Storm D.R., et al., "Effect of Small Changes in Orientation on Reaction Rate," Journal of the American Chemical Society, Aug. 1972, vol. 94 (16), pp. 5815-5825.
Suh W.K., et al., "The B7 Family Member B7-H3 Preferentially Down-regulates T Helper Type 1-mediated Immune Responses," Nature Immunology, Sep. 2003, vol. 4 (9), pp. 899-906.
Sun C., et al., "Enabling ScFvs as Multi-Drug Carriers: a Dendritic Approach," Bioorganic & Medicinal Chemistry, 2003, vol. 11 (8), pp. 1761-1768.
Sun C., et al., "Syntheses of Dendritic Linkers Containing Chlorambucil Residues for the Preparation of Antibody-Multidrug Immunoconjugates," Bioorganic & Medicinal Chemistry Letters, 2002, vol. 12 (16), pp. 2213-2215.
Sun Y., et al., "B7-H3 and B7-H4 Expression in Non-small-cell Lung Cancer," Lung Cancer, Aug. 2006, vol. 53 (2), pp. 143-151.
Suwanborirux K., et al., "Ansamitocin P-3, a Maytansinoid, From Claopodium Crispifolium and Anomodon Attenuatus or Associated Actinomycetes," Experientia, Jan. 1990, vol. 46 (1), pp. 117-120.
Takeda S., et al., "Construction of Chimaeric Processed Immunoglobulin Genes Containing Mouse Variable and Human Constant Region Sequences," Nature, 1985, vol. 314 (6010), pp. 452-454.
Tao Z.F., et al., "Discovery of a Potent and Selective Bcl-xl Inhibitor With in Vivo Activity," ACS Medicinal Chemistry Letters, 2014, vol. 5 (10), pp. 1088-1093.
Thorpe P.E., et al., "New Coupling Agents for the Synthesis of Immunotoxins Containing a Hindered Disulfide Bond with Improved Stability in Vivo," Cancer Research, Nov. 1987, vol. 47 (22), pp. 5924-5931.
Thorpe P.E., et al., "The Preparation and Cytotoxic Properties of Antibody-toxin Conjugates," Immunological Reviews, 1982, vol. 62, pp. 119-158.
Thorpe P.E. et al., "Antibody Carriers of Cytotoxic Agents in Cancer Therapy: A Review," in: Monoclonal Antibodies '84: Biological and Clinical Applications, 1985, pp. 474-512.
Tian F., et al., "A General Approach to Site-specific Antibody Drug Conjugates," Proceedings of the National Academy of Sciences of the United States of America, 2014, vol. 111 (5), pp. 1766-1771.
Tolstoshev P., "Gene Therapy, Concepts, Current Trials and Future Directions," Annual Review of Pharmacology and Toxicology, 1993, vol. 32, pp. 573-596.
Tumey L.N., et al., "Mild Method for Succinimide Hydrolysis on ADCs: Impact on ADC Potency, Stability, Exposure, and Efficacy," Bioconjugate Chemistry, Oct. 2014, vol. 25 (10), pp. 1871-1880.
Umana P., et al., "Engineered Glycoforms of an Antineuroblastoma IgG1 with Optimized Antibody-dependent Cellular Cytotoxic Activity," Nature Biotechnology, 1999, vol. 17 (2), pp. 176-180.

Urlaub G., et al., "Isolation of Chinese Hamster Cell Mutants Deficient in Dihydrofolate Reductase Activity," Proceedings of the National Academy of Sciences, 1980, vol. 77 (7), pp. 4216-4220.
Verhoeyen M., et al., "Reshaping Human Antibodies: Grafting an Antilysozyme Activity," Science, 1988, vol. 239, pp. 1534-1536.
Walker J.R., et al, "Synthesis and Preliminary Chemotherapeutic Evaluation of the Fully C-linked Glucuronide of N-(4-hydroxyphenyl)retinamide," Bioorganic & Medicinal Chemistry, May 2006, vol. 14 (9), pp. 3038-3048.
Walker M.A., et al., "Monoclonal Antibody Mediated Intracellular Targeting of Tallysomycin S(10B)," Bioorganic & Medicinal Chemistry Letters, 2004, vol. 14 (16), pp. 4323-4327.
Walker M.A., et al., "Synthesis of an Immunoconjugate of Camptothecin," Bioorganic & Medicinal Chemistry Letters, 2002, vol. 12 (2), pp. 217-219.
Wallick S.C., et al., "Glycosylation of a VH Residue of a Monoclonal Antibody against Alpha (1-6) Dextran Increases its Affinity for Antigen," Journal of Experimental Medicine, 1988, vol. 168 (3), pp. 1099-1109.
Wang L., et al., "B7-H3 Promotes Acute and Chronic Allograft Rejection," European Journal of Immunology, Feb. 2005, vol. 35 (2), pp. 428-438.
Wani N.C., et al., "Plant Antitumor Agents: Colubrinol Acetate and Colubrinol, Antileukemic ansa Macrolides from Colubrina Texensis," Journal of the Chemical Society, Chemical Communications, 1973, vol. 390, pp. 1973.
Ward E.S., et al., "Binding Activities of a Repertoire of Single Immunoglobulin Variable Domains Secreted from *Escherichia coli*," Nature, 1989, vol. 341 (6242), pp. 544-546.
Wawrzynczak et al., "Antibody Conjugates in Radioimaging and Therapy of Cancer": in Immunoconjugates, Vogel C.W. ed., Oxford Univ. Press, 1987, 5 pages.
Wright A., et al., "Antibody Variable Region Glycosylation: Position Effects on Antigen Binding and Carbohydrate Structure," The EMBO Journal, 1991, vol. 10 (10), pp. 2717-2723.
Wu C.P., et al., "Relationship Between Co-stimulatory Molecule B7-H3 Expression and Gastric Carcinoma Histology and Prognosis," World Journal of Gastroenterology, Jan. 2006, vol. 12 (3), pp. 457-459.
Wu G., et al., "Delivery Systems for Gene Therapy," Biotherapy, 1991, vol. 3 (1), pp. 87-95.
Wu G.Y., et al., "Receptor-mediated in Vitro Gene Transformation by a Soluble DNA Carrier System," Journal of Biological Chemistry, 1987, vol. 262 (10), pp. 4429-4432.
Yamamoto Y., et al., "Radical Reaction Initiated and Stereocontrolled by Zinc Chloride," Heterocycles, 1998, vol. 47 (2), pp. 765-780.
Yamato I., et al., "Clinical Importance of B7-H3 Expression in Human Pancreatic Cancer," British Journal of Cancer, Nov. 2009, vol. 101 (10), pp. 1709-1716.
Yang M., et al., "Direct Lactonization of 2-arylacetic Acids Through Pd(II)-catalyzed C-h Activation/c-o Formation," Organic Letters, 2013, vol. 15 (3), pp. 690-693.
Zamore P.D., "Ancient Pathways Programmed by Small RNAs," Science, May 2002, vol. 296 (5571), pp. 1265-1269.
Zeleznick L.D., et al., "Treatment of Leukemic (L-1210) Mice with Double-stranded Polyribonucleotides," Proceedings of the Society for Experimental Biology and Medicine, Jan. 1969, vol. 130 (1), pp. 126-128.
Zhang J.Y., et al., "Apoptosis-based Anticancer Drugs," Nature Reviews. Drug Discovery, Feb. 2002, vol. 1 (2), pp. 101-102.
Zhao R.Y., et al., "Synthesis and Evaluation of Hydrophilic Linkers for Antibody-Maytansinoid Conjugates," Journal of Medicinal Chemistry, 2011, vol. 54 (10), pp. 3606-3623.
Co-pending U.S. Appl. No. 16/308,463, filed on Jun. 7, 2017 (corresponding to WO2017/214282).
Co-pending U.S. Appl. No. 16/308,622, filed on Jun. 7, 2017 (corresponding to WO2017/214322).
Co-pending U.S. Appl. No. 16/308,742, filed on Jun. 7, 2017 (corresponding to WO2017/214339).
Co-pending U.S. Appl. No. 16/308,755, filed on Jun. 8, 2017 (corresponding to WO2017/214456).
Co-pending U.S. Appl. No. 16/308,766, filed on Jun. 8, 2017 (corresponding to WO2017/214462).

(56) References Cited

OTHER PUBLICATIONS

Co-pending U.S. Appl. No. 16/308,774, filed on Jun. 8, 2017 (corresponding to WO2017/214458).
Co-pending U.S. Appl. No. 16/358,963, filed on Mar. 20, 2019.
Co-pending U.S. Appl. No. 16/675784, filed on Nov. 6, 2019.
International Search Report and Written Opinion for Application No. PCT/US2017/036445, dated Nov. 21, 2017, 33 pages.
Koenig S., et al., "Targeting B7-H3 in Cancer," Medicographia, 2014, vol. 36 (3), pp. 285-292.
Leong S.R., et al., "An Anti-B7-H4 Antibody—Drug Conjugate for the Treatment of Breast Cancer," Molecular Pharmaceutics, 2015, vol. 12 (6), pp. 1717-1729.

ANTI-B7-H3 ANTIBODIES AND ANTIBODY DRUG CONJUGATES

RELATED APPLICATIONS

This application claims priority to U.S. Provisional Application No. 62/347,476, filed on Jun. 8, 2016, and to U.S. Provisional Application No. 62/366,511, filed on Jul. 25, 2016. The entire contents of the foregoing applications are expressly incorporated herein by reference.

SEQUENCE LISTING

The instant application contains a Sequence Listing which has been submitted electronically in ASCII format and is hereby incorporated by reference in its entirety. Said ASCII copy, created on Jun. 7, 2017, is named 117813-12603_ST25.txt and is 159,744 bytes in size.

BACKGROUND OF THE INVENTION

The B7 homology 3 protein (B7-H3) (also known as CD276 and B7RP-2, and referred to herein as "B7-H3") is a type I transmembrane glycoprotein of the immunoglobulin superfamily. Human B7-H3 contains a putative signal peptide, V-like and C-like Ig domains, a transmembrane region and a cytoplasmic domain. Exon duplication in humans results in the expression of two B7-H3 isoforms having either a single IgV-IgC-like domain (2IgB7-H3 isoform) or a IgV-IgC-IgV-IgC-like domain (4IgB7-H3 isoform) containing several conserved cysteine residues. The predominant B7-H3 isoform in human tissues and cell lines is the 4IgB7-H3 isoform (Steinberger et al., J. Immunol. 172(4): 2352-9 (2004)).

B7-H3 has been reported as having both co-stimulatory and co-inhibitory signaling functions (see, e.g., Chapoval et al., Nat. Immunol. 2: 269-74 (2001); Suh et al., Nat. Immunol. 4: 899-906 (2003); Prasad et al., J. Immunol. 173: 2500-6 (2004); and Wang et al., Eur. J. Immunol. 35: 428-38 (2005)). For example, in vitro studies have shown B7-H3's co-stimulatory function since B7-H3 was able to increase proliferation of cytotoxic T-lymphocytes (CTLs) and upregulate interferon gamma (IFN-γ) production in the presence of anti-CD3 antibody to mimic the T cell receptor signal (Chapoval et al., 2001). Moreover, in vivo studies using cardiac allografts in B7-H3−/− mice showed decreased production of key cytokine, chemokine and chemokine receptor mRNA transcripts (e.g., IL-2, IFN-γ, monocyte chemoattractant protein (MCP-1) and IFN-inducible protein (IP)-10) as compared to wild-type control (Wang et al., 2005). In contrast, B7-H3 co-inhibitory function has been observed, for example, in mice where B7-H3 protein inhibited T-cell activation and effector cytokine production (Suh et al., 2003). Although no ligands have been identified for human B7-H3, murine B7-H3 has been found to bind to the triggering receptor expressed on myeloid cells (TREM-) like transcript 2 (TLT-2), a modulator of adaptive an innate immunity cellular responses. Binding of murine B7-H3 to TLT-2 on CD8+ T-cells enhances T-cell effector functions such as proliferation, cytotoxicity and cytokine production (Hashiguchi et al., Proc. Nat'l. Acad. Sci. U.S.A. 105(30): 10495-500 (2008)).

B7-H3 is not constitutively expressed in many immune cells (e.g., natural killer (NK) cells, T-cells, and antigen-presenting cells (APCs)), however, its expression can be induced. Further, the expression of B7-H3 is not restricted to immune cells. B7-H3 transcripts are expressed in a variety of human tissues including colon, heart, liver, placenta, prostate, small intestine, testis, and uterus, as well as osteoblasts, fibroblasts, epithelial cells, and other cells of non-lymphoid lineage, potentially indicating immunological and non-immunological functions (Nygren et al. Front Biosci. 3:989-93 (2011)). However, protein expression in normal tissue is typically maintained at a low level and thus, may be subject to post-transcriptional regulation.

B7-H3 is also expressed in a variety of human cancers, including prostate cancer, clear cell renal cell carcinoma, glioma, melanoma, lung cancer, non-small cell lung cancer (NSCLC), small cell lung cancer, pancreatic cancer, gastric cancer, acute myeloid leukemia (AML), non-Hodgkin's lymphoma (NHL), ovarian cancer, colorectal cancer, colon cancer, renal cancer, hepatocellular carcinoma, kidney cancer, head and neck cancer, hypopharyngeal squamous cell carcinoma, glioblastoma, neuroblastoma, breast cancer, endometrial cancer, and urothelial cell carcinoma. Although the role of B7-H3 in cancer cells is unclear, its expression may orchestrate signaling events that may protect cancer cells from innate and adaptive immune responses. For example, B7-H3 is overexpressed in high-grade prostatic intraepithelial neoplasia and adenocarcinomas of the prostate, and high expression levels of B7-H3 in these cancerous cells is associated with an increased risk of cancer progression after surgery (Roth et al. Cancer Res. 67(16): 7893-900 (2007)). Further, tumor B7-H3 expression in NSCLC inversely correlated with the number of tumor-infiltrating lymphocytes and significantly correlated with lymph node metastasis (Sun et al. Lung Cancer 53(2): 143-51 (2006)). The level of circulating soluble B7-H3 in NSCLC patients has also been associated with higher tumor stage, tumor size, lymph node metastasis, and distant metastasis (Yamato et al., Br. J. Cancer 101(10):1709-16 (2009)).

B7-H3 may also play an important role in T-cell-mediated antitumor responses in a context dependent manner. For example, gastric cancer tumor cell expression of B7-H3 positively correlated with survival time, infiltration depth, and tissue type (Wu et al., World J. Gastroenterol. 12(3): 457-9 (2006)). Further, high expression of B7-H3 in pancreatic tumor cells was associated with patient survival after surgical resection and significantly correlated with the number of tumor-infiltrating CD8+ T-cells (Loos et al., BMC Cancer 9:463 (2009).

Antibody drug conjugates (ADC) represent a relatively new class of therapeutics comprising an antibody conjugated to a cytotoxic drug via a chemical linker. The therapeutic concept of ADCs is to combine binding capabilities of an antibody with a drug, where the antibody is used to deliver the drug to a tumor cell by means of binding to a target surface antigen, including target surface antigens that are overexpressed in the tumor cells.

There remains a need in the art for anti-B7-H3 antibodies and anti-B7-H3 ADCs that can be used for therapeutic purposes in the treatment of cancer.

SUMMARY OF THE INVENTION

In certain aspects, the present invention provides for antibodies and antibody drug conjugates (ADCs) that specifically bind to human B7-H3. In certain aspects, the present invention provides novel ADCs that can selectively deliver Bcl-xL inhibitors to target cancer cells, e.g., B7-H3 expressing cells.

In one aspect, the present invention provides an antoi-B7-H3 antibody, or antigen binding portion thereof, that binds to human B7-H3 (hB7-H3), wherein the antibody, or antigen binding portion thereof, comprises a heavy chain variable region comprising a CDR3 having the amino acid sequence of SEQ ID NO: 12 and a light chain variable region comprising a CDR3 having the amino acid sequence of SEQ ID NO: 15.

In one embodiment, the anti-B7-H3 antibody, or antigen binding portion thereof, comprises a heavy chain variable region comprising a CDR2 having the amino acid sequence of SEQ ID NO: 140 and a light chain variable region comprising a CDR2 having the amino acid sequence of SEQ ID NO: 7.

In one embodiment, the anti-B7-H3 antibody, or antigen binding portion thereof, comprises a heavy chain variable region comprising a CDR1 having the amino acid sequence of SEQ ID NO: 10 and a light chain variable region comprising a CDR1 having the amino acid sequence of either SEQ ID NO: 136 or 138.

In one aspect, the present invention provides an anti-B7-H3 antibody, or antigen binding portion thereof, that binds to human B7-H3 (hB7-H3), wherein the antibody, or antigen binding portion thereof, comprises a heavy chain variable region comprising a CDR3 having the amino acid sequence of SEQ ID NO: 35 and a light chain variable region comprising a CDR3 having the amino acid sequence of SEQ ID NO: 39.

In one embodiment, the anti-B7-H3 antibody, or antigen binding portion thereof, comprises a heavy chain variable region comprising a CDR2 having the amino acid sequence of SEQ ID NO: 34, and a light chain variable region comprising a CDR2 having the amino acid sequence of SEQ ID NO: 38.

In one embodiment, the anti-B7-H3 antibody, or antigen binding portion thereof, comprises a heavy chain variable region comprising a CDR1 having the amino acid sequence of SEQ ID NO: 33 and a light chain variable region comprising a CDR1 having the amino acid sequence of either SEQ ID NO: 37.

In one embodiment, the anti-B7-H3 antibody, or antigen binding portion thereof, is an IgG isotype.

In one embodiment, the anti-B7-H3 antibody, or antigen binding portion thereof, is an IgG1 or an IgG4 isotype.

In one embodiment, the anti-B7-H3 antibody, or antigen binding portion thereof, has a $K_D$ of $1.5 \times 10^{-8}$ or less as determined by surface plasmon resonance.

In one aspect, the present invention provides an anti-B7-H3 antibody, or antigen-binding portion thereof, that binds to hB7-H3, said antibody, or antigen-binding portion thereof, comprising either (i) a heavy chain variable region comprising a CDR set of SEQ ID NOs: 10, 11, and 12, and a light chain variable region comprising a CDR set of SEQ ID NOs: 14, 7, and 15, or (ii) a heavy chain variable region comprising a CDR set of SEQ ID NOs: 33, 34, and 35, and a light chain variable region comprising a CDR set of SEQ ID NOs: 37, 38, and 39.

In one aspect, the present invention provides an anti-B7-H3 antibody that binds to human B7-H3 (hB7-H3), wherein the antibody comprises a heavy chain variable region comprising a CDR3 having the amino acid sequence of SEQ ID NO: 12 and a light chain variable region comprising a CDR3 having the amino acid sequence of SEQ ID NO: 15.

In one embodiment, the anti-B7-H3 antibody comprises a heavy chain variable region comprising a CDR2 having the amino acid sequence of SEQ ID NO: 140 and a light chain variable region comprising a CDR2 having the amino acid sequence of SEQ ID NO: 7.

In one embodiment, the anti-B7-H3 antibody comprises a heavy chain variable region comprising a CDR1 having the amino acid sequence of SEQ ID NO: 10 and a light chain variable region comprising a CDR1 having the amino acid sequence of either SEQ ID NO: 136 or 138.

In one aspect, the present invention provides an anti-B7-H3 antibody that binds to human B7-H3 (hB7-H3), wherein the antibody, or antigen binding portion thereof, comprises a heavy chain variable region comprising a CDR3 having the amino acid sequence of SEQ ID NO: 35 and a light chain variable region comprising a CDR3 having the amino acid sequence of SEQ ID NO: 39.

In one embodiment, the anti-B7-H3 antibody comprises a heavy chain variable region comprising a CDR2 having the amino acid sequence of SEQ ID NO: 34, and a light chain variable region comprising a CDR2 having the amino acid sequence of SEQ ID NO: 38.

In one embodiment, the anti-B7-H3 antibody comprises a heavy chain variable region comprising a CDR1 having the amino acid sequence of SEQ ID NO: 33 and a light chain variable region comprising a CDR1 having the amino acid sequence of either SEQ ID NO: 37.

In one embodiment, the anti-B7-H3 antibody is an IgG isotype.

In one embodiment, the anti-B7-H3 antibody is an IgG1 or an IgG4 isotype.

In one embodiment, the anti-B7-H3 antibody has a $K_D$ of $1.5 \times 10^{-8}$ or less as determined by surface plasmon resonance.

In one aspect, the present invention provides an anti-B7-H3 antibody that binds to hB7-H3, said antibody comprising either (i) a heavy chain variable region comprising a CDR set of SEQ ID NOs: 10, 11, and 12, and a light chain variable region comprising a CDR set of SEQ ID NOs: 14, 7, and 15, or (ii) a heavy chain variable region comprising a CDR set of SEQ ID NOs: 33, 34, and 35, and a light chain variable region comprising a CDR set of SEQ ID NOs: 37, 38, and 39.

In one embodiment, the anti-B7-H3 antibody, or antigen binding portion thereof, is humanized.

In one embodiment, the anti-B7-H3 antibody, or antigen binding portion thereof, further comprises a human acceptor framework. In one embodiment, the human acceptor framework comprises an amino acid sequence selected from the group consisting of SEQ ID Nos: 155, 156, 164, 165, 166, and 167. In one embodiment, the human acceptor framework comprises at least one framework region amino acid substitution. In one embodiment, the amino acid sequence of the framework is at least 65% identical to the sequence of said human acceptor framework and comprises at least 70 amino acid residues identical to said human acceptor framework.

In one embodiment, the human acceptor framework comprises at least one framework region amino acid substitution at a key residue, said key residue selected from the group consisting of a residue adjacent to a CDR; a glycosylation site residue; a rare residue; a residue capable of interacting with human B7-H3; a residue capable of interacting with a CDR; a canonical residue; a contact residue between heavy chain variable region and light chain variable region; a residue within a Vernier zone; and a residue in a region that overlaps between a Chothia-defined variable heavy chain CDR1 and a Kabat-defined first heavy chain framework. In one embodiment, the key residue is selected from the group consisting of 48H, 67H, 69H, 71H, 73H, 94H, and 2L. In one embodiment, the key residue substitution is in the variable heavy chain region and is selected from the group consisting of M48I, V67A, I69L, A71V, K73R, and R94G. In one embodiment, the key residue substitution is in the variable light chain region and is I2V.

In one aspect, the present invention provides an anti-B7-H3 antibody, or antigen-binding portion thereof, that binds to hB7-H3 comprising a heavy chain variable region comprising a CDR set of SEQ ID NOs: 25, 26, and 27, and a light chain variable region comprising a CDR set of SEQ ID NOs: 29, 30, and 31. In one embodiment, the anti-B7-H3 antibody, or antigen binding portion thereof, is humanized In one embodiment, the anti-B7-H3 antibody, or antigen binding portion thereof, further comprises a human acceptor framework.

In one embodiment, the human acceptor framework comprises an amino acid sequence selected from the group consisting of SEQ ID NOs: 155 to 158. In one embodiment, the human acceptor framework comprises at least one framework region amino acid substitution. In one embodiment, the amino acid sequence of the framework is at least 65% identical to the sequence of said human acceptor framework and comprises at least 70 amino acid residues identical to said human acceptor framework. In one embodiment, the amino acid sequence of the framework is at least 85% identical, 90% identical, 95% identical, 96% identical, 97% identical, 98% identical, or 99% identical to the sequence of the human acceptor framework and comprises at least 70, at least 75, at least 80, or at least 85 amino acid residues identical to the human acceptor framework.

In one embodiment, the human acceptor framework comprises at least one framework region amino acid substitution at a key residue, said key residue selected from the group consisting of: a residue adjacent to a CDR; a glycosylation site residue; a rare residue; a residue capable of interacting with human B7-H3; a residue capable of interacting with a CDR; a canonical residue; a contact residue between heavy chain variable region and light chain variable region; a residue within a Vernier zone; and a residue in a region that overlaps between a Chothia-defined variable heavy chain CDR1 and a Kabat-defined first heavy chain framework. In one embodiment, the key residue is selected from the group consisting of 69H, 46L, 47L, 64L, and 71L. In one embodiment, the key residue substitution is in the variable heavy chain region and is L69I. In one embodiment, the key residue substitution is in the variable light chain region and is selected from the group consisting of L46P, L47W, G64V, and F71H.

In one aspect, the present invention provides an anti-hB7-H3 antibody, or antigen-binding portion thereof, comprising a heavy chain CDR1 comprising an amino acid sequence as set forth in SEQ ID NO: 10, a heavy chain CDR2 comprising an amino acid sequence as set forth in SEQ ID NO: 140, a heavy chain CDR3 comprising an amino acid sequence as set forth in SEQ ID NO: 12, a light chain CDR1 comprising an amino acid sequence as set forth in SEQ ID NO: 136 or 138, a light chain CDR2 comprising an amino acid sequence as set forth in SEQ ID NO: 7, and a light chain CDR3 comprising an amino acid sequence as set forth in SEQ ID NO: 15.

In another aspect, the present invention provides an anti-hB7-H3 antibody, or antigen-binding portion thereof, comprising a heavy chain CDR1 comprising an amino acid sequence as set forth in SEQ ID NO: 33, a heavy chain CDR2 comprising an amino acid sequence as set forth in SEQ ID NO: 34, a heavy chain CDR3 comprising an amino acid sequence as set forth in SEQ ID NO: 35, a light chain CDR1 comprising an amino acid sequence as set forth in SEQ ID NO: 37, a light chain CDR2 comprising an amino acid sequence as set forth in SEQ ID NO: 38, and a light chain CDR3 comprising an amino acid sequence as set forth in SEQ ID NO: 39.

In one embodiment, the anti-hB7-H3 antibody, or antigen-binding portion thereof, comprises a heavy chain variable domain comprising an amino acid sequence set forth in SEQ ID NO: 139 and a light chain variable domain comprising an amino acid sequence set forth in SEQ ID NO: 135.

In one embodiment, the anti-hB7-H3 antibody, or antigen-binding portion thereof, comprises a heavy chain comprising an amino acid sequence having at least 90%, 95%, 96%, 97%, 98%, or 99% identity to SEQ ID NO: 139, and/or a light chain comprising an amino acid sequence having at least 90%, 95%, 96%, 97%, 98%, or 99% identity to SEQ ID NO: 135.

In one embodiment, the anti-hB7-H3 antibody, or antigen-binding portion thereof, comprises a heavy chain variable domain comprising an amino acid sequence set forth in SEQ ID NO: 139 and a light chain variable domain comprising an amino acid sequence set forth in SEQ ID NO: 137.

In one embodiment, the anti-hB7-H3 antibody, or antigen-binding portion thereof, comprises a heavy chain comprising an amino acid sequence having at least 90%, 95%, 96%, 97%, 98%, or 99% identity to SEQ ID NO: 139, and/or a light chain comprising an amino acid sequence having at least 90%, 95%, 96%, 97%, 98%, or 99% identity to SEQ ID NO: 137.

In one embodiment, the anti-hB7-H3 antibody, or antigen-binding portion thereof, comprises a heavy chain variable domain comprising an amino acid sequence set forth in SEQ ID NO: 147 and a light chain variable domain comprising an amino acid sequence set forth in SEQ ID NO: 144.

In one embodiment, the anti-hB7-H3 antibody, or antigen-binding portion thereof, comprises a heavy chain comprising an amino acid sequence having at least 90%, 95%, 96%, 97%, 98%, or 99% identity to SEQ ID NO: 147, and/or a light chain comprising an amino acid sequence having at least 90%, 95%, 96%, 97%, 98%, or 99% identity to SEQ ID NO: 144.

In one aspect, the present invention provides an anti-hB7-H3 antibody comprising a heavy chain CDR1 comprising an amino acid sequence as set forth in SEQ ID NO: 10, a heavy chain CDR2 comprising an amino acid sequence as set forth in SEQ ID NO: 140, a heavy chain CDR3 comprising an amino acid sequence as set forth in SEQ ID NO: 12, a light chain CDR1 comprising an amino acid sequence as set forth in SEQ ID NO: 136 or 138, a light chain CDR2 comprising an amino acid sequence as set forth in SEQ ID NO: 7, and a light chain CDR3 comprising an amino acid sequence as set forth in SEQ ID NO: 15.

In another aspect, the present invention provides an anti-hB7-H3 antibody comprising a heavy chain CDR1 comprising an amino acid sequence as set forth in SEQ ID NO: 33, a heavy chain CDR2 comprising an amino acid sequence as set forth in SEQ ID NO: 34, a heavy chain CDR3 comprising an amino acid sequence as set forth in SEQ ID NO: 35, a light chain CDR1 comprising an amino acid sequence as set forth in SEQ ID NO: 37, a light chain CDR2 comprising an amino acid sequence as set forth in SEQ ID NO: 38, and a light chain CDR3 comprising an amino acid sequence as set forth in SEQ ID NO: 39.

In one embodiment, the anti-hB7-H3 antibody comprises a heavy chain variable domain comprising an amino acid sequence set forth in SEQ ID NO: 139 and a light chain variable domain comprising an amino acid sequence set forth in SEQ ID NO: 135.

In one embodiment, the anti-hB7-H3 antibody comprises a heavy chain comprising an amino acid sequence having at least 90%, 95%, 96%, 97%, 98%, or 99% identity to SEQ ID NO: 139, and/or a light chain comprising an amino acid sequence having at least 90%, 95%, 96%, 97%, 98%, or 99% identity to SEQ ID NO: 135.

In one embodiment, the anti-hB7-H3 antibody comprises a heavy chain variable domain comprising an amino acid sequence set forth in SEQ ID NO: 139 and a light chain variable domain comprising an amino acid sequence set forth in SEQ ID NO: 137.

In one embodiment, the anti-hB7-H3 antibody comprises a heavy chain comprising an amino acid sequence having at least 90%, 95%, 96%, 97%, 98%, or 99% identity to SEQ ID NO: 139, and/or a light chain comprising an amino acid sequence having at least 90%, 95%, 96%, 97%, 98%, or 99% identity to SEQ ID NO: 137.

In one embodiment, the anti-hB7-H3 antibody comprises a heavy chain variable domain comprising an amino acid sequence set forth in SEQ ID NO: 147 and a light chain variable domain comprising an amino acid sequence set forth in SEQ ID NO: 144.

In one embodiment, the anti-hB7-H3 antibody comprises a heavy chain comprising an amino acid sequence having at least 90%, 95%, 96%, 97%, 98%, or 99% identity to SEQ ID NO: 147, and/or a light chain comprising an amino acid sequence having at least 90%, 95%, 96%, 97%, 98%, or 99% identity to SEQ ID NO: 144.

In one embodiment, the anti-hB7-H3 antibody, or antigen-binding portion thereof, comprises a heavy chain CDR set corresponding to antibody huAb13v1, and a light chain CDR set corresponding to antibody huAb13v1. In one embodiment, the anti-hB7-H3 antibody, or antigen-binding portion thereof, comprises a heavy chain variable region corresponding to antibody huAb13v1, and a light chain variable region corresponding to antibody huAb13v1.

In one embodiment, the anti-hB7-H3 antibody, or antigen-binding portion thereof, comprises a heavy chain CDR set corresponding to antibody huAb3v2.5, and a light chain CDR set corresponding to antibody huAb3v2.5. In one embodiment, the anti-hB7-H3 antibody, or antigen-binding portion thereof, comprises a heavy chain variable region corresponding to antibody huAb3v2.5, and a light chain variable region corresponding to antibody huAb3v2.5.

In one embodiment, the antibody, or antigen binding portion thereof, binds cynomolgus B7-H3.

In one embodiment, the antibody, or antigen binding portion thereof, has a dissociation constant ($K_D$) to hB7-H3 selected from the group consisting of: at most about $10^{-7}$ M; at most about $10^{-8}$ M; at most about $10^{-9}$ M; at most about $10^{-10}$ M; at most about $10^{-11}$ M; at most about $10^{-12}$ M; and at most $10^{-13}$ M.

In one embodiment, the antibody, or antigen binding portion thereof, comprises a heavy chain immunoglobulin constant domain of a human IgM constant domain, a human IgG1 constant domain, a human IgG2 constant domain, a human IgG3 constant domain, a human IgG4 constant domain, a human IgA constant domain, or a human IgE constant domain.

In one embodiment, the antibody is an IgG having four polypeptide chains which are two heavy chains and two light chains.

In one embodiment, the antibody, or antigen-binding portion thereof, comprises the heavy chain immunoglobulin constant region domain is a human IgG1 constant domain.

In one embodiment, the human IgG1 constant domain comprises an amino acid sequence of SEQ ID NO: 159 or SEQ ID NO: 160.

In one aspect, the present invention provides an isolated antibody, or antigen binding portion thereof, that binds to human B7-H3 (hB7-H3), wherein the antibody, or antigen binding portion thereof, comprises a heavy chain comprising the amino acid sequence of SEQ ID NO: 168 and a light chain comprising the amino acid sequence of SEQ ID NO: 169.

In one aspect, the present invention provides an isolated antibody, or antigen binding portion thereof, that binds to human B7-H3 (hB7-H3), wherein the antibody, or antigen binding portion thereof, comprises a heavy chain comprising the amino acid sequence of SEQ ID NO: 170 and a light chain comprising the amino acid sequence of SEQ ID NO: 171.

In one aspect, the present invention provides an isolated antibody, or antigen binding portion thereof, that binds to human B7-H3 (hB7-H3), wherein the antibody, or antigen binding portion thereof, comprises a heavy chain comprising the amino acid sequence of SEQ ID NO: 172 and a light chain comprising the amino acid sequence of SEQ ID NO: 173.

In one embodiment, the antibody, or antigen binding portion thereof, further comprises a light chain immunoglobulin constant domain comprising a human Ig kappa constant domain or a human Ig lambda constant domain.

In one embodiment, the anti-hB7-H3 antibody, or antigen-binding portion thereof, competes with the antibody, or antigen binding portion thereof, of any one of the anti-hB7-H3 antibodies, or antigen-binding portions thereof, disclosed herein.

In one aspect, the present invention provides a pharmaceutical composition comprising the anti-hB7-H3 antibody, or antigen binding portion thereof, as disclosed herein, and a pharmaceutically acceptable carrier.

In another aspect, the present invention provides an anti-hB7-H3 Antibody Drug Conjugate (ADC) comprising an anti-hB7-H3 antibody disclosed herein conjugated to a drug via a linker In one embodiment, the drug is an auristatin or a pyrrolobenzodiazepine (PBD). In one embodiment, the drug is a Bcl-xL inhibitor.

In one aspect, the present invention provides an anti-hB7-H3 antibody drug conjugate (ADC) comprising a drug linked to an anti-human B7-H3 (hB7-H3) antibody by way of a linker, wherein the drug is a Bcl-xL inhibitor according to structural formula (IIa), (IIb), (IIc), or (IId):

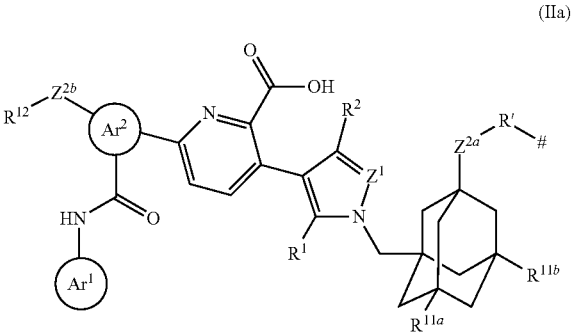

(IIa)

-continued

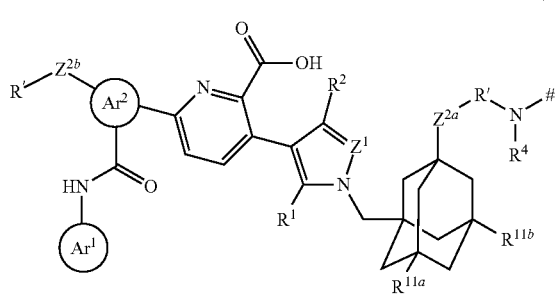
(IIb)

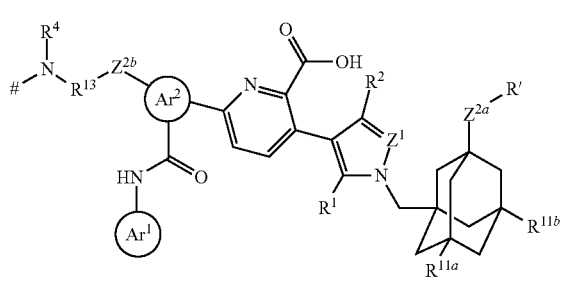
(IIc)

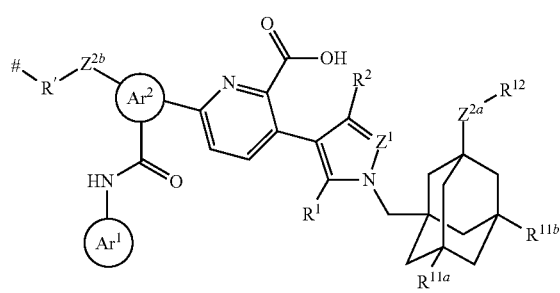
(IId)

wherein:
Ar¹ is selected from

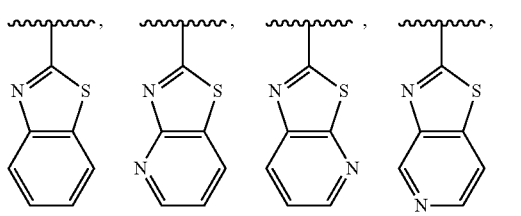

, and

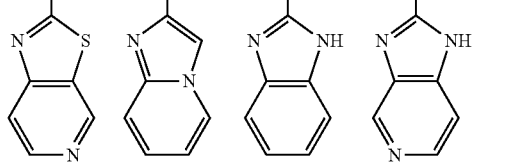

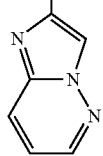

and is optionally substituted with one or more substituents independently selected from halo, hydroxy, nitro, lower alkyl, lower heteroalkyl, $C_{1-4}$alkoxy, amino, cyano and halomethyl;

Ar² is selected from

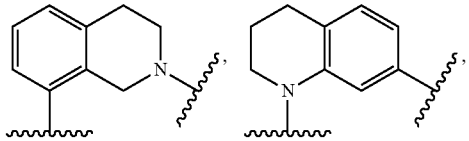

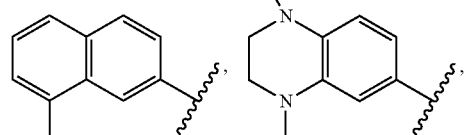

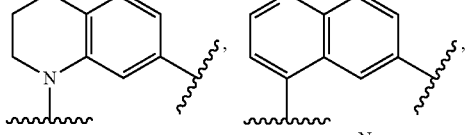

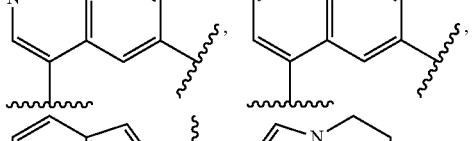

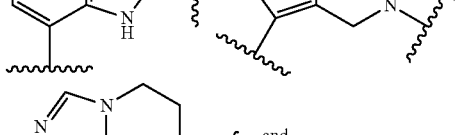, and

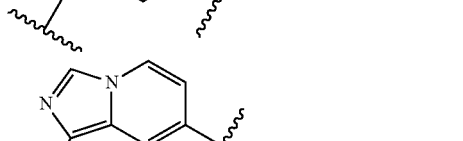

or an N-oxide thereof, and is optionally substituted with one or more substituents independently selected from halo, hydroxy, nitro, lower alkyl, lower heteroalkyl, $C_{1-4}$alkoxy, amino, cyano and halomethyl, wherein the $R^{12}$—$Z^{2b}$—, R'—$Z^{2b}$—, #—N($R^4$)—$R^{13}$—$Z^{2b}$—, or #—R'—$Z^{2b}$— substituents are attached to Ar² at any Ar² atom capable of being substituted; Z¹ is selected from N, CH, C-halo, C—CH₃ and C—CN; $Z^{2a}$ and $Z^{2b}$ are each, independently from one another, selected from a bond, $NR^6$, $CR^{6a}R^{6b}$, O, S, S(O), S(O)₂, $NR^6C(O)$—, —$NR^{6a}C(O)NR^{6b}$—, and $NR^6C(O)O$—;

R' is

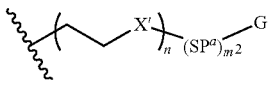

or

-continued

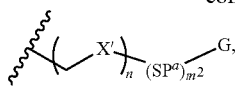

wherein #, where attached to R', is attached to R' at any R' atom capable of being substituted; X' is selected at each occurrence from —N($R^{10}$)—, —N($R^{10}$)C(O)—, —N($R^{10}$)S(O)$_2$—, —S(O)$_2$N($R^{10}$)—, and —O—; n is selected from 0-3; $R^{10}$ is independently selected at each occurrence from hydrogen, lower alkyl, heterocycle, aminoalkyl, G-alkyl, and —(CH$_2$)$_2$—O—(CH$_2$)$_2$—O—(CH$_2$)$_2$—NH$_2$; G at each occurrence is independently selected from a polyol, a polyethylene glycol with between 4 and 30 repeating units, a salt and a moiety that is charged at physiological pH; SP$^a$ is independently selected at each occurrence from oxygen, —S(O)$_2$N(H)—, —N(H)S(O)$_2$—, —N(H)C(O)—, —C(O)N(H)—, —N(H)—, arylene, heterocyclene, and optionally substituted methylene; wherein methylene is optionally substituted with one or more of —NH(CH$_2$)$_2$G, NH$_2$, C$_{1-8}$ alkyl, and carbonyl; m$^2$ is selected from 0-12; $R^1$ is selected from hydrogen, methyl, halo, halomethyl, ethyl, and cyano; $R^2$ is selected from hydrogen, methyl, halo, halomethyl and cyano; $R^3$ is selected from hydrogen, methyl, ethyl, halomethyl and haloethyl; $R^4$ is selected from hydrogen, lower alkyl and lower heteroalkyl or is taken together with an atom of $R^{13}$ to form a cycloalkyl or heterocyclyl ring having between 3 and 7 ring atoms; $R^6$, $R^{6a}$ and $R^{6b}$ are each, independent from one another, selected from hydrogen, optionally substituted lower alkyl, optionally substituted lower heteroalkyl, optionally substituted cycloalkyl and optionally substituted heterocyclyl, or are taken together with an atom from $R^4$ and an atom from $R^{13}$ to form a cycloalkyl or heterocyclyl ring having between 3 and 7 ring atoms; $R^{11a}$ and $R^{11b}$ are each, independently of one another, selected from hydrogen, halo, methyl, ethyl, halomethyl, hydroxyl, methoxy, CN, and SCH$_3$; $R^{12}$ is optionally R' or is selected from hydrogen, halo, cyano, optionally substituted alkyl, optionally substituted heteroalkyl, optionally substituted heterocyclyl, and optionally substituted cycloalkyl; $R^{13}$ is selected from optionally substituted C$_{1-8}$ alkylene, optionally substituted heteroalkylene, optionally substituted heterocyclene, and optionally substituted cycloalkylene; and # represents a point of attachment to a linker; and wherein the anti-hB7-H3 antibody binds to B7-H3 (SEQ ID NO: 149) with a dissociation constant (K$_d$) of about 1×10$^{-6}$M or less. In a further embodiment, the antibody comprises a heavy chain variable domain comprising the amino acid sequence set forth in SEQ ID NO: 147 and a light chain variable domain comprising the amino acid sequence set forth in SEQ ID NO: 144; binds to B7-H3 (SEQ ID NO: 149) with a dissociation constant (K$_d$) of about 1×10$^{-6}$ M or less, as determined by surface plasmon resonance; and/or inhibits tumor growth in an in vivo human small-cell lung carcinoma (SCLC) xenograft assay with a tumor growth inhibition % (TGI %) of at least about 50% relative to a human IgG antibody which is not specific for B7-H3, wherein the human IgG antibody is administered in the SCLC xenograft assay at the same dose and frequency as the anti-hB7-H3 antibody.

In one embodiment, the ADC is a compound according to structural formula (I):

  (I)

wherein D is the Bcl-xL inhibitor drug of formula (IIa), (IIb), (IIc) or (IId); L is the linker; Ab is the anti-hB7-H3 antibody; LK represents a covalent linkage linking the linker (L) to the anti-hB7-H3 antibody (Ab); and m is an integer ranging from 1 to 20.

In one embodiment, G at each occurrence is a salt or a moiety that is charged at physiological pH.

In one embodiment, G at each occurrence is a salt of a carboxylate, a sulfonate, a phosphonate, or ammonium.

In one embodiment, G at each occurrence is a moiety that is charged at physiological pH selected from the group consisting of carboxylate, a sulfonate, a phosphonate, and an amine.

In one embodiment, G at each occurrence is a moiety containing a polyethylene glycol with between 4 and 30 repeating units, or a polyol.

In one embodiment, the polyol is a sugar.

In one embodiment, the ADC is of the formula (IIa) or formula (IId), and R' includes at least one substitutable nitrogen suitable for attachment to a linker.

In one embodiment, G is selected at each occurrence from:

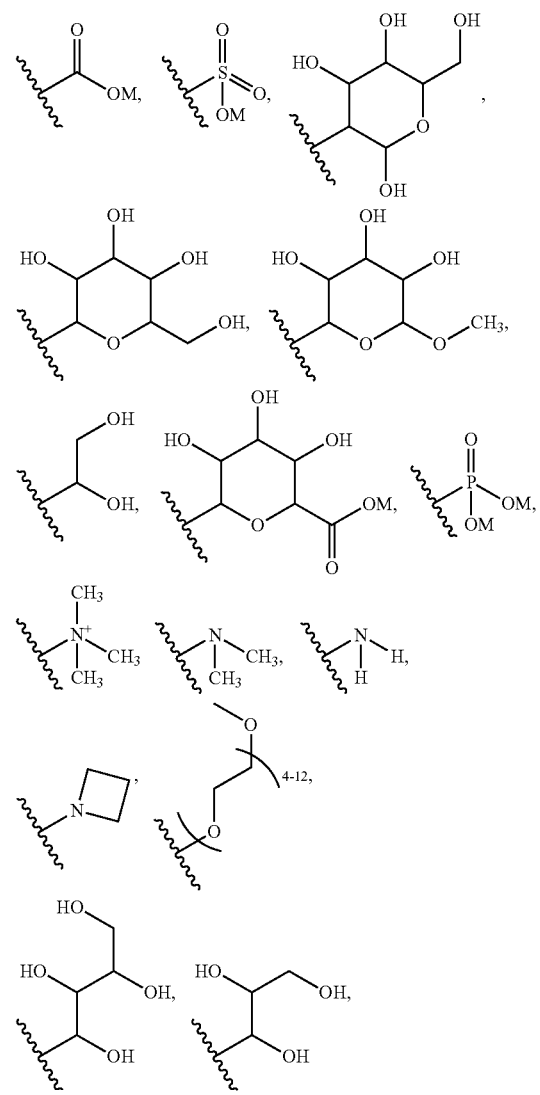

-continued
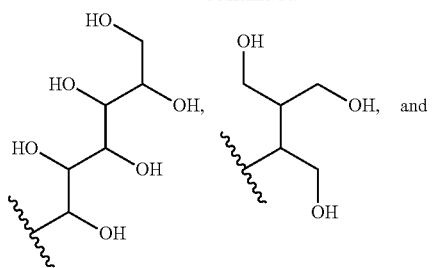
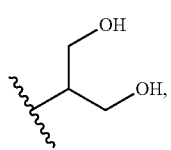
wherein M is hydrogen or a positively charged counterion.
In one embodiment, R' is selected from
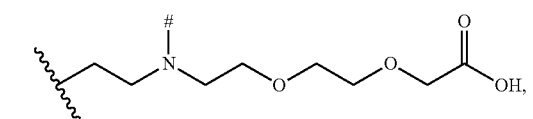
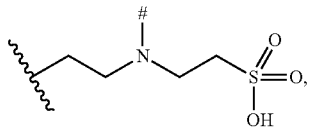
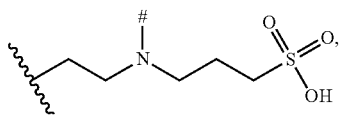
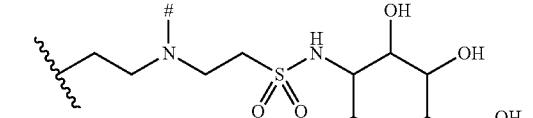
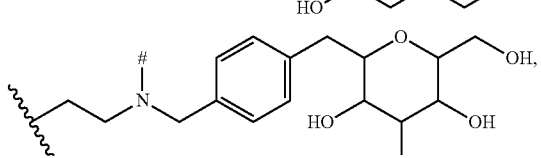
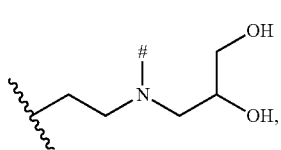
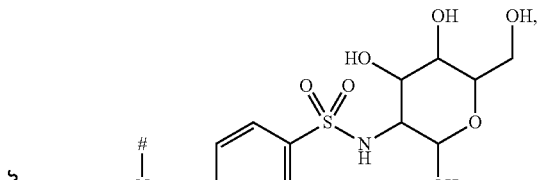
-continued
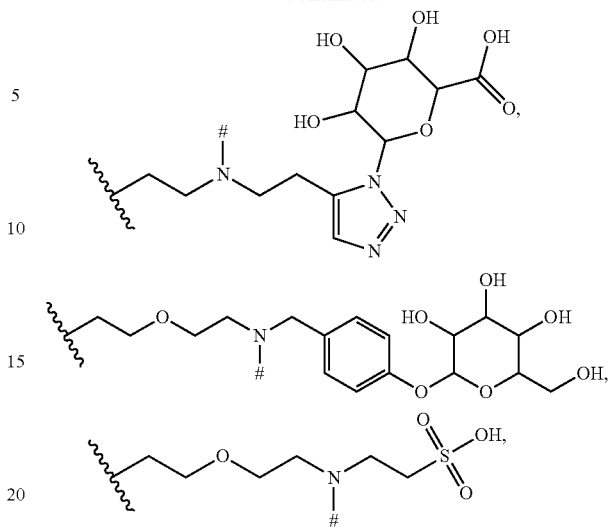
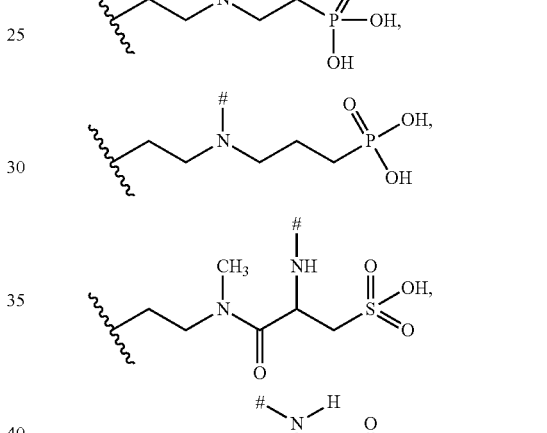
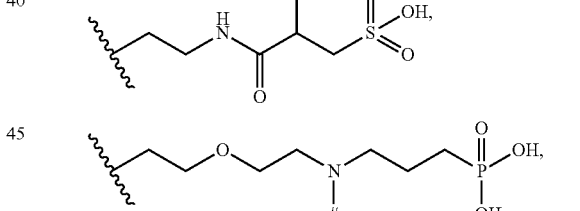
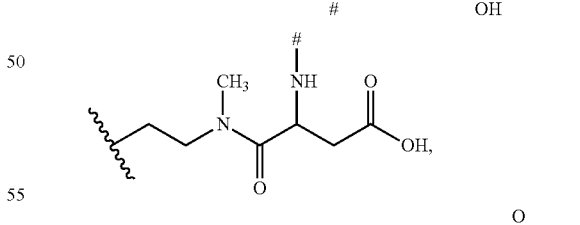
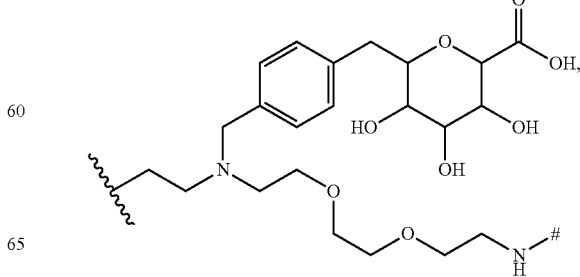

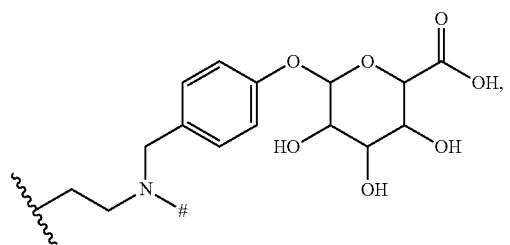
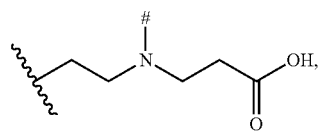
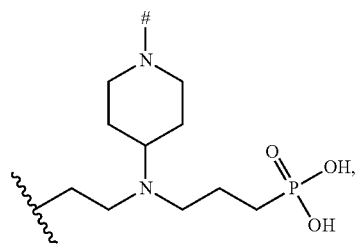
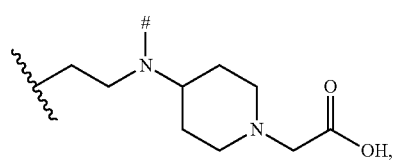
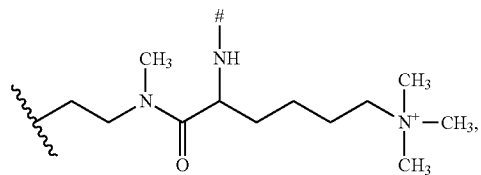
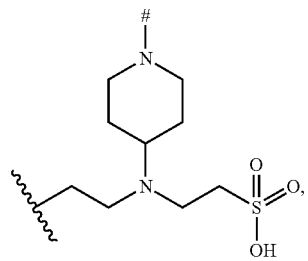
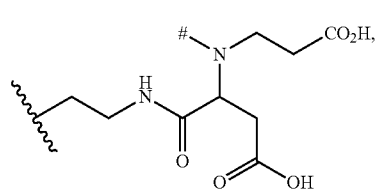
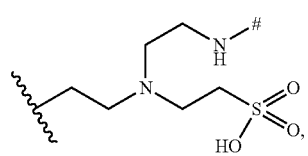
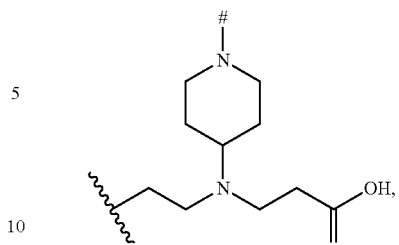
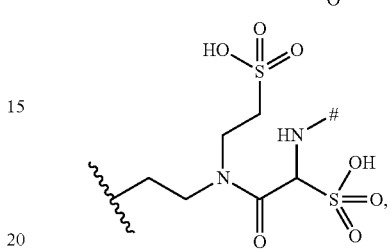
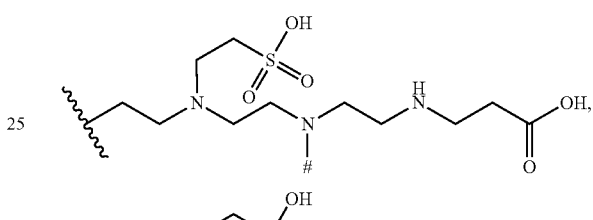
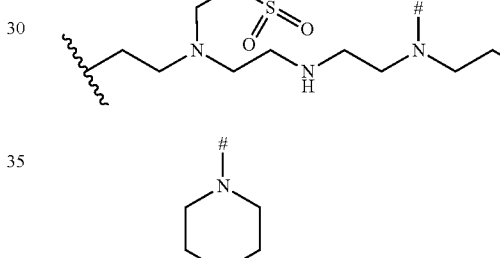
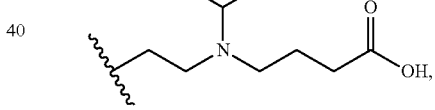
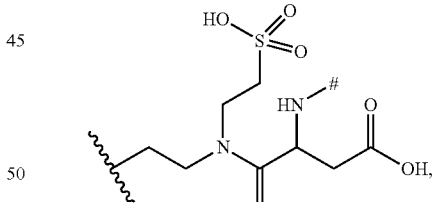
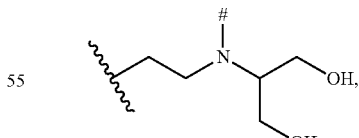
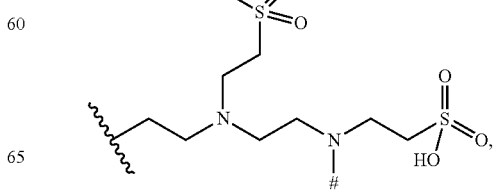

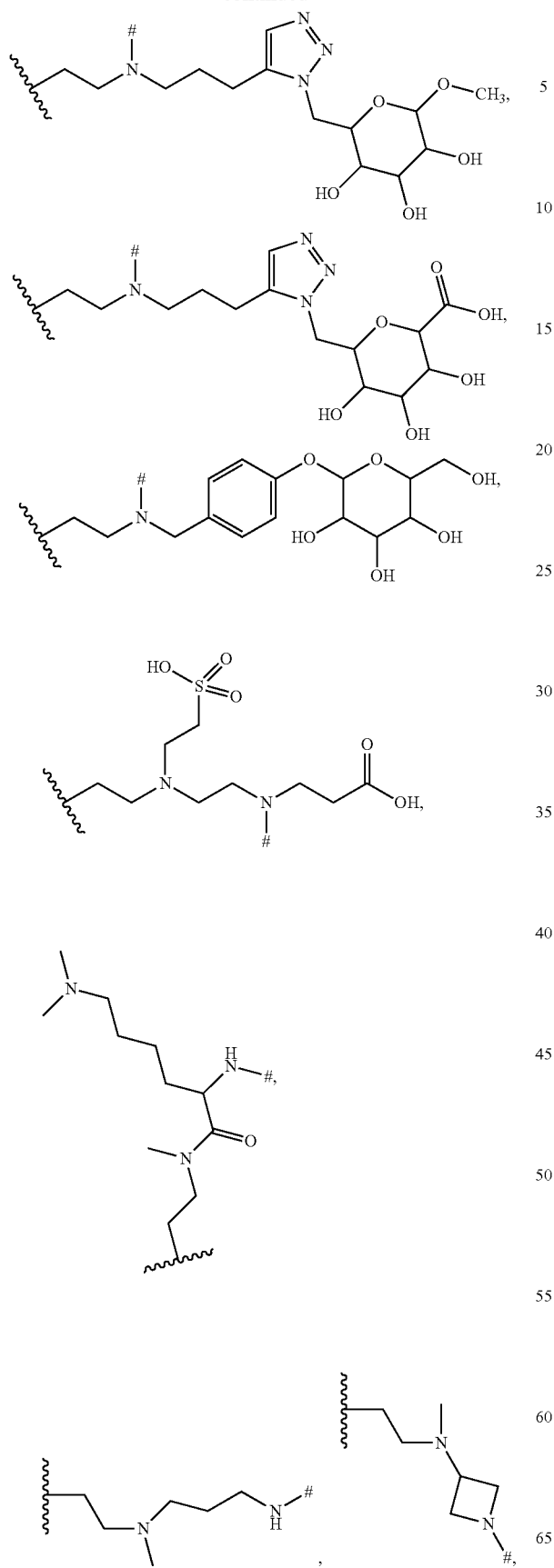
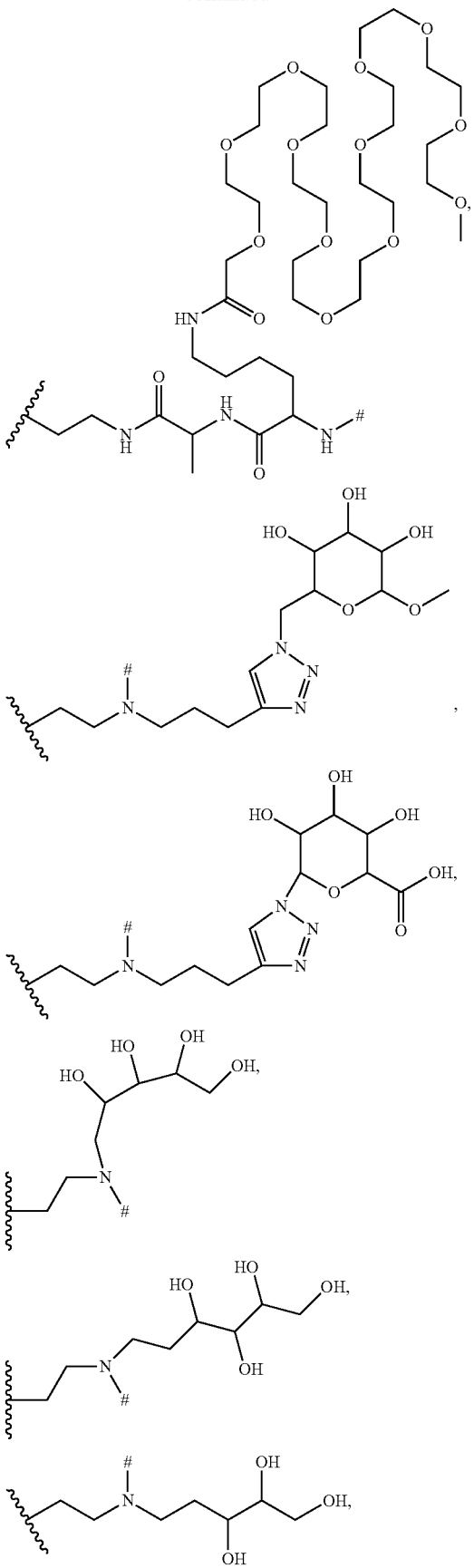

-continued

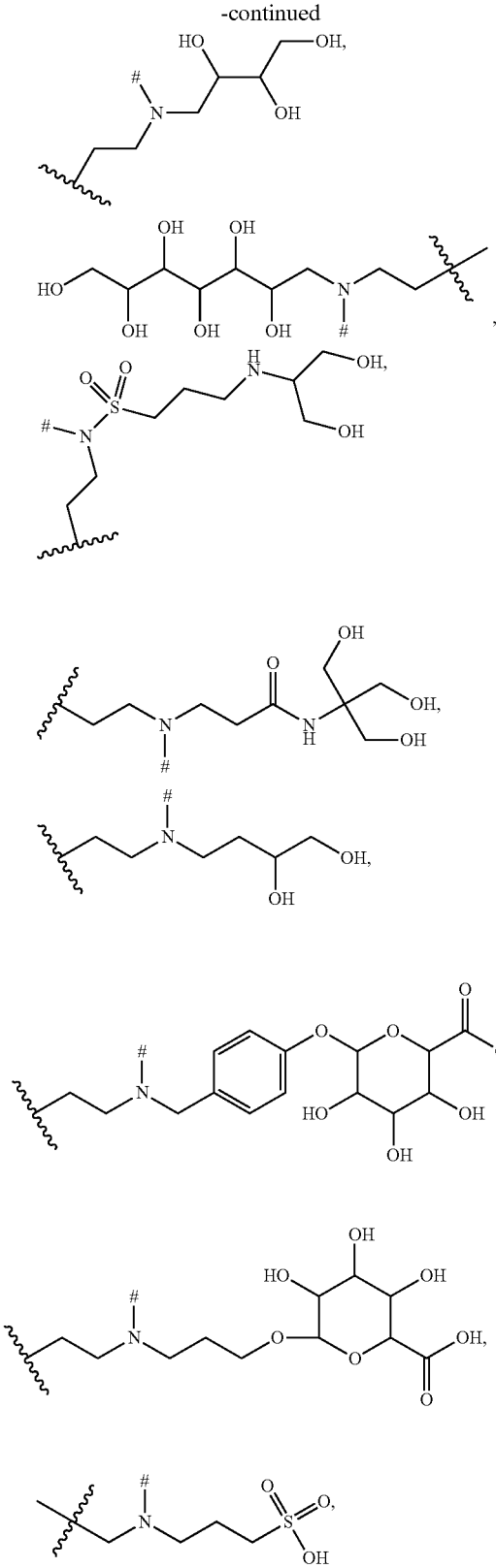

wherein # represents either a hydrogen atom in the Bcl-xL inhibitor drug of the ADCs of formula (IIb) or (IIc) or the point of attachment in the Bcl-xL inhibitor drug of the ADCs of formula (IIa) or (IId) to a linker L.

In one embodiment, $Ar^1$ is selected from

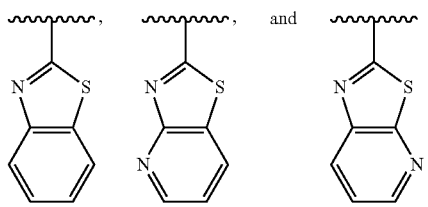

and is optionally substituted with one or more substituents independently selected from halo, cyano, methyl, and halomethyl.

In one embodiment, $Ar^1$ is

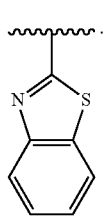

In one embodiment, $Ar^2$ is

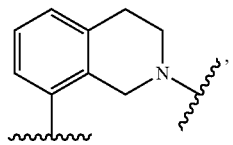 [SMILES: *c1cccc2c1CN(*)CC2]

optionally substituted with one or more substituents.

In one embodiment, $Ar^2$ is selected from

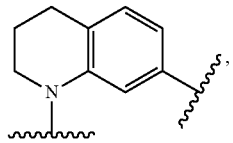

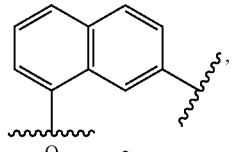

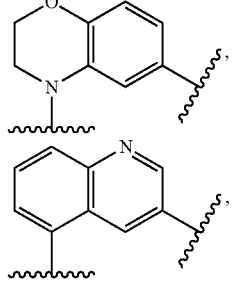

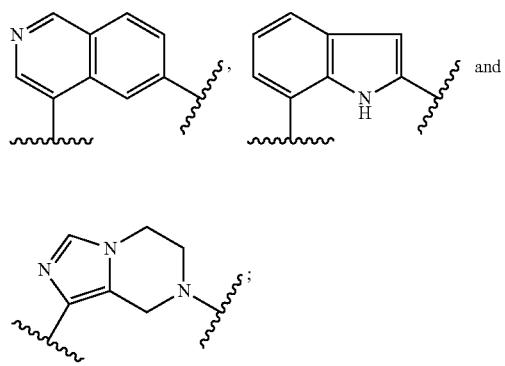

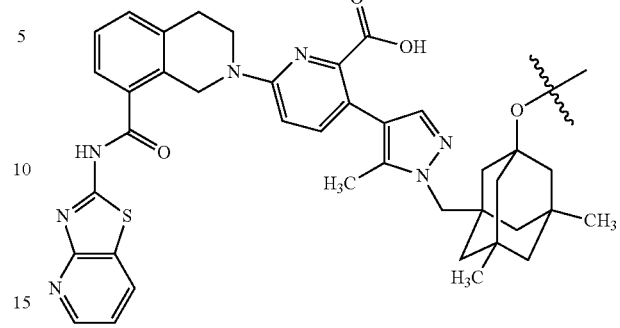

and is optionally substituted with one or more substituents.

In one embodiment, $Ar^2$ is substituted with one or more solubilizing groups.

In one embodiment, each solubilizing group is, independently of the others, selected from a moiety containing a polyol, a polyethylene glycol with between 4 and 30 repeating units, a salt, or a moiety that is charged at physiological pH.

In one embodiment, $Ar^2$ is substituted with one or more solubilizing groups.

In one embodiment, each solubilizing group is, independently of the others, selected from a moiety containing a polyol, a polyethylene glycol with between 4 and 30 repeating units, a salt, or a moiety that is charged at physiological pH.

In one embodiment, $Z^1$ is N.

In one embodiment, $Z^{2a}$ is O.

In one embodiment, $R^1$ is methyl or chloro.

In one embodiment, $R^2$ is hydrogen or methyl.

In one embodiment, $R^2$ is hydrogen.

In one embodiment, $Z^{2b}$ is O.

In one embodiment, $Z^{2b}$ is NH or $CH_2$.

In one embodiment, the ADC is a compound according to structural formula (IIa).

In one embodiment, the ADC is a compound according to structural formula (IIa) which includes a core selected from structures (C.1)-(C.21):

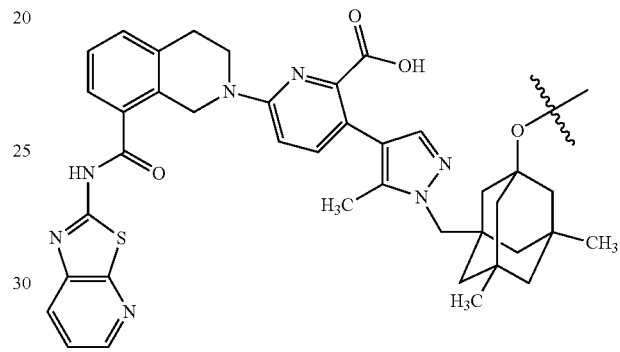

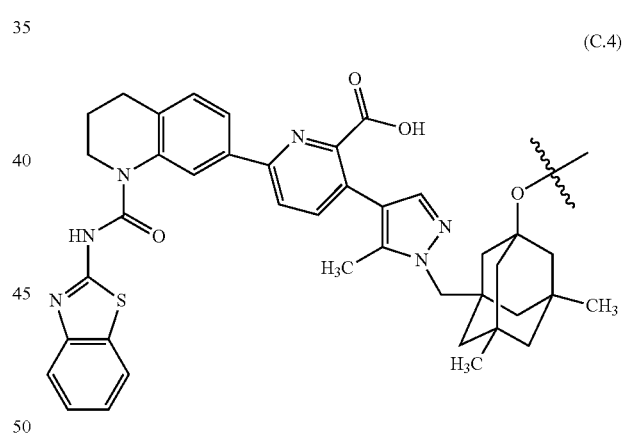

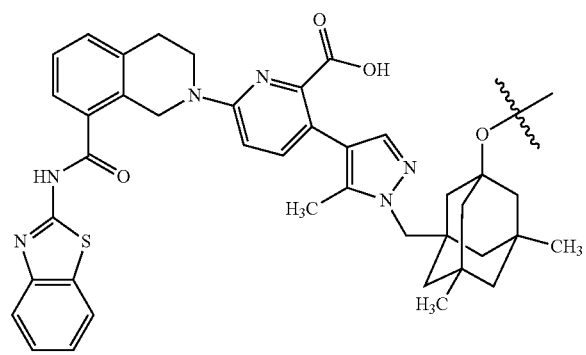

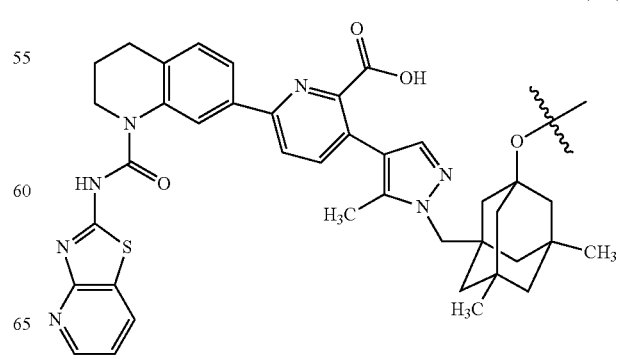

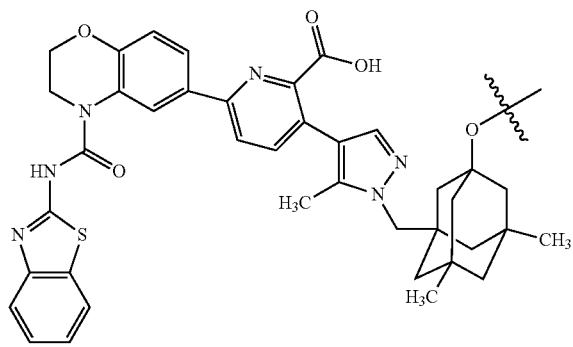
(C.6)
(C.7)
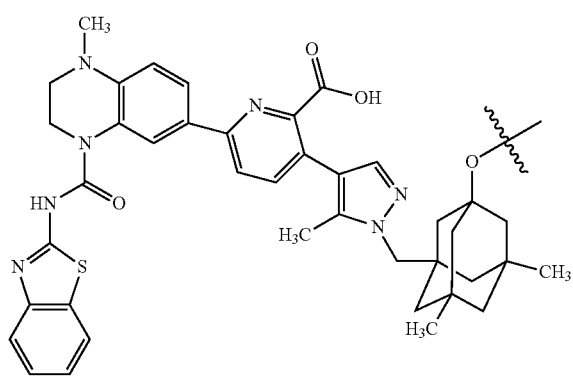
(C.8)
(C.9)
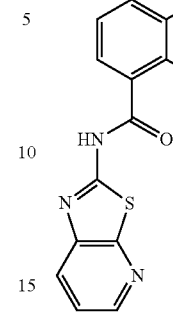
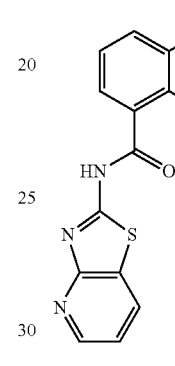
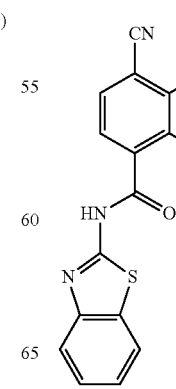
(C.10)
(C.11)
(C.12)
(C.13)

(C.14)
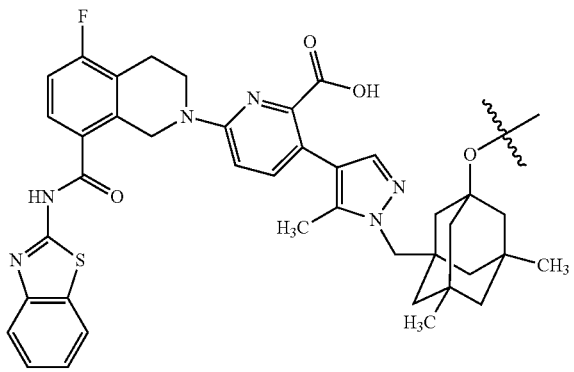
(C.15)
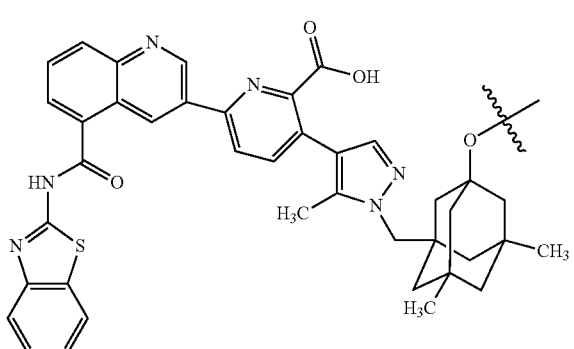
(C.16)
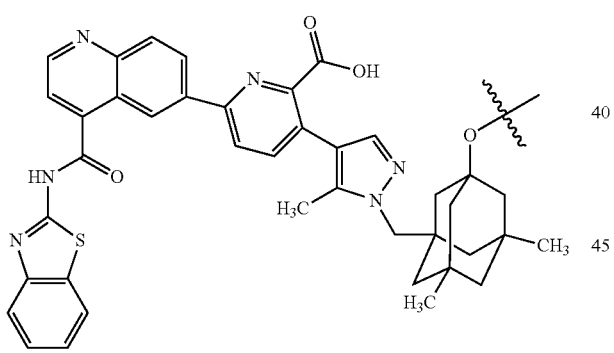
(C.17)
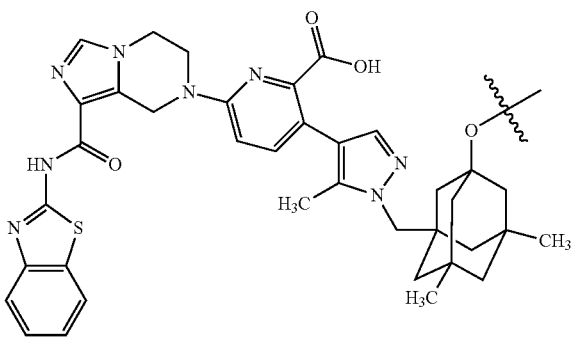
(C.18)
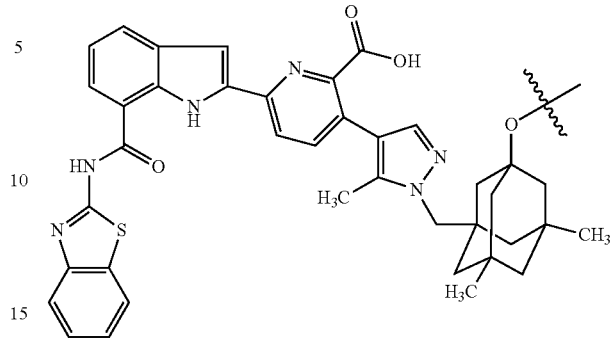
(C.19)
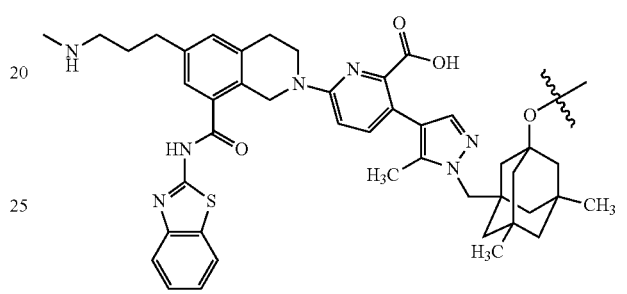
(C.20)
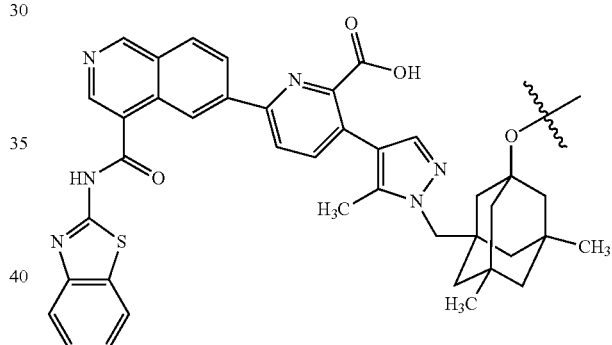
(C.21)
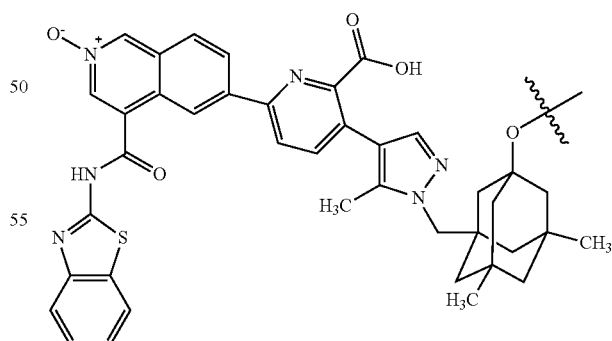
In one embodiment, the ADC is a compound according to structural formula (IIa.1):

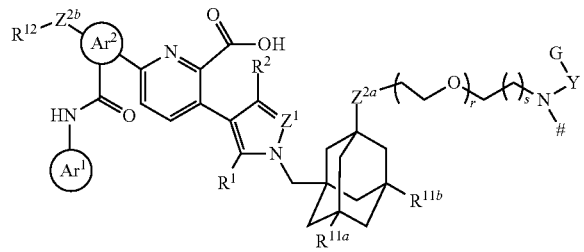

(IIa.1)

wherein Y is optionally substituted $C_1$-$C_8$ alkylene; r is 0 or 1; and s is 1, 2 or 3.

In one embodiment, the ADC is a compound according to structural formula (IIa.2):

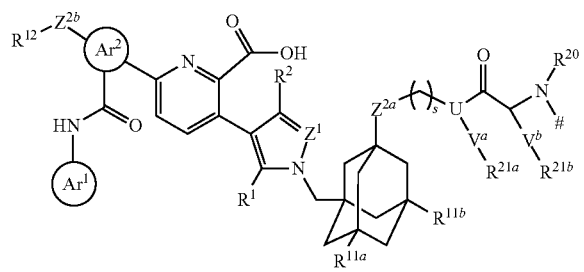

(IIa.2)

wherein U is selected from N, O and CH, with the proviso that when U is O, then $V^a$ and $R^{21a}$ are absent; $R^{20}$ is selected from H and $C_1$-$C_4$ alkyl; $R^{21a}$ and $R^{21b}$ are each, independently from one another, absent or selected from H, $C_1$-$C_4$ alkyl and G, where G is selected from a polyol, PEG4-30, a salt and a moiety that is charged at physiological pH; $V^a$ and $V^b$ are each, independently from one another, absent or selected from a bond, and an optionally substituted alkylene; $R^{20}$ is selected from H and $C_1$-$C_4$ alkyl; and s is 1, 2 or 3.

In one embodiment, the ADC is a compound according to structural formula (IIa.3):

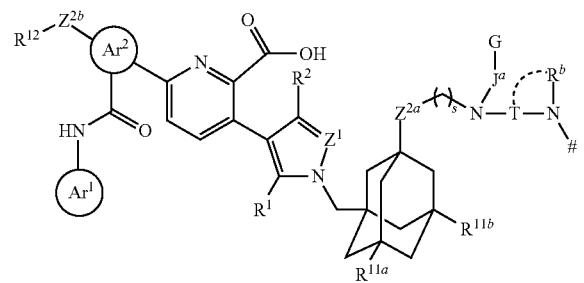

(IIa.3)

wherein $R^b$ is selected from H, $C_1$-$C_4$ alkyl and $J^b$-G or is optionally taken together with an atom of T to form a ring having between 3 and 7 atoms; $J^a$ and $J^b$ are each, independently from one another, selected from optionally substituted $C_1$-$C_8$ alkylene and optionally substituted phenylene; T is selected from optionally substituted $C_1$-$C_5$ alkylene, $CH_2CH_2OCH_2CH_2OCH_2CH_2$, $CH_2CH_2OCH_2CH_2OCH_2CH_2OCH_2$ and a polyethylene glycol containing from 4 to 10 ethylene glycol units; G is selected from a polyol, PEG4-30, a salt and a moiety that is charged at physiological pH; and s is 1, 2 or 3.

In one embodiment, the ADC is a compound according to structural formula (IIb).

In one embodiment, the ADC is a compound according to structural formula (IIb.1):

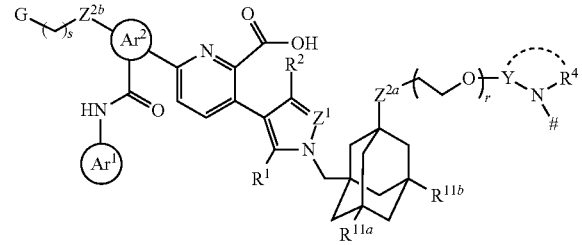

(IIb.1)

wherein Y is optionally substituted $C_1$-$C_8$ alkylene; G is selected from a polyol, PEG4-30, a salt and a moiety that is charged at physiological pH; r is 0 or 1; and s is 1, 2 or 3.

In one embodiment, the ADC is a compound according to structural formula (IIc).

In one embodiment, the ADC is a compound according to structural formula (IIc.1):

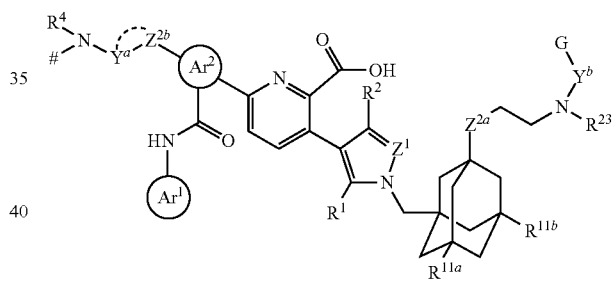

(IIc.1)

wherein $Y^a$ is optionally substituted $C_1$-$C_8$ alkylene; $Y^b$ is optionally substituted $C_1$-$C_8$ alkylene; $R^{23}$ is selected from H and $C_1$-$C_4$ alkyl; and G is selected from a polyol, PEG4-30, a salt and a moiety that is charged at physiological pH.

In one embodiment, the ADC is a compound according to structural formula (IIc.2):

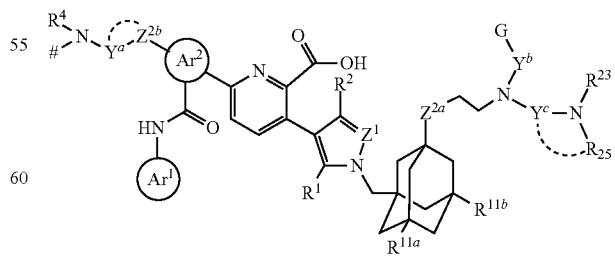

(IIc.2)

wherein $Y^a$ is optionally substituted $C_1$-$C_8$ alkylene; $Y^b$ is optionally substituted $C_1$-$C_8$ alkylene; $Y^c$ is optionally substituted $C_1$-$C_8$ alkylene; $R^{23}$ is selected from H and $C_1$-$C_4$ alkyl; $R^{25}$ is $Y^b$-G or is taken together with an atom of $Y^c$ to form a ring having 4-6 ring atoms; and G is selected from a polyol, PEG4-30, a salt and a moiety that is charged at physiological pH.

In one embodiment, the Bcl-xL inhibitor is selected from the group consisting of the following compounds modified in that the hydrogen corresponding to the # position of structural formula (IIa), (IIb), (IIc), or (IId) is not present forming a monoradical:

6-[8-(1,3-benzothiazol-2-ylcarbamoyl)-3,4-dihydroisoquinolin-2(1H)-yl]-3-[1-({3-[2-({2-[2-(carboxymethoxy)ethoxy]ethyl}amino)ethoxy]-5,7-dimethyltricyclo[3.3.1.1$^{3,7}$]dec-1-yl}methyl)-5-methyl-1H-pyrazol-4-yl]pyridine-2-carboxylic acid;

6-[8-(1,3-benzothiazol-2-ylcarbamoyl)-3,4-dihydroisoquinolin-2(1H)-yl]-3-{1-[(3,5-dimethyl-7-{2-[(2-sulfoethyl)amino]ethoxy}tricyclo[3.3.1.1$^{3,7}$]dec-1-yl)methyl]-5-methyl-1H-pyrazol-4-yl}pyridine-2-carboxylic acid;

2-{[(2-{[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl]amino}ethyl)sulfonyl]amino}-2-deoxy-D-glucopyranose;

6-[8-(1,3-benzothiazol-2-ylcarbamoyl)-3,4-dihydroisoquinolin-2(1H)-yl]-3-{1-[(3,5-dimethyl-7-{2-[(4-{[(3R,4R,5S,6R)-3,4,5-trihydroxy-6-(hydroxymethyl)tetrahydro-2H-pyran-2-yl]methyl}benzyl)amino]ethoxy}tricyclo[3.3.1.13,7]dec-1-yl)methyl]-5-methyl-1H-pyrazol-4-yl}pyridine-2-carboxylic acid;

6-[8-(1,3-benzothiazol-2-ylcarbamoyl)-3,4-dihydroisoquinolin-2(1H)-yl]-3-{1-[(3,5-dimethyl-7-{2-[(3-sulfopropyl)amino]ethoxy}tricyclo[3.3.1.1$^{3,7}$]dec-1-yl)methyl]-5-methyl-1H-pyrazol-4-yl}pyridine-2-carboxylic acid;

6-[8-(1,3-benzothiazol-2-ylcarbamoyl)-3,4-dihydroisoquinolin-2(1H)-yl]-3-{1-[(3-{2-[(2,3-dihydroxypropyl)amino]ethoxy}-5,7-dimethyltricyclo[3.3.1.1$^{3,7}$]dec-1-yl)methyl]-5-methyl-1H-pyrazol-4-yl}pyridine-2-carboxylic acid;

2-({[4-({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl]amino}methyl)phenyl]sulfonyl}amino)-2-deoxy-beta-D-glucopyranose;

8-(1,3-benzothiazol-2-ylcarbamoyl)-2-{6-carboxy-5-[1-({3-[2-({2-[1-(beta-D-glucopyranuronosyl)-1H-1,2,3-triazol-4-yl]ethyl}amino)ethoxy]-5,7-dimethyltricyclo[3.3.1.1$^{3,7}$]dec-1-yl}methyl)-5-methyl-1H-pyrazol-4-yl]pyridin-2-yl}-1,2,3,4-tetrahydroisoquinoline;

3-[1-({3-[2-(2-[{4-(beta-D-allopyranosyloxy)benzyl]amino}ethoxy)ethoxy]-5,7-dimethyltricyclo[3.3.1.1$^{3,7}$]dec-1-yl}methyl)-5-methyl-1H-pyrazol-4-yl]-6-[8-(1,3-benzothiazol-2-ylcarbamoyl)-3,4-dihydroisoquinolin-2(1H)-yl]pyridine-2-carboxylic acid;

6-[8-(1,3-benzothiazol-2-ylcarbamoyl)-3,4-dihydroisoquinolin-2(1H)-yl]-3-(1-{[3,5-dimethyl-7-(2-{2-[(2-sulfoethyl)amino]ethoxy}ethoxy)tricyclo[3.3.1.1$^{3,7}$]dec-1-yl]methyl}-5-methyl-1H-pyrazol-4-yl)pyridine-2-carboxylic acid;

6-[8-(1,3-benzothiazol-2-ylcarbamoyl)-3,4-dihydroisoquinolin-2(1H)-yl]-3-{1-[(3,5-dimethyl-7-{2-[(2-phosphonoethyl)amino]ethoxy}tricyclo[3.3.1.1$^{3,7}$]dec-1-yl)methyl]-5-methyl-1H-pyrazol-4-yl}pyridine-2-carboxylic acid;

6-[8-(1,3-benzothiazol-2-ylcarbamoyl)-3,4-dihydroisoquinolin-2(1H)-yl]-3-{1-[(3,5-dimethyl-7-{2-[methyl(3-sulfo-L-alanyl)amino]ethoxy}tricyclo[3.3.1.1$^{3,7}$]dec-1-yl)methyl]-5-methyl-1H-pyrazol-4-yl}pyridine-2-carboxylic acid;

6-[8-(1,3-benzothiazol-2-ylcarbamoyl)-3,4-dihydroisoquinolin-2(1H)-yl]-3-{1-[(3,5-dimethyl-7-{2-[(3-phosphonopropyl)amino]ethoxy}tricyclo[3.3.1.1$^{3,7}$]dec-1-yl)methyl]-5-methyl-1H-pyrazol-4-yl}pyridine-2-carboxylic acid;

6-[8-(1,3-benzothiazol-2-ylcarbamoyl)-3,4-dihydroisoquinolin-2(1H)-yl]-3-{1-[(3,5-dimethyl-7-{2-[(3-sulfo-L-alanyl)amino]ethoxy}tricyclo[3.3.1.1$^{3,7}$]dec-1-yl)methyl]-5-methyl-1H-pyrazol-4-yl}pyridine-2-carboxylic acid;

6-[8-(1,3-benzothiazol-2-ylcarbamoyl)-3,4-dihydroisoquinolin-2(1H)-yl]-3-(1-{[3,5-dimethyl-7-(2-{2-[(3-phosphonopropyl)amino]ethoxy}ethoxy)tricyclo[3.3.1.1$^{3,7}$]dec-1-yl]methyl}-5-methyl-1H-pyrazol-4-yl)pyridine-2-carboxylic acid;

3-{1-[(3-{2-[L-alpha-aspartyl(methyl)amino]ethoxy}-5,7-dimethyltricyclo[3.3.1.1$^{3,7}$]dec-1-yl)methyl]-5-methyl-1H-pyrazol-4-yl}-6-[8-(1,3-benzothiazol-2-ylcarbamoyl)-3,4-dihydroisoquinolin-2(1H)-yl]pyridine-2-carboxylic acid;

6-{4-[({2-[2-(2-aminoethoxy)ethoxy]ethyl}[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl]amino)methyl]benzyl}-2,6-anhydro-L-acid;

4-({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl]amino}methyl)phenyl hexopyranosiduronic acid;

6-[1-(1,3-benzothiazol-2-ylcarbamoyl)-1,2,3,4-tetrahydroquinolin-7-yl]-3-{1-[(3,5-dimethyl-7-{2-[(2-phosphonoethyl)amino]ethoxy}tricyclo[3.3.1.1$^{3,7}$]dec-1-yl)methyl]-5-methyl-1H-pyrazol-4-yl}pyridine-2-carboxylic acid;

6-[1-(1,3-benzothiazol-2-ylcarbamoyl)-1,2,3,4-tetrahydroquinolin-7-yl]-3-{1-[(3,5-dimethyl-7-{2-[methyl(3-sulfo-L-alanyl)amino]ethoxy}tricyclo[3.3.1.1$^{3,7}$]dec-1-yl)methyl]-5-methyl-1H-pyrazol-4-yl}pyridine-2-carboxylic acid;

3-{1-[(3,5-dimethyl-7-{2-[(2-sulfoethyl)amino]ethoxy}tricyclo[3.3.1.1$^{3,7}$]dec-1-yl)methyl]-5-methyl-1H-pyrazol-4-yl}-6-[8-([1,3]thiazolo[5,4-b]pyridin-2-ylcarbamoyl)-3,4-dihydroisoquinolin-2(1H)-yl]pyridine-2-carboxylic acid;

3-{1-[(3,5-dimethyl-7-{2-[(2-sulfoethyl)amino]ethoxy}tricyclo[3.3.1.1$^{3,7}$]dec-1-yl)methyl]-5-methyl-1H-pyrazol-4-yl}-6-[8-([1,3]thiazolo[4,5-b]pyridin-2-ylcarbamoyl)-3,4-dihydroisoquinolin-2(1H)-yl]pyridine-2-carboxylic acid;

6-[1-(1,3-benzothiazol-2-ylcarbamoyl)-1,2,3,4-tetrahydroquinolin-7-yl]-3-{1-[(3,5-dimethyl-7-{2-[(2-sulfoethyl)amino]ethoxy}tricyclo[3.3.1.1$^{3,7}$]dec-1-yl)methyl]-5-methyl-1H-pyrazol-4-yl}pyridine-2-carboxylic acid;

6-[8-(1,3-benzothiazol-2-ylcarbamoyl)-3,4-dihydroisoquinolin-2(1H)-yl]-3-{1-[(3-{2-[(2-carboxyethyl)amino]ethoxy}-5,7-dimethyltricyclo[3.3.1.1$^{3,7}$]dec-1-yl)methyl]-5-methyl-1H-pyrazol-4-yl}pyridine-2-carboxylic acid;

6-[8-(1,3-benzothiazol-2-ylcarbamoyl)-3,4-dihydroisoquinolin-2(1H)-yl]-3-{1-[(3,5-dimethyl-7-{2-[(3-phosphonopropyl)(piperidin-4-yl)amino]ethoxy}tricyclo[3.3.1.1$^{3,7}$]dec-1-yl)methyl]-5-methyl-1H-pyrazol-4-yl}pyridine-2-carboxylic acid;

3-{1-[(3-{2-[D-alpha-aspartyl(methyl)amino]ethoxy}-5,7-dimethyltricyclo[3.3.1.1$^{3,7}$]dec-1-yl)methyl]-5-methyl-1H-pyrazol-4-yl}-6-[8-(1,3-benzothiazol-2-ylcarbamoyl)-3,4-dihydroisoquinolin-2(1H)-yl]pyridine-2-carboxylic acid;

6-[8-(1,3-benzothiazol-2-ylcarbamoyl)-3,4-dihydroisoquinolin-2(1H)-yl]-3-(1-{[3-(2-{[1-(carboxymethyl)piperidin-4-yl]amino}ethoxy)-5,7-dimethyltricyclo[3.3.1.1$^{3,7}$]dec-1-yl]methyl}-5-methyl-1H-pyrazol-4-yl)pyridine-2-carboxylic acid;

N-[(5S)-5-amino-6-{[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](methyl)amino}-6-oxohexyl]-N,N-dimethylmethanaminium;

6-[8-(1,3-benzothiazol-2-ylcarbamoyl)-3,4-dihydroisoquinolin-2(1H)-yl]-3-{1-[(3,5-dimethyl-7-{2-[piperidin-4-yl(2-sulfoethyl)amino]ethoxy}tricyclo[3.3.1.1$^{3,7}$]dec-1-yl)methyl]-5-methyl-1H-pyrazol-4-yl}pyridine-2-carboxylic acid;

6-[8-(1,3-benzothiazol-2-ylcarbamoyl)-5-(3-phosphonopropoxy)-3,4-dihydroisoquinolin-2(1H)-yl]-3-[1-({3,5-dimethyl-7-[2-(methylamino)ethoxy]tricyclo[3.3.1.1$^{3,7}$]dec-1-yl}methyl)-5-methyl-1H-pyrazol-4-yl]pyridine-2-carboxylic acid;

6-[8-(1,3-benzothiazol-2-ylcarbamoyl)-3,4-dihydroisoquinolin-2(1H)-yl]-3-(1-{[3-(2-{[N-(2-carboxyethyl)-L-alpha-aspartyl]amino}ethoxy)-5,7-dimethyltricyclo[3.3.1.1$^{3,7}$]dec-1-yl]methyl}-5-methyl-1H-pyrazol-4-yl)pyridine-2-carboxylic acid;

3-{1-[(3-{2-[(2-aminoethyl)(2-sulfoethyl))amino]ethoxy}-5,7-dimethyltricyclo[3.3.1.1$^{3,7}$]dec-1-yl)methyl]-5-methyl-1H-pyrazol-4-yl}-6-[8-(1,3-benzothiazol-2-ylcarbamoyl)-3,4-dihydroisoquinolin-2(1H)-yl]pyridine-2-carboxylic acid;

6-[5-(2-aminoethoxy)-8-(1,3-benzothiazol-2-ylcarbamoyl)-3,4-dihydroisoquinolin-2(1H)-yl]-3-[1-({3,5-dimethyl-7-[2-(methylamino)ethoxy]tricyclo[3.3.1.1$^{3,7}$]dec-1-yl}methyl)-5-methyl-1H-pyrazol-4-yl]pyridine-2-carboxylic acid;

6-[8-(1,3-benzothiazol-2-ylcarbamoyl)naphthalen-2-yl]-3-{1-[(3,5-dimethyl-7-{2-[(3-sulfopropyl)amino]ethoxy}tricyclo[3.3.1.1$^{3,7}$]dec-1-yl)methyl]-5-methyl-1H-pyrazol-4-yl}pyridine-2-carboxylic acid;

6-[8-(1,3-benzothiazol-2-ylcarbamoyl)-3,4-dihydroisoquinolin-2(1H)-yl]-3-{1-[(3-{2-[(2-carboxyethyl)(piperidin-4-yl)amino]ethoxy}-5,7-dimethyltricyclo[3.3.1.1$^{3,7}$]dec-1-yl)methyl]-5-methyl-1H-pyrazol-4-yl}pyridine-2-carboxylic acid;

6-[8-(1,3-benzothiazol-2-ylcarbamoyl)-3,4-dihydroisoquinolin-2(1H)-yl]-3-{1-[(3,5-dimethyl-7-{2-[(3-sulfo-L-alanyl)(2-sulfoethyl)amino]ethoxy}tricyclo[3.3.1.1$^{3,7}$]dec-1-yl)methyl]-5-methyl-1H-pyrazol-4-yl}pyridine-2-carboxylic acid;

6-[8-(1,3-benzothiazol-2-ylcarbamoyl)-3,4-dihydroisoquinolin-2(1H)-yl]-3-{1-[(3-{2-[{2-[(2-carboxyethyl)amino]ethyl}(2-sulfoethyl)amino]ethoxy}-5,7-dimethyltricyclo[3.3.1.1$^{3,7}$]dec-1-yl)methyl]-5-methyl-1H-pyrazol-4-yl}pyridine-2-carboxylic acid;

3-{1-[(3,5-dimethyl-7-{2-[(3-phosphonopropyl)amino]ethoxy}tricyclo[3.3.1.1$^{3,7}$]dec-1-yl)methyl]-5-methyl-1H-pyrazol-4-yl}-6-[8-([1,3]thiazolo[4,5-b]pyridin-2-ylcarbamoyl)-3,4-dihydroisoquinolin-2(1H)-yl]pyridine-2-carboxylic acid;

3-{1-[(3,5-dimethyl-7-{2-[(3-phosphonopropyl)amino]ethoxy}tricyclo[3.3.1.1$^{3,7}$]dec-1-yl)methyl]-5-methyl-1H-pyrazol-4-yl]-6-[8-([1,3]thiazolo[5,4-b]pyridin-2-ylcarbamoyl)-3,4-dihydroisoquinolin-2(1H)-yl]pyridine-2-carboxylic acid;

6-[8-(1,3-benzothiazol-2-ylcarbamoyl)-5-(carboxymethoxy)-3,4-dihydroisoquinolin-2(1H)-yl]-3-[1-({3,5-dimethyl-7-[2-(methylamino)ethoxy]tricyclo[3.3.1.1$^{3,7}$]dec-1-yl}methyl)-5-methyl-1H-pyrazol-4-yl]pyridine-2-carboxylic acid;

6-[8-(1,3-benzothiazol-2-ylcarbamoyl)-3,4-dihydroisoquinolin-2(1H)-yl]-3-{1-[(3-{2-[(3-carboxypropyl)(piperidin-4-yl)amino]ethoxy}-5,7-dimethyltricyclo[3.3.1.1$^{3,7}$]dec-1-yl)methyl]-5-methyl-1H-pyrazol-4-yl}pyridine-2-carboxylic acid;

6-[8-(1,3-benzothiazol-2-ylcarbamoyl)naphthalen-2-yl]-3-{1-[(3,5-dimethyl-7-{2-[(2-sulfoethyl)amino]ethoxy}tricyclo[3.3.1.1$^{3,7}$]dec-1-yl)methyl]-5-methyl-1H-pyrazol-4-yl}pyridine-2-carboxylic acid;

3-{1-[(3-{2-[L-alpha-aspartyl(2-sulfoethyl)amino]ethoxy}-5,7-dimethyltricyclo[3.3.1.1$^{3,7}$]dec-1-yl)methyl]-5-methyl-1H-pyrazol-4-yl}-6-[8-(1,3-benzothiazol-2-ylcarbamoyl)-3,4-dihydroisoquinolin-2(1H)-yl]pyridine-2-carboxylic acid;

6-[8-(1,3-benzothiazol-2-ylcarbamoyl)-3,4-dihydroisoquinolin-2(1H)-yl]-3-{1-[(3-{2-[(1,3-dihydroxypropan-2-yl)amino]ethoxy}-5,7-dimethyltricyclo[3.3.1.1$^{3,7}$]dec-1-yl)methyl]-5-methyl-1H-pyrazol-4-yl}pyridine-2-carboxylic acid;

6-[5-(2-aminoethoxy)-8-(1,3-benzothiazol-2-ylcarbamoyl)-3,4-dihydroisoquinolin-2(1H)-yl]-3-{1-[(3,5-dimethyl-7-{2-[methyl(2-sulfoethyl)amino]ethoxy}tricyclo[3.3.1.1$^{3,7}$]dec-1-yl)methyl]-5-methyl-1H-pyrazol-4-yl}pyridine-2-carboxylic acid;

6-[8-(1,3-benzothiazol-2-ylcarbamoyl)-5-{2-[(2-sulfoethyl)amino]ethoxy}-3,4-dihydroisoquinolin-2(1H)-yl]-3-{1-[(3,5-dimethyl-7-{2-[methyl(2-sulfoethyl)amino]ethoxy}tricyclo[3.3.1.1$^{3,7}$]dec-1-yl)methyl]-5-methyl-1H-pyrazol-4-yl}pyridine-2-carboxylic acid;

6-[8-(1,3-benzothiazol-2-ylcarbamoyl)-3,4-dihydroisoquinolin-2(1H)-yl]-3-{1-[(3,5-dimethyl-7-{2-[(2-sulfoethyl){2-[(2-sulfoethyl)amino]ethyl}amino]ethoxy}tricyclo[3.3.1.1$^{3,7}$]dec-1-yl)methyl]-5-methyl-1H-pyrazol-4-yl}pyridine-2-carboxylic acid;

6-[8-(1,3-benzothiazol-2-ylcarbamoyl)-5-{2-[(2-carboxyethyl)amino]ethoxy}-3,4-dihydroisoquinolin-2(1H)-yl]-3-{1-[(3,5-dimethyl-7-{2-[methyl(2-sulfoethyl)amino]ethoxy}tricyclo[3.3.1.1$^{3,7}$]dec-1-yl)methyl]-5-methyl-1H-pyrazol-4-yl}pyridine-2-carboxylic acid;

3-{1-[(3,5-dimethyl-7-{2-[(3-phosphonopropyl)(piperidin-4-yl)amino]ethoxy}tricyclo[3.3.1.1$^{3,7}$]dec-1-yl)methyl]-5-methyl-1H-pyrazol-4-yl}-6-[8-([1,3]thiazolo[4,5-b]pyridin-2-ylcarbamoyl)-3,4-dihydroisoquinolin-2(1H)-yl]pyridine-2-carboxylic acid;

6-[4-(1,3-benzothiazol-2-ylcarbamoyl)-3,4-dihydro-2H-1,4-benzoxazin-6-yl]-3-{1-[(3,5-dimethyl-7-{2-[(2-sulfoethyl)amino]ethoxy}tricyclo[3.3.1.1$^{3,7}$]dec-1-yl)methyl]-5-methyl-1H-pyrazol-4-yl}pyridine-2-carboxylic acid;

6-[8-(1,3-benzothiazol-2-ylcarbamoyl)-5-(3-sulfopropoxy)-3,4-dihydroisoquinolin-2(1H)-yl]-3-[1-({3,5-dimethyl-7-[2-(methylamino)ethoxy]tricyclo[3.3.1.1$^{3,7}$]dec-1-yl}methyl)-5-methyl-1H-pyrazol-4-yl]pyridine-2-carboxylic acid;

3-{1-[(3,5-dimethyl-7-{2-[(2-sulfoethyl)amino]ethoxy}tricyclo[3.3.1.1$^{3,7}$]dec-1-yl)methyl]-5-methyl-1H-pyrazol-4-yl}-6-[1-([1,3]thiazolo[4,5-b]pyridin-2-ylcarbamoyl)-1,2,3,4-tetrahydroquinolin-7-yl]pyridine-2-carboxylic acid;

3-{1-[(3,5-dimethyl-7-{2-[(2-sulfoethyl)amino]ethoxy tricyclo[3.3.1.1$^{3,7}$]dec-1-yl)methyl]-5-methyl-1H-pyrazol-4-yl}-6-[8-([1,3]thiazolo[4,5-b]pyridin-2-ylcarbamoyl)naphthalen-2-yl]pyridine-2-carboxylic acid;

(1ξ)-1-({2-[5-(1-{[3-(2-aminoethoxy)-5,7-dimethyltricyclo[3.3.1.1$^{3,7}$]dec-1-yl]methyl}-5-methyl-1H-pyrazol-4-yl)-6-carboxypyridin-2-yl]-8-(1,3-benzothiazol-2-ylcarbamoyl)-1,2,3,4-tetrahydroisoquinolin-5-yl}methyl)-1,5-anhydro-D-glucitol;

6-[8-(1,3-benzothiazol-2-ylcarbamoyl)-3,4-dihydroisoquinolin-2(1H)-yl]-3-{1-[(3-{2-[(3-carboxypropyl)amino]ethoxy}-5,7-dimethyltricyclo[3.3.1.1$^{3,7}$]dec-1-yl)methyl]-5-methyl-1H-pyrazol-4-yl}pyridine-2-carboxylic acid;

6-[8-(1,3-benzothiazol-2-ylcarbamoyl)naphthalen-2-yl]-3-{1-[(3,5-dimethyl-7-{2-[(3-phosphonopropyl)amino]ethoxy}tricyclo[3.3.1.1$^{3,7}$]dec-1-yl)methyl]-5-methyl-1H-pyrazol-4-yl}pyridine-2-carboxylic acid;

6-[8-(1,3-benzothiazol-2-ylcarbamoyl)-3,4-dihydroisoquinolin-2(1H)-yl]-3-(1-{[3-(2-{[4-(beta-D-glucopyranosyloxy)benzyl]amino}ethoxy)-5,7-dimethyltricyclo[3.3.1.1$^{3,7}$]dec-1-yl]methyl}-5-methyl-1H-pyrazol-4-yl)pyridine-2-carboxylic acid;

3-(1-{[3-(2-{[4-(beta-D-allopyranosyloxy)benzyl]amino}ethoxy)-5,7-dimethyltricyclo[3.3.1.1$^{3,7}$]dec-1-yl]methyl}-5-methyl-1H-pyrazol-4-yl)-6-[8-(1,3-benzothiazol-2-ylcarbamoyl)-3,4-dihydroisoquinolin-2(1H)-yl]pyridine-2-carboxylic acid;

3-{1-[(3-{2-[azetidin-3-yl(2-sulfoethyl)amino]ethoxy}-5,7-dimethyltricyclo[3.3.1.1$^{3,7}$]dec-1-yl)methyl]-5-methyl-1H-pyrazol-4-yl}-6-[8-(1,3-benzothiazol-2-ylcarbamoyl)-3,4-dihydroisoquinolin-2(1H)-yl]pyridine-2-carboxylic acid;

3-{1-[(3-{2-[(3-aminopropyl)(2-sulfoethyl)amino]ethoxy}-5,7-dimethyltricyclo[3.3.1.1$^{3,7}$]dec-1-yl)methyl]-5-methyl-1H-pyrazol-4-yl}-6-[8-(1,3-benzothiazol-2-ylcarbamoyl)-3,4-dihydroisoquinolin-2(1H)-yl]pyridine-2-carboxylic acid;

6-[1-(1,3-benzothiazol-2-ylcarbamoyl)-1,2,3,4-tetrahydroquinolin-7-yl]-3-{1-[(3-{2-[(2-carboxyethyl)amino]ethoxy}-5,7-dimethyltricyclo[3.3.1.1$^{3,7}$]dec-1-yl)methyl]-5-methyl-1H-pyrazol-4-yl}pyridine-2-carboxylic acid;

6-[8-(1,3-benzothiazol-2-ylcarbamoyl)-3,4-dihydroisoquinolin-2(1H)-yl]-3-{1-[(3-{2-[(N$^6$,N$^6$-dimethyl-L-lysyl)(methyl)amino]ethoxy}-5,7-dimethyltricyclo[3.3.1.1$^{3,7}$]dec-1-yl)methyl]-5-methyl-1H-pyrazol-4-yl}pyridine-2-carboxylic acid;

3-{1-[(3-{2-[(3-aminopropyl)(methyl)amino]ethoxy}-5,7-dimethyltricyclo[3.3.1.1$^{3,7}$]dec-1-yl)methyl]-5-methyl-1H-pyrazol-4-yl}-6-[1-(1,3-benzothiazol-2-ylcarbamoyl)-1,2,3,4-tetrahydroquinolin-7-yl]pyridine-2-carboxylic acid;

3-{1-[(3-{2-[azetidin-3-yl(methyl)amino]ethoxy}-5,7-dimethyltricyclo[3.3.1.1$^{3,7}$]dec-1-yl)methyl]-5-methyl-1H-pyrazol-4-yl}-6-[1-(1,3-benzothiazol-2-ylcarbamoyl)-1,2,3,4-tetrahydroquinolin-7-yl]pyridine-2-carboxylic acid;

N$^6$-(37-oxo-2,5,8,11,14,17,20,23,26,29,32,35-dodecaoxaheptatriacontan-37-yl)-L-lysyl-N-[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl]-L-alaninamide;

methyl 6-[4-(3-{[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl]amino}propyl)-1H-1,2,3-triazol-1-yl]-6-deoxy-beta-L-glucopyranoside;

6-[8-(1,3-benzothiazol-2-ylcarbamoyl)naphthalen-2-yl]-3-{1-[(3-{2-[(2-carboxyethyl)amino]ethoxy}-5,7-dimethyltricyclo[3.3.1.1$^{3,7}$]dec-1-yl)methyl]-5-methyl-1H-pyrazol-4-yl}pyridine-2-carboxylic acid;

6-[5-(1,3-benzothiazol-2-ylcarbamoyl)quinolin-3-yl]-3-{1-[(3,5-dimethyl-7-{2-[(2-sulfoethyl)amino]ethoxy}tricyclo[3.3.1.1$^{3,7}$]dec-1-yl)methyl]-5-methyl-1H-pyrazol-4-yl}pyridine-2-carboxylic acid;

6-[4-(1,3-benzothiazol-2-ylcarbamoyl)quinolin-6-yl]-3-{1-[(3,5-dimethyl-7-{2-[(2-sulfoethyl)amino]ethoxy}tricyclo[3.3.1.1$^{3,7}$]dec-1-yl)methyl]-5-methyl-1H-pyrazol-4-yl}pyridine-2-carboxylic acid;

6-[5-(1,3-benzothiazol-2-ylcarbamoyl)quinolin-3-yl]-3-{1-[(3-{2-[(2-carboxyethyl)amino]ethoxy}-5,7-dimethyltricyclo[3.3.1.1$^{3,7}$]dec-1-yl)methyl]-5-methyl-1H-pyrazol-4-yl}pyridine-2-carboxylic acid;

6-[1-(1,3-benzothiazol-2-ylcarbamoyl)-5,6-dihydroimidazo[1,5-a]pyrazin-7(8H)-yl]-3-{1-[(3,5-dimethyl-7-{2-[(2-sulfoethyl)amino]ethoxy}tricyclo[3.3.1.1$^{3,7}$]dec-1-yl)methyl]-5-methyl-1H-pyrazol-4-yl}pyridine-2-carboxylic acid;

8-(1,3-benzothiazol-2-ylcarbamoyl)-2-{6-carboxy-5-[1-({3-[2-({3-[1-(beta-D-glucopyranuronosyl)-1H-1,2,3-triazol-4-yl]propyl}amino)ethoxy]-5,7-dimethyltricyclo[3.3.1.1$^{3,7}$]dec-1-yl}methyl)-5-methyl-1H-pyrazol-4-yl]pyridin-2-yl}-1,2,3,4-tetrahydroisoquinoline;

6-[7-(1,3-benzothiazol-2-ylcarbamoyl)-1H-indol-2-yl]-3-{1-[(3,5-dimethyl-7-{2-[(2-sulfoethyl)amino]ethoxy}tricyclo[3.3.1.1$^{3,7}$]dec-1-yl)methyl]-5-methyl-1H-pyrazol-4-yl}pyridine-2-carboxylic acid;

6-[8-(1,3-benzothiazol-2-ylcarbamoyl)-6-[3-(methylamino)propyl]-3,4-dihydroisoquinolin-2(1H)-yl]-3-{1-[(3,5-dimethyl-7-{2-[(2-sulfoethyl)amino]ethoxy}tricyclo[3.3.1.1$^{3,7}$]dec-1-yl)methyl]-5-methyl-1H-pyrazol-4-yl}pyridine-2-carboxylic acid;

5-{[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl]amino}-5-deoxy-D-arabinitol;

1-{[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl]amino}-1,2-dideoxy-D-arabino-hexitol;

6-[4-(1,3-benzothiazol-2-ylcarbamoyl)isoquinolin-6-yl]-3-{1-[(3,5-dimethyl-7-{2-[(2-sulfoethyl)amino]ethoxy}tricyclo[3.3.1.1$^{3,7}$]dec-1-yl)methyl]-5-methyl-1H-pyrazol-4-yl}pyridine-2-carboxylic acid;

6-[8-(1,3-benzothiazol-2-ylcarbamoyl)-3,4-dihydroisoquinolin-2(1H)-yl]-3-(1-{[3-(2-{[3-hydroxy-2-(hydroxymethyl)propyl]amino}ethoxy)-5,7-dimethyltricyclo[3.3.1.1$^{3,7}$]dec-1-yl]methyl}-5-methyl-1H-pyrazol-4-yl)pyridine-2-carboxylic acid;

1-{[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl]amino}-1,2-dideoxy-D-erythro-pentitol;

6-[8-(1,3-benzothiazol-2-ylcarbamoyl)-3,4-dihydroisoquinolin-2(1H)-yl]-3-(1-{[3,5-dimethyl-7-(2-{[(2S,3S)-2,3,4-trihydroxybutyl]amino}ethoxy)tricyclo[3.3.1.1$^{3,7}$]dec-1-yl]methyl}-5-methyl-1H-pyrazol-4-yl)pyridine-2-carboxylic acid;

6-[8-(1,3-benzothiazol-2-ylcarbamoyl)-3,4-dihydroisoquinolin-2(1H)-yl]-3-(1-{[3-(2-{[(2S,3S,4R,5R,6R)-2,3,4,5,6,7-hexahydroxyheptyl]amino}ethoxy)-5,7-dimethyltricyclo[3.3.1.1³,⁷]dec-1-yl]methyl}-5-methyl-1H-pyrazol-4-yl)pyridine-2-carboxylic acid;

6-[8-(1,3-benzothiazol-2-ylcarbamoyl)-3,4-dihydroisoquinolin-2(1H)-yl]-3-{1-[(3-{2-[({3-[(1,3-dihydroxypropan-2-yl)amino]propyl}sulfonyl)amino]ethoxy}-5,7-dimethyltricyclo[3.3.1.1³,⁷]dec-1-yl)methyl]-5-methyl-1H-pyrazol-4-yl}pyridine-2-carboxylic acid;

6-[8-(1,3-benzothiazol-2-ylcarbamoyl)-3,4-dihydroisoquinolin-2(1H)-yl]-3-{1-[(3-{2-[(3-{[1,3-dihydroxy-2-(hydroxymethyl)propan-2-yl]amino}-3-oxopropyl)amino]ethoxy}-5,7-dimethyltricyclo[3.3.1.1³,⁷]dec-1-yl)methyl]-5-methyl-1H-pyrazol-4-yl}pyridine-2-carboxylic acid;

6-[8-(1,3-benzothiazol-2-ylcarbamoyl)-3,4-dihydroisoquinolin-2(1H)-yl]-3-(1-{[3-(2-{[(3S)-3,4-dihydroxybutyl]amino}ethoxy)-5,7-dimethyltricyclo[3.3.1.1³,⁷]dec-1-yl]methyl}-5-methyl-1H-pyrazol-4-yl)pyridine-2-carboxylic acid;

4-({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1³,⁷]dec-1-yl}oxy)ethyl]amino}methyl)phenyl beta-D-glucopyranosiduronic acid;

3-{[2-({3-[(4-{6-[8-(1,3-benzothiazol-2-ylcarbamoyl)naphthalen-2-yl]-2-carboxypyridin-3-yl}-5-methyl-1H-pyrazol-1-yl)methyl]-5,7-dimethyltricyclo[3.3.1.1³,⁷]dec-1-yl}oxy)ethyl]amino}propyl beta-D-glucopyranosiduronic acid;

6-[4-(1,3-benzothiazol-2-ylcarbamoyl)-2-oxidoisoquinolin-6-yl]-3-[1-({3,5-dimethyl-7-[2-(methylamino)ethoxy]tricyclo[3.3.1.1³,⁷]dec-1-yl}methyl)-5-methyl-1H-pyrazol-4-yl]pyridine-2-carboxylic acid;

6-{8-[(1,3-benzothiazol-2-yl)carbamoyl]-3,4-dihydroisoquinolin-2(1H)-yl}-3-{1-[(3,5-dimethyl-7-{2-[(2-sulfoethyl)amino]acetamido}tricyclo[3.3.1.1³,⁷]decan-1-yl)methyl]-5-methyl-1H-pyrazol-4-yl}pyridine-2-carboxylic acid;

6-[8-(1,3-benzothiazol-2-ylcarbamoyl)-3,4-dihydroisoquinolin-2(1H)-yl]-3-(1-{[3,5-dimethyl-7-({2-[(2-sulfoethyl)amino]ethyl}sulfanyl)tricyclo[3.3.1.1³,⁷]dec-1-yl]methyl}-5-methyl-1H-pyrazol-4-yl)pyridine-2-carboxylic acid; and 6-{8-[(1,3-benzothiazol-2-yl)carbamoyl]-3,4-dihydroisoquinolin-2(1H)-yl}-3-{1-[(3,5-dimethyl-7-{3-[(2-sulfoethyl)amino]propyl}tricyclo[3.3.1.1³,⁷]decan-1-yl)methyl]-5-methyl-1H-pyrazol-4-yl}pyridine-2-carboxylic acid.

In one embodiment, the linker is cleavable by a lysosomal enzyme. In one embodiment, the lysosomal enzyme is Cathepsin B.

In one embodiment, the linker comprises a segment according to structural formula (IVa), (IVb), (IVc), or (IVd):

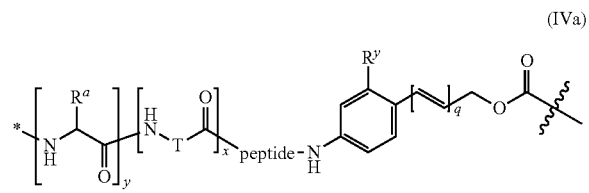

(IVa)

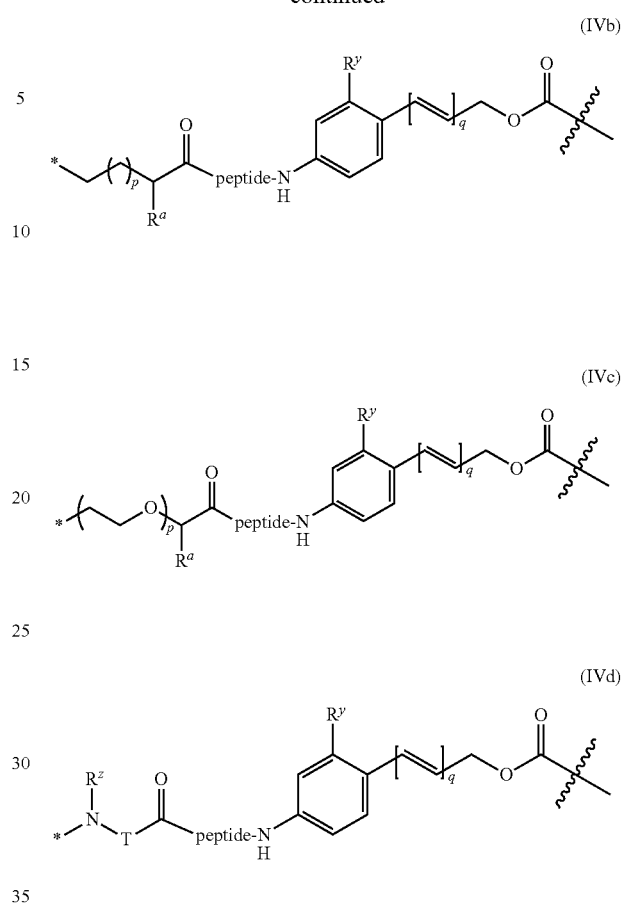

wherein peptide represents a peptide (illustrated N→C, wherein peptide includes the amino and carboxy "termini") a cleavable by a lysosomal enzyme; T represents a polymer comprising one or more ethylene glycol units or an alkylene chain, or combinations thereof;

$R^a$ is selected from hydrogen, $C_{1-6}$ alkyl, $SO_3H$ and $CH_2SO_3H$; $R^y$ is hydrogen or $C_{1-4}$ alkyl-(O)$_1$—$(C_{1-4}$ alkylene)$_s$-$G^1$ or $C_{1-4}$ alkyl-(N)—[$(C_{1-4}$ alkylene)-$G^1$]2; $R^z$ is $C_{1-4}$ alkyl-(O), —$(C_{1-4}$ alkylene)$_s$-$G^2$; $G^1$ is $SO_3H$, $CO_2H$, PEG 4-32, or sugar moiety; $G^2$ is $SO_3H$, $CO_2H$, or PEG 4-32 moiety; r is 0 or 1; s is 0 or 1; p is an integer ranging from 0 to 5; q is 0 or 1; x is 0 or 1; y is 0 or 1; ⌇ represents the point of attachment of the linker to the Bcl-xL inhibitor; and * represents the point of attachment to the remainder of the linker.

In one embodiment, the peptide is selected from the group consisting of Val-Cit; Cit-Val; Ala-Ala; Ala-Cit; Cit-Ala; Asn-Cit; Cit-Asn; Cit-Cit; Val-Glu; Glu-Val; Ser-Cit; Cit-Ser; Lys-Cit; Cit-Lys; Asp-Cit; Cit-Asp; Ala-Val; Val-Ala; Phe-Lys; Lys-Phe; Val-Lys; Lys-Val; Ala-Lys; Lys-Ala; Phe-Cit; Cit-Phe; Leu-Cit; Cit-Leu; Ile-Cit; Cit-Ile; Phe-Arg; Arg-Phe; Cit-Trp; and Trp-Cit.

In one embodiment, the lysosomal enzyme is f-glucuronidase or β-galactosidase.

In one embodiment, the linker comprises a segment according to structural formula (Va), (Vb), (Vc), (Vd), or (Ve):

(Va)
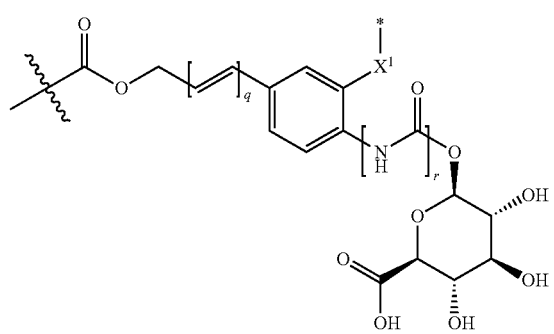
(Vb)
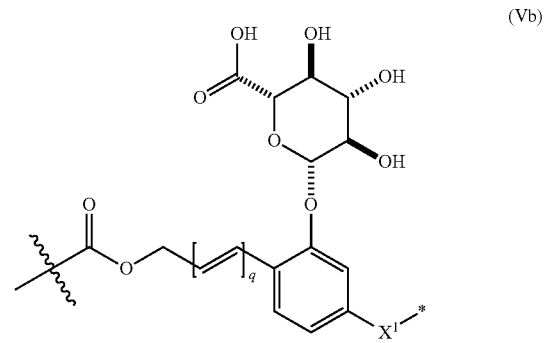
(Vc)
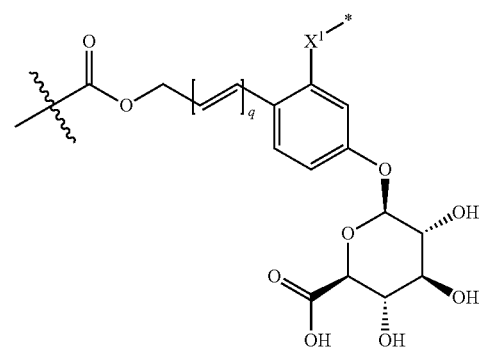
(Vd)
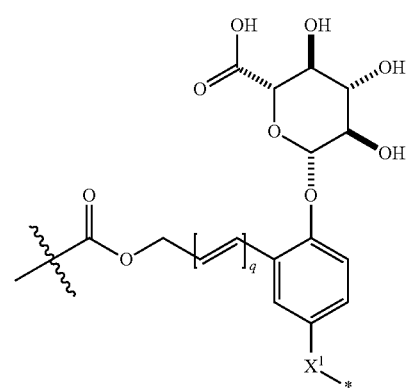
(Ve)
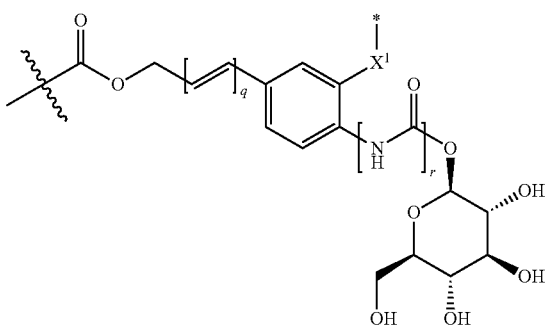
wherein q is 0 or 1; r is 0 or 1; $X^1$ is $CH_2$, O or NH; ⁄ represents the point of attachment of the linker to the drug; and * represents the point of attachment to the remainder of the linker.
In one embodiment, the linker comprises a segment according to structural formula (VIIIa), (VIIIb), or (VIIIc):
(VIIIa)
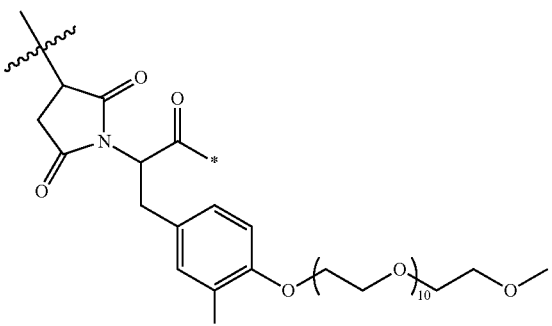
(hydrolyzed form)
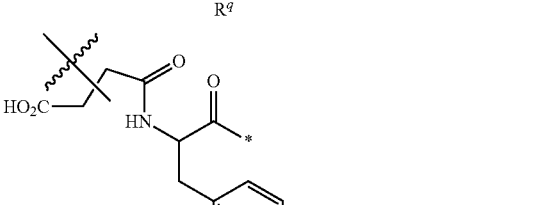
(VIIIb)
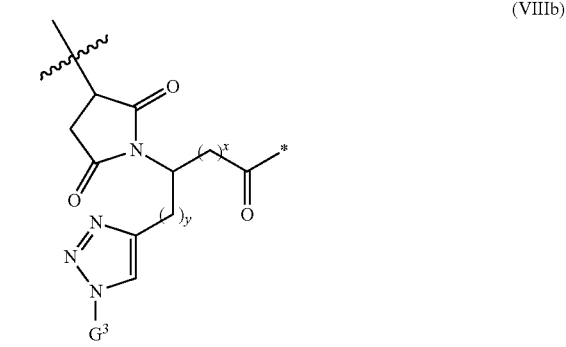

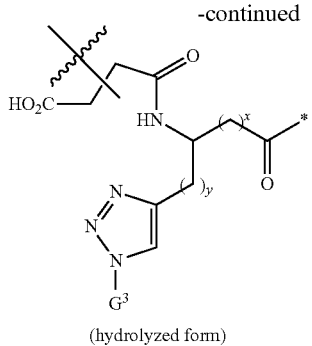

(hydrolyzed form)

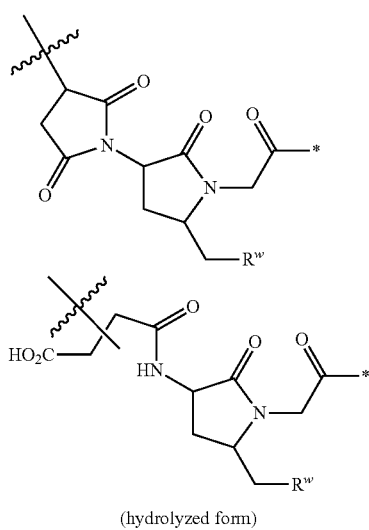

(VIIIc)

(hydrolyzed form)

or a hydrolyzed derivative thereof, wherein: $R^9$ is H or —O—$(CH_2CH_2O)_{11}$—$CH_3$; x is 0 or 1; y is 0 or 1; $G^3$ is —$CH_2CH_2CH_2SO_3H$ or —$CH_2CH_2O$—$(CH_2CH_2O)_{11}$—$CH_3$; $R^w$ is —O—$CH_2CH_2SO_3H$ or —NH(CO)—$CH_2CH_2O(CH\ CH_2O)_{12}$—$CH_3$; * represents the point of attachment to the remainder of the linker; and ∤ represents the point of attachment of the linker to the antibody.

In one embodiment, the linker comprises a polyethylene glycol segment having from 1 to 6 ethylene glycol units.

In one embodiment, m is 2, 3 or 4.

In one embodiment, linker L is selected from IVa or IVb.

In one embodiment, linker L is selected from the group consisting of IVa.1-IVa.8, IVb.1-IVb.19, IVc.1-IVc.7, IVd.1-IVd.4, Va.1-Va.12, Vb.1-Vb.10, Vc. 1-Vc.11, Vd.1-Vd.6, Ve.1-Ve.2, VIa.1, VIc.1-VIc.2, VId.1-VId.4, VIIa.1-VIIa.4, VIIb.1-VIIb.8, VIIc.1-VIIc.6 in either the closed or open form.

In one embodiment, the linker L is selected from the group consisting of IVb.2, IVc.5, IVc.6, IVc.7, IVd.4, Vb.9, VIIa.1, VIIa.3, VIIc.1, VIIc.4, and VIIc.5, wherein the maleimide of each linker has reacted with the antibody Ab, forming a covalent attachment as either a succinimide (closed form) or succinamide (open form).

In one embodiment, the linker L is selected from the group consisting of IVb.2, IVc.5, IVc.6, IVd.4, VIIa.1, VIIa.3, VIIc.1, VIIc.4, VIIc.5, wherein the maleimide of each linker has reacted with the antibody Ab, forming a covalent attachment as either a succinimide (closed form) or succinamide (open form).

In one embodiment, the linker L is selected from the group consisting of IVb.2, VIIa.3, IVc.6, and VIIc.1, wherein ∤ is the attachment point to drug D and @ is the attachment point to the LK, wherein when the linker is in the open form as shown below, @ can be either at the α-position or β-position of the carboxylic acid next to it:

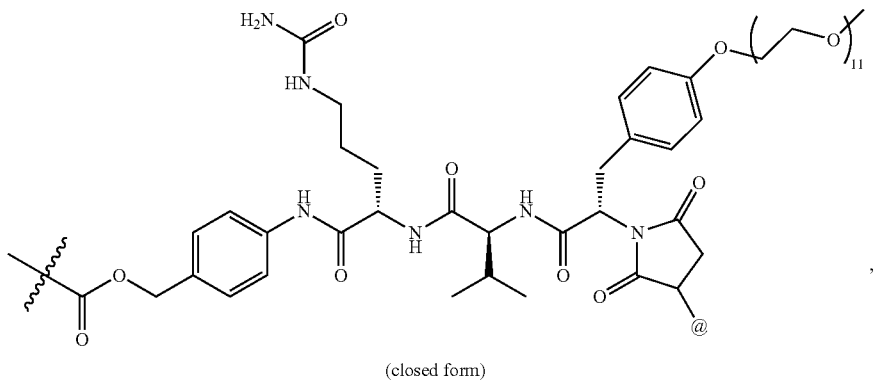

VIIa.3

(closed form)

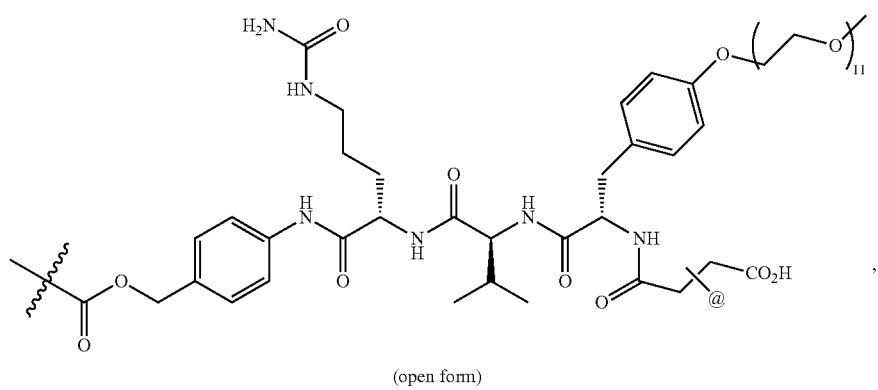
VIIa.3
(open form)
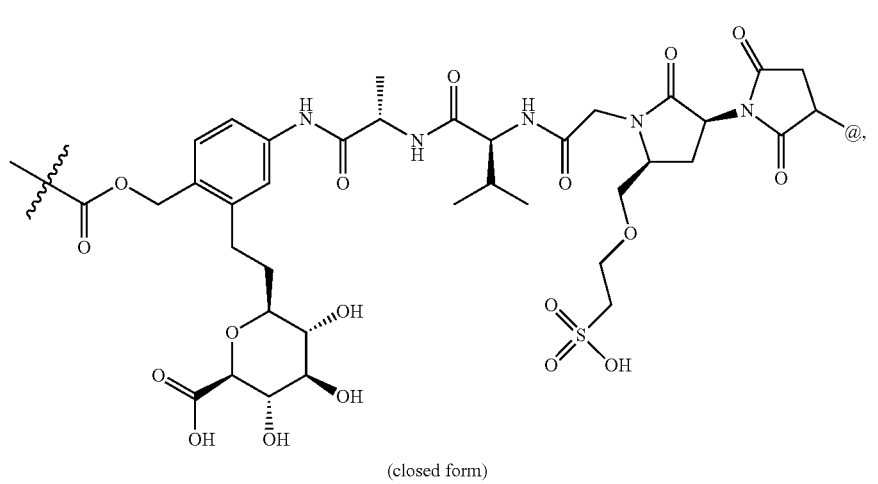
VIIc.1
(closed form)
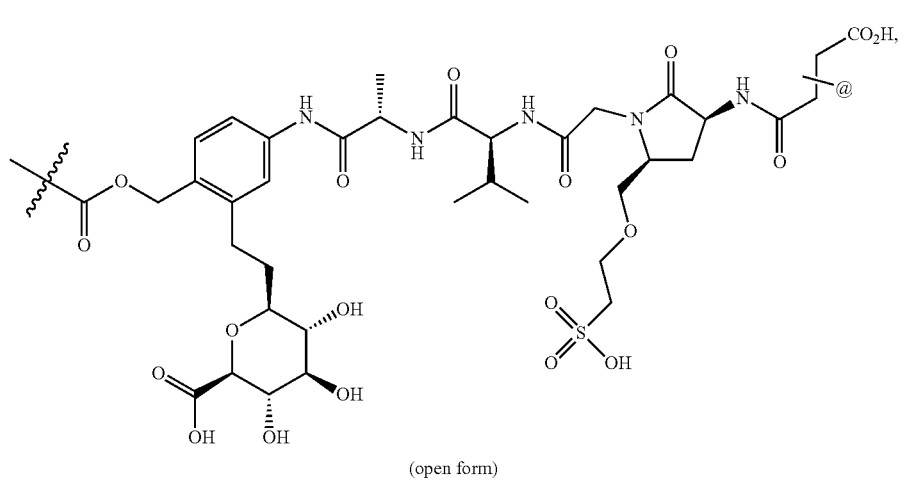
VIIc.1
(open form)

-continued

IVc.6

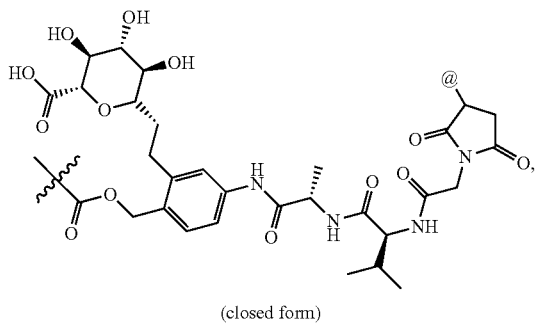

(closed form)

IVc.6

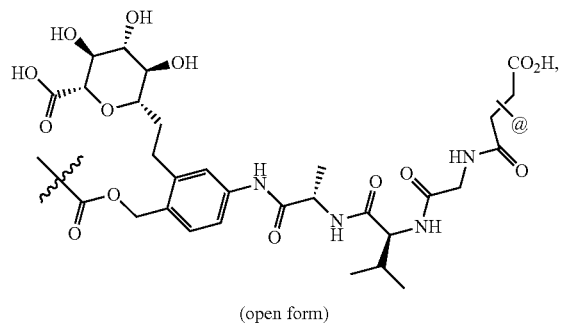

(open form)

IVb.2

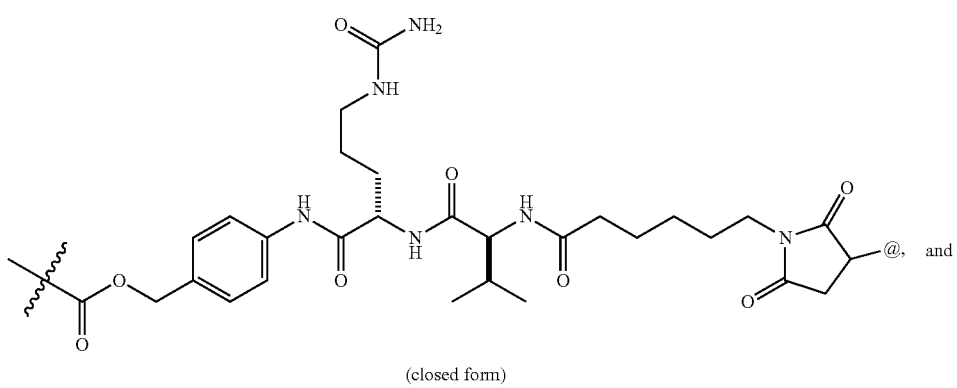

(closed form)

, and

IVb.2

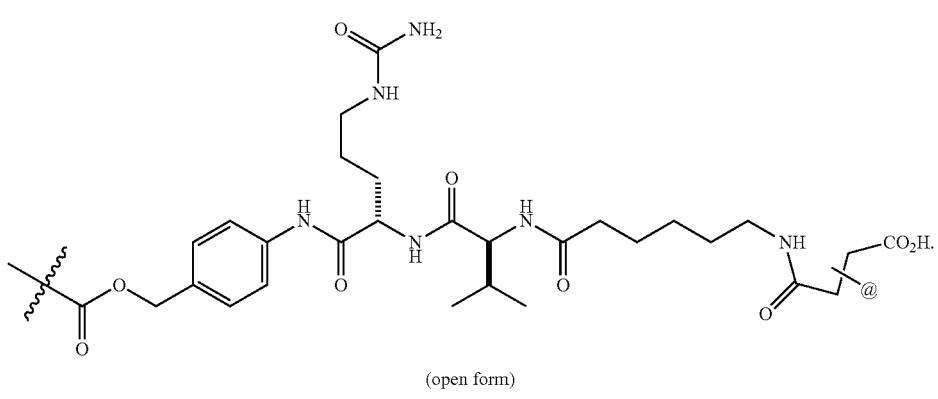

(open form)

In one embodiment, LK is a linkage formed with an amino group on the anti-hB7H3 antibody Ab.

In one embodiment, LK is an amide or a thiourea.

In one embodiment, LK is a linkage formed with a sulfhydryl group on the anti-hB7-H3 antibody Ab.

In one embodiment, LK is a thioether.

In one embodiment, LK is selected from the group consisting of amide, thiourea and thioether; and m is an integer ranging from 1 to 8.

In one embodiment, D is a Bcl-xL inhibitor as described herein; L is selected from the group consisting of linkers IVa.1-IVa.8, IVb.1-IVb.19, IVc.1-IVc.7, IVd.1-IVd.4, Va.1-Va.12, Vb.1-Vb.10, Vc.1-Vc.11, Vd.1-Vd.6, Ve.1-Ve.2, VIa.1, VIc.1-VIc.2, VId.1-VId.4, VIIa.1-VIIa.4, VIIb.1-VIIb.8, and VIIc.1-VIIc.6, wherein each linker has reacted with the antibody, Ab, forming a covalent attachment; LK is thioether; and m is an integer ranging from 1 to 8.

In one embodiment, D is the Bcl-xL inhibitor selected from the group consisting of the following compounds modified in that the hydrogen corresponding to the # position of structural formula (IIa), (IIb), (IIc), or (IId) is not present, forming a monoradical:

6-[8-(1,3-benzothiazol-2-ylcarbamoyl)-3,4-dihydroisoquinolin-2(1H)-yl]-3-{1-[(3,5-dimethyl-7-{2-[(2-sulfoethyl)amino]ethoxy}tricyclo[3.3.1.1$^{3,7}$]dec-1-yl)methyl]-5-methyl-1H-pyrazol-4-yl}pyridine-2-carboxylic acid;

6-[8-(1,3-benzothiazol-2-ylcarbamoyl)-3,4-dihydroisoquinolin-2(1H)-yl]-3-{1-[(3-{2-[(2-carboxyethyl)amino]ethoxy}-5,7-dimethyltricyclo[3.3.1.1$^{3,7}$]dec-1-yl)methyl]-5-methyl-1H-pyrazol-4-yl}pyridine-2-carboxylic acid;

6-[8-(1,3-benzothiazol-2-ylcarbamoyl)naphthalen-2-yl]-3-{1-[(3,5-dimethyl-7-{2-[(2-sulfoethyl)amino]ethoxy}tricyclo[3.3.1.1$^{3,7}$]dec-1-yl)methyl]-5-methyl-1H-pyrazol-4-yl}pyridine-2-carboxylic acid;

1-{[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl]amino}-1,2-dideoxy-D-arabino-hexitol;

6-[8-(1,3-benzothiazol-2-ylcarbamoyl)-3,4-dihydroisoquinolin-2(1H)-yl]-3-(1-{[3-(2-{[3-hydroxy-2-(hydroxymethyl)propyl]amino}ethoxy)-5,7-dimethyltricyclo[3.3.1.1$^{3,7}$]dec-1-yl]methyl}-5-methyl-1H-pyrazol-4-yl)pyridine-2-carboxylic acid; and 6-[8-(1,3-benzothiazol-2-ylcarbamoyl)-3,4-dihydroisoquinolin-2(1H)-yl]-3-(1-{[3-(2-{[(3S)-3,4-dihydroxybutyl]amino}ethoxy)-5,7-dimethyltricyclo[3.3.1.1$^{3,7}$]dec-1-yl]methyl}-5-methyl-1H-pyrazol-4-yl)pyridine-2-carboxylic acid;

L is selected from the group consisting of linkers IVb.2, IVc.5, IVc.6, IVc.7, IVd.4, Vb.9, Vc.11, VIIa.1, VIIa.3, VIIc.1, VIIc.4, and VIIc.5 in either closed or open forms; LK is thioether; and m is an integer ranging from 2 to 4.

In one embodiment, the ADC is selected from the group consisting of formulae i-vi:

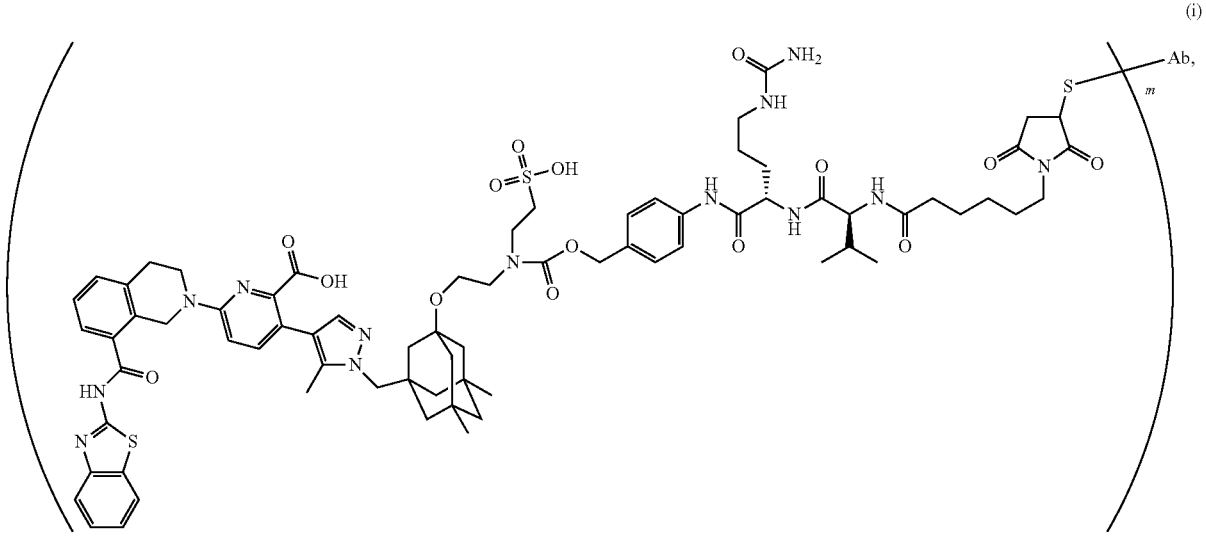

(i)

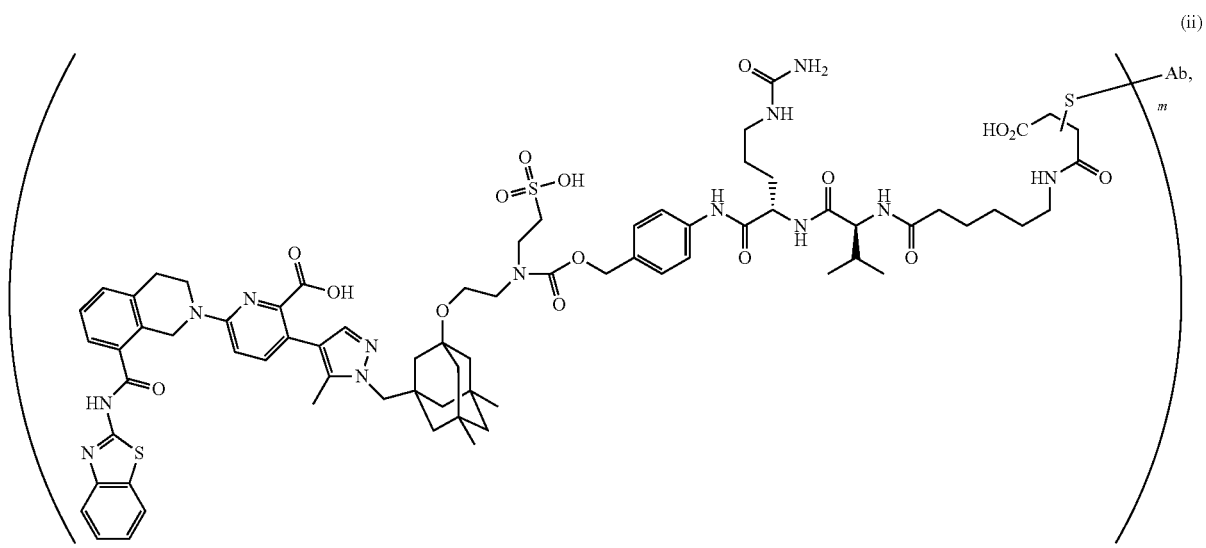

(ii)

-continued

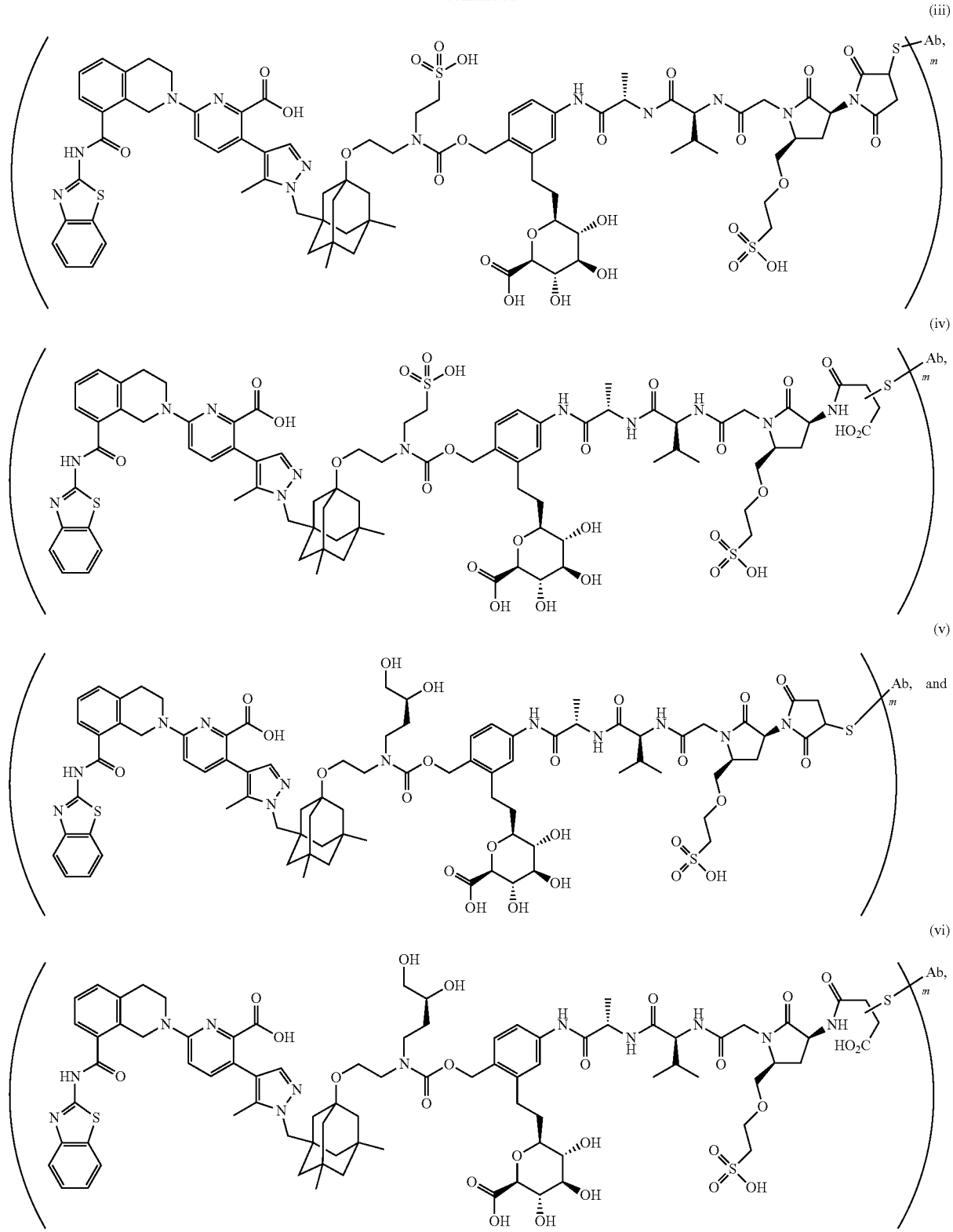

wherein m is an integer from 1 to 6. In one embodiment, Ab is an anti-hB7-H3 antibody, wherein the anti-hB7-H3 antibody comprises a heavy chain CDR3 domain comprising the amino acid sequence set forth in SEQ ID NO: 35, a heavy chain CDR2 domain comprising the amino acid sequence set forth in SEQ ID NO: 34, and a heavy chain CDR1 domain comprising the amino acid sequence set forth in SEQ ID NO: 33; and a light chain CDR3 domain comprising the amino acid sequence set forth in SEQ ID NO: 39, a light chain CDR2 domain comprising the amino acid sequence set forth in SEQ ID NO: 38, and a light chain CDR1 domain comprising the amino acid sequence set forth in SEQ ID NO: 37. In one embodiment, the Ab is an anti-hB7-H3 antibody, wherein the anti-hB7H3 antibody comprises a heavy chain variable region comprising the amino acid sequence set forth in SEQ ID NO: 147, and a light chain variable region comprising the amino acid sequence set forth in SEQ ID NO: 144. In one embodiment, Ab is an anti-hB7-H3 antibody, wherein the anti-hB7-H3 antibody comprises a heavy chain constant region comprising the amino acid sequence set forth in SEQ ID NO: 160 and/or a light chain constant region comprising the amino acid sequence set forth in SEQ ID NO: 161. In one embodiment, Ab is an anti-hB7-H3 antibody, wherein the anti-hB7-H3 antibody comprises a heavy chain comprising the amino acid sequence set forth in SEQ ID NO: 168, and a light chain comprising the amino acid sequence set forth in SEQ ID NO: 169. In one embodiment, Ab is an anti-hB7-H3 antibody, wherein the anti-hB7-H3 antibody comprises a heavy chain CDR3 domain comprising the amino acid sequence set forth in SEQ ID NO: 12, a heavy chain CDR2 domain comprising the amino acid sequence set forth in SEQ ID NO: 140, and a heavy chain CDR1 domain comprising the amino acid sequence set forth in SEQ ID NO: 10; and a light chain CDR3 domain comprising the amino acid sequence set forth in SEQ ID NO: 15, a light chain CDR2 domain comprising the amino acid sequence set forth in SEQ ID NO: 7, and a light chain CDR1 domain comprising the amino acid sequence set forth in SEQ ID NO: 136. In one embodiment, the Ab is an anti-hB7-H3 antibody, wherein the anti-hB7H3 antibody comprises a heavy chain variable region comprising the amino acid sequence set forth in SEQ ID NO: 139, and a light chain variable region comprising the amino acid sequence set forth in SEQ ID NO: 135. In one embodiment, Ab is an anti-hB7-H3 antibody, wherein the anti-hB7-H3 antibody comprises a heavy chain constant region comprising the amino acid sequence set forth in SEQ ID NO: 160 and/or a light chain constant region comprising the amino acid sequence set forth in SEQ ID NO: 161. In one embodiment, Ab is an anti-hB7-H3 antibody, wherein the anti-hB7-H3 antibody comprises a heavy chain comprising the amino acid sequence set forth in SEQ ID NO: 170, and a light chain comprising the amino acid sequence set forth in SEQ ID NO: 171.

In one embodiment, m is an integer from 2 to 6. In one embodiment, m is 2.

In one embodiment, the ADC comprises an anti-hB7-H3 antibody comprising a heavy chain CDR3 domain comprising the amino acid sequence set forth in SEQ ID NO: 12, a heavy chain CDR2 domain comprising the amino acid sequence set forth in SEQ ID NO: 140, and a heavy chain CDR1 domain comprising the amino acid sequence set forth in SEQ ID NO: 10; a light chain CDR3 domain comprising the amino acid sequence set forth in SEQ ID NO: 15, a light chain CDR2 domain comprising the amino acid sequence set forth in SEQ ID NO: 7, and a light chain CDR1 domain comprising the amino acid sequence set forth in SEQ ID NO: 136 or 138.

In one embodiment, the ADC comprises an antibody comprising a heavy chain variable region comprising the amino acid sequence set forth in SEQ ID NO: 139, and a light chain variable region comprising the amino acid sequence set forth in SEQ ID NO: 135.

In one embodiment, the ADC comprises an the antibody comprising a heavy chain variable region comprising the amino acid sequence set forth in SEQ ID NO: 139, and a light chain variable region comprising the amino acid sequence set forth in SEQ ID NO: 137.

In one embodiment, the ADC comprises an antibody comprising a light chain CDR3 domain comprising the amino acid sequence set forth in SEQ ID NO: 39, a light chain CDR2 domain comprising the amino acid sequence set forth in SEQ ID NO: 38, and a light chain CDR1 domain comprising the amino acid sequence set forth in SEQ ID NO: 37; and a heavy chain CDR3 domain comprising the amino acid sequence set forth in SEQ ID NO: 35, a heavy chain CDR2 domain comprising the amino acid sequence set forth in SEQ ID NO: 34, and a heavy chain CDR1 domain comprising the amino acid sequence set forth in SEQ ID NO: 33.

In one embodiment, the ADC comprises an antibody comprising a heavy chain variable region comprising the amino acid sequence set forth in SEQ ID NO: 147, and a light chain variable region comprising the amino acid sequence set forth in SEQ ID NO: 144.

In one embodiment, the ADC is selected from the group consisting of huAb3v2.5-CZ, huAb3v2.5-TX, huAb3v2.5-TV, huAb3v2.5-YY, huAb3v2.5-AAA, huAb3v2.5-AAD, huAb3v2.6-CZ, huAb3v2.6-TX, huAb3v2.6-TV, huAb3v2.6-YY, huAb3v2.6-AAD, huAb13v1-CZ, huAb13v1-TX, huAb13v1-TV, huAb13v1-YY, huAb13v1-AAA, huAb13v1-AAD, wherein CZ, TX, TV, YY, AAA, and AAD are synthons disclosed in Table B, and wherein the conjugated synthons are either in open or closed form.

In one aspect, the present invention provides a pharmaceutical composition comprising an effective amount of an ADC described herein, and a pharmaceutically acceptable carrier.

In another aspect, the present invention provides a pharmaceutical composition comprising an ADC mixture comprising a plurality of ADCs described herein, and a pharmaceutically acceptable carrier.

In one embodiment, the ADC mixture has an average drug to antibody ratio (DAR) of 1.5 to 4.

In one embodiment, the ADC mixture comprises ADCs each having a DAR of 1.5 to 8.

In one aspect, the present invention provides a method for treating cancer, comprising administering a therapeutically effective amount of an ADC described herein to a subject in need thereof.

In one embodiment, the cancer is selected from the group consisting of small cell lung cancer, non small cell lung cancer, breast cancer, ovarian cancer, a glioblastoma, prostate cancer, pancreatic cancer, colon cancer, gastric cancer, melanoma, hepatocellular carcinoma, head and neck cancer, kidney cancer, leukemia, e.g., acute myeloid leukemia (AML), and lymphoma, e.g., non-Hodgkin's lymphoma (NHL).

In one embodiment, the cancer is a squamous cell carcinoma. In one embodiment, the squamous cell carcinoma is squamous lung cancer or squamous head and neck cancer.

In one embodiment, the cancer is triple negative breast cancer.

In one embodiment, the cancer is non-small cell lung cancer.

In one embodiment, the cancer is characterized as having an activating EGFR mutation. In one embodiment, the activating EGFR mutation is selected from the group consisting of an exon 19 deletion mutation, a single-point substitution mutation L858R in exon 21, a T790M point mutation, and combinations thereof.

In one aspect, the present invention provides a method for inhibiting or decreasing solid tumor growth in a subject having a solid tumor, said method comprising administering an effective amount of an ADC described herein to the subject having the solid tumor, such that the solid tumor growth is inhibited or decreased.

In one embodiment, the solid tumor is a non-small cell lung carcinoma.

In one embodiment, the ADC is administered in combination with an additional agent or an additional therapy.

In one embodiment, the additional agent is selected from the group consisting of an anti-PD1 antibody (e.g. pembrolizumab), an anti-PD-L1 antibody (e.g., atezolizumab), an anti-CTLA-4 antibody (e.g. ipilimumab), a MEK inhibitor (e.g. trametinib), an ERK inhibitor, a BRAF inhibitor (e.g. dabrafenib), osimertinib, erlotinib, gefitinib, sorafenib, a CDK9 inhibitor (e.g. dinaciclib), a MCL-1 inhibitor, temozolomide, a Bcl-2 inhibitor (e.g. venetoclax), a Bcl-xL inhibitor, ibrutinib, a mTOR inhibitor (e.g. everolimus), a PI3K inhibitor (e.g. buparlisib), duvelisib, idelalisib, an AKT inhibitor, a HER2 inhibitor (e.g. lapatinib), a taxane (e.g. docetaxel, paclitaxel, nab-paclitaxel), an ADC comprising an auristatin, an ADC comprising a PBD (e.g. rovalpituzumab tesirine), an ADC comprising a maytansinoid (e.g. TDM1), a TRAIL agonist, a proteasome inhibitor (e.g. bortezomib), and a nicotinamide phosphoribosyltransferase (NAMPT) inhibitor.

In one embodiment, the anti-B7-H3 ADCs of the invention are administered in combination with venetoclax to a human subject for the treatment of small cell lung cancer (SCLC).

In one embodiment, the additional therapy is radiation.

In one embodiment, the additional agent is a chemotherapeutic agent.

In one aspect, the present invention provides a process for the preparation of an ADC according to structural formula (I):

(I)

wherein:

D is the Bcl-xL inhibitor drug of formula (IIa), (IIb), (IIc), or (IId) as disclosed herein;

L is the linker as disclosed herein;

Ab is an hB7-H3 antibody, wherein the hB7-H3 antibody comprises the heavy and light chain CDRs of huAb3v2.5, huAb3v2.6, or huAb13v1;

LK represents a covalent linkage linking linker L to antibody Ab; and m is an integer ranging from 1 to 20;

the process comprising:

treating an antibody in an aqueous solution with an effective amount of a disulfide reducing agent at 30-40° C. for at least 15 minutes, and then cooling the antibody solution to 20-27° C.;

adding to the reduced antibody solution a solution of water/dimethyl sulfoxide comprising a synthon selected from the group of 2.1 to 2.176 (Table B);

adjusting the pH of the solution to a pH of 7.5 to 8.5;

allowing the reaction to run for 48 to 80 hours to form the ADC;

wherein the mass is shifted by 18±2 amu for each hydrolysis of a succinimide to a succinamide as measured by electron spray mass spectrometry; and wherein the ADC is optionally purified by hydrophobic interaction chromatography.

In one embodiment, m is 2.

In another aspect, the present invention provides an ADC prepared by the process as described above.

DETAILED DESCRIPTION OF THE INVENTION

Figure 1:
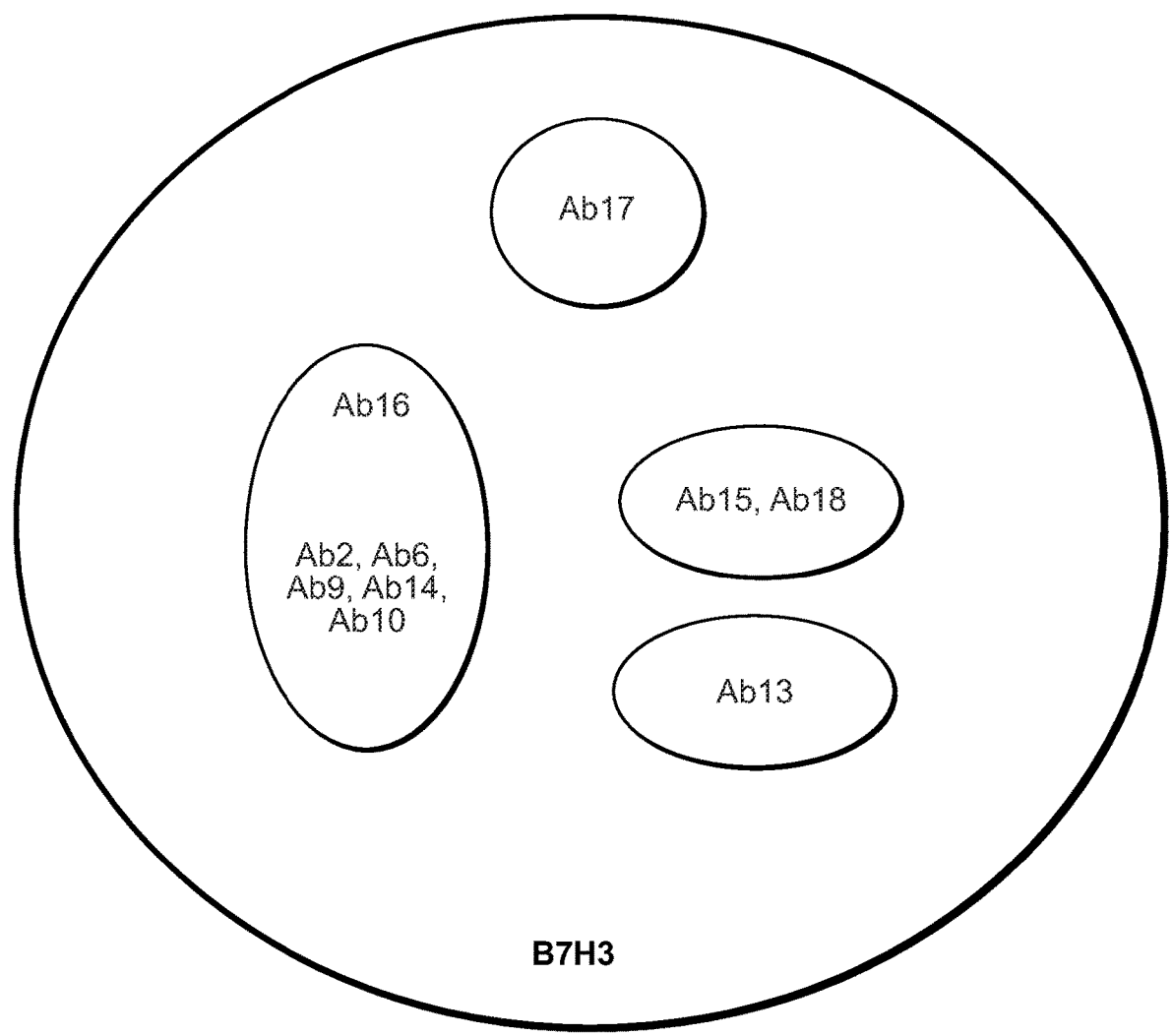
FIG. 1 is a graphical representation of the epitope grouping of murine anti-B7-H3 hybridoma antibodies as determined by pair-wise binding assays.

Various aspects of the invention relate to anti-B7-H3 antibodies and antibody fragments, anti-B7-H3 ADCs, and pharmaceutical compositions thereof, as well as nucleic acids, recombinant expression vectors and host cells for making such antibodies and fragments. Methods of using the antibodies, fragments, and ADCs described herein to detect human B7-H3, to inhibit human B7-H3 activity (in vitro or in vivo), and to treat cancers are also encompassed by the invention. In certain embodiments, the invention provides anti-B7-H3 ADCs, including ADCs comprising Bcl-xL inhibitors, synthons useful for synthesizing the ADCs, compositions comprising the ADCs, methods of making the ADCs, and various methods of using the ADCs.

As will be appreciated by skilled artisans, the ADCs disclosed herein are "modular" in nature. Throughout the instant disclosure, various specific embodiments of the various "modules" comprising the ADCs, as well as the synthons useful for synthesizing the ADCs, are described. As specific non-limiting examples, specific embodiments of antibodies, linkers, and Bcl-xL inhibitors that may comprise the ADCs and synthons are described. It is intended that all of the specific embodiments described may be combined with each other as though each specific combination were explicitly described individually.

It will also be appreciated by skilled artisans that the various ADCs and/or ADC synthons described herein may be in the form of salts, and in certain embodiments, particularly pharmaceutically acceptable salts. The compounds of the present disclosure that possess a sufficiently acidic, a sufficiently basic, or both functional groups, can react with any of a number of inorganic bases, and inorganic and organic acids, to form a salt. Alternatively, compounds that are inherently charged, such as those with a quaternary nitrogen, can form a salt with an appropriate counterion, e.g., a halide such as a bromide, chloride, or fluoride.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenyl-sulfonic acid, carbonic acid, succinic acid, citric acid, etc. Base addition salts include those derived from inorganic bases, such as ammonium and alkali or alkaline earth metal hydroxides, carbonates, bicarbonates, and the like.

In the disclosure below, if both structural diagrams and nomenclature are included and if the nomenclature conflicts with the structural diagram, the structural diagram controls.

An outline of the Detailed Description of the Invention is provided below:

I. Definitions
II. Anti-B7-H3 Antibodies
  II.A. Anti-B7-H3 Chimeric Antibodies
  II.B. Humanized Anti-B7-H3 Antibodies
III. Anti-B7-H3 Antibody Drug Conjugates (ADCs)
  III.A. Anti-B7-H3/Bcl-xL Inhibitor ADCs
    III.A.1. Bcl-xL Inhibitors
    III.A.2 Bcl-xL Linkers
      Cleavable Linkers
      Non-Cleavable Linkers
      Groups Used to Attach Linkers to Anti-B7-H3 Antibodies
      Linker Selection Considerations
    III.A.3. Bcl-xL ADC Synthons
    III.A.4 Methods of Synthesis of Bcl-xL ADCs
    III.A.5. General Methods for Synthesizing Bcl-xL Inhibitors
    III.A.6. General Methods for Synthesizing Synthons
    III.A.7. General Methods for Synthesizing Anti-B7-H3 ADCs
  III.B. Anti-B7-H3 ADCs: Other Exemplary Drugs for Conjugation
  III.C. Anti-B7-H3 ADCs: Other Exemplary Linkers
IV. Purification of Anti-B7-H3 ADCs
V. Uses of Anti-B7-H3 Antibodies and Anti-B7-H3 ADCs
VI. Pharmaceutical Compositions I. Definitions In order that the invention may be more readily understood, certain terms are first defined. In addition, it should be noted that whenever a value or range of values of a parameter are recited, it is intended that values and ranges intermediate to the recited values are also intended to be part of this invention.

The term "anti-B7-H3 antibody" refers to an antibody that specifically binds to B7-H3. An antibody "which binds" an antigen of interest, i.e., B7-H3, is one capable of binding that antigen with sufficient affinity such that the antibody is useful in targeting a cell expressing the antigen. In a preferred embodiment, the antibody specifically binds to human B7-H3 (hB7-H3). Examples of anti-B7-H3 antibodies are disclosed in the examples below. Unless otherwise indicated, the term "anti-B7-H3 antibody" is meant to refer to an antibody which binds to wild type B7-H3 (e.g., a 4IgB7-H3 isoform of B7-H3) or any variant of B7-H3. The amino acid sequence of wild type human B7-H3 is provided below as SEQ ID NO: 149, where the signal peptide (amino acid residues 1-28) is underlined.

(SEQ ID NO: 149)
MLRRRGSPGMGVHVGAALGALWFCLTGALEVQVPEDPVVALVGTDAT

LCCSFSPEPGFSLAQLNLIWQLTDTKQLVHSFAEGQDQGSAYANRTA

LFPDLLAQGNASLRLQRVRVADEGSFTCFVSIRDFGSAAVSLQVAAP

YSKPSMTLEPNKDLRPGDTVTITCSSYQGYPEAEVFWQDGQGVPLTG

NVTTSQMANEQGLFDVHSILRVVLGANGTYSCLVRNPVLQQDAHSSV

-continued

TITPQRSPTGAVEVQVPEDPVVALVGTDATLRCSFSPEPGESLAQLN

LIWQLTDTKQLVHSFTEGRDQGSAYANRTALFPDLLAQGNASLRLQR

VRVADEGSFTCFVSIRDFGSAAVSLQVAAPYSKPSMTLEPNKDLRPG

DTVTITCSSYRGYPEAEVFWQDGQGVPLTGNVTTSQMANEQGLFDVH

SVLRVVLGANGTYSCLVRNPVLQQDAHGSVTITGQPMTFPPEALWVT

VGLSVCLIALLVALAFVCWRKIKQSCEEENAGAEDQDGEGEGSKTAL

QPLKHSDSKEDDGQEIA

Thus, in one embodiment of the invention, the antibody or ADC binds human B7-H3 as defined in SEQ ID NO: 149. The extracellular domain (ECD) of human B7-H3 is provided in SEQ ID NO: 152 (inclusive of a His tag). As such, in one embodiment of the invention, the antibody of ADC binds the ECD of human B7-H3 as described in the ECD of SEQ ID NO: 152.

The terms "specific binding" or "specifically binding", as used herein, in reference to the interaction of an antibody or an ADC with a second chemical species, mean that the interaction is dependent upon the presence of a particular structure (e.g., an antigenic determinant or epitope) on the chemical species; for example, an antibody recognizes and binds to a specific protein structure rather than to proteins generally. If an antibody or ADC is specific for epitope "A", the presence of a molecule containing epitope A (or free, unlabeled A), in a reaction containing labeled "A" and the antibody, will reduce the amount of labeled A bound to the antibody or ADC. By way of example, an antibody "binds specifically" to a target if the antibody, when labeled, can be competed away from its target by the corresponding non-labeled antibody. In one embodiment, an antibody specifically binds to a target, e.g., B7-H3, if the antibody has a $K_D$ for the target of at least about $10^{-4}$ M, $10^{-5}$ M, $10^{-6}$ M, 10-7 M, $10^{-8}$ M, $10^{-9}$ M, $10^{-10}$ M, $10^{-11}$ M, $10^{-12}$ M, or less (less meaning a number that is less than $10^{-12}$, e.g. $10^{-13}$). In one embodiment, the term "specific binding to B7-H3" or "specifically binds to B7-H3," as used herein, refers to an antibody or an ADC that binds to B7-H3 and has a dissociation constant ($K_D$) of $1.0 \times 10^{-7}$ M or less, as determined by surface plasmon resonance. It shall be understood, however, that the antibody or ADC may be capable of specifically binding to two or more antigens which are related in sequence. For example, in one embodiment, an antibody can specifically bind to both human and a non-human (e.g., mouse or non-human primate) orthologs of B7-H3.

The term "antibody" refers to an immunoglobulin molecule that specifically binds to an antigen and comprises a heavy (H) chain(s) and a light (L chain(s). Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. An antibody can be of any type (e.g., IgG, IgE, IgM, IgD, IgA and IgY) and class (e.g., IgG1, IgG2, IgG 3, IgG4, IgA1 and IgA2) or subclass.

While the term "antibody" is not intended to include antigen binding portions of an antibody (defined below), it is intended, in certain embodiments, to include a small number of amino acid deletions from the carboxy end of the heavy chain(s). In one embodiment, an antibody comprises a heavy chain having 1-5 amino acid deletions the carboxy end of the heavy chain. In one embodiment, an antibody is a monoclonal antibody which is an IgG, having four polypeptide chains, two heavy (H) chains, and two light (L chains) that can bind to hB7-H3. In one embodiment, an antibody is a monoclonal IgG antibody comprising a lambda or a kappa light chain.

The term "antigen binding portion" or "antigen binding fragment" of an antibody (or simply "antibody portion" or "antibody fragment"), as used herein, refers to one or more fragments of an antibody that retain the ability to specifically bind to an antigen (e.g., hB7-H3). It has been shown that the antigen binding function of an antibody can be performed by fragments of a full-length antibody. Such antibody embodiments may also be bispecific, dual specific, or multi-specific formats; specifically binding to two or more different antigens. Examples of binding fragments encompassed within the term "antigen binding portion" of an antibody include (i) a Fab fragment, a monovalent fragment consisting of the VL, VH, CL and CH1 domains; (ii) a F(ab')₂ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546, Winter et al., PCT publication WO 90/05144 A1 herein incorporated by reference), which comprises a single variable domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen binding portion" of an antibody. In certain embodiments of the invention, scFv molecules may be incorporated into a fusion protein. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poljak, R. J., et al. (1994) *Structure* 2:1121-1123). Such antibody binding portions are known in the art (Kontermann and Dubel eds., *Antibody Engineering* (2001) Springer-Verlag. New York. 790 pp. (ISBN 3-540-41354-5).

An IgG is a class of antibody comprising two heavy chains and two light chains arranged in a Y-shape. An IgG constant domain refers to a heavy or light chain constant domain. Exemplary human IgG heavy chain and light chain constant domain amino acid sequences are known in the art and represented below in Table A.

TABLE A

Sequences of human IgG heavy chain constant domains and light chain constant domains

| Protein | Sequence Identifier | Sequence |
|---|---|---|
| Ig gamma-1 constant region | SEQ ID NO: 159 | ASTKGPSVFPLAPSSKSTSGGTAALGCLVKDY FPEPVTVSWNSGALTSGVHTFPAVLQSSGLYS LSSVVTVPSSSLGTQTYICNVNHKPSNTKVDK KVEPKSCDKTHTCPPCPAPELLGGPSVFLFPP KPKDTLMISRTPEVTCVVVDVSHEDPEVKFNW YVDGVEVHNAKTKPREEQYNSTYRVVSVLTVL HQDWLNGKEYKCKVSNKALPAPIEKTISKAKG QPREPQVYTLPPSREEMTKNQVSLTCLVKGFY PSDIAVEWESNGQPENNYKTTPPVLDSDGSFF LYSKLTVDKSRWQQGNVFSCSVMHEALHNHYT QKSLSLSPGK |
| Ig gamma-1 constant region mutant | SEQ ID NO: 160 | ASTKGPSVFPLAPSSKSTSGGTAALGCLVKDY FPEPVTVSWNSGALTSGVHTFPAVLQSSGLYS LSSVVTVPSSSLGTQTYICNVNHKPSNTKVDK KVEPKSCDKTHTCPPCPAPEAAGGPSVFLFPP KPKDTLMISRTPEVICVVVDVSHEDPEVKFNW YVDGVEVHNAKTKPREEQYNSTYRVVSVLTVL HQDWLNGKEYKCKVSNKALPAPIEKTISKAKG QPREPQVYTLPPSREEMTKNQVSLTCLVKGFY PSDIAVEWESNGQPENNYKTTPPVLDSDGSFF LYSKLTVDKSRWQQGNVFSCSVMHEALHNHYT QKSLSLSPGK |
| Ig Kappa constant region | SEQ ID NO: 161 | RTVAAPSVFIFPPSDEQLKSGTASVVCLLNNF YPREAKVQWKVDNALQSGNSQESVTEQDSKDS TYSLSSTLTLSKADYEKHKVYACEVTHQGLSS PVTKSFNRGEC |
| Ig Lambda constant | SEQ ID NO: 162 | QPKAAPSVTLFPPSSEELQANKATLVCLISDF YPGAVTVAWKADSSPVKAGVETTTPSKQSNNK |

TABLE A-continued

Sequences of human IgG heavy chain constant domains and light chain constant domains

| Protein | Sequence Identifier | Sequence |
|---|---|---|
| region | | YAASSYLSLTPEQWKSHRSYSCQVTHEGSTVE KTVAPTECS |

An "isolated antibody", as used herein, is intended to refer to an antibody that is substantially free of other antibodies having different antigenic specificities (e.g., an isolated antibody that specifically binds B7-H3 is substantially free of antibodies that specifically bind antigens other than B7-H3). An isolated antibody that specifically binds B7-H3 may, however, have cross-reactivity to other antigens, such as B7-H3 molecules from other species. Moreover, an isolated antibody may be substantially free of other cellular material and/or chemicals.

The term "humanized antibody" refers to antibodies which comprise heavy and light chain variable region sequences from a nonhuman species (e.g., a mouse) but in which at least a portion of the VH and/or VL sequence has been altered to be more "human-like", i.e., more similar to human germline variable sequences. In particular, the term "humanized antibody" is an antibody or a variant, derivative, analog or fragment thereof which immunospecifically binds to an antigen of interest and which comprises a framework (FR) region having substantially the amino acid sequence of a human antibody and a complementary determining region (CDR) having substantially the amino acid sequence of a non-human antibody. As used herein, the term "substantially" in the context of a CDR refers to a CDR having an amino acid sequence at least 80%, preferably at least 85%, at least 90%, at least 95%, at least 98% or at least 99% identical to the amino acid sequence of a non-human antibody CDR. A humanized antibody comprises substantially all of at least one, and typically two, variable domains (Fab, Fab', F(ab')$_2$, FabC, Fv) in which all or substantially all of the CDR regions correspond to those of a non-human immunoglobulin (i.e., donor antibody) and all or substantially all of the framework regions are those of a human immunoglobulin consensus sequence. Preferably, a humanized antibody also comprises at least a portion of an immunoglobulin constant region (Fc), typically that of a human immunoglobulin. In some embodiments, a humanized antibody contains both the light chain as well as at least the variable domain of a heavy chain. The antibody also may include the CH1, hinge, CH2, CH3, and CH4 regions of the heavy chain. In some embodiments, a humanized antibody only contains a humanized light chain. In other embodiments, a humanized antibody only contains a humanized heavy chain. In specific embodiments, a humanized antibody only contains a humanized variable domain of a light chain and/or humanized heavy chain.

The humanized antibody can be selected from any class of immunoglobulins, including IgM, IgG, IgD, IgA and IgE, and any isotype, including without limitation IgG1, IgG2, IgG3 and IgG4. The humanized antibody may comprise sequences from more than one class or isotype, and particular constant domains may be selected to optimize desired effector functions using techniques well-known in the art.

The terms "Kabat numbering," "Kabat definitions," and "Kabat labeling" are used interchangeably herein. These terms, which are recognized in the art, refer to a system of numbering amino acid residues which are more variable (i.e., hypervariable) than other amino acid residues in the heavy and light chain variable regions of an antibody, or an antigen binding portion thereof (Kabat et al. (1971) *Ann. NY Acad, Sci.* 190:382-391 and, Kabat, E. A., et al. (1991) *Sequences of Proteins of Immunological Interest, Fifth Edition*, U.S. Department of Health and Human Services, NIH Publication No. 91-3242). For the heavy chain variable region, the hypervariable region ranges from amino acid positions 31 to 35 for CDR1, amino acid positions 50 to 65 for CDR2, and amino acid positions 95 to 102 for CDR3. For the light chain variable region, the hypervariable region ranges from amino acid positions 24 to 34 for CDR1, amino acid positions 50 to 56 for CDR2, and amino acid positions 89 to 97 for CDR3.

As used herein, the term "CDR" refers to the complementarity determining region within antibody variable sequences. There are three CDRs in each of the variable regions of the heavy chain (HC) and the light chain (LC), which are designated CDR1, CDR2 and CDR3 (or specifically HC CDR1, HC CDR2, HC CDR3, LC CDR1, LC CDR2, and LC CDR3), for each of the variable regions. The term "CDR set" as used herein refers to a group of three CDRs that occur in a single variable region capable of binding the antigen. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Chothia and coworkers (Chothia & Lesk, J. Mol. Biol. 196:901-917 (1987) and Chothia et al., Nature 342:877-883 (1989)) found that certain sub-portions within Kabat CDRs adopt nearly identical peptide backbone conformations, despite having great diversity at the level of amino acid sequence. These sub-portions were designated as L1, L2 and L3 or H1, H2 and H3 where the "L" and the "H" designates the light chain and the heavy chains regions, respectively. These regions may be referred to as Chothia CDRs, which have boundaries that overlap with Kabat CDRs. Other boundaries defining CDRs overlapping with the Kabat CDRs have been described by Padlan (FASEB J. 9:133-139 (1995)) and MacCallum (J. Mol. Biol. 262(5):732-45 (1996)). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although preferred embodiments use Kabat or Chothia defined CDRs.

As used herein, the term "framework" or "framework sequence" refers to the remaining sequences of a variable region minus the CDRs. Because the exact definition of a CDR sequence can be determined by different systems, the meaning of a framework sequence is subject to correspondingly different interpretations. The six CDRs (CDR-L1, CDR-L2, and CDR-L3 of light chain and CDR-H1, CDR-H2, and CDR-H3 of heavy chain) also divide the framework regions on the light chain and the heavy chain into four sub-regions (FR1, FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FR's within the variable region of a single, naturally occurring immunoglobulin chain. As used herein, a FR represents one of the four sub-regions, and FRs represents two or more of the four sub-regions constituting a framework region.

The framework and CDR regions of a humanized antibody need not correspond precisely to the parental sequences, e.g., the donor antibody CDR or the consensus framework may be mutagenized by substitution, insertion and/or deletion of at least one amino acid residue so that the CDR or framework residue at that site does not correspond to either the donor antibody or the consensus framework. In a preferred embodiment, such mutations, however, will not be extensive. Usually, at least 80%, preferably at least 85%, more preferably at least 90%, and most preferably at least 95% of the humanized antibody residues will correspond to those of the parental FR and CDR sequences. As used herein, the term "consensus framework" refers to the framework region in the consensus immunoglobulin sequence. As used herein, the term "consensus immunoglobulin sequence" refers to the sequence formed from the most frequently occurring amino acids (or nucleotides) in a family of related immunoglobulin sequences (See e.g., Winnaker, From Genes to Clones (Verlagsgesellschaft, Weinheim, Germany 1987). In a family of immunoglobulins, each position in the consensus sequence is occupied by the amino acid occurring most frequently at that position in the family. If two amino acids occur equally frequently, either can be included in the consensus sequence.

The term "human acceptor framework", as used herein, is meant to refer to a framework of an antibody or antibody fragment thereof comprising the amino acid sequence of a VH or VL framework derived from a human antibody or antibody fragment thereof or a human consensus sequence framework into which CDR's from a non-human species may be incorporated.

"Percent (%) amino acid sequence identity" with respect to a peptide or polypeptide sequence is defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. In one embodiment, the invention includes an amino acid sequence having at least 80%, at least 85%, at least 90%, at least 95%, at least 96%, at least 97%, at least 98%, or at least 99% identity to an amino acid sequence set forth in any one of SEQ ID NOs: 1 to 148.

The term "multivalent antibody" is used herein to denote an antibody comprising two or more antigen binding sites. In certain embodiments, the multivalent antibody may be engineered to have the three or more antigen binding sites, and is generally not a naturally occurring antibody.

The term "multispecific antibody" refers to an antibody capable of binding two or more unrelated antigens. In one embodiment, the multispecific antibody is a bispecific antibody that is capable of binding to two unrelated antigens, e.g., a bispecific antibody, or antigen-binding portion thereof, that binds B7-H3 and CD3.

The term "dual variable domain" or "DVD," as used interchangeably herein, are antigen binding proteins that comprise two or more antigen binding sites and are tetravalent or multivalent binding proteins. Such DVDs may be monospecific, i.e., capable of binding one antigen or multispecific, i.e. capable of binding two or more antigens. DVD binding proteins comprising two heavy chain DVD polypeptides and two light chain DVD polypeptides are referred to a DVD Ig. Each half of a DVD Ig comprises a heavy chain DVD polypeptide, and a light chain DVD polypeptide, and two antigen binding sites. Each binding site comprises a heavy chain variable domain and a light chain variable domain with a total of 6 CDRs involved in antigen binding per antigen binding site. In one embodiment, the CDRs described herein are used in an anti-B7-H3 DVD.

The term "chimeric antigen receptor" or "CAR" refers to a recombinant protein comprising at least (1) an antigen-binding region, e.g., a variable heavy or light chain of an antibody, (2) a transmembrane domain to anchor the CAR into a T cell, and (3) one or more intracellular signaling domains.

The term "activity" includes activities such as the binding specificity/affinity of an antibody or ADC for an antigen, for example, an anti-hB7-H3 antibody that binds to an hB7-H3 antigen and/or the neutralizing potency of an antibody, for example, an anti-hB7-H3 antibody whose binding to hB7-H3 inhibits the biological activity of hB7-H3, e.g., inhibition of proliferation of B7-H3 expressing cell lines, e.g., human H146 lung carcinoma cells, human H1650 lung carcinoma cells, or human EBC1 lung carcinoma cells.

The term "non small-cell lung carcinoma (NSCLC) xenograft assay," as used herein, refers to an in vivo assay used to determine whether an anti-B7-H3 antibody or ADC, can inhibit tumor growth (e.g., further growth) and/or decrease tumor growth resulting from the transplantation of NSCLC cells into an immunodeficient mouse. An NSCLC xenograft assay includes transplantation of NSCLC cells into an immunodeficient mouse such that a tumor grows to a desired size, e.g., 200-250 mm$^3$, whereupon the antibody or ADC is administered to the mouse to determine whether the antibody or ADC can inhibit and/or decrease tumor growth. In certain embodiments, the activity of the antibody or ADC is determined according to the percent tumor growth inhibition (% TGI) relative to a control antibody, e.g., a human IgG antibody (or collection thereof) which does not specifically bind tumor cells, e.g., is directed to an antigen not associated with cancer or is obtained from a source which is noncancerous (e.g., normal human serum). In such embodiments, the antibody (or ADC) and the control antibody are administered to the mouse at the same dose, with the same frequency, and via the same route. In one embodiment, the mouse used in the NSCLC xenograft assay is a severe combined immunodeficiency (SCID) mouse and/or an athymic CD-1 nude mouse. Examples of NSCLC cells that may be used in the NSCLC xenograft assay include, but are not limited to, H1299 cells (NCI-H1299 [H-1299] (ATCC® CRL-5803)), H1975 cells (NCI-H1975 cells [H1975] (ATCC® CRL-5908™)), and EBC-1 cells.

The term "small-cell lung carcinoma (SCLC) xenograft assay," as used herein, refers to an in vivo assay used to determine whether an anti-B7-H3 antibody or ADC, can inhibit tumor growth (e.g., further growth) and/or decrease tumor growth resulting from the transplantation of SCLC cells into an immunodeficient mouse. An SCLC xenograft assay includes transplantation of SCLC cells into an immunodeficient mouse such that a tumor grows to a desired size, e.g., 200-250 mm$^3$, whereupon the antibody or ADC is administered to the mouse to determine whether the antibody or ADC can inhibit and/or decrease tumor growth. In certain embodiments, the activity of the antibody or ADC is determined according to the percent tumor growth inhibition (% TGI) relative to a control antibody, e.g., a human IgG antibody (or collection thereof) which does not specifically bind tumor cells, e.g., is directed to an antigen not associated with cancer or is obtained from a source which is noncancerous (e.g., normal human serum). In such embodiments, the antibody (or ADC) and the control antibody are administered to the mouse at the same dose, with the same frequency, and via the same route. In one embodiment, the mouse used in the NSCLC xenograft assay is a severe combined immunodeficiency (SCID) mouse and/or an athymic CD-1 nude mouse. Examples of SCLC cells that may be used in the SCLC xenograft assay include, but are not limited to, H146 cells (NCI-H146 cells [H146] (ATCC® HTB-173™)), and H847 cells (NCI-H847 [H847] (ATCC® CRL-5846™)). The term "epitope" refers to a region of an antigen that is bound by an antibody or ADC. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics. In certain embodiments, an antibody is said to specifically bind an antigen when it preferentially recognizes its target antigen in a complex mixture of proteins and/or macromolecules.

The term "surface plasmon resonance", as used herein, refers to an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Jönsson, U., et al. (1993) *Ann. Biol. Clin.* 51:19-26; Jönsson, U., et al. (1991) *Biotechniques* 11:620-627; Johnsson, B., et al. (1995) *J. Mol. Recognit.* 8:125-131; and Johnsson, B., et al. (1991) *Anal. Biochem.* 198:268-277. In one embodiment, surface plasmon resonance is determined according to the methods described in Example 2.

The term "$k_{on}$" or "$k_a$", as used herein, is intended to refer to the on rate constant for association of an antibody to the antigen to form the antibody/antigen complex.

The term "$k_{off}$" or "$k_d$", as used herein, is intended to refer to the off rate constant for dissociation of an antibody from the antibody/antigen complex.

The term "$K_D$", as used herein, is intended to refer to the equilibrium dissociation constant of a particular antibody-antigen interaction (e.g., huAb13 antibody and B7-H3). $K_D$ is calculated by $k_d/k_a$.

The term "competitive binding", as used herein, refers to a situation in which a first antibody competes with a second antibody, for a binding site on a third molecule, e.g., an antigen. In one embodiment, competitive binding between two antibodies is determined using FACS analysis.

The term "competitive binding assay" is an assay used to determine whether two or more antibodies bind to the same epitope. In one embodiment, a competitive binding assay is a competition fluorescent activated cell sorting (FACS) assay which is used to determine whether two or more antibodies bind to the same epitope by determining whether the fluorescent signal of a labeled antibody is reduced due to the introduction of a non-labeled antibody, where competition for the same epitope will lower the level of fluorescence.

The term "labeled antibody" as used herein, refers to an antibody, or an antigen binding portion thereof, with a label incorporated that provides for the identification of the binding protein, e.g., an antibody. Preferably, the label is a detectable marker, e.g., incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). Examples of labels for polypeptides include, but are not limited to, the following: radioisotopes or radionuclides (e.g., $^3$H, $^{14}$C, $^{35}$S, $^{99}$Y, $^{99}$Tc, $^{111}$In, $^{125}$I, $^{131}$I, $^{177}$Lu, $^{166}$Ho, or $^{153}$Sm); fluorescent labels (e.g., FITC, rhodamine, lanthanide phosphors), enzymatic labels (e.g., horseradish peroxidase, luciferase, alkaline phosphatase); chemiluminescent markers; biotinyl groups; predetermined polypeptide epitopes recognized by a secondary reporter (e.g., leucine zipper pair sequences, binding sites for secondary antibodies, metal binding domains, epitope tags); and magnetic agents, such as gadolinium chelates.

The term "antibody-drug-conjugate" or "ADC" refers to a binding protein, such as an antibody or antigen binding fragment thereof, chemically linked to one or more chemical drug(s) (also referred to herein as agent(s), warhead(s), and payload(s)) that may optionally be therapeutic or cytotoxic agents. In a preferred embodiment, an ADC includes an antibody, a drug, (e.g. a cytotoxic drug), and a linker that enables attachment or conjugation of the drug to the antibody. An ADC typically has anywhere from 1 to 8 drugs conjugated to the antibody, including drug loaded species of 2, 4, 6, or 8. Non-limiting examples of drugs that may be included in the ADCs are mitotic inhibitors, antitumor antibiotics, immunomodulating agents, vectors for gene therapy, alkylating agents, antiangiogenic agents, antimetabolites, boron-containing agents, chemoprotective agents, hormones, antihormone agents, corticosteroids, photoactive therapeutic agents, oligonucleotides, radionuclide agents, topoisomerase inhibitors, kinase inhibitors (e.g., TEC-family kinase inhibitors and serine/threonine kinase inhibitors), and radiosensitizers. In one embodiment, the drug is a Bcl-xL inhibitor.

The terms "anti-B7-H3 antibody drug conjugate" or "anti-B7-H3 ADC", used interchangeably herein, refer to an ADC comprising an antibody that specifically binds to B7-H3, whereby the antibody is conjugated to one or more chemical agent(s). In one embodiment, the anti-B7-H3 ADC comprises antibody huAb13v1, huAb3v2.5, or huAb3v2.6 conjugated to an auristatin, e.g., MMAE or MMAF. In one embodiment, the anti-B7-H3 ADC comprises antibody huAb13v1, huAb3v2.5, or huAb3v2.6 conjugated to a Bcl-xL inhibitor. In a preferred embodiment, the anti-B7-H3 ADC binds to human B7-H3 (hB7-H3).

The term "Bcl-xL inhibitor", as used herein, refers to a compound which antagonizes Bcl-xL activity in a cell. In one embodiment, a Bcl-xL inhibitor promotes apoptosis of a cell by inhibiting Bcl-xL activity.

The term "auristatin", as used herein, refers to a family of antimitotic agents. Auristatin derivatives are also included within the definition of the term "auristatin". Examples of auristatins include, but are not limited to, auristatin E (AE), monomethylauristatin E (MMAE), monomethylauristatin F (MMAF), and synthetic analogs of dolastatin. In one embodiment, an anti-B7-H3 antibody described herein is conjugated to an auristatin to form an anti-B7-H3 ADC.

As used herein, the term "Ab-vcMMAE" is used to refer to an ADC comprising an antibody conjugated to monomethylauristatin E (MMAE) via a maleimidocaproyl valine citrulline p-aminobenzyloxycarbamyl (PABA) linker.

As used herein, the term "mcMMAF" is used to refer to a linker/drug combination of maleimidocaproyl-monomethylauristatin F (MMAF).

The term "drug-to-antibody ratio" or "DAR" refers to the number of drugs, e.g., Bcl-xL inhibitor, attached to the antibody of the ADC. The DAR of an ADC can range from 1 to 8, although higher loads, e.g., 20, are also possible depending on the number of linkage site on an antibody. The term DAR may be used in reference to the number of drugs loaded onto an individual antibody, or, alternatively, may be used in reference to the average or mean DAR of a group of ADCs.

The term "undesired ADC species", as used herein, refers to any drug loaded species which is to be separated from an ADC species having a different drug load. In one embodiment, the term undesired ADC species may refer to drug loaded species of 6 or more, i.e., ADCs with a DAR of 6 or more, including DAR6, DAR7, DAR8, and DAR greater than 8 (i.e., drug loaded species of 6, 7, 8, or greater than 8). In a separate embodiment, the term undesired ADC species may refer to drug loaded species of 8 or more, i.e., ADCs with a DAR of 8 or more, including DAR8, and DAR greater than 8 (i.e., drug loaded species of 8, or greater than 8).

The term "ADC mixture", as used herein, refers to a composition containing a heterogeneous DAR distribution of ADCs. In one embodiment, an ADC mixture contains ADCs having a distribution of DARs of 1 to 8, e.g., 1.5, 2, 4, 6, and 8 (i.e., drug loaded species of 2, 4, 6, and 8). Notably, degradation products may result such that DARs of 1, 3, 5, and 7 may also be included in the mixture. Further, ADCs within the mixture may also have DARs greater than 8. The ADC mixture results from interchain disulfide reduction followed by conjugation. In one embodiment, the ADC mixture comprises both ADCs with a DAR of 4 or less (i.e., a drug loaded species of 4 or less) and ADCs with a DAR of 6 or more (i.e., a drug loaded species of 6 or more).

The term a "xenograft assay", as used herein, refers to a human tumor xenograft assay, wherein human tumor cells are transplanted, either under the skin or into the organ type in which the tumor originated, into immunocompromised mice that do not reject human cells.

The term "cancer" is meant to refer to or describe the physiological condition in mammals that is typically characterized by unregulated cell growth. Examples of cancer include, but are not limited to, carcinoma, lymphoma, blastoma, sarcoma, and leukemia or lymphoid malignancies. More particular examples of such cancers include glioblastoma, acute myeloid leukemia (AML), non-Hodgkin's lymphoma (NHL), non-small cell lung cancer, lung cancer, colon cancer, colorectal cancer, head and neck cancer, breast cancer (e.g., triple negative breast cancer), pancreatic cancer, squamous cell tumors, squamous cell carcinoma (e.g., squamous cell lung cancer or squamous cell head and neck cancer), anal cancer, skin cancer, and vulvar cancer. In one embodiment, the antibodies or ADCs of the invention are administered to a patient having a tumor(s) that overexpresses B7-H3. In one embodiment, the antibodies or ADCs of the invention are administered to a patient having a solid tumor which is likely to over-express B7-H3. In one embodiment, the antibodies or ADCs of the invention are administered to a patient having squamous cell non-small cell lung cancer (NSCLC). In one embodiment, the antibodies or ADCs of the invention are administered to a patient having solid tumors, including advanced solid tumors. In one embodiment, the antibodies or ADCs of the invention are administered to a patient having prostate cancer. In one embodiment, the antibodies or ADCs of the invention are administered to a patient having non-small cell lung cancer. In one embodiment, the antibodies or ADCs of the invention are administered to a patient having a glioblastoma. In one embodiment, the antibodies or ADCs of the invention are administered to a patient having colon cancer. In one embodiment, the antibodies or ADCs of the invention are administered to a patient having head and neck cancer. In one embodiment, the antibodies or ADCs of the invention are administered to a patient having kidney cancer. In one embodiment, the antibodies or ADCs of the invention are administered to a patient having clear cell renal cell carcinoma. In one embodiment, the antibodies or ADCs of the invention are administered to a patient having glioma. In one embodiment, the antibodies or ADCs of the invention are administered to a patient having melanoma. In one embodiment, the antibodies or ADCs of the invention are administered to a patient having pancreatic cancer. In one embodiment, the antibodies or ADCs of the invention are administered to a patient having gastric cancer. In one embodiment, the antibodies or ADCs of the invention are administered to a patient having ovarian cancer. In one embodiment, the antibodies or ADCs of the invention are administered to a patient having colorectal cancer. In one embodiment, the antibodies or ADCs of the invention are administered to a patient having renal cancer. In one embodiment, the antibodies or ADCs of the invention are administered to a patient having small cell lung cancer. In one embodiment, the antibodies or ADCs of the invention are administered to a patient having hepatocellular carcinoma. In one embodiment, the antibodies or ADCs of the invention are administered to a patient having hypopharyngeal squamous cell carcinoma. In one embodiment, the antibodies or ADCs of the invention are administered to a patient having neuroblastoma. In one embodiment, the antibodies or ADCs of the invention are administered to a patient having breast cancer. In one embodiment, the antibodies or ADCs of the invention are administered to a patient having endometrial cancer. In one embodiment, the antibodies or ADCs of the invention are administered to a patient having urothelial cell carcinoma. In one embodiment, the antibodies or ADCs of the invention are administered to a patient having acute myeloid leukemia (AML). In one embodiment, the antibodies or ADCs of the invention are administered to a patient having non-Hodgkin's lymphoma (NHL).

The term "B7-H3 expressing tumor," as used herein, refers to a tumor which expresses B7-H3 protein. In one embodiment, B7-H3 expression in a tumor is determined using immunohistochemical staining of tumor cell membranes, where any immunohistochemical staining above background level in a tumor sample indicates that the tumor is a B7-H3 expressing tumor. Methods for detecting expression of B7-H3 in a tumor are known in the art, and include immunohistochemical assays. In contrast, a "B7-H3 negative tumor" is defined as a tumor having an absence of B7-H3 membrane staining above background in a tumor sample as determined by immunohistochemical techniques.

The terms "overexpress," "overexpression," or "overexpressed" interchangeably refer to a gene that is transcribed or translated at a detectably greater level, usually in a cancer cell, in comparison to a normal cell. Overexpression therefore refers to both overexpression of protein and RNA (due to increased transcription, post transcriptional processing, translation, post translational processing, altered stability, and altered protein degradation), as well as local overexpression due to altered protein traffic patterns (increased nuclear localization), and augmented functional activity, e.g., as in an increased enzyme hydrolysis of substrate. Thus, overexpression refers to either protein or RNA levels. Overexpression can also be by 50%, 60%, 70%, 80%, 90% or more in comparison to a normal cell or comparison cell. In certain embodiments, the anti-B7-H3 antibodies or ADCs of the invention are used to treat solid tumors likely to overexpress B7-H3.

The term "gene amplification", as used herein, refers to a cellular process characterized by the production of multiple copies of any particular piece of DNA. For example, a tumor cell may amplify, or copy, chromosomal segments as a result of cell signals and sometimes environmental events. The process of gene amplification leads to the production of additional copies of the gene. In one embodiment, the gene is B7-H3, i.e., "B7-H3 amplification." In one embodiment, the compositions and methods disclosed herein are used to treat a subject having B7-H3 amplified cancer.

The term "administering" as used herein is meant to refer to the delivery of a substance (e.g., an anti-B7-H3 antibody or ADC) to achieve a therapeutic objective (e.g., the treatment of a B7-H3-associated disorder). Modes of administration may be parenteral, enteral and topical. Parenteral administration is usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The term "combination therapy" or "combination" in the context of a therapeutic method (e.g., a treatment method), as used herein, refers to the administration of two or more therapeutic substances, e.g., an anti-B7-H3 antibody or ADC and an additional therapeutic agent. The additional therapeutic agent may be administered concomitant with, prior to, or following the administration of the anti-B7-H3 antibody or ADC.

As used herein, the term "effective amount" or "therapeutically effective amount" refers to the amount of a drug, e.g., an antibody or ADC, which is sufficient to reduce or ameliorate the severity and/or duration of a disorder, e.g., cancer, or one or more symptoms thereof, prevent the advancement of a disorder, cause regression of a disorder, prevent the recurrence, development, onset or progression of one or more symptoms associated with a disorder, detect a disorder, or enhance or improve the prophylactic or therapeutic effect(s) of another therapy (e.g., prophylactic or therapeutic agent). The effective amount of an antibody or ADC may, for example, inhibit tumor growth (e.g., inhibit an increase in tumor volume), decrease tumor growth (e.g., decrease tumor volume), reduce the number of cancer cells, and/or relieve to some extent one or more of the symptoms associated with the cancer. The effective amount may, for example, improve disease free survival (DFS), improve overall survival (OS), or decrease likelihood of recurrence.

Various chemical substituents are defined below. In some instances, the number of carbon atoms in a substituent (e.g., alkyl, alkanyl, alkenyl, alkynyl, cycloalkyl, heterocyclyl, heteroaryl, and aryl) is indicated by the prefix "$C_x$-$C_y$," or "$C_{x-y}$," wherein x is the minimum and y is the maximum number of carbon atoms. Thus, for example, "$C_1$-$C_6$ alkyl" refers to an alkyl containing from 1 to 6 carbon atoms. Illustrating further, "$C_3$-$C_8$ cycloalkyl" means a saturated hydrocarbyl ring containing from 3 to 8 carbon ring atoms. If a substituent is described as being "substituted," a hydrogen atom on a carbon or nitrogen is replaced with a non-hydrogen group. For example, a substituted alkyl substituent is an alkyl substituent in which at least one hydrogen atom on the alkyl is replaced with a non-hydrogen group. To illustrate, monofluoroalkyl is alkyl substituted with a fluoro radical, and difluoroalkyl is alkyl substituted with two fluoro radicals. It should be recognized that if there is more than one substitution on a substituent, each substitution may be identical or different (unless otherwise stated). If a substituent is described as being "optionally substituted", the substituent may be either (1) not substituted or (2) substituted. Possible substituents include, but are not limited to, $C_1$-$C_6$ alkyl, $C_2$-$C_6$ alkenyl, $C_2$-$C_6$ alkynyl, aryl, cycloalkyl, heterocyclyl, heteroaryl, halogen, $C_1$-$C_6$ haloalkyl, oxo, —CN, $NO_2$, —$OR^{xa}$, —$OC(O)R^{xz}$, —$OC(O)N(R^{xa})_2$, —$SR^{xa}$, —$S(O)_2R^{xa}$, —$S(O)_2N(R^{xa})_2$, —$C(O)R^{xa}$, —$C(O)OR^{xa}$, —$C(O)N(R^{xa})_2$, —$C(O)N(R^{xa})S(O)_2R^{xz}$, —$N(R^{xa})_2$, —$N(R^{xa})C(O)R^{xz}$, —$N(R^{xa})S(O)_2R^{xz}$, —$N(R^{xa})C(O)O(R^{xz})$, —$N(R^{xa})C(O)N(R^{xa})_2$, —$N(R^{xa})S(O)_2N(R^{xa})_2$, —($C_1$-$C_6$ alkylenyl)-CN, —($C_1$-$C_6$ alkylenyl)-$OR^{xa}$, —($C_1$-$C_6$ alkylenyl)-OC(O)$R^{xz}$, —($C_1$-$C_6$ alkylenyl)-OC(O)N($R^{xa}$)$_2$, —($C_1$-$C_6$ alkylenyl)-$SR^{xa}$, —($C_1$-$C_6$ alkylenyl)-S(O)$_2R^{xa}$, —($C_1$-$C_6$ alkylenyl)-S(O)$_2$N($R^a$)$_2$, —($C_1$-$C_6$ alkylenyl)-C(O)$R^{xa}$, —($C_1$-$C_6$ alkylenyl)-C(O)O$R^{xa}$, —($C_1$-$C_6$ alkylenyl)-C(O)N($R^{xa}$)$_2$, —($C_1$-$C_6$ alkylenyl)-C(O)N($R^{xa}$)S(O)$_2R^{xz}$, —($C_1$-$C_6$ alkylenyl)-N($R^a$)$_2$, —($C_1$-$C_6$ alkylenyl)-N($R^{xa}$)C(O)$R^z$, —($C_1$-$C_6$ alkylenyl)-N($R^{xa}$)S(O)$_2R^{xz}$, —($C_1$-$C_6$ alkylenyl)-N($R^{xa}$)C(O)O($R^z$), —($C_1$-$C_6$ alkylenyl)-N($R^{xa}$)C(O)N($R^{xa}$)$_2$, or —($C_1$-$C_6$ alkylenyl)-N($R^{xa}$)S(O)$_2$N($R^{xa}$)$_2$; wherein $R^{xa}$, at each occurrence, is independently hydrogen, aryl, cycloalkyl, heterocyclyl, heteroaryl, $C_1$-$C_6$ alkyl, or $C_1$-$C_6$ haloalkyl; and $R^{xz}$, at each occurrence, is independently aryl, cycloalkyl, heterocyclyl, heteroaryl, $C_1$-$C_6$ alkyl or $C_1$-$C_6$ haloalkyl.

Various ADCs, synthons and Bcl-xL inhibitors comprising the ADCs and/or synthons are described in some embodiments herein by reference to structural formulae including substituents. It is to be understood that the various groups comprising substituents may be combined as valence and stability permit. Combinations of substituents and variables envisioned by this disclosure are only those that result in the formation of stable compounds. As used herein, the term "stable" refers to compounds that possess stability sufficient to allow manufacture and that maintain the integrity of the compound for a sufficient period of time to be useful for the purpose detailed herein.

As used herein, the following terms are intended to have the following meanings:

The term "alkoxy" refers to a group of the formula —$OR^{xa}$, where $R^{xa}$ is an alkyl group. Representative alkoxy groups include methoxy, ethoxy, propoxy, tert-butoxy and the like.

The term "alkoxyalkyl" refers to an alkyl group substituted with an alkoxy group and may be represented by the general formula —$R^bOR^{xa}$ where $R^b$ is an alkylene group and $R^{xa}$ is an alkyl group.

The term "alkyl" by itself or as part of another substituent refers to a saturated or unsaturated branched, straight-chain or cyclic monovalent hydrocarbon radical that is derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl, cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. Where specific levels of saturation are intended, the nomenclature "alkanyl," "alkenyl" and/or "alkynyl" are used, as defined below. The term "lower alkyl" refers to alkyl groups with 1 to 6 carbons.

The term "alkanyl" by itself or as part of another substituent refers to a saturated branched, straight-chain or cyclic alkyl derived by the removal of one hydrogen atom from a single carbon atom of a parent alkane. Typical alkanyl groups include, but are not limited to, methyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

The term "alkenyl" by itself or as part of another substituent refers to an unsaturated branched, straight-chain or cyclic alkyl having at least one carbon-carbon double bond derived by the removal of one hydrogen atom from a single carbon atom of a parent alkene. Typical alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

The term "alkynyl" by itself or as part of another substituent refers to an unsaturated branched, straight-chain or cyclic alkyl having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

The term "alkylamine" refers to a group of the formula —$NHR^{xa}$ and "dialkylamine" refers to a group of the formula —$NR^aR^{xa}$, where each $R^{xa}$ is, independently of the others, an alkyl group.

The term "alkylene" refers to an alkane, alkene or alkyne group having two terminal monovalent radical centers derived by the removal of one hydrogen atom from each of the two terminal carbon atoms. Typical alkylene groups include, but are not limited to, methylene; and saturated or unsaturated ethylene; propylene; butylene; and the like. The term "lower alkylene" refers to alkylene groups with 1 to 6 carbons.

The term "heteroalkylene" refers to a divalent alkylene having one or more —$CH_2$— groups replaced with a thio, oxy, or —$NR^{x3}$— where $R^{x3}$ is selected from hydrogen, lower alkyl and lower heteroalkyl. The heteroalkylene can be linear, branched, cyclic, bicyclic, or a combination thereof and can include up to 10 carbon atoms and up to 4 heteroatoms. The term "lower heteroalkylene" refers to alkylene groups with 1 to 4 carbon atoms and 1 to 3 heteroatoms.

The term "aryl" means an aromatic carbocyclyl containing from 6 to 14 carbon ring atoms. An aryl may be monocyclic or polycyclic (i.e., may contain more than one ring). In the case of polycyclic aromatic rings, only one ring the polycyclic system is required to be aromatic while the remaining ring(s) may be saturated, partially saturated or unsaturated. Examples of aryls include phenyl, naphthalenyl, indenyl, indanyl, and tetrahydronaphthyl.

The term "arylene" refers to an aryl group having two monovalent radical centers derived by the removal of one hydrogen atom from each of the two ring carbons. An exemplary arylene group is a phenylene.

An alkyl group may be substituted by a "carbonyl" which means that two hydrogen atoms from a single alkanylene carbon atom are removed and replaced with a double bond to an oxygen atom.

The prefix "halo" indicates that the substituent which includes the prefix is substituted with one or more independently selected halogen radicals. For example, haloalkyl means an alkyl substituent in which at least one hydrogen radical is replaced with a halogen radical. Typical halogen radicals include chloro, fluoro, bromo and iodo. Examples of haloalkyls include chloromethyl, 1-bromoethyl, fluoromethyl, difluoromethyl, trifluoromethyl, and 1,1,1-trifluoroethyl. It should be recognized that if a substituent is substituted by more than one halogen radical, those halogen radicals may be identical or different (unless otherwise stated).

The term "haloalkoxy" refers to a group of the formula —$OR^c$, where $R^c$ is a haloalkyl.

The terms "heteroalkyl," "heteroalkanyl," "heteroalkenyl," "heteroalkynyl," and "heteroalkylene" refer to alkyl, alkanyl, alkenyl, alkynyl, and alkylene groups, respectively, in which one or more of the carbon atoms, e.g., 1, 2 or 3 carbon atoms, are each independently replaced with the same or different heteroatoms or heteroatomic groups. Typical heteroatoms and/or heteroatomic groups which can replace the carbon atoms include, but are not limited to, —O—, —S—, —S—O—, —$NR^c$—, —PH, —S(O)—, —$S(O)_2$—, —$S(O)NR^c$—, —$S(O)_2NR^c$—, and the like, including combinations thereof, where each $R^c$ is independently hydrogen or $C_1$-$C_6$ alkyl. The term "lower heteroalkyl" refers to between 1 and 4 carbon atoms and between 1 and 3 heteroatoms.

The terms "cycloalkyl" and "heterocyclyl" refer to cyclic versions of "alkyl" and "heteroalkyl" groups, respectively. For heterocyclyl groups, a heteroatom can occupy the position that is attached to the remainder of the molecule. A cycloalkyl or heterocyclyl ring may be a single-ring (monocyclic) or have two or more rings (bicyclic or polycyclic).

Monocyclic cycloalkyl and heterocyclyl groups will typically contains from 3 to 7 ring atoms, more typically from 3 to 6 ring atoms, and even more typically 5 to 6 ring atoms. Examples of cycloalkyl groups include, but are not limited to, cyclopropyl; cyclobutyls such as cyclobutanyl and cyclobutenyl; cyclopentyls such as cyclopentanyl and cyclopentenyl; cyclohexyls such as cyclohexanyl and cyclohexenyl; and the like. Examples of monocyclic heterocyclyls include, but are not limited to, oxetane, furanyl, dihydrofuranyl, tetrahydrofuranyl, tetrahydropyranyl, thiophenyl (thiofuranyl), dihydrothiophenyl, tetrahydrothiophenyl, pyrrolyl, pyrrolinyl, pyrrolidinyl, imidazolyl, imidazolinyl, imidazolidinyl, pyrazolyl, pyrazolinyl, pyrazolidinyl, triazolyl, tetrazolyl, oxazolyl, oxazolidinyl, isoxazolidinyl, isoxazolyl, thiazolyl, isothiazolyl, thiazolinyl, isothiazolinyl, thiazolidinyl, isothiazolidinyl, thiodiazolyl, oxadiazolyl (including 1,2,3-oxadiazolyl, 1,2,4-oxadiazolyl, 1,2,5-oxadiazolyl (furazanyl), or 1,3,4-oxadiazolyl), oxatriazolyl (including 1,2,3,4-oxatriazolyl or 1,2,3,5-oxatriazolyl), dioxazolyl (including 1,2,3-dioxazolyl, 1,2,4-dioxazolyl, 1,3,2-dioxazolyl, or 1,3,4-dioxazolyl), 1,4-dioxanyl, dioxothiomorpholinyl, oxathiazolyl, oxathiolyl, oxathiolanyl, pyranyl, dihydropyranyl, thiopyranyl, tetrahydrothiopyranyl, pyridinyl (azinyl), piperidinyl, diazinyl (including pyridazinyl (1,2-diazinyl), pyrimidinyl (1,3-diazinyl), or pyrazinyl (1,4-diazinyl)), piperazinyl, triazinyl (including 1,3,5-triazinyl, 1,2,4-triazinyl, and 1,2,3-triazinyl)), oxazinyl (including 1,2-oxazinyl, 1,3-oxazinyl, or 1,4-oxazinyl)), oxathiazinyl (including 1,2,3-oxathiazinyl, 1,2,4-oxathiazinyl, 1,2,5-oxathiazinyl, or 1,2,6-oxathiazinyl)), oxadiazinyl (including 1,2,3-oxadiazinyl, 1,2,4-oxadiazinyl, 1,4,2-oxadiazinyl, or 1,3,5-oxadiazinyl)), morpholinyl, azepinyl, oxepinyl, thiepinyl, diazepinyl, pyridonyl (including pyrid-2(1H)-onyl and pyrid-4(1H)-onyl), furan-2(5H)-onyl, pyrimidonyl (including pyramid-2(1H)-onyl and pyramid-4(3H)-onyl), oxazol-2(3H)-onyl, 1H-imidazol-2(3H)-onyl, pyridazin-3(2H)-onyl, and pyrazin-2(1H)-onyl.

Polycyclic cycloalkyl and heterocyclyl groups contain more than one ring, and bicyclic cycloalkyl and heterocyclyl groups contain two rings. The rings may be in a bridged, fused or spiro orientation. Polycyclic cycloalkyl and heterocyclyl groups may include combinations of bridged, fused and/or spiro rings. In a spirocyclic cycloalkyl or heterocyclyl, one atom is common to two different rings. An example of a spirocycloalkyl is spiro[4.5]decane and an example of a spiroheterocyclyls is a spiropyrazoline.

In a bridged cycloalkyl or heterocyclyl, the rings share at least two common non-adjacent atoms. Examples of bridged cycloalkyls include, but are not limited to, adamantyl and norbornanyl rings. Examples of bridged heterocyclyls include, but are not limited to, 2-oxatricyclo[3.3.1.1$^{3,7}$]decanyl.

In a fused-ring cycloalkyl or heterocyclyl, two or more rings are fused together, such that two rings share one common bond. Examples of fused-ring cycloalkyls include decalin, naphthylene, tetralin, and anthracene. Examples of fused-ring heterocyclyls containing two or three rings include imidazopyrazinyl (including imidazo[1,2-a]pyrazinyl), imidazopyridinyl (including imidazo[1,2-a]pyridinyl), imidazopyridazinyl (including imidazo[1,2-b]pyridazinyl), thiazolopyridinyl (including thiazolo[5,4-c]pyridinyl, thiazolo[5,4-b]pyridinyl, thiazolo[4,5-b]pyridinyl, and thiazolo[4,5-c]pyridinyl), indolizinyl, pyranopyrrolyl, 4H-quinolizinyl, purinyl, naphthyridinyl, pyridopyridinyl (including pyrido[3,4-b]-pyridinyl, pyrido[3,2-b]-pyridinyl, or pyrido[4,3-b]-pyridinyl), and pteridinyl. Other examples of fused-ring heterocyclyls include benzo-fused heterocyclyls, such as dihydrochromenyl, tetrahydroisoquinolinyl, indolyl, isoindolyl (isobenzazolyl, pseudoisoindolyl), indoleninyl (pseudoindolyl), isoindazolyl (benzpyrazolyl), benzazinyl (including quinolinyl (1-benzazinyl) or isoquinolinyl (2-benzazinyl)), phthalazinyl, quinoxalinyl, quinazolinyl, benzodiazinyl (including cinnolinyl (1,2-benzodiazinyl) or quinazolinyl (1,3-benzodiazinyl)), benzopyranyl (including chromanyl or isochromanyl), benzoxazinyl (including 1,3,2-benzoxazinyl, 1,4,2-benzoxazinyl, 2,3,1-benzoxazinyl, or 3,1,4-benzoxazinyl), benzo[d]thiazolyl, and benzisoxazinyl (including 1,2-benzisoxazinyl or 1,4-benzisoxazinyl).

The term "cycloalkylene" refers to a cycloalkyl group having two monovalent radical centers derived by the removal of one hydrogen atom from each of two ring carbons. Exemplary cycloalkylene groups include:

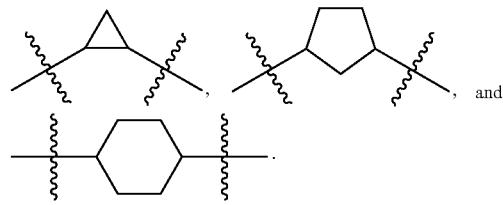

The term "heteroaryl" refers to an aromatic heterocyclyl containing from 5 to 14 ring atoms. A heteroaryl may be a single ring or 2 or 3 fused rings. Examples of heteroaryls include 6-membered rings such as pyridyl, pyrazyl, pyrimidinyl, pyridazinyl, and 1,3,5-, 1,2,4- or 1,2,3-triazinyl; 5-membered ring substituents such as triazolyl, pyrrolyl, imidazyl, furanyl, thiophenyl, pyrazolyl, oxazolyl, isoxazolyl, thiazolyl, 1,2,3-, 1,2,4-, 1,2,5-, or 1,3,4-oxadiazolyl and isothiazolyl; 6/5-membered fused ring substituents such as imidazopyrazinyl (including imidazo[1,2-a]pyrazinyl) imidazopyridinyl (including imidazo[1,2-a]pyridinyl), imidazopyridazinyl (including imidazo[1,2-b]pyridazinyl), thiazolopyridinyl (including thiazolo[5,4-c]pyridinyl, thiazolo[5,4-b]pyridinyl, thiazolo[4,5-b]pyridinyl, and thiazolo[4,5-c]pyridinyl), benzo[d]thiazolyl, benzothiofuranyl, benzisoxazolyl, benzoxazolyl, purinyl, and anthranilyl; and 6/6-membered fused rings such as benzopyranyl, quinolinyl, isoquinolinyl, cinnolinyl, quinazolinyl, and benzoxazinyl. Heteroaryls may also be heterocycles having aromatic (4N+2 pi electron) resonance contributors such as pyridonyl (including pyrid-2(1H)-onyl and pyrid-4(1H)-onyl), pyrimidonyl (including pyramid-2(1H)-onyl and pyramid-4(3H)-onyl), pyridazin-3(2H)-onyl and pyrazin-2(1H)-onyl.

The term "sulfonate" as used herein means a salt or ester of a sulfonic acid.

The term "methyl sulfonate" as used herein means a methyl ester of a sulfonic acid group.

The term "carboxylate" as used herein means a salt or ester of a carboxylic acid.

The term "polyol", as used herein, means a group containing more than two hydroxyl groups independently or as a portion of a monomer unit. Polyols include, but are not limited to, reduced $C_2$-$C_6$ carbohydrates, ethylene glycol, and glycerin.

The term "sugar" when used in context of "$G^1$" includes O-glycoside, N-glycoside, S-glycoside and C-glycoside (C-glycoslyl) carbohydrate derivatives of the monosaccharide and disaccharide classes and may originate from naturally-occurring sources or may be synthetic in origin.

For example "sugar" when used in context of "$G^1$" includes derivatives such as but not limited to those derived from glucuronic acid, galacturonic acid, galactose, and glucose among others. Suitable sugar substitutions include but are not limited to hydroxyl, amine, carboxylic acid, sulfonic acid, phosphonic acid, esters, and ethers.

The term "NHS ester" means the N-hydroxysuccinimide ester derivative of a carboxylic acid.

The term "amine" includes primary, secondary and tertiary aliphatic amines, including cyclic versions.

The term salt when used in context of "or salt thereof" include salts commonly used to form alkali metal salts and to form addition salts of free acids or free bases. In general, these salts typically may be prepared by conventional means by reacting, for example, the appropriate acid or base with a compound of the invention Where a salt is intended to be administered to a patient (as opposed to, for example, being in use in an in vitro context), the salt preferably is pharmaceutically acceptable and/or physiologically compatible. The term "pharmaceutically acceptable" is used adjectivally in this patent application to mean that the modified noun is appropriate for use as a pharmaceutical product or as a part of a pharmaceutical product. The term "pharmaceutically acceptable salt" includes salts commonly used to form alkali metal salts and to form addition salts of free acids or free bases. In general, these salts typically may be prepared by conventional means by reacting, for example, the appropriate acid or base with a compound of the invention.

Various aspects of the invention are described in further detail in the following subsections.

II. Anti-B7-H3 Antibodies

One aspect of the invention provides anti-B7-H3 antibodies, or antigen binding portions thereof. In one embodiment, the present invention provides chimeric anti-B7-H3 antibodies, or antigen binding portions thereof. In yet another embodiment, the present invention provides humanized anti-B7-H3 antibodies, or antigen binding portions thereof. In another aspect, the invention features antibody drug conjugates (ADCs) comprising an anti-B7-H3 antibody described herein and at least one drug(s), such as, but not limited to, a Bcl-xL inhibitor or an auristatin. The antibodies or ADCs of the invention have characteristics including, but not limited to, binding to wild-type human B7-H3 in vitro, binding to wild-type human B7-H3 on tumor cells expressing B7-H3, and decreasing or inhibiting xenograft tumor growth in a mouse model.

One aspect of the invention features an anti-human B7-H3 (anti-hB7-H3) Antibody Drug Conjugate (ADC) comprising an anti-hB7-H3 antibody conjugated to a drug via a linker, wherein the drug is a Bcl-xL inhibitor. Exemplary anti-B7-H3 antibodies (and sequences thereof) that can be used in the ADCs are described herein.

The anti-B7-H3 antibodies described herein provide the ADCs of the invention with the ability to bind to B7-H3 such that the cytotoxic Bcl-xL drug attached to the antibody may be delivered to the B7-H3-expressing cell, particularly a B7-H3 expressing cancer cell.

While the term "antibody" is used throughout, it should be noted that antibody fragments (i.e., antigen-binding portions of an anti-B7-H3antibody) are also included in the invention and may be included in the embodiments (methods and compositions) described throughout. For example, an anti-B7-H3antibody fragment may be conjugated to the Bcl-xL inhibitors described herein. Thus, it is within the scope of the invention that in certain embodiments, antibody fragments of the anti-B7-H3antibodies described herein are conjugated to Bcl-xL inhibitors (including those described below in Section III.A) via linkers (including those described below in Section III.A). In certain embodiments, the anti-B7-H3 antibody binding portion is a Fab, a Fab', a F(ab')2, a Fv, a disulfide linked Fv, an scFv, a single domain antibody, or a diabody.

II.A. Anti-B7-H3 Chimeric Antibodies

A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, Science 229:1202 (1985); Oi et al., BioTechniques 4:214 (1986); Gillies et al., (1989) J. Immunol. Methods 125:191-202; U.S. Pat. Nos. 5,807,715; 4,816,567; and 4,816,397, which are incorporated herein by reference in their entireties. In addition, techniques developed for the production of "chimeric antibodies" (Morrison et al., 1984, Proc. Natl. Acad. Sci. 81:851-855; Neuberger et al., 1984, Nature 312:604-608; Takeda et al., 1985, Nature 314:452-454, each of which are incorporated herein by reference in their entireties) by splicing genes from a mouse antibody molecule of appropriate antigen specificity together with genes from a human antibody molecule of appropriate biological activity can be used.

As described in Example 3, eighteen anti-B7-H3 murine antibodies were identified having high specific binding activity against human and cynomolgus B7-H3. Chimeric antibodies, in the context of a human immunoglobulin constant region, were generated from these eighteen antibodies.

Thus, in one aspect, the present invention is directed to an anti-B7-H3 antibody, or antigen-binding portion thereof, having a heavy chain variable region including an amino acid sequence set forth in SEQ ID NOs: 1, 9, 16, 24, 32, 40, 48, 56, 64, 72, 80, 87, 95, 101, or 108; and/or a light chain variable region including an amino acid sequence set forth in SEQ ID NOs: 5, 13, 20, 28, 36, 44, 52, 60, 68, 76, 84, 91, 98, 105, or 112.

In another aspect, the present invention is directed to an anti-B7-H3 antibody, or antigen-binding portion thereof, having a heavy chain variable region including an amino acid sequence as set forth in SEQ ID NO: 1, and a light chain variable region including an amino acid sequence set forth in SEQ ID NO: 5.

In another aspect, the present invention is directed to an anti-B7-H3 antibody, or antigen-binding portion thereof, having a heavy chain variable domain region including (a) a CDR1 having an amino acid sequence as set forth in SEQ ID NO: 2; (b) a CDR2 having an amino acid sequence as set forth in SEQ ID NO: 3; and (c) a CDR3 having an amino acid sequence as set forth in SEQ ID NO: 4; and a light chain variable region including (a) a CDR1 having an amino acid sequence as set forth in SEQ ID NO: 6; (b) a CDR2 having an amino acid sequence as set forth in SEQ ID NO: 7; and (c) a CDR3 having an amino acid sequence as set forth in SEQ ID NO: 8.

In another aspect, the present invention is directed to an anti-B7-H3 antibody, or antigen-binding portion thereof, having a heavy chain variable region including an amino acid sequence as set forth in SEQ ID NO: 9, and a light chain variable region including an amino acid sequence set forth in SEQ ID NO: 13.

In another aspect, the present invention is directed to an anti-B7-H3 antibody, or antigen-binding portion thereof, having a heavy chain variable domain region including (a) a CDR1 having an amino acid sequence as set forth in SEQ ID NO: 10; (b) a CDR2 having an amino acid sequence as set forth in SEQ ID NO: 11; and (c) a CDR3 having an amino acid sequence as set forth in SEQ ID NO: 12; and a light chain variable region including (a) a CDR1 having an amino acid sequence as set forth in SEQ ID NO: 14 (b) a CDR2 having an amino acid sequence as set forth in SEQ ID NO: 7; and (c) a CDR3 having an amino acid sequence as set forth in SEQ ID NO: 15.

In another aspect, the present invention is directed to an anti-B7-H3 antibody, or antigen-binding portion thereof, having a heavy chain variable region including an amino acid sequence as set forth in SEQ ID NO: 16, and a light chain variable region including an amino acid sequence set forth in SEQ ID NO: 20.

In another aspect, the present invention is directed to an anti-B7-H3 antibody, or antigen-binding portion thereof, having a heavy chain variable domain region including (a) a CDR1 having an amino acid sequence as set forth in SEQ ID NO: 17; (b) a CDR2 having an amino acid sequence as set forth in SEQ ID NO: 18; and (c) a CDR3 having an amino acid sequence as set forth in SEQ ID NO: 19; and a light chain variable region including (a) a CDR1 having an amino acid sequence as set forth in SEQ ID NO: 21; (b) a CDR2 having an amino acid sequence as set forth in SEQ ID NO: 22; and (c) a CDR3 having an amino acid sequence as set forth in SEQ ID NO: 23.

In another aspect, the present invention is directed to an anti-B7-H3 antibody, or antigen-binding portion thereof, having a heavy chain variable region including an amino acid sequence as set forth in SEQ ID NO: 24, and a light chain variable region including an amino acid sequence set forth in SEQ ID NO: 28.

In another aspect, the present invention is directed to an anti-B7-H3 antibody, or antigen-binding portion thereof, having a heavy chain variable domain region including (a) a CDR1 having an amino acid sequence as set forth in SEQ ID NO: 25; (b) a CDR2 having an amino acid sequence as set forth in SEQ ID NO: 26; and (c) a CDR3 having an amino acid sequence as set forth in SEQ ID NO: 27; and a light chain variable region including (a) a CDR1 having an amino acid sequence as set forth in SEQ ID NO: 29; (b) a CDR2 having an amino acid sequence as set forth in SEQ ID NO: 30; and (c) a CDR3 having an amino acid sequence as set forth in SEQ ID NO: 31.

In another aspect, the present invention is directed to an anti-B7-H3 antibody, or antigen-binding portion thereof, having a heavy chain variable region including an amino acid sequence as set forth in SEQ ID NO: 32, and a light chain variable region including an amino acid sequence set forth in SEQ ID NO: 36.

In another aspect, the present invention is directed to an anti-B7-H3 antibody, or antigen-binding portion thereof, having a heavy chain variable domain region including (a) a CDR1 having an amino acid sequence as set forth in SEQ ID NO: 33; (b) a CDR2 having an amino acid sequence as set forth in SEQ ID NO: 34; and (c) a CDR3 having an amino acid sequence as set forth in SEQ ID NO: 35; and a light chain variable region including (a) a CDR1 having an amino acid sequence as set forth in SEQ ID NO: 37; (b) a CDR2 having an amino acid sequence as set forth in SEQ ID NO: 38; and (c) a CDR3 having an amino acid sequence as set forth in SEQ ID NO: 182.

In another aspect, the present invention is directed to an anti-B7-H3 antibody, or antigen-binding portion thereof, having a heavy chain variable region including an amino acid sequence as set forth in SEQ ID NO: 40, and a light chain variable region including an amino acid sequence set forth in SEQ ID NO: 44.

In another aspect, the present invention is directed to an anti-B7-H3 antibody, or antigen-binding portion thereof, having a heavy chain variable domain region including (a) a CDR1 having an amino acid sequence as set forth in SEQ ID NO: 41; (b) a CDR2 having an amino acid sequence as set forth in SEQ ID NO: 42; and (c) a CDR3 having an amino acid sequence as set forth in SEQ ID NO: 43; and a light chain variable region including (a) a CDR1 having an amino acid sequence as set forth in SEQ ID NO: 45; (b) a CDR2 having an amino acid sequence as set forth in SEQ ID NO: 46; and (c) a CDR3 having an amino acid sequence as set forth in SEQ ID NO: 47.

In another aspect, the present invention is directed to an anti-B7-H3 antibody, or antigen-binding portion thereof, having a heavy chain variable region including an amino acid sequence as set forth in SEQ ID NO: 48, and a light chain variable region including an amino acid sequence set forth in SEQ ID NO: 52.

In another aspect, the present invention is directed to an anti-B7-H3 antibody, or antigen-binding portion thereof, having a heavy chain variable domain region including (a) a CDR1 having an amino acid sequence as set forth in SEQ ID NO: 49; (b) a CDR2 having an amino acid sequence as set forth in SEQ ID NO: 50; and (c) a CDR3 having an amino acid sequence as set forth in SEQ ID NO: 51; and a light chain variable region including (a) a CDR1 having an amino acid sequence as set forth in SEQ ID NO: 53; (b) a CDR2 having an amino acid sequence as set forth in SEQ ID NO: 54; and (c) a CDR3 having an amino acid sequence as set forth in SEQ ID NO: 55.

In another aspect, the present invention is directed to an anti-B7-H3 antibody, or antigen-binding portion thereof, having a heavy chain variable region including an amino acid sequence as set forth in SEQ ID NO: 56, and a light chain variable region including an amino acid sequence set forth in SEQ ID NO: 60.

In another aspect, the present invention is directed to an anti-B7-H3 antibody, or antigen-binding portion thereof, having a heavy chain variable domain region including (a) a CDR1 having an amino acid sequence as set forth in SEQ ID NO: 57; (b) a CDR2 having an amino acid sequence as set forth in SEQ ID NO: 58; and (c) a CDR3 having an amino acid sequence as set forth in SEQ ID NO: 59; and a light chain variable region including (a) a CDR1 having an amino acid sequence as set forth in SEQ ID NO: 61; (b) a CDR2 having an amino acid sequence as set forth in SEQ ID NO: 62; and (c) a CDR3 having an amino acid sequence as set forth in SEQ ID NO: 63.

In another aspect, the present invention is directed to an anti-B7-H3 antibody, or antigen-binding portion thereof, having a heavy chain variable region including an amino acid sequence as set forth in SEQ ID NO: 64, and a light chain variable region including an amino acid sequence set forth in SEQ ID NO: 68.

In another aspect, the present invention is directed to an anti-B7-H3 antibody, or antigen-binding portion thereof, having a heavy chain variable domain region including (a) a CDR1 having an amino acid sequence as set forth in SEQ ID NO: 65; (b) a CDR2 having an amino acid sequence as set forth in SEQ ID NO: 66; and (c) a CDR3 having an amino acid sequence as set forth in SEQ ID NO: 67; and a light chain variable region including (a) a CDR1 having an amino acid sequence as set forth in SEQ ID NO: 69; (b) a CDR2 having an amino acid sequence as set forth in SEQ ID NO: 70; and (c) a CDR3 having an amino acid sequence as set forth in SEQ ID NO: 71.

In another aspect, the present invention is directed to an anti-B7-H3 antibody, or antigen-binding portion thereof, having a heavy chain variable region including an amino acid sequence as set forth in SEQ ID NO: 72, and a light chain variable region including an amino acid sequence set forth in SEQ ID NO: 76.

In another aspect, the present invention is directed to an anti-B7-H3 antibody, or antigen-binding portion thereof, having a heavy chain variable domain region including (a) a CDR1 having an amino acid sequence as set forth in SEQ ID NO: 73; (b) a CDR2 having an amino acid sequence as set forth in SEQ ID NO: 74; and (c) a CDR3 having an amino acid sequence as set forth in SEQ ID NO: 75; and a light chain variable region including (a) a CDR1 having an amino acid sequence as set forth in SEQ ID NO: 77; (b) a CDR2 having an amino acid sequence as set forth in SEQ ID NO: 78; and (c) a CDR3 having an amino acid sequence as set forth in SEQ ID NO: 79.

In another aspect, the present invention is directed to an anti-B7-H3 antibody, or antigen-binding portion thereof, having a heavy chain variable region including an amino acid sequence as set forth in SEQ ID NO: 80, and a light chain variable region including an amino acid sequence set forth in SEQ ID NO: 84.

In another aspect, the present invention is directed to an anti-B7-H3 antibody, or antigen-binding portion thereof, having a heavy chain variable domain region including (a) a CDR1 having an amino acid sequence as set forth in SEQ ID NO: 81; (b) a CDR2 having an amino acid sequence as set forth in SEQ ID NO: 82; and (c) a CDR3 having an amino acid sequence as set forth in SEQ ID NO: 83; and a light chain variable region including (a) a CDR1 having an amino acid sequence as set forth in SEQ ID NO: 85; (b) a CDR2 having an amino acid sequence as set forth in SEQ ID NO: 7; and (c) a CDR3 having an amino acid sequence as set forth in SEQ ID NO: 86.

In another aspect, the present invention is directed to an anti-B7-H3 antibody, or antigen-binding portion thereof, having a heavy chain variable region including an amino acid sequence as set forth in SEQ ID NO: 87, and a light chain variable region including an amino acid sequence set forth in SEQ ID NO: 91.

In another aspect, the present invention is directed to an anti-B7-H3 antibody, or antigen-binding portion thereof, having a heavy chain variable domain region including (a) a CDR1 having an amino acid sequence as set forth in SEQ ID NO: 88; (b) a CDR2 having an amino acid sequence as set forth in SEQ ID NO: 89; and (c) a CDR3 having an amino acid sequence as set forth in SEQ ID NO: 90; and a light chain variable region including (a) a CDR1 having an amino acid sequence as set forth in SEQ ID NO: 92; (b) a CDR2 having an amino acid sequence as set forth in SEQ ID NO: 93; and (c) a CDR3 having an amino acid sequence as set forth in SEQ ID NO: 94.

In another aspect, the present invention is directed to an anti-B7-H3 antibody, or antigen-binding portion thereof, having a heavy chain variable region including an amino acid sequence as set forth in SEQ ID NO: 95, and a light chain variable region including an amino acid sequence set forth in SEQ ID NO: 98.

In another aspect, the present invention is directed to an anti-B7-H3 antibody, or antigen-binding portion thereof, having a heavy chain variable domain region including (a) a CDR1 having an amino acid sequence as set forth in SEQ ID NO: 49; (b) a CDR2 having an amino acid sequence as set forth in SEQ ID NO: 96; and (c) a CDR3 having an amino acid sequence as set forth in SEQ ID NO: 97; and a light chain variable region including (a) a CDR1 having an amino acid sequence as set forth in SEQ ID NO: 99; (b) a CDR2 having an amino acid sequence as set forth in SEQ ID NO: 93; and (c) a CDR3 having an amino acid sequence as set forth in SEQ ID NO: 100.

In another aspect, the present invention is directed to an anti-B7-H3 antibody, or antigen-binding portion thereof, having a heavy chain variable region including an amino acid sequence as set forth in SEQ ID NO: 101, and a light chain variable region including an amino acid sequence set forth in SEQ ID NO: 105.

In another aspect, the present invention is directed to an anti-B7-H3 antibody, or antigen-binding portion thereof, having a heavy chain variable domain region including (a) a CDR1 having an amino acid sequence as set forth in SEQ ID NO: 102; (b) a CDR2 having an amino acid sequence as set forth in SEQ ID NO: 103; and (c) a CDR3 having an amino acid sequence as set forth in SEQ ID NO: 104; and a light chain variable region including (a) a CDR1 having an amino acid sequence as set forth in SEQ ID NO: 106; (b) a CDR2 having an amino acid sequence as set forth in SEQ ID NO: 46; and (c) a CDR3 having an amino acid sequence as set forth in SEQ ID NO: 107.

In another aspect, the present invention is directed to an anti-B7-H3 antibody, or antigen-binding portion thereof, having a heavy chain variable region including an amino acid sequence as set forth in SEQ ID NO: 108, and a light chain variable region including an amino acid sequence set forth in SEQ ID NO: 112.

In another aspect, the present invention is directed to an anti-B7-H3 antibody, or antigen-binding portion thereof, having a heavy chain variable domain region including (a) a CDR1 having an amino acid sequence as set forth in SEQ ID NO: 109; (b) a CDR2 having an amino acid sequence as set forth in SEQ ID NO: 110; and (c) a CDR3 having an amino acid sequence as set forth in SEQ ID NO: 111; and a light chain variable region including (a) a CDR1 having an amino acid sequence as set forth in SEQ ID NO: 113; (b) a CDR2 having an amino acid sequence as set forth in SEQ ID NO: 114; and (c) a CDR3 having an amino acid sequence as set forth in SEQ ID NO: 115.

II.B. Humanized Anti-B7-H3 Antibodies

The chimeric antibodies disclosed herein may be used in the production of humanized anti-B7-H3 antibodies. For example, following the generation and characterization of chimeric anti-B7-H3 antibodies chAb1-chAb18, antibodies chAb3, chAb13, and chAb18 were selected for humanization. Specifically, six different humanized antibodies were created based on chAb3 (referred to herein as huAb3v1, huAb3v2, huAb3v3, huAb3v4, huAb3v5, and huAb3v6 (see Examples 12 and 13), nine different humanized antibodies were created based on chAb13 (referred to herein as huAb13v1, huAb13v2, huAb13v3, huAb13v4, huAb13v5, huAb13v6, huAb13v7, huAb13v8, huAb13v9), and ten different humanized antibodies were created based on chAb18 (referred to herein as huAb18v1, huAb18v2, huAb18v3, huAb18v4, huAb18v5, huAb18v6, huAb18v7, huAb18v8, huAb18v9, and huAb18v10 (see Examples 9 and 10)). Tables 8, 12, 16, 18, and 19 provide the amino acid sequences of CDR, VH and VL regions of humanized chAb3, chAb13, and chAb18, respectively.

Generally, humanized antibodies are antibody molecules from non-human species antibody that binds the desired antigen having one or more complementarity determining regions (CDRs) from the non-human species and framework regions from a human immunoglobulin molecule. Known human Ig sequences are disclosed, e.g., www.ncbi.nlm.nih.gov/entrez-/query.fcgi;
www.atcc.org/phage/hdb.html; www.sciquest.com/;
www.abcam.com/;
www.antibodyresource.com/onlinecomp.html;
www.public.iastate.edu/.about.pedro/research_tools.html;
www.mgen.uni-heidelberg.de/SD/IT/IT.html;

www.whfreeman.com/immunology/CH-05/kuby05.htm;
www.library.thinkquest.org/12429/Immune/Antibody.html;
www.hhmi.org/grants/lectures/1996/vlab/; www.path.cam.ac.uk/.about.mrc7/m-ikeimages.html;
www.antibodyresource.com/; mcb.harvard.edu/BioLinks/ Immuno-logy.html.www.immunologylink.com/; path-box.wustl.edu/.about.hcenter/index.-html;
www.biotech.ufl.edu/.about.hcl/; www.pebio.com/pa/340913/340913.html-;
www.nal.usda.gov/awic/pubs/antibody/; www.m.ehime-u.acjp/.about.yasuhito-/Elisa.html;
www.biodesign.com/table.asp; www.icnet.uk/axp/facs/davies/lin-ks.html;
www.biotech.ufl.edu/.about.fccl/protocol.html; www.isac-net.org/sites_geo.html; aximtl.imt.uni-marburg.de/.about.rek/AEP-Start.html; baserv.uci.kun.nl/.about.jraats/linksl.html; www.recab.uni-hd.de/immuno.bme.nwu.edu/;
www.mrc-cpe.cam.ac.uk/imt-doc/pu-blic/INTRO.html;
www.ibt.unam.mx/vir/V_mice.html; imgt.cnusc.fr:8104/;
www.biochem.ucl.ac.uk/.about.martin/abs/index.html; antibody.bath.ac.uk/; abgen.cvm.tamu.edu/lab/wwwabgen.html; www.unizh.ch/.about.honegger/AHOsem-inar/Slide01.html; www.cryst.bbk.ac.uk/.about.ubcg07s/;
www.nimr.mrc.ac.uk/CC/ccaewg/ccaewg.htm; www.path.cam.ac.uk/.about.mrc7/h-umanisation/TAHHP.html;
www.ibt.unam.mx/vir/structure/stat_aim.html;
www.biosci.missouri.edu/smithgp/index.html; www.cryst.bioc.cam.ac.uk/.abo-ut.fmolina/Web-pages/Pept/spot-tech.html;
www.jerini.de/fr roducts.htm; www.patents.ibm.com/ibm.html.Kabat et al., Sequences of Proteins of Immunological Interest, U.S. Dept. Health (1983), each entirely incorporated herein by reference. Such imported sequences can be used to reduce immunogenicity or reduce, enhance or modify binding, affinity, on-rate, off-rate, avidity, specificity, half-life, or any other suitable characteristic, as known in the art.

Framework residues in the human framework regions may be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.) Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding. Antibodies can be humanized using a variety of techniques known in the art, such as but not limited to those described in Jones et al., Nature 321:522 (1986); Verhoeyen et al., Science 239:1534 (1988)), Sims et al., J. Immunol. 151: 2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), Padlan, Molecular Immunology 28(4/5):489-498 (1991); Studnicka et al., Protein Engineering 7(6):805-814 (1994); Roguska. et al., PNAS 91:969-973 (1994); PCT publication WO 91/09967, PCT/: US98/16280, US96/18978, US91/09630, US91/05939, US94/01234, GB89/01334, GB91/01134, GB92/01755; WO90/14443, WO90/14424, WO90/14430, EP 229246, EP 592,106; EP 519,596, EP 239,400, U.S. Pat. Nos. 5,565,332, 5,723,323, 5,976,862, 5,824,514, 5,817,483, 5,814,476, 5,763,192, 5,723,323, 5,766886, 5,714,352, 6,204,023, 6,180,370, 5,693,762, 5,530,101, 5,585,089, 5,225,539; 4,816,567, each entirely incorporated herein by reference, included references cited therein.

Humanized Anti-B7-H3 Antibodies Derived from chAb3

Six humanized antibodies based on chAb3 were created. The sequences of each are as follows:

A) huAb3v1 (VH amino acid sequence set forth in SEQ ID NO: 125 and VH CDR1, CDR2, and CDR3 amino acid sequences set forth in SEQ ID NOs: 10, 11, and 12, respectively; and VL amino acid sequence set forth in SEQ ID NO: 128 and VL CDR1, CDR2, and CDR3 amino acid sequences set forth in SEQ ID NOs: 14, 7, and 15, respectively);

B) huAb3v2 (VH amino acid sequence set forth in SEQ ID NO: 127 and VH CDR1, CDR2, and CDR3 amino acid sequences set forth in SEQ ID NOs: 10, 11, and 12, respectively; and VL amino acid sequence set forth in SEQ ID NO: 128 and VL CDR1, CDR2, and CDR3 amino acid sequences set forth in SEQ ID NOs: 14, 7, and 15, respectively);

C) huAb3v3 (VH amino acid sequence set forth in SEQ ID NO: 126 and VH CDR1, CDR2, and CDR3 amino acid sequences set forth in SEQ ID NOs: 10, 11, and 12, respectively; and VL amino acid sequence set forth in SEQ ID NO: 129 and VL CDR1, CDR2, and CDR3 amino acid sequences set forth in SEQ ID NOs: 14, 7, and 15, respectively);

D) huAb3v4 (VH amino acid sequence set forth in SEQ ID NO: 125 and VH CDR1, CDR2, and CDR3 amino acid sequences set forth in SEQ ID NOs: 10, 11, and 12, respectively; and VL amino acid sequence set forth in SEQ ID NO: 130 and VL CDR1, CDR2, and CDR3 amino acid sequences set forth in SEQ ID NOs: 14, 7, and 15, respectively);

E) huAb3v5 (VH amino acid sequence set forth in SEQ ID NO: 127 and VH CDR1, CDR2, and CDR3 amino acid sequences set forth in SEQ ID NOs: 10, 11, and 12, respectively; and VL amino acid sequence set forth in SEQ ID NO: 130 and VL CDR1, CDR2, and CDR3 amino acid sequences set forth in SEQ ID NOs: 14, 7, and 15, respectively); and F) huAb3v6 (VH amino acid sequence set forth in SEQ ID NO: 126 and VH CDR1, CDR2, and CDR3 amino acid sequences set forth in SEQ ID NOs: 10, 11, and 12, respectively; and VL amino acid sequence set forth in SEQ ID NO: 130 and VL CDR1, CDR2, and CDR3 amino acid sequences set forth in SEQ ID NOs: 14, 7, and 15, respectively).

Of the six humanized versions of chAb3, huAb3v2 was selected for further modified in order to remove potential deamidation or isomerization sites in the light chain CDR1 or in the heavy chain CDR2. Nine variants of the humanized antibody huAb3v2 were generated, and are referred to herein as huAb3v2.1, huAb3v2.2, huAb3v2.3, huAb3v2.4, huAb3v2.5, huAb3v2.6, huAb3v2.7, huAb3v2.8, and huAb3v2.9 (CDR and variable domain sequences are provided in Table 16). The nine variants of the huAb3v2 antibody include the following:

A) huAb3v2.1 (VH amino acid sequence set forth in SEQ ID NO: 131 and VH CDR1, CDR2, and CDR3 amino acid sequences set forth in SEQ ID NOs: 10, 132, and 12, respectively; and VL amino acid sequence set forth in SEQ ID NO: 133 and VL CDR1, CDR2, and CDR3 amino acid sequences set forth in SEQ ID NOs: 134, 7, and 15, respectively);

B) huAb3v2.2 (VH amino acid sequence set forth in SEQ ID NO: 131 and VH CDR1, CDR2, and CDR3 amino acid sequences set forth in SEQ ID NOs: 10, 132, and 12, respectively; and VL amino acid sequence set forth in SEQ ID NO: 135 and VL CDR1, CDR2, and CDR3 amino acid sequences set forth in SEQ ID NOs: 136, 7, and 15, respectively);

C) huAb3v2.3 (VH amino acid sequence set forth in SEQ ID NO: 131 and VH CDR1, CDR2, and CDR3 amino acid sequences set forth in SEQ ID NOs: 10, 132, and 12, respectively; and VL amino acid sequence set forth in SEQ ID NO: 137 and VL CDR1, CDR2, and CDR3 amino acid sequences set forth in SEQ ID NOs: 138, 7, and 15, respectively);

D) huAb3v2.4 (VH amino acid sequence set forth in SEQ ID NO: 139 and VH CDR1, CDR2, and CDR3 amino acid sequences set forth in SEQ ID NOs: 10, 140, and 12, respectively; and VL amino acid sequence set forth in SEQ ID NO: 133 and VL CDR1, CDR2, and CDR3 amino acid sequences set forth in SEQ ID NOs: 134, 7, and 15, respectively);

E) huAb3v2.5 (VH amino acid sequence set forth in SEQ ID NO: 139 and VH CDR1, CDR2, and CDR3 amino acid sequences set forth in SEQ ID NOs: 10, 140, and 12, respectively; and VL amino acid sequence set forth in SEQ ID NO: 135 and VL CDR1, CDR2, and CDR3 amino acid sequences set forth in SEQ ID NOs: 136, 7, and 15, respectively);

F) huAb3v2.6 (VH amino acid sequence set forth in SEQ ID NO: 139 and VH CDR1, CDR2, and CDR3 amino acid sequences set forth in SEQ ID NOs: 10, 140, and 12, respectively; and VL amino acid sequence set forth in SEQ ID NO: 137 and VL CDR1, CDR2, and CDR3 amino acid sequences set forth in SEQ ID NOs: 138, 7, and 15, respectively);

G) huAb3v2.7 (VH amino acid sequence set forth in SEQ ID NO: 141 and VH CDR1, CDR2, and CDR3 amino acid sequences set forth in SEQ ID NOs: 10, 142, and 12, respectively; and VL amino acid sequence set forth in SEQ ID NO: 133 and VL CDR1, CDR2, and CDR3 amino acid sequences set forth in SEQ ID NOs: 134, 7, and 15, respectively);

H) huAb3v2.8 (VH amino acid sequence set forth in SEQ ID NO: 141 and VH CDR1, CDR2, and CDR3 amino acid sequences set forth in SEQ ID NOs: 10, 142, and 12, respectively; and VL amino acid sequence set forth in SEQ ID NO: 135 and VL CDR1, CDR2, and CDR3 amino acid sequences set forth in SEQ ID NOs: 136, 7, and 15, respectively); and I) huAb3v2.9 (VH amino acid sequence set forth in SEQ ID NO: 141 and VH CDR1, CDR2, and CDR3 amino acid sequences set forth in SEQ ID NOs: 10, 142, and 12, respectively; and VL amino acid sequence set forth in SEQ ID NO: 137 and VL CDR1, CDR2, and CDR3 amino acid sequences set forth in SEQ ID NOs: 138, 7, and 15, respectively).

Thus, in one aspect, the present invention provides antibodies comprising variable and/or CDR sequences from a humanized antibody derived from chAb3. In one embodiment, the invention features anti-B7-H3 antibodies which are derived from Ab3 have improved characteristics, e.g., improved binding affinity to isolated B7-H3 protein and improved binding to B7-H3 expressing cells, as described in the Examples below. Collectively these novel antibodies are referred to herein as "Ab3 variant antibodies." Generally, the Ab3 variant antibodies retain the same epitope specificity as Ab3. In various embodiments, anti-B7-H3 antibodies, or antigen binding fragments thereof, of the invention are capable of modulating a biological function of B7-H3.

In one aspect, the present invention provides a humanized antibody, or antigen binding portion thereof, having a heavy chain variable region including an amino acid sequence set forth in SEQ ID NOs: 125, 126, 127, 131, 139, or 141; and/or a light chain variable region including an amino acid sequence set forth in SEQ ID NOs: 128, 129, 130, 133, 135, or 137.

In another aspect, the present invention is directed to an anti-B7-H3 antibody, or antigen binding portion thereof, of the invention comprises a heavy chain variable region comprising a CDR1 domain comprising an amino acid sequence as set forth in SEQ ID NO: 10; a CDR2 domain comprising an amino acid sequence as set forth in SEQ ID NO: 11, 132, 140, or 142; and a CDR3 domain comprising an amino acid sequence as set forth in SEQ ID NO: 12; and a light chain variable region comprising a CDR1 domain comprising an amino acid sequence as set forth in SEQ ID NO: 14, 134, 136, or 138; a CDR2 domain comprising an amino acid sequence as set forth in SEQ ID NO: 7; and a CDR3 domain comprising an amino acid sequence as set forth in SEQ ID NO: 15.

In one aspect, the present invention is directed to an anti-B7-H3 antibody, or antigen-binding portion thereof, having a heavy chain variable region including an amino acid sequence as set forth in SEQ ID NO: 125, and a light chain variable region including an amino acid sequence set forth in SEQ ID NO: 128.

In one aspect, the present invention is directed to an anti-B7-H3 antibody, or antigen-binding portion thereof, having a heavy chain variable region including an amino acid sequence as set forth in SEQ ID NO: 127, and a light chain variable region including an amino acid sequence set forth in SEQ ID NO: 128.

In one aspect, the present invention is directed to an anti-B7-H3 antibody, or antigen-binding portion thereof, having a heavy chain variable region including an amino acid sequence as set forth in SEQ ID NO: 126, and a light chain variable region including an amino acid sequence set forth in SEQ ID NO: 129.

In one aspect, the present invention is directed to an anti-B7-H3 antibody, or antigen-binding portion thereof, having a heavy chain variable region including an amino acid sequence as set forth in SEQ ID NO: 125, and a light chain variable region including an amino acid sequence set forth in SEQ ID NO: 130.

In one aspect, the present invention is directed to an anti-B7-H3 antibody, or antigen-binding portion thereof, having a heavy chain variable region including an amino acid sequence as set forth in SEQ ID NO: 127, and a light chain variable region including an amino acid sequence set forth in SEQ ID NO: 130.

In one aspect, the present invention is directed to an anti-B7-H3 antibody, or antigen-binding portion thereof, having a heavy chain variable region including an amino acid sequence as set forth in SEQ ID NO: 126, and a light chain variable region including an amino acid sequence set forth in SEQ ID NO: 130.

In another aspect, the present invention is directed to a humanized anti-B7-H3 antibody, or antigen-binding portion thereof, having a heavy chain variable domain region including (a) a CDR1 having an amino acid sequence as set forth in SEQ ID NO: 10; (b) a CDR2 having an amino acid sequence as set forth in SEQ ID NO: 11; and (c) a CDR3 having an amino acid sequence as set forth in SEQ ID NO: 12; and a light chain variable region including (a) a CDR1 having an amino acid sequence as set forth in SEQ ID NO: 14; (b) a CDR2 having an amino acid sequence as set forth in SEQ ID NO: 7; and (c) a CDR3 having an amino acid sequence as set forth in SEQ ID NO: 15.

In one aspect, the present invention is directed to an anti-B7-H3 antibody, or antigen-binding portion thereof, having a heavy chain variable region including an amino acid sequence as set forth in SEQ ID NO: 131, and a light chain variable region including an amino acid sequence set forth in SEQ ID NO: 133.

In another aspect, the present invention is directed to a humanized anti-B7-H3 antibody, or antigen-binding portion thereof, having a heavy chain variable domain region including (a) a CDR1 having an amino acid sequence as set forth in SEQ ID NO: 10; (b) a CDR2 having an amino acid sequence as set forth in SEQ ID NO: 132; and (c) a CDR3 having an amino acid sequence as set forth in SEQ ID NO: 12; and a light chain variable region including (a) a CDR1 having an amino acid sequence as set forth in SEQ ID NO: 134; (b) a CDR2 having an amino acid sequence as set forth in SEQ ID NO: 7; and (c) a CDR3 having an amino acid sequence as set forth in SEQ ID NO: 15.

In one aspect, the present invention is directed to an anti-B7-H3 antibody, or antigen-binding portion thereof, having a heavy chain variable region including an amino acid sequence as set forth in SEQ ID NO: 131, and a light chain variable region including an amino acid sequence set forth in SEQ ID NO: 135.

In another aspect, the present invention is directed to a humanized anti-B7-H3 antibody, or antigen-binding portion thereof, having a heavy chain variable domain region including (a) a CDR1 having an amino acid sequence as set forth in SEQ ID NO: 10; (b) a CDR2 having an amino acid sequence as set forth in SEQ ID NO: 132; and (c) a CDR3 having an amino acid sequence as set forth in SEQ ID NO: 12; and a light chain variable region including (a) a CDR1 having an amino acid sequence as set forth in SEQ ID NO: 136; (b) a CDR2 having an amino acid sequence as set forth in SEQ ID NO: 7; and (c) a CDR3 having an amino acid sequence as set forth in SEQ ID NO: 15.

In one aspect, the present invention is directed to an anti-B7-H3 antibody, or antigen-binding portion thereof, having a heavy chain variable region including an amino acid sequence as set forth in SEQ ID NO: 131, and a light chain variable region including an amino acid sequence set forth in SEQ ID NO: 137.

In another aspect, the present invention is directed to a humanized anti-B7-H3 antibody, or antigen-binding portion thereof, having a heavy chain variable domain region including (a) a CDR1 having an amino acid sequence as set forth in SEQ ID NO: 10; (b) a CDR2 having an amino acid sequence as set forth in SEQ ID NO: 132; and (c) a CDR3 having an amino acid sequence as set forth in SEQ ID NO: 12; and a light chain variable region including (a) a CDR1 having an amino acid sequence as set forth in SEQ ID NO: 138; (b) a CDR2 having an amino acid sequence as set forth in SEQ ID NO: 7; and (c) a CDR3 having an amino acid sequence as set forth in SEQ ID NO: 15.

In one aspect, the present invention is directed to an anti-B7-H3 antibody, or antigen-binding portion thereof, having a heavy chain variable region including an amino acid sequence as set forth in SEQ ID NO: 139, and a light chain variable region including an amino acid sequence set forth in SEQ ID NO: 133.

In another aspect, the present invention is directed to a humanized anti-B7-H3 antibody, or antigen-binding portion thereof, having a heavy chain variable domain region including (a) a CDR1 having an amino acid sequence as set forth in SEQ ID NO: 10; (b) a CDR2 having an amino acid sequence as set forth in SEQ ID NO: 140; and (c) a CDR3 having an amino acid sequence as set forth in SEQ ID NO: 12; and a light chain variable region including (a) a CDR1 having an amino acid sequence as set forth in SEQ ID NO: 134; (b) a CDR2 having an amino acid sequence as set forth in SEQ ID NO: 7; and (c) a CDR3 having an amino acid sequence as set forth in SEQ ID NO: 15.

In one aspect, the present invention is directed to an anti-B7-H3 antibody, or antigen-binding portion thereof, having a heavy chain variable region including an amino acid sequence as set forth in SEQ ID NO: 139, and a light chain variable region including an amino acid sequence set forth in SEQ ID NO: 135.

In another aspect, the present invention is directed to a humanized anti-B7-H3 antibody, or antigen-binding portion thereof, having a heavy chain variable domain region including (a) a CDR1 having an amino acid sequence as set forth in SEQ ID NO: 10; (b) a CDR2 having an amino acid sequence as set forth in SEQ ID NO: 140; and (c) a CDR3 having an amino acid sequence as set forth in SEQ ID NO: 12; and a light chain variable region including (a) a CDR1 having an amino acid sequence as set forth in SEQ ID NO: 136; (b) a CDR2 having an amino acid sequence as set forth in SEQ ID NO: 7; and (c) a CDR3 having an amino acid sequence as set forth in SEQ ID NO: 15.

In another aspect, the present invention is directed to an anti-B7-H3 antibody, or antigen-binding portion thereof, having a heavy chain comprising the amino acid sequence of SEQ ID NO: 170 and a light chain comprising the amino acid sequence of SEQ ID NO: 171.

In one aspect, the present invention is directed to an anti-B7-H3 antibody, or antigen-binding portion thereof, having a heavy chain variable region including an amino acid sequence as set forth in SEQ ID NO: 139, and a light chain variable region including an amino acid sequence set forth in SEQ ID NO: 137.

In another aspect, the present invention is directed to a humanized anti-B7-H3 antibody, or antigen-binding portion thereof, having a heavy chain variable domain region including (a) a CDR1 having an amino acid sequence as set forth in SEQ ID NO: 10; (b) a CDR2 having an amino acid sequence as set forth in SEQ ID NO: 140; and (c) a CDR3 having an amino acid sequence as set forth in SEQ ID NO: 12; and a light chain variable region including (a) a CDR1 having an amino acid sequence as set forth in SEQ ID NO: 138; (b) a CDR2 having an amino acid sequence as set forth in SEQ ID NO: 7; and (c) a CDR3 having an amino acid sequence as set forth in SEQ ID NO: 15.

In another aspect, the present invention is directed to an anti-B7-H3 antibody, or antigen-binding portion thereof, having a heavy chain comprising the amino acid sequence of SEQ ID NO: 172 and a light chain comprising the amino acid sequence of SEQ ID NO: 173. In one aspect, the present invention is directed to an anti-B7-H3 antibody, or antigen-binding portion thereof, having a heavy chain variable region including an amino acid sequence as set forth in SEQ ID NO: 141, and a light chain variable region including an amino acid sequence set forth in SEQ ID NO: 133.

In another aspect, the present invention is directed to a humanized anti-B7-H3 antibody, or antigen-binding portion thereof, having a heavy chain variable domain region including (a) a CDR1 having an amino acid sequence as set forth in SEQ ID NO: 10; (b) a CDR2 having an amino acid sequence as set forth in SEQ ID NO: 142; and (c) a CDR3 having an amino acid sequence as set forth in SEQ ID NO: 12; and a light chain variable region including (a) a CDR1 having an amino acid sequence as set forth in SEQ ID NO: 134; (b) a CDR2 having an amino acid sequence as set forth in SEQ ID NO: 7; and (c) a CDR3 having an amino acid sequence as set forth in SEQ ID NO: 15.

In one aspect, the present invention is directed to an anti-B7-H3 antibody, or antigen-binding portion thereof, having a heavy chain variable region including an amino acid sequence as set forth in SEQ ID NO: 141, and a light chain variable region including an amino acid sequence set forth in SEQ ID NO: 135.

In another aspect, the present invention is directed to a humanized anti-B7-H3 antibody, or antigen-binding portion thereof, having a heavy chain variable domain region including (a) a CDR1 having an amino acid sequence as set forth in SEQ ID NO: 10; (b) a CDR2 having an amino acid sequence as set forth in SEQ ID NO: 142; and (c) a CDR3 having an amino acid sequence as set forth in SEQ ID NO: 12; and a light chain variable region including (a) a CDR1 having an amino acid sequence as set forth in SEQ ID NO: 136; (b) a CDR2 having an amino acid sequence as set forth in SEQ ID NO: 7; and (c) a CDR3 having an amino acid sequence as set forth in SEQ ID NO: 15.

In one aspect, the present invention is directed to an anti-B7-H3 antibody, or antigen-binding portion thereof, having a heavy chain variable region including an amino acid sequence as set forth in SEQ ID NO: 141, and a light chain variable region including an amino acid sequence set forth in SEQ ID NO: 137.

In another aspect, the present invention is directed to a humanized anti-B7-H3 antibody, or antigen-binding portion thereof, having a heavy chain variable domain region including (a) a CDR1 having an amino acid sequence as set forth in SEQ ID NO: 10; (b) a CDR2 having an amino acid sequence as set forth in SEQ ID NO: 142; and (c) a CDR3 having an amino acid sequence as set forth in SEQ ID NO: 12; and a light chain variable region including (a) a CDR1 having an amino acid sequence as set forth in SEQ ID NO: 138; (b) a CDR2 having an amino acid sequence as set forth in SEQ ID NO: 7; and (c) a CDR3 having an amino acid sequence as set forth in SEQ ID NO: 15.

Humanized Anti-B7-H3 Antibodies Derived from chAb13

The nine different humanized antibodies created based on chAb13 include the following:

A) huAb13v1 (VH amino acid sequence set forth in SEQ ID NO: 147 and VH CDR1, CDR2, and CDR3 amino acid sequences set forth in SEQ ID NOs: 33, 34, and 35, respectively; and VL amino acid sequence set forth in SEQ ID NO: 144 and VL CDR1, CDR2, and CDR3 amino acid sequences set forth in SEQ ID NOs: 37, 38, and 39, respectively);

B) huAb13v2 (VH amino acid sequence set forth in SEQ ID NO: 146 and VH CDR1, CDR2, and CDR3 amino acid sequences set forth in SEQ ID NOs: 33, 34, and 35, respectively; and VL amino acid sequence set forth in SEQ ID NO: 143 and VL CDR1, CDR2, and CDR3 amino acid sequences set forth in SEQ ID NOs: 37, 38, and 39, respectively);

C) huAb13v3 (VH amino acid sequence set forth in SEQ ID NO: 146 and VH CDR1, CDR2, and CDR3 amino acid sequences set forth in SEQ ID NOs: 33, 34, and 35, respectively; and VL amino acid sequence set forth in SEQ ID NO: 144 and VL CDR1, CDR2, and CDR3 amino acid sequences set forth in SEQ ID NOs: 37, 38, and 39, respectively);

D) huAb13v4 (VH amino acid sequence set forth in SEQ ID NO: 146 and VH CDR1, CDR2, and CDR3 amino acid sequences set forth in SEQ ID NOs: 33, 34, and 35, respectively; and VL amino acid sequence set forth in SEQ ID NO: 145 and VL CDR1, CDR2, and CDR3 amino acid sequences set forth in SEQ ID NOs: 37, 38, and 39, respectively);

E) huAb13v5 (VH amino acid sequence set forth in SEQ ID NO: 147 and VH CDR1, CDR2, and CDR3 amino acid sequences set forth in SEQ ID NOs: 33, 34, and 35, respectively; and VL amino acid sequence set forth in SEQ ID NO: 143 and VL CDR1, CDR2, and CDR3 amino acid sequences set forth in SEQ ID NOs: 37, 38, and 39, respectively);

F) huAb13v6 (VH amino acid sequence set forth in SEQ ID NO: 147 and VH CDR1, CDR2, and CDR3 amino acid sequences set forth in SEQ ID NOs: 33, 34, and 35, respectively; and VL amino acid sequence set forth in SEQ ID NO: 145 and VL CDR1, CDR2, and CDR3 amino acid sequences set forth in SEQ ID NOs: 37, 38, and 39, respectively);

G) huAb13v7 (VH amino acid sequence set forth in SEQ ID NO: 148 and VH CDR1, CDR2, and CDR3 amino acid sequences set forth in SEQ ID NOs: 33, 34, and 35, respectively; and VL amino acid sequence set forth in SEQ ID NO: 143 and VL CDR1, CDR2, and CDR3 amino acid sequences set forth in SEQ ID NOs: 37, 38, and 39, respectively);

H) huAb13v8 (VH amino acid sequence set forth in SEQ ID NO: 148 and VH CDR1, CDR2, and CDR3 amino acid sequences set forth in SEQ ID NOs: 33, 34, and 35, respectively; and VL amino acid sequence set forth in SEQ ID NO: 144 and VL CDR1, CDR2, and CDR3 amino acid sequences set forth in SEQ ID NOs: 37, 38, and 39, respectively);

I) huAb13v9 (VH amino acid sequence set forth in SEQ ID NO: 148 and VH CDR1, CDR2, and CDR3 amino acid sequences set forth in SEQ ID NOs: 33, 34, and 35, respectively; and VL amino acid sequence set forth in SEQ ID NO: 145 and VL CDR1, CDR2, and CDR3 amino acid sequences set forth in SEQ ID NOs: 37, 38, and 39, respectively).

Thus, in one aspect the present invention provides antibodies comprising variable and/or CDR sequences from a humanized antibody derived from chAb13. In one embodiment, the invention features anti-B7-H3 antibodies which are derived from chAb13 have improved characteristics, e.g., improved binding affinity to isolated B7-H3 protein and improved binding to B7-H3 expressing cells, as described in the Examples below. Collectively these novel antibodies are referred to herein as "Ab13 variant antibodies." Generally, the Ab13 variant antibodies retain the same epitope specificity as Ab13. In various embodiments, anti-B7-H3 antibodies, or antigen binding fragments thereof, of the invention are capable of modulating a biological function of B7-H3.

In one aspect, the present invention provides a humanized antibody, or antigen binding portion thereof, having a heavy chain variable region including an amino acid sequence set forth in SEQ ID NOs: 146, 147, or 148; and/or a light chain variable region including an amino acid sequence set forth in SEQ ID NOs: 143, 144, or 145.

In another aspect, the present invention is directed to an anti-B7-H3 antibody, or antigen binding portion thereof, of the invention comprises a heavy chain variable region comprising a CDR1 domain comprising an amino acid sequence as set forth in SEQ ID NO: 33; a CDR2 domain comprising an amino acid sequence as set forth in SEQ ID NO: 34; and a CDR3 domain comprising an amino acid sequence as set forth in SEQ ID NO: 35; and a light chain variable region comprising a CDR1 domain comprising an amino acid sequence as set forth in SEQ ID NO: 37; a CDR2 domain comprising an amino acid sequence as set forth in SEQ ID NO: 38; and a CDR3 domain comprising an amino acid sequence as set forth in SEQ ID NO: 39.

In one aspect, the present invention is directed to an anti-B7-H3 antibody, or antigen-binding portion thereof, having a heavy chain variable region including an amino acid sequence as set forth in SEQ ID NO: 147, and a light chain variable region including an amino acid sequence set forth in SEQ ID NO: 144. In one embodiment, the invention provides an anti-B7H3 antibody comprising the CDR sequences set forth in the variable regions of huAb13v1 (SEQ ID NOs. 144 and 147).

In one aspect, the present invention is directed to an anti-B7-H3 antibody, or antigen binding portion thereof, having a heavy chain comprising the amino acid sequence of SEQ ID NO: 168 and a light chain comprising the amino acid sequence of SEQ ID NO: 169.

In one aspect, the present invention is directed to an anti-B7-H3 antibody, or antigen-binding portion thereof, having a heavy chain variable region including an amino acid sequence as set forth in SEQ ID NO: 146, and a light chain variable region including an amino acid sequence set forth in SEQ ID NO: 143.

In one aspect, the present invention is directed to an anti-B7-H3 antibody, or antigen-binding portion thereof, having a heavy chain variable region including an amino acid sequence as set forth in SEQ ID NO: 146, and a light chain variable region including an amino acid sequence set forth in SEQ ID NO: 144.

In one aspect, the present invention is directed to an anti-B7-H3 antibody, or antigen-binding portion thereof, having a heavy chain variable region including an amino acid sequence as set forth in SEQ ID NO: 146, and a light chain variable region including an amino acid sequence set forth in SEQ ID NO: 145.

In one aspect, the present invention is directed to an anti-B7-H3 antibody, or antigen-binding portion thereof, having a heavy chain variable region including an amino acid sequence as set forth in SEQ ID NO: 147, and a light chain variable region including an amino acid sequence set forth in SEQ ID NO: 143.

In one aspect, the present invention is directed to an anti-B7-H3 antibody, or antigen-binding portion thereof, having a heavy chain variable region including an amino acid sequence as set forth in SEQ ID NO: 147, and a light chain variable region including an amino acid sequence set forth in SEQ ID NO: 145.

In one aspect, the present invention is directed to an anti-B7-H3 antibody, or antigen-binding portion thereof, having a heavy chain variable region including an amino acid sequence as set forth in SEQ ID NO: 148, and a light chain variable region including an amino acid sequence set forth in SEQ ID NO: 143.

In one aspect, the present invention is directed to an anti-B7-H3 antibody, or antigen-binding portion thereof, having a heavy chain variable region including an amino acid sequence as set forth in SEQ ID NO: 148, and a light chain variable region including an amino acid sequence set forth in SEQ ID NO: 144.

In one aspect, the present invention is directed to an anti-B7-H3 antibody, or antigen-binding portion thereof, having a heavy chain variable region including an amino acid sequence as set forth in SEQ ID NO: 148, and a light chain variable region including an amino acid sequence set forth in SEQ ID NO: 145.

Humanized Anti-B7-H3 Antibodies Derived from chAb18

The ten different humanized antibodies created based on chAb18 include the following:

A) huAb18v1 (VH amino acid sequence set forth in SEQ ID NO: 116 and VH CDR1, CDR2, and CDR3 amino acid sequences set forth in SEQ ID NOs: 25, 26, and 27, respectively; and VL amino acid sequence set forth in SEQ ID NO: 120 and VL CDR1, CDR2, and CDR3 amino acid sequences set forth in SEQ ID NOs: 29, 30, and 31, respectively);

B) huAb18v2 (VH amino acid sequence set forth in SEQ ID NO: 118 and VH CDR1, CDR2, and CDR3 amino acid sequences set forth in SEQ ID NOs: 25, 119, and 27, respectively; and VL amino acid sequence set forth in SEQ ID NO: 120 and VL CDR1, CDR2, and CDR3 amino acid sequences set forth in SEQ ID NOs: 29, 30, and 31, respectively);

C) huAb18v3 (VH amino acid sequence set forth in SEQ ID NO: 117 and VH CDR1, CDR2, and CDR3 amino acid sequences set forth in SEQ ID NOs: 25, 26, and 27, respectively; and VL amino acid sequence set forth in SEQ ID NO: 121 and VL CDR1, CDR2, and CDR3 amino acid sequences set forth in SEQ ID NOs: 29, 30, and 31, respectively);

D) huAb18v4 (VH amino acid sequence set forth in SEQ ID NO: 118 and VH CDR1, CDR2, and CDR3 amino acid sequences set forth in SEQ ID NOs: 25, 119, and 27, respectively; and VL amino acid sequence set forth in SEQ ID NO: 121 and VL CDR1, CDR2, and CDR3 amino acid sequences set forth in SEQ ID NOs: 29, 30, and 31, respectively);

E) huAb18v5 (VH amino acid sequence set forth in SEQ ID NO: 116 and VH CDR1, CDR2, and CDR3 amino acid sequences set forth in SEQ ID NOs: 25, 26, and 27, respectively; and VL amino acid sequence set forth in SEQ ID NO: 123 and VL CDR1, CDR2, and CDR3 amino acid sequences set forth in SEQ ID NOs: 29, 30, and 31, respectively);

F) huAb18v6 (VH amino acid sequence set forth in SEQ ID NO: 118 and VH CDR1, CDR2, and CDR3 amino acid sequences set forth in SEQ ID NOs: 25, 119, and 27, respectively; and VL amino acid sequence set forth in SEQ ID NO: 123 and VL CDR1, CDR2, and CDR3 amino acid sequences set forth in SEQ ID NOs: 29, 30, and 31, respectively);

G) huAb18v7 (VH amino acid sequence set forth in SEQ ID NO: 118 and VH CDR1, CDR2, and CDR3 amino acid sequences set forth in SEQ ID NOs: 25, 119, and 27, respectively; and VL amino acid sequence set forth in SEQ ID NO: 124 and VL CDR1, CDR2, and CDR3 amino acid sequences set forth in SEQ ID NOs: 29, 30, and 31, respectively);

H) huAb18v8 (VH amino acid sequence set forth in SEQ ID NO: 117 and VH CDR1, CDR2, and CDR3 amino acid sequences set forth in SEQ ID NOs: 25, 26, and 27, respectively; and VL amino acid sequence set forth in SEQ ID NO: 122 and VL CDR1, CDR2, and CDR3 amino acid sequences set forth in SEQ ID NOs: 29, 30, and 31, respectively);

I) huAb18v9 (VH amino acid sequence set forth in SEQ ID NO: 117 and VH CDR1, CDR2, and CDR3 amino acid sequences set forth in SEQ ID NOs: 25, 26, and 27, respectively; and VL amino acid sequence set forth in SEQ ID NO: 124 and VL CDR1, CDR2, and CDR3 amino acid sequences set forth in SEQ ID NOs: 29, 30, and 31, respectively); and J) huAb18v10 (VH amino acid sequence set forth in SEQ ID NO: 118 and VH CDR1, CDR2, and CDR3 amino acid sequences set forth in SEQ ID NOs: 25, 119, and 27, respectively; and VL amino acid sequence set forth in SEQ ID NO: 122 and VL CDR1, CDR2, and CDR3 amino acid sequences set forth in SEQ ID NOs: 29, 30, and 31, respectively).

Thus, in one aspect the present invention provides antibodies comprising variable and/or CDR sequences from a humanized antibody derived from chAb18. In one embodiment, the invention features anti-B7-H3 antibodies which are derived from Ab18 have improved characteristics, e.g., improved binding affinity to isolated B7-H3 protein and improved binding to B7-H3 expressing cells, as described in the Examples below. Collectively these novel antibodies are referred to herein as "Ab18 variant antibodies." Generally, the Ab18 variant antibodies retain the same epitope specificity as Ab18. In various embodiments, anti-B7-H3 antibodies, or antigen binding fragments thereof, of the invention are capable of modulating a biological function of B7-H3.

In one aspect, the present invention provides a humanized antibody, or antigen binding portion thereof, having a heavy chain variable region including an amino acid sequence set forth in SEQ ID NOs: 116, 117, or 118; and/or a light chain variable region including an amino acid sequence set forth in SEQ ID NOs: 120, 121, 122, 123 or 124.

In another aspect, the present invention is directed to an anti-B7-H3 antibody, or antigen binding portion thereof, of the invention comprises a heavy chain variable region comprising a CDR1 domain comprising an amino acid sequence as set forth in SEQ ID NO: 25; a CDR2 domain comprising an amino acid sequence as set forth in SEQ ID NO: 26 or 119; and a CDR3 domain comprising an amino acid sequence as set forth in SEQ ID NO: 27; and a light chain variable region comprising a CDR1 domain comprising an amino acid sequence as set forth in SEQ ID NO: 29; a CDR2 domain comprising an amino acid sequence as set forth in SEQ ID NO: 30; and a CDR3 domain comprising an amino acid sequence as set forth in SEQ ID NO: 31.

In one aspect, the present invention is directed to an anti-B7-H3 antibody, or antigen-binding portion thereof, having a heavy chain variable region including an amino acid sequence as set forth in SEQ ID NO: 116, and a light chain variable region including an amino acid sequence set forth in SEQ ID NO: 120.

In another aspect, the present invention is directed to a humanized anti-B7-H3 antibody, or antigen-binding portion thereof, having a heavy chain variable domain region including (a) a CDR1 having an amino acid sequence as set forth in SEQ ID NO: 25; (b) a CDR2 having an amino acid sequence as set forth in SEQ ID NO: 26; and (c) a CDR3 having an amino acid sequence as set forth in SEQ ID NO: 27; and a light chain variable region including (a) a CDR1 having an amino acid sequence as set forth in SEQ ID NO: 29; (b) a CDR2 having an amino acid sequence as set forth in SEQ ID NO: 30; and (c) a CDR3 having an amino acid sequence as set forth in SEQ ID NO: 31.

In one aspect, the present invention is directed to an anti-B7-H3 antibody, or antigen-binding portion thereof, having a heavy chain variable region including an amino acid sequence as set forth in SEQ ID NO: 118, and a light chain variable region including an amino acid sequence set forth in SEQ ID NO: 120.

In another aspect, the present invention is directed to a humanized anti-B7-H3 antibody, or antigen-binding portion thereof, having a heavy chain variable domain region including (a) a CDR1 having an amino acid sequence as set forth in SEQ ID NO: 25; (b) a CDR2 having an amino acid sequence as set forth in SEQ ID NO: 119; and (c) a CDR3 having an amino acid sequence as set forth in SEQ ID NO: 27; and a light chain variable region including (a) a CDR1 having an amino acid sequence as set forth in SEQ ID NO: 29; (b) a CDR2 having an amino acid sequence as set forth in SEQ ID NO: 30; and (c) a CDR3 having an amino acid sequence as set forth in SEQ ID NO: 31.

In one aspect, the present invention is directed to an anti-B7-H3 antibody, or antigen-binding portion thereof, having a heavy chain variable region including an amino acid sequence as set forth in SEQ ID NO: 117, and a light chain variable region including an amino acid sequence set forth in SEQ ID NO: 121.

In one aspect, the present invention is directed to an anti-B7-H3 antibody, or antigen-binding portion thereof, having a heavy chain variable region including an amino acid sequence as set forth in SEQ ID NO: 118, and a light chain variable region including an amino acid sequence set forth in SEQ ID NO: 121.

In one aspect, the present invention is directed to an anti-B7-H3 antibody, or antigen-binding portion thereof, having a heavy chain variable region including an amino acid sequence as set forth in SEQ ID NO: 116, and a light chain variable region including an amino acid sequence set forth in SEQ ID NO: 123.

In one aspect, the present invention is directed to an anti-B7-H3 antibody, or antigen-binding portion thereof, having a heavy chain variable region including an amino acid sequence as set forth in SEQ ID NO: 118, and a light chain variable region including an amino acid sequence set forth in SEQ ID NO: 123.

In one aspect, the present invention is directed to an anti-B7-H3 antibody, or antigen-binding portion thereof, having a heavy chain variable region including an amino acid sequence as set forth in SEQ ID NO: 118, and a light chain variable region including an amino acid sequence set forth in SEQ ID NO: 124.

In one aspect, the present invention is directed to an anti-B7-H3 antibody, or antigen-binding portion thereof, having a heavy chain variable region including an amino acid sequence as set forth in SEQ ID NO: 117, and a light chain variable region including an amino acid sequence set forth in SEQ ID NO: 122.

In one aspect, the present invention is directed to an anti-B7-H3 antibody, or antigen-binding portion thereof, having a heavy chain variable region including an amino acid sequence as set forth in SEQ ID NO: 117, and a light chain variable region including an amino acid sequence set forth in SEQ ID NO: 124.

In one aspect, the present invention is directed to an anti-B7-H3 antibody, or antigen-binding portion thereof, having a heavy chain variable region including an amino acid sequence as set forth in SEQ ID NO: 118, and a light chain variable region including an amino acid sequence set forth in SEQ ID NO: 122.

In one aspect, the present invention provides a humanized antibody, or antigen binding portion thereof, having a heavy chain variable region including an amino acid sequence set forth in SEQ ID NOs: 116, 117, 118, 146, 147, 148, 125, 126, 127, 131, 139, or 141; and/or a light chain variable region including an amino acid sequence set forth in SEQ ID NOs: 120, 121, 122, 123, 124, 143, 144, 145, 128, 129, 130, 133, 135, or 137.

In another aspect, the present invention is directed to an anti-B7-H3 antibody, or antigen binding portion thereof, of the invention comprises a heavy chain variable region comprising a CDR1 domain comprising an amino acid sequence as set forth in SEQ ID NO: 10, 25, or 33; a CDR2 domain comprising an amino acid sequence as set forth in SEQ ID NO: 11, 26, 34, 119, 132, 140, or 142; and a CDR3 domain comprising an amino acid sequence as set forth in SEQ ID NO: 12, 27, or 35; and a light chain variable region comprising a CDR1 domain comprising an amino acid sequence as set forth in SEQ ID NO: 14, 29, 37, 134, 136, or 138; a CDR2 domain comprising an amino acid sequence as set forth in SEQ ID NO: 7, 30, or 38; and a CDR3 domain comprising an amino acid sequence as set forth in SEQ ID NO: 15, 31 or 39.

In another aspect, the invention provides an anti-B7-H3 antibody, or antigen binding fragment thereof, that specifically competes with an anti-B7-H3 antibody, or fragment thereof, as described herein, wherein said competition can be detected in a competitive binding assay using said antibody, the human B7-H3 polypeptide, and the anti-B7-H3 antibody or fragment thereof.

In particular embodiments, the competing antibody, or antigen binding portion thereof, is an antibody, or antigen binding portion thereof, that competes with huAb3v2.5, huAb3v2.6, or huAb13v1.

In one embodiment, the anti-B7-H3 antibodies, or antigen binding portions thereof, of the invention bind to the extracellular domain of human B7-H3 (SEQ ID NO: 152) with a dissociation constant ($K_D$) of about $1\times10^{-6}$ M or less, as determined by surface plasmon resonance. Alternatively, the antibodies, or antigen binding portions thereof, bind to human B7-H3 with a $K_D$ of between about $1\times10^{-6}$ M and about $1\times10^{-11}$ M, as determined by surface plasmon resonance. In a further alternative, antibodies, or antigen binding portions thereof, bind to human B7-H3 with a $K_D$ of between about $1\times10^{-6}$ M and about $1\times10^{-7}$ M, as determined by surface plasmon resonance. Alternatively, antibodies, or antigen binding portions thereof, of the invention binds to human B7-H3 with a $K_D$ of between about $1\times10^{-6}$ M and about $5\times10^{-11}$ M, about $1\times10^{-6}$ M and about $5\times10^{-10}$ M; a $K_D$ of between about $1\times10^{-6}$ M and about $1\times10^{-9}$ M; a $K_D$ of between about $1\times10^{-6}$ M and about $5\times10^{-9}$ M; a $K_D$ of between about $1\times10^{-6}$ M and about $1\times10^{-8}$ M; a $K_D$ of between about $1\times10^{-6}$ M and about $5\times10^{-8}$ M; a $K_D$ of between about $1\times10^{-7}$ M and about $3.4\times10^{-11}$ M; a $K_D$ of between about $5.9\times10^{-7}$ M; and about $2.2\times10^{-7}$ M, as determined by surface plasmon resonance.

In one embodiment, the antibodies, or antigen binding portions thereof, of the invention bind to human B7-H3 (SEQ ID NO: 149) with a $K_D$ of about $1\times10^{-6}$ M or less, as determined by surface plasmon resonance. Alternatively, the antibodies, or antigen binding portions thereof, of the invention bind to human B7-H3 (SEQ ID NO: 149) with a $K_D$ of between about $8.2\times10^{-9}$ M and about $6.3\times10^{-10}$ M; a $K_D$ of between about $8.2\times10^{-9}$ M and about $2.0\times10^{-9}$ M; a $K_D$ of between about $2.3\times10^{-9}$ M and about $1.5\times10^{-10}$ M, as determined by surface plasmon resonance.

The foregoing establish a novel family of B7-H3 binding proteins, isolated in accordance with this invention, and including antigen binding polypeptides that comprise the CDR sequences listed in the Sequence Table provided herein.

Anti-B7-H3 antibodies provided herein may comprise a heavy chain variable region comprising CDR1, CDR2 and CDR3 sequences and a light chain variable region comprising CDR1, CDR2 and CDR3 sequences, wherein one or more of these CDR sequences comprise specified amino acid sequences based on the antibodies described herein (e.g., huAb13v1 or huAb3v2.5), or conservative modifications thereof, and wherein the antibodies retain the desired functional properties of the anti-B7-H3antibodies described herein. Accordingly, the anti-B7-H3 antibody, or antigen binding portion thereof, may comprise a heavy chain variable region comprising CDR1, CDR2, and CDR3 sequences and a light chain variable region comprising CDR1, CDR2, and CDR3 sequences, wherein: (a) the heavy chain variable region CDR3 sequence comprises SEQ ID NO: 12 or 35, and conservative modifications thereof, e.g., 1, 2, 3, 4, 5, 1-2, 1-3, 1-4 or 1-5 conservative amino acid substitutions; (b) the light chain variable region CDR3 sequence comprises SEQ ID NO: 15 or 39, and conservative modifications thereof, e.g., 1, 2, 3, 4, 5, 1-2, 1-3, 1-4 or 1-5 conservative amino acid substitutions; (c) the antibody specifically binds to B7-H3, and (d) the antibody exhibits 1, 2, 3, 4, 5, 6, or all of the following functional properties described herein, e.g., binding to soluble human B7-H3. In a one embodiment, the heavy chain variable region CDR2 sequence comprises SEQ ID NO: 140 or 34, and conservative modifications thereof, e.g., 1, 2, 3, 4, 5, 1-2, 1-3, 1-4 or 1-5 conservative amino acid substitutions; and the light chain variable region CDR2 sequence comprises SEQ ID NO: 7 or 38, and conservative modifications thereof, e.g., 1, 2, 3, 4, 5, 1-2, 1-3, 1-4 or 1-5 conservative amino acid substitutions. In another preferred embodiment, the heavy chain variable region CDR1 sequence comprises SEQ ID NO: 10 or 33, and conservative modifications thereof, e.g., 1, 2, 3, 4, 5, 1-2, 1-3, 1-4 or 1-5 conservative amino acid substitutions; and the light chain variable region CDR1 sequence comprises SEQ ID NO: 136, 138, or 37, and conservative modifications thereof, e.g., 1, 2, 3, 4, 5, 1-2, 1-3, 1-4 or 1-5 conservative amino acid substitutions.

Conservative amino acid substitutions may also be made in portions of the antibodies other than, or in addition to, the CDRs. For example, conservative amino acid modifications may be made in a framework region or in the Fc region. A variable region or a heavy or light chain may comprise 1, 2, 3, 4, 5, 1-2, 1-3, 1-4, 1-5, 1-10, 1-15, 1-20, 1-25, or 1-50 conservative amino acid substitutions relative to the anti-B7-H3 antibody sequences provided herein. In certain embodiments, the anti-B7-H3antibody comprises a combination of conservative and non-conservative amino acid modification.

To generate and to select CDRs having preferred B7-H3 binding and/or neutralizing activity with respect to hB7-H3, standard methods known in the art for generating antibodies, or antigen binding portions thereof, and assessing the B7-H3 binding and/or neutralizing characteristics of those antibodies, or antigen binding portions thereof, may be used, including but not limited to those specifically described herein.

In certain embodiments, the antibody comprises a heavy chain constant region, such as an IgG1, IgG2, IgG3, IgG4, IgA, IgE, IgM, or IgD constant region. In certain embodiments, the anti-B7-H3 antibody, or antigen binding portion thereof, comprises a heavy chain immunoglobulin constant domain selected from the group consisting of a human IgG constant domain, a human IgM constant domain, a human IgE constant domain, and a human IgA constant domain. In further embodiments, the antibody, or antigen binding portion thereof, has an IgG1 heavy chain constant region, an IgG2 heavy chain constant region, an IgG3 constant region, or an IgG4 heavy chain constant region. Preferably, the heavy chain constant region is an IgG1 heavy chain constant region or an IgG4 heavy chain constant region. Furthermore, the antibody can comprise a light chain constant region, either a kappa light chain constant region or a lambda light chain constant region. Preferably, the antibody comprises a kappa light chain constant region. Alternatively, the antibody portion can be, for example, a Fab fragment or a single chain Fv fragment.

In certain embodiments, the anti-B7-H3 antibody binding portion is a Fab, a Fab', a F(ab')2, a Fv, a disulfide linked Fv, an scFv, a single domain antibody, or a diabody.

In certain embodiments, the anti-B7-H3 antibody, or antigen binding portion thereof, is a multispecific antibody, e.g. a bispecific antibody.

Replacements of amino acid residues in the Fc portion to alter antibody effector function have been described (Winter, et al. U.S. Pat. Nos. 5,648,260 and 5,624,821, incorporated by reference herein). The Fc portion of an antibody mediates several important effector functions e.g. cytokine induction, ADCC, phagocytosis, complement dependent cytotoxicity (CDC) and half-life/clearance rate of antibody and antigen-antibody complexes. In some cases these effector functions are desirable for therapeutic antibody but in other cases might be unnecessary or even deleterious, depending on the therapeutic objectives. Certain human IgG isotypes, particularly IgG1 and IgG3, mediate ADCC and CDC via binding to FcγRs and complement C1q, respectively. Neonatal Fc receptors (FcRn) are the critical components determining the circulating half-life of antibodies. In still another embodiment at least one amino acid residue is replaced in the constant region of the antibody, for example the Fc region of the antibody, such that effector functions of the antibody are altered.

One embodiment of the invention includes a recombinant chimeric antigen receptor (CAR) comprising the binding regions of the antibodies described herein, e.g., the heavy and/or light chain CDRs of huAb13v1. A recombinant CAR, as described herein, may be used to redirect T cell specificity to an antigen in a human leukocyte antigen (HLA)-independent fashion. Thus, CARs of the invention may be used in immunotherapy to help engineer a human subject's own immune cells to recognize and attack the subject's tumor (see, e.g., U.S. Pat. Nos. 6,410,319; 8,389,282; 8,822,647; 8,906,682; 8,911,993; 8,916,381; 8,975,071; and U.S. Patent Appln. Publ. No. US20140322275, each of which is incorporated by reference herein with respect to CAR technology). This type of immunotherapy is called adoptive cell transfer (ACT), and may be used to treat cancer in a subject in need thereof.

An anti-B7-H3 CAR of the invention preferably contains a extracellular antigen-binding domain specific for B7-H3, a transmembrane domain which is used to anchor the CAR into a T cell, and one or more intracellular signaling domains. In one embodiment of the invention, the CAR includes a transmembrane domain that comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154. In one embodiment of the invention, the CAR comprises a costimulatory domain, e.g., a costimulatory domain comprising a functional signaling domain of a protein selected from the group consisting of OX40, CD2, CD27, CD28, CD5, ICAM-1, LFA-1 (CD11a/CD18), ICOS (CD278), and 4-1BB (CD137). In certain embodiments of the invention, the CAR comprises an scFv comprising the CDR or variable regions described herein e.g., CDRs or variable regions from the huAb13v1 antibody, a transmembrane domain, a co-stimulatory domain (e.g., a functional signaling domain from CD28 or 4-1BB), and a signaling domain comprising a functional signaling domain from CD3 (e.g., CD3-zeta).

In certain embodiments, the invention incudes a T cell comprising a CAR (also referred to as a CAR T cell) comprising antigen binding regions, e.g. CDRs, of the antibodies described herein or an scFv described herein.

In certain embodiments of the invention, the CAR comprises a heavy chain variable region comprising a CDR1 domain comprising an amino acid sequence as set forth in SEQ ID NO: 10, 25, or 33; a CDR2 domain comprising an amino acid sequence as set forth in SEQ ID NO: 11, 26, 34, 119, 132, 140, or 142; and a CDR3 domain comprising an amino acid sequence as set forth in SEQ ID NO: 12, 27, or 35; and a light chain variable region comprising a CDR1 domain comprising an amino acid sequence as set forth in SEQ ID NO: 14, 29, 37, 134, 136, or 138; a CDR2 domain comprising an amino acid sequence as set forth in SEQ ID NO: 7, 30, or 38; and a CDR3 domain comprising an amino acid sequence as set forth in SEQ ID NO: 15, 31 or 39.

In certain embodiments of the invention, the CAR comprises a heavy chain variable domain region including (a) a CDR1 having an amino acid sequence as set forth in SEQ ID NO: 10; (b) a CDR2 having an amino acid sequence as set forth in SEQ ID NO: 11; and (c) a CDR3 having an amino acid sequence as set forth in SEQ ID NO: 12; and a light chain variable region including (a) a CDR1 having an amino acid sequence as set forth in SEQ ID NO: 14; (b) a CDR2 having an amino acid sequence as set forth in SEQ ID NO: 7; and (c) a CDR3 having an amino acid sequence as set forth in SEQ ID NO: 15.

In certain embodiments of the invention, the CAR comprises a heavy chain variable domain region including (a) a CDR1 having an amino acid sequence as set forth in SEQ ID NO: 10; (b) a CDR2 having an amino acid sequence as set forth in SEQ ID NO: 132; and (c) a CDR3 having an amino acid sequence as set forth in SEQ ID NO: 12; and a light chain variable region including (a) a CDR1 having an amino acid sequence as set forth in SEQ ID NO: 134; (b) a CDR2 having an amino acid sequence as set forth in SEQ ID NO: 7; and (c) a CDR3 having an amino acid sequence as set forth in SEQ ID NO: 15.

In certain embodiments of the invention, the CAR comprises a heavy chain variable domain region including (a) a CDR1 having an amino acid sequence as set forth in SEQ ID NO: 10; (b) a CDR2 having an amino acid sequence as set forth in SEQ ID NO: 132; and (c) a CDR3 having an amino acid sequence as set forth in SEQ ID NO: 12; and a light chain variable region including (a) a CDR1 having an amino acid sequence as set forth in SEQ ID NO: 136; (b) a CDR2 having an amino acid sequence as set forth in SEQ ID NO: 7; and (c) a CDR3 having an amino acid sequence as set forth in SEQ ID NO: 15.

In certain embodiments of the invention, the CAR comprises a heavy chain variable domain region including (a) a CDR1 having an amino acid sequence as set forth in SEQ ID NO: 10; (b) a CDR2 having an amino acid sequence as set forth in SEQ ID NO: 132; and (c) a CDR3 having an amino acid sequence as set forth in SEQ ID NO: 12; and a light chain variable region including (a) a CDR1 having an amino acid sequence as set forth in SEQ ID NO: 138; (b) a CDR2 having an amino acid sequence as set forth in SEQ ID NO: 7; and (c) a CDR3 having an amino acid sequence as set forth in SEQ ID NO: 15.

In certain embodiments of the invention, the CAR comprises a heavy chain variable domain region including (a) a CDR1 having an amino acid sequence as set forth in SEQ ID NO: 10; (b) a CDR2 having an amino acid sequence as set forth in SEQ ID NO: 140; and (c) a CDR3 having an amino acid sequence as set forth in SEQ ID NO: 12; and a light chain variable region including (a) a CDR1 having an amino acid sequence as set forth in SEQ ID NO: 134; (b) a CDR2 having an amino acid sequence as set forth in SEQ ID NO: 7; and (c) a CDR3 having an amino acid sequence as set forth in SEQ ID NO: 15.

In certain embodiments of the invention, the CAR comprises a heavy chain variable domain region including (a) a CDR1 having an amino acid sequence as set forth in SEQ ID NO: 10; (b) a CDR2 having an amino acid sequence as set forth in SEQ ID NO: 140; and (c) a CDR3 having an amino acid sequence as set forth in SEQ ID NO: 12; and a light chain variable region including (a) a CDR1 having an amino acid sequence as set forth in SEQ ID NO: 136; (b) a CDR2 having an amino acid sequence as set forth in SEQ ID NO: 7; and (c) a CDR3 having an amino acid sequence as set forth in SEQ ID NO: 15.

In certain embodiments of the invention, the CAR comprises a heavy chain variable domain region including (a) a CDR1 having an amino acid sequence as set forth in SEQ ID NO: 10; (b) a CDR2 having an amino acid sequence as set forth in SEQ ID NO: 140; and (c) a CDR3 having an amino acid sequence as set forth in SEQ ID NO: 12; and a light chain variable region including (a) a CDR1 having an amino acid sequence as set forth in SEQ ID NO: 138; (b) a CDR2 having an amino acid sequence as set forth in SEQ ID NO: 7; and (c) a CDR3 having an amino acid sequence as set forth in SEQ ID NO: 15.

In certain embodiments of the invention, the CAR comprises a heavy chain variable domain region including (a) a CDR1 having an amino acid sequence as set forth in SEQ ID NO: 10; (b) a CDR2 having an amino acid sequence as set forth in SEQ ID NO: 142; and (c) a CDR3 having an amino acid sequence as set forth in SEQ ID NO: 12; and a light chain variable region including (a) a CDR1 having an amino acid sequence as set forth in SEQ ID NO: 134; (b) a CDR2 having an amino acid sequence as set forth in SEQ ID NO: 7; and (c) a CDR3 having an amino acid sequence as set forth in SEQ ID NO: 15.

In certain embodiments of the invention, the CAR comprises a heavy chain variable domain region including (a) a CDR1 having an amino acid sequence as set forth in SEQ ID NO: 10; (b) a CDR2 having an amino acid sequence as set forth in SEQ ID NO: 142; and (c) a CDR3 having an amino acid sequence as set forth in SEQ ID NO: 12; and a light chain variable region including (a) a CDR1 having an amino acid sequence as set forth in SEQ ID NO: 136; (b) a CDR2 having an amino acid sequence as set forth in SEQ ID NO: 7; and (c) a CDR3 having an amino acid sequence as set forth in SEQ ID NO: 15.

In certain embodiments of the invention, the CAR comprises a heavy chain variable domain region including (a) a CDR1 having an amino acid sequence as set forth in SEQ ID NO: 10; (b) a CDR2 having an amino acid sequence as set forth in SEQ ID NO: 142; and (c) a CDR3 having an amino acid sequence as set forth in SEQ ID NO: 12; and a light chain variable region including (a) a CDR1 having an amino acid sequence as set forth in SEQ ID NO: 138; (b) a CDR2 having an amino acid sequence as set forth in SEQ ID NO: 7; and (c) a CDR3 having an amino acid sequence as set forth in SEQ ID NO: 15.

In certain embodiments of the invention, the CAR comprises a heavy chain variable region comprising a CDR1 domain comprising an amino acid sequence as set forth in SEQ ID NO: 33; a CDR2 domain comprising an amino acid sequence as set forth in SEQ ID NO: 34; and a CDR3 domain comprising an amino acid sequence as set forth in SEQ ID NO: 35; and a light chain variable region comprising a CDR1 domain comprising an amino acid sequence as set forth in SEQ ID NO: 37; a CDR2 domain comprising an amino acid sequence as set forth in SEQ ID NO: 38; and a CDR3 domain comprising an amino acid sequence as set forth in SEQ ID NO: 39.

In certain embodiments of the invention, the CAR comprises a heavy chain variable region comprising a CDR1 domain comprising an amino acid sequence as set forth in SEQ ID NO: 25; a CDR2 domain comprising an amino acid sequence as set forth in SEQ ID NO: 26 or 119; and a CDR3 domain comprising an amino acid sequence as set forth in SEQ ID NO: 27; and a light chain variable region comprising a CDR1 domain comprising an amino acid sequence as set forth in SEQ ID NO: 29; a CDR2 domain comprising an amino acid sequence as set forth in SEQ ID NO: 30; and a CDR3 domain comprising an amino acid sequence as set forth in SEQ ID NO: 31.

In certain embodiments of the invention, the CAR comprises a heavy chain variable domain region including (a) a CDR1 having an amino acid sequence as set forth in SEQ ID NO: 25; (b) a CDR2 having an amino acid sequence as set forth in SEQ ID NO: 26; and (c) a CDR3 having an amino acid sequence as set forth in SEQ ID NO: 27; and a light chain variable region including (a) a CDR1 having an amino acid sequence as set forth in SEQ ID NO: 29; (b) a CDR2 having an amino acid sequence as set forth in SEQ ID NO: 30; and (c) a CDR3 having an amino acid sequence as set forth in SEQ ID NO: 31.

In certain embodiments of the invention, the CAR comprises a heavy chain variable domain region including (a) a CDR1 having an amino acid sequence as set forth in SEQ ID NO: 25; (b) a CDR2 having an amino acid sequence as set forth in SEQ ID NO: 119; and (c) a CDR3 having an amino acid sequence as set forth in SEQ ID NO: 27; and a light chain variable region including (a) a CDR1 having an amino acid sequence as set forth in SEQ ID NO: 29; (b) a CDR2 having an amino acid sequence as set forth in SEQ ID NO: 30; and (c) a CDR3 having an amino acid sequence as set forth in SEQ ID NO: 31.

One embodiment of the invention includes a labeled anti-B7-H3 antibody, or antibody portion thereof, where the antibody is derivatized or linked to one or more functional molecule(s) (e.g., another peptide or protein). For example, a labeled antibody can be derived by functionally linking an antibody or antibody portion of the invention (by chemical coupling, genetic fusion, noncovalent association or otherwise) to one or more other molecular entities, such as another antibody (e.g., a bispecific antibody or a diabody), a detectable agent, a pharmaceutical agent, a protein or peptide that can mediate the association of the antibody or antibody portion with another molecule (such as a streptavidin core region or a polyhistidine tag), and/or a cytotoxic or therapeutic agent selected from the group consisting of a mitotic inhibitor, an antitumor antibiotic, an immunomodulating agent, a vector for gene therapy, an alkylating agent, an antiangiogenic agent, an antimetabolite, a boron-containing agent, a chemoprotective agent, a hormone, an antihormone agent, a corticosteroid, a photoactive therapeutic agent, an oligonucleotide, a radionuclide agent, a topoisomerase inhibitor, a kinase inhibitor, a radiosensitizer, and a combination thereof.

Useful detectable agents with which an antibody or antibody portion thereof, may be derivatized include fluorescent compounds. Exemplary fluorescent detectable agents include fluorescein, fluorescein isothiocyanate, rhodamine, 5-dimethylamine-1-napthalenesulfonyl chloride, phycoerythrin and the like. An antibody may also be derivatized with detectable enzymes, such as alkaline phosphatase, horseradish peroxidase, glucose oxidase and the like. When an antibody is derivatized with a detectable enzyme, it is detected by adding additional reagents that the enzyme uses to produce a detectable reaction product. For example, when the detectable agent horseradish peroxidase is present the addition of hydrogen peroxide and diaminobenzidine leads to a colored reaction product, which is detectable. An antibody may also be derivatized with biotin, and detected through indirect measurement of avidin or streptavidin binding.

In one embodiment, the antibody of the invention is conjugated to an imaging agent. Examples of imaging agents that may be used in the compositions and methods described herein include, but are not limited to, a radiolabel (e.g., indium), an enzyme, a fluorescent label, a luminescent label, a bioluminescent label, a magnetic label, and biotin.

In one embodiment, the antibodies or ADCs are linked to a radiolabel, such as, but not limited to, indium ($^{111}$In). $^{111}$Indium may be used to label the antibodies and ADCs described herein for use in identifying B7-H3 positive tumors. In a certain embodiment, anti-B7-H3 antibodies (or ADCs) described herein are labeled with $^{111}$I via a bifunctional chelator which is a bifunctional cyclohexyl diethylenetriaminepentaacetic acid (DTPA) chelate (see U.S. Pat. Nos. 5,124,471; 5,434,287; and 5,286,850, each of which is incorporated herein by reference).

Another embodiment of the invention provides a glycosylated binding protein wherein the anti-B7-H3 antibody or antigen binding portion thereof comprises one or more carbohydrate residues. Nascent in vivo protein production may undergo further processing, known as post-translational modification. In particular, sugar (glycosyl) residues may be added enzymatically, a process known as glycosylation. The resulting proteins bearing covalently linked oligosaccharide side chains are known as glycosylated proteins or glycoproteins. Antibodies are glycoproteins with one or more carbohydrate residues in the Fc domain, as well as the variable domain. Carbohydrate residues in the Fc domain have important effect on the effector function of the Fc domain, with minimal effect on antigen binding or half-life of the antibody (R. Jefferis, *Biotechnol. Prog.* 21 (2005), pp. 11-16). In contrast, glycosylation of the variable domain may have an effect on the antigen binding activity of the antibody. Glycosylation in the variable domain may have a negative effect on antibody binding affinity, likely due to steric hindrance (Co, M. S., et al., *Mol. Immunol.* (1993) 30:1361-1367), or result in increased affinity for the antigen (Wallick, S. C., et al., *Exp. Med.* (1988) 168:1099-1109; Wright, A., et al., *EMBO J.* (1991) 10:2717-2723).

One aspect of the invention is directed to generating glycosylation site mutants in which the O- or N-linked glycosylation site of the binding protein has been mutated. One skilled in the art can generate such mutants using standard well-known technologies. Glycosylation site mutants that retain the biological activity, but have increased or decreased binding activity, are another object of the invention.

In still another embodiment, the glycosylation of the anti-B7-H3 antibody or antigen binding portion of the invention is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region glycosylation sites to thereby eliminate glycosylation at that site. Such aglycosylation may increase the affinity of the antibody for antigen. Such an approach is described in further detail in PCT Publication WO2003016466A2, and U.S. Pat. Nos. 5,714,350 and 6,350,861, each of which is incorporated herein by reference in its entirety.

Additionally or alternatively, a modified anti-B7-H3 antibody of the invention can be made that has an altered type of glycosylation, such as a hypofucosylated antibody having reduced amounts of fucosyl residues or an antibody having increased bisecting GlcNAc structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. See, for example, Shields, R. L. et al. (2002) *J. Biol. Chem.* 277:26733-26740; Umana et al. (1999) *Nat. Biotech.* 17:176-1, as well as, European Patent No: EP 1,176,195; PCT Publications WO 03/035835; WO 99/54342 80, each of which is incorporated herein by reference in its entirety.

Protein glycosylation depends on the amino acid sequence of the protein of interest, as well as the host cell in which the protein is expressed. Different organisms may produce different glycosylation enzymes (e.g., glycosyltransferases and glycosidases), and have different substrates (nucleotide sugars) available. Due to such factors, protein glycosylation pattern, and composition of glycosyl residues, may differ depending on the host system in which the particular protein is expressed. Glycosyl residues useful in the invention may include, but are not limited to, glucose, galactose, mannose, fucose, n-acetylglucosamine and sialic acid. Preferably the glycosylated binding protein comprises glycosyl residues such that the glycosylation pattern is human.

Differing protein glycosylation may result in differing protein characteristics. For instance, the efficacy of a therapeutic protein produced in a microorganism host, such as yeast, and glycosylated utilizing the yeast endogenous pathway may be reduced compared to that of the same protein expressed in a mammalian cell, such as a CHO cell line. Such glycoproteins may also be immunogenic in humans and show reduced half-life in vivo after administration. Specific receptors in humans and other animals may recognize specific glycosyl residues and promote the rapid clearance of the protein from the bloodstream. Other adverse effects may include changes in protein folding, solubility, susceptibility to proteases, trafficking, transport, compartmentalization, secretion, recognition by other proteins or factors, antigenicity, or allergenicity. Accordingly, a practitioner may prefer a therapeutic protein with a specific composition and pattern of glycosylation, for example glycosylation composition and pattern identical, or at least similar, to that produced in human cells or in the species-specific cells of the intended subject animal.

Expressing glycosylated proteins different from that of a host cell may be achieved by genetically modifying the host cell to express heterologous glycosylation enzymes. Using recombinant techniques, a practitioner may generate antibodies or antigen binding portions thereof exhibiting human protein glycosylation. For example, yeast strains have been genetically modified to express non-naturally occurring glycosylation enzymes such that glycosylated proteins (glycoproteins) produced in these yeast strains exhibit protein glycosylation identical to that of animal cells, especially human cells (U.S. patent Publication Nos. 20040018590 and 20020137134 and PCT publication WO2005100584 A2).

Antibodies may be produced by any of a number of techniques. For example, expression from host cells, wherein expression vector(s) encoding the heavy and light chains is (are) transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is possible to express antibodies in either prokaryotic or eukaryotic host cells, expression of antibodies in eukaryotic cells is preferable, and most preferable in mammalian host cells, because such eukaryotic cells (and in particular mammalian cells) are more likely than prokaryotic cells to assemble and secrete a properly folded and immunologically active antibody.

Preferred mammalian host cells for expressing the recombinant antibodies of the invention include Chinese Hamster Ovary (CHO cells) (including dhfr-CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *Mol. Biol.* 159:601-621), NS0 myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Host cells can also be used to produce functional antibody fragments, such as Fab fragments or scFv molecules. It will be understood that variations on the above procedure are within the scope of the invention. For example, it may be desirable to transfect a host cell with DNA encoding functional fragments of either the light chain and/or the heavy chain of an antibody of this invention. Recombinant DNA technology may also be used to remove some, or all, of the DNA encoding either or both of the light and heavy chains that is not necessary for binding to the antigens of interest. The molecules expressed from such truncated DNA molecules are also encompassed by the antibodies of the invention. In addition, bifunctional antibodies may be produced in which one heavy and one light chain are an antibody of the invention and the other heavy and light chain are specific for an antigen other than the antigens of interest by crosslinking an antibody of the invention to a second antibody by standard chemical crosslinking methods.

In a preferred system for recombinant expression of an antibody, or antigen binding portion thereof, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium. Still further the invention provides a method of synthesizing a recombinant antibody of the invention by culturing a host cell in a suitable culture medium until a recombinant antibody is synthesized. Recombinant antibodies of the invention may be produced using nucleic acid molecules corresponding to the amino acid sequences disclosed herein The method can further comprise isolating the recombinant antibody from the culture medium.

The N- and C-termini of antibody polypeptide chains of the present invention may differ from the expected sequence due to commonly observed post-translational modifications. For example, C-terminal lysine residues are often missing from antibody heavy chains. Dick et al. (2008) Biotechnol. Bioeng. 100:1132. N-terminal glutamine residues, and to a lesser extent glutamate residues, are frequently converted to pyroglutamate residues on both light and heavy chains of therapeutic antibodies. Dick et al. (2007) Biotechnol. Bioeng. 97:544; Liu et al. (2011) JBC 28611211; Liu et al. (2011) J. Biol. Chem. 286:11211.

III. Anti-B7-H3 Antibody Drug Conjugates (ADCs)

Anti-B7-H3 antibodies described herein may be conjugated to a drug moiety to form an anti-B7-H3 Antibody Drug Conjugate (ADC). Antibody-drug conjugates (ADCs) may increase the therapeutic efficacy of antibodies in treating disease, e.g., cancer, due to the ability of the ADC to selectively deliver one or more drug moiety(s) to target tissues, such as a tumor-associated antigen, e.g., B7-H3 expressing tumors. Thus, in certain embodiments, the invention provides anti-B7-H3 ADCs for therapeutic use, e.g., treatment of cancer.

Anti-B7-H3 ADCs of the invention comprise an anti-B7-H3 antibody, i.e., an antibody that specifically binds to B7-H3, linked to one or more drug moieties. The specificity of the ADC is defined by the specificity of the antibody, i.e., anti-B7-H3. In one embodiment, an anti-B7-H3 antibody is linked to one or more cytotoxic drug(s) which is delivered internally to a transformed cancer cell expressing B7-H3.

Examples of drugs that may be used in the anti-B7-H3 ADC of the invention are provided below, as are linkers that may be used to conjugate the antibody and the one or more drug(s). The terms "drug," "agent," and "drug moiety" are used interchangeably herein. The terms "linked" and "conjugated" are also used interchangeably herein and indicate that the antibody and moiety are covalently linked.

In some embodiments, the ADC has the following formula (formula I):

wherein Ab is the antibody, e.g., anti-B7-H3 antibody huAb13v1, huAb3v2.5, or huAb3v2.6, and (L) is a linker, (D) is a drug, and LK represents a covalent linkage linking linker L to antibody Ab; and m is an integer ranging from 1 to 20. D is a drug moiety having, for example, cytostatic, cytotoxic, or otherwise therapeutic activity against a target cell, e.g., a cell expressing B7-H3. In some embodiments, m ranges from 1 to 8, 1 to 7, 1 to 6, 2 to 6, 1 to 5, 1 to 4, 1 to 3, 1 to 2, 1.5 to 8, 1.5 to 7, 1.5 to 6, 1.5 to 5, 1.5 to 4, 2 to 6, 1 to 5, 1 to 4, 1 to 3, 1 to 2,or 2 to 4. The DAR of an ADC is equivalent to the "m" referred to in Formula I. In one embodiment, the ADC has a formula of Ab-(LK-L-D)$_m$, wherein Ab is an anti-B7-H3 antibody, e.g. huAb13v1, huAb3v2.5, or huAb3v2.6, L is a linker, D is a drug, e.g., a Bcl-xL inhibitor or an auristatin such as MMAF or MMAE, and m is 2 to 4 (equivalent to a DAR of 2-4). Additional details regarding drugs (D of Formula I) and linkers (L of Formula I) that may be used in the ADCs of the invention, as well as alternative ADC structures, are described below.

III. A. Anti-B7-H3 ADCs: Bcl-xL Inhibitors, Linkers, Synthons, and Methods of Making Same Dysregulated apoptotic pathways have also been implicated in the pathology of cancer. The implication that down-regulated apoptosis (and more particularly the Bcl-2 family of proteins) is involved in the onset of cancerous malignancy has revealed a novel way of targeting this still elusive disease. Research has shown, for example, the anti-apoptotic proteins, Bcl 2 and Bcl-xL, are over-expressed in many cancer cell types. See, Zhang, 2002, Nature Reviews/Drug Discovery 1:101; Kirkin et al., 2004, Biochimica Biophysica Acta 1644:229-249; and Amundson et al., 2000, Cancer Research 60:6101-6110. The effect of this deregulation is the survival of altered cells which would otherwise have undergone apoptosis in normal conditions. The repetition of these defects associated with unregulated proliferation is thought to be the starting point of cancerous evolution.

Aspects of the disclosure concern anti-hB7-H3 ADCs comprising an anti-hB7-H3 antibody conjugated to a drug via a linker, wherein the drug is a Bcl-xL inhibitor. In specific embodiments, the ADCs are compounds according to structural formula (I) below, or a pharmaceutically acceptable salt thereof, wherein Ab represents the anti-hB7-H3 antibody, D represents a Bcl-xL inhibitor drug (i.e., a compound of formula (IIa), (IIb), (IIc), or (IId) as shown below), L represents a linker, LK represents a covalent linkage linking the linker (L) to the anti-hB7-H3 antibody (Ab) and m represents the number of D-L-LK units linked to the antibody, which is an integer ranging from 1 to 20. In certain embodiments, m is 2, 3 or 4. In some embodiments, m ranges from 1 to 8, 1 to 7, 1 to 6, 2 to 6, 1 to 5, 1 to 4, 2 to 4, 1 to 3, 1 to 2, or is 1.

Specific embodiments of various Bcl-xL inhibitors per se, and various Bcl-xL inhibitors (D), linkers (L) and anti-B7-H3 antibodies (Ab) that can comprise the ADCs described herein, as well as the number of Bcl-xL inhibitors linked to the ADCs, are described in more detail below.

Examples of Bcl-xL inhibitors that may be used in the anti-B7-H3 ADC of the invention are provided below, as are linkers that may be used to conjugate the antibody and the one or more Bcl-xL inhibitor(s). The terms "linked" and "conjugated" are also used interchangeably herein and indicate that the antibody and moiety are covalently linked.

III.A.1. Bcl-xL Inhibitors

One aspect of the instant disclosure concerns Bcl-xL inhibitors that have low cell permeability. The compounds are generally heterocyclic in nature and include one or more solubilizing groups that impart the compounds with high water solubility and low cell permeability. The solubilizing groups are generally groups that are capable of hydrogen bonding, forming dipole-dipole interactions, and/or that include a polyethylene glycol polymer containing from 1 to 30 units, one or more polyols, one or more salts, or one or more groups that are charged at physiological pH.

The Bcl-xL inhibitors may be used as compounds or salts per se in the various methods described herein, or may be included as a component part of an ADC.

Specific embodiments of Bcl-xL inhibitors that may be used in unconjugated form, or that may be included as part of an ADC include compounds according to structural formulae (IIa), (IIb), (IIc), or (IId). In the present invention, when the Bcl-xL inhibitors are included as part of an ADC, # shown in structural formula (IIa), (IIb), (IIc), or (IId) below represents a point of attachment to a linker, which indicates that they are represented in a monoradical form.

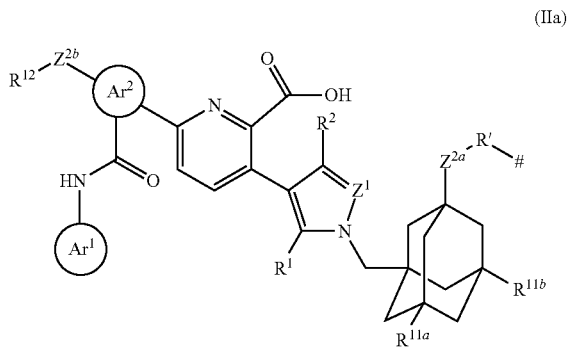

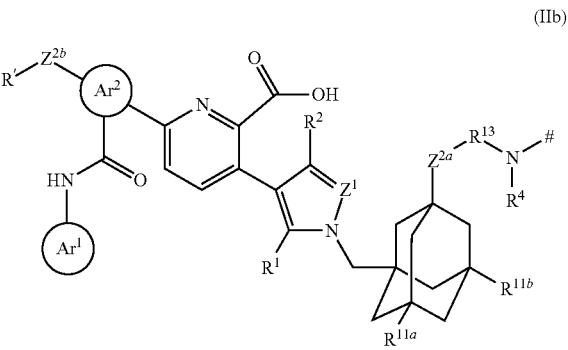

-continued (IIc)

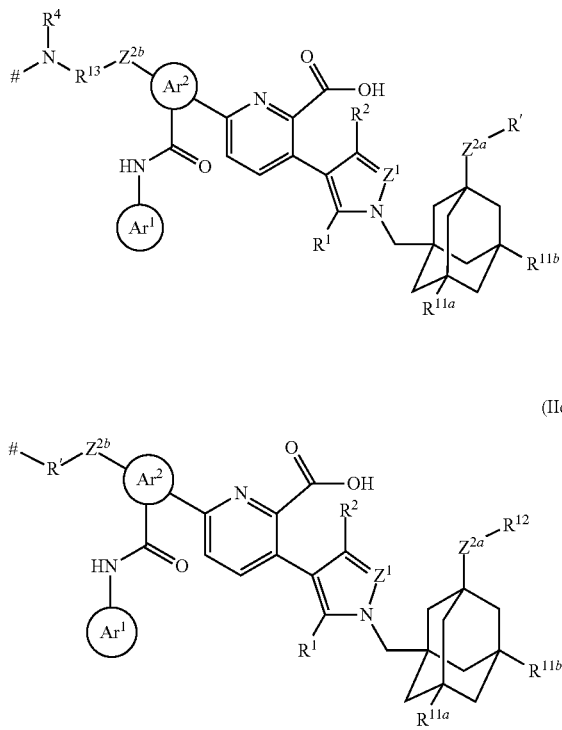

(IId)

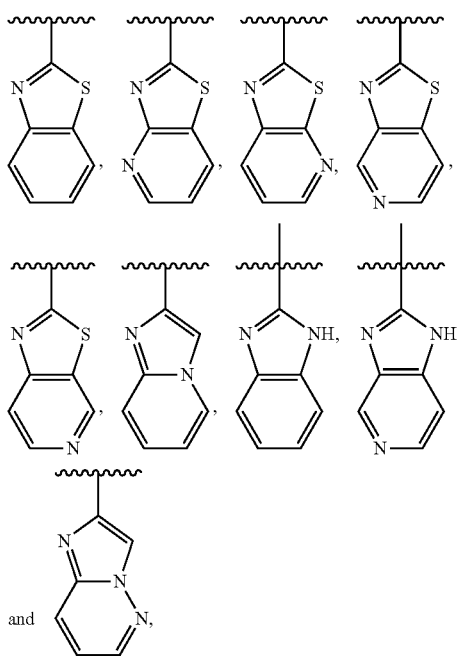

or a pharmaceutically acceptable salt thereof, wherein:

$Ar^1$ is selected from

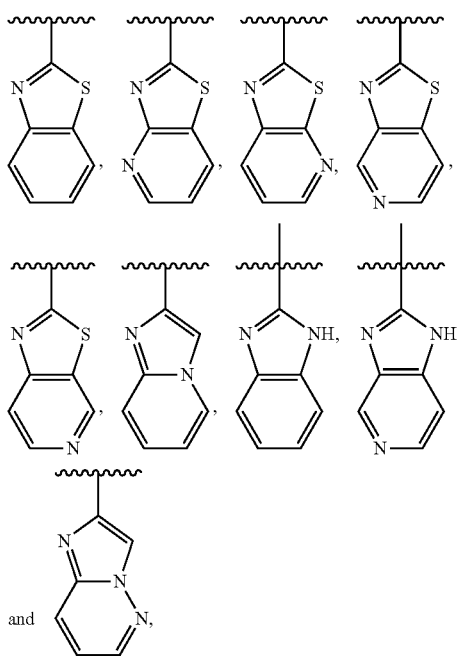

and is optionally substituted with one or more substituents independently selected from halo, hydroxy, nitro, lower alkyl, lower heteroalkyl, $C_{1-4}$alkoxy, amino, cyano and halomethyl;

$Ar^2$ is selected from

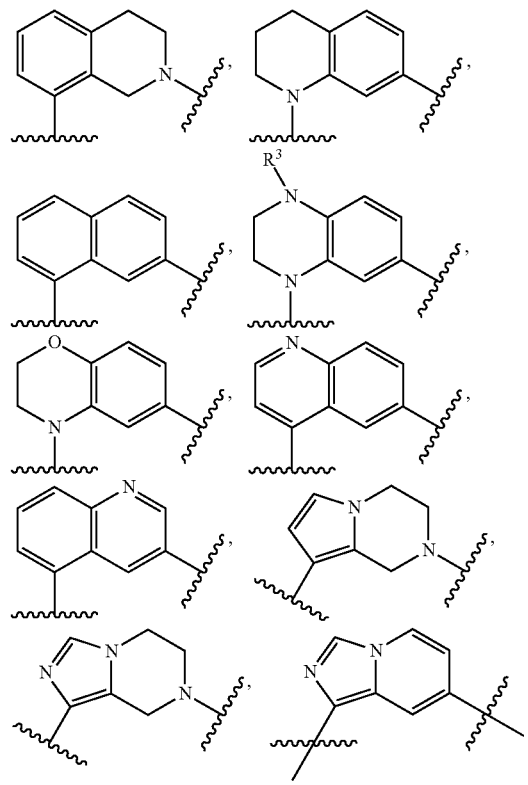

and is optionally substituted with one or more substituents independently selected from halo, hydroxy, nitro, lower alkyl, lower heteroalkyl, $C_{1-4}$alkoxy, amino, cyano and halomethyl, wherein the $R^{12}$—$Z^{2b}$—, $R'$—$Z^{2b}$-, #—$N(R^4)$—$R^{13}$—$Z^{2b}$—, or #—$R'$—$Z^{2b}$— substituents are attached to $Ar^2$ at any $Ar^2$ atom capable of being substituted;

$Z^1$ is selected from N, CH, C-halo, C—$CH_3$ and C—CN;

$Z^{2a}$ and $Z^{2b}$ are each, independently from one another, selected from a bond, $NR^6$, $CR^{6a}R^{6b}$, O, S, S(O), S(O)$_2$, —$NR^6C(O)$—, —$NR^{6a}C(O)NR^{6b}$—, and —$NR^6C(O)O$—;

R' is a alkylene, heteroalkylene, cycloalkylene, heterocyclene, aryl or heteroaryl independently substituted at one or more carbon or heteroatoms with a solubilizing moiety containing a group selected from a polyol, a polyethylene glycol containing from 4 to 30 ethylene glycol units, a salt, and a group that is charged at physiological pH and combinations thereof, wherein #, where attached to R', is attached to R' at any R' atom capable of being substituted;

$R^1$ is selected from hydrogen, methyl, halo, halomethyl, ethyl, and cyano;

$R^2$ is selected from hydrogen, methyl, halo, halomethyl and cyano;

$R^3$ is selected from hydrogen, methyl, ethyl, halomethyl and haloethyl;

$R^4$ is selected from hydrogen, lower alkyl and lower heteroalkyl or is taken together with an atom of $R^{13}$ to form a cycloalkyl or heterocyclyl ring having between 3 and 7 ring atoms;

$R^6$, $R^{6a}$ and $R^{6b}$ are each, independent from one another, selected from hydrogen, optionally substituted lower alkyl, optionally substituted lower heteroalkyl, optionally substituted cycloalkyl and optionally substituted heterocyclyl, or are taken together with an atom from $R^4$ and an atom from $R^{13}$ to form a cycloalkyl or heterocyclyl ring having between 3 and 7 ring atoms;

$R^{11a}$ and $R^{11b}$ are each, independently of one another, selected from hydrogen, halo, methyl, ethyl, halomethyl, hydroxyl, methoxy, CN, and $SCH_3$;

$R^{12}$ is optionally R' or is selected from hydrogen, halo, cyano, optionally substituted alkyl, optionally substituted heteroalkyl, optionally substituted heterocyclyl, and optionally substituted cycloalkyl;

$R^{13}$ is selected from optionally substituted $C_{1-8}$ alkylene, optionally substituted heteroalkylene, optionally substituted heterocyclene, and optionally substituted cycloalkylene; and # represents the point of attachment to a linker L.

One embodiment of Bcl-xL inhibitors that may be used in unconjugated form, or that may be included as part of an ADC include compounds according to structural formulae (IIa), (IIb), (IIc), or (IId):

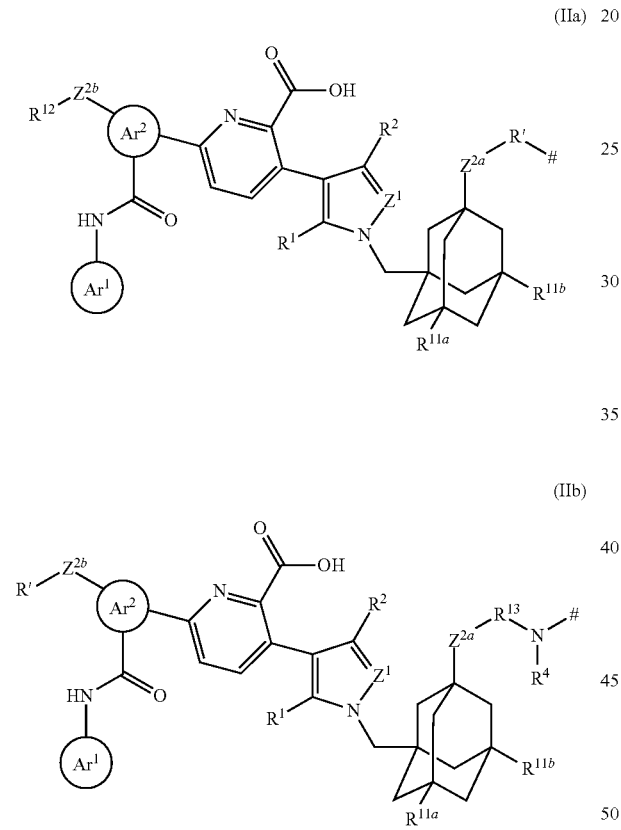

(IIa)

(IIb)

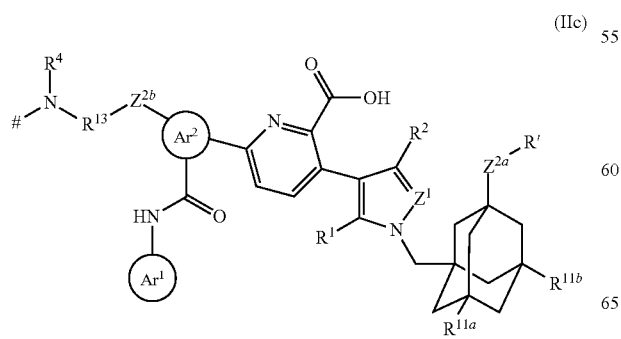

(IIc)

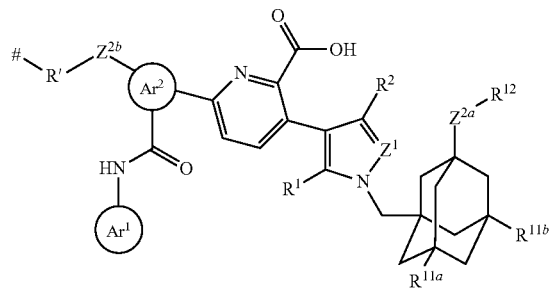

(IId)

or a pharmaceutically acceptable salt thereof, wherein:

$Ar^1$ is selected from

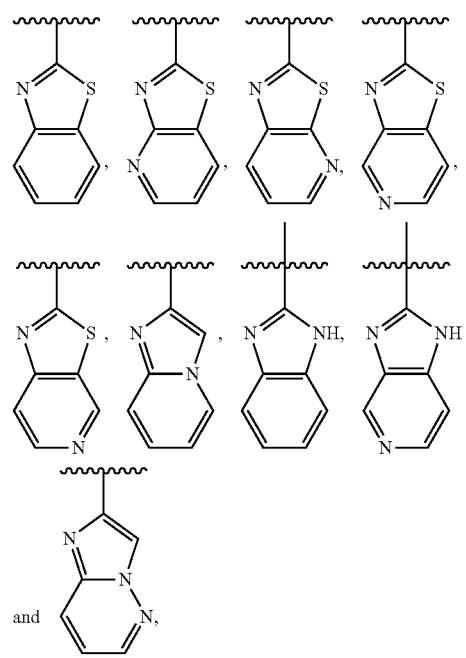

and is optionally substituted with one or more substituents independently selected from halo, hydroxy, nitro, lower alkyl, lower heteroalkyl, $C_{1-4}$alkoxy, amino, cyano and halomethyl;

$Ar^2$ is selected from

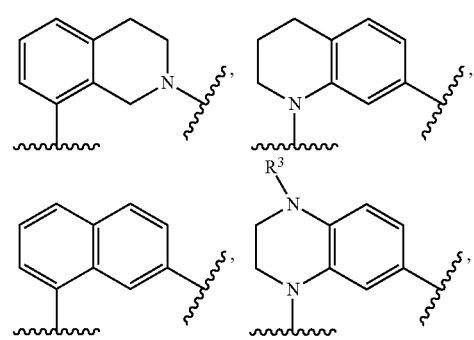

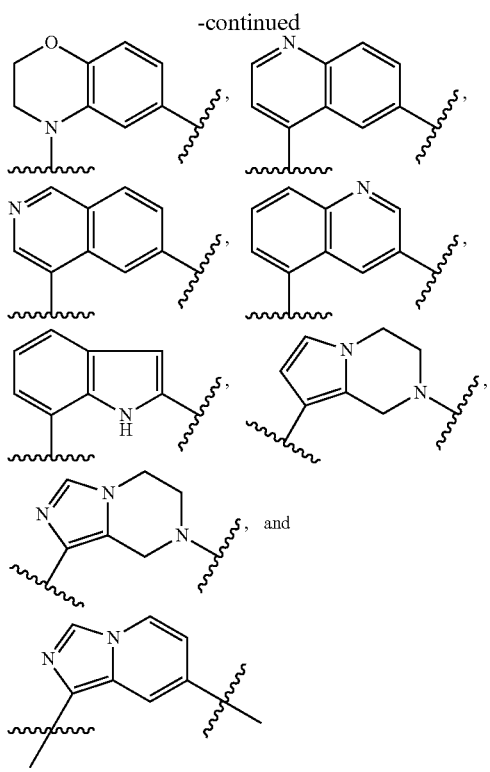

or an N-oxide thereof, and is optionally substituted with one or more substituents independently selected from halo, hydroxy, nitro, lower alkyl, lower heteroalkyl, $C_{1-4}$alkoxy, amino, cyano and halomethyl, wherein the $R^{12}$—$Z^{2b}$—, $R'$—$Z^{2b}$—, #—$N(R^4)$—$R^{13}$—$Z^{2b}$—, or #—$R'$—$Z^{2b}$— substituents are attached to $Ar^2$ at any $Ar^2$ atom capable of being substituted;

$Z^1$ is selected from N, CH, C-halo, C—$CH_3$ and C—CN;

$Z^{2a}$ and $Z^{2b}$ are each, independently from one another, selected from a bond, $NR^6$, $CR^{6a}R^{6b}$, O, S, S(O), $S(O)_2$, —$NR^6C(O)$—, —$NR^{6a}C(O)NR^{6b}$—, and —$NR^6C(O)O$—;

R' is

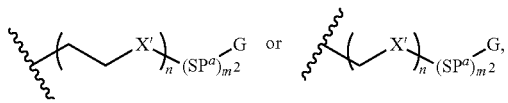

wherein #, where attached to R', is attached to R' at any R' atom capable of being substituted;

X' is selected at each occurrence from —$N(R^{10})$—, —$N(R^{10})C(O)$—, —$N(R^{10})S(O)_2$—, —$S(O)_2N(R^{10})$—, and —O—;

n is selected from 0-3;

$R^{10}$ is independently selected at each occurrence from hydrogen, lower alkyl, heterocycle, aminoalkyl, G-alkyl, and —$(CH_2)_2$—O—$(CH_2)_2$—O—$(CH_2)_2$—$NH_2$;

G at each occurrence is independently selected from a polyol, a polyethylene glycol with between 4 and 30 repeating units, a salt and a moiety that is charged at physiological pH;

$SP^a$ is independently selected at each occurrence from oxygen, —$S(O)_2N(H)$—, —$N(H)S(O)_2$—, —$N(H)C(O)$—, —$C(O)N(H)$—, —$N(H)$—, arylene, heterocyclene, and optionally substituted methylene; wherein methylene is optionally substituted with one or more of —$NH(CH_2)_2G$, $NH_2$, $C_{1-8}$alkyl, and carbonyl;

$m^2$ is selected from 0-12;

$R^1$ is selected from hydrogen, methyl, halo, halomethyl, ethyl, and cyano;

$R^2$ is selected from hydrogen, methyl, halo, halomethyl and cyano;

$R^3$ is selected from hydrogen, methyl, ethyl, halomethyl and haloethyl;

$R^4$ is selected from hydrogen, lower alkyl and lower heteroalkyl or is taken together with an atom of $R^{13}$ to form a cycloalkyl or heterocyclyl ring having between 3 and 7 ring atoms;

$R^6$, $R^{6a}$ and $R^{6b}$ are each, independent from one another, selected from hydrogen, optionally substituted lower alkyl, optionally substituted lower heteroalkyl, optionally substituted cycloalkyl and optionally substituted heterocyclyl, or are taken together with an atom from $R^4$ and an atom from $R^{13}$ to form a cycloalkyl or heterocyclyl ring having between 3 and 7 ring atoms;

$R^{11a}$ and $R^{11b}$ are each, independently of one another, selected from hydrogen, halo, methyl, ethyl, halomethyl, hydroxyl, methoxy, CN, and $SCH_3$;

$R^{12}$ is optionally R' or is selected from hydrogen, halo, cyano, optionally substituted alkyl, optionally substituted heteroalkyl, optionally substituted heterocyclyl, and optionally substituted cycloalkyl;

$R^{13}$ is selected from optionally substituted $C_{1-8}$ alkylene, optionally substituted heteroalkylene, optionally substituted heterocyclene, and optionally substituted cycloalkylene; and # represents the point of attachment to a linker L.

When a Bcl-xL inhibitor of structural formulae (IIa)-(IId) is not a component of an ADC, # in formulae (IIa)-(IId) represents the point of attachment to a hydrogen atom. When the Bcl-xL inhibitor is a component of an ADC, # in formulae (IIa)-(IId) represents the point of attachment to the linker. When a Bcl-xL inhibitor is a component of an ADC, the ADC may comprise one or more Bcl-xL inhibitors, which may be the same or different, but are typically the same.

In certain embodiments, R' is a $C_2$-$C_8$ heteroalkylene substituted with one or more moieties containing a salt and/or a group that is charged at physiological pH. The salt may be selected, for example, from the salt of a carboxylate, a sulfonate, a phosphonate, and an ammonium ion. For example, the salt may be the sodium or potassium salt of a carboxylate, sulfonate or phosphonate or the chloride salt of an ammonium ion. The group that is charged at physiological pH may be any group that is charged at a physiological pH, including, by way of example and not limitation, a zwitterionic group. In certain embodiments a group that is a salt is a dipolar moiety such as, but not limited to, N-oxides of amines including certain heterocyclyls such as, but not limited to, pyridine and quinoline. In specific embodiments the group that is charged at physiological pH is selected independently at each occurrence, from carboxylate, sulfonate, phosphonate, and amine.

In certain embodiments, R' is a $C_2$-$C_8$ heteroalkylene substituted with one or more moieties containing polyethylene glycol or a polyol such as a diol or a sugar moiety.

In certain embodiments, R' may be substituted with groups in addition to a solubilizing moiety. For example, R' may be substituted with one or more of the same or different alkyl, heteroalkyl, cycloalkyl, heterocyclyl, aryl, heteroaryl, or halo groups.

In certain embodiments, R' is represented by the formula:

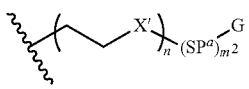

or a pharmaceutically acceptable salt thereof, wherein:

X' is selected at each occurrence from —N(R$^{10}$)— and —O—;

n is selected from 1-3;

R$^{10}$ is individually selected at each occurrence from hydrogen, alkyl, heterocycle, aminoalkyl, G-alkyl, heterocycle, and —(CH$_2$)$_2$—O—(CH$_2$)$_2$—O—(CH$_2$)$_2$—NH$_2$;

G at each occurrence is independently selected from a polyol, a polyethylene glycol with between 4 and 30 repeating unit (referred to herein as PEG4-30), a salt and a moiety that is charged at physiological pH;

SP$^a$ is independently selected at each occurrence from oxygen, sulfonamide, arylene, heterocyclene, and optionally substituted methylene; wherein methylene is optionally substituted with one or more of —NH(CH$_2$)$_2$G, amine and carbonyl; and m$^2$ is selected from 0-6, wherein there is at least one substitutable nitrogen in R' that is attached to a linker or a hydrogen atom at a substitutable nitrogen atom of R'.

In certain embodiments, R' is

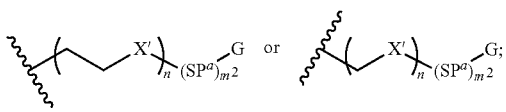

X' is selected at each occurrence from —N(R$^{10}$)—, —N(R$^{10}$)C(O)—, —N(R$^{10}$)S(O)$_2$—, —S(O)$_2$N(R$^{10}$)—, and —O—;

n is selected from 0-3;

R$^{10}$ is independently selected at each occurrence from hydrogen, alkyl, heterocycle, aminoalkyl, G-alkyl, heterocycle, and —(CH$_2$)$_2$—O—(CH$_2$)$_2$—O—(CH$_2$)$_2$—NH$_2$;

G at each occurrence is independently selected from a polyol, a polyethylene glycol with between 4 and 30 repeating units, a salt and a moiety that is charged at physiological pH;

SP$^a$ is independently selected at each occurrence from oxygen-S(O)$_2$N(H)—, —N(H)S(O)$_2$—, —N(H)C(O)—, —C(O)N(H)—, —N(H)—, arylene, heterocyclene, and optionally substituted methylene; wherein methylene is optionally substituted with one or more of —NH(CH$_2$)$_2$G, amine, alkyl, and carbonyl;

m$^2$ is selected from 0-12, and

, where attached to R', is attached to R' at any R' atom capable of being substituted.

In certain embodiments, G at each occurrence is a salt or a moiety that is charged at physiological pH.

In certain embodiments, G at each occurrence is a salt of a carboxylate, a sulfonate, a phosphonate, or ammonium.

In certain embodiments, G at each occurrence is a moiety that is charged at physiological pH selected from the group consisting of carboxylate, a sulfonate, a phosphonate, and an amine.

In certain embodiments, G at each occurrence is a moiety containing a polyethylene glycol with between 4 and 30 repeating units, or a polyol.

In certain embodiments, the polyol is a sugar.

In certain embodiments, R' of formula (IIa) or (IId) includes at least one substitutable nitrogen suitable for attachment to a linker.

In certain embodiments, G is selected independently at each occurrence from:

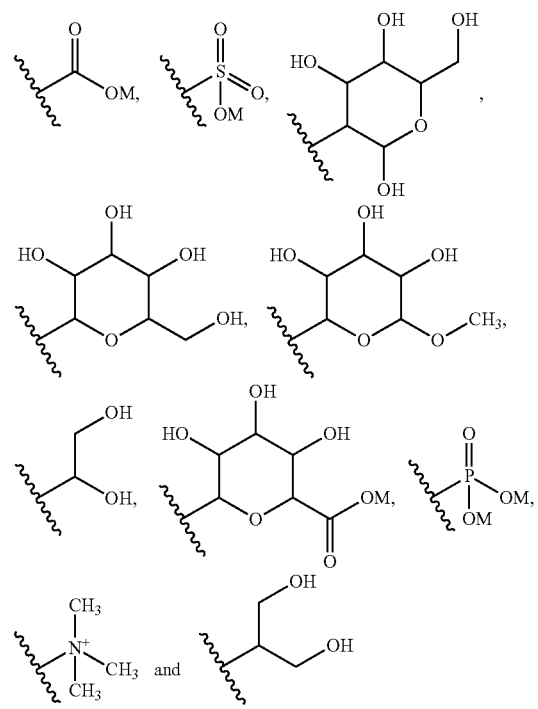

wherein M is hydrogen or a positively charged counterion. In certain embodiments, M is Na$^+$, K$^+$ or Li$^+$. In certain embodiments, M is hydrogen. In particular embodiments, G is SO$_3$H.

In certain embodiments, G is selected independently at each occurrence from:

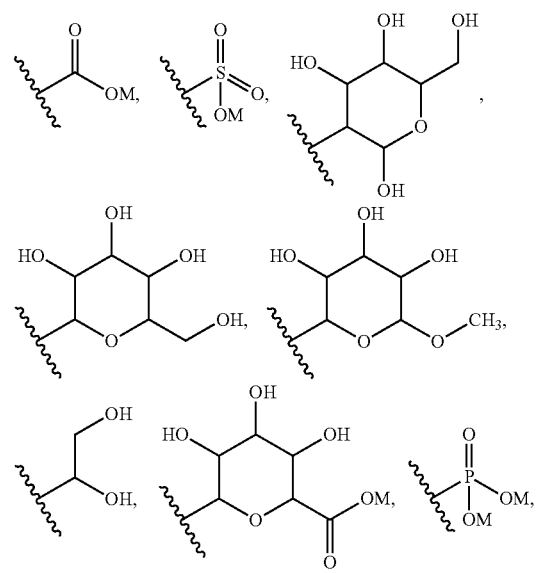

109
-continued
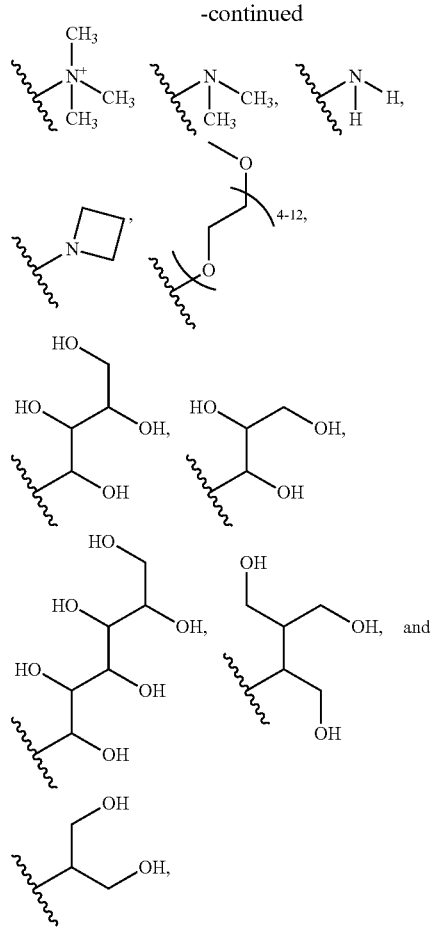
wherein M is hydrogen or a positively charged counterion.
In certain embodiments, M is hydrogen.
In particular embodiments, G is $SO_3H$.
In certain embodiments, R' is selected from:
110
-continued
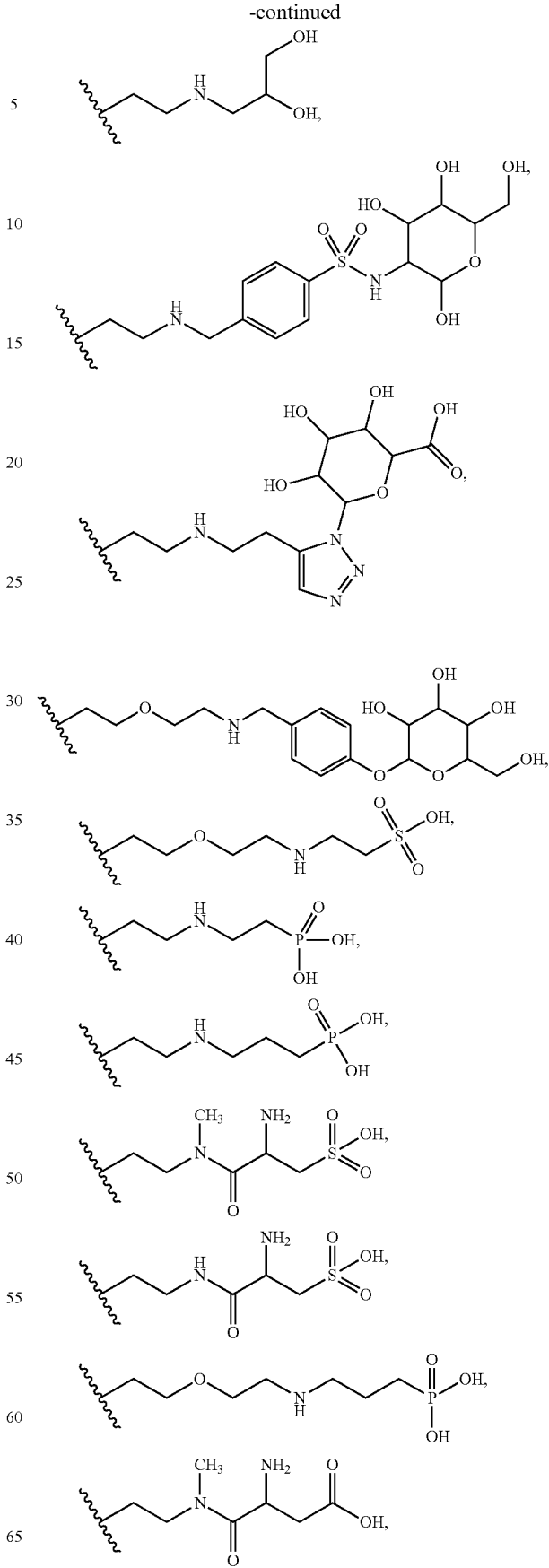

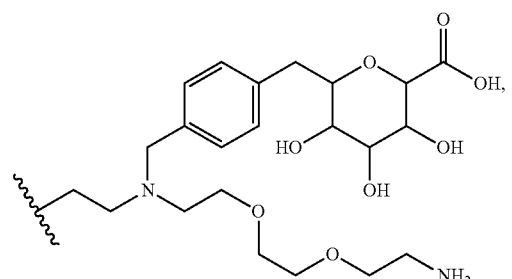
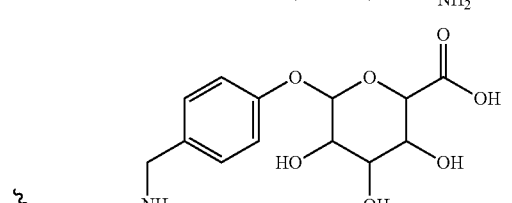
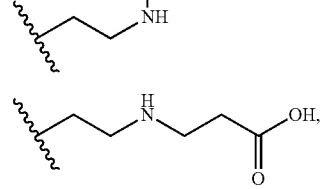
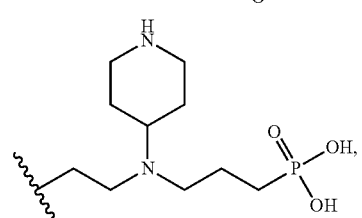
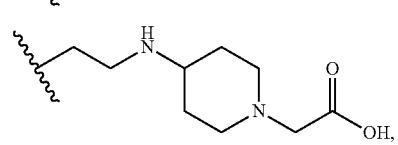
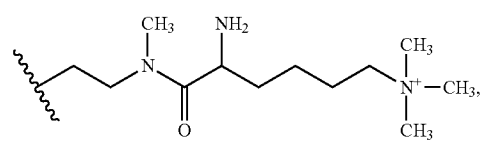
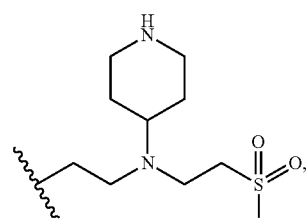
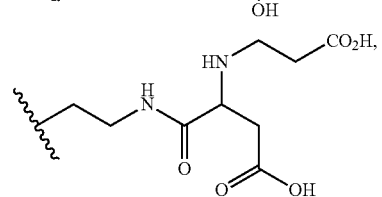
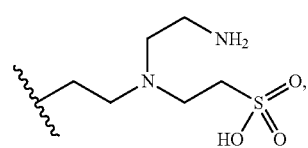
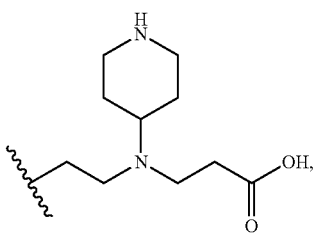
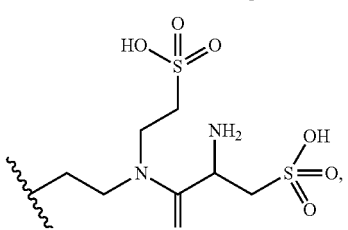
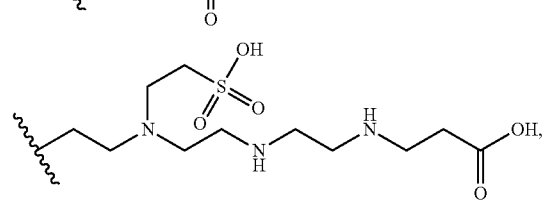
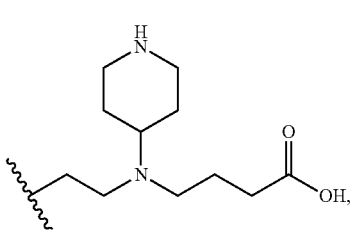
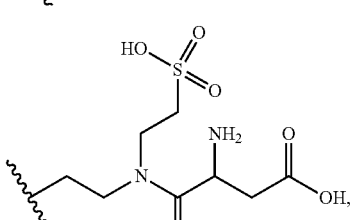
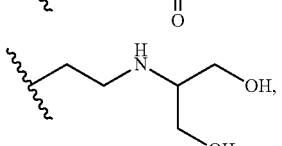
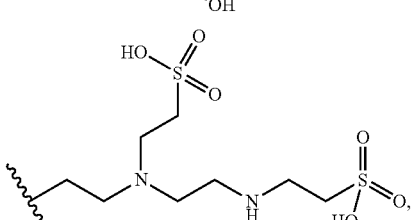
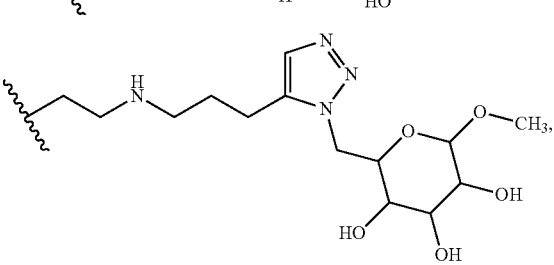

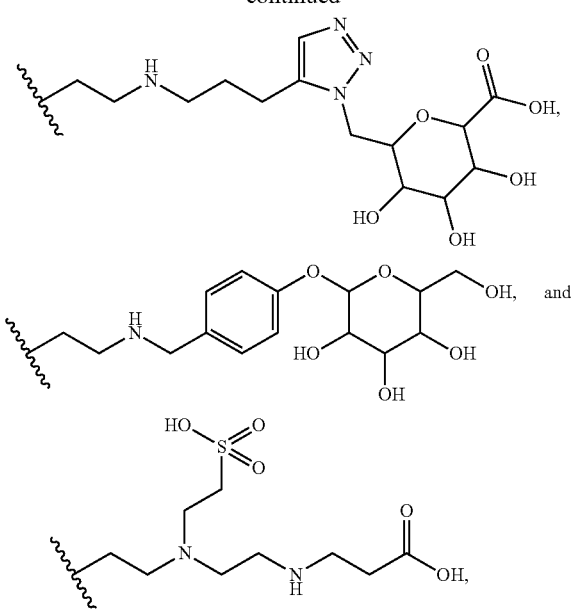
or a salt thereof. When Bcl-xL inhibitors of this embodiment are included in an ADC, the linker of the ADC is linked to the nitrogen atom of an available primary or secondary amine group.
In certain embodiments, R' is selected from:
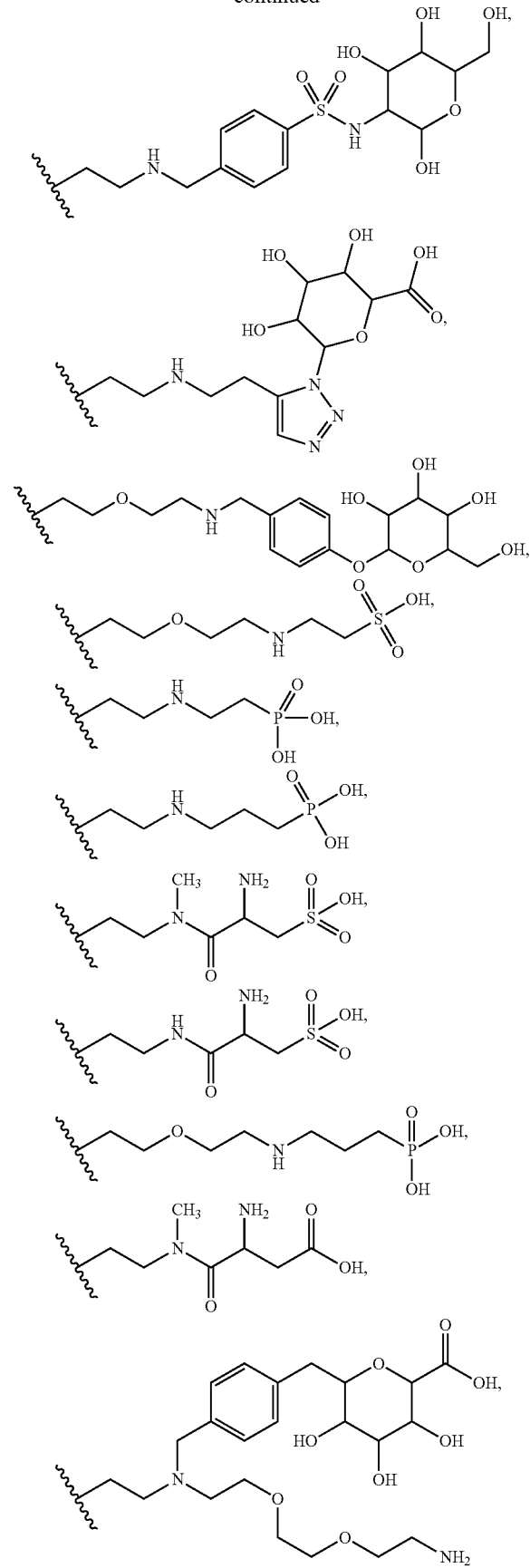

115
-continued
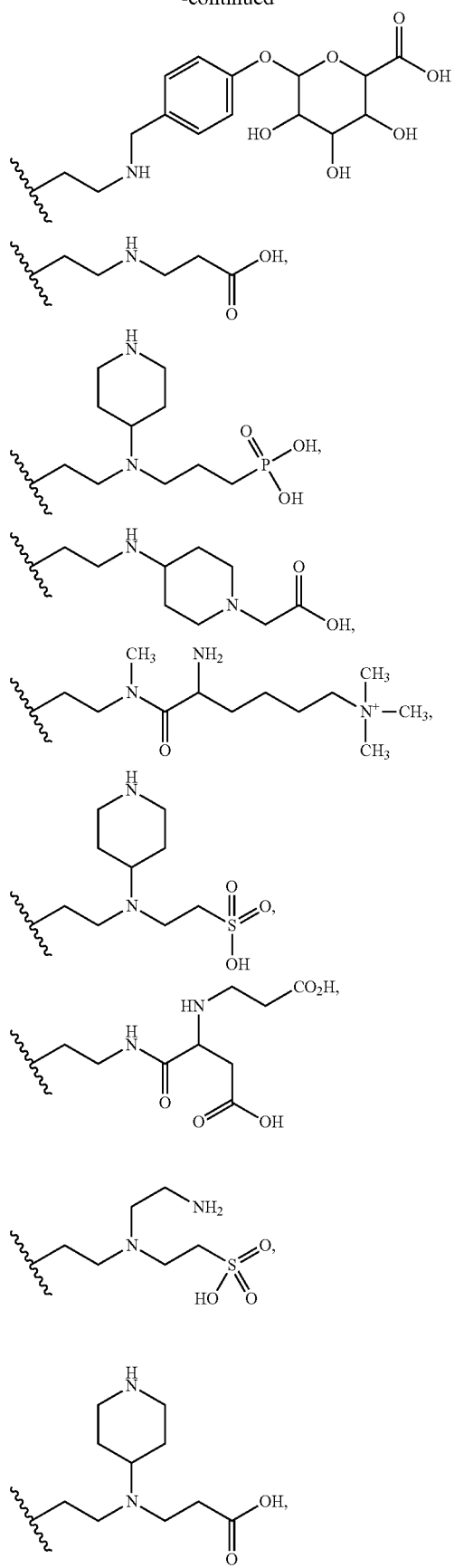
116
-continued
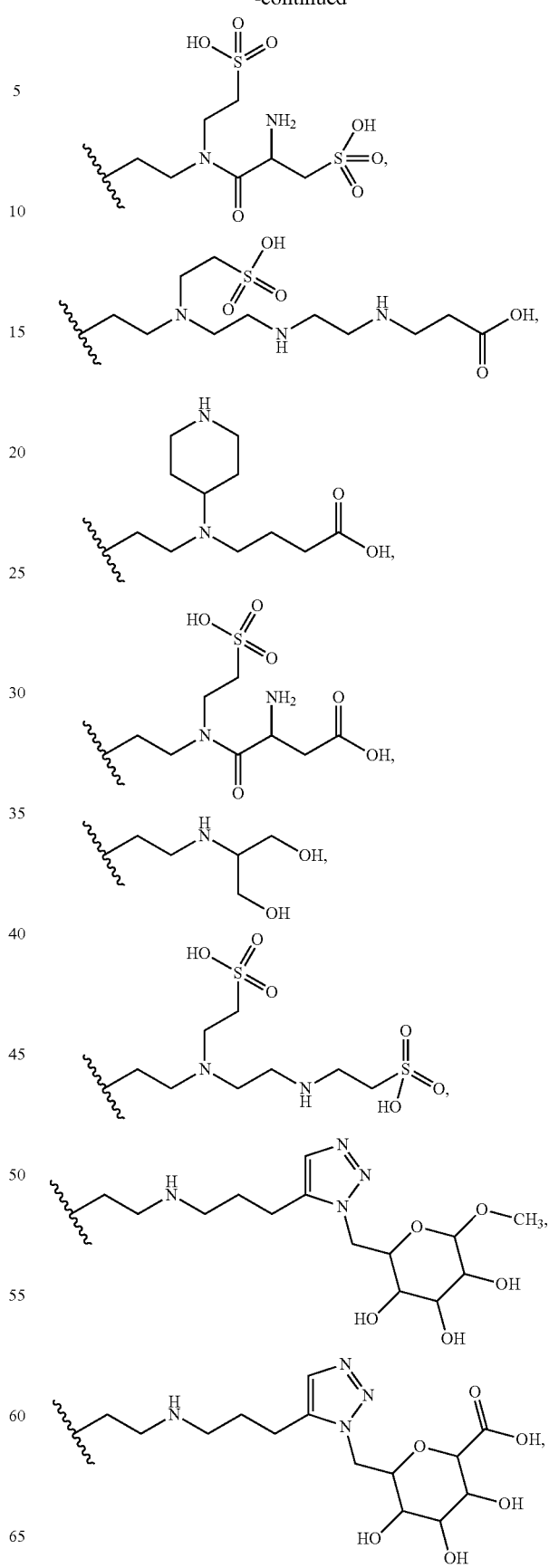

117
-continued
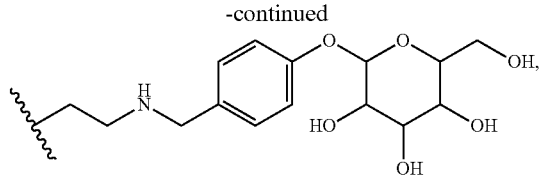
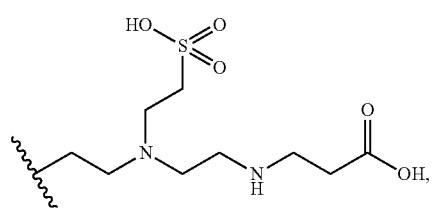
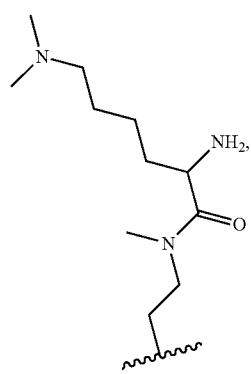
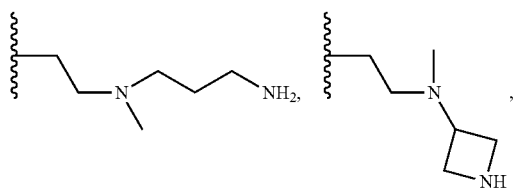
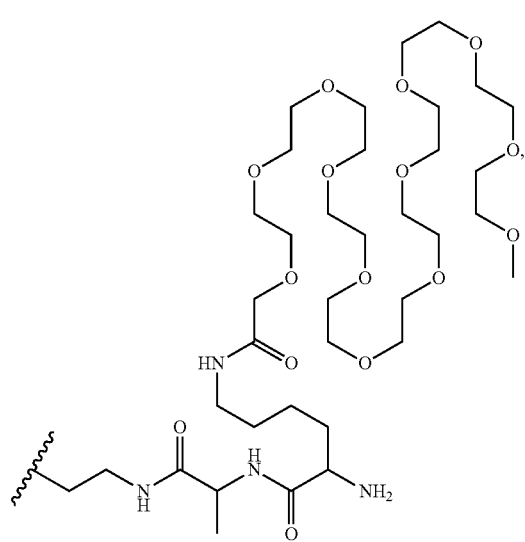
118
-continued
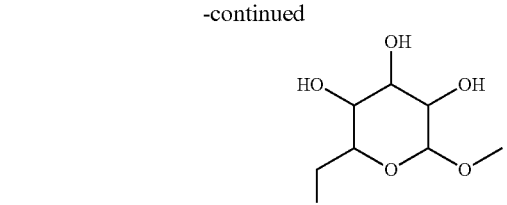
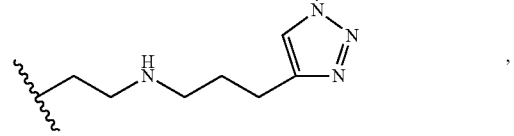
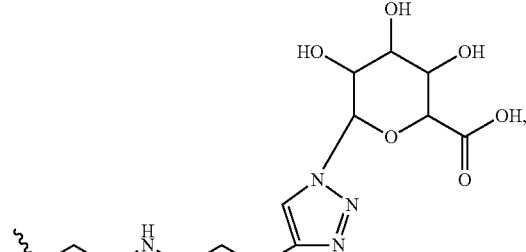
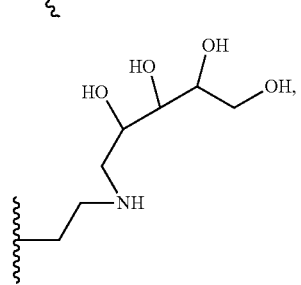
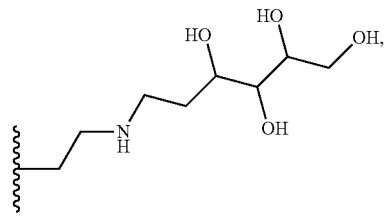
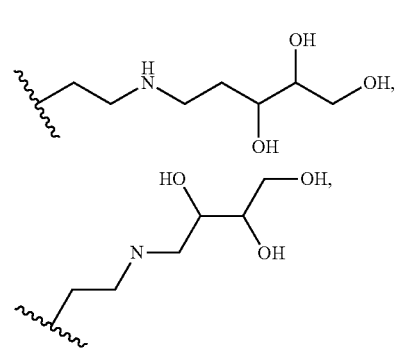
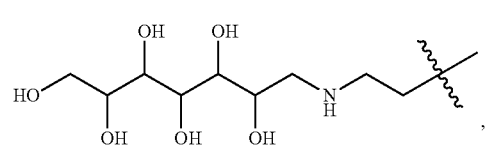

119
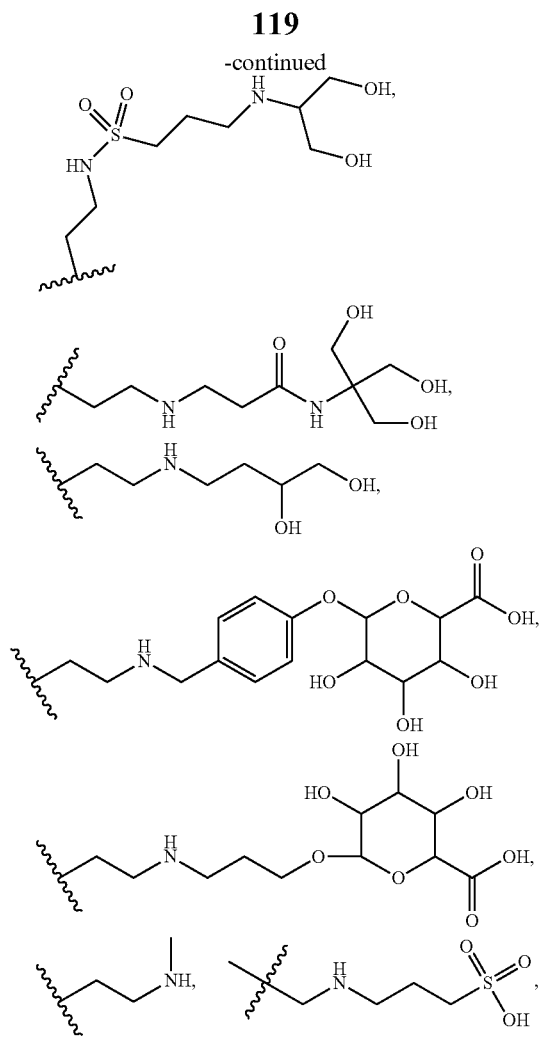
or a salt thereof. When Bcl-xL inhibitors of this embodiment are included in an ADC, the linker of the ADC is linked to the nitrogen atom of an available primary or secondary amine group.
In certain embodiments, R' is selected from
120
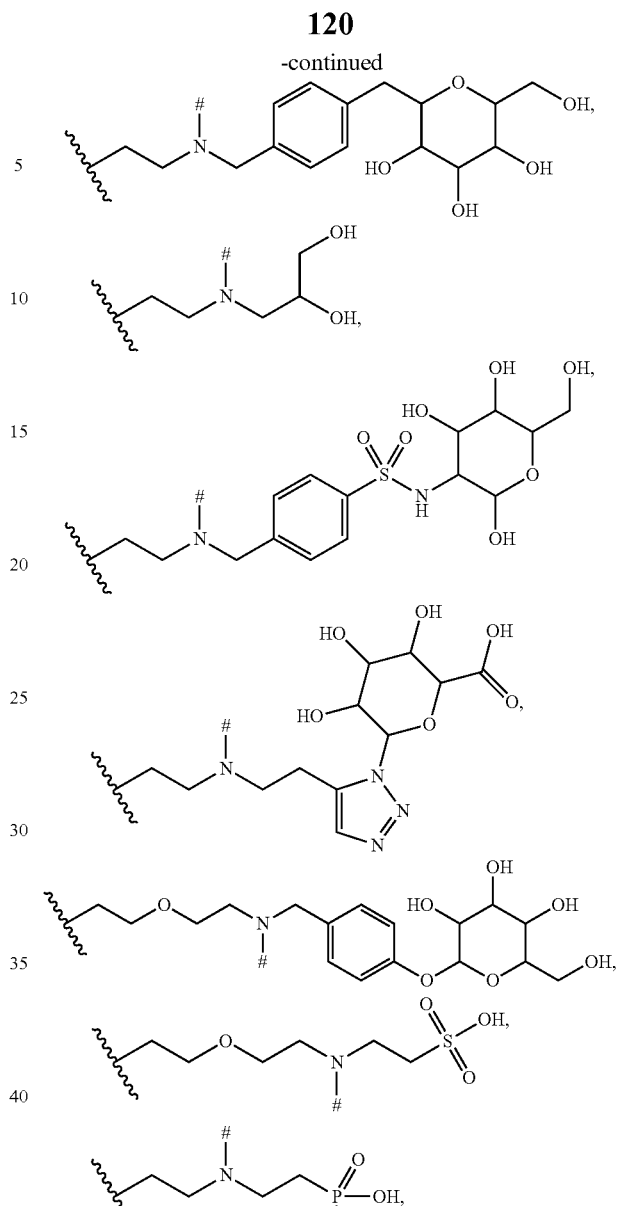

121
-continued
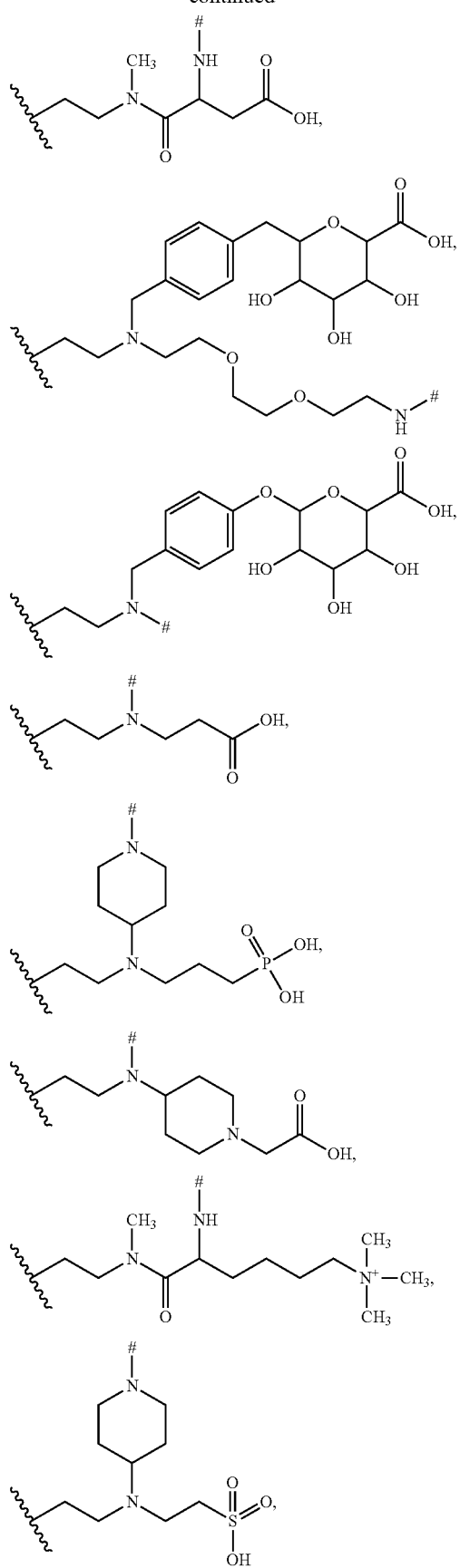
122
-continued
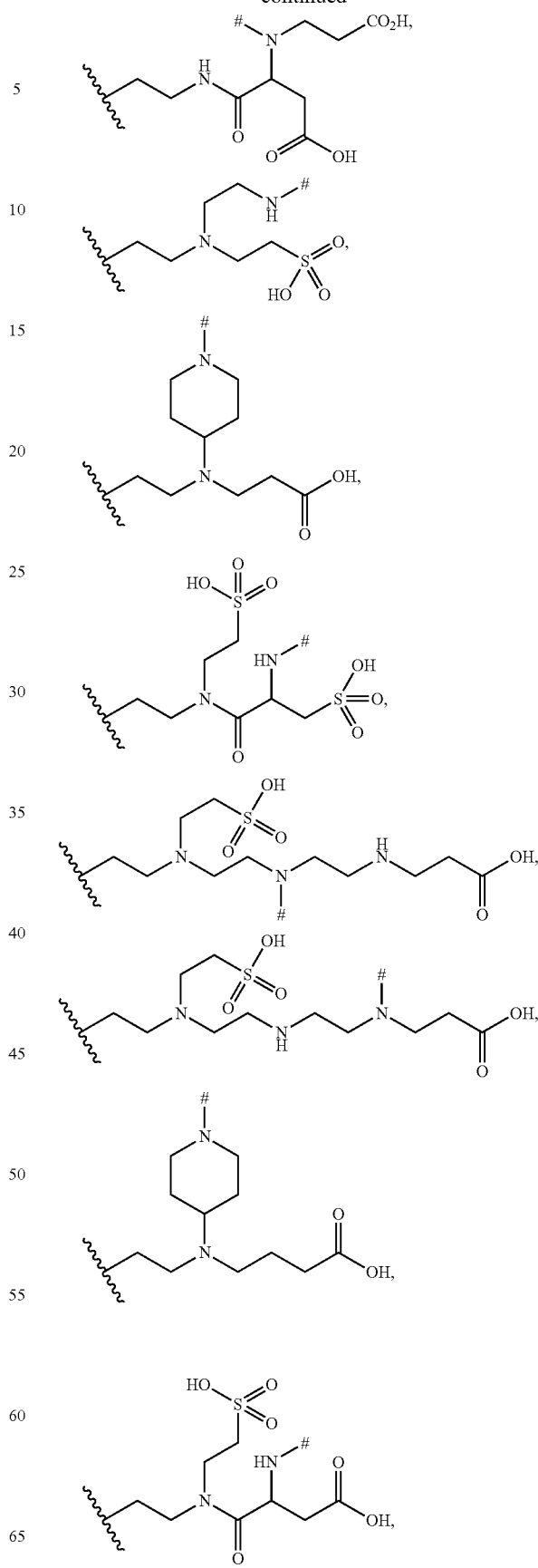

123
-continued
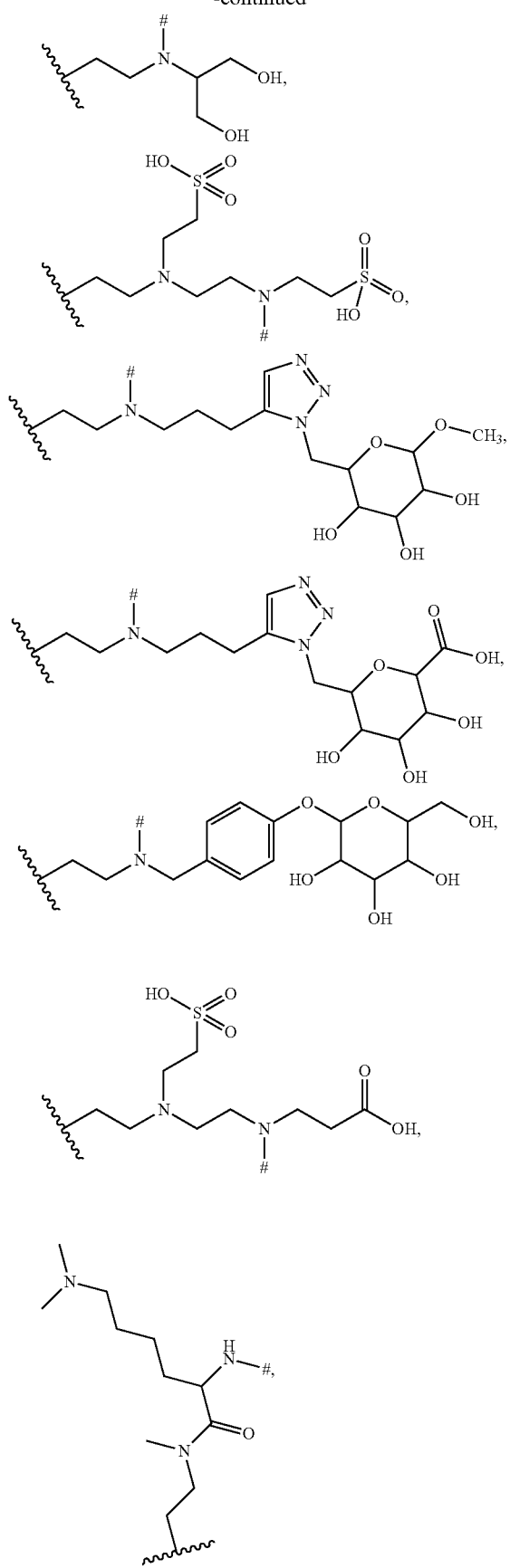
124
-continued
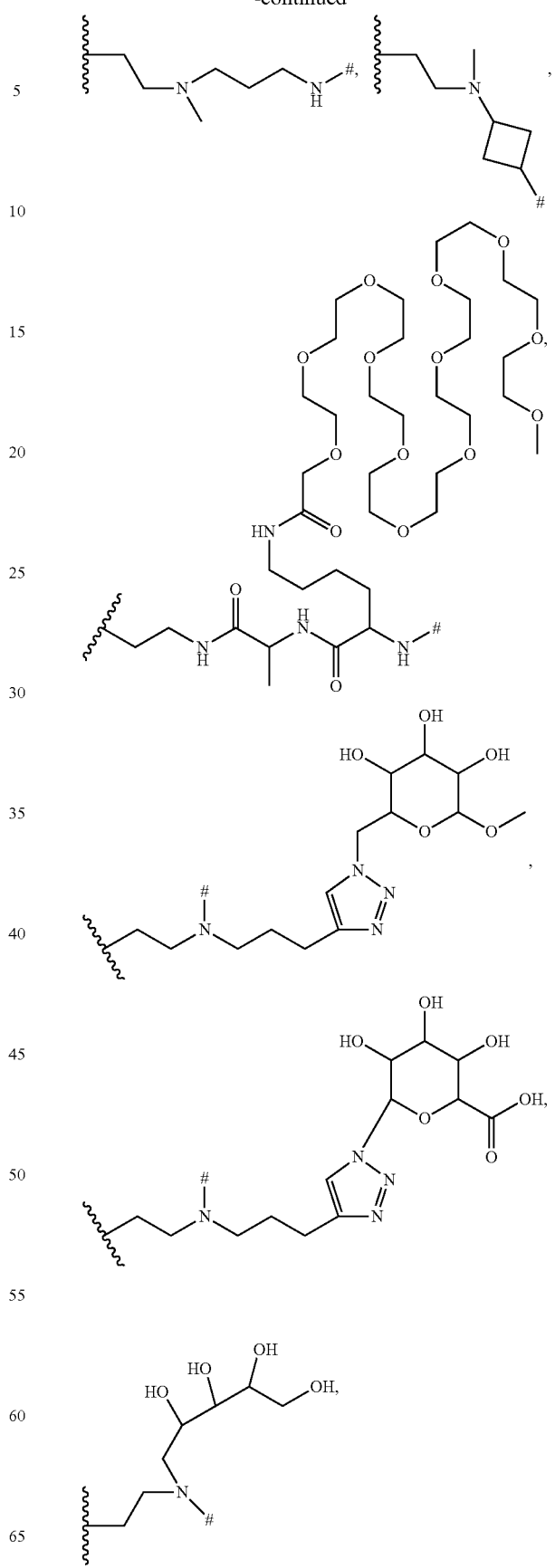

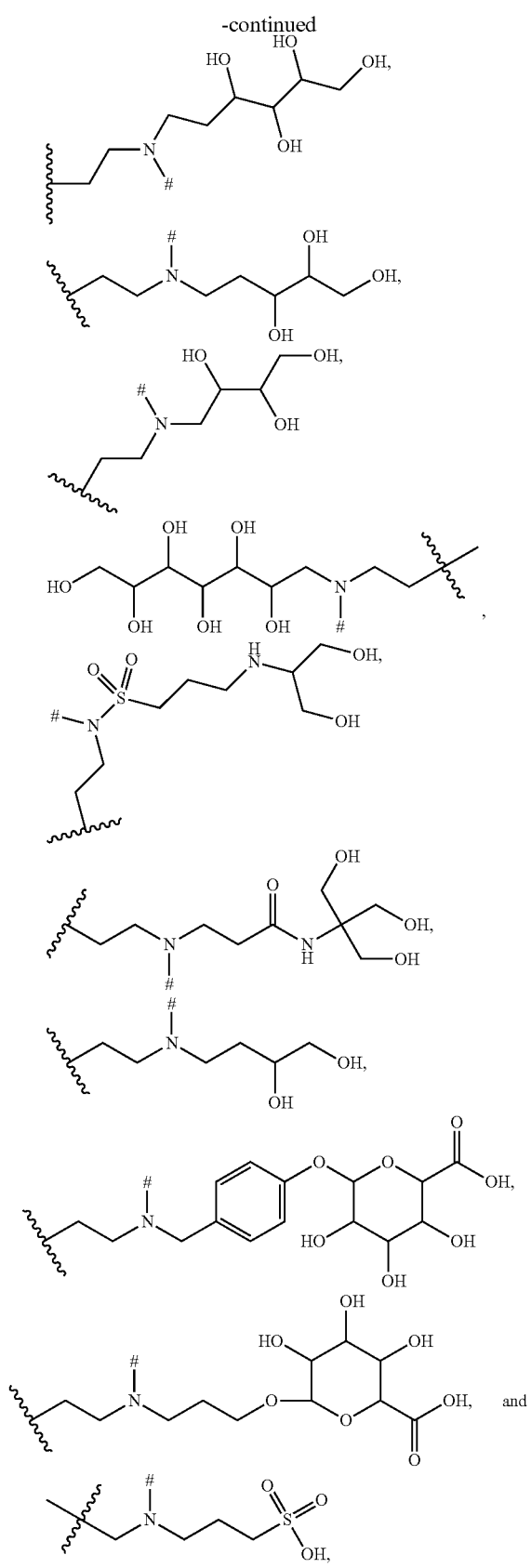

wherein # represents either a hydrogen atom in the Bcl-xL inhibitor drug of the ADCs of formula (IIb) or (IIc) or the point of attachment in the Bcl-xL inhibitor drug of the ADCs of formula (IIa) or (IId) to a linker L.

In certain embodiments, $Ar^1$ of formulae (IIa)-(IId) is selected from

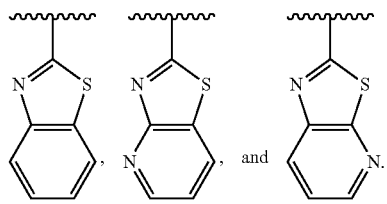

In certain embodiments, $Ar^1$ of formulae (IIa)-(IId) is selected from

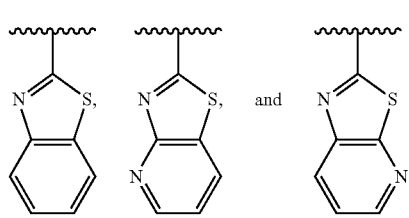

and is optionally substituted with one or more substituents independently selected from halo, cyano, methyl, and halomethyl. In particular embodiments, $Ar^1$ is

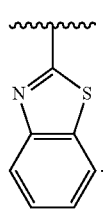

In certain embodiments, $Ar^2$ is

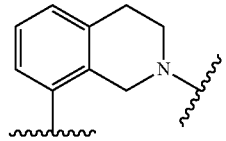 [SMILES: *c1cccc2c1CN(*)CC2]

optionally substituted with one or more substituents, wherein the $R^{12}-Z^{2b}-$, $R'-Z^{2b}-$, $\#-N(R^4)-R^{13}-Z^{2b}-$, or $\#-R'-Z^{2b}-$ substituents are attached to $Ar^2$ at any $Ar^2$ atom capable of being substituted.

In certain embodiments, $Ar^2$ is selected from:

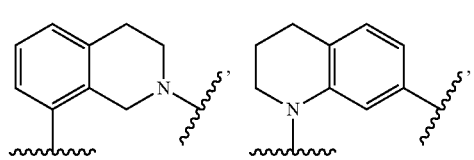

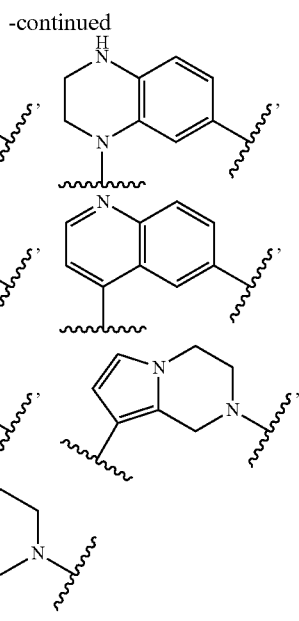

and is optionally substituted with one or more substituents, wherein the $R^{12}$—$Z^{2b}$—, $R'$—$Z^{2b}$—, #—$N(R^4)$—$R^{13}$—$Z^{2b}$—, or #—$R'$—$Z^{2b}$— substituents are attached to $Ar^2$ at any $Ar^2$ atom capable of being substituted. In certain embodiments, $Ar^2$ is selected from:

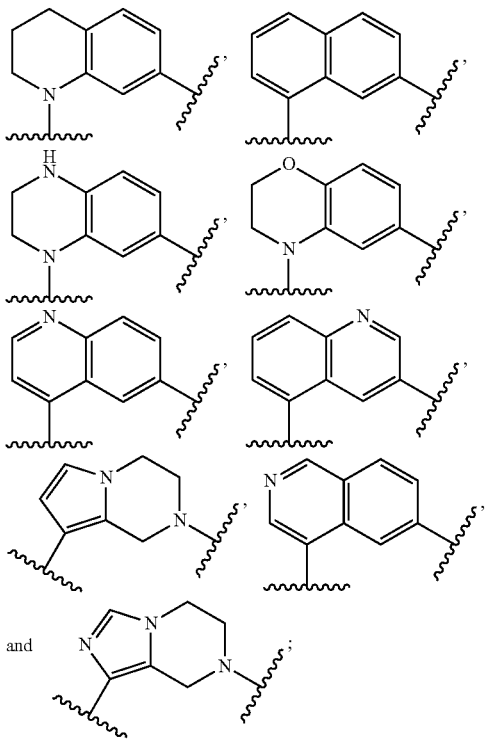

and is optionally substituted with one or more substituents, wherein the $R^{12}$—$Z^{2b}$—, $R'$—$Z^{2b}$—, #—$N(R^4)$—$R^{13}$—$Z^{2b}$—, or # $R'$—$Z^{2b}$— substituents are attached to $Ar^2$ at any $Ar^2$ atom capable of being substituted. In certain embodiments, $Ar^2$ is substituted with one or more solubilizing group. In certain embodiments, the each solubilizing group is, independently of the others, selected from a moiety containing a polyol, a polyethylene glycol with between 4 and 30 repeating units, a salt, or a moiety that is charged at physiological pH.

In certain embodiments, $Z^1$ of formulae (IIa)-(IId) is N.

In certain embodiments, $Z^{2a}$ of formulae (IIa)-(IId) is O. In certain embodiments, $Z^{2a}$ of formulae (IIa)-(IId) is $CR^{6a}R^{6b}$. In certain embodiments, $Z^{2a}$ of formulae (IIa)-(IId) is S. In certain embodiments, $Z^{2a}$ of formulae (IIa)-(IId) is —$NR^6C(O)$—. In particular embodiments, $R^6$ is hydrogen.

In certain embodiments, $Z^{2b}$ of formulae (IIa)-(IId) is O. In certain embodiments, $Z^{2b}$ of formulae (IIa)-(IId) is NH or $CH_2$.

In certain embodiments, $R^1$ of formulae (IIa)-(IId) is selected from methyl and chloro.

In certain embodiments, $R^2$ of formulae (IIa)-(IId) is selected from hydrogen and methyl. In particular embodiments, $R^2$ is hydrogen.

In certain embodiments the Bcl-xL inhibitor is a compound of formula (IIa). In certain embodiments in which the Bcl-xL inhibitor is a compound of formula (IIa), the compound has the structural formula (IIa.1),

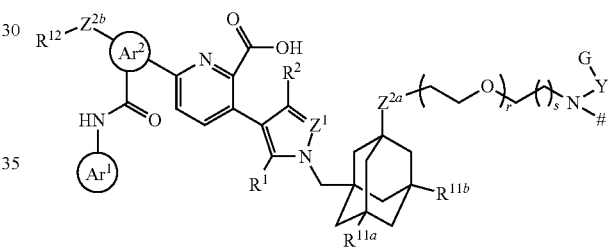

(IIa.1)

or salts thereof, wherein:

$Ar^1$, $Ar^2$, $Z^1$, $Z^{2a}$, $Z^{2b}$, $R^1$, $R^2$, $R^{1a}$, $R^{11b}$, $R^{12}$, G and # are defined as above;

Y is optionally substituted $C_1$-$C_8$ alkylene;

r is 0 or 1; and s is 1, 2 or 3.

In certain embodiments in which the Bcl-xL inhibitor is a compound of formula (IIa.1), r is 0 and s is 1.

In certain embodiments in which the Bcl-xL inhibitor is a compound of formula (IIa.1), r is 0 and s is 2.

In certain embodiments in which the Bcl-xL inhibitor is a compound of formula (IIa.1), r is 1 and s is 2.

In certain embodiments in which the Bcl-xL inhibitor is a compound of formula (IIa.1), $Z^{2a}$ is selected from O, NH, $CH_2$ and S. In particular embodiments, $Z^{2a}$ is O. In certain embodiments, $Z^{2a}$ of formula (IIa.1) is —$CR^{6a}R^{6b}$—. In certain embodiments, $Z^{2a}$ of formula (IIa.1) is $CH_2$. In certain embodiments, $Z^{2a}$ of formula (IIa.1) is S. In certain embodiments, $Z^{2a}$ of formula (IIa.1) is —$NR^6C(O)$—.

In certain embodiments in which the Bcl-xL inhibitor is a compound of formula (IIa.1), Y is selected from ethylene, propylene and butylene. In particular embodiments, Y is selected from ethylene and propylene.

In certain embodiments in which the Bcl-xL inhibitor is a compound of formula (IIa.1), G is selected from

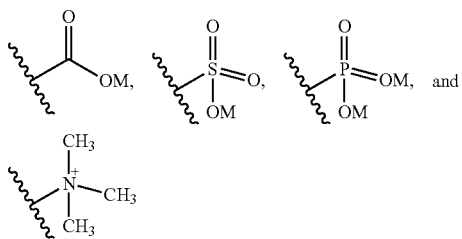

wherein M is hydrogen or a positively charged counterion. In particular embodiments, G is

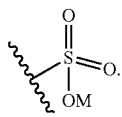

In particular embodiments, G is SO$_3$H.

In certain embodiments in which the Bcl-xL inhibitor is a compound of formula (IIa.1), Ar$^2$ is selected from

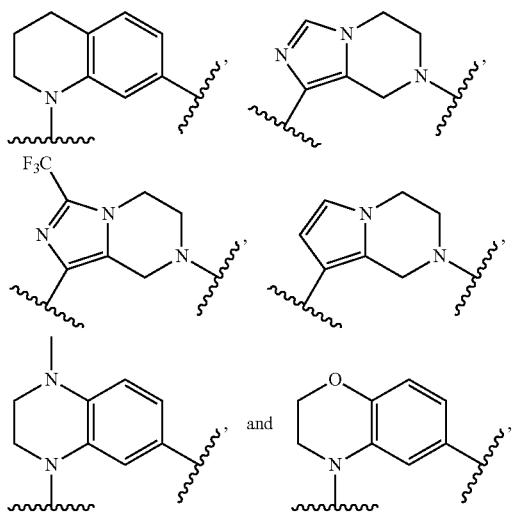

wherein the R$^{12}$—Z$^{2b}$— substituent is attached to Ar$^2$ at any Ar$^2$ atom capable of being substituted.

In certain embodiments in which the Bcl-xL inhibitor is a compound of formula (IIa.1), Ar$^2$ is selected from

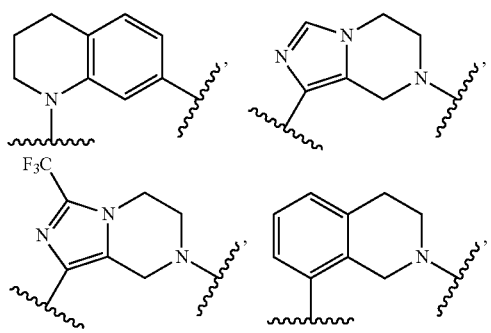

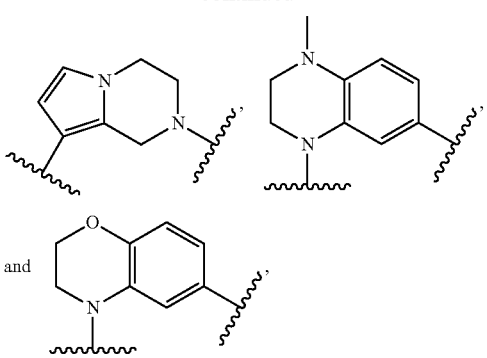

wherein the R$_{12}$—Z$^{2b}$— substituent is attached to Ar$^2$ at any Ar$^2$ atom capable of being substituted.

In particular embodiments in which the Bcl-xL inhibitor is a compound of formula (IIa.1), Ar$^2$ is

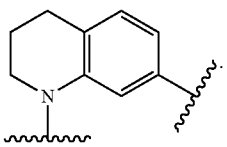 [SMILES: *c1ccc2c(c1)N(*)CCC2]

In particular embodiments in which the Bcl-xL inhibitor is a compound of formula (IIa.1), Ar$^2$ is

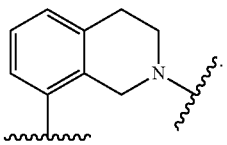 [SMILES: *c1cccc2c1CN(*)CC2]

In certain embodiments in which the Bcl-xL inhibitor is a compound of formula (IIa.1), Z$^{2b}$—R$^{12}$ is selected from H, F, CN, OCH$_3$, OH, NH$_2$, OCH$_2$CH$_2$OCH$_3$, N(CH$_3$)C(=O) CH$_3$, CH$_2$N(CH$_3$)C(=O)CH$_3$SCH$_3$, C(=O)N(CH$_3$)$_2$ and OCH$_2$CH$_2$N(CH$_3$)(C(=O)CH$_3$). In particular embodiments, Z$^{2b}$—R$^{12}$ is selected from H, F and CN. In particular embodiments, Z$^{2b}$—R$^{12}$ is H.

In embodiments where Z$^{2b}$—R$^{12}$ is substituted with hydroxyl (OH), the oxygen can serve as the point of attachment to a linking group (See Section 4.4.1.1).

In certain embodiments in which the Bcl-xL inhibitor is a compound of formula (IIa.1), Ar$^1$ is

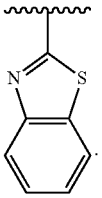 [SMILES: *c1nc2ccccc2s1]

In certain embodiments in which the Bcl-xL inhibitor is a compound of formula (IIa.1), the group

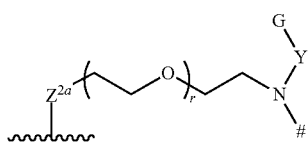

bonded to the adamantane ring is selected from:

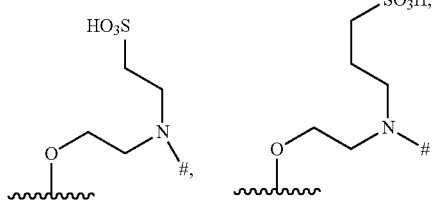

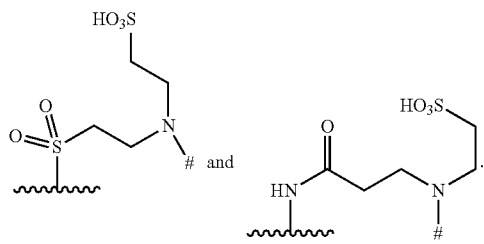

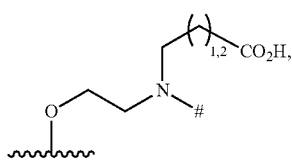

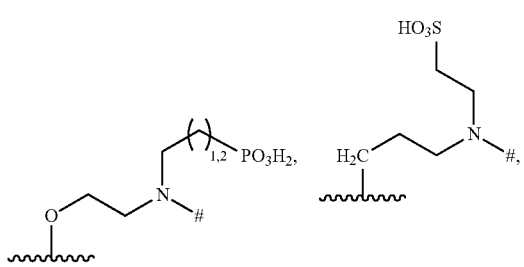

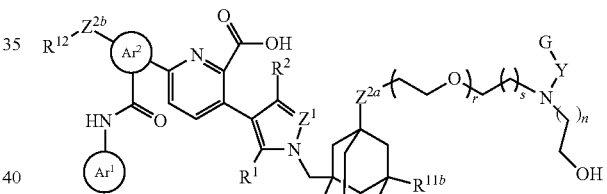

In certain embodiments, a compound of formula (IIa.1) may be converted into the compound of formula IIa.1.1, wherein n is selected from 1-3:

IIa.1.1

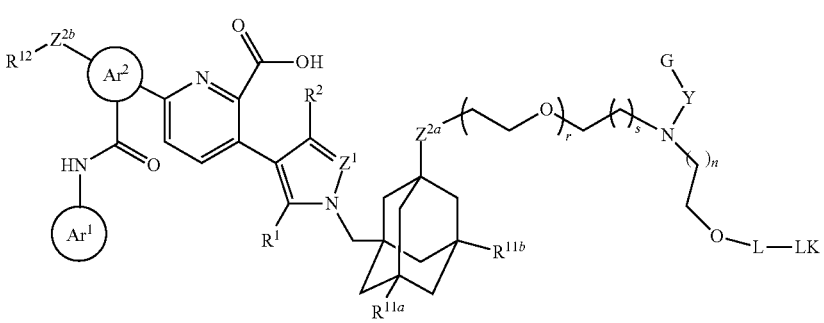

In certain embodiments, the compound of formula IIa.1.1 can be converted into a compound of formula IIa.1.2, wherein L represents a linker and LK represents a linkage formed between a reactive functional group on linker L and a complementary functional group on antibody.

(IIa.2)

In certain embodiments in which the Bcl-xL inhibitor is a compound of formula (IIa), the compound has the structural formula (IIa.2), (IIa.2)

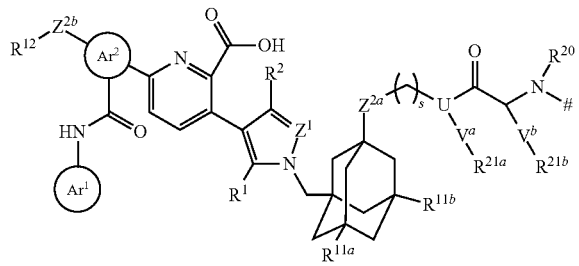

or salts thereof, wherein:

$Ar^1$, $Ar^2$, $Z^1$, $Z^{2a}$, $Z^{2b}$, $R^1$, $R^2$, $R^{11a}$, $R^{11b}$, $R^{12}$ and # are defined as above;

U is selected from N, O and CH, with the proviso that when U is O, then $V^a$ and $R^{21a}$ are absent;

$R^{20}$ is selected from H and $C_1$-$C_4$ alkyl;

$R^{21a}$ and $R^{21b}$ are each, independently from one another, absent or selected from H, $C_1$-$C_4$ alkyl and G, where G is selected from a polyol, PEG4-30, a salt and a moiety that is charged at physiological pH;

$V^a$ and $V^b$ are each, independently from one another, absent or selected from a bond, and an optionally substituted alkylene;

$R^{20}$ is selected from H and $C_1$-$C_4$ alkyl; and s is 1, 2 or 3.

In certain embodiments in which the Bcl-xL inhibitor is a compound of formula (IIa.2), s is 2.

In certain embodiments in which the Bcl-xL inhibitor is a compound of formula (IIa.2), $Z^{2a}$ is selected from O, NH, $CH_2$ and S. In particular embodiments, $Z^{2a}$ is O. In certain embodiments, $Z^{2a}$ of formula (IIa.2) is $CR^{6a}R^{6b}$. In certain embodiments, $Z^{2a}$ of formula (IIa.2) is $CH_2$. In certain embodiments, $Z^{2a}$ of formula (IIa.2) is S. In certain embodiments, $Z^{2a}$ of formula (IIa.2) is —$NR^6C(O)$—.

In certain embodiments in which the Bcl-xL inhibitor is a compound of formula (IIa.2), U is selected from N and O. In particular embodiments, U is O.

In certain embodiments in which the Bcl-xL inhibitor is a compound of formula (IIa.2), $V^a$ is a bond, $R^{21a}$ is a $C_1$-$C_4$ alkyl group, $V^b$ is selected from methylene and ethylene and R21b is G. In particular embodiments, $V^a$ is a bond, $R^{21a}$ is a methyl group and $V^b$ is selected from methylene and ethylene and $R^{21b}$ is G.

In certain embodiments in which the Bcl-xL inhibitor is a compound of formula (IIa.2), $V^a$ is selected from methylene and ethylene, $R^{21a}$ is G, $V^b$ is selected from methylene and ethylene and $R^{21b}$ is G. In particular embodiments, $V^a$ is ethylene, $R^{21a}$ is G, $V^b$ is selected from methylene and ethylene and $R^{21b}$ is G.

In certain embodiments in which the Bcl-xL inhibitor is a compound of formula (IIa.2), G is selected from

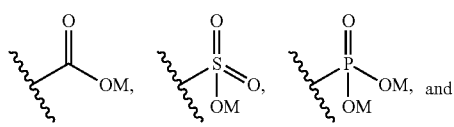

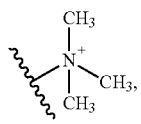

wherein M is hydrogen or a positively charged counterion. In particular embodiments, G is In particular embodiments, G is $SO_3H$.

In certain embodiments in which the Bcl-xL inhibitor is a compound of formula (IIa.2), $R^{20}$ is selected from hydrogen and a methyl group.

In certain embodiments in which the Bcl-xL inhibitor is a compound of formula (IIa.2), $Ar^2$ is selected from wherein the $R^2$—$Z^{2b}$— substituent is attached to $Ar^2$ at any $Ar^2$ atom capable of being substituted.

In certain embodiments in which the Bcl-xL inhibitor is a compound of formula (IIa.2), $Ar^2$ is selected from

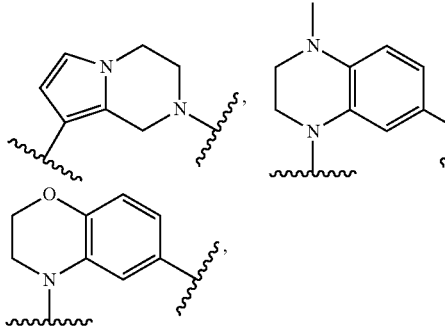

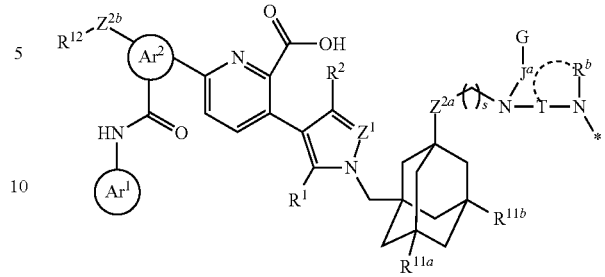

(IIa.3)

$R^{12}$—$Z^{2b}$— substituent is attached to $Ar^2$ at any $Ar^2$ atom capable of being substituted.

In particular embodiments in which the Bcl-xL inhibitor is a compound of formula (IIa.2), $Ar^2$ is

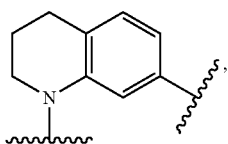 [SMILES: *c1ccc2c(c1)N(*)CCC2]

wherein the $R^{12}$—$Z^{2b}$— substituent is attached to $Ar^2$ at any $Ar^2$ atom capable of being substituted.

In certain embodiments in which the Bcl-xL inhibitor is a compound of formula (IIa.2), $Z^{2b}$—$R^{12}$ is selected from H, F, CN, $OCH_3$, OH, $NH_2$, $OCH_2CH_2OCH_3$, $N(CH_3)C(=O)CH_3$, $CH_2N(CH_3)C(=O)CH_3SCH_3$, $C(=O)N(CH_3)_2$ and $OCH_2CH_2N(CH_3)(C(=O)CH_3)$. In particular embodiments, $Z^{2b}$—$R^{12}$ is selected from H, F and CN. In particular embodiments, $Z^{2b}$—$R^{12}$ is H. In certain embodiments in which the Bcl-xL inhibitor is a compound of formula (IIa.2), $Ar^1$ is

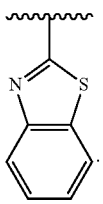 [SMILES: *c1nc2ccccc2s1]

In particular embodiments in which the Bcl-xL inhibitor is a compound of formula (IIa.2), $Ar^2$ is

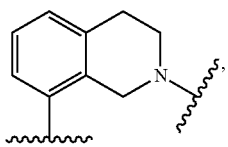 [SMILES: *c1cccc2c1CN(*)CC2]

wherein the $R^{12}$—$Z^{2b}$— substituent is attached to $Ar^2$ at any $Ar^2$ atom capable of being substituted.

In certain embodiments in which the Bcl-xL inhibitor is a compound of formula (IIa), the compound has the structural formula (IIa.3), or salts thereof, wherein:

$Ar^1$, $Ar^2$, $Z^1$, $Z^{2a}$, $Z^{2b}$, $R^1$, $R^2$, $R^{11a}$, $R^{11b}$, $R^{12}$ and # are defined as above; $R^b$ is selected from H, $C_1$-$C_4$ alkyl and $J^b$-G or is optionally taken together with an atom of T to form a ring having between 3 and 7 atoms;

$J^a$ and $J^b$ are each, independently from one another, selected from optionally substituted $C_1$-$C_8$ alkylene and optionally substituted phenylene;

T is selected from optionally substituted $C_1$-$C_8$ alkylene, $CH_2CH_2OCH_2CH_2OCH_2CH_2$, $CH_2CH_2OCH_2CH_2OCH_2CH_2OCH_2$ and a polyethylene glycol containing from 4 to 10 ethylene glycol units;

G is selected from a polyol, PEG4-30, a salt and a moiety that is charged at physiological pH; and s is 1, 2 or 3.

In certain embodiments in which the Bcl-xL inhibitor is a compound of formula (IIa.3), s is 1.

In certain embodiments in which the Bcl-xL inhibitor is a compound of formula (IIa.3), s is 2.

In certain embodiments in which the Bcl-xL inhibitor is a compound of formula (IIa.3), $Z^{2a}$ is selected from O, $CH_2$ and S. In particular embodiments, $Z^{2a}$ is O. In certain embodiments, $Z^{2a}$ of formula (IIa.3) is $CR^{6a}R^{6b}$. In certain embodiments, $Z^{2a}$ of formula (IIa.3) is $CH_2$. In certain embodiments, $Z^{2a}$ of formula (IIa.3) is S. In certain embodiments, $Z^{2a}$ of formula (IIa.3) is —$NR^6C(O)$—.

In certain embodiments in which the Bcl-xL inhibitor is a compound of formula (IIa.3), $J^a$ is selected from methylene and ethylene and $R^b$ is $J^b$-G, wherein $J^b$ is methylene or ethylene. In some such embodiments, T is ethylene. In other such embodiments, T is $CH_2CH_2OCH_2CH_2OCH_2CH_2$. In other such embodiments, T is a polyethylene glycol containing from 4 to 10 ethylene glycol units.

In certain embodiments in which the Bcl-xL inhibitor is a compound of formula (IIa.3), $J^a$ is selected from methylene and ethylene and $R^b$ is taken together with an atom of T to form a ring having 4-6 ring atoms.

In certain embodiments in which the Bcl-xL inhibitor is a compound of formula (IIa.3), $J^a$ is selected from methylene and ethylene and $R^b$ is H or alkyl. In some such embodiments, T is ethylene.

In other such embodiments, T is $CH_2CH_2OCH_2CH_2OCH_2CH_2$.

In certain embodiments in which the Bcl-xL inhibitor is a compound of formula (IIa.3), G is selected from

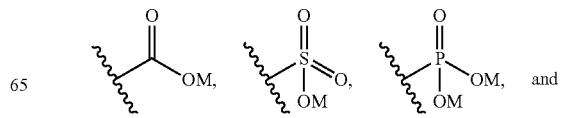

and

-continued

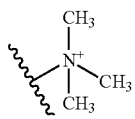

wherein M is hydrogen or a positively charged counterion. In particular embodiments, G is

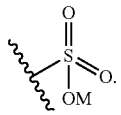

In particular embodiments, G is SO$_3$H.

In certain embodiments in which the Bcl-xL inhibitor is a compound of formula (IIa.3), R$^{20}$ is selected from hydrogen and a methyl group.

In certain embodiments in which the Bcl-xL inhibitor is a compound of formula (IIa.3), Ar$^2$ is selected from

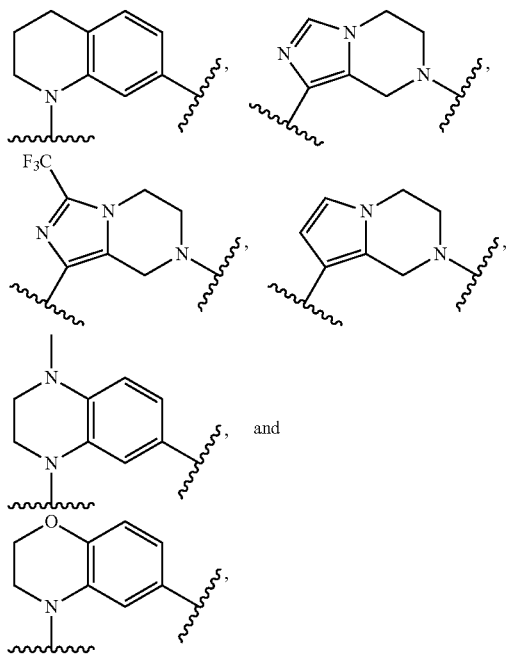

and

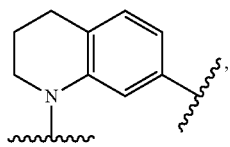 [SMILES: *c1ccc2c(c1)N(*)CCC2]

wherein the R$^{12}$—Z$^{2b}$— substituent is attached to Ar$^2$ at any Ar$^2$ atom capable of being substituted.

In particular embodiments in which the Bcl-xL inhibitor is a compound of formula (IIa.3), Ar$^2$ is

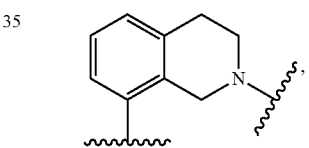

herein the R$^{12}$—Z$^{2b}$— substituent is attached to Ar$^2$ at any Ar$^2$ atom capable of being substituted. In certain embodiments in which the Bcl-xL inhibitor is a compound of formula (IIa.3), Ar$^2$ is selected from

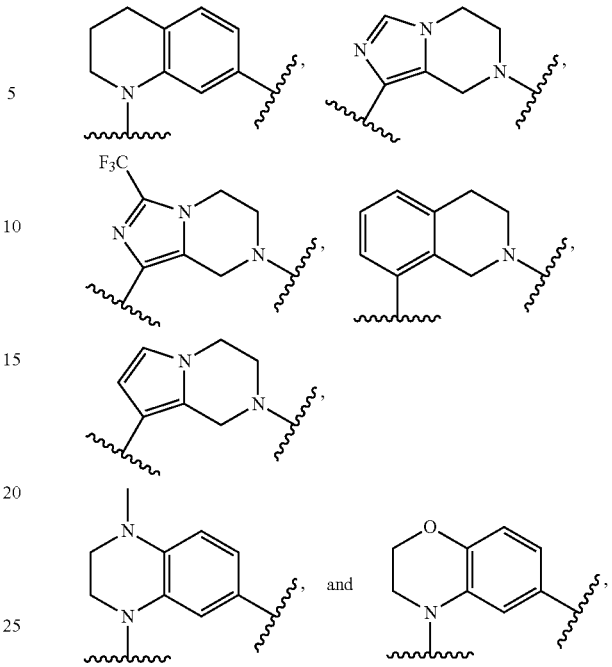

and wherein the R$^{12}$—Z$^{2b}$— substituent is attached to Ar$^2$ at any Ar$^2$ atom capable of being substituted. In particular embodiments in which the Bcl-xL inhibitor is a compound of formula (IIa.3), Ar$^2$ is

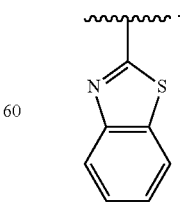

wherein the R$^{12}$—Z$^{2b}$— substituent is attached to Ar$^2$ at any Ar$^2$ atom capable of being substituted.

In certain embodiments in which the Bcl-xL inhibitor is a compound of formula (IIa.3), Z$^{2b}$—R$^{12}$ is selected from H, F, CN, OCH$_3$, OH, NH$_2$, OCH$_2$CH$_2$OCH$_3$, N(CH$_3$)C(=O)CH$_3$, CH$_2$N(CH$_3$)C(=O)CH$_3$SCH$_3$, C(=O)N(CH$_3$)$_2$ and OCH$_2$CH$_2$N(CH$_3$)(C(=O)CH$_3$). In particular embodiments, Z$^{2b}$—R$^{12}$ is selected from H, F and CN. In particular embodiments, Z$^{2b}$—R$^{12}$ is H.

In certain embodiments in which the Bcl-xL inhibitor is a compound of formula (IIa.3), Ar$^1$ is In certain embodiments in which the Bcl-xL inhibitor is a compound of formula (IIa.3), the group

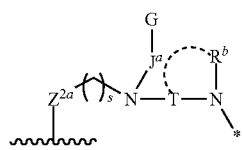
is selected from:
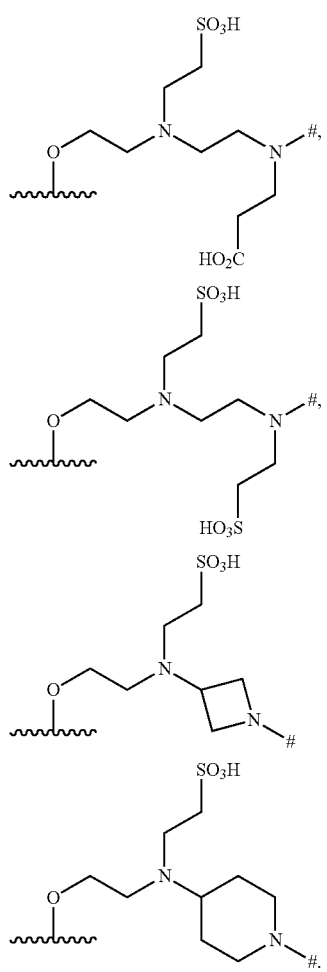
In certain embodiments in which the Bcl-xL inhibitor is a compound of formula (IIa.3), the group
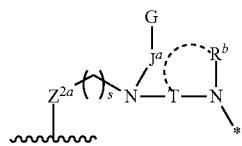
is selected from:
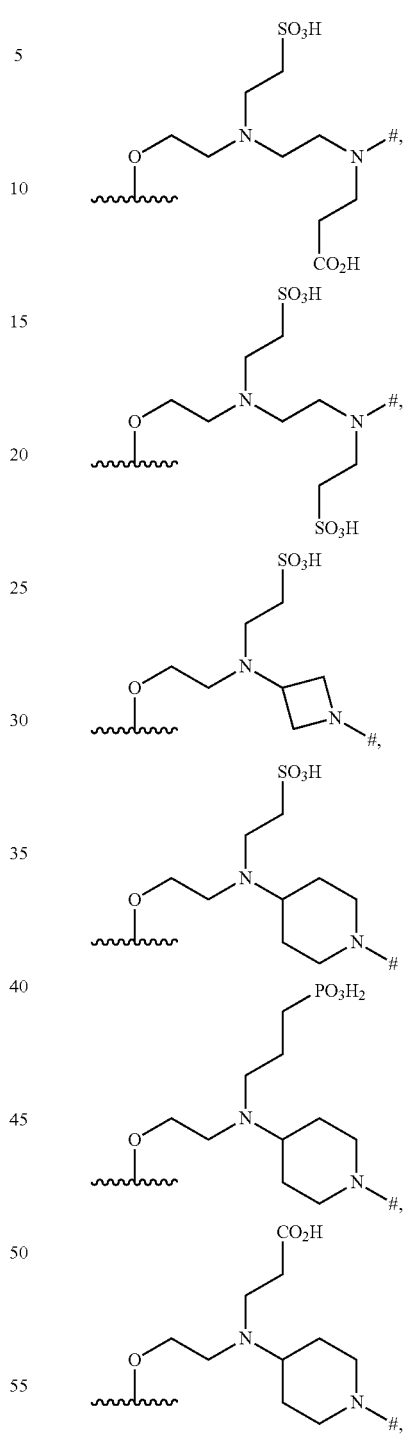
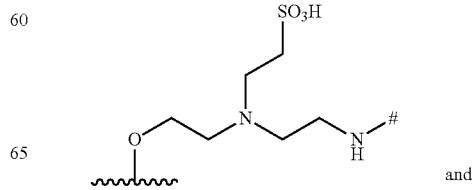
and -continued

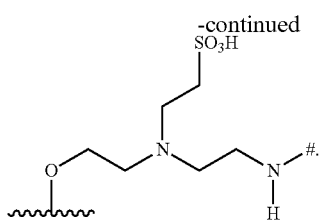

In certain embodiments the Bcl-xL inhibitor is a compound of formula (IIb). In certain embodiments in which the Bcl-xL inhibitor is a compound of formula (IIb), the compound has the structural formula (IIb. 1), (IIb.1)

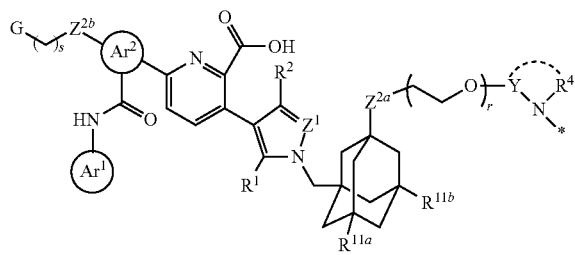

or salts thereof, wherein:

$Ar^1, Ar^2, Z^{2a}, Z^{2b}, R^1, R^2, R^4, R^{11a}, R^{11b}$ and # are defined as above;

Y is optionally substituted $C_1$-$C_8$ alkylene;

G is selected from a polyol, PEG4-30, a salt and a moiety that is charged at physiological pH;

r is 0 or 1; and s is 1, 2 or 3.

In certain embodiments in which the Bcl-xL inhibitor is a compound of formula (IIb. 1), s is 1.

In certain embodiments in which the Bcl-xL inhibitor is a compound of formula (IIb. 1), s is 2. In certain embodiments in which the Bcl-xL inhibitor is a compound of formula (IIb. 1), s is 3.

In certain embodiments in which the Bcl-xL inhibitor is a compound of formula (IIb. 1), $Z^{2a}$ is selected from O, $CH_2$, NH and S. In particular embodiments, $Z^{2a}$ is O. In certain embodiments, $Z^{2a}$ of formula (IIb.1) is $CR^{6a}R^{6b}$. In certain embodiments, $Z^{2a}$ of formula (IIb.1) is $CH_2$. In certain embodiments, $Z^{2a}$ of formula (IIb. 1) is S. In certain embodiments, $Z^{2a}$ of formula (IIb.1) is —$NR^6C(O)$—.

In certain embodiments in which the Bcl-xL inhibitor is a compound of formula (IIb. 1), $Z^{2b}$ is selected from O, $CH_2$, NH, $NCH_3$ and S. In particular embodiments, $Z^{2b}$ is O. In particular embodiments, $Z^{2b}$ is NH. In particular embodiments, $Z^{2b}$ is $NCH_3$.

In certain embodiments in which the Bcl-xL inhibitor is a compound of formula (IIb. 1), Y is ethylene and r is 0.

In certain embodiments in which the Bcl-xL inhibitor is a compound of formula (IIb. 1), Y is ethylene and r is 1.

In certain embodiments in which the Bcl-xL inhibitor is a compound of formula (IIb. 1), $R^4$ is H or methyl. In particular embodiments, $R^4$ is methyl. In other embodiments, $R^4$ is H.

In certain embodiments in which the Bcl-xL inhibitor is a compound of formula (IIb. 1), $R^4$ is taken together with an atom of Y to form a ring having 4-6 ring atoms. In particular embodiments, the ring is a cyclobutane ring. In other embodiments, the ring is a piperazine ring. In other embodiments, the ring is a morpholine ring.

In certain embodiments in which the Bcl-xL inhibitor is a compound of formula (IIb. 1), G is selected from

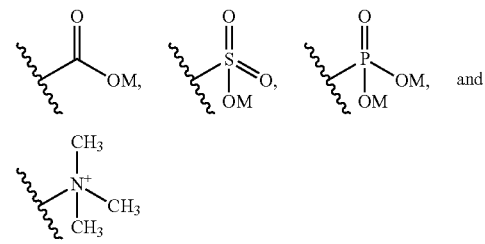

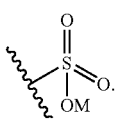

wherein M is hydrogen or a positively charged counterion. In particular embodiments, G is

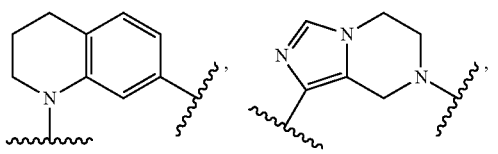

In other embodiments, G is $SO_3H$. In particular embodiments, G is $NH_2$. In other embodiments, G is $PO_3H_2$. In particular embodiments, G is $NH_2$. In particular embodiments, G is C(O)OH. In particular embodiments, G is polyol.

In certain embodiments in which the Bcl-xL inhibitor is a compound of formula (IIb. 1), $Ar^2$ is selected from

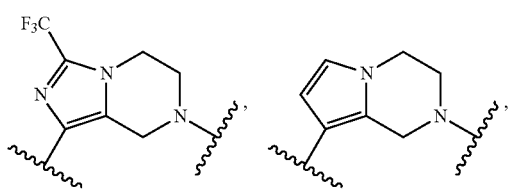

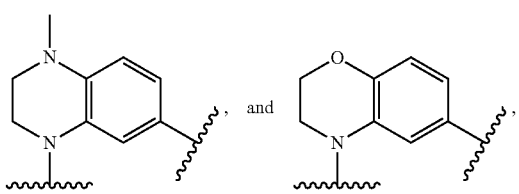

wherein the G-$(CH_2)_s$—$Z^{2b}$— substituent is attached to $Ar^2$ at any $Ar^2$ atom capable of being substituted.

In particular embodiments in which the Bcl-xL inhibitor is a compound of formula (IIb. 1), $Ar^2$ is

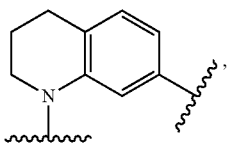

wherein the G-(CH$_2$)$_s$—Z$^{2b}$— substituent is attached to Ar$^2$ at any Ar$^2$ atom capable of being substituted. In certain embodiments in which the Bcl-xL inhibitor is a compound of formula (IIb.1), Ar$^2$ is selected from

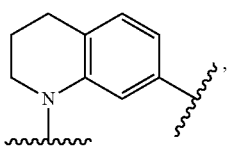 [SMILES: *c1ccc2c(c1)N(*)CCC2] 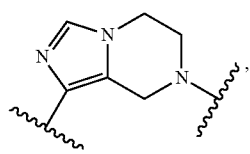

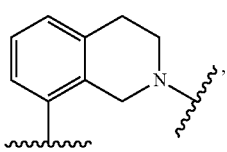 [SMILES: *c1cccc2c1CN(*)CC2] 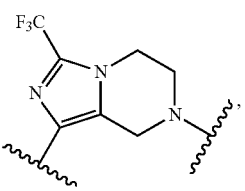

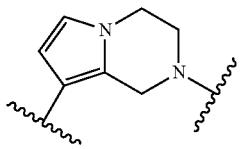

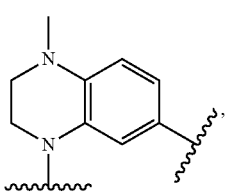 and 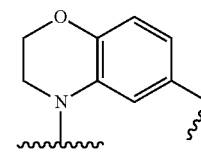

wherein the G-(CH$_2$)$_s$—Z$^{2b}$— substituent is attached to Ar$^2$ at any Ar$^2$ atom capable of being substituted. In particular embodiments in which the Bcl-xL inhibitor is a compound of formula (IIb. 1), Ar$^2$ is

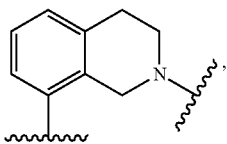

wherein the G-(CH$_2$)$_s$—Z$^{2b}$— substituent is attached to Ar$^2$ at any Ar$^2$ atom capable of being substituted.

In certain embodiments in which the Bcl-xL inhibitor is a compound of formula (IIb. 1), Ar$^1$ is

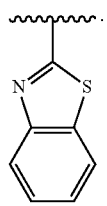 [SMILES: *c1nc2ccccc2s1]

In certain embodiments in which the Bcl-xL inhibitor is a compound of formula (IIb. 1), the group

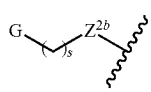

is selected from:

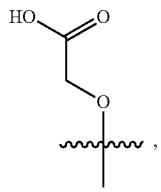 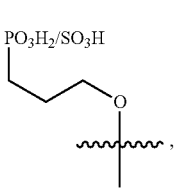

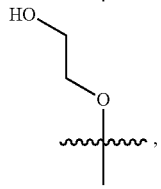 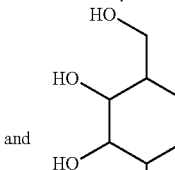

In certain embodiments in which the Bcl-xL inhibitor is a compound of formula (IIb. 1), the group

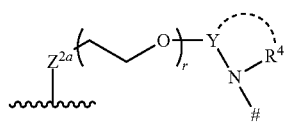

is selected from:

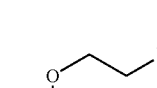 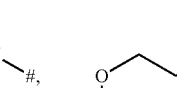 and

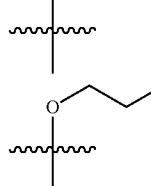 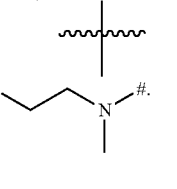

In certain embodiments in which the Bcl-xL inhibitor is a compound of formula (IIb. 1), the group

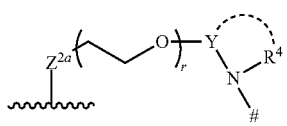

is selected from:

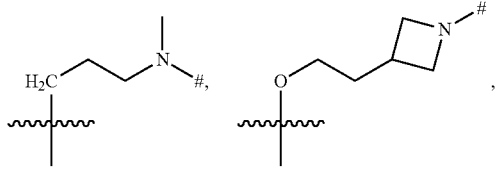

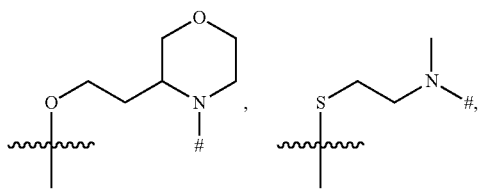

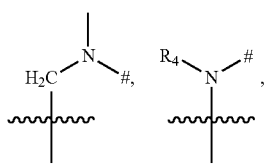

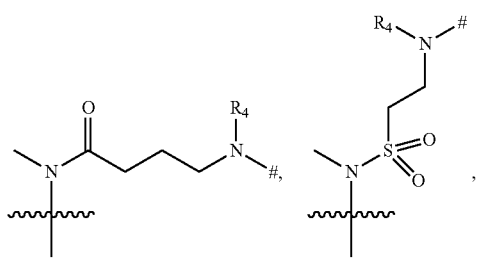

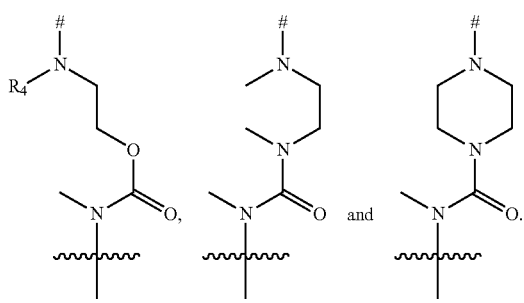

In certain embodiments the Bcl-xL inhibitor is a compound of formula (IIc). In certain embodiments in which the Bcl-xL inhibitor is a compound of formula (IIc), the compound has the structural formula (IIc.1)

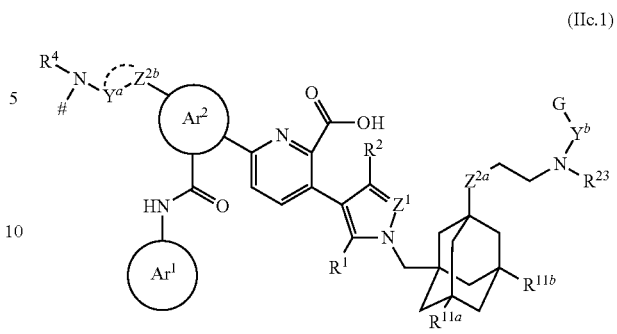

(IIc.1)

or salts thereof, wherein:

$Ar^1$, $Ar^2$, $Z^1$, $Z^{2a}$, $Z^{2b}$, $R^1$, $R^2$, $R^4$, $R^{11a}$, $R^{11b}$ and # are defined as above;

$Y^a$ is optionally substituted $C_1$-$C_8$ alkylene;

$Y^b$ is optionally substituted $C_1$-$C_8$ alkylene;

$R^{23}$ is selected from H and $C_1$-$C_4$ alkyl; and

G is selected from a polyol, PEG4-30, a salt and a moiety that is charged at physiological pH;

In certain embodiments in which the Bcl-xL inhibitor is a compound of formula (IIc. 1), $Z^{2a}$ is selected from O, $CH_2$, NH and S. In particular embodiments, $Z^{2a}$ is O. In certain embodiments, $Z^{2a}$ of formula (IIc.1) is $CR^{6a}R^{6b}$. In certain embodiments, $Z^{2a}$ of formula (IIc.1) is S. In certain embodiments, $Z^{2a}$ of formula (IIc.1) is —$NR^6C(O)$—.

In certain embodiments in which the Bcl-xL inhibitor is a compound of formula (IIc. 1), $Z^{2b}$ is selected from O, $CH_2$, NH, $NCH_3$ and S. In particular embodiments, $Z^{2b}$ is O. In particular embodiments, $Z^{2b}$ is NH. In particular embodiments, $Z^{2b}$ is $NCH_3$.

In certain embodiments in which the Bcl-xL inhibitor is a compound of formula (IIc. 1), $Z^{2b}$ is a bond. In some such embodiments $Y^a$ is methylene or ethylene.

In certain embodiments in which the Bcl-xL inhibitor is a compound of formula (IIc. 1), $Z^{2b}$ is O. In some such embodiments $Y^a$ is methylene, ethylene, or propylene.

In certain embodiments in which the Bcl-xL inhibitor is a compound of formula (IIc. 1), $Z^{2b}$ is $NR^6$, where $R^6$ is defined as above. In some such embodiments, $R^6$ is taken together with an atom from $Y^a$ to form a cycloalkyl or heterocyclyl ring having between 3 and 7 ring atoms. In some such embodiments, the ring has 5 atoms.

In certain embodiments in which the Bcl-xL inhibitor is a compound of formula (IIc. 1), $Y^a$ is ethylene.

In certain embodiments in which the Bcl-xL inhibitor is a compound of formula (IIc. 1), $Y^a$ is methylene.

In certain embodiments in which the Bcl-xL inhibitor is a compound of formula (IIc.1), $Y^a$ is propylene.

In certain embodiments in which the Bcl-xL inhibitor is a compound of formula (IIc. 1), $R^4$ is H or methyl. In particular embodiments, $R^4$ is H.

In certain embodiments in which the Bcl-xL inhibitor is a compound of formula (IIc. 1), $Y^b$ is ethylene or propylene. In particular embodiments, $Y^b$ is ethylene.

In certain embodiments in which the Bcl-xL inhibitor is a compound of formula (IIc. 1), $R^{23}$ is methyl.

In certain embodiments in which the Bcl-xL inhibitor is a compound of formula (IIc.1), $R^{23}$ is H.

In certain embodiments in which the Bcl-xL inhibitor is a compound of formula (IIc. 1), G is selected from

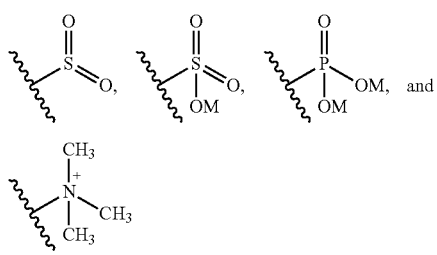

wherein M is hydrogen or a positively charged counterion. In particular embodiments, G is

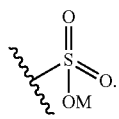

In particular embodiments, G is SO$_3$H.

In certain embodiments in which the Bcl-xL inhibitor is a compound of formula (IIc.1), Ar$^2$ is selected from

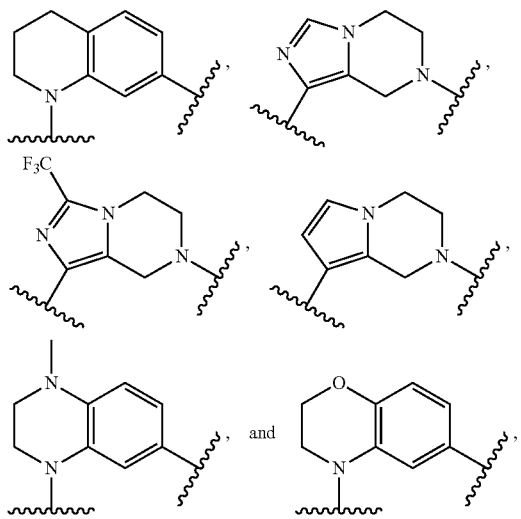

wherein the #—N(R$^4$)—Y$^a$—Z$^{2b}$— substituent is attached to Ar$^2$ at any Ar$^2$ atom capable of being substituted.

In particular embodiments in which the Bcl-xL inhibitor is a compound of formula (IIc. 1), Ar$^2$ is

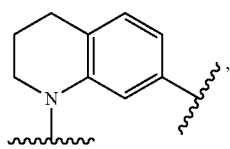 [SMILES: *c1ccc2c(c1)N(*)CCC2]

wherein the #—N(R$^4$) Y$^a$—Z$^{2b}$— substituent is attached to Ar$^2$ at any Ar$^2$ atom capable of being substituted. In certain embodiments in which the Bcl-xL inhibitor is a compound of formula (IIc.1), Ar$^2$ is selected from

—N(R$^4$)—Y$^a$—Z$^{2b}$— substituent is attached to Ar$^2$ at any Ar$^2$ atom capable of being substituted. In particular embodiments in which the Bcl-xL inhibitor is a compound of formula (IIc. 1), Ar$^2$ is

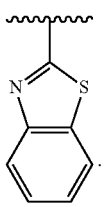

wherein the #—N(R$^4$)$^a$—Z$^{2b}$— substituent is attached to Ar$^2$ at any Ar$^2$ atom capable of being substituted.

In certain embodiments in which the Bcl-xL inhibitor is a compound of formula (IIc. 1), Ar$^1$ is

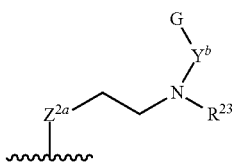

In certain embodiments in which the Bcl-xL inhibitor is a compound of formula (IIc. 1), the group is selected from:

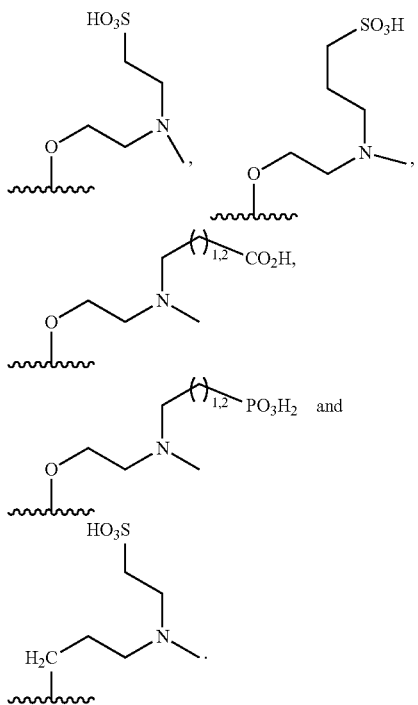

In other embodiments in which the Bcl-xL inhibitor is a compound of formula (IIc. 1), the group

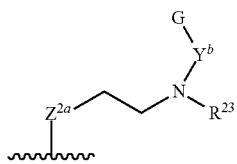

is selected from:

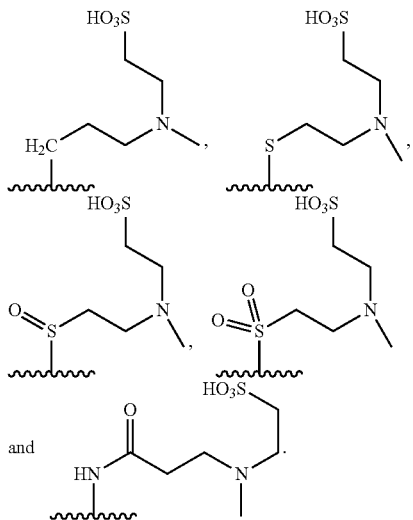

In certain embodiments in which the Bcl-xL inhibitor is a compound of formula (IIc), the compound has the structural formula (IIc.2),

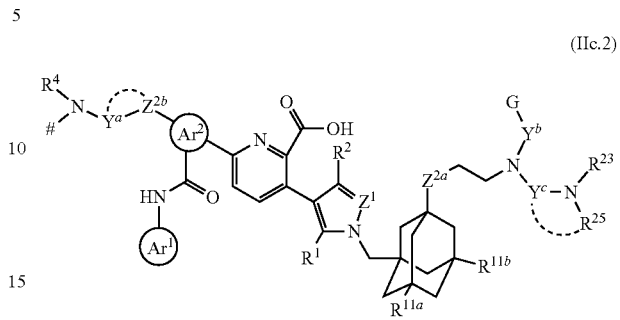

(IIc.2)

or salts thereof, wherein:

$Ar^1$, $Ar^2$, $Z^1$, $Z^{2a}$, $Z^{2b}$, $R^1$, $R^2$, $R^4$, $R^{11a}$, $R^{11b}$ and # are defined as above;

$Y^a$ is optionally substituted $C_1$-$C_8$ alkylene;
$Y^b$ is optionally substituted $C_1$-$C_8$ alkylene;
$Y^c$ is optionally substituted $C_1$-$C_8$ alkylene;
$R^{23}$ is selected from H and $C_1$-$C_4$ alkyl;
$R^{25}$ is $Y^b$-G or is taken together with an atom of $Y^c$ to form a ring having 4-6 ring atoms; and G is selected from a polyol, PEG4-30, a salt and a moiety that is charged at physiological pH.

In certain embodiments in which the Bcl-xL inhibitor is a compound of formula (IIc.2), $Z^{2a}$ is selected from O, $CH_2$, NH and S. In particular embodiments, $Z^{2a}$ is O. In certain embodiments, $Z^{2a}$ of formula (IIc.2) is $CR^{6a}R^{6b}$. In certain embodiments, $Z^{2a}$ of formula (IIc.2) is S. In certain embodiments, $Z^{2a}$ of formula (IIc.2) is —$NR^6C(O)$—. In certain embodiments in which the Bcl-xL inhibitor is a compound of formula (IIc.2), $Z^{2b}$ is selected from O, $CH_2$, NH, $NCH_3$ and S. In particular embodiments, $Z^{2b}$ is O. In particular embodiments, $Z^{2b}$ is NH. In particular embodiments, $Z^{2b}$ is $NCH_3$.

In certain embodiments in which the Bcl-xL inhibitor is a compound of formula (IIc.2), $Z^{2b}$ is a bond. In some such embodiments $Y^a$ is methylene or ethylene.

In certain embodiments in which the Bcl-xL inhibitor is a compound of formula (IIc.2), $Z^{2b}$ is $NR^6$, where $R^6$ is defined as above. In some such embodiments, $R^6$ is taken together with an atom from $Y^a$ to form a cycloalkyl or heterocyclyl ring having between 3 and 7 ring atoms. In some such embodiments, the ring has 5 atoms.

In certain embodiments in which the Bcl-xL inhibitor is a compound of formula (IIc.2), $Y^a$ is ethylene.

In certain embodiments in which the Bcl-xL inhibitor is a compound of formula (IIc.2), $Y^a$ is methylene.

In certain embodiments in which the Bcl-xL inhibitor is a compound of formula (IIc.2), $R^4$ is H or methyl.

In certain embodiments in which the Bcl-xL inhibitor is a compound of formula (IIc.2), $Y^b$ is ethylene or propylene. In particular embodiments, $Y^b$ is ethylene.

In certain embodiments in which the Bcl-xL inhibitor is a compound of formula (IIc.2), $Y^c$ is ethylene or propylene. In particular embodiments, $Y^b$ is ethylene.

In certain embodiments in which the Bcl-xL inhibitor is a compound of formula (IIc.2), $R^{25}$ is taken together with an atom of $Y^C$ to form a ring having 4 or 5 ring atoms.

In certain embodiments in which the Bcl-xL inhibitor is a compound of formula (IIc.2), $R^{23}$ is methyl.

In certain embodiments in which the Bcl-xL inhibitor is a compound of formula (IIc.2), G is selected from

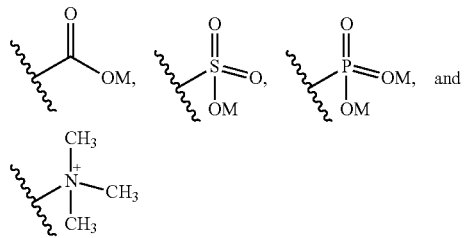

wherein M is hydrogen or a positively charged counterion. In particular embodiments, G is

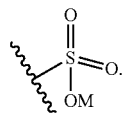

In particular embodiments, G is SO₃H.

In certain embodiments in which the Bcl-xL inhibitor is a compound of formula (IIc.2), Ar² is selected from

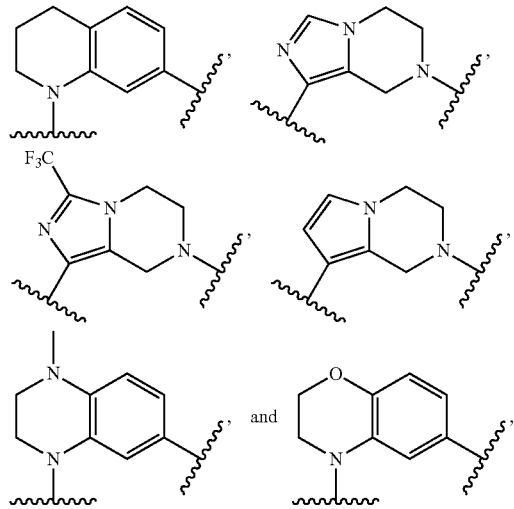

wherein the #—N(R⁴)—Y$^a$—Z$^{2b}$— substituent is attached to Ar² at any Ar² atom capable of being substituted.

In particular embodiments in which the Bcl-xL inhibitor is a compound of formula (IIc.2), Ar² is

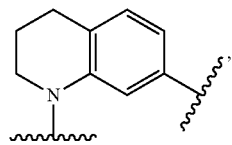 [SMILES: *c1ccc2c(c1)N(*)CCC2]

wherein the #—N(R⁴)—Y$^a$—Z$^{2b}$— substituent is attached to Ar² at any Ar² atom capable of being substituted. In certain embodiments in which the Bcl-xL inhibitor is a compound of formula (IIc.2), Ar² is selected from

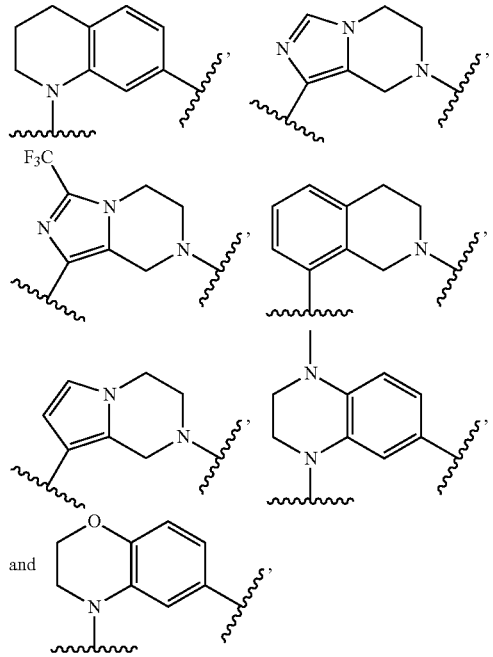

wherein the #—N(R⁴)—Y$^a$—Z$^{2b}$— substituent is attached to Ar² at any Ar² atom capable of being substituted. In particular embodiments in which the Bcl-xL inhibitor is a compound of formula (IIc.2), Ar² is

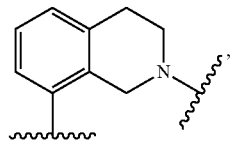

wherein the #—N(R⁴)—Y$^a$—Z$^{2b}$— substituent is attached to Ar² at any Ar² atom capable of being substituted.

In certain embodiments in which the Bcl-xL inhibitor is a compound of formula (IIc.2), Ar¹ is

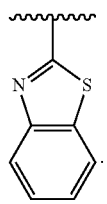 [SMILES: *c1nc2ccccc2s1]

In certain embodiments in which the Bcl-xL inhibitor is a compound of formula (IIc.2), the group

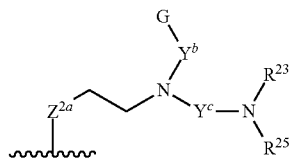

is selected from:

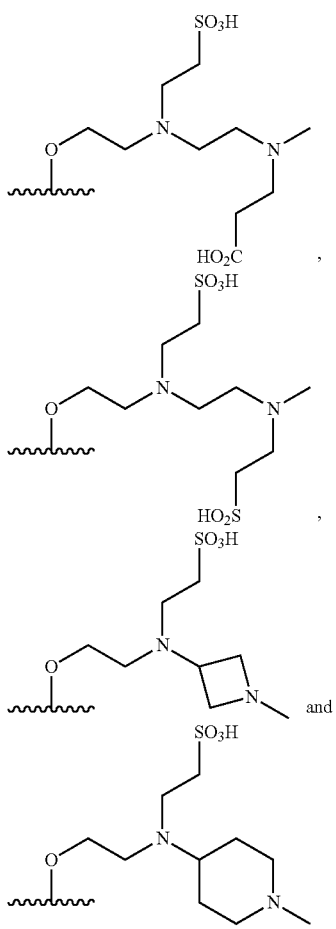

and

In certain embodiments in which the Bcl-xL inhibitor is a compound of formula (IId), the compound has the structural formula (IId.1),

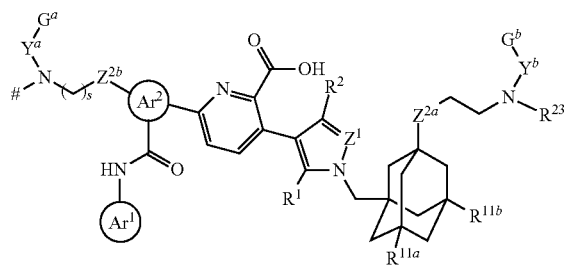

(IId.1)

or salts thereof, wherein:
Ar$^1$, Ar$^2$, Z$^1$, Z$^{2a}$, Z$^{2b}$, R$^1$, R$^2$, R$^{11a}$, R$^{11b}$ and # are defined as above;
Y$^a$ is optionally substituted alkylene;
Y$^b$ is optionally substituted alkylene;
R$^{23}$ is selected from H and C$_1$-C$_4$ alkyl;
G$^a$ is selected from a polyol, PEG4-30, a salt and a moiety that is charged at physiological pH;
G$^b$ is selected from a polyol, PEG4-30, a salt and a moiety that is charged at physiological pH;

In certain embodiments in which the Bcl-xL inhibitor is a compound of formula (IId. 1), s is 1.

In certain embodiments in which the Bcl-xL inhibitor is a compound of formula (IId. 1), s is 2.

In certain embodiments in which the Bcl-xL inhibitor is a compound of formula (IId. 1), Z$^{2a}$ is selected from O, NH, CH$_2$ and S. In particular embodiments, Z$^{2a}$ is O. In certain embodiments, Z$^{2a}$ of formula (IId.1) is CR$^{6a}$R$^{6b}$. In certain embodiments, Z$^{2a}$ of formula (IId.1) is S. In certain embodiments, Z$^{2a}$ of formula (IId. 1) is —NR$^6$C(O)—.

In certain embodiments in which the Bcl-xL inhibitor is a compound of formula (IId. 1), Z$^{2b}$ is selected from O, NH, CH$_2$ and S. In particular embodiments, Z$^{2b}$ is O.

In certain embodiments in which the Bcl-xL inhibitor is a compound of formula (IId. 1), Y$^a$ is selected from ethylene, propylene and butylene. In particular embodiments, Y is ethylene.

In certain embodiments in which the Bcl-xL inhibitor is a compound of formula (IId. 1), Y$^a$ is selected from ethylene, propylene and butylene. In particular embodiments, Y is ethylene.

In certain embodiments in which the Bcl-xL inhibitor is a compound of formula (IId. 1), G$^a$ is selected from

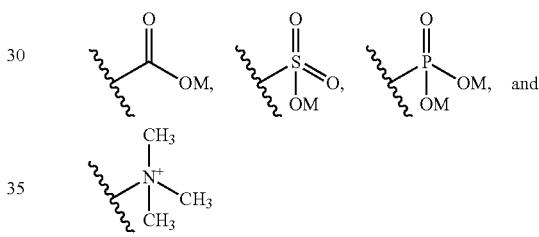

wherein M is hydrogen or a positively charged counterion. In particular embodiments, G$^a$ is

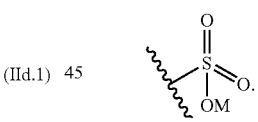

In particular embodiments, G$^a$ is SO$_3$H. In particular embodiments, G$^a$ is CO$_2$H.

In certain embodiments in which the Bcl-xL inhibitor is a compound of formula (IId. 1), G$^b$ is selected from

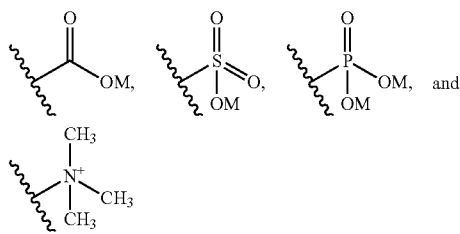

wherein M is hydrogen or a positively charged counterion. In particular embodiments, G$^b$ is

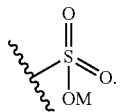

In particular embodiments, $G^b$ is $SO_3H$. In particular embodiments, $G^b$ is $CO_2H$.

In certain embodiments in which the Bcl-xL inhibitor is a compound of formula (IId. 1), $R^{23}$ is methyl.

In certain embodiments in which the Bcl-xL inhibitor is a compound of formula (IId. 1), $Ar^2$ is selected from

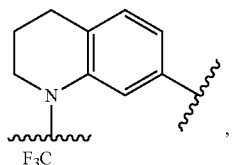 , 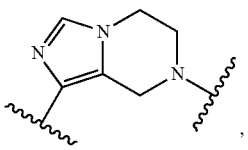 ,

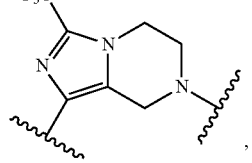 , 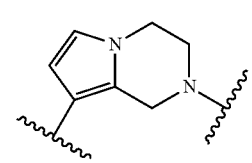 ,

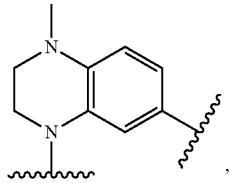 , and 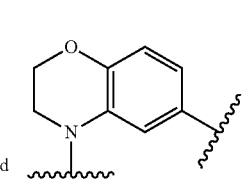 , wherein the $G^a$-$Y^a$—N(#)—$(CH_2)_s$—$Z^{2b}$— substituent is attached to $Ar^2$ at any $Ar^2$ atom capable of being substituted.

In particular embodiments in which the Bcl-xL inhibitor is a compound of formula (IId. 1), $Ar^2$ is

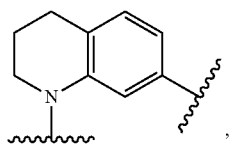 [SMILES: *c1ccc2c(c1)N(*)CCC2] , wherein the $G^a$-$Y^a$—N(#)—$(CH_2)_s$—$Z^{2b}$— substituent is attached to $Ar^2$ at any $Ar^2$ atom capable of being substituted. In certain embodiments in which the Bcl-xL inhibitor is a compound of formula (IId. 1), $Ar^2$ is selected from

 , 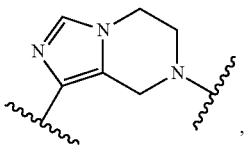 ,

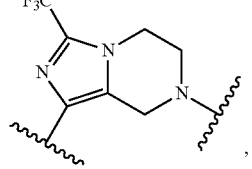 , 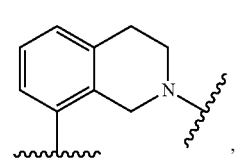 [SMILES: *c1cccc2c1CN(*)CC2] ,

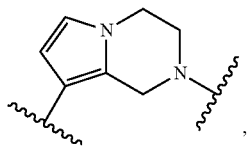

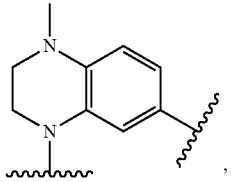 , and 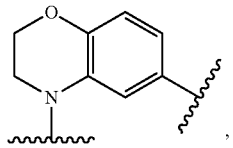 , wherein the $G^a$-$Y^a$—N(#)—$(CH_2)_s$—$Z^{2b}$— substituent is attached to $Ar^2$ at any $Ar^2$ atom capable of being substituted.

In particular embodiments in which the Bcl-xL inhibitor is a compound of formula (IId. 1), $Ar^2$ is

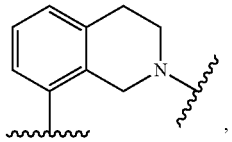 , wherein the $G^a$-$Y^a$—N(#)—$(CH_2)_s$—$Z^{2b}$— substituent is attached to $Ar^2$ at any $Ar^2$ atom capable of being substituted.

In certain embodiments in which the Bcl-xL inhibitor is a compound of formula (IId. 1), $Ar^1$ is

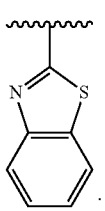

In certain embodiments, $R^{11a}$ and $R^{11b}$ of formulae (IIa)-(IId) are the same. In a particular embodiment, $R^{11a}$ and $R^{11b}$ are each methyl.

In certain embodiments, the compounds of formulae (IIa)-(IId) include one of the following cores (C.1)-(C.21):

(C.1)

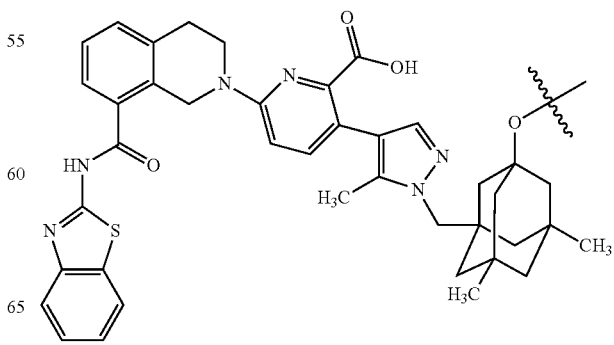

(C.2)
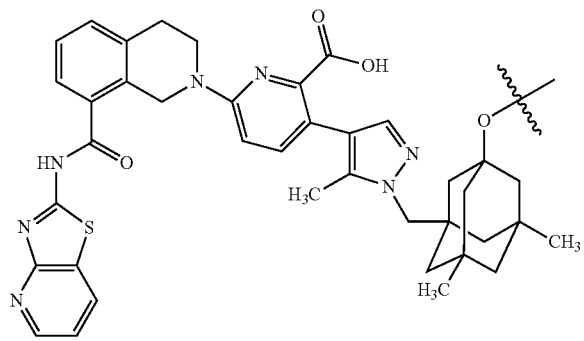
(C.3)
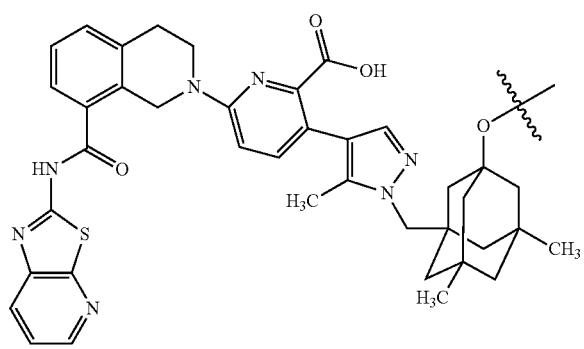
(C.4)
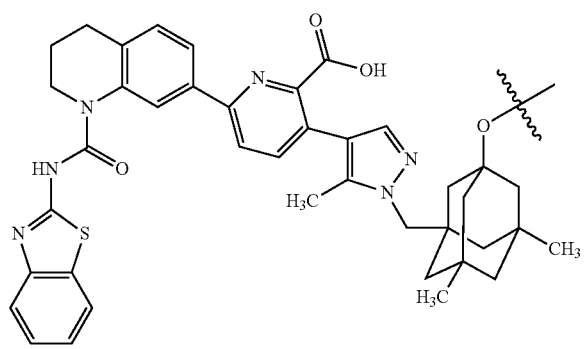
(C.5)
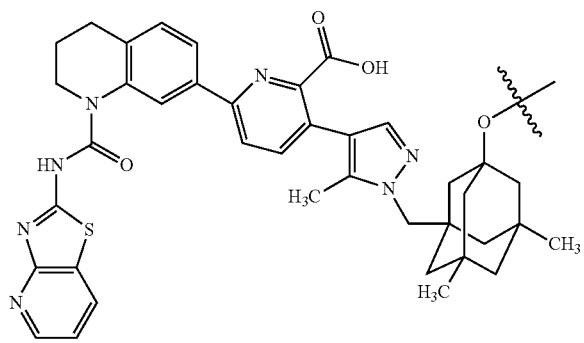
(C.6)
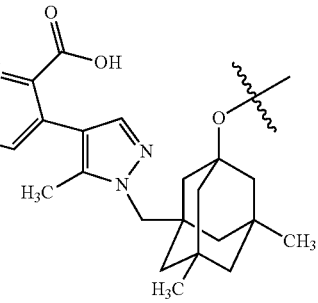
(C.7)
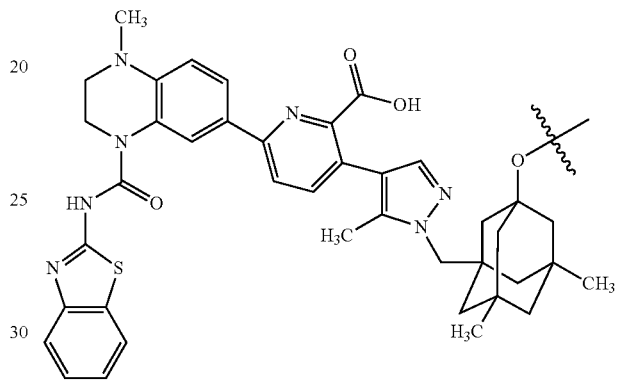
(C.8)
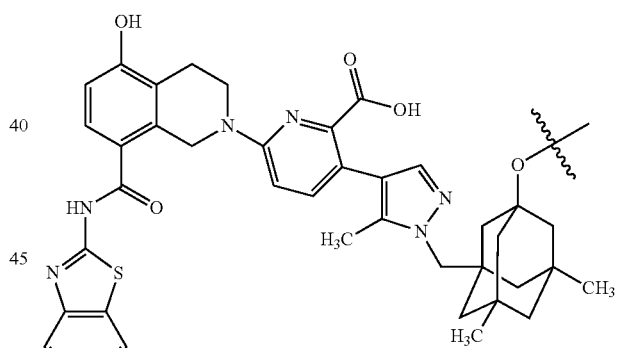
(C.9)
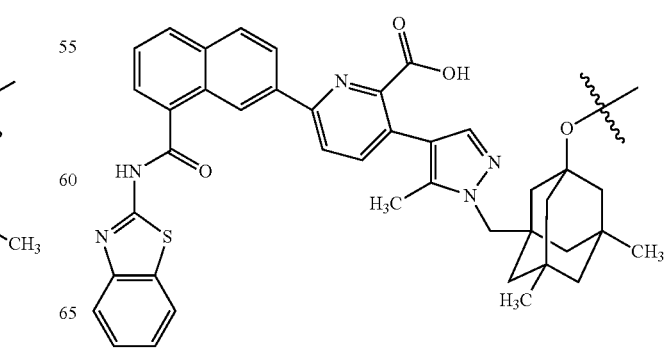

-continued
(C.10)
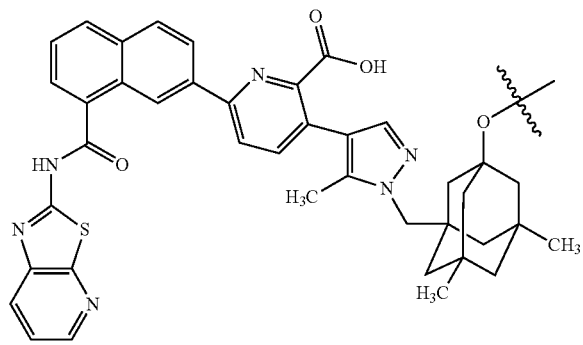
(C.11)
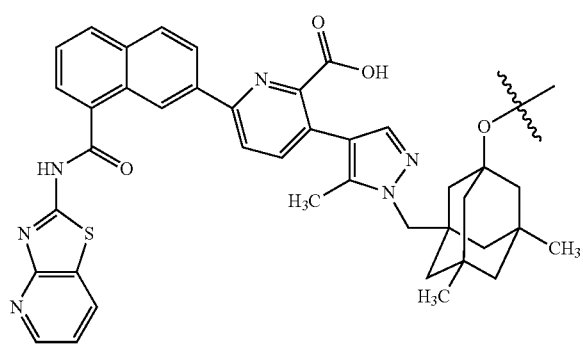
(C.12)
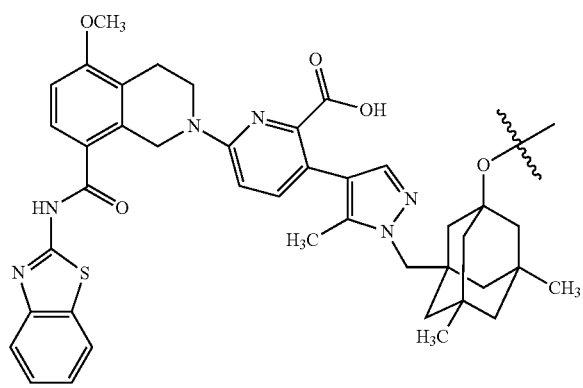
(C.13)
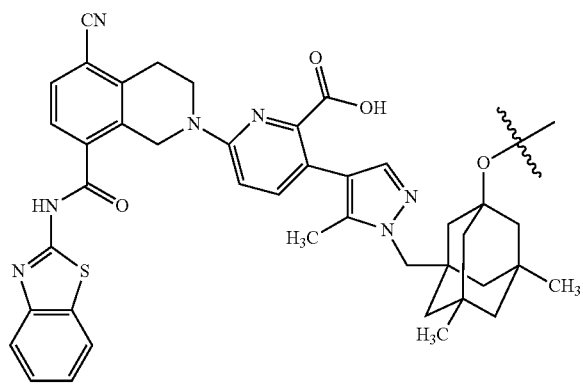
-continued
(C.14)
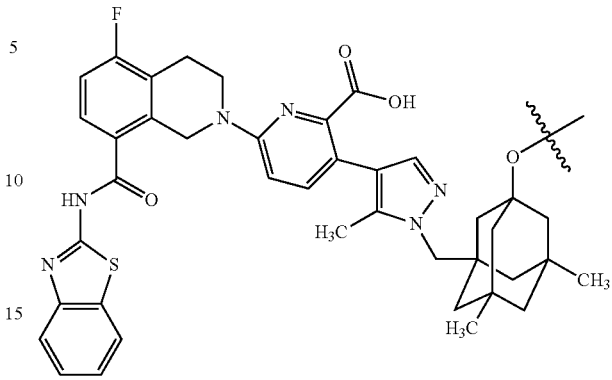
(C.15)
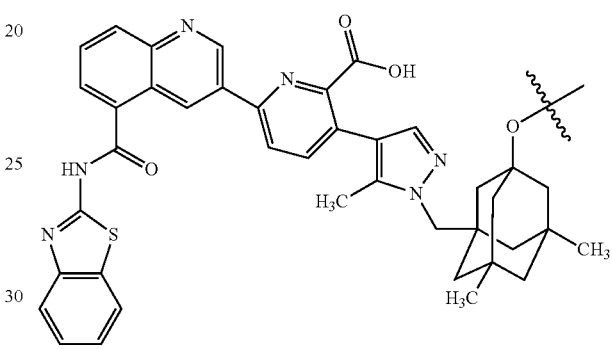
(C.16)
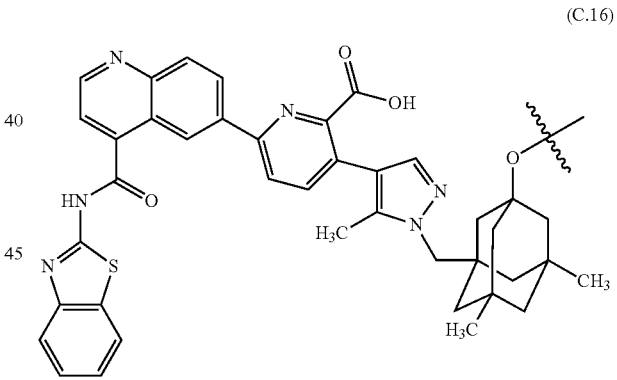
(C.17)
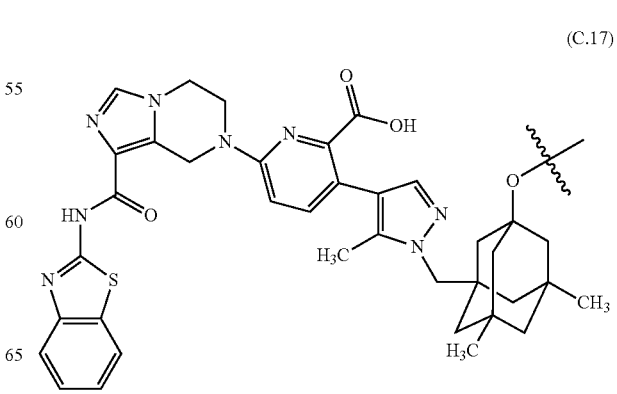

-continued

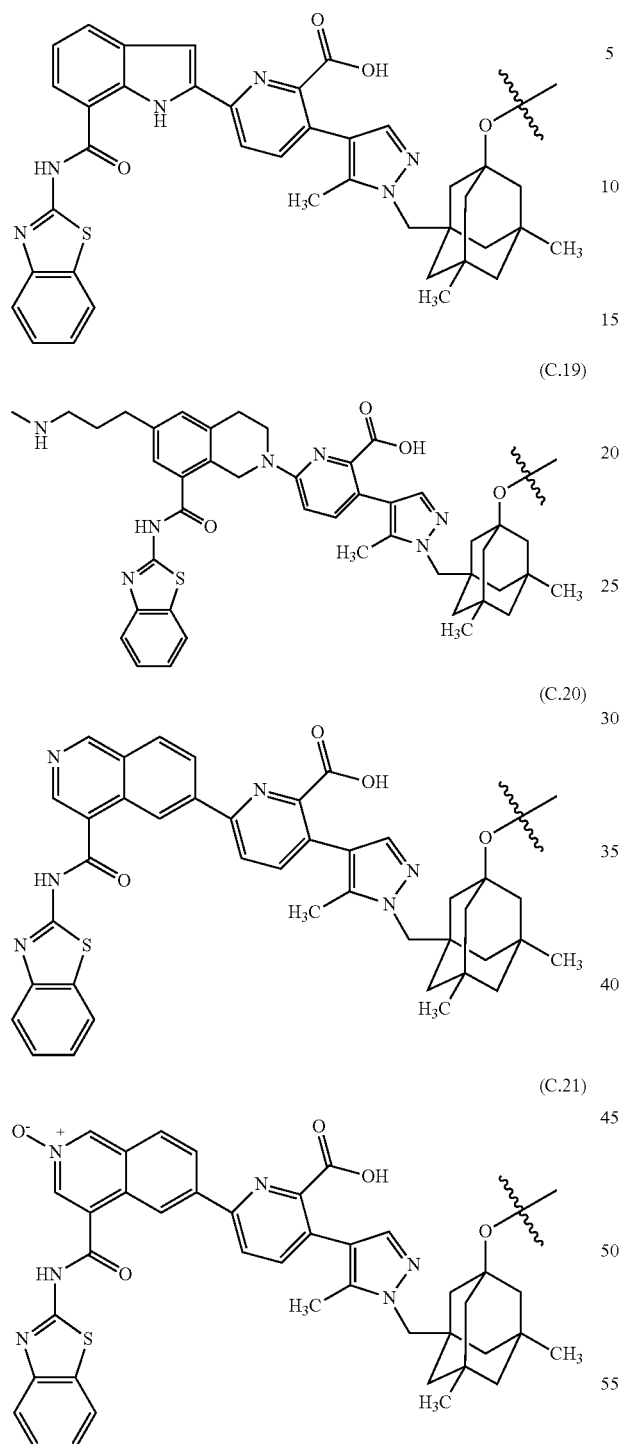

(C.18)
(C.19)
(C.20)
(C.21)

Exemplary Bcl-xL inhibitors according to structural formulae (IIa)-(IId) that may be used in the methods described herein in unconjugated form and/or included in the ADCs described herein include the following compounds, and/or salts thereof:

| App Ex. No. | Bcl-xL Inhibitor Cmpd No |
|---|---|
| 1.1 | W2.01 |
| 1.2 | W2.02 |
| 1.3 | W2.03 |
| 1.5 | W2.05 |
| 1.6 | W2.06 |
| 1.7 | W2.07 |
| 1.8 | W2.08 |
| 1.9 | W2.09 |
| 1.10 | W2.10 |
| 1.11 | W2.11 |
| 1.12 | W2.12 |
| 1.13 | W2.13 |
| 1.14 | W2.14 |
| 1.15 | W2.15 |
| 1.16 | W2.16 |
| 1.17 | W2.17 |
| 1.18 | W2.18 |
| 1.19 | W2.19 |
| 1.20 | W2.20 |
| 1.21 | W2.21 |
| 1.22 | W2.22 |
| 1.23 | W2.23 |
| 1.24 | W2.24 |
| 1.25 | W2.25 |
| 1.26 | W2.26 |
| 1.27 | W2.27 |
| 1.28 | W2.28 |
| 1.29 | W2.29 |
| 1.30 | W2.30 |
| 1.31 | W2.31 |
| 1.32 | W2.32 |
| 1.33 | W2.33 |
| 1.34 | W2.34 |
| 1.35 | W2.35 |
| 1.36 | W2.36 |
| 1.37 | W2.37 |
| 1.38 | W2.38 |
| 1.39 | W2.39 |
| 1.40 | W2.40 |
| 1.41 | W2.41 |
| 1.42 | W2.42 |
| 1.43 | W2.43 |
| 1.44 | W2.44 |
| 1.45 | W2.45 |
| 1.46 | W2.46 |
| 1.47 | W2.47 |
| 1.48 | W2.48 |
| 1.49 | W2.49 |
| 1.50 | W2.50 |
| 1.51 | W2.51 |
| 1.52 | W2.52 |
| 1.53 | W2.53 |
| 1.54 | W2.54 |
| 1.55 | W2.55 |
| 1.56 | W2.56 |
| 1.57 | W2.57 |
| 1.58 | W2.58 |
| 1.59 | W2.59 |
| 1.60 | W2.60 |
| 1.61 | W2.61 |
| 1.62 | W2.62 |
| 1.63 | W2.63 |
| 1.64 | W2.64 |
| 1.65 | W2.65 |
| 1.66 | W2.66 |
| 1.67 | W2.67 |
| 1.68 | W2.68 |
| 1.69 | W2.69 |
| 1.70 | W2.70 |
| 1.71 | W2.71 |
| 1.72 | W2.72 |
| 1.73 | W2.73 |
| 1.74 | W2.74 |
| 1.75 | W2.75 |
| 1.76 | W2.76 |
| 1.77 | W2.77 |
| 1.78 | W2.78 |
| 1.79 | W2.79 |
| 1.80 | W2.80 |

| App Ex. No. | Bcl-xL Inhibitor Cmpd No |
|---|---|
| 1.81 | W2.81 |
| 1.82 | W2.82 |
| 1.83 | W2.83 |
| 1.84 | W2.84 |
| 1.85 | W2.85 |
| 1.86 | W2.86 |
| 1.87 | W2.87 |
| 1.88 | W2.88 |
| 1.89 | W2.89 |
| 1.90 | W2.90 |
| 1.91 | W2.91 |

Notably, when the Bcl-xL inhibitor of the present application is in conjugated form, the hydrogen corresponding to the # position of structural formulae (IIa)-(IId) is not present, forming a monoradical. For example, compound W2.01 (Example 1.1) is 6-[8-(1,3-benzothiazol-2-ylcarbamoyl)-3,4-dihydroisoquinolin-2(1H)-yl]-3-[1-({3-[2-({2-[2-(carboxymethoxy)ethoxy]ethyl}amino)ethoxy]-5,7-dimethyltricyclo[3.3.1.13,7]dec-1-yl}methyl)-5-methyl-1H-pyrazol-4-yl]pyridine-2-carboxylic acid.

When it is in unconjugated form, it has the following structure:

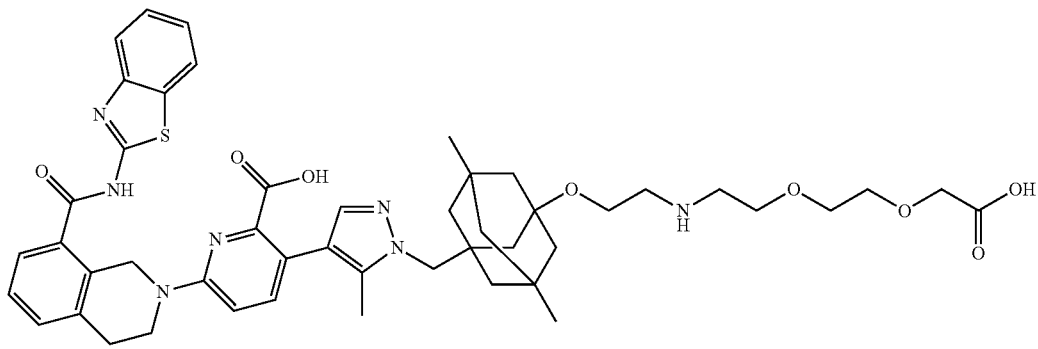 [SMILES: Cc1c(-c2ccc(N3CCc4cccc(C(=O)Nc5nc6ccccc6s5)c4C3)nc2C(=O)O)cnn1CC12CC3(C)CC(C)(C1)CC(OCCNCCOCCOCC(=O)O)(C3)C2]

When the same compound is included in the ADCs as shown in structural formula (IIa) or (IIb), the hydrogen corresponding to the # position is not present, forming a monoradical.

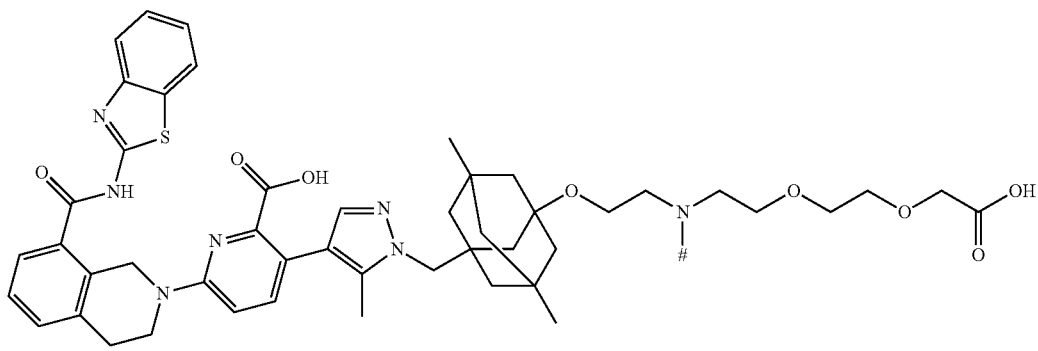

In certain embodiments, the Bcl-xL inhibitors according to structural formulae (IIa)-(IId) are selected from the group consisting of W2.01, W2.02, W2.03, W2.04, W2.05, W2.06, W2.07, W2.08, W2.09, W2.10, W2.11, W2.12, W2.13, W2.14, W2.15, W2.16, W2.17, W2.18, W2.19, W2.20, W2.21, W2.22, W2.23, W2.24, W2.25, W2.26, W2.27, W2.28, W2.29, W2.30, W2.31, W2.32, W2.33, W2.34, W2.35, W2.36, W2.37, W2.38, W2.39, W2.40, W2.41, W2.42, W2.43, W2.44, W2.45, W2.46, W2.47, W2.48, W2.49, W2.50, W2.51, W2.52, W2.53, W2.54, W2.55, W2.56, W2.57, W2.58, W2.59, W2.60, W2.61, W2.62, W2.63, W2.64, W2.65, W2.66, W2.67, W2.68, W2.69, W2.70, W2.71, W2.72, W2.73, W2.74, W2.75, W2.76, W2.77, W2.78, W2.79, W2.80, W2.81, W2.82, W2.83, W2.84, W2.85, W2.86, W2.87, W2.88, W2.89, W2.90, and W2.91, or pharmaceutically acceptable salts thereof.

In certain embodiments, the ADC, or a pharmaceutically acceptable salt thereof, comprises a drug linked to an antibody by way of a linker, wherein the drug is a Bcl-xL inhibitor selected from the group consisting of W2.01, W2.02, W2.03, W2.04, W2.05, W2.06, W2.07, W2.08, W2.09, W2.10, W2.11, W2.12, W2.13, W2.14, W2.15, W2.16, W2.17, W2.18, W2.19, W2.20, W2.21, W2.22, W2.23, W2.24, W2.25, W2.26, W2.27, W2.28, W2.29, W2.30, W2.31, W2.32, W2.33, W2.34, W2.35, W2.36, W2.37, W2.38, W2.39, W2.40, W2.41, W2.42, W2.43, W2.44, W2.45, W2.46, W2.47, W2.48, W2.49, W2.50, W2.51, W2.52, W2.53, W2.54, W2.55, W2.56, W2.57, W2.58, W2.59, W2.60, W2.61, W2.62, W2.63, W2.64, W2.65, W2.66, W2.67, W2.68, W2.69, W2.70, W2.71, W2.72, W2.73, W2.74, W2.75, W2.76, W2.77, W2.78, W2.79, W2.80, W2.81, W2.82, W2.83, W2.84, W2.85, W2.86, W2.87, W2.88, W2.89, W2.90, and W2.91.

In certain embodiments, the ADC, or a pharmaceutically acceptable salt thereof, the Bcl-xL inhibitor is selected from the group consisting of the following compounds modified in that the hydrogen corresponding to the # position of structural formula (IIa), (IIb), (IIc), or (IId) is not present forming a monoradical:

6-[8-(1,3-benzothiazol-2-ylcarbamoyl)-3,4-dihydroisoquinolin-2(1H)-yl]-3-[1-({3-[2-({2-[2-(carboxymethoxy)ethoxy]ethyl}amino)ethoxy]-5,7-dimethyltricyclo[3.3.1.1$^{3,7}$]dec-1-yl}methyl)-5-methyl-1H-pyrazol-4-yl]pyridine-2-carboxylic acid;

6-[8-(1,3-benzothiazol-2-ylcarbamoyl)-3,4-dihydroisoquinolin-2(1H)-yl]-3-{1-[(3,5-dimethyl-7-{2-[(2-sulfoethyl)amino]ethoxy}tricyclo[3.3.1.1$^{3,7}$]dec-1-yl)methyl]-5-methyl-1H-pyrazol-4-yl}pyridine-2-carboxylic acid;

2-{[(2-{[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl]amino}ethyl)sulfonyl]amino}-2-deoxy-D-glucopyranose;

6-[8-(1,3-benzothiazol-2-ylcarbamoyl)-3,4-dihydroisoquinolin-2(1H)-yl]-3-{1-[(3,5-dimethyl-7-{2-[(4-{[(3R,4R,5S,6R)-3,4,5-trihydroxy-6-(hydroxymethyl)tetrahydro-2H-pyran-2-yl]methyl}benzyl)amino]ethoxy}tricyclo[3.3.1.1$^{3,7}$]dec-1-yl)methyl]-5-methyl-1H-pyrazol-4-yl}pyridine-2-carboxylic acid 6-[8-(1,3-benzothiazol-2-ylcarbamoyl)-3,4-dihydroisoquinolin-2(1H)-yl]-3-{1-[(3,5-dimethyl-7-{2-[(3-sulfopropyl)amino]ethoxy}tricyclo[3.3.1.1$^{3,7}$]dec-1-yl)methyl]-5-methyl-1H-pyrazol-4-yl}pyridine-2-carboxylic acid;

6-[8-(1,3-benzothiazol-2-ylcarbamoyl)-3,4-dihydroisoquinolin-2(1H)-yl]-3-{1-[(3-{2-[(2,3-dihydroxypropyl)amino]ethoxy}-5,7-dimethyltricyclo[3.3.1.1$^{3,7}$]dec-1-yl)methyl]-5-methyl-1H-pyrazol-4-yl}pyridine-2-carboxylic acid;

2-({[4-({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl]amino}methyl)phenyl]sulfonyl}amino)-2-deoxy-beta-D-glucopyranose;

8-(1,3-benzothiazol-2-ylcarbamoyl)-2-{6-carboxy-5-[1-({3-[2-({2-[1-(beta-D-glucopyranuronosyl)-1H-1,2,3-triazol-4-yl]ethyl}amino)ethoxy]-5,7-dimethyltricyclo[3.3.1.1$^{3,7}$]dec-1-yl}methyl)-5-methyl-1H-pyrazol-4-yl]pyridin-2-yl}-1,2,3,4-tetrahydroisoquinoline;

3-[1-({3-[2-(2-{[4-(beta-D-allopyranosyloxy)benzyl]amino}ethoxy)ethoxy]-5,7-dimethyltricyclo[3.3.1.1$^{3,7}$]dec-1-yl}methyl)-5-methyl-1H-pyrazol-4-yl]-6-[8-(1,3-benzothiazol-2-ylcarbamoyl)-3,4-dihydroisoquinolin-2(1H)-yl]pyridine-2-carboxylic acid;

6-[8-(1,3-benzothiazol-2-ylcarbamoyl)-3,4-dihydroisoquinolin-2(1H)-yl]-3-(1-{[3,5-dimethyl-7-(2-{2-[(2-sulfoethyl)amino]ethoxy}ethoxy)tricyclo[3.3.1.1$^{3,7}$]dec-1-yl]methyl}-5-methyl-1H-pyrazol-4-yl)pyridine-2-carboxylic acid;

6-[8-(1,3-benzothiazol-2-ylcarbamoyl)-3,4-dihydroisoquinolin-2(1H)-yl]-3-{1-[(3,5-dimethyl-7-{2-[(2-phosphonoethyl)amino]ethoxy}tricyclo[3.3.1.1$^{3,7}$]dec-1-yl)methyl]-5-methyl-1H-pyrazol-4-yl}pyridine-2-carboxylic acid;

6-[8-(1,3-benzothiazol-2-ylcarbamoyl)-3,4-dihydroisoquinolin-2(1H)-yl]-3-{1-[(3,5-dimethyl-7-{2-[methyl(3-sulfo-L-alanyl)amino]ethoxy}tricyclo[3.3.1.1$^{3,7}$]dec-1-yl)methyl]-5-methyl-1H-pyrazol-4-yl}pyridine-2-carboxylic acid;

6-[8-(1,3-benzothiazol-2-ylcarbamoyl)-3,4-dihydroisoquinolin-2(1H)-yl]-3-{1-[(3,5-dimethyl-7-{2-[(3-phosphonopropyl)amino]ethoxy}tricyclo[3.3.1.1$^{3,7}$]dec-1-yl)methyl]-5-methyl-1H-pyrazol-4-yl}pyridine-2-carboxylic acid;

6-[8-(1,3-benzothiazol-2-ylcarbamoyl)-3,4-dihydroisoquinolin-2(1H)-yl]-3-{1-[(3,5-dimethyl-7-{2-[(3-sulfo-L-alanyl)amino]ethoxy tricyclo[3.3.1.1$^{3,7}$]dec-1-yl)methyl]-5-methyl-1H-pyrazol-4-yl}pyridine-2-carboxylic acid;

6-[8-(1,3-benzothiazol-2-ylcarbamoyl)-3,4-dihydroisoquinolin-2(1H)-yl]-3-(1-{[3,5-dimethyl-7-(2-{2-[(3-phosphonopropyl)amino]ethoxy}ethoxy)tricyclo[3.3.1.1$^{3,7}$]dec-1-yl]methyl}-5-methyl-1H-pyrazol-4-yl)pyridine-2-carboxylic acid;

3-{1-[(3-{2-[L-alpha-aspartyl(methyl)amino]ethoxy}-5,7-dimethyltricyclo[3.3.1.1$^{3,7}$]dec-1-yl)methyl]-5-methyl-1H-pyrazol-4-yl}-6-[8-(1,3-benzothiazol-2-ylcarbamoyl)-3,4-dihydroisoquinolin-2(1H)-yl]pyridine-2-carboxylic acid;

6-{4-[({2-[2-(2-aminoethoxy)ethoxy]ethyl}[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl]amino)methyl]benzyl}-2,6-anhydro-L-gulonic acid;

4-({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl]amino}methyl)phenyl hexopyranosiduronic acid;

6-[1-(1,3-benzothiazol-2-ylcarbamoyl)-1,2,3,4-tetrahydroquinolin-7-yl]-3-{1-[(3,5-dimethyl-7-{2-[(2-phosphonoethyl)amino]ethoxy}tricyclo[3.3.1.1$^{3,7}$]dec-1-yl)methyl]-5-methyl-1H-pyrazol-4-yl}pyridine-2-carboxylic acid;

6-[1-(1,3-benzothiazol-2-ylcarbamoyl)-1,2,3,4-tetrahydroquinolin-7-yl]-3-{1-[(3,5-dimethyl-7-{2-[methyl(3-sulfo-L-alanyl)amino]ethoxy}tricyclo[3.3.1.1$^{3,7}$]dec-1-yl)methyl]-5-methyl-1H-pyrazol-4-yl}pyridine-2-carboxylic acid;

3-{1-[(3,5-dimethyl-7-{2-[(2-sulfoethyl)amino]ethoxy}tricyclo[3.3.1.1$^{3,7}$]dec-1-yl)methyl]-5-methyl-1H-pyrazol-4-yl}-6-[8-([1,3]thiazolo[5,4-b]pyridin-2-ylcarbamoyl)-3,4-dihydroisoquinolin-2(1H)-yl]pyridine-2-carboxylic acid;

3-{1-[(3,5-dimethyl-7-{2-[(2-sulfoethyl)amino]ethoxy}tricyclo[3.3.1.1$^{3,7}$]dec-1-yl)methyl]-5-methyl-1H-pyrazol-4-yl}-6-[8-([1,3]thiazolo[4,5-b]pyridin-2-ylcarbamoyl)-3,4-dihydroisoquinolin-2(1H)-yl]pyridine-2-carboxylic acid;

6-[1-(1,3-benzothiazol-2-ylcarbamoyl)-1,2,3,4-tetrahydroquinolin-7-yl]-3-{1-[(3,5-dimethyl-7-{2-[(2-sulfoethyl)amino]ethoxy}tricyclo[3.3.1.1$^{3,7}$]dec-1-yl)methyl]-5-methyl-1H-pyrazol-4-yl}pyridine-2-carboxylic acid;

6-[8-(1,3-benzothiazol-2-ylcarbamoyl)-3,4-dihydroisoquinolin-2(1H)-yl]-3-{1-[(3-{2-[(2-carboxyethyl)amino]ethoxy}-5,7-dimethyltricyclo[3.3.1.1$^{3,7}$]dec-1-yl)methyl]-5-methyl-1H-pyrazol-4-yl}pyridine-2-carboxylic acid;

6-[8-(1,3-benzothiazol-2-ylcarbamoyl)-3,4-dihydroisoquinolin-2(1H)-yl]-3-{1-[(3,5-dimethyl-7-{2-[(3-phosphonopropyl)(piperidin-4-yl)amino]ethoxy}tricyclo[3.3.1.1$^{3,7}$]dec-1-yl)methyl]-5-methyl-1H-pyrazol-4-yl}pyridine-2-carboxylic acid;

3-{1-[(3-{2-[D-alpha-aspartyl(methyl)amino]ethoxy}-5,7-dimethyltricyclo[3.3.1.1$^{3,7}$]dec-1-yl)methyl]-5-methyl-1H-pyrazol-4-yl}-6-[8-(1,3-benzothiazol-2-ylcarbamoyl)-3,4-dihydroisoquinolin-2(1H)-yl]pyridine-2-carboxylic acid;

6-[8-(1,3-benzothiazol-2-ylcarbamoyl)-3,4-dihydroisoquinolin-2(1H)-yl]-3-(1-{[3-(2-{[1-(carboxymethyl)piperidin-4-yl]amino}ethoxy)-5,7-dimethyltricyclo[3.3.1.1$^{3,7}$]dec-1-yl]methyl}-5-methyl-1H-pyrazol-4-yl)pyridine-2-carboxylic acid;

N-[(5S)-5-amino-6-{[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](methyl)amino}-6-oxohexyl]-N,N-dimethylmethanaminium;

6-[8-(1,3-benzothiazol-2-ylcarbamoyl)-3,4-dihydroisoquinolin-2(1H)-yl]-3-{1-[(3,5-dimethyl-7-{2-[piperidin-4-yl(2-sulfoethyl)amino]ethoxy}tricyclo[3.3.1.1$^{3,7}$]dec-1-yl)methyl]-5-methyl-1H-pyrazol-4-yl}pyridine-2-carboxylic acid;

6-[8-(1,3-benzothiazol-2-ylcarbamoyl)-5-(3-phosphonopropoxy)-3,4-dihydroisoquinolin-2(1H)-yl]-3-[1-({3,5-dimethyl-7-[2-(methylamino)ethoxy]tricyclo[3.3.1.1$^{3,7}$]dec-1-yl}methyl)-5-methyl-1H-pyrazol-4-yl]pyridine-2-carboxylic acid;

6-[8-(1,3-benzothiazol-2-ylcarbamoyl)-3,4-dihydroisoquinolin-2(1H)-yl]-3-(1-{[3-(2-{[N-(2-carboxyethyl)-L-alpha-aspartyl]amino}ethoxy)-5,7-dimethyltricyclo[3.3.1.1$^{3,7}$]dec-1-yl]methyl}-5-methyl-1H-pyrazol-4-yl)pyridine-2-carboxylic acid;

3-{1-[(3-{2-[(2-aminoethyl)(2-sulfoethyl)amino]ethoxy}-5,7-dimethyltricyclo[3.3.1.1$^{3,7}$]dec-1-yl)methyl]-5-methyl-1H-pyrazol-4-yl}-6-[8-(1,3-benzothiazol-2-ylcarbamoyl)-3,4-dihydroisoquinolin-2(1H)-yl]pyridine-2-carboxylic acid;

6-[5-(2-aminoethoxy)-8-(1,3-benzothiazol-2-ylcarbamoyl)-3,4-dihydroisoquinolin-2(1H)-yl]-3-[1-({3,5-dimethyl-7-[2-(methylamino)ethoxy]tricyclo[3.3.1.1$^{3,7}$]dec-1-yl}methyl)-5-methyl-1H-pyrazol-4-yl]pyridine-2-carboxylic acid;

6-[8-(1,3-benzothiazol-2-ylcarbamoyl)naphthalen-2-yl]-3-{1-[(3,5-dimethyl-7-{2-[(3-sulfopropyl)amino]ethoxy}tricyclo[3.3.1.1$^{3,7}$]dec-1-yl)methyl]-5-methyl-1H-pyrazol-4-yl}pyridine-2-carboxylic acid;

6-[8-(1,3-benzothiazol-2-ylcarbamoyl)-3,4-dihydroisoquinolin-2(1H)-yl]-3-{1-[(3-{2-[(2-carboxyethyl)(piperidin-4-yl)amino]ethoxy}-5,7-dimethyltricyclo[3.3.1.1$^{3,7}$]dec-1-yl)methyl]-5-methyl-1H-pyrazol-4-yl}pyridine-2-carboxylic acid;

6-[8-(1,3-benzothiazol-2-ylcarbamoyl)-3,4-dihydroisoquinolin-2(1H)-yl]-3-{1-[(3,5-dimethyl-7-{2-[(3-sulfo-L-alanyl)(2-sulfoethyl)amino]ethoxy}tricyclo[3.3.1.1$^{3,7}$]dec-1-yl)methyl]-5-methyl-1H-pyrazol-4-yl}pyridine-2-carboxylic acid;

6-[8-(1,3-benzothiazol-2-ylcarbamoyl)-3,4-dihydroisoquinolin-2(1H)-yl]-3-{1-[(3-{2-[{2-[(2-carboxyethyl)amino]ethyl}(2-sulfoethyl)amino]ethoxy}-5,7-dimethyltricyclo[3.3.1.1$^{3,7}$]dec-1-yl)methyl]-5-methyl-1H-pyrazol-4-yl}pyridine-2-carboxylic acid;

3-{1-[(3,5-dimethyl-7-{2-[(3-phosphonopropyl)amino]ethoxy}tricyclo[3.3.1.1$^{3,7}$]dec-1-yl)methyl]-5-methyl-1H-pyrazol-4-yl}-6-[8-([1,3]thiazolo[4,5-b]pyridin-2-ylcarbamoyl)-3,4-dihydroisoquinolin-2(1H)-yl]pyridine-2-carboxylic acid;

3-{1-[(3,5-dimethyl-7-{2-[(3-phosphonopropyl)amino]ethoxy}tricyclo[3.3.1.1$^{3,7}$]dec-1-yl)methyl]-5-methyl-1H-pyrazol-4-yl}-6-[8-([1,3]thiazolo[5,4-b]pyridin-2-ylcarbamoyl)-3,4-dihydroisoquinolin-2(1H)-yl]pyridine-2-carboxylic acid;

6-[8-(1,3-benzothiazol-2-ylcarbamoyl)-5-(carboxymethoxy)-3,4-dihydroisoquinolin-2(1H)-yl]-3-[1-({3,5-dimethyl-7-[2-(methylamino)ethoxy]tricyclo[3.3.1.1$^{3,7}$]dec-1-yl}methyl)-5-methyl-1H-pyrazol-4-yl]pyridine-2-carboxylic acid;

6-[8-(1,3-benzothiazol-2-ylcarbamoyl)-3,4-dihydroisoquinolin-2(1H)-yl]-3-{1-[(3-{2-[(3-carboxypropyl)(piperidin-4-yl)amino]ethoxy}-5,7-dimethyltricyclo[3.3.1.1$^{3,7}$]dec-1-yl)methyl]-5-methyl-1H-pyrazol-4-yl}pyridine-2-carboxylic acid;

6-[8-(1,3-benzothiazol-2-ylcarbamoyl)naphthalen-2-yl]-3-{1-[(3,5-dimethyl-7-{2-[(2-sulfoethyl)amino]ethoxy}tricyclo[3.3.1.1$^{3,7}$]dec-1-yl)methyl]-5-methyl-1H-pyrazol-4-yl}pyridine-2-carboxylic acid;

3-{1-[(3-{2-[L-alpha-aspartyl(2-sulfoethyl)amino]ethoxy}-5,7-dimethyltricyclo[3.3.1.1$^{3,7}$]dec-1-yl)methyl]-5-methyl-1H-pyrazol-4-yl}-6-[8-(1,3-benzothiazol-2-ylcarbamoyl)-3,4-dihydroisoquinolin-2(1H)-yl]pyridine-2-carboxylic acid;

6-[8-(1,3-benzothiazol-2-ylcarbamoyl)-3,4-dihydroisoquinolin-2(1H)-yl]-3-{1-[(3-{2-[(1,3-dihydroxypropan-2-yl)amino]ethoxy}-5,7-dimethyltricyclo[3.3.1.1$^{3,7}$]dec-1-yl)methyl]-5-methyl-1H-pyrazol-4-yl}pyridine-2-carboxylic acid;

6-[5-(2-aminoethoxy)-8-(1,3-benzothiazol-2-ylcarbamoyl)-3,4-dihydroisoquinolin-2(1H)-yl]-3-{1-[(3,5-dimethyl-7-{2-[methyl(2-sulfoethyl)amino]ethoxy}tricyclo[3.3.1.1$^{3,7}$]dec-1-yl)methyl]-5-methyl-1H-pyrazol-4-yl}pyridine-2-carboxylic acid;

6-[8-(1,3-benzothiazol-2-ylcarbamoyl)-5-{2-[(2-sulfoethyl)amino]ethoxy}-3,4-dihydroisoquinolin-2(1H)-yl]-3-{1-[(3,5-dimethyl-7-{2-[methyl(2-sulfoethyl)amino]ethoxy}tricyclo[3.3.1.1$^{3,7}$]dec-1-yl)methyl]-5-methyl-1H-pyrazol-4-yl}pyridine-2-carboxylic acid;

6-[8-(1,3-benzothiazol-2-ylcarbamoyl)-3,4-dihydroisoquinolin-2(1H)-yl]-3-{1-[(3,5-dimethyl-7-{2-[(2-sulfoethyl){2-[(2-sulfoethyl)amino]ethyl}amino]ethoxy}tricyclo[3.3.1.1$^{3,7}$]dec-1-yl)methyl]-5-methyl-1H-pyrazol-4-yl}pyridine-2-carboxylic acid;

6-[8-(1,3-benzothiazol-2-ylcarbamoyl)-5-{2-[(2-carboxyethyl)amino]ethoxy}-3,4-dihydroisoquinolin-2(1H)-yl]-3-{1-[(3,5-dimethyl-7-{2-[methyl(2-sulfoethyl)amino]ethoxy}tricyclo[3.3.1.1$^{3,7}$]dec-1-yl)methyl]-5-methyl-1H-pyrazol-4-yl}pyridine-2-carboxylic acid;

3-{1-[(3,5-dimethyl-7-{2-[(3-phosphonopropyl)(piperidin-4-yl)amino]ethoxy}tricyclo[3.3.1.1$^{3,7}$]dec-1-yl)methyl]-5-methyl-1H-pyrazol-4-yl}-6-[8-([1,3]thiazolo[4,5-b]pyridin-2-ylcarbamoyl)-3,4-dihydroisoquinolin-2(1H)-yl]pyridine-2-carboxylic acid;

6-[4-(1,3-benzothiazol-2-ylcarbamoyl)-3,4-dihydro-2H-1,4-benzoxazin-6-yl]-3-{1-[(3,5-dimethyl-7-{2-[(2-sulfoethyl)amino]ethoxy}tricyclo[3.3.1.1$^{3,7}$]dec-1-yl)methyl]-5-methyl-1H-pyrazol-4-yl}pyridine-2-carboxylic acid;

6-[8-(1,3-benzothiazol-2-ylcarbamoyl)-5-(3-sulfopropoxy)-3,4-dihydroisoquinolin-2(1H)-yl]-3-[1-({3,5-dimethyl-7-[2-(methylamino)ethoxy]tricyclo[3.3.1.1$^{3,7}$]dec-1-yl}methyl)-5-methyl-1H-pyrazol-4-yl]pyridine-2-carboxylic acid;

3-{1-[(3,5-dimethyl-7-{2-[(2-sulfoethyl)amino]ethoxy}tricyclo[3.3.1.1$^{3,7}$]dec-1-yl)methyl]-5-methyl-1H-pyrazol-4-yl}-6-[1-([1,3]thiazolo[4,5-b]pyridin-2-ylcarbamoyl)-1,2,3,4-tetrahydroquinolin-7-yl]pyridine-2-carboxylic acid;

3-{1-[(3,5-dimethyl-7-{2-[(2-sulfoethyl)amino]ethoxy}tricyclo[3.3.1.1$^{3,7}$]dec-1-yl)methyl]-5-methyl-1H-pyrazol-4-yl}-6-[8-([1,3]thiazolo[4,5-b]pyridin-2-ylcarbamoyl)naphthalen-2-yl]pyridine-2-carboxylic acid;

(1ξ)-1-({2-[5-(1-{[3-(2-aminoethoxy)-5,7-dimethyltricyclo[3.3.1.1$^{3,7}$]dec-1-yl]methyl}-5-methyl-1H-pyrazol-4-yl)-

6-carboxypyridin-2-yl]-8-(1,3-benzothiazol-2-ylcarbamoyl)-1,2,3,4-tetrahydroisoquinolin-5-yl}methyl)-1,5-anhydro-D-glucitol;

6-[8-(1,3-benzothiazol-2-ylcarbamoyl)-3,4-dihydroisoquinolin-2(1H)-yl]-3-{1-[(3-{2-[(3-carboxypropyl)amino]ethoxy}-5,7-dimethyltricyclo[3.3.1.1$^{3,7}$]dec-1-yl)methyl]-5-methyl-1H-pyrazol-4-yl}pyridine-2-carboxylic acid;

6-[8-(1,3-benzothiazol-2-ylcarbamoyl)naphthalen-2-yl]-3-{1-[(3,5-dimethyl-7-{2-[(3-phosphonopropyl)amino]ethoxy}tricyclo[3.3.1.1$^{3,7}$]dec-1-yl)methyl]-5-methyl-1H-pyrazol-4-yl}pyridine-2-carboxylic acid;

6-[8-(1,3-benzothiazol-2-ylcarbamoyl)-3,4-dihydroisoquinolin-2(1H)-yl]-3-(1-{[3-(2-{[4-(beta-D-glucopyranosyloxy)benzyl]amino}ethoxy)-5,7-dimethyltricyclo[3.3.1.1$^{3,7}$]dec-1-yl]methyl}-5-methyl-1H-pyrazol-4-yl)pyridine-2-carboxylic acid;

3-(1-{[3-(2-{[4-(beta-D-allopyranosyloxy)benzyl]amino}ethoxy)-5,7-dimethyltricyclo[3.3.1.1$^{3,7}$]dec-1-yl]methyl}-5-methyl-1H-pyrazol-4-yl)-6-[8-(1,3-benzothiazol-2-ylcarbamoyl)-3,4-dihydroisoquinolin-2(1H)-yl]pyridine-2-carboxylic acid;

3-{1-[(3-{2-[azetidin-3-yl(2-sulfoethyl)amino]ethoxy}-5,7-dimethyltricyclo[3.3.1.1$^{3,7}$]dec-1-yl)methyl]-5-methyl-1H-pyrazol-4-yl}-6-[8-(1,3-benzothiazol-2-ylcarbamoyl)-3,4-dihydroisoquinolin-2(1H)-yl]pyridine-2-carboxylic acid;

3-{1-[(3-{2-[(3-aminopropyl)(2-sulfoethyl)amino]ethoxy}-5,7-dimethyltricyclo[3.3.1.1$^{3,7}$]dec-1-yl)methyl]-5-methyl-1H-pyrazol-4-yl}-6-[8-(1,3-benzothiazol-2-ylcarbamoyl)-3,4-dihydroisoquinolin-2(1H)-yl]pyridine-2-carboxylic acid;

6-[1-(1,3-benzothiazol-2-ylcarbamoyl)-1,2,3,4-tetrahydroquinolin-7-yl]-3-{1-[(3-{2-[(2-carboxyethyl)amino]ethoxy}-5,7-dimethyltricyclo[3.3.1.1$^{3,7}$]dec-1-yl)methyl]-5-methyl-1H-pyrazol-4-yl}pyridine-2-carboxylic acid;

6-[8-(1,3-benzothiazol-2-ylcarbamoyl)-3,4-dihydroisoquinolin-2(1H)-yl]-3-{1-[(3-{2-[(N$^6$,N$^6$-dimethyl-L-lysyl)(methyl)amino]ethoxy}-5,7-dimethyltricyclo[3.3.1.1$^{3,7}$]dec-1-yl)methyl]-5-methyl-1H-pyrazol-4-yl}pyridine-2-carboxylic acid;

3-{1-[(3-{2-[(3-aminopropyl)(methyl)amino]ethoxy}-5,7-dimethyltricyclo[3.3.1.1$^{3,7}$]dec-1-yl)methyl]-5-methyl-1H-pyrazol-4-yl}-6-[1-(1,3-benzothiazol-2-ylcarbamoyl)-1,2,3,4-tetrahydroquinolin-7-yl]pyridine-2-carboxylic acid;

3-{1-[(3-{2-[azetidin-3-yl(methyl)amino]ethoxy}-5,7-dimethyltricyclo[3.3.1.1$^{3,7}$]dec-1-yl)methyl]-5-methyl-1H-pyrazol-4-yl}-6-[1-(1,3-benzothiazol-2-ylcarbamoyl)-1,2,3,4-tetrahydroquinolin-7-yl]pyridine-2-carboxylic acid;

N$^6$-(37-oxo-2,5,8,11,14,17,20,23,26,29,32,35-dodecaoxa-heptatriacontan-37-yl)-L-lysyl-N-[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl]-L-alaninamide;

methyl 6-[4-(3-{[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl]amino}propyl)-1H-1,2,3-triazol-1-yl]-6-deoxy-beta-L-glucopyranoside;

6-[8-(1,3-benzothiazol-2-ylcarbamoyl)naphthalen-2-yl]-3-{1-[(3-{2-[(2-carboxyethyl)amino]ethoxy}-5,7-dimethyltricyclo[3.3.1.1$^{3,7}$]dec-1-yl)methyl]-5-methyl-1H-pyrazol-4-yl}pyridine-2-carboxylic acid;

6-[5-(1,3-benzothiazol-2-ylcarbamoyl)quinolin-3-yl]-3-{1-[(3,5-dimethyl-7-{2-[(2-sulfoethyl)amino]ethoxy}tricyclo[3.3.1.1$^{3,7}$]dec-1-yl)methyl]-5-methyl-1H-pyrazol-4-yl}pyridine-2-carboxylic acid;

6-[4-(1,3-benzothiazol-2-ylcarbamoyl)quinolin-6-yl]-3-{1-[(3,5-dimethyl-7-{2-[(2-sulfoethyl)amino]ethoxy}tricyclo[3.3.1.1$^{3,7}$]dec-1-yl)methyl]-5-methyl-1H-pyrazol-4-yl}pyridine-2-carboxylic acid;

6-[5-(1,3-benzothiazol-2-ylcarbamoyl)quinolin-3-yl]-3-{1-[(3-{2-[(2-carboxyethyl)amino]ethoxy}-5,7-dimethyltricyclo[3.3.1.1$^{3,7}$]dec-1-yl)methyl]-5-methyl-1H-pyrazol-4-yl}pyridine-2-carboxylic acid;

6-[1-(1,3-benzothiazol-2-ylcarbamoyl)-5,6-dihydroimidazo[1,5-a]pyrazin-7(8H)-yl]-3-{1-[(3,5-dimethyl-7-{2-[(2-sulfoethyl)amino]ethoxy}tricyclo[3.3.1.1$^{3,7}$]dec-1-yl)methyl]-5-methyl-1H-pyrazol-4-yl}pyridine-2-carboxylic acid;

8-(1,3-benzothiazol-2-ylcarbamoyl)-2-{6-carboxy-5-[1-({3-[2-({3-[1-(beta-D-glucopyranuronosyl)-1H-1,2,3-triazol-4-yl]propyl}amino)ethoxy]-5,7-dimethyltricyclo[3.3.1.1$^{3,7}$]dec-1-yl}methyl)-5-methyl-1H-pyrazol-4-yl]pyridin-2-yl}-1,2,3,4-tetrahydroisoquinoline;

6-[7-(1,3-benzothiazol-2-ylcarbamoyl)-1H-indol-2-yl]-3-{1-[(3,5-dimethyl-7-{2-[(2-sulfoethyl)amino]ethoxy}tricyclo[3.3.1.1$^{3,7}$]dec-1-yl)methyl]-5-methyl-1H-pyrazol-4-yl}pyridine-2-carboxylic acid;

6-[8-(1,3-benzothiazol-2-ylcarbamoyl)-6-[3-(methylamino)propyl]-3,4-dihydroisoquinolin-2(1H)-yl]-3-{1-[(3,5-dimethyl-7-{2-[(2-sulfoethyl)amino]ethoxy}tricyclo[3.3.1.1$^{3,7}$]dec-1-yl)methyl]-5-methyl-1H-pyrazol-4-yl}pyridine-2-carboxylic acid;

5-{[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl]amino}-5-deoxy-D-arabinitol;

1-{[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl]amino}-1,2-dideoxy-D-arabino-hexitol;

6-[4-(1,3-benzothiazol-2-ylcarbamoyl)isoquinolin-6-yl]-3-{1-[(3,5-dimethyl-7-{2-[(2-sulfoethyl)amino]ethoxy}tricyclo[3.3.1.1$^{3,7}$]dec-1-yl)methyl]-5-methyl-1H-pyrazol-4-yl}pyridine-2-carboxylic acid;

6-[8-(1,3-benzothiazol-2-ylcarbamoyl)-3,4-dihydroisoquinolin-2(1H)-yl]-3-(1-{[3-(2-{[3-hydroxy-2-(hydroxymethyl)propyl]amino}ethoxy)-5,7-dimethyltricyclo[3.3.1.1$^{3,7}$]dec-1-yl]methyl}-5-methyl-1H-pyrazol-4-yl)pyridine-2-carboxylic acid;

1-{[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl]amino}-1,2-dideoxy-D-erythro-pentitol;

6-[8-(1,3-benzothiazol-2-ylcarbamoyl)-3,4-dihydroisoquinolin-2(1H)-yl]-3-(1-{[3,5-dimethyl-7-(2-{[(2S,3S)-2,3,4-trihydroxybutyl]amino}ethoxy)tricyclo[3.3.1.1$^{3,7}$]dec-1-yl]methyl}-5-methyl-1H-pyrazol-4-yl)pyridine-2-carboxylic acid;

6-[8-(1,3-benzothiazol-2-ylcarbamoyl)-3,4-dihydroisoquinolin-2(1H)-yl]-3-(1-{[3-(2-{[(2S,3S,4R,5R,6R)-2,3,4,5,6,7-hexahydroxyheptyl]amino}ethoxy)-5,7-dimethyltricyclo[3.3.1.1$^{3,7}$]dec-1-yl]methyl}-5-methyl-1H-pyrazol-4-yl)pyridine-2-carboxylic acid;

6-[8-(1,3-benzothiazol-2-ylcarbamoyl)-3,4-dihydroisoquinolin-2(1H)-yl]-3-{1-[(3-{2-[({3-[(1,3-dihydroxypropan- 2-yl)amino]propyl}sulfonyl)amino]ethoxy}-5,7-dimethyltricyclo[3.3.1.1$^{3,7}$]dec-1-yl)methyl]-5-methyl-1H-pyrazol-4-yl}pyridine-2-carboxylic acid;

6-[8-(1,3-benzothiazol-2-ylcarbamoyl)-3,4-dihydroisoquinolin-2(1H)-yl]-3-{1-[(3-{2-[(3-{[1,3-dihydroxy-2-(hydroxymethyl)propan-2-yl]amino}-3-oxopropyl)amino]ethoxy}-5,7-dimethyltricyclo[3.3.1.1$^{3,7}$]dec-1-yl)methyl]-5-methyl-1H-pyrazol-4-yl}pyridine-2-carboxylic acid;

6-[8-(1,3-benzothiazol-2-ylcarbamoyl)-3,4-dihydroisoquinolin-2(1H)-yl]-3-(1-{[3-(2-{[(3S)-3,4-dihydroxybutyl]amino}ethoxy)-5,7-dimethyltricyclo[3.3.1.1$^{3,7}$]dec-1-yl]methyl}-5-methyl-1H-pyrazol-4-yl)pyridine-2-carboxylic acid;

4-({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl]amino}methyl)phenyl beta-D-glucopyranosiduronic acid;

3-{[2-({3-[(4-{6-[8-(1,3-benzothiazol-2-ylcarbamoyl)naphthalen-2-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl]amino}propyl beta-D-glucopyranosiduronic acid;

6-[4-(1,3-benzothiazol-2-ylcarbamoyl)-2-oxidoisoquinolin-6-yl]-3-[1-({3,5-dimethyl-7-[2-(methylamino)ethoxy]tricyclo[3.3.1.1$^{3,7}$]dec-1-yl}methyl)-5-methyl-1H-pyrazol-4-yl]pyridine-2-carboxylic acid;

6-{8-[(1,3-benzothiazol-2-yl)carbamoyl]-3,4-dihydroisoquinolin-2(1H)-yl}-3-{1-[(3,5-dimethyl-7-{2-[(2-sulfoethyl)amino]acetamido}tricyclo[3.3.1.1$^{3,7}$]decan-1-yl)methyl]-5-methyl-1H-pyrazol-4-yl}pyridine-2-carboxylic acid;

6-[8-(1,3-benzothiazol-2-ylcarbamoyl)-3,4-dihydroisoquinolin-2(1H)-yl]-3-(1-{[3,5-dimethyl-7-({2-[(2-sulfoethyl)amino]ethyl}sulfanyl)tricyclo[3.3.1.1$^{3,7}$]dec-1-yl]methyl}-5-methyl-1H-pyrazol-4-yl)pyridine-2-carboxylic acid; and 6-{8-[(1,3-benzothiazol-2-yl)carbamoyl]-3,4-dihydroisoquinolin-2(1H)-yl}-3-{1-[(3,5-dimethyl-7-{3-[(2-sulfoethyl)amino]propyl}tricyclo[3.3.1.1$^{3,7}$]decan-1-yl)methyl]-5-methyl-1H-pyrazol-4-yl}pyridine-2-carboxylic acid;

and a pharmaceutically acceptable salt thereof.

The Bcl-xL inhibitors bind to and inhibit anti-apoptotic Bcl-xL proteins, inducing apoptosis. The ability of specific Bcl-xL inhibitors according to structural formulae (IIa)-(IId) to bind to and inhibit Bcl-xL activity may be confirmed in standard binding and activity assays, including, for example, the TR-FRET Bcl-xL binding assays described in Tao et al., 2014, ACS Med. Chem. Lett., 5:1088-1093. A specific TR-FRET Bcl-xL binding assay that can be used to confirm Bcl-xL binding is provided in Example 4, below. Typically, Bcl-xL inhibitors useful as inhibitors per se and in the ADCs described herein will exhibit a $K_i$ in the binding assay of Example 5 of less than about 1 nM, but may exhibit a significantly lower $K_i$, for example a $K_i$ of less than about 1, 0.1, or even 0.01 nM.

Bcl-xL inhibitory activity may also be confirmed in standard cell-based cytotoxicity assays, such as the FL5.12 cellular and Molt-4 cytotoxicity assays described in Tao et al., 2014, ACS Med. Chem. Lett., 5:1088-1093. A specific Molt-4 cellular cytotoxicity assay that may be used to confirm Bcl-xL inhibitory activity of specific Bcl-xL inhibitors that are able to permeate cell membranes is provided in Examples 5 and 6, below. Typically, such cell-permeable Bcl-xL inhibitors will exhibit an $EC_{50}$ of less than about 500 nM in the Molt-4 cytotoxicity assay of Examples 5 and 6, but may exhibit a significantly lower $EC_{50}$, for example an $EC_{50}$ of less than about 250, 100, 50, 20, 10 or even 5 nM.

Owing to the presence of solubilizing groups, many of the Bcl-xL inhibitors described herein are expected to exhibit low or very low cell permeability, and therefore will not yield significant activity in certain cellular assays due to the inability of the compound to traverse the cell membrane, including the Molt-4 cellular toxicity assay of Examples 5 and 6. Bcl-xL inhibitory activity of compounds that do not freely traverse cell membranes may be confirmed in cellular assays with permeabilized cells. The process of mitochondrial outer-membrane permeabilization (MOMP) is controlled by the Bcl-2 family proteins. Specifically, MOMP is promoted by the pro-apoptotic Bcl-2 family proteins Bax and Bak which, upon activation oligomerize on the outer mitochondrial membrane and form pores, leading to release of cytochrome c (cyt c). The release of cyt c triggers formulation of the apoptosome which, in turn, results in caspase activation and other events that commit the cell to undergo programmed cell death (see, Goldstein et al., 2005, *Cell Death and Differentiation* 12:453-462). The oligomerization action of Bax and Bak is antagonized by the anti-apoptotic Bcl-2 family members, including Bcl-2 and Bcl-xL. Bcl-xL inhibitors, in cells that depend upon Bcl-xL for survival, can cause activation of Bax and/or Bak, MOMP, release of cyt c and downstream events leading to apoptosis. The process of cyt c release can be measured via western blot of both mitochondrial and cytosolic fractions of cells and used as a proxy measurement of apoptosis in cells.

As a means of detecting Bcl-xL inhibitory activity and consequent release of cyt c for Bcl-xL inhibitors with low cell permeability, the cells can be treated with an agent that causes selective pore formation in the plasma, but not mitochondrial, membrane. Specifically, the cholesterol/phospholipid ratio is much higher in the plasma membrane than the mitochondrial membrane. As a result, short incubation with low concentrations of the cholesterol-directed detergent digitonin selectively permeabilizes the plasma membrane without significantly affecting the mitochondrial membrane. This agent forms insoluble complexes with cholesterol leading to the segregation of cholesterol from its normal phospholipid binding sites. This action, in turn, leads to the formation of holes about 40-50 Å wide in the lipid bilayer. Once the plasma membrane is permeabilized, cytosolic components able to pass over digitonin-formed holes can be washed out, including the cytochrome C that was released from mitochondria to cytosol in the apoptotic cells (Campos, 2006, *Cytometry A* 69(6):515-523).

Typically, Bcl-xL inhibitors will yield an $EC_{50}$ of less than about 10 nM in the Molt-4 cell permeabilized cyt c assay of Examples 5 and 6, although the compounds may exhibit significantly lower $EC_{50}$s, for example, less than about 5, 1, or even 0.5 nM. As demonstrated in Example 6, Bcl-xL inhibitors having low or very low cell permeability that do not exhibit activity in the standard Molt-4 cellular toxicity assay with non-permeablized cells exhibit potent functional activity, as measured by release of cyt c, in cellular cytotoxicity assays with permeabilized cells. In addition to cytochrome c release, mitochondria undergoing apoptosis frequently lose their transmembrane mitochondrial membrane potential (Bouchier-Hayes et al., 2008, *Methods* 44(3): 222-228). JC-1 is a cationic carbocyanine dye that accumulates in mitochondria and fluoresces red when mitochondria are healthy and is lost when the mitochondrial membrane is compromised (percentage depolarization; Smiley et al., 1991, *Proc. Natl. Acad. Sci. USA*, 88: 3671-3675;

Reers et al., 1991: *Biochemistry*, 30: 4480-4486). This loss in signal can be detected in permeabilized cells using a fluorimeter (excitation 545 nm and emission of 590 nm) and is therefore fully quantitative, enhancing both reproducibility and throughput. Typically, Bcl-xL inhibitors will yield an $EC_{50}$ of less than about 10 nM in the Molt-4 cell permeabilized JC-1 assay of Examples 5 and 6, although the compounds may exhibit significantly lower $EC_{50}s$, for example, less than about 5, 1, 0.5 or even 0.05 nM. As demonstrated in Example 6, Bcl-xL inhibitors having low or very low cell permeability that do not exhibit activity in the standard Molt-4 cellular toxicity assay with non-permeablized cells exhibit potent functional activity, as measured by their loss of transmembrane mitochondrial membrane potential in the JC-1 assay, in cellular cytotoxicity assays with permeabilized cells. Low permeability Bcl-xL inhibitors also exhibit potent activity when administered to cells in the form of ADCs (see, e.g., Example 8).

Although many of the Bcl-xL inhibitors of structural formulae (IIa)-(IId) selectively or specifically inhibit Bcl-xL over other anti-apoptotic Bcl-2 family proteins, selective and/or specific inhibition of Bcl-xL is not necessary. The Bcl-xL inhibitors and ADCs comprising the compounds may also, in addition to inhibiting Bcl-xL, inhibit one or more other anti-apoptotic Bcl-2 family proteins, such as, for example, Bcl-2. In some embodiments, the Bcl-xL inhibitors and/or ADCs are selective and/or specific for Bcl-xL. By specific or selective is meant that the particular Bcl-xL inhibitor and/or ADC binds or inhibits Bcl-xL to a greater extent than Bcl-2 under equivalent assay conditions. In specific embodiments, the Bcl-xL inhibitors and/or ADCs exhibit in the range of about 10-fold, 100-fold, or even greater specificity or selectivity for Bcl-xL than Bcl-2 in binding assays.

III.A.2. Bcl-xL Linkers

In the ADCs described herein, the Bcl-xL inhibitors are linked to the antibody by way of linkers. The linker linking a Bcl-xL inhibitor to the antibody of an ADC may be short, long, hydrophobic, hydrophilic, flexible or rigid, or may be composed of segments that each independently has one or more of the above-mentioned properties such that the linker may include segments having different properties. The linkers may be polyvalent such that they covalently link more than one Bcl-xL inhibitor to a single site on the antibody, or monovalent such that covalently they link a single Bcl-xL inhibitor to a single site on the antibody.

As will be appreciated by skilled artisans, the linkers link the Bcl-xL inhibitors to the antibody by forming a covalent linkage to the Bcl-xL inhibitor at one location and a covalent linkage to antibody at another. The covalent linkages are formed by reaction between functional groups on the linker and functional groups on the inhibitors and antibody. As used herein, the expression "linker" is intended to include (i) unconjugated forms of the linker that include a functional group capable of covalently linking the linker to a Bcl-xL inhibitor and a functional group capable of covalently linking the linker to an antibody; (ii) partially conjugated forms of the linker that include a functional group capable of covalently linking the linker to an antibody and that is covalently linked to a Bcl-xL inhibitor, or vice versa; and (iii) fully conjugated forms of the linker that is covalently linked to both a Bcl-xL inhibitor and an antibody. In some specific embodiments of intermediate synthons and ADCs described herein, moieties comprising the functional groups on the linker and covalent linkages formed between the linker and antibody are specifically illustrated as $R^x$ and LK, respectively.

The linkers are preferably, but need not be, chemically stable to conditions outside the cell, and may be designed to cleave, immolate and/or otherwise specifically degrade inside the cell. Alternatively, linkers that are not designed to specifically cleave or degrade inside the cell may be used. A wide variety of linkers useful for linking drugs to antibodies in the context of ADCs are known in the art. Any of these linkers, as well as other linkers, may be used to link the Bcl-xL inhibitors to the antibody of the ADCs described herein.

Exemplary polyvalent linkers that may be used to link many Bcl-xL inhibitors to an antibody are described, for example, in U.S. Pat. No. 8,399,512; U.S. Published Application No. 2010/0152725; U.S. Pat. Nos. 8,524,214; 8,349,308; U.S. Published Application No. 2013/189218; U.S. Published Application No. 2014/017265; WO 2014/093379; WO 2014/093394; WO 2014/093640, the contents of which are incorporated herein by reference in their entireties. For example, the Fleximer® linker technology developed by Mersana et al. has the potential to enable high-DAR ADCs with good physicochemical properties. As shown below, the Fleximer® linker technology is based on incorporating drug molecules into a solubilizing poly-acetal backbone via a sequence of ester bonds. The methodology renders highly-loaded ADCs (DAR up to 20) whilst maintaining good physicochemical properties. This methodology could be utilized with Bcl-xL inhibitors as shown in the Scheme below.

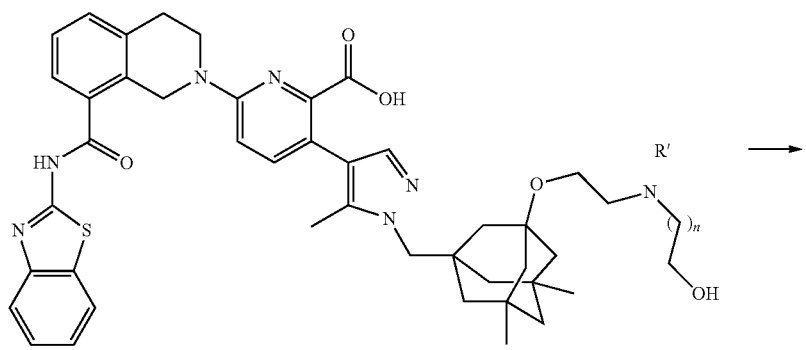

-continued

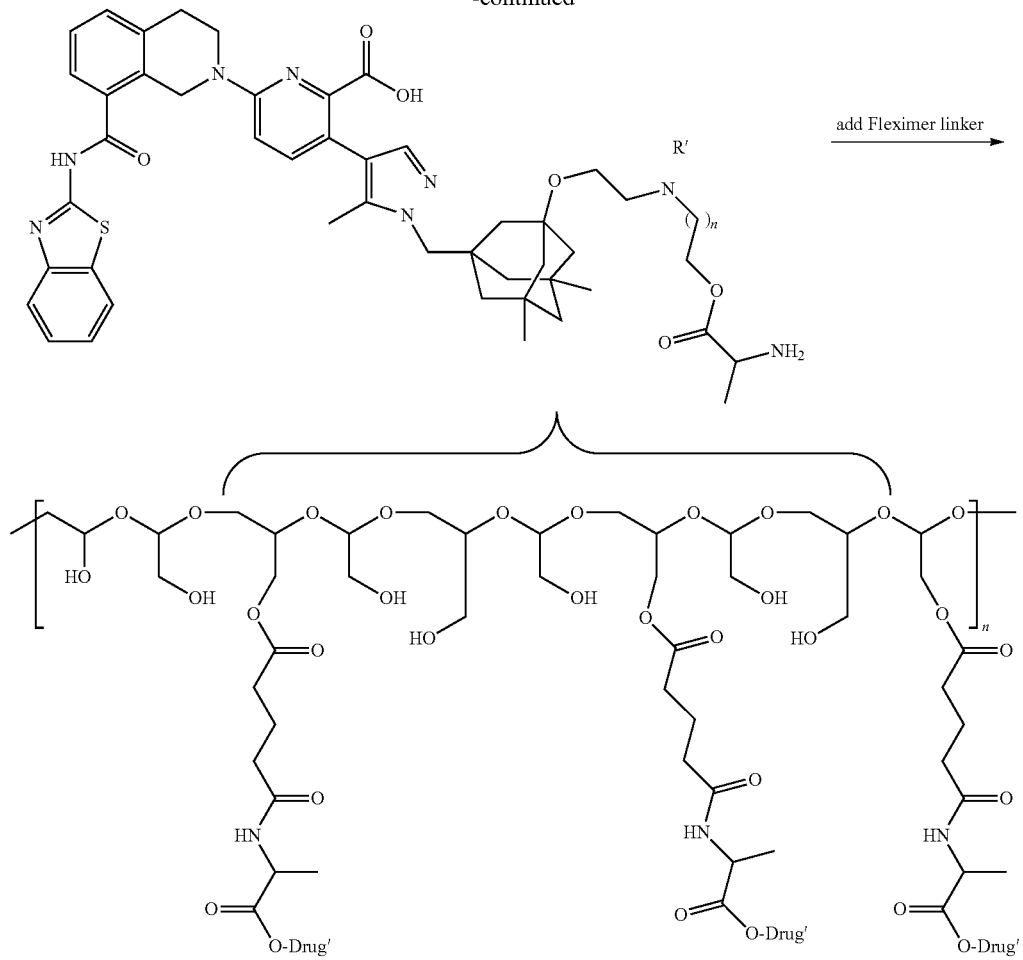

To utilize the Fleximer® linker technology depicted in the scheme above, an aliphatic alcohol can be present or introduced into the Bcl-xL inhibitor. The alcohol moiety is then conjugated to an alanine moiety, which is then synthetically incorporated into the Fleximer® linker. Liposomal processing of the ADC in vitro releases the parent alcohol-containing drug.

Additional examples of dendritic type linkers can be found in US 2006/116422; US 2005/271615; de Groot et al., (2003) Angew. Chem. Int. Ed. 42:4490-4494; Amir et al., (2003) Angew. Chem. Int. Ed. 42:4494-4499; Shamis et al., (2004) J. Am. Chem. Soc. 126:1726-1731; Sun et al., (2002) Bioorganic & Medicinal Chemistry Letters 12:2213-2215; Sun et al., (2003) Bioorganic & Medicinal Chemistry 11:1761-1768; King et al., (2002) Tetrahedron Letters 43:1987-1990.

Exemplary monovalent linkers that may be used are described, for example, in Nolting, 2013, Antibody-Drug Conjugates, Methods in Molecular Biology 1045:71-100; Kitson et al., 2013, CROs/CMOs—Chemica Oggi—Chemistry Today 31(4): 30-36; Ducry et al., 2010, Bioconjugate Chem. 21:5-13; Zhao et al., 2011, J. Med. Chem. 54:3606-3623; U.S. Pat. Nos. 7,223,837; 8,568,728; 8,535,678; and WO2004010957, the content of each of which is incorporated herein by reference in their entireties.

By way of example and not limitation, some cleavable and noncleavable linkers that may be included in the ADCs described herein are described below.

Cleavable Linkers

In certain embodiments, the linker selected is cleavable in vitro and in vivo. Cleavable linkers may include chemically or enzymatically unstable or degradable linkages. Cleavable linkers generally rely on processes inside the cell to liberate the drug, such as reduction in the cytoplasm, exposure to acidic conditions in the lysosome, or cleavage by specific proteases or other enzymes within the cell. Cleavable linkers generally incorporate one or more chemical bonds that are either chemically or enzymatically cleavable while the remainder of the linker is noncleavable.

In certain embodiments, a linker comprises a chemically labile group such as hydrazone and/or disulfide groups. Linkers comprising chemically labile groups exploit differential properties between the plasma and some cytoplasmic compartments. The intracellular conditions to facilitate drug release for hydrazone containing linkers are the acidic environment of endosomes and lysosomes, while the disulfide containing linkers are reduced in the cytosol, which contains high thiol concentrations, e.g., glutathione. In certain embodiments, the plasma stability of a linker comprising a chemically labile group may be increased by introducing steric hindrance using substituents near the chemically labile group.

Acid-labile groups, such as hydrazone, remain intact during systemic circulation in the blood's neutral pH environment (pH 7.3-7.5) and undergo hydrolysis and release the drug once the ADC is internalized into mildly acidic endosomal (pH 5.0-6.5) and lysosomal (pH 4.5-5.0) compartments of the cell. This pH dependent release mechanism has been associated with nonspecific release of the drug. To increase the stability of the hydrazone group of the linker, the linker may be varied by chemical modification, e.g., substitution, allowing tuning to achieve more efficient release in the lysosome with a minimized loss in circulation.

Hydrazone-containing linkers may contain additional cleavage sites, such as additional acid-labile cleavage sites and/or enzymatically labile cleavage sites. ADCs including exemplary hydrazone-containing linkers include the following structures:

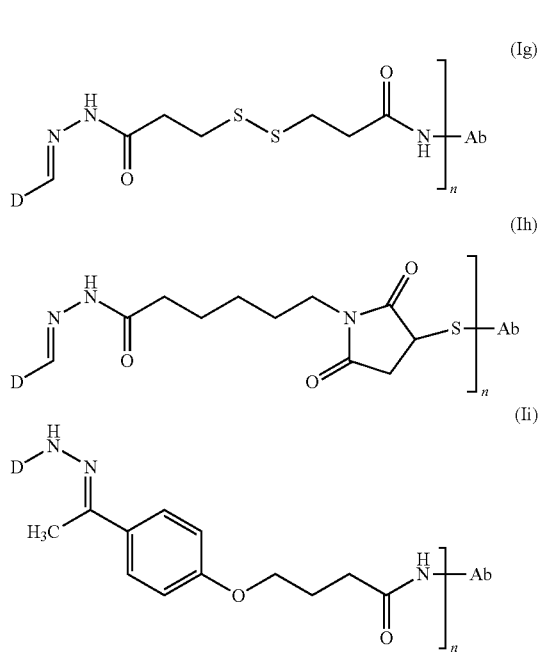

wherein D and Ab represent the drug and Ab, respectively, and n represents the number of drug-linkers linked to the antibody. In certain linkers such as linker (Ig), the linker comprises two cleavable groups—a disulfide and a hydrazone moiety. For such linkers, effective release of the unmodified free drug requires acidic pH or disulfide reduction and acidic pH. Linkers such as (Ih) and (Ii) have been shown to be effective with a single hydrazone cleavage site.

Other acid-labile groups that may be included in linkers include cis-aconityl-containing linkers. cis-Aconityl chemistry uses a carboxylic acid juxtaposed to an amide bond to accelerate amide hydrolysis under acidic conditions.

Cleavable linkers may also include a disulfide group. Disulfides are thermodynamically stable at physiological pH and are designed to release the drug upon internalization inside cells, wherein the cytosol provides a significantly more reducing environment compared to the extracellular environment. Scission of disulfide bonds generally requires the presence of a cytoplasmic thiol cofactor, such as (reduced) glutathione (GSH), such that disulfide-containing linkers are reasonable stable in circulation, selectively releasing the drug in the cytosol. The intracellular enzyme protein disulfide isomerase, or similar enzymes capable of cleaving disulfide bonds, may also contribute to the preferential cleavage of disulfide bonds inside cells. GSH is reported to be present in cells in the concentration range of 0.5-10 mM compared with a significantly lower concentration of GSH or cysteine, the most abundant low-molecular weight thiol, in circulation at approximately 5 µM. Tumor cells, where irregular blood flow leads to a hypoxic state, result in enhanced activity of reductive enzymes and therefore even higher glutathione concentrations. In certain embodiments, the in vivo stability of a disulfide-containing linker may be enhanced by chemical modification of the linker, e.g., use of steric hindrance adjacent to the disulfide bond.

ADCs including exemplary disulfide-containing linkers include the following structures:

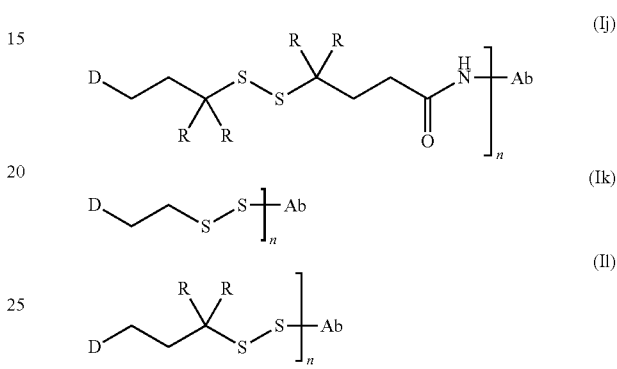

wherein D and Ab represent the drug and antibody, respectively, n represents the number of drug-linkers linked to the antibody and R is independently selected at each occurrence from hydrogen or alkyl, for example. In certain embodiments, increasing steric hindrance adjacent to the disulfide bond increases the stability of the linker. Structures such as (Ij) and (Il) show increased in vivo stability when one or more R groups is selected from a lower alkyl such as methyl.

Another type of linker that may be used is a linker that is specifically cleaved by an enzyme. Such linkers are typically peptide-based or include peptidic regions that act as substrates for enzymes. Peptide based linkers tend to be more stable in plasma and extracellular milieu than chemically labile linkers. Peptide bonds generally have good serum stability, as lysosomal proteolytic enzymes have very low activity in blood due to endogenous inhibitors and the unfavorably high pH value of blood compared to lysosomes. Release of a drug from an antibody occurs specifically due to the action of lysosomal proteases, e.g., cathepsin and plasmin. These proteases may be present at elevated levels in certain tumor tissues. In certain embodiments, the linker is cleavable by a lysosomal enzyme. In certain embodiments, the linker is cleavable by a lysosomal enzyme, and the lysosomal enzyme is Cathepsin B. In certain embodiments, the linker is cleavable by a lysosomal enzyme, and the lysosomal enzyme is β-glucuronidase or β-galactosidase. In certain embodiments, the linker is cleavable by a lysosomal enzyme, and the lysosomal enzyme is β-glucuronidase. In certain embodiments, the linker is cleavable by a lysosomal enzyme, and the lysosomal enzyme is β-galactosidase.

Those skilled in the art recognize the importance of cleavable linkers that are stable to plasma, yet are readily cleaved by a lysosomal enzyme. Disclosed herein, in certain embodiments, are linkers, cleavable by the lysosomal enzymes β-glucuronidase or β-galactosidase, that show improved plasma stability and reduced non-specific release of small molecule drug.

In exemplary embodiments, the cleavable peptide is selected from tetrapeptides such as Gly-Phe-Leu-Gly, Ala-Leu-Ala-Leu or dipeptides such as Val-Cit, Val-Ala, and Phe-Lys. In certain embodiments, dipeptides are preferred over longer polypeptides due to hydrophobicity of the longer peptides.

A variety of dipeptide-based cleavable linkers useful for linking drugs such as doxorubicin, mitomycin, camptothecin, tallysomycin and auristatin/auristatin family members to antibodies have been described (see, Dubowchik et al., 1998, *J. Org. Chem.* 67:1866-1872; Dubowchik et al., 1998, *Bioorg. Med. Chem. Lett.* 8:3341-3346; Walker et al., 2002, *Bioorg. Med. Chem. Lett.* 12:217-219; Walker et al., 2004, *Bioorg. Med. Chem. Lett.* 14:4323-4327; and Francisco et al., 2003, *Blood* 102:1458-1465, the contents of each of which are incorporated herein by reference). All of these dipeptide linkers, or modified versions of these dipeptide linkers, may be used in the ADCs described herein. Other dipeptide linkers that may be used include those found in ADCs such as Seattle Genetics' Brentuximab Vendotin SGN-35 (Adcetris™), Seattle Genetics SGN-75 (anti-CD-70, MC-monomethyl auristatin F(MMAF), Celldex Therapeutics glembatumumab (CDX-011) (anti-NMB, Val-Cit-monomethyl auristatin E(MMAE), and Cytogen PSMA-ADC (PSMA-ADC-1301) (anti-PSMA, Val-Cit-MMAE).

Enzymatically cleavable linkers may include a self-immolative spacer to spatially separate the drug from the site of enzymatic cleavage. The direct attachment of a drug to a peptide linker can result in proteolytic release of an amino acid adduct of the drug, thereby impairing its activity. The use of a self-immolative spacer allows for the elimination of the fully active, chemically unmodified drug upon amide bond hydrolysis.

One self-immolative spacer is the bifunctional para-aminobenzyl alcohol group, which is linked to the peptide through the amino group, forming an amide bond, while amine containing drugs may be attached through carbamate functionalities to the benzylic hydroxyl group of the linker (to give a p-amidobenzylcarbamate, PABC). The resulting prodrugs are activated upon protease-mediated cleavage, leading to a 1,6-elimination reaction releasing the unmodified drug, carbon dioxide, and remnants of the linker group. The following scheme depicts the fragmentation of p-amidobenzyl carbamate and release of the drug:

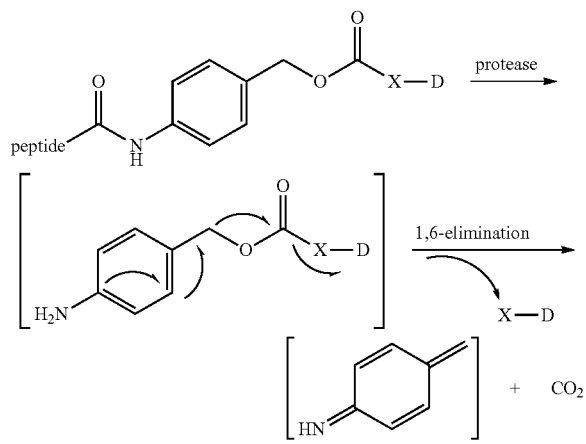

wherein X-D represents the unmodified drug. Heterocyclic variants of this self-immolative group have also been described. See U.S. Pat. No. 7,989,434.

In certain embodiments, the enzymatically cleavable linker is a β-glucuronic acid-based linker. Facile release of the drug may be realized through cleavage of the β-glucuronide glycosidic bond by the lysosomal enzyme β-glucuronidase. This enzyme is present abundantly within lysosomes and is overexpressed in some tumor types, while the enzyme activity outside cells is low. β-Glucuronic acid-based linkers may be used to circumvent the tendency of an ADC to undergo aggregation due to the hydrophilic nature of β-glucuronides. In certain embodiments, β-glucuronic acid-based linkers are preferred as linkers for ADCs linked to hydrophobic drugs. The following scheme depicts the release of the drug from and ADC containing a β-glucuronic acid-based linker:

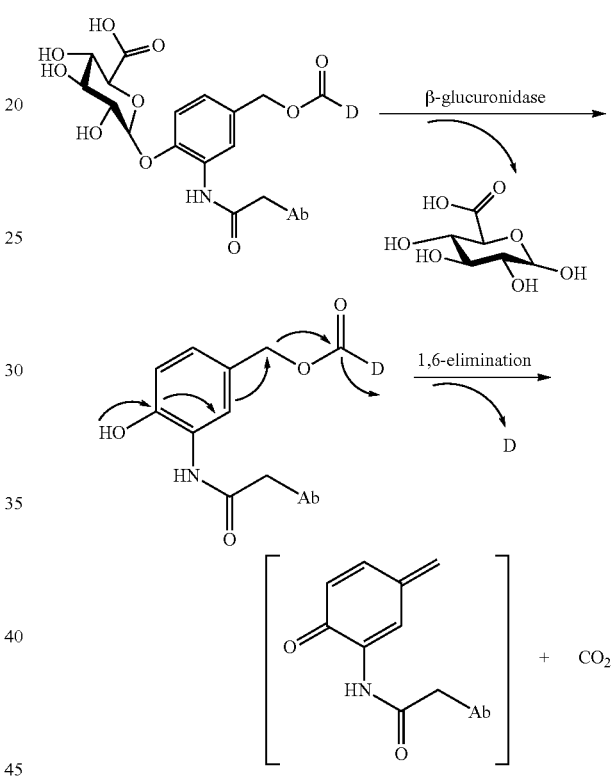

A variety of cleavable β-glucuronic acid-based linkers useful for linking drugs such as auristatins, camptothecin and doxorubicin analogues, CBI minor-groove binders, and psymberin to antibodies have been described (see, Jeffrey et al., 2006, *Bioconjug. Chem.* 17:831-840; Jeffrey et al., *Bioorg. Med. Chem. Lett.* 17:2278-2280; and Jiang et al., 2005, *J. Am. Chem. Soc.* 127:11254-11255, the contents of each of which are incorporated herein by reference). All of these β-glucuronic acid-based linkers may be used in the ADCs described herein. In certain embodiments, the enzymatically cleavable linker is a β-galactoside-based linker. β-Galactoside is present abundantly within lysosomes, while the enzyme activity outside cells is low. Additionally, Bcl-xL inhibitors containing a phenol group can be covalently bonded to a linker through the phenolic oxygen. One such linker, described in U.S. Published App. No. 2009/0318668, relies on a methodology in which a diamino-ethane "SpaceLink" is used in conjunction with traditional "PABO"-based self-immolative groups to deliver phenols. The cleavage of the linker is depicted schematically below using a Bcl-xL inhibitor of the disclosure.

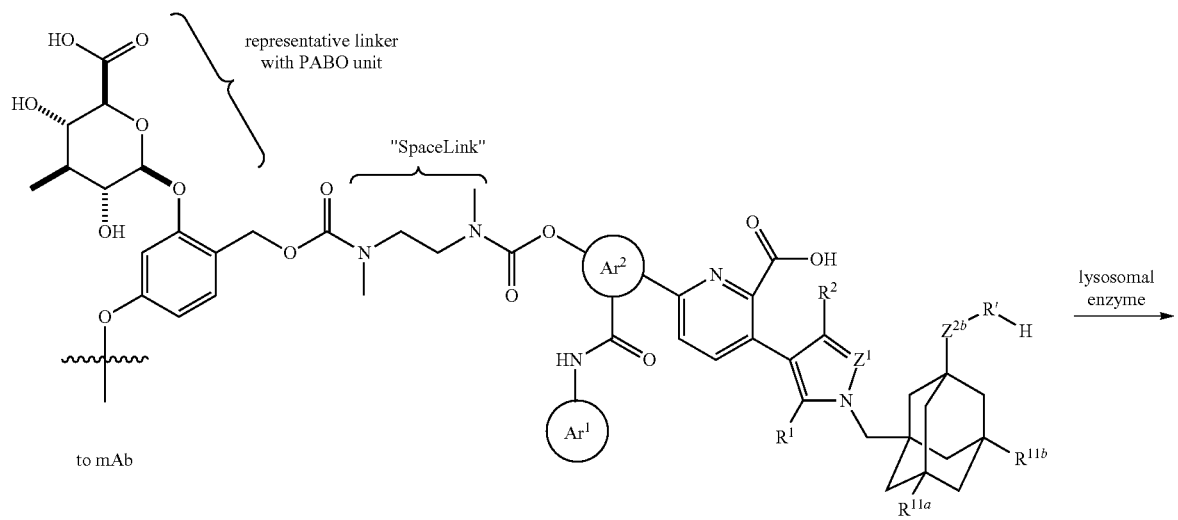

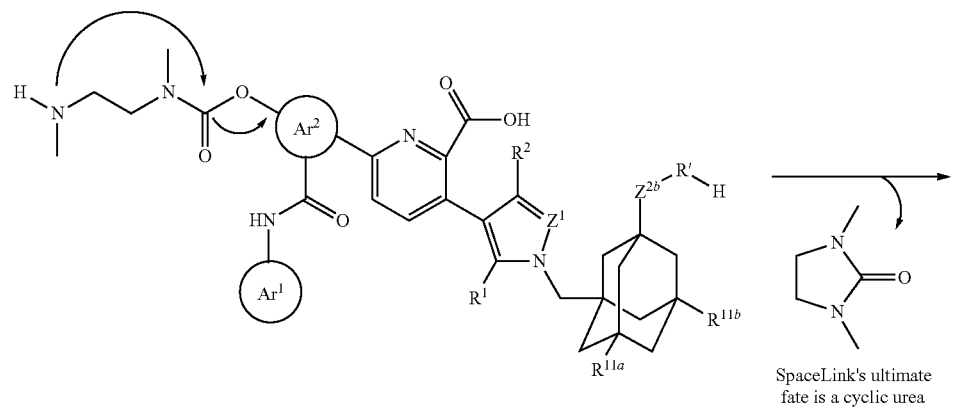

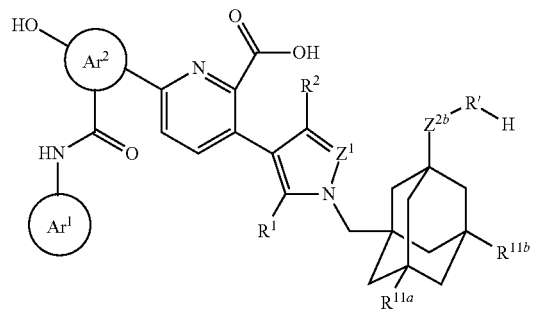

Cleavable linkers may include noncleavable portions or segments, and/or cleavable segments or portions may be included in an otherwise non-cleavable linker to render it cleavable. By way of example only, polyethylene glycol (PEG) and related polymers may include cleavable groups in the polymer backbone. For example, a polyethylene glycol or polymer linker may include one or more cleavable groups such as a disulfide, a hydrazone or a dipeptide.

Other degradable linkages that may be included in linkers include ester linkages formed by the reaction of PEG carboxylic acids or activated PEG carboxylic acids with alcohol groups on a biologically active agent, wherein such ester groups generally hydrolyze under physiological conditions to release the biologically active agent. Hydrolytically degradable linkages include, but are not limited to, carbonate linkages; imine linkages resulting from reaction of an amine and an aldehyde; phosphate ester linkages formed by reacting an alcohol with a phosphate group; acetal linkages that are the reaction product of an aldehyde and an alcohol; orthoester linkages that are the reaction product of a formate and an alcohol; and oligonucleotide linkages formed by a phosphoramidite group, including but not limited to, at the end of a polymer, and a 5' hydroxyl group of an oligonucleotide.

In certain embodiments, the linker comprises an enzymatically cleavable peptide moiety, for example, a linker comprising structural formula (IVa), (IVb), (IVc) or (IVd):

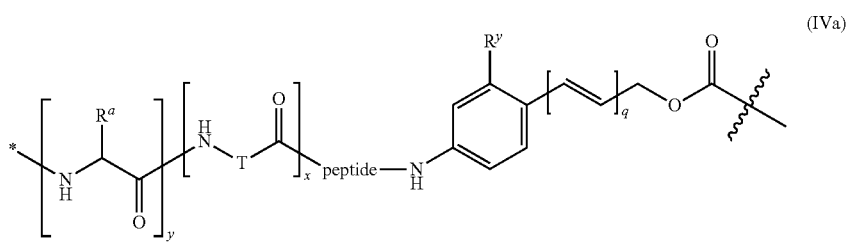
(IVa)

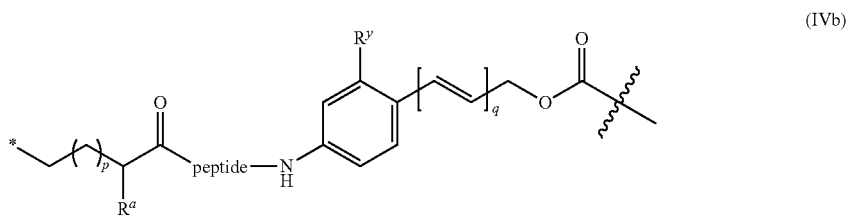
(IVb)

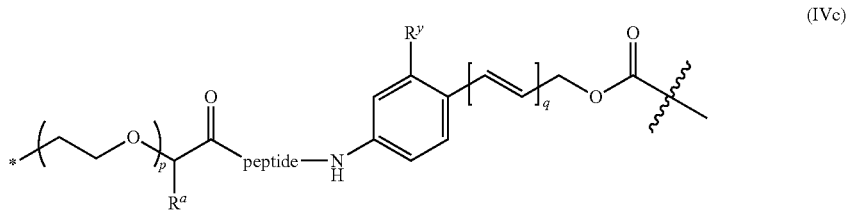
(IVc)

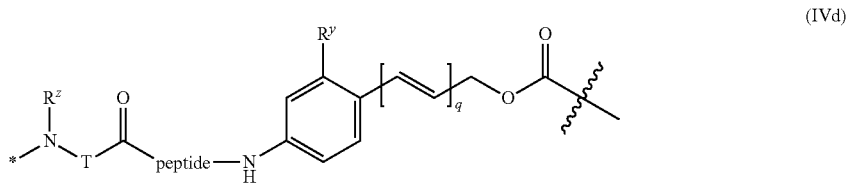
(IVd)

or a pharmaceutically acceptable salt thereof, wherein:
- peptide represents a peptide (illustrated N→C, wherein peptide includes the amino and carboxy "termini") cleavable by a lysosomal enzyme;
- T represents a polymer comprising one or more ethylene glycol units or an alkylene chain, or combinations thereof;
- $R^a$ is selected from hydrogen, $C_{16}$ alkyl, $SO_3H$ and $CH_2SO_3H$;
- $R^y$ is hydrogen or $C_{1-4}$ alkyl-(O), —$(C_{1-4}$ alkylene$)_s$-$G^1$ or $C_{1-4}$ alkyl-(N)—[$(C_{1-4}$ alkylene)-$G^1$]$_2$;
- $R^z$ is $C_{1-4}$ alkyl-(O), —$(C_{1-4}$ alkylene$)_s$-$G^2$;
- $G^1$ is $SO_3H$, $CO_2H$, PEG 4-32, or sugar moiety;
- $G^2$ is $SO_3H$, $CO_2H$, or PEG 4-32 moiety;
- r is 0 or 1;
- s is 0 or 1;
- p is an integer ranging from 0 to 5;
- q is 0 or 1;
- x is 0 or 1;
- y is 0 or 1;
- ⨏ represents the point of attachment of the linker to the Bcl-xL inhibitor; and
- \* represents the point of attachment to the remainder of the linker.

In certain embodiments, the linker comprises an enzymatically cleavable peptide moiety, for example, a linker comprising structural formula (IVa), (IVb), (IVc), or (IVd), or a pharmaceutically acceptable salt thereof.

In certain embodiments, the peptide is selected from a tripeptide or a dipeptide. In particular embodiments, the dipeptide is selected from: Val-Cit; Cit-Val; Ala-Ala; Ala-Cit; Cit-Ala; Asn-Cit; Cit-Asn; Cit-Cit; Val-Glu; Glu-Val; Ser-Cit; Cit-Ser; Lys-Cit; Cit-Lys; Asp-Cit; Cit-Asp; Ala-Val; Val-Ala; Phe-Lys; Lys-Phe; Val-Lys; Lys-Val; Ala-Lys; Lys-Ala; Phe-Cit; Cit-Phe; Leu-Cit; Cit-Leu; Ile-Cit; Cit-Ile; Phe-Arg; Arg-Phe; Cit-Trp; and Trp-Cit; or a pharmaceutically acceptable salt thereof.

Exemplary embodiments of linkers according to structural formula (IVa) that may be included in the ADCs described herein include the linkers illustrated below (as illustrated, the linkers include a group suitable for covalently linking the linker to an antibody):

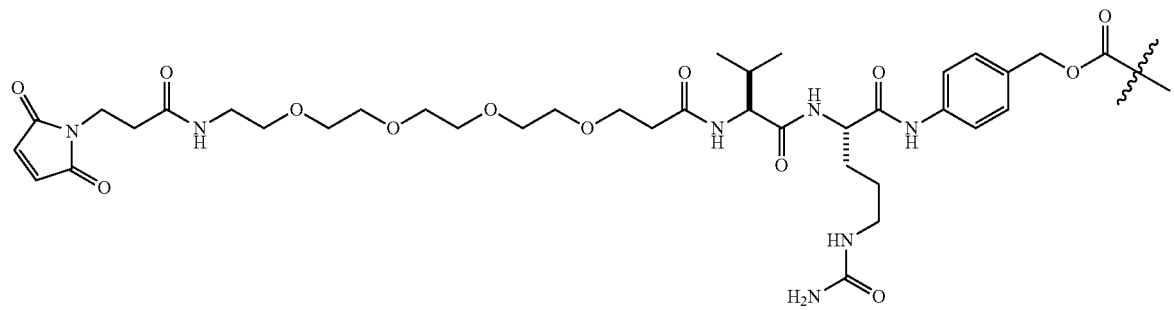
(IVa.1)
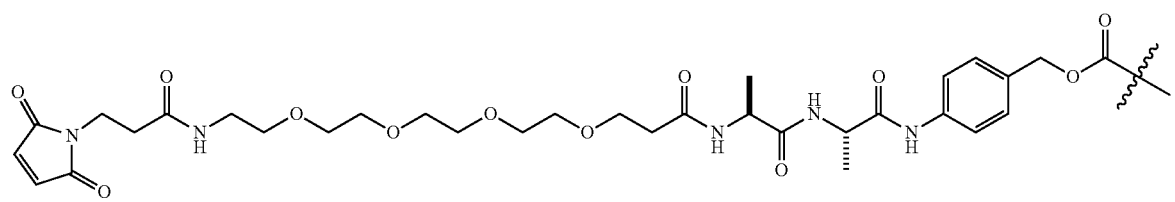
(IVa.2)
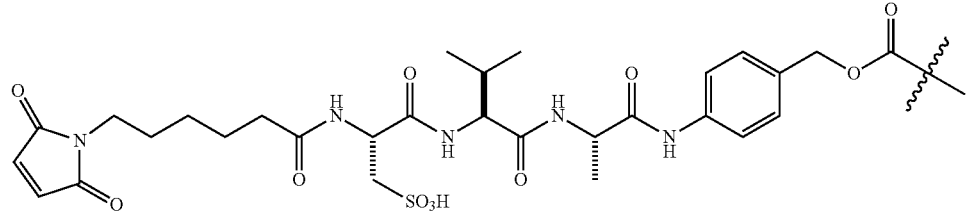
(IVa.3)
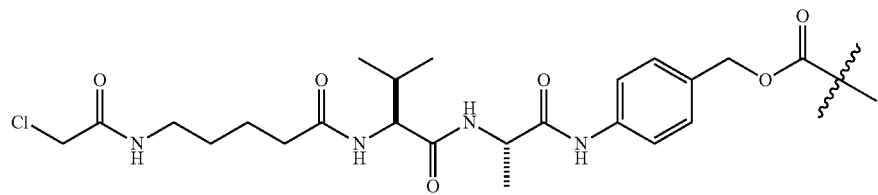
(IVa.4)
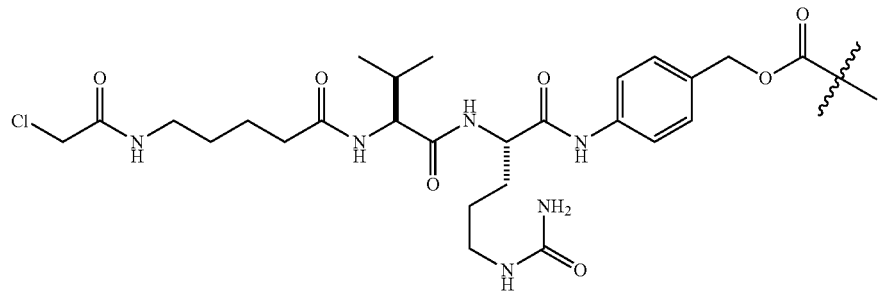
(IVa.5)

(IVa.6)
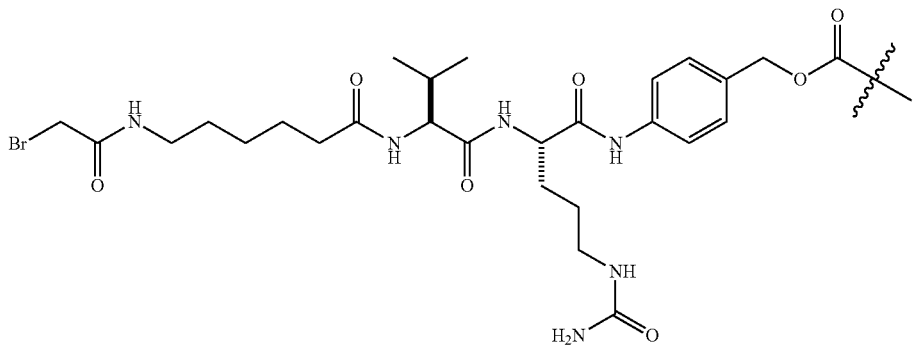
(IVa.7)
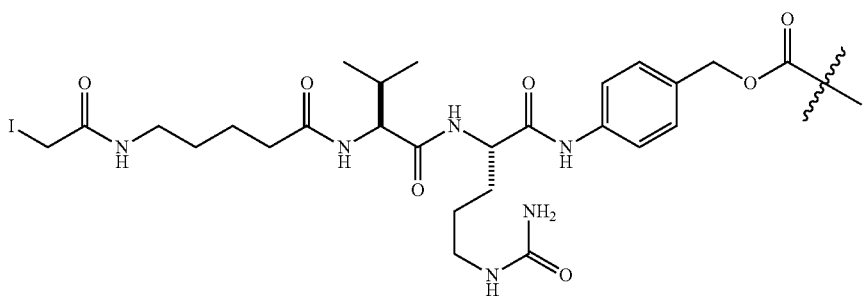
(IVa.8)
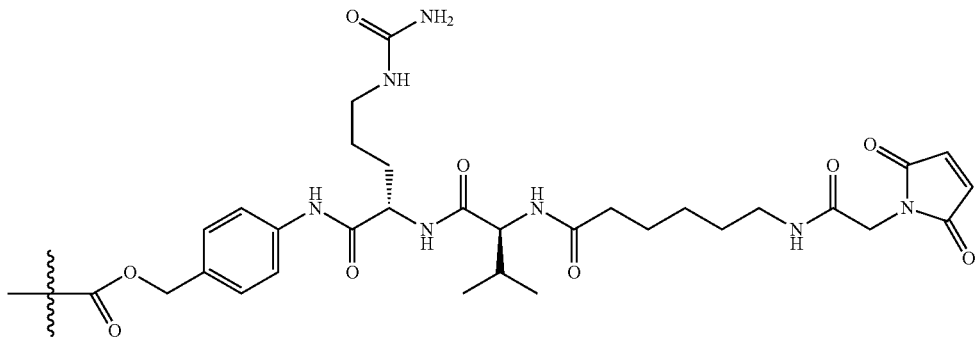
Exemplary embodiments of linkers according to structural formula (IVb), (IVc), or (IVd) that may be included in the ADCs described herein include the linkers illustrated below (as illustrated, the linkers include a group suitable for covalently linking the linker to an antibody):
(IVb.1)
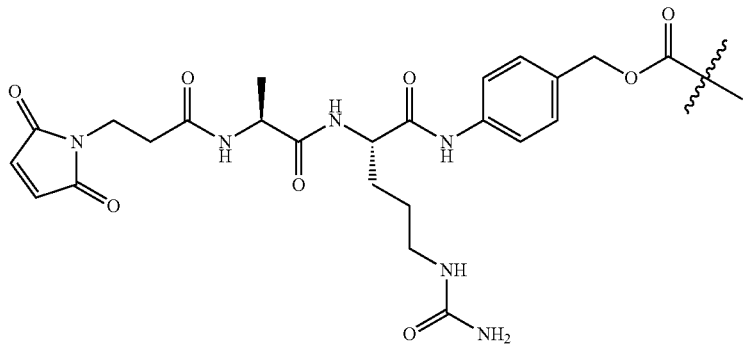

-continued
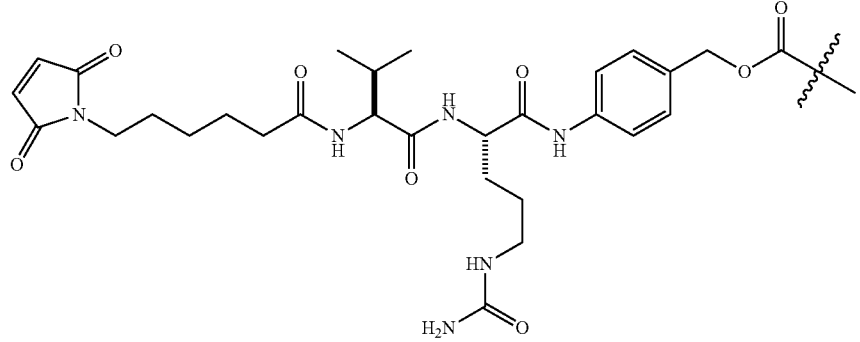
(IVb.2)
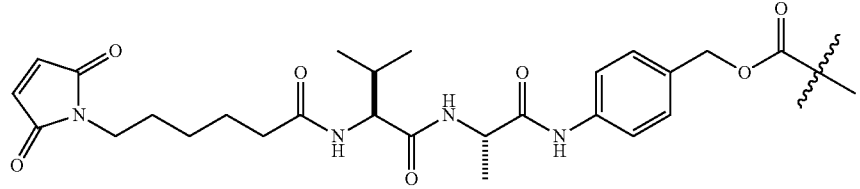
(IVb.3)
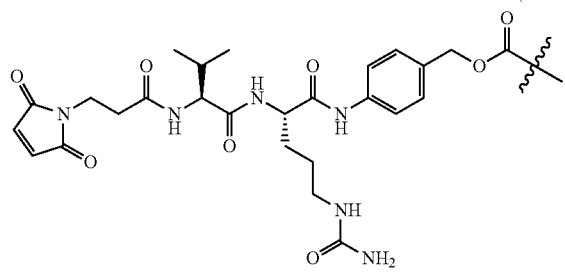
(IVb.4)
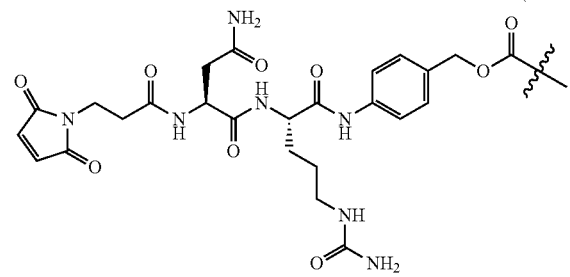
(IVb.5)
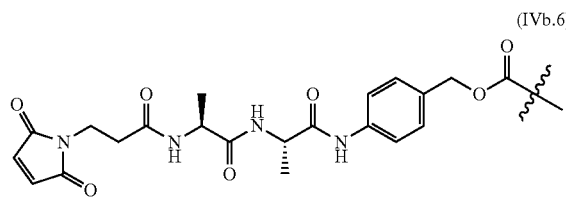
(IVb.6)
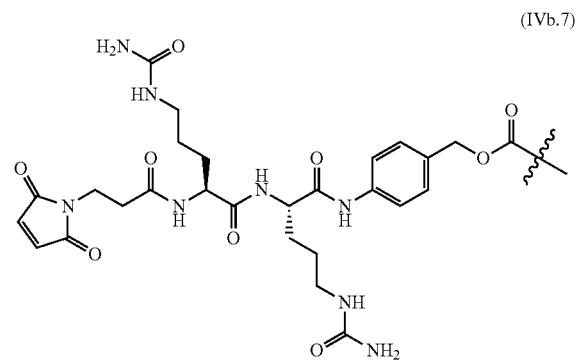
(IVb.7)
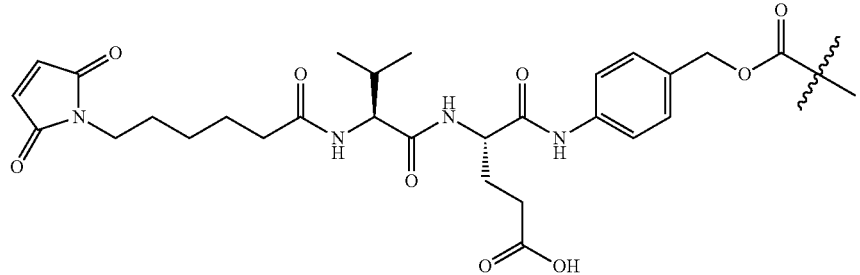
(IVb.8)

-continued
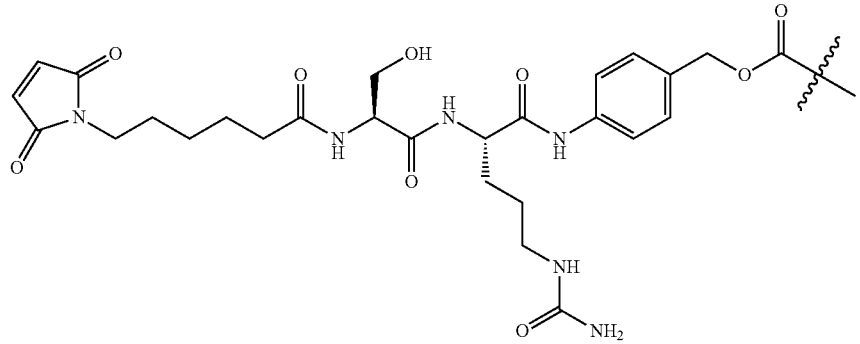
(IVb.9)
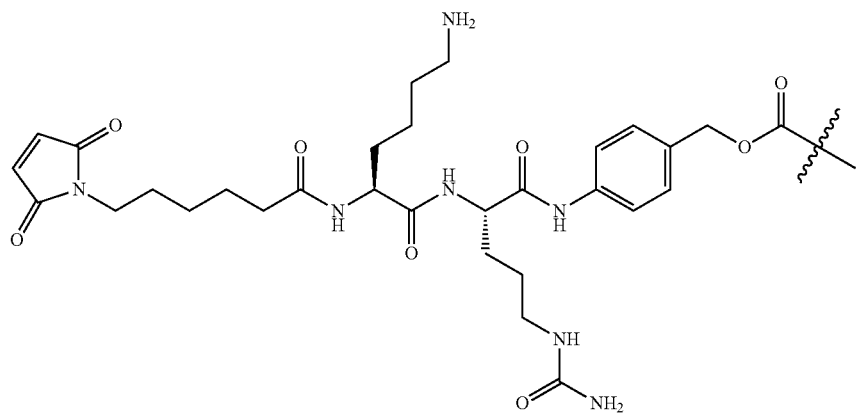
(IVb.10)
(IVb.11) (IVb.12)
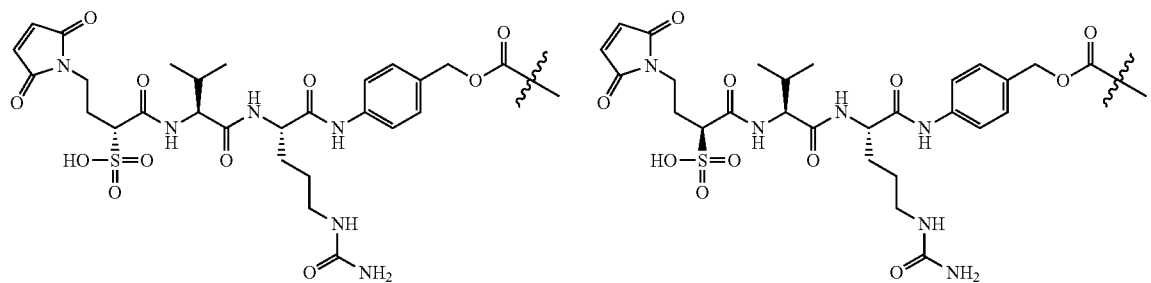
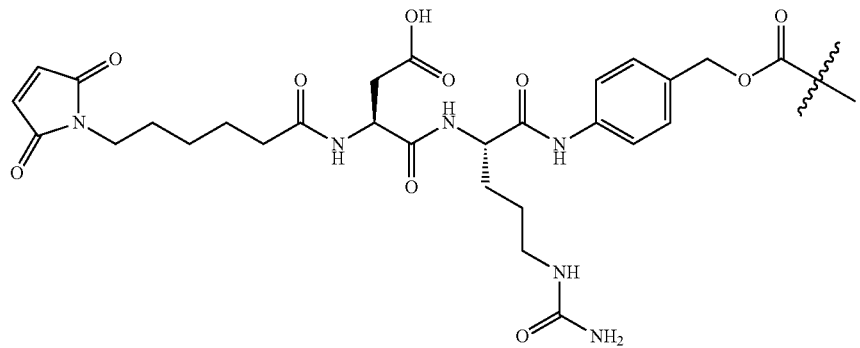
(IVb.13)

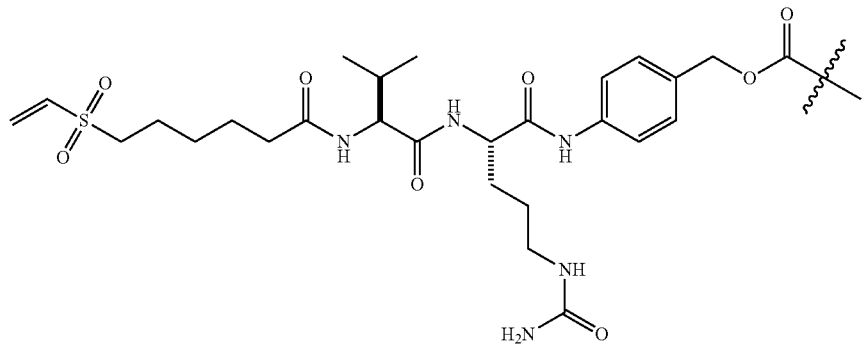
(IVb.14)
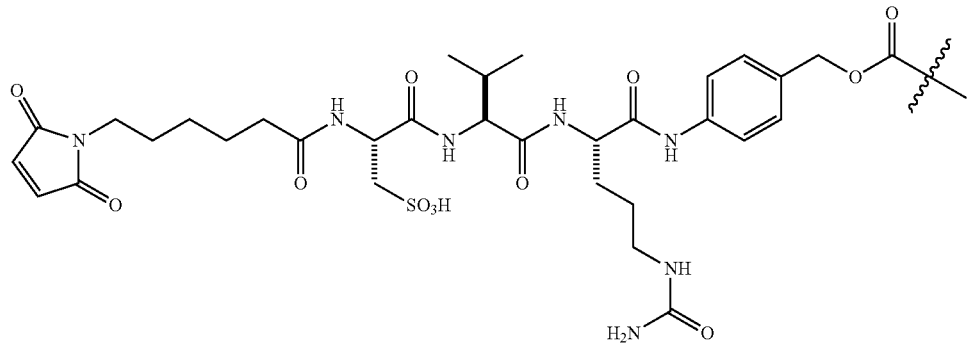
(IVb.15)
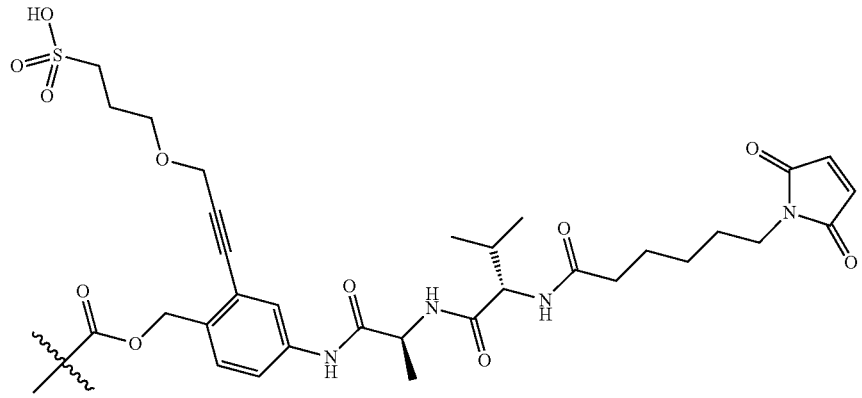
(IVb.16)
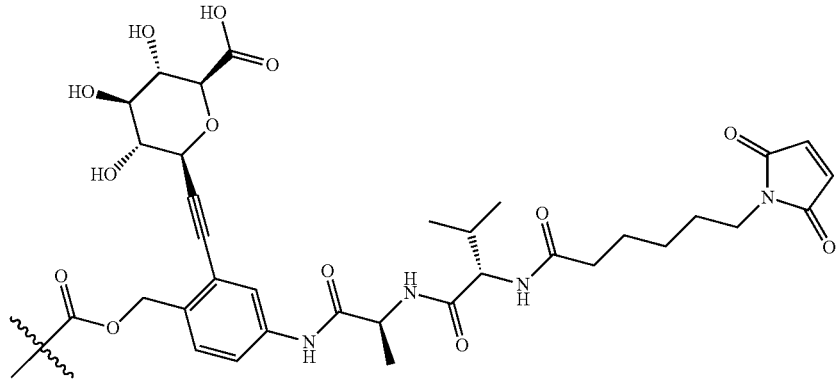
(IVb.17)

(IVb.18)
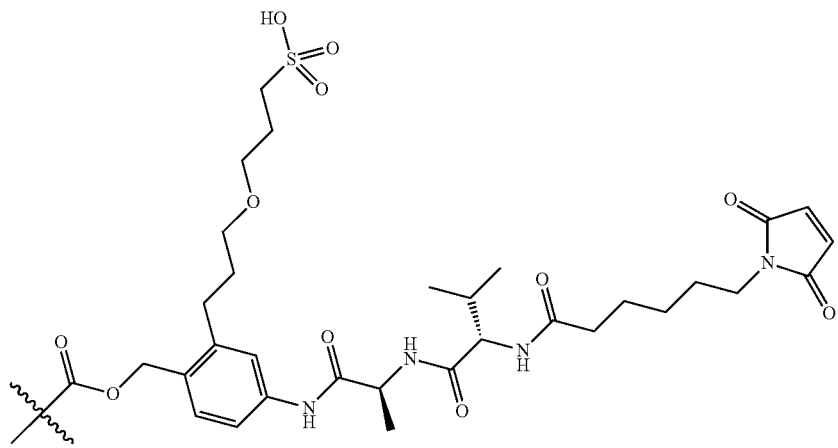
(IVb.19)
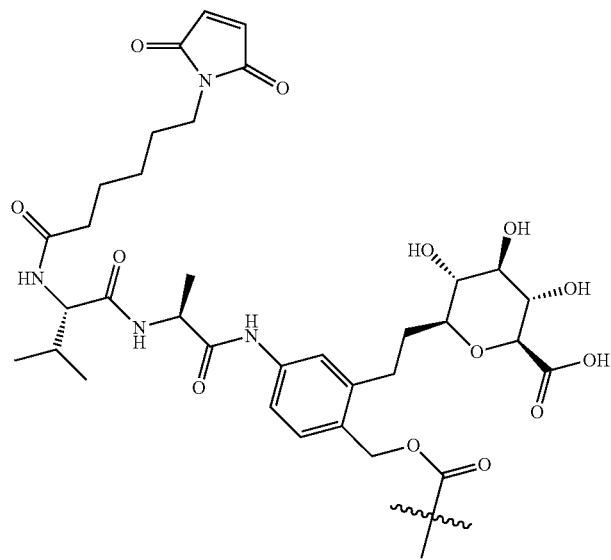
(IVc.1)
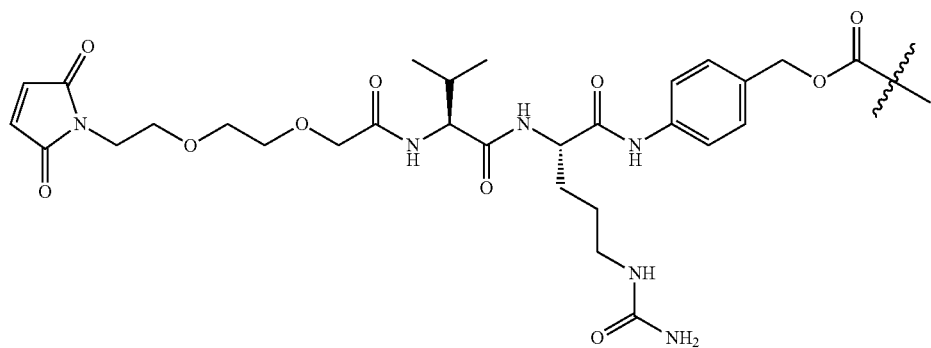

-continued
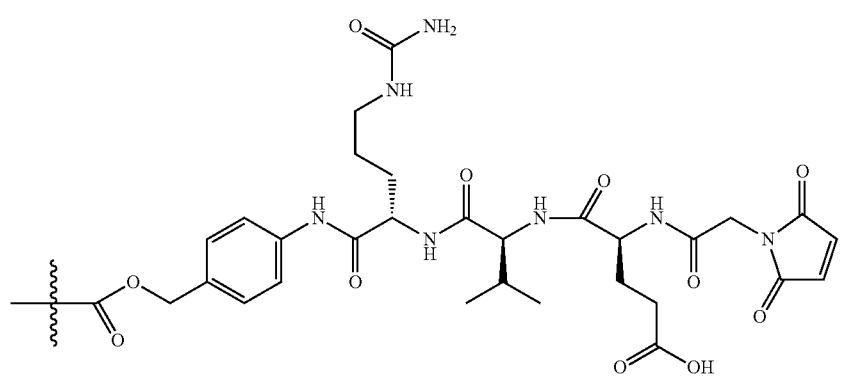
(IVc.2)
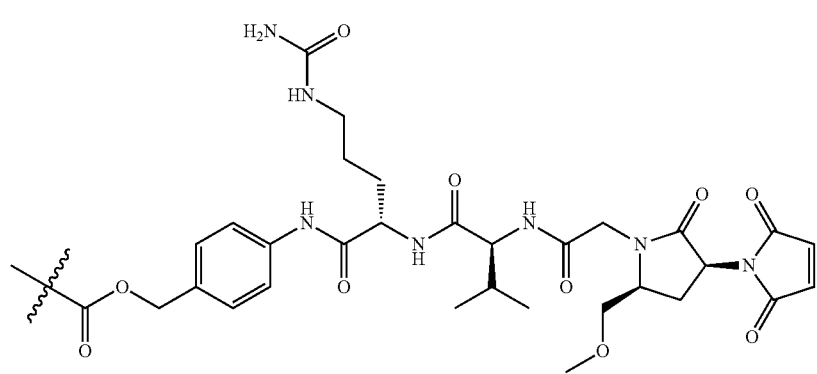
(IVc.3)
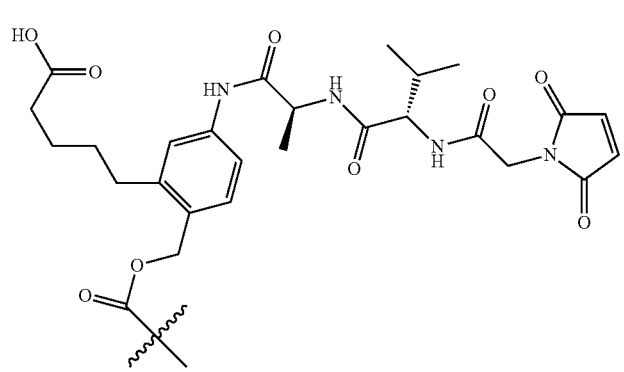
(IVc.4)
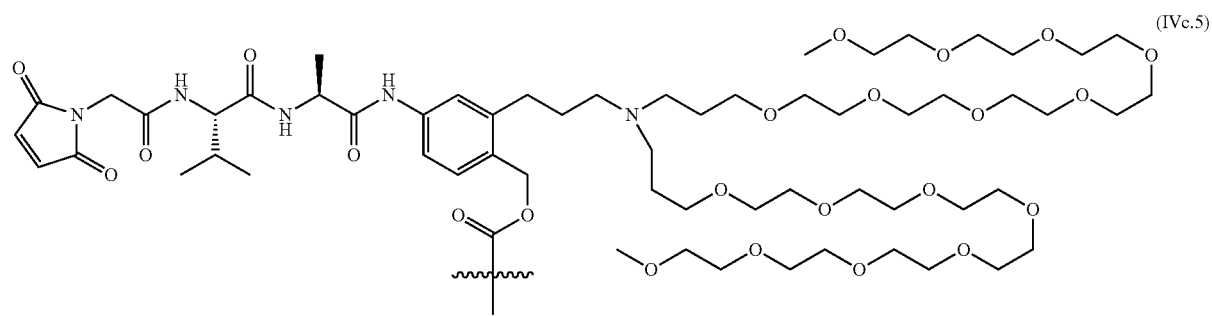
(IVc.5)

-continued
(IVc.6)
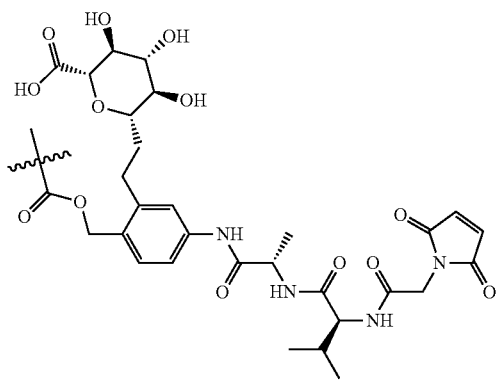
(IVc.7)
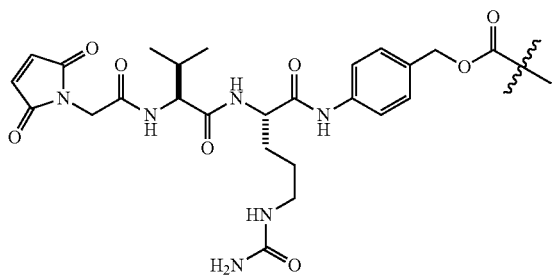
(IVd.1)
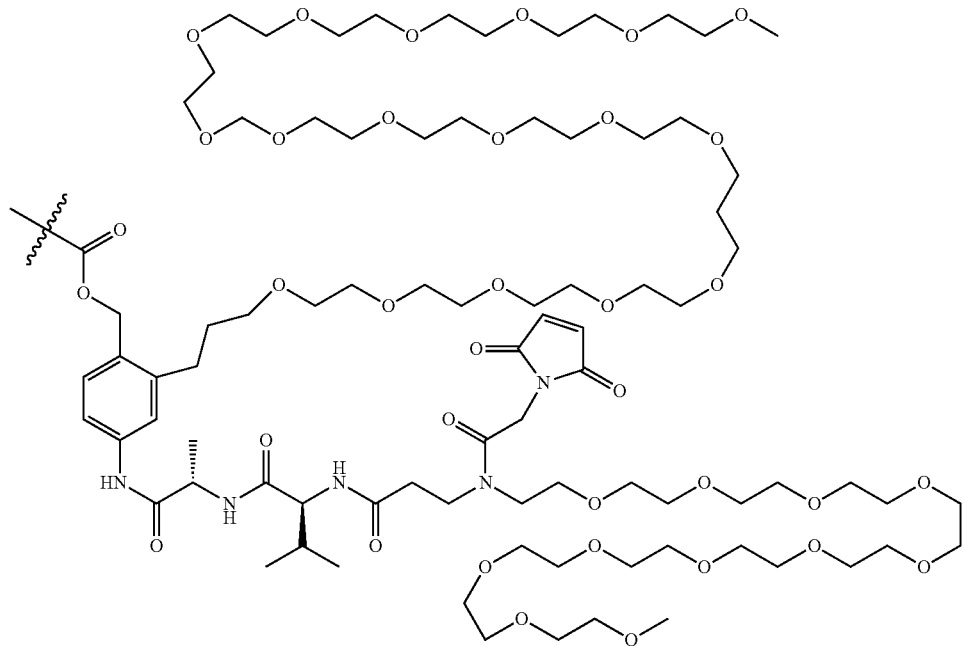
(IVd.2)
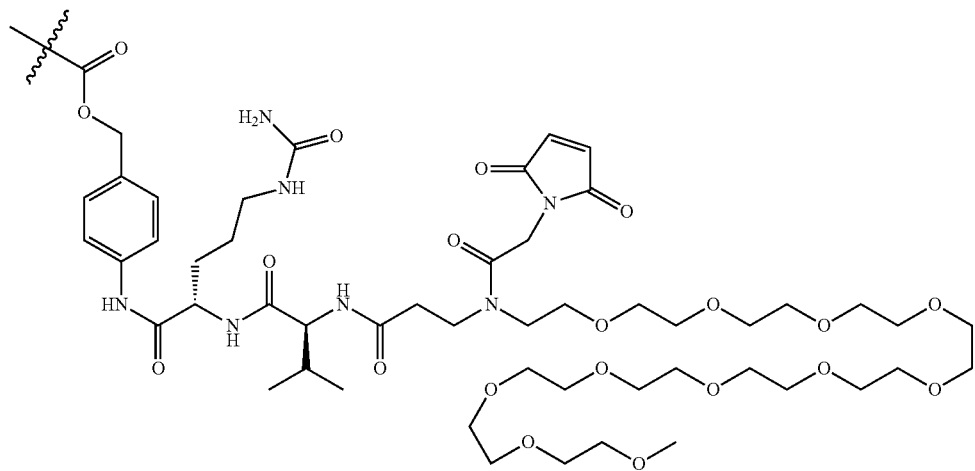

-continued
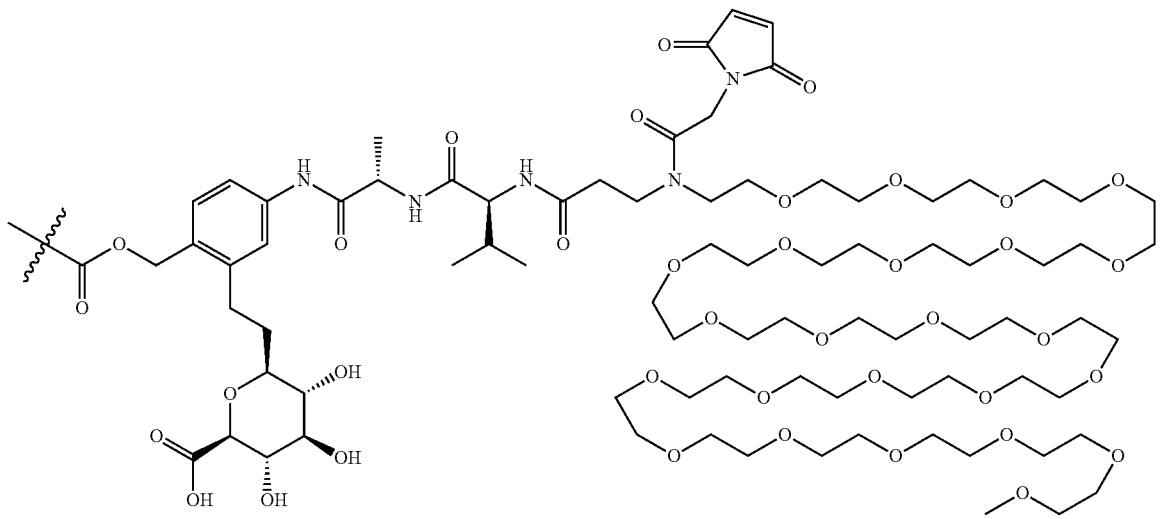
(IVd.3)
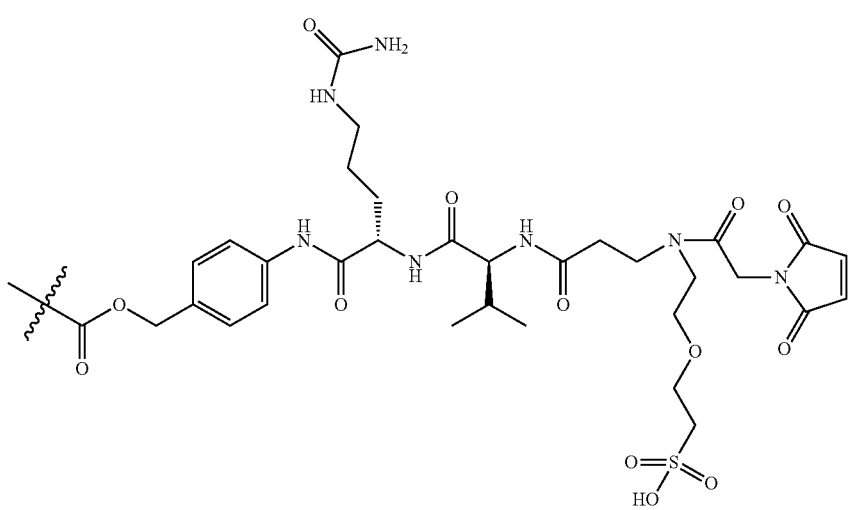
(IVd.4)
In certain embodiments, the linker comprises an enzymatically cleavable sugar moiety, for example, a linker comprising structural formula (Va), (Vb), (Vc), (Vd), or (Ve):
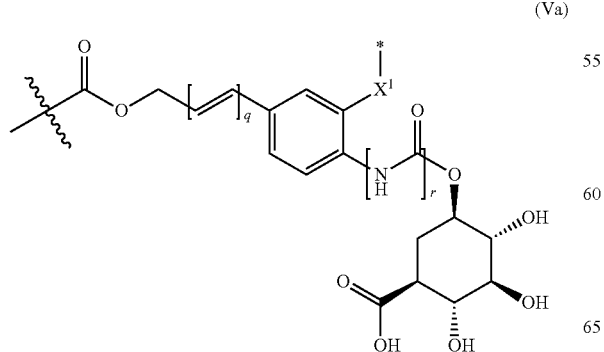
(Va)
-continued
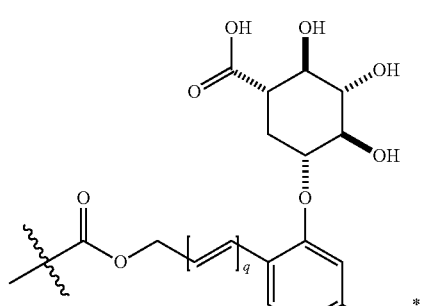
(Vb)

(Vc)

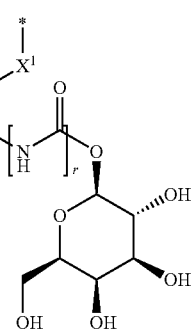

(Ve)

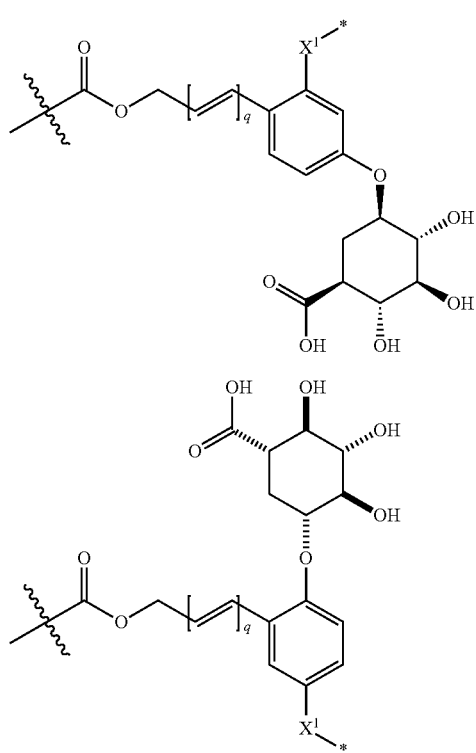

(Vd)

or a pharmaceutically acceptable salt thereof, wherein:
q is 0 or 1;
r is 0 or 1;
$X^1$ is $CH_2$, O or NH;
✓ represents the point of attachment of the linker to the drug; and
* represents the point of attachment to the remainder of the linker.

Exemplary embodiments of linkers according to structural formula (Va) that may be included in the ADCs described herein include the linkers illustrated below (as illustrated, the linkers include a group suitable for covalently linking the linker to an antibody):

(Va.1)

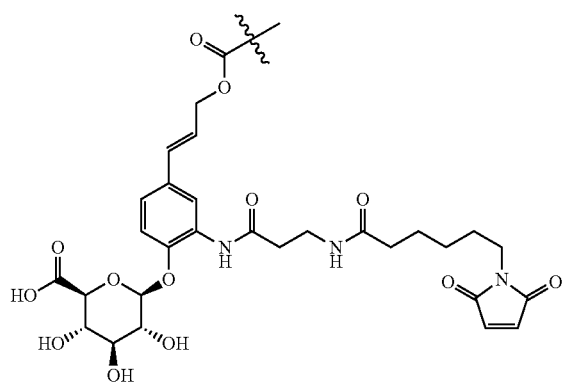

(Va.2)

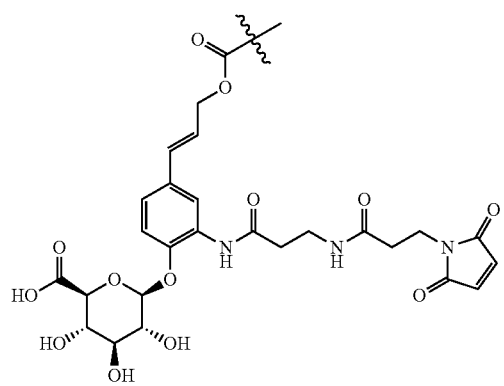

(Va.3)

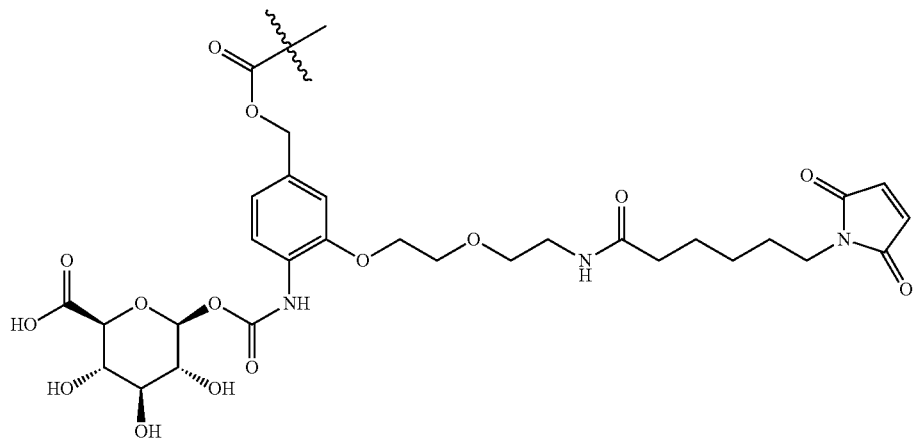

(Va.4)
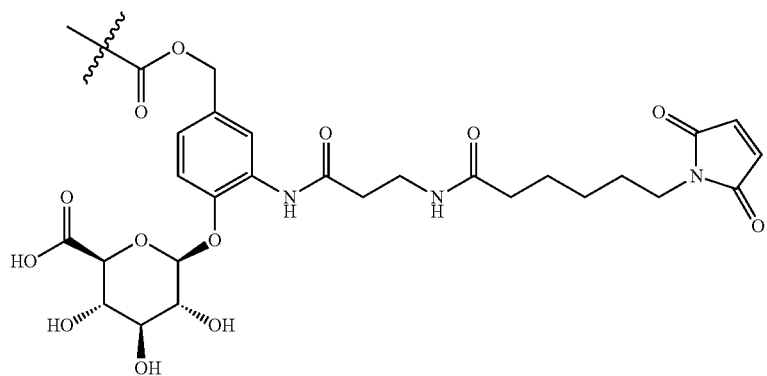
(Va.5)
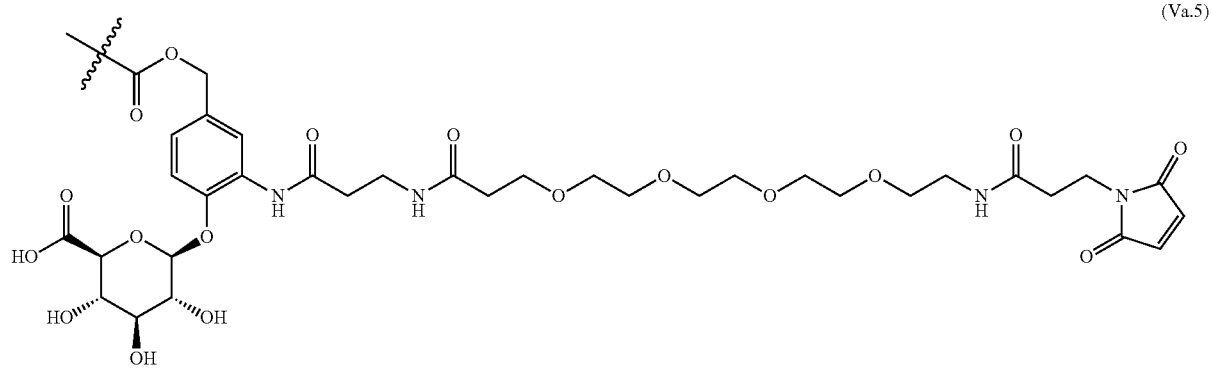
(Va.6)
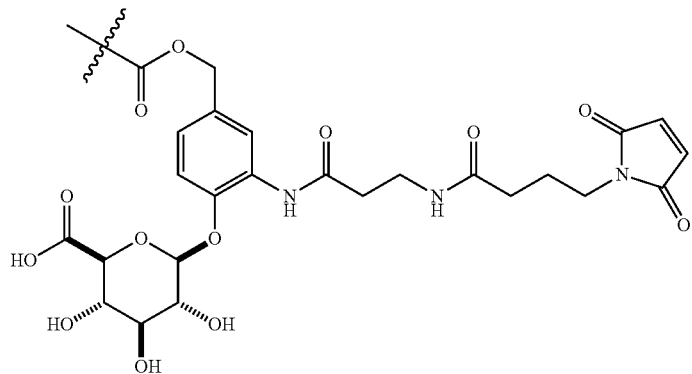
(Va.7)
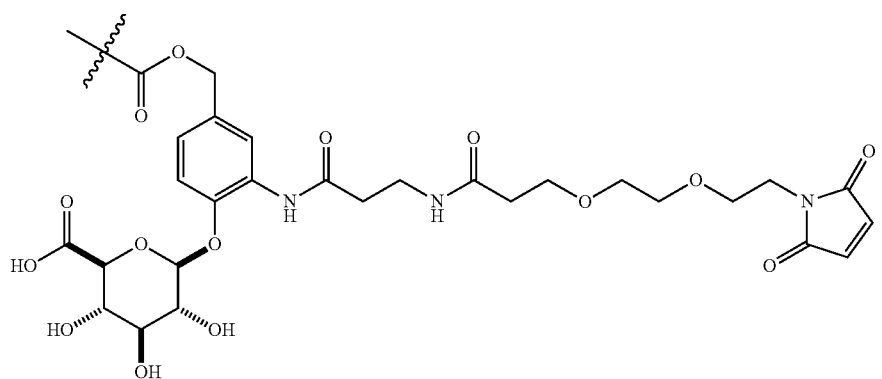

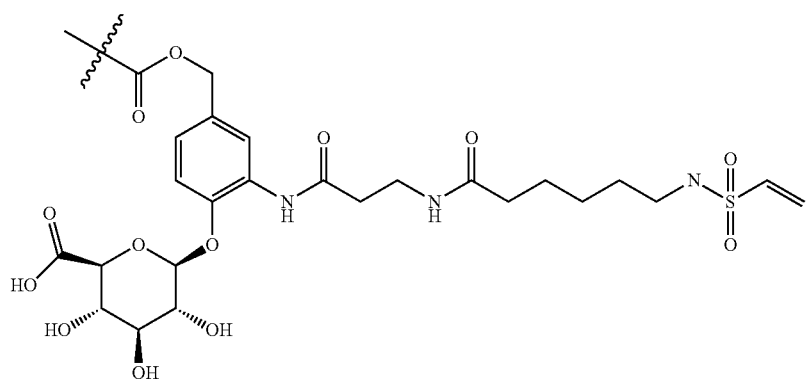
(Va.8)
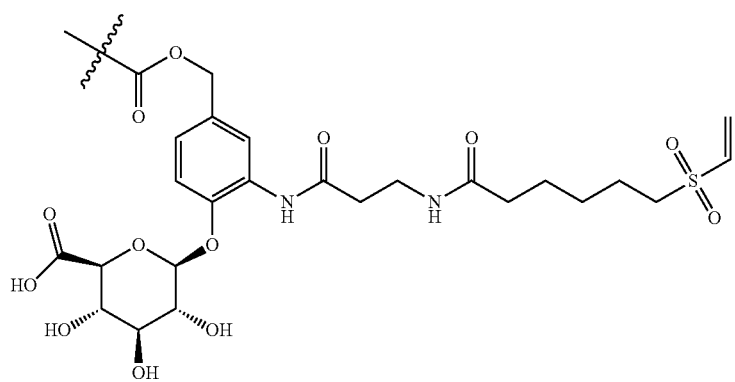
(Va.9)
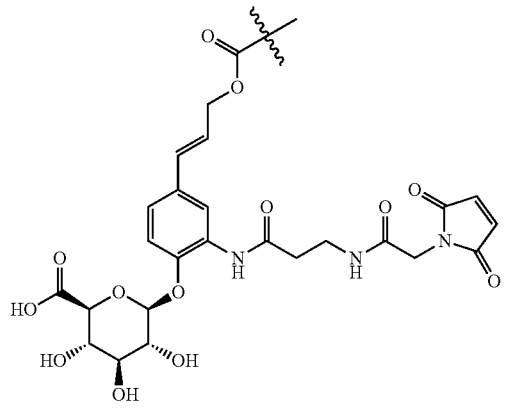
(Va.10) (Va.11)

-continued
(Va.12)
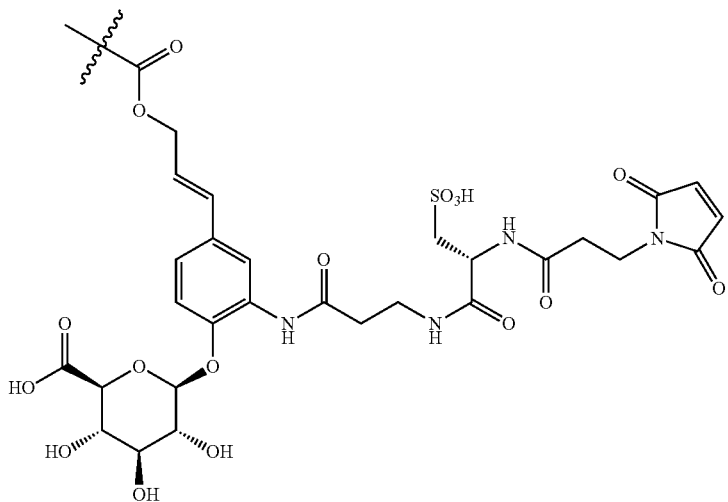
Exemplary embodiments of linkers according to structural formula (Vb) that may be included in the ADCs described herein include the linkers illustrated below (as illustrated, the linkers include a group suitable for covalently linking the linker to an antibody):
(Vb.1)
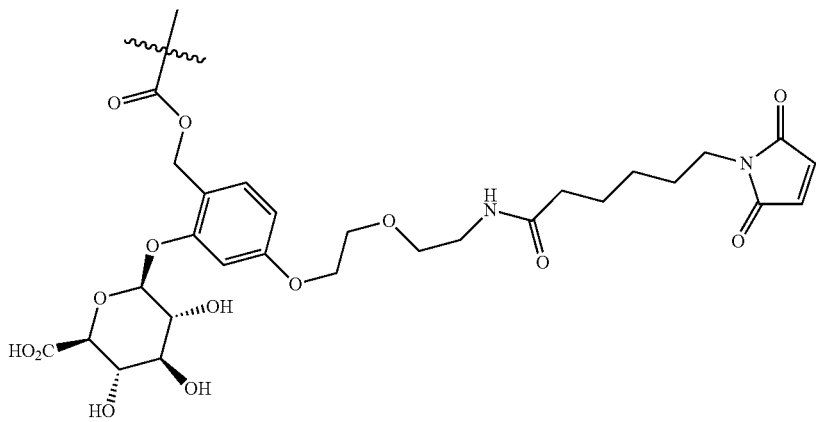
(Vb.2)
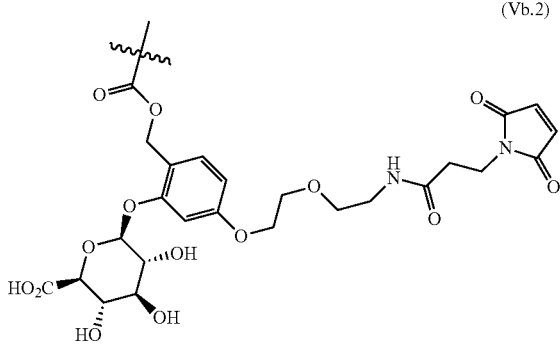
(Vb.3)
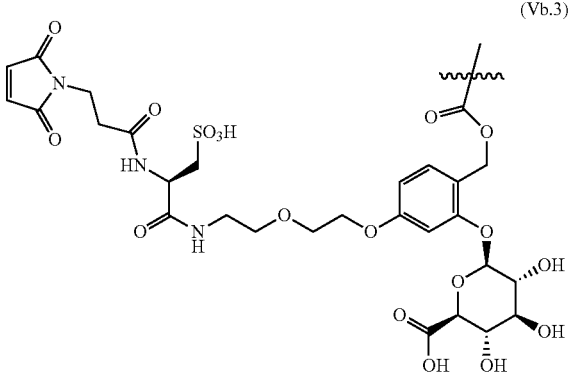

-continued
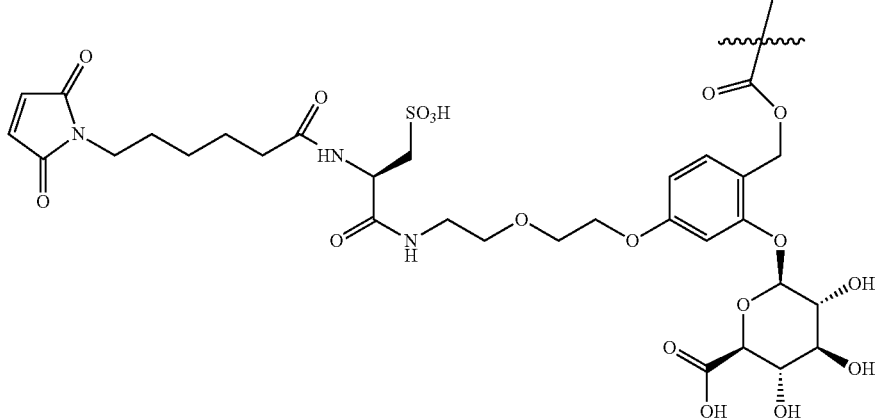
(Vb.4)
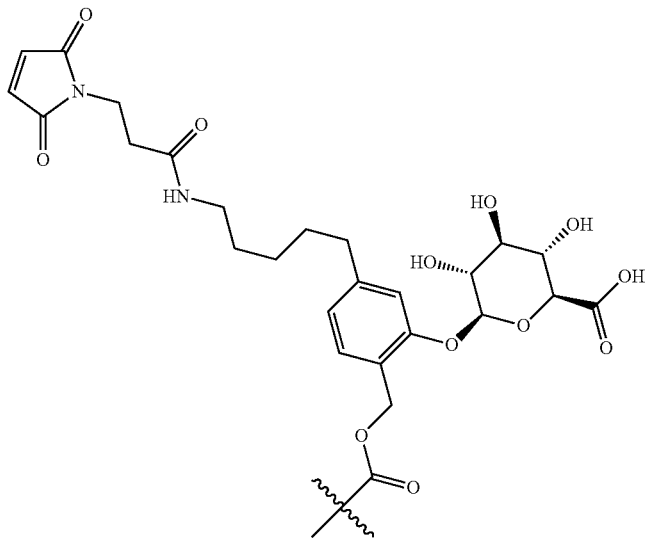
(Vb.5)
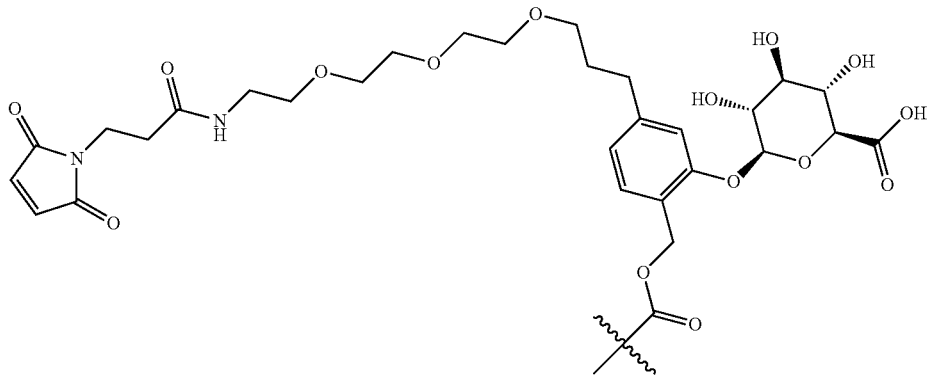
(Vb.6)

-continued
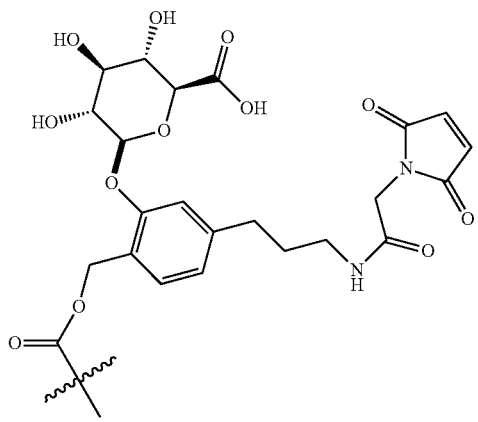
(Vb.7)
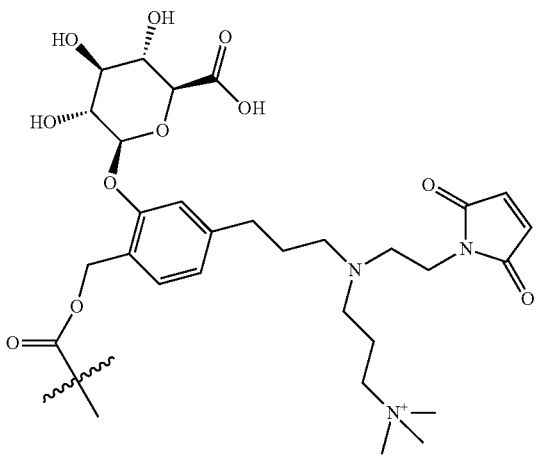
(Vb.8)
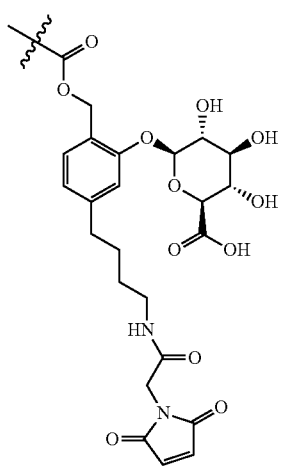
(Vb.9)
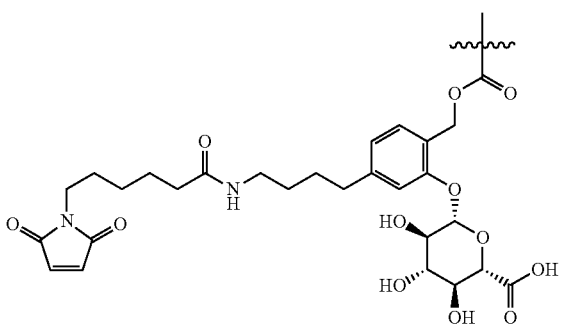
(Vb.10)
Exemplary embodiments of linkers according to structural formula (Vc) that may be included in the ADCs described herein include the linkers illustrated below (as illustrated, the linkers include a group suitable for covalently linking the linker to an antibody):
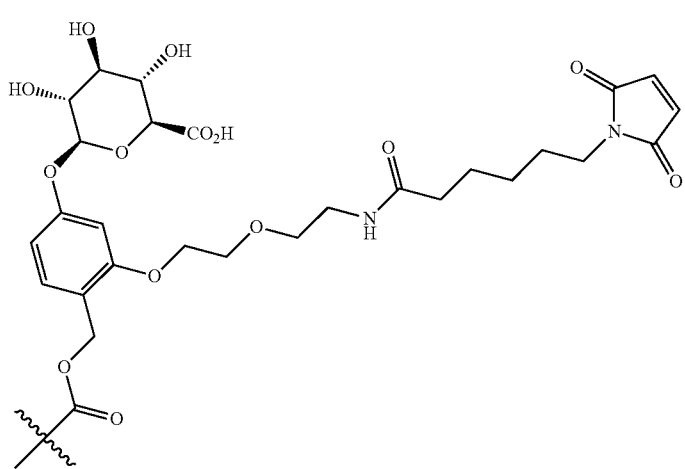
(Vc.1)

-continued
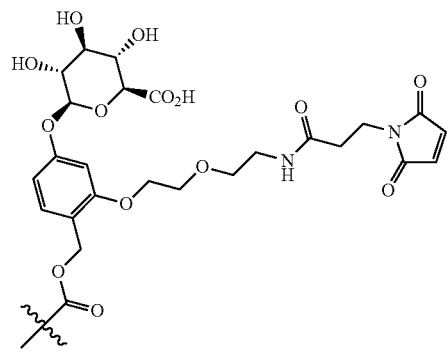
(Vc.2)
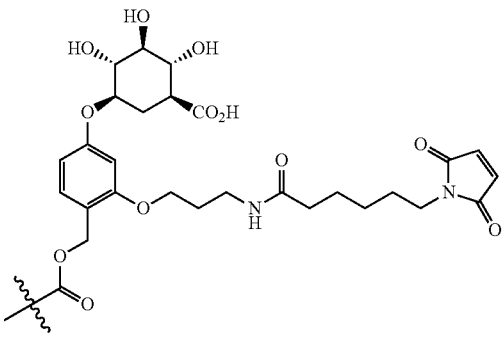
(Vc.3)
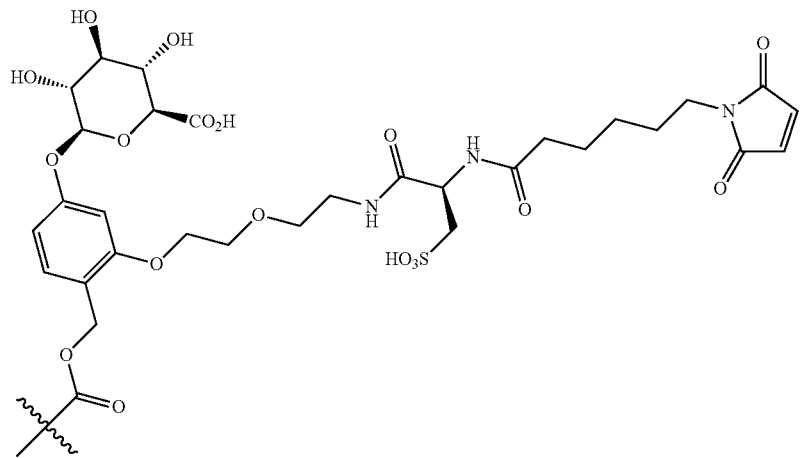
(Vc.4)
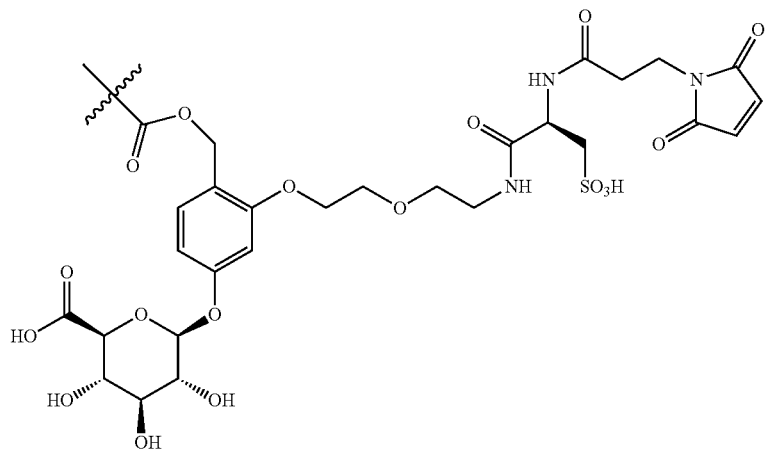
(Vc.5)

(Vc.6)
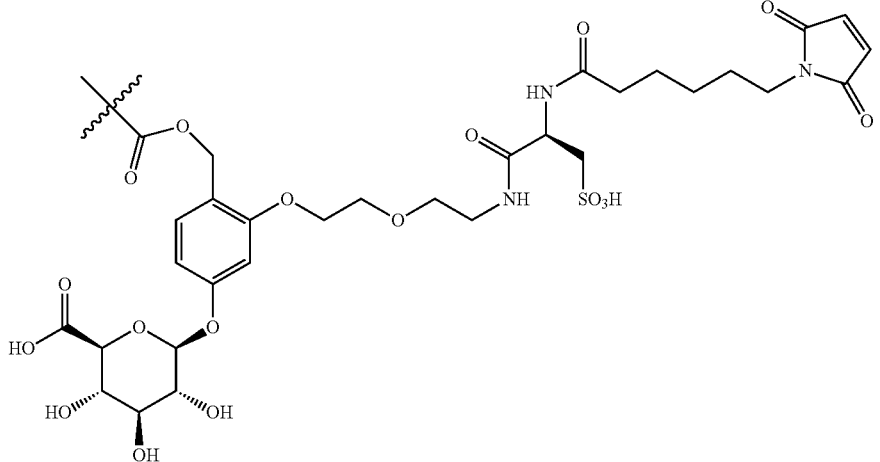
(Vc.7)
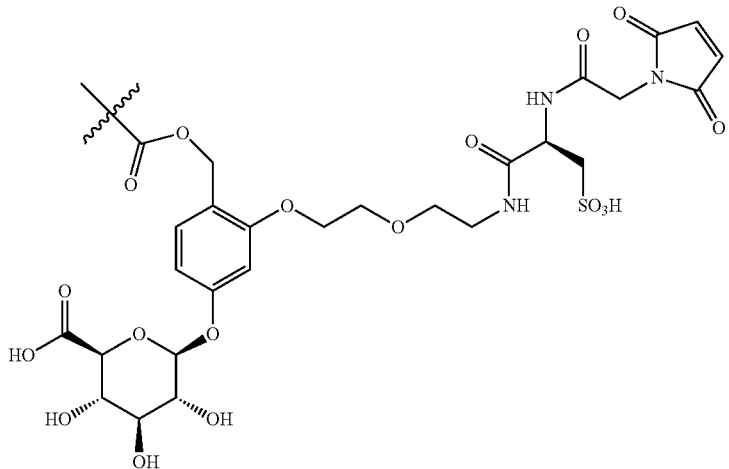
(Vc.8)
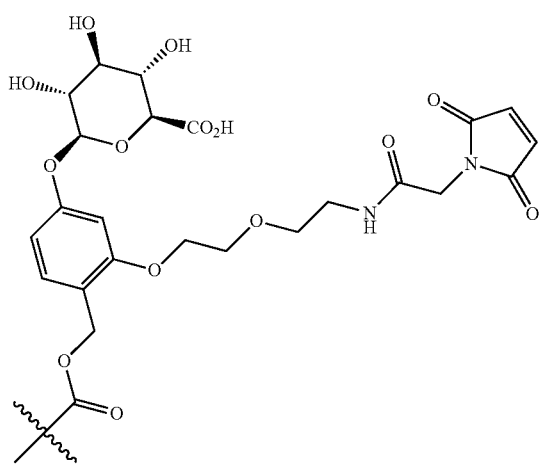

(Vc.9)
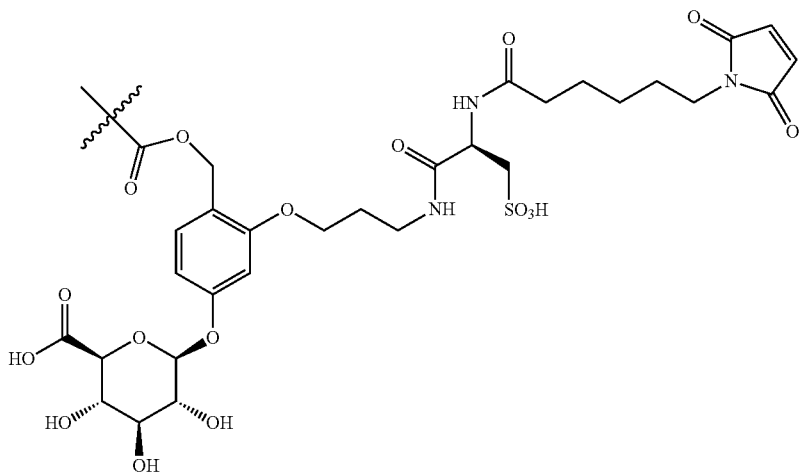
(Vc.10) (Vc.11)
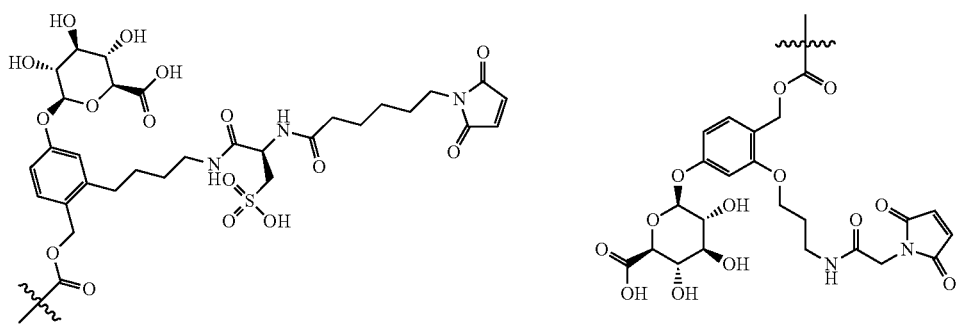
Exemplary embodiments of linkers according to structural formula (Vd) that may be included in the ADCs described herein include the linkers illustrated below (as illustrated, the linkers include a group suitable for covalently linking the linker to an antibody):
(Vd.1) (Vd.2)
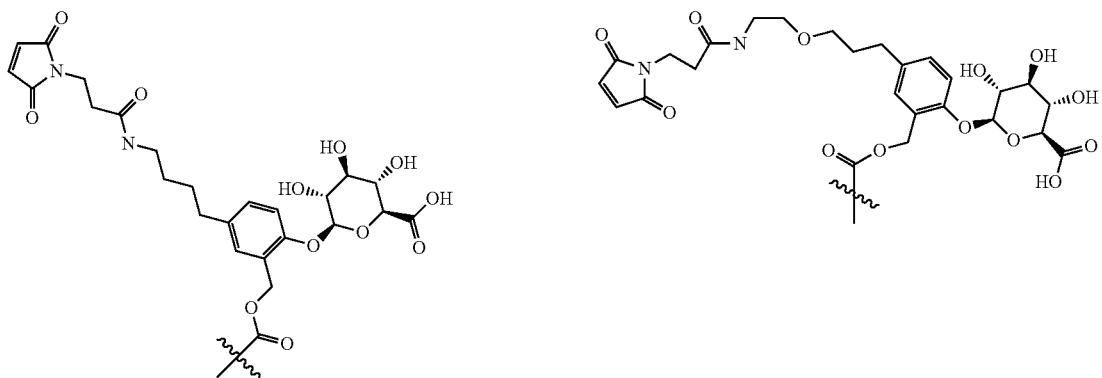

(Vd.3)
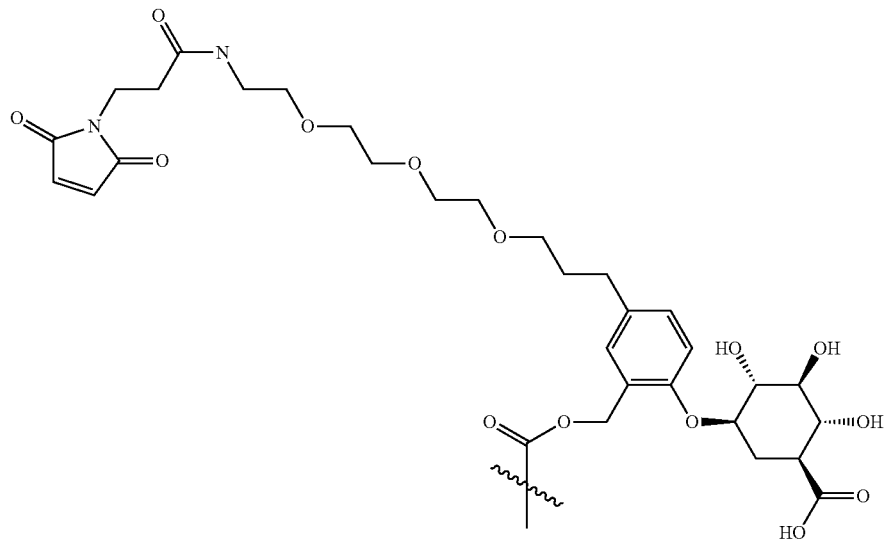
(Vd.4)
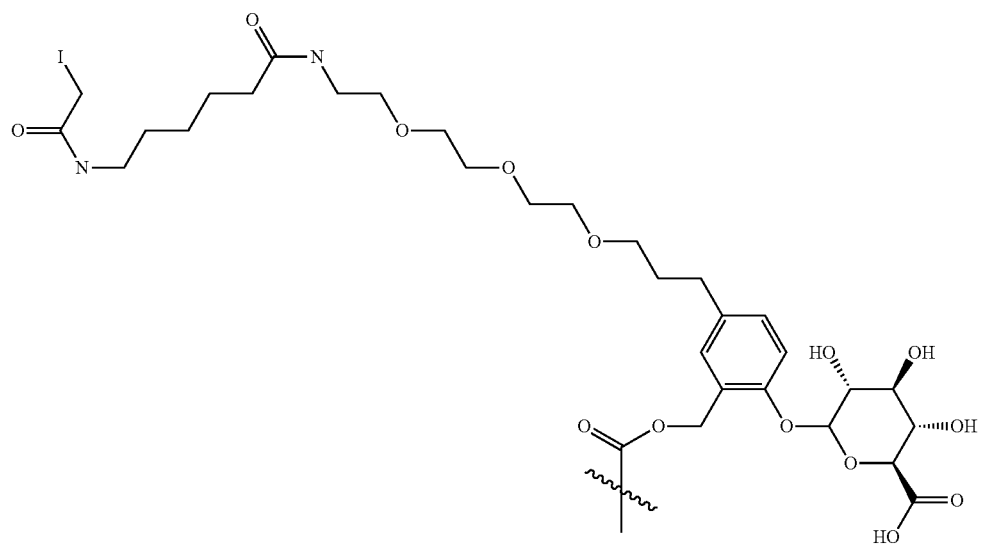
(Vd.5)
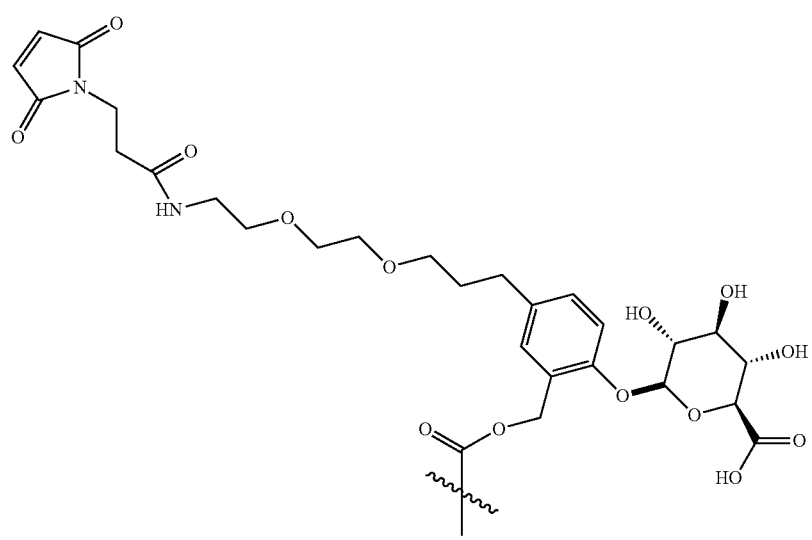

(Vd.6)

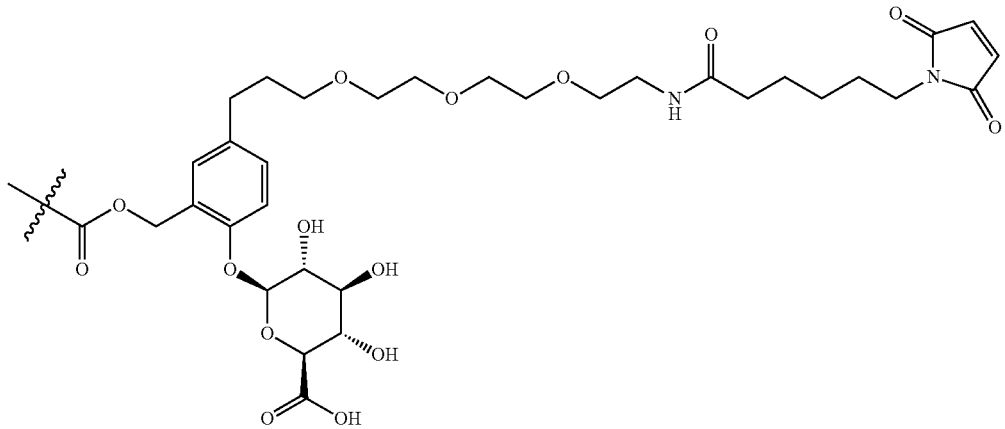

Exemplary embodiments of linkers according to structural formula (Ve) that may be included in the ADCs described herein include the linkers illustrated below (as illustrated, the linkers include a group suitable for covalently linking the linker to an antibody):

(Ve.1)

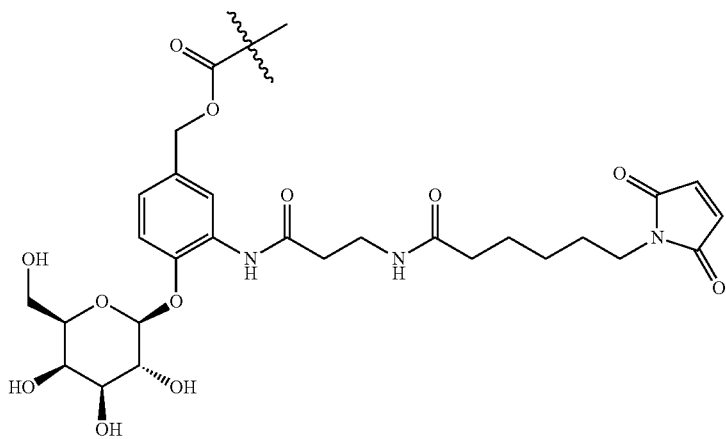

(Ve.2)

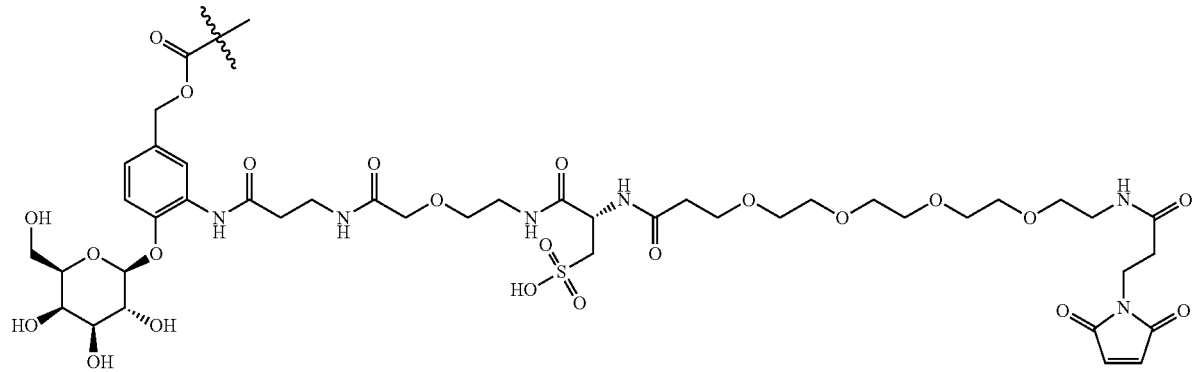

Non-Cleavable Linkers

Although cleavable linkers may provide certain advantages, the linkers comprising the ADC described herein need not be cleavable. For noncleavable linkers, the drug release does not depend on the differential properties between the plasma and some cytoplasmic compartments. The release of the drug is postulated to occur after internalization of the ADC via antigen-mediated endocytosis and delivery to lysosomal compartment, where the antibody is degraded to the level of amino acids through intracellular proteolytic degradation. This process releases a drug derivative, which is formed by the drug, the linker, and the amino acid residue to which the linker was covalently attached. The amino-acid drug metabolites from conjugates with noncleavable linkers are more hydrophilic and generally less membrane permeable, which leads to less bystander effects and less nonspecific toxicities compared to conjugates with a cleavable linker. In general, ADCs with noncleavable linkers have greater stability in circulation than ADCs with cleavable linkers. Non-cleavable linkers may be alkylene chains, or maybe polymeric in natures, such as, for example, based upon polyalkylene glycol polymers, amide polymers, or may include segments of alkylene chains, polyalkylene glycols and/or amide polymers. In certain embodiments, the linker comprises a polyethylene glycol segment having from 1 to 6 ethylene glycol units.

A variety of non-cleavable linkers used to link drugs to antibodies have been described. (See, Jeffrey et al., 2006, *Bioconjug. Chem.* 17; 831-840; Jeffrey et al., 2007, *Bioorg. Med. Chem. Lett.* 17:2278-2280; and Jiang et al., 2005, *J. Am. Chem. Soc.* 127:11254-11255, the contents of which are incorporated herein by reference). All of these linkers may be included in the ADCs described herein.

In certain embodiments, the linker is non-cleavable in vivo, for example a linker according to structural formula (VIa), (VIb), (VIc) or (VId) (as illustrated, the linkers include a group suitable for covalently linking the linker to an antibody:

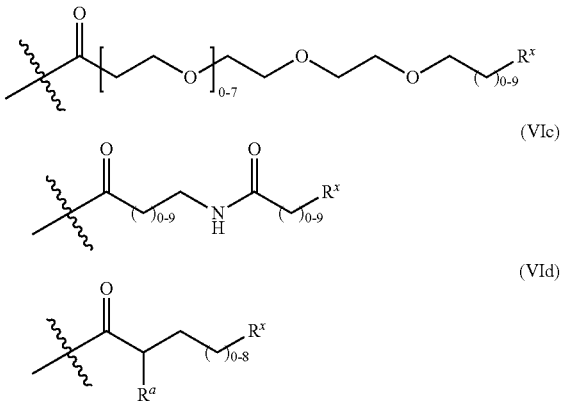

or a pharmaceutically acceptable salt thereof, wherein:
- $R^a$ is selected from hydrogen, alkyl, sulfonate and methyl sulfonate;
- $R^x$ is a moiety including a functional group capable of covalently linking the linker to an antibody; and
- ∤ represents the point of attachment of the linker to the Bcl-xL inhibitor.

Exemplary embodiments of linkers according to structural formula (VIa)-(VId) that may be included in the ADCs described herein include the linkers illustrated below (as illustrated, the linkers include a group suitable for covalently linking the linker to an antibody, and ∤ represents the point of attachment to a Bcl-xL inhibitor):

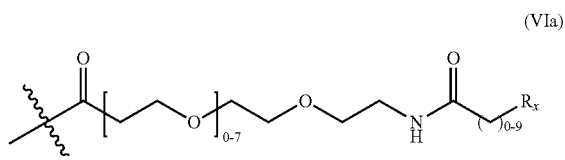

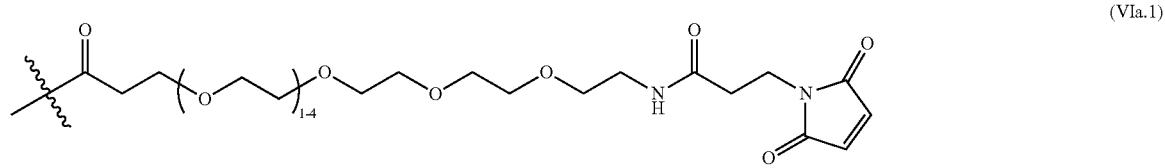

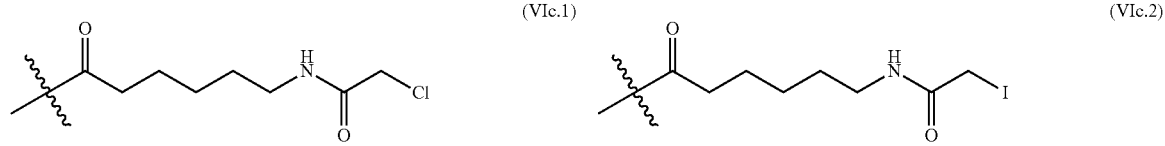

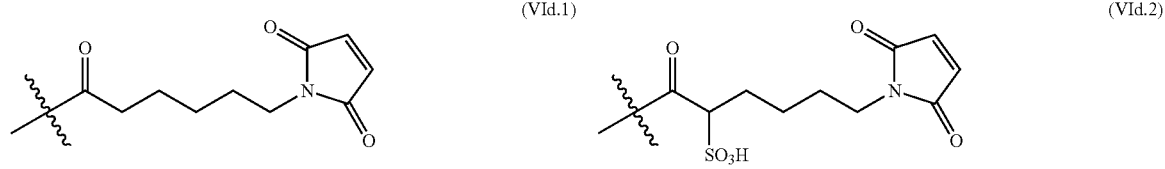

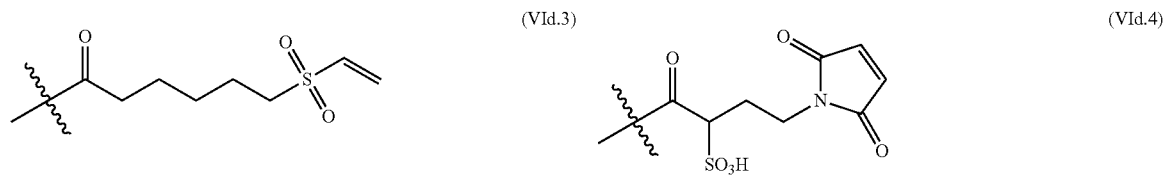

Groups Used to Attach Linkers to Anti-B7-H3 Antibodies

Attachment groups can be electrophilic in nature and include: maleimide groups, activated disulfides, active esters such as NHS esters and HOBt esters, haloformates, acid halides, alkyl and benzyl halides such as haloacetamides. As discussed below, there are also emerging technologies related to "self-stabilizing" maleimides and "bridging disulfides" that can be used in accordance with the disclosure.

Loss of the drug-linker from the ADC has been observed as a result of a maleimide exchange process with albumin, cysteine or glutathione (Alley et al., 2008, *Bioconjugate Chem.* 19: 759-769). This is particularly prevalent from highly solvent-accessible sites of conjugation while sites that are partially accessible and have a positively charged environment promote maleimide ring hydrolysis (Junutula et al., 2008, *Nat. Biotechnol.* 26: 925-932). A recognized solution is to hydrolyze the succinimide formed from conjugation as this is resistant to deconjugation from the antibody, thereby making the ADC stable in serum. It has been reported previously that the succinimide ring will undergo hydrolysis under alkaline conditions (Kalia et al., 2007, *Bioorg. Med. Chem. Lett.* 17: 6286-6289). One example of a "self-stabilizing" maleimide group that hydrolyzes spontaneously under antibody conjugation conditions to give an ADC species with improved stability is depicted in the schematic below. See U.S. Published Application No. 2013/0309256, International Application Publication No. WO 2013/173337, Tumey et al., 2014, Bioconjugate Chem. 25: 1871-1880, and Lyon et al., 2014, *Nat. Biotechnol.* 32: 1059-1062. Thus, the maleimide attachment group is reacted with a sulfhydryl of an antibody to give an intermediate succinimide ring. The hydrolyzed form of the attachment group is resistant to deconjugation in the presence of plasma proteins.

Normal system:

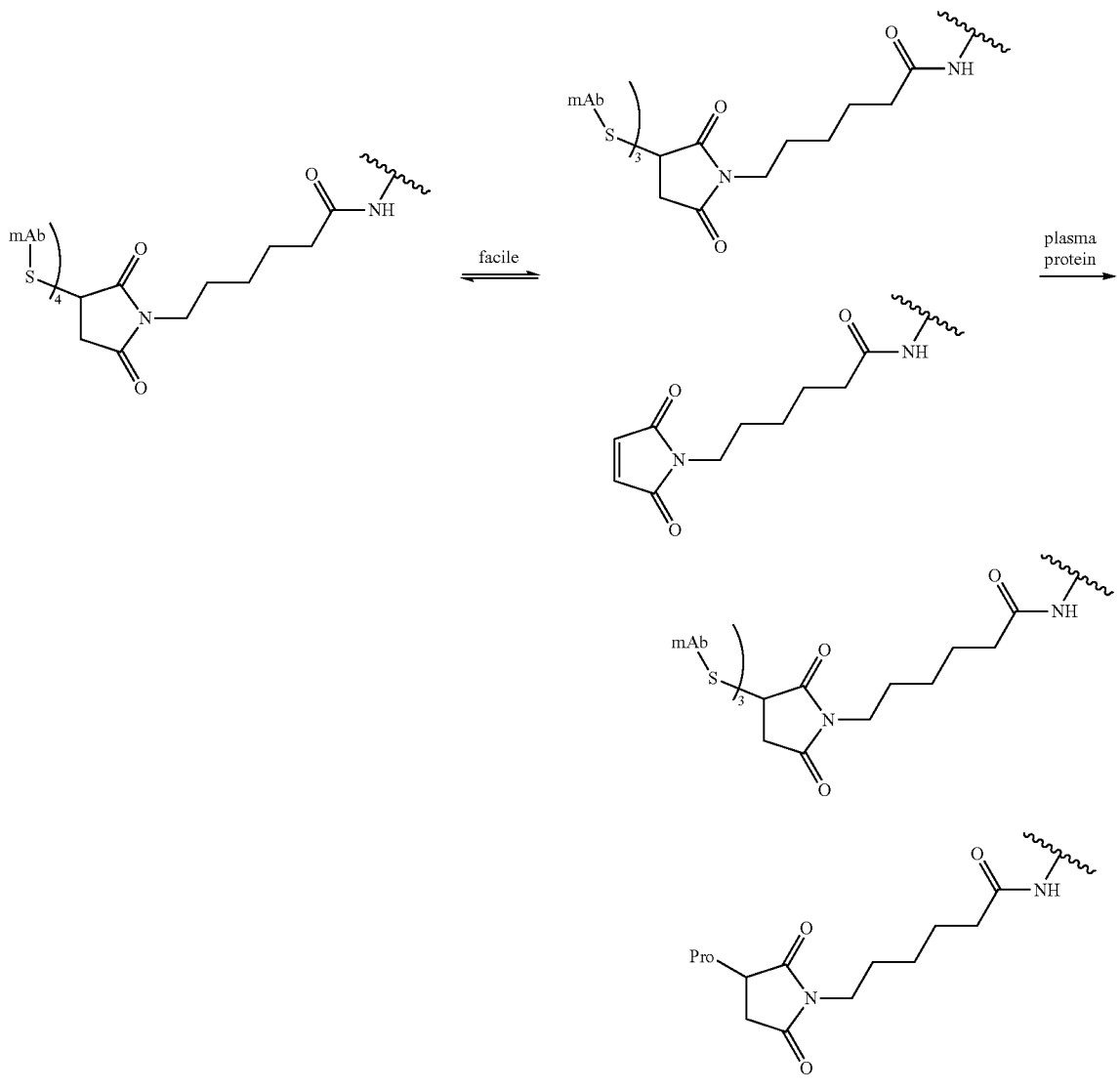

Leads to "DAR loss" over time

Self-stabilizing attachment

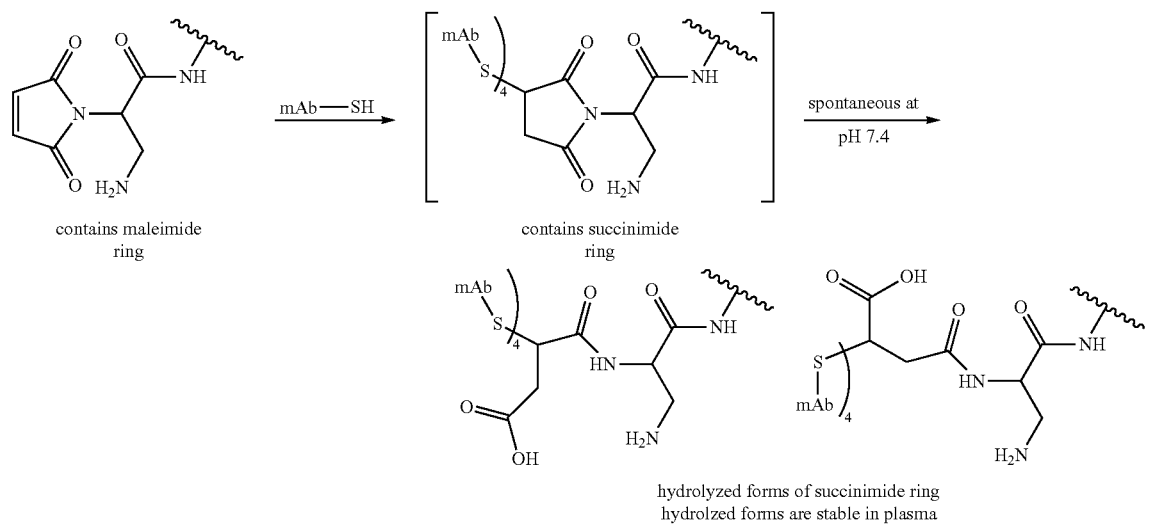

contains maleimide ring → contains succinimide ring → hydrolyzed forms of succinimide ring; hydrolzed forms are stable in plasma As shown above, the maleimide ring of a linker may react with an antibody Ab, forming a covalent attachment as either a succinimide (closed form) or succinamide (open form).

Polytherics has disclosed a method for bridging a pair of sulfhydryl groups derived from reduction of a native hinge disulfide bond. See, Badescu et al., 2014, *Bioconjugate Chem.* 25:1124-1136. The reaction is depicted in the schematic below. An advantage of this methodology is the ability to synthesize homogenous DAR4 ADCs by full reduction of IgGs (to give 4 pairs of sulfhydryls) followed by reaction with 4 equivalents of the alkylating agent. ADCs containing "bridged disulfides" are also claimed to have increased stability.

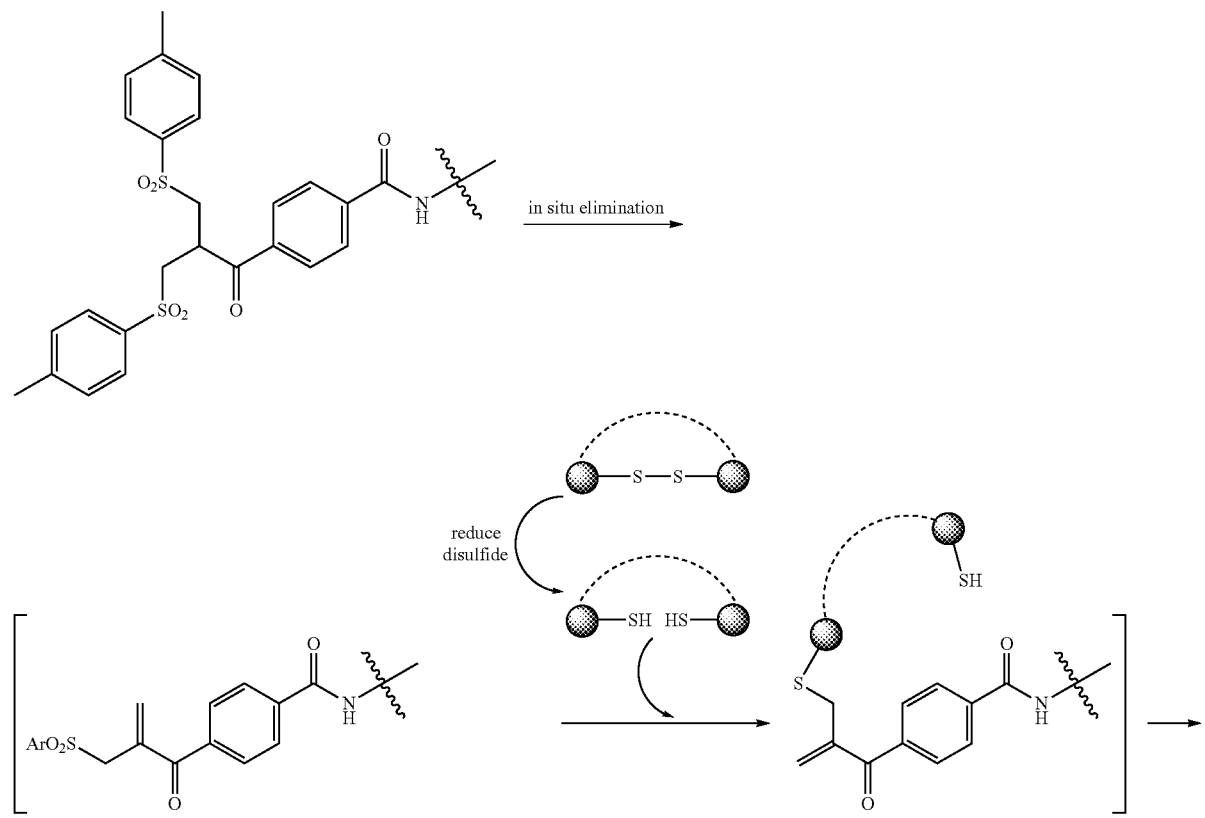

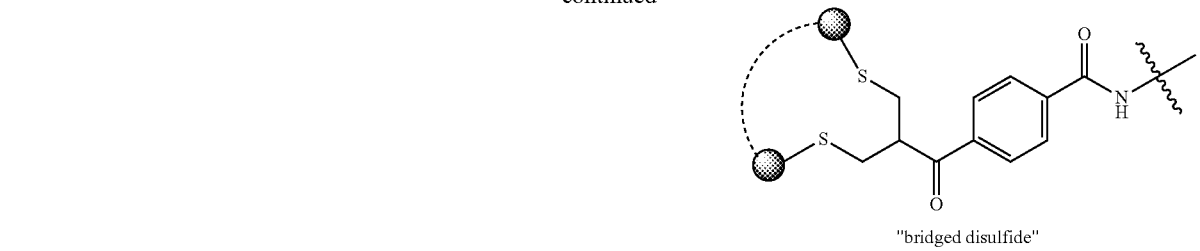

"bridged disulfide"

Similarly, as depicted below, a maleimide derivative that is capable of bridging a pair of sulfhydryl groups has been developed. See U.S. Published Application No. 2013/0224228.

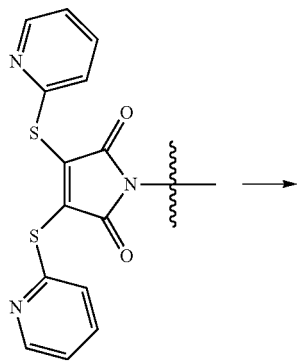

→

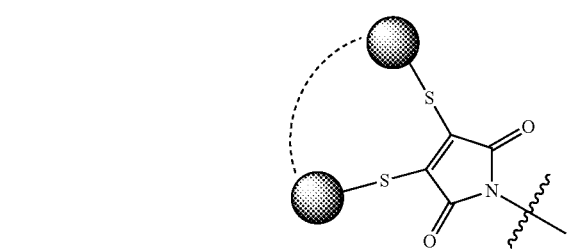

In certain embodiments the attachment moiety comprises the structural formulae (VIIa), (VIIb), or (VIIc):

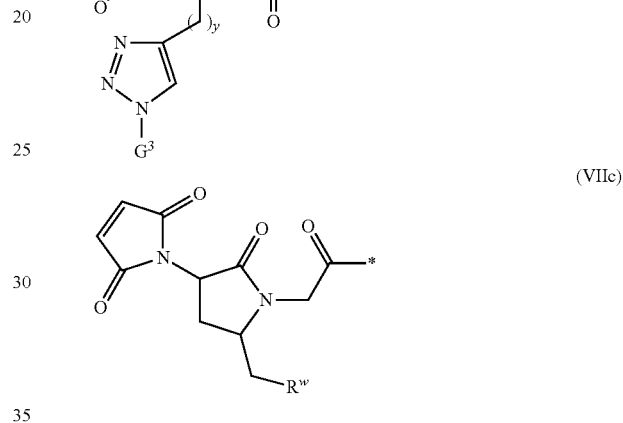

or a pharmaceutically acceptable salt thereof, wherein:

R9 is H or —O—$(CH_2CH_2O)_{11}$—$CH_3$;

x is 0 or 1;

y is 0 or 1;

$G^3$ is —$CH_2CH_2CH_2SO_3H$ or —$CH_2CH_2O$—$(CH_2CH_2O)_{11}$—$CH_3$;

$R^w$ is —O—$CH_2CH_2SO_3H$ or —NH(CO)—$CH_2CH_2O$—$(CH_2CH_2O)_{12}$—$CH_3$; and \* represents the point of attachment to the remainder of the linker.

In certain embodiments, the linker comprises a segment according to structural formulae (VIIIa), (VIIIb), or (VIIIc):

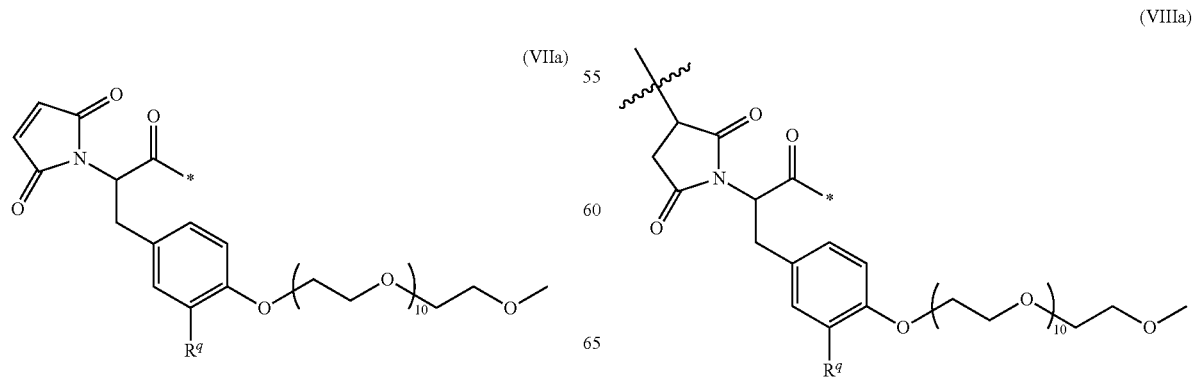

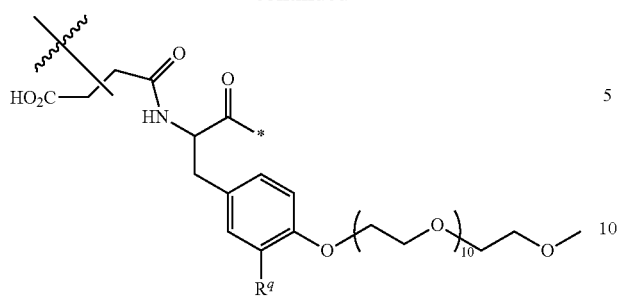

(hydrolyzed form)

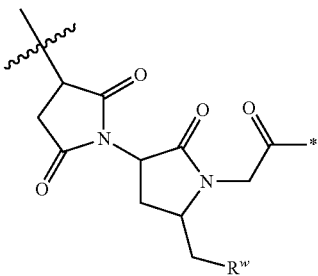

(VIIIc)

(VIIIb)

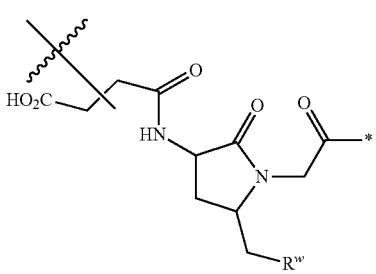

(hydrolyzed form)

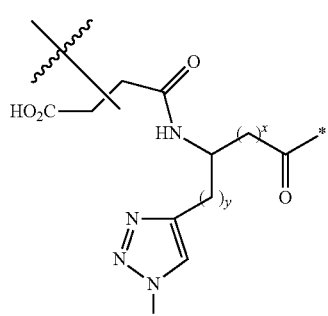

(hydrolyzed form)

or a hydrolyzed derivative or a pharmaceutically acceptable salt thereof, wherein:
$R^9$ is H or —O—$(CH_2CH_2O)_{11}$—$CH_3$;
x is 0 or 1;
y is 0 or 1;
$G^3$ is —$CH_2CH_2CH_2SO_3H$ or —$CH_2CH_2O$—$(CH_2CH_2O)_{11}$—$CH_3$;
$R^w$ is —O—$CH_2CH_2SO_3H$ or —NH(CO)—$CH_2CH_2O$—$(CH_2CH_2O)_{12}$—$CH_3$;
* represents the point of attachment to the remainder of the linker; and
⌇ represents the point of attachment of the linker to the antibody.

Exemplary embodiments of linkers according to structural formula (VIIa) and (VIIb) that may be included in the ADCs described herein include the linkers illustrated below (as illustrated, the linkers include a group suitable for covalently linking the linker to an antibody):

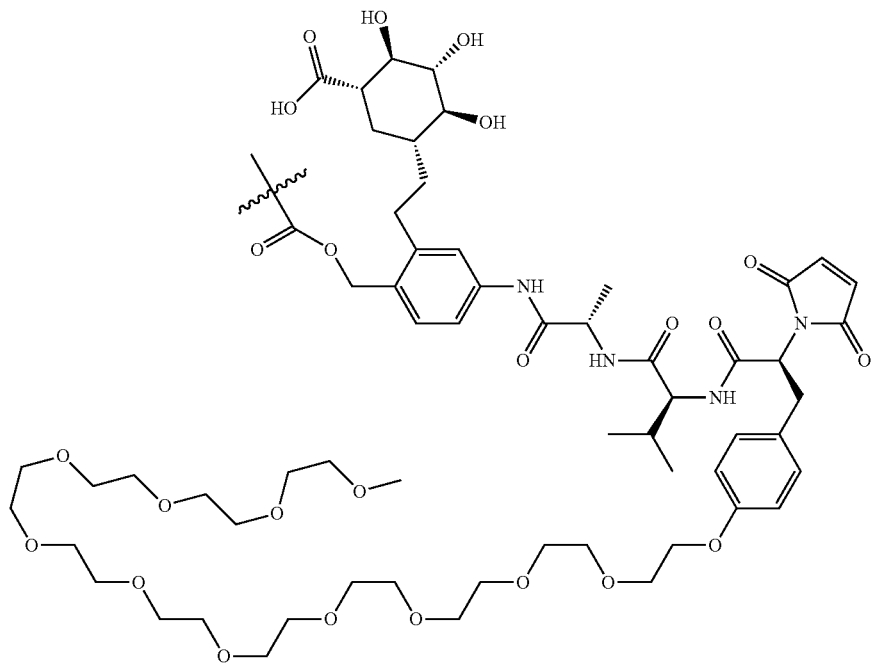
(VIIa.1)
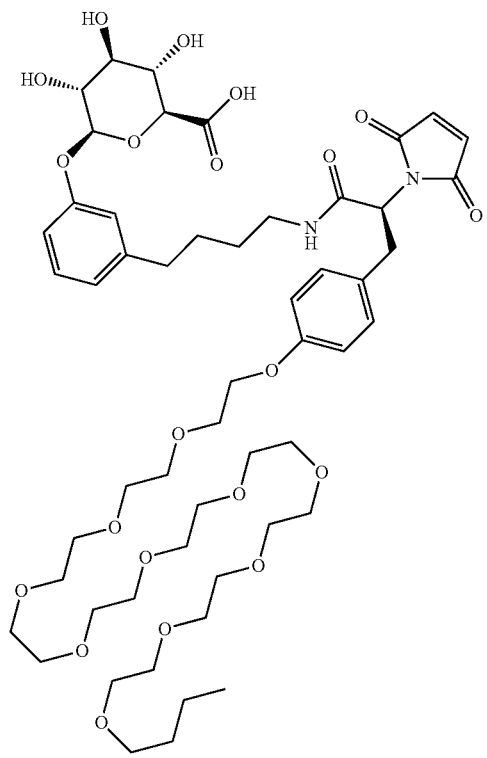
(VIIa.2)

-continued
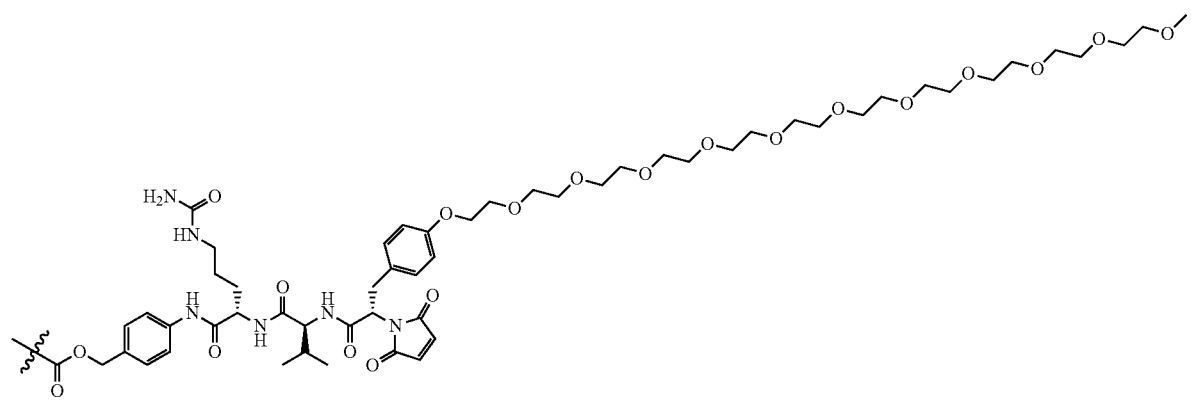
(VIIa.3)
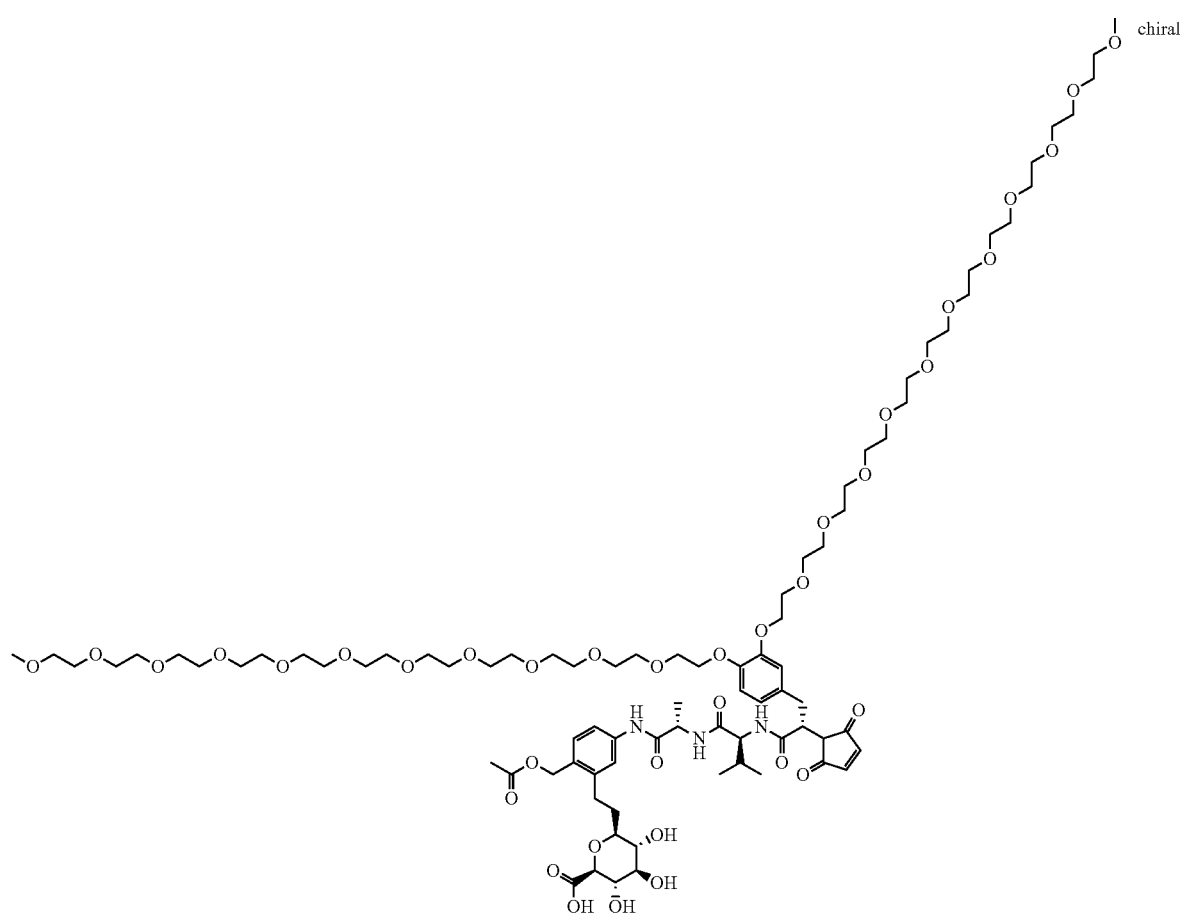
(VIIa.4)

-continued
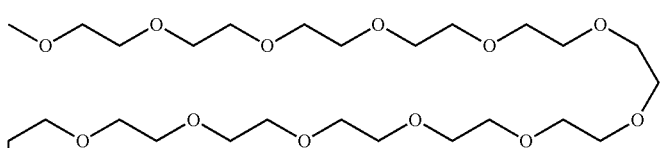
(VIIb.1)
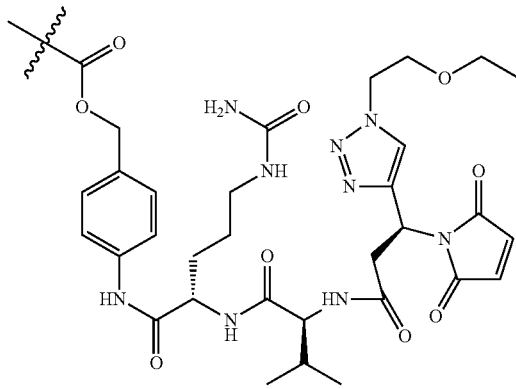
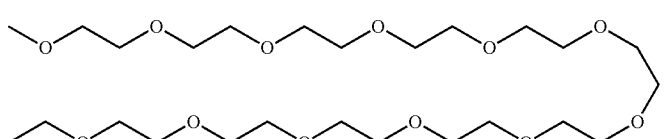
(VIIb.2)
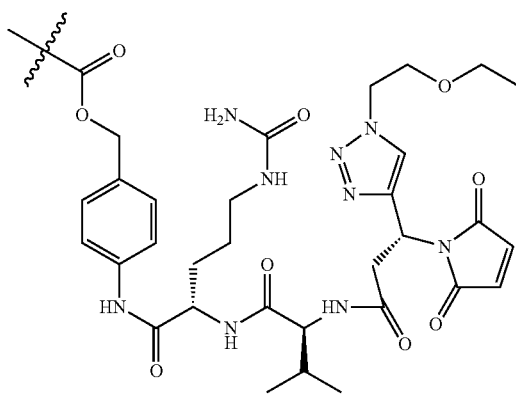
(VIIb.3)
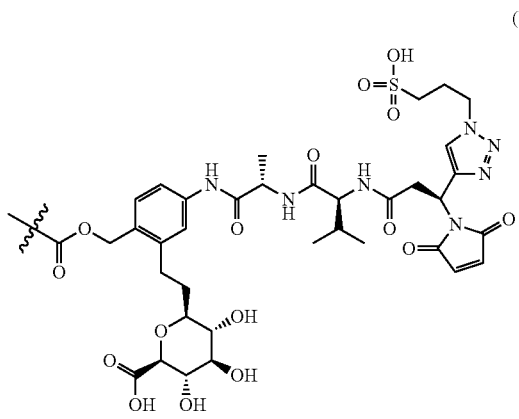
(VIIb.4)
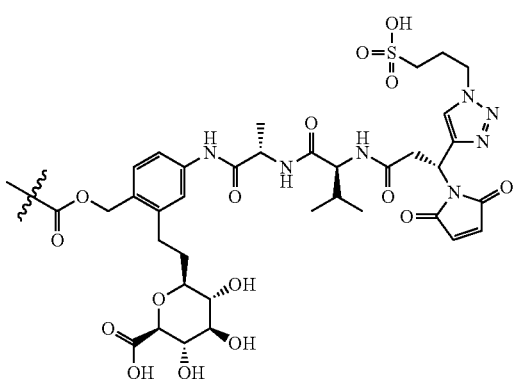

-continued
(VIIb.6)
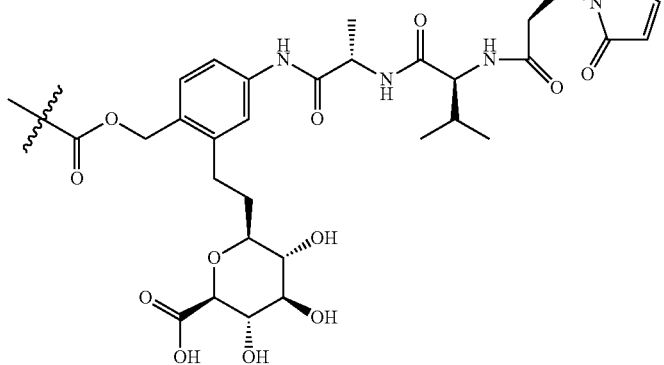
(VIIb.7)
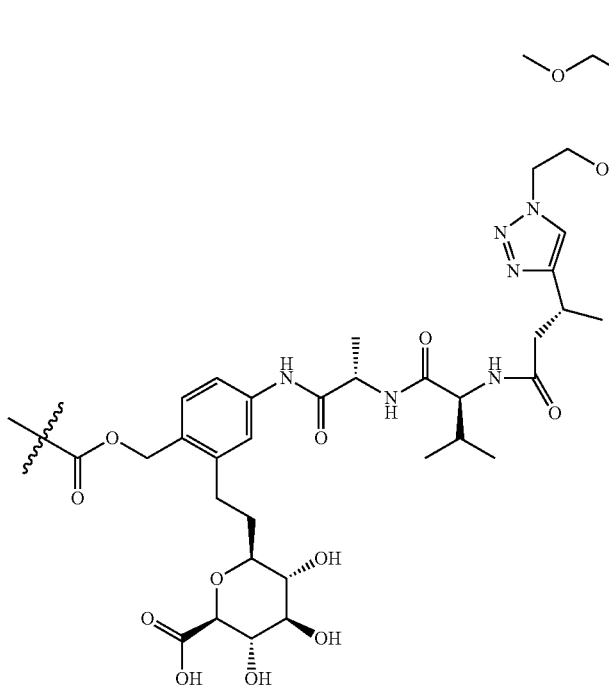

-continued
(VIIb.8)
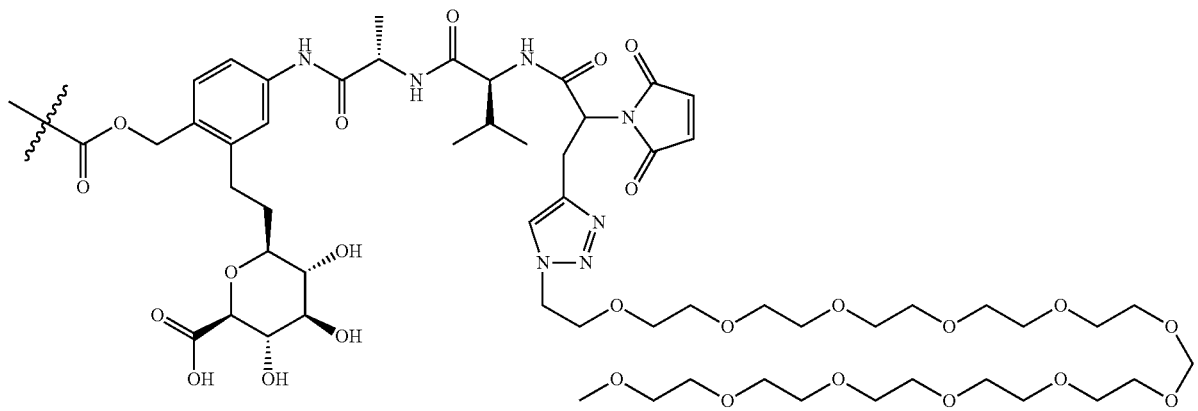
Exemplary embodiments of linkers according to structural formula (VIIc) that may be included in the ADCs described herein include the linkers illustrated below (as illustrated, the linkers include a group suitable for covalently linking the linker to an antibody):
(VIIc.1)
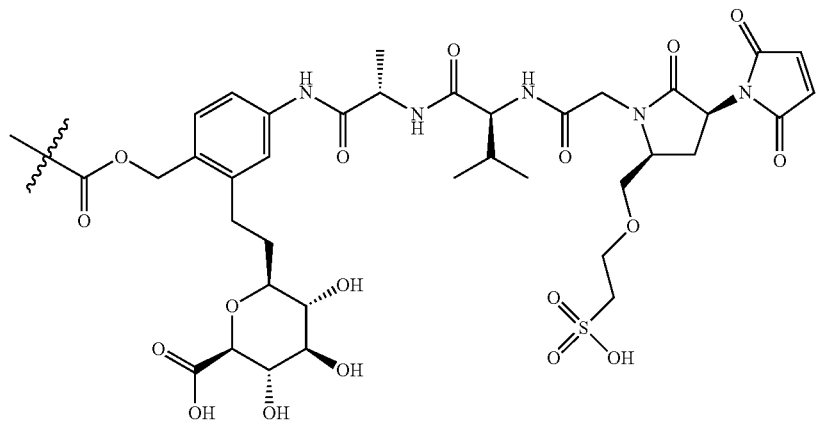
(VIIc.2)
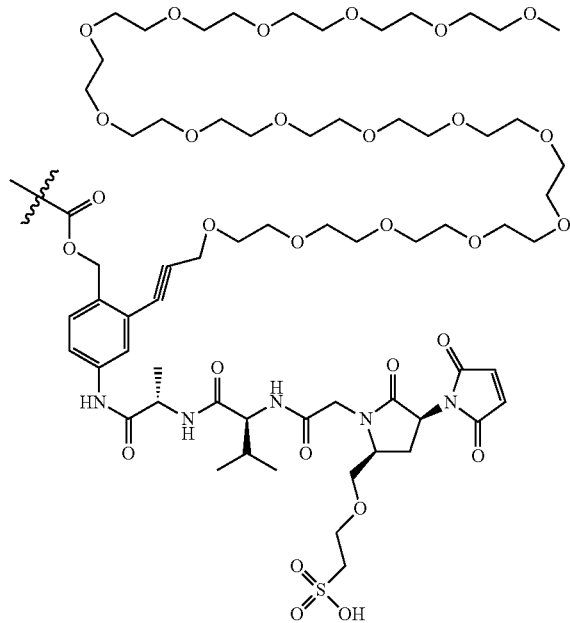

(VIIc.3)
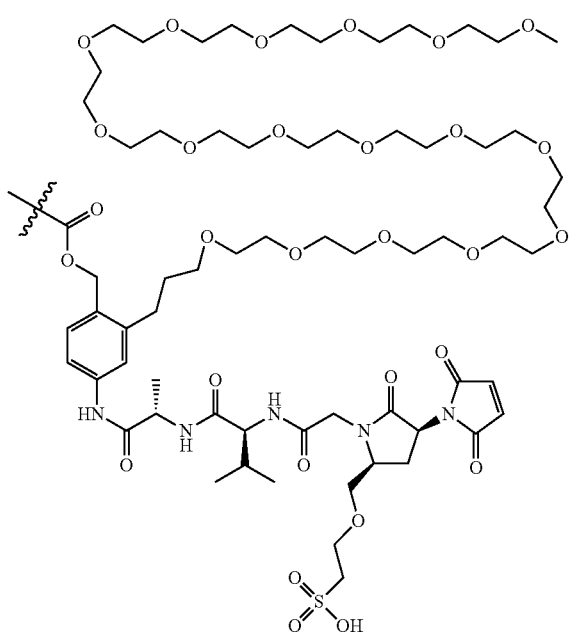
(VIIc.4)
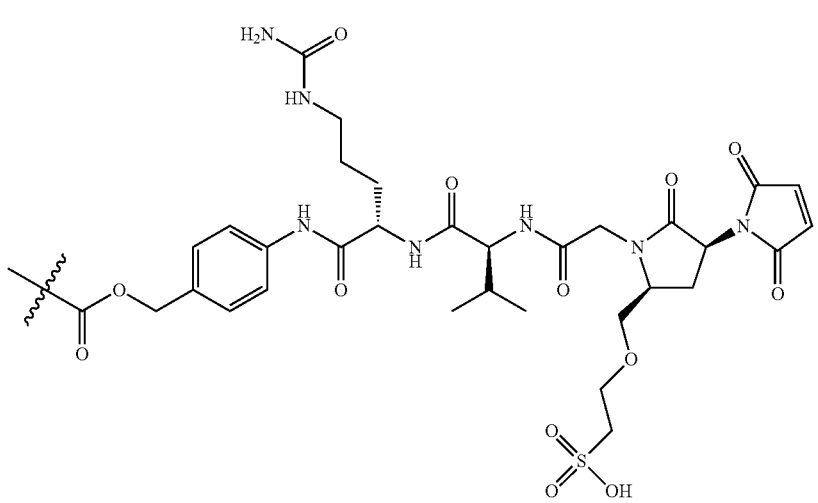
(VIIc.5)
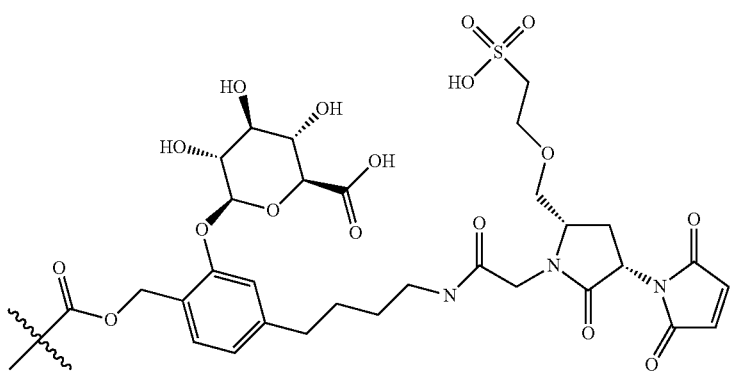

-continued (VIIc.6)

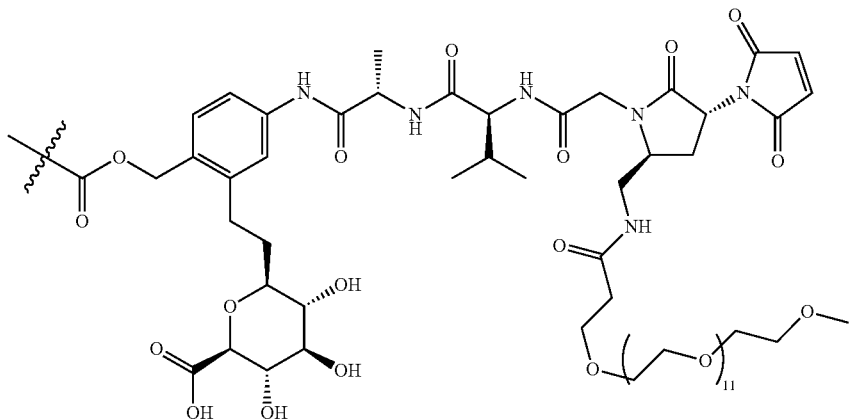

In certain embodiments, L is selected from the group consisting of IVa.1-IVa.8, IVb.1-IVb.19, IVc.1-IVc.7, IVd.1-IVd.4, Va.1-Va.12, Vb.1-Vb.10, Vc. 1-Vc.11, Vd.1-Vd.6, Ve.1-Ve.2, VIa.1, VIc.1-VIc.2, VId.1-VId.4, VIIa.1-VIIa.4, VIIb.1-VIIb.8, VIIc.1-VIIc.6 in either the closed or open form, and a pharmaceutically acceptable salt thereof.

In certain embodiments, L is selected from the group consisting of IVb.2, IVc.5, IVc.6, IVc.7, IVd.4, Vb.9, VIIa.1, VIIa.3, VIIc.1, VIIc.4, and VIIc.5, wherein the maleimide of each linker has reacted with the antibody Ab, forming a covalent attachment as either a succinimide (closed form) or succinamide (open form), and a pharmaceutically acceptable salt thereof.

In certain embodiments, L is selected from the group consisting of IVb.2, IVc.5, IVc.6, IVd.4, VIIa.1, VIIa.3, VIIc.1, VIIc.4, VIIc.5, wherein the maleimide of each linker has reacted with the antibody Ab, forming a covalent attachment as either a succinimide (closed form) or succinamide (open form), and a pharmaceutically acceptable salt thereof.

In certain embodiments, L is selected from the group consisting of IVb.2, VIIa.3, IVc.6, and VIIc.1, wherein ╱ is the attachment point to drug D and @ is the attachment point to the LK, wherein when the linker is in the open form as shown below, @ can be either at the α-position or β-position of the carboxylic acid next to it:

VIIa.3

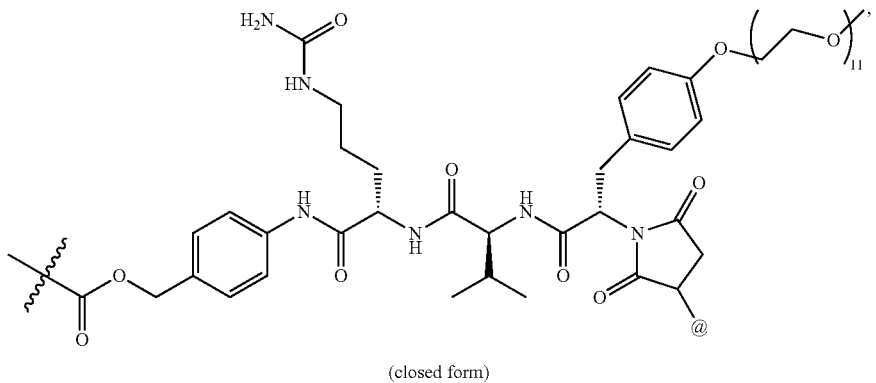

(closed form)

VIIa.3

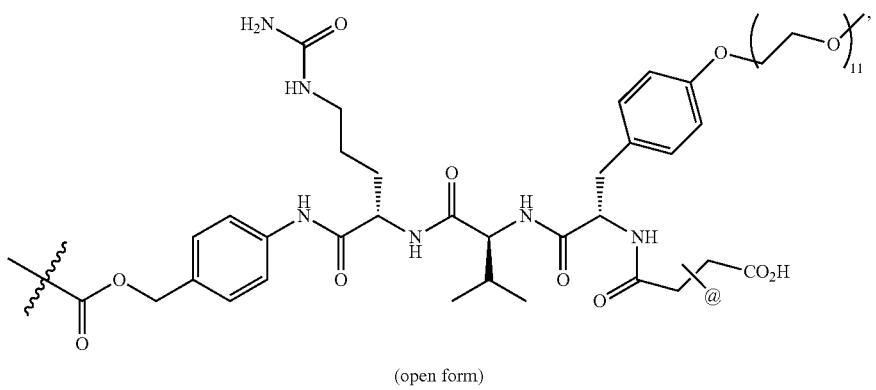

(open form)

-continued
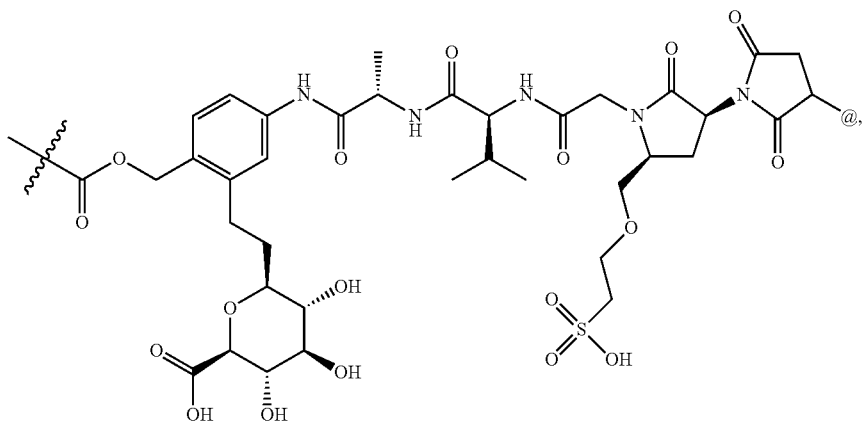
VIIc.1
(closed form)
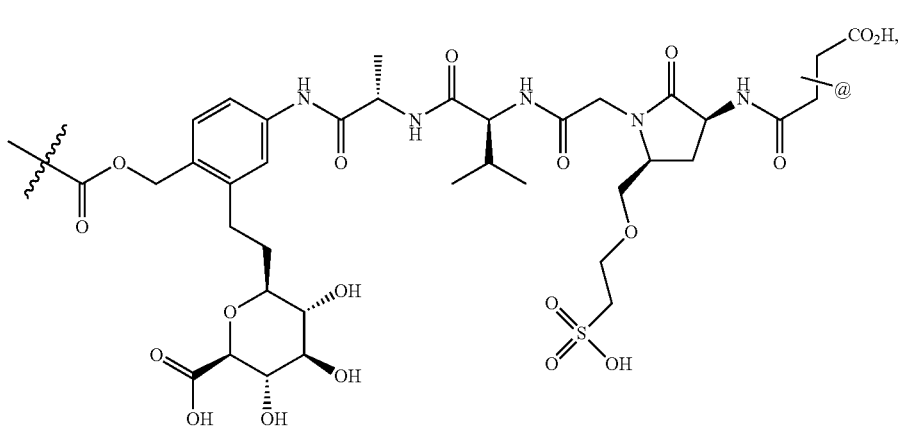
VIIc.1
(open form)
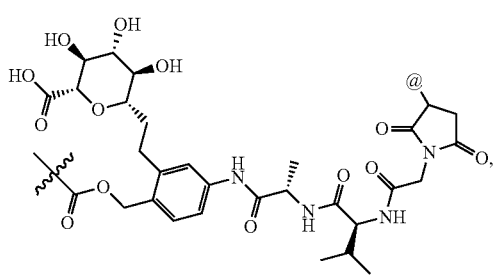
IVc.6
(closed form)
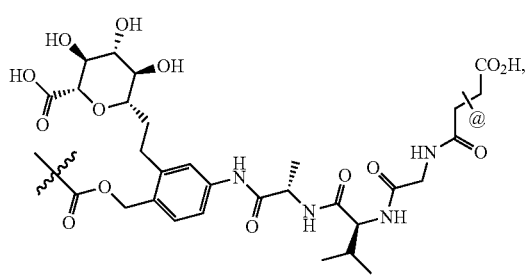
IVc.6
(open form)
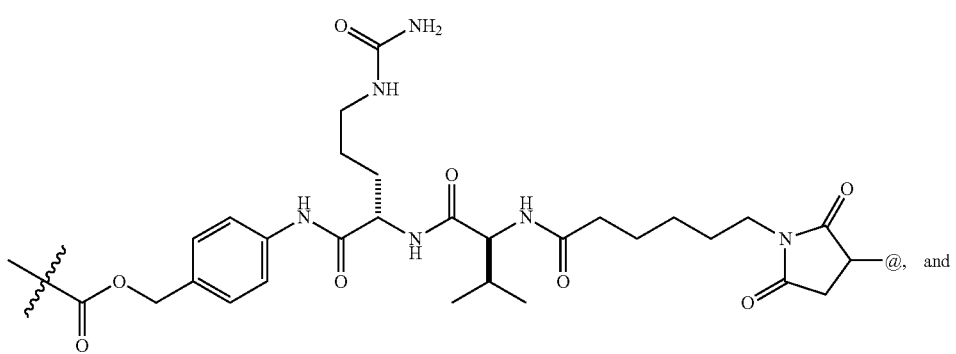
IVb.2
(closed form)
and

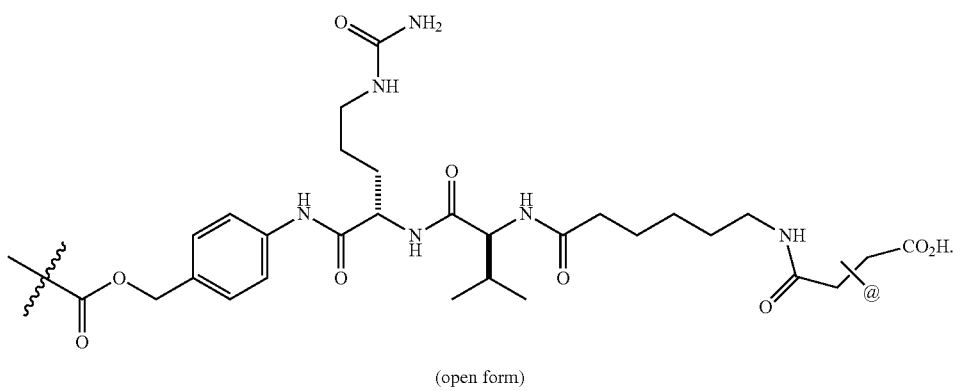

(open form)

Bcl-xL Linker Selection Considerations

As is known by skilled artisans, the linker selected for a particular ADC may be influenced by a variety of factors, including but not limited to, the site of attachment to the antibody (e.g., lys, cys or other amino acid residues), structural constraints of the drug pharmacophore and the lipophilicity of the drug. The specific linker selected for an ADC should seek to balance these different factors for the specific antibody/drug combination. For a review of the factors that are influenced by choice of linkers in ADCs, see Nolting, Chapter 5 "Linker Technology in Antibody-Drug Conjugates," In: Antibody-Drug Conjugates: Methods in Molecular Biology, vol. 1045, pp. 71-100, Laurent Ducry (Ed.), Springer Science & Business Medica, LLC, 2013.

For example, ADCs have been observed to effect killing of bystander antigen-negative cells present in the vicinity of the antigen-positive tumor cells. The mechanism of bystander cell killing by ADCs has indicated that metabolic products formed during intracellular processing of the ADCs may play a role. Neutral cytotoxic metabolites generated by metabolism of the ADCs in antigen-positive cells appear to play a role in bystander cell killing while charged metabolites may be prevented from diffusing across the membrane into the medium and therefore cannot affect bystander killing. In certain embodiments, the linker is selected to attenuate the bystander killing effect caused by cellular metabolites of the ADC. In certain embodiments, the linker is selected to increase the bystander killing effect.

The properties of the linker may also impact aggregation of the ADC under conditions of use and/or storage. Typically, ADCs reported in the literature contain no more than 3-4 drug molecules per antibody molecule (see, e.g., Chari, 2008, Acc Chem Res 41:98-107). Attempts to obtain higher drug-to-antibody ratios ("DAR") often failed, particularly if both the drug and the linker were hydrophobic, due to aggregation of the ADC (see King et al., 2002, J Med Chem 45:4336-4343; Hollander et al., 2008, Bioconjugate Chem 19:358-361; Burke et al., 2009 Bioconjugate Chem 20:1242-1250). In many instances, DARs higher than 3-4 could be beneficial as a means of increasing potency. In instances where the Bcl-xL inhibitor is hydrophobic in nature, it may be desirable to select linkers that are relatively hydrophilic as a means of reducing ADC aggregation, especially in instances where DARS greater than 3-4 are desired. Thus, in certain embodiments, the linker incorporates chemical moieties that reduce aggregation of the ADCs during storage and/or use. A linker may incorporate polar or hydrophilic groups such as charged groups or groups that become charged under physiological pH to reduce the aggregation of the ADCs. For example, a linker may incorporate charged groups such as salts or groups that deprotonate, e.g., carboxylates, or protonate, e.g., amines, at physiological pH.

Exemplary polyvalent linkers that have been reported to yield DARs as high as 20 that may be used to link numerous Bcl-xL inhibitors to an antibody are described in U.S. Pat. No. 8,399,512; U.S. Published Application No. 2010/0152725; U.S. Pat. Nos. 8,524,214; 8,349,308; U.S. Published Application No. 2013/189218; U.S. Published Application No. 2014/017265; WO 2014/093379; WO 2014/093394; WO 2014/093640, the content of which are incorporated herein by reference in their entireties.

In particular embodiments, the aggregation of the ADCs during storage or use is less than about 40% as determined by size-exclusion chromatography (SEC). In particular embodiments, the aggregation of the ADCs during storage or use is less than 35%, such as less than about 30%, such as less than about 25%, such as less than about 20%, such as less than about 15%, such as less than about 10%, such as less than about 5%, such as less than about 4%, or even less, as determined by size-exclusion chromatography (SEC).

III.A.3. Bcl-xL ADC Synthons

Antibody-Drug Conjugate synthons are synthetic intermediates used to form ADCs. The synthons are generally compounds according to structural formula (III):

or a pharmaceutically acceptable salt thereof, wherein D is a Bcl-xL inhibitor as previously described, L is a linker as previously described, and $R^x$ is a reactive group suitable for linking the synthon to an antibody.

In specific embodiments, the intermediate synthons are compounds according to structural formulae (IIIa), (IIIb), (IIIc) and (IIId), below, or a pharmaceutically acceptable salt thereof, where the various substituents $Ar^1$, $Ar^2$, $Z^1$, $Z^{2a}$, $Z^{2b}$, R', $R^1$, $R^2$, $R^4$, $R^{11a}$, $R^{11b}$, $R^{12}$ and $R^{13}$ are as previously defined for structural formulae (IIa), (IIb), (IIc) and (IId), respectively, L is a linker as previously described and $R^x$ is a functional group as described above:

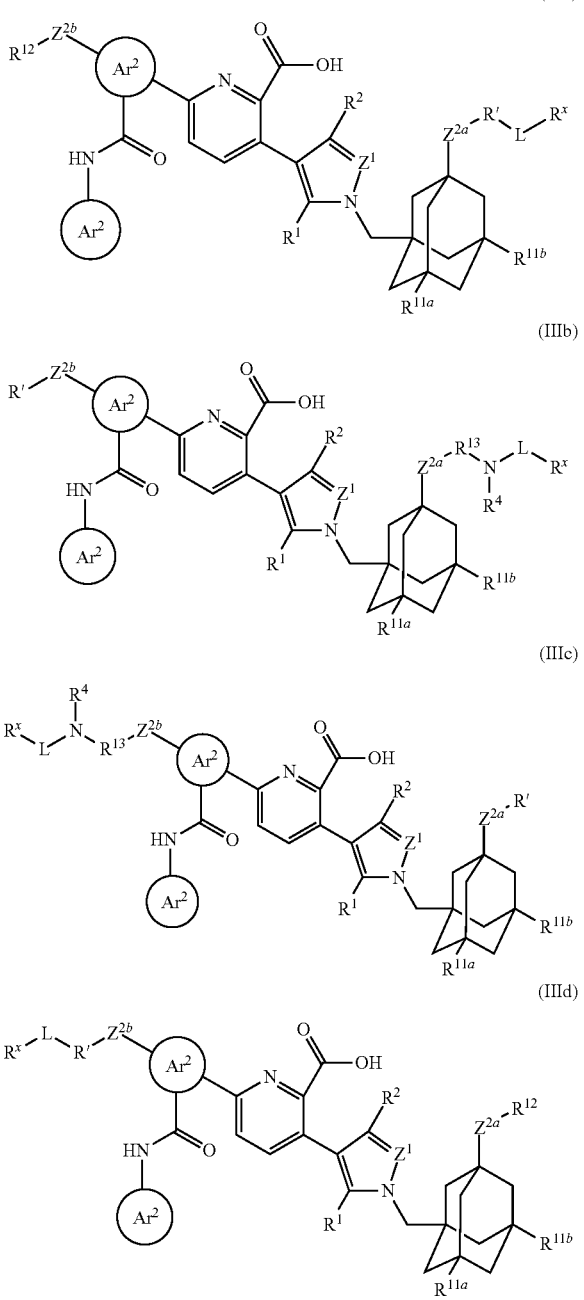

To synthesize an ADC, an intermediate synthon according to structural formula (III), or a salt thereof, is contacted with an antibody of interest under conditions in which functional group $R^x$ reacts with a "complementary" functional group on the antibody, $F^x$, to form a covalent linkage.

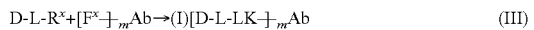

The identities of groups $R^x$ and $F^x$ will depend upon the chemistry used to link the synthon to the antibody. Generally, the chemistry used should not alter the integrity of the antibody, for example its ability to bind its target. Preferably, the binding properties of the conjugated antibody will closely resemble those of the unconjugated antibody. A variety of chemistries and techniques for conjugating molecules to biological molecules such as antibodies are known in the art and in particular to antibodies, are well-known. See, e.g., Amon et al., "Monoclonal Antibodies For Immunotargeting Of Drugs In Cancer Therapy," in: *Monoclonal Antibodies And Cancer Therapy*, Reisfeld et al. Eds., Alan R. Liss, Inc., 1985; Hellstrom et al., "Antibodies For Drug Delivery," in: *Controlled Drug Delivery*, Robinson et al., Eds., Marcel Dekker, Inc., 2nd Ed. 1987; Thorpe, "Antibody Carriers Of Cytotoxic Agents In Cancer Therapy: A Review," in: *Monoclonal Antibodies '84: Biological And Clinical Applications*, Pinchera et al., Eds., 1985; "Analysis, Results, and Future Prospective of the Therapeutic Use of Radiolabeled Antibody In Cancer Therapy," in: *Monoclonal Antibodies For Cancer Detection And Therapy*, Baldwin et al., Eds., Academic Press, 1985; Thorpe et al., 1982, *Immunol. Rev.* 62:119-58; PCT publication WO 89/12624. Any of these chemistries may be used to link the synthons to an antibody.

Typically, the synthons are linked to the side chains of amino acid residues of the antibody, including, for example, the primary amino group of accessible lysine residues or the sulthydryl group of accessible cysteine residues. Free sulfhydryl groups may be obtained by reducing interchain disulfide bonds. In certain embodiments, LK is a linkage formed with an amino group on the anti-hB7-H3 antibody Ab. In certain embodiments, LK is an amide, thioether, or thiourea. In certain embodiments, LK is an amide or thiourea. In certain embodiments, LK is a linkage formed with a sulfhydryl group on the anti-hB7-H3 antibody Ab. In certain embodiments, LK is a thioether. In certain embodiments, LK is an amide, thioether, or thiourea; and m is an integer ranging from 1 to 8.

A number of functional groups $R^x$ and chemistries useful for linking synthons to accessible lysine residues are known, and include by way of example and not limitation NHS-esters and isothiocyanates.

A number of functional groups $R^x$ and chemistries useful for linking synthons to accessible free sulfhydryl groups of cysteine residues are known, and include by way of example and not limitation haloacetyls and maleimides.

However, conjugation chemistries are not limited to available side chain groups. Side chains such as amines may be converted to other useful groups, such as hydroxyls, by linking an appropriate small molecule to the amine. This strategy can be used to increase the number of available linking sites on the antibody by conjugating multifunctional small molecules to side chains of accessible amino acid residues of the antibody. Functional groups R suitable for covalently linking the synthons to these "converted" functional groups are then included in the synthons.

The antibody may also be engineered to include amino acid residues for conjugation. An approach for engineering antibodies to include non-genetically encoded amino acid residues useful for conjugating drugs in the context of ADCs is described in Axup et al., 2003, *Proc Natl Acad Sci* 109:16101-16106 and Tian et al., 2014, *Proc Natl Acad Sci* 111:1776-1771 as are chemistries and functional groups useful for linking synthons to the non-encoded amino acids.

Exemplary synthons useful for making ADCs described herein include, but are not limited to, the following synthons listed below in Table B.

TABLE B
| Example No. | Synthon Code | Synthon Structure |
|---|---|---|
| 2.1 | CZ | 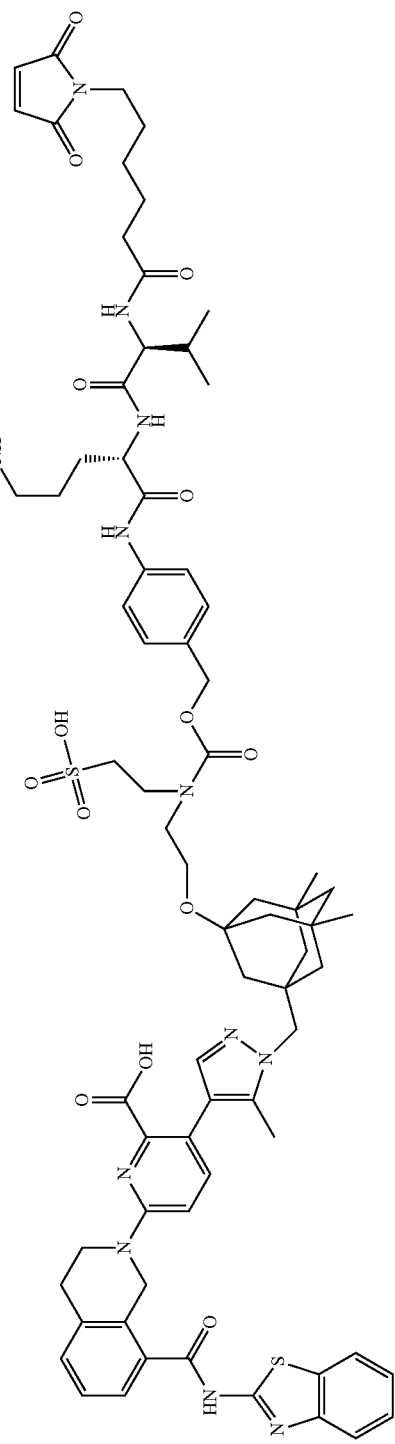 |
| 2.2 | DH | 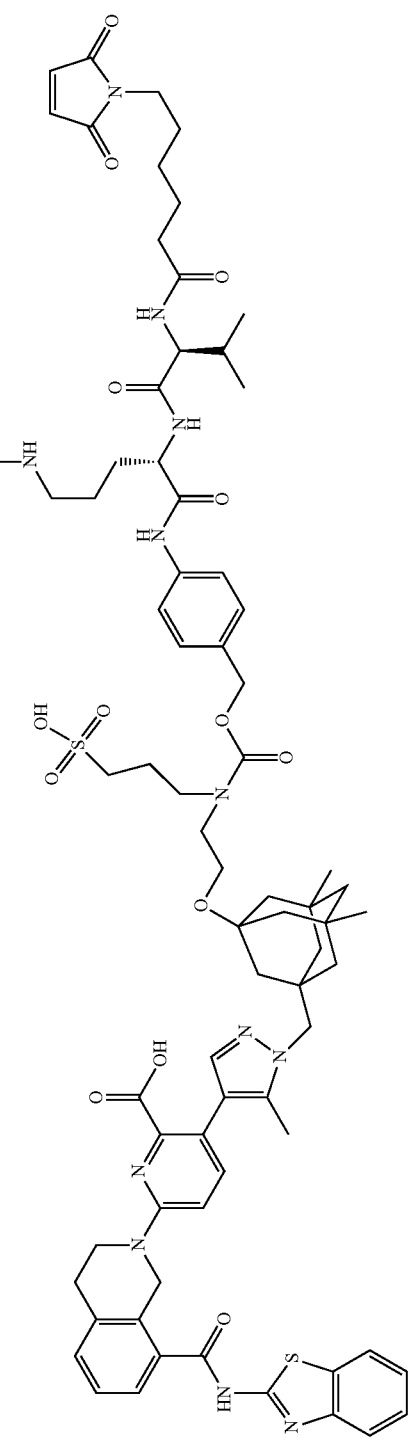 |

TABLE B-continued
| Example No. | Synthon Code | Synthon Structure |
|---|---|---|
| 2.4 | EP | 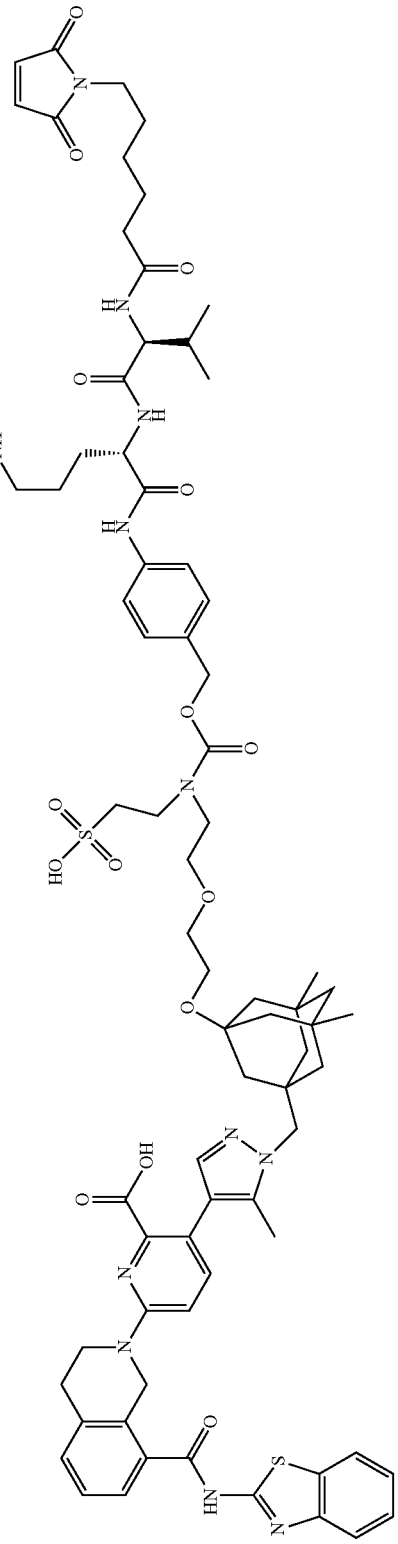 |
| 2.5 | EF | 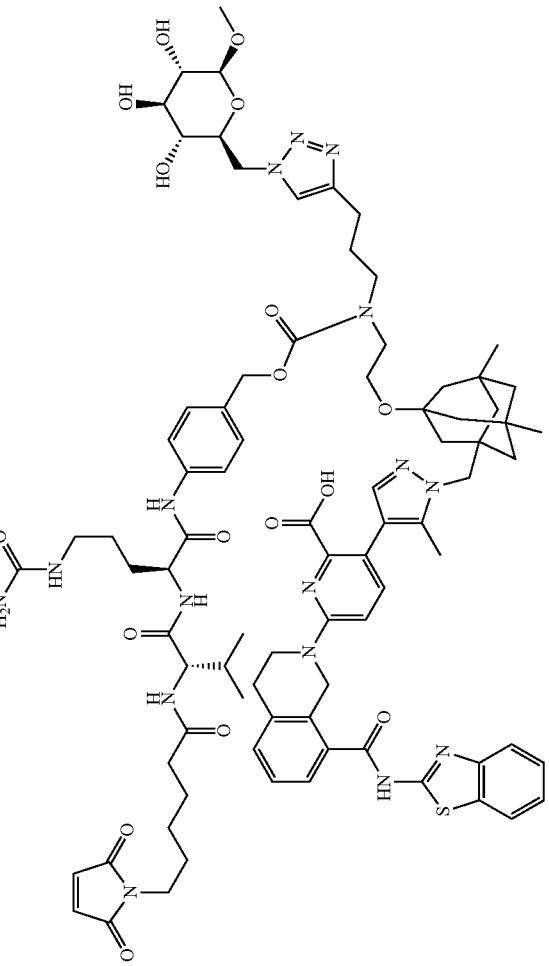 |

TABLE B-continued

| Example No. | Synthon Code | Synthon Structure |
|---|---|---|
| 2.6 | EG | |
| 2.7 | EH | |

TABLE B-continued
| Example No. | Synthon Code | Synthon Structure |
|---|---|---|
| 2.8 | ER | 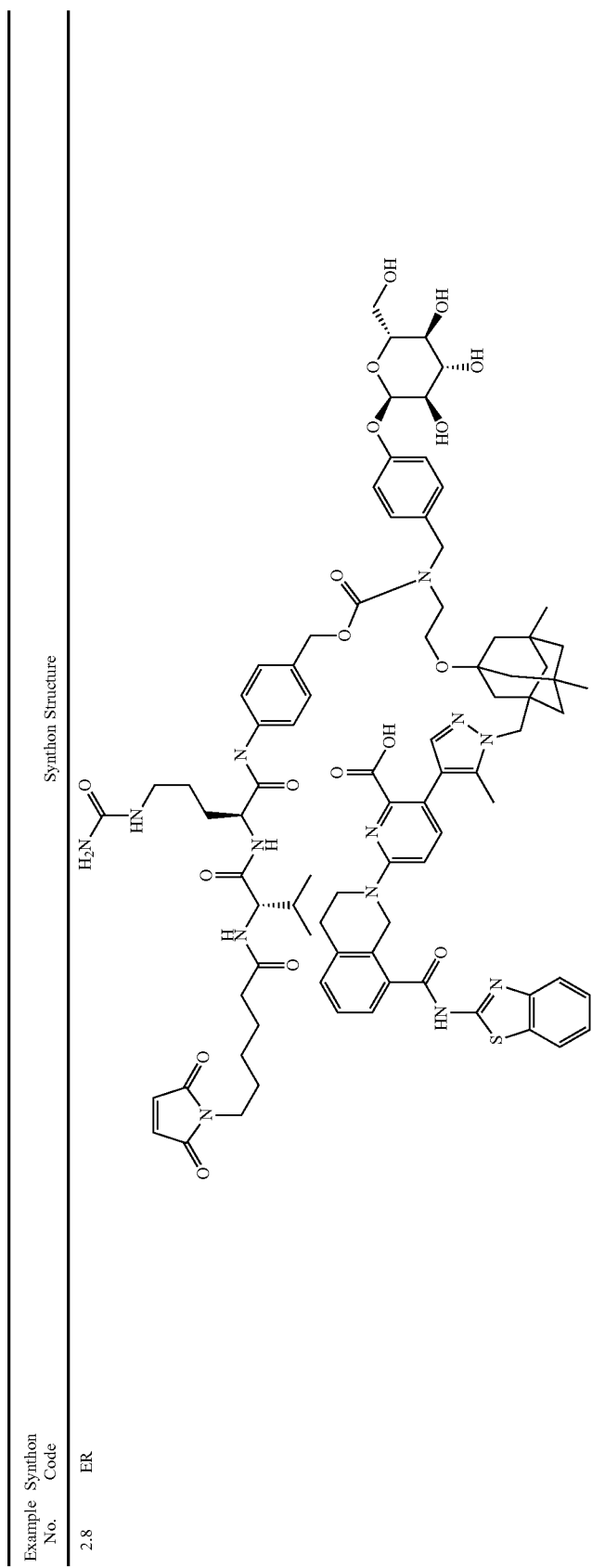 |

TABLE B-continued
| Example No. | Synthon Code | Synthon Structure |
|---|---|---|
| 2.9 | ES | 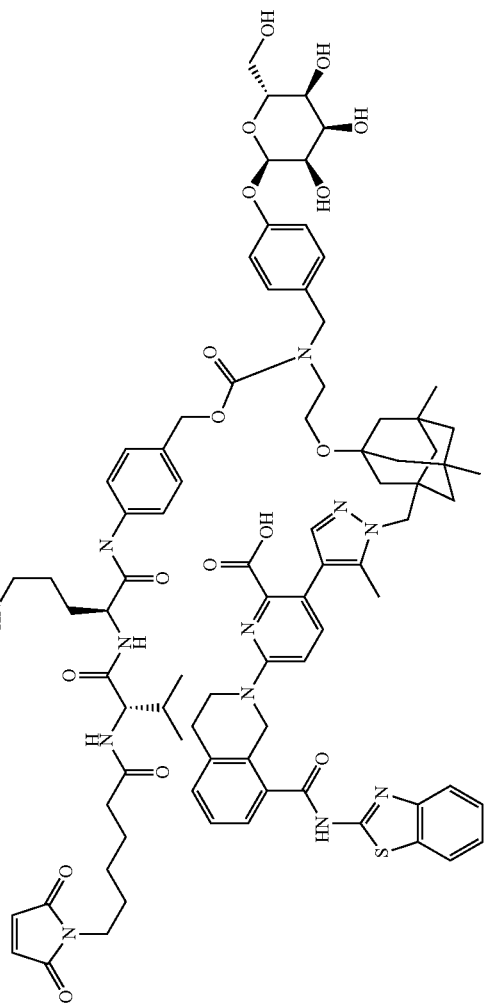 |
| 2.10 | EQ | 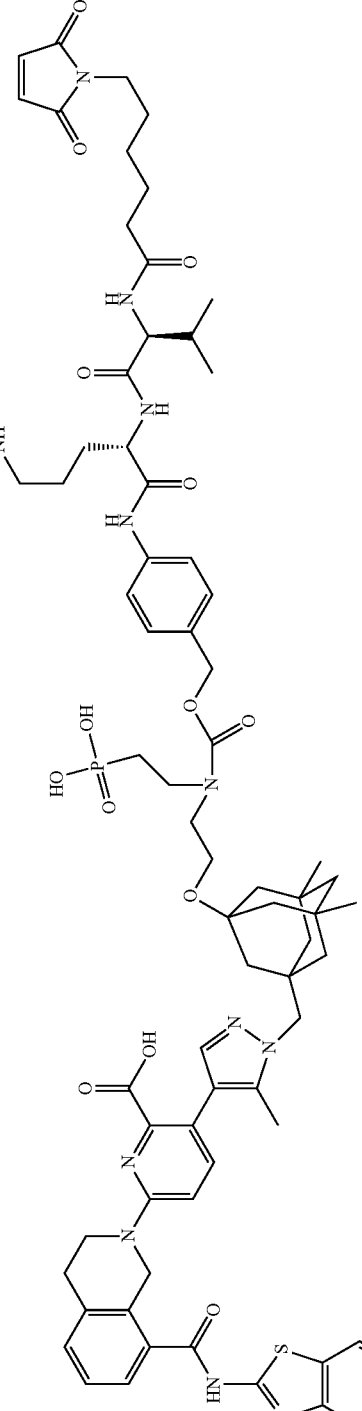 |

TABLE B-continued
| Example No. | Synthon Code | Synthon Structure |
|---|---|---|
| 2.11 | EU | 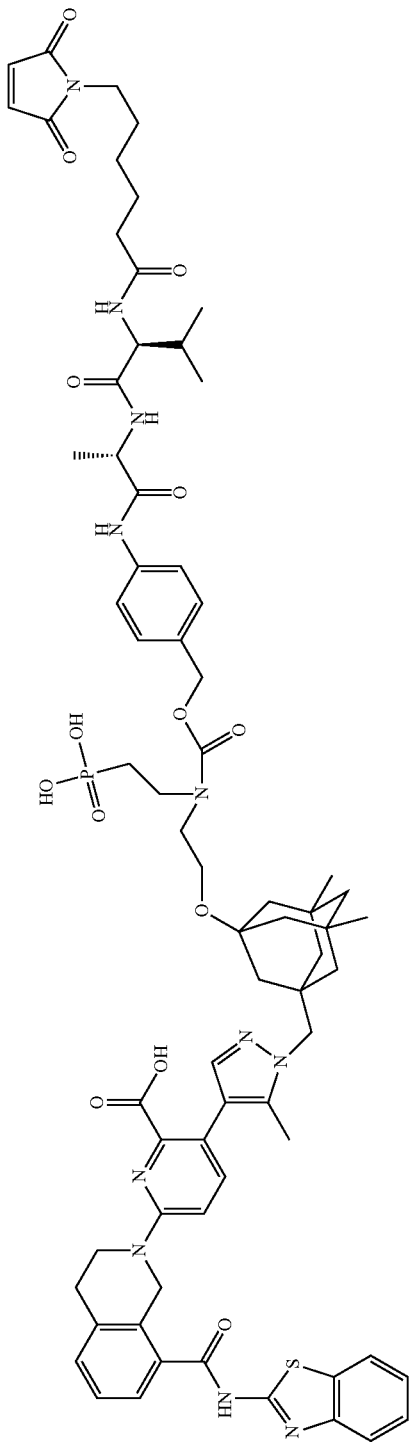 |
| 2.12 | EV | 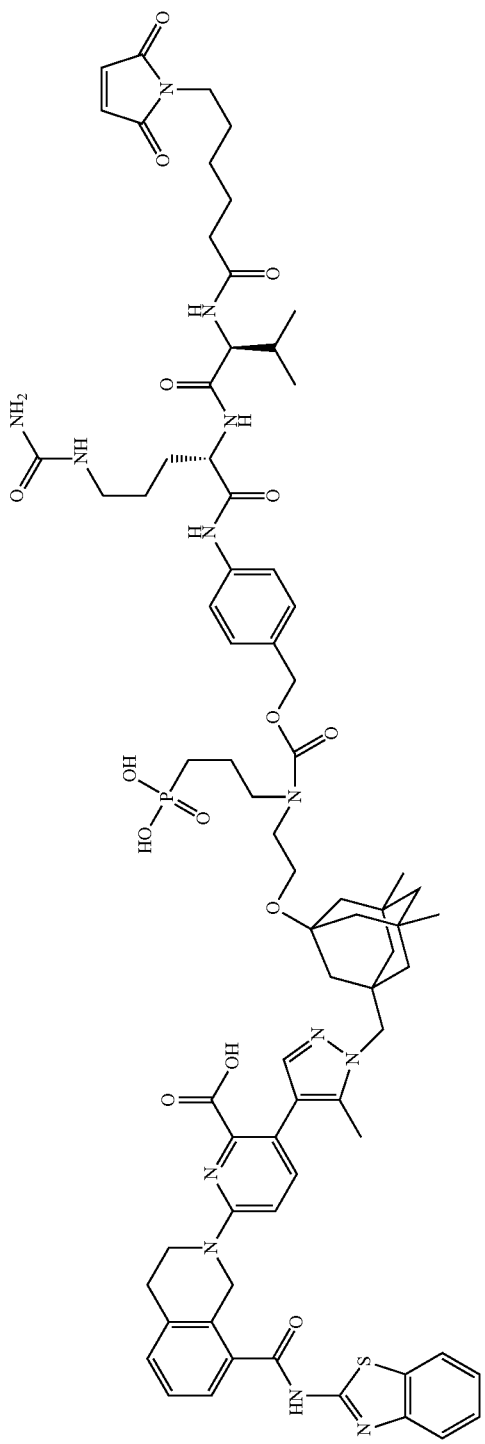 |

TABLE B-continued

| Example No. | Synthon Code | Synthon Structure |
|---|---|---|
| 2.13 | EW | |
| 2.14 | EX | |

TABLE B-continued
| Example No. | Synthon Code | Synthon Structure |
|---|---|---|
| 2.15 | EY | 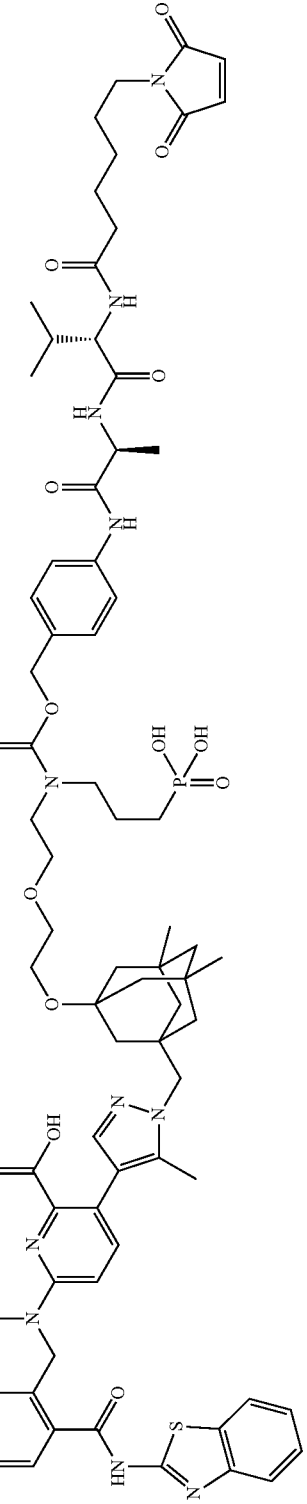 |
| 2.16 | EZ | 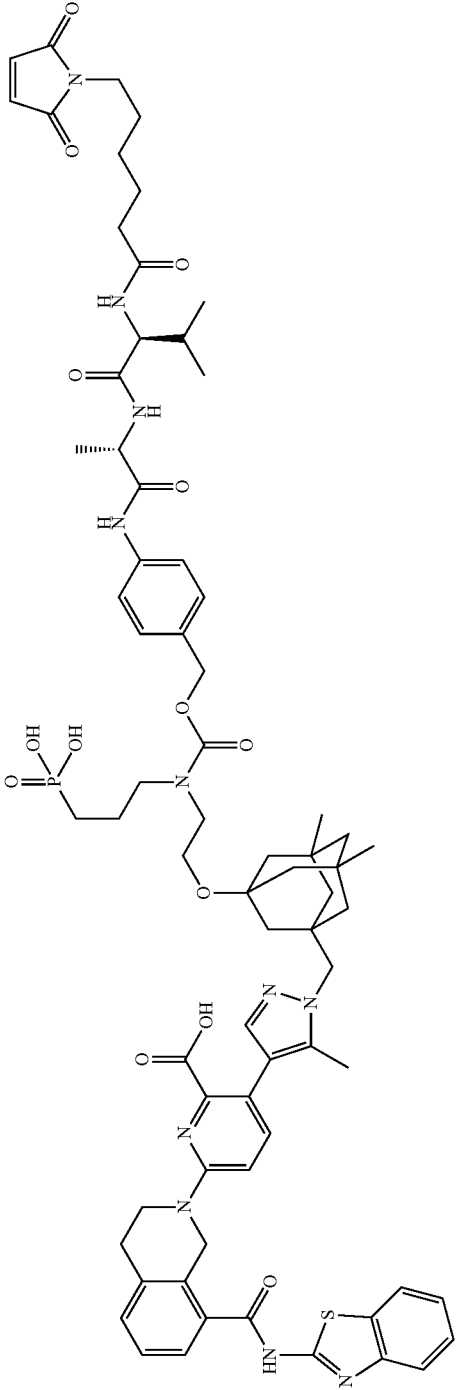 |

TABLE B-continued
| Example No. | Synthon Code | Synthon Structure |
|---|---|---|
| 2.17 | FD | 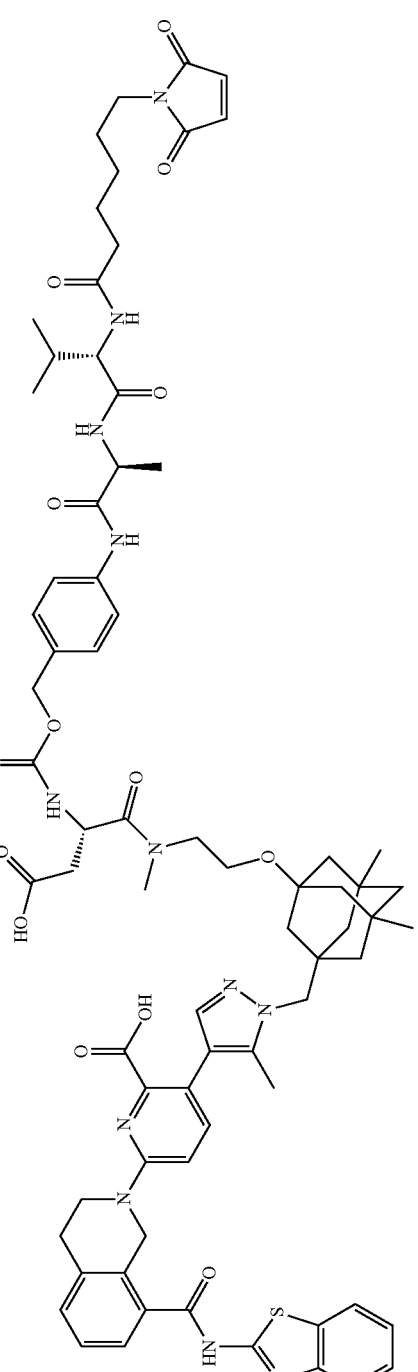 |
| 2.18 | FS | 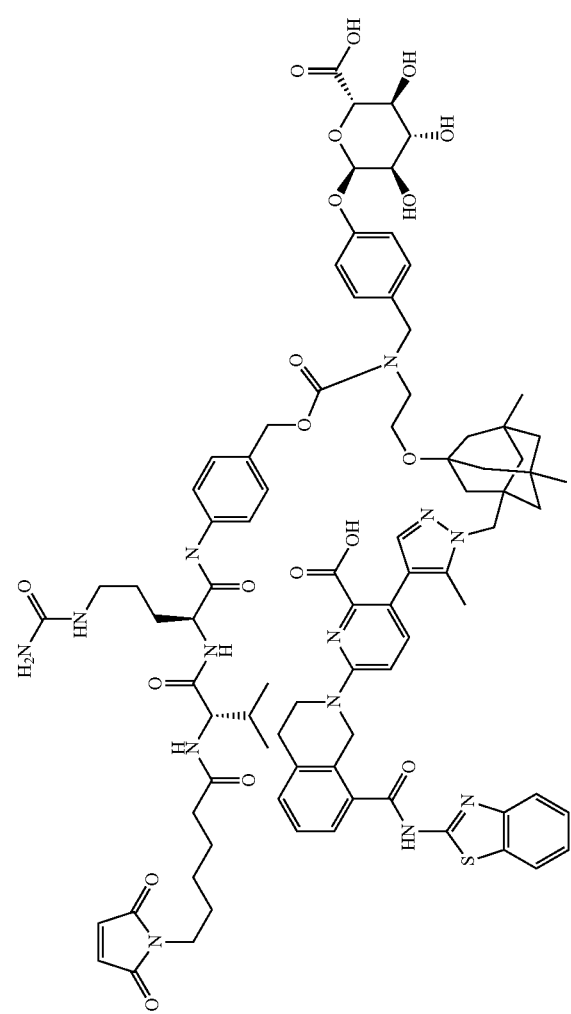 |

TABLE B-continued
| Example No. | Synthon Code | Synthon Structure |
|---|---|---|
| 2.19 | FI | 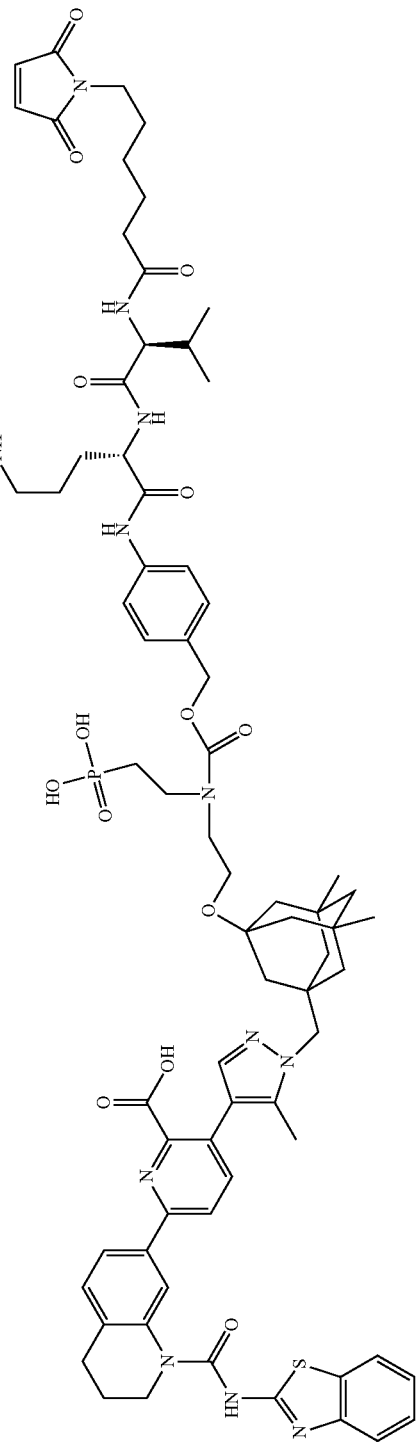 |

TABLE B-continued
| Example No. | Synthon Code | Synthon Structure |
|---|---|---|
| 2.20 | FV | 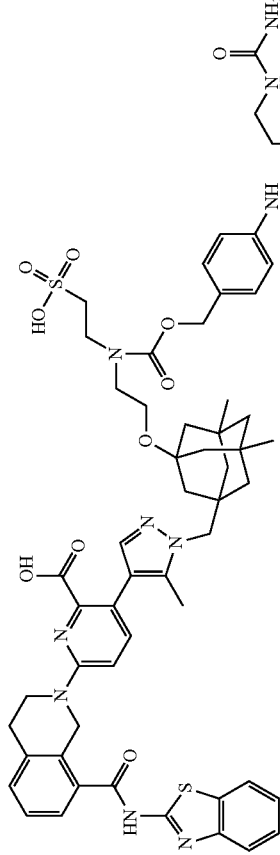 |
| 2.21 | GC | 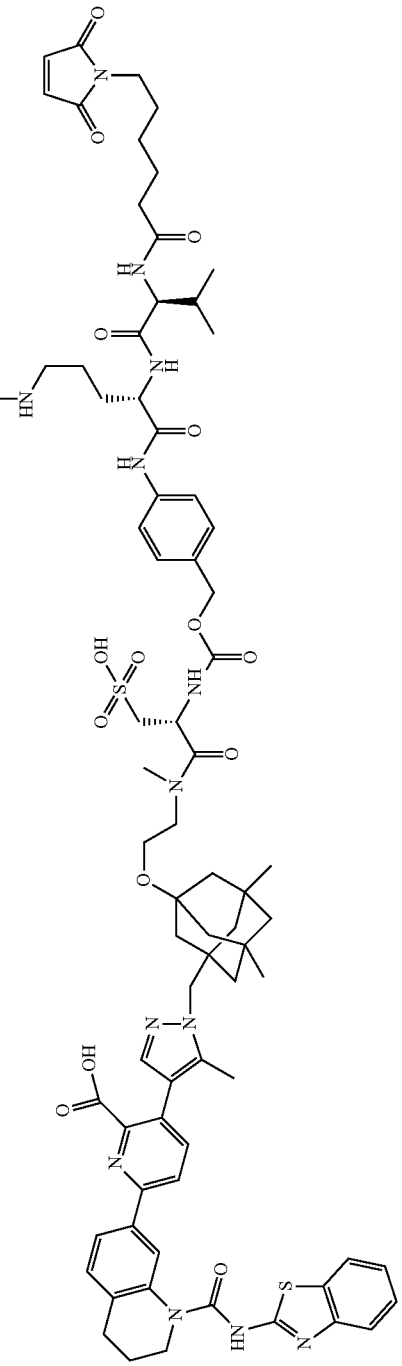 |

TABLE B-continued

Synthon Structure

| Example No. | Synthon Code |
|---|---|
| 2.22 | GB |
| 2.23 | FW |

TABLE B-continued

| Example No. | Synthon Code | Synthon Structure |
|---|---|---|
| 2.24 | GD | |
| 2.25 | GK | |

TABLE B-continued
| Example No. | Synthon Code | Synthon Structure |
|---|---|---|
| 2.26 | GJ | 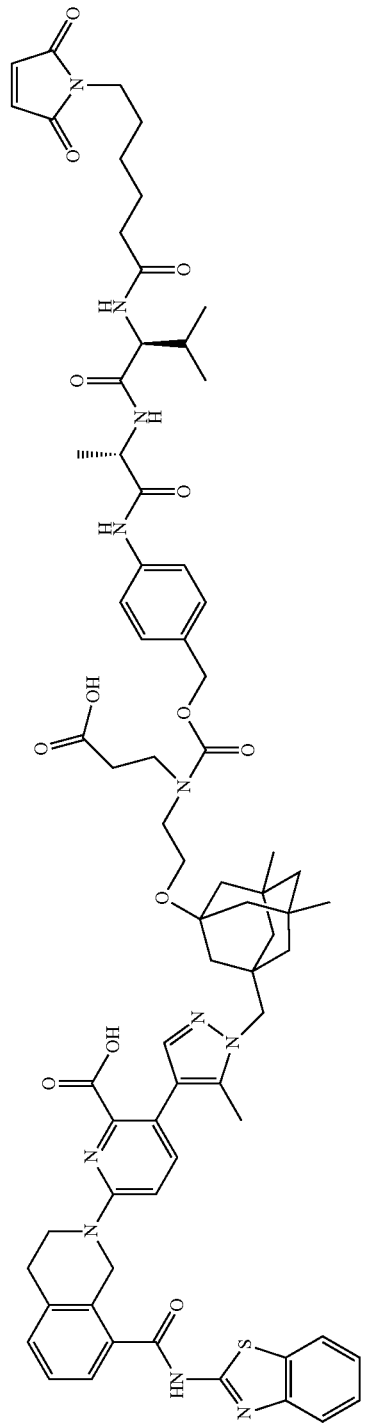 |
| 2.27 | GW | 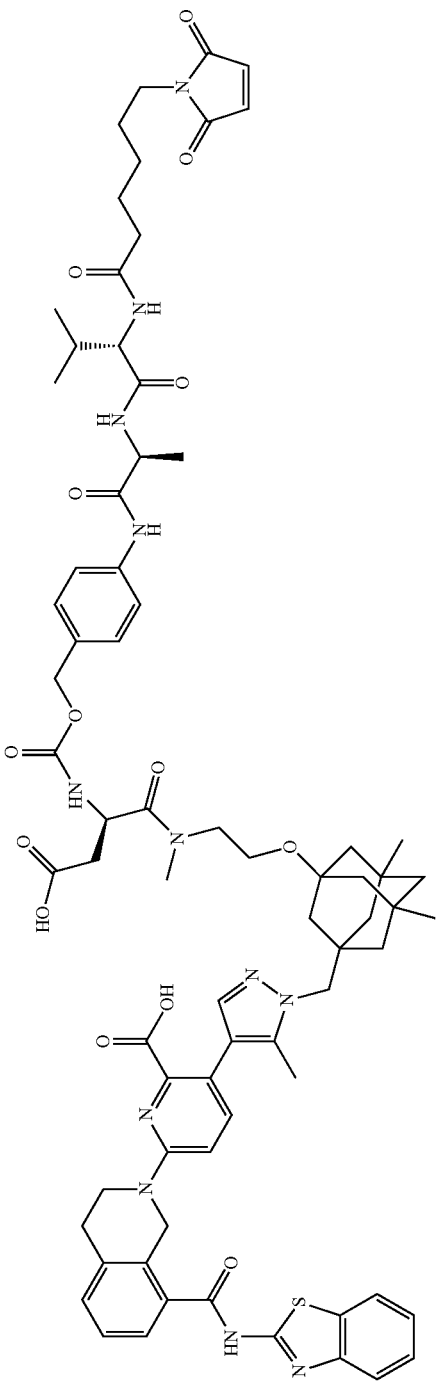 |

TABLE B-continued
| Example No. | Synthon Code | Synthon Structure |
|---|---|---|
| 2.28 | HF | 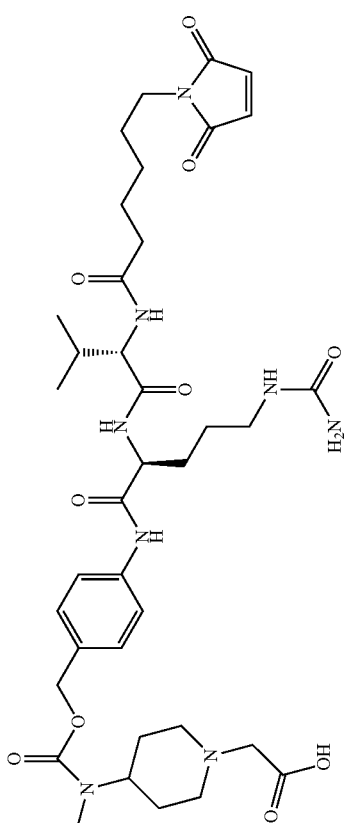 |

TABLE B-continued

| Example No. | Synthon Code | Synthon Structure |
|---|---|---|
| 2.29 | HG | |
| 2.30 | HP | |

TABLE B-continued

| Example No. | Synthon Code | Synthon Structure |
|---|---|---|
| 2.31 | HR | |
| 2.32 | HU | |

TABLE B-continued

| Example No. | Synthon Code | Synthon Structure |
|---|---|---|
| 2.33 | HT | |
| 2.34 | HV | |

TABLE B-continued

| Example No. | Synthon Code | Synthon Structure |
|---|---|---|
| 2.35 | HZ | |
| 2.36 | IA | |

TABLE B-continued
| Example No. | Synthon Code | Synthon Structure |
|---|---|---|
| 2.37 | IF | 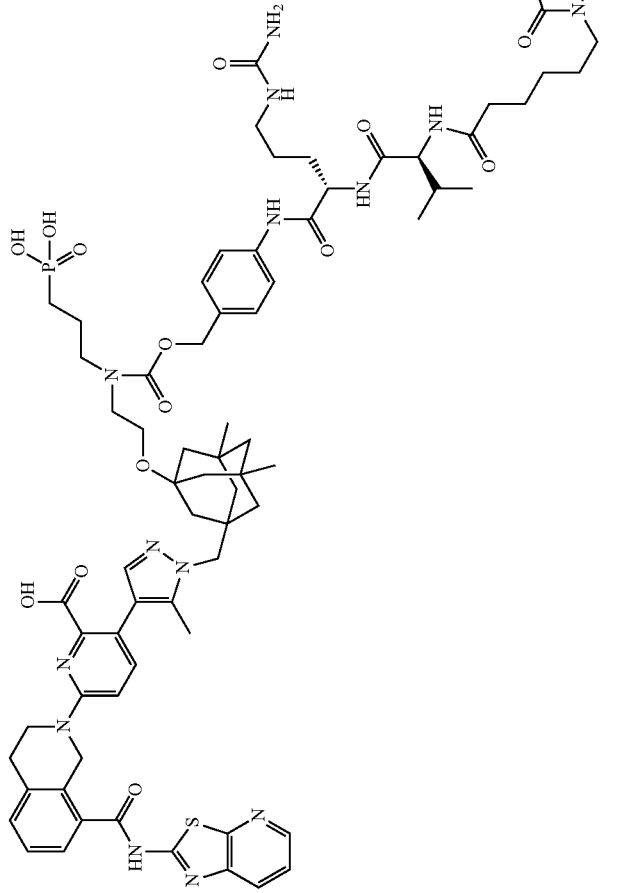 |
| 2.38 | IG | 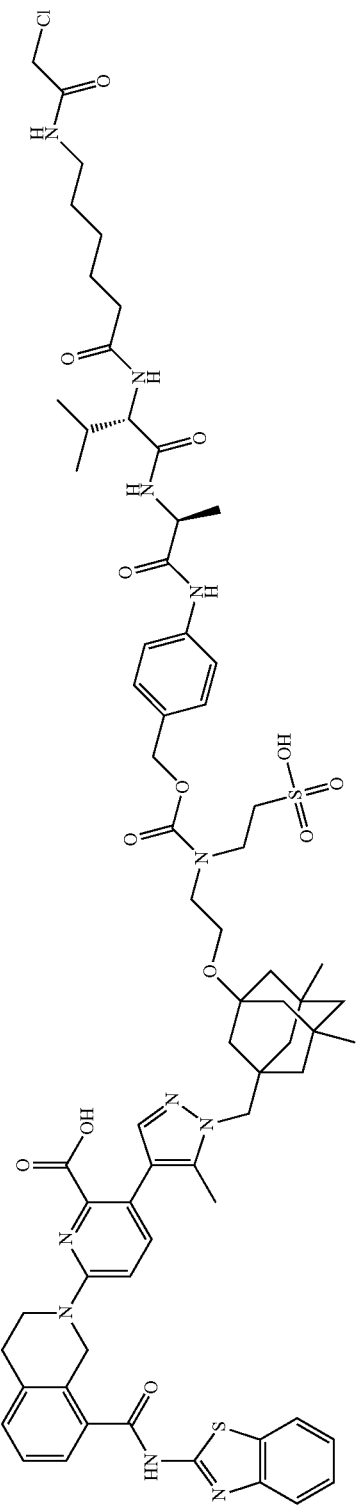 |

TABLE B-continued

| Example No. | Synthon Code | Synthon Structure |
|---|---|---|
| 2.39 | IH | (structure) |
| 2.40 | IJ | (structure) |

TABLE B-continued
| Example No. | Synthon Code | Synthon Structure |
|---|---|---|
| 2.41 | IK | 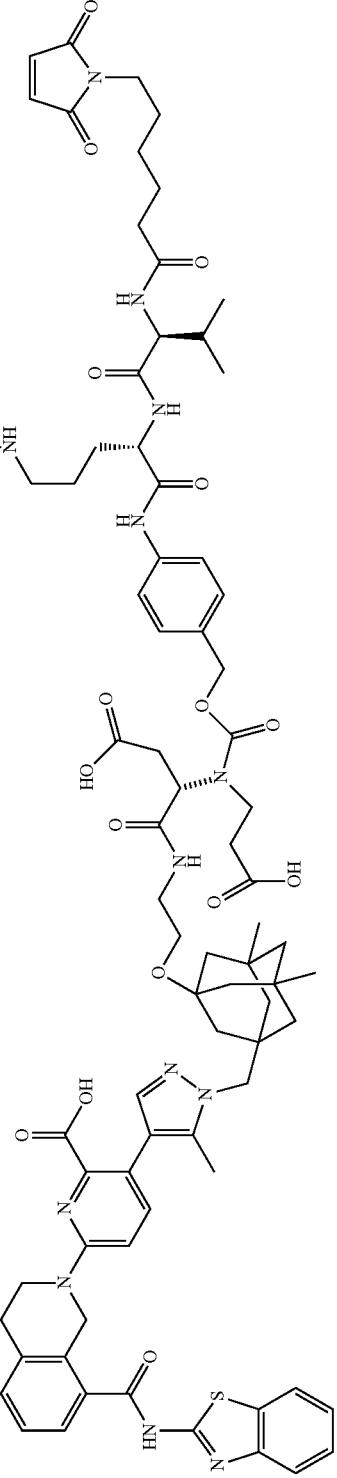 |
| 2.42 | IL | 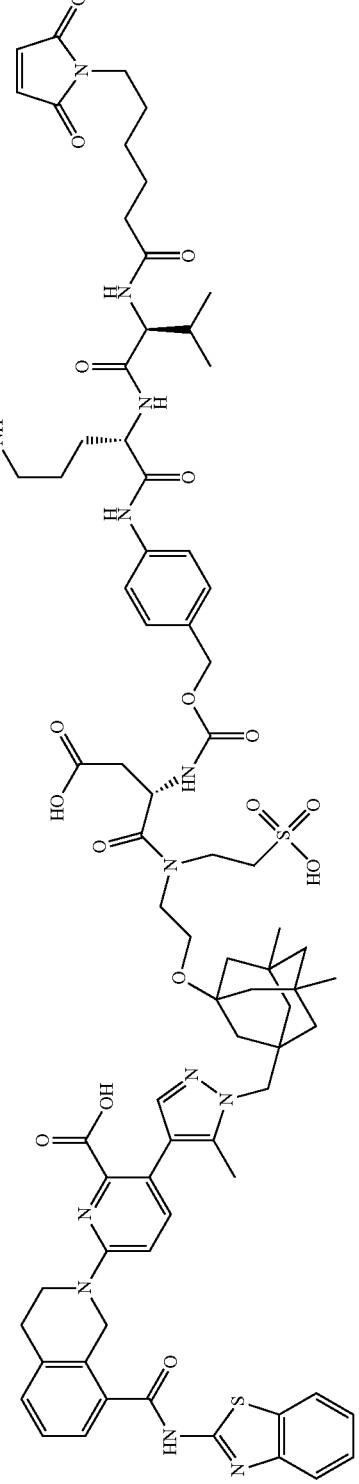 |

TABLE B-continued

| Example No. | Synthon Code | Synthon Structure |
|---|---|---|
| 2.43 | IM | |
| 2.44 | IO | |

TABLE B-continued

Synthon Structure

| Example No. | Synthon Code |
|---|---|
| 2.45 | IP |
| 2.46 | IS |

TABLE B-continued
Synthon Structure
| Example No. | Synthon Code | Synthon Structure |
|---|---|---|
| 2.47 | IU | 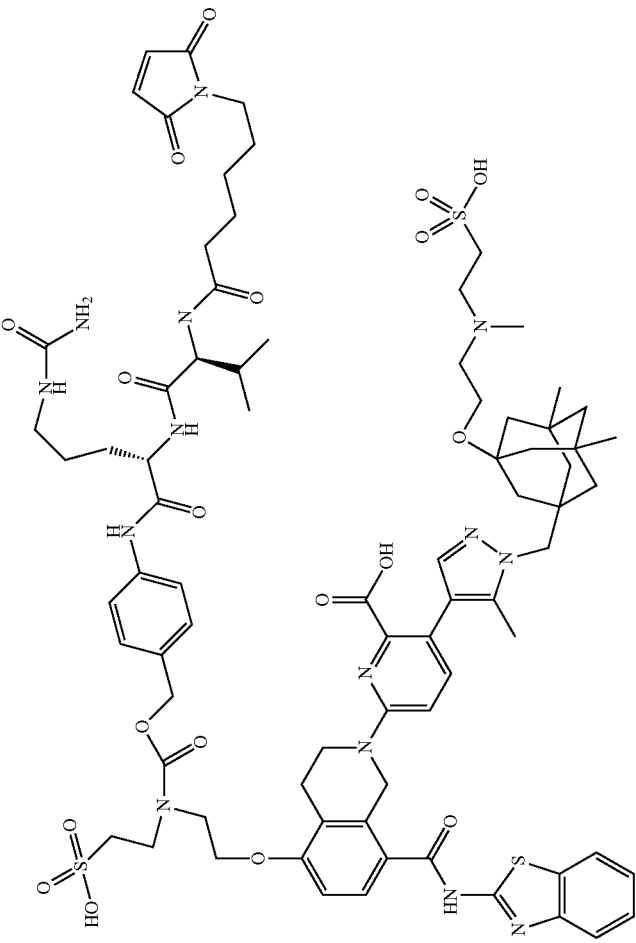 |
| 2.48 | IV | 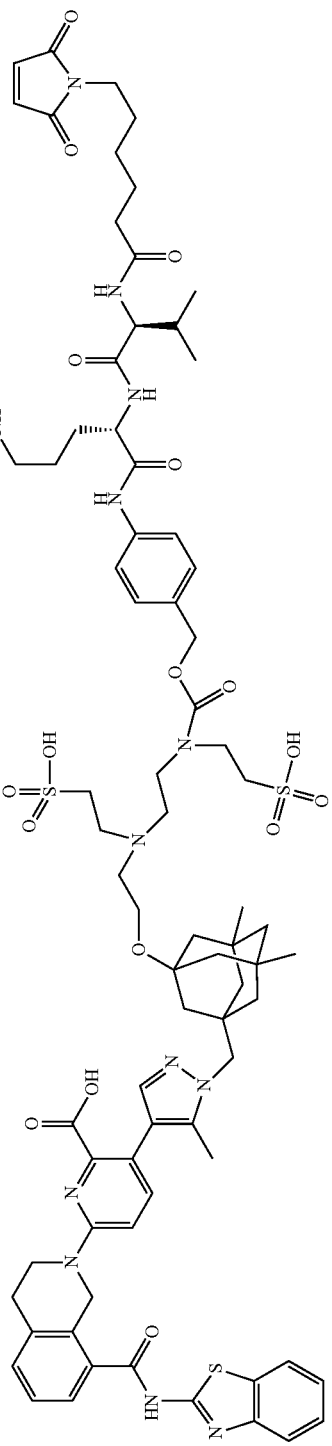 |

TABLE B-continued
| Example No. | Synthon Code | Synthon Structure |
|---|---|---|
| 2.49 | IZ | 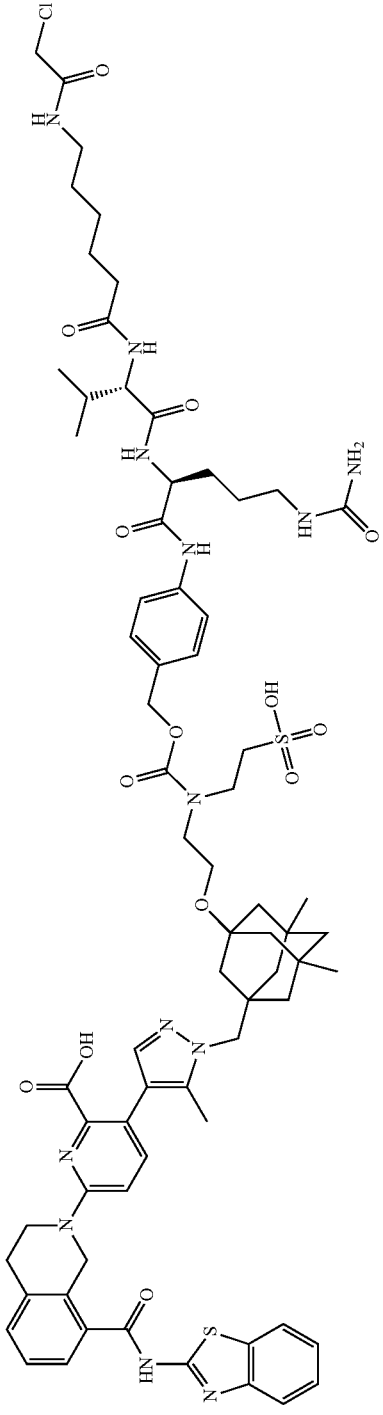 |
| 2.50 | JD | 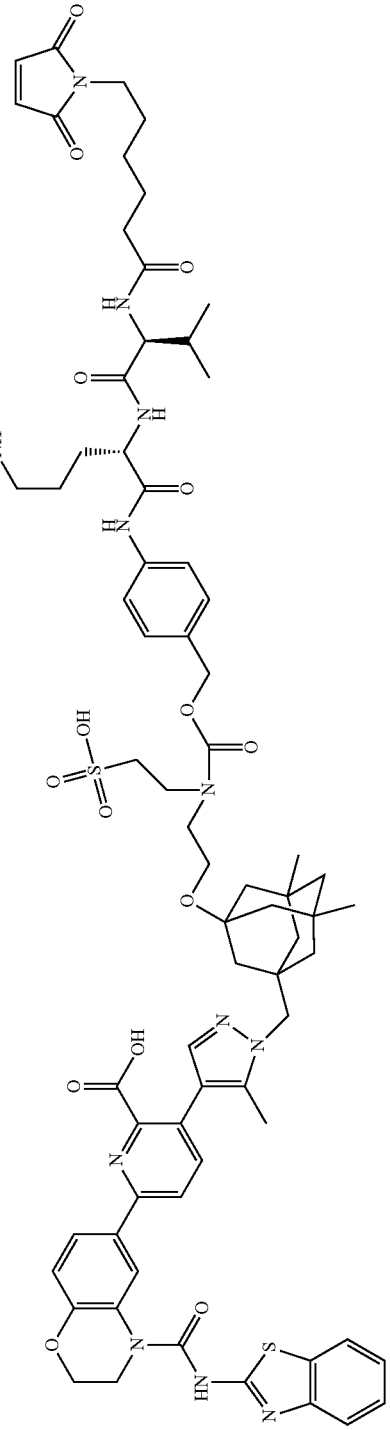 |

TABLE B-continued
Synthon Structure
| Example No. | Synthon Code | Synthon Structure |
|---|---|---|
| 2.51 | JF | 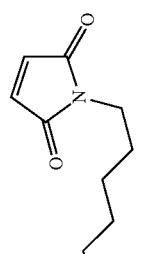 |

TABLE B-continued
| Example No. | Synthon Code | Synthon Structure |
|---|---|---|
| 2.52 | JK | 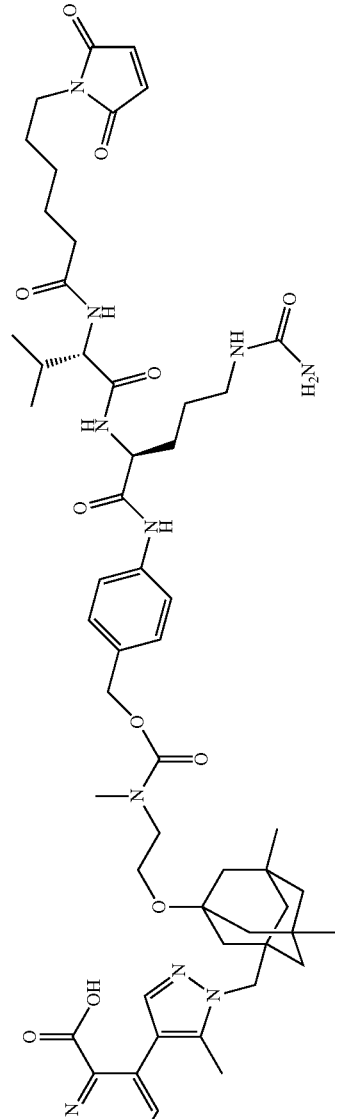 |
| 2.53 | JJ | 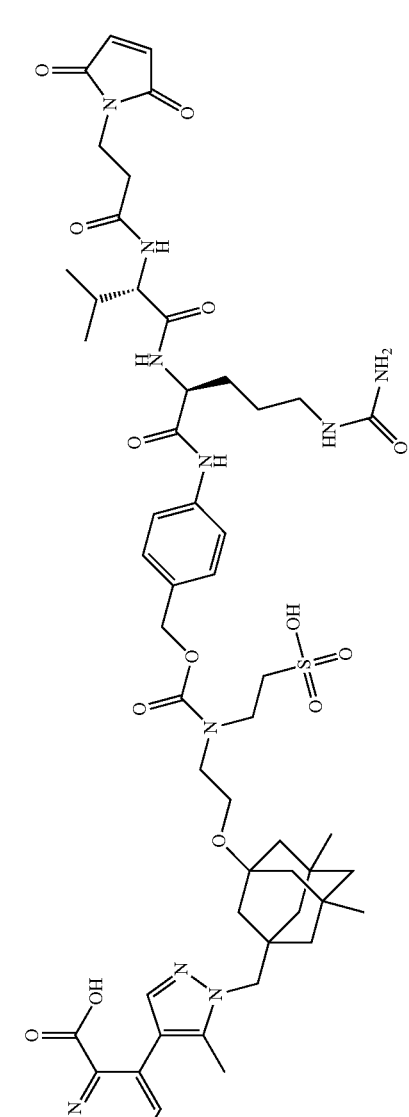 |

TABLE B-continued
| Example No. | Synthon Code | Synthon Structure |
|---|---|---|
| 2.54 | JL | 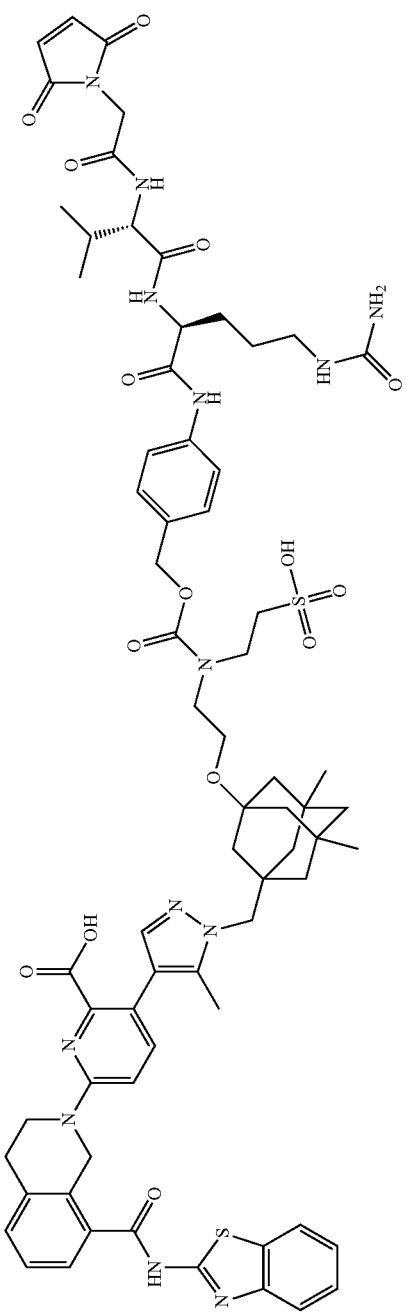 |
| 2.55 | FE | 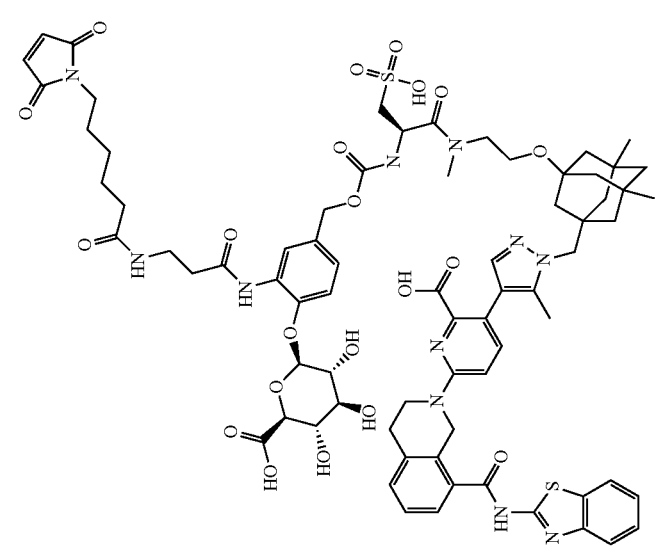 |

TABLE B-continued
| Example No. | Synthon Code | Synthon Structure |
|---|---|---|
| 2.56 | GG | 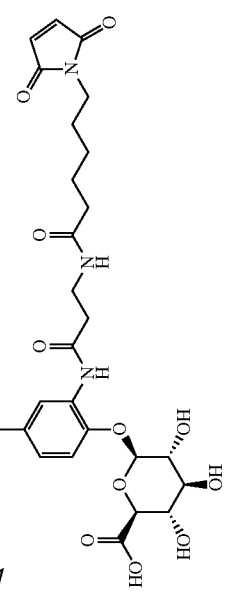 |
| 2.57 | GM | 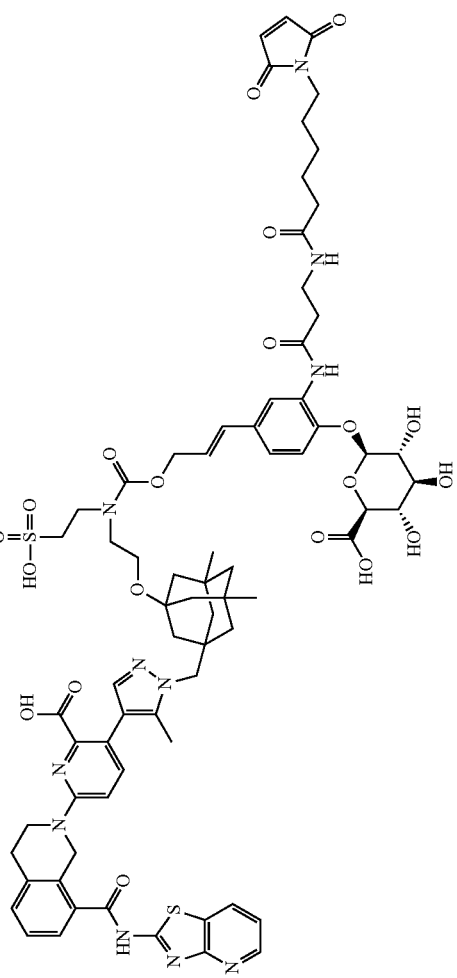 |

TABLE B-continued

| Example No. | Synthon Code | Synthon Structure |
|---|---|---|
| 2.58 | HD | |
| 2.59 | HS | |

TABLE B-continued
| Example No. | Synthon Code | Synthon Structure |
|---|---|---|
| 2.60 | HW | 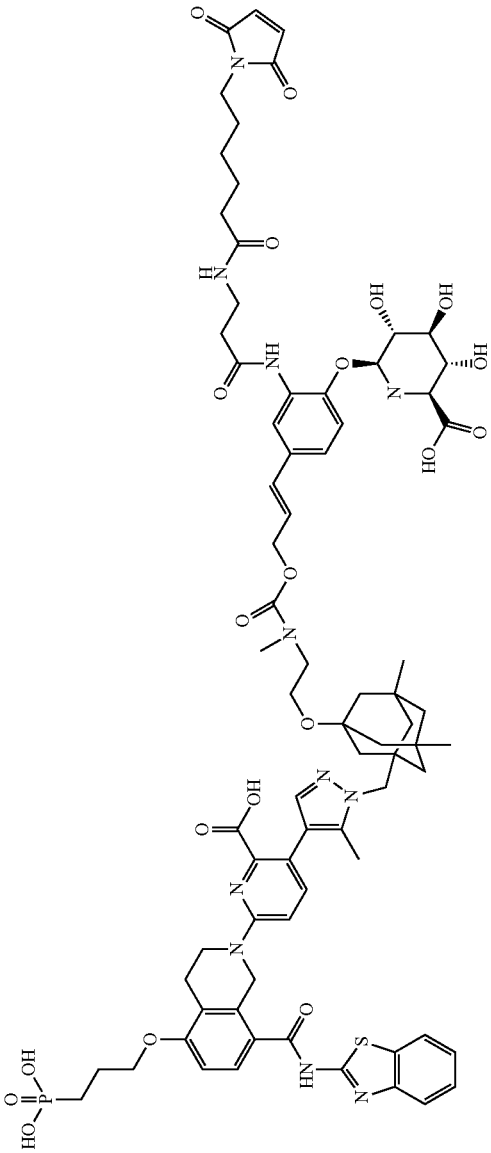 |
| 2.61 | HX | 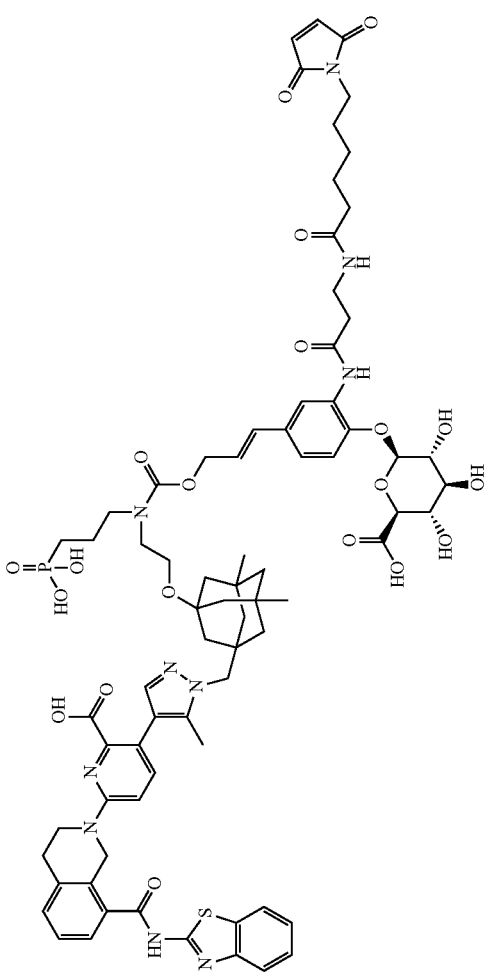 |

TABLE B-continued

| Example No. | Synthon Code | Synthon Structure |
|---|---|---|
| 2.62 | HY | |
| 2.63 | IB | |

TABLE B-continued
| Example No. | Synthon Code | Synthon Structure |
|---|---|---|
| 2.64 | IE | 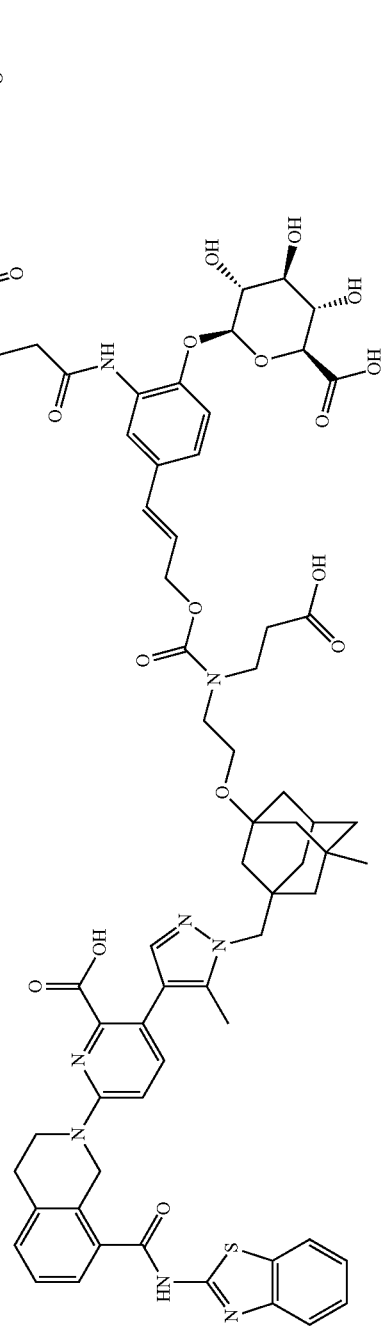 |

TABLE B-continued
| Example No. | Synthon Code | Synthon Structure |
|---|---|---|
| 2.65 | II | 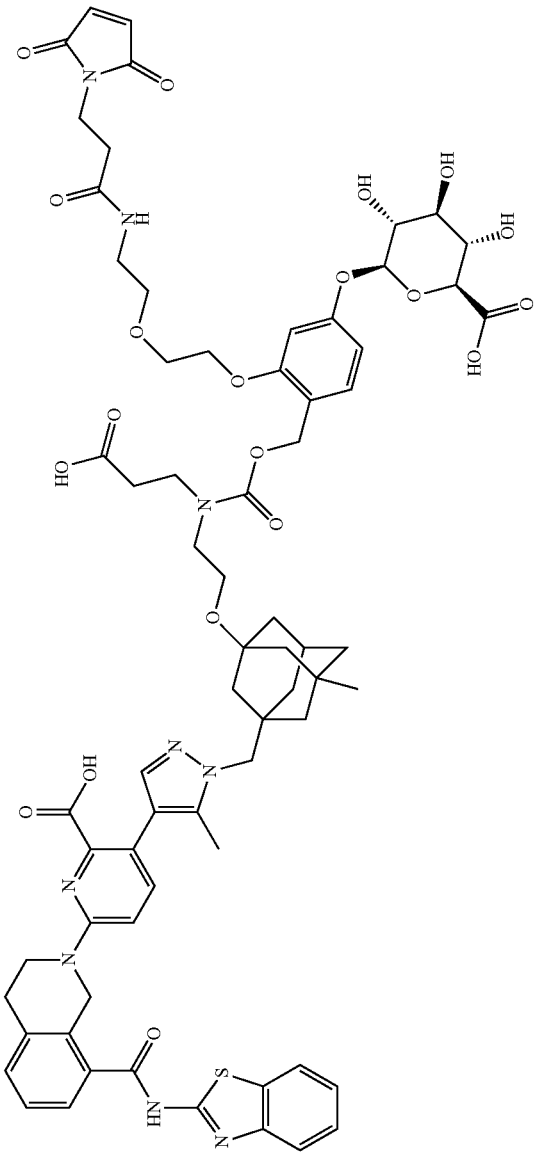 |
| 2.66 | KY | 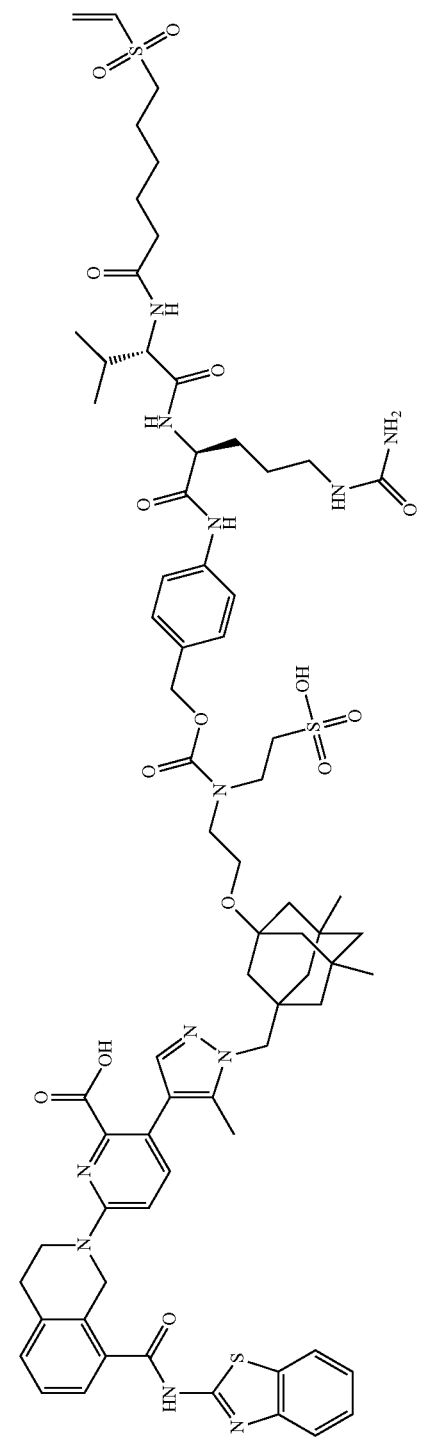 |

TABLE B-continued
| Example No. | Synthon Code | Synthon Structure |
|---|---|---|
| 2.67 | IW | 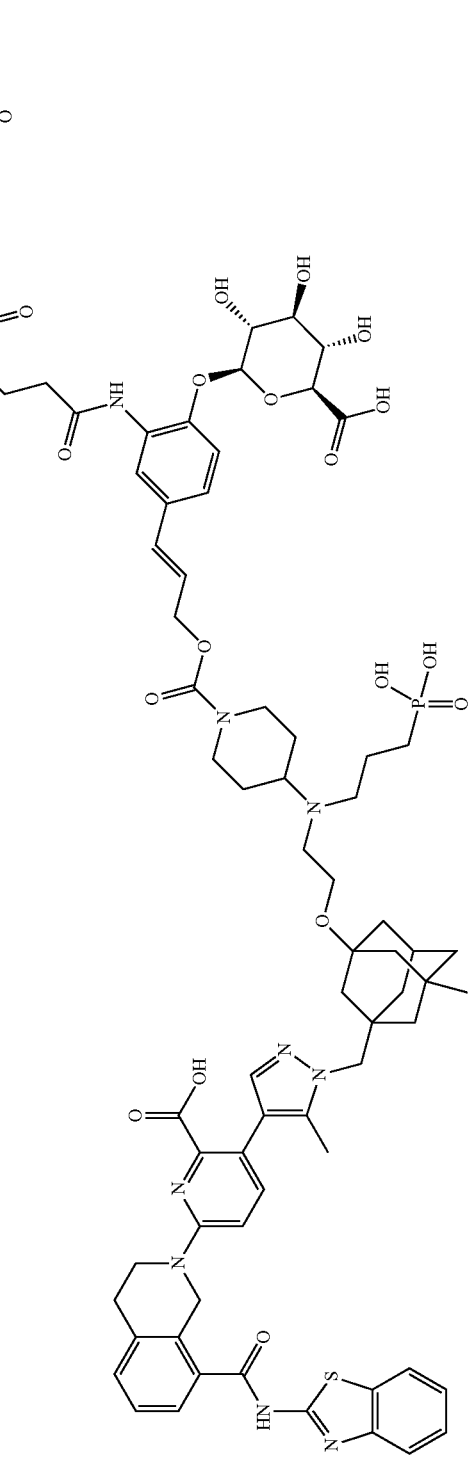 |

TABLE B-continued

| Example No. | Synthon Code | Synthon Structure |
|---|---|---|
| 2.68 | IY | |
| 2.69 | JA | |

TABLE B-continued
| Example No. | Synthon Code | Synthon Structure |
|---|---|---|
| 2.77 | EA | 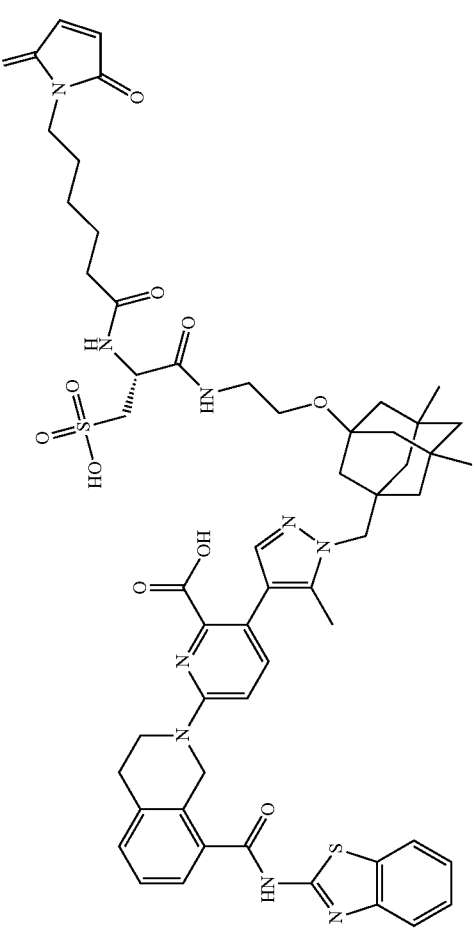 |
| 2.78 | FJ | 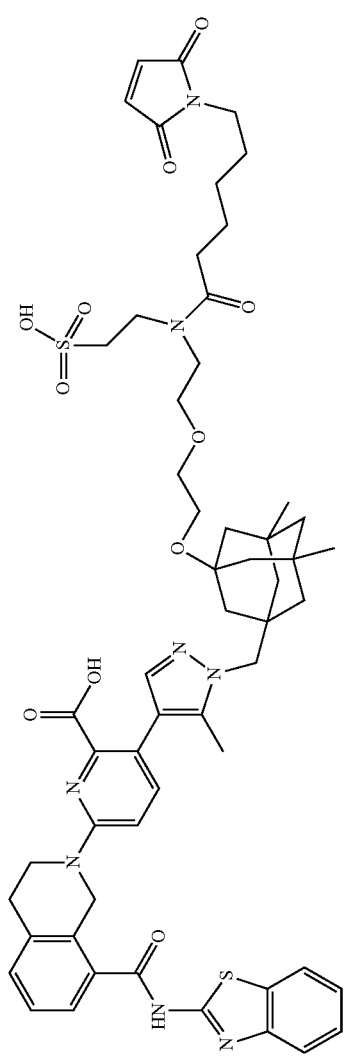 |

TABLE B-continued

| Example No. | Synthon Code | Synthon Structure |
|---|---|---|
| 2.79 | FK | |
| 2.80 | FQ | |
| 2.81 | FR | |

TABLE B-continued
| Example No. | Synthon Code | Synthon Structure |
|---|---|---|
| 2.82 | JE | 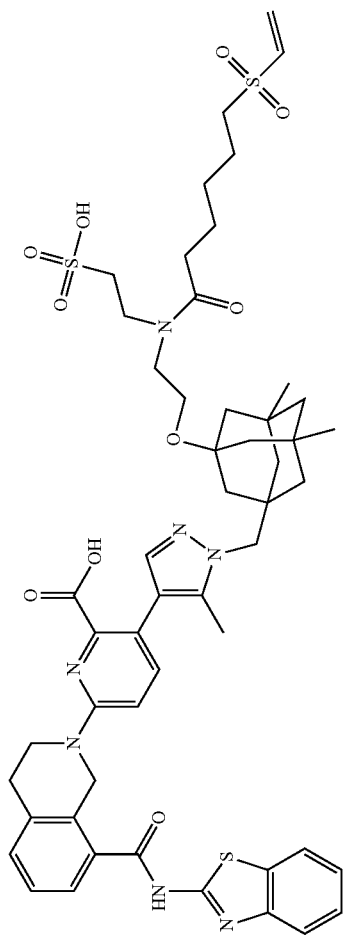 |
| 2.83 | JM | 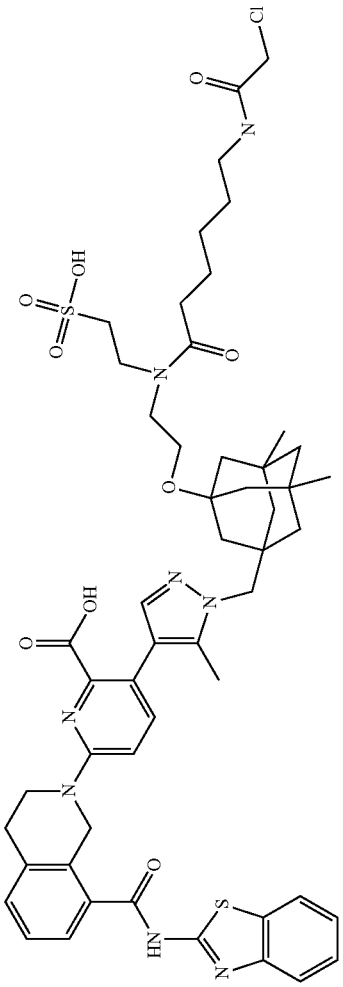 |

TABLE B-continued
| Example No. | Synthon Code | Synthon Structure |
|---|---|---|
| 2.84 | LE | 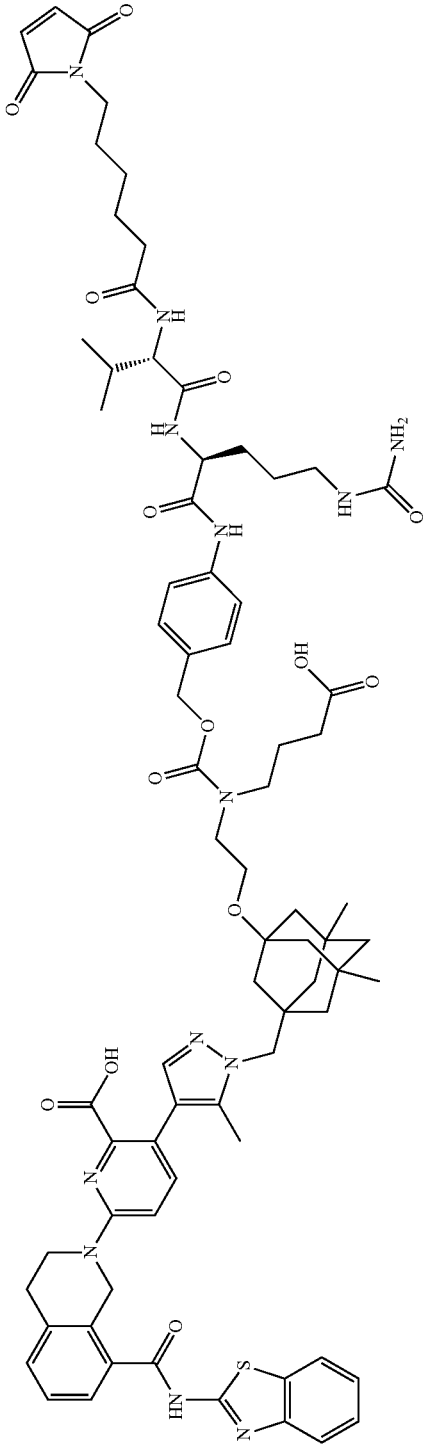 |
| 2.85 | LH | 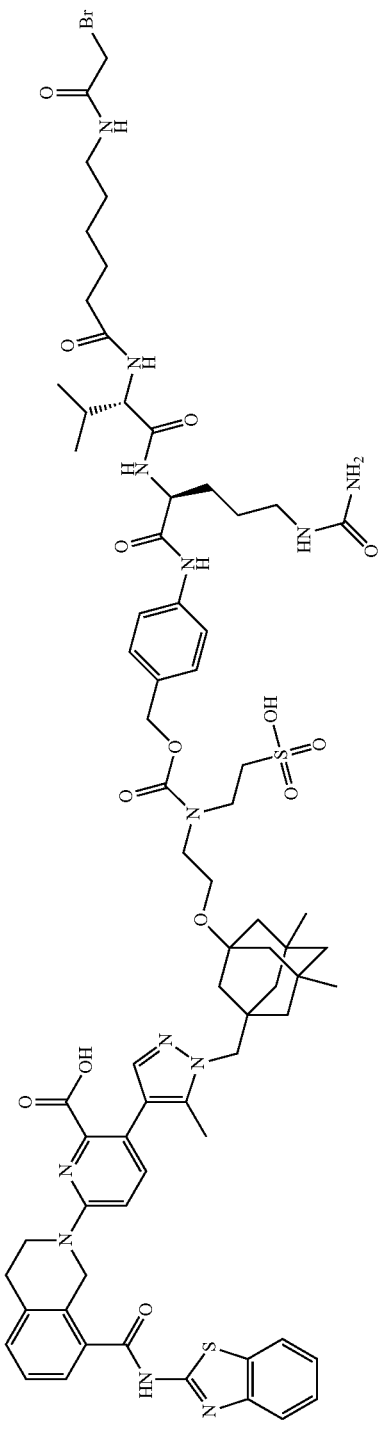 |

TABLE B-continued
| Example No. | Synthon Code | Synthon Structure |
|---|---|---|
| 2.86 | LJ | 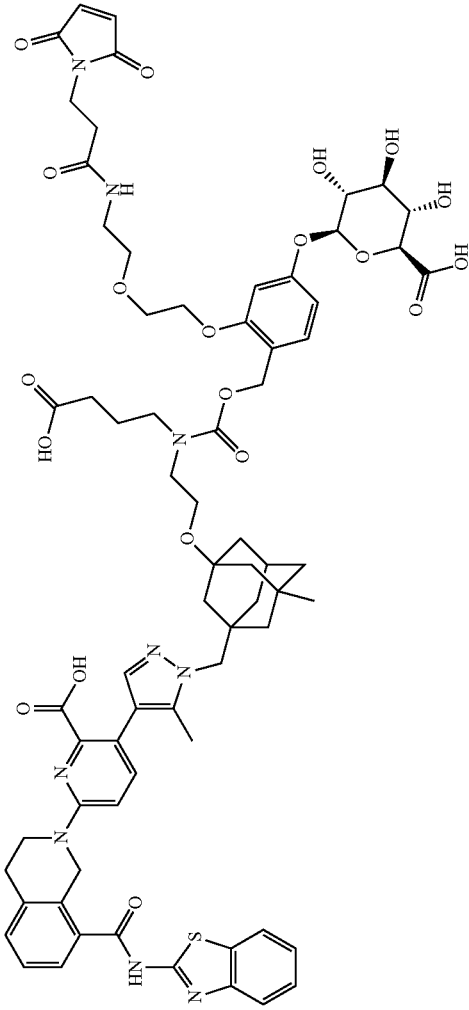 |
| 2.87 | MA | 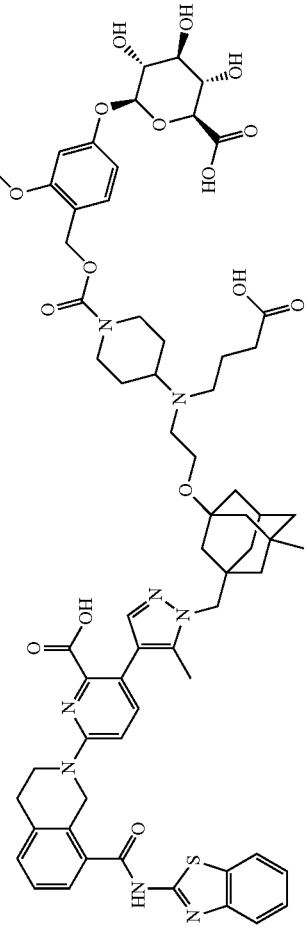 |

TABLE B-continued
| Example No. | Synthon Code | Synthon Structure |
|---|---|---|
| 2.88 | MD | 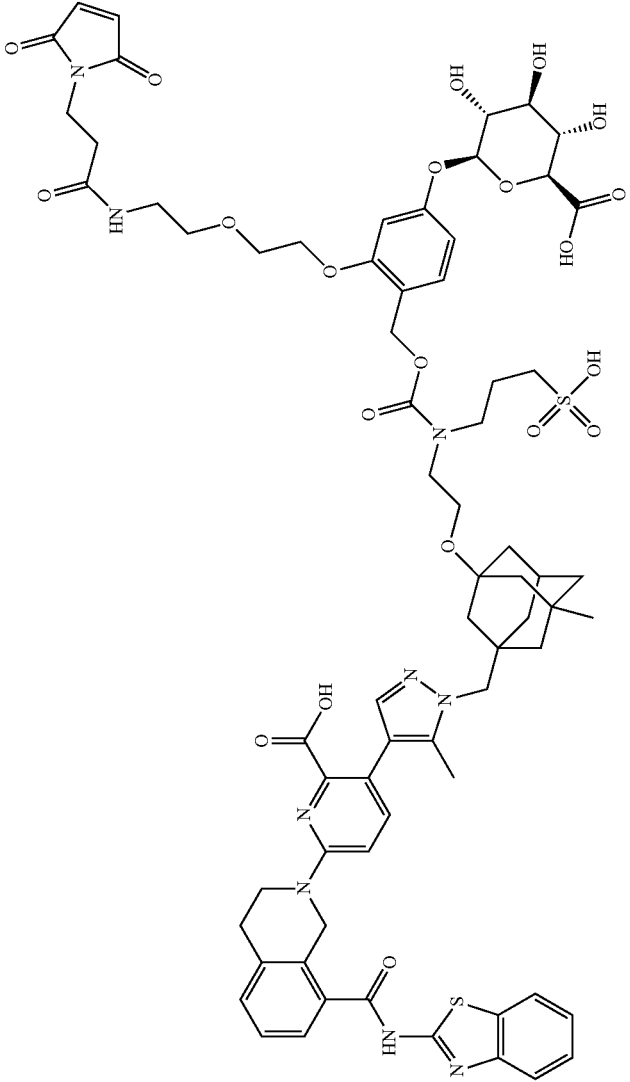 |
| 2.89 | MG | 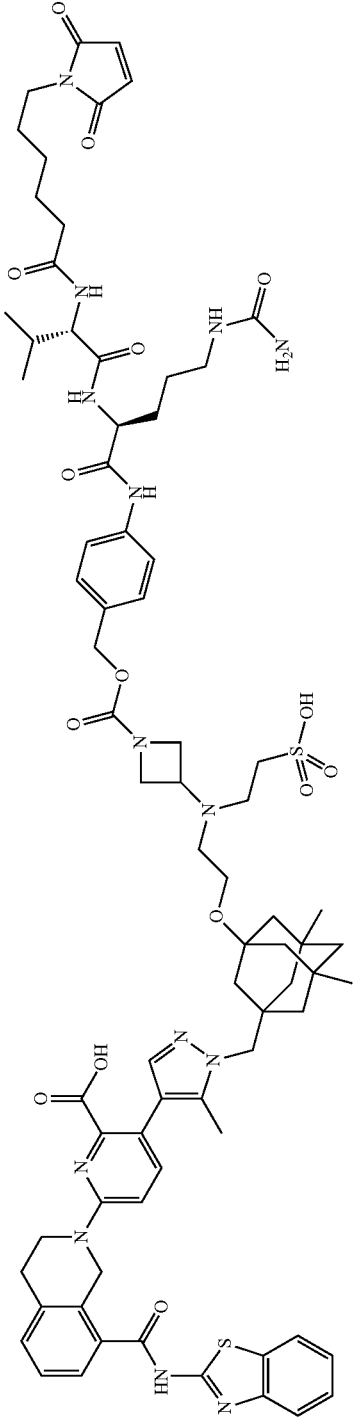 |

TABLE B-continued

| Example No. | Synthon Code | Synthon Structure |
|---|---|---|
| 2.90 | MS | |
| 2.91 | MR | |
| 2.92 | MQ | |

TABLE B-continued
| Example No. | Synthon Code | Synthon Structure |
|---|---|---|
| 2.93 | MZ | 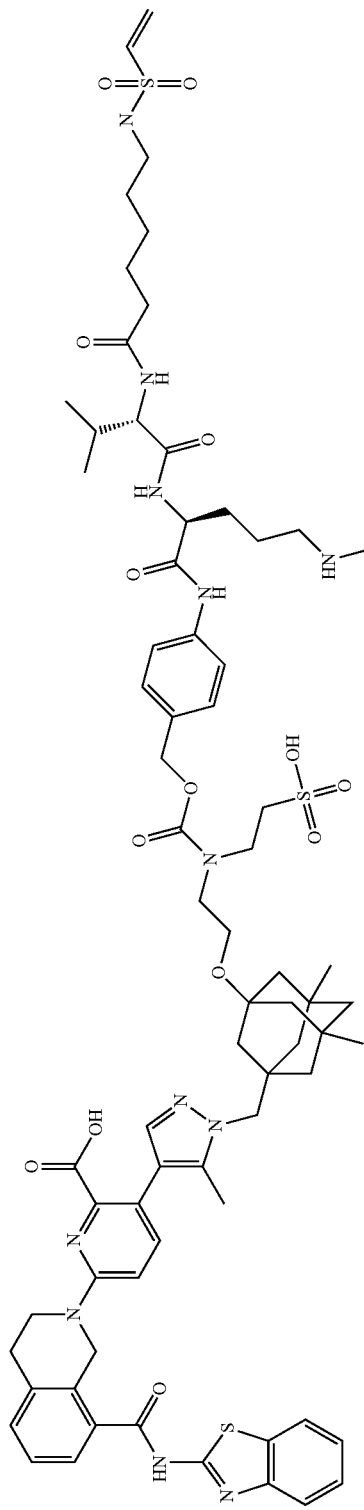 |
| 2.94 | NA | 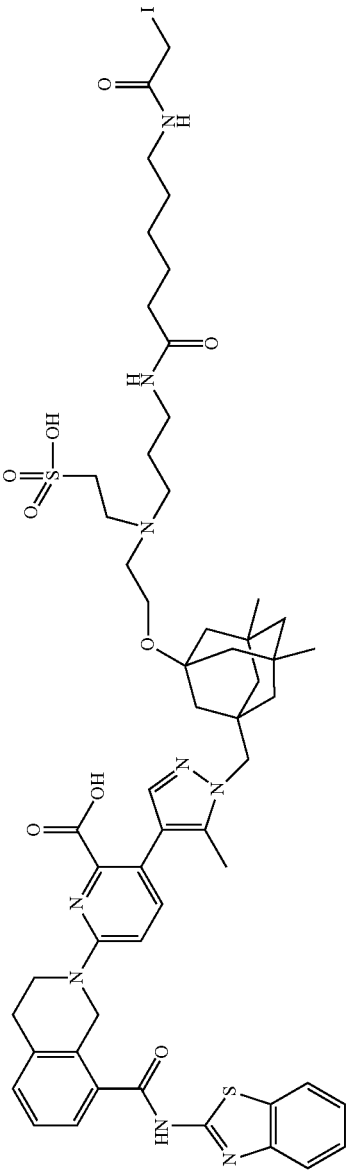 |

TABLE B-continued
| Example No. | Synthon Code | Synthon Structure |
|---|---|---|
| 2.95 | NB | 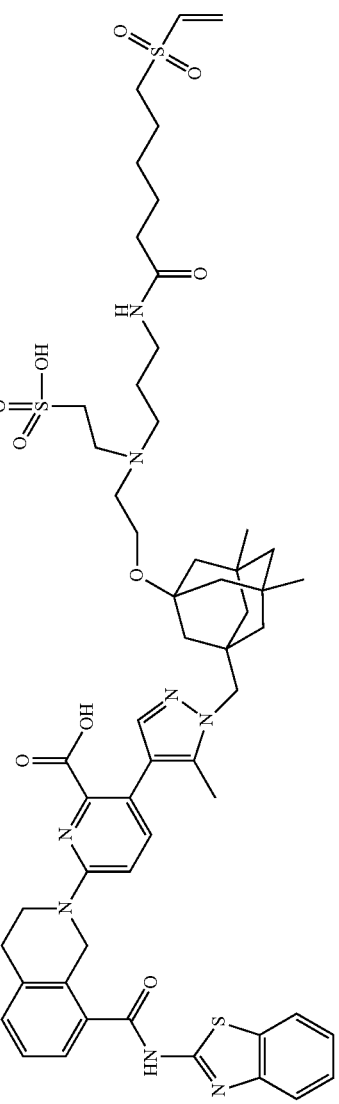 |
| 2.96 | NP | 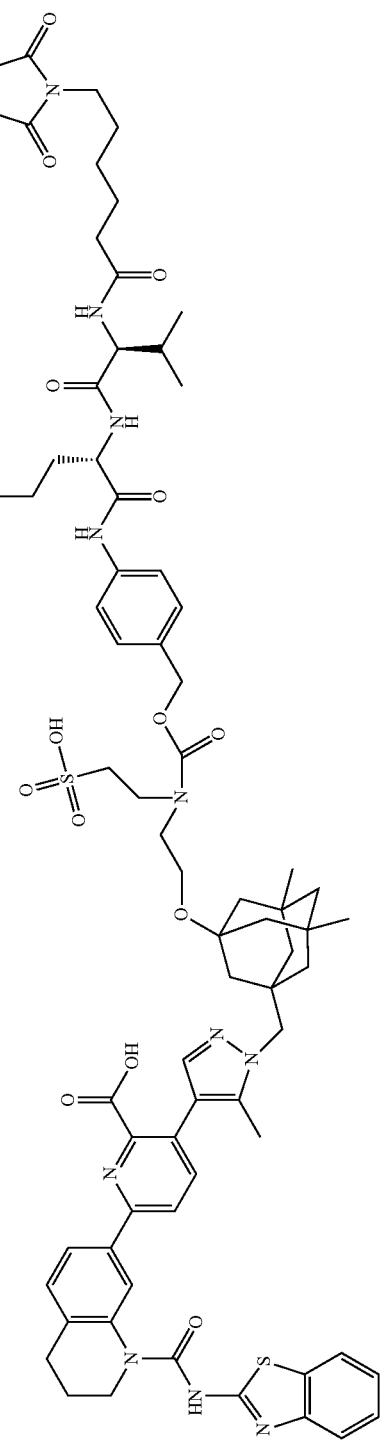 |

TABLE B-continued

Synthon Structure

| Example No. | Synthon Code |
|---|---|
| 2.97 | NN |
| 2.98 | NO |

TABLE B-continued

Synthon Structure

| Example No. | Synthon Code |
|---|---|
| 2.101 | OK |
| 2.102 | OW |

TABLE B-continued

Synthon Structure

| Example No. | Synthon Code |
|---|---|
| 2.103 | PC |
| 2.104 | PI |

TABLE B-continued
Synthon Structure
| Example No. | Synthon Code | Synthon Structure |
|---|---|---|
| 2.105 | PJ | 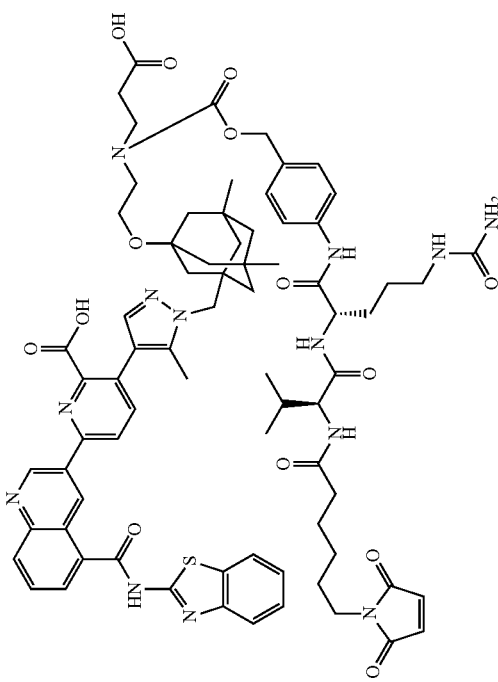 |
| 2.106 | PU | 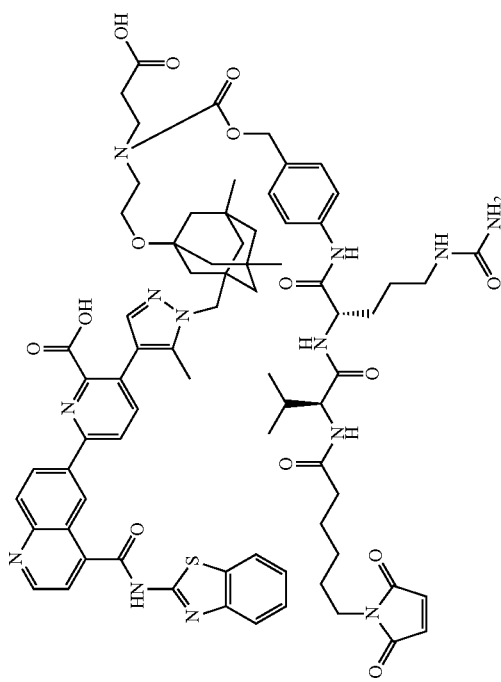 |

TABLE B-continued
| Example No. | Synthon Code | Synthon Structure |
|---|---|---|
| 2.107 | PV | 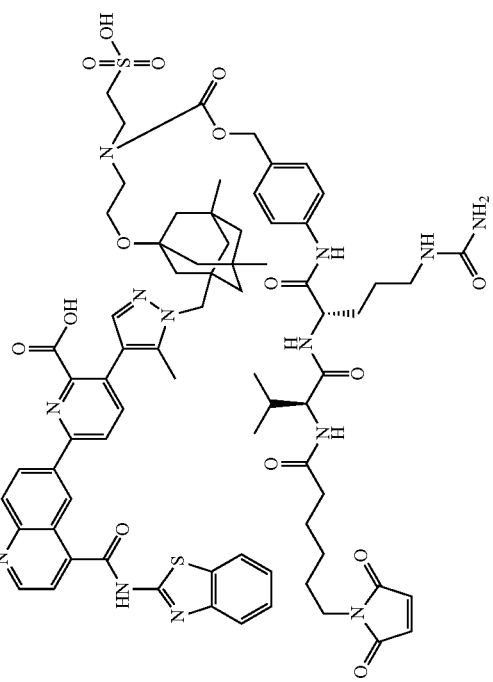 |
| 2.108 | PW | 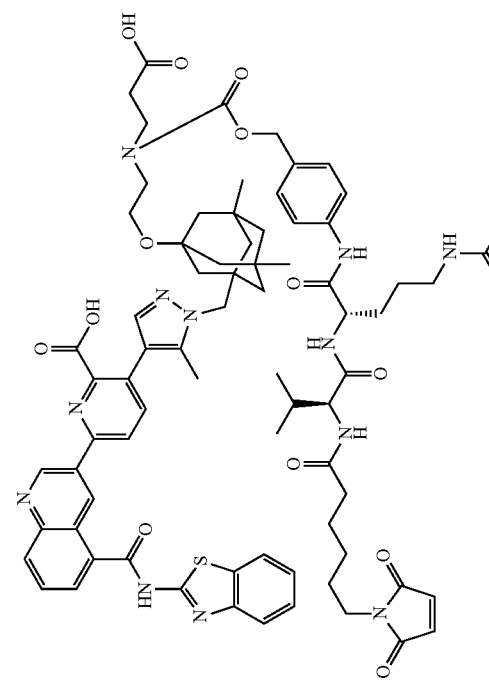 |

TABLE B-continued
| Example No. | Synthon Code | Synthon Structure |
|---|---|---|
| 2.109 | QW | 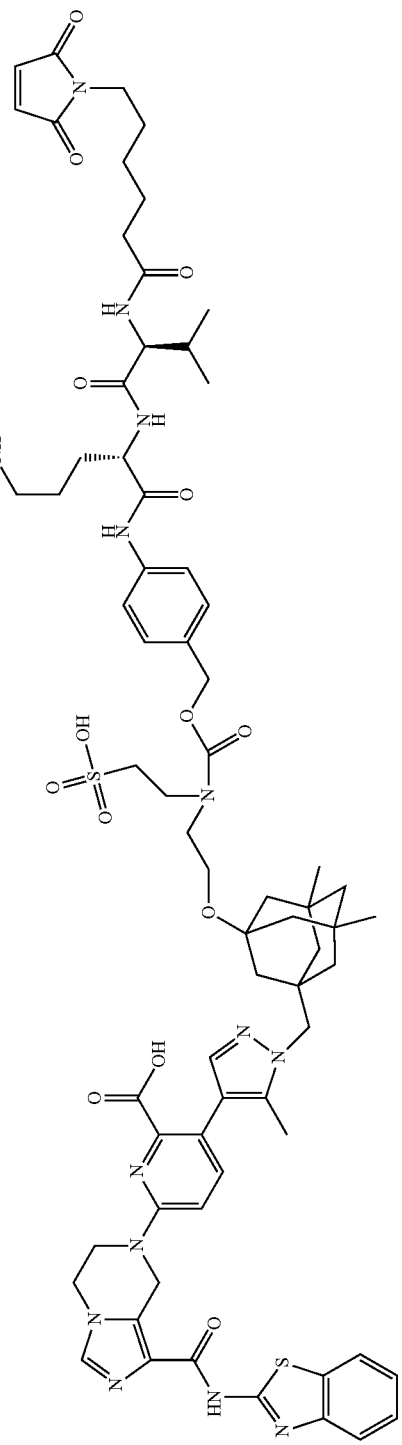 |
| 2.110 | RM | 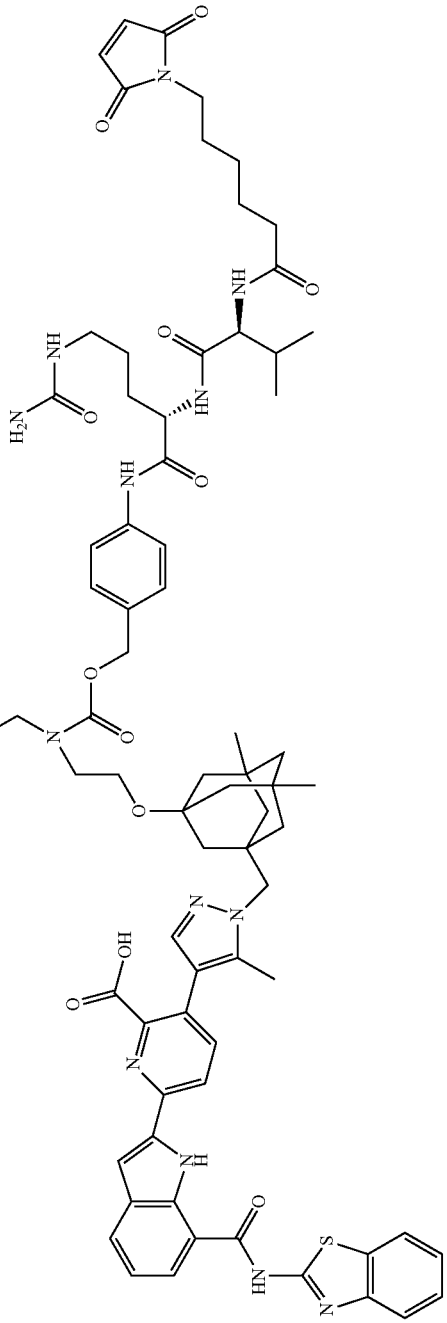 |

TABLE B-continued
| Example No. | Synthon Code | Synthon Structure |
|---|---|---|
| 2.111 | RR | 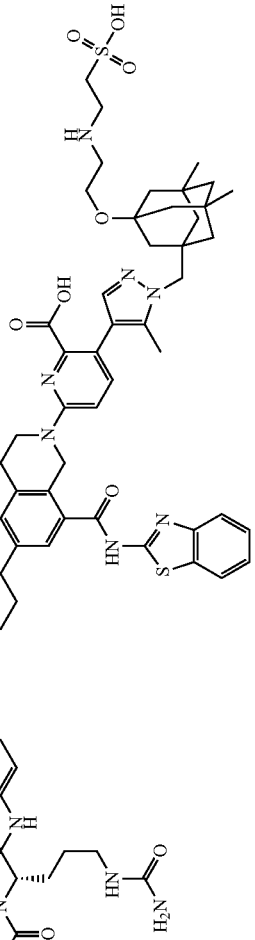 |
| 2.112 | SJ | 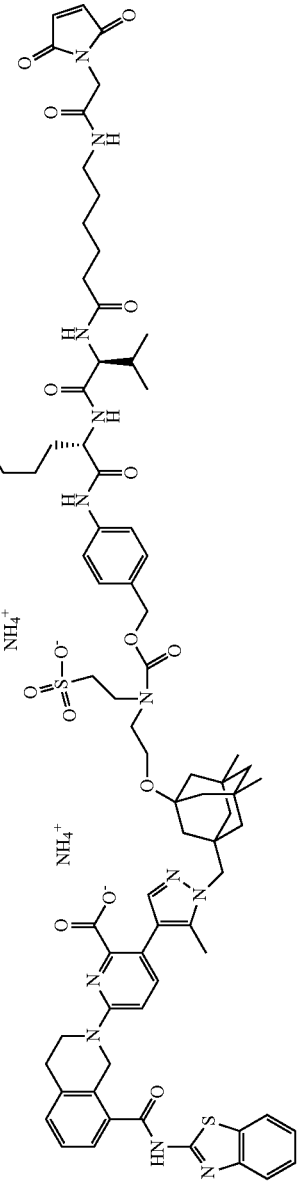 |

TABLE B-continued
Synthon Structure
| Example No. | Synthon Code |
|---|---|
| 2.113 | SM |
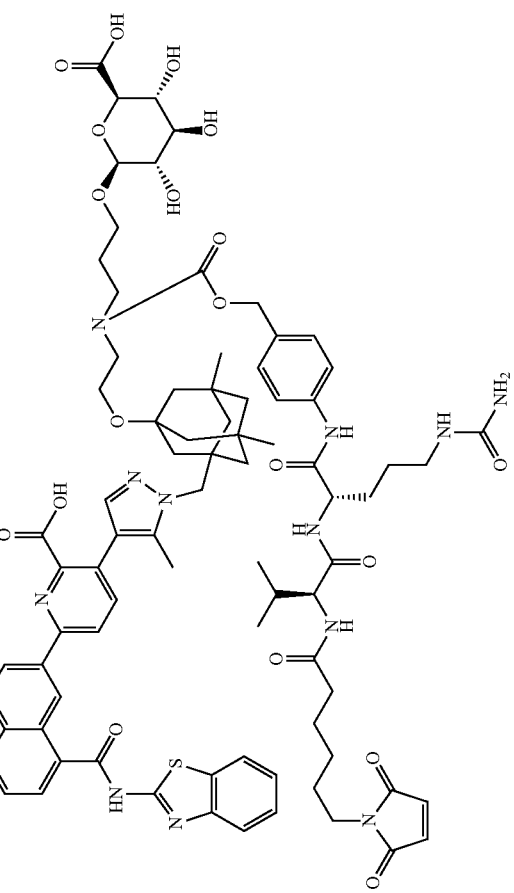

TABLE B-continued
| Example No. | Synthon Code | Synthon Structure |
|---|---|---|
| 2.114 | SN | 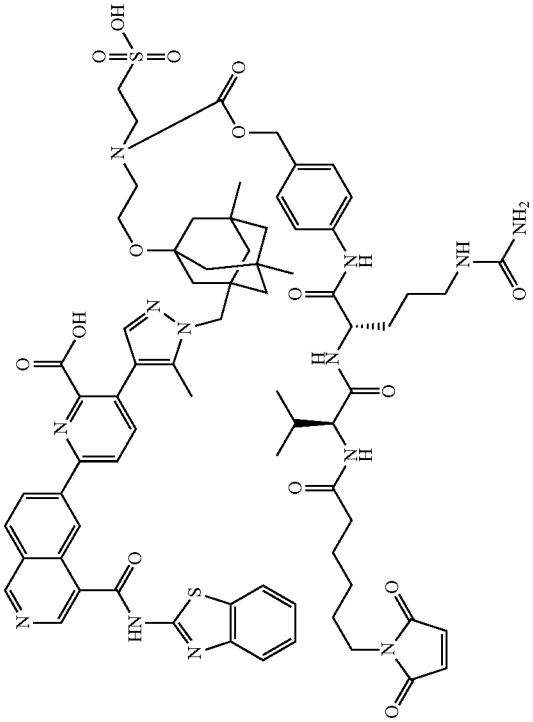 |
| 2.115 | SS | 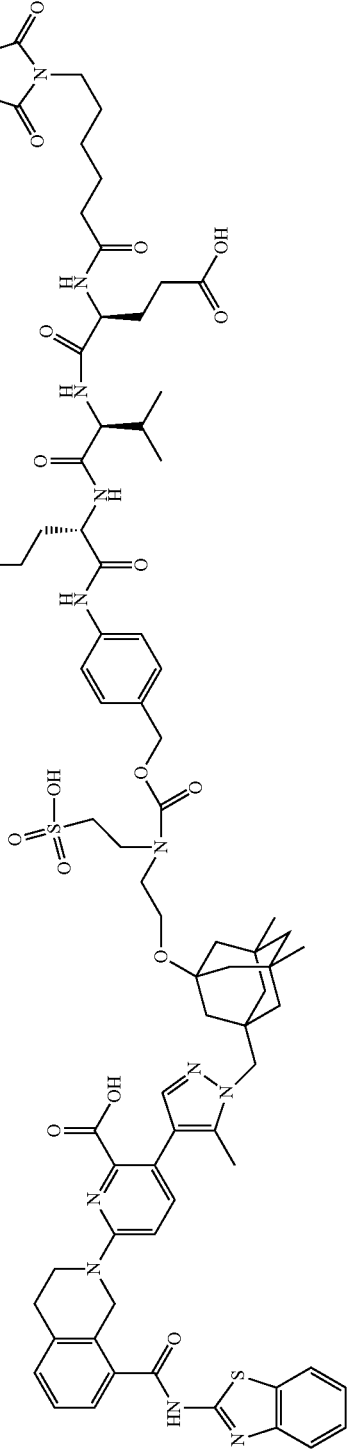 |

TABLE B-continued

Synthon Structure

| Example No. | Synthon Code |
|---|---|
| 2.116 | TA |
| 2.117 | TW |

TABLE B-continued
Synthon Structure
| Example No. | Synthon Code | Synthon Structure |
|---|---|---|
| 2.118 | ST | 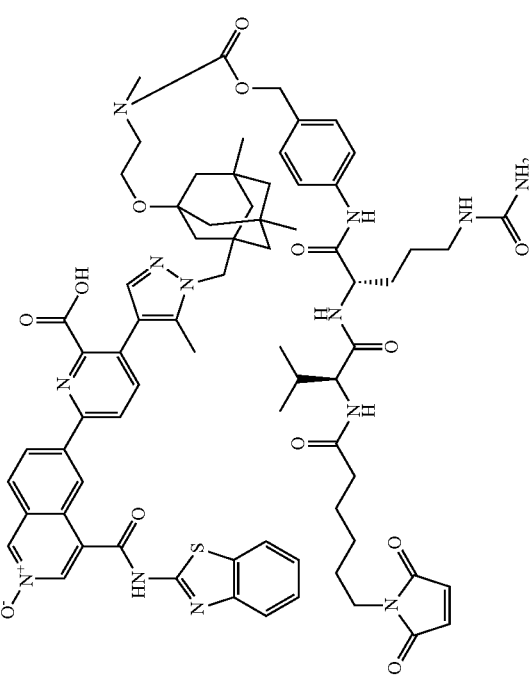 |
| 2.119 | ZL | 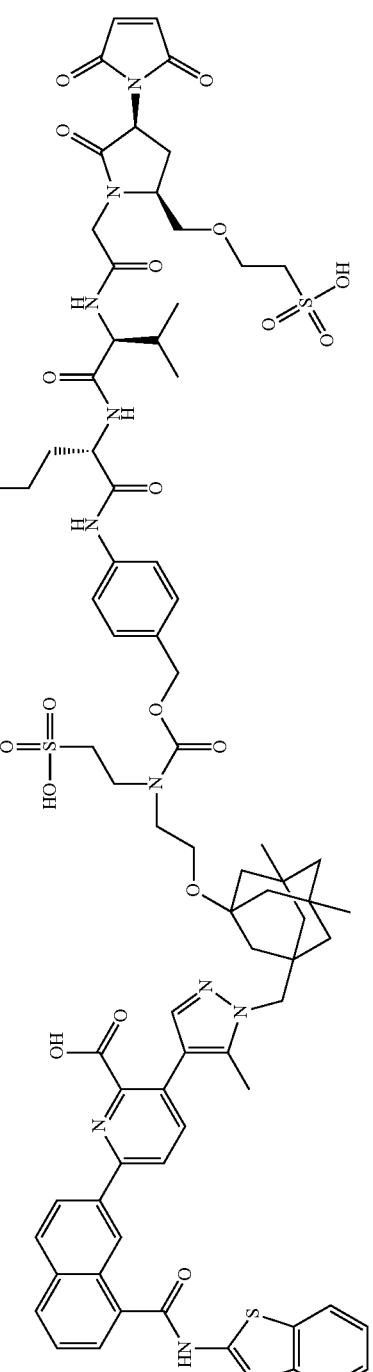 |

TABLE B-continued
| Example No. | Synthon Code | Synthon Structure |
|---|---|---|
| 2.120 | SX | 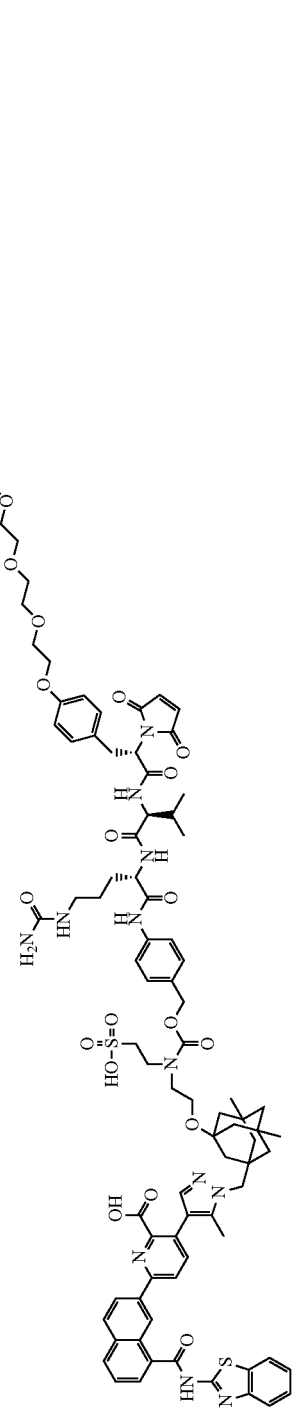 |
| 2.121 | SW | 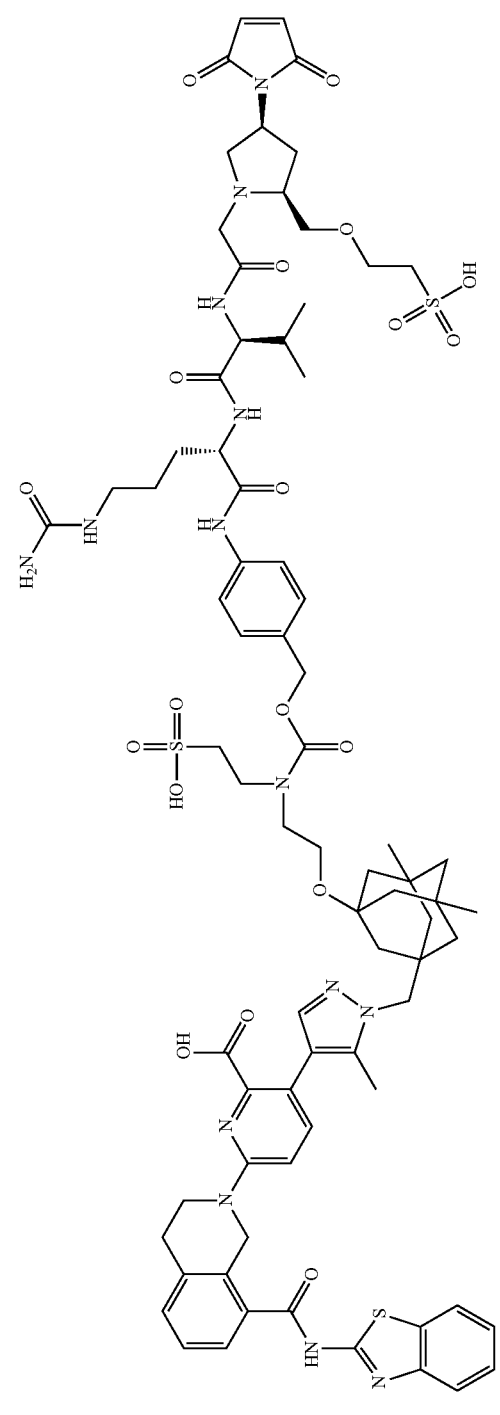 |

TABLE B-continued
| Example No. | Synthon Code | Synthon Structure |
|---|---|---|
| 2.122 | TV | 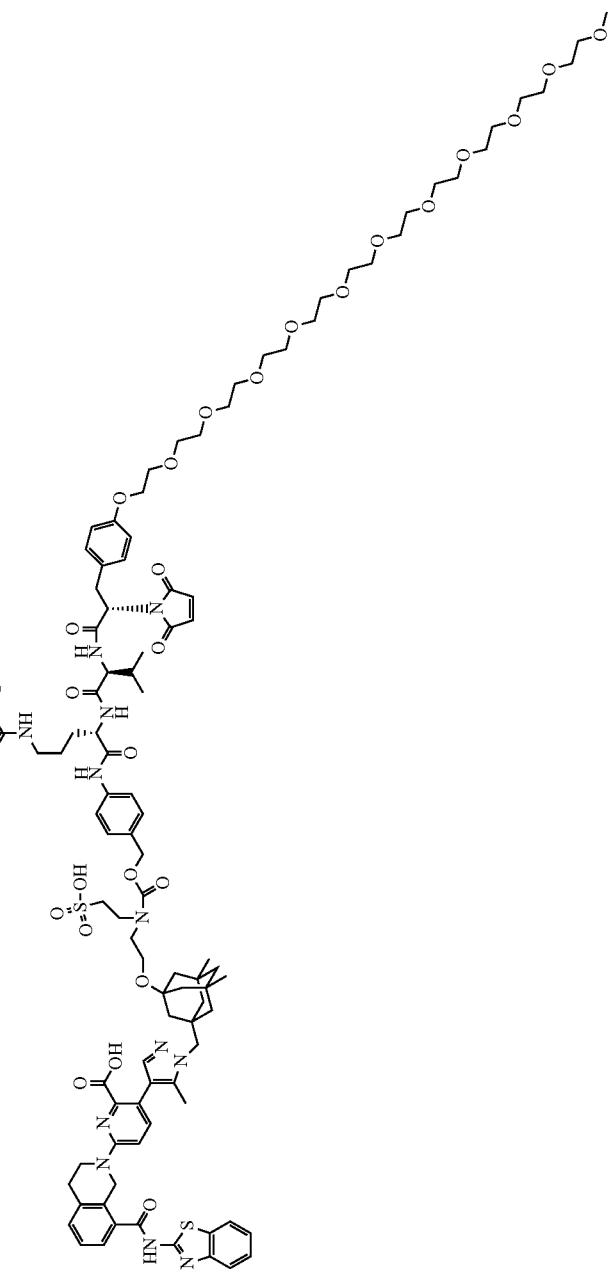 |
| 2.123 | SZ | 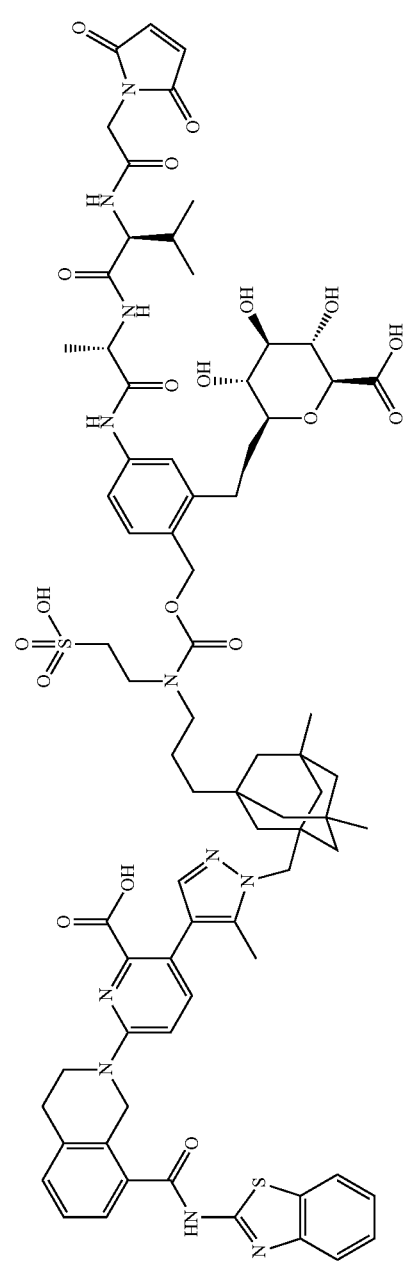 |

TABLE B-continued

Synthon Structure

| Example No. | Synthon Code |
|---|---|
| 2.124 | ZM |
| 2.125 | SV |

TABLE B-continued
| Example No. | Synthon Code | Synthon Structure |
|---|---|---|
| 2.126 | SY | 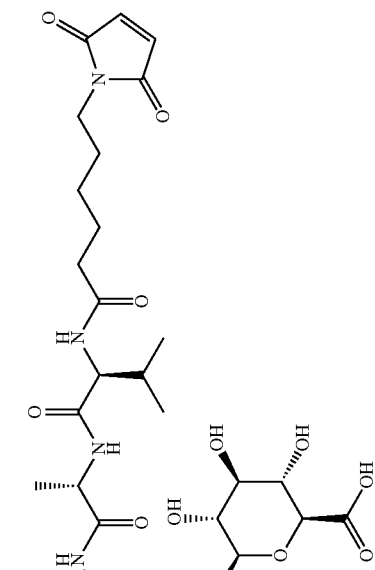 |
| 2.127 | TK | 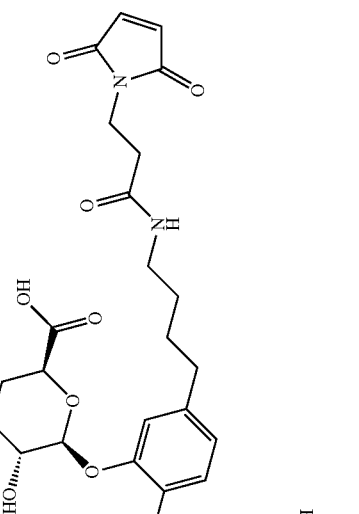 |

TABLE B-continued
| Example No. | Synthon Code | Synthon Structure |
|---|---|---|
| 2.128 | TR | 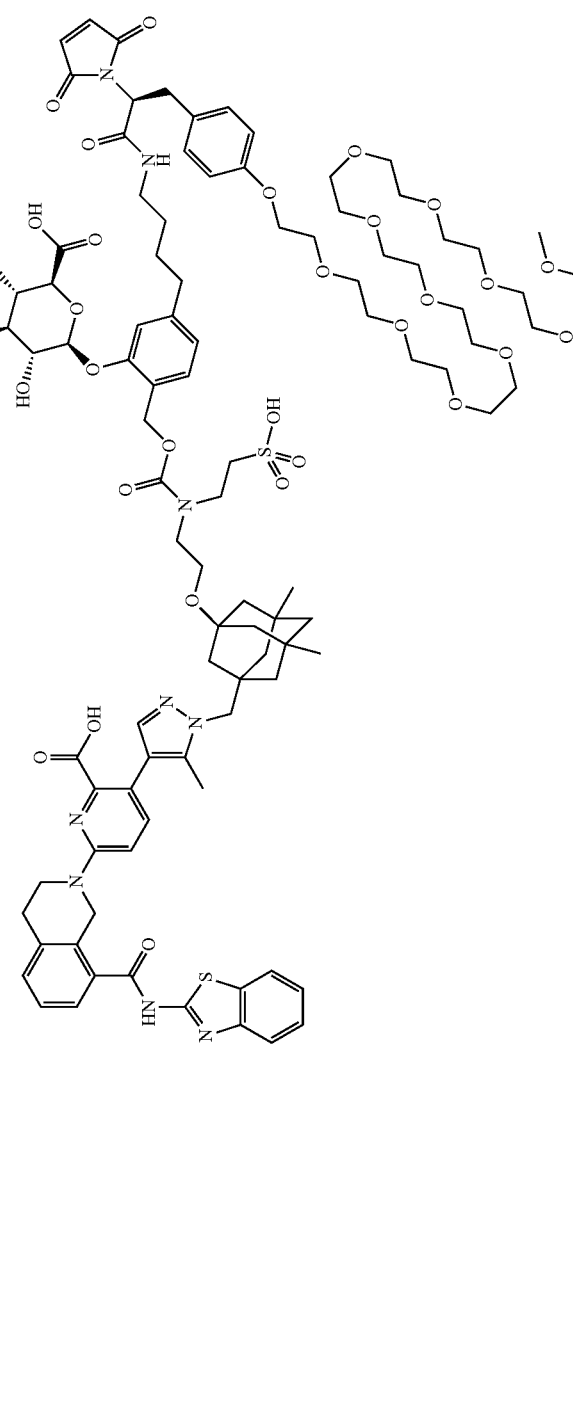 |

TABLE B-continued

| Example No. | Synthon Code | Synthon Structure |
|---|---|---|
| 2.129 | TY | |
| 2.130 | TX | |

TABLE B-continued

Synthon Structure

| Example No. | Synthon Code |
|---|---|
| 2.131 | TZ |
| 2.132 | UA |

TABLE B-continued
| Example No. | Synthon Code | Synthon Structure |
|---|---|---|
| 2.133 | UJ | 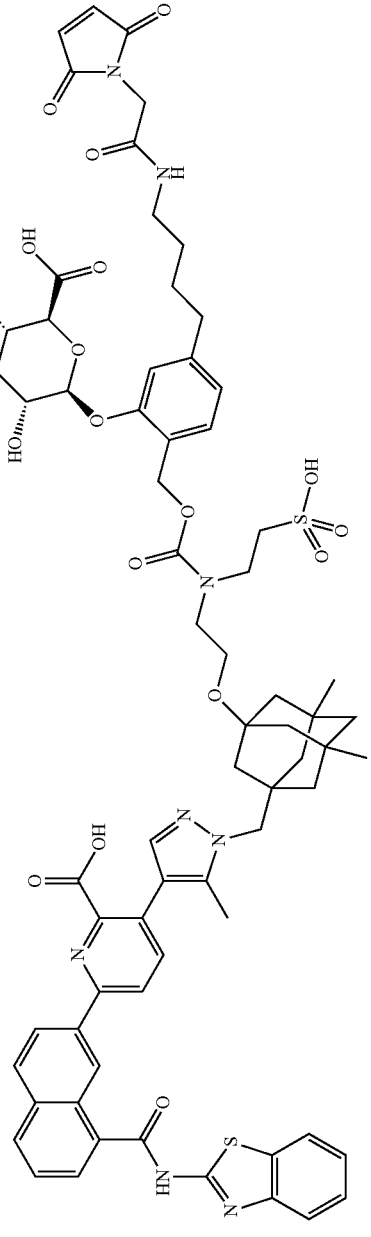 |
| 2.134 | UK | 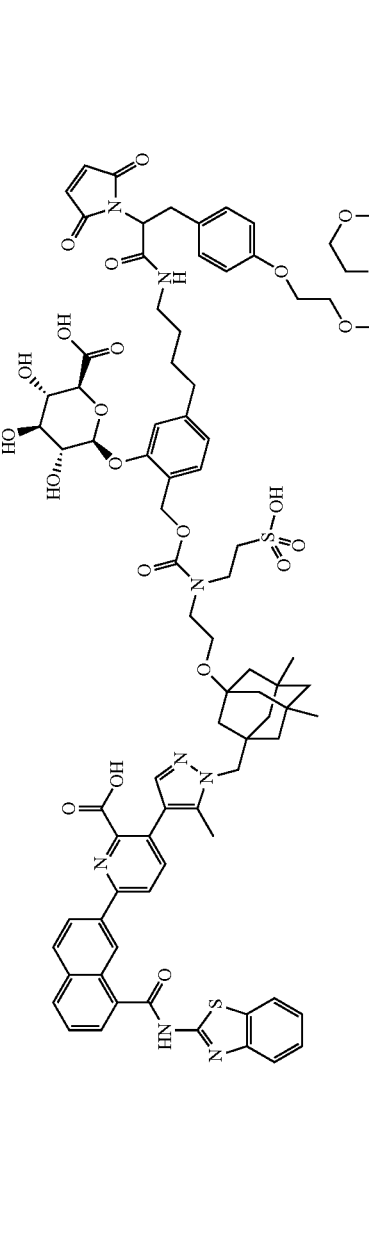 |

TABLE B-continued
| Example No. | Synthon Code | Synthon Structure |
|---|---|---|
| 2.135 | UU | 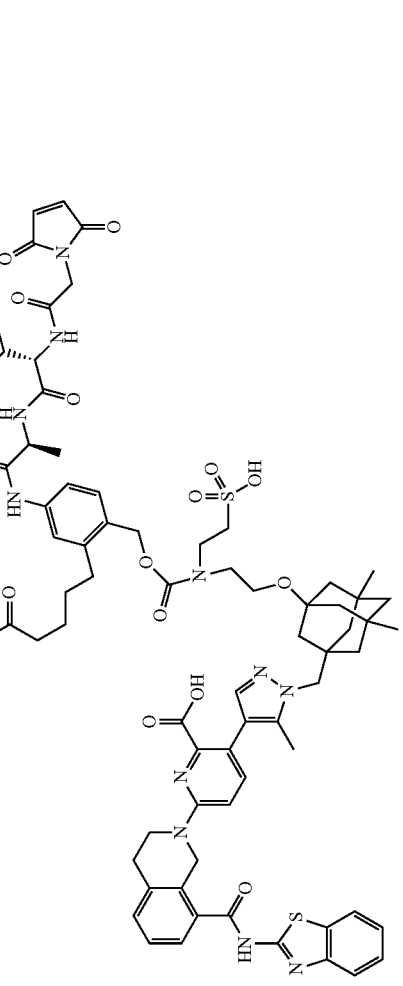 |
| 2.136 | UV | 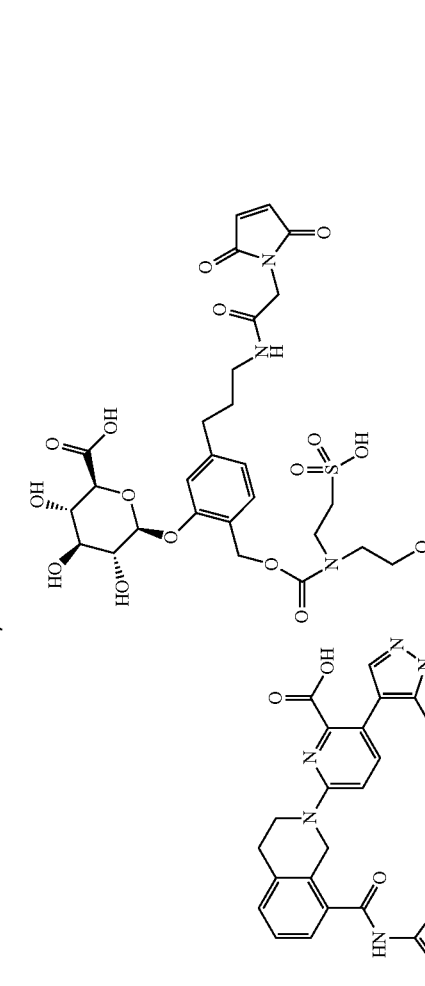 |

TABLE B-continued

Synthon Structure

| Example No. | Synthon Code |
|---|---|
| 2.137 | UZ |
| 2.138 | VB |

TABLE B-continued
Synthon Structure
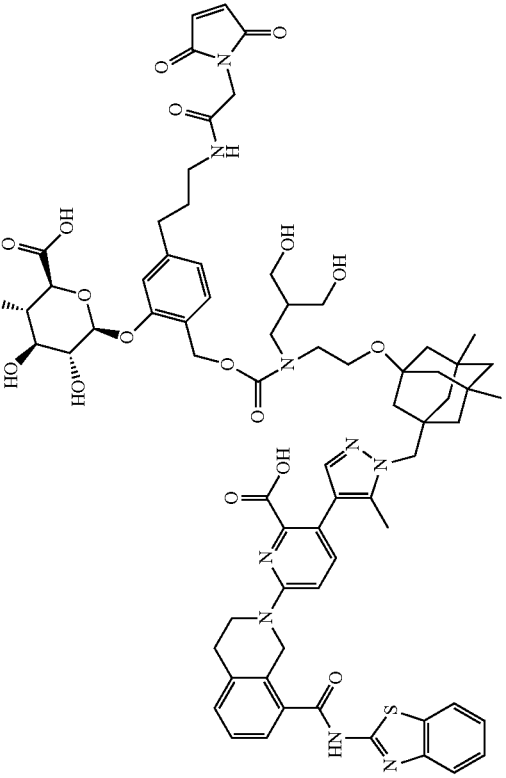
| Example No. | Synthon Code |
|---|---|
| 2.139 | VC |

TABLE B-continued
| Example No. | Synthon Code | Synthon Structure |
|---|---|---|
| 2.140 | VS | 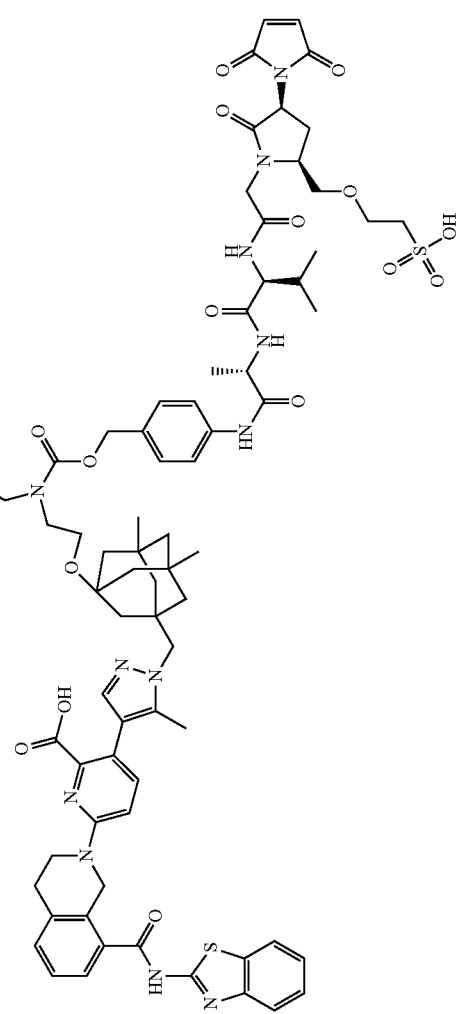 |

TABLE B-continued

| Example No. | Synthon Code | Synthon Structure |
|---|---|---|
| 2.141 | VT | |
| 2.142 | VY | |

TABLE B-continued
Example No. | Synthon Code | Synthon Structure
--- | --- | ---
2.143 | WI | 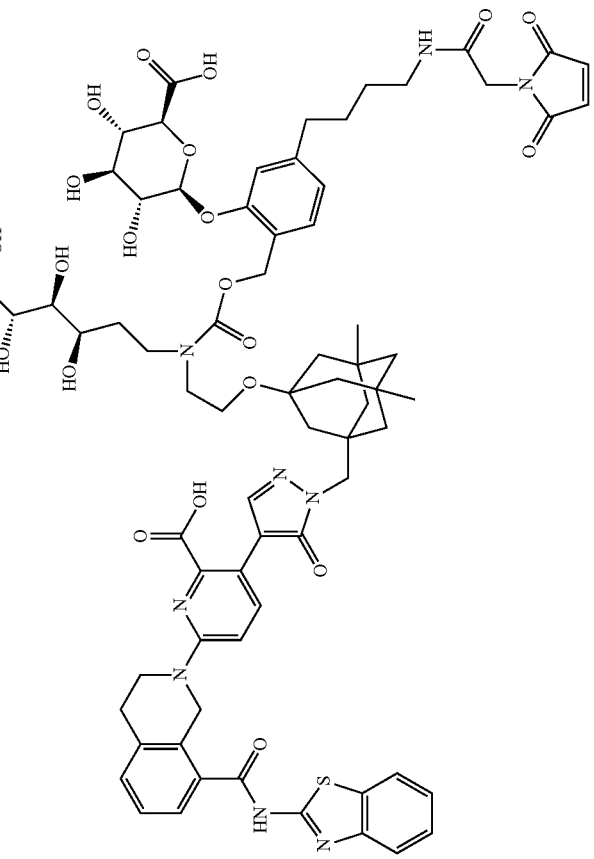

TABLE B-continued
Synthon Structure
| Example No. | Synthon Code |
|---|---|
| 2.144 | WK |
| 2.145 | WP |
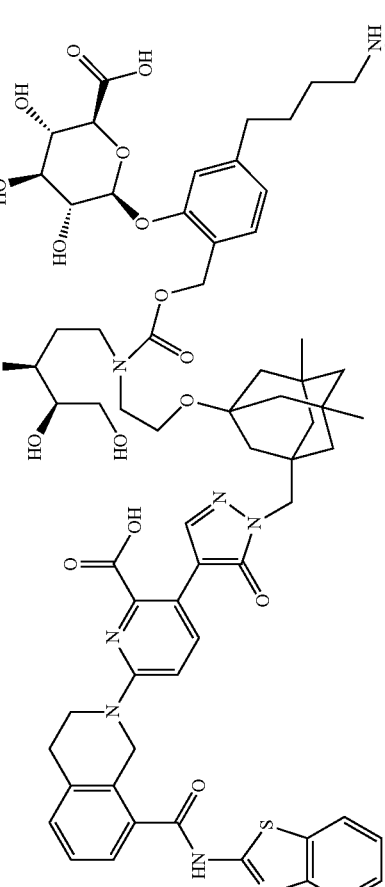

TABLE B-continued
| Example No. | Synthon Code | Synthon Structure |
|---|---|---|
| 2.146 | XD | 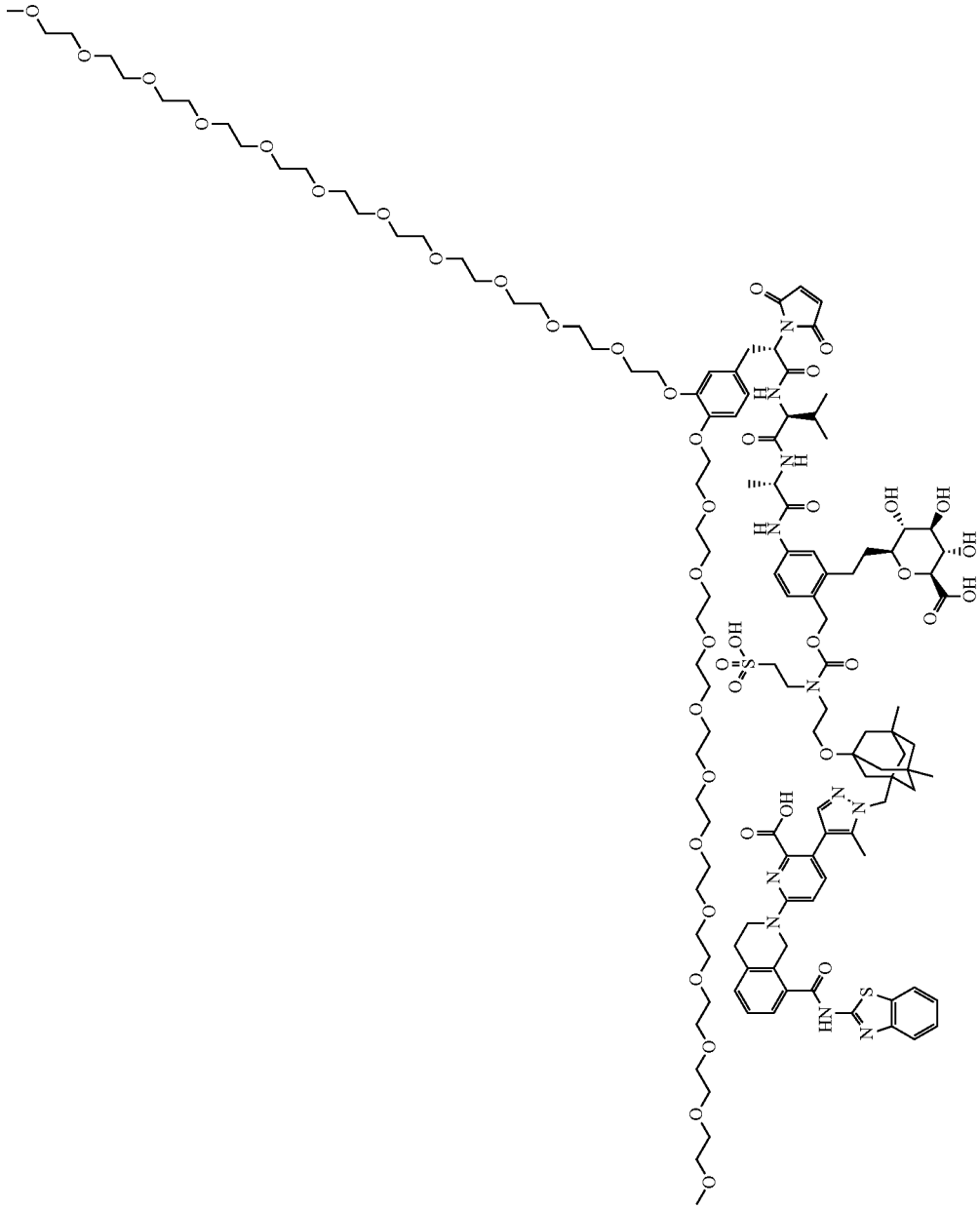 |

TABLE B-continued
| Example No. | Synthon Code | Synthon Structure |
|---|---|---|
| 2.147 | XK | 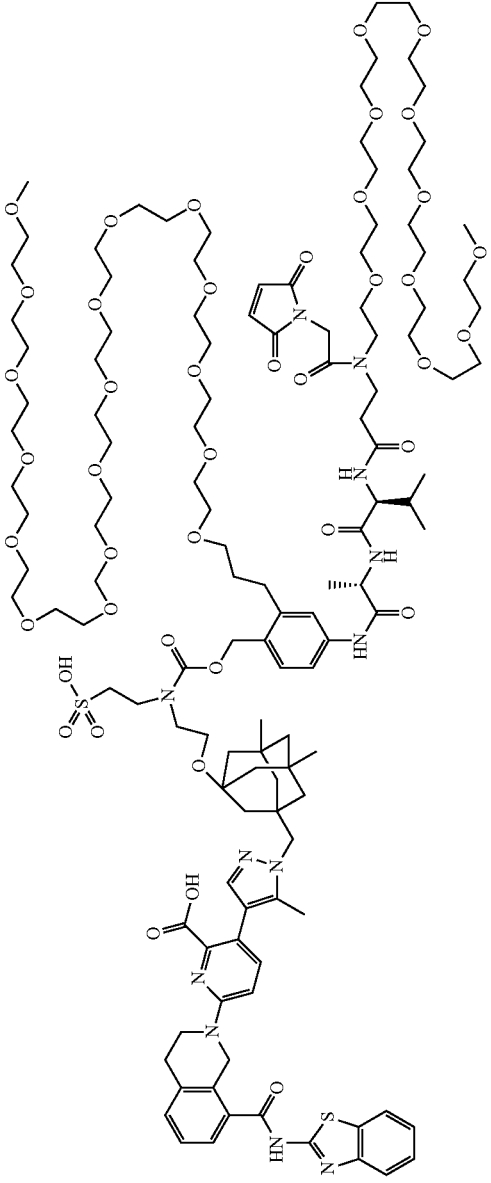 |
| 2.148 | XL | 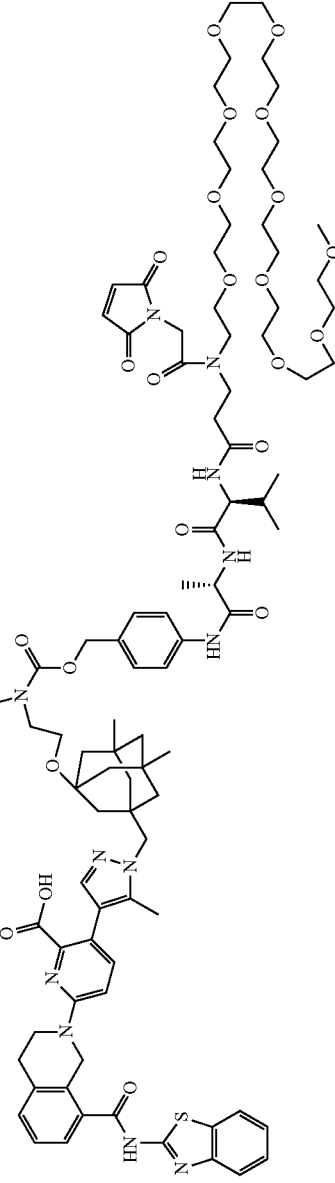 |

TABLE B-continued
| Example No. | Synthon Code | Synthon Structure |
|---|---|---|
| 2.149 | YJ | 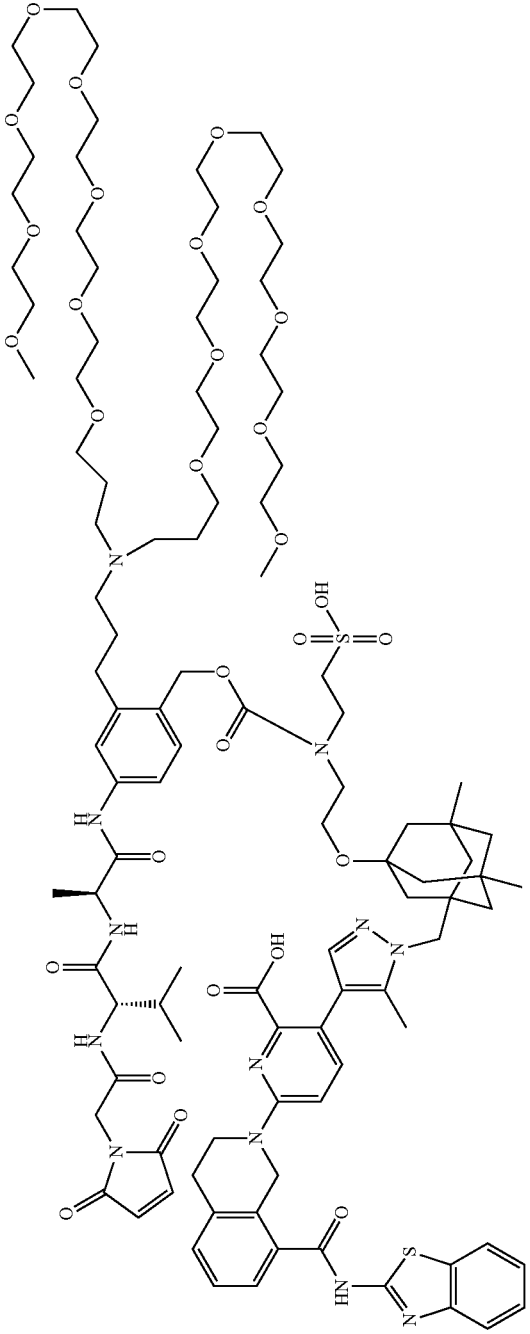 |
| 2.150 | YQ | 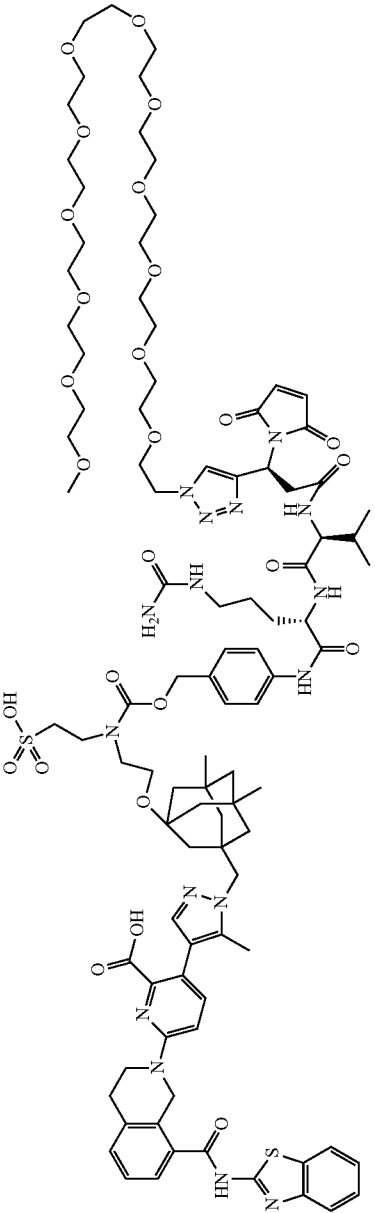 |

TABLE B-continued
Synthon Structure
| Example No. | Synthon Code |
|---|---|
| 2.151 | YR |
| 2.152 | YS |
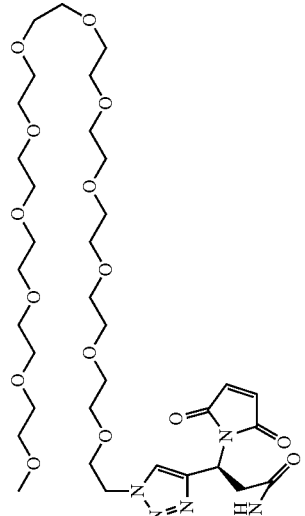

TABLE B-continued

Synthon Structure

| Example No. | Synthon Code |
|---|---|
| 2.153 | YY |
| 2.154 | YT |

TABLE B-continued

Synthon Structure

| Example No. | Synthon Code |
|---|---|
| 2.155 | YU |
| 2.156 | YV |

TABLE B-continued
| Example No. | Synthon Code | Synthon Structure |
|---|---|---|
| 2.157 | YW | 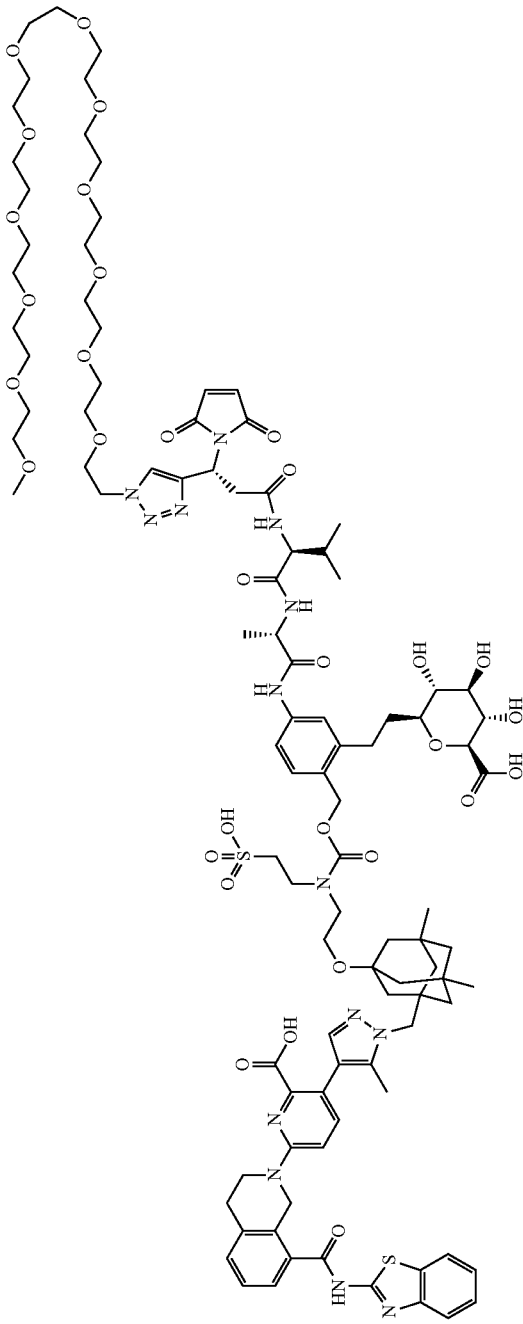 |
| 2.158 | ZB | 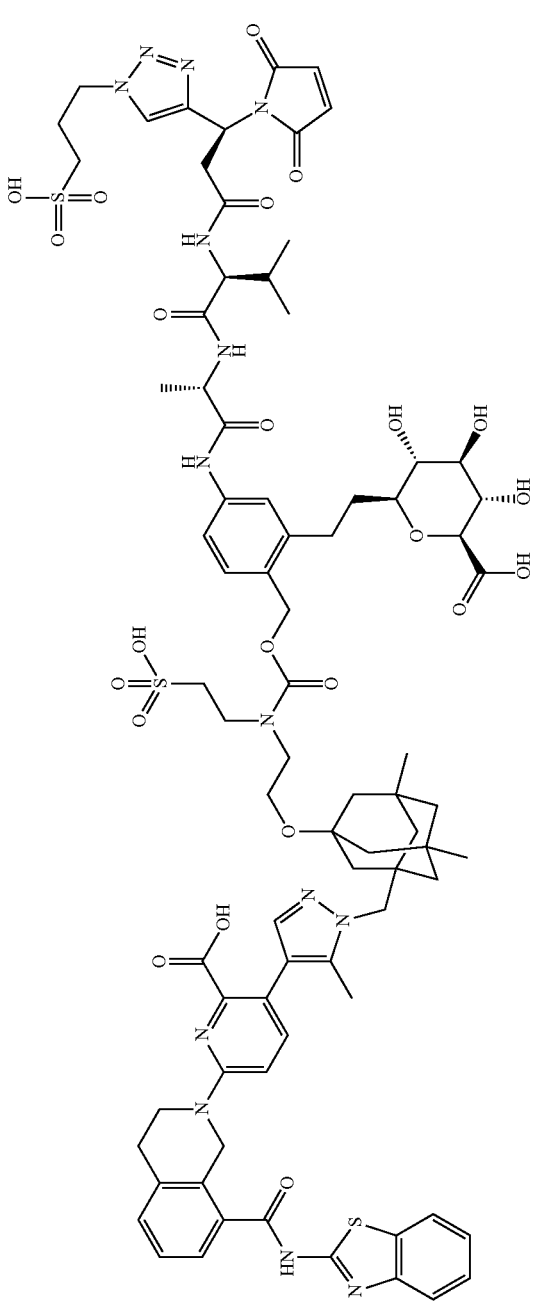 |

TABLE B-continued
| Example No. | Synthon Code | Synthon Structure |
|---|---|---|
| 2.159 | ZC | 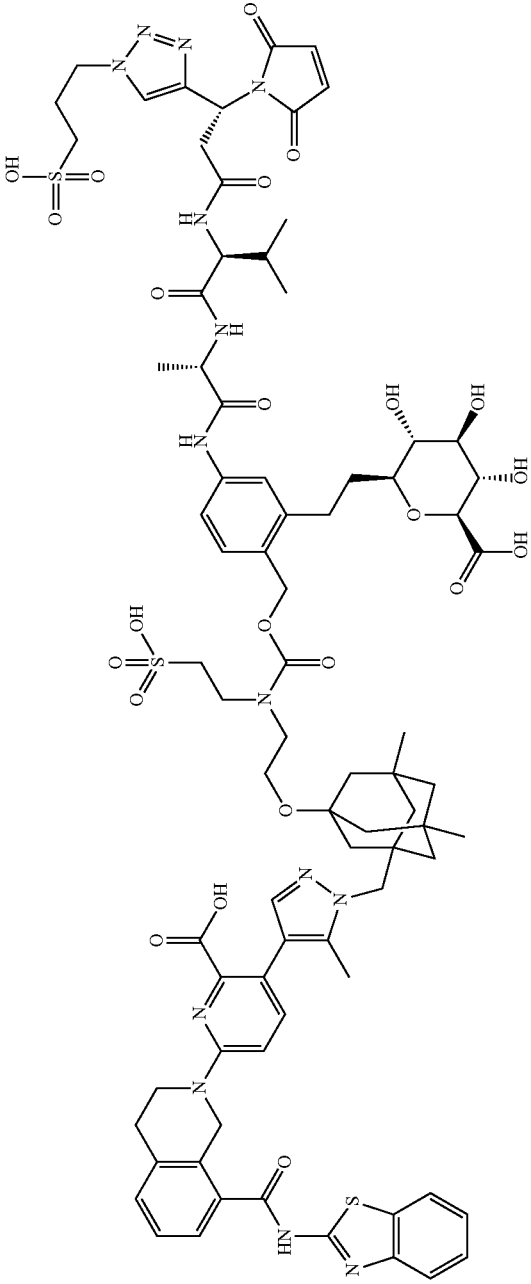 |
| 2.160 | ZJ | 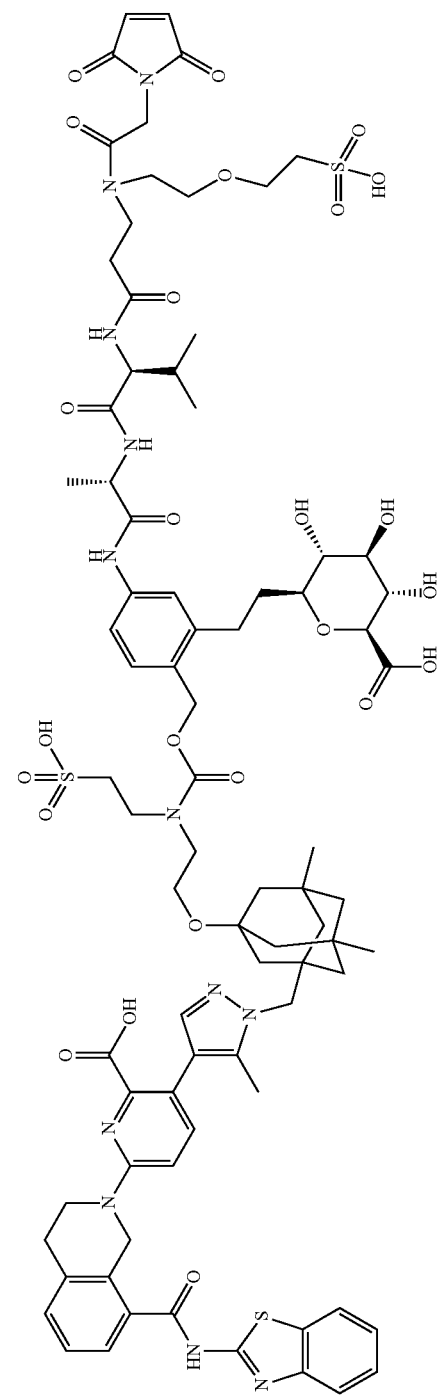 |

TABLE B-continued
| Example No. | Synthon Code | Synthon Structure |
|---|---|---|
| 2.161 | ZE | 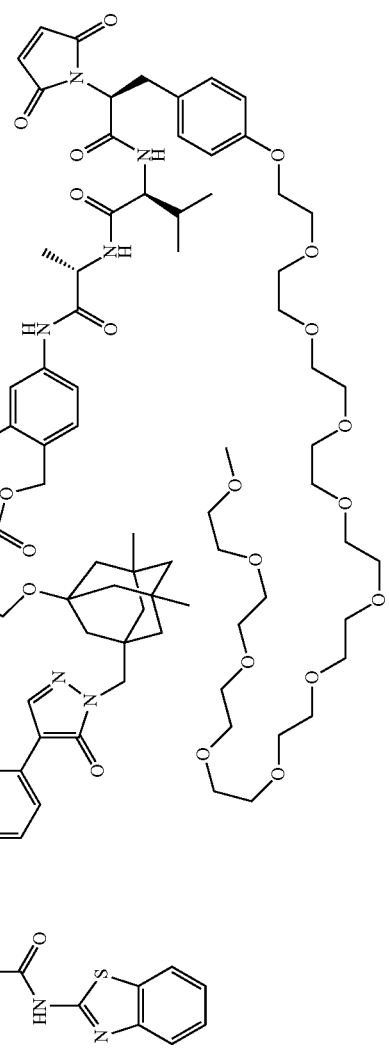 |

TABLE B-continued
| Example No. | Synthon Code | Synthon Structure |
|---|---|---|
| 2.162 | ZS | 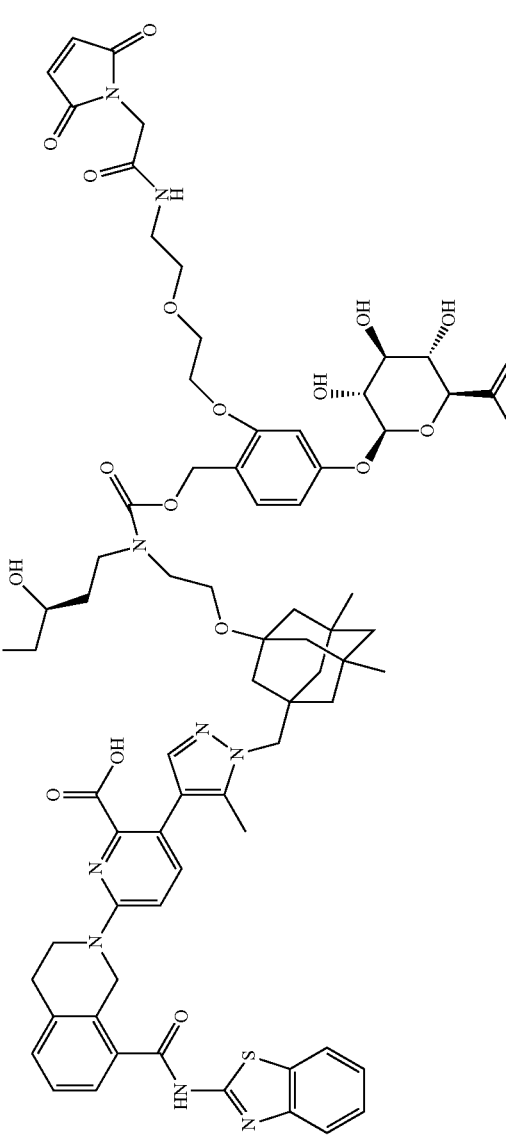 |
| 2.163 | ZW | 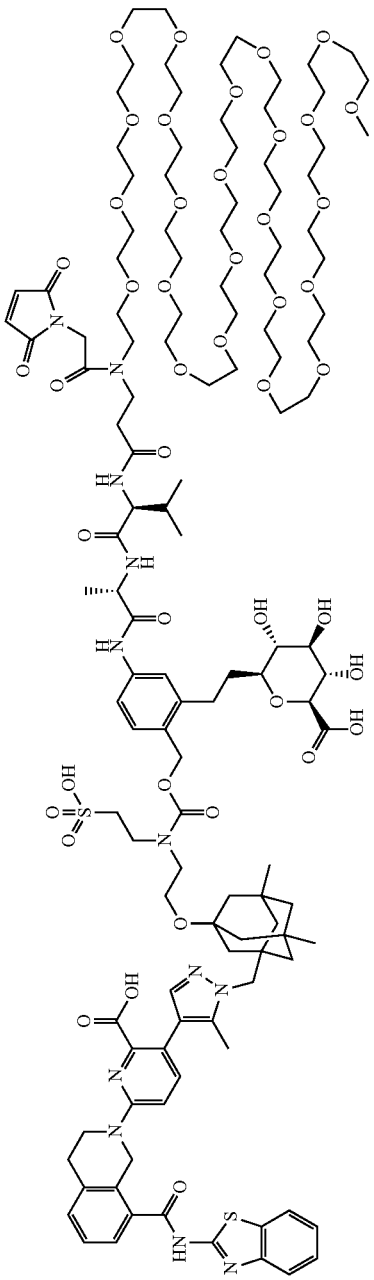 |

TABLE B-continued
| Example No. | Synthon Code | Synthon Structure |
|---|---|---|
| 2.164 | ZX | 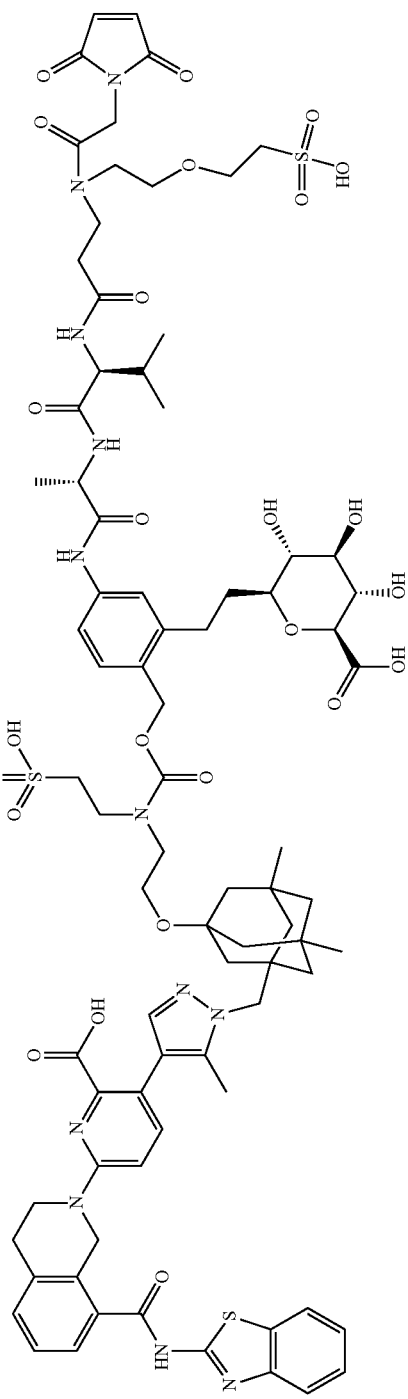 |
| 2.166 | AAA | 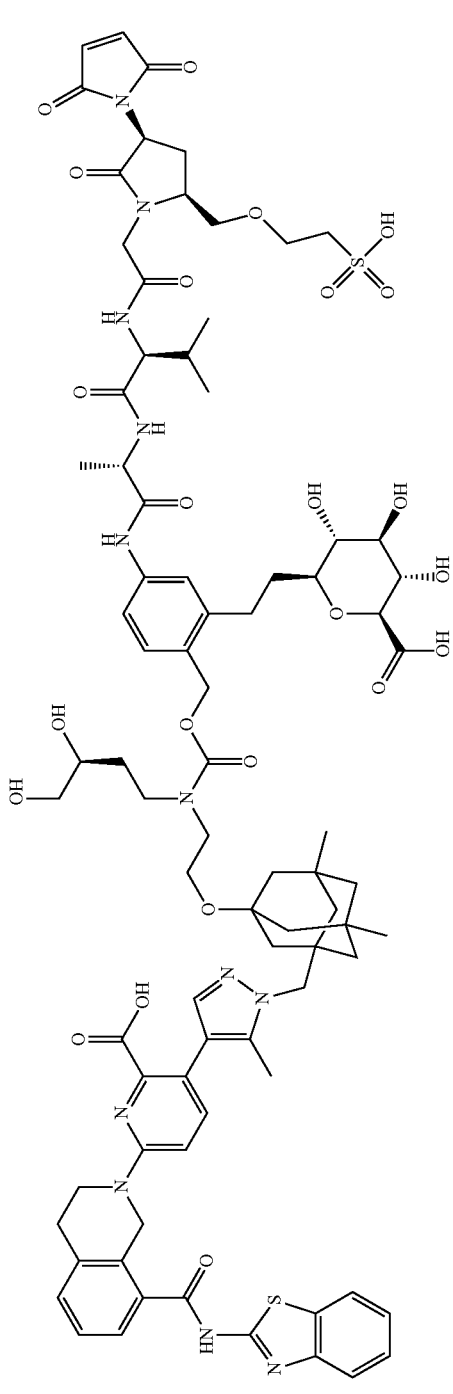 |

TABLE B-continued

| Example No. | Synthon Code | Synthon Structure |
|---|---|---|
| 2.167 | AAD | |
| 2.168 | AAE | |

TABLE B-continued

| Example No. | Synthon Code | Synthon Structure |
|---|---|---|
| 2.169 | ABG | |
| 2.170 | ABL | |

TABLE B-continued
| Example No. | Synthon Code | Synthon Structure |
|---|---|---|
| 2.171 | ABN | 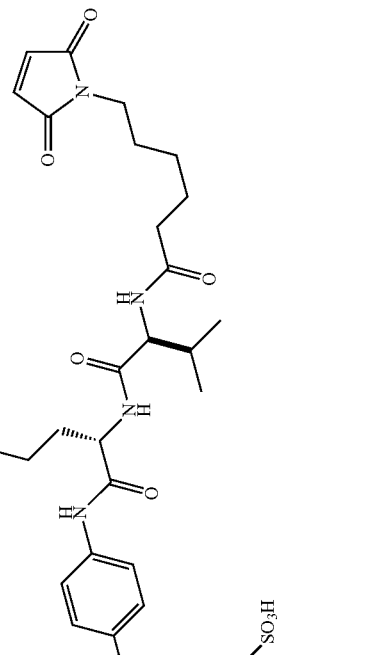 |
| 2.172 | AAF | 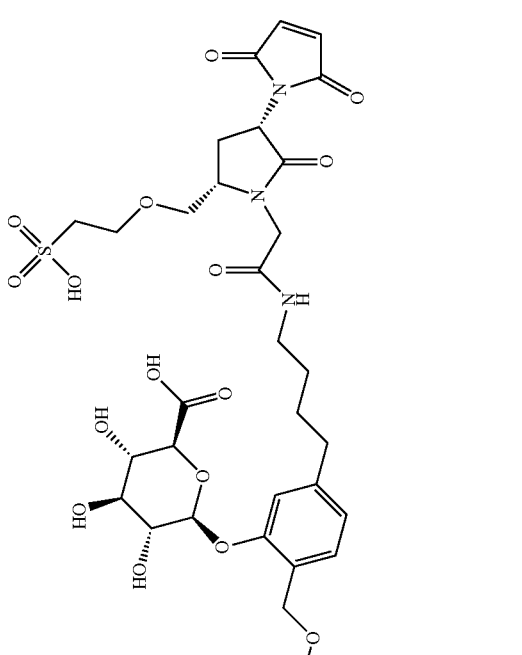 |

TABLE B-continued
Example No. | Synthon Code | Synthon Structure
---|---|---
2.173 | ABO | 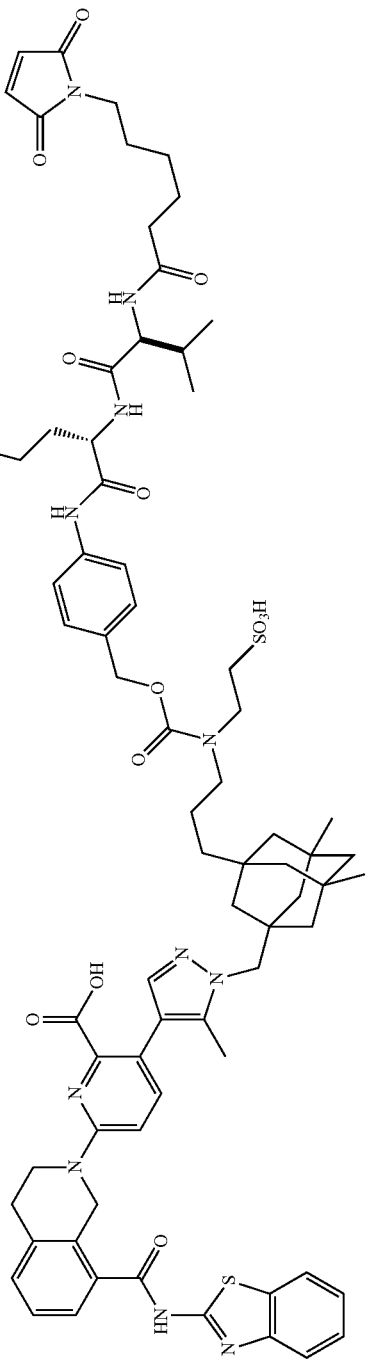

TABLE B-continued
| Example No. | Synthon Code | Synthon Structure |
|---|---|---|
| 2.174 | ABM | 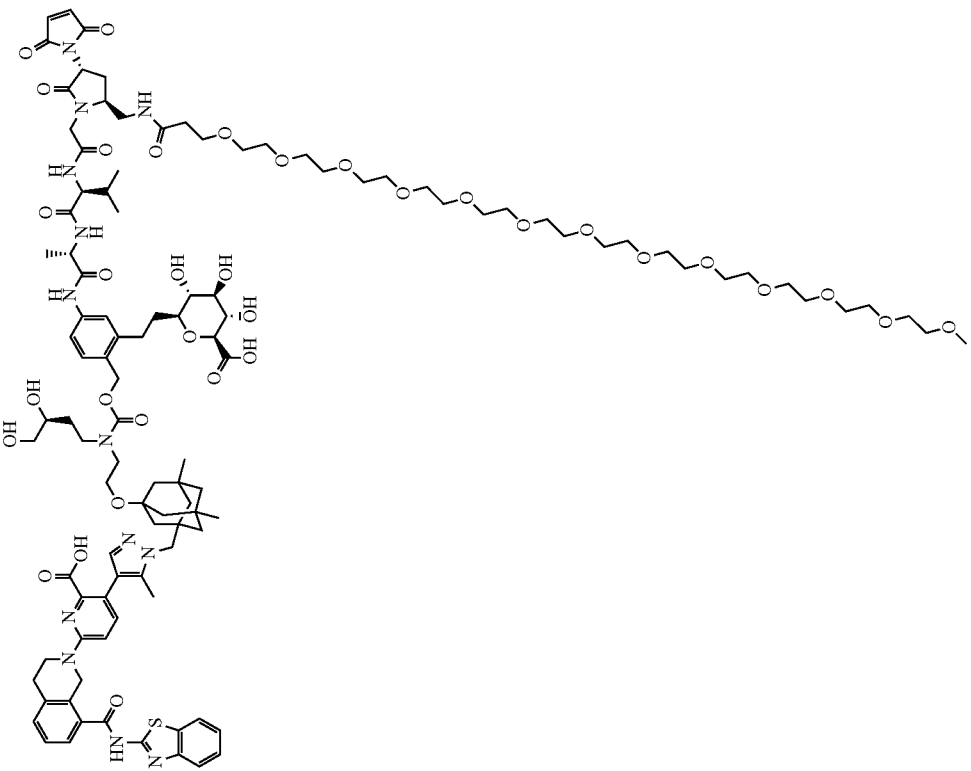 |

TABLE B-continued

| Example No. | Synthon Code | Synthon Structure |
|---|---|---|
| 2.175 | ABU | |
| 2.176 | ABV | |

TABLE B-continued

Synthon Structure

| Example No. | Synthon Code |
|---|---|
| 2.177 (control) | LB |
| 2.178 (control) | WD |

TABLE B-continued

| Example No. | Synthon Code | Synthon Structure |
|---|---|---|
| 2.179 (control) | ZZ | |
| 2.180 (control) | ZT | |

TABLE B-continued

| Example No. | Synthon Code | Synthon Structure |
|---|---|---|
| 2.181 (control) | XW | |
| 2.182 (control) | SE | |

TABLE B-continued
| Example No. | Synthon Code | Synthon Structure |
|---|---|---|
| 2.183 (control) | SR | 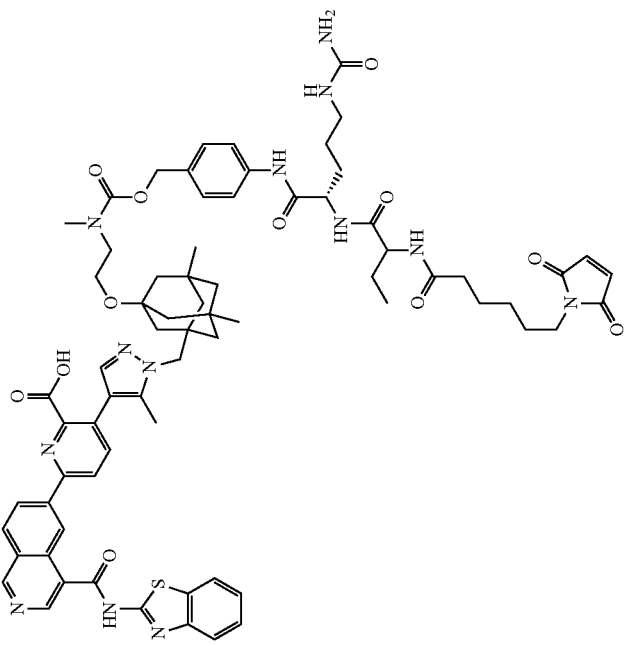 |
| 2.184 (control) | YG | 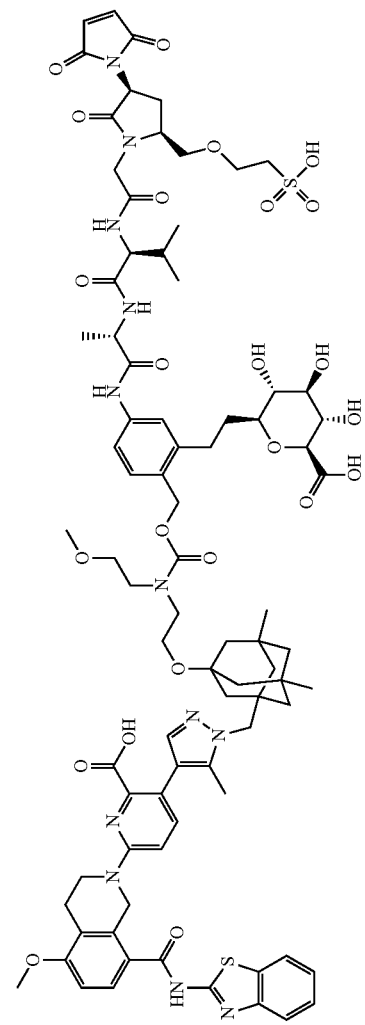 |

TABLE B-continued
| Example No. | Synthon Code | Synthon Structure |
|---|---|---|
| 2.185 (control) | KZ | 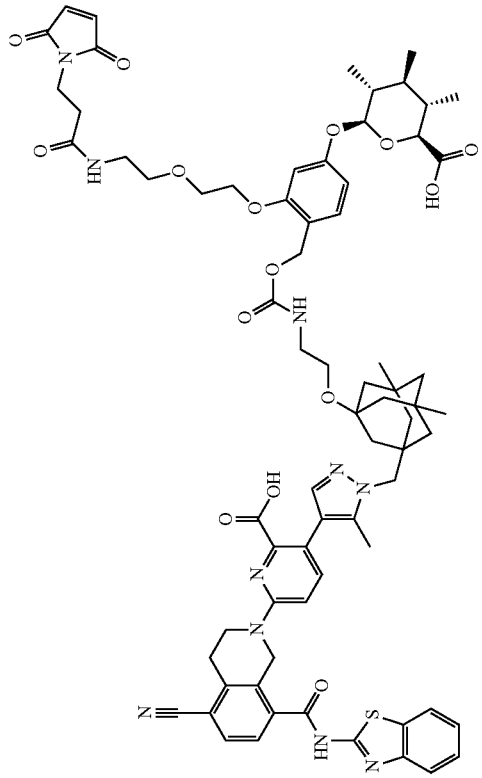 |

In certain embodiments, the synthon is selected from the group consisting of synthon examples 2.1, 2.2, 2.4, 2.5, 2.6, 2.7, 2.8, 2.9, 2.10, 2.11, 2.12, 2.13, 2.14, 2.15, 2.16, 2.17, 2.18, 2.19, 2.20, 2.21, 2.22, 2.23, 2.24, 2.25, 2.26, 2.27, 2.28, 2.29, 2.30, 2.31, 2.32, 2.33, 2.34, 2.35, 2.36, 2.37, 2.38, 2.39, 2.40, 2.41, 2.42, 2.43, 2.44, 2.45, 2.46, 2.47, 2.48, 2.49, 2.50, 2.51, 2.52, 2.53, 2.54, 2.55, 2.56, 2.57, 2.58, 2.59, 2.60, 2.61, 2.62, 2.63, 2.64, 2.65, 2.66, 2.67, 2.68, 2.69, 2.77, 2.78, 2.79, 2.80, 2.81, 2.82, 2.83, 2.84, 2.85, 2.86, 2.87, 2.88, 2.89, 2.90, 2.91, 2.92, 2.93, 2.94, 2.95, 2.96, 2.97, 2.98, 2.101, 2.102, 2.103, 2.104, 2.105, 2.106, 2.107, 2.108, 2.109, 2.110, 2.111, 2.112, 2.113, 2.114, 2.115, 2.116, 2.117, 2.118, 2.119, 2.120, 2.121, 2.122, 2.123, 2.124, 2.125, 2.126, 2.127, 2.128, 2.129, 2.130, 2.131, 2.132, 2.133, 2.134, 2.135, 2.136, 2.137, 2.138, 2.139, 2.140, 2.141, 2.142, 2.143, 2.144, 2.145, 2.146, 2.147, 2.148, 2.149, 2.150, 2.151, 2.152, 2.153, 2.154, 2.155, 2.156, 2.157, 2.158, 2.159, 2.160, 2.161, 2.162, 2.163, 2.164, 2.166, 2.167, 2.168, 2.169, 2.170, 2.171, 2.172, 2.173, 2.174, 2.175, and 2.176, or a pharmaceutically acceptable salt thereof. The compound names of these synthon are provided below:

N-[6-(2,5-dioxo-2,5-dihydro-1H-pyrrol-1-yl)hexanoyl]-L-valyl-N-{4-[({[2-({3-[(4-{6-[8-(1,3-benzothiazol-2-yl-carbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]phenyl}-N$^5$-carbamoyl-L-ornithinamide;

N-[6-(2,5-dioxo-2,5-dihydro-1H-pyrrol-1-yl)hexanoyl]-L-valyl-N-{4-[({[2-({3-[(4-{6-[8-(1,3-benzothiazol-2-yl-carbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](3-sulfopropyl)carbamoyl}oxy)methyl]phenyl}-N$^5$-carbamoyl-L-ornithinamide;

N-[6-(2,5-dioxo-2,5-dihydro-1H-pyrrol-1-yl)hexanoyl]-L-valyl-N-[4-({[{2-[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethoxy]ethyl}(2-sulfoethyl)carbamoyl]oxy}methyl)phenyl]-N$^5$-carbamoyl-L-ornithinamide;

methyl 6-[4-(3-{[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl]([4-({N-[6-(2,5-dioxo-2,5-dihydro-1H-pyrrol-1-yl)hexanoyl]-L-valyl-N$^5$-carbamoyl-L-ornithyl}amino)benzyl]oxy}carbonyl)amino}propyl)-1H-1,2,3-triazol-1-yl]-6-deoxy-beta-L-glucopyranoside;

N-[6-(2,5-dioxo-2,5-dihydro-1H-pyrrol-1-yl)hexanoyl]-L-valyl-N-(4-{[([2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl]{3-[1-(beta-D-glucopyranuronosyl)-1H-1,2,3-triazol-4-yl]propyl}carbamoyl)oxy]methyl}phenyl)-N$^5$-carbamoyl-L-ornithinamide;

N-[6-(2,5-dioxo-2,5-dihydro-1H-pyrrol-1-yl)hexanoyl]-L-valyl-N-{4-[({[(2R)-1-{[2-({3-[(4-{6-[8-(1,3-benzothi-azol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](methyl)amino}-1-oxo-3-sulfopropan-2-yl]carbamoyl}oxy)methyl]phenyl}-L-alaninamide;

N-[6-(2,5-dioxo-2,5-dihydro-1H-pyrrol-1-yl)hexanoyl]-L-valyl-N-{4-[({[2-({3-[(4-{6-[8-(1,3-benzothiazol-2-yl-carbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl][4-(beta-D-glucopyranosyloxy)benzyl]carbamoyl}oxy)methyl]phenyl}-N$^5$-carbamoyl-L-ornithinamide;

N-[6-(2,5-dioxo-2,5-dihydro-1H-pyrrol-1-yl)hexanoyl]-L-valyl-N-{4-[({[4-(beta-D-allopyranosyloxy)benzyl][2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl]carbamoyl}oxy)methyl]phenyl}-N$^5$-carbamoyl-L-ornithinamide;

N-[6-(2,5-dioxo-2,5-dihydro-1H-pyrrol-1-yl)hexanoyl]-L-valyl-N-{4-[({[2-({3-[(4-{6-[8-(1,3-benzothiazol-2-yl-carbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-phosphonoethyl)carbamoyl}oxy)methyl]phenyl}-N$^5$-carbamoyl-L-ornithinamide;

N-[6-(2,5-dioxo-2,5-dihydro-1H-pyrrol-1-yl)hexanoyl]-L-valyl-N-{4-[({[2-({3-[(4-{6-[8-(1,3-benzothiazol-2-yl-carbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-phosphonoethyl)carbamoyl}oxy)methyl]phenyl}-L-alaninamide;

N-[6-(2,5-dioxo-2,5-dihydro-1H-pyrrol-1-yl)hexanoyl]-L-valyl-N-{4-[({[2-({3-[(4-{6-[8-(1,3-benzothiazol-2-yl-carbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](3-phosphonopropyl)carbamoyl}oxy)methyl]phenyl}-N$^5$-carbamoyl-L-ornithinamide;

N-[6-(2,5-dioxo-2,5-dihydro-1H-pyrrol-1-yl)hexanoyl]-L-valyl-N-[4-({[{2-[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethoxy]ethyl}(3-phosphonopropyl)carbamoyl]oxy}methyl)phenyl]-N$^5$-carbamoyl-L-ornithinamide;

N-[6-(2,5-dioxo-2,5-dihydro-1H-pyrrol-1-yl)hexanoyl]-L-valyl-N-[4-({[{2-[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethoxy]ethyl}(3-phosphonopropyl)carbamoyl]oxy}methyl)phenyl]-L-alaninamide;

N-[6-(2,5-dioxo-2,5-dihydro-1H-pyrrol-1-yl)hexanoyl]-L-valyl-N-{4-[({[2-({3-[(4-{6-[8-(1,3-benzothiazol-2-yl-carbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](3-phosphonopropyl)carbamoyl}oxy)methyl]phenyl}-L-alaninamide;

6-[8-(1,3-benzothiazol-2-ylcarbamoyl)-3,4-dihydroisoquinolin-2(1H)-yl]-3-(1-{[3-(2-{[(2S)-3-carboxy-2-({[(4-{[(2S)-2-{[(2S)-2-{[6-(2,5-dioxo-2,5-dihydro-1H-pyrrol-1-yl)hexanoyl]amino}-3-methylbutanoyl]amino}propanoyl]amino}benzyl)oxy]carbonyl}amino)

propanoyl](methyl)amino}ethoxy)-5,7-dimethyltricyclo[3.3.1.1$^{3,7}$]dec-1-yl]methyl}-5-methyl-1H-pyrazol-4-yl)pyridine-2-carboxylic acid;

N-[6-(2,5-dioxo-2,5-dihydro-1H-pyrrol-1-yl)hexanoyl]-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl][4-(beta-D-glucopyranuronosyloxy)benzyl]carbamoyl}oxy)methyl]phenyl}-N$^5$-carbamoyl-L-ornithinamide;

N-[6-(2,5-dioxo-2,5-dihydro-1H-pyrrol-1-yl)hexanoyl]-L-valyl-N-{4-[({[2-({3-[(4-{6-[1-(1,3-benzothiazol-2-ylcarbamoyl)-1,2,3,4-tetrahydroquinolin-7-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-phosphonoethyl)carbamoyl}oxy)methyl]phenyl}-N$^5$-carbamoyl-L-ornithinamide;

N-[6-(2,5-dioxo-2,5-dihydro-1H-pyrrol-1-yl)hexanoyl]-L-valyl-N-{4-[({[2-({3-[(4-{2-carboxy-6-[8-([1,3]thiazolo[5,4-b]pyridin-2-ylcarbamoyl)-3,4-dihydroisoquinolin-2(1H)-yl]pyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]phenyl}-L-ornithinamide;

N-[6-(2,5-dioxo-2,5-dihydro-1H-pyrrol-1-yl)hexanoyl]-L-valyl-N-{4-[({[(2R)-1-{[2-({3-[(4-{6-[1-(1,3-benzothiazol-2-ylcarbamoyl)-1,2,3,4-tetrahydroquinolin-7-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](methyl)amino}-1-oxo-3-sulfopropan-2-yl]carbamoyl}oxy)methyl]phenyl}-N$^5$-carbamoyl-L-ornithinamide;

N-[6-(2,5-dioxo-2,5-dihydro-1H-pyrrol-1-yl)hexanoyl]-L-valyl-N-{4-[({[(2R)-1-{[2-({3-[(4-{6-[1-(1,3-benzothiazol-2-ylcarbamoyl)-1,2,3,4-tetrahydroquinolin-7-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](methyl)amino}-1-oxo-3-sulfopropan-2-yl]carbamoyl}oxy)methyl]phenyl}-L-alaninamide;

N-[6-(2,5-dioxo-2,5-dihydro-1H-pyrrol-1-yl)hexanoyl]-L-valyl-N$^5$-carbamoyl-N-{4-[({[2-({3-[(4-{2-carboxy-6-[8-([1,3]thiazolo[4,5-b]pyridin-2-ylcarbamoyl)-3,4-dihydroisoquinolin-2(1H)-yl]pyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]phenyl}-L-ornithinamide;

N-[6-(2,5-dioxo-2,5-dihydro-1H-pyrrol-1-yl)hexanoyl]-L-valyl-N-{4-[({[2-({3-[(4-{6-[1-(1,3-benzothiazol-2-ylcarbamoyl)-1,2,3,4-tetrahydroquinolin-7-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]phenyl}-N$^5$-carbamoyl-L-ornithinamide;

N-[6-(2,5-dioxo-2,5-dihydro-1H-pyrrol-1-yl)hexanoyl]-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-carboxyethyl)carbamoyl}oxy)methyl]phenyl}-N$^5$-carbamoyl-L-ornithinamide;

N-[6-(2,5-dioxo-2,5-dihydro-1H-pyrrol-1-yl)hexanoyl]-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-carboxyethyl)carbamoyl}oxy)methyl]phenyl}-L-alaninamide;

6-[8-(1,3-benzothiazol-2-ylcarbamoyl)-3,4-dihydroisoquinolin-2(1H)-yl]-3-(1-{[3-(2-{[(2R)-3-carboxy-2-({[(4-{[(2S)-2-{[(2S)-2-{[6-(2,5-dioxo-2,5-dihydro-1H-pyrrol-1-yl)hexanoyl]amino}-3-methylbutanoyl]amino}propanoyl]amino}benzyl)oxy]carbonyl}amino)propanoyl](methyl)amino}eth oxy)-5,7-dimethyltricyclo[3.3.1.1$^{3,7}$]dec-1-yl]methyl}-5-methyl-1H-pyrazol-4-yl)pyridine-2-carboxylic acid;

N-[6-(2,5-dioxo-2,5-dihydro-1H-pyrrol-1-yl)hexanoyl]-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl][1-(carboxymethyl)piperidin-4-yl]carbamoyl}oxy)methyl]phenyl}-N$^5$-carbamoyl-L-ornithinamide;

(S)-6-((2-((3-((4-(6-(8-(benzo[d]thiazol-2-ylcarbamoyl)-3,4-dihydroisoquinin-2(1H)-yl)-2-carboxypyridin-3-yl)-5-methyl-1H-pyrazol-1-yl)methyl)-5,7-dimethyladaman-tan-1-yl)oxy)ethyl)(methyl)amino)-5-((((4-((S)-2-((S)-2-(6-(2,5-dioxo-2,5-dihydro-1H-pyrrol-1-yl)hexanamido)-3-methylbutanamido)-5-ureidopentanamido)benzyl)oxy)carbonyl)amino)-N,N,N-trimethyl-6-oxohexan-1-aminium salt;

N-[6-(2,5-dioxo-2,5-dihydro-1H-pyrrol-1-yl)hexanoyl]-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]phenyl}-L-alaninamide;

N-[6-(2,5-dioxo-2,5-dihydro-1H-pyrrol-1-yl)hexanoyl]-L-valyl-N-[4-({[(4-{[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)amino}piperidin-1-yl)carbonyl]oxy}methyl)phenyl]-N$^5$-carbamoyl-L-ornithinamide;

N-[6-(2,5-dioxo-2,5-dihydro-1H-pyrrol-1-yl)hexanoyl]-L-valyl-N-{4-[({[2-({3-[(4-{6-[8-(1,3-benzothiazol-2-ylcarbamoyl)-5-(3-phosphonopropoxy)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](methyl)carbamoyl}oxy)methyl]phenyl}-N$^5$-carbamoyl-L-ornithinamide;

N-[6-(2,5-dioxo-2,5-dihydro-1H-pyrrol-1-yl)hexanoyl]-L-valyl-N-[4-({[(4-{[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](3-phosphonopropyl)amino}piperidin-1-yl)carbonyl]oxy}methyl)phenyl]-N$^5$-carbamoyl-L-ornithinamide;

N-[6-(2,5-dioxo-2,5-dihydro-1H-pyrrol-1-yl)hexanoyl]-L-valyl-N-{4-[({[2-({3-[(4-{6-[8-(1,3-benzothiazol-2-ylcarbamoyl)naphthalen-2-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](3-phosphonopropyl)carbamoyl}oxy)methyl]phenyl}-N$^5$-carbamoyl-L-ornithinamide;

N-[6-(2,5-dioxo-2,5-dihydro-1H-pyrrol-1-yl)hexanoyl]-L-valyl-N-[4-({[(4-{[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-carboxyethyl)amino}piperidin-1-yl)carbonyl]oxy}methyl)phenyl]-N$^5$-carbamoyl-L-ornithinamide;

N-[6-(2,5-dioxo-2,5-dihydro-1H-pyrrol-1-yl)hexanoyl]-L-valyl-N$^5$-{4-({[(4-{[2-({3-[(4-{2-carboxy-6-[8-([1,3]thiazolo[4,5-b]pyridin-2-ylcarbamoyl)-3,4-dihydroisoquinolin-2(1H)-yl]pyridin-3-yl}-5-methyl-1H-pyrazol-1-yl)methyl]-5,7-dimethyltricyclo[3.3.1.1$^{3,7}$]dec-1-yl}oxy)ethyl](3-phosphonopropyl)carbamoyl}oxy)methyl]phenyl}-L-ornithinamide;

N-[6-(2,5-dioxo-2,5-dihydro-1H-pyrrol-1-yl)hexanoyl]-L-valyl-N-{4-[({[2-({3-[(4-{2-carboxy-6-[8-([1,3]thiazolo[5,4-b]pyridin-2-ylcarbamoyl)-3,4-dihydroisoquinolin-2(1H)-yl]pyridin-3-yl}-5-methyl-1H-pyrazol-1-yl)methyl]-5,7-dimethyltricyclo[3.3.1.1$^{3,7}$]dec-1-yl}oxy)ethyl](3-phosphonopropyl)carbamoyl}oxy)methyl]phenyl}-L-ornithinamide;

N-{6-[(chloroacetyl)amino]hexanoyl}-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]phenyl}-L-alaninamide;

N-[6-(2,5-dioxo-2,5-dihydro-1H-pyrrol-1-yl)hexanoyl]-L-valyl-N-{4-[({[2-({3-[(4-{6-[8-(1,3-benzothiazol-2-ylcarbamoyl)-5-(carboxymethoxy)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](methyl)carbamoyl}oxy)methyl]phenyl}-N$^5$-carbamoyl-L-ornithinamide;

N-[6-(2,5-dioxo-2,5-dihydro-1H-pyrrol-1-yl)hexanoyl]-L-valyl-N-[4-({[(2-{[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)amino}ethyl)(2-carboxyethyl)carbamoyl]oxy}methyl)phenyl]-N$^5$-carbamoyl-L-ornithinamide;

6-[8-(1,3-benzothiazol-2-ylcarbamoyl)-3,4-dihydroisoquinolin-2(1H)-yl]-3-[1-({3-[2-({[(2S)-2-[{[(4-{[(2S)-5-(carbamoylamino)-2-{[(2S)-2-{[6-(2,5-dioxo-2,5-dihydro-1H-pyrrol-1-yl)hexanoyl]amino}-3-methylbutanoyl]amino}pentanoyl]amino}benzyl)oxy]carbonyl}(2-carboxyethyl)amino]-3-carboxypropanoyl}amino)ethoxy]-5,7-dimethyltricyclo[3.3.1.1$^{3,7}$]dec-1-yl}methyl)-5-methyl-1H-pyrazol-4-yl]pyridine-2-carboxylic acid;

6-[8-(1,3-benzothiazol-2-ylcarbamoyl)-3,4-dihydroisoquinolin-2(1H)-yl]-3-(1-{[3-(2-{[(2S)-2-({[(4-{[(2S)-5-(carbamoylamino)-2-{[(2S)-2-{[6-(2,5-dioxo-2,5-dihydro-1H-pyrrol-1-yl)hexanoyl]amino}-3-methylbutanoyl]amino}pentanoyl]amino}benzyl)oxy]carbonyl}amino)-3-carboxypropanoyl](2-sulfoethyl)amino}ethoxy)-5,7-dimethyltricyclo[3.3.1.1$^{3,7}$]dec-1-yl]methyl}-5-methyl-1H-pyrazol-4-yl)pyridine-2-carboxylic acid;

N-[6-(2,5-dioxo-2,5-dihydro-1H-pyrrol-1-yl)hexanoyl]-L-valyl-N-[4-({[(4-{[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](3-carboxypropyl)amino}piperidin-1-yl)carbonyl]oxy}methyl)phenyl]-N$^5$-carbamoyl-L-ornithinamide;

4-[(1E)-3-({[2-({3-[(4-{6-[8-(1,3-benzothiazol-2-ylcarbamoyl)-5-(carboxymethoxy)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](methyl)carbamoyl}oxy)prop-1-en-1-yl]-2-({N-[6-(2,5-dioxo-2,5-dihydro-1H-pyrrol-1-yl)hexanoyl]-beta-alanyl}amino)phenyl beta-D-glucopyranosiduronic acid;

N-[6-(2,5-dioxo-2,5-dihydro-1H-pyrrol-1-yl)hexanoyl]-L-valyl-N-{4-[({[2-({3-[(4-{6-[8-(1,3-benzothiazol-2-ylcarbamoyl)naphthalen-2-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]phenyl}-N$^5$-carbamoyl-L-ornithinamide;

N-[6-(2,5-dioxo-2,5-dihydro-1H-pyrrol-1-yl)hexanoyl]-L-valyl-N-[4-({[(2-{[8-(1,3-benzothiazol-2-ylcarbamoyl)-2-(6-carboxy-5-{1-[(3,5-dimethyl-7-{2-[methyl(2-sulfoethyl)amino]ethoxy}tricyclo[3.3.1.1$^{3,7}$]dec-1-yl)methyl]-5-methyl-1H-pyrazol-4-yl}pyridin-2-yl)-1,2,3,4-tetrahydroisoquinolin-5-yl]oxy}ethyl)carbamoyl]oxy}methyl)phenyl]-N$^5$-carbamoyl-L-ornithinamide;

N-[6-(2,5-dioxo-2,5-dihydro-1H-pyrrol-1-yl)hexanoyl]-L-valyl-N-[4-({[(2-{[8-(1,3-benzothiazol-2-ylcarbamoyl)-2-(6-carboxy-5-{1-[(3,5-dimethyl-7-{2-[methyl(2-sulfoethyl)amino]ethoxy}tricyclo[3.3.1.1$^{3,7}$]dec-1-yl)methyl]-5-methyl-1H-pyrazol-4-yl}pyridin-2-yl)-1,2,3,4-tetrahydroisoquinolin-5-yl]oxy}ethyl)(2-sulfoethyl)carbamoyl]oxy}methyl)phenyl]-N$^5$-carbamoyl-L-ornithinamide;

N-[6-(2,5-dioxo-2,5-dihydro-1H-pyrrol-1-yl)hexanoyl]-L-valyl-N-[4-({[(2-{[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)amino}ethyl)(2-sulfoethyl)carbamoyl]oxy}methyl)phenyl]-N$^5$-carbamoyl-L-ornithinamide;

N-{6-[(chloroacetyl)amino]hexanoyl}-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]phenyl}-N$^5$-carbamoyl-L-ornithinamide;

N-[6-(2,5-dioxo-2,5-dihydro-1H-pyrrol-1-yl)hexanoyl]-L-valyl-N-{4-[({[2-({3-[(4-{6-[4-(1,3-benzothiazol-2-ylcarbamoyl)-3,4-dihydro-2H-1,4-benzoxazin-6-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]phenyl}-N$^5$-carbamoyl-L-ornithinamide;

N-[6-(2,5-dioxo-2,5-dihydro-1H-pyrrol-1-yl)hexanoyl]-L-valyl-N-[4-({[(2-{[8-(1,3-benzothiazol-2-ylcarbamoyl)-2-(6-carboxy-5-{1-[(3,5-dimethyl-7-{2-[methyl(2-sulfoethyl)amino]ethoxy}tricyclo[3.3.1.1$^{3,7}$]dec-1-yl)methyl]-5-methyl-1H-pyrazol-4-yl}pyridin-2-yl)-1,2,3,4-tetrahydroisoquinolin-5-yl]oxy}ethyl)(2-carboxyethyl)carbamoyl]oxy}methyl)phenyl]-N$^5$-carbamoyl-L-ornithinamide;

N-[6-(2,5-dioxo-2,5-dihydro-1H-pyrrol-1-yl)hexanoyl]-L-valyl-N-{4-[({[2-({3-[(4-{6-[8-(1,3-benzothiazol-2-ylcarbamoyl)-5-(3-sulfopropoxy)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](methyl)carbamoyl}oxy)methyl]phenyl}-N$^5$-carbamoyl-L-ornithinamide;

N-[3-(2,5-dioxo-2,5-dihydro-1H-pyrrol-1-yl)propanoyl]-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]phenyl}-N$^5$-carbamoyl-L-ornithinamide;

N-[(2,5-dioxo-2,5-dihydro-1H-pyrrol-1-yl)acetyl]-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7- dimethyltricyclo[3.3.1.1$^{3,7}$]dec-1-yl}oxy)ethyl](2-sulfoethyl)carbamoyl}oxy)methyl]phenyl}-N$^5$-carbamoyl-L-ornithinamide;

6-[8-(1,3-benzothiazol-2-ylcarbamoyl)-3,4-dihydroisoquinolin-2(1H)-yl]-3-(1-{[3-(2-{[(2S)-2-({[(4-{[(2S,3R,4S,5S,6S)-6-carboxy-3,4,5-trihydroxytetrahydro-2H-pyran-2-yl]oxy}-3-[(3-{[6-(2,5-dioxo-2,5-dihydro-1H-pyrrol-1-yl)hexanoyl]amino}propanoyl)amino]benzyl)oxy]carbonyl}amino)-3-sulfopropanoyl](methyl)amino}ethoxy)-5,7-dimethyltricyclo[3.3.1.1$^{3,7}$]dec-1-yl]methyl}-5-methyl-1H-pyrazol-4-yl)pyridine-2-carboxylic acid;

4-[(1E)-3-({[2-({3-[(4-{2-carboxy-6-[8-([1,3]thiazolo[5,4-b]pyridin-2-ylcarbamoyl)-3,4-dihydroisoquinolin-2(1H)-yl]pyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)prop-1-en-1-yl]-2-({N-[6-(2,5-dioxo-2,5-dihydro-1H-pyrrol-1-yl)hexanoyl]-beta-alanyl}amino)phenyl beta-D-glucopyranosiduronic acid;

4-[(1E)-3-({[2-({3-[(4-{2-carboxy-6-[8-([1,3]thiazolo[4,5-b]pyridin-2-ylcarbamoyl)-3,4-dihydroisoquinolin-2(1H)-yl]pyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)prop-1-en-1-yl]-2-({N-[6-(2,5-dioxo-2,5-dihydro-1H-pyrrol-1-yl)hexanoyl]-beta-alanyl}amino)phenyl beta-D-glucopyranosiduronic acid;

4-[(1E)-3-({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)prop-1-en-1-yl]-2-({N-[6-(2,5-dioxo-2,5-dihydro-1H-pyrrol-1-yl)hexanoyl]-beta-alanyl}amino)phenyl beta-D-glucopyranosiduronic acid;

4-[(1E)-3-({[2-({3-[(4-{2-carboxy-6-[8-([1,3]thiazolo[5,4-b]pyridin-2-ylcarbamoyl)-3,4-dihydroisoquinolin-2(1H)-yl]pyridin-3-yl}-5-methyl-1H-pyrazol-1-yl)methyl]-5,7-dimethyltricyclo[3.3.1.1$^{3,7}$]dec-1-yl}oxy)ethyl](3-phosphonopropyl)carbamoyl}oxy)prop-1-en-1-yl]-2-({N-[6-(2,5-dioxo-2,5-dihydro-1H-pyrrol-1-yl)hexanoyl]-beta-alanyl}amino)phenyl beta-D-glucopyranosiduronic acid;

4-[(1E)-3-({{[2-({3-[(4-{6-[8-(1,3-benzothiazol-2-ylcarbamoyl)-5-(3-phosphonopropoxy)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](methyl)carbamoyl}oxy)prop-1-en-1-yl]-2-({N-[6-(2,5-dioxo-2,5-dihydro-1H-pyrrol-1-yl)hexanoyl]-beta-alanyl}amino)phenyl beta-D-glucopyranosiduronic acid;

4-[(1E)-3-({{[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](3-phosphonopropyl)carbamoyl}oxy)prop-1-en-1-yl]-2-({N-[6-(2,5-dioxo-2,5-dihydro-1H-pyrrol-1-yl)hexanoyl]-beta-alanyl}amino)phenyl beta-D-glucopyranosiduronic acid;

4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]-3-[2-(2-{[3-(2,5-dioxo-2,5-dihydro-1H-pyrrol-1-yl)propanoyl]amino}ethoxy)ethoxy]phenyl beta-D-glucopyranosiduronic acid;

4-[(1E)-3-({[2-({3-[(4-{2-carboxy-6-[8-([1,3]thiazolo[4,5-b]pyridin-2-ylcarbamoyl)-3,4-dihydroisoquinolin-2(1H)-yl]pyridin-3-yl}-5-methyl-1H-pyrazol-1-yl)methyl]-5,7-dimethyltricyclo[3.3.1.1$^{3,7}$]dec-1-yl}oxy)ethyl](3-phosphonopropyl)carbamoyl}oxy)prop-1-en-1-yl]-2-({N-[6-(2,5-dioxo-2,5-dihydro-1H-pyrrol-1-yl)hexanoyl]-beta-alanyl}amino)phenyl beta-D-glucopyranosiduronic acid;

6-[8-(1,3-benzothiazol-2-ylcarbamoyl)-3,4-dihydroisoquinolin-2(1H)-yl]-3-{1-[(3-{2-[(2-carboxyethyl)({[(2E)-3-(4-{[(2S,3R,4S,5S,6S)-6-carboxy-3,4,5-trihydroxytetrahydro-2H-pyran-2-yl]oxy}-3-[(3-([6-(2,5-dihydro-1H-pyrrol-1-yl)hexanoyl]amino}propanoyl)amino]phenyl)prop-2-en-1-yl]oxy}carbonyl)amino]ethoxy}-5,7-dimethyltricyclo[3.3.1.1$^{3,7}$]dec-1-yl)methyl]-5-methyl-1H-pyrazol-4-yl}pyridine-2-carboxylic acid;

6-[8-(1,3-benzothiazol-2-ylcarbamoyl)-3,4-dihydroisoquinolin-2(1H)-yl]-3-{1-[(3-{2-[(2-carboxyethyl){[(4-{[(2S,3R,4S,5S,6S)-6-carboxy-3,4,5-trihydroxytetrahydro-2H-pyran-2-yl]oxy}-2-[2-(2-{[3-(2,5-dioxo-2,5-dihydro-1H-pyrrol-1-yl)propanoyl]amino}ethoxy)ethoxy]benzyl)oxy]carbonyl}amino]ethoxy}-5,7-dimethyltricyclo[3.3.1.1$^{3,7}$]dec-1-yl)methyl]-5-methyl-1H-pyrazol-4-yl}pyridine-2-carboxylic acid;

N-[6-(ethenylsulfonyl)hexanoyl]-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]phenyl}-N$^5$-carbamoyl-L-ornithinamide;

4-[(1E)-3-{[(4-{[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](3-phosphonopropyl)amino}piperidin-1-yl)carbonyl]oxy}prop-1-en-1-yl]-2-({N-[6-(2,5-dioxo-2,5-dihydro-1H-pyrrol-1-yl)hexanoyl]-beta-alanyl}amino)phenyl beta-D-glucopyranosiduronic acid;

4-[(1E)-3-{[(4-{[2-({3-[(4-{2-carboxy-6-[8-([1,3]thiazolo[4,5-b]pyridin-2-ylcarbamoyl)-3,4-dihydroisoquinolin-2(1H)-yl]pyridin-3-yl}-5-methyl-1H-pyrazol-1-yl)methyl]-5,7-dimethyltricyclo[3.3.1.1$^{3,7}$]dec-1-yl}oxy)ethyl](3-phosphonopropyl)amino}piperidin-1-yl)carbonyl]oxy}prop-1-en-1-yl]-2-({N-[6-(2,5-dioxo-2,5-dihydro-1H-pyrrol-1-yl)hexanoyl]-beta-alanyl}amino)phenyl beta-D-glucopyranosiduronic acid;

4-[(1E)-3-({[2-({[3-[(4-{6-[8-(1,3-benzothiazol-2-ylcarbamoyl)naphthalen-2-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)prop-1-en-1-yl]-2-({N-[6-(2,5-dioxo-2,5-dihydro-1H-pyrrol-1-yl)hexanoyl]-beta-alanyl}amino)phenyl beta-D-glucopyranosiduronic acid;

6-[8-(1,3-benzothiazol-2-ylcarbamoyl)-3,4-dihydroisoquinolin-2(1H)-yl]-3-[1-({3-[2-({N-[6-(2,5-dioxo-2,5-dihydro-1H-pyrrol-1-yl)hexanoyl]-3-sulfo-L-alanyl}amino)ethoxy]-5,7-dimethyltricyclo[3.3.1.1$^{3,7}$]dec-1-yl}methyl)-5-methyl-1H-pyrazol-4-yl]pyridine-2-carboxylic acid; 6-[8-(1,3-benzothiazol-2-ylcarbamoyl)-3,4-dihydroisoquinolin-2(1H)-yl]-3-[1-({3-[2-(2-{[6-(2,5-dioxo-2,5-dihydro-1H-pyrrol-1-yl)hexanoyl](2-sulfoethyl)amino}ethoxy)ethoxy]-5,7-dimethyltricyclo[3.3.1.1$^{3,7}$]dec-1-yl}methyl)-5-methyl-1H-pyrazol-4-yl]pyridine-2-carboxylic acid;

6-[8-(1,3-benzothiazol-2-ylcarbamoyl)-3,4-dihydroisoquinolin-2(1H)-yl]-3-(1-{[3-(2-{[6-(2,5-dioxo-2,5-dihydro-1H-pyrrol-1-yl)hexanoyl](2-sulfoethyl)amino}ethoxy)-5, 7-dimethyltricyclo[3.3.1.1$^{3,7}$]dec-1-yl]methyl}-5-methyl-1H-pyrazol-4-yl)pyridine-2-carboxylic acid;

6-[8-(1,3-benzothiazol-2-ylcarbamoyl)-3,4-dihydroisoquinolin-2(1H)-yl]-3-{1-[(3-{[1-(2,5-dioxo-2,5-dihydro-1H-pyrrol-1-yl)-21-oxo-22-(2-sulfoethyl)-3,6,9,12,15,18-hexaoxa-22-azatetracosan-24-yl]oxy}-5,7-dimethyltricyclo[3.3.1.1$^{3,7}$]dec-1-yl)methyl]-5-methyl-1H-pyrazol-4-yl}pyridine-2-carboxylic acid;

6-[8-(1,3-benzothiazol-2-ylcarbamoyl)-3,4-dihydroisoquinolin-2(1H)-yl]-3-{1-[(3-{[1-(2,5-dioxo-2,5-dihydro-1H-pyrrol-1-yl)-21-oxo-22-(2-sulfoethyl)-3,6,9,12,15,18,25-heptaoxa-22-azaheptacosan-27-yl]oxy}-5,7-dimethyltricyclo[3.3.1.1$^{3,7}$]dec-1-yl)methyl]-5-methyl-1H-pyrazol-4-yl}pyridine-2-carboxylic acid;

6-[8-(1,3-benzothiazol-2-ylcarbamoyl)-3,4-dihydroisoquinolin-2(1H)-yl]-3-(1-{[3-(2-{[6-(ethenylsulfonyl)hexanoyl](2-sulfoethyl)amino}ethoxy)-5,7-dimethyltricyclo[3.3.1.1$^{3,7}$]dec-1-yl]methyl}-5-methyl-1H-pyrazol-4-yl)pyridine-2-carboxylic acid;

6-[8-(1,3-benzothiazol-2-ylcarbamoyl)-3,4-dihydroisoquinolin-2(1H)-yl]-3-{1-[(3-{2-[{6-[(chloroacetyl)amino]hexanoyl}(2-sulfoethyl)amino]ethoxy}-5,7-dimethyltricyclo[3.3.1.1$^{3,7}$]dec-1-yl)methyl]-5-methyl-1H-pyrazol-4-yl}pyridine-2-carboxylic acid;

N-[6-(2,5-dioxo-2,5-dihydro-1H-pyrrol-1-yl)hexanoyl]-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](3-carboxypropyl)carbamoyl}oxy)methyl]phenyl}-N$^5$-carbamoyl-L-ornithinamide;

N-{6-[(bromoacetyl)amino]hexanoyl}-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]phenyl}-N$^5$-carbamoyl-L-ornithinamide;

4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](3-carboxypropyl)carbamoyl}oxy)methyl]-3-[2-(2-{[3-(2,5-dioxo-2,5-dihydro-1H-pyrrol-1-yl)propanoyl]amino}ethoxy)ethoxy]phenyl beta-D-glucopyranosiduronic acid;

4-({[(4-{[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](3-carboxypropyl)amino}piperidin-1-yl)carbonyl]oxy}methyl)-3-[2-(2-{[3-(2,5-dioxo-2,5-dihydro-1H-pyrrol-1-yl)propanoyl]amino}ethoxy)ethoxy]phenyl beta-D-glucopyranosiduronic acid;

4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](3-sulfopropyl)carbamoyl}oxy)methyl]-3-[2-(2-{[3-(2,5-dioxo-2,5-dihydro-1H-pyrrol-1-yl)propanoyl]amino}ethoxy)ethoxy]phenyl beta-D-glucopyranosiduronic acid;

N-[6-(2,5-dioxo-2,5-dihydro-1H-pyrrol-1-yl)hexanoyl]-L-valyl-N-[4-({[(3-{[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)amino}azetidin-1-yl)carbonyl]oxy}methyl)phenyl]-N$^5$-carbamoyl-L-ornithinamide;

6-[8-(1,3-benzothiazol-2-ylcarbamoyl)-3,4-dihydroisoquinolin-2(1H)-yl]-3-{1-[(3-{[26-(2,5-dioxo-2,5-dihydro-1H-pyrrol-1-yl)-8,24-dioxo-3-(2-sulfoethyl)-11,14,17,20-tetraoxa-3,7,23-triazahexacos-1-yl]oxy}-5,7-dimethyltricyclo[3.3.1.1$^{3,7}$]dec-1-yl)methyl]-5-methyl-1H-pyrazol-4-yl}pyridine-2-carboxylic acid;

N-[6-(2,5-dioxo-2,5-dihydro-1H-pyrrol-1-yl)hexanoyl]-L-valyl-N-[4-({[(3-{[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)amino}prop yl)carbamoyl]oxy}methyl)phenyl]-N$^5$-carbamoyl-L-ornithinamide;

N-{6-[(iodoacetyl)amino]hexanoyl}-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]phenyl}-N$^5$-carbamoyl-L-ornithinamide;

N-{6-[(ethenylsulfonyl)amino]hexanoyl}-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]phenyl}-N$^5$-carbamoyl-L-ornithinamide;

N-{6-[(ethenylsulfonyl)amino]hexanoyl}-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]phenyl}-N$^5$-carbamoyl-L-ornithinamide;

6-[8-(1,3-benzothiazol-2-ylcarbamoyl)-3,4-dihydroisoquinolin-2(1H)-yl]-3-{1-[(3-{2-[(3-{[6-(ethenylsulfonyl)hexanoyl]amino}propyl)(2-sulfoethyl)amino]ethoxy}-5,7-dimethyltricyclo[3.3.1.1$^{3,7}$]dec-1-yl)methyl]-5-methyl-1H-pyrazol-4-yl}pyridine-2-carboxylic acid;

N-[3-(2,5-dioxo-2,5-dihydro-1H-pyrrol-1-yl)propanoyl]-L-valyl-N-{4-[({[2-({3-[(4-{6-[1-(1,3-benzothiazol-2-ylcarbamoyl)-1,2,3,4-tetrahydroquinolin-7-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]phenyl}-N$^5$-carbamoyl-L-ornithinamide;

6-[8-(1,3-benzothiazol-2-ylcarbamoyl)-3,4-dihydroisoquinolin-2(1H)-yl]-3-{1-[(3-{2-[(2-carboxyethyl) {[(2-{[(2S,3R,4S,5S,6S)-6-carboxy-3,4,5-trihydroxytetrahydro-2H-pyran-2-yl]oxy}-4-[2-(2-{[3-(2,5-dioxo-2,5-dihydro-1H-pyrrol-1-yl)propanoyl]amino}ethoxy)ethoxy]benzyl)oxy]carbonyl}amino]ethoxy}-5,7-dimethyltricyclo[3.3.1.1$^{3,7}$]dec-1-yl)methyl]-5-methyl-1H-pyrazol-4-yl}pyridine-2-carboxylic acid;

N-[6-(2,5-dioxo-2,5-dihydro-1H-pyrrol-1-yl)hexanoyl]-3-sulfo-L-alanyl-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-carboxyethyl)carbamoyl}oxy)methyl]phenyl}-N-carbamoyl-L-ornithinamide;

6-[8-(1,3-benzothiazol-2-ylcarbamoyl)-3,4-dihydroisoquinolin-2(1H)-yl]-3-{1-[(3-{[(43S,46S)-43-({[(4-{[(2S)-2-{[(2S)-2-{[6-(2,5-dioxo-2,5-dihydro-1H-pyrrol-1-yl)hexanoyl]amino}-3-methylbutanoyl]amino}propanoyl]amino}benzyl)oxy]carbonyl}amino)-46-methyl-37,44,47-trioxo-2,5,8,11,14,17,20,23,26,29,32,35-dodecaoxa- 38,45,48-triazapentacontan-50-yl]oxy}-5,7-dimethyltricyclo[3.3.1.1$^{3,7}$]dec-1-yl)methyl]-5-methyl-1H-pyrazol-4-yl}pyridine-2-carboxylic acid;

N-[6-(2,5-dioxo-2,5-dihydro-1H-pyrrol-1-yl)hexanoyl]-L-valyl-N-{4-[({[2-({3-[(4-{6-[1-(1,3-benzothiazol-2-yl-carbamoyl)-1,2,3,4-tetrahydroquinolin-7-yl]-2-carboxy-pyridin-3-yl}-5-methyl-1H-pyrazol-1-yl)methyl]-5,7-dimethyltricyclo[3.3.1.1$^{3,7}$]dec-1-yl}oxy)ethyl](2-carboxyethyl)carbamoyl}oxy)methyl]phenyl}-N$^5$-carbamoyl-L-ornithinamide;

N-[6-(2,5-dioxo-2,5-dihydro-1H-pyrrol-1-yl)hexanoyl]-L-valyl-N-{4-[({[2-({3-[(4-{6-[8-(1,3-benzothiazol-2-yl-carbamoyl)naphthalen-2-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-carboxyethyl)carbamoyl}oxy)methyl]phenyl}-N$^5$-carbamoyl-L-ornithinamide;

6-[8-(1,3-benzothiazol-2-ylcarbamoyl)naphthalen-2-yl]-3-{1-[(3-{2-[(2-carboxyethyl) {(2-{[(2R,3S,4R,5R,6R)-6-carboxy-3,4,5-trihydroxytetrahydro-2H-pyran-2-yl]oxy}-4-[2-(2-{[6-(2,5-dioxo-2,5-dihydro-1H-pyrrol-1-yl)hexanoyl]amino}ethoxy)ethoxy]benzyl)oxy]carbonyl}amino]ethoxy}-5,7-dimethyltricyclo[3.3.1.1$^{3,7}$]dec-1-yl)methyl]-5-methyl-1H-pyrazol-4-yl}pyridine-2-carboxylic acid;

N-[6-(2,5-dioxo-2,5-dihydro-1H-pyrrol-1-yl)hexanoyl]-L-valyl-N-{4-[({[2-({3-[(4-{6-[5-(1,3-benzothiazol-2-yl-carbamoyl)quinolin-3-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoy}oxy)methyl]phenyl}-N$^5$-carbamoyl-L-ornithinamide;

N-[6-(2,5-dioxo-2,5-dihydro-1H-pyrrol-1-yl)hexanoyl]-L-valyl-N-{4-[({[2-({3-[(4-{6-[4-(1,3-benzothiazol-2-yl-carbamoyl)quinolin-6-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-carboxyethyl)carbamoyl}oxy)methyl]phenyl}-N$^5$-carbamoyl-L-ornithinamide;

N-[6-(2,5-dioxo-2,5-dihydro-1H-pyrrol-1-yl)hexanoyl]-L-valyl-N-{4-[({[2-({3-[(4-{6-[4-(1,3-benzothiazol-2-yl-carbamoyl)quinolin-6-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]phenyl}-N$^5$-carbamoyl-L-ornithinamide;

N-[6-(2,5-dioxo-2,5-dihydro-1H-pyrrol-1-yl)hexanoyl]-L-valyl-N-{4-[({[2-({3-[(4-{6-[5-(1,3-benzothiazol-2-yl-carbamoyl)quinolin-3-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-carboxyethyl)carbamoyl}oxy)methyl]phenyl}-N$^5$-carbamoyl-L-ornithinamide;

N-[6-(2,5-dioxo-2,5-dihydro-1H-pyrrol-1-yl)hexanoyl]-L-valyl-N-{4-[({[2-({3-[(4-{6-[1-(1,3-benzothiazol-2-yl-carbamoyl)-5,6-dihydroimidazo[1,5-a]pyrazin-7(8H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]phenyl}-N$^5$-carbamoyl-L-ornithinamide;

N-[6-(2,5-dioxo-2,5-dihydro-1H-pyrrol-1-yl)hexanoyl]-L-valyl-N-{4-[({[2-({3-[(4-{6-[7-(1,3-benzothiazol-2-yl-carbamoyl)-1H-indol-2-yl]-2-carboxypyridin-3-yl}-5-methyl-H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]phenyl}-N$^5$-carbamoyl-L-ornithinamide;

N-[6-(2,5-dioxo-2,5-dihydro-1H-pyrrol-1-yl)hexanoyl]-L-valyl-N-[4-({[{3-[8-(1,3-benzothiazol-2-ylcarbamoyl)-2-(6-carboxy-5-{1-[(3,5-dimethyl-7-{2-[(2-sulfoethyl)amino]ethoxy}tricyclo[3.3.1.1$^{3,7}$]dec-1-yl)methyl]-5-methyl-1H-pyrazol-4-yl}pyridin-2-yl)-1,2,3,4-tetrahydroisoquinolin-6-yl]propyl}(methyl)carbamoyl]oxy}methyl)phenyl]-N$^5$-carbamoyl-L-ornithinamide;

N-(6-{[((2,5-dioxo-2,5-dihydro-1H-pyrrol-1-yl) acetyl]amino}hexanoyl)-L-valyl-N-{4-[(1 [2-(13-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-11-yl}oxy)ethyl](2-sulfoethyl)carbamoyl}oxy)methyl]phenyl}-N$^5$-carbamoyl-L-ornithinamide;

N-[6-(2,5-dioxo-2,5-dihydro-1H-pyrrol-1-yl)hexanoyl]-L-valyl-N-(4-[(([2-((3-[(4-{6-[8-(1,3-benzothiazol-2-ylcarbamoyl)naphthalen-2-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl][3-(beta-L-glucopyranuronosyloxy)propyl]carbamoyl}oxy)methyl]phenyl}-N$^5$-carbamoyl-L-ornithinamide;

N-[6-(2,5-dioxo-2,5-dihydro-1H-pyrrol-1-yl)hexanoyl]-L-valyl-N-(4-[(([2-((3-[(4-{6-[4-(1,3-benzothiazol-2-ylcarbamoyl)isoquinolin-6-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]phenyl}-N$^5$-carbamoyl-L-ornithinamide;

N-[6-(2,5-dioxo-2,5-dihydro-1H-pyrrol-1-yl)hexanoyl]-L-alpha-glutamyl-L-valyl-N-{4-[(1 [2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]phenyl}-N$^5$-carbamoyl-L-ornithinamide;

N-[(2,5-dioxo-2,5-dihydro-1H-pyrrol-1-yl)acetyl]-L-alpha-glutamyl-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]phenyl}-N$^5$-carbamoyl-L-ornithinamide;

1-{[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl]({[4-({N-[6-(2,5-dioxo-2,5-dihydro-1H-pyrrol-1-yl)hexanoyl]-D-valyl-N$^5$-carbamoyl-D-ornithyl}amino)benzyl]oxy}carbonyl)amino}-1,2-dideoxy-D-arabino-hexitol;

N-[6-(2,5-dioxo-2,5-dihydro-1H-pyrrol-1-yl)hexanoyl]-L-valyl-N-(4-[(([2-((3-[(4-{6-[4-(1,3-benzothiazol-2-ylcarbamoyl)-2-oxidoisoquinolin-6-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](methyl)carbamoyl}oxy)methyl]phenyl}-N$^5$-carbamoyl-L-ornithinamide;

N-({(3S,5S)-3-(2,5-dioxo-2,5-dihydro-1H-pyrrol-1-yl)-2-oxo-5-[(2-sulfoethoxy)methyl]pyrrolidin-1-yl}acetyl)-L-valyl-N-{4-[({[2-({3-[(4-{6-[8-(1,3-benzothiazol-2-yl-carbamoyl)naphthalen-2-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]phenyl}-N$^5$-carbamoyl-L-ornithinamide;

N-{(2S)-2-(2,5-dioxo-2,5-dihydro-1H-pyrrol-1-yl)-3-[4-(2,5,8,11,14,17,20,23,26,29,32-undecaoxatetratriacontan-34-yloxy)phenyl]propanoyl}-L-valyl-N-{4-[({[2-({3-[(4-

{6-[8-(1,3-benzothiazol-2-ylcarbamoyl)naphthalen-2-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]phenyl}-N$^5$-carbamoyl-L-ornithinamide;

N-({(3S,5S)-3-(2,5-dioxo-2,5-dihydro-1H-pyrrol-1-yl)-2-oxo-5-[(2-sulfoethoxy)methyl]pyrrolidin-1-yl}acetyl)-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]phenyl}-N$^5$-carbamoyl-L-ornithinamide;

N-{(2S)-2-(2,5-dioxo-2,5-dihydro-1H-pyrrol-1-yl)-3-[4-(2,5,8,11,14,17,20,23,26,29,32-undecaoxatetratriacontan-34-yloxy)phenyl]propanoyl}-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]phenyl}-N$^5$-carbamoyl-L-ornithinamide;

(6S)-2,6-anhydro-6-(2-{2-[({[2-({3-[(4-{6-[8-(1,3-benzothiazol-2-ylcarbamoyl)-3,4-dihydroisoquinolin-2(1H)-yl]-2-carboxypyridin-3-yl-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]-5-({N-[(2,5-dioxo-2,5-dihydro-1H-pyrrol-1-yl)acetyl]-L-valyl-L-alanyl}amino)phenyl ethyl)-L-gulonic acid;

3-{[2-({3-[(4-{6-[8-(1,3-benzothiazol-2-ylcarbamoyl)naphthalen-2-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl]({[4-(4-{1 [6-(2,5-dioxo-2,5-dihydro-1H-pyrrol-1-yl)hexanoyl]amino}butyl)-2-(beta-D-glucopyranuronosyloxy)benzyl]oxy}carbonyl)amino}propyl beta-D-glucopyranosiduronic acid;

N-{[(3S,5S)-3-(2,5-dioxo-2,5-dihydro-1H-pyrrol-1-yl)-5-(methoxymethyl)-2-oxopyrrolidin-1-yl]acetyl}-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]phenyl}-N$^5$-carbamoyl-L-ornithinamide;

(6S)-2,6-anhydro-6-(2-{2-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]-5-({N-[6-(2,5-dioxo-2,5-dihydro-1H-pyrrol-1-yl)hexanoyl]-L-valyl-L-alanyl}amino)phenyl}ethyl)-L-gulonic acid;

2-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]-5-(4-{[3-(2,5-dioxo-2,5-dihydro-1H-pyrrol-1-yl)propanoyl]amino}butyl)phenyl beta-D-glucopyranosiduronic acid;

2-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]-5-[4-({(2S)-2-(2,5-dioxo-2,5-dihydro-1H-pyrrol-1-yl)-3-[4-(2,5,8,11,14,17,20,23,26,29,32-undecaoxatetratriacontan-34-yloxy)phenyl]propanoyl}amino)butyl]phenyl beta-D-glucopyranosiduronic acid;

(6S)-2,6-anhydro-6-(2-{2-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]-5-[(N-{(2S)-2-(2,5-dioxo-2,5-dihydro-1H-pyrrol-1-yl)-3-[4-(2,5,8,11,14,17,20,23,26,29,32-undecaoxatetratriacontan-34-yloxy)phenyl]propanoyl}-L-valyl-L-alanyl)amino]phenyl}ethyl)-L-gulonic acid;

6-(8-(benzo[d]thiazol-2-ylcarbamoyl)-3,4-dihydroisoquinolin-2(1H)-yl)-3-(1-((3-(2-((((2-(2-((2S,3R,4R,5S,6S)-6-carboxy-3,4,5-trihydroxytetrahydro-2H-pyran-2-yl)ethyl)-4-((S)-2-((S)-2-(2-((3S,5S)-3-(2,5-dioxo-2,5-dihydro-1H-pyrrol-1-yl)-2-oxo-5-((2-sulfoethoxy)methyl)pyrrolidin-1-yl)acetamido)-3-methylbutanamido)propanamido)benzyl)oxy)carbonyl)(2-sulfoethyl)amino)ethoxy)-5,7-dimethyladamantan-1-yl)methyl)-5-methyl-1H-pyrazol-4-yl)picolinic acid;

6-(8-(benzo[d]thiazol-2-ylcarbamoyl)-3,4-dihydroisoquinolin-2(1H)-yl)-3-(1-((3-(2-((((2-(((2S,3R,4S,5S,6S)-6-carboxy-3,4,5-trihydroxytetrahydro-2H-pyran-2-yl)oxy)-4-(4-(2-((3S,5S)-3-(2,5-dioxo-2,5-dihydro-1H-pyrrol-1-yl)-2-oxo-5-((2-sulfoethoxy)methyl)pyrrolidin-1-yl)acetamido)butyl)benzyl)oxy)carbonyl)(2-sulfoethyl)amino)ethoxy)-5,7-dimethyladamantan-1-yl)methyl)-5-methyl-1H-pyrazol-4-yl)picolinic acid;

2-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]-5-(4-{[(2,5-dioxo-2,5-dihydro-1H-pyrrol-1-yl)acetyl]amino}butyl)phenyl beta-D-glucopyranosiduronic acid;

2-[({[2-({3-[(4-{6-[8-(1,3-benzothiazol-2-ylcarbamoyl)naphthalen-2-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]-5-(4-{[(2,5-dioxo-2,5-dihydro-1H-pyrrol-1-yl)acetyl]amino}butyl)phenyl beta-D-glucopyranosiduronic acid;

2-[({[2-({3-[(4-{6-[8-(1,3-benzothiazol-2-ylcarbamoyl)naphthalen-2-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]-5-[4-({(2S)-2-(2,5-dioxo-2,5-dihydro-1H-pyrrol-1-yl)-3-[4-(2,5,8,11,14,17,20,23,26,29,32-undecaoxatetratriacontan-34-yloxy)phenyl]propanoyl}amino)butyl]phenyl beta-D-glucopyranosiduronic acid;

N-[(2,5-dioxo-2,5-dihydro-1H-pyrrol-1-yl)acetyl]-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]-3-(4-carboxybutyl)phenyl}-L-alaninamide;

2-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]-5-(3-{[(2,5-dioxo-2,5-dihydro-1H-pyrrol-1-yl)acetyl]amino}propyl)phenyl beta-D-glucopyranosiduronic acid;

6-[8-(1,3-benzothiazol-2-ylcarbamoyl)-3,4-dihydroisoquinolin-2(1H)-yl]-3-{1-[(3-{2-[({[2-{[(2S,3R,4S,5S,6S)-6-carboxy-3,4,5-trihydroxytetrahydro-2H-pyran-2-yl]oxy}-4-(4-{[(2,5-dioxo-2,5-dihydro-1H-pyrrol-1-yl)acetyl]

amino}butyl)benzyl]oxy}carbonyl)(3-{[1,3-dihydroxy-2-(hydroxymethyl)propan-2-yl]amino}-3-oxopropyl)amino]ethoxy}-5,7-dimethyltricyclo[3.3.1.1$^{3,7}$]dec-1-yl)methyl]-5-methyl-1H-pyrazol-4-yl}pyridine-2-carboxylic acid;

6-(8-(benzo[d]thiazol-2-ylcarbamoyl)naphthalen-2-yl)-3-(1-((3-(2-((((2-(((2S,3R,4S,5S,6S)-6-carboxy-3,4,5-trihydroxytetrahydro-2H-pyran-2-yl)oxy)-4-(4-(2-((3S,5S)-3-(2,5-dioxo-2,5-dihydro-1H-pyrrol-1-yl)-2-oxo-5-((2-sulfoethoxy)methyl)pyrrolidin-1-yl)acetamido)butyl)benzyl)oxy)carbonyl)(2-sulfoethyl)amino)ethoxy)-5,7-dimethyladamantan-1-yl)methyl)-5-methyl-1H-pyrazol-4-yl)picolinic acid;

2-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl][3-hydroxy-2-(hydroxymethyl)propyl]carbamoyl}oxy)methyl]-5-(3-{[(2,5-dioxo-2,5-dihydro-1H-pyrrol-1-yl)acetyl]amino}propyl)phenyl beta-D-glucopyranosiduronic acid;

N-({(3S,5S)-3-(2,5-dioxo-2,5-dihydro-1H-pyrrol-1-yl)-2-oxo-5-[(2-sulfoethoxy)methyl]pyrrolidin-1-yl}acetyl)-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]-3-(2,5,8,11,14,17,20,23,26,29,32,35,38,41,44,47,50-heptadecaoxatripentacont-52-yn-53-yl)phenyl}-L-alaninamide;

N-({(3S,5S)-3-(2,5-dioxo-2,5-dihydro-1H-pyrrol-1-yl)-2-oxo-5-[(2-sulfoethoxy)methyl]pyrrolidin-1-yl}acetyl)-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]-3-(2,5,8,11,14,17,20,23,26,29,32,35,38,41,44,47,50-heptadecaoxatripentacontan-53-yl)phenyl}-L-alaninamide;

2-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl][(3S)-3,4-dihydroxybutyl]carbamoyl}oxy)methyl]-5-(3-{[(2,5-dioxo-2,5-dihydro-1H-pyrrol-1-yl)acetyl]amino}propyl)phenyl beta-D-glucopyranosiduronic acid;

1-{[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl]({[4-(4-{[(2,5-dioxo-2,5-dihydro-1H-pyrrol-1-yl)acetyl]amino}butyl)-2-(beta-D-glucopyranuronosyloxy)benzyl]oxy}carbonyl)amino}-1,2-dideoxy-D-arabino-hexitol;

1-{[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl]({[4-(4-{[(2,5-dioxo-2,5-dihydro-1H-pyrrol-1-yl)acetyl]amino}butyl)-2-(beta-D-glucopyranuronosyloxy)benzyl]oxy}carbonyl)amino}-1,2-dideoxy-D-erythro-pentitol;

N-[(2,5-dioxo-2,5-dihydro-1H-pyrrol-1-yl)acetyl]-L-valyl-N-{4-[({[2-({3-[(4-{6-[8-(1,3-benzothiazol-2-ylcarbamoyl)naphthalen-2-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl }oxy)methyl]-3-[27-(2,5,8,11,14,17,20,23-octaoxahexacosan-26-yl)-2,5,8,11,14,17,20,23-octaoxa-27-azatriacontan-30-yl]phenyl}-L-alaninamide;

(6S)-2,6-anhydro-6-(2-{2-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]-5-({N-[(2S)-3-[3,4-bis(2,5,8,11,14,17,20,23,26,29,32-undecaoxatetratriacontan-34-yloxy)phenyl]-2-(2,5-dioxo-2,5-dihydro-1H-pyrrol-1-yl)propanoyl]-L-valyl-L-alanyl}amino)phenyl}ethyl)-L-gulonic acid;

N-[(2,5-dioxo-2,5-dihydro-1H-pyrrol-1-yl)acetyl]-N-(2,5,8,11,14,17,20,23,26,29,32-undecaoxatetratriacontan-34-yl)-beta-alanyl-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl J}oxy)methyl]-3-(2,5,8,11,14,17,20,23,26,29,32,35,38,41,44,47,50-heptadecaoxatripentacontan-53-yl)phenyl J}-L-alaninamide;

N-[(2,5-dioxo-2,5-dihydro-1H-pyrrol-1-yl)acetyl]-N-(2,5,8,11,14,17,20,23,26,29,32-undecaoxatetratriacontan-34-yl)-beta-alanyl-L-valyl-N-{4-[({[2-(3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]phenyl}-N$^5$-carbamoyl-L-ornithinamide;

N-[(2,5-dioxo-2,5-dihydro-1H-pyrrol-1-yl)acetyl]-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]-3-[27-(2,5,8,11,14,17,20,23-octaoxahexacosan-26-yl)-2,5,8,11,14,17,20,23-octaoxa-27-azatriacontan-30-yl]phenyl}-L-alaninamide;

N-{(3S)-3-(2,5-dioxo-2,5-dihydro-1H-pyrrol-1-yl)-3-[1-(2,5,8,11,14,17,20,23,26,29,32,35-dodecaoxaheptatriacontan-37-yl)-1H-1,2,3-triazol-4-yl]propanoyl}-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]phenyl}-N$^5$-carbamoyl-L-ornithinamide;

N-((3R)-3-(2,5-dioxo-2,5-dihydro-1H-pyrrol-1-yl)-3-[1-(2,5,8,11,14,17,20,23,26,29,32,35-dodecaoxaheptatriacontan-37-yl)-1H-1,2,3-triazol-4-yl]propanoyl}-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]phenyl}-N$^5$-carbamoyl-L-ornithinamide;

6-[8-(1,3-benzothiazol-2-ylcarbamoyl)-3,4-dihydroisoquinolin-2(1H)-yl]-3-[1-({3-[2-({[(2-{2-[(2S,3R,4R,5S,6S)-6-carboxy-3,4,5-trihydroxytetrahydro-2H-pyran-2-yl]ethyl}-4-{[(2S)-2-{[(2S)-2-{[(2,5-dioxo-2,5-dihydro-1H-pyrrol-1-yl)acetyl]amino}-3-methylbutanoyl]amino}propanoyl]amino}benzyl)oxy]carbonyl}[(3R,4S,5R)-3,4,5,6-tetrahydroxyhexyl]amino)ethoxy]-5,7-dimethyltricyclo[3.3.1.1$^{3,7}$]dec-1-yl}methyl)-5-methyl-1H-pyrazol-4-yl]pyridine-2-carboxylic acid;

6-[8-(1,3-benzothiazol-2-ylcarbamoyl)-3,4-dihydroisoquinolin-2(1H)-yl]-3-[1-({3-[2-({[(2-{2-[(2S,3R,4R,5S,6S)-6-carboxy-3,4,5-trihydroxytetrahydro-2H-pyran-2-yl]

ethyl}-4-{[(2S)-2-({(2S)-2-[({1 (3S,5S)-3-(2,5-dioxo-2,5-dihydro-1H-pyrrol-1-yl)-2-oxo-5-[(2-sulfoethoxy)methyl]pyrrolidin-1-yl}acetyl)amino]-3-methylbutanoyl}amino)propanoyl]amino}benzyl)oxy]carbonyl}[(3R,4S,5R)-3,4,5,6-tetrahydroxyhexyl]amino)ethoxy]-5,7-dimethyltricyclo[3.3.1.1$^{3,7}$]dec-1-yl}methyl)-5-methyl-1H-pyrazol-4-yl]pyridine-2-carboxylic acid;

(6S)-2,6-anhydro-6-(2-{2-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]-5-({N-[(2,5-dioxo-2,5-dihydro-1H-pyrrol-1-yl)acetyl]-N-(2,5,8,11,14,17,20,23,26,29,32-undecaoxatetratriacontan-34-yl)-beta-alanyl-L-valyl-L-alanyl}amino)phenyl}ethyl)-L-gulonic acid;

(6S)-2,6-anhydro-6-(2-{2-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]-5-[(N-{2-(2,5-dioxo-2,5-dihydro-1H-pyrrol-1-yl)-3-[1-(2,5,8,11,14,17,20,23,26,29,32,35-dodecaoxaheptatriacontan-37-yl)-1H-1,2,3-triazol-4-yl]propanoyl}-L-valyl-L-alanyl)amino]phenyl}ethyl)-L-gulonic acid;

(6S)-2,6-anhydro-6-(2-{2-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]-5-[(N-{(3S)-3-(2,5-dioxo-2,5-dihydro-1H-pyrrol-1-yl)-3-[1-(2,5,8,11,14,17,20,23,26,29,32,35-dodecaoxaheptatriacontan-37-yl)-1H-1,2,3-triazol-4-yl]propanoyl}-L-valyl-L-alanyl)amino]phenyl}ethyl)-L-gulonic acid;

(6S)-2,6-anhydro-6-(2-{2-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]-5-[(N-{(3R)-3-(2,5-dioxo-2,5-dihydro-1H-pyrrol-1-yl)-3-[1-(2,5,8,11,14,17,20,23,26,29,32,35-dodecaoxaheptatriacontan-37-yl)-1H-1,2,3-triazol-4-yl]propanoyl}-L-valyl-L-alanyl)amino]phenyl}ethyl)-L-gulonic acid;

(6S)-2,6-anhydro-6-(2-{2-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]-5-[(N-{(3S)-3-(2,5-dioxo-2,5-dihydro-1H-pyrrol-1-yl)-3-[1-(3-sulfopropyl)-1H-1,2,3-triazol-4-yl]propanoyl}-L-valyl-L-alanyl)amino]phenyl}ethyl)-L-gulonic acid;

(6S)-2,6-anhydro-6-(2-{2-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]-5-[(N-{(3R)-3-(2,5-dioxo-2,5-dihydro-1H-pyrrol-1-yl)-3-[1-(3-sulfopropyl)-1H-1,2,3-triazol-4-yl]propanoyl}-L-valyl-L-alanyl)amino]phenyl}ethyl)-L-gulonic acid;

(6S)-2,6-anhydro-6-(2-{2-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]-5-({N-[(2,5-dioxo-2,5-dihydro-1H-pyrrol-1-yl)acetyl]-N-[2-(2-sulfoethoxy)ethyl]-beta-alanyl-L-valyl-L-alanyl}amino)phenyl}ethyl)-L-gulonic acid;

6-{8-[(1,3-benzothiazol-2-yl)carbamoyl]-3,4-dihydroisoquinolin-2(1H)-yl}-3-[1-({3-[2-({[(2-{2-[(2S,3R,4R,5S,6S)-6-carboxy-3,4,5-trihydroxyoxan-2-yl]ethyl}-4-{[(2S)-2-{[(2S)-2-{[(2S)-2-(2,5-dioxo-2,5-dihydro-1H-pyrrol-1-yl)-3-{4-[(2,5,8,11,14,17,20,23,26,29,32-undecaoxatetratriacontan-34-yl)oxy]phenyl}propanoyl]amino}-3-methylbutanoyl]amino}propanoyl]amino}phenyl)methoxy]carbonyl}[(3R,4S,5R)-3,4,5,6-tetrahydroxyhexyl]amino)ethoxy]-5,7-dimethyltricyclo[3.3.1.1$^{3,7}$]decan-1-yl}methyl)-5-methyl-1H-pyrazol-4-yl]pyridine-2-carboxylic acid;

4-{[({2-[(3-{[4-(6-{8-[(1,3-benzothiazol-2-yl)carbamoyl]-3,4-dihydroisoquinolin-2(1H)-yl}-2-carboxypyridin-3-yl)-5-methyl-1H-pyrazol-1-yl]methyl}-5,7-dimethyltricyclo[3.3.1.1$^{3,7}$]decan-1-yl)oxy]ethyl][(3S)-3,4-dihydroxybutyl]carbamoyl)oxy]methyl}-3-(2-{2-[2-(2,5-dioxo-2,5-dihydro-1H-pyrrol-1-yl)acetamido]ethoxy}ethoxy)phenyl beta-D-glucopyranosiduronic acid;

2,6-anhydro-8-[2-({[{2-[(3-{[4-(6-{8-[(1,3-benzothiazol-2-yl)carbamoyl]-3,4-dihydroisoquinolin-2(1H)-yl}-2-carboxypyridin-3-yl)-5-methyl-1H-pyrazol-1-yl]methyl}-5,7-dimethyltricyclo[3.3.1.1$^{3,7}$]decan-1-yl)oxy]ethyl}(2-sulfoethyl)carbamoyl]oxy}methyl)-5-{[(79S,82S)-74-[(2,5-dioxo-2,5-dihydro-1H-pyrrol-1-yl)acetyl]-82-methyl-77,80,83-trioxo-79-(propan-2-yl)-2,5,8,11,14,17,20,23,26,29,32,35,38,41,44,47,50,53,56,59,62,65,68,71-tetracosaoxa-74,78,81-triazatrioctacontan-83-yl]amino}phenyl]-7,8-dideoxy-L-glycero-L-gulo-octonic acid;

6-{8-[(1,3-benzothiazol-2-yl)carbamoyl]-3,4-dihydroisoquinolin-2(1H)-yl}-3-{1-[(3-{2-[{[(4-{[(2S,5S)-2-[3-(carbamoylamino)propyl]-10-[(2,5-dioxo-2,5-dihydro-1H-pyrrol-1-yl)acetyl]-4,7-dioxo-5-(propan-2-yl)-15-sulfo-13-oxa-3,6,10-triazapentadecanan-1-oyl]amino}phenyl)methoxy]carbonyl}(2-sulfoethyl)amino]ethoxy}-5,7-dimethyltricyclo[3.3.1.1$^{3,7}$]decan-1-yl)methyl]-5-methyl-1H-pyrazol-4-yl}pyridine-2-carboxylic acid;

6-(8-(benzo[d]thiazol-2-ylcarbamoyl)-3,4-dihydroisoquinolin-2(1H)-yl)-3-(1-((3-(2-((((2-(2-((2S,3R,4R,5S,6S)-6-carboxy-3,4,5-trihydroxytetrahydro-2H-pyran-2-yl)ethyl)-4-((S)-2-((S)-2-((3S,5S)-3-(2,5-dioxo-2,5-dihydro-1H-pyrrol-1-yl)-2-oxo-5-((2-sulfoethoxy)methyl)pyrrolidin-1-yl)acetamido)-3-methylbutanamido)propanamido)benzyl)oxy)carbonyl)((S)-3,4-dihydroxybutyl)amino)ethoxy)-5,7-dimethyladamantan-1-yl)methyl)-5-methyl-1H-pyrazol-4-yl)picolinic acid;

2,6-anhydro-8-(2-{[({2-[(3-{[4-(6-{8-[(1,3-benzothiazol-2-yl)carbamoyl]-3,4-dihydroisoquinolin-2(1H)-yl}-2-carboxypyridin-3-yl)-5-methyl-1H-pyrazol-1-yl]methyl}-5,7-dimethyltricyclo[3.3.1.1$^{3,7}$]decan-1-yl)oxy]ethyl}[(3S)-3,4-dihydroxybutyl]carbamoyl)oxy]methyl}-5-{[(2S)-2-({(2S)-2-[2-(2,5-dioxo-2,5-dihydro-1H-pyrrol-1-yl)acetamido]-3-methylbutanoyl}amino)propanoyl]amino}phenyl)-7,8-dideoxy-L-glycero-L-gulo-octonic acid;

2-{[({2-[(3-{[4-(6-{8-[(1,3-benzothiazol-2-yl)carbamoyl]-3,4-dihydroisoquinolin-2(1H)-yl}-2-carboxypyridin-3-yl)-5-methyl-1H-pyrazol-1-yl]methyl}-5,7-dimethyltricyclo[3.3.1.1$^{3,7}$]decan-1-yl)oxy]ethyl}[(3S)-3,4-dihydroxybutyl]carbamoyl)oxy]methyl}-5-{4-[2-(2,5-dioxo-2,5-dihydro-1H-pyrrol-1-yl)acetamido]butyl}phenyl beta-D-glucopyranosiduronic acid;

6-{8-[(1,3-benzothiazol-2-yl)carbamoyl]-3,4-dihydroiso-
quinolin-2(1H)-yl}-3-{1-[(3-{2-[{[(4-{[(2S)-5-(carbam-
oylamino)-2-{[(2S)-2-{[6-(2,5-dioxo-2,5-dihydro-1H-
pyrrol-1-yl)hexanoyl]amino}-3-methylbutanoyl]
amino}pentanoyl]amino}phenyl)methoxy]carbonyl}(2-
sulfoethyl)amino]acetamido}-5,7-dimethyltricyclo
[3.3.1.1$^{3,7}$]decan-1-yl)methyl]-5-methyl-1H-pyrazol-4-
yl}pyridine-2-carboxylic acid;

N-[6-(2,5-dioxo-2,5-dihydro-1H-pyrrol-1-yl)hexanoyl]-L-
valyl-N-{4-[({[2-({3-[(4-{6-[8-(1,3-benzothiazol-2-yl-
carbamoyl)-3,4-dihydroisoquinolin-2(1H)-yl]-2-carboxy-
pyridin-3-yl}-5-methyl-1H-pyrazol-1-yl)methyl]-5,7-
dimethyltricyclo[3.3.1.1$^{3,7}$]dec-1-yl}sulfanyl)ethyl](2-
sulfoethyl)carbamoyl}oxy)methyl]phenyl}-N$^5$-
carbamoyl-L-ornithinamide;

N-[6-(2,5-dioxo-2,5-dihydro-1H-pyrrol-1-yl)hexanoyl]-L-
valyl-N-[4-({[(3-{3-[(4-{6-[8-(1,3-benzothiazol-2-ylcar-
bamoyl)-3,4-dihydroisoquinolin-2(1H)-yl]-2-carboxy-
pyridin-3-yl}-5-methyl-1H-pyrazol-1-yl)methyl]-5,7-
dimethyltricyclo[3.3.1.1$^{3,7}$]dec-1-yl}propyl)(2-
sulfoethyl)carbamoyl]oxy}methyl)phenyl]-N$^5$-
carbamoyl-L-ornithinamide;

2-[({[2-({3-[(4-{6-[8-(1,3-benzothiazol-2-ylcarbamoyl)-3,
4-dihydroisoquinolin-2(1H)-yl]-2-carboxypyridin-3-yl}-
5-methyl-1H-pyrazol-1-yl)methyl]-5,7-dimethyltricyclo
[3.3.1.1$^{3,7}$]dec-1-yl}oxy)ethyl][(3S)-3,4-dihydroxybutyl]
carbamoyl}oxy)methyl]-5-{4-[({(3S,5S)-3-(2,5-dioxo-2,
5-dihydro-1H-pyrrol-1-yl)-2-oxo-5-[(2-sulfoethoxy)
methyl]pyrrolidin-1-yl}acetyl)amino]butyl}phenyl beta-
D-glucopyranosiduronic acid;

2,6-anhydro-8-[2-([{2-[(3-{[4-(6-{8-[(1,3-benzothiazol-2-
yl)carbamoyl]-3,4-dihydroisoquinolin-2(1H)-yl}-2-car-
boxypyridin-3-yl)-5-methyl-1H-pyrazol-1-yl]methyl}-5,
7-dimethyltricyclo[3.3.1.1$^{3,7}$]decan-1-yl)oxy]ethyl}(2-
sulfoethyl)carbamoyl]oxy}methyl)-5-{[N-({(3R,5S)-3-
(2,5-dioxo-2,5-dihydro-1H-pyrrol-1-yl)-2-oxo-5-[(2-
sulfoethoxy)methyl]pyrrolidin-1-yl}acetyl)-L-valyl-L-
alanyl]amino}phenyl]-7,8-dideoxy-L-glycero-L-gulo-
octonic acid;

2,6-anhydro-8-{2-(({[{2-[(3-{[4-(6-{8-[(1,3-benzothiazol-
2-yl)carbamoyl]-3,4-dihydroisoquinolin-2(1H)-yl}-2-
carboxypyridin-3-yl)-5-methyl-1H-pyrazol-1-yl]
methyl}-5,7-dimethyltricyclo[3.3.1.1$^{3,7}$]decan-1-yl)oxy]
ethyl}(2-sulfoethyl)carbamoyl]oxy}methyl)-5-[(N-
{[(3R,5S)-3-(2,5-dioxo-2,5-dihydro-1H-pyrrol-1-yl)-2-
oxo-5-(41-oxo-2,5,8,11,14,17,20,23,26,29,32,35,38-tri-
decaoxa-42-azatritetracontan-43-yl)pyrrolidin-1-yl]
acetyl}-L-valyl-L-alanyl]amino]phenyl}-7,8-dideoxy-L-
glycero-L-gulo-octonic acid;

(6S)-2,6-anhydro-6-(2-{2-[({[2-({3-[(4-{6-[8-(1,3-benzo-
thiazol-2-ylcarbamoyl)-3,4-dihydroisoquinolin-2(1H)-
yl]-2-carboxypyridin-3-yl}-5-methyl-1H-pyrazol-1-yl)
methyl]-5,7-dimethyltricyclo[3.3.1.1$^{3,7}$]dec-1-yl}oxy)
ethyl][(3S)-3,4-dihydroxybutyl]carbamoyl}oxy)methyl]-
5-({N-[(2,5-dioxo-2,5-dihydro-1H-pyrrol-1-yl)acetyl]-N-
(2,5,8,11,14,17,20,23,26,29,32-
undecaoxatetratriacontan-34-yl)-b-alanyl-L-valyl-L-
alanyl}amino)phenyl}ethyl)-L-gulonic acid; and (6S)-2,6-anhydro-6-(2-{2-[({[2-({3-[(4-{6-[8-(1,3-benzo-
thiazol-2-ylcarbamoyl)-3,4-dihydroisoquinolin-2(1H)-
yl]-2-carboxypyridin-3-yl-5-methyl-1H-pyrazol-1-yl)
methyl]-5,7-dimethyltricyclo[3.3.1.1$^{3,7}$]dec-1-yl}oxy)
ethyl][(3S)-3,4-dihydroxybutyl]carbamoyl}oxy)methyl]-
5-(({N-[(2,5-dioxo-2,5-dihydro-1H-pyrrol-1-yl)acetyl]-
N-[2-(2-sulfoethoxy)ethyl]-b-alanyl-L-valyl-L-
alanyl}amino)phenyl}ethyl)-L-gulonic acid.

In certain embodiments, the ADC, or a pharmaceutically acceptable salt thereof,

D is the Bcl-xL inhibitor selected from the group consisting of the following compounds modified in that the hydrogen corresponding to the # position of structural formula (IIa), (IIb), (IIc), or (IId) is not present, forming a monoradical:

W2.01, W2.02, W2.03, W2.04, W2.05, W2.06, W2.07, W2.08, W2.09, W2.10, W2.11, W2.12, W2.13, W2.14, W2.15, W2.16, W2.17, W2.18, W2.19, W2.20, W2.21, W2.22, W2.23, W2.24, W2.25, W2.26, W2.27, W2.28, W2.29, W2.30, W2.31, W2.32, W2.33, W2.34, W2.35, W2.36, W2.37, W2.38, W2.39, W2.40, W2.41, W2.42, W2.43, W2.44, W2.45, W2.46, W2.47, W2.48, W2.49, W2.50, W2.51, W2.52, W2.53, W2.54, W2.55, W2.56, W2.57, W2.58, W2.59, W2.60, W2.61, W2.62, W2.63, W2.64, W2.65, W2.66, W2.67, W2.68, W2.69, W2.70, W2.71, W2.72, W2.73, W2.74, W2.75, W2.76, W2.77, W2.78, W2.79, W2.80, W2.81, W2.82, W2.83, W2.84, W2.85, W2.86, W2.87, W2.88, W2.89, W2.90, and W2.91, and a pharmaceutically acceptable salt thereof;

L is selected from the group consisting of linkers IVa.1-IVa.8, IVb.1-IVb.19, IVc.1-IVc.7, IVd.1-IVd.4, Va.1-Va.12, Vb. 1-Vb.10, Vc.1-Vc.11, Vd.1-Vd.6, Ve.1-Ve.2, VIa.1, VIc. 1-VIc.2, VId.1-VId.4, VIIa.1-VIIa.4, VIIb.1-VIIb.8, VIIc.1-VIIc.6, wherein each linker has reacted with the antibody, Ab, forming a covalent attachment;

LK is thioether; and m is an integer ranging from 1 to 8.

In certain embodiments, the ADC, or a pharmaceutically acceptable salt thereof,

D is the Bcl-xL inhibitor selected from the group consisting of the following compounds modified in that the hydrogen corresponding to the # position of structural formula (IIa), (IIb), (IIc), or (IId) is not present, forming a monoradical:

6-[8-(1,3-benzothiazol-2-ylcarbamoyl)-3,4-dihydroisoqui-
nolin-2(1H)-yl]-3-{1-[(3,5-dimethyl-7-{2-[(2-sulfoethyl)
amino]ethoxy tricyclo[3.3.1.1$^{3,7}$]dec-1-yl)methyl]-5-
methyl-1H-pyrazol-4-yl}pyridine-2-carboxylic acid;

6-[8-(1,3-benzothiazol-2-ylcarbamoyl)-3,4-dihydroisoqui-
nolin-2(1H)-yl]-3-{1-[(3-{2-[(2-carboxyethyl)amino]
ethoxy}-5,7-dimethyltricyclo[3.3.1.1$^{3,7}$]dec-1-yl)
methyl]-5-methyl-1H-pyrazol-4-yl}pyridine-2-
carboxylic acid;

6-[8-(1,3-benzothiazol-2-ylcarbamoyl)naphthalen-2-yl]-3-
{1-[(3,5-dimethyl-7-{2-[(2-sulfoethyl)amino]
ethoxy}tricyclo[3.3.1.1$^{3,7}$]dec-1-yl)methyl]-5-methyl-
1H-pyrazol-4-yl}pyridine-2-carboxylic acid;

1-{[2-({3-[(4-{6-[8-(1,3-benzothiazol-2-ylcarbamoyl)-3,4-
dihydroisoquinolin-2(1H)-yl]-2-carboxypyridin-3-yl}-5-
methyl-1H-pyrazol-1-yl)methyl]-5,7-dimethyltricyclo
[3.3.1.1$^{3,7}$]dec-1-yl}oxy)ethyl]amino}-1,2-dideoxy-D-
arabino-hexitol;

6-[8-(1,3-benzothiazol-2-ylcarbamoyl)-3,4-dihydroisoqui-
nolin-2(1H)-yl]-3-(1-{[3-(2-{[3-hydroxy-2-(hydroxym-
ethyl)propyl]amino}ethoxy)-5,7-dimethyltricyclo
[3.3.1.1$^{3,7}$]dec-1-yl]methyl}-5-methyl-1H-pyrazol-4-yl)
pyridine-2-carboxylic acid;

6-[8-(1,3-benzothiazol-2-ylcarbamoyl)-3,4-dihydroisoqui-
nolin-2(1H)-yl]-3-(1-{[3-(2-{[(3S)-3,4-dihydroxybutyl]
amino}ethoxy)-5,7-dimethyltricyclo[3.3.1.1$^{3,7}$]dec-1-yl]
methyl}-5-methyl-1H-pyrazol-4-yl)pyridine-2-
carboxylic acid;

and pharmaceutically acceptable salts thereof;

L is selected from the group consisting of linkers IVb.2, IVc.5, IVc.6, IVc.7, IVd.4, Vb.9, Vc.11, VIIa.1, VIIa.3, VIIc.1, VIIc.4, and VIIc.5 in either closed or open forms and a pharmaceutically acceptable salt thereof;

LK is thioether; and m is an integer ranging from 2 to 4.

To form an ADC, the maleimide ring of a synthon (for example, the synthons listed in Table B) may react with an antibody Ab, forming a covalent attachment as either a succinimide (closed form) or succinamide (open form). Similarly, other functional groups, e.g. acetyl halide or vinyl sulfone may react with an antibody, Ab, forming a covalent attachment.

In certain embodiments, the ADC, or a pharmaceutically acceptable salt thereof, is selected from the group consisting of AbA-CZ, AbA-TX, AbA-TV, AbA-YY, AbA-AAA, AbA-AAD, AbB-CZ, AbB-TX, AbB-TV, AbB-YY, AbB-AAD, AbG-CZ, AbG-TX, AbG-TV, AbG-YY, AbG-AAA, AbG-AAD, AbK-CZ, AbK-TX, AbK-TV, AbK-YY, AbK-AAA, AbK-AAD, wherein CZ, TX, TV, YY, AAA, and AAD are synthons disclosed in Table B, and wherein the conjugated synthons are either in open or closed form.

In one embodiment, the ADC, or a pharmaceutically acceptable salt thereof, is:

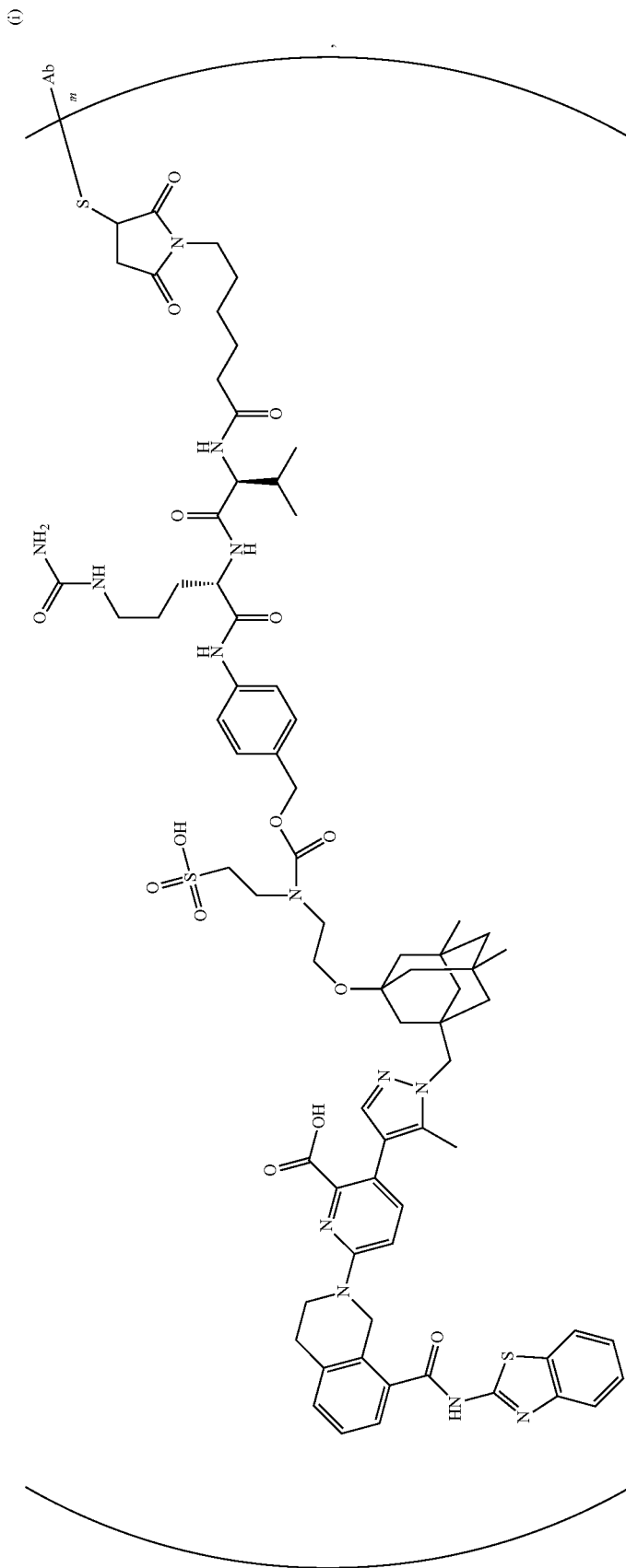

wherein m is 2, Ab is either an anti-hB7-H3 antibody, wherein the anti-hB7-H3 antibody comprises a heavy chain CDR3 domain comprising the amino acid sequence set forth in SEQ ID NO: 35, a heavy chain CDR2 domain comprising the amino acid sequence set forth in SEQ ID NO: 34, and a heavy chain CDR1 domain comprising the amino acid sequence set forth in SEQ ID NO: 33; and a light chain CDR3 domain comprising the amino acid sequence set forth in SEQ ID NO: 39, a light chain CDR2 domain comprising the amino acid sequence set forth in SEQ ID NO: 38, and a light chain CDR1 domain comprising the amino acid sequence set forth in SEQ ID NO: 37; or an anti-hB7-H3 antibody, wherein the anti-hB7H3 antibody comprises a heavy chain variable region comprising the amino acid sequence set forth in SEQ ID NO: 147, and a light chain variable region comprising the amino acid sequence set forth in SEQ ID NO: 144; or an anti-hB7-H3 antibody, wherein the anti-hB7-H3 antibody comprises a heavy chain comprising the amino acid sequence set forth in SEQ ID NO: 168, and a light chain comprising the amino acid sequence set forth in SEQ ID NO: 169.

In one embodiment, the ADC, or a pharmaceutically acceptable salt thereof, is:

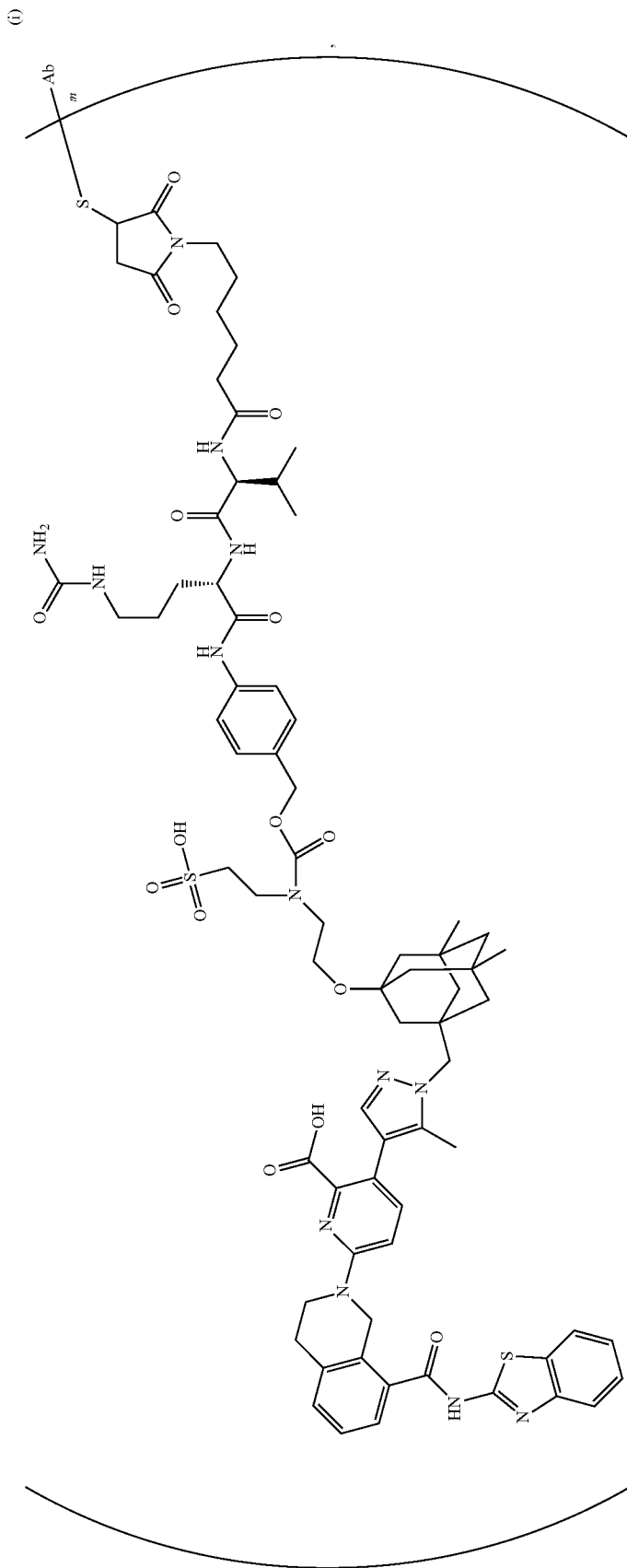

wherein m is 2, Ab is either an anti-hB7-H3 antibody, wherein the anti-hB7-H3 antibody comprises a heavy chain CDR3 domain comprising the amino acid sequence set forth in SEQ ID NO: 12, a heavy chain CDR2 domain comprising the amino acid sequence set forth in SEQ ID NO: 140, and a heavy chain CDR1 domain comprising the amino acid sequence set forth in SEQ ID NO: 10; and a light chain CDR3 domain comprising the amino acid sequence set forth in SEQ ID NO: 15, a light chain CDR2 domain comprising the amino acid sequence set forth in SEQ ID NO: 7, and a light chain CDR1 domain comprising the amino acid sequence set forth in SEQ ID NO: 136; or an anti-hB7-H3 antibody, wherein the anti-hB7H3 antibody comprises a heavy chain variable region comprising the amino acid sequence set forth in SEQ ID NO: 139, and a light chain variable region comprising the amino acid sequence set forth in SEQ ID NO: 135; or an anti-hB7-H3 antibody, wherein the anti-hB7-H3 antibody comprises a heavy chain comprising the amino acid sequence set forth in SEQ ID NO: 170, and a light chain comprising the amino acid sequence set forth in SEQ ID NO: 171.

In one embodiment, the ADC, or a pharmaceutically acceptable salt thereof, is:

(ii)
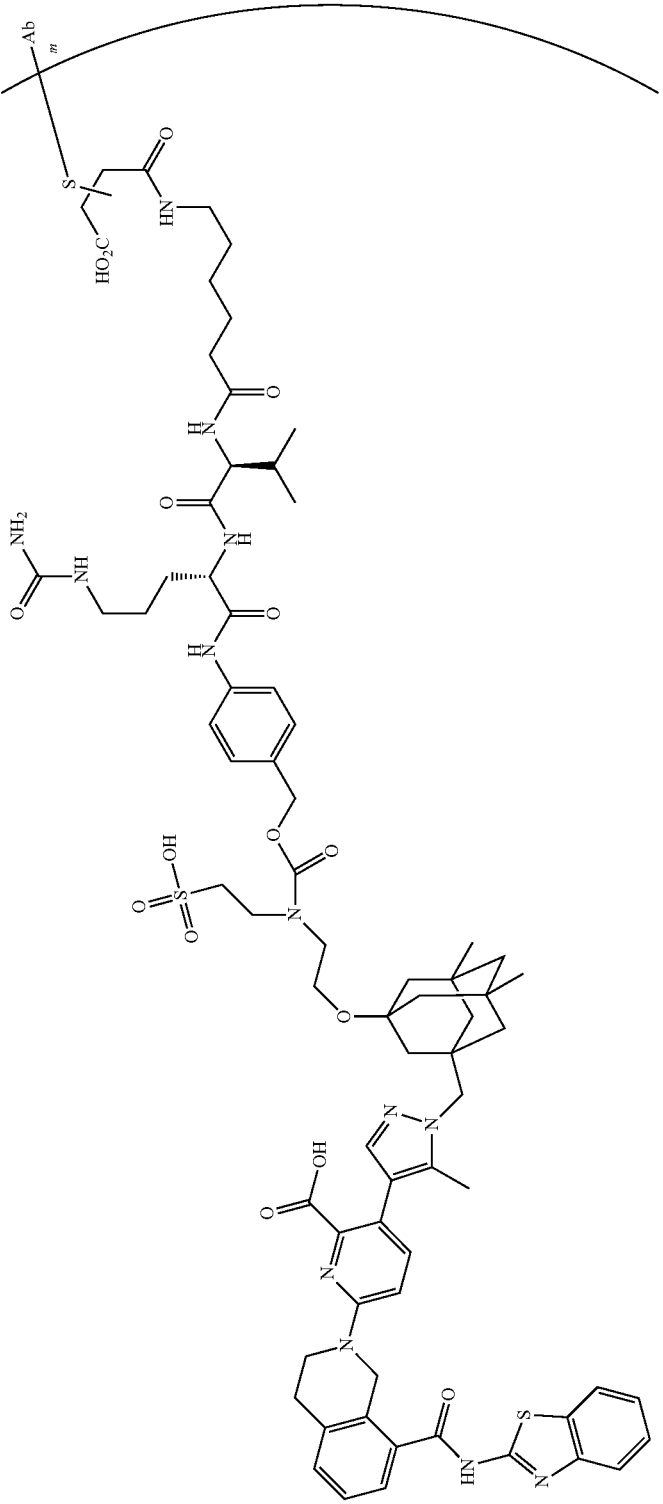

wherein m is 2, Ab is either an anti-hB7-H3 antibody, wherein the anti-hB7-H3 antibody comprises a heavy chain CDR3 domain comprising the amino acid sequence set forth in SEQ ID NO: 35, a heavy chain CDR2 domain comprising the amino acid sequence set forth in SEQ ID NO: 34, and a heavy chain CDR1 domain comprising the amino acid sequence set forth in SEQ ID NO: 33; and a light chain CDR3 domain comprising the amino acid sequence set forth in SEQ ID NO: 39, a light chain CDR2 domain comprising the amino acid sequence set forth in SEQ ID NO: 38, and a light chain CDR1 domain comprising the amino acid sequence set forth in SEQ ID NO: 37; or an anti-hB7-H3 antibody, wherein the anti-hB7H3 antibody comprises a heavy chain variable region comprising the amino acid sequence set forth in SEQ ID NO: 147, and a light chain variable region comprising the amino acid sequence set forth in SEQ ID NO: 144; or an anti-hB7-H3 antibody, wherein the anti-hB7-H3 antibody comprises a heavy chain comprising the amino acid sequence set forth in SEQ ID NO: 168, and a light chain comprising the amino acid sequence set forth in SEQ ID NO: 169.

In one embodiment, the ADC, or a pharmaceutically acceptable salt thereof, is:

(ii)
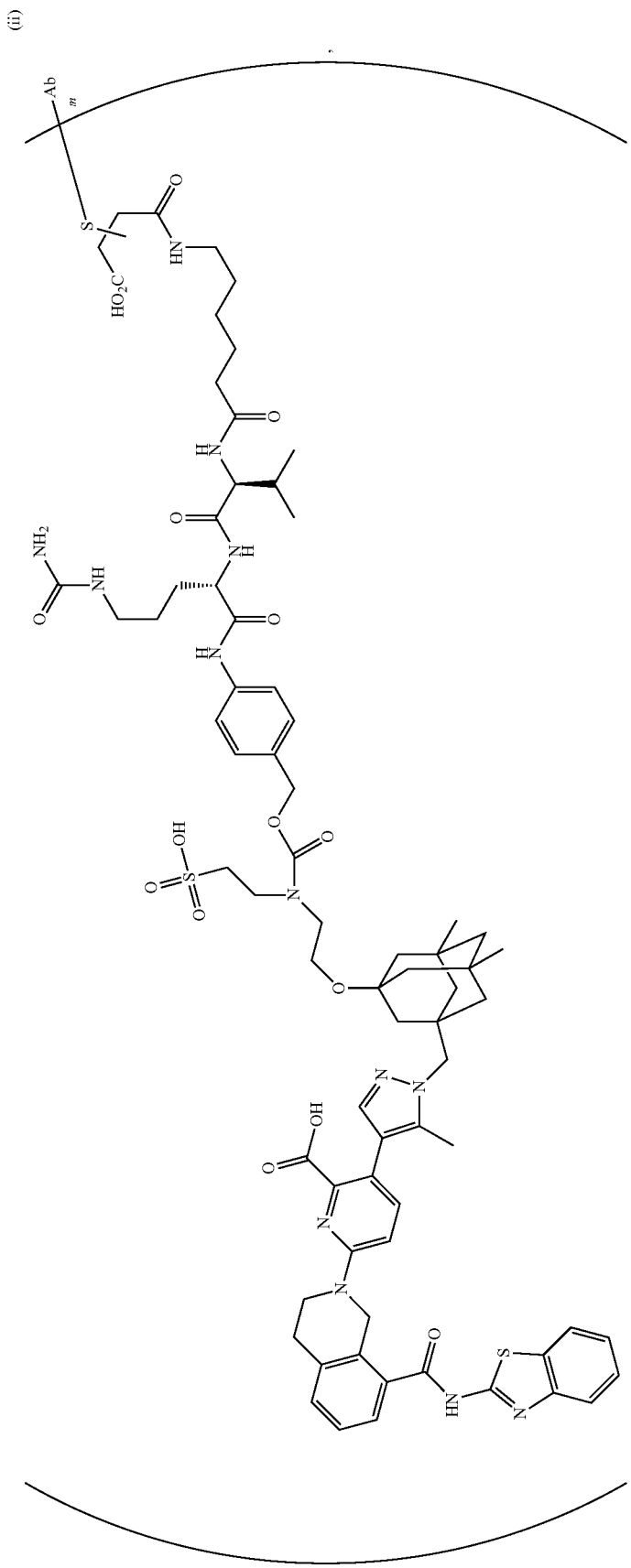

wherein m is 2, Ab is either an anti-hB7-H3 antibody, wherein the anti-hB7-H3 antibody comprises a heavy chain CDR3 domain comprising the amino acid sequence set forth in SEQ ID NO: 12, a heavy chain CDR2 domain comprising the amino acid sequence set forth in SEQ ID NO: 140, and a heavy chain CDR1 domain comprising the amino acid sequence set forth in SEQ ID NO: 10; and a light chain CDR3 domain comprising the amino acid sequence set forth in SEQ ID NO: 15, a light chain CDR2 domain comprising the amino acid sequence set forth in SEQ ID NO: 7, and a light chain CDR1 domain comprising the amino acid sequence set forth in SEQ ID NO: 136; or an anti-hB7-H3 antibody, wherein the anti-hB7H3 antibody comprises a heavy chain variable region comprising the amino acid sequence set forth in SEQ ID NO: 139, and a light chain variable region comprising the amino acid sequence set forth in SEQ ID NO: 135; or an anti-hB7-H3 antibody, wherein the anti-hB7-H3 antibody comprises a heavy chain comprising the amino acid sequence set forth in SEQ ID NO: 170, and a light chain comprising the amino acid sequence set forth in SEQ ID NO: 171.

In one embodiment, the ADC, or a pharmaceutically acceptable salt thereof, is:

CDR3 domain comprising the amino acid sequence set forth in SEQ ID NO: 35, a heavy chain CDR2 domain comprising the amino acid sequence set forth in SEQ ID NO: 34, and a heavy chain CDR1 domain comprising the amino acid sequence set forth in SEQ ID NO: 33; and a light chain CDR3 domain comprising the amino acid sequence set forth in SEQ ID NO: 39, a light chain CDR2 domain comprising the amino acid sequence set forth in SEQ ID NO: 38, and a light chain CDR1 domain comprising the amino acid sequence set forth in SEQ ID NO: 37; or an anti-hB7-H3 antibody, wherein the anti-hB7H3 antibody comprises a heavy chain variable region comprising the amino acid sequence set forth in SEQ ID NO: 147, and a light chain variable region comprising the amino acid sequence set forth in SEQ ID NO: 144; or an anti-hB7-H3 antibody, wherein the anti-hB7-H3 antibody comprises a heavy chain comprising the amino acid sequence set forth in SEQ ID NO: 168, and a light chain comprising the amino acid sequence set forth in SEQ ID NO: 169.

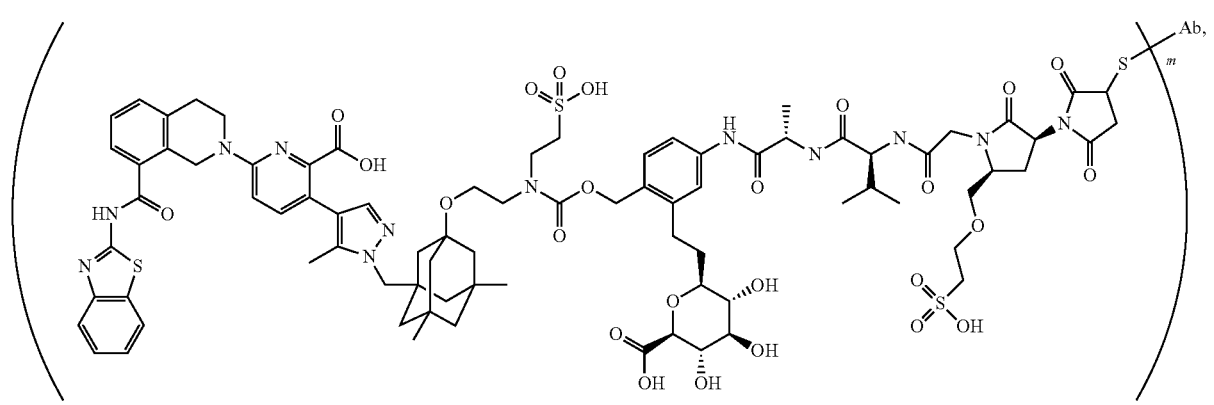

(iii)

wherein m is 2, Ab is either an anti-hB7-H3 antibody, wherein the anti-hB7-H3 antibody comprises a heavy chain In one embodiment, the ADC, or a pharmaceutically acceptable salt thereof, is:

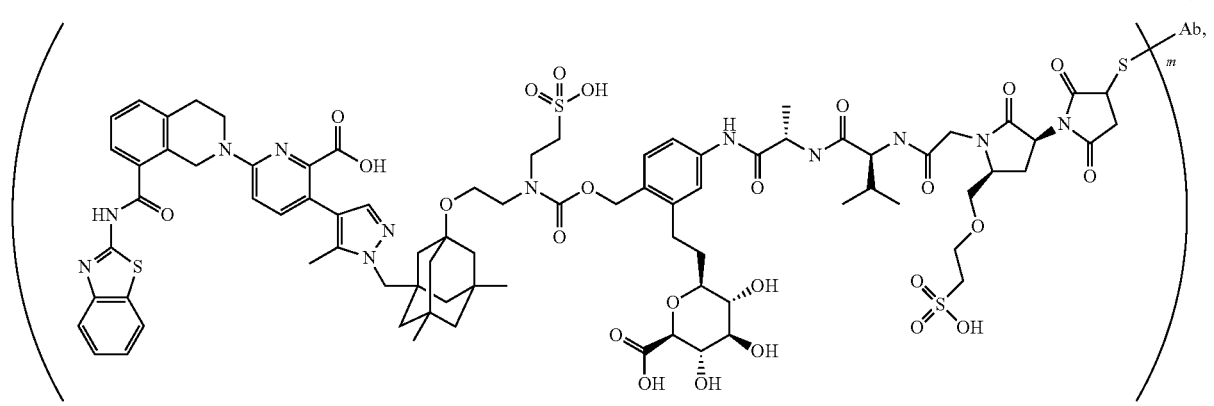

(iii)

wherein m is 2, Ab is either an anti-hB7-H3 antibody, wherein the anti-hB7-H3 antibody comprises a heavy chain CDR3 domain comprising the amino acid sequence set forth in SEQ ID NO: 12, a heavy chain CDR2 domain comprising the amino acid sequence set forth in SEQ ID NO: 140, and a heavy chain CDR1 domain comprising the amino acid sequence set forth in SEQ ID NO: 10; and a light chain CDR3 domain comprising the amino acid sequence set forth in SEQ ID NO: 15, a light chain CDR2 domain comprising the amino acid sequence set forth in SEQ ID NO: 7, and a light chain CDR1 domain comprising the amino acid sequence set forth in SEQ ID NO: 136; or an anti-hB7-H3 antibody, wherein the anti-hB7H3 antibody comprises a heavy chain variable region comprising the amino acid sequence set forth in SEQ ID NO: 139, and a light chain variable region comprising the amino acid sequence set forth in SEQ ID NO: 135; or an anti-hB7-H3 antibody, wherein the anti-hB7-H3 antibody comprises a heavy chain comprising the amino acid sequence set forth in SEQ ID NO: 170, and a light chain comprising the amino acid sequence set forth in SEQ ID NO: 171.

In one embodiment, the ADC, or a pharmaceutically acceptable salt thereof, is (iv)

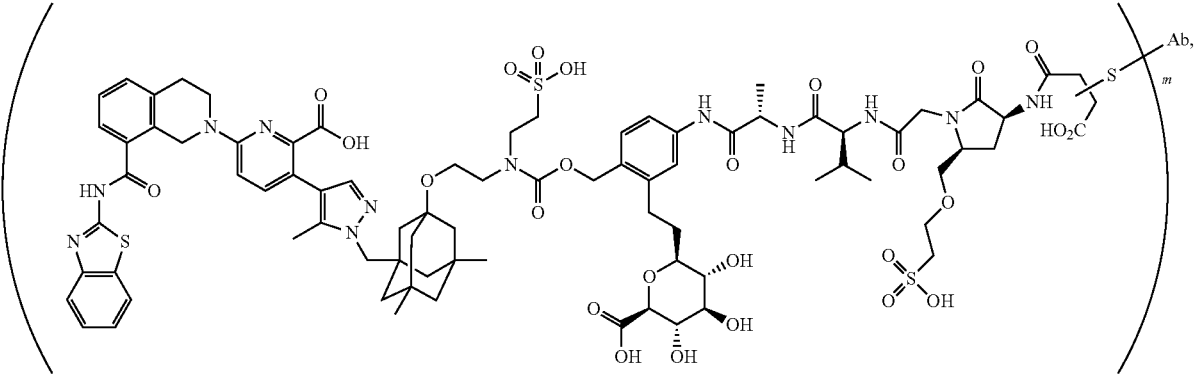

wherein m is 2, Ab is either an anti-hB7-H3 antibody, wherein the anti-hB7-H3 antibody comprises a heavy chain CDR3 domain comprising the amino acid sequence set forth in SEQ ID NO: 35, a heavy chain CDR2 domain comprising the amino acid sequence set forth in SEQ ID NO: 34, and a heavy chain CDR1 domain comprising the amino acid sequence set forth in SEQ ID NO: 33; and a light chain CDR3 domain comprising the amino acid sequence set forth in SEQ ID NO: 39, a light chain CDR2 domain comprising the amino acid sequence set forth in SEQ ID NO: 38, and a light chain CDR1 domain comprising the amino acid sequence set forth in SEQ ID NO: 37; or an anti-hB7-H3 antibody, wherein the anti-hB7H3 antibody comprises a heavy chain variable region comprising the amino acid sequence set forth in SEQ ID NO: 147, and a light chain variable region comprising the amino acid sequence set forth in SEQ ID NO: 144; or an anti-hB7-H3 antibody, wherein the anti-hB7-H3 antibody comprises a heavy chain comprising the amino acid sequence set forth in SEQ ID NO: 168, and a light chain comprising the amino acid sequence set forth in SEQ ID NO: 169.

In one embodiment, the ADC, or a pharmaceutically acceptable salt thereof, is:

(iv)

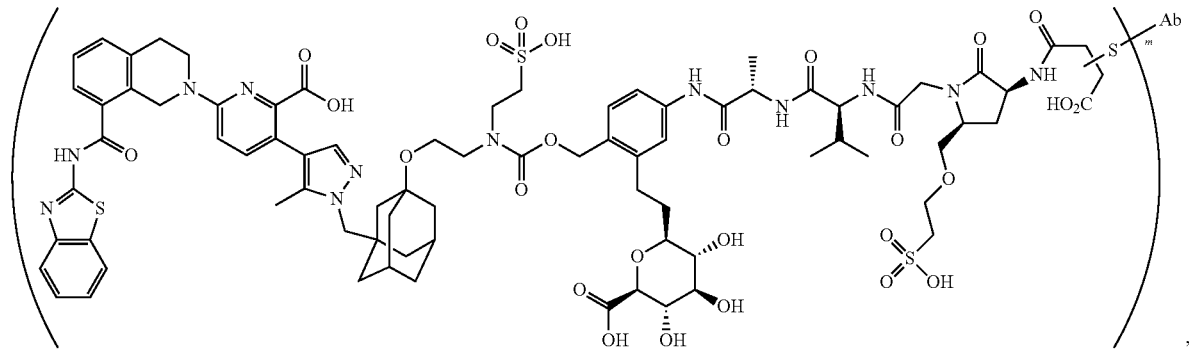

wherein m is 2, Ab is either an anti-hB7-H3 antibody, wherein the anti-hB7-H3 antibody comprises a heavy chain CDR3 domain comprising the amino acid sequence set forth in SEQ ID NO: 12, a heavy chain CDR2 domain comprising the amino acid sequence set forth in SEQ ID NO: 140, and a heavy chain CDR1 domain comprising the amino acid sequence set forth in SEQ ID NO: 10; and a light chain CDR3 domain comprising the amino acid sequence set forth in SEQ ID NO: 15, a light chain CDR2 domain comprising the amino acid sequence set forth in SEQ ID NO: 7, and a light chain CDR1 domain comprising the amino acid sequence set forth in SEQ ID NO: 136; or an anti-hB7-H3 antibody, wherein the anti-hB7H3 antibody comprises a heavy chain variable region comprising the amino acid sequence set forth in SEQ ID NO: 139, and a light chain variable region comprising the amino acid sequence set forth in SEQ ID NO: 135; or an anti-hB7-H3 antibody, wherein the anti-hB7-H3 antibody comprises a heavy chain comprising the amino acid sequence set forth in SEQ ID NO: 170, and a light chain comprising the amino acid sequence set forth in SEQ ID NO: 171.

In one embodiment, the ADC, or a pharmaceutically acceptable salt thereof, is:

(v)

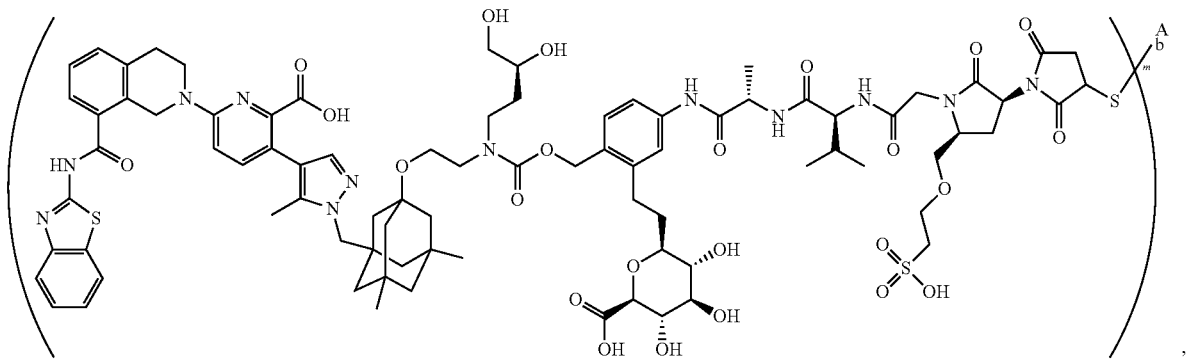

wherein m is 2, Ab is either an anti-hB7-H3 antibody, wherein the anti-hB7-H3 antibody comprises a heavy chain CDR3 domain comprising the amino acid sequence set forth in SEQ ID NO: 35, a heavy chain CDR2 domain comprising the amino acid sequence set forth in SEQ ID NO: 34, and a heavy chain CDR1 domain comprising the amino acid sequence set forth in SEQ ID NO: 33; and a light chain CDR3 domain comprising the amino acid sequence set forth in SEQ ID NO: 39, a light chain CDR2 domain comprising the amino acid sequence set forth in SEQ ID NO: 38, and a light chain CDR1 domain comprising the amino acid sequence set forth in SEQ ID NO: 37; or an anti-hB7-H3 antibody, wherein the anti-hB7H3 antibody comprises a heavy chain variable region comprising the amino acid sequence set forth in SEQ ID NO: 147, and a light chain variable region comprising the amino acid sequence set forth in SEQ ID NO: 144; or an anti-hB7-H3 antibody, wherein the anti-hB7-H3 antibody comprises a heavy chain comprising the amino acid sequence set forth in SEQ ID NO: 168, and a light chain comprising the amino acid sequence set forth in SEQ ID NO: 169.

In one embodiment, the ADC, or a pharmaceutically acceptable salt thereof, is:

(v)

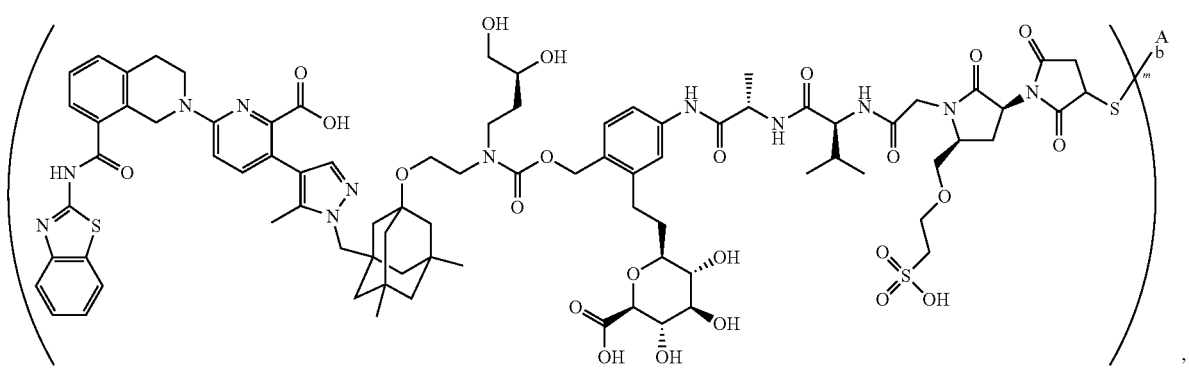

wherein m is 2, Ab is either an anti-hB7-H3 antibody, wherein the anti-hB7-H3 antibody comprises a heavy chain CDR3 domain comprising the amino acid sequence set forth in SEQ ID NO: 12, a heavy chain CDR2 domain comprising the amino acid sequence set forth in SEQ ID NO: 140, and a heavy chain CDR1 domain comprising the amino acid sequence set forth in SEQ ID NO: 10; and a light chain CDR3 domain comprising the amino acid sequence set forth in SEQ ID NO: 15, a light chain CDR2 domain comprising the amino acid sequence set forth in SEQ ID NO: 7, and a light chain CDR1 domain comprising the amino acid sequence set forth in SEQ ID NO: 136; or an anti-hB7-H3 antibody, wherein the anti-hB7H3 antibody comprises a heavy chain variable region comprising the amino acid sequence set forth in SEQ ID NO: 139, and a light chain variable region comprising the amino acid sequence set forth in SEQ ID NO: 135; or an anti-hB7-H3 antibody, wherein the anti-hB7-H3 antibody comprises a heavy chain comprising the amino acid sequence set forth in SEQ ID NO: 170, and a light chain comprising the amino acid sequence set forth in SEQ ID NO: 171.

In one embodiment, the ADC, or a pharmaceutically acceptable salt thereof, is:

(vi)

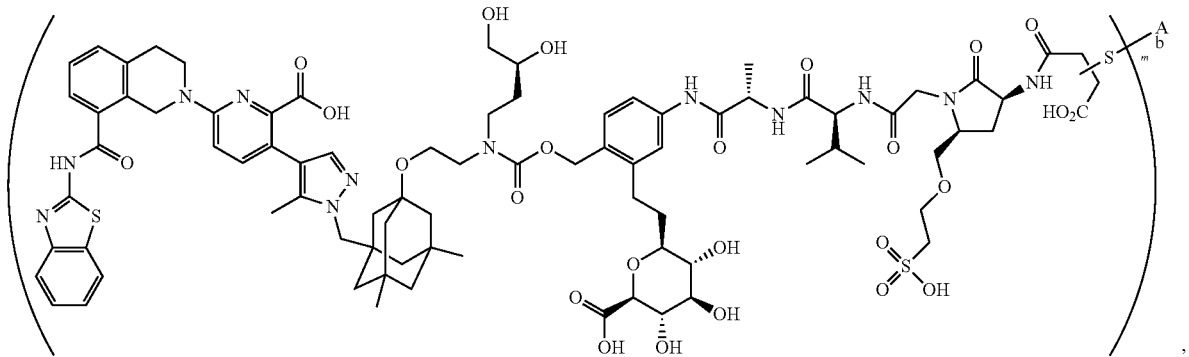

wherein m is 2, Ab is either an anti-hB7-H3 antibody, wherein the anti-hB7-H3 antibody comprises a heavy chain CDR3 domain comprising the amino acid sequence set forth in SEQ ID NO: 35, a heavy chain CDR2 domain comprising the amino acid sequence set forth in SEQ ID NO: 34, and a heavy chain CDR1 domain comprising the amino acid sequence set forth in SEQ ID NO: 33; and a light chain CDR3 domain comprising the amino acid sequence set forth in SEQ ID NO: 39, a light chain CDR2 domain comprising the amino acid sequence set forth in SEQ ID NO: 38, and a light chain CDR1 domain comprising the amino acid sequence set forth in SEQ ID NO: 37; or an anti-hB7-H3 antibody, wherein the anti-hB7H3 antibody comprises a heavy chain variable region comprising the amino acid sequence set forth in SEQ ID NO: 147, and a light chain variable region comprising the amino acid sequence set forth in SEQ ID NO: 144; or an anti-hB7-H3 antibody, wherein the anti-hB7-H3 antibody comprises a heavy chain comprising the amino acid sequence set forth in SEQ ID NO: 168, and a light chain comprising the amino acid sequence set forth in SEQ ID NO: 169.

In one embodiment, the ADC, or a pharmaceutically acceptable salt thereof, is:

(vi)

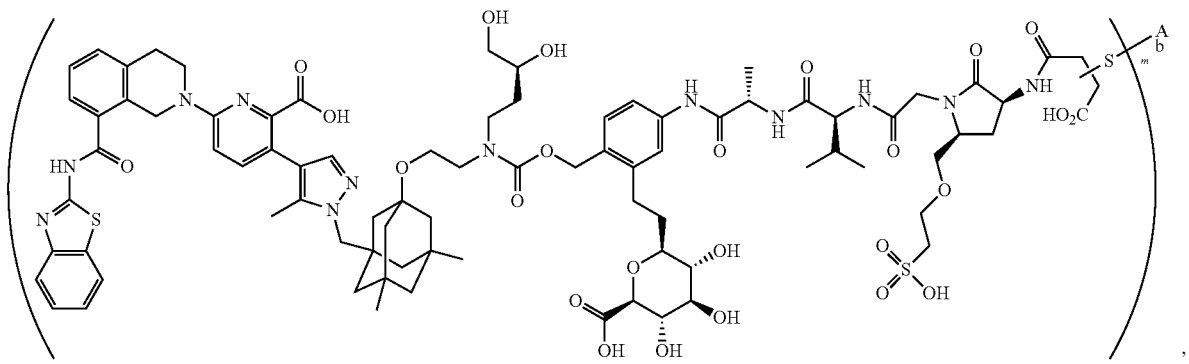

wherein m is 2, Ab is either an anti-hB7-H3 antibody, wherein the anti-hB7-H3 antibody comprises a heavy chain CDR3 domain comprising the amino acid sequence set forth in SEQ ID NO: 12, a heavy chain CDR2 domain comprising the amino acid sequence set forth in SEQ ID NO: 140, and a heavy chain CDR1 domain comprising the amino acid sequence set forth in SEQ ID NO: 10; and a light chain CDR3 domain comprising the amino acid sequence set forth in SEQ ID NO: 15, a light chain CDR2 domain comprising the amino acid sequence set forth in SEQ ID NO: 7, and a light chain CDR1 domain comprising the amino acid sequence set forth in SEQ ID NO: 136; or an anti-hB7-H3 antibody, wherein the anti-hB7H3 antibody comprises a heavy chain variable region comprising the amino acid sequence set forth in SEQ ID NO: 139, and a light chain variable region comprising the amino acid sequence set forth in SEQ ID NO: 135; or an anti-hB7-H3 antibody, wherein the anti-hB7-H3 antibody comprises a heavy chain comprising the amino acid sequence set forth in SEQ ID NO: 170, and a light chain comprising the amino acid sequence set forth in SEQ ID NO: 171.

Bcl-xL inhibitors, including warheads and synthons, and methods of making the same, are described in US 2016/0339117 (AbbVie Inc.), which is incorporated by reference herein.

III.A.4. Methods of Synthesis of Bcl-xL ADCs

The Bcl-xL inhibitors and synthons described herein may be synthesized using standard, known techniques of organic chemistry. General schemes for synthesizing Bcl-xL inhibitors and synthons that may be used as-is or modified to synthesize the full scope of Bcl-xL inhibitors and synthons described herein are provided below. Specific methods for synthesizing exemplary Bcl-xL inhibitors and synthons that may be useful for guidance are provided in the Examples section. ADCs may likewise be prepared by standard methods, such as methods analogous to those described in Hamblett et al., 2004, "Effects of Drug Loading on the Antitumor Activity of a Monoclonal Antibody Drug Conjugate", *Clin. Cancer Res.* 10:7063-7070; Doronina et al., 2003, "Development of potent and highly efficacious monoclonal antibody auristatin conjugates for cancer therapy," *Nat. Biotechnol.* 21(7):778-784; and Francisco et al., 2003, *Blood* 102:1458-1465. For example, ADCs with four drugs per antibody may be prepared by partial reduction of the antibody with an excess of a reducing reagent such as DTT or TCEP at 37° C. for 30 min, then the buffer exchanged by elution through SEPHADEX® G-25 resin with 1 mM DTPA in DPBS. The eluent is diluted with further DPBS, and the thiol concentration of the antibody may be measured using 5,5'-dithiobis(2-nitrobenzoic acid) [Ellman's reagent]. An excess, for example 5-fold, of a linker-drug synthon is added at 4° C. for 1 hr, and the conjugation reaction may be quenched by addition of a substantial excess, for example 20-fold, of cysteine. The resulting ADC mixture may be purified on SEPHADEX G-25 equilibrated in PBS to remove unreacted synthons, desalted if desired, and purified by size-exclusion chromatography. The resulting ADC may then be then sterile filtered, for example, through a 0.2 µm filter, and lyophilized if desired for storage. In certain embodiments, all of the interchain cysteine disulfide bonds are replaced by linker-drug conjugates. One embodiment pertains to a method of making an ADC, comprising contacting a synthon described herein with an antibody under conditions in which the synthon covalently links to the antibody Examples of the foregoing Bcl-xL inhibitors, linkers, and synthons thereof, as well as methods of making the same, can be found in US Patent Publication No. US 2016/0339117, the entire contents of which are incorporated by reference herein.

Specific methods for synthesizing exemplary ADCs that may be used to synthesize the full range of ADCs described herein are provided in the Examples section.

III.A.5. General Methods for Synthesizing Bcl-xL Inhibitors

In the schemes below, the various substituents $Ar^1$, $Ar^2$, $Z^1$, $R^4$, $R^{10}$, $R^{11a}$ and $R^{11b}$ are as defined in the Detailed Description section.

5.1.1. Synthesis of Compound (6)

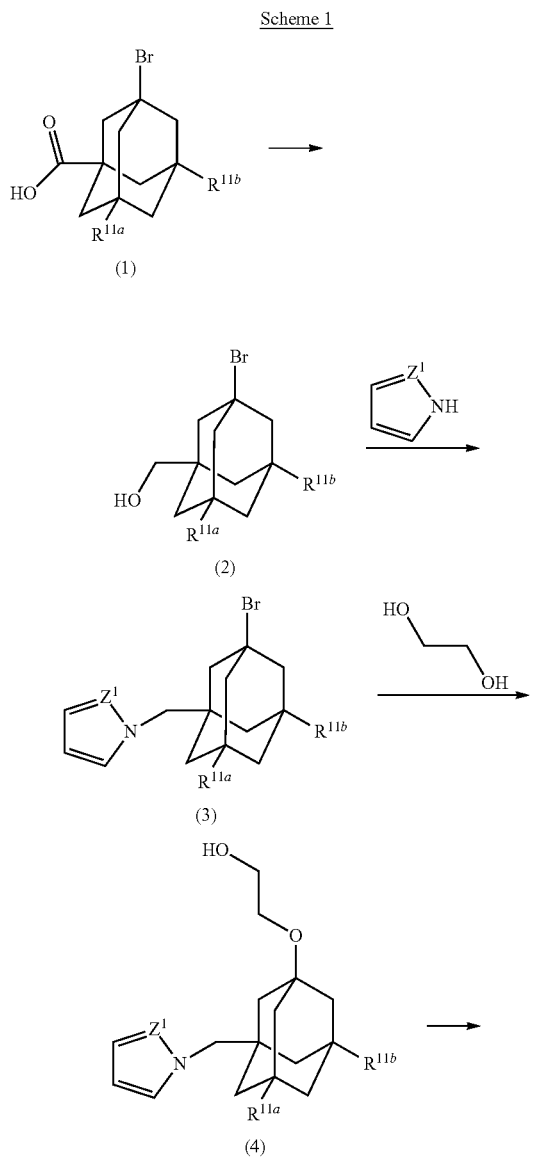

5.1.2. Synthesis of Compound (12)

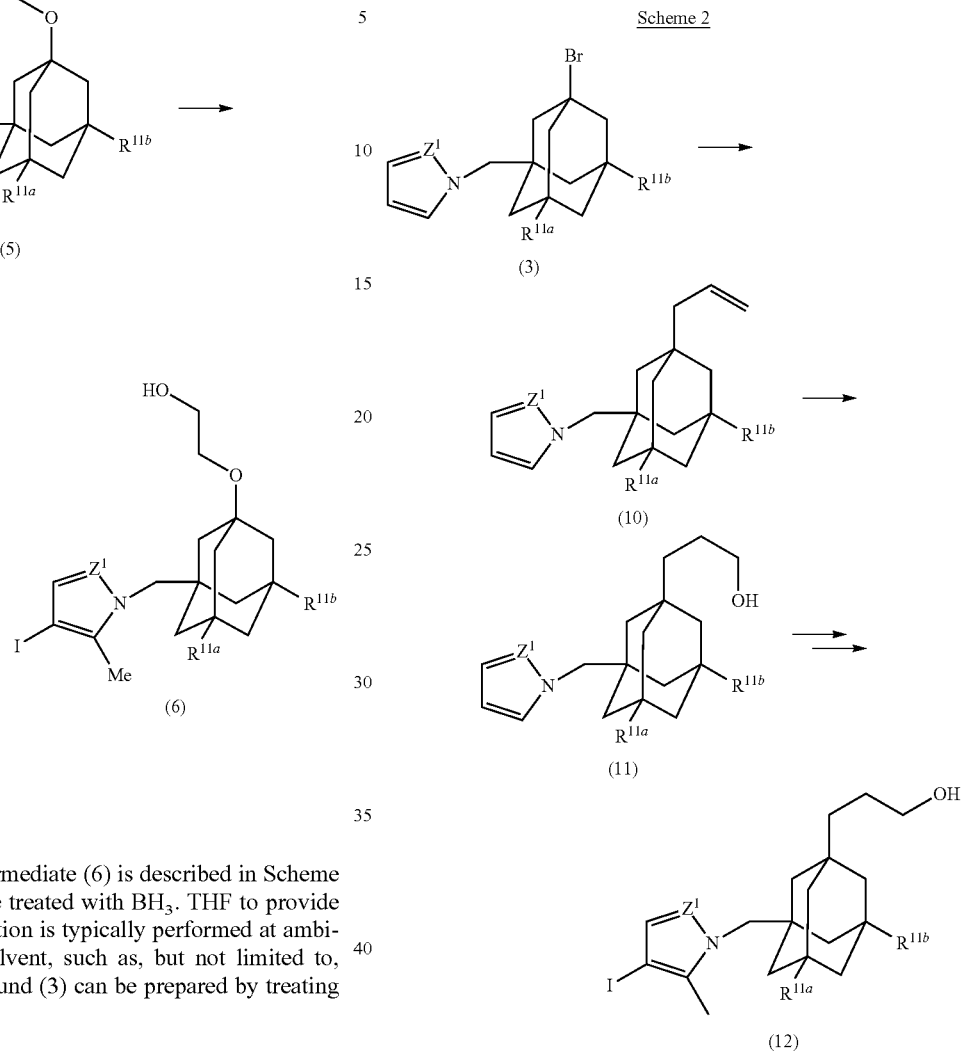

Scheme 2

The synthesis of intermediate (12) is described in Scheme 2. Compound (3) can be treated with tri-n-butyl-allylstannane in the presence of ZnCl₂.Et₂O or N, N'-azoisobutyronitrile (AIBN) to provide compound (10) (Yamamoto et al., 1998, *Heterocycles* 47:765-780). The reaction is typically performed at −78° C. in a solvent, such as, but not limited to dichloromethane. Compound (10) can be treated under standard conditions known in the art for hydroboration/oxidation to provide compound (11). For example, treatment of compound (10) with a reagent such as BH₃.THF in a solvent such as, but not limited to, tetrahydrofuran followed by treatment of the intermediate alkylborane adduct with an oxidant such as, but not limited to, hydrogen peroxide in the presence of a base such as, but not limited to, sodium hydroxide would provide compound (11) (Brown et al., 1968, *J. Am. Chem. Soc.* 86:397). Typically the addition of BH₃.THF is performed at low temperature before warming to ambient temperature, which is followed by the addition of hydrogen peroxide and sodium hydroxide to generate the alcohol product. Compound (12) can be generated according to Scheme 1, as previously described for compound (6).

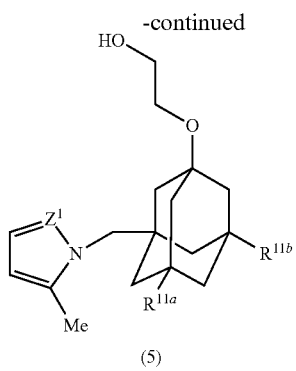

The synthesis of an intermediate (6) is described in Scheme 1. Compound (1) can be treated with BH₃. THF to provide compound (2). The reaction is typically performed at ambient temperature in a solvent, such as, but not limited to, tetrahydrofuran. Compound (3) can be prepared by treating compound (2) with

in the presence of cyanomethylenetributylphosphorane. The reaction is typically performed at an elevated temperature in a solvent such as, but not limited to, toluene. Compound (3) can be treated with ethane-1,2-diol in the presence of a base such as, but not limited to, triethylamine, to provide compound (4). The reaction is typically performed at an elevated temperature, and the reaction may be performed under microwave conditions. Compound (4) can be treated with a strong base, such as, but not limited to, n-butyllithium, followed by the addition of iodomethane, to provide compound (5). The addition and reaction is typically performed in a solvent such as, but not limited to, tetrahydrofuran, at a reduced temperature before warming up to ambient temperature for work up. Compound (5) can be treated with N-iodosuccinimide to provide compound (6). The reaction is typically performed at ambient temperature is a solvent such as, but not limited to, N,N-dimethylformamide.

5.1.3. Synthesis of Compound (15)

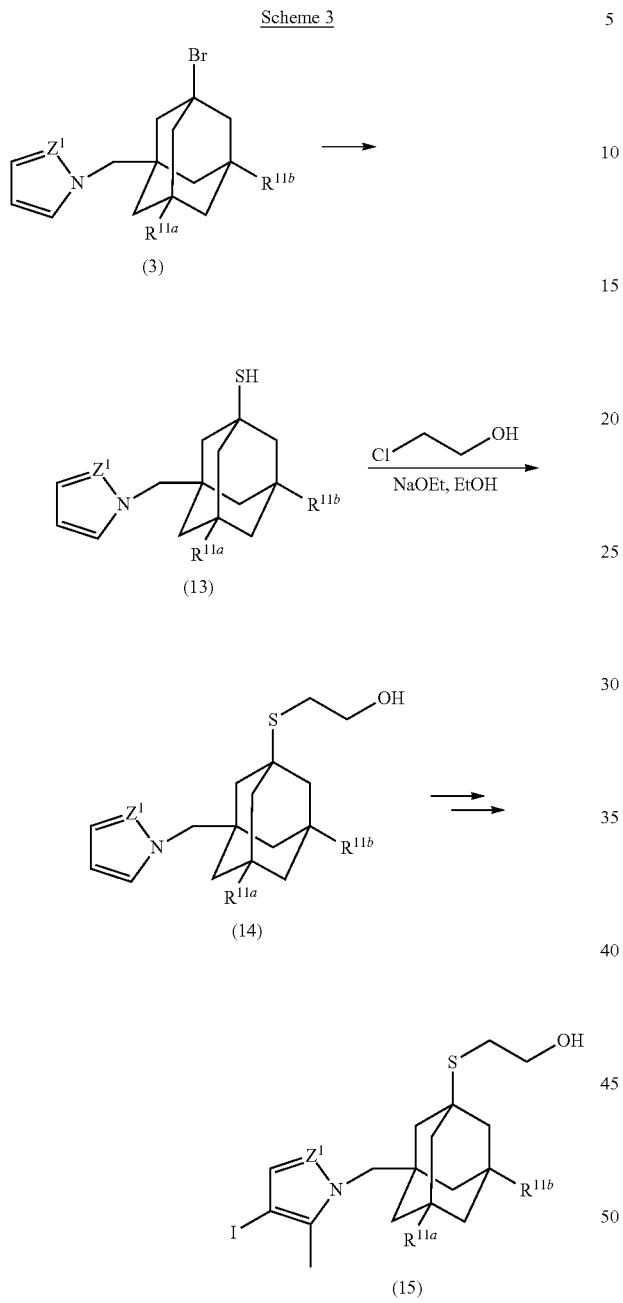

5.1.4. Synthesis of Compound (22)

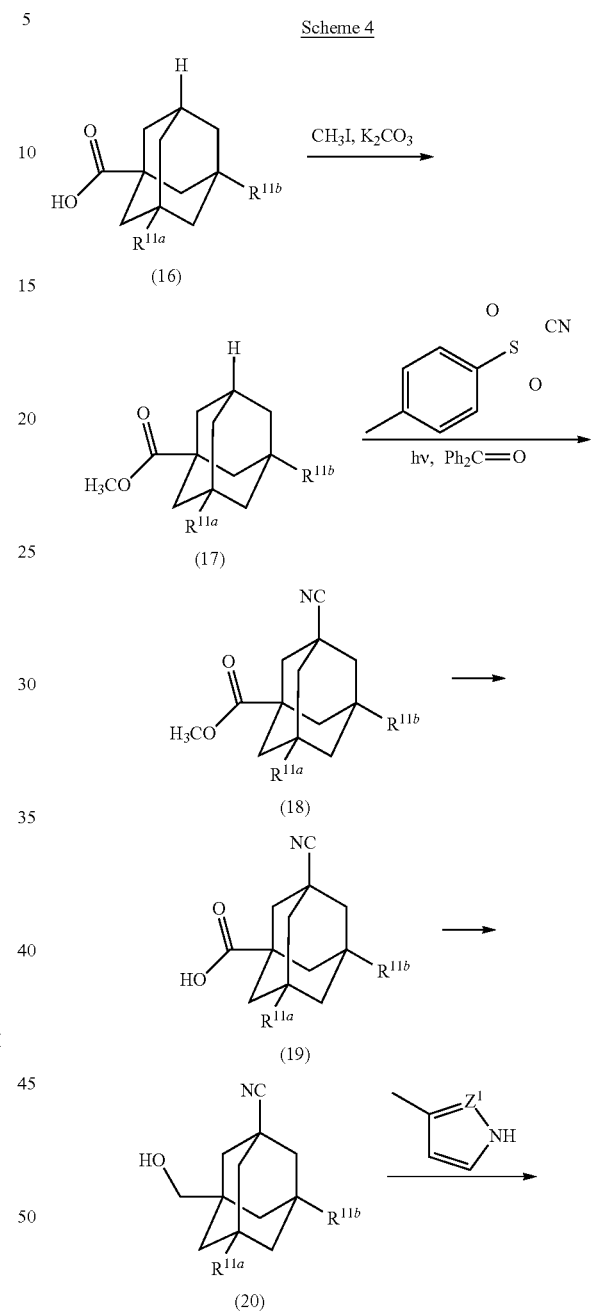

The synthesis of intermediate (15) is described in Scheme 3. Compound (3) can be reacted with thiourea in a solvent mixture of acetic acid and 48% aqueous HBr solution at 100° C. to yield an intermediate that can be subsequently treated with sodium hydroxide in a solvent mixture such as, but not limited to, 20% v/v ethanol in water to provide compound (13). Compound (13) can be reacted with 2-chloroethanol in the presence of a base such as, but not limited to, sodium ethoxide to provide compound (14). The reaction is typically performed at ambient or elevated temperatures in a solvent such as, but not limited to, ethanol. Compound (15) can be generated according to Scheme 1, as previously described for compound (6).

-continued

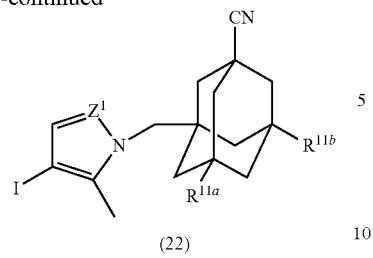

(22)

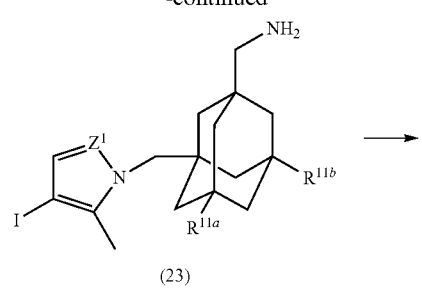

(23)

The synthesis of compound (22) is described in Scheme 4. Compound (16) can be reacted with iodomethane in the presence of a base such as, but not limited to, potassium carbonate to provide compound (17). The reaction is typically conducted at ambient or elevated temperature in a solvent such as, but not limited to, acetone or N,N-dimethylformamide. Compound (17) can be reacted under photochemical conditions with tosyl cyanide in the presence of benzophenone to provide compound (18) (see Kamijo et al., 2011, *Org. Lett.*, 13:5928-5931). The reaction is typically run at ambient temperature in a solvent such as, but not limited to, acetonitrile or benzene using a Riko 100W medium pressure mercury lamp as the light source. Compound (18) can be reacted with lithium hydroxide in a solvent system such as, but not limited to, mixtures of water and tetrahydrofuran or water and methanol to provide compound (19). Compound (19) can be treated with $BH_3 \cdot THF$ to provide compound (20). The reaction is typically performed at ambient temperature in a solvent, such as, but not limited to, tetrahydrofuran. Compound (21) can be prepared by treating compound (20) with

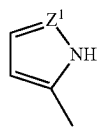

in the presence of cyanomethylenetributylphosphorane. The reaction is typically performed at an elevated temperature in a solvent such as, but not limited to, toluene. Compound (21) can be treated with N-iodosuccinimide to provide compound (22). The reaction is typically performed at ambient temperature is a solvent such as, but not limited to, N,N-dimethylformamide.

5.1.5. Synthesis of Compound (24)

Scheme 5

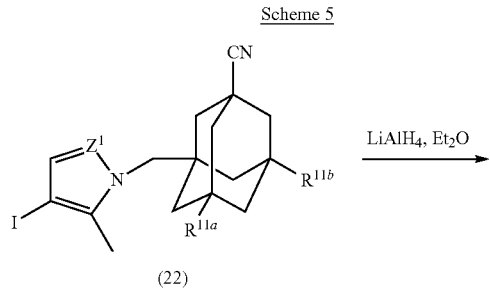

(22)

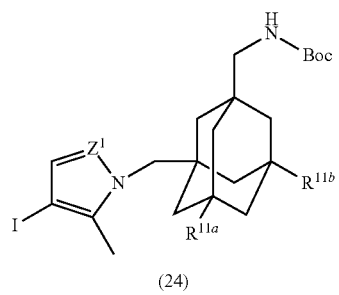

(24)

The synthesis of pyrazole compound (24), is described in Scheme 5. Compound (22) can be treated with a reducing agent such as, but not limited to, lithium aluminum hydride in a solvent such as, but not limited to, diethyl ether or tetrahydrofuran to provide compound (23). Typically the reaction is performed at 0° C. before warming to ambient or elevated temperature. Compound (23) can be reacted with di-tert-butyl dicarbonate under standard conditions described herein or in the literature to provide compound (24).

5.1.6. Synthesis of Compound (24a)

Scheme 6

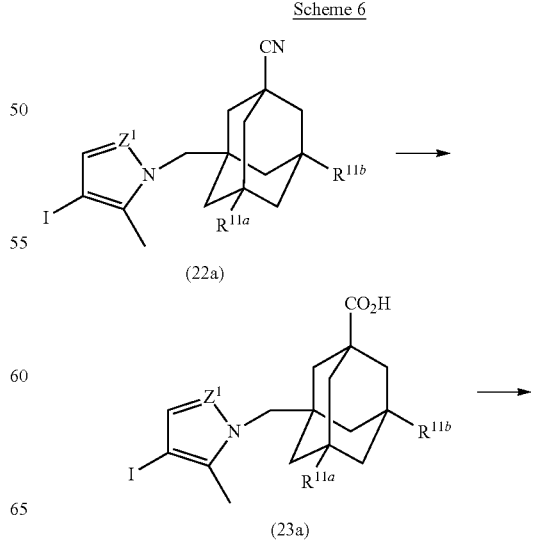

-continued

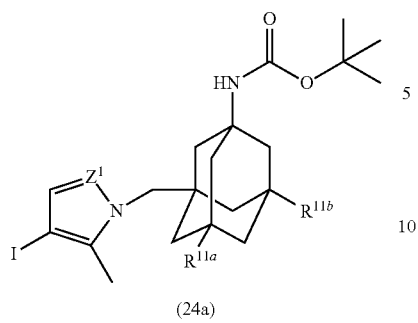

(24a)

The synthesis of intermediate (24a) is described in Scheme 6. Compound (22a) can be hydrolyzed using conditions described in the literature to provide compound (23a). Typically the reaction is run in the presence of potassium hydroxide in a solvent such as, but not limited to, ethylene glycol at elevated temperatures (see Roberts et al., 1994, *J. Org. Chem.* 59:6464-6469; Yang et al, 2013, *Org. Lett.*, 15:690-693). Compound (24a) can be made from compound (23a) by Curtius rearrangement using conditions described in the literature. For example, compound (23a) can be reacted with sodium azide in the presence of tetrabutylammonium bromide, zinc(II) triflate and di-tert-butyl dicarbonate to provide compound (24a) (see Lebel et al., *Org. Lett.*, 2005, 7:4107-4110). Typically the reaction is run at elevated temperatures, preferably from 40-50° C., in a solvent such as, but not limited to, tetrahydrofuran.

5.1.7. Synthesis of Compound (29)

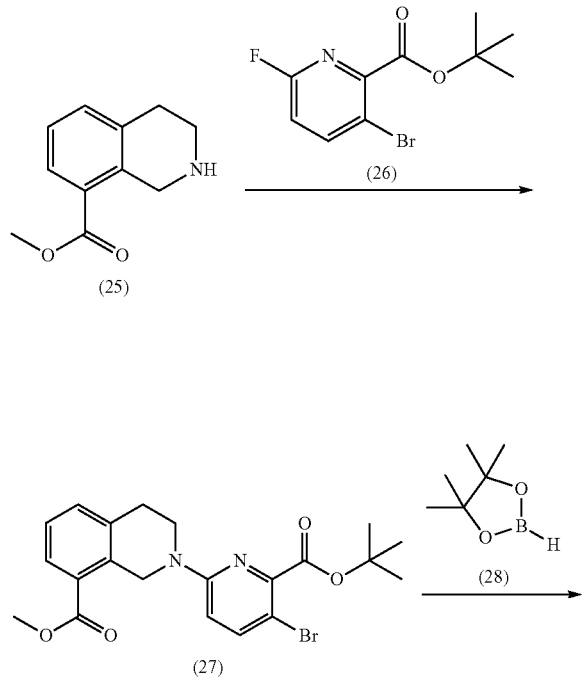

As shown in Scheme 7, compounds of formula (27) can be prepared by reacting compounds of formula (25) with tert-butyl 3-bromo-6-fluoropicolinate (26) in the presence of a base, such as, but not limited to, N,N-diisopropylethylamine, or triethylamine. The reaction is typically performed under an inert atmosphere at an elevated temperature in a solvent, such as, but not limited to, dimethyl sulfoxide. Compounds of formula (27) can be reacted with 4,4,5,5-tetramethyl-1,3,2-dioxaborolane (28), under borylation conditions described herein or in the literature to provide compounds of formula (29).

5.1.8. Synthesis of Compound (38)

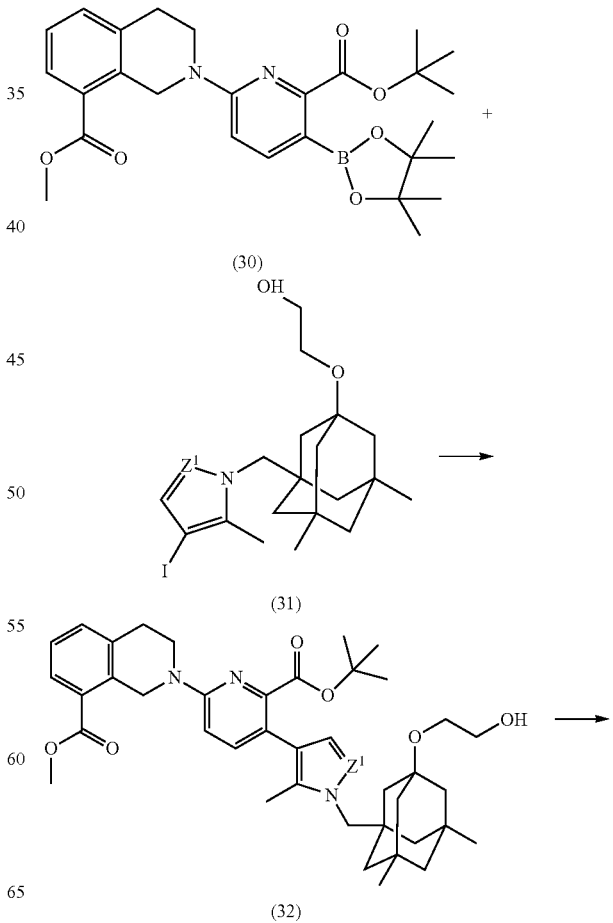

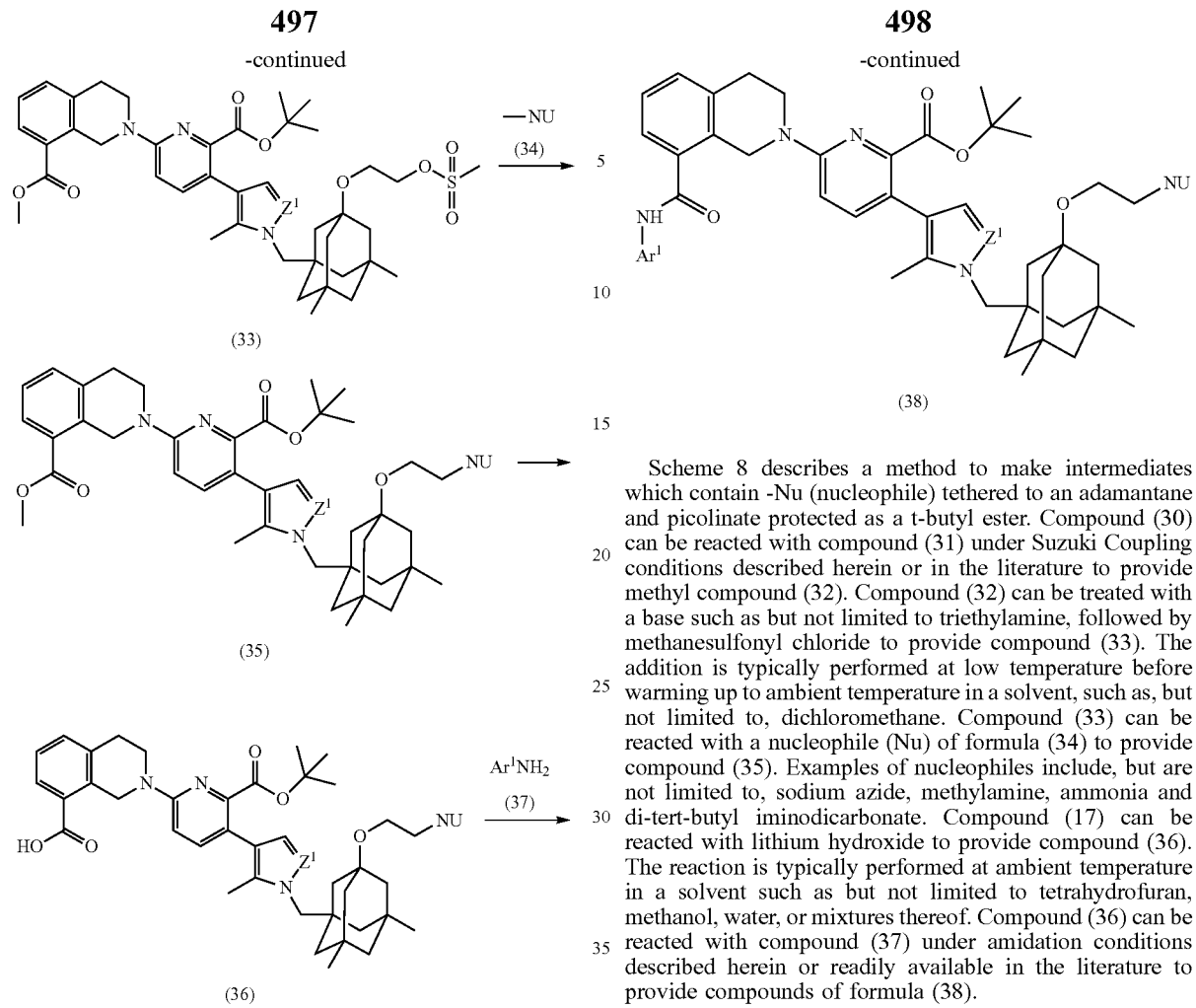

Scheme 8 describes a method to make intermediates which contain -Nu (nucleophile) tethered to an adamantane and picolinate protected as a t-butyl ester. Compound (30) can be reacted with compound (31) under Suzuki Coupling conditions described herein or in the literature to provide methyl compound (32). Compound (32) can be treated with a base such as but not limited to triethylamine, followed by methanesulfonyl chloride to provide compound (33). The addition is typically performed at low temperature before warming up to ambient temperature in a solvent, such as, but not limited to, dichloromethane. Compound (33) can be reacted with a nucleophile (Nu) of formula (34) to provide compound (35). Examples of nucleophiles include, but are not limited to, sodium azide, methylamine, ammonia and di-tert-butyl iminodicarbonate. Compound (17) can be reacted with lithium hydroxide to provide compound (36). The reaction is typically performed at ambient temperature in a solvent such as but not limited to tetrahydrofuran, methanol, water, or mixtures thereof. Compound (36) can be reacted with compound (37) under amidation conditions described herein or readily available in the literature to provide compounds of formula (38).

5.1.9. Synthesis of Compounds (42) and (43)

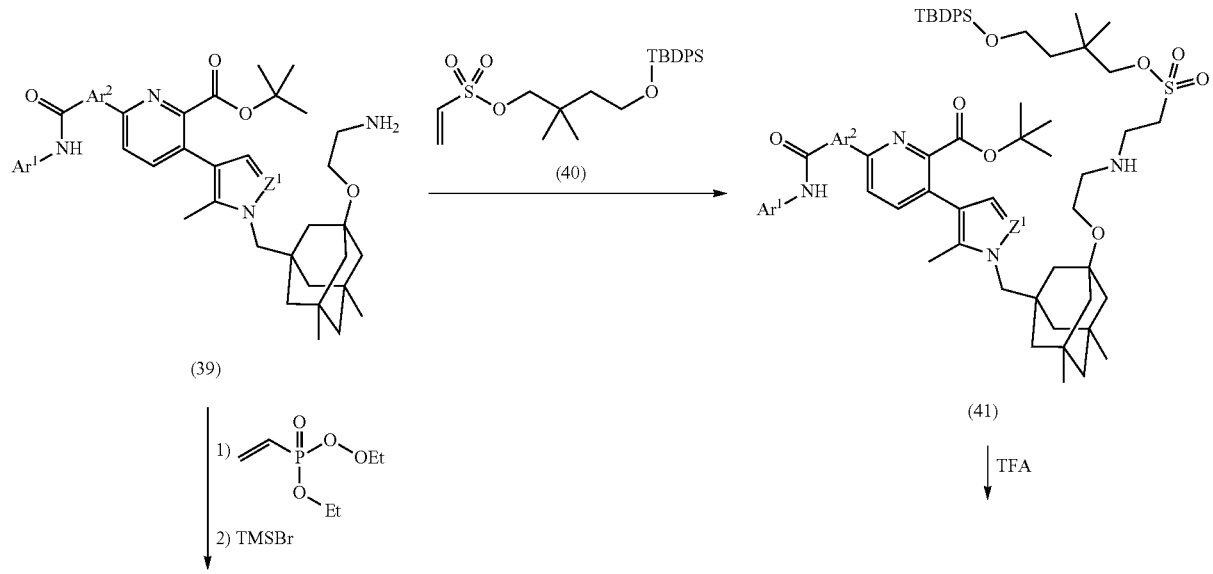

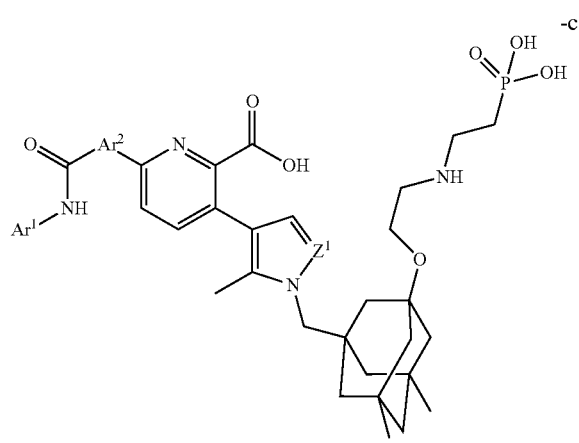

(42)

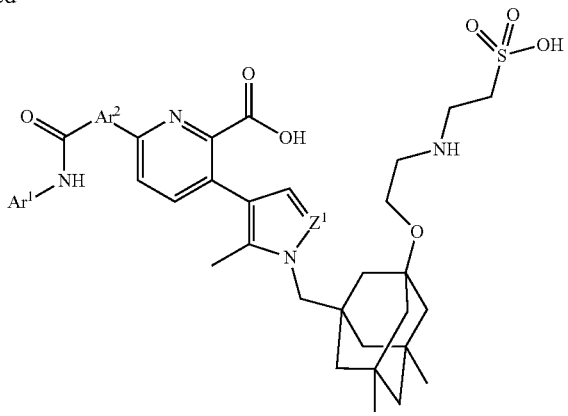

(43)

Scheme 9 shows representative methods used to make solubilized Bcl-xL inhibitors. Bcl-xL inhibitors can be synthesized using the general approach of modifying a primary amine with a solubilizing group and then attaching the resulting secondary amine to a linker as described in later schemes. For example, compound (41) can be prepared by reacting compound (39) with compound (40). The reaction is typically performed at ambient temperature in a solvent such as but not limited to N,N-dimethylformamide. Compound (41) can be reacted with trifluoroacetic acid to provide compound (43). The reaction is typically performed at ambient temperature in a solvent such as but not limited to dichloromethane. Another example shown in Scheme 9 is the reaction of compound (39) with diethyl vinylphosphonate, followed by reaction with bromotrimethylsilane and allyltrimethylsilane to provide compound (42). Other examples to introduce solubilizing groups on the Bcl-xL inhibitors described herein include, but are not limited to, reductive amination reactions, alkylations, and amidation reactions.

5.1.10. Synthesis of Compound (47)

Scheme 10

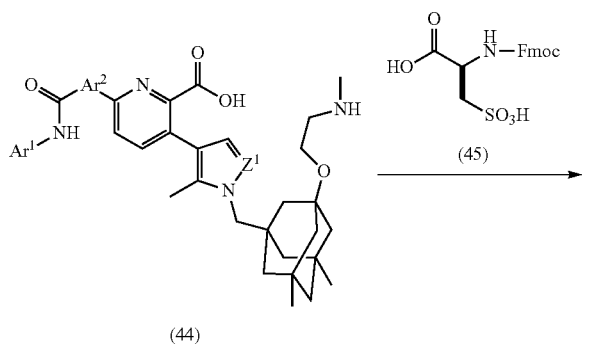

(44)

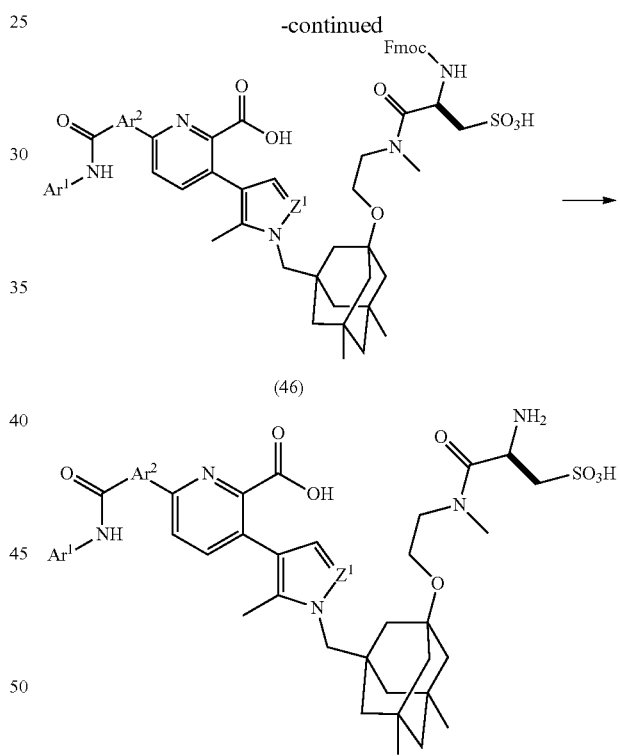

(46)

(47)

Scheme 10 shows introduction of a solubilizing group by amidation reaction. Bcl-xL inhibitors can be synthesized using the general approach of modifying a primary or secondary amine with a solubilizing group and then attaching the resulting amine to a linker as described in later schemes. For example, compound (45) can be treated sequentially with HATU and compound (44), to provide compound (46). Compound (46) can be treated with diethylamine in solvents such as, but not limited to, N,N-dimethylformamide to give compound (47).

5.1.11. Synthesis of Compound (51)
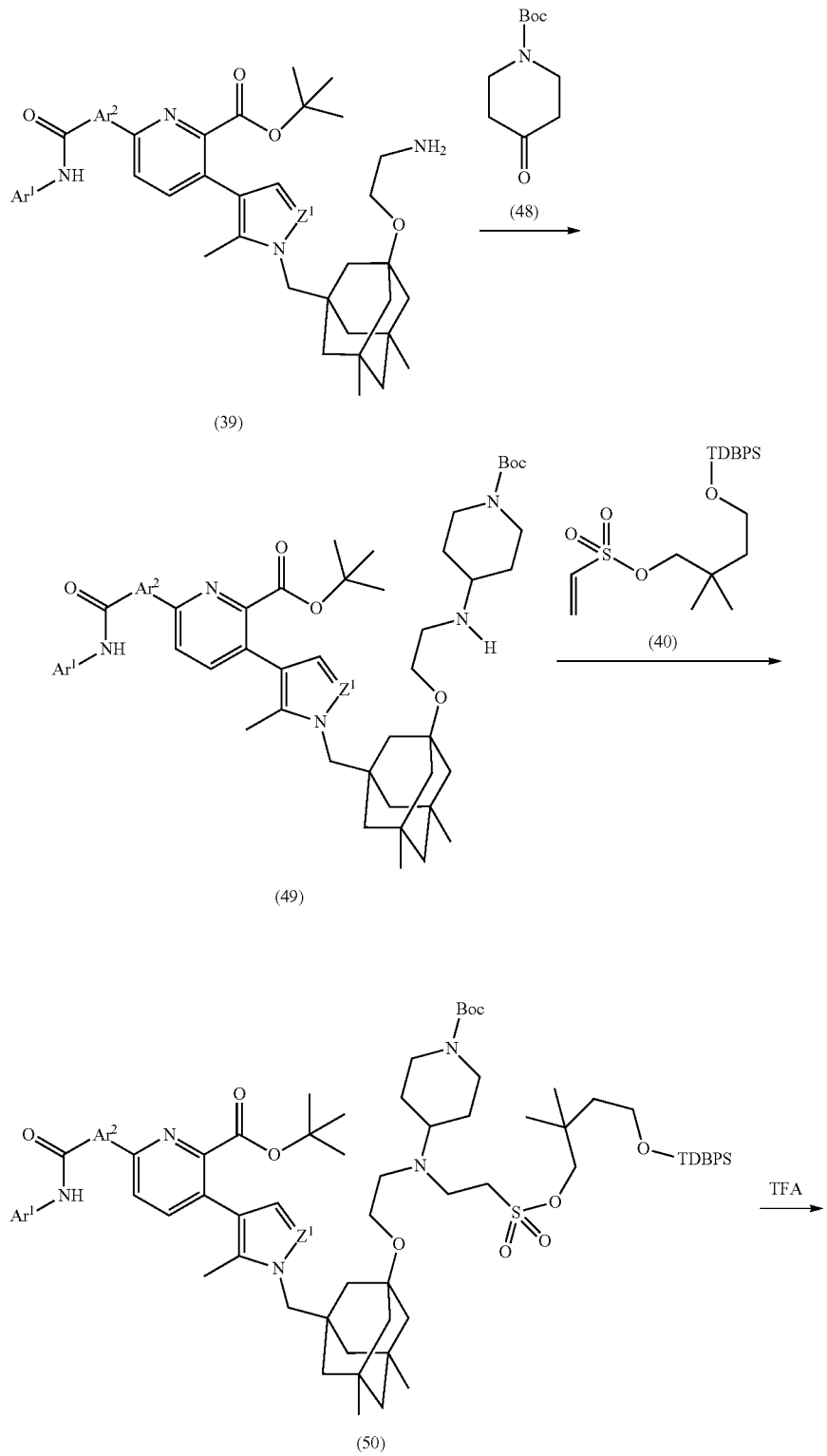
Scheme 11

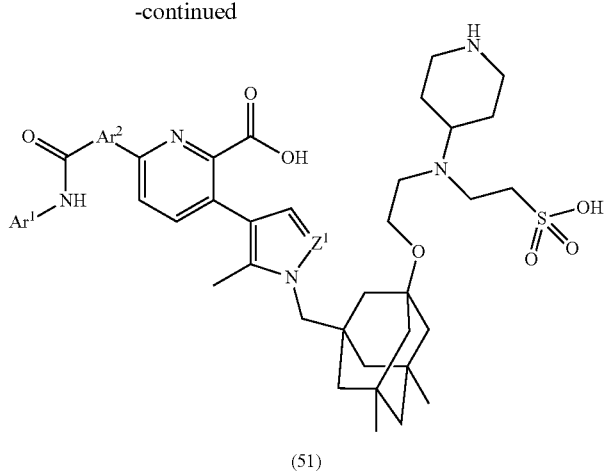

(51)

Scheme 11 shows representative methods to make solubilized Bcl-xL inhibitors. Bcl-xL inhibitors can be synthesized using the general approach of modifying a primary amine with a spacer to give a differentially protected diamine. The unprotected secondary amine can be modified with a solubilizing group. Deprotection of a protected amine then reveals a site for linker attachment, as described in later schemes. For example, compound (39) can be reductively alkylated with reagents such as, but not limited to tert-butyl 4-oxopiperidine-1-carboxylate (48), under conditions known in the art, to provide a secondary amine (49).

Compound (50) can be prepared by reacting compound (49) with 4-((tert-butyldiphenylsilyl)oxy)-2,2-dimethylbutyl ethenesulfonate (40). The reaction is typically performed at ambient temperature in a solvent such as but not limited to N,N-dimethylformamide. Compound (40) can be reacted with trifluoroacetic acid to provide compound (51). The reaction is typically performed at ambient temperature in a solvent such as but not limited to dichloromethane.

5.1.12. Synthesis of Compound (61)

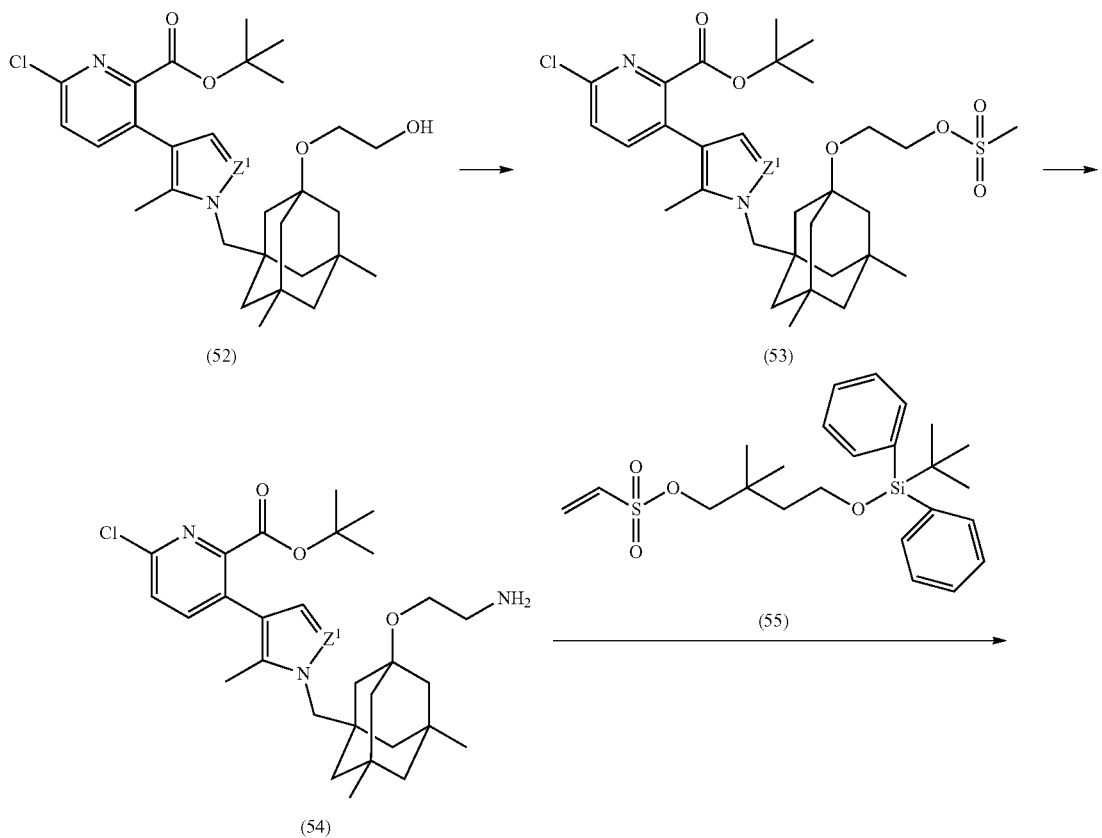

-continued
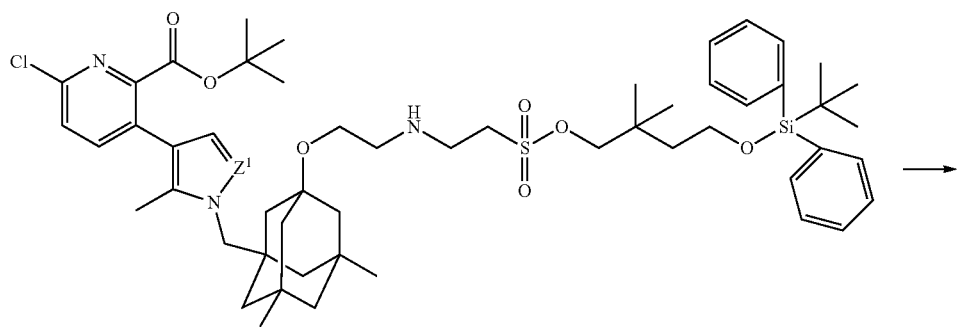
(56)
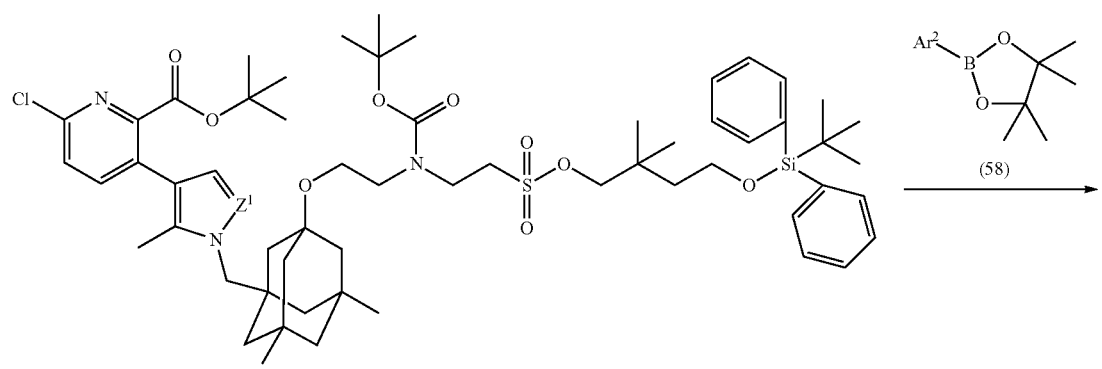
(57)
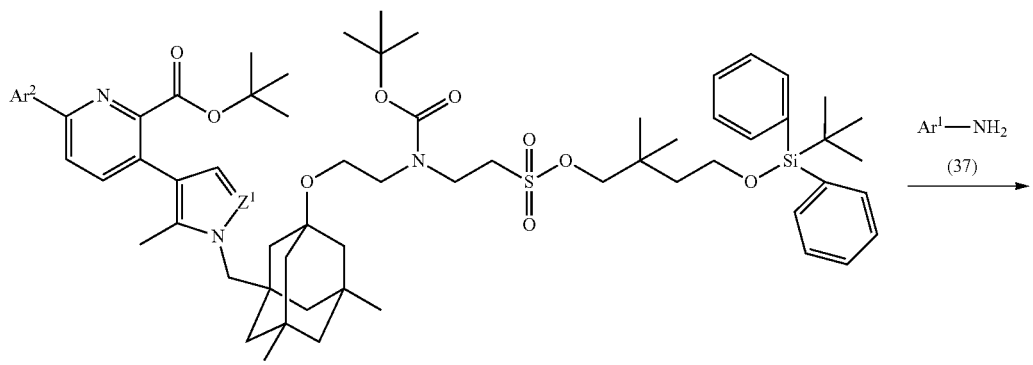
(59)
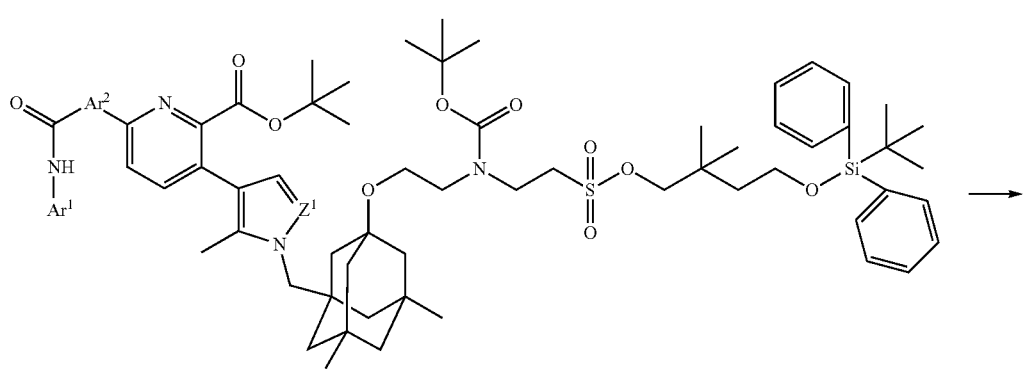
(60)

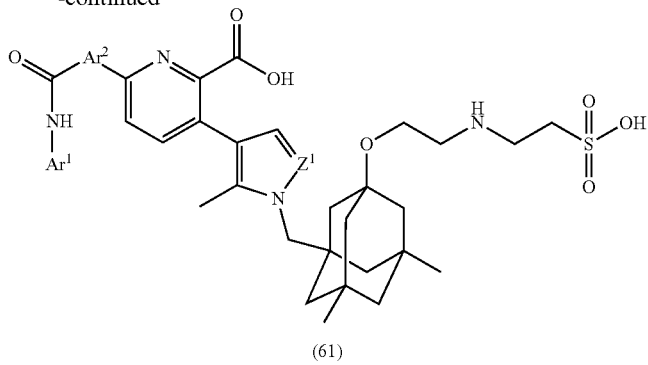

(61)

Scheme 12 describes a method to synthesize solubilized Bcl-xL inhibitors. Compound (52) can be reacted with methanesulfonyl chloride, in the presence of a base, such as, but not limited to, triethylamine, to provide compound (53). The reaction is typically performed at a low temperature in a solvent such as but not limited to dichloromethane. Compound (53) can be treated with ammonia in methanol to provide compound (54). The reaction is typically performed at an elevated temperature, and the reaction may be performed under microwave conditions. Compound (56) can be prepared by reacting compound (55) in the presence of a base such as but not limited to N,N-diisopropylethylamine. The reaction is typically performed at ambient temperature in a solvent such as but not limited to N,N-dimethylformamide. Compound (56) can be treated with di-t-butyldicarbonate and 4-(dimethylamino)pyridine to provide compound (57). The reaction is typically performed at ambient temperature in a solvent such as but not limited to tetrahydrofuran. Compound (59) can be prepared by reacting compound (57) with a boronate ester (or the equivalent boronic acid) of formula (58), under Suzuki Coupling conditions described herein or in the literature. Bis(2,5-dioxopyrrolidin-1-yl) carbonate can be reacted with compound (37), followed by reaction with compound (59), to provide compound (60). The reaction is typically performed at ambient temperature in a solvent such as, but not limited to, acetonitrile. Compound (61) can be prepared by treating compound (60) with trifluoroacetic acid. The reaction is typically performed at ambient temperature in a solvent such as but not limited to dichloromethane.

5.1.13. Synthesis of Compound (70)

Scheme 13

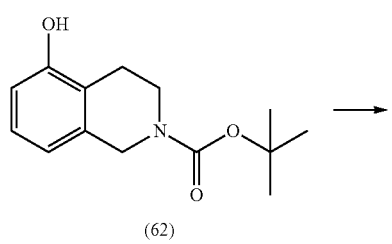

(62)

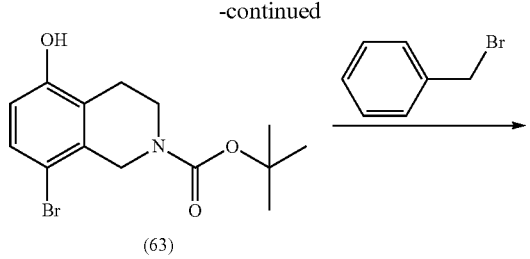

(63)

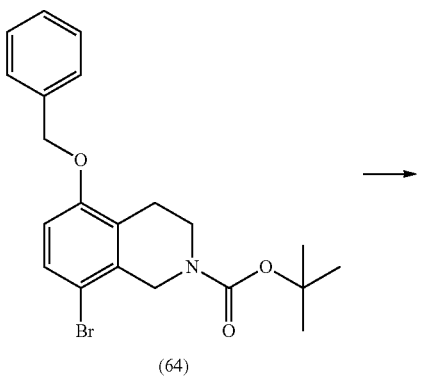

(64)

(65)

509
-continued

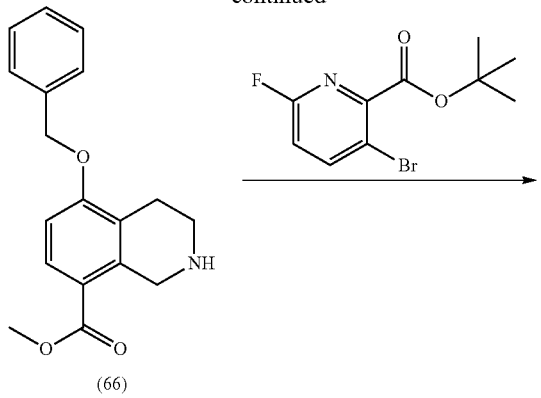
(66)

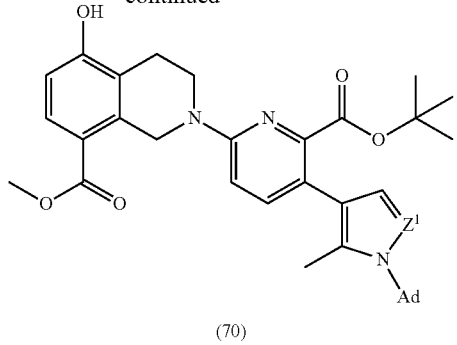
(68)

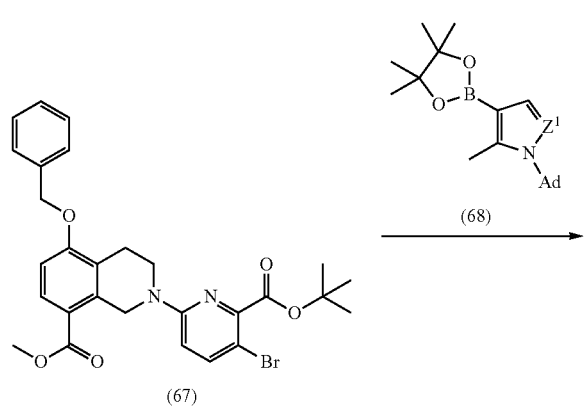
(67)

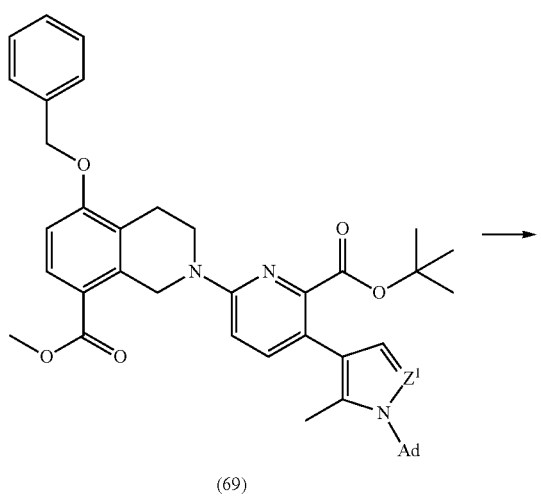
(69)

510
-continued

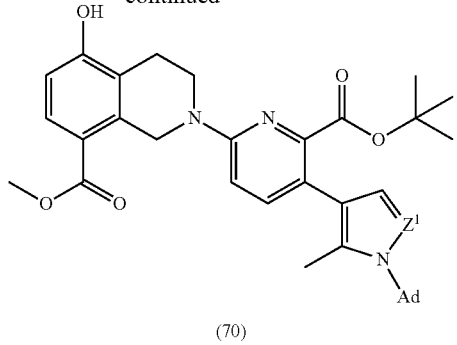

(70)

Scheme 13 describes the synthesis of 5-hydroxy tetrahydroisoquinoline intermediates. Compound (63) can be prepared by treating compound (62) with N-bromosuccinimide. The reaction is typically performed at ambient temperature is a solvent such as, but not limited to, N,N-dimethylformamide. Compound (63) can be reacted with benzyl bromide in the presence of a base, such as, but not limited to, potassium carbonate, to provide compound (64). The reaction is typically performed at an elevated temperature, in a solvent such as, but not limited to, acetone. Compound (64) can be treated with carbon monoxide and methanol in the presence of a base, such as, but not limited to, triethylamine, and a catalyst, such as, but not limited to, compound (65). The reaction is typically performed at an elevated temperature under an inert atmosphere. Compound (65) can be treated with an acid, such as, but not limited to, hydrochloric acid in dioxane, to provide compound (66). The reaction is typically performed at ambient temperature in a solvent, such as, but not limited to, tetrahydrofuran. Compound (67) can be prepared by reacting compound (66) with tert-butyl 3-bromo-6-fluoropicolinate in the presence of a base, such as, but not limited to, triethylamine. The reaction is typically performed under an inert atmosphere at an elevated temperature in a solvent, such as, but not limited to, dimethyl sulfoxide. Compound (67) can be reacted with a boronic acid of formula (68), wherein Ad is the methyladamantane moiety of the compounds of the disclosure (e.g., the compounds of formulae (IIa)-(IId)), under Suzuki Coupling conditions described herein or in the literature to provide compound (69). Compound (70) can be prepared by reacting compound (69) with hydrogen in the presence of Pd(OH)$_2$. The reaction is typically performed at an elevated temperature in a solvent such as, but not limited to tetrahydrofuran.

5.1.14. Synthesis of Compound (75)
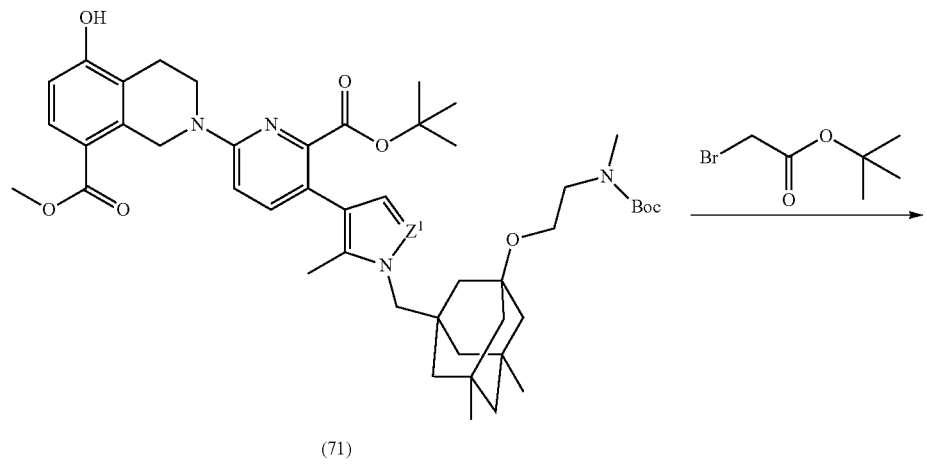
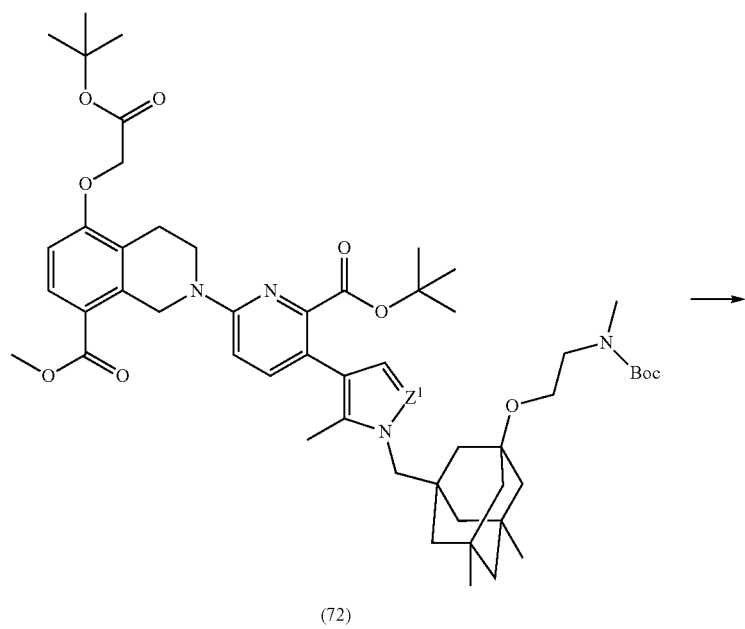

-continued
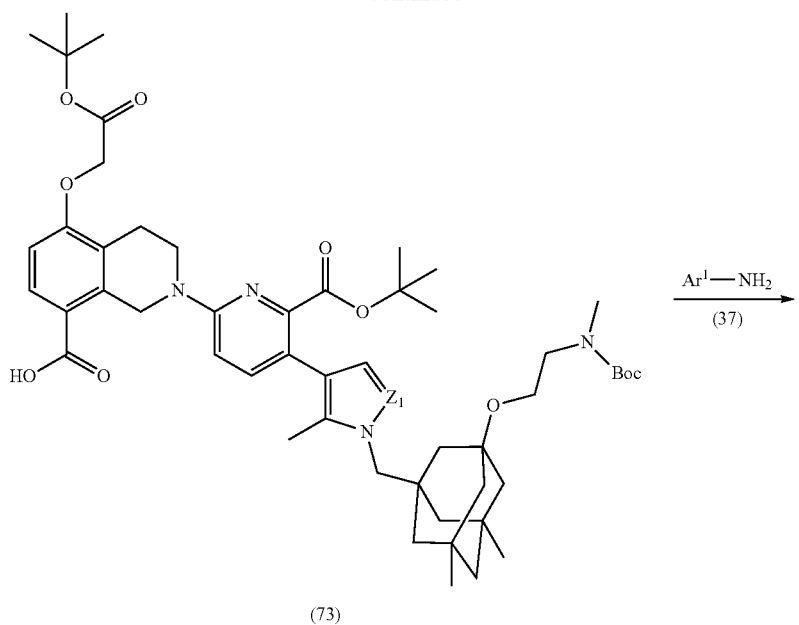
(73)
$Ar^1$—$NH_2$
(37)
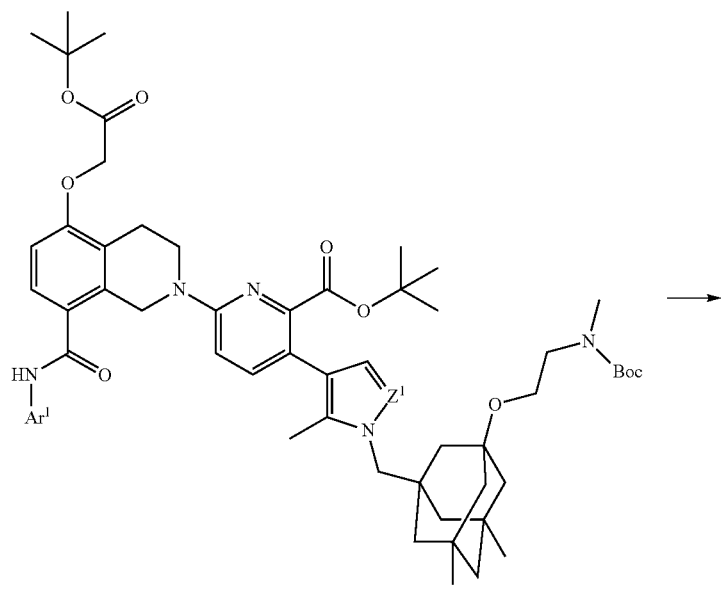
(74)

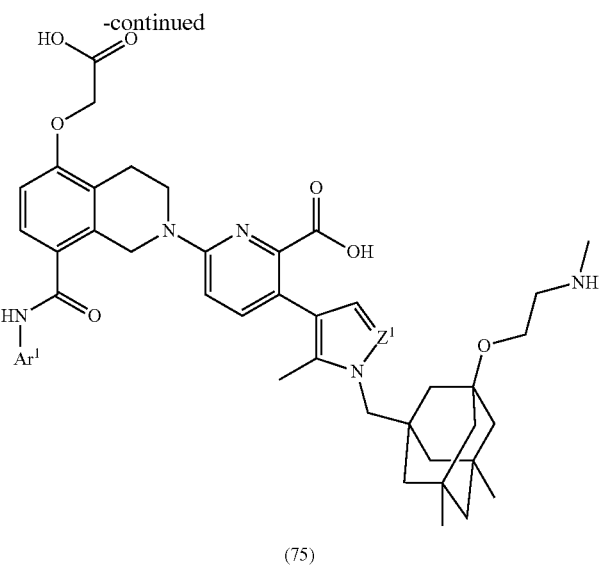

(75)

Scheme 14 shows representative methods used to make solubilized Bcl-xL inhibitors. Bcl-xL inhibitors can be synthesized using the general approach of modifying an $Ar^2$ substituent with a solubilizing group and then attaching an amine to a linker as described in later schemes. For example, compound (71) can be reacted with tert-butyl 2-bromoacetate in the presence of a base such as, but not limited to, potassium carbonate in a solvent such as, but not limited, to N,N-dimethylformamide. Compound (72) can be treated with aqueous lithium hydroxide in a solvent such as, but not limited to, methanol, tetrahydrofuran or mixtures thereof to provide compound (73). Compound (74) can be obtained by amidation of compound (73) with compound (37) under conditions previously described. Compound (74) can be treated with acids such as, but not limited to trifluoroacetic acid or HCl, to provide a Bcl-xL inhibitor of the formula (75). The reaction is typically performed at ambient temperature in solvents such as, but not limited to, dichloromethane or 1,4-dioxane.

III.A.6. General Methods for Synthesizing Bcl-xL Synthons

In the schemes below, the various substituents $Ar^1$, $Ar^2$, $Z^1$, Y, G, $R^{11a}$ and $R^{11b}$ are as defined in the Detailed Description section.

5.2.1. Synthesis of Compound (89)

Scheme 15

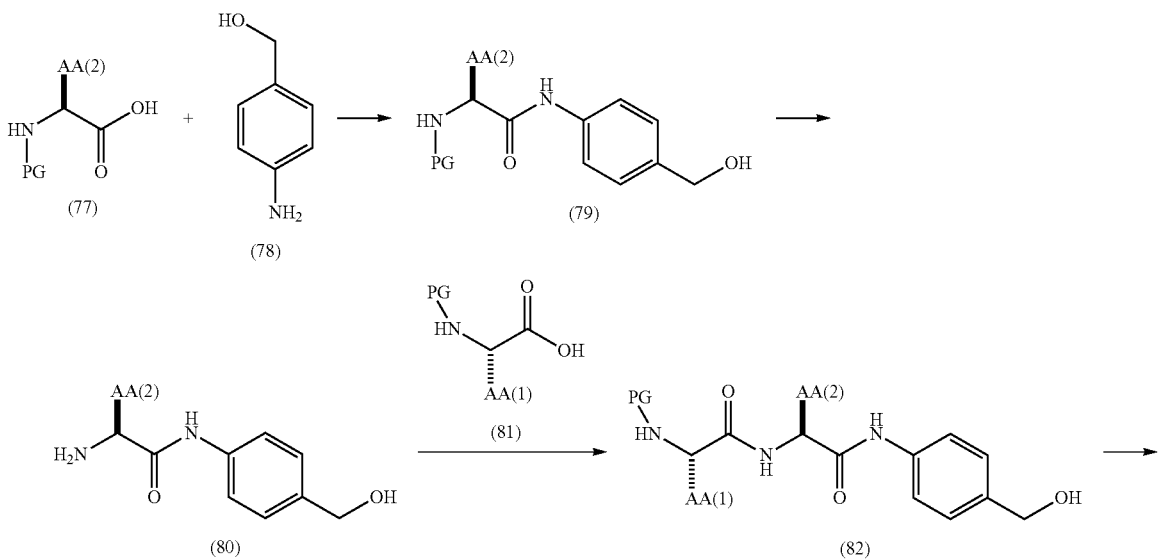

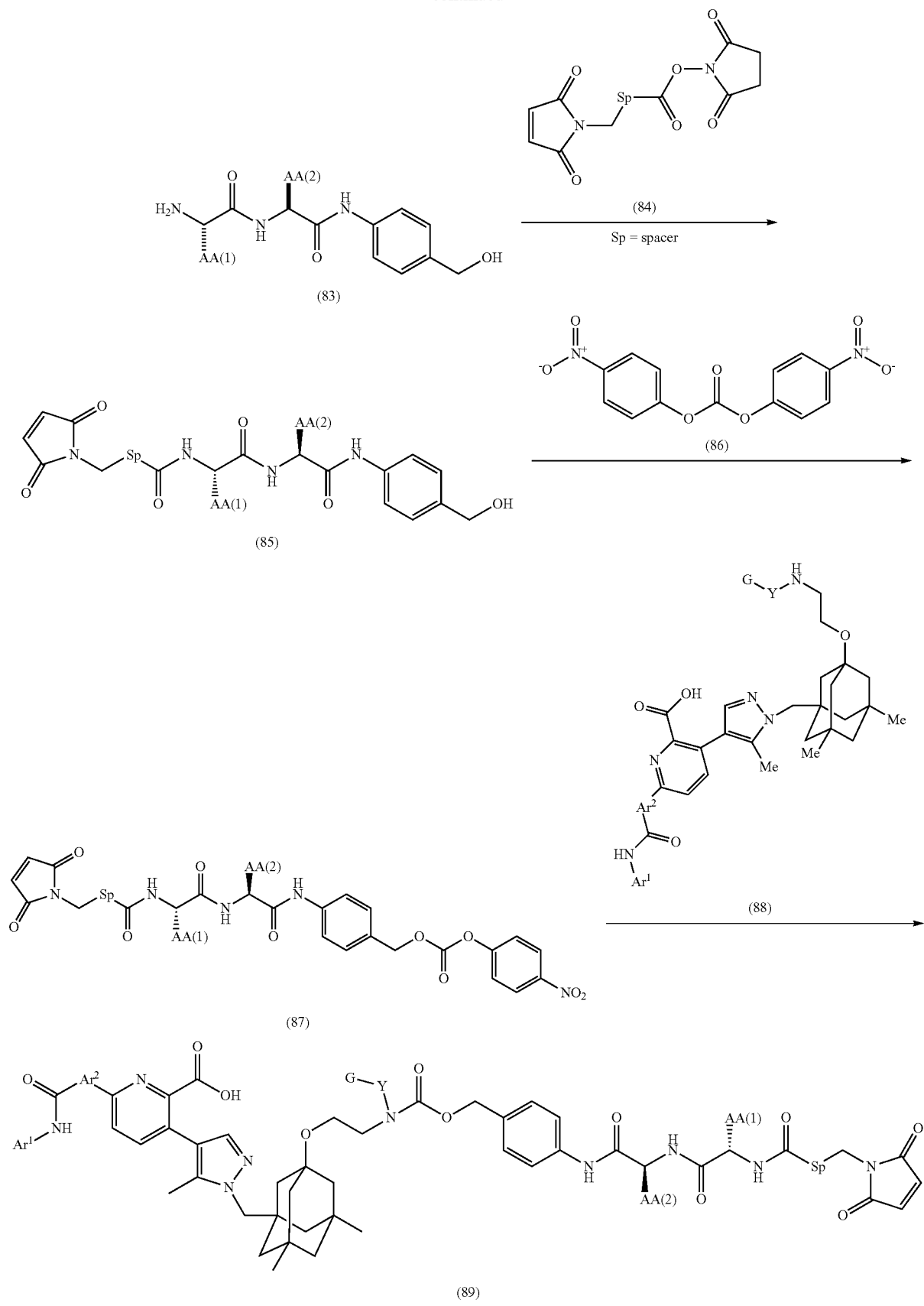

As shown in scheme 15, compounds of formula (77), wherein PG is an appropriate base labile protecting group and AA(2) is Cit, Ala, or Lys, can be reacted with 4-(aminophenyl)methanol (78), under amidation conditions described herein or readily available in the literature to provide compound (79). Compound (80) can be prepared by reacting compound (79) with a base such as, but not limited to, diethylamine. The reaction is typically performed at ambient temperature in a solvent such as but not limited to N,N-dimethylformamide. Compound (81), wherein PG is an appropriate base or acid labile protecting group and AA(1) is Val or Phe, can be reacted with compound (80), under amidation conditions described herein or readily available in the literature to provide compound (82). Compound (83) can be prepared by treating compound (82) with diethylamine or trifluoroacetic acid, as appropriate. The reaction is typically performed at ambient temperature in a solvent such as but not limited to dichloromethane. Compound (84), wherein Sp is a spacer, can be reacted with compound (83) to provide compound (85). The reaction is typically performed at ambient temperature in a solvent such as but not limited to N,N-dimethylformamide. Compound (85) can be reacted with bis(4-nitrophenyl) carbonate (86) in the presence of a base such as, but not limited to N,N-diisopropylethylamine, to provide compounds (87). The reaction is typically performed at ambient temperature in a solvent such as but not limited to N,N-dimethylformamide. Compounds (87) can be reacted with compound (88) in the presence of a base such as, but not limited to, N,N-diisopropylethylamine, to provide compound (89). The reaction is typically performed at ambient temperature in a solvent such as, but not limited to, N,N-dimethylformamide.

5.2.2. Synthesis of Compounds (94) and (96)

Scheme 16
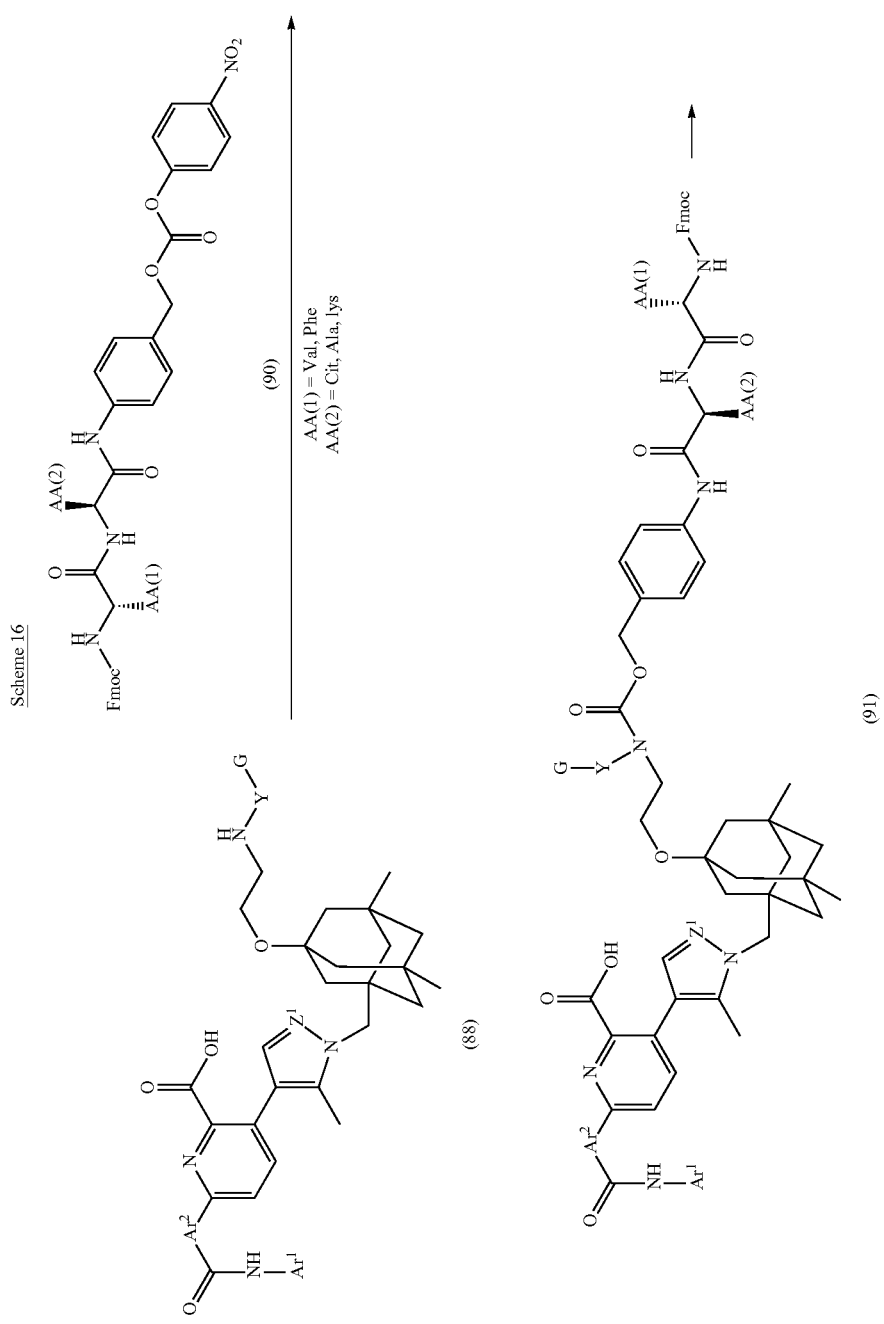

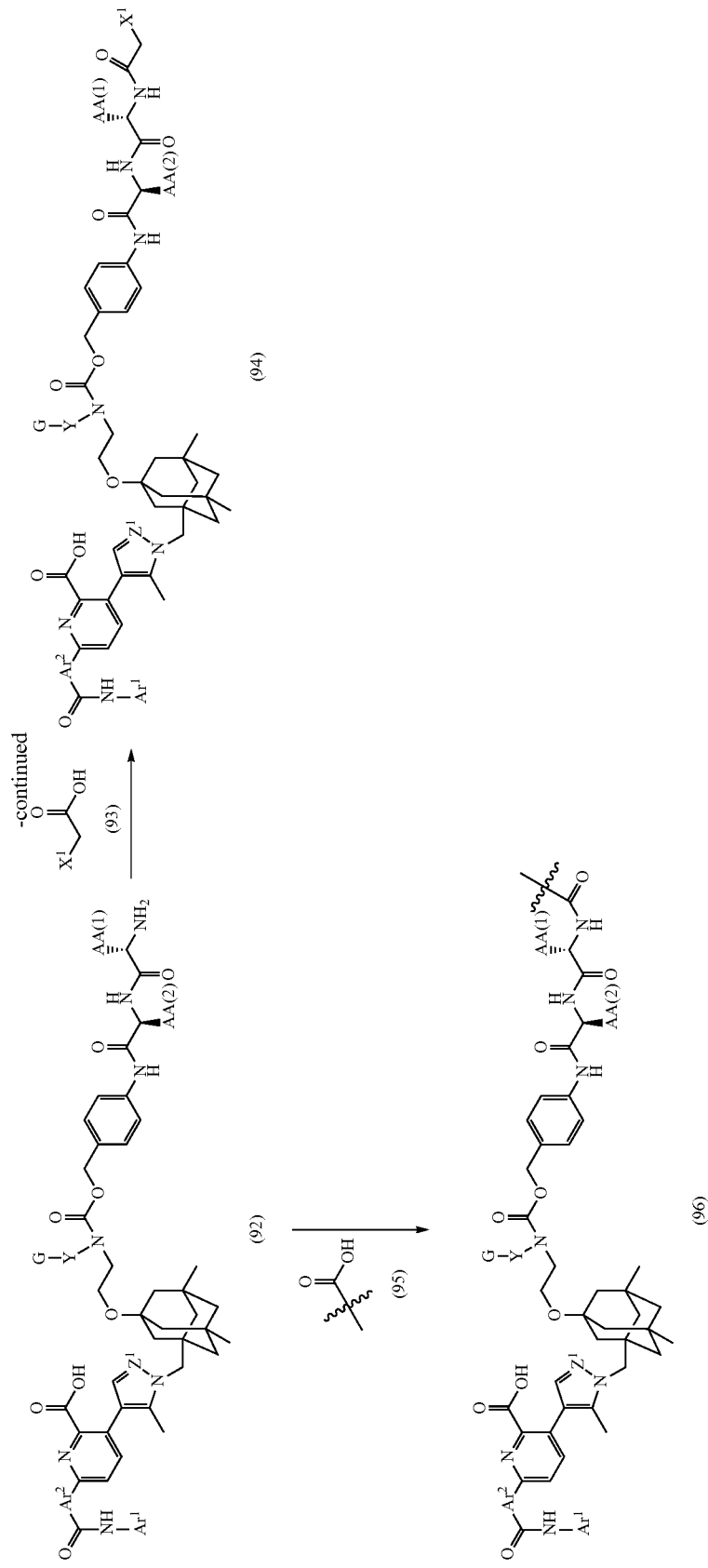

Scheme 16 describes the installment of alternative mAb-linker attachments to dipeptide Synthons. Compound (88) can be reacted with compound (90) in the presence of a base such as, but not limited to, N,N-diisopropylamine to provide compound (91). The reaction is typically performed at ambient temperature in a solvent such as but not limited to N,N-dimethylformamide. Compound (92) can be prepared by reacting compound (91) with diethylamine. The reaction is typically performed at ambient temperature in a solvent such as but not limited to N,N-dimethylformamide. Compound (93), wherein $X^1$ is Cl, Br, or I, can be reacted with compound (92), under amidation conditions described herein or readily available in the literature to provide compound (94). Compound (92) can be reacted with compounds of formula (95) under amidation conditions described herein or readily available in the literature to provide compound (96).

5.2.3. Synthesis of Compound (106)

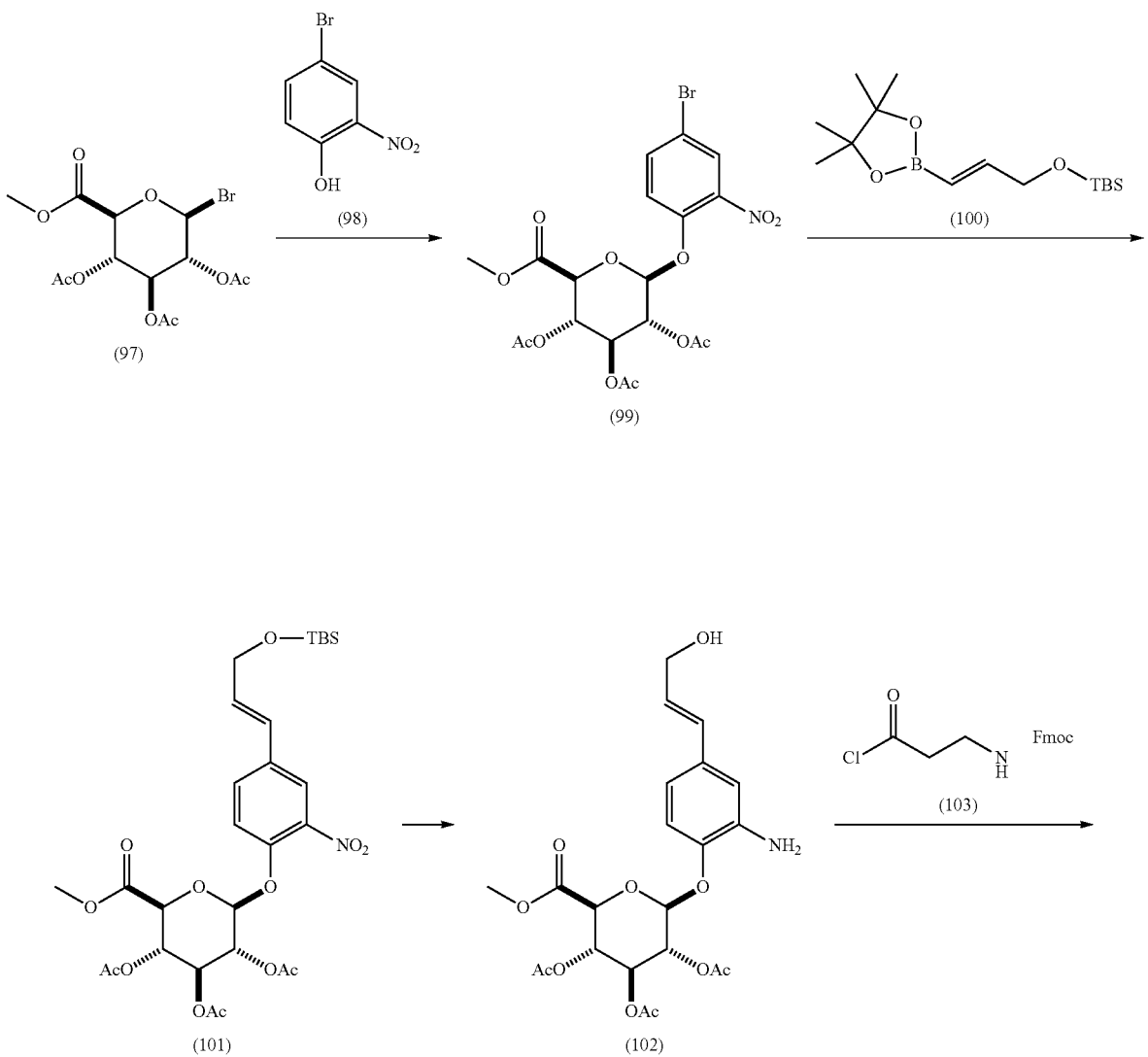

Scheme 17

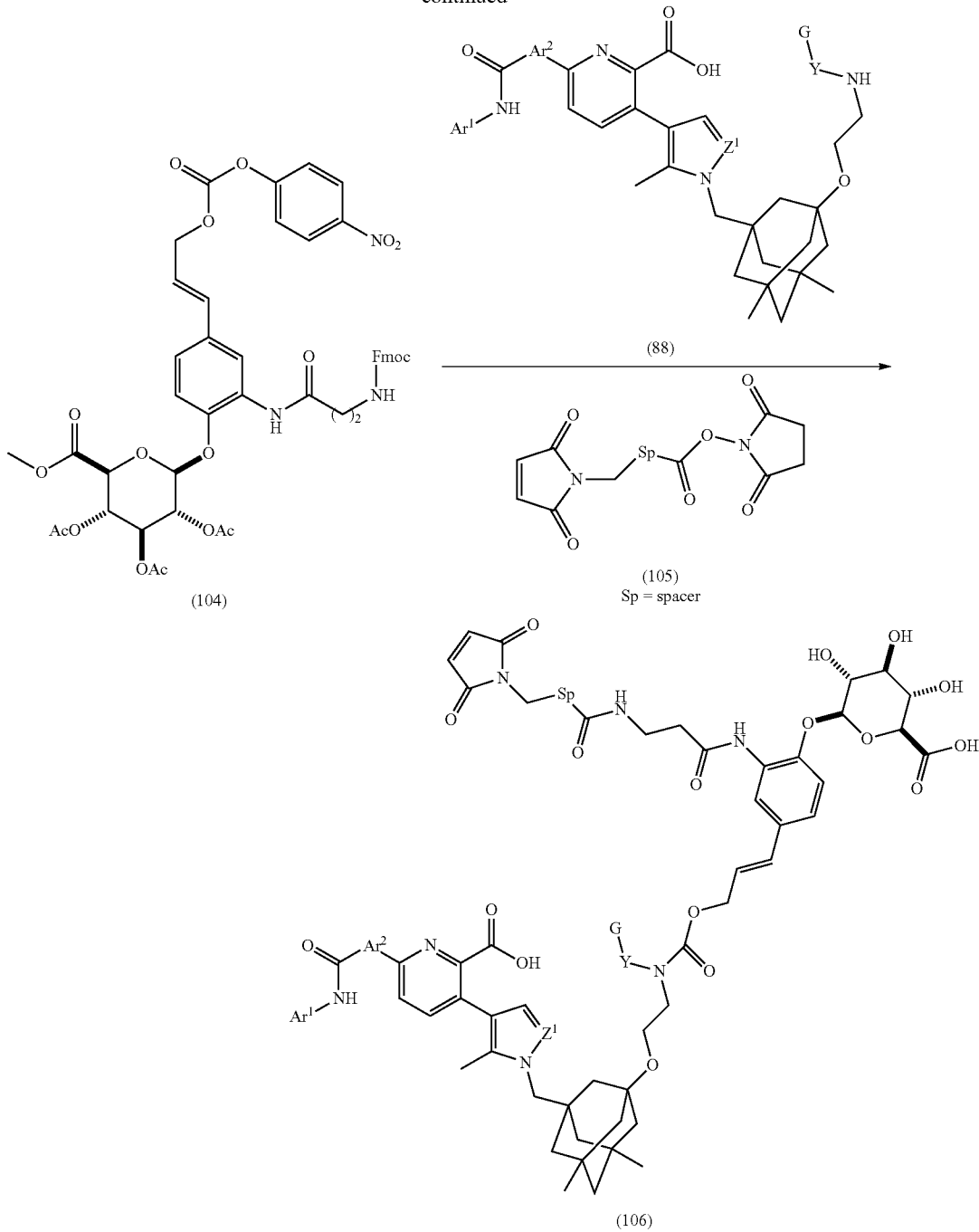

Scheme 17 describes the synthesis of vinyl glucuronide linker intermediates and synthons. (2R,3R,4S,5S,6S)-2-Bromo-6-(methoxycarbonyl)tetrahydro-2H-pyran-3,4,5-triyl triacetate (97) can be treated with silver oxide, followed by 4-bromo-2-nitrophenol (98) to provide (2S,3R,4S,5S,6S)-2-(4-bromo-2-nitrophenoxy)-6-(methoxycarbonyl)tetrahydro-2H-pyran-3,4,5-triyl triacetate (99). The reaction is typically performed at ambient temperature in a solvent, such as, but not limited to, acetonitrile. (2S,3R,4S,5S,6S)-2-(4-Bromo-2-nitrophenoxy)-6-(methoxycarbonyl)tetrahydro-2H-pyran-3,4,5-triyl triacetate (99) can be reacted with (E)-tert-butyldimethyl((3-(4,4,5,5-tetramethyl-1,3,2-dioxaborolan-2-yl)allyl)oxy)silane (100) in the presence of a base such as, but not limited to, sodium carbonate, and a catalyst such as but not limited to tris(dibenzylideneacetone)dipalladium (Pd$_2$(dba)$_3$), to provide (2S,3R,4S,5S,6S)-2-(4-((E)-3-((tert-butyldimethylsilyl)oxy)prop-1-en-1-yl)-2-nitrophenoxy)-6-(methoxycarbonyl)tetrahydro-2H-pyran-3,4,5-triyl triacetate (101). The reaction is typically performed at an elevated temperature in a solvent, such as, but not limited to, tetrahydrofuran. (2S,3R,4S,5S,6S)-2-(2-amino-4-((E)-3-hydroxyprop-1-en-1-yl)phenoxy)-6-(methoxycarbonyl)tetrahydro-2H-pyran-3,4,5-triyl triacetate (102) can be prepared by reacting (2S,3R,4S,5S,6S)-2-(4-((E)-3-((tert-butyldimethylsilyl)oxy)prop-1-en-1-yl)-2-nitrophenoxy)-6-(methoxycarbonyl)tetrahydro-2H-pyran-3,4,5-triyl triacetate (101) with zinc in the presence of an acid such as, but not limited to, hydrochloric acid. The addition is typically performed at low temperature before warming to ambient temperature in a solvent such as, but not limited to, tetrahydrofuran, water, or mixtures thereof. (2S,3R,4S,5S,6S)-2-(2-amino-4-((E)-3-hydroxyprop-1-en-1-yl)phenoxy)-6-(methoxycarbonyl)tetrahydro-2H-pyran-3,4,5-triyl triacetate (102) can be reacted with (9H-fluoren-9-yl)methyl (3-chloro-3-oxopropyl)carbamate (103), in the presence of a base such as, but not limited to, N,N-diisopropylethylamine, to provide (2S,3R,4S,5S,6S)-2-(2-(3-((((9H-fluoren-9-yl)methoxy)carbonyl)amino)propanamido)-4-((E)-3-hydroxyprop-1-en-1-yl)phenoxy)-6-(methoxycarbonyl)tetrahydro-2H-pyran-3,4,5-triyl triacetate (104). The addition is typically performed at low temperature before warming to ambient temperature in a solvent such as, but not limited to, dichloromethane. Compound (88) can be reacted with (2S,3R,4S,5S,6S)-2-(2-(3-((((9H-fluoren-9-yl)methoxy)carbonyl)amino)propanamido)-4-((E)-3-hydroxyprop-1-en-1-yl)phenoxy)-6-(methoxycarbonyl)tetrahydro-2H-pyran-3,4,5-triyl triacetate (104) in the presence of a base such as, but not limited to, N-ethyl-N-isopropylpropan-2-amine, followed by work up and reaction with compound (105) in the presence of a base such as, but not limited to, N,N-diisopropylethylamine to provide compound (106). The reactions are typically performed at ambient temperature in a solvent such as, but not limited to N,N-dimethylformamide.

5.2.4. Synthesis of Compound (115)

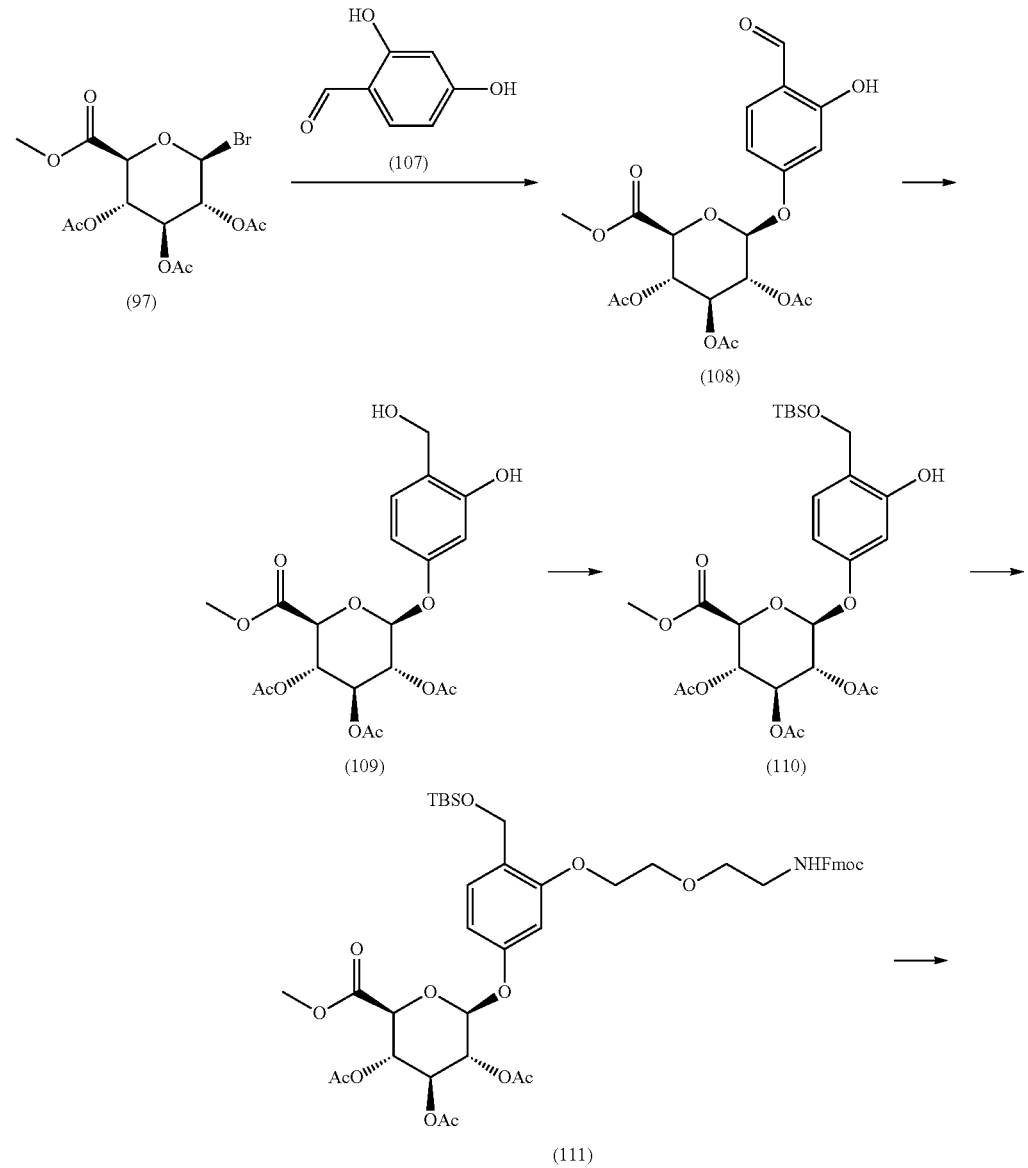

Scheme 18

-continued
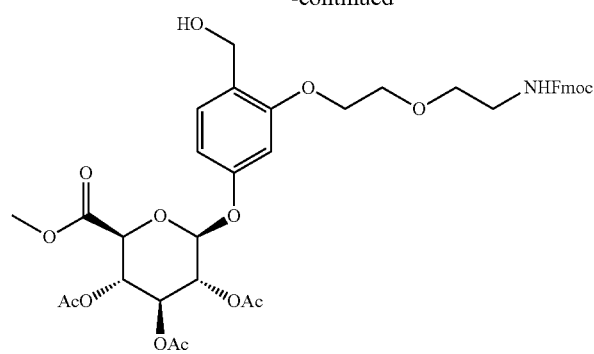
(112)
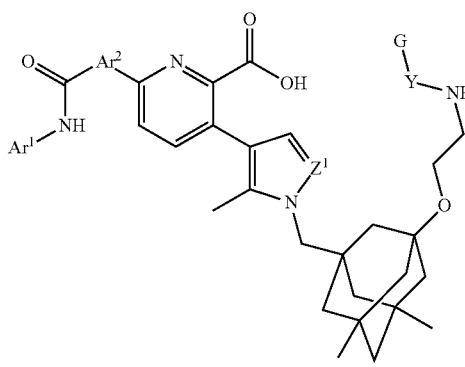
(88)
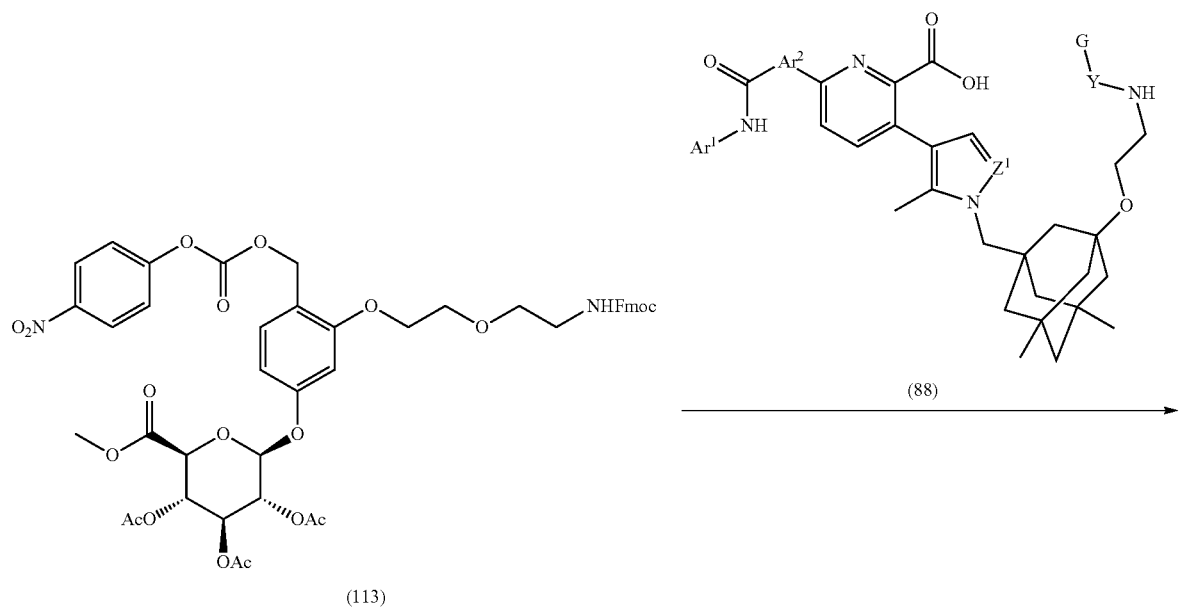
(113)
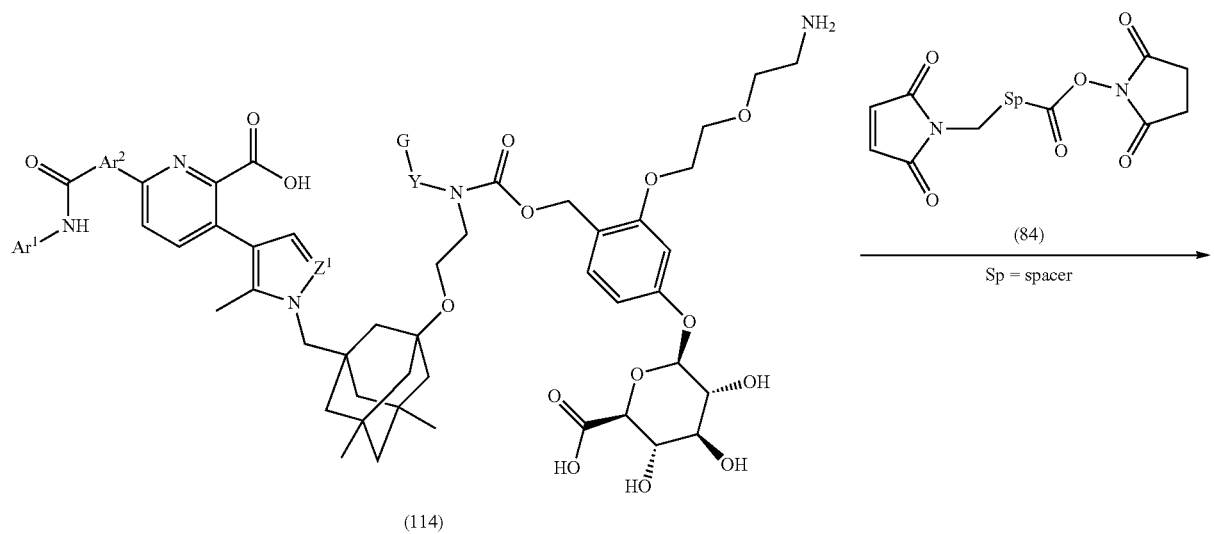
(114)
(84)
Sp = spacer

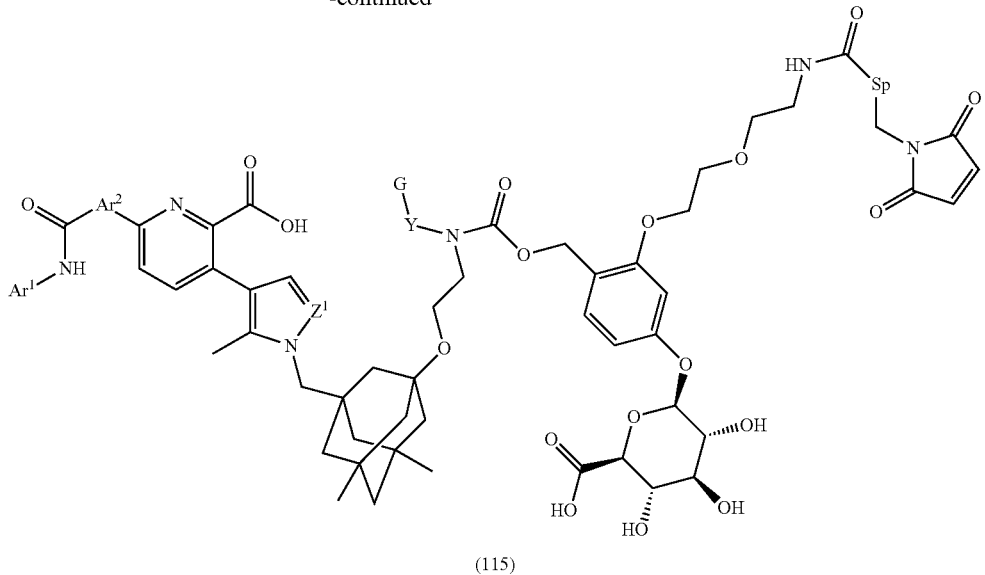

(115)

Scheme 18 describes the synthesis of a representative 2-ether glucuronide linker intermediate and synthon. (2S,3R,4S,5S,6S)-2-Bromo-6-(methoxycarbonyl)tetrahydro-2H-pyran-3,4,5-triyl triacetate (97) can be reacted with 2,4-dihydroxybenzaldehyde (107) in the presence of silver carbonate to provide (2S,3R,4S,5S,6S)-2-(4-formyl-3-hydroxyphenoxy)-6-(methoxycarbonyl)tetrahydro-2H-pyran-3,4,5-triyl triacetate (108). The reaction is typically performed at an elevated temperature in a solvent, such as, but not limited to, acetonitrile. (2S,3R,4S,5S,6S)-2-(4-Formyl-3-hydroxyphenoxy)-6-(methoxycarbonyl)tetrahydro-2H-pyran-3,4,5-triyl triacetate (108) can be treated with sodium borohydride to provide (2S,3R,4S,5S,6S)-2-(3-hydroxy-4-(hydroxymethyl)phenoxy)-6-(methoxycarbonyl)tetrahydro-2H-pyran-3,4,5-triyl triacetate (109). The addition is typically performed at low temperature before warming to ambient temperature in a solvent such as but not limited to tetrahydrofuran, methanol, or mixtures thereof. (2S,3R,4S,5S,6S)-2-(4-(((tert-butyldimethylsilyl)oxy)methyl)-3-hydroxyphenoxy)-6-(methoxycarbonyl)tetrahydro-2H-pyran-3,4,5-triyl triacetate (110) can be prepared by reacting (2S,3R,4S,5S,6S)-2-(3-hydroxy-4-(hydroxymethyl)phenoxy)-6-(methoxycarbonyl)tetrahydro-2H-pyran-3,4,5-triyl triacetate (109) with tert-butyldimethylsilyl chloride in the presence of imidazole. The reaction is typically performed at low temperature in a solvent, such as, but not limited to, dichloromethane. (2S,3R,4S,5S,6S)-2-(3-(2-(2-((((9H-Fluoren-9-yl)methoxy)carbonyl)amino)ethoxy)ethoxy)-4-(((tert-butyldimethylsilyl)oxy)methyl)phenoxy)-6-(methoxycarbonyl)tetrahydro-2H-pyran-3,4,5-triyl triacetate (111) can be prepared by reacting (2S,3R,4S,5S,6S)-2-(4-(((tert-butyldimethylsilyl)oxy)methyl)-3-hydroxyphenoxy)-6-(methoxycarbonyl)tetrahydro-2H-pyran-3,4,5-triyl triacetate (110) with (9H-fluoren-9-yl)methyl (2-(2-hydroxyethoxy)ethyl)carbamate in the presence of triphenylphosphine and a azodicarboxylate such as, but not limited to, di-tert-butyl diazene-1,2-dicarboxylate. The reaction is typically performed at ambient temperature in a solvent such as but not limited to toluene. (2S,3R,4S,5S,6S)-2-(3-(2-(2-((((9H-Fluoren-9-yl)methoxy)carbonyl)amino)ethoxy)ethoxy)-4-(((tert-butyldimethylsilyl)oxy)methyl)phenoxy)-6-(methoxycarbonyl)tetrahydro-2H-pyran-3,4,5-triyl triacetate (111) can be treated with acetic acid to provide (2S,3R,4S,5S,6S)-2-(3-(2-(2-((((9H-fluoren-9-yl)methoxy)carbonyl)amino)ethoxy)ethoxy)-4-(hydroxymethyl)phenoxy)-6-(methoxycarbonyl)tetrahydro-2H-pyran-3,4,5-triyl triacetate (112). The reaction is typically performed at ambient temperature in a solvent such as but not limited to water, tetrahydrofuran, or mixtures thereof. (2S,3R,4S,5S,6S)-2-(3-(2-(2-((((9H-Fluoren-9-yl)methoxy)carbonyl)amino)ethoxy)ethoxy)-4-((((4-nitrophenoxy)carbonyl)oxy)methyl)phenoxy)-6-(methoxycarbonyl)tetrahydro-2H-pyran-3,4,5-triyl triacetate (113) can be prepared by reacting (2S,3R,4S,5S,6S)-2-(3-(2-(2-((((9H-fluoren-9-yl)methoxy)carbonyl)amino)ethoxy)ethoxy)-4-(hydroxymethyl)phenoxy)-6-(methoxycarbonyl)tetrahydro-2H-pyran-3,4,5-triyl triacetate (112) with bis(4-nitrophenyl) carbonate in the presence of a base such as but not limited to N-ethyl-N-isopropylpropan-2-amine. The reaction is typically performed at ambient temperature in a solvent such as but not limited to N,N-dimethylformamide. (2S,3R,4S,5S,6S)-2-(3-(2-(2-((((9H-Fluoren-9-yl)methoxy)carbonyl)amino)ethoxy)ethoxy)-4-((((4-nitrophenoxy)carbonyl)oxy)methyl)phenoxy)-6-(methoxycarbonyl)tetrahydro-2H-pyran-3,4,5-triyl triacetate (113) can be treated with compound (88) in the presence of a base such as but not limited to N-ethyl-N-isopropylpropan-2-amine, followed by treatment with lithium hydroxide to provide a compound (114). The reaction is typically performed at ambient temperature in a solvent such as but not limited to N,N-dimethylformamide, tetrahydrofuran, methanol, or mixtures thereof. Compound (115) can be prepared by reacting compound (114) with compound (84) in the presence of a base such as but not limited to N-ethyl-N-isopropylpropan-2-amine. The reaction is typically performed at ambient temperature in a solvent such as but not limited to N,N-dimethylformamide.

5.2.5. Synthesis of Compound (119)
Scheme 19
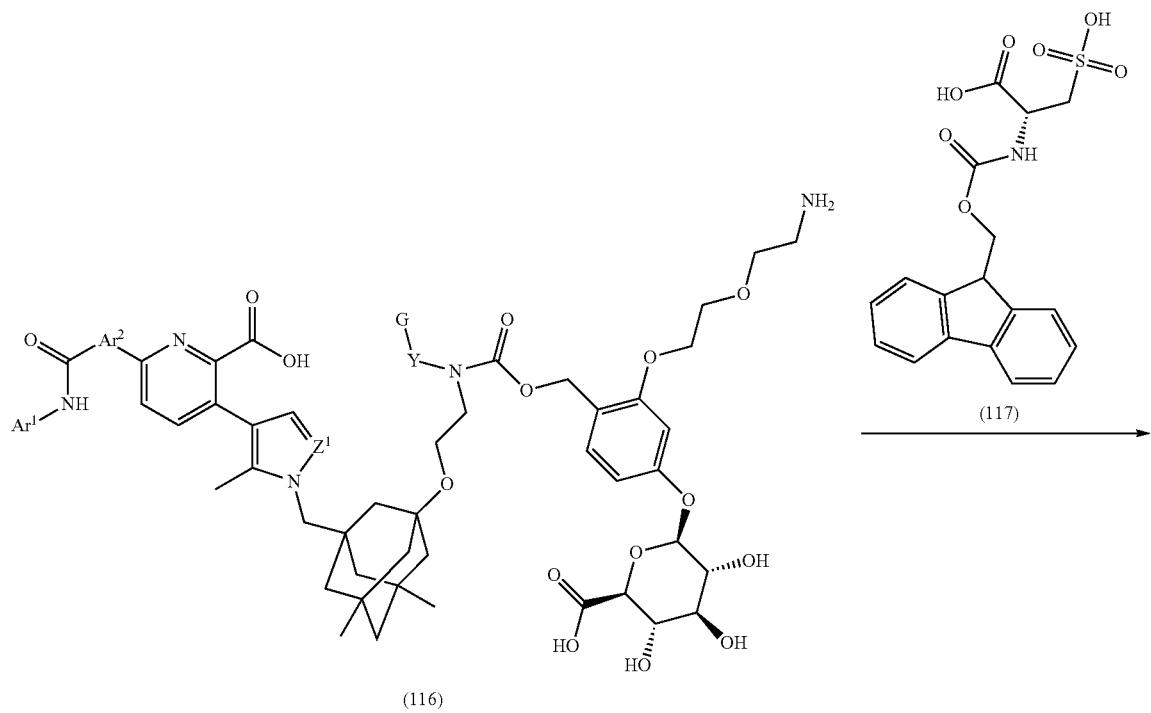
(116) (117)
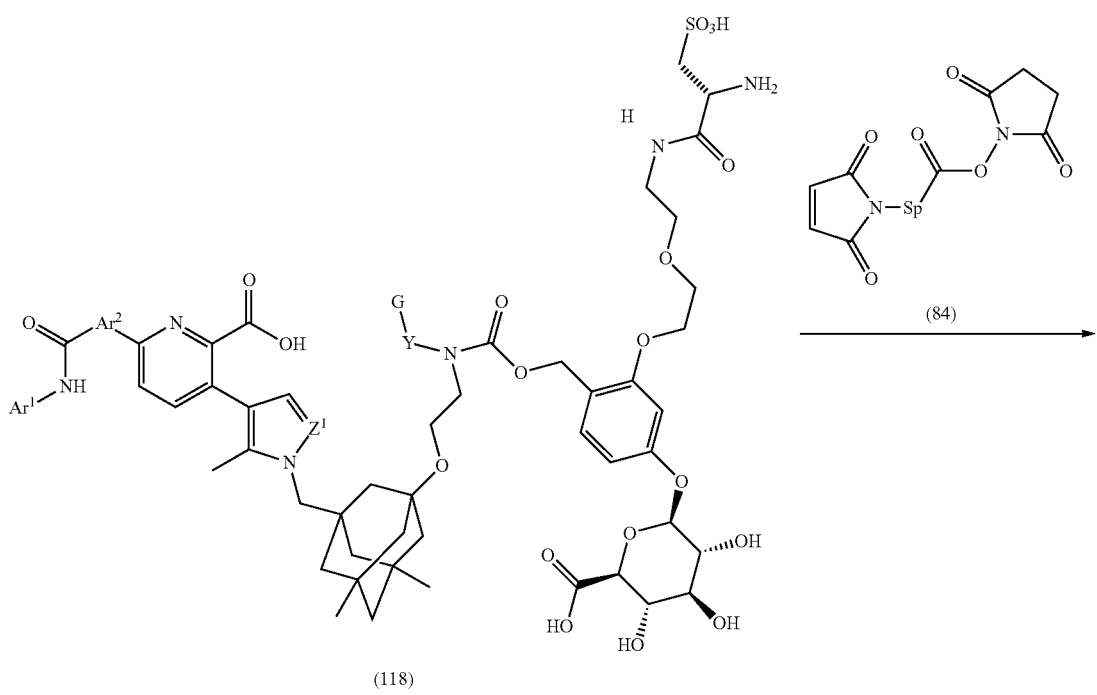
(118) (84)

-continued

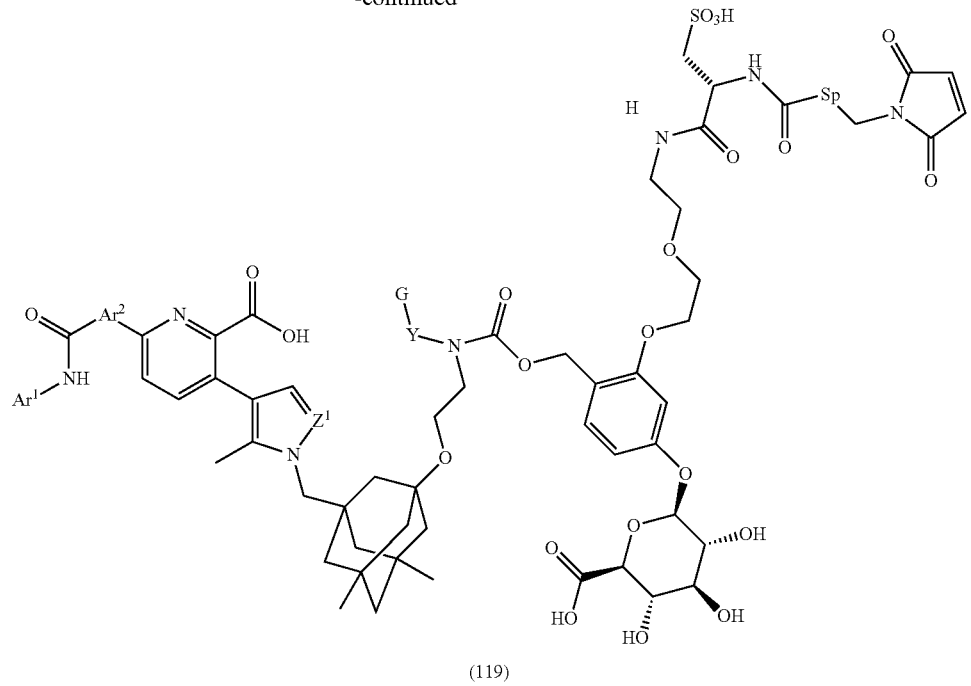

(119)

Scheme 19 describes the introduction of a second solubilizing group to a sugar linker. Compound (116) can be reacted with (R)-2-((((9H-fluoren-9-yl)methoxy)carbonyl)amino)-3-sulfopropanoic acid (117), under amidation conditions described herein or readily available in the literature, followed by treatment with a base such as but not limited to diethylamine, to provide compound (118). Compound (118) can be reacted with compound (84), wherein Sp is a spacer, under amidation conditions described herein or readily available in the literature, to provide compound (119).

5.2.6. Synthesis of Compound (129)

Scheme 20

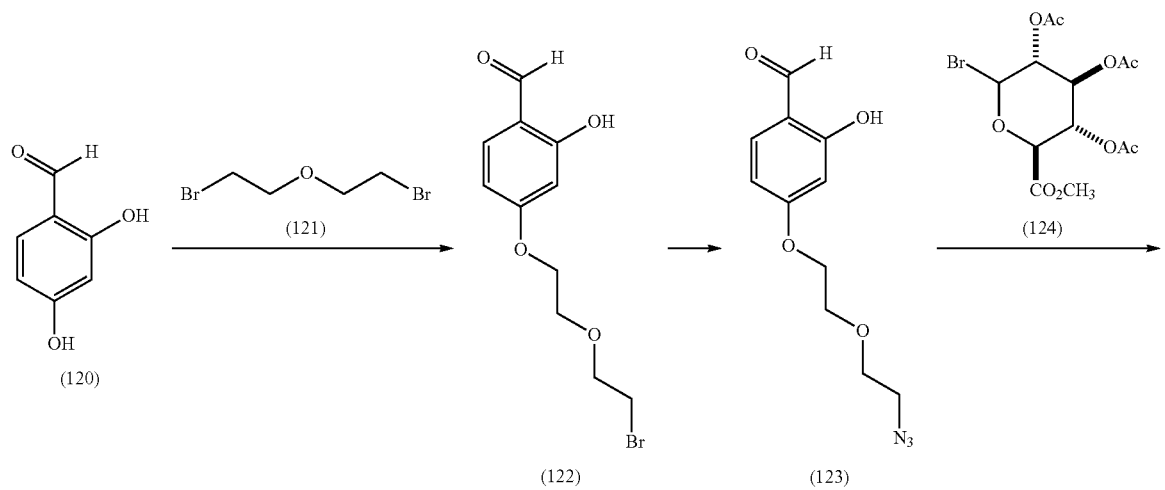

539
540
-continued
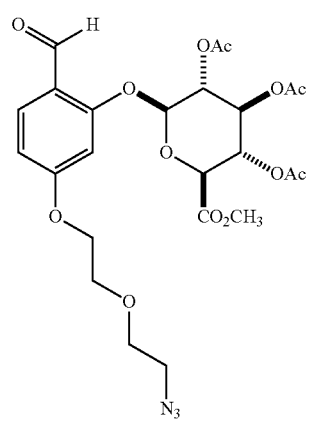
(125)
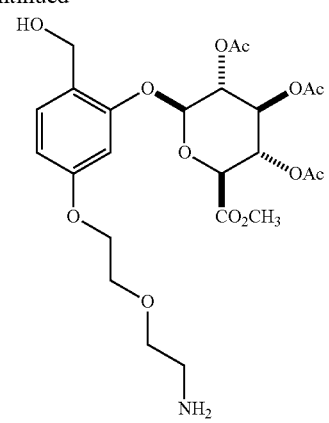
(126)
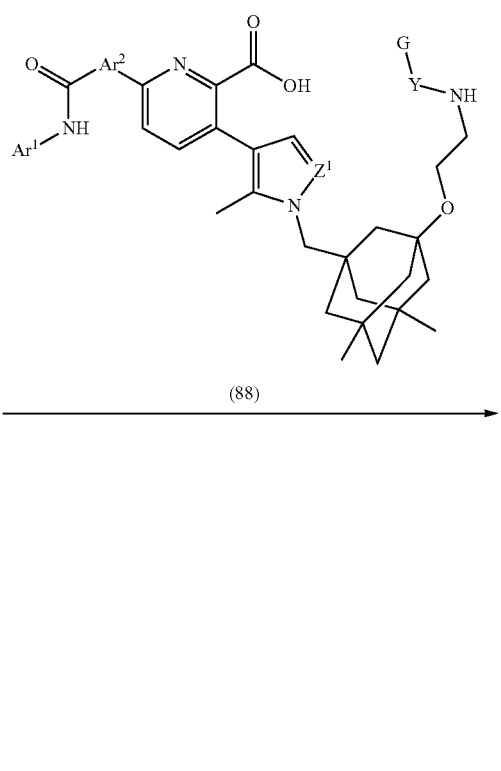
(127)
(88)

541 542

-continued

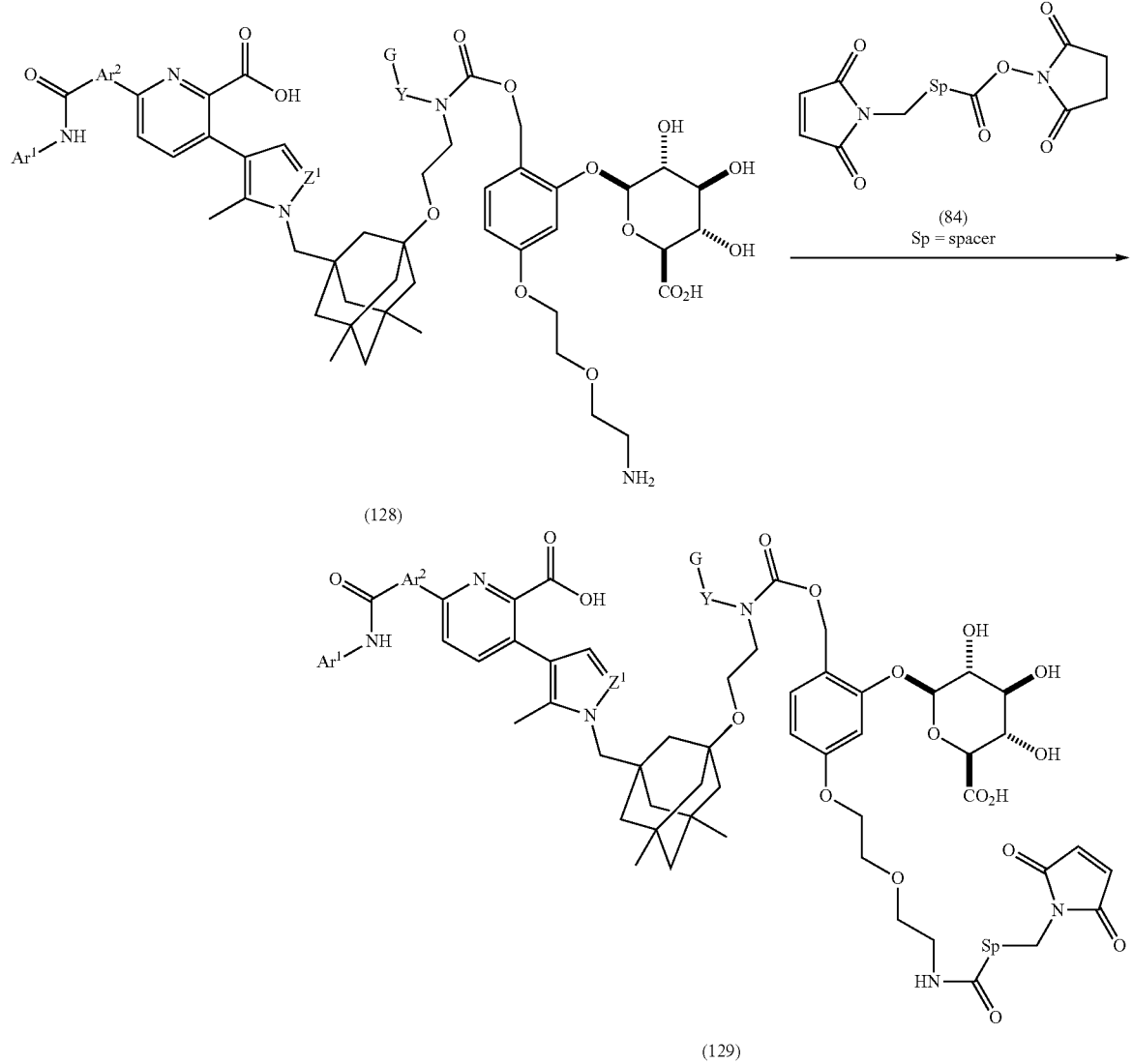

Scheme 20 describes the synthesis of 4-ether glucuronide linker intermediates and synthons. 4-(2-(2-Bromoethoxy)ethoxy)-2-hydroxybenzaldehyde (122) can be prepared by reacting 2,4-dihydroxybenzaldehyde (120) with 1-bromo-2-(2-bromoethoxy)ethane (121) in the presence of a base such as, but not limited to, potassium carbonate. The reaction is typically performed at an elevated temperature in a solvent such as but not limited to acetonitrile. 4-(2-(2-Bromoethoxy)ethoxy)-2-hydroxybenzaldehyde (122) can be treated with sodium azide to provide 4-(2-(2-azidoethoxy)ethoxy)-2-hydroxybenzaldehyde (123). The reaction is typically performed at ambient temperature in a solvent such as but not limited to N,N-dimethylformamide. (2S,3R,4S,5S,6S)-2-(5-(2-(2-Azidoethoxy)ethoxy)-2-formylphenoxy)-6-(methoxycarbonyl)tetrahydro-2H-pyran-3,4,5-triyl triacetate (125) can be prepared by reacting 4-(2-(2-azidoethoxy)ethoxy)-2-hydroxybenzaldehyde (123) with (3R,4S,5S,6S)-2-bromo-6-(methoxycarbonyl)tetrahydro-2H-pyran-3,4,5-triyl triacetate (124) in the presence of silver oxide. The reaction is typically performed at ambient temperature in a solvent such as, but not limited to, acetonitrile. Hydrogenation of (2S,3R,4S,5S,6S)-2-(5-(2-(2-azidoethoxy)ethoxy)-2-formyl- phenoxy)-6-(methoxycarbonyl)tetrahydro-2H-pyran-3,4,5-triyl triacetate (125) in the presence of Pd/C will provide (2S,3R,4S,5S,6S)-2-(5-(2-(2-aminoethoxy)ethoxy)-2-(hydroxymethyl)phenoxy)-6-(methoxycarbonyl)tetrahydro-2H-pyran-3,4,5-triyl triacetate (126). The reaction is typically performed at ambient temperature in a solvent such as, but not limited to, tetrahydrofuran. (2S,3R,4S,5S,6S)-2-(5-(2-(2-((((9H-Fluoren-9-yl)methoxy)carbonyl)amino)ethoxy)ethoxy)-2-(hydroxymethyl)phenoxy)-6-(methoxycarbonyl)tetrahydro-2H-pyran-3,4,5-triyl triacetate (127) can be prepared by treating (2S,3R,4S,5S,6S)-2-(5-(2-(2-aminoethoxy)ethoxy)-2-(hydroxymethyl)phenoxy)-6-(methoxycarbonyl)tetrahydro-2H-pyran-3,4,5-triyl triacetate (126) with (9H-fluoren-9-yl)methyl carbonochloridate in the presence of a base, such as, but not limited to, N-ethyl-N-isopropylpropan-2-amine. The reaction is typically performed at low temperature in a solvent such as, but not limited to, dichloromethane. Compound (88) can be reacted with (2S,3R,4S,5S,6S)-2-(5-(2-(2-((((9H-Fluoren-9-yl)methoxy)carbonyl)amino)ethoxy)ethoxy)-2-(hydroxymethyl)phenoxy)-6-(methoxycarbonyl)tetrahydro-2H-pyran-3,4,5-triyl triacetate (127) in the presence of a base, such as, but not limited to, N-ethyl-N-isopropylpropan-2-amine, followed by treatment with lithium hydroxide to provide compound (128). The reaction is typically performed at low temperature in a solvent such as, but not limited to, N,N-dimethylformamide. Compound (129) can be prepared by reacting compound (128) with compound (84) in the presence of a base such as, but not limited to, N-ethyl-N-isopropylpropan-2-amine. The reaction is typically performed at ambient temperature in a solvent such as but not limited to N,N-dimethylformamide.

5.2.7. Synthesis of Compound (139)

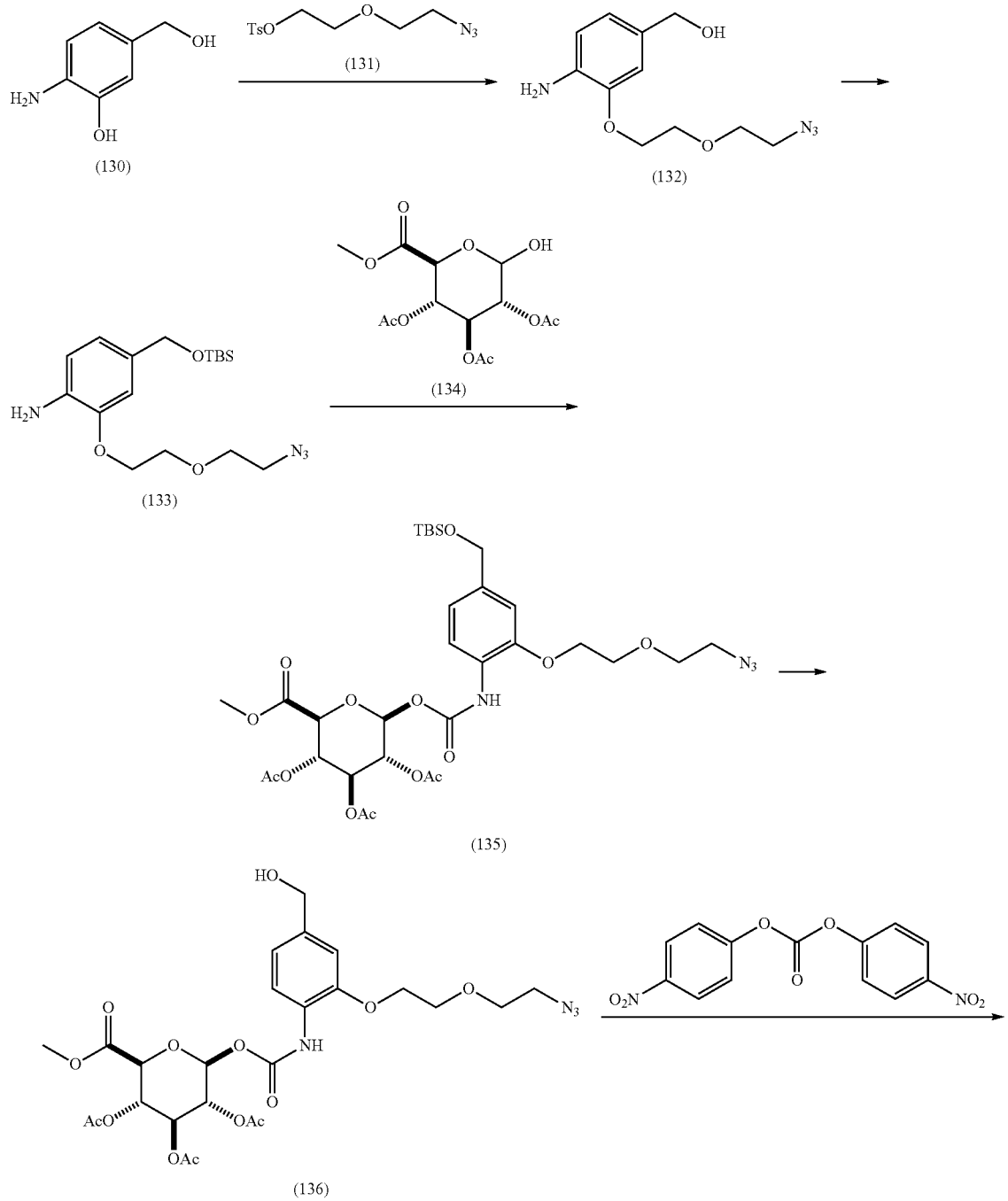

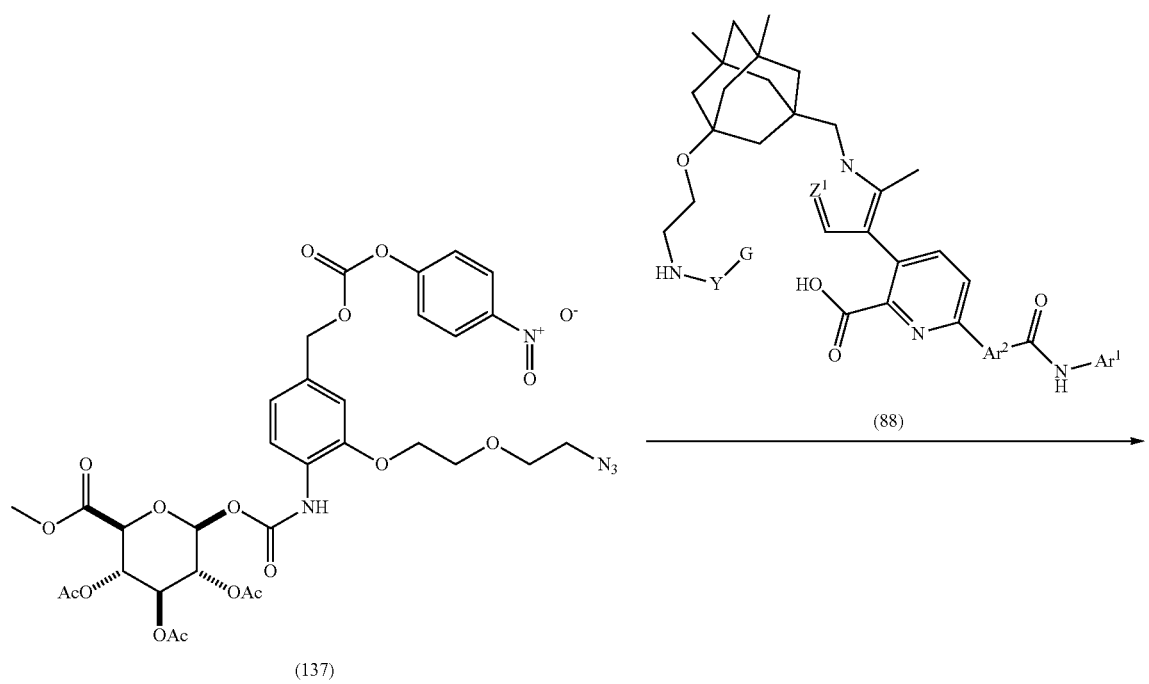
(137)
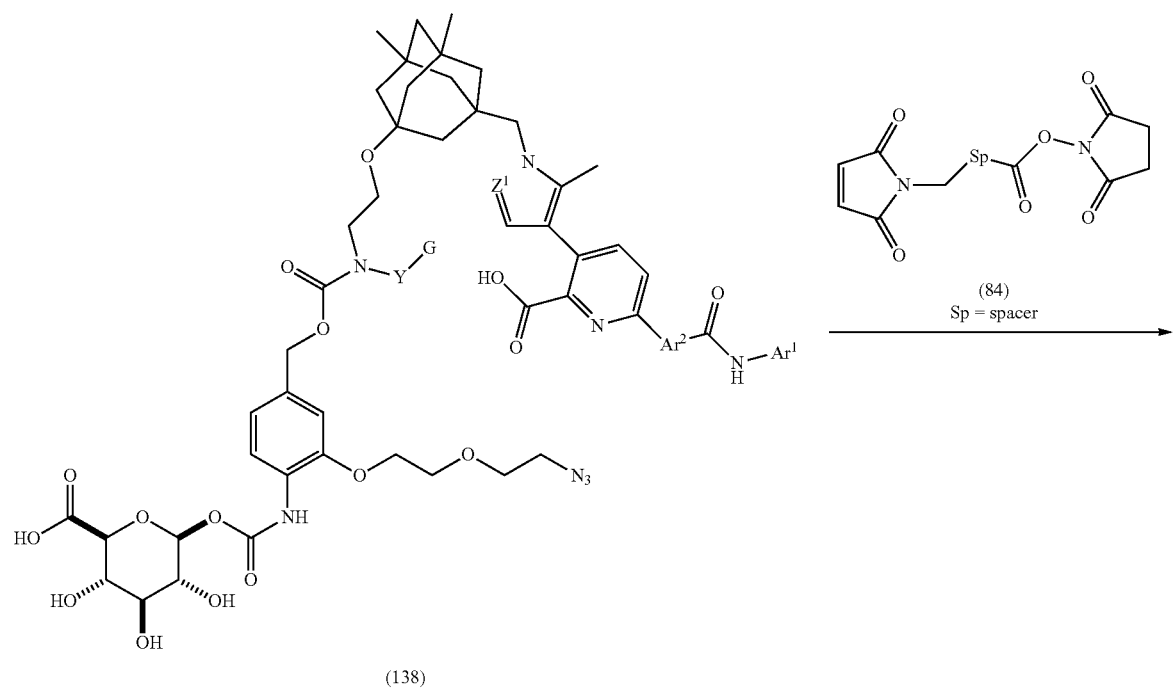
(138)

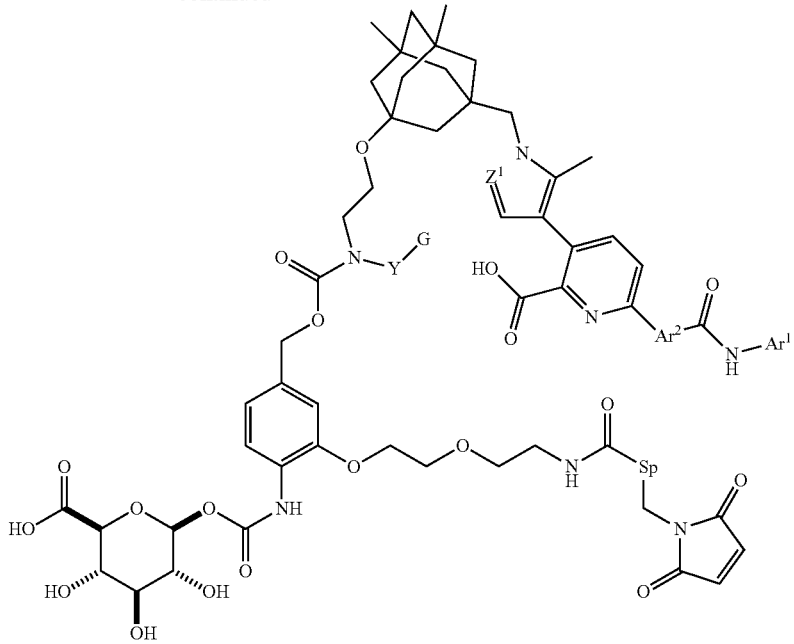

(139)

Scheme 21 describes the synthesis of carbamate glucuronide intermediates and synthons. 2-Amino-5-(hydroxymethyl)phenol (130) can be treated with sodium hydride and then reacted with 2-(2-azidoethoxy)ethyl 4-methylbenzenesulfonate (131) to provide (4-amino-3-(2-(2-azidoethoxy)ethoxy)phenyl)methanol (132). The reaction is typically performed at an elevated temperature in a solvent such as, but not limited to N,N-dimethylformamide. 2-(2-(2-Azidoethoxy)ethoxy)-4-(((tert-butyldimethylsilyl)oxy)methyl)aniline (133) can be prepared by reacting (4-amino-3-(2-(2-azidoethoxy)ethoxy)phenyl)methanol (132) with tert-butyldimethylchlorosilane in the presence of imidazole. The reaction is typically performed at ambient temperature in a solvent such as, but not limited to tetrahydrofuran. 2-(2-(2-Azidoethoxy)ethoxy)-4-(((tert-butyldimethylsilyl)oxy)methyl)aniline (133) can be treated with phosgene, in the presence of a base such as but not limited to triethylamine, followed by reaction with (3R,4S,5S,6S)-2-hydroxy-6-(methoxycarbonyl)tetrahydro-2H-pyran-3,4,5-triyl triacetate (134) in the presence of a base such as but not limited to triethylamine, to provide 2S,3R,4S,5S,6S)-2-(((2-(2-(2-azidoethoxy)ethoxy)-4-(((tert-butyldimethylsilyl)oxy)methyl)phenyl)carbamoyl)oxy)-6-(methoxycarbonyl)tetrahydro-2H-pyran-3,4,5-triyl triacetate (135). The reaction is typically performed in a solvent such as, but not limited to, toluene, and the additions are typically performed at low temperature, before warming up to ambient temperature after the phosgene addition and heating at an elevated temperature after the (3R,4S,5S,6S)-2-hydroxy-6-(methoxycarbonyl)tetrahydro-2H-pyran-3,4,5-triyl triacetate (134) addition. (2S,3R,4S,5S,6S)-2-(((2-(2-(2-Azidoethoxy)ethoxy)-4-(hydroxymethyl)phenyl)carbamoyl)oxy)-6-(methoxycarbonyl)tetrahydro-2H-pyran-3,4,5-triyl triacetate (136) can be prepared by reacting 2S,3R,4S,5S,6S)-2-(((2-(2-(2-azidoethoxy)ethoxy)-4-(((tert-butyldimethylsilyl)oxy)methyl)phenyl)carbamoyl)oxy)-6-(methoxycarbonyl)tetrahydro-2H-pyran-3,4,5-triyl triacetate (135) with p-toluenesulfonic acid monohydrate. The reaction is typically performed at ambient temperature in a solvent such as, but not limited to methanol. (2S,3R,4S,5S,6S)-2-(((2-(2-(2-Azidoethoxy)ethoxy)-4-(hydroxymethyl)phenyl)carbamoyl)oxy)-6-(methoxycarbonyl)tetrahydro-2H-pyran-3,4,5-triyl triacetate (136) can be reacted with bis(4-nitrophenyl) carbonate in the presence of a base such as, but not limited to, N,N-diisopropylethylamine, to provide (2S,3R,4S,5S,6S)-2-(((2-(2-(2-azidoethoxy)ethoxy)-4-((((4-nitrophenoxy)carbonyl)oxy)methyl)phenyl)carbamoyl)oxy)-6-(methoxycarbonyl)tetrahydro-2H-pyran-3,4,5-triyl triacetate (137). The reaction is typically performed at ambient temperature in a solvent such as, but not limited to, N,N-dimethylformamide. (2S,3R,4S,5S,6S)-2-(((2-(2-(2-Azidoethoxy)ethoxy)-4-((((4-nitrophenoxy)carbonyl)oxy)methyl)phenyl)carbamoyl)oxy)-6-(methoxycarbonyl)tetrahydro-2H-pyran-3,4,5-triyl triacetate (137) can be reacted with compound in the presence of a base such as, but not limited to, N,N-diisopropylethylamine, followed by treatment with aqueous lithium hydroxide, to provide compound (138). The first step is typically conducted at ambient temperature in a solvent such as, but not limited to N,N-dimethylformamide, and the second step is typically conducted at low temperature in a solvent such as but not limited to methanol. Compound (138) can be treated with tris(2-carboxyethyl))phosphine hydrochloride, followed by reaction with compound (84) in the presence of a base such as, but not limited to, N,N-diisopropylethylamine, to provide compound (139). The reaction with tris(2-carboxyethyl))phosphine hydrochloride is typically performed at ambient temperature in a solvent such as, but not limited to, tetrahydrofuran, water, or mixtures thereof, and the reaction with N-succinimidyl 6-maleimidohexanoate is typically performed at ambient temperature in a solvent such as, but not limited to, N,N-dimethylformamide.

5.2.8. Synthesis of Compound (149)
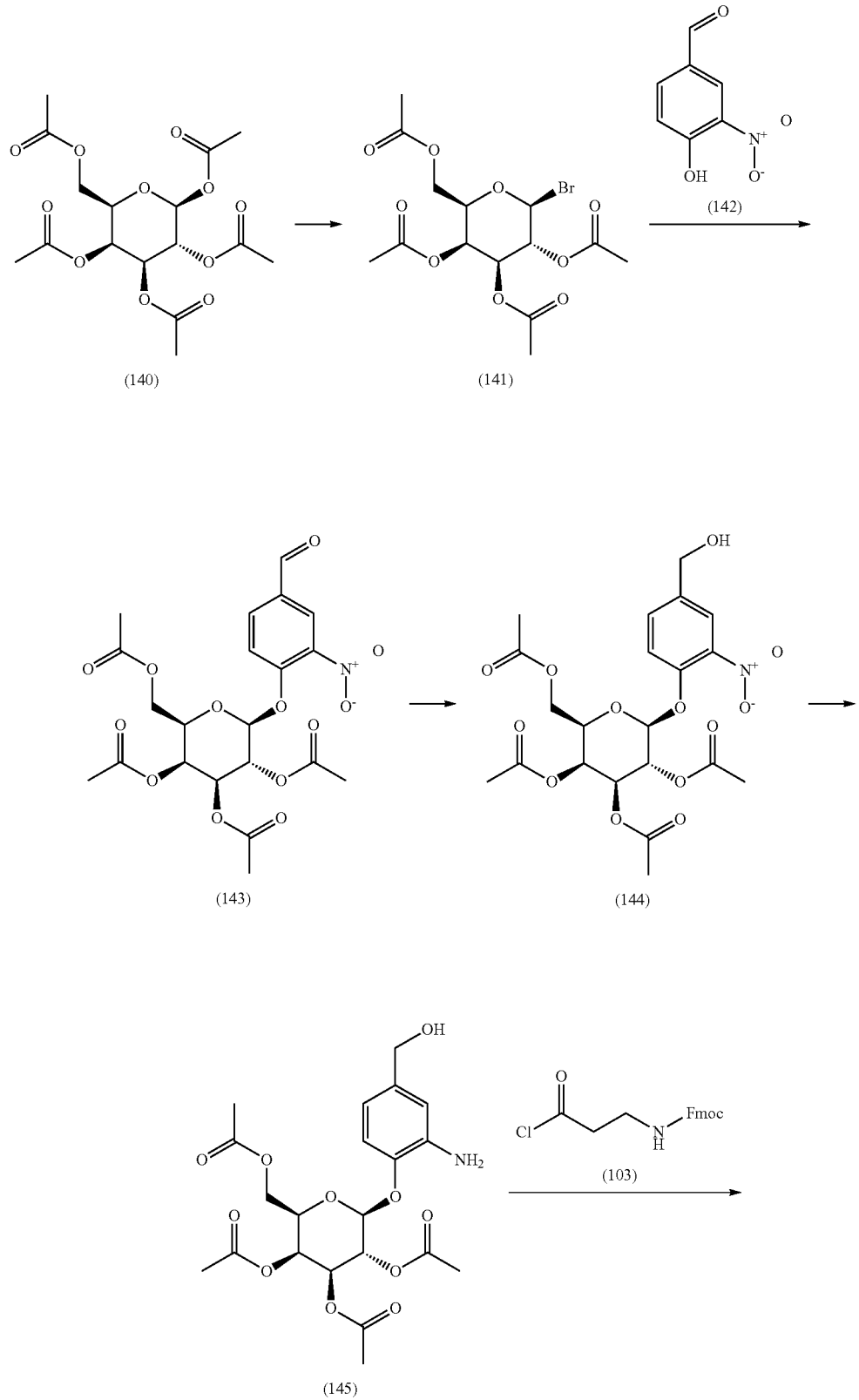

-continued
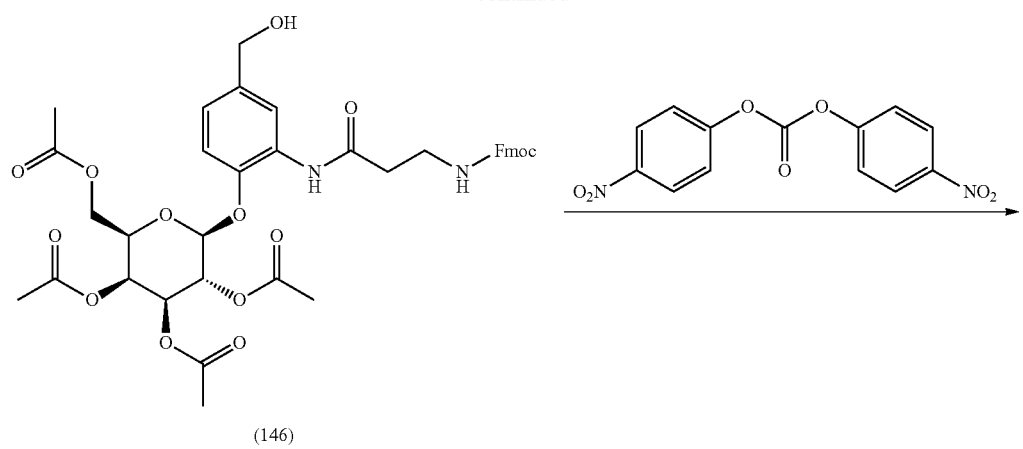
(146)
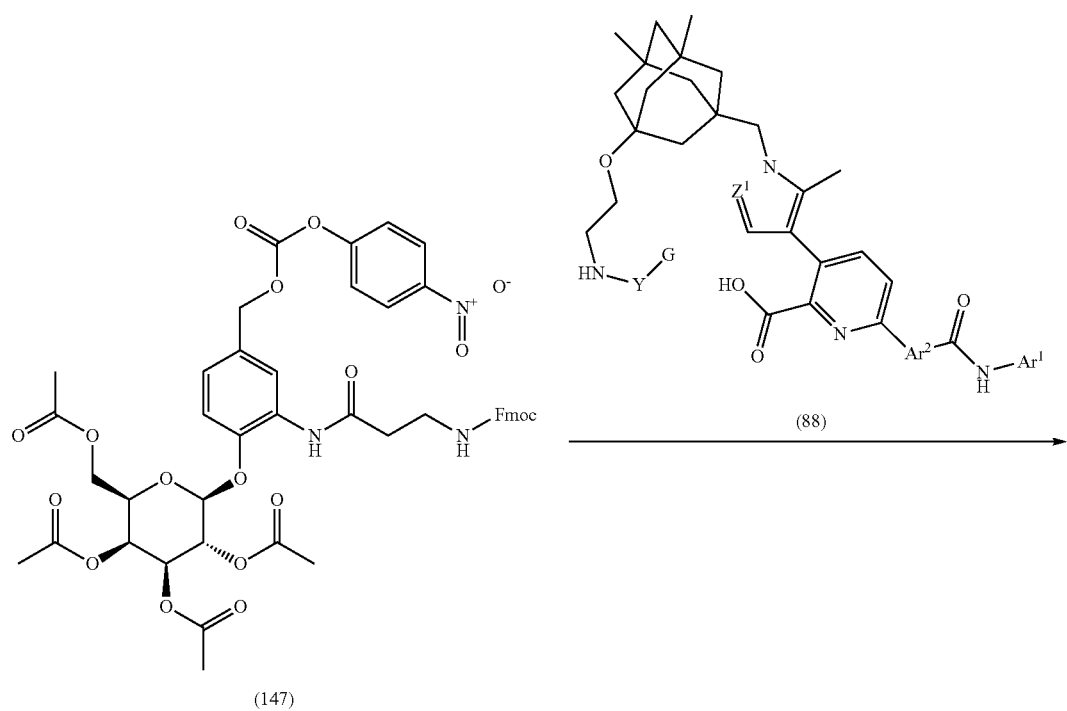
(147)

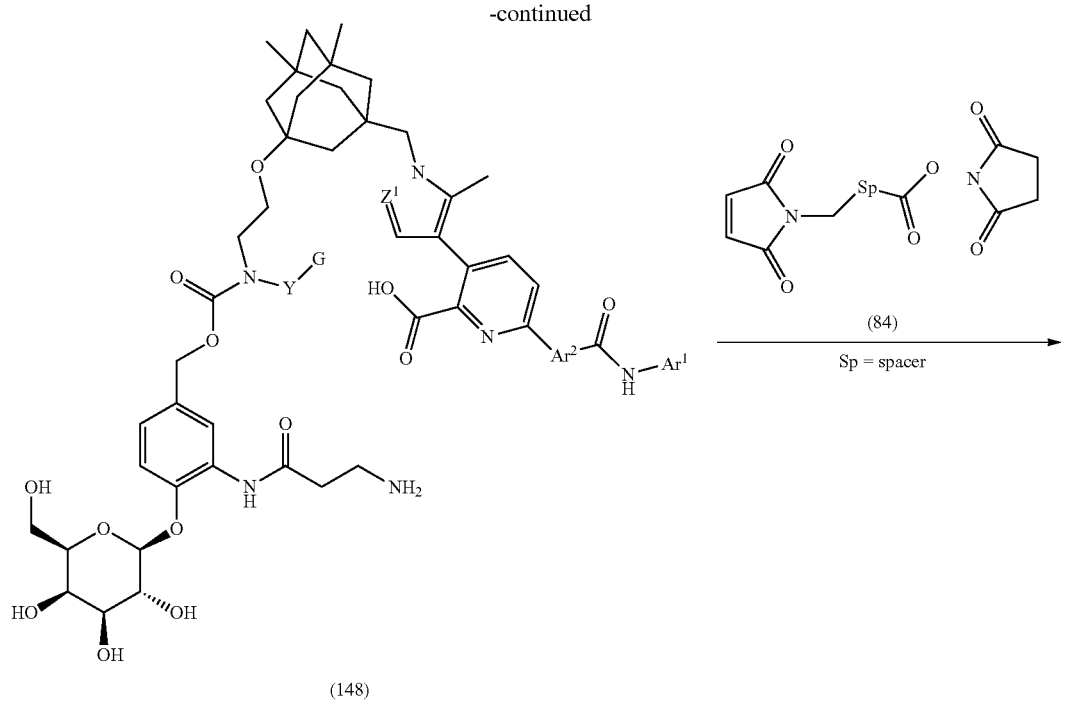

(148)

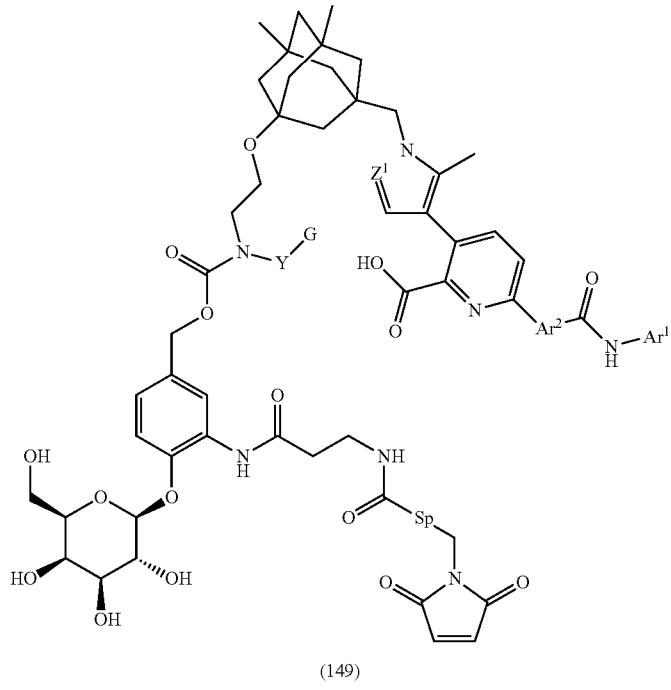

(149)

Scheme 22 describes the synthesis of galactoside linker intermediates and synthons. (2S,3R,4S,5S,6R)-6-(Acetoxymethyl)tetrahydro-2H-pyran-2,3,4,5-tetrayl tetraacetate (140) can be treated with HBr in acetic acid to provide (2R,3S,4S,5R,6S)-2-(acetoxymethyl)-6-bromotetrahydro-2H-pyran-3,4,5-triyl triacetate (141). The reaction is typically performed at ambient temperature under a nitrogen atmosphere. (2R,3S,4S,5R,6S)-2-(Acetoxymethyl)-6-(4-formyl-2-nitrophenoxy)tetrahydro-2H-pyran-3,4,5-triyl triacetate (143) can be prepared by treating (2R,3S,4S,5R,6S)-2-(acetoxymethyl)-6-bromotetrahydro-2H-pyran-3,4,5-triyl triacetate (141) with silver(I) oxide in the presence of 4-hydroxy-3-nitrobenzaldehyde (142). The reaction is typically performed at ambient temperature in a solvent such as, but not limited to, acetonitrile. (2R,3S,4S,5R,6S)-2-(Acetoxymethyl)-6-(4-formyl-2-nitrophenoxy)tetrahydro-2H-pyran-3,4,5-triyl triacetate (143) can be treated with sodium borohydride to provide (2R,3S,4S,5R,6S)-2-(acetoxymethyl)-6-(4-(hydroxymethyl)-2-nitrophenoxy)tetrahydro-2H-pyran-3,4,5-triyl triacetate (144). The reaction is typically performed at low temperature in a solvent such as but not limited to tetrahydrofuran, methanol, or mixtures thereof. (2R,3S,4S,5R,6S)-2-(Acetoxymethyl)-6-(2-amino-4-(hydroxymethyl)phenoxy)tetrahydro-2H-pyran-3,4,5-triyl triacetate (145) can be prepared by treating (2R,3S,4S,5R, 6S)-2-(acetoxymethyl)-6-(4-(hydroxymethyl)-2-nitrophenoxy)tetrahydro-2H-pyran-3,4,5-triyl triacetate (144) with zinc in the presence of hydrochloric acid. The reaction is typically performed at low temperature, under a nitrogen atmosphere, in a solvent such as, but not limited to, tetrahydrofuran. (2S,3R,4S,5S,6R)-2-(2-(3-((((9H-Fluoren-9-yl)methoxy)carbonyl)amino)propanamido)-4-(hydroxymethyl)phenoxy)-6-(acetoxymethyl)tetrahydro-2H-pyran-3,4,5-triyl triacetate (146) can be prepared by reacting (2R,3S,4S,5R,6S)-2-(acetoxymethyl)-6-(2-amino-4-(hydroxymethyl)phenoxy)tetrahydro-2H-pyran-3,4,5-triyl triacetate (145) with (9H-fluoren-9-yl)methyl (3-chloro-3-oxopropyl)carbamate (103) in the presence of a base such as, but not limited to, N,N-diisopropylethylamine. The reaction is typically performed at low temperature, in a solvent such as, but not limited to, dichloromethane. (2S,3R,4S,5S,6R)-2-(2-(3-((((9H-Fluoren-9-yl)methoxy)carbonyl)amino)propanamido)-4-(hydroxymethyl)phenoxy)-6-(acetoxymethyl) tetrahydro-2H-pyran-3,4,5-triyl triacetate (146) can be reacted with bis(4-nitrophenyl)carbonate in the presence of a base such as, but not limited to, N,N-diisopropylethylamine, to provide (2S,3R,4S,5S,6R)-2-(2-(3-((((9H-fluoren-9-yl)methoxy)carbonyl)amino)propanamido)-4-(((((4-nitrophenoxy)carbonyl)oxy)methyl)phenoxy)-6-(acetoxymethyl) tetrahydro-2H-pyran-3,4,5-triyl triacetate (147). The reaction is typically performed at low temperature, in a solvent such as, but not limited to, N,N-dimethylformamide. (2S,3R,4S,5S,6R)-2-(2-(3-((((9H-Fluoren-9-yl)methoxy)carbonyl)amino)propanamido)-4-(((((4-nitrophenoxy)carbonyl)oxy)methyl)phenoxy)-6-(acetoxymethyl)tetrahydro-2H-pyran-3,4,5-triyl triacetate (147) can be reacted with compound (88) in the presence of a base such as, but not limited to N,N-diisopropylethylamine, followed by treatment with lithium hydroxide, to provide compound (148). The first step is typically performed at low temperature, in a solvent such as, but not limited to, N,N-dimethylformamide, and the second step is typically performed at ambient temperature, in a solvent such as, but not limited to, methanol. Compound (148) can be treated with compound (84), wherein Sp is a spacer, in the presence of a base, such as, but not limited to N,N-diisopropylethylamine, to provide compound (149). The reaction is typically performed at ambient temperature, in a solvent such as, but not limited to, N,N-dimethylformamide.

III.A.7. General Methods for Synthesizing Anti-B7-H3 ADCs

The present invention also discloses a process to prepare an anti-B7-H3 ADC according to structural formula (I):

wherein D, L, LK, Ab and m are as defined in the Detailed Description section. The process comprises:

treating an antibody in an aqueous solution with an effective amount of a disulfide reducing agent at 30-40° C. for at least 15 minutes, and then cooling the antibody solution to 20-27° C.;

adding to the reduced antibody solution a solution of water/dimethyl sulfoxide comprising a synthon selected from the group of 2.1 to 2.176 (Table B);

adjusting the pH of the solution to a pH of 7.5 to 8.5;

allowing the reaction to run for 48 to 80 hours to form the ADC;

wherein the mass is shifted by 18±2 amu for each hydrolysis of a succinimide to a succinamide as measured by electron spray mass spectrometry; and wherein the ADC is optionally purified by hydrophobic interaction chromatography.

In certain embodiments, the antibody is an hB7-H3 antibody, wherein the hB7-H3 antibody comprises the heavy and light chain CDRs of huAb3v2.5, huAb3v2.6, or huAb13v1.

The present invention is also directed to an anti-B7-H3 ADC prepared by the above-described process.

In certain embodiments, the anti-B7-H3 ADC disclosed in the present application is formed by contacting an antibody that binds an hB7-H3 cell surface receptor or tumor associated antigen expressed on a tumor cell with a drug-linker synthon under conditions in which the drug-linker synthon covalently links to the antibody through a maleimide moiety as shown in formulae (IIe) and (IIf), or through an acetyl halide as shown in (IIg), or through a vinyl sulfone as shown in (IIh).

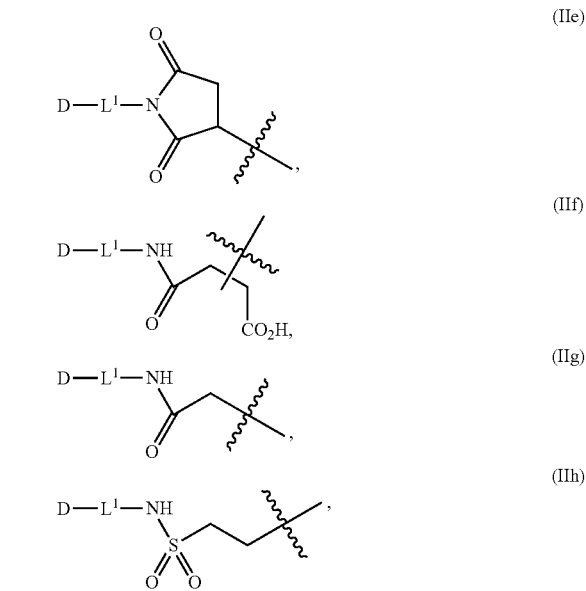

wherein D is the Bcl-xL inhibitor drug according to structural formula (IIa), (IIb), (IIc) or (IId) as described above and $L^1$ is the portion of the linker not formed from the maleimide, acetyl halide or vinyl sulfone upon attachment of the synthon to the antibody; and wherein the drug-linker synthon is selected from the group consisting of synthon examples 2.1 to 2.176 (Table B), or a pharmaceutically acceptable salt thereof.

In certain embodiments, the contacting step is carried out under conditions such that the anti-B7-H3 ADC has a DAR of 2, 3 or 4.

III.B. Anti-B7-H3 ADCs: Other Exemplary Drugs for Conjugation

Anti-B7-H3 antibodies may be used in ADCs to target one or more drug(s) to a cell of interest, e.g., a cancer cell expressing B7-H3. The anti-B7-H3 ADCs of the invention provide a targeted therapy that may, for example, reduce the side effects often seen with anti-cancer therapies, as the one or more drug(s) is delivered to a specific cell.

Auristatins

Anti-B7-H3 antibodies of the invention, e.g., the huAb13v1, huAb3v2.5, or huAb3v2.6 antibody, may be conjugated to at least one auristatin. Auristatins represent a group of dolastatin analogs that have generally been shown to possess anticancer activity by interfering with microtubule dynamics and GTP hydrolysis, thereby inhibiting cellular division. For example, auristatin E (U.S. Pat. No. 5,635,483) is a synthetic analogue of the marine natural product dolastatin 10, a compound that inhibits tubulin polymerization by binding to the same site on tubulin as the anticancer drug vincristine (G. R. Pettit, Prog. Chem. Org. Nat. Prod, 70: 1-79 (1997)). Dolastatin 10, auristatin PE, and auristatin E are linear peptides having four amino acids, three of which are unique to the dolastatin class of compounds. Exemplary embodiments of the auristatin subclass of mitotic inhibitors include, but are not limited to, monomethyl auristatin D (MMAD or auristatin D derivative), monomethyl auristatin E (MMAE or auristatin E derivative), monomethyl auristatin F (MMAF or auristatin F derivative), auristatin F phenylenediamine (AFP), auristatin EB (AEB), auristatin EFP (AEFP), and 5-benzoylvaleric acid-AE ester (AEVB). The synthesis and structure of auristatin derivatives are described in U.S. Patent Application Publication Nos. 2003-0083263, 2005-0238649 and 2005-0009751; International Patent Publication No. WO 04/010957, International Patent Publication No. WO 02/088172, and U.S. Pat. Nos. 6,323,315; 6,239,104; 6,034,065; 5,780,588; 5,665,860; 5,663,149; 5,635,483; 5,599,902; 5,554,725; 5,530,097; 5,521,284; 5,504,191; 5,410,024; 5,138,036; 5,076,973; 4,986,988; 4,978,744; 4,879,278; 4,816,444; and 4,486,414, each of which is incorporated by reference herein.

In one embodiment, anti-B7-H3 antibodies of the invention, e.g., huAb13v1, huAb3v2.5, or huAb3v2.6, are conjugated to at least one MMAE (mono-methyl auristatin E). Monomethyl auristatin E (MMAE, vedotin) inhibits cell division by blocking the polymerization of tubulin. However, due to its super toxicity, auristatin E cannot be used as a drug itself. Auristatin E can be linked to a monoclonal antibody (mAb) that recognizes a specific marker expression in cancer cells and directs MMAE to the cancer cells. In one embodiment, the linker linking MMAE to the anti-B7-H3 antibody is stable in extracellular fluid (i.e., the medium or environment that is external to cells), but is cleaved by cathepsin once the ADC has bound to the specific cancer cell antigen and entered the cancer cell, thus releasing the toxic MMAE and activating the potent anti-mitotic mechanism.

In one embodiment, an anti-B7-H3 antibody described herein, e.g., huAb13v1, huAb3v2.5, or huAb3v2.6, is conjugated to at least one MMAF (monomethyllauristatin F). Monomethyl auristatin F (MMAF) inhibits cell division by blocking the polymerization of tubulin. It has a charged C-terminal phenylalanine residue that attenuates its cytotoxic activity compared to its uncharged counterpart MMAE. However, due to its super toxicity, auristatin F cannot be used as a drug itself, but can be linked to a monoclonal antibody (mAb) that directs it to the cancer cells. In one embodiment, the linker to the anti-B7-H3 antibody is stable in extracellular fluid, but is cleaved by cathepsin once the conjugate has entered a tumor cell, thus activating the anti-mitotic mechanism.

The structures of MMAF and MMAE are provided below.

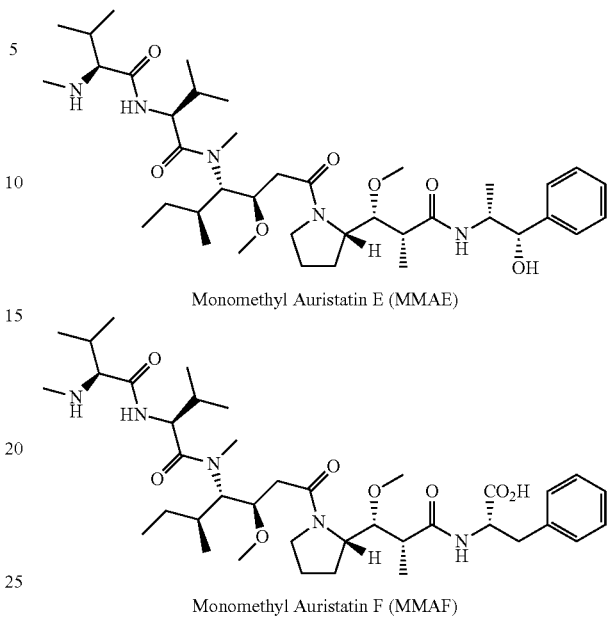

Monomethyl Auristatin E (MMAE)

Monomethyl Auristatin F (MMAF)

Figure 3:
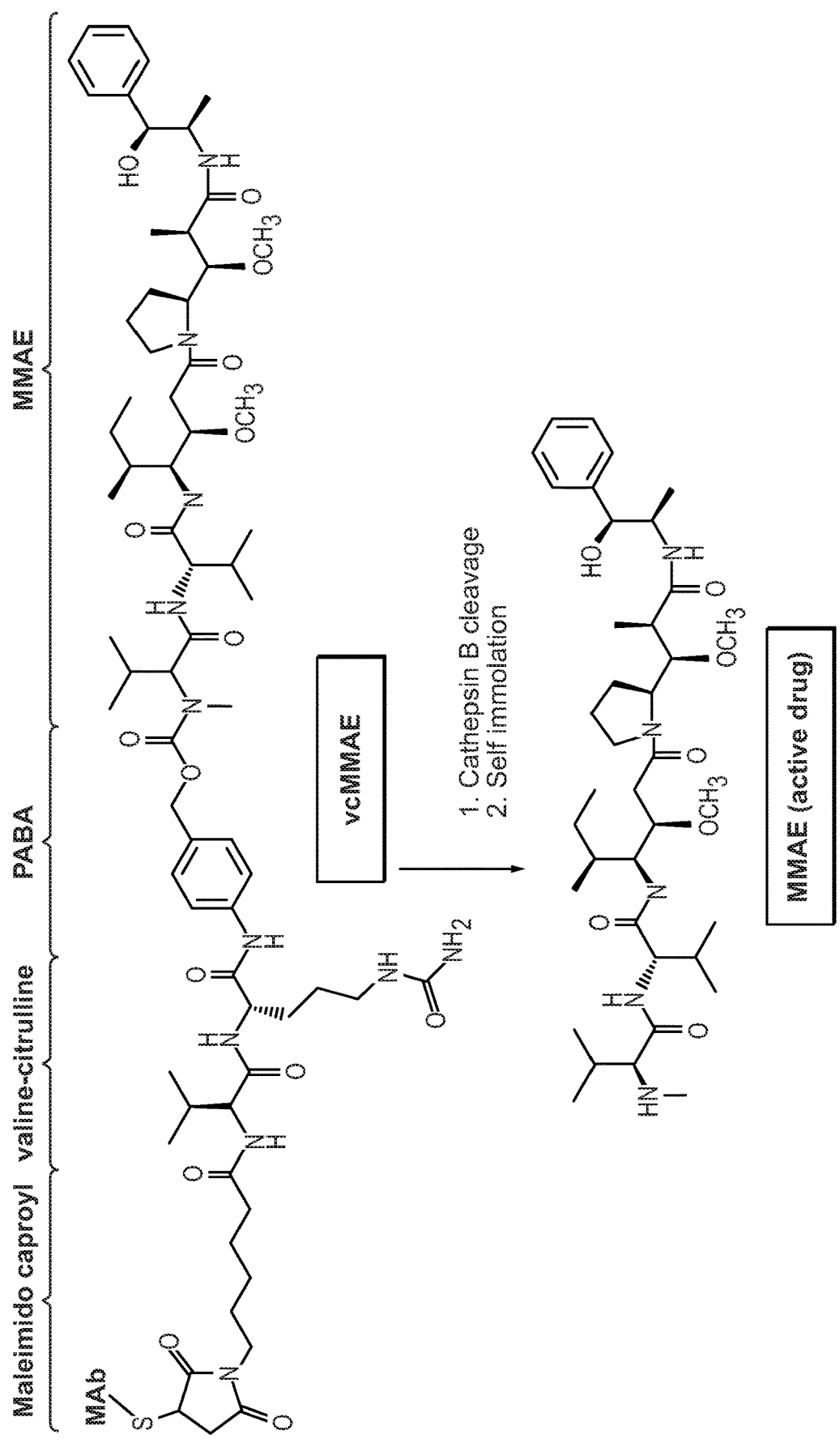
FIG. 3 depicts the structure of an antibody-maleimidocaproyl-vc-PABA-MMAE ADC.

An example of huAb13v1, huAb3v2.5, or huAb3v2.6-vcMMAE is also provided in FIG. 3. Notably, FIG. 3 describes a situation where the antibody (e.g., huAb13v1, huAb3v2.5, or huAb3v2.6) is coupled to a single drug and, therefore, has a DAR of 1. In certain embodiments, the ADC will have a DAR of 2 to 8, or, alternatively, 2 to 4.

Other Drugs for Conjugation

Examples of drugs that may be used in ADCs, i.e., drugs that may be conjugated to the anti-B7-H3 antibodies of the invention, are provided below, and include mitotic inhibitors, antitumor antibiotics, immunomodulating agents, gene therapy vectors, alkylating agents, antiangiogenic agents, antimetabolites, boron-containing agents, chemoprotective agents, hormone agents, glucocorticoids, photoactive therapeutic agents, oligonucleotides, radioactive isotopes, radiosensitizers, topoisomerase inhibitors, kinase inhibitors, and combinations thereof.

1. Mitotic Inhibitors

In one aspect, anti-B7-H3 antibodies may be conjugated to one or more mitotic inhibitor(s) to form an ADC for the treatment of cancer. The term "mitotic inhibitor", as used herein, refers to a cytotoxic and/or therapeutic agent that blocks mitosis or cell division, a biological process particularly important to cancer cells. A mitotic inhibitor disrupts microtubules such that cell division is prevented, often by effecting microtubule polymerization (e.g., inhibiting microtubule polymerization) or microtubule depolymerization (e.g., stabilizing the microtubule cytoskeleton against depolymerization). Thus, in one embodiment, an anti-B7-H3 antibody of the invention is conjugated to one or more mitotic inhibitor(s) that disrupts microtubule formation by inhibiting tubulin polymerization. In another embodiment, an anti-B7-H3 antibody of the invention is conjugated to one or more mitotic inhibitor(s) that stabilizes the microtubule cytoskeleton from depolymerization. In one embodiment, the mitotic inhibitor used in the ADCs of the invention is Ixempra (ixabepilone). Examples of mitotic inhibitors that may be used in the anti-B7-H3 ADCs of the invention are provided below. Included in the genus of mitotic inhibitors are auristatins, described above.

a. Dolastatins

The anti-B7-H3 antibodies of the invention may be conjugated to at least one dolastatin to form an ADC. Dolastatins are short peptidic compounds isolated from the Indian Ocean sea hare *Dolabella auricularia* (see Pettit et al., J. Am. Chem. Soc., 1976, 98, 4677). Examples of dolastatins include dolastatin 10 and dolastatin 15. Dolastatin 15, a seven-subunit depsipeptide derived from *Dolabella auricularia*, and is a potent antimitotic agent structurally related to the antitubulin agent dolastatin 10, a five-subunit peptide obtained from the same organism. Thus, in one embodiment, the anti-B7-H3 ADC of the invention comprises an anti-B7-H3 antibody, as described herein, and at least one dolastatin. Auristatins, described above, are synthetic derivatives of dolastatin 10.

b. Maytansinoids

The anti-B7-H3 antibodies of the invention may be conjugated to at least one maytansinoid to form an ADC. Maytansinoids are potent antitumor agents that were originally isolated from members of the higher plant families Celastraceae, Rhamnaceae, and Euphorbiaceae, as well as some species of mosses (Kupchan et al, J. Am. Chem. Soc. 94:1354-1356 [1972]; Wani et al, J. Chem. Soc. Chem. Commun. 390: [1973]; Powell et al, J. Nat. Prod. 46:660-666 [1983]; Sakai et al, J. Nat. Prod. 51:845-850 [1988]; and Suwanborirux et al, Experientia 46:117-120 [1990]). Evidence suggests that maytansinoids inhibit mitosis by inhibiting polymerization of the microtubule protein tubulin, thereby preventing formation of microtubules (see, e.g., U.S. Pat. No. 6,441,163 and Remillard et al., Science, 189, 1002-1005 (1975)). Maytansinoids have been shown to inhibit tumor cell growth in vitro using cell culture models, and in vivo using laboratory animal systems. Moreover, the cytotoxicity of maytansinoids is 1,000-fold greater than conventional chemotherapeutic agents, such as, for example, methotrexate, daunorubicin, and vincristine (see, e.g., U.S. Pat. No. 5,208,020).

Maytansinoids to include maytansine, maytansinol, C-3 esters of maytansinol, and other maytansinol analogues and derivatives (see, e.g., U.S. Pat. Nos. 5,208,020 and 6,441,163, each of which is incorporated by reference herein). C-3 esters of maytansinol can be naturally occurring or synthetically derived. Moreover, both naturally occurring and synthetic C-3 maytansinol esters can be classified as a C-3 ester with simple carboxylic acids, or a C-3 ester with derivatives of N-methyl-L-alanine, the latter being more cytotoxic than the former. Synthetic maytansinoid analogues are described in, for example, Kupchan et al., J. Med. Chem., 21, 31-37 (1978).

Suitable maytansinoids for use in ADCs of the invention can be isolated from natural sources, synthetically produced, or semi-synthetically produced. Moreover, the maytansinoid can be modified in any suitable manner, so long as sufficient cytotoxicity is preserved in the ultimate conjugate molecule. In this regard, maytansinoids lack suitable functional groups to which antibodies can be linked. A linking moiety desirably is utilized to link the maytansinoid to the antibody to form the conjugate, and is described in more detail in the linker section below. The structure of an exemplary maytansinoid, mertansine (DM1), is provided below.

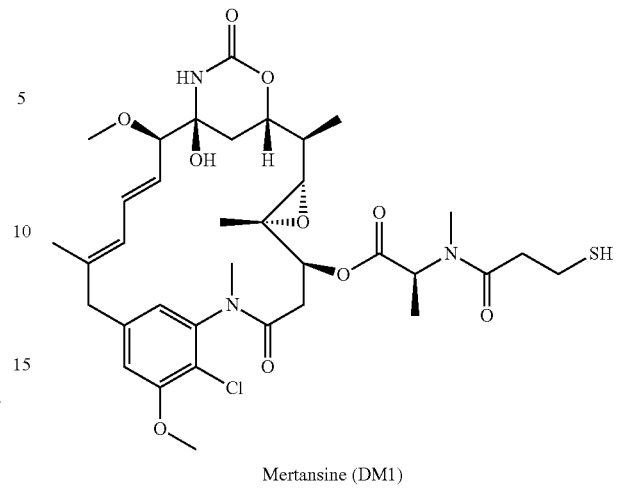

Mertansine (DM1)

Representative examples of maytansinoids include, but are not limited to, DM1 ($N^{2'}$-deacetyl-$N^{2'}$-(3-mercapto-1-oxopropyl)-maytansine; also referred to as mertansine, drug maytansinoid 1; ImmunoGen, Inc.; see also Chari et al. (1992) *Cancer Res* 52:127), DM2, DM3 ($N^{2'}$-deacetyl-$N^{2'}$-(4-mercapto-1-oxopentyl)-maytansine), DM4 (4-methyl-4-mercapto-1-oxopentyl)-maytansine), and maytansinol (a synthetic maytansinoid analog). Other examples of maytansinoids are described in U.S. Pat. No. 8,142,784, incorporated by reference herein.

Ansamitocins are a group of maytansinoid antibiotics that have been isolated from various bacterial sources. These compounds have potent antitumor activities. Representative examples include, but are not limited to ansamitocin P1, ansamitocin P2, ansamitocin P3, and ansamitocin P4.

In one embodiment of the invention, an anti-B7-H3 antibody is conjugated to at least one DM1. In one embodiment, an anti-B7-H3 antibody is conjugated to at least one DM2. In one embodiment, an anti-B7-H3 antibody is conjugated to at least one DM3. In one embodiment, an anti-B7-H3 antibody is conjugated to at least one DM4.

d. Plant Alkaloids

The anti-B7-H3 antibodies of the invention may be conjugated to at least one plant alkaloid, e.g., a taxane or *vinca* alkaloid. Plant alkaloids are chemotherapy treatments derived made from certain types of plants. The *vinca* alkaloids are made from the periwinkle plant (*catharanthus rosea*), whereas the taxanes are made from the bark of the Pacific Yew tree (*taxus*). Both the *vinca* alkaloids and taxanes are also known as antimicrotubule agents, and are described in more detail below.

Taxanes

Anti-B7-H3 antibodies described herein may be conjugated to at least one taxane. The term "taxane" as used herein refers to the class of antineoplastic agents having a mechanism of microtubule action and having a structure that includes the taxane ring structure and a stereospecific side chain that is required for cytostatic activity. Also included within the term "taxane" are a variety of known derivatives, including both hydrophilic derivatives, and hydrophobic derivatives. Taxane derivatives include, but not limited to, galactose and mannose derivatives described in International Patent Application No. WO 99/18113; piperazino and other derivatives described in WO 99/14209; taxane derivatives described in WO 99/09021, WO 98/22451, and U.S. Pat. No. 5,869,680; 6-thio derivatives described in WO 98/28288; sulfenamide derivatives described in U.S. Pat. No. 5,821,263; and taxol derivative described in U.S. Pat. No. 5,415,869, each of which is incorporated by reference herein. Taxane compounds have also previously been described in U.S. Pat. Nos. 5,641,803, 5,665,671, 5,380,751, 5,728,687, 5,415,869, 5,407,683, 5,399,363, 5,424,073, 5,157,049, 5,773,464, 5,821,263, 5,840,929, 4,814,470, 5,438,072, 5,403,858, 4,960,790, 5,433,364, 4,942,184, 5,362,831, 5,705,503, and 5,278,324, all of which are expressly incorporated by reference. Further examples of taxanes include, but are not limited to, docetaxel (Taxotere; Sanofi Aventis), paclitaxel (Abraxane or Taxol; Abraxis Oncology), carbazitaxel, tesetaxel, opaxio, larotaxel, taxoprexin, BMS-184476, hongdoushan A, hongdoushan B, and hongdoushan C, and nanoparticle paclitaxel (ABI-007/Abraxene; Abraxis Bioscience).

In one embodiment, the anti-B7-H3 antibody of the invention is conjugated to at least one docetaxel molecule. In one embodiment, the anti-B7-H3 antibody of the invention is conjugated to at least one paclitaxel molecule.

Vinca alkaloids

In one embodiment, the anti-B7-H3 antibody is conjugated to at least one vinca alkaloid.

Vinca alkaloids are a class of cell-cycle-specific drugs that work by inhibiting the ability of cancer cells to divide by acting upon tubulin and preventing the formation of microtubules. Examples of vinca alkaloids that may be used in the ADCs of the invention include, but are not limited to, vindesine sulfate, vincristine, vinblastine, and vinorelbine.

2. Antitumor Antibiotics

Anti-B7-H3 antibodies of the invention may be conjugated to one or more antitumor antibiotic(s) for the treatment of cancer. As used herein, the term "antitumor antibiotic" means an antineoplastic drug that blocks cell growth by interfering with DNA and is made from a microorganism. Often, antitumor antibiotics either break up DNA strands or slow down or stop DNA synthesis. Examples of antitumor antibiotics that may be included in the anti-B7-H3 ADCs of the invention include, but are not limited to, actinomycines (e.g., pyrrolo[2,1-c][1,4]benzodiazepines), anthracyclines, calicheamicins, and duocarmycins, described in more detail below.

a. Actinomycins

The anti-B7-H3 antibodies of the invention may be conjugated to at least one actinomycin. Actinomycins are a subclass of antitumor antibiotics isolated from bacteria of the genus *Streptomyces. Representative examples actinomycins include, but are not limited to, actinomycin D* (Cosmegen [also known as actinomycin, dactinomycin, actinomycin IV, actinomycin C1], Lundbeck, Inc.), anthramycin, chicamycin A, DC-81, mazethramycin, neothramycin A, neothramycin B, porothramycin, prothracarcin B, SG2285, sibanomicin, sibiromycin, and tomaymycin. In one embodiment, the anti-B7-H3 antibody of the invention is conjugated to at least one pyrrolobenzodiazepine (PBD). Examples of PBDs include, but are not limited to, anthramycin, chicamycin A, DC-81, mazethramycin, neothramycin A, neothramycin B, porothramycin, prothracarcin B, SG2000 (SJG-136), SG2202 (ZC-207), SG2285 (ZC-423), sibanomicin, sibiromycin and tomaymycin. Thus, in one embodiment, anti-B7-H3 antibodies of the invention are conjugated to at least one actinomycin, e.g., actinomycin D, or at least one PBD, e.g., a pyrrolobenzodiazepine (PBD) dimer.

The structures of PBDs can be found, for example, in U.S. Patent Application Pub. Nos. 2013/0028917 and 2013/0028919, and in WO 2011/130598 A1, each of which are incorporated herein by reference in their entirety. The generic structure of a PBD is provided below.

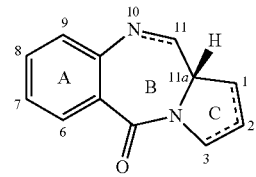

PBDs differ in the number, type and position of substituents, in both their aromatic A rings and pyrrolo C rings, and in the degree of saturation of the C ring. In the B-ring, there is generally an imine (N=C), a carbinolamine (NH—CH(OH)), or a carbinolamine methyl ether (NH—CH(OMe)) at the N10-C11 position which is the electrophilic center responsible for alkylating DNA. All of the known natural products have an (S)-configuration at the chiral C11α position which provides them with a right-handed twist when viewed from the C ring towards the A ring. The PBD examples provided herein may be conjugated to the anti-B7-H3 antibodies of the invention. Further examples of PBDs which may be conjugated to the anti-B7-H3 antibodies of the invention can be found, for example, in U.S. Patent Application Publication Nos. 2013/0028917 A1 and 2013/0028919 A1, in U.S. Pat. No. 7,741,319 B2, and in WO 2011/130598 A1 and WO 2006/111759 A1, each of which are incorporated herein by reference in their entirety.

A representative PBD dimer having the following formula XXX may be conjugated to the anti-B7-H3 antibodies of the invention:

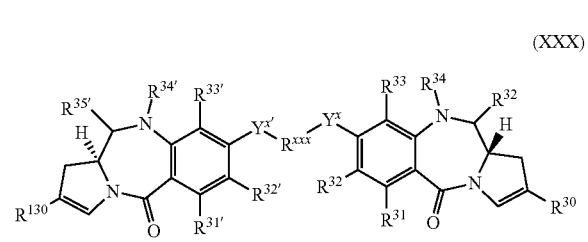

(XXX)

wherein:
$R^{30}$ is of formula XXXI:

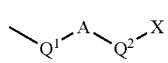

(XXXI)

where A is a $C_{5-7}$ aryl group, X is a group conjugated to the Linker unit selected from the group consisting of —O—, —S—, —C(O)O—, —C(O)—, —NH(C=O)—, and —N($R^N$)—, wherein R is selected from the group consisting of H, $C_{1-4}$ alkyl and $(C_2H_4O)_mCH_3$, where s is 1 to 3, and either:

(i) $Q^1$ is a single bond, and $Q^2$ is selected from the group consisting of a single bond and —Z—$(CH_2)_n$—, where Z is selected from the group consisting of a single bond, O, S and NH and n is from 1 to 3; or (ii) Q is —CH=CH—, and Q is a single bond;

$R^{130}$ is a $C_{5-10}$ aryl group, optionally substituted by one or more substituents selected from the group consisting of halo, nitro, cyano, $C_{1-12}$ alkoxy, $C_{3-20}$ heterocycloalkoxy, $C_{5-20}$ aryloxy, heteroaryloxy, alkylalkoxy, arylalkoxy, alkyl aryloxy, heteroarylalkoxy, alkylheteroaryloxy, $C_{1-7}$ alkyl, $C_{3-7}$ heterocyclyl and bis-oxy-$C_{1-3}$ alkylene;

$R^{31}$ and $R^{33}$ are independently selected from the group consisting of H, $R^x$, OH, $OR^x$, SH, $SR^x$, $NH_2$, $NHR^x$, $NR^xR^{xx'}$, nitro, $Me_3Sn$ and halo;

where R and R' are independently selected from the group consisting of optionally substituted $C_{1-12}$ alkyl, $C_{3-20}$ heterocyclyl and $C_{5-20}$ aryl groups;

$R^{32}$ is selected from the group consisting of H, $R^x$, OH, $OR^x$, SH, $SR^x$, $NH_2$, $NHR^X$, $NHR^xR^{xx}$, nitro, $Me_3Sn$ and halo;

either:
(a) $R^{34}$ is H, and $R^{11}$ is OH, $OR^{x4}$, where $R^{x4}$ is $C_{1-4}$ alkyl;
(b) $R^{34}$ and $R^{35}$ form a nitrogen-carbon double bond between the nitrogen and carbon atoms to which they are bound; or
(c) $R^{34}$ is H and $R^{35}$ is $SO_2M$, where z is 2 or 3;

$R^{xxx}$ is a $C_{3-12}$ alkylene group, which chain may be interrupted by one or more heteroatoms, selected from the group consisting of O, S, NH, and an aromatic ring;

$Y^x$ and $Y^{x'}$ are is selected from the group consisting of O, S, and NH;

$R^{31'}$, $R^{32'}$, $R^{33'}$ are selected from the same groups as $R^{31}$, $R^{32}$ and $R^{33}$ respectively and $R^{34'}$ and $R^{35'}$ are the same as $R^{34}$ and $R^{35}$, and each M is a monovalent pharmaceutically acceptable cation or both M groups together are a divalent pharmaceutically acceptable cation.

$C_{1-12}$ alkyl: The term "$C_{1-12}$ alkyl" as used herein, pertains to a monovalent moiety obtained by removing a hydrogen atom from a carbon atom of a hydrocarbon compound having from 1 to 12 carbon atoms, which may be aliphatic or alicyclic, and which may be saturated or unsaturated (e.g. partially unsaturated, fully unsaturated). Thus, the term "alkyl" includes the sub-classes alkenyl, alkynyl, cycloalkyl, etc., discussed below.

Examples of saturated alkyl groups include, but are not limited to, methyl ($C_1$), ethyl ($C_2$), propyl ($C_3$), butyl ($C_4$), pentyl ($C_5$), hexyl ($C_6$) and heptyl ($C_7$).

Examples of saturated linear alkyl groups include, but are not limited to, methyl ($C_1$), ethyl ($C_2$), n-propyl ($C_3$), n-butyl ($C_4$), n-pentyl (amyl) ($C_5$), n-hexyl ($C_6$) and n-heptyl ($C_7$).

Examples of saturated branched alkyl groups include iso-propyl ($C_3$), iso-butyl ($C_4$), sec-butyl ($C_4$), tert-butyl ($C_4$), iso-pentyl ($C_5$), and neo-pentyl ($C_5$).

$C_{3-20}$ heterocyclyl: The term "$C_{3-20}$ heterocyclyl" as used herein, pertains to a monovalent moiety obtained by removing a hydrogen atom from a ring atom of a heterocyclic compound, which moiety has from 3 to 20 ring atoms, of which from 1 to 10 are ring heteroatoms. Preferably, each ring has from 3 to 7 ring atoms, of which from 1 to 4 are ring heteroatoms.

In this context, the prefixes (e.g. $C_{3-20}$, $C_{3-7}$, $C_{5-6}$, etc.) denote the number of ring atoms, or range of number of ring atoms, whether carbon atoms or heteroatoms. For example, the term "$C_{5-6}$heterocyclyl", as used herein, pertains to a heterocyclyl group having 5 or 6 ring atoms.

Examples of monocyclic heterocyclyl groups include, but are not limited to, those derived from:

$N_1$: aziridine ($C_3$), azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$); $O_1$: oxirane ($C_3$), oxetane ($C_4$), oxolane (tetrahydrofuran) ($C_5$), oxole (dihydrofuran) ($C_5$), oxane (tetrahydropyran) ($C_6$), dihydropyran ($C_6$), pyran ($C_6$), oxepin ($C_7$); $S_1$: thiirane ($C_3$), thietane ($C_4$), thiolane (tetrahydrothiophene) ($C_5$), thiane (tetrahydrothiopyran) ($C_6$), thiepane ($C_7$); $O_2$: dioxolane ($C_5$), dioxane ($C_6$), and dioxepane ($C_7$); $O_3$: trioxane ($C_6$); $N_2$: imidazolidine ($C_5$), pyrazolidine (diazolidine) ($C_5$), imidazoline ($C_5$), pyrazoline (dihydropyrazole) ($C_5$), piperazine ($C_6$); $N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$); $N_1S_1$: thiazoline ($C_5$), thiazolidine ($C_5$), thiomorpholine ($C_6$); $N_2O_1$: oxadiazine ($C_6$); $O_1S_1$: oxathiole ($C_5$) and oxathiane (thioxane) ($C_6$); and, $N_1O_1S_1$: oxathiazine ($C_6$).

Examples of substituted monocyclic heterocyclyl groups include those derived from saccharides, in cyclic form, for example, furanoses ($C_5$), such as arabinofuranose, lyxofuranose, ribofuranose, and xylofuranse, and pyranoses ($C_6$), such as allopyranose, altropyranose, glucopyranose, mannopyranose, gulopyranose, idopyranose, galactopyranose, and talopyranose.

$C_{5-20}$ aryl: The term "$C_{5-20}$ aryl", as used herein, pertains to a monovalent moiety obtained by removing a hydrogen atom from an aromatic ring atom of an aromatic compound, which moiety has from 3 to 20 ring atoms. Preferably, each ring has from 5 to 7 ring atoms.

In this context, the prefixes (e.g. $C_{3-20}$, $C_{5-7}$, $C_{5-6}$, etc.) denote the number of ring atoms, or range of number of ring atoms, whether carbon atoms or heteroatoms. For example, the term "$C_{5-6}$ aryl" as used herein, pertains to an aryl group having 5 or 6 ring atoms.

In one embodiment, the anti-B7-H3 antibodies of the invention may be conjugated to a PBD dimer having the following formula XXXIa:

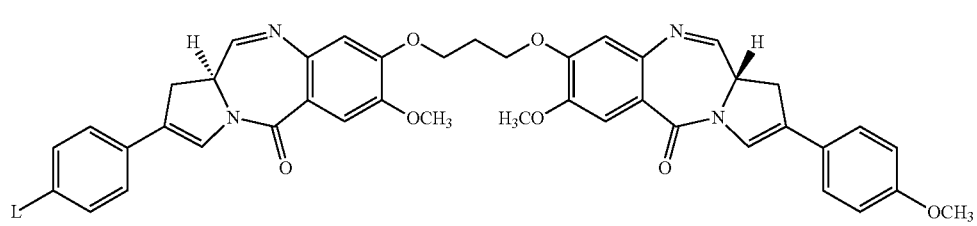

(XXXIa)

wherein the above structure describes the PBD dimer SG2202 (ZC-207) and is conjugated to the anti-B7-H3 antibody of the invention via a linker L. SG2202 (ZC-207) is disclosed in, for example, U.S. Patent App. Pub. No. 2007/0173497, which is incorporated herein by reference in its entirety.

Figure 4:
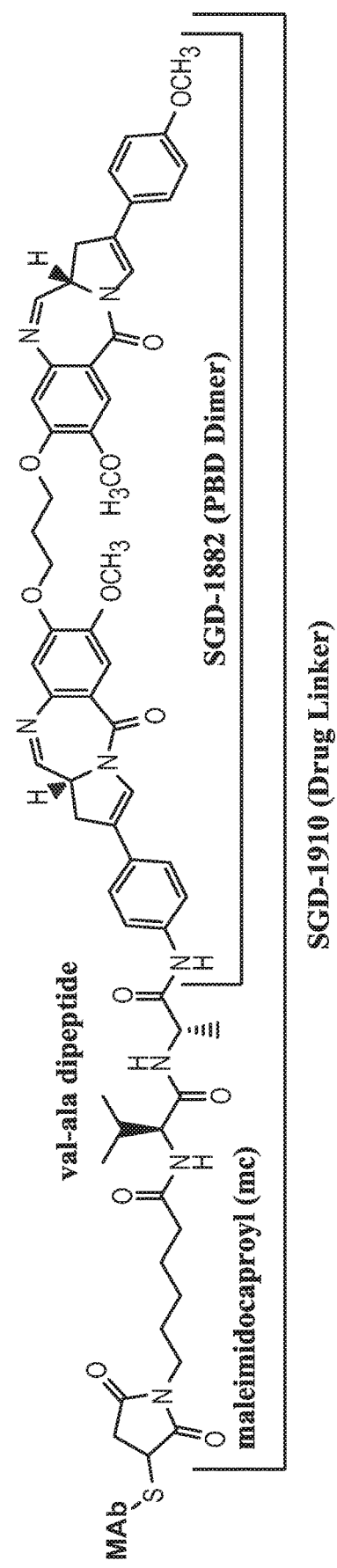
FIG. 4 depicts the structure of a PBD dimer (SGD-1882) conjugated to an antibody (Ab) via a maleimidocaproyl-valine-alanine linker (collectively referred to as SGD-1910).

In another embodiment, a PBD dimer, SGD-1882, is conjugated to anti-B7-H3 antibody of the invention via a drug linker, as depicted in FIG. 4. SGD-1882 is disclosed in Sutherland et al. (2013) *Blood* 122(8): 1455 and in U.S Patent App. Pub. No. 2013/0028919, which is incorporated herein by reference in its entirety. As described in FIG. 4, the PBD dimer SGD-1882 may be conjugated to an antibody via an mc-val-ala-dipeptide linker (collectively referred to as SGD-1910 in FIG. 4). In a certain embodiment, an anti-B7-H3 antibody, as disclosed herein, is conjugated to the PBD dimer described in FIG. 4. Thus, in a further embodiment, the invention includes an anti-B7-H3 antibody, as disclosed herein, conjugated to a PBD dimer via a mc-val-ala-dipeptide linker, as described in FIG. 4. In certain embodiments, the invention includes an anti-B7-H3 antibody comprising a heavy chain variable region comprising a CDR3 domain comprising the amino acid sequence of SEQ ID NO: 35, a CDR2 domain comprising the amino acid sequence of SEQ ID NO: 34, and a CDR1 domain comprising the amino acid sequence of SEQ ID NO: 33, and a light chain variable region comprising a CDR3 domain comprising the amino acid sequence of SEQ ID NO: 39, a CDR2 domain comprising the amino acid sequence of SEQ ID NO: 38, and a CDR1 domain comprising the amino acid sequence of SEQ ID NO: 37, conjugated to a PBD, including, but not limited to, the PBD dimer described in FIG. 4. In certain embodiments, the invention includes an anti-B7-H3 antibody comprising a heavy chain variable region comprising a CDR3 domain comprising the amino acid sequence of SEQ ID NO: 12, a CDR2 domain comprising the amino acid sequence of SEQ ID NO: 140, and a CDR1 domain comprising the amino acid sequence of SEQ ID NO: 10, and a light chain variable region comprising a CDR3 domain comprising the amino acid sequence of SEQ ID NO: 15, a CDR2 domain comprising the amino acid sequence of SEQ ID NO: 7, and a CDR1 domain comprising the amino acid sequence of SEQ ID NO: 136, conjugated to a PBD, including, but not limited to, the PBD dimer described in FIG. 4. In certain embodiments, the invention includes an anti-B7-H3 antibody comprising a heavy chain variable region comprising a CDR3 domain comprising the amino acid sequence of SEQ ID NO: 12, a CDR2 domain comprising the amino acid sequence of SEQ ID NO: 140, and a CDR1 domain comprising the amino acid sequence of SEQ ID NO: 10, and a light chain variable region comprising a CDR3 domain comprising the amino acid sequence of SEQ ID NO: 15, a CDR2 domain comprising the amino acid sequence of SEQ ID NO: 7, and a CDR1 domain comprising the amino acid sequence of SEQ ID NO: 138, conjugated to a PBD, including, but not limited to, the PBD dimer described in FIG. 4. In certain embodiments, the invention includes an anti-B7-H3 antibody comprising the heavy chain variable region of huAb13v1 as defined by the amino acid sequence set forth in SEQ ID NO: 147, or huAb3v2.5 or huAb3v2.6 as defined by the amino acid sequence set forth in SEQ ID NO: 139, and a light chain variable region comprising the amino acid sequence of SEQ ID NO: 144, 135, or 137 corresponding to huAb13v1, huAb3v2.5, or huAb3v2.6, respectively, wherein the antibody is conjugated to a PBD, such as, but not limited to, the exemplary PBD dimer of FIG. 4.

b. Anthracyclines

Anti-B7-H3 antibodies of the invention may be conjugated to at least one anthracycline. Anthracyclines are a subclass of antitumor antibiotics isolated from bacteria of the genus *Streptomyces*. Representative examples include, but are not limited to daunorubicin (Cerubidine, Bedford Laboratories), doxorubicin (Adriamycin, Bedford Laboratories; also referred to as doxorubicin hydrochloride, hydroxy-daunorubicin, and Rubex), epirubicin (Ellence, Pfizer), and idarubicin (Idamycin; Pfizer Inc.). Thus, in one embodiment, the anti-B7-H3 antibody of the invention is conjugated to at least one anthracycline, e.g., doxorubicin.

c. Calicheamicins

The anti-B7-H3 antibodies of the invention may be conjugated to at least one calicheamicin. Calicheamicins are a family of enediyne antibiotics derived from the soil organism *Micromonospora echinospora*. Calicheamicins bind the minor groove of DNA and induce double-stranded DNA breaks, resulting in cell death with a 100 fold increase over other chemotherapeutics (Damle et al. (2003) *Curr Opin Pharmacol* 3:386). Preparation of calicheamicins that may be used as drug conjugates in the invention have been described, see U.S. Pat. Nos. 5,712,374; 5,714,586; 5,739,116; 5,767,285; 5,770,701; 5,770,710; 5,773,001; and 5,877,296. Structural analogues of calicheamicin which may be used include, but are not limited to, $\gamma_1^1$, $\alpha_2^1$, $\alpha_3^1$, N-acetyl-$\gamma_1^1$, PSAG and $\theta_1^1$ (Hinman et al., Cancer Research 53:3336-3342 (1993), Lode et al., Cancer Research 58:2925-2928 (1998) and the aforementioned U.S. Pat. Nos. 5,712,374; 5,714,586; 5,739,116; 5,767,285; 5,770,701; 5,770,710; 5,773,001; and 5,877,296). Thus, in one embodiment, the anti-B7-H3 antibody of the invention is conjugated to at least one calicheamicin.

d. Duocarmycins

Anti-B7-H3 antibodies of the invention may be conjugated to at least one duocarmycin. Duocarmycins are a subclass of antitumor antibiotics isolated from bacteria of the genus *Streptomyces*. (see Nagamura and Saito (1998) Chemistry of *Heterocyclic Compounds*, Vol. 34, No. 12). Duocarmycins bind to the minor groove of DNA and alkylate the nucleobase adenine at the N3 position (Boger (1993) *Pure and Appl Chem* 65(6): 1123; and Boger and Johnson (1995) *PNAS USA* 92:3642). Synthetic analogs of duocarmycins include, but are not limited to, adozelesin, bizelesin, and carzelesin. Thus, in one embodiment, the anti-B7-H3 antibody of the invention is conjugated to at least one duocarmycin.

e. Other Antitumor Antibiotics

In addition to the foregoing, additional antitumor antibiotics that may be used in the anti-B7-H3 ADCs of the invention include bleomycin (Blenoxane, Bristol-Myers Squibb), mitomycin, and plicamycin (also known as mithramycin).

3. Immunomodulating Agents

In one aspect, anti-B7-H3 antibodies of the invention may be conjugated to at least one immunomodulating agent. As used herein, the term "immunomodulating agent" refers to an agent that can stimulate or modify an immune response. In one embodiment, an immunomodulating agent is an immunostimulator that enhances a subject's immune response. In another embodiment, an immunomodulating agent is an immunosuppressant that prevents or decreases a subject's immune response. An immunomodulating agent may modulate myeloid cells (monocytes, macrophages, dendritic cells, megakaryocytes and granulocytes) or lymphoid cells (T cells, B cells and natural killer (NK) cells) and any further differentiated cell thereof. Representative examples include, but are not limited to, *bacillus* calmette-guerin (BCG) and levamisole (Ergamisol). Other examples of immunomodulating agents that may be used in the ADCs of the invention include, but are not limited to, cancer vaccines, cytokines, and immunomodulating gene therapy.

a. Cancer Vaccines

Anti-B7-H3 antibodies of the invention may be conjugated to a cancer vaccine. As used herein, the term "cancer vaccine" refers to a composition (e.g., a tumor antigen and a cytokine) that elicits a tumor-specific immune response. The response is elicited from the subject's own immune system by administering the cancer vaccine, or, in the case of the instant invention, administering an ADC comprising an anti-B7-H3 antibody and a cancer vaccine. In preferred embodiments, the immune response results in the eradication of tumor cells in the body (e.g., primary or metastatic tumor cells). The use of cancer vaccines generally involves the administration of a particular antigen or group of antigens that are, for example, present on the surface a particular cancer cell, or present on the surface of a particular infectious agent shown to facilitate cancer formation. In some embodiments, the use of cancer vaccines is for prophylactic purposes, while in other embodiments, the use is for therapeutic purposes. Non-limiting examples of cancer vaccines that may be used in the anti-B7-H3 ADCs of the invention include, recombinant bivalent human papillomavirus (HPV) vaccine types 16 and 18 vaccine (Cervarix, GlaxoSmithKline), recombinant quadrivalent human papillomavirus (HPV) types 6, 11, 16, and 18 vaccine (Gardasil, Merck & Company), and sipuleucel-(Provenge, Dendreon). Thus, in one embodiment, the anti-B7-H3 antibody of the invention is conjugated to at least one cancer vaccine that is either an immunostimulator or is an immunosuppressant.

b. Cytokines

The anti-B7-H3 antibodies of the invention may be conjugated to at least one cytokine. The term "cytokine" generally refers to proteins released by one cell population which act on another cell as intercellular mediators. Cytokines directly stimulate immune effector cells and stromal cells at the tumor site and enhance tumor cell recognition by cytotoxic effector cells (Lee and Margolin (2011) *Cancers* 3:3856). Numerous animal tumor model studies have demonstrated that cytokines have broad anti-tumor activity and this has been translated into a number of cytokine-based approaches for cancer therapy (Lee and Margoli, supra). Recent years have seen a number of cytokines, including GM-CSF, IL-7, IL-12, IL-15, IL-18 and IL-21, enter clinical trials for patients with advanced cancer (Lee and Margoli, supra).

Examples of cytokines that may be used in the ADCs of the invention include, but are not limited to, parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor; mullerian-inhibiting substance; mouse gonadotropin-associated peptide; inhibin; activin; vascular endothelial growth factor; integrin; thrombopoietin (TPO); nerve growth factors such as NGF; platelet-growth factor; transforming growth factors (TGFs); insulin-like growth factor-I and -II; erythropoietin (EPO); osteoinductive factors; interferons such as interferon α, β, and γ, colony stimulating factors (CSFs); granulocyte-macrophage-C-SF (GM-CSF); and granulocyte-CSF (G-CSF); interleukins (ILs) such as IL-1, IL-1α, IL-2, IL-3, IL-4, IL-5, IL-6, IL-7, IL-8, IL-9, IL-11, IL-12; tumor necrosis factor; and other polypeptide factors including LIF and kit ligand (KL). As used herein, the term cytokine includes proteins from natural sources or from recombinant cell culture and biologically active equivalents of the native sequence cytokines. Thus, in one embodiment, the invention provides an ADC comprising an anti-B7-H3 antibody described herein and a cytokine.

c. Colony-Stimulating Factors (CSFs)

The anti-B7-H3 antibodies of the invention may be conjugated to at least one colony stimulating factor (CSF). Colony stimulating factors (CSFs) are growth factors that assist the bone marrow in making white blood cells. Some cancer treatments (e.g., chemotherapy) can affect white blood cells (which help fight infection); therefore, colony-stimulating factors may be introduced to help support white blood cell levels and strengthen the immune system. Colony-stimulating factors may also be used following a bone marrow transplant to help the new marrow start producing white blood cells. Representative examples of CSFs that may be used in the anti-B7-H3 ADCs of the invention include, but are not limited to erythropoietin (Epoetin), filgrastim (Neopogen (also known as granulocyte colony-stimulating factor (G-CSF); Amgen, Inc.), sargramostim (leukine (granulocyte-macrophage colony-stimulating factor and GM-CSF); Genzyme Corporation), promegapoietin, and Oprelvekin (recombinant IL-11; Pfizer, Inc.). Thus, in one embodiment, the invention provides an ADC comprising an anti-B7-H3 antibody described herein and a CSF.

4. Gene Therapy

The anti-B7-H3 antibody of the invention may be conjugated to at least one nucleic acid (directly or indirectly via a carrier) for gene therapy. Gene therapy generally refers to the introduction of genetic material into a cell whereby the genetic material is designed to treat a disease. As it pertains to immunomodulatory agents, gene therapy is used to stimulate a subject's natural ability to inhibit cancer cell proliferation or kill cancer cells. In one embodiment, the anti-B7-H3 ADC of the invention comprises a nucleic acid encoding a functional, therapeutic gene that is used to replace a mutated or otherwise dysfunctional (e.g. truncated) gene associated with cancer. In other embodiments, the anti-B7-H3 ADC of the invention comprises a nucleic acid that encodes for or otherwise provides for the production of a therapeutic protein to treat cancer. The nucleic acid that encodes the therapeutic gene may be directly conjugated to the anti-B7-H3 antibody, or alternatively, may be conjugated to the anti-B7-H3 antibody through a carrier. Examples of carriers that may be used to deliver a nucleic acid for gene therapy include, but are not limited to, viral vectors or liposomes.

5. Alkylating Agents

The anti-B7-H3 antibodies of the invention may be conjugated to one or more alkylating agent(s). Alkylating agents are a class of antineoplastic compounds that attaches an alkyl group to DNA. Examples of alkylating agents that may be used in the ADCs of the invention include, but are not limited to, alkyl sulfonates, ethylenimimes, methylamine derivatives, epoxides, nitrogen mustards, nitrosoureas, triazines, and hydrazines.

a. Alkyl Sulfonates

The anti-B7-H3 antibodies of the invention may be conjugated to at least one alkyl sulfonate. Alkyl sulfonates are a subclass of alkylating agents with a general formula: $R—SO_2—O—R^1$, wherein R and $R^1$ are typically alkyl or aryl groups. A representative example of an alkyl sulfonate includes, but is not limited to, busulfan (Myleran, GlaxoSmithKline; Busulfex IV, PDL BioPharma, Inc.).

b. Nitrogen Mustards

The anti-B7-H3 antibodies of the invention may be conjugated to at least one nitrogen mustard. Representative examples of this subclass of anti-cancer compounds include, but are not limited to chlorambucil (Leukeran, GlaxoSmithKline), cyclophosphamide (Cytoxan, Bristol-Myers Squibb; Neosar, Pfizer, Inc.), estramustine (estramustine phosphate sodium or Estracyt), Pfizer, Inc.), ifosfamide (Ifex, Bristol- Myers Squibb), mechlorethamine (Mustargen, Lundbeck Inc.), and melphalan (Alkeran or L-Pam or phenylalanine mustard; GlaxoSmithKline).

c. Nitrosoureas

The anti-B7-H3 antibody of the invention may be conjugated to at least one nitrosourea. Nitrosoureas are a subclass of alkylating agents that are lipid soluble. Representative examples include, but are not limited to, carmustine (BCNU [also known as BiCNU, N,N-Bis(2-chloroethyl)-N-nitrosourea, or 1,3-bis (2-chloroethyl)-1-nitrosourea], Bristol-Myers Squibb), fotemustine (also known as Muphoran), lomustine (CCNU or 1-(2-chloro-ethyl)-3-cyclohexyl-1-nitrosourea, Bristol-Myers Squibb), nimustine (also known as ACNU), and streptozocin (Zanosar, Teva Pharmaceuticals).

d. Triazines and Hydrazines

The anti-B7-H3 antibody of the invention may be conjugated to at least one triazine or hydrazine. Triazines and hydrazines are a subclass of nitrogen-containing alkylating agents. In some embodiments, these compounds spontaneously decompose or can be metabolized to produce alkyl diazonium intermediates that facilitate the transfer of an alkyl group to nucleic acids, peptides, and/or polypeptides, thereby causing mutagenic, carcinogenic, or cytotoxic effects. Representative examples include, but are not limited to dacarbazine (DTIC-Dome, Bayer Healthcare Pharmaceuticals Inc.), procarbazine (Mutalane, Sigma-Tau Pharmaceuticals, Inc.), and temozolomide (Temodar, Schering Plough).

e. Other Alkylating Agents

The anti-B7-H3 antibodies of the invention may be conjugated to at least one ethylenimine, methylamine derivative, or epoxide. Ethylenimines are a subclass of alkylating agents that typically containing at least one aziridine ring. Epoxides represent a subclass of alkylating agents that are characterized as cyclic ethers with only three ring atoms.

Representatives examples of ethylenimines include, but are not limited to thiopeta (Thioplex, Amgen), diaziquone (also known as aziridinyl benzoquinone (AZQ)), and mitomycin C. Mitomycin C is a natural product that contains an aziridine ring and appears to induce cytoxicity through cross-linking DNA (Dorr R T, et al. *Cancer Res.* 1985; 45:3510; Kennedy K A, et al *Cancer Res.* 1985; 45:3541). Representative examples of methylamine derivatives and their analogs include, but are not limited to, altretamine (Hexalen, MGI Pharma, Inc.), which is also known as hexamethylamine and hexastat. Representative examples of epoxides of this class of anti-cancer compound include, but are not limited to dianhydrogalactitol. Dianhydrogalactitol (1,2:5,6-dianhydrodulcitol) is chemically related to the aziridines and generally facilitate the transfer of an alkyl group through a similar mechanism as described above. Dibromodulcitol is hydrolyzed to dianhydrogalactitol and thus is a pro-drug to an epoxide (Sellei C, et al. *Cancer Chemother Rep.* 1969; 53:377).

6. Antiangiogenic Agents

In one aspect, the anti-B7-H3 antibodies described herein are conjugated to at least one antiangiogenic agent. Antiangiogenic agents inhibit the growth of new blood vessels. Antiangiogenic agents exert their effects in a variety of ways. In some embodiments, these agents interfere with the ability of a growth factor to reach its target. For example, vascular endothelial growth factor (VEGF) is one of the primary proteins involved in initiating angiogenesis by binding to particular receptors on a cell surface. Thus, certain antiangiogenic agents, that prevent the interaction of VEGF with its cognate receptor, prevent VEGF from initiating angiogenesis. In other embodiments, these agents interfere with intracellular signaling cascades. For example, once a particular receptor on a cell surface has been triggered, a cascade of other chemical signals is initiated to promote the growth of blood vessels. Thus, certain enzymes, for example, some tyrosine kinases, that are known to facilitate intracellular signaling cascades that contribute to, for example, cell proliferation, are targets for cancer treatment. In other embodiments, these agents interfere with intercellular signaling cascades. Yet, in other embodiments, these agents disable specific targets that activate and promote cell growth or by directly interfering with the growth of blood vessel cells. Angiogenesis inhibitory properties have been discovered in more than 300 substances with numerous direct and indirect inhibitory effects.

Representative examples of antiangiogenic agents that may be used in the ADCs of the invention include, but are not limited to, angiostatin, ABX EGF, C1-1033, PKI-166, EGF vaccine, EKB-569, GW2016, ICR-62, EMD 55900, CP358, PD153035, AG1478, IMC-C225 (Erbitux, ZD1839 (Iressa), OSI-774, Erlotinib (tarceva), angiostatin, arrestin, endostatin, BAY 12-9566 and w/fluorouracil or doxorubicin, canstatin, carboxyamidotriozole and with paclitaxel, EMD121974, S-24, vitaxin, dimethylxanthenone acetic acid, IM862, Interleukin-12, Interleukin-2, NM-3, HuMV833, PTK787, RhuMab, angiozyme (ribozyme), IMC-1C11, Neovastat, marimstat, prinomastat, BMS-275291, COL-3, MM1270, SU101, SU6668, SU11248, SU5416, with paclitaxel, with gemcitabine and cisplatin, and with irinotecan and cisplatin and with radiation, tecogalan, temozolomide and PEG interferon c2b, tetrathiomolybdate, TNP-470, thalidomide, CC-5013 and with taxotere, tumstatin, 2-methoxyestradiol, VEGF trap, mTOR inhibitors (deforolimus, everolimus (Afinitor, Novartis Pharmaceutical Corporation), and temsirolimus (Torisel, Pfizer, Inc.)), kinase inhibitors (e.g., erlotinib (Tarceva, Genentech, Inc.), imatinib (Gleevec, Novartis Pharmaceutical Corporation), gefitinib (Iressa, AstraZeneca Pharmaceuticals), dasatinib (Sprycel, Brystol-Myers Squibb), sunitinib (Sutent, Pfizer, Inc.), nilotinib (Tasigna, Novartis Pharmaceutical Corporation), lapatinib (Tykerb, GlaxoSmithKline Pharmaceuticals), sorafenib (Nexavar, Bayer and Onyx), phosphoinositide 3-kinases (PI3K), Osimertinib, Cobimetinib, Trametinib, Dabrafenib, Dinaciclib).

7. Antimetabolites

The anti-B7-H3 antibodies of the invention may be conjugated to at least one antimetabolite. Antimetabolites are types of chemotherapy treatments that are very similar to normal substances within the cell. When the cells incorporate an antimetabolite into the cellular metabolism, the result is negative for the cell, e.g., the cell is unable to divide. Antimetabolites are classified according to the substances with which they interfere. Examples of antimetabolites that may be used in the ADCs of the invention include, but are not limited to, a folic acid antagonist (e.g., methotrexate), a pyrimidine antagonist (e.g., 5-Fluorouracil, Foxuridine, Cytarabine, Capecitabine, and Gemcitabine), a purine antagonist (e.g., 6-Mercaptopurine and 6-Thioguanine) and an adenosine deaminase inhibitor (e.g., Cladribine, Fludarabine, Nelarabine and Pentostatin), as described in more detail below.

a. Antifolates

The anti-B7-H3 antibodies of the invention may be conjugated to at least one antifolate. Antifolates are a subclass of antimetabolites that are structurally similar to folate. Representative examples include, but are not limited to, methotrexate, 4-amino-folic acid (also known as aminopterin and 4-aminopteroic acid), lometrexol (LMTX), pemetrexed (Alimpta, Eli Lilly and Company), and trimetrexate (Neutrexin, Ben Venue Laboratories, Inc.)

b. Purine Antagonists

The anti-B7-H3 antibodies of the invention may be conjugated to at least one purine antagonist. Purine analogs are a subclass of antimetabolites that are structurally similar to the group of compounds known as purines. Representative examples of purine antagonists include, but are not limited to, azathioprine (Azasan, Salix; Imuran, GlaxoSmithKline), cladribine (Leustatin [also known as 2-CdA], Janssen Biotech, Inc.), mercaptopurine (Purinethol [also known as 6-mercaptoethanol], GlaxoSmithKline), fludarabine (Fludara, Genzyme Corporation), pentostatin (Nipent, also known as 2'-deoxycoformycin (DCF)), 6-thioguanine (Lanvis [also known as thioguanine], GlaxoSmithKline).

c. Pyrimidine Antagonists

The anti-B7-H3 antibodies of the invention may be conjugated to at least one pyrimidine antagonist. Pyrimidine antagonists are a subclass of antimetabolites that are structurally similar to the group of compounds known as purines. Representative examples of pyrimidine antagonists include, but are not limited to azacitidine (Vidaza, Celgene Corporation), capecitabine (Xeloda, Roche Laboratories), Cytarabine (also known as cytosine arabinoside and arabinosylcytosine, Bedford Laboratories), decitabine (Dacogen, Eisai Pharmaceuticals), 5-fluorouracil (Adrucil, Teva Pharmaceuticals; Efudex, Valeant Pharmaceuticals, Inc), 5-fluoro-2'-deoxyuridine 5'-phosphate (FdUMP), 5-fluorouridine triphosphate, and gemcitabine (Gemzar, Eli Lilly and Company).

8. Boron-Containing Agents

The anti-B7-H3 antibody of the invention may be conjugated to at least one boron containing agent. Boron-containing agents comprise a class of cancer therapeutic compounds which interfere with cell proliferation. Representative examples of boron containing agents include, but are not limited, to borophycin and bortezomib (Velcade, Millenium Pharmaceuticals).

9. Chemoprotective Agents

The anti-B7-H3 antibodies of the invention may be conjugated to at least one chemoprotective agent. Chemoprotective drugs are a class of compounds, which help protect the body against specific toxic effects of chemotherapy. Chemoprotective agents may be administered with various chemotherapies in order to protect healthy cells from the toxic effects of chemotherapy drugs, while simultaneously allowing the cancer cells to be treated with the administered chemotherapeutic. Representative chemoprotective agents include, but are not limited to amifostine (Ethyol, Medimmune, Inc.), which is used to reduce renal toxicity associated with cumulative doses of cisplatin, dexrazoxane (Totect, Apricus Pharma; Zinecard), for the treatment of extravasation caused by the administration of anthracycline (Totect), and for the treatment of cardiac-related complications caused by the administration of the antitumor antibiotic doxorubicin (Zinecard), and mesna (Mesnex, Bristol-Myers Squibb), which is used to prevent hemorrhagic cystitis during chemotherapy treatment with ifocfamide.

10. Hormone Agents

The anti-B7-H3 antibody of the invention may be conjugated to at least one hormone agent. A hormone agent (including synthetic hormones) is a compound that interferes with the production or activity of endogenously produced hormones of the endocrine system. In some embodiments, these compounds interfere with cell growth or produce a cytotoxic effect. Non-limiting examples include androgens, estrogens, medroxyprogesterone acetate (Provera, Pfizer, Inc.), and progestins.

11. Antihormone Agents

The anti-B7-H3 antibodies of the invention may be conjugated to at least one antihormone agent. An "antihormone" agent is an agent that suppresses the production of and/or prevents the function of certain endogenous hormones. In one embodiment, the antihormone agent interferes with the activity of a hormone selected from the group comprising androgens, estrogens, progesterone, and goanadotropin-releasing hormone, thereby interfering with the growth of various cancer cells. Representative examples of antihormone agents include, but are not limited to, aminoglutethimide, anastrozole (Arimidex, AstraZeneca Pharmaceuticals), bicalutamide (Casodex, AstraZeneca Pharmaceuticals), cyproterone acetate (Cyprostat, Bayer PLC), degarelix (Firmagon, Ferring Pharmaceuticals), exemestane (Aromasin, Pfizer Inc.), flutamide (Drogenil, Schering-Plough Ltd), fulvestrant (Faslodex, AstraZeneca Pharmaceuticals), goserelin (Zolodex, AstraZeneca Pharmaceuticals), letrozole (Femara, Novartis Pharmaceuticals Corporation), leuprolide (Prostap), lupron, medroxyprogesterone acetate (Provera, Pfizer Inc.), Megestrol acetate (Megace, Bristol-Myers Squibb Company), tamoxifen (Nolvadex, AstraZeneca Pharmaceuticals), and triptorelin (Decapetyl, Ferring).

12. Corticosteroids

The anti-B7-H3 antibodies of the invention may be conjugated to at least one corticosteroid. Corticosteroids may be used in the ADCs of the invention to decrease inflammation. An example of a corticosteroid includes, but is not limited to, a glucocorticoid, for example, prednisone (Deltasone, Pharmacia & Upjohn Company, a division of Pfizer, Inc.).

13. Photoactive Therapeutic Agents

The anti-B7-H3 antibodies of the invention may be conjugated to at least one photoactive therapeutic agent. Photoactive therapeutic agents include compounds that can be deployed to kill treated cells upon exposure to electromagnetic radiation of a particular wavelength. Therapeutically relevant compounds absorb electromagnetic radiation at wavelengths which penetrate tissue. In preferred embodiments, the compound is administered in a non-toxic form that is capable of producing a photochemical effect that is toxic to cells or tissue upon sufficient activation. In other preferred embodiments, these compounds are retained by cancerous tissue and are readily cleared from normal tissues. Non-limiting examples include various chromagens and dyes.

14. Oligonucleotides

The anti-B7-H3 antibodies of the invention may be conjugated to at least one oligonucleotide. Oligonucleotides are made of short nucleic acid chains that work by interfering with the processing of genetic information. In some embodiments, the oligonucleotides for use in ADCs are unmodified single-stranded and/or double-stranded DNA or RNA molecules, while in other embodiments, these therapeutic oligonucleotides are chemically-modified single-stranded and/or double-stranded DNA or RNA molecules. In one embodiment, the oligonulceotides used in the ADCs are relatively short (19-25 nucleotides) and hybridize to a unique nucleic acid sequence in the total pool of nucleic acid targets present in cells. Some of the important oligonucleotide technologies include the antisense oligonucleotides (including RNA interference (RNAi)), aptamers, CpG oligonucleotides, and ribozymes.

a. Antisense Oligonucleotides

The anti-B7-H3 antibody of the invention may be conjugated to at least one antisense oligonucleotide. Antisense oligonucleotides are designed to bind to RNA through Watson-Crick hybridization. In some embodiments the antisense oligonucleotide is complementary to a nucleotide encoding a region, domain, portion, or segment of B7-H3. In some embodiments, the antisense oligonucleotide comprises from about 5 to about 100 nucleotides, from about 10 to about 50 nucleotides, from about 12 to about 35, and from about 18 to about 25 nucleotides. In some embodiments, the oligonucleotide is at least 50%, at least 60%, at least 70%, at least 80%, at least 90%, at least 95%, at least 96%, at least 97%, at least 98%, at least 99%, or at least 100% homologous to a region, portion, domain, or segment of the B7-H3 gene. In some embodiments there is substantial sequence homology over at least 15, 20, 25, 30, 35, 40, 50, or 100 consecutive nucleotides of the B7-H3 gene. In preferred embodiments, the size of these antisense oligonucleotides ranges from 12 to 25 nucleotides in length, with the majority of antisense oligonucleotides being 18 to 21 nucleotides in length. There are multiple mechanisms that can be exploited to inhibit the function of the RNA once the oligonucleotide binds to the target RNA (Crooke S T. (1999). *Biochim. Biophys. Acta,* 1489, 30-42). The best-characterized antisense mechanism results in cleavage of the targeted RNA by endogenous cellular nucleases, such as RNase H or the nuclease associated with the RNA interference mechanism. However, oligonucleotides that inhibit expression of the target gene by non-catalytic mechanisms, such as modulation of splicing or translation arrest, can also be potent and selective modulators of gene function.

Another RNase-dependent antisense mechanism that has recently received much attention is RNAi (Fire et al. (1998). *Nature,* 391, 806-811; Zamore P D. (2002). *Science,* 296, 1265-1269). RNA interference (RNAi) is a post-transcriptional process where a double stranded RNA inhibits gene expression in a sequence specific fashion. In some embodiments, the RNAi effect is achieved through the introduction of relatively longer double-stranded RNA (dsRNA), while in preferred embodiments, this RNAi effect is achieved by the introduction of shorter double-stranded RNAs, e.g. small interfering RNA (siRNA) and/or microRNA (miRNA). In yet another embodiment, RNAi can also be achieved by introducing of plasmid that generate dsRNA complementary to target gene. In each of the foregoing embodiments, the double-stranded RNA is designed to interfere with the gene expression of a particular the target sequence within cells. Generally, the mechanism involves conversion of dsRNA into short RNAs that direct ribonucleases to homologous mRNA targets (summarized, Ruvkun, Science 2294:797 (2001)), which then degrades the corresponding endogenous mRNA, thereby resulting in the modulation of gene expression. Notably, dsRNA has been reported to have antiproliferative properties, which makes it possible also to envisage therapeutic applications (Aubel et al., *Proc. Natl. Acad. Sci.,* USA 88:906 (1991)). For example, synthetic dsRNA has been shown to inhibit tumor growth in mice (Levy et al. *Proc. Nat. Acad. Sci. USA,* 62:357-361 (1969)), is active in the treatment of leukemic mice (Zeleznick et al., *Proc. Soc. Exp. Biol. Med.* 130:126-128 (1969)), and inhibits chemically induced tumorigenesis in mouse skin (Gelboin et al., *Science* 167:205-207 (1970)). Thus, in a preferred embodiment, the invention provides for the use of antisense oligonucleotides in ADCs for the treatment of breast cancer. In other embodiments, the invention provides compositions and methods for initiating antisense oligonucleotide treatment, wherein dsRNA interferes with target cell expression of B7-H3 at the mRNA level. dsRNA, as used above, refers to naturally-occurring RNA, partially purified RNA, recombinantly produced RNA, synthetic RNA, as well as altered RNA that differs from naturally-occurring RNA by the inclusion of non-standard nucleotides, non-nucleotide material, nucleotide analogs (e.g. locked nucleic acid (LNA)), deoxyribonucleotides, and any combination thereof. RNA of the invention need only be sufficiently similar to natural RNA that it has the ability to mediate the antisense oligonucleotide-based modulation described herein.

b. Aptamers

The anti-B7-H3 antibodies of the invention may be conjugated to at least one aptamer. An aptamer is a nucleic acid molecule that has been selected from random pools based on its ability to bind other molecules. Like antibodies, aptamers can bind target molecules with extraordinary affinity and specificity. In many embodiments, aptamers assume complex, sequence-dependent, three-dimensional shapes that allow them to interact with a target protein, resulting in a tightly bound complex analogous to an antibody-antigen interaction, thereby interfering with the function of said protein. The particular capacity of aptamers to bind tightly and specifically to their target protein underlines their potential as targeted molecular therapies.

c. CpG oligonucleotides

The anti-B7-H3 antibodies of the invention may be conjugated to at least one CpG oligonucleotide. Bacterial and viral DNA are known to be a strong activators of both the innate and specific immunity in humans. These immunologic characteristics have been associated with unmethylated CpG dinucleotide motifs found in bacterial DNA. Owing to the fact that these motifs are rare in humans, the human immune system has evolved the ability to recognize these motifs as an early indication of infection and subsequently initiate immune responses. Therefore, oligonucleotides containing this CpG motif can be exploited to initiate an antitumor immune response.

d. Ribozymes

The anti-B7-H3 antibody of the invention may be conjugated to at least one ribozyme. Ribozymes are catalytic RNA molecules ranging from about 40 to 155 nucleotides in length. The ability of ribozymes to recognize and cut specific RNA molecules makes them potential candidates for therapeutics. A representative example includes angiozyme.

15. Radionuclide Agents (Radioactive Isotopes)

The anti-B7-H3 antibodies of the invention may be conjugated to at least one radionuclide agent. Radionuclide agents comprise agents that are characterized by an unstable nucleus that is capable of undergoing radioactive decay. The basis for successful radionuclide treatment depends on sufficient concentration and prolonged retention of the radionuclide by the cancer cell. Other factors to consider include the radionuclide half-life, the energy of the emitted particles, and the maximum range that the emitted particle can travel. In preferred embodiments, the therapeutic agent is a radionuclide selected from the group consisting of $^{111}$In, $^{177}$Lu, $^{212}$Bi, $^{213}$Bi, $^{211}$At, $^{62}$Cu, $^{64}$Cu, $^{67}$Cu, $^{90}$Y, $^{125}$I, $^{131}$I, $^{32}$P, $^{33}$P, $^{47}$Sc, $^{111}$Ag, $^{67}$Ga, $^{142}$Pr, $^{153}$Sm, $^{161}$Tb, $^{166}$Dy, $^{166}$Ho, $^{186}$Re, $^{188}$Re, $^{189}$Re, $^{212}$Pb, $^{223}$Ra, $^{225}$Ac, $^{59}$Fe, $^{75}$Se, $^{77}$As, $^{89}$Sr, $^{99}$Mo, $^{105}$Rh, $^{109}$Pd, $^{143}$Pr, $^{149}$Pm, $^{169}$Er, $^{194}$Ir, $^{198}$Au, $^{199}$Au, and $^{211}$Pb. Also preferred are radionuclides that substantially decay with Auger-emitting particles. For example, Co-58, Ga-67, Br-80m, Tc-99m, Rh-103m, Pt-109, In-111 1, Sb-119, 1-125, Ho-161, Os-189m and Ir-192. Decay energies of useful beta-particle-emitting nuclides are preferably Dy-152, At-211, Bi-212, Ra-223, Rn-219, Po-215, Bi-21 1, Ac-225, Fr-221, At-217, Bi-213 and Fm-255. Decay energies of useful alpha-particle-emitting radionuclides are preferably 2,000-10,000 keV, more preferably 3,000-8,000 keV, and most preferably 4,000-7,000 keV. Additional potential radioisotopes of use include $^{11}$C, $^{13}$N, $^{15}$O, $^{75}$Br, $^{198}$Au, $^{224}$Ac, $^{126}$I, $^{133}$I, $^{77}$Br, $^{113}$In, $^{95}$Ru, $^{97}$Ru, $^{103}$Ru, $^{105}$Ru, $^{107}$Hg, $^{203}$Hg, $^{121m}$Te, $^{122m}$Te, $^{125m}$Te, $^{165}$Tm, $^{167}$Tm, $^{168}$Tm, $^{197}$Pt, $^{109}$Pd, $^{105}$Rh, $^{142}$Pr, $^{143}$Pr, $^{161}$Tb, $^{166}$Ho, $^{199}$Au, $^{57}$Co, $^{58}$Co, $^{51}$Cr, $^{59}$Fe, $^{75}$Se, $^{201}$Tl, $^{225}$Ac, $^{76}$Br, $^{169}$Yb, and the like.

16. Radiosensitizers

The anti-B7-H3 antibodies of the invention may be conjugated to at least one radiosensitizer. The term "radiosensitizer," as used herein, is defined as a molecule, preferably a low molecular weight molecule, administered to animals in therapeutically effective amounts to increase the sensitivity of the cells to be radiosensitized to electromagnetic radiation and/or to promote the treatment of diseases that are treatable with electromagnetic radiation. Radiosensitizers are agents that make cancer cells more sensitive to radiation therapy, while typically having much less of an effect on normal cells. Thus, the radiosensitizer can be used in combination with a radiolabeled antibody or ADC. The addition of the radiosensitizer can result in enhanced efficacy when compared to treatment with the radiolabeled antibody or antibody fragment alone. Radiosensitizers are described in D. M. Goldberg (ed.), Cancer Therapy with Radiolabeled Antibodies, CRC Press (1995). Examples of radiosensitizers include gemcitabine, 5-fluorouracil, taxane, and cisplatin.

Radiosensitizers may be activated by the electromagnetic radiation of X-rays. Representative examples of X-ray activated radiosensitizers include, but are not limited to, the following: metronidazole, misonidazole, desmethylmisonidazole, pimonidazole, etanidazole, nimorazole, mitomycin C, RSU 1069, SR 4233, E09, RB 6145, nicotinamide, 5-bromodeoxyuridine (BUdR), 5-iododeoxyuridine (IUdR), bromodeoxycytidine, fluorodeoxyuridine (FUdR), hydroxyurea, cisplatin, and therapeutically effective analogs and derivatives of the same. Alternatively, radiosensitizers may be activated using photodynamic therapy (PDT). Representative examples of photodynamic radiosensitizers include, but are not limited to, hematoporphyrin derivatives, Photofrin(r), benzoporphyrin derivatives, NPe6, tin etioporphyrin (SnET2), pheoborbide a, bacteriochlorophyll a, naphthalocyanines, phthalocyanines, zinc phthalocyanine, and therapeutically effective analogs and derivatives of the same.

16. Topoisomerase Inhibitors

The anti-B7-H3 antibodies of the invention may be conjugated to at least one topoisomerase inhibitor. Topoisomerase inhibitors are chemotherapy agents designed to interfere with the action of topoisomerase enzymes (topoisomerase I and II), which are enzymes that control the changes in DNA structure by catalyzing then breaking and rejoining of the phosphodiester backbone of DNA strands during the normal cell cycle. Representative examples of DNA topoisomerase I inhibitors include, but are not limited to, camptothecins and its derivatives irinotecan (CPT-11, Camptosar, Pfizer, Inc.) and topotecan (Hycamtin, GlaxoSmithKline Pharmaceuticals). Representative examples of DNA topoisomerase II inhibitors include, but are not limited to, amsacrine, daunorubicin, doxotrubicin, epipodophyllotoxins, ellipticines, epirubicin, etoposide, razoxane, and teniposide.

17. Kinase Inhibitors

The anti-B7-H3 antibodies of the invention may be conjugated to at least one kinase inhibitor.

By blocking the ability of protein kinases to function, tumor growth may be inhibited. Examples of kinase inhibitors that may be used in the ADCs of the invention include, but are not limited to, Axitinib, Bosutinib, Cediranib, Dasatinib, Erlotinib, Gefitinib, Imatinib, Lapatinib, Lestaurtinib, Nilotinib, Semaxanib, Sunitinib, Osimertinib, Cobimetinib, Trametinib, Dabrafenib, Dinaciclib, and Vandetanib.

18. Other Agents

Examples of other agents that may be used in the ADCs of the invention include, but are not limited to, abrin (e.g. abrin A chain), alpha toxin, *Aleurites fordii* proteins, amatoxin, crotin, curcin, dianthin proteins, diptheria toxin (e.g. diphtheria A chain and nonbinding active fragments of diphtheria toxin), deoxyribonuclease (Dnase), gelonin, mitogellin, modeccin A chain, *Momordica charantia* inhibitor, neomycin, onconase, phenomycin, *Phytolaca americana* proteins (PAPI, PAPII, and PAP-S), pokeweed antiviral protein, *Pseudomonas* endotoxin, *Pseudomonas* exotoxin (e.g. exotoxin A chain (from *Pseudomonas aeruginosa*)), restrictocin, ricin A chain, ribonuclease (Rnase), *Sapaonaria officinalis* inhibitor, saporin, alpha-sarcin, Staphylcoccal enterotoxin-A, tetanus toxin, cisplatin, carboplatin, and oxaliplatin (Eloxatin, Sanofi Aventis), proteasome inhibitors (e.g. PS-341 [bortezomib or Velcade]), HDAC inhibitors (vorinostat (Zolinza, Merck & Company, Inc.)), belinostat, entinostat, mocetinostat, and panobinostat), COX-2 inhibitors, substituted ureas, heat shock protein inhibitors (e.g. Geldanamycin and its numerous analogs), adrenocortical suppressants, and the tricothecenes. (See, for example, WO 93/21232). Other agents also include asparaginase (Espar, Lundbeck Inc.), hydroxyurea, levamisole, mitotane (Lysodren, Bristol-Myers Squibb), and tretinoin (Renova, Valeant Pharmaceuticals Inc.).

III.C. Anti-B7-H3 ADCs: Other Exemplary Linkers

In addition to the linkers mentioned above, other exemplary linkers include, but are not limited to, 6-maleimidocaproyl, maleimidopropanoyl ("MP"), valine-citrulline ("val-cit" or "vc"), alanine-phenylalanine ("ala-phe"), p-aminobenzyloxycarbonyl (a "PAB"), N-Succinimidyl 4-(2-pyridylthio)pentanoate ("SPP"), and 4-(N-maleimidomethyl)cyclohexane-1 carboxylate ("MCC").

In one aspect, an anti-B7-H3 antibody is conjugated to a drug, (such as auristatin, e.g., MMAE), via a linker comprising maleimidocaproyl ("mc"), valine citrulline (val-cit or "vc"), and PABA (referred to as a "mc-vc-PABA linker"). Maleimidocaproyl acts as a linker to the anti-B7-H3 antibody and is not cleavable. Val-cit is a dipeptide that is an amino acid unit of the linker and allows for cleavage of the linker by a protease, specifically the protease cathepsin B. Thus, the val-cit component of the linker provides a means for releasing the auristatin from the ADC upon exposure to the intracellular environment. Within the linker, p-aminobenzylalcohol (PABA) acts as a spacer and is self immolative, allowing for the release of the MMAE. The structure of the mc-vc-PABA-MMAE linker is provided in FIG. 3.

As described above, suitable linkers include, for example, cleavable and non-cleavable linkers. A linker may be a "cleavable linker," facilitating release of a drug. Nonlimiting exemplary cleavable linkers include acid-labile linkers (e.g., comprising hydrazone), protease-sensitive (e.g., peptidase-sensitive) linkers, photolabile linkers, or disulfide-containing linkers (Chari et al., Cancer Research 52:127-131 (1992); U.S. Pat. No. 5,208,020). A cleavable linker is typically susceptible to cleavage under intracellular conditions. Suitable cleavable linkers include, for example, a peptide linker cleavable by an intracellular protease, such as lysosomal protease or an endosomal protease. In exemplary embodiments, the linker can be a dipeptide linker, such as a valine-citrulline (val-cit) or a phenylalanine-lysine (phe-lys) linker.

Linkers are preferably stable extracellularly in a sufficient manner to be therapeutically effective. Before transport or delivery into a cell, the ADC is preferably stable and remains intact, i.e. the antibody remains conjugated to the drug moiety. Linkers that are stable outside the target cell may be cleaved at some efficacious rate once inside the cell. Thus, an effective linker will: (i) maintain the specific binding properties of the antibody; (ii) allow delivery, e.g., intracellular delivery, of the drug moiety; and (iii) maintain the therapeutic effect, e.g., cytotoxic effect, of a drug moiety.

In one embodiment, the linker is cleavable under intracellular conditions, such that cleavage of the linker sufficiently releases the drug from the antibody in the intracellular environment to be therapeutically effective. In some embodiments, the cleavable linker is pH-sensitive, i.e., sensitive to hydrolysis at certain pH values. Typically, the pH-sensitive linker is hydrolyzable under acidic conditions. For example, an acid-labile linker that is hydrolyzable in the lysosome (e.g., a hydrazone, semicarbazone, thiosemicarbazone, cis-aconitic amide, orthoester, acetal, ketal, or the like) can be used. (See, e.g., U.S. Pat. Nos. 5,122,368; 5,824,805; 5,622,929; Dubowchik and Walker, 1999, *Pharm. Therapeutics* 83:67-123; Neville et al., 1989, *Biol. Chem.* 264: 14653-14661.) Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, e.g., a thioether attached to the therapeutic agent via an acylhydrazone bond (see, e.g., U.S. Pat. No. 5,622,929).

In other embodiments, the linker is cleavable under reducing conditions (e.g., a disulfide linker). A variety of disulfide linkers are known in the art, including, for example, those that can be formed using SATA (N-succinimidyl-5-acetylthioacetate), SPDP (N-succinimidyl-3-(2-pyridyldithio)propionate), SPDB (N-succinimidyl-3-(2-pyridyldithio)butyrate) and SMPT (N-succinimidyloxycarbonyl-alpha-methyl-alpha-(2-pyridyl-dithio)toluene), SPDB and SMPT. (See, e.g., Thorpe et al., 1987, Cancer Res. 47:5924-5931; Wawrzynczak et al., In *Immunoconjugates: Antibody Conjugates in Radioimagery and Therapy of Cancer* (C. W. Vogel ed., Oxford U. Press, 1987. See also U.S. Pat. No. 4,880,935).

In some embodiments, the linker is cleavable by a cleaving agent, e.g., an enzyme, that is present in the intracellular environment (e.g., within a lysosome or endosome or caveolea). The linker can be, e.g., a peptidyl linker that is cleaved by an intracellular peptidase or protease enzyme, including, but not limited to, a lysosomal or endosomal protease. In some embodiments, the peptidyl linker is at least two amino acids long or at least three amino acids long. Cleaving agents can include cathepsins B and D and plasmin, all of which are known to hydrolyze dipeptide drug derivatives resulting in the release of active drug inside target cells (see, e.g., Dubowchik and Walker, 1999, Pharm. Therapeutics 83:67-123). Most typical are peptidyl linkers that are cleavable by enzymes that are present in B7-H3-expressing cells. Examples of such linkers are described, e.g., in U.S. Pat. No. 6,214,345, incorporated herein by reference in its entirety and for all purposes. In a specific embodiment, the peptidyl linker cleavable by an intracellular protease is a Val-Cit linker or a Phe-Lys linker (see, e.g., U.S. Pat. No. 6,214,345, which describes the synthesis of doxorubicin with the val-cit linker). One advantage of using intracellular proteolytic release of the therapeutic agent is that the agent is typically attenuated when conjugated and the serum stabilities of the conjugates are typically high.

In other embodiments, the linker is a malonate linker (Johnson et al., 1995, Anticancer Res. 15:1387-93), a maleimidobenzoyl linker (Lau et al., 1995, *Bioorg-Med-Chem.* 3(10):1299-1304), or a 3'-N-amide analog (Lau et al., 1995, *Bioorg-Med-Chem.* 3(10): 1305-12).

In yet other embodiments, the linker unit is not cleavable and the drug is released, for example, by antibody degradation. See U.S. Publication No. 20050238649 incorporated by reference herein in its entirety. An ADC comprising a non-cleavable linker may be designed such that the ADC remains substantially outside the cell and interacts with certain receptors on a target cell surface such that the binding of the ADC initiates (or prevents) a particular cellular signaling pathway.

In some embodiments, the linker is substantially hydrophilic linker (e.g., PEG4Mal and sulfo-SPDB). A hydrophilic linker may be used to reduce the extent to which the drug may be pumped out of resistant cancer cells through MDR (multiple drug resistance) or functionally similar transporters.

In other embodiments, upon cleavage, the linker functions to directly or indirectly inhibit cell growth and/or cell proliferation. For example, in some embodiments, the linker, upon cleavage, can function as an intercalating agent, thereby inhibiting macromolecular biosynthesis (e.g. DNA replication, RNA transcription, and/or protein synthesis).

In other embodiments, the linker is designed to facilitate bystander killing (the killing of neighboring cells) through diffusion of the linker-drug and/or the drug alone to neighboring cells. In other, embodiments, the linker promotes cellular internalization.

The presence of a sterically hindered disulfide can increase the stability of a particular disulfide bond, enhancing the potency of the ADC. Thus, in one embodiment, the linker includes a sterically hindered disulfide linkage. A sterically hindered disulfide refers to a disulfide bond present within a particular molecular environment, wherein the environment is characterized by a particular spatial arrangement or orientation of atoms, typically within the same molecule or compound, which prevents or at least partially inhibits the reduction of the disulfide bond. Thus, the presence of bulky (or sterically hindering) chemical moieties and/or bulky amino acid side chains proximal to the disulfide bond prevents or at least partially inhibits the disulfide bond from potential interactions that would result in the reduction of the disulfide bond.

Notably, the aforementioned linker types are not mutually exclusive. For example, in one embodiment, the linker used in the anti-B7-H3 ADCs described herein is a non-cleavable linker that promotes cellular internalization.

In some embodiments, a linker component comprises a "stretcher unit" that links an antibody to another linker component or to a drug moiety. An illustrative stretcher unit described in U.S. Pat. No. 8,309,093, incorporated by reference herein. In certain embodiments, the stretcher unit is linked to the anti-B7-H3 antibody via a disulfide bond between a sulfur atom of the anti-B7-H3 antibody unit and a sulfur atom of the stretcher unit. A representative stretcher unit of this embodiment is depicted in U.S. Pat. No. 8,309,093, incorporated by reference herein. In yet other embodiments, the stretcher contains a reactive site that can form a bond with a primary or secondary amino group of an antibody. Examples of these reactive sites include but are not limited to, activated esters such as succinimide esters, 4 nitrophenyl esters, pentafluorophenyl esters, tetrafluorophenyl esters, anhydrides, acid chlorides, sulfonyl chlorides, isocyanates and isothiocyanates. Representative stretcher units of this embodiment are depicted in U.S. Pat. No. 8,309,093, incorporated by reference herein.

In some embodiments, the stretcher contains a reactive site that is reactive to a modified carbohydrate's (—CHO) group that can be present on an antibody. For example, a carbohydrate can be mildly oxidized using a reagent such as sodium periodate and the resulting (—CHO) unit of the oxidized carbohydrate can be condensed with a Stretcher that contains a functionality such as a hydrazide, an oxime, a primary or secondary amine, a hydrazine, a thiosemicarbazone, a hydrazine carboxylate, and an arylhydrazide such as those described by Kaneko et al., 1991, *Bioconjugate Chem.* 2:133-41. Representative Stretcher units of this embodiment are depicted in U.S. Pat. No. 8,309,093, incorporated by reference herein.

In some embodiments, a linker component comprises an "amino acid unit". In some such embodiments, the amino acid unit allows for cleavage of the linker by a protease, thereby facilitating release of the drug from the immunoconjugate upon exposure to intracellular proteases, such as lysosomal enzymes (Doronina et al. (2003) *Nat. Biotechnol.* 21:778-784). Exemplary amino acid units include, but are not limited to, dipeptides, tripeptides, tetrapeptides, and pentapeptides. Exemplary dipeptides include, but are not limited to, valine-citrulline (vc or val-cit), alanine-phenylalanine (af or ala-phe); phenylalanine-lysine (fk or phe-lys); phenylalanine-homolysine (phe-homolys); and N-methyl-valine-citrulline (Me-val-cit). Exemplary tripeptides include, but are not limited to, glycine-valine-citrulline (gly-val-cit) and glycine-glycine-glycine (gly-gly-gly). An amino acid unit may comprise amino acid residues that occur naturally and/or minor amino acids and/or non-naturally occurring amino acid analogs, such as citrulline Amino acid units can be designed and optimized for enzymatic cleavage by a particular enzyme, for example, a tumor-associated protease, cathepsin B, C and D, or a plasmin protease.

In one embodiment, the amino acid unit is valine-citrulline (vc or val-cit). In another aspect, the amino acid unit is phenylalanine-lysine (i.e., fk). In yet another aspect of the amino acid unit, the amino acid unit is N-methylvaline-citrulline. In yet another aspect, the amino acid unit is 5-aminovaleric acid, homo phenylalanine lysine, tetraisoquinolinecarboxylate lysine, cyclohexylalanine lysine, isonepecotic acid lysine, beta-alanine lysine, glycine serine valine glutamine and isonepecotic acid.

Alternatively, in some embodiments, the amino acid unit is replaced by a glucuronide unit that links a stretcher unit to a spacer unit if the stretcher and spacer units are present, links a stretcher unit to the drug moiety if the spacer unit is absent, and links the linker unit to the drug if the stretcher and spacer units are absent. The glucuronide unit includes a site that can be cleaved by a β-glucuronidase enzyme (See also US 2012/0107332, incorporated by reference herein). In some embodiments, the glucuronide unit comprises a sugar moiety (Su) linked via a glycoside bond (—O'—) to a self-immolative group (Z) of the formula as depicted below (See also US 2012/0107332, incorporated by reference herein).

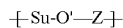

The glycosidic bond (—O'—) is typically a f-glucuronidase-cleavage site, such as a bond cleavable by human, lysosomal β-glucuronidase. In the context of a glucuronide unit, the term "self-immolative group" refers to a di- or tri-functional chemical moiety that is capable of covalently linking together two or three spaced chemical moieties (i.e., the sugar moiety (via a glycosidic bond), a drug moiety (directly or indirectly via a spacer unit), and, in some embodiments, a linker (directly or indirectly via a stretcher unit) into a stable molecule. The self-immolative group will spontaneously separate from the first chemical moiety (e.g., the spacer or drug unit) if its bond to the sugar moiety is cleaved.

In some embodiments, the sugar moiety (Su) is cyclic hexose, such as a pyranose, or a cyclic pentose, such as a furanose. In some embodiments, the pyranose is a glucuronide or hexose. The sugar moiety is usually in the β-D conformation. In a specific embodiment, the pyranose is a β-D-glucuronide moiety (i.e., β-D-glucuronic acid linked to the self-immolative group —Z— via a glycosidic bond that is cleavable by β-glucuronidase). In some embodiments, the sugar moiety is unsubstituted (e.g., a naturally occurring cyclic hexose or cyclic pentose). In other embodiments, the sugar moiety can be a substituted β-D-glucuronide (i.e., glucuronic acid substituted with one or more group, such as hydrogen, hydroxyl, halogen, sulfur, nitrogen or lower alkyl. In some embodiments, the glucuronide unit has one of the formulas as described in US 2012/0107332, incorporated by reference herein.

In some embodiments, the linker comprises a spacer unit (—Y—), which, when present, links an amino acid unit (or Glucuronide unit, see also US 2012/0107332, incorporated by reference herein) to the drug moiety when an amino acid unit is present. Alternately, the spacer unit links the stretcher unit to the drug moiety when the amino acid unit is absent. The spacer unit may also links the drug unit to the antibody unit when both the amino acid unit and stretcher unit are absent.

Spacer units are of two general types: non self-immolative or self-immolative. A non self-immolative spacer unit is one in which part or all of the spacer unit remains bound to the drug moiety after cleavage, particularly enzymatic, of an amino acid unit (or glucuronide unit) from the antibody-drug conjugate. Examples of a non self-immolative spacer unit include, but are not limited to a (glycine-glycine) spacer unit and a glycine spacer unit (see U.S. Pat. No. 8,309,093, incorporated by reference herein)). Other examples of self-immolative spacers include, but are not limited to, aromatic compounds that are electronically similar to the PAB group such as 2-aminoimidazol-5-methanol derivatives (Hay et al., 1999, Bioorg. Med. Chem. Lett. 9:2237) and ortho or para-aminobenzylacetals. Spacers can be used that undergo cyclization upon amide bond hydrolysis, such as substituted and unsubstituted 4-aminobutyric acid amides (Rodrigues et al., 1995, Chemistry Biology 2:223), appropriately substituted bicyclo[2.2.1] and bicyclo[2.2.2] ring systems (Storm et al., 1972, J. Amer. Chem. Soc. 94:5815) and 2-aminophenylpropionic acid amides (Amsberry et al., 1990, J. Org. Chem. 55:5867). Elimination of amine-containing drugs that are substituted at the α-position of glycine (Kingsbury et al., 1984, J. Med. Chem. 27:1447) are also examples of self-immolative spacers.

Other examples of self-immolative spacers include, but are not limited to, aromatic compounds that are electronically similar to the PAB group such as 2-aminoimidazol-5-methanol derivatives (see, e.g., Hay et al., 1999, *Bioorg. Med. Chem. Lett.* 9:2237) and ortho or para-aminobenzylacetals. Spacers can be used that undergo cyclization upon amide bond hydrolysis, such as substituted and unsubstituted 4-aminobutyric acid amides (see, e.g., Rodrigues et al., 1995, *Chemistry Biology* 2:223), appropriately substituted bicyclo[2.2.1] and bicyclo[2.2.2] ring systems (see, e.g., Storm et al., 1972, *J. Amer. Chem. Soc.* 94:5815) and 2-aminophenylpropionic acid amides (see, e.g., Amsberry et al., 1990, J. Org. Chem. 55:5867). Elimination of amine-containing drugs that are substituted at the a-position of glycine (see, e.g., Kingsbury et al., 1984, *J. Med. Chem.* 27:1447) are also examples of self-immolative spacers.

Other suitable spacer units are disclosed in Published U.S. Patent Application No. 2005-0238649, the disclosure of which is incorporated by reference herein.

Another approach for the generation of ADCs involves the use of heterobifunctional cross-linkers which link the anti-B7-H3 antibody to the drug moiety. Examples of cross-linkers that may be used include N-succinimidyl 4-(5-nitro-2-pyridyldithio)-pentanoate or the highly water-soluble analog N-sulfosuccinimidyl 4-(5-nitro-2-pyridyldithio)-pentanoate, N-succinimidyl-4-(2-pyridyldithio) butyrate (SPDB), N-succinimidyl-4-(5-nitro-2-pyridyldithio) butyrate (SNPB), and N-sulfosuccinimidyl-4-(5-nitro-2-pyridyldithio) butyrate (SSNPB), N-succinimidyl-4-methyl-4-(5-nitro-2-pyridyldithio)pentanoate (SMNP), N-succinimidyl-4-(5-N,N-dimethylcarboxamido-2-pyridyldithio) butyrate (SCPB) or N-sulfosuccinimidyl-4-(5-N,N-dimethylcarboxamido-2-pyridyldithio) butyrate (SSCPB)). The antibodies of the invention may be modified with the cross-linkers N-succinimidyl 4-(5-nitro-2-pyridyldithio)-pentanoate, N-sulfosuccinimidyl 4-(5-nitro-2-pyridyldithio)-pentanoate, SPDB, SNPB, SSNPB, SMNP, SCPB, or SSCPB can then react with a small excess of a particular drug that contains a thiol moiety to give excellent yields of an ADC. Preferably, the cross-linkers are compounds of the formula as depicted in U.S. Pat. No. 6,913,748, incorporated by reference herein.

In one embodiment, charged linkers (also referred to as pro-charged linkers) are used to conjugate anti-B7-H3 antibodies to drugs to form ADCs. Charged linkers include linkers that become charged after cell processing. The presence of a charged group(s) in the linker of a particular ADC or on the drug after cellular processing provides several advantages, such as (i) greater water solubility of the ADC, (ii) ability to operate at a higher concentration in aqueous solutions, (iii) ability to link a greater number of drug molecules per antibody, potentially resulting in higher potency, (iv) potential for the charged conjugate species to be retained inside the target cell, resulting in higher potency, and (v) improved sensitivity of multidrug resistant cells, which would be unable to export the charged drug species from the cell. Examples of some suitable charged or pro-charged cross-linkers and their synthesis are shown in FIGS. 1 to 10 of U.S. Pat. No. 8,236,319, and are incorporated by reference herein. Preferably, the charged or pro-charged cross-linkers are those containing sulfonate, phosphate, carboxyl or quaternary amine substituents that significantly increase the solubility of the ADCs, especially for ADCs with 2 to 20 conjugated drugs. Conjugates prepared from linkers containing a pro-charged moiety would produce one or more charged moieties after the conjugate is metabolized in a cell.

Additional examples of linkers that can be used with the compositions and methods include valine-citrulline; maleimidocaproyl; amino benzoic acids; p-aminobenzylcarbamoyl (PAB); lysosomal enzyme-cleavable linkers; maleimidocaproyl-polyethylene glycol (MC(PEG)6-OH); N-methyl-valine citrulline; N-succinimidyl 4-(N-maleimidomethyl)cyclohexane-1-carboxylate (SMCC); N-Succinimidyl 4-(2-pyridyldithio)butanoate (SPDB); and N-Succinimidyl 4-(2-pyridylthio)pentanoate (SPP) (See also US 2011/0076232). Another linker for use in the invention includes an avidin-biotin linkage to provide an avidin-biotin-containing ADC (See also U.S. Pat. No. 4,676,980, PCT publication Nos. WO1992/022332A2, WO1994/016729A1, WO1995/015770A1, WO1997/031655A2, WO1998/035704A1, WO1999/019500A1, WO2001/09785A2, WO2001/090198A1, WO2003/093793A2, WO2004/050016A2, WO2005/081898A2, WO2006/083562A2, WO2006/089668A1, WO2007/150020A1, WO2008/135237A1, WO2010/111198A1, WO2011/057216A1, WO2011/058321A1, WO2012/027494A1, and EP77671B1), wherein some such linkers are resistant to biotinidase cleavage. Additional linkers that may be used in the invention include a cohesin/dockerin pair to provide a cohesion-dockerin-containing ADC (See PCT publication Nos. WO2008/097866A2, WO2008/097870A2, WO2008/103947A2, and WO2008/103953A2).

Additional linkers for use in the invention may contain non-peptide polymers (examples include, but are not limited to, polyethylene glycol, polypropylene glycol, polyoxyethylated polyols, polyvinyl alcohol, polysaccharides, dextran, polyvinyl ethyl ether, PLA (poly(lactic acid)), PLGA (poly (lactic acid-glycolic acid)), and combinations thereof, wherein a preferred polymer is polyethylene glycol) (See also PCT publication No. WO2011/000370). Additional linkers are also described in WO 2004-010957, U.S. Publication No. 20060074008, U.S. Publication No. 20050238649, and U.S. Publication No. 20060024317, each of which is incorporated by reference herein in its entirety).

For an ADC comprising a maytansinoid, many positions on maytansinoids can serve as the position to chemically link the linking moiety. In one embodiment, maytansinoids comprise a linking moiety that contains a reactive chemical group are C-3 esters of maytansinol and its analogs where the linking moiety contains a disulfide bond and the chemical reactive group comprises a N-succinimidyl or N-sulfosuccinimidyl ester. For example, the C-3 position having a hydroxyl group, the C-14 position modified with hydroxymethyl, the C-15 position modified with hydroxy and the C-20 position having a hydroxy group are all useful. The linking moiety most preferably is linked to the C-3 position of maytansinol.

The conjugation of the drug to the antibody via a linker can be accomplished by any technique known in the art. A number of different reactions are available for covalent attachment of drugs and linkers to antibodies. This may be accomplished by reaction of the amino acid residues of the antibody, including the amine groups of lysine, the free carboxylic acid groups of glutamic and aspartic acid, the sulfhydryl groups of cysteine and the various moieties of the aromatic amino acids.

One of the most commonly used non-specific methods of covalent attachment is the carbodiimide reaction to link a carboxy (or amino) group of a compound to amino (or carboxy) groups of the antibody. Additionally, bifunctional agents such as dialdehydes or imidoesters have been used to link the amino group of a compound to amino groups of an antibody. Also available for attachment of drugs to antibodies is the Schiff base reaction. This method involves the periodate oxidation of a drug that contains glycol or hydroxy groups, thus forming an aldehyde which is then reacted with the binding agent. Attachment occurs via formation of a Schiff base with amino groups of the antibody. Isothiocyanates can also be used as coupling agents for covalently attaching drugs to antibodies. Other techniques are known to the skilled artisan and within the scope of the invention.

In certain embodiments, an intermediate, which is the precursor of the linker, is reacted with the drug under appropriate conditions. In certain embodiments, reactive groups are used on the drug or the intermediate. The product of the reaction between the drug and the intermediate, or the derivatized drug, is subsequently reacted with the anti-B7-H3 antibody under appropriate conditions. The synthesis and structure of exemplary linkers, stretcher units, amino acid units, self-immolative spacer units are described in U.S. Patent Application Publication Nos. 20030083263, 20050238649 and 20050009751, each if which is incorporated herein by reference.

Stability of the ADC may be measured by standard analytical techniques such as mass spectroscopy, HPLC, and the separation/analysis technique LC/MS.

IV. Purification of Anti-B7-H3 ADCs

Purification of the ADCs may be achieved in such a way that ADCs having certain DARs are collected. For example, HIC resin may be used to separate high drug loaded ADCs from ADCs having optimal drug to antibody ratios (DARs), e.g. a DAR of 4 or less. In one embodiment, a hydrophobic resin is added to an ADC mixture such that undesired ADCs, i.e., higher drug loaded ADCs, bind the resin and can be selectively removed from the mixture. In certain embodiments, separation of the ADCs may be achieved by contacting an ADC mixture (e.g., a mixture comprising a drug loaded species of ADC of 4 or less and a drug loaded species of ADC of 6 or more) with a hydrophobic resin, wherein the amount of resin is sufficient to allow binding of the drug loaded species which is being removed from the ADC mixture. The resin and ADC mixture are mixed together, such that the ADC species being removed (e.g., a drug loaded species of 6 or more) binds to the resin and can be separated from the other ADC species in the ADC mixture. The amount of resin used in the method is based on a weight ratio between the species to be removed and the resin, where the amount of resin used does not allow for significant binding of the drug loaded species that is desired. Thus, methods may be used to reduce the average DAR to less than 4. Further, the purification methods described herein may be used to isolate ADCs having any desired range of drug loaded species, e.g., a drug loaded species of 4 or less, a drug loaded species of 3 or less, a drug loaded species of 2 or less, a drug loaded species of 1 or less.

Certain species of molecule(s) binds to a surface based on hydrophobic interactions between the species and a hydrophobic resin. In one embodiment, method of the invention refers to a purification process that relies upon the intermixing of a hydrophobic resin and a mixture of ADCs, wherein the amount of resin added to the mixture determines which species (e.g., ADCs with a DAR of 6 or more) will bind. Following production and purification of an antibody from an expression system (e.g., a mammalian expression system), the antibody is reduced and coupled to a drug through a conjugation reaction. The resulting ADC mixture often contains ADCs having a range of DARs, e.g., 1 to 8. In one embodiment, the ADC mixture comprises a drug loaded species of 4 or less and a drug loaded species of 6 or more. According to the methods of the invention, the ADC mixture may be purified using a process, such as, but not limited to, a batch process, such that ADCs having a drug loaded species of 4 or less are selected and separated from ADCs having a higher drug load (e.g., ADCs having a drug loaded species of 6 or more). Notably, the purification methods described herein may be used to isolate ADCs having any desired range of DAR, e.g., a DAR of 4 or less, a DAR of 3 or less, or a DAR of 2 or less.

Thus, in one embodiment, an ADC mixture comprising a drug loaded species of 4 or less and a drug loaded species of 6 or more may be contacted with a hydrophobic resin to form a resin mixture, wherein the amount of hydrophobic resin contacted with the ADC mixture is sufficient to allow binding of the drug loaded species of 6 or more to the resin but does not allow significant binding of the drug load species of 4 or less; and removing the hydrophobic resin from the ADC mixture, such that the composition comprising ADCs is obtained, wherein the composition comprises less than 15% of the drug loaded species of 6 or more, and wherein the ADC comprises an antibody conjugated to a Bcl-xL inhibitor. In a separate embodiment, the method of the invention comprises contacting an ADC mixture comprising a drug loaded species of 4 or less and a drug loaded species of 6 or more with a hydrophobic resin to form a resin mixture, wherein the amount of hydrophobic resin contacted with the ADC mixture is sufficient to allow binding of the drug loaded species of 6 or more to the resin but does not allow significant binding of the drug load species of 4 or less; and removing the hydrophobic resin from the ADC mixture, such that the composition comprising ADCs is obtained, wherein the composition comprises less than 15% of the drug loaded species of 6 or more, and wherein the ADC comprises an antibody conjugated to a Bcl-xL inhibitor, wherein the hydrophobic resin weight is 3 to 12 times the weight of the drug loaded species of 6 or more in the ADC mixture.

The ADC separation method described herein method may be performed using a batch purification method. The batch purification process generally includes adding the ADC mixture to the hydrophobic resin in a vessel, mixing, and subsequently separating the resin from the supernatant. For example, in the context of batch purification, a hydrophobic resin may be prepared in or equilibrated to the desired equilibration buffer. A slurry of the hydrophobic resin may thus be obtained. The ADC mixture may then be contacted with the slurry to adsorb the specific species of ADC(s) to be separated by the hydrophobic resin. The solution comprising the desired ADCs that do not bind to the hydrophobic resin material may then be separated from the slurry, e.g., by filtration or by allowing the slurry to settle and removing the supernatant. The resulting slurry can be subjected to one or more washing steps. In order to elute bound ADCs, the salt concentration can be decreased. In one embodiment, the process used in the invention includes no more than 50 g of hydrophobic resin.

Thus, a batch method may be used to contact an ADC mixture comprising a drug loaded species of 4 or less and a drug loaded species of 6 or more with a hydrophobic resin to form a resin mixture, wherein the amount of hydrophobic resin contacted with the ADC mixture is sufficient to allow binding of the drug loaded species of 6 or more to the resin but does not allow significant binding of the drug load species of 4 or less; and removing the hydrophobic resin from the ADC mixture, such that the composition comprising ADCs is obtained, wherein the composition comprises less than 15% of the drug loaded species of 6 or more, and wherein the ADC comprises an antibody conjugated to a Bcl-xL inhibitor. In a separate embodiment, a batch method is used to contact an ADC mixture comprising a drug loaded species of 4 or less and a drug loaded species of 6 or more with a hydrophobic resin to form a resin mixture, wherein the amount of hydrophobic resin contacted with the ADC mixture is sufficient to allow binding of the drug loaded species of 6 or more to the resin but does not allow significant binding of the drug load species of 4 or less; and removing the hydrophobic resin from the ADC mixture, such that the composition comprising ADCs is obtained, wherein the composition comprises less than 15% of the drug loaded species of 6 or more, and wherein the ADC comprises an antibody conjugated to a Bcl-xL inhibitor, wherein the hydrophobic resin weight is 3 to 12 times the weight of the drug loaded species of 6 or more in the ADC mixture.

Alternatively, in a separate embodiment, purification may be performed using a circulation process, whereby the resin is packed in a container and the ADC mixture is passed over the hydrophobic resin bed until the specific species of ADC(s) to be separated have been removed. The supernatant (containing the desired ADC species) is then pumped from the container and the resin bed may be subjected to washing steps.

A circulation process may be used to contact an ADC mixture comprising a drug loaded species of 4 or less and a drug loaded species of 6 or more with a hydrophobic resin to form a resin mixture, wherein the amount of hydrophobic resin contacted with the ADC mixture is sufficient to allow binding of the drug loaded species of 6 or more to the resin but does not allow significant binding of the drug load species of 4 or less; and removing the hydrophobic resin from the ADC mixture, such that the composition comprising ADCs is obtained, wherein the composition comprises less than 15% of the drug loaded species of 6 or more, and wherein the ADC comprises an antibody conjugated to a Bcl-xL inhibitor. In a separate embodiment, a circulation process is used to contact an ADC mixture comprising a drug loaded species of 4 or less and a drug loaded species of 6 or more with a hydrophobic resin to form a resin mixture, wherein the amount of hydrophobic resin contacted with the ADC mixture is sufficient to allow binding of the drug loaded species of 6 or more to the resin but does not allow significant binding of the drug load species of 4 or less; and removing the hydrophobic resin from the ADC mixture, such that the composition comprising ADCs is obtained, wherein the composition comprises less than 15% of the drug loaded species of 6 or more, and wherein the ADC comprises an antibody conjugated to a Bcl-xL inhibitor, wherein the hydrophobic resin weight is 3 to 12 times the weight of the drug loaded species of 6 or more in the ADC mixture.

Alternatively, a flow through process may be used to purify an ADC mixture to arrive at a composition comprising a majority of ADCs having a certain desired DAR. In a flow through process, resin is packed in a container, e.g., a column, and the ADC mixture is passed over the packed resin such that the desired ADC species does not substantially bind to the resin and flows through the resin, and the undesired ADC species is bound to the resin. A flow through process may be performed in a single pass mode (where the ADC species of interest are obtained as a result of a single pass through the resin of the container) or in a multi-pass mode (where the ADC species of interest are obtained as a result of multiple passes through the resin of the container). The flow through process is performed such that the weight of resin selected binds to the undesired ADC population, and the desired ADCs (e.g., DAR 2-4) flow over the resin and are collected in the flow through after one or multiple passes.

A flow through process may be used to contact an ADC mixture comprising a drug loaded species of 4 or less and a drug loaded species of 6 or more with a hydrophobic resin, wherein the amount of hydrophobic resin contacted with the ADC mixture is sufficient to allow binding of the drug loaded species of 6 or more to the resin but does not allow significant binding of the drug load species of 4 or less, where the drug load species of 4 or less passes over the resin and is subsequently collected after one or multiple passes, such that the composition comprising the desired ADCs (e.g. DAR 2-4) is obtained, wherein the composition comprises less than 15% of the drug loaded species of 6 or more, and wherein the ADC comprises an antibody conjugated to a Bcl-xL inhibitor. In a separate embodiment, a flow through process is used to contact an ADC mixture comprising a drug loaded species of 4 or less and a drug loaded species of 6 or more with a hydrophobic resin by passing the ADC mixture over the resin, wherein the amount of hydrophobic resin contacted with the ADC mixture is sufficient to allow binding of the drug loaded species of 6 or more to the resin but does not allow significant binding of the drug load species of 4 or less, where the drug load species of 4 or less passes over the resin and is subsequently collected, such that the composition comprising ADCs is obtained, wherein the composition comprises less than 15% of the drug loaded species of 6 or more, and wherein the ADC comprises an antibody conjugated to an a drug, e.g., a Bcl-xL inhibitor, wherein the amount of hydrophobic resin weight is 3 to 12 times the weight of the drug loaded species of 6 or more in the ADC mixture.

Following a flow through process, the resin may be washed with a one or more washes following in order to further recover ADCs having the desired DAR range (found in the wash filtrate). For example, a plurality of washes having decreasing conductivity may be used to further recover ADCs having the DAR of interest. The elution material obtained from the washing of the resin may be subsequently combined with the filtrate resulting from the flow through process for improved recovery of ADCs having the DAR of interest.

The aforementioned batch, circulation, and flow through process purification methods are based on the use of a hydrophobic resin to separate high vs. low drug loaded species of ADC. Hydrophobic resin comprises hydrophobic groups which interact with the hydrophobic properties of the ADCs. Hydrophobic groups on the ADC interact with hydrophobic groups within the hydrophobic resin. The more hydrophobic a protein is the stronger it will interact with the hydrophobic resin.

Hydrophobic resin normally comprises a base matrix (e.g., cross-linked agarose or synthetic copolymer material) to which hydrophobic ligands (e.g., alkyl or aryl groups) are coupled. Many hydrophobic resins are available commercially. Examples include, but are not limited to, Phenyl Sepharose™ 6 Fast Flow with low or high substitution (Pharmacia LKB Biotechnology, AB, Sweden); Phenyl Sepharose™ High Performance (Pharmacia LKB Biotechnology, AB, Sweden); Octyl Sepharose™ High Performance (Pharmacia LKB Biotechnology, AB, Sweden); Fractogel™ EMD Propyl or Fractogel™ EMD Phenyl columns (E. Merck, Germany); Macro-Prep™ Methyl or Macro-Prep™. t-Butyl Supports (Bio-Rad, California); WP HI-Propyl $(C_3)$™ (J. T. Baker, New Jersey); and Toyopearl™ ether, hexyl, phenyl or butyl (TosoHaas, PA). In one embodiment, the hydrophobic resin is a butyl hydrophobic resin. In another embodiment, the hydrophobic resin is a phenyl hydrophobic resin. In another embodiment, the hydrophobic resin is a hexyl hydrophobic resin, an octyl hydrophobic resin, or a decyl hydrophobic resin. In one embodiment, the hydrophobic resin is a methacrylic polymer having n-butyl ligands (e.g. TOYOPEARL® Butyl-600M).

Further methods for purifying ADC mixtures to obtain a composition having a desired DAR are described in U.S. application Ser. No. 14/210,602 (U.S. Patent Appln. Publication No. US 2014/0286968), incorporated by reference in its entirety.

In certain embodiments of the invention, ADCs described herein having a DAR2 are purified from ADCs having higher or lower DARs. Such purified DAR2 ADCs are referred to herein as "E2". Purification methods for achieving a composition having E2 anti-B7-H3 ADCs. In one embodiment, of the invention provides a composition comprising an ADC mixture, wherein at least 75% of the ADCs are anti-B7H3 ADCs (like those described herein) having a DAR2. In another embodiment, the invention provides a composition comprising an ADC mixture, wherein at least 80% of the ADCs are anti-B7H3 ADCs (like those described herein) having a DAR2. In another embodiment, the invention provides a composition comprising an ADC mixture, wherein at least 85% of the ADCs are anti-B7H3 ADCs (like those described herein) having a DAR2. In another embodiment, the invention provides a composition comprising an ADC mixture, wherein at least 90% of the ADCs are anti-B7H3 ADCs (like those described herein) having a DAR2.

V. Uses of Anti-B7-H3 Antibodies and Anti-B7-H3 ADCs

The antibodies and ADCs of the invention preferably are capable of neutralizing human B7-H3 activity both in vivo and in vitro. Accordingly, such antibodies and ADCs of the invention can be used to inhibit hB7-H3 activity, e.g., in a cell culture containing hB7-H3, in human subjects or in other mammalian subjects having B7-H3 with which an antibody of the invention cross-reacts. In one embodiment, the invention provides a method for inhibiting hB7-H3 activity comprising contacting hB7-H3 with an antibody or ADC of the invention such that hB7-H3 activity is inhibited. For example, in a cell culture containing, or suspected of containing hB7-H3, an antibody or antibody portion of the invention can be added to the culture medium to inhibit hB7-H3 activity in the culture.

In another embodiment, of the invention a method for reducing hB7-H3 activity in a subject, advantageously from a subject suffering from a disease or disorder in which B7-H3 activity is detrimental. The invention provides methods for reducing B7-H3 activity in a subject suffering from such a disease or disorder, which method comprises administering to the subject an antibody or ADC of the invention such that B7-H3 activity in the subject is reduced. Preferably, the B7-H3 is human B7-H3, and the subject is a human subject. Alternatively, the subject can be a mammal expressing a B7-H3 to which antibodies of the invention are capable of binding. Still further the subject can be a mammal into which B7-H3 has been introduced (e.g., by administration of B7-H3 or by expression of a B7-H3 transgene). Antibodies or ADCs of the invention can be administered to a human subject for therapeutic purposes. Moreover, antibodies or ADCS of the invention can be administered to a non-human mammal expressing a B7-H3 with which the antibody is capable of binding for veterinary purposes or as an animal model of human disease. Regarding the latter, such animal models may be useful for evaluating the therapeutic efficacy of antibodies of the invention (e.g., testing of dosages and time courses of administration).

As used herein, the term "a disorder in which B7-H3 expression is detrimental" is intended to include diseases and other disorders in which the presence of B7-H3 in a subject suffering from the disorder has been shown to be expressed, or has been shown to be or is suspected of being either responsible for the pathophysiology of the disorder or a factor that contributes to the disorder. For example, the ADCs of the invention may be used to target tumor cells that are expressing B7-H3. Non-limiting examples of disorders that can be treated with the ADCs of the invention, for example, an ADC comprising huAb13v1, include, but are not limited to, a variety of cancers including, but not limited to, small cell lung cancer, non small cell lunch cancer (NSCLC), breast cancer, ovarian cancer, lung cancer, a glioma, prostate cancer, pancreatic cancer, colon cancer, head and neck cancer, leukemia, e.g., acute myeloid leukemia (AML), lymphoma, e.g., non-Hodgkin's lymphoma (NHL), and kidney cancer. Other examples of cancer that may be treated using the compositions and methods disclosed herein include squamous cell carcinoma (e.g., squamous lung cancer or squamous head and neck cancer), triple negative breast cancer, non-small cell lung cancer, colorectal cancer, and mesothelioma. In one embodiment, the antibodies or ADCs disclosed herein are used to treat a solid tumor, e.g., inhibit growth of or decrease size of a solid tumor, overexpressing B7-H3 or which is B7-H3 positive. In one embodiment, the invention is directed to the treatment of squamous lung cancer associated with B7-H3 expression. In another embodiment, the antibodies and ADCs disclosed herein are used to treat triple negative breast cancer (TNBC). Diseases and disorders described herein may be treated by anti-B7-H3 antibodies or ADCs of the invention, as well as pharmaceutical compositions comprising such anti-B7-H3 antibodies or ADCs.

In certain embodiments, the cancer may be characterized as having EGFR overexpression. In one embodiment, the ADCs of the invention may be used to treating cancer associated with an activating EGFR mutation. Examples of such mutations include, but are not limited to, an exon 19 deletion mutation, a single-point substitution mutation L858R in exon 21, a T790M point mutation, and combinations thereof.

In certain embodiments, the antibodies or ADCs disclosed herein are administered to a subject in need thereof in order to treat advanced solid tumor types likely to exhibit elevated levels of B7-H3. Examples of such tumors include, but are not limited to, small cell lung cancer, breast cancer, ovarian cancer, head and neck squamous cell carcinoma, non-small cell lung cancer, triple negative breast cancer, colorectal carcinoma, and glioblastoma multiforme.

In certain embodiments, the invention includes a method for inhibiting or decreasing solid tumor growth in a subject having a solid tumor, said method comprising administering an anti-B7-H3 antibody or ADC described herein, to the subject having the solid tumor, such that the solid tumor growth is inhibited or decreased. In certain embodiments, the solid tumor is a non-small cell lung carcinoma or a glioblastoma. In further embodiments, the solid tumor is a B7-H3-expressing solid tumors. In further embodiments, the solid tumor is an B7-H3 overexpressing solid tumors. In certain embodiments the anti-B7-H3 antibodies or ADCs described herein are administered to a subject having glioblastoma multiforme, alone or in combination with an additional agent, e.g., radiation and/or temozolomide.

In certain embodiments the anti-B7-H3 ADCs described herein are are administered to a subject having small cell lung cancer, alone or in combination with an additional agent, e.g., ABT-199 (venetoclax).

In certain embodiments the anti-B7-H3 ADCs described herein are administered to a subject having non-small cell lung cancer, alone or in combination with an additional agent, e.g., a taxane. In certain embodiments the anti-B7-H3 antibodies or ADCs described herein are administered to a subject having breast cancer, alone or in combination with an additional agent, e.g., a taxane. In certain embodiments the anti-B7-H3 antibodies or ADCs described herein are administered to a subject having ovarian cancer, alone or in combination with an additional agent, e.g., a taxane.

Other combination therapies which are included in the invention are the administration of an anti-B7-H3 ADC with an agent selected from the group consisting of an anti-PD1 antibody (e.g. pembrolizumab), an anti-PD-L1 antibody (e.g., atezolizumab), an anti-CTLA-4 antibody (e.g. ipilimumab), a MEK inhibitor (e.g. trametinib), an ERK inhibitor, a BRAF inhibitor (e.g. dabrafenib), osimertinib, erlotinib, gefitinib, sorafenib, a CDK9 inhibitor (e.g. dinaciclib), a MCL-1 inhibitor, temozolomide, a Bcl-xL inhibitor, a Bcl-2 inhibitor (e.g. venetoclax), ibrutinib, a mTOR inhibitor (e.g. everolimus), a PI3K inhibitor (e.g. buparlisib), duvelisib, idelalisib, an AKT inhibitor, a HER2 inhibitor (e.g. lapatinib), a taxane (e.g., docetaxel, paclitaxel, nab-paclitaxel), venetoclax, an ADC comprising an auristatin, an ADC comprising a PBD (e.g. rovalpituzumab tesirine), an ADC comprising a maytansinoid (e.g. TDM1), a TRAIL agonist, a proteasome inhibitor (e.g. bortezomib), and a nicotinamide phosphoribosyltransferase (NAMPT) inhibitor.

Combination therapies include administration of an ADC of the invention prior to, concurrently with, or following administration of an additional therapeutic agent, including those described above.

In certain embodiments, the invention includes a method for inhibiting or decreasing solid tumor growth in a subject having a solid tumor which was identified as an B7-H3 expressing or B7-H3 overexpressing tumor, said method comprising administering an anti-B7-H3 antibody or ADC described herein, to the subject having the solid tumor, such that the solid tumor growth is inhibited or decreased. Methods for identifying B7-H3 expressing tumors (e.g., B7-H3 overexpressing tumors) are known in the art, and include FDA-approved tests and validation assays. For example, the B7-H3 assay is a qualitative immunohistochemical (IHC) kit system used to identify B7-H3 expression in normal and neoplastic tissues routinely-fixed for histological evaluation. In addition, PCR-based assays may also be used for identifying B7-H3 overexpressing tumors. The amplified PCR products may be subsequently analyzed, for example, by gel electrophoresis using standard methods known in the art to determine the size of the PCR products. Such tests may be used to identify tumors that may be treated with the methods and compositions described herein.

Any of the methods for gene therapy available in the art can be used according to the invention. For general reviews of the methods of gene therapy, see Goldspiel et al., 1993, *Clinical Pharmacy* 12:488-505; Wu and Wu, 1991, *Biotherapy* 3:87-95; Tolstoshev, 1993, *Ann. Rev. Pharmacol. Toxicol.* 32:573-596; Mulligan, *Science* 260:926-932 (1993); and Morgan and Anderson, 1993, *Ann. Rev. Biochem.* 62:191-217; May, 1993, *TIBTECH* 11(5):155-215. Methods commonly known in the art of recombinant DNA technology which can be used are described in Ausubel et al. (eds.), *Current Protocols in Molecular Biology*, John Wiley & Sons, N Y (1993); and Kriegler, Gene Transfer and Expression, A Laboratory Manual, Stockton Press, NY (1990). Detailed description of various methods of gene therapy is provided in US20050042664 A1 which is incorporated herein by reference.

In another aspect, this application features a method of treating (e.g., curing, suppressing, ameliorating, delaying or preventing the onset of, or preventing recurrence or relapse of) or preventing a B7-H3-associated disorder, in a subject. The method includes: administering to the subject an B7-H3 binding agent, e.g., an anti-B7-H3 antibody or fragment thereof as described herein, in an amount sufficient to treat or prevent the B7-H3-associated disorder. The B7-H3 antagonist, e.g., the anti-B7-H3 antibody or fragment thereof, can be administered to the subject, alone or in combination with other therapeutic modalities as described herein.

Antibodies or ADCs of the invention, or antigen binding portions thereof can be used alone or in combination to treat such diseases. It should be understood that the antibodies of the invention or antigen binding portion thereof can be used alone or in combination with an additional agent, e.g., a therapeutic agent, said additional agent being selected by the skilled artisan for its intended purpose. For example, the additional agent can be a therapeutic agent art-recognized as being useful to treat the disease or condition being treated by the antibody of the invention. The additional agent also can be an agent that imparts a beneficial attribute to the therapeutic composition, e.g., an agent which affects the viscosity of the composition.

It should further be understood that the combinations which are to be included within this invention are those combinations useful for their intended purpose. The agents set forth below are illustrative for purposes and not intended to be limited. The combinations, which are part of this invention, can be the antibodies of the invention and at least one additional agent selected from the lists below. The combination can also include more than one additional agent, e.g., two or three additional agents if the combination is such that the formed composition can perform its intended function.

The combination therapy can include one or more B7-H3 antagonists, e.g., anti-B7-H3 antibodies or fragments thereof, formulated with, and/or co-administered with, one or more additional therapeutic agents, e.g., one or more cytokine and growth factor inhibitors, immunosuppressants, anti-inflammatory agents (e.g., systemic anti-inflammatory agents), anti-fibrotic agents, metabolic inhibitors, enzyme inhibitors, and/or cytotoxic or cytostatic agents, mitotic inhibitors, antitumor antibiotics, immunomodulating agents, vectors for gene therapy, alkylating agents, antiangiogenic agents, antimetabolites, boron-containing agents, chemoprotective agents, hormones, antihormone agents, corticosteroids, photoactive therapeutic agents, oligonucleotides, radionuclide agents, topoisomerase inhibitors, kinase inhibitors, or radiosensitizers, as described in more herein.

In a particular embodiment, the anti-B7-H3 binding proteins described herein, for example, anti-B7-H3 antibodies, are used in combination with an anti-cancer agent or an antineoplastic agent. The terms "anti-cancer agent" and "antineoplastic agent" refer to drugs used to treat malignancies, such as cancerous growths. Drug therapy may be used alone, or in combination with other treatments such as surgery or radiation therapy. Several classes of drugs may be used in cancer treatment, depending on the nature of the organ involved. For example, breast cancers are commonly stimulated by estrogens, and may be treated with drugs which inactive the sex hormones. Similarly, prostate cancer may be treated with drugs that inactivate androgens, the male sex hormone. Anti-cancer agents that may be used in conjunction with the anti-B7-H3 antibodies or ADCs of the invention include, among others, an anti-PD1 antibody (e.g., pembrolizumab), an anti-PD-L1 antibody (e.g., atezolizumab), an anti-CTLA-4 antibody (e.g., ipilimumab), a MEK inhibitor (e.g., trametinib), an ERK inhibitor, a BRAF inhibitor (e.g., dabrafenib), osimertinib (AZD9291), erlotinib, gefitinib, sorafenib, a CDK9 inhibitor (e.g., dinaciclib), a MCL-1 inhibitor, temozolomide, a Bcl-xL inhibitor, a Bcl-2 inhibitor (e.g., venetoclax), ibrutinib, a mTOR inhibitor (e.g., everolimus), a PI3K inhibitor (e.g., buparlisib), duvelisib, idelalisib, an AKT inhibitor, a HER2 inhibitor (e.g., lapatinib), Herceptin, a taxane (e.g., docetaxel, paclitaxel, nab-paclitaxel), an ADC comprising an auristatin, an ADC comprising a PBD (e.g., rovalpituzumab tesirine), an ADC comprising a maytansinoid (e.g., TDM1), a TRAIL agonist, a proteasome inhibitor (e.g., bortezomib), and a nicotinamide phosphoribosyltransferase (NAMPT) inhibitor, as well as the following agents:

| Anti-Cancer Agent | Comments | Examples |
| --- | --- | --- |
| Antibodies | Antibodies which bind IGF-1R (insulin-like growth factor type 1 receptor), which is expressed on the cell surface of most human cancers | A12 (fully humanized mAb)<br>19D12 (fully humanized mAb)<br>Cp751-871 (fully humanized mAb)<br>H7C10 (humanized mAb)<br>alphaIR3 (mouse)<br>ScFV/FC (mouse/human chimera)<br>EM/164 (mouse) |
| | Antibodies which bind EGFR; Mutations affecting EGFR expression or activity could result in cancer | Matuzumab (EMD72000)<br>Erbitux ®/Cetuximab (Imclone)<br>Vectibix ®/Panitumumab (Amgen)<br>mAb 806<br>Nimotuxumab (TheraCIM) |
| | Antibodies which bind cMET (Mesechymal epithelial transition factor); a member of the MET family of receptor tyrosine kinases) | AVEO (AV299) (AVEO)<br>AMG102 (Amgen)<br>5D5 (OA-5d5) (Genentech)<br>H244G11 (Pierre Fabre) |
| | Anti-ErbB3 antibodies | Ab #14 (MM 121-14)<br>Herceptin ® (Trastuzumab; Genentech)<br>1B4C3; 2D1D12 (U3 Pharma AG) |
| Small Molecules Targeting IGF1R | Insulin-like growth factor type 1 receptor which is expressed on the cell surface of many human cancers | NVP-AEW541-A<br>BMS-536,924 (1H-benzoimidazol-2-yl)-1H-pyridin-2-one)<br>BMS-554,417<br>Cycloligan<br>TAE226<br>PQ401 |
| Small Molecules Targeting EGFR | EGFR; Overexpression or mutations affecting EGFR expression or activity could result in cancer | Iressa ®/Gefitinib (AstraZeneca)<br>CI-1033 (PD 183805) (Pfizer)<br>Lapatinib (GW-572016) (GlaxoSmithKline)<br>Tykerb ®/Lapatinib Ditosylate (Smith Kline Beecham)<br>Tarceva ®/Erlotinib HCL (OSI-774) (OSI Pharma)<br>PKI-166 (Novartis)<br>PD-158780<br>EKB-569<br>Tyrphostin AG 1478 (4-(3-Chloroanillino)-6,7-dimethoxyquinazoline) |
| Small Molecules Targeting cMET | cMET (Mesenchymal epithelial transition factor); a member of the MET family of receptor tyrosine kinases) | PHA665752<br>ARQ 197 |
| Antimetabolites | | Flourouracil (5-FU)<br>Capecitabine/XELODA ® (HLR Roche)<br>5-Trifluoromethyl-2'-deoxyuridine<br>Methotrexate sodium (Trexall) (Barr)<br>Raltitrexed/Tomudex ® (AstraZeneca)<br>Pemetrexed/Alimta ® (Lilly)<br>Tegafur<br>Cytosine Arabinoside (Cytarabine, Ara-C)/Thioguanine ® (GlaxoSmithKline)<br>5-azacytidine<br>6-mercaptopurine (Mercaptopurine, 6-MP)<br>Azathioprine/Azasan ® (AAIPHARMA LLC)<br>6-thioguanine (6-TG)/Purinethol ® (TEVA)<br>Pentostatin/Nipent ® (Hospira Inc.)<br>Fludarabine phosphate/Fludara ® (Bayer Health Care)<br>Cladribine (2-CdA, 2-chlorodeoxyadenosine)/Leustatin ® (Ortho Biotech) |

-continued

| Anti-Cancer Agent | Comments | Examples |
|---|---|---|
| Alkylating agents | An alkylating antineoplastic agent is an alkylating agent that attaches an alkyl group to DNA. Since cancer cells generally proliferate unrestrictively more than do healthy cells they are more sensitive to DNA damage, and alkylating agents are used clinically to treat a variety of tumors. | Ribonucleotide Reductase Inhibitor (RNR) Cyclophosphamide/Cytoxan (BMS) Neosar (TEVA) Ifosfamide/Mitoxana ® (ASTA Medica) Thiotepa (Bedford, Abraxis, Teva) BCNU→ 1,3-bis(2-chloroethyl)-1-nitosourea CCNU→ 1, -(2-chloroethyl)-3-cyclohexyl-1-nitrosourea (methyl CCNU) Hexamethylmelamine (Altretamine, HMM)/ Hexalen ® (MGI Pharma Inc.) Busulfan/Myleran (GlaxoSmithKline) Procarbazine HCL/Matulane (Sigma Tau Pharmaceuticals, Inc.) Dacarbazine (DTIC) Chlorambucil/Leukara ® (SmithKline Beecham) Melphalan/Alkeran ® (GlaxoSmithKline) Cisplatin (Cisplatinum, CDDP)/Platinol (Bristol Myers) Carboplatin/Paraplatin (BMS) Oxaliplatin/Eloxitan ® (Sanofi-Aventis US) |
| Topoisomerase inhibitors | Topoisomerase inhibitors are chemotherapy agents designed to interfere with the action of topoisomerase enzymes (topoisomerase I and II), which are enzymes that control the changes in DNA structure by catalyzing the breaking and rejoining of the phosphodiester backbone of DNA strands during the normal cell cycle. | Doxorubicin HCL/Doxil ® (Alza) Daunorubicin citrate/Daunoxome ® (Gilead) Mitoxantrone HCL/Novantrone (EMD Serono) Actinomycin D Etoposide/Vepesid ® (BMS)/Etopophos ® (Hospira, Bedford, Teva Parenteral, Etc.) Topotecan HCL/Hycamtin ® (GlaxoSmithKline) Teniposide (VM-26)/Vumon ® (BMS) Irinotecan HCL(CPT-ll/Camptosar ® (Pharmacia & Upjohn) |
| Microtubule targeting agents | Microtubules are one of the components of the cytoskeleton. They have diameter of ~24 nm and length varying from several micrometers to possibly millimeters in axons of nerve cells. Microtubules serve as structural components within cells and are involved in many cellular processes including mitosis, cytokinesis, and vesicular transport. | Vincristine/Oncovin ® (Lilly) Vinblastine sulfate/Velban ®(discontinued) (Lilly) Vinorelbine tartrate/Navelbine ® (PierreFabre) Vindesine sulphate/Eldisine ® (Lilly) Paclitaxel/Taxol ® (BMS) Docetaxel/Taxotere ® (Sanofi Aventis US) Nanoparticle paclitaxel (ABI-007)/ Abraxane ® (Abraxis BioScience, Inc.) Ixabepilone/IXEMPRA ™ (BMS) |
| Kinase inhibitors | Kinases are enzymes that catalyze the transfer of phosphate groups from high-energy, phosphate-donating molecules to specific substrates, and are utilized to transmit signals and regulate complex processes in cells. | Imatinib mesylate/Gleevec (Novartis) Sunitinib malate/Sutent ® (Pfizer) Sorafenib tosylate/Nexavar ® (Bayer) Nilotinib hydrochloride monohydrate/ Tasigna ® (Novartis), Osimertinib, Cobimetinib, Trametinib, Dabrafenib, Dinaciclib |
| Protein synthesis inhibitors | Induces cell apoptosis | L-asparaginase/Elspar ® (Merck & Co.) |
| Immunotherapeutic agents | Induces cancer patients to exhibit immune responsiveness | Alpha interferon Angiogenesis Inhibitor/Avastin ® (Genentech) IL-2→ Interleukin 2 (Aldesleukin)/Proleukin ® (Chiron) IL-12→ Interleukin 12 |
| | Antibody/small molecule immune checkpoint modulators | Anti-CTLA-4 and PR-1 therapies Yervoy ® (ipilimumab; Bristol-Myers Squibb) Opdivo ® (nivolumab; Bristol-Myers Squibb) Keytrada ® (pembrolizumab; Merck) |
| Hormones | Hormone therapies associated with menopause and aging seek to increase the amount of certain hormones in your body to compensate for age- or disease-related hormonal declines. Hormone therapy | Toremifene citrate/Fareston ® (GTX, Inc.) Fulvestrant/Faslodex ® (AstraZeneca) Raloxifene HCL/Evista ® (Lilly) Anastrazole/Arimidex ® (AstraZeneca) Letrozole/Femara ® (Novartis) Fadrozole (CGS 16949A) Exemestane/Aromasin ® (Pharmacia & Upjohn) |

-continued

| Anti-Cancer Agent | Comments | Examples |
|---|---|---|
| | as a cancer treatment either reduces the level of specific hormones or alters the cancer's ability to use these hormones to grow and spread. | Leuprolide acetate/Eligard ® (QTL USA)<br>Lupron ® (TAP Pharm)<br>Goserelin acetate/Zoladex ® (AstraZeneca)<br>Triptorelin pamoate/Trelstar ® (Watson Labs)<br>Buserelin/Suprefact ® (Sanofi Aventis)<br>Nafarelin/Synarel ® (Pfizer)<br>Cetrorelix/Cetrotide ® (EMD Serono)<br>Bicalutamide/Casodex ® (AstraZeneca)<br>Nilutamide/Nilandron ® (Aventis Pharm.)<br>Megestrol acetate/Megace ® (BMS)<br>Somatostatin Analogs (Octreotide acetate/Sandostatin ® (Novartis) |
| Glucocorticoids | Anti-inflammatory drugs used to reduce swelling that causes cancer pain. | Prednisolone<br>Dexamethasone/Decadron ® (Wyeth) |
| Aromatose inhibitors | Includes imidazoles | Ketoconazole |
| mTOR inhibitors | the mTOR signaling pathway was originally discovered during studies of the immunosuppressive agent rapamycin. This highly conserved pathway regulates cell proliferation and metabolism in response to environmental factors, linking cell growth factor receptor signaling via phosphoinositide-3-kinase(PI-3K) to cell growth, proliferation, and angiogenesis. | Sirolimus (Rapamycin)/Rapamune ® (Wyeth)<br>Temsirolimus (CCI-779)/Torisel ® (Wyeth)<br>Deforolimus (AP23573)/(Ariad Pharm.)<br>Everolimus (RAD00I)/Certican ® (Novartis) |

In addition to the above anti-cancer agents, the anti-B7-H3 antibodies and ADCs described herein may be administered in combination with the agents described herein. Further, the aforementioned anti-cancer agents may also be used in the ADCs of the invention.

In particular embodiments, the anti-B7-H3 antibodies or ADCs can be administered alone or with another anti-cancer agent which acts in conjunction with or synergistically with the antibody to treat the disease associated with B7-H3 activity. Such anti-cancer agents include, for example, agents well known in the art (e.g., cytotoxins, chemotherapeutic agents, small molecules and radiation). Examples of anti-cancer agents include, but are not limited to, Panorex (Glaxo-Welcome), Rituxan (IDEC/Genentech/Hoffman la Roche), Mylotarg (Wyeth), Campath (Millennium), Zevalin (IDEC and Schering AG), Bexxar (Corixa/GSK), Erbitux (Imclone/BMS), Avastin (Genentech) and Herceptin (Genentech/Hoffman la Roche). Other anti-cancer agents include, but are not limited to, those disclosed in U.S. Pat. No. 7,598,028 and International Publication No. WO2008/100624, the contents of which are hereby incorporated by reference. One or more anti-cancer agents may be administered either simultaneously or before or after administration of an antibody or antigen binding portion thereof of the invention.

In particular embodiments of the invention, the anti-B7-H3 antibodies or ADCs described herein can be used in a combination therapy with an apoptotic agent, such as a Bcl-xL inhibitor or a Bcl-2 (B-cell lymphoma 2) inhibitor (e.g., ABT-199 (venetoclax)) to treat cancer, such as leukemia, in a subject. In one embodiment, the anti-B7-H3 antibodies or ADCs described herein can be used in a combination therapy with a Bcl-xL inhibitor for treating cancer. In one embodiment, the anti-B7-H3 antibodies or ADCs described herein can be used in a combination therapy with venetoclax for treating cancer.

In particular embodiments of the invention, the anti-B7-H3 antibodies or ADCs described herein can be used in a combination therapy with an inhibitor of NAMPT (see examples of inhibitors in US 2013/0303509; AbbVie, Inc., incorporated by reference herein) to treat a subject in need thereof. NAMPT (also known as pre-B-cell-colony-enhancing factor (PBEF) and visfatin) is an enzyme that catalyzes the phosphoribosylation of nicotinamide and is the rate-limiting enzyme in one of two pathways that salvage NAD. In one embodiment of the invention, anti-B7-H3 antibodies and ADCs described herein are administered in combination with a NAMPT inhibitor for the treatment of cancer in a subject.

In particular embodiments of the invention, the anti-B7-H3 antibodies or ADCs described herein can be used in a combination therapy with SN-38, which is the active metabolite of the topoisomerase inhibitor irinotecan.

In other embodiments of the invention, the anti-B7-H3 antibodies or ADCs described herein can be used in a combination therapy with a PARP (poly ADP ribose polymerase) inhibitor, e.g., veliparib, to treat cancer, including breast, ovarian and non-small cell lung cancers.

Further examples of additional therapeutic agents that can be co-administered and/or formulated with anti-B7-H3 antibodies or anti-B7-H3 ADCs described herein, include, but are not limited to, one or more of: inhaled steroids; beta-agonists, e.g., short-acting or long-acting beta-agonists; antagonists of leukotrienes or leukotriene receptors; combination drugs such as ADVAIR; IgE inhibitors, e.g., anti-IgE antibodies (e.g., XOLAIR®, omalizumab); phosphodiesterase inhibitors (e.g., PDE4 inhibitors); xanthines; anticholinergic drugs; mast cell-stabilizing agents such as cromolyn; IL-4 inhibitors; IL-5 inhibitors; eotaxin/CCR3 inhibitors; antagonists of histamine or its receptors including H1, H2, H3, and H4, and antagonists of prostaglandin D or its receptors (DP1 and CRTH2). Such combinations can be used to treat, for example, asthma and other respiratory disorders. Other examples of additional therapeutic agents that can be co-administered and/or formulated with anti-B7-H3 antibodies or anti-B7-H3 ADCs described herein, include, but are not limited to, one or more of, an anti-PD1 antibody (e.g., pembrolizumab), an anti-PD-L1 antibody (e.g., atezolizumab), an anti-CTLA-4 antibody (e.g., ipilimumab), a MEK inhibitor (e.g., trametinib), an ERK inhibitor, a BRAF inhibitor (e.g., dabrafenib), osimertinib (AZD9291), erlotinib, gefitinib, sorafenib, a CDK9 inhibitor (e.g., dinaciclib), a MCL-1 inhibitor, temozolomide, a Bcl-xL inhibitor, a Bcl-2 inhibitor (e.g., venetoclax), ibrutinib, a mTOR inhibitor (e.g., everolimus), a PI3K inhibitor (e.g., buparlisib), duvelisib, idelalisib, an AKT inhibitor, a HER2 inhibitor (e.g., lapatinib), Herceptin, a taxane (e.g., docetaxel, paclitaxel, nab-paclitaxel), an ADC comprising an auristatin, an ADC comprising a PBD (e.g., rovalpituzumab tesirine), an ADC comprising a maytansinoid (e.g., TDM1), a TRAIL agonist, a proteasome inhibitor (e.g., bortezomib), and a nicotinamide phosphoribosyltransferase (NAMPT) inhibitor. Additional examples of therapeutic agents that can be co-administered and/or formulated with one or more anti-B7-H3 antibodies or fragments thereof include one or more of: TNF antagonists (e.g., a soluble fragment of a TNF receptor, e.g., p55 or p75 human TNF receptor or derivatives thereof, e.g., 75 kD TNFR-IgG (75 kD TNF receptor-IgG fusion protein, ENBREL)); TNF enzyme antagonists, e.g., TNF converting enzyme (TACE) inhibitors; muscarinic receptor antagonists; TGF-beta antagonists; interferon gamma; perfenidone; chemotherapeutic agents, e.g., methotrexate, leflunomide, or a sirolimus (rapamycin) or an analog thereof, e.g., CCI-779; COX2 and cPLA2 inhibitors; NSAIDs; immunomodulators; p38 inhibitors, TPL-2, MK-2 and NFkB inhibitors, among others.

Other preferred combinations are cytokine suppressive anti-inflammatory drug(s) (CSAIDs); antibodies to or antagonists of other human cytokines or growth factors, for example, IL-1, IL-2, IL-3, IL-4, IL-5, IL-6, IL-7, IL-8, IL-15, IL-16, IL-18, IL-21, IL-31, interferons, EMAP-II, GM-CSF, FGF, EGF, PDGF, and edothelin-1, as well as the receptors of these cytokines and growth factors. Antibodies of the invention, or antigen binding portions thereof, can be combined with antibodies to cell surface molecules such as CD2, CD3, CD4, CD8, CD25, CD28, CD30, CD40, CD45, CD69, CD80 (B7.1), CD86 (B7.2), CD90, CTLA, CTLA-4, PD-1, or their ligands including CD154 (gp39 or CD40L).

Preferred combinations of therapeutic agents may interfere at different points in the inflammatory cascade; preferred examples include TNF antagonists like chimeric, humanized or human TNF antibodies, adalimumab, (HUMIRA; D2E7; PCT Publication No. WO 97/29131 and U.S. Pat. No. 6,090,382, incorporated by reference herein), CA2 (Remicade™), CDP 571, and soluble p55 or p75 TNF receptors, derivatives, thereof, (p75TNFR1gG (Enbrel™) or p55TNFR1gG (Lenercept), and also TNF converting enzyme (TACE) inhibitors; similarly IL-1 inhibitors (Interleukin-1-converting enzyme inhibitors, IL-1RA etc.) may be effective for the same reason. Other preferred combinations include Interleukin 4.

The pharmaceutical compositions of the invention may include a "therapeutically effective amount" or a "prophylactically effective amount" of an antibody or antibody portion of the invention. A "therapeutically effective amount" refers to an amount effective, at dosages and for periods of time necessary, to achieve the desired therapeutic result. A therapeutically effective amount of the antibody or antibody portion may be determined by a person skilled in the art and may vary according to factors such as the disease state, age, sex, and weight of the individual, and the ability of the antibody or antibody portion to elicit a desired response in the individual. A therapeutically effective amount is also one in which any toxic or detrimental effects of the antibody, or antibody portion, are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of an ADC, an antibody or antibody portion of the invention is 0.1-20 mg/kg, more preferably 1-10 mg/kg. In one embodiment, the dose of the antibody or ADC described herein is 1 to 6 mg/kg, including the individual doses recited therein, e.g., 1 mg/kg, 2 mg/kg, 3 mg/kg, 4 mg/kg, 5 mg/kg, and 6 mg/kg. In another embodiment, the dose of the antibody or ADC described herein is 1 to 200 µg/kg, including the individual doses recited therein, e.g., 1 µg/kg, 2 µg/kg, 3 µg/kg, 4 µg/kg, 5 µg/kg, 10 µg/kg, 20 µg/kg, 30 µg/kg, 40 µg/kg, 50 µg/kg, 60 µg/kg, 80 µg/kg, 100 µg/kg, 120 µg/kg, 140 µg/kg, 160 µg/kg, 180 µg/kg and 200 µg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

In one embodiment, an anti-B7-H3 ADC, including an ADC comprising antibody huAb13v1, huAb3v2.5, or huAb3v2.6, is administered to a subject in need thereof, e.g., a subject having cancer, at a dose of 0.1 to 30 mg/kg. In another embodiment, the anti-B7-H3 antibody, e.g., huAb13v1, huAb3v2.5, huAb3v2.6, or an antigen binding portion thereof, is administered to a subject in need thereof, e.g., a subject having cancer, as an ADC at a dose of 1 to 15 mg/kg. In another embodiment, the anti-B7-H3 antibody, e.g., huAb13v1, huAb3v2.5, huAb3v2.6, or an antigen binding portion thereof, is administered to a subject in need thereof, e.g., a subject having cancer, as an ADC at a dose of 1 to 10 mg/kg. In another embodiment, the anti-B7-H3 antibody, e.g., huAb13v1, huAb3v2.5, huAb3v2.6, or an antigen binding portion thereof, is administered to a subject in need thereof, e.g., a subject having cancer, as an ADC at a dose of 2 to 3. In another embodiment, the anti-B7-H3 antibody, e.g., huAb13v1, huAb3v2.5, huAb3v2.6, or an antigen binding portion thereof, is administered to a subject in need thereof, e.g., a subject having cancer, as an ADC at a dose of 1 to 4 mg/kg.

In one embodiment, an anti-B7-H3 antibody or ADC described herein, e.g., huAb13v1, huAb3v2.5, huAb3v2.6, is administered to a subject in need thereof, e.g., a subject having cancer, as an ADC at a dose of 1 to 200 µg/kg. In another embodiment, the anti-B7-H3 antibody, e.g., huAb13v1, huAb3v2.5, huAb3v2.6, or an antigen binding portion thereof, is administered to a subject in need thereof, e.g., a subject having cancer, as an ADC at a dose of 5 to 150 µg/kg. In another embodiment, the anti-B7-H3 antibody, e.g., huAb13v1, huAb3v2.5, huAb3v2.6, or an antigen binding portion thereof, is administered to a subject in need thereof, e.g., a subject having cancer, as an ADC at a dose of 5 to 100 µg/kg. In another embodiment, the anti-B7-H3 antibody, e.g., huAb13v1, huAb3v2.5, huAb3v2.6, or an antigen binding portion thereof, is administered to a subject in need thereof, e.g., a subject having cancer, as an ADC at a dose of 5 to 90 µg/kg. In another embodiment, the anti-B7-H3 antibody, e.g., huAb13v1, huAb3v2.5, huAb3v2.6, or an antigen binding portion thereof, is administered to a subject in need thereof, e.g., a subject having cancer, as an ADC at a dose of 5 to 80 µg/kg. In another embodiment, the anti-B7-H3 antibody, e.g., huAb13v1, huAb3v2.5, huAb3v2.6, or an antigen binding portion thereof, is administered to a subject in need thereof, e.g., a subject having cancer, as an ADC at a dose of 5 to 70 µg/kg. In another embodiment, the anti-B7-H3 antibody, e.g., huAb13v1, huAb3v2.5, huAb3v2.6, or an antigen binding portion thereof, is administered to a subject in need thereof, e.g., a subject having cancer, as an ADC at a dose of 5 to 60 µg/kg. In another embodiment, the anti-B7-H3 antibody, e.g., huAb13v1, huAb3v2.5, huAb3v2.6, or an antigen binding portion thereof, is administered to a subject in need thereof, e.g., a subject having cancer, as an ADC at a dose of 10 to 80 µg/kg.

Doses described above may be useful for the administration of either anti-B7-H3 ADCs or antibodies disclosed herein.

In another aspect, this application provides a method for detecting the presence of B7-H3 in a sample in vitro (e.g., a biological sample, such as serum, plasma, tissue, and biopsy). The subject method can be used to diagnose a disorder, e.g., a cancer. The method includes: (i) contacting the sample or a control sample with the anti-B7-H3 antibody or fragment thereof as described herein; and (ii) detecting formation of a complex between the anti-B7-H3 antibody or fragment thereof, and the sample or the control sample, wherein a statistically significant change in the formation of the complex in the sample relative to the control sample is indicative of the presence of B7-H3 in the sample.

Given their ability to bind to human B7-H3, the anti-human B7-H3 antibodies, or portions thereof, of the invention, (as well as ADCs thereof) can be used to detect human B7-H3 (e.g., in a biological sample, such as serum or plasma), using a conventional immunoassay, such as an enzyme linked immunosorbent assays (ELISA), an radioimmunoassay (RIA) or tissue immunohistochemistry. In one aspect, the invention provides a method for detecting human B7-H3 in a biological sample comprising contacting a biological sample with an antibody, or antibody portion, of the invention and detecting either the antibody (or antibody portion) bound to human B7-H3 or unbound antibody (or antibody portion), to thereby detect human B7-H3 in the biological sample. The antibody is directly or indirectly labeled with a detectable substance to facilitate detection of the bound or unbound antibody. Suitable detectable substances include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{3}H$, $^{14}C$, $^{35}S$, $^{90}Y$, $^{99}Tc$, $^{111}In$, $^{125}I$, $^{131}I$, $^{177}Lu$, $^{166}Ho$, or $^{153}Sm$.

Alternative to labeling the antibody, human B7-H3 can be assayed in biological fluids by a competition immunoassay utilizing rhB7-H3 standards labeled with a detectable substance and an unlabeled anti-human B7-H3 antibody. In this assay, the biological sample, the labeled rhB7-H3 standards and the anti-human B7-H3 antibody are combined and the amount of labeled rhB7-H3 standard bound to the unlabeled antibody is determined. The amount of human B7-H3 in the biological sample is inversely proportional to the amount of labeled rhB7-H3 standard bound to the anti-B7-H3 antibody. Similarly, human B7-H3 can also be assayed in biological fluids by a competition immunoassay utilizing rhB7-H3 standards labeled with a detectable substance and an unlabeled anti-human B7-H3 antibody.

In yet another aspect, this application provides a method for detecting the presence of B7-H3 in vivo (e.g., in vivo imaging in a subject). The subject method can be used to diagnose a disorder, e.g., a B7-H3-associated disorder. The method includes: (i) administering the anti-B7-H3 antibody or fragment thereof as described herein to a subject or a control subject under conditions that allow binding of the antibody or fragment to B7-H3; and (ii) detecting formation of a complex between the antibody or fragment and B7-H3, wherein a statistically significant change in the formation of the complex in the subject relative to the control subject is indicative of the presence of B7-H3.

VI. Pharmaceutical Compositions

The invention also provides pharmaceutical compositions comprising an antibody, or antigen binding portion thereof, or ADC of the invention and a pharmaceutically acceptable carrier. The pharmaceutical compositions comprising antibodies or ADCs of the invention are for use in, but not limited to, diagnosing, detecting, or monitoring a disorder, in preventing, treating, managing, or ameliorating of a disorder or one or more symptoms thereof, and/or in research. In a specific embodiment, a composition comprises one or more antibodies of the invention. In another embodiment, the pharmaceutical composition comprises one or more antibodies or ADCs of the invention and one or more prophylactic or therapeutic agents other than antibodies or ADCs of the invention for treating a disorder in which B7-H3 activity is detrimental. Preferably, the prophylactic or therapeutic agents known to be useful for or having been or currently being used in the prevention, treatment, management, or amelioration of a disorder or one or more symptoms thereof.

In accordance with these embodiments, the composition may further comprise of a carrier, diluent or excipient.

The antibodies and antibody-portions or ADCs of the invention can be incorporated into pharmaceutical compositions suitable for administration to a subject. Typically, the pharmaceutical composition comprises an antibody or antibody portion of the invention and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody or antibody portion or ADC.

Various delivery systems are known and can be used to administer one or more antibodies or ADCs of the invention or the combination of one or more antibodies of the invention and a prophylactic agent or therapeutic agent useful for preventing, managing, treating, or ameliorating a disorder or one or more symptoms thereof, e.g., encapsulation in liposomes, microparticles, microcapsules, recombinant cells capable of expressing the antibody or antibody fragment, receptor-mediated endocytosis (see, e.g., Wu and Wu, J. Biol. Chem. 262:4429-4432 (1987)), construction of a nucleic acid as part of a retroviral or other vector, etc. Methods of administering a prophylactic or therapeutic agent of the invention include, but are not limited to, parenteral administration (e.g., intradermal, intramuscular, intraperitoneal, intravenous and subcutaneous), epidural administration, intratumoral administration, and mucosal administration (e.g., intranasal and oral routes). In addition, pulmonary administration can be employed, e.g., by use of an inhaler or nebulizer, and formulation with an aerosolizing agent. See, e.g., U.S. Pat. Nos. 6,019,968, 5,985,320, 5,985,309, 5,934,272, 5,874,064, 5,855,913, 5,290,540, and 4,880,078; and PCT Publication Nos. WO 92/19244, WO 97/32572, WO 97/44013, WO 98/31346, and WO 99/66903, each of which is incorporated herein by reference their entireties. In one embodiment, an antibody of the invention, combination therapy, or a composition of the invention is administered using Alkermes AIR® pulmonary drug delivery technology (Alkermes, Inc., Cambridge, Mass.). In a specific embodiment, prophylactic or therapeutic agents of the invention are administered intramuscularly, intravenously, intratumorally, orally, intranasally, pulmonary, or subcutaneously. The prophylactic or therapeutic agents may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

In a specific embodiment, it may be desirable to administer the prophylactic or therapeutic agents of the invention locally to the area in need of treatment; this may be achieved by, for example, and not by way of limitation, local infusion, by injection, or by means of an implant, said implant being of a porous or non-porous material, including membranes and matrices, such as sialastic membranes, polymers, fibrous matrices (e.g., Tissuel®), or collagen matrices. In one embodiment, an effective amount of one or more antibodies of the invention antagonists is administered locally to the affected area to a subject to prevent, treat, manage, and/or ameliorate a disorder or a symptom thereof. In another embodiment, an effective amount of one or more antibodies of the invention is administered locally to the affected area in combination with an effective amount of one or more therapies (e.g., one or more prophylactic or therapeutic agents) other than an antibody of the invention of a subject to prevent, treat, manage, and/or ameliorate a disorder or one or more symptoms thereof.

In another embodiment, the prophylactic or therapeutic agent of the invention can be delivered in a controlled release or sustained release system. In one embodiment, a pump may be used to achieve controlled or sustained release (see Langer, supra; Sefton, 1987, CRC Crit. Ref Biomed. Eng. 14:20; Buchwald et al., 1980, Surgery 88:507; Saudek et al., 1989, N. Engl. J. Med. 321:574). In another embodiment, polymeric materials can be used to achieve controlled or sustained release of the therapies of the invention (see e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J., Macromol. Sci. Rev. Macromol. Chem. 23:61; see also Levy et al., 1985, Science 228:190; During et al., 1989, Ann. Neurol. 25:351; Howard et al., 1989, J. Neurosurg. 7 1:105); U.S. Pat. Nos. 5,679,377; 5,916,597; 5,912,015; 5,989,463; 5,128,326; PCT Publication No. WO 99/15154; and PCT Publication No. WO 99/20253. Examples of polymers used in sustained release formulations include, but are not limited to, poly(2-hydroxy ethyl methacrylate), poly(methyl methacrylate), poly (acrylic acid), poly(ethylene-co-vinyl acetate), poly(methacrylic acid), polyglycolides (PLG), polyanhydrides, poly (N-vinyl pyrrolidone), poly(vinyl alcohol), polyacrylamide, poly(ethylene glycol), polylactides (PLA), poly(lactide-co-glycolides) (PLGA), and polyorthoesters. In a preferred embodiment, the polymer used in a sustained release formulation is inert, free of leachable impurities, stable on storage, sterile, and biodegradable. In yet another embodiment, a controlled or sustained release system can be placed in proximity of the prophylactic or therapeutic target, thus requiring only a fraction of the systemic dose (see, e.g., Goodson, in Medical Applications of Controlled Release, supra, vol. 2, pp. 115-138 (1984)).

Controlled release systems are discussed in the review by Langer (1990, Science 249:1527-1533). Any technique known to one of skill in the art can be used to produce sustained release formulations comprising one or more therapeutic agents of the invention. See, e.g., U.S. Pat. No. 4,526,938, PCT publication WO 91/05548, PCT publication WO 96/20698, Ning et al., 1996, "Intratumoral Radioimmunotherapy of a Human Colon Cancer Xenograft Using a Sustained-Release Gel," Radiotherapy & Oncology 39:179-189, Song et al., 1995, "Antibody Mediated Lung Targeting of Long-Circulating Emulsions," PDA Journal of Pharmaceutical Science & Technology 50:372-397, Cleek et al., 1997, "Biodegradable Polymeric Carriers for a bFGF Antibody for Cardiovascular Application," Pro. Int'l. Symp. Control. Rel. Bioact. Mater. 24:853-854, and Lam et al., 1997, "Microencapsulation of Recombinant Humanized Monoclonal Antibody for Local Delivery," Proc. Int'l. Symp. Control Rel. Bioact. Mater. 24:759-760, each of which is incorporated herein by reference in their entireties.

In a specific embodiment, where the composition of the invention is a nucleic acid encoding a prophylactic or therapeutic agent, the nucleic acid can be administered in vivo to promote expression of its encoded prophylactic or therapeutic agent, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see, e.g., Joliot et al., 1991, *Proc. Natl. Acad. Sci. USA* 88:1864-1868). Alternatively, a nucleic acid can be introduced intracellularly and incorporated within host cell DNA for expression by homologous recombination.

A pharmaceutical composition of the invention is formulated to be compatible with its intended route of administration. Examples of routes of administration include, but are not limited to, parenteral, e.g., intravenous, intradermal, subcutaneous, oral, intranasal (e.g., inhalation), transdermal (e.g., topical), transmucosal, and rectal administration. In a specific embodiment, the composition is formulated in accordance with routine procedures as a pharmaceutical composition adapted for intravenous, subcutaneous, intramuscular, oral, intranasal, or topical administration to human beings. Typically, compositions for intravenous administration are solutions in sterile isotonic aqueous buffer. Where necessary, the composition may also include a solubilizing agent and a local anesthetic such as lignocaine to ease pain at the site of the injection.

If the method of the invention comprises intranasal administration of a composition, the composition can be formulated in an aerosol form, spray, mist or in the form of drops. In particular, prophylactic or therapeutic agents for use according to the invention can be conveniently delivered in the form of an aerosol spray presentation from pressurized packs or a nebulizer, with the use of a suitable propellant (e.g., dichlorodifluoromethane, trichlorofluoromethane, dichlorotetrafluoroethane, carbon dioxide or other suitable gas). In the case of a pressurized aerosol the dosage unit may be determined by providing a valve to deliver a metered amount. Capsules and cartridges (composed of, e.g., gelatin) for use in an inhaler or insufflator may be formulated containing a powder mix of the compound and a suitable powder base such as lactose or starch.

If the method of the invention comprises oral administration, compositions can be formulated orally in the form of tablets, capsules, cachets, gel caps, solutions, suspensions, and the like. Tablets or capsules can be prepared by conventional means with pharmaceutically acceptable excipients such as binding agents (e.g., pregelatinised maize starch, polyvinylpyrrolidone, or hydroxypropyl methylcellulose); fillers (e.g., lactose, microcrystalline cellulose, or calcium hydrogen phosphate); lubricants (e.g., magnesium stearate, talc, or silica); disintegrants (e.g., potato starch or sodium starch glycolate); or wetting agents (e.g., sodium lauryl sulphate). The tablets may be coated by methods well-known in the art. Liquid preparations for oral administration may take the form of, but not limited to, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, flavoring, coloring, and sweetening agents as appropriate. Preparations for oral administration may be suitably formulated for slow release, controlled release, or sustained release of a prophylactic or therapeutic agent(s).

The method of the invention may comprise pulmonary administration, e.g., by use of an inhaler or nebulizer, of a composition formulated with an aerosolizing agent. See, e.g., U.S. Pat. Nos. 6,019,968, 5,985,320, 5,985,309, 5,934,272, 5,874,064, 5,855,913, 5,290,540, and 4,880,078; and PCT Publication Nos. WO 92/19244, WO 97/32572, WO 97/44013, WO 98/31346, and WO 99/66903, each of which is incorporated herein by reference their entireties. In a specific embodiment, an antibody of the invention, combination therapy, and/or composition of the invention is administered using Alkermes AIR® pulmonary drug delivery technology (Alkermes, Inc., Cambridge, Mass.).

The method of the invention may comprise administration of a composition formulated for parenteral administration by injection (e.g., by bolus injection or continuous infusion). Formulations for injection may be presented in unit dosage form (e.g., in ampoules or in multi-dose containers) with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle (e.g., sterile pyrogen-free water) before use.

The methods of the invention may additionally comprise of administration of compositions formulated as depot preparations. Such long acting formulations may be administered by implantation (e.g., subcutaneously or intramuscularly) or by intramuscular injection. Thus, for example, the compositions may be formulated with suitable polymeric or hydrophobic materials (e.g., as an emulsion in an acceptable oil) or ion exchange resins, or as sparingly soluble derivatives (e.g., as a sparingly soluble salt).

The methods of the invention encompass administration of compositions formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

Generally, the ingredients of compositions are supplied either separately or mixed together in unit dosage form, for example, as a dry lyophilized powder or water free concentrate in a hermetically sealed container such as an ampoule or sachette indicating the quantity of active agent. Where the mode of administration is infusion, composition can be dispensed with an infusion bottle containing sterile pharmaceutical grade water or saline. Where the mode of administration is by injection, an ampoule of sterile water for injection or saline can be provided so that the ingredients may be mixed prior to administration.

In particular, the invention also provides that one or more of the prophylactic or therapeutic agents, or pharmaceutical compositions of the invention is packaged in a hermetically sealed container such as an ampoule or sachette indicating the quantity of the agent. In one embodiment, one or more of the prophylactic or therapeutic agents, or pharmaceutical compositions of the invention is supplied as a dry sterilized lyophilized powder or water free concentrate in a hermetically sealed container and can be reconstituted (e.g., with water or saline) to the appropriate concentration for administration to a subject. Preferably, one or more of the prophylactic or therapeutic agents or pharmaceutical compositions of the invention is supplied as a dry sterile lyophilized powder in a hermetically sealed container at a unit dosage of at least 5 mg, at least 10 mg, at least 15 mg, at least 25 mg, at least 35 mg, at least 45 mg, at least 50 mg, at least 75 mg, or at least 100 mg. The lyophilized prophylactic or therapeutic agents or pharmaceutical compositions of the invention should be stored at between 2° C. and 8° C. in its original container and the prophylactic or therapeutic agents, or pharmaceutical compositions of the invention should be administered within 1 week, within 5 days, within 72 hours, within 48 hours, within 24 hours, within 12 hours, within 6 hours, within 5 hours, within 3 hours, or within 1 hour after being reconstituted. In an alternative embodiment, one or more of the prophylactic or therapeutic agents or pharmaceutical compositions of the invention is supplied in liquid form in a hermetically sealed container indicating the quantity and concentration of the agent. Preferably, the liquid form of the administered composition is supplied in a hermetically sealed container at least 0.25 mg/ml, at least 0.5 mg/ml, at least 1 mg/ml, at least 2.5 mg/ml, at least 5 mg/ml, at least 8 mg/ml, at least 10 mg/ml, at least 15 mg/kg, at least 25 mg/ml, at least 50 mg/ml, at least 75 mg/ml or at least 100 mg/ml. The liquid form should be stored at between 2° C. and 8° C. in its original container.

The antibodies and antibody-portions of the invention can be incorporated into a pharmaceutical composition suitable for parenteral administration. Preferably, the antibody or antibody-portions will be prepared as an injectable solution containing 0.1-250 mg/ml antibody. The injectable solution can be composed of either a liquid or lyophilized dosage form in a flint or amber vial, ampule or pre-filled syringe. The buffer can be L-histidine (1-50 mM), optimally 5-10 mM, at pH 5.0 to 7.0 (optimally pH 6.0). Other suitable buffers include but are not limited to, sodium succinate, sodium citrate, sodium phosphate or potassium phosphate. Sodium chloride can be used to modify the toxicity of the solution at a concentration of 0-300 mM (optimally 150 mM for a liquid dosage form). Cryoprotectants can be included for a lyophilized dosage form, principally 0-10% sucrose (optimally 0.5-1.0%). Other suitable cryoprotectants include trehalose and lactose. Bulking agents can be included for a lyophilized dosage form, principally 1-10% mannitol (optimally 2-4%). Stabilizers can be used in both liquid and lyophilized dosage forms, principally 1-50 mM L-methionine (optimally 5-10 mM). Other suitable bulking agents include glycine, arginine, can be included as 0-0.05% polysorbate-80 (optimally 0.005-0.01%). Additional surfactants include but are not limited to polysorbate 20 and BRIJ surfactants. The pharmaceutical composition comprising the antibodies and antibody-portions of the invention prepared as an injectable solution for parenteral administration, can further comprise an agent useful as an adjuvant, such as those used to increase the absorption, or dispersion of a therapeutic protein (e.g., antibody). A particularly useful adjuvant is hyaluronidase, such as Hylenex® (recombinant human hyaluronidase). Addition of hyaluronidase in the injectable solution improves human bioavailability following parenteral administration, particularly subcutaneous administration. It also allows for greater injection site volumes (i.e. greater than 1 ml) with less pain and discomfort, and minimum incidence of injection site reactions. (see WO2004078140, US2006104968 incorporated herein by reference).

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans with other antibodies. The preferred mode of administration is parenteral (e.g., intravenous, subcutaneous, intraperitoneal, intramuscular). In a preferred embodiment, the antibody is administered by intravenous infusion or injection. In another preferred embodiment, the antibody is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., antibody or antibody portion) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile, lyophilized powders for the preparation of sterile injectable solutions, the preferred methods of preparation are vacuum drying and spray-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including, in the composition, an agent that delays absorption, for example, monostearate salts and gelatin.

The antibodies and antibody-portions or ADCs of the invention can be administered by a variety of methods known in the art, although for many therapeutic applications, the preferred route/mode of administration is subcutaneous injection, intravenous injection or infusion. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

In certain embodiments, an antibody or antibody portion or ADC of the invention may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

In other embodiments, an antibody or antibody portion or ADC of the invention may be conjugated to a polymer-based species such that said polymer-based species may confer a sufficient size upon said antibody or antibody portion of the invention such that said antibody or antibody portion of the invention benefits from the enhanced permeability and retention effect (EPR effect) (See also PCT Publication No. WO2006/042146A2 and U.S. Publication Nos. 2004/0028687A1, 2009/0285757A1, and 2011/0217363A1, and U.S. Pat. No. 7,695,719 (each of which is incorporated by reference herein in its entirety and for all purposes).

Supplementary active compounds can also be incorporated into the compositions. In certain embodiments, an antibody or antibody portion or ADC of the invention is formulated with and/or co-administered with one or more additional therapeutic agents that are useful for treating disorders in which B7-H3 activity is detrimental. For example, an anti-hB7-H3 antibody or antibody portion or ADC of the invention may be formulated and/or co-administered with one or more additional antibodies that bind other targets (e.g., antibodies that bind cytokines or that bind cell surface molecules). Furthermore, one or more antibodies of the invention may be used in combination with two or more of the foregoing therapeutic agents. Such combination therapies may advantageously utilize lower dosages of the administered therapeutic agents, thus avoiding possible toxicities or complications associated with the various monotherapies.

In certain embodiments, an antibody or ADC to B7-H3 or fragment thereof is linked to a half-life extending vehicle known in the art. Such vehicles include, but are not limited to, the Fc domain, polyethylene glycol, and dextran. Such vehicles are described, e.g., in U.S. application Ser. No. 09/428,082 and published PCT Application No. WO 99/25044, which are hereby incorporated by reference for any purpose.

It will be readily apparent to those skilled in the art that other suitable modifications and adaptations of the methods of the invention described herein are obvious and may be made using suitable equivalents without departing from the scope of the invention or the embodiments disclosed herein. Having now described the invention in detail, the same will be more clearly understood by reference to the following examples, which are included for purposes of illustration only and are not intended to be limiting

EXAMPLES

Example 1: Synthesis of Exemplary Bcl-xL Inhibitors

This example provides synthetic methods for exemplary Bcl-xL inhibitory compounds W2.01-W2.91. Bcl-xL inhibitors (W2.01-W2.91) and synthons (Examples 2.1-2.176) were named using ACD/Name 2012 release (Build 56084, 5 Apr. 2012, Advanced Chemistry Development Inc., Toronto, Ontario), ACD/Name 2014 release (Build 66687, 25 Oct. 2013, Advanced Chemistry Development Inc., Toronto, Ontario), ChemDraw® Ver. 9.0.7 (CambridgeSoft, Cambridge, Mass.), ChemDraw® Ultra Ver. 12.0 (CambridgeSoft, Cambridge, Mass.), or ChemDraw® Professional Ver. 15.0.0.106. Bcl-xL inhibitor and synthon intermediates were named with ACD/Name 2012 release (Build 56084, 5 Apr. 2012, Advanced Chemistry Development Inc., Toronto, Ontario), ACD/Name 2014 release (Build 66687, 25 Oct. 2013, Advanced Chemistry Development Inc., Toronto, Ontario), ChemDraw® Ver. 9.0.7 (CambridgeSoft, Cambridge, Mass.), ChemDraw® Ultra Ver. 12.0 (CambridgeSoft, Cambridge, Mass.), or ChemDraw® Professional Ver. 15.0.0.106.

1.1 Synthesis of 6-[8-(1,3-benzothiazol-2-ylcarbamoyl)-3,4-dihydroisoquinolin-2(1H)-yl]-3-[1-({3-[2-({2-[2-(carboxymethoxy)ethoxy]ethyl}amino)ethoxy]-5,7-dimethyltricyclo[3.3.1.1$^{3,7}$]dec-1-yl}methyl)-5-methyl-1H-pyrazol-4-yl]pyridine-2-carboxylic acid (Compound W2.01)

1.1.1 3-bromo-5,7-dimethyladamantanecarboxylic acid

Into a 50 mL round-bottomed flask at 0° C., was added bromine (16 mL). Iron powder (7 g) was added, and the reaction was stirred at 0° C. for 30 minutes. 3,5-Dimethyladamantane-1-carboxylic acid (12 g) was added. The mixture was warmed up to room temperature and stirred for 3 days. A mixture of ice and concentrated HCl was poured into the reaction mixture. The resulting suspension was treated twice with Na$_2$SO$_3$ (50 g in 200 mL water) and extracted three times with dichloromethane. The combined organics were washed with 1N aqueous HCl, dried over sodium sulfate, filtered, and concentrated to give the title compound.

1.1.2 3-bromo-5,7-dimethyladamantanemethanol

To a solution of Example 1.1.1 (15.4 g) in tetrahydrofuran (200 mL) was added BH$_3$ (1M in tetrahydrofuran, 150 mL), and the mixture was stirred at room temperature overnight. The reaction mixture was then carefully quenched by adding methanol dropwise. The mixture was then concentrated under vacuum, and the residue was balanced between ethyl acetate (500 mL) and 2N aqueous HCl (100 mL). The aqueous layer was further extracted twice with ethyl acetate, and the combined organic extracts were washed with water and brine, dried over sodium sulfate, and filtered. Evaporation of the solvent gave the title compound.

1.1.3 1-((3-bromo-5,7-dimethyltricyclo[3.3.1.1$^{3,7}$]dec-1-yl)methyl)-1H-pyrazole To a solution of Example 1.1.2 (8.0 g) in toluene (60 mL) was added 1H-pyrazole (1.55 g) and cyanomethylenetributylphosphorane (2.0 g), and the mixture was stirred at 90° C. overnight. The reaction mixture was concentrated, and the residue was purified by silica gel column chromatography (10:1 heptane:ethyl acetate) to give the title compound. MS (ESI) m/e 324.2 (M+H)$^+$.

1.1.4 2-{[3,5-dimethyl-7-(1H-pyrazol-1-ylmethyl)tricyclo[3.3.1.1$^{3,7}$]dec-1-yl]oxy}ethanol To a solution of Example 1.1.3 (4.0 g) in ethane-1,2-diol (12 mL) was added triethylamine (3 mL). The mixture was stirred at 150° C. under microwave conditions (Biotage Initiator) for 45 minutes. The mixture was poured into water (100 mL) and extracted three times with ethyl acetate. The combined organic extracts were washed with water and brine, dried over sodium sulfate, and filtered. Evaporation of the solvent gave a residue that was purified by silica gel chromatography, eluting with 20% ethyl acetate in heptane, followed by 5% methanol in dichloromethane, to give the title compound. MS (ESI) m/e 305.2 (M+H)$^+$.

1.1.5 2-({3,5-dimethyl-7-[(5-methyl-1H-pyrazol-1-yl)methyl]tricyclo[3.3.1.1$^{3,7}$]dec-1-yl}oxy)ethanol To a cooled (−78° C.) solution of Example 1.1.4 (6.05 g) in tetrahydrofuran (100 mL) was added n-BuLi (40 mL, 2.5M in hexane), and the mixture was stirred at −78° C. for 1.5 hours. Iodomethane (10 mL) was added through a syringe, and the mixture was stirred at −78° C. for 3 hours. The reaction mixture was then quenched with aqueous NH$_4$Cl and extracted twice with ethyl acetate, and the combined organic extracts were washed with water and brine. After drying over sodium sulfate, the solution was filtered and concentrated, and the residue was purified by silica gel column chromatography, eluting with 5% methanol in dichloromethane, to give the title compound. MS (ESI) m/e 319.5 (M+H)$^+$.

1.1.6 1-({3,5-dimethyl-7-[2-(hydroxy)ethoxy]tricyclo[3.3.1.1$^{3,7}$]dec-1-yl}methyl)-4-iodo-5-methyl-1H-pyrazole To a solution of Example 1.1.5 (3.5 g) in N,N-dimethylformamide (30 mL) was added N-iodosuccinimide (3.2 g), and the mixture was stirred at room temperature for 1.5 hours. The reaction mixture was diluted with ethyl acetate (600 mL) and washed with aqueous NaHSO$_3$, water and brine. The organic layer was dried over sodium sulfate, filtered and concentrated under reduced pressure. The residue was purified by silica gel chromatography, eluting with 20% ethyl acetate in dichloromethane, to give the title compound. MS (ESI) m/e 445.3 (M+H)$^+$.

1.1.7 1-((3-(2-((tert-butyldimethylsilyl)oxy)ethoxy)-5,7-dimethyladamantan-1-yl)methyl)-4-iodo-5-methyl-1H-pyrazole Tert-butyldimethylsilyl trifluoromethanesulfonate (5.34 mL) was added to a solution of Example 1.1.6 (8.6 g) and 2,6-lutidine (3.16 mL) in dichloromethane (125 mL) at −40° C., and the reaction was allowed to warm to room temperature overnight. The mixture was concentrated, and the residue was purified by silica gel chromatography, eluting with 5-20% ethyl acetate in heptanes, to give the title compound. MS (ESI) m/e 523.4 (M+H)$^+$.

1.1.8 1-((3-(2-((tert-butyldimethylsilyl)oxy)ethoxy)-5,7-dimethyladamantan-1-yl)methyl)-5-methyl-4-(4,4,5,5-tetramethyl-1,3,2-dioxaborolan-2-yl)-1H-pyrazole n-Butyllithium (8.42 mL, 2.5M in hexanes) was added to Example 1.1.7 (9.8 g) in 120 mL tetrahydrofuran at −78° C., and the reaction was stirred for 1 minute. Trimethyl borate (3.92 mL) was added, and the reaction stirred for 5 minutes. Pinacol (6.22 g) was added, and the reaction was allowed to warm to room temperature and was stirred 2 hours. The reaction was quenched with pH 7 buffer, and the mixture was poured into ether. The layers were separated, and the organic layer was concentrated under reduced pressure. The residue was purified by silica gel chromatography, eluting with 1-25% ethyl acetate in heptanes, to give the title compound.

1.1.9 6-fluoro-3-bromopicolinic acid

A slurry of 6-amino-3-bromopicolinic acid (25 g) in 400 mL 1:1 dichloromethane/chloroform was added to nitrosonium tetrafluoroborate (18.2 g) in dichloromethane (100 mL) at 5° C. over 1 hour. The resulting mixture was stirred for another 30 minutes, then warmed to 35° C. and stirred overnight. The reaction was cooled to room temperature, and then adjusted to pH 4 with aqueous NaH$_2$PO$_4$ solution. The resulting solution was extracted three times with dichloromethane, and the combined extracts were washed with brine, dried over sodium sulfate, filtered and concentrated to provide the title compound.

1.1.10 Tert-butyl 3-bromo-6-fluoropicolinate

Para-toluenesulfonyl chloride (27.6 g) was added to a solution of Example 1.1.9 (14.5 g) and pyridine (26.7 mL) in dichloromethane (100 mL) and tert-butanol (80 mL) at 0° C. The reaction was stirred for 15 minutes, and then warmed to room temperature, and stirred overnight. The solution was concentrated and partitioned between ethyl acetate and aqueous Na$_2$CO$_3$ solution. The layers were separated, and the aqueous layer extracted with ethyl acetate. The organic layers were combined, rinsed with aqueous Na$_2$CO$_3$ solution and brine, dried over sodium sulfate, filtered, and concentrated to provide the title compound.

1.1.11 methyl 2-(5-bromo-6-(tert-butoxycarbonyl)pyridin-2-yl)-1,2,3,4-tetrahydroisoquinoline-8-carboxylate To a solution of methyl 1,2,3,4-tetrahydroisoquinoline-8-carboxylate hydrochloride (12.37 g) and Example 1.1.10 (15 g) in dimethyl sulfoxide (100 mL) was added N,N-diisopropylethylamine (12 mL), and the mixture was stirred at 50° C. for 24 hours. The mixture was then diluted with ethyl acetate (500 mL) and washed with water and brine. The organic layer was dried over sodium sulfate, filtered and concentrated under reduced pressure. The residue was purified by silica gel chromatography, eluting with 20% ethyl acetate in hexane, to give the title compound. MS (ESI) m/e 448.4 (M+H)$^+$.

1.1.12 methyl 2-(6-(tert-butoxycarbonyl)-5-(1-((3-(2-((tert-butyldimethylsilyl)oxy)ethoxy)-5,7-dimethyladamantan-1-yl)methyl)-5-methyl-1H-pyrazol-4-yl)pyridin-2-yl)-1,2,3,4-tetrahydroisoquinoline-8-carboxylate A mixture of Example 1.1.11 (3.08 g), Example 1.1.8 (5 g), tris(dibenzylideneacetone)dipalladium(0) (126 mg), 1,3,5,7-tetramethyl-8-tetradecyl-2,4,6-trioxa-8-phosphaadamantane (170 mg), and K$_3$PO$_4$ (3.65 g) in 1,4-dioxane (25 mL) and water (25 mL) was heated to 90° C. for 2 hours. The mixture was cooled and poured into 1:1 diethyl ether:ethyl acetate. The layers were separated, and the organic was washed with saturated aqueous NaH$_2$PO$_4$ solution, water (2×), and brine. The organic layer was dried over sodium sulfate, filtered, and concentrated. The residue was purified by silica gel chromatography, eluting with 1-25% ethyl acetate in heptanes, to give the title compound. MS (ESI) m/e 799.6 (M+H)$^+$.

1.1.13 2-(6-(tert-butoxycarbonyl)-5-(1-((3-(2-((tert-butyldimethylsilyl)oxy)ethoxy)-5,7-dimethyladamantan-1-yl)methyl)-5-methyl-1H-pyrazol-4-yl)pyridin-2-yl)-1,2,3,4-tetrahydroisoquinoline-8-carboxylic acid Example 1.1.12 (5 g) and lithium hydroxide monohydrate (0.276 g) were stirred together in a solvent mixture of tetrahydrofuran (50 mL), methanol (5 mL) and water (15 mL) at 70° C. for 2 days. The reaction was cooled, acidified with 1M aqueous HCl solution, and extracted twice with ethyl acetate. The combined organic layers were washed with brine, dried over sodium sulfate, filtered, and concentrated. The residue was dissolved in dichloromethane (100 mL), cooled at −40° C., and 2,6-lutidine (1.8 mL) and tert-butyldimethylsilyl trifluoromethanesulfonate (3.28 g) were added. The reaction was allowed to warm to room temperature and was stirred for 2 hours. The mixture was diluted with ether, and the layers were separated. The organic layer was concentrated. The residue was dissolved in tetrahydrofuran and treated with saturated aqueous $K_2CO_3$ solution for 1 hour. This mixture was acidified with concentrated HCl and extracted twice with ethyl acetate. The combined organic layers were dried over sodium sulfate, filtered, and concentrated under reduced pressure. The residue was purified by silica gel chromatography, eluting with 10-100% ethyl acetate in heptanes then 5% methanol in ethyl acetate, to give the title compound. MS (ESI) m/e 785.6 $(M+H)^+$.

1.1.14 tert-butyl 6-(8-(benzo[d]thiazol-2-ylcarbamoyl)-3,4-dihydroisoquinolin-2(1H)-yl)-3-(1-((3-(2-hydroxyethoxy)-5,7-dimethyladamantan-1-yl)methyl)-5-methyl-1H-pyrazol-4-yl)picolinate Example 1.1.13 (970 mg), N,N-diisopropylethylamine (208 mg), and 2-(3H-[1,2,3]triazolo[4,5-b]pyridin-3-yl)-1,1,3,3-tetramethylisouronium hexafluorophosphate (HATU) (970 mg) were stirred in 7 mL N,N-dimethylformamide at 0° C. for 10 minutes. Benzo[d]thiazol-2-amine (278 mg) was added, and the mixture was stirred for 24 hours at 50° C. The mixture was cooled and diluted with ethyl acetate. The organic layer was washed with water and brine, dried over sodium sulfate, filtered, and concentrated. The residue was dissolved in tetrahydrofuran (50 mL), and tetrabutyl ammonium fluoride (10 mL, 1M in tetrahydrofuran) was added. The reaction was stirred for 1 hour, poured into ethyl acetate and washed with pH 7 buffer and brine. The organic layer was dried over sodium sulfate, filtered, and concentrated under reduced pressure. The residue was purified by silica gel chromatography, eluting with 10-100% ethyl acetate in heptanes, to give the title compound. MS (ESI) m/e 803.7 $(M+H)^+$.

1.1.15 tert-butyl 6-(8-(benzo[d]thiazol-2-ylcarbamoyl)-3,4-dihydroisoquinolin-2(1H)-yl)-3-(1-((3,5-dimethyl-7-(2-oxoethoxy)adamantan-1-yl)methyl)-5-methyl-1H-pyrazol-4-yl)picolinate To an ambient solution of Example 1.1.14 (100 mg) in dichloromethane (1.3 mL) was added Dess-Martin periodinane (58.1 mg) in a single portion. The reaction was stirred for 0.5 hours, and additional Dess-Martin periodinane (8 mg) was added. The reaction was stirred for 1 hour and quenched by the addition of ~10% aqueous NaOH solution and dichloromethane. The layers were separated, and the organic layer was washed with ~10% aqueous NaOH solution. The organic layer was dried with anhydrous sodium sulfate, filtered and concentrated under reduced pressure to a solid, which was used in the subsequent reaction without further purification. MS (ESI) m/e 801.3 $(M+H)^+$.

1.1.16 2-(2-(2-((2-((3-((4-(6-(8-(benzo[d]thiazol-2-ylcarbamoyl)-3,4-dihydroisoquinolin-2(1H)-yl)-2-(tert-butoxycarbonyl)pyridin-3-yl)-5-methyl-1H-pyrazol-1-yl)methyl)-5,7-dimethyladamantan-1-yl)oxy)ethyl)amino)ethoxy)ethoxy)acetic acid To an ambient solution of 2-(2-(2-aminoethoxy)ethoxy)acetic acid (22 mg) and Example 1.1.15 (100 mg) in methanol (1.3 mL) was added $MP-CNBH_3$ (65 mg, 2.49 mmol/g loading). The reaction was gently shaken overnight and filtered through a 0.4 micron filter. The crude material was purified by reverse phase HPLC using a Gilson system, eluting with 20-80% acetonitrile in water containing 0.1% v/v trifluoroacetic acid. The desired fractions were combined and freeze-dried to provide the title compound. MS (ESI) m/e 948.3 $(M+H)^+$.

1.1.17 6-(8-(benzo[d]thiazol-2-ylcarbamoyl)-3,4-dihydroisoquinolin-2(1H)-yl)-3-(1-((3-(2-((2-(2-(carboxymethoxy)ethoxy)ethyl)amino)ethoxy)-5,7-dimethyladamantan-1-yl)methyl)-5-methyl-1H-pyrazol-4-yl)picolinic acid To an ambient solution of Example 1.1.16 (15 mg) in dichloromethane (1 mL) was added trifluoroacetic acid (1 mL). The reaction was stirred for 16 hours and then concentrated under reduced pressure. The residue was purified by reverse phase HPLC using a Gilson system, eluting with 20-80% acetonitrile in water containing 0.1% v/v trifluoroacetic acid. The desired fractions were combined and freeze-dried to provide the title compound. $^1$H NMR (400 MHz, dimethyl sulfoxide-$d_6$) δ ppm 12.70 (bs, 2H), 8.29 (s, 1H), 8.03 (d, 1H), 7.79 (d, 1H), 7.62 (d, 1H), 7.53-7.42 (m, 3H), 7.40-7.32 (m, 2H), 7.29 (s, 1H), 6.96 (d, 1H), 4.96 (bs, 2H), 4.03 (s, 2H), 3.90 (t, 2H), 3.84 (s, 2H), 3.68 (t, 2H), 3.63-3.54 (m, 6H), 3.17-3.04 (m, 4H), 3.00 (t, 2H), 2.10 (s, 3H), 1.45-1.40 (m, 2H), 1.36-1.20 (m, 4H), 1.21-0.96 (m, 7H), 0.91-0.81 (m, 6H). MS (ESI) m/e 892.3 $(M+H)^+$.

1.2 Synthesis of 6-[8-(1,3-benzothiazol-2-ylcarbamoyl)-3,4-dihydroisoquinolin-2(1H)-yl]-3-{1-[(3,5-dimethyl-7-{2-[(2-sulfoethyl)amino]ethoxy}tricyclo[3.3.1.1$^{3,7}$]dec-1-yl)methyl]-5-methyl-1H-pyrazol-4-yl}pyridine-2-carboxylic acid (Compound W2.02)

1.2.1 methyl 2-(6-(tert-butoxycarbonyl)-5-(4,4,5,5-tetramethyl-1,3,2-dioxaborolan-2-yl)pyridin-2-yl)-1,2,3,4-tetrahydroisoquinoline-8-carboxylate To a solution of Example 1.1.11 (2.25 g) and [1,1'-bis(diphenylphosphino)ferrocene]dichloropalladium(II) (205 mg) in acetonitrile (30 mL) was added triethylamine (3 mL) and pinacolborane (2 mL), and the mixture was stirred at reflux for 3 hours. The mixture was diluted with ethyl acetate (200 mL) and washed with water and brine. The organic layer was dried over sodium sulfate, filtered and concentrated under reduced pressure. Purification of the residue by silica gel chromatography, eluting with 20% ethyl acetate in hexane, provided the title compound.

1.2.2 methyl 2-(6-(tert-butoxycarbonyl)-5-(1-((3-(2-hydroxyethoxy)-5,7-dimethyladamantan-1-yl)methyl)-5-methyl-1H-pyrazol-4-yl)pyridin-2-yl)-1,2,3,4-tetrahydroisoquinoline-8-carboxylate To a solution of Example 1.2.1 (2.25 g) in tetrahydrofuran (30 mL) and water (10 mL) was added Example 1.1.6 (2.0 g), 1,3,5,7-tetramethyl-6-phenyl-2,4,8-trioxa-6-phosphaadamantane (329 mg), tris(dibenzylideneacetone)dipalladium(0) (206 mg) and potassium phosphate tribasic (4.78 g). The mixture was refluxed overnight, cooled and diluted with ethyl acetate (500 mL). The resulting mixture was washed with water and brine, and the organic layer was dried over sodium sulfate, filtered and concentrated. The residue was purified by flash chromatography, eluting with 20% ethyl acetate in heptanes followed by 5% methanol in dichloromethane, to provide the title compound.

1.2.3 methyl 2-(6-(tert-butoxycarbonyl)-5-(1-((3,5-dimethyl-7-(2-((methylsulfonyl)oxy)ethoxy)adamantan-1-yl)methyl)-5-methyl-1H-pyrazol-4-yl)pyridin-2-yl)-1,2,3,4-tetrahydroisoquinoline-8-carboxylate To a cold solution of Example 1.2.2 (3.32 g) in dichloromethane (100 mL) in an ice-bath was sequentially added triethylamine (3 mL) and methanesulfonyl chloride (1.1 g). The reaction mixture was stirred at room temperature for 1.5 hours and diluted with ethyl acetate, and washed with water and brine. The organic layer was dried over sodium sulfate, filtered, and concentrated to provide the title compound.

1.2.4 methyl 2-(5-(1-((3-(2-azidoethoxy)-5,7-dimethyladamantan-1-yl)methyl)-5-methyl-1H-pyrazol-4-yl)-6-(tert-butoxycarbonyl)pyridin-2-yl)-1,2,3,4-tetrahydroisoquinoline-8-carboxylate To a solution of Example 1.2.3 (16.5 g) in N,N-dimethylformamide (120 mL) was added sodium azide (4.22 g). The mixture was heated at 80° C. for 3 hours, cooled, diluted with ethyl acetate and washed with water and brine. The organic layer was dried over sodium sulfate, filtered, and concentrated. The residue was purified by flash chromatography, eluting with 20% ethyl acetate in heptanes, to provide the title compound.

1.2.5 2-(5-(1-((3-(2-azidoethoxy)-5,7-dimethyladamantan-1-yl)methyl)-5-methyl-1H-pyrazol-4-yl)-6-(tert-butoxycarbonyl)pyridin-2-yl)-1,2,3,4-tetrahydroisoquinoline-8-carboxylic acid To a solution of Example 1.2.4 (10 g) in a mixture of tetrahydrofuran (60 mL), methanol (30 mL) and water (30 mL) was added lithium hydroxide monohydrate (1.2 g). The mixture was stirred at room temperature overnight and neutralized with 2% aqueous HCl. The resulting mixture was concentrated, and the residue was dissolved in ethyl acetate (800 mL), and washed with brine. The organic layer was dried over sodium sulfate, filtered, and concentrated to provide the title compound.

1.2.6 tert-butyl 3-(1-((3-(2-azidoethoxy)-5,7-dimethyladamantan-1-yl)methyl)-5-methyl-1H-pyrazol-4-yl)-6-(8-(benzo[d]thiazol-2-ylcarbamoyl)-3,4-dihydroisoquinolin-2(1H)-yl)picolinate A mixture of Example 1.2.5 (10 g), benzo[d]thiazol-2-amine (3.24 g), fluoro-N,N,N',N'-tetramethylformamidinium hexafluorophosphate (5.69 g) and N,N-diisopropylethylamine (5.57 g) in N,N-dimethylformamide (20 mL) was heated at 60° C. for 3 hours, cooled and diluted with ethyl acetate. The resulting mixture was washed with water and brine. The organic layer was dried over sodium sulfate, filtered, and concentrated. The residue was purified by flash chromatography, eluting with 20% ethyl acetate in dichloromethane to give the title compound.

1.2.7 tert-butyl 3-(1-((3-(2-aminoethoxy)-5,7-dimethyladamantan-1-yl)methyl)-5-methyl-1H-pyrazol-4-yl)-6-(8-(benzo[d]thiazol-2-ylcarbamoyl)-3,4-dihydroisoquinolin-2(1H)-yl)picolinate To a solution of Example 1.2.6 (2.0 g) in tetrahydrofuran (30 mL) was added Pd/C (10%, 200 mg). The mixture was stirred under a hydrogen atmosphere overnight. The insoluble material was filtered off and the filtrate was concentrated to provide the title compound.

1.2.8 tert-butyl 6-[8-(1,3-benzothiazol-2-ylcarbamoyl)-3,4-dihydroisoquinolin-2(1H)-yl]-3-[1-({3,5-dimethyl-7-[(2,2,7,7-tetramethyl-10,10-dioxido-3,3-diphenyl-4,9-dioxa-$10^6$-thia-13-aza-3-silapentadecan-15-yl)oxy]tricyclo[3.3.1.1$^{3,7}$]dec-1-yl}methyl)-5-methyl-1H-pyrazol-4-yl]pyridine-2-carboxylate To a solution of Example 1.2.7 (500 mg) in N,N-dimethylformamide (8 mL) was added 4-((tert-butyldiphenylsilyl)oxy)-2,2-dimethylbutyl ethenesulfonate (334 mg). The reaction was stirred at room temperature overnight and methylamine (0.3 mL) was added to quench the reaction. The resulting mixture was stirred for 20 minutes and purified by reverse-phase chromatography using an Analogix system (C18 column), eluting with 50-100% acetonitrile in water containing 0.1% v/v trifluoroacetic acid, to provide the title compound.

1.2.9 6-[8-(1,3-benzothiazol-2-ylcarbamoyl)-3,4-dihydroisoquinolin-2(1H)-yl]-3-{1-[(3,5-dimethyl-7-{2-[(2-sulfoethyl)amino]ethoxy}tricyclo[3.3.1.1$^{3,7}$]dec-1-yl)methyl]-5-methyl-1H-pyrazol-4-yl}pyridine-2-carboxylic acid Example 1.2.8 (200 mg) in dichloromethane (5 mL) was treated with trifluoroacetic acid (2.5 mL) overnight. The reaction mixture was concentrated and purified by reverse phase chromatography (C18 column), eluting with 20-60% acetonitrile in water containing 0.1% v/v trifluoroacetic acid, to provide the title compound. $^1$H NMR (500 MHz, dimethyl sulfoxide-d$_6$) δ ppm 12.86 (s, 1H), 8.32 (s, 2H), 8.02 (d, 1H), 7.78 (d, 1H), 7.60 (d, 1H), 7.51 (d, 1H), 7.40-7.49 (m, 2H), 7.31-7.39 (m, 2H), 7.27 (s, 1H), 6.95 (d, 1H), 4.94 (s, 2H), 3.87 (t, 2H), 3.81 (s, 2H), 3.15-3.25 (m, 2H), 3.03-3.13 (m, 2H), 3.00 (t, 2H), 2.79 (t, 2H), 2.09 (s, 3H), 1.39 (s, 2H), 1.22-1.34 (m, 4H), 0.94-1.18 (m, 6H), 0.85 (s, 6H). MS (ESI) m/e 854.1 (M+H)$^+$.

1.3 Synthesis of 2-{[(2-{[2-({3-[(4-{6-[8-(1,3-ben-zothiazol-2-ylcarbamoyl)-3,4-dihydroisoquinolin-2(1H)-yl]-2-carboxypyridin-3-yl}-5-methyl-1H-pyra-zol-1-yl)methyl]-5,7-dimethyltricyclo[3.3.1.1$^{3,7}$]dec-1-yl}oxy)ethyl]amino}ethyl)sulfonyl]amino}-2-deoxy-D-glucopyranose (Compound W2.03)

1.3.1 3-(1-((3-(2-aminoethoxy)-5,7-dimethylada-mantan-1-yl)methyl)-5-methyl-1H-pyrazol-4-yl)-6-(8-(benzo[d]thiazol-2-ylcarbamoyl)-3,4-dihydroiso-quinolin-2(1H)-yl)picolinic acid Example 1.2.7 (200 mg) in dichloromethane (2.5 mL) was treated with trifluoroacetic acid (2.5 mL) overnight. The reaction mixture was concentrated, and the residue was purified by reverse phase chromatography (C18 column), eluting with 20-60% acetonitrile in water containing 0.1% v/v trifluoroacetic acid, to provide the title compound. MS (ESI) m/e 746.2 (M+H)$^+$.

1.3.2 (3R,4R,5S,6R)-6-(acetoxymethyl)-3-(vinylsul-fonamido)tetrahydro-2H-pyran-2,4,5-triyl triacetate To a suspension of (3R,4R,5S,6R)-6-(acetoxymethyl)-3-aminotetrahydro-2H-pyran-2,4,5-triyl triacetate (7.7 g) in dichloromethane (100 mL) at 0° C. was added 2-chloroeth-anesulfonyl chloride (4.34 g). The mixture was stirred at 0° C. for 15 minutes, and triethylamine (12.1 mL) was added. The mixture was stirred at 0° C. for 1 hour, warmed to room temperature and stirred for 2 days. The mixture was diluted with dichloromethane and washed with water and brine. The organic layer was dried over sodium sulfate, filtered, and concentrated to provide the title compound.

1.3.3 N-((3R,4R,5S,6R)-2,4,5-trihydroxy-6-(hy-droxymethyl)tetrahydro-2H-pyran-3-yl)ethenesulfo-namide To a solution of Example 1.3.2 (6.74 g) in methanol (150 mL) was added triethylamine (10 mL). The mixture was stirred for 4 days and concentrated. The residue was dissolved in methanol and treated with Dowex HCR-5 until the solution was neutral. The mixture was filtered, and the filtrate was concentrated. The residue was purified by chromatography using a column of Sephadex LH-20 (100 g), eluting with methanol to provide the title compound.

1.3.4 2-{[(2-{[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl]amino}ethyl)sulfonyl]amino}-2-deoxy-D-glucopyranose A mixture of Example 1.3.1 (23.5 mg), Example 1.3.3 (42.4 mg), and N,N-diisopropylethylamine (55 µL) in N,N-dimethylformamide (1 mL) and water (0.3 mL) was stirred for 5 days. The mixture was purified by reverse phase chromatography (C18 column), eluting with 20-60% acetonitrile in water containing 0.1% v/v trifluoroacetic acid, to provide the title compound. $^1$H NMR (400 MHz, dimethyl sulfoxide-d$_6$) δ ppm 12.85 (s, 1H), 8.42 (s, 1H), 8.42 (s, 1H), 8.03 (d, 1H), 7.79 (d, 1H), 7.55-7.66 (m, 1H), 7.46-7.54 (m, 2H), 7.42-7.47 (m, 1H), 7.33-7.40 (m, 2H), 7.29 (s, 1H), 6.96 (d, 1H), 4.96 (s, 2H), 3.89 (t, 2H), 3.83 (s, 2H), 2.97-3.14 (m, 6H), 2.10 (s, 3H), 1.44 (s, 2H), 1.22-1.39 (m, 4H), 0.97-1.20 (m, 6H), 0.87 (s, 6H). MS (ESI) m/e 1015.3 (M+H)$^+$.

1.4 this Paragraph was Intentionally Left Blank

1.5 Synthesis of 6-[8-(1,3-benzothiazol-2-ylcarbam-oyl)-3,4-dihydroisoquinolin-2(1H)-yl]-3-{1-[(3,5-dimethyl-7-{2-[(4-{[(3R,4R,5S,6R)-3,4,5-trihy-droxy-6-(hydroxymethyl)tetrahydro-2H-pyran-2-yl]methyl}benzyl)amino]ethoxy}tricyclo[3.3.1.13,7]dec-1-yl)methyl]-5-methyl-1H-pyrazol-4-yl}pyridine-2-carboxylic acid (Compound W2.05)

1.5.1 [4-((3S,4R,5R,6R)-3,4,5-Tris-methoxymethoxy-6-methoxymethoxymethyl-tetra-hydro-pyran-2-ylmethyl)-phenyl]-methanol The title compound was prepared according to J. R. Walker et al., Bioorg. Med. Chem. 2006, 14, 3038-3048. MS (ESI) m/e 478 (M+NH$_4$)$^+$.

1.5.2 4-((3S,4R,5R,6R)-3,4,5-Tris-methoxymethoxy-6-methoxymethoxymethyl-tetra-hydro-pyran-2-ylmethyl)-benzaldehyde Example 1.5.1 (1.000 g) was dissolved in dichloromethane (25 mL), and Dess-Martin periodinane (1.013 g) was added. The solution was stirred 16 hours at room temperature. The solution was diluted with diethyl ether (25 mL) and 2 M aqueous sodium carbonate solution (25 mL) was added. The mixture was extracted with diethyl ether three times. The organic extracts were combined, washed with brine, and dried over anhydrous sodium sulfate. After filtration, the solution was concentrated under reduced pressure and purified by silica gel chromatography, eluting with 50-70% ethyl acetate in heptanes. The solvent was evaporated under reduced pressure to provide the title compound. MS (ESI) m/e 476 (M+NH$_4$)$^+$.

1.5.3 Acetic acid (2R,3R,4R,5S)-3,4,5-triacetoxy-6-(4-formyl-benzyl)-tetrahydro-pyran-2-ylmethyl ester Example 1.5.2 (660 mg) was dissolved in methanol (145 mL). 6 M Hydrochloric acid (8 mL) was added, and the solution was stirred at room temperature for two days. The solvents were removed under reduced pressure, azeotroping with ethyl acetate three times. The material was dried under vacuum for four days. The material was dissolved in N,N-dimethylformamide (50 mL). Acetic anhydride (12 mL), pyridine (6 mL), and N,N-dimethylpyridin-4-amine (10 mg) were added sequentially, and the solution was stirred at room temperature for 16 hours. The solution was diluted with water (150 mL) and extracted with ethyl acetate (50 mL) three times. The organics were combined, washed with water, washed with brine, and dried over anhydrous sodium sulfate. After filtration, the solution was concentrated under reduced pressure and purified by chromatography on silica gel, eluting with 40-50% ethyl acetate in heptanes. The solvent was evaporated under reduced pressure to provide the title compound.

1.5.4 (2R,3R,4R,5S)-2-(acetoxymethyl)-6-(4-(((2-((3-((4-(6-(8-(benzo[d]thiazol-2-ylcarbamoyl)-3,4-dihydroisoquinolin-2(1H)-yl)-2-(tert-butoxycarbo-nyl)pyridin-3-yl)-5-methyl-1H-pyrazol-1-yl)methyl)-5,7-dimethyladamantan-1-yl)oxy)ethyl)amino)methyl)benzyl)tetrahydro-2H-pyran-3,4,5-triyl triacetate Example 1.5.7 (40 mg) and Example 1.5.3 (22.5 mg) were stirred in dichloromethane (1 mL) at room temperature for 10 minutes. Sodium triacetoxyborohydride (14 mg) was added, and the solution was stirred at room temperature for 16 hours. The material was purified by chromatography on silica gel, eluting with 10% methanol in dichloromethane. The solvent was evaporated under reduced pressure to provide the title compound. MS (ESI) m/e 1236 (M+H)+.

1.5.5 6-[8-(1,3-benzothiazol-2-ylcarbamoyl)-3,4-dihydroisoquinolin-2(1H)-yl]-3-{1-[(3,5-dimethyl-7-{2-[(4-{[(3R,4R,5S,6R)-3,4,5-trihydroxy-6-(hydroxymethyl)tetrahydro-2H-pyran-2-yl]methyl}benzyl)amino]ethoxy}tricyclo[3.3.1.1$^{3,7}$]dec-1-yl)methyl]-5-methyl-1H-pyrazol-4-yl}pyridine-2-carboxylic acid Example 1.5.4 (68 mg) was dissolved in methanol (0.5 mL). Aqueous lithium hydroxide solution (2M, 1 mL) was added, and the solution was stirred at room temperature for 4.5 hours. Acetic acid (0.1 mL) was added, and the solvents were removed under vacuum. The material was then dissolved in trifluoroacetic acid (2 mL) and stirred at room temperature for 16 hours. The solution was concentrated under vacuum. The residue was purified by reverse phase HPLC using a Gilson PLC 2020 with a 150×30 mm C18 column, eluting with 20-70% acetonitrile in water containing 0.1% v/v trifluoroacetic acid. The desired fractions were combined and freeze-dried to provide the title compound. $^1$H NMR (400 MHz, dimethyl sulfoxide-d$_6$) δ ppm 12.86 (bs, 1H), 8.68 (bs, 2H), 8.04 (d, 1H), 7.80 (d, 1H), 7.62 (d, 1H), 7.51-7.43 (m, 3H), 7.39-7.24 (m, 6H), 6.96 (d, 1H), 5.23 (t, 1H), 4.96 (s, 2H), 4.56 (d, 1H), 4.42 (dd, 1H), 4.11 (m, 2H), 3.89 (t, 2H), 3.83 (s, 2H), 3.61-3.56 (m, 3H), 3.39 (dd, 1H), 3.22 (t, 1H), 3.15 (t, 1H), 3.09 (d, 1H), 3.01 (m, 6H), 2.89 (t, 1H), 2.60 (m, 1H), 2.10 (s, 3H), 1.43 (s, 2H), 1.30 (q, 4H), 1.14 (m, 4H), 1.03 (q, 2H), 0.86 (s, 6H). MS (ESI) m/e 1012 (M+H)+.

1.6 Synthesis of 6-[8-(1,3-benzothiazol-2-ylcarbamoyl)-3,4-dihydroisoquinolin-2(1H)-yl]-3-{1-[(3,5-dimethyl-7-{2-[(3-sulfopropyl)amino]ethoxy}tricyclo[3.3.1.1$^{3,7}$]dec-1-yl)methyl]-5-methyl-1H-pyrazol-4-yl}pyridine-2-carboxylic acid (Compound W2.06)

1.6.1 3-((2-((3-((4-(6-(8-(benzo[d]thiazol-2-ylcarbamoyl)-3,4-dihydroisoquinolin-2(1H)-yl)-2-(tert-butoxycarbonyl)pyridin-3-yl)-5-methyl-1H-pyrazol-1-yl)methyl)-5,7-dimethyladamantan-1-yl)oxy)ethyl)amino)propane-1-sulfonic acid A mixture of Example 1.2.7 (100 mg), 1,2-oxathiolane 2,2-dioxide (13 mg) and N,N-diisopropylethylamine (19.07 μL) in N,N-dimethylformamide (2 mL) was heated to 50° C. overnight. The reaction was cooled and purified by reverse phase HPLC (C18 column), eluting with 20-60% acetonitrile in water containing 0.1% v/v trifluoroacetic acid, to provide the title compound. MS (ESI) m/e 924.1 (M+H)+.

1.6.2 6-[8-(1,3-benzothiazol-2-ylcarbamoyl)-3,4-dihydroisoquinolin-2(1H)-yl]-3-{1-[(3,5-dimethyl-7-{2-[(3-sulfopropyl)amino]ethoxy}tricyclo[3.3.1.1$^{3,7}$]dec-1-yl)methyl]-5-methyl-1H-pyrazol-4-yl}pyridine-2-carboxylic acid Example 1.6.1 (40 mg) in dichloromethane (2.5 mL) was treated with trifluoroacetic acid (2.5 mL) overnight. The reaction mixture was concentrated, and the residue was purified by reverse phase chromatography (C18 column), eluting with 20-60% acetonitrile in water containing 0.1% v/v trifluoroacetic acid, to provide the title compound. $^1$H NMR (400 MHz, dimethyl sulfoxide-d$_6$) δ ppm 12.86 (s, 1H), 8.52 (s, 2H), 8.04 (d, 1H), 7.79 (d, 1H), 7.61 (d, 1H), 7.41-7.55 (m, 3H), 7.32-7.39 (m, 2H), 7.29 (s, 1H), 6.96 (d, 1H), 4.96 (s, 2H), 3.89 (t, 2H), 3.49-3.58 (m, 2H), 2.94-3.12 (m, 6H), 2.56-2.64 (m, 2H), 1.88-1.99 (m, 2H), 1.41 (s, 2H), 1.22-1.36 (m, 4H), 0.96-1.20 (m, 6H), 0.86 (s, 6H). MS (ESI) m/e 868.3 (M+H)+.

1.7 Synthesis of 6-[8-(1,3-benzothiazol-2-ylcarbamoyl)-3,4-dihydroisoquinolin-2(1H)-yl]-3-{1-[(3-{2-[(2,3-dihydroxypropyl)amino]ethoxy}-5,7-dimethyltricyclo[3.3.1.1$^{3,7}$]dec-1-yl)methyl]-5-methyl-1H-pyrazol-4-yl}pyridine-2-carboxylic acid (Compound W2.07)

To a solution of Example 1.2.7 (30 mg) in dichloromethane (3 mL) was added 2,3-dihydroxypropanal (3.6 mg), and NaCNBH$_3$ on resin (200 mg). The mixture was stirred overnight, filtered, and the solvent was evaporated. The residue was dissolved in dimethyl sulfoxide/methanol (1:1, 3 mL) and purified by reverse phase HPLC using a Gilson system, eluting with 10-85% acetonitrile in 0.1% trifluoroacetic acid in water, to give the title compound. $^1$H NMR (400 MHz, dimethyl sulfoxide-d$_6$) δ ppm 12.85 (s, 1H), 8.27 (s, 2H), 8.03 (d, 1H), 7.79 (d, 1H), 7.61 (t, 1H), 7.33-7.54 (m, 6H), 7.29 (s, 1H), 6.96 (d, 1H), 4.96 (s, 3H), 3.72-3.89 (m, 8H), 3.25-3.64 (m, 6H), 2.99-3.10 (m, 4H), 2.11 (s, 3H), 1.00-1.52 (m, 8H), 0.86 (s, 6H). MS (ESI) m/e 820.3 (M+H)+.

1.8 Synthesis of 2-({[4-({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl]amino}methyl)phenyl]sulfonyl}amino)-2-deoxy-beta-D-glucopyranose (Compound W2.08)

1.8.1 (2R,3S,4S,5R,6S)-6-(acetoxymethyl)-3-(4-formylphenylsulfonamido)tetrahydro-2H-pyran-2,4,5-triyl triacetate 4-Formylbenzene-1-sulfonyl chloride (100 mg) and (2S, 3R,4R,5S,6R)-6-(acetoxymethyl)-3-aminotetrahydro-2H-pyran-2,4,5-triyl triacetate hydrochloride (563 mg) were added to 1,2-dichloroethane (4 mL). N,N-Diisopropylethylamine (0.51 mL) was added, and the solution was heated at 55° C. for three days. The solution was concentrated under reduced pressure and purified by flash column chromatography on silica gel, eluting with 70% ethyl acetate in heptanes. The solvent was evaporated under reduced pressure, and the material was dissolved in acetone (4 mL). Hydrochloric acid (1M, 4 mL) was added, and the solution was stirred at room temperature for 16 hours. The solution was then extracted with 70% ethyl acetate in heptanes (20 mL). The organic layer was washed with brine and dried over anhydrous sodium sulfate. After filtration, the solvent was evaporated under reduced pressure to provide the title compound. MS (ESI) m/e 514 (M+H)+.

1.8.2 (2R,3S,4S,5R,6S)-6-(acetoxymethyl)-3-(4-(((2-((3-((4-(6-(8-(benzo[d]thiazol-2-ylcarbamoyl)-3,4-dihydroisoquinolin-2(1H)-yl)-2-(tert-butoxycarbonyl)pyridin-3-yl)-5-methyl-1H-pyrazol-1-yl)methyl)-5,7-dimethyladamantan-1-yl)oxy)ethyl)amino)methyl)phenylsulfonamido)tetrahydro-2H-pyran-2,4,5-triyl triacetate The title compound was prepared by substituting Example 1.8.1 for Example 1.5.3 in Example 1.5.4. MS (ESI) m/e 1301 (M+H)⁺.

1.8.3 2-({[4-({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1³,⁷]dec-1-yl}oxy)ethyl]amino}methyl)phenyl]sulfonyl}amino)-2-deoxy-beta-D-glucopyranose The title compound was prepared by substituting Example 1.8.2 for Example 1.5.4 in Example 1.5.5. ¹H NMR (400 MHz, dimethyl sulfoxide-d₆) δ ppm 12.86 (bs, 1H), 8.87 (bs, 2H), 8.04 (d, 1H), 7.91 (d, 2H), 7.79 (d, 1H), 7.70-7.55 (m, 3H), 7.52-7.42 (m, 3H), 7.39-7.33 (m, 2H), 7.29 (m, 1H), 6.96 (d, 1H), 4.96 (bs, 2H), 4.85 (dd, 1H), 4.62-4.52 (m, 2H), 4.32 (m, 2H), 3.89 (t, 2H), 3.83 (s, 2H), 3.70-3.35 (m, 10H), 3.02 (m, 4H), 2.91 (m, 1H), 2.10 (s, 3H), 1.44 (bs, 2H), 1.37-1.22 (m, 4H), 1.18-0.98 (m, 6H), 0.93-0.82 (m, 6H). MS (ESI) m/e 1075 (M+H)⁺.

1.9 Synthesis of 8-(1,3-benzothiazol-2-ylcarbamoyl)-2-{6-carboxy-5-[1-({3-[2-({2-[1-(beta-D-glucopyranuronosyl)-1H-1,2,3-triazol-4-yl]ethyl}amino)ethoxy]-5,7-dimethyltricyclo[3.3.1.1³,⁷]dec-1-yl}methyl)-5-methyl-1H-pyrazol-4-yl]pyridin-2-yl}-1,2,3,4-tetrahydroisoquinoline (Compound W2.09)

1.9.1 (2R,3R,4S,5S,6S)-2-(4-(2-hydroxyethyl)-1H-1,2,3-triazol-1-yl)-6-(methoxycarbonyl)tetrahydro-2H-pyran-3,4,5-triyl triacetate To a solution of (2R,3R,4S,5S,6S)-2-azido-6-(methoxycarbonyl)tetrahydro-2H-pyran-3,4,5-triyl triacetate (720 mg) in t-butanol (8 mL) and water (4 mL) was added but-3-yn-1-ol (140 mg), copper(II) sulfate pentahydrate (5.0 mg) and sodium ascorbate (40 mg). The mixture was stirred 20 minutes at 100° C. under microwave conditions (Biotage Initiator). The reaction mixture was diluted with ethyl acetate (300 mL), washed with water and brine, and dried over sodium sulfate. Filtration and evaporation of the solvent provided the title compound. MS (ESI) m/e 430.2 (M+H)⁺.

1.9.2 (2S,3S,4S,5R,6R)-2-(methoxycarbonyl)-6-(4-(2-oxoethyl)-1H-1,2,3-triazol-1-yl)tetrahydro-2H-pyran-3,4,5-triyl triacetate To a solution of dimethyl sulfoxide (0.5 mL) in dichloromethane (10 mL) at −78° C. was added oxalyl chloride (0.2 mL). The mixture was stirred 20 minutes at −78° C., and a solution of (2R,3R,4S,5S,6S)-2-(4-(2-hydroxyethyl)-1H-1,2,3-triazol-1-yl)-6-(methoxycarbonyl)tetrahydro-2H-pyran-3,4,5-triyl triacetate (233 mg) in dichloromethane (10 mL) was added through a syringe. After 20 minutes, triethylamine (1 mL) was added to the mixture, and the mixture was stirred for 30 minutes while the temperature was allowed to rise to room temperature. The reaction mixture was diluted with ethyl acetate (300 mL), washed with water and brine, and dried over sodium sulfate. Filtration and evaporation of the solvent gave the crude product, which was used in the next reaction without further purification. MS (ESI) m/e 429.2 (M+H)⁺.

1.9.3 8-(1,3-benzothiazol-2-ylcarbamoyl)-2-{6-carboxy-5-[1-({3-[2-({2-[1-(beta-D-glucopyranuronosyl)-1H-1,2,3-triazol-4-yl]ethyl}amino)ethoxy]-5,7-dimethyltricyclo[3.3.1.1³,⁷]dec-1-yl}methyl)-5-methyl-1H-pyrazol-4-yl]pyridin-2-yl}-1,2,3,4-tetrahydroisoquinoline To a solution of Example 1.3.1 (150 mg) in dichloromethane (10 mL) was added Example 1.9.2 (86 mg) and NaBH₃CN on resin (2.49 mmol/g, 200 mg), and the mixture was stirred overnight. The reaction mixture was then filtered and concentrated. The residue was dissolved in tetrahydrofuran/methanol/H₂O (2:1:1, 12 mL) and lithium hydroxide monohydrate (50 mg) was added. The mixture was stirred overnight. The mixture was concentrated, and the residue was purified by reverse phase HPLC using a Gilson system, eluting with 10-85% acetonitrile in 0.1% trifluoroacetic acid in water, to provide the title compound. ¹H NMR (400 MHz, dimethyl sulfoxide-d₆) δ ppm 12.84 (s, 1H), 8.48 (s, 2H), 8.20 (s, 1H), 8.03 (d, 1H), 7.79 (d, 1H), 7.62 (d, 1H), 7.32-7.53 (m, 5H), 7.29 (s, 1H), 6.96 (d, 1H), 5.66 (d, 1H), 4.96 (s, 2H), 4.00 (d, 1H), 3.76-3.92 (m, 6H), 3.22-3.26 (m, 2H), 2.96-3.15 (m, 8H), 2.10 (s, 3H), 0.99-1.52 (m, 14H), 0.87 (s, 6H). MS (ESI) m/e 1028.3 (M+H)⁺.

1.10 Synthesis of 3-[1-({3-[2-(2-{[4-(beta-D-allopyranosyloxy)benzyl]amino}ethoxy)ethoxy]-5,7-dimethyltricyclo[3.3.1.1³,⁷]dec-1-yl}methyl)-5-methyl-1H-pyrazol-4-yl]-6-[8-(1,3-benzothiazol-2-ylcarbamoyl)-3,4-dihydroisoquinolin-2(1H)-yl]pyridine-2-carboxylic acid (Compound W2.10)

1.10.1 2-(2-((3-((1H-pyrazol-1-yl)methyl)-5,7-dimethyladamantan-1-yl)oxy)ethoxy)ethanol The title compound was prepared as in Example 1.1.4 by substituting ethane-1,2-diol with 2,2'-oxydiethanol. MS (ESI) m/e 349.2 (M+H)⁺.

1.10.2 2-(2-((3,5-dimethyl-7-((5-methyl-1H-pyrazol-1-yl)methyl)adamantan-1-yl)oxy)ethoxy)ethanol The title compound was prepared as in Example 1.1.5 by substituting Example 1.1.4 with Example 1.10.1. MS (ESI) m/e 363.3 (M+H)⁺.

1.10.3 2-(2-((3-((4-iodo-5-methyl-1H-pyrazol-1-yl)methyl)-5,7-dimethyladamantan-1-yl)oxy)ethoxy)ethanol The title compound was prepared as in Example 1.1.6 by substituting Example 1.1.5 with Example 1.10.2. MS (ESI) m/e 489.2 (M+H)⁺.

1.10.4 2-(2-((3-((4-iodo-5-methyl-1H-pyrazol-1-yl)methyl)-5,7-dimethyladamantan-1-yl)oxy)ethoxy) ethyl methanesulfonate To a cooled solution of Example 1.10.3 (6.16 g) in dichloromethane (100 mL) was added triethylamine (4.21 g)

followed by methanesulfonyl chloride (1.6 g), and the mixture was stirred at room temperature for 1.5 hours. The reaction mixture was then diluted with ethyl acetate (600 mL) and washed with water and brine. After drying over sodium sulfate, the solution was filtered and concentrated, and the residue was used in the next reaction without further purification. MS (ESI) m/e 567.2 (M+H)$^+$.

1.10.5 2-(2-((3-((4-iodo-5-methyl-1H-pyrazol-1-yl)methyl)-5,7-dimethyladamantan-1-yl)oxy)ethoxy)ethanamine A solution of Example 1.10.4 (2.5 g) in 7N ammonia in methanol (15 mL) was stirred at 100° C. for 20 minutes under microwave conditions (Biotage Initiator). The reaction mixture was concentrated under vacuum, and the residue was diluted with ethyl acetate (400 mL) and washed with aqueous NaHCO$_3$, water and brine. After drying over sodium sulfate, the solution was filtered and concentrated, and the residue was used in the next reaction without further purification. MS (ESI) m/e 488.2 (M+H)$^+$.

1.10.6 tert-butyl (2-(2-((3-((4-iodo-5-methyl-1H-pyrazol-1-yl)methyl)-5,7-dimethyladamantan-1-yl)oxy)ethoxy)ethyl)carbamate To a solution of Example 1.10.5 (2.2 g) in tetrahydrofuran (30 mL) was added di-tert-butyl dicarbonate (1.26 g) and 4-dimethylaminopyridine (100 mg). The mixture was stirred at room temperature for 1.5 hours and was diluted with ethyl acetate (300 mL). The solution was washed with saturated aqueous NaHCO$_3$, water (60 mL) and brine (60 mL). The organic layer was dried with sodium sulfate, filtered and concentrated. The residue was purified by silica gel chromatography, eluting with 20% ethyl acetate in dichloromethane, to give the title compound. MS (ESI) m/e 588.2 (M+H)$^+$.

1.10.7 methyl 2-(6-(tert-butoxycarbonyl)-5-(1-((3-(2-(2-((tert-butoxycarbonyl)amino)ethoxy)ethoxy)-5,7-dimethyladamantan-1-yl)methyl)-5-methyl-1H-pyrazol-4-yl)pyridin-2-yl)-1,2,3,4-tetrahydroisoquinoline-8-carboxylate The title compound was prepared as in Example 1.2.2 by substituting Example 1.1.6 with Example 1.10.6. MS (ESI) m/e 828.5 (M+H)$^+$.

1.10.8 2-(6-(tert-butoxycarbonyl)-5-(1-((3-(2-(2-((tert-butoxycarbonyl)amino)ethoxy)ethoxy)-5,7-dimethyladamantan-1-yl)methyl)-5-methyl-1H-pyrazol-4-yl)pyridin-2-yl)-1,2,3,4-tetrahydroisoquinoline-8-carboxylic acid The title compound was prepared as in Example 1.2.5 by substituting Example 1.2.4 with Example 1.10.7. MS (ESI) m/e 814.5 (M+H)$^+$.

1.10.10 tert-butyl 6-(8-(benzo[d]thiazol-2-ylcarbamoyl)-3,4-dihydroisoquinolin-2(1H)-yl)-3-(1-((3-(2-(2-((tert-butoxycarbonyl)amino)ethoxy)ethoxy)-5,7-dimethyladamantan-1-yl)methyl)-5-methyl-1H-pyrazol-4-yl)picolinate The title compound was prepared as in Example 1.2.6 by substituting Example 1.2.5 with Example 1.10.8. MS (ESI) m/e 946.2 (M+H)$^+$.

1.10.11 3-(1-((3-(2-(2-aminoethoxy)ethoxy)-5,7-dimethyladamantan-1-yl)methyl)-5-methyl-1H-pyrazol-4-yl)-6-(8-(benzo[d]thiazol-2-ylcarbamoyl)-3,4-dihydroisoquinolin-2(1H)-yl)picolinic acid The title compound was prepared as in Example 1.1.17 by substituting Example 1.1.16 with Example 1.10.9.

1.10.12 3-[1-({3-[2-(2-{[4-(beta-D-allopyranosyloxy)benzyl]amino}ethoxy)ethoxy]-5,7-dimethyltricyclo[3.3.1.1$^{3,7}$]dec-1-yl}methyl)-5-methyl-1H-pyrazol-4-yl]-6-[8-(1,3-benzothiazol-2-ylcarbamoyl)-3,4-dihydroisoquinolin-2(1H)-yl]pyridine-2-carboxylic acid To a solution of Example 1.10.10 (88 mg) and triethylamine (0.04 mL) in dichloromethane (1.5 mL) was added 4-(((2S,3R,4R,5S,6R)-3,4,5-trihydroxy-6-(hydroxymethyl)tetrahydro-2H-pyran-2-yl)oxy)benzaldehyde (27.7 mg), methanol (1 mL), MP-CNBH$_3$ (2.49 mmol/g, 117 mg) and acetic acid (18 μL). The reaction mixture was stirred overnight. The reaction was filtered, and the filtrate was concentrated. The residue was purified by purified by reverse phase chromatography (C18 column), eluting with 20-60% acetonitrile in water containing 0.1% v/v trifluoroacetic acid, to provide the title compound. $^1$H NMR (400 MHz, dimethyl sulfoxide-d$_6$) δ ppm 7.99 (d, 1H), 7.77 (d, 1H), 7.60 (d, 1H), 7.40-7.50 (m, 2H), 7.29-7.39 (m, 6H), 6.96 (d, 2H), 6.76 (d, 1H), 5.11 (d, 2H), 4.92 (s, 2H), 3.83-3.96 (m, 4H), 3.77 (s, 2H), 3.60-3.72 (m, 4H), 3.01 (d, 2H), 2.80 (t, 2H), 2.09 (s, 3H), 0.98-1.32 (m, 14H), 0.82 (s, 6H). MS (ESI) m/e 1058.3 (M+H)$^+$.

1.11 Synthesis of 6-[8-(1,3-benzothiazol-2-ylcarbamoyl)-3,4-dihydroisoquinolin-2(1H)-yl]-3-(1-{[3,5-dimethyl-7-(2-{2-[(2-sulfoethyl)amino]ethoxy}ethoxy)tricyclo[3.3.1.1$^{3,7}$]dec-1-yl]methyl}-5-methyl-1H-pyrazol-4-yl)pyridine-2-carboxylic acid (Compound W2.11)

1.11.1 tert-butyl 3-(1-((3-(2-(2-aminoethoxy)ethoxy)-5,7-dimethyladamantan-1-yl)methyl)-5-methyl-1H-pyrazol-4-yl)-6-(8-(benzo[d]thiazol-2-ylcarbamoyl)-3,4-dihydroisoquinolin-2(1H)-yl)picolinate Example 1.10.9 (6.8 g) was dissolved in 50% trifluoroacetic acid in dichloromethane (10 mL) and stirred for 20 minutes, and the solvents were removed under vacuum. The residue was purified by reverse phase chromatography, eluting with 20-80% acetonitrile in water containing 0.1% trifluoroacetic acid, to provide the title compound. MS (ESI) m/e 790.2 (M+H)$^+$.

1.11.2 tert-butyl 6-(8-(benzo[d]thiazol-2-ylcarbamoyl)-3,4-dihydroisoquinolin-2(1H)-yl)-3-(1-((3,5-dimethyl-7-(2-(2-((2-(phenoxysulfonyl)ethyl)amino)ethoxy)ethoxy)adamantan-1-yl)methyl)-5-methyl-1H-pyrazol-4-yl)picolinate To a solution of Example 1.11.1 (200 mg) and N,N-diisopropylethylamine (146 μL) in tetrahydrofuran (3 mL) at 0° C. was added phenyl ethenesulfonate (46 mg). The reaction mixture was stirred at 0° C. for 30 minutes, gradually warmed to room temperature, stirred overnight and concentrated to provide the title compound.

1.11.3 6-(8-(benzo[d]thiazol-2-ylcarbamoyl)-3,4-dihydroisoquinolin-2(1H)-yl)-3-(1-((3,5-dimethyl-7-(2-(2-((2-(phenoxysulfonyl)ethyl)amino)ethoxy)ethoxy)adamantan-1-yl)methyl)-5-methyl-1H-pyrazol-4-yl)picolinic acid A solution of Example 1.11.2 (100 mg) in dichloromethane (5 mL) was treated with trifluoroacetic acid (2.5 mL) overnight and concentrated to provide the title compound. MS (APCI) m/e 974.9 (M+H)+.

1.11.4 6-[8-(1,3-benzothiazol-2-ylcarbamoyl)-3,4-dihydroisoquinolin-2(1H)-yl]-3-(1-{[3,5-dimethyl-7-(2-{2-[(2-sulfoethyl)amino]ethoxy}ethoxy)tricyclo[3.3.1.1$^{3,7}$]dec-1-yl]methyl}-5-methyl-1H-pyrazol-4-yl)pyridine-2-carboxylic acid To a solution of Example 1.11.3 (195 mg) in tetrahydrofuran (3 mL) and methanol (2 mL) was slowly added 1M sodium hydroxide aqueous solution (2 mL). The mixture was stirred overnight, and NaOH pellets (0.5 g) were added. The resulting mixture was heated at 40° C. for 3 hours, cooled and concentrated. The concentrate was purified by reverse phase chromatography (C18 column), eluting with 10-70% acetonitrile in 10 mM aqueous NH$_4$OAc solution, to provide the title compound. $^1$H NMR (400 MHz, dimethyl sulfoxide-d$_6$) δ ppm 8.04 (d, 1H), 7.79 (d, 1H), 7.61 (d, 1H), 7.41-7.51 (m, 3H), 7.32-7.39 (m, 2H), 7.29 (s, 1H), 6.88 (d, 1H), 4.93 (s, 2H), 3.89 (t, 2H), 3.81 (s, 2H), 3.60-3.66 (m, 4H), 3.13-3.19 (m, 2H), 3.05-3.10 (m, 2H), 3.01 (t, 2H), 2.79 (t, 2H), 2.11 (s, 3H), 1.34 (s, 2H), 1.26 (s, 4H), 0.96-1.22 (m, 6H), 0.85 (s, 6H). MS (ESI) m/e 898.2 (M+H)+.

1.12 Synthesis of 6-[8-(1,3-benzothiazol-2-ylcarbamoyl)-3,4-dihydroisoquinolin-2(1H)-yl]-3-{1-[(3,5-dimethyl-7-{2-[(2-phosphonoethyl)amino]ethoxy}tricyclo[3.3.1.1$^{3,7}$]dec-1-yl)methyl]-5-methyl-1H-pyrazol-4-yl}pyridine-2-carboxylic acid (Compound W2.12)

1.12.1 tert-butyl 6-(8-(benzo[d]thiazol-2-ylcarbamoyl)-3,4-dihydroisoquinolin-2(1H)-yl)-3-(1-((3-(2-((2-(diethoxyphosphoryl)ethyl)amino)ethoxy)-5,7-dimethyladamantan-1-yl)methyl)-5-methyl-1H-pyrazol-4-yl)picolinate To a solution of Example 1.2.7 (307 mg) in tetrahydrofuran (5 mL) was added diethyl vinylphosphonate (176 mg) in water (2 mL). The reaction mixture was stirred at 70° C. for 3 days, and a few drops of acetic acid were added. The mixture was purified by reverse phase chromatography (C18 column), eluting with 10-70% acetonitrile in water containing 0.1% v/v trifluoroacetic acid, to provide the title compound. MS (APCI) m/e 966.8 (M+H)+.

1.12.2 6-[8-(1,3-benzothiazol-2-ylcarbamoyl)-3,4-dihydroisoquinolin-2(1H)-yl]-3-{1-[(3,5-dimethyl-7-{2-[(2-phosphonoethyl)amino]ethoxy}tricyclo[3.3.1.1$^{3,7}$]dec-1-yl)methyl]-5-methyl-1H-pyrazol-4-yl}pyridine-2-carboxylic acid To a solution of Example 1.12.1 (170 mg) in dichloromethane (2.5 mL) was added bromotrimethylsilane (82 µL) and allyltrimethylsilane (50.4 µL). The reaction mixture was stirred overnight and water (0.02 mL) was added. The resulting mixture was stirred overnight and concentrated. The residue was purified by reverse phase chromatography (C18 column), eluting with 20-60% acetonitrile in water containing 0.1% trifluoroacetic acid, to provide the title compound. $^1$H NMR (500 MHz, dimethyl sulfoxide-d$_6$) δ ppm 8.35 (s, 2H), 8.03 (d, 1H), 7.79 (d, 1H), 7.62 (d, 1H), 7.41-7.53 (m, 3H), 7.33-7.40 (m, 2H), 7.29 (s, 1H), 6.96 (d, 1H), 4.96 (s, 2H), 3.89 (t, 2H), 3.83 (s, 2H), 3.09 (s, 4H), 3.01 (t, 2H), 2.10 (s, 3H), 1.85-2.00 (m, 2H), 1.43 (s, 2H), 1.19-1.37 (m, 4H), 1.14 (s, 6H), 0.87 (s, 6H). MS (APCI) m/e 854.4 (M+H)+.

1.13 Synthesis of 6-[8-(1,3-benzothiazol-2-ylcarbamoyl)-3,4-dihydroisoquinolin-2(1H)-yl]-3-{1-[(3,5-dimethyl-7-{2-[methyl(3-sulfo-L-alanyl)amino]ethoxy}tricyclo[3.3.1.1$^{3,7}$]dec-1-yl)methyl]-5-methyl-1H-pyrazol-4-yl}pyridine-2-carboxylic acid (Compound W2.13)

1.13.1 2-({3-[(4-iodo-5-methyl-1H-pyrazol-1-yl)methyl]-5,7-dimethyltricyclo[3.3.1.1$^{3,7}$]dec-1-yl}oxy)ethyl methanesulfonate To a cooled solution of Example 1.1.6 (6.16 g) in dichloromethane (100 mL) was added triethylamine (4.21 g) followed by methanesulfonyl chloride (1.6 g), and the mixture was stirred at room temperature for 1.5 hours. The reaction mixture was diluted with ethyl acetate (600 mL) and washed with water and brine. After drying over sodium sulfate, the solution was filtered and concentrated, and the residue was used in the next reaction without further purification. MS (ESI) m/e 523.4 (M+H)+.

1.13.2 1-({3,5-dimethyl-7-[2-(methylamino)ethoxy]tricyclo[3.3.1.1$^{3,7}$]dec-1-yl}methyl)-4-iodo-5-methyl-1H-pyrazole A solution of Example 1.13.1 (2.5 g) in 2M methylamine in methanol (15 mL) was stirred at 100° C. for 20 minutes under microwave conditions (Biotage Initiator). The reaction mixture was concentrated under vacuum, and the residue was diluted with ethyl acetate (400 mL) and washed with aqueous NaHCO$_3$, water and brine. After drying over sodium sulfate, the solution was filtered and concentrated, and the residue was used in the next reaction without further purification. MS (ESI) m/e 458.4 (M+H)+.

1.13.3 tert-butyl[2-({3-[(4-iodo-5-methyl-1H-pyrazol-1-yl)methyl]-5,7-dimethyltricyclo[3.3.1.1$^{3,7}$]dec-1-yl}oxy)ethyl]methylcarbamate To a solution of Example 1.13.2 (2.2 g) in tetrahydrofuran (30 mL) was added di-tert-butyl dicarbonate (1.26 g) and a catalytic amount of 4-dimethylaminopyridine. The mixture was stirred at room temperature for 1.5 hours and diluted with ethyl acetate (300 mL). The solution was washed with saturated aqueous NaHCO$_3$, water (60 mL) and brine (60 mL). The organic layer was dried with sodium sulfate, filtered and concentrated. The residue was purified by silica gel chromatography, eluting with 20% ethyl acetate in dichloromethane, to give the title compound. MS (ESI) m/e 558.5 (M+H)+.

1.13.4 methyl 2-(6-(tert-butoxycarbonyl)-5-(1-((3-(2-((tert-butoxycarbonyl)(methyl)amino)ethoxy)-5,7-dimethyltricyclo[3.3.1.1$^{3,7}$]dec-1-yl)methyl)-5-methyl-1H-pyrazol-4-yl)pyridin-2-yl)-1,2,3,4-tetrahydroisoquinoline-8-carboxylate To a solution of Example 1.2.1 (4.94 g) in tetrahydrofuran (60 mL) and water (20 mL) was added Example 1.13.3 (5.57 g), 1,3,5,7-tetramethyl-8-tetradecyl-2,4,6-trioxa-8-phosphaadamantane (412 mg), tris(dibenzylideneacetone)dipalladium(0) (457 mg), and $K_3PO_4$ (11 g), and the mixture was stirred at reflux for 24 hours. The reaction mixture was cooled and diluted with ethyl acetate (500 mL), washed with water and brine. The organic layer was dried over sodium sulfate, filtered and concentrated under reduced pressure. Purification of the residue by silica gel chromatography, eluting with 20% ethyl acetate in heptane, provided the title compound. MS (ESI) m/e 799.1 $(M+H)^+$.

1.13.5 2-(6-(tert-butoxycarbonyl)-5-(1-((3-(2-((tert-butoxycarbonyl)(methyl)amino)ethoxy)-5,7-dimethyltricyclo[3.3.1.1$^{3,7}$]dec-1-yl)methyl)-5-methyl-1H-pyrazol-4-yl)pyridin-2-yl)-1,2,3,4-tetrahydroisoquinoline-8-carboxylic acid To a solution of Example 1.13.4 (10 g) in tetrahydrofuran (60 mL), methanol (30 mL) and water (30 mL) was added lithium hydroxide monohydrate (1.2 g), and the mixture was stirred at room temperature for 24 hours. The reaction mixture was neutralized with 2% aqueous HCl and concentrated under vacuum. The residue was diluted with ethyl acetate (800 mL) and washed with water and brine, and dried over sodium sulfate. Filtration and evaporation of the solvent provided the title compound. MS (ESI) m/e 785.1 $(M+H)^+$.

1.13.6 tert-butyl 6-[8-(1,3-benzothiazol-2-ylcarbamoyl)-3,4-dihydroisoquinolin-2(1H)-yl]-3-{1-[(3-{2-[(tert-butoxycarbonyl)(methyl)amino]ethoxy}-5,7-dimethyltricyclo[3.3.1.1$^{3,7}$]dec-1-yl)methyl]-5-methyl-1H-pyrazol-4-yl}pyridine-2-carboxylate To a solution of Example 1.13.5 (10 g) in N,N-dimethylformamide (20 mL) was added benzo[d]thiazol-2-amine (3.24 g), fluoro-N,N,N',N'-tetramethylformamidinium hexafluorophosphate (5.69 g) and N,N-diisopropylethylamine (5.57 g), and the mixture was stirred at 60° C. for 3 hours. The reaction mixture was diluted with ethyl acetate (800 mL) and washed with water and brine, and dried over sodium sulfate. Filtration and evaporation of the solvent and silica gel purification of the residue, eluting with 20% ethyl acetate in dichloromethane, provided the title compound. MS (ESI) m/e 915.5 $(M+H)^+$.

1.13.7 6-[8-(1,3-benzothiazol-2-ylcarbamoyl)-3,4-dihydroisoquinolin-2(1H)-yl]-3-[1-({3,5-dimethyl-7-[2-(methylamino)ethoxy]tricyclo[3.3.1.1$^{3,7}$]dec-1-yl}methyl)-5-methyl-1H-pyrazol-4-yl]pyridine-2-carboxylic acid To a solution of Example 1.13.6 (5 g) in dichloromethane (20 mL) was added trifluoroacetic acid (10 mL), and the mixture was stirred overnight. The solvent was evaporated under vacuum, and the residue was dissolved in dimethyl sulfoxide/methanol (1:1, 10 mL). The mixture was purified by reverse phase chromatography using an Analogix system and a C18 column (300 g), and eluting with 10-85% acetonitrile and 0.1% trifluoroacetic acid in water, to give the title compound.

1.13.8 6-[8-(1,3-benzothiazol-2-ylcarbamoyl)-3,4-dihydroisoquinolin-2(1H)-yl]-3-{1-[(3,5-dimethyl-7-{2-[methyl(3-sulfo-L-alanyl)amino]ethoxy}tricyclo[3.3.1.1$^{3,7}$]dec-1-yl)methyl]-5-methyl-1H-pyrazol-4-yl}pyridine-2-carboxylic acid A solution of (R)-2-(((((9H-fluoren-9-yl)methoxy)carbonyl)amino)-3-sulfopropanoic acid (0.020 g), N,N-diisopropylethylamine (0.045 mL) and O-(7-azabenzotriazol-1-yl)-N,N,N',N'-tetramethyluronium hexafluorophosphate (HATU, 0.020 g) were stirred together in N,N-dimethylformamide (0.75 mL) at room temperature. After stirring for 30 minutes, Example 1.13.7 (0.039 g) was added, and the reaction stirred for an additional 1 hour. Diethylamine (0.027 mL) was added to the reaction and stirring was continued for 3 hours. The reaction was diluted with water (0.75 mL) and N,N-dimethylformamide (1 mL), neutralized with trifluoroacetic acid (0.039 mL) and purified by reverse phase HPLC using a Gilson system, eluting with 20-80% acetonitrile in water containing 0.1% v/v trifluoroacetic acid. The desired fractions were combined and freeze-dried to provide the title compound. $^1$H NMR (400 MHz, dimethyl sulfoxide-d$_6$) δ ppm 12.89 (s, 1H), 8.11-8.02 (m, 4H), 7.84 (d, 1H), 7.66 (d, 1H), 7.60-7.45 (m, 3H), 7.45-7.36 (m, 2H), 7.34 (d, 1H), 7.00 (dd, 1H), 5.00 (s, 2H), 4.57-4.40 (m, 1H), 3.93 (t, 2H), 3.90-3.84 (m, 2H), 3.58-3.43 (m, 2H), 3.41-3.21 (m, 2H), 3.18-3.02 (m, 3H), 2.95-2.85 (m, 2H), 2.76 (td, 2H), 2.14 (d, 3H), 1.51-0.85 (m, 18H). MS (ESI) m/e 911.2 $(M+H)^+$.

1.14 Synthesis of 6-[8-(1,3-benzothiazol-2-ylcarbamoyl)-3,4-dihydroisoquinolin-2(1H)-yl]-3-{1-[(3,5-dimethyl-7-{2-[(3-phosphonopropyl)amino]ethoxy}tricyclo[3.3.1.1$^{3,7}$]dec-1-yl)methyl]-5-methyl-1H-pyrazol-4-yl}pyridine-2-carboxylic acid (Compound W2.14)

1.14.1 di-tert-butyl (3-hydroxypropyl)phosphonate

NaH (60% in mineral oil, 400 mg) was added to di-tert-butylphosphonate (1.93 g) in N,N-dimethylformamide (30 mL), and the reaction was stirred at room temperature for 30 minutes. (3-Bromopropoxy)(tert-butyl)dimethylsilane (2.1 g) was added, and the reaction was stirred overnight. The mixture was diluted with diethyl ether (300 mL), and the solution was washed three times with water, and brine, then dried over sodium sulfate, filtered, and concentrated. The residue was dissolved in 20 mL tetrahydrofuran, and tetrabutyl ammonium fluoride (TBAF, 1M in tetrahydrofuran, 9 mL) was added. The solution was stirred for 20 minutes, and then pH 7 buffer (50 mL) was added. The mixture was taken up in diethyl ether, and separated, and the organic layer was washed with brine, and then concentrated. The crude product was chromatographed on silica gel using 10-100% ethyl acetate in heptanes, followed by 5% methanol in ethyl acetate to provide the title compound.

1.14.2 di-tert-butyl (3-oxopropyl)phosphonate

Example 1.14.1 (200 mg) and Dess-Martin periodinane (370 mg) were stirred in dichloromethane (5 mL) for 2 hours. The mixture was taken up in ethyl acetate, and washed twice with 1M aqueous NaOH solution, and brine, and then concentrated. The crude product was chromatographed on silica gel, using 50-100% ethyl acetate in heptanes followed by 10% methanol in ethyl acetate, to provide the title compound.

1.14.3 tert-butyl 6-(8-(benzo[d]thiazol-2-ylcarbamoyl)-3,4-dihydroisoquinolin-2(1H)-yl)-3-(1-((3-(2-((3-(diethoxyphosphoryl)propyl)amino)ethoxy)-5,7-dimethyladamantan-1-yl)methyl)-5-methyl-1H-pyrazol-4-yl)picolinate The title compound was prepared as described in Example 1.10.11, replacing Example 1.10.10 and 4-(((2S,3R,4R,5S, 6R)-3,4,5-trihydroxy-6-(hydroxymethyl)tetrahydro-2H-pyran-2-yl)oxy)benzaldehyde with Example 1.2.7 and Example 1.14.2, respectively. MS (APCI) m/e 980.9 (M+H)$^+$.

1.14.5 6-[8-(1,3-benzothiazol-2-ylcarbamoyl)-3,4-dihydroisoquinolin-2(1H)-yl]-3-{1-[(3,5-dimethyl-7-{2-[(3-phosphonopropyl)amino]ethoxy}tricyclo[3.3.1.1$^{3,7}$]dec-1-yl)methyl]-5-methyl-1H-pyrazol-4-yl}pyridine-2-carboxylic acid The title compound was prepared as described in Example 1.12.2, replacing Example 1.12.1 with Example 1.14.3. $^1$H NMR (400 MHz, dimethyl sulfoxide-d$_6$) δ ppm 8.37 (s, 2H), 8.03 (d, 1H), 7.79 (d, 1H), 7.62 (d, 1H), 7.42-7.53 (m, 3H), 7.33-7.40 (m, 2H), 7.29 (s, 1H), 6.96 (d, 1H), 4.96 (s, 2H), 3.86-3.93 (m, 2H), 3.52-3.59 (m, 2H), 2.93-3.06 (m, 6H), 2.10 (s, 3H), 1.71-1.89 (m, 2H), 1.53-1.65 (m, 2H), 1.43 (s, 2H), 1.23-1.37 (m, 4H), 0.96-1.19 (m, 6H), 0.87 (s, 6H). MS (APCI) m/e 868.3 (M+H)$^+$.

1.15 Synthesis of 6-[8-(1,3-benzothiazol-2-ylcarbamoyl)-3,4-dihydroisoquinolin-2(1H)-yl]-3-{1-[(3,5-dimethyl-7-{2-[(3-sulfo-L-alanyl)amino]ethoxy}tricyclo[3.3.1.1$^{3,7}$]dec-1-yl)methyl]-5-methyl-1H-pyrazol-4-yl}pyridine-2-carboxylic acid (Compound W2.15)

A solution of (R)-2-((((9H-fluoren-9-yl)methoxy)carbonyl)amino)-3-sulfopropanoic acid (0.050 g) and O-(7-azabenzotriazol-1-yl)-N,N,N',N'-tetramethyluronium hexafluorophosphate (0.049 g) were dissolved in N,N-dimethylformamide (1 mL) and N,N-diisopropylethylamine (0.102 mL) was added. After stirring for 15 minutes, Example 1.3.1 (0.100 g) was added, and the reaction stirred for an additional 3 hours. Diethylamine (0.061 mL) was added to the reaction and stirring was continued overnight. The reaction was neutralized with 2,2,2-trifluoroacetic acid (0.090 mL) and diluted with N,N-dimethylformamide (1 mL) and water (1 mL). The mixture was purified by reverse phase HPLC using a Gilson system, eluting with 20-80% acetonitrile in water containing 0.1% v/v trifluoroacetic acid. The desired fractions were combined and freeze-dried to provide the title compound. $^1$H NMR (500 MHz, dimethyl sulfoxide-d$_6$) δ ppm 12.86 (s, 1H), 8.63 (t, 1H), 8.15-8.01 (m, 4H), 7.79 (d, 1H), 7.62 (d, 1H), 7.56-7.41 (m, 3H), 7.40-7.33 (m, 2H), 7.30 (s, 1H), 6.96 (d, 1H), 4.96 (s, 2H), 4.08-3.97 (m, 1H), 3.89 (t, 2H), 3.82 (s, 2H), 3.42-3.31 (m, 2H), 3.28-3.17 (m, 1H), 3.16-3.06 (m, 1H), 3.01 (t, 2H), 2.97 (dd, 1H), 2.76 (dd, 1H), 2.10 (s, 3H), 1.39 (s, 2H), 1.32-1.20 (m, 4H), 1.19-1.07 (m, 4H), 1.07-0.95 (m, 2H), 0.85 (s, 6H). MS (ESI) m/e 897.2 (M+H)$^+$.

1.16 Synthesis of 6-[8-(1,3-benzothiazol-2-ylcarbamoyl)-3,4-dihydroisoquinolin-2(1H)-yl]-3-(1-{[3,5-dimethyl-7-(2-{2-[(3-phosphonopropyl)amino]ethoxy}ethoxy)tricyclo[3.3.1.1$^{3,7}$]dec-1-yl]methyl}-5-methyl-1H-pyrazol-4-yl)pyridine-2-carboxylic acid (Compound W2.16)

1.16.1 tert-butyl 6-(8-(benzo[d]thiazol-2-ylcarbamoyl)-3,4-dihydroisoquinolin-2(1H)-yl)-3-(1-((3-(2-(2-((3-di-tert-butoxyphosphoryl)propyl)amino)ethoxy)ethoxy)-5,7-dimethyladamantan-1-yl)methyl)-5-methyl-1H-pyrazol-4-yl)picolinate Example 1.10.10 (338 mg) and Example 1.14.2 (120 mg) were dissolved in ethanol (20 mL), and the solution was concentrated. The residue was again taken up in ethanol (20 mL) and concentrated. The residue was then dissolved in dichloromethane (10 mL) and to this was added sodium triacetoxyborohydride (119 mg), and the reaction was stirred overnight. The crude mixture was chromatographed on silica gel, using 1% triethylamine in 95:5 ethyl acetate/methanol, to provide the title compound. MS (ESI) 1080.3 (M+H)$^+$.

1.16.2 6-[8-(1,3-benzothiazol-2-ylcarbamoyl)-3,4-dihydroisoquinolin-2(1H)-yl]-3-(1-{[3,5-dimethyl-7-(2-{2-[(3-phosphonopropyl)amino]ethoxy}ethoxy)tricyclo[3.3.1.1$^{3,7}$]dec-1-yl]methyl}-5-methyl-1H-pyrazol-4-yl)pyridine-2-carboxylic acid Example 1.16.1 (22 mg) was stirred in dichloromethane (3 mL) and trifluoroacetic acid (3 mL) for 2 days. The mixture was concentrated and chromatographed via reverse phase on a Biotage Isolera One system using a 40 g C18 column and eluting with 10-90% acetonitrile in 0.1% trifluoroacetic acid/water, to provide the title compound as a trifluoroacetic acid salt. $^1$H NMR (400 MHz, dimethyl sulfoxide-d$_6$) δ ppm □8.62 (bs, 1H), 8.10 (d, 1H), 7.86 (d, 1H), 7.68 (d, 1H), 7.57 (d, 1H), 7.54 (dd, 1H), 7.50 (d, 1H), 7.42 (m, 2H), 7.35 (s, 1H), 7.02 (d, 1H), 5.02 (s, 2H), 3.94 (m, 2H), 3.97 (m, 2H), 3.68 (m, 2H), 3.55 (m, 2H), 3.15 (m, 1H), 3.09 (m, 4H), 2.55 (m, 4H), 2.15 (s, 3H), 1.86 (m, 1H), 1.66 (m, 2H), 1.45 (m, 2H), 1.31 (m, 4H), 1.19 (m, 4H), 1.08 (m, 2H), 0.90 (s, 6H). MS (ESI) 912.2 (M+H)$^+$.

1.17 Synthesis of 3-{1-[(3-{2-[L-alpha-aspartyl(methyl)amino]ethoxy}-5,7-dimethyltricyclo[3.3.1.1$^{3,7}$]dec-1-yl)methyl]-5-methyl-1H-pyrazol-4-yl}-6-[8-(1,3-benzothiazol-2-ylcarbamoyl)-3,4-dihydroisoquinolin-2(1H)-yl]pyridine-2-carboxylic acid (Compound W2.17)

1.17.1 6-[8-(1,3-benzothiazol-2-ylcarbamoyl)-3,4-dihydroisoquinolin-2(1H)-yl]-3-{1-[(3-{2-[{(2S)-4-tert-butoxy-2-[(tert-butoxycarbonyl)amino]-4-oxobutanoyl}(methyl)amino]ethoxy}-5,7-dimethyltricyclo[3.3.1.1$^{3,7}$]dec-1-yl)methyl]-5-methyl-1H-pyrazol-4-yl}pyridine-2-carboxylic acid A solution of Example 1.13.7 (0.060 g), (S)-4-tert-butyl 1-(2,5-dioxopyrrolidin-1-yl) 2-((tert-butoxycarbonyl)amino)succinate (0.034 g) and N,N-diisopropylethylamine were stirred together in dichloromethane (1 mL). After stirring overnight, the reaction was loaded onto silica gel and eluted using a gradient of 0.5-5% methanol/dichloromethane to give the title compound.

1.17.2 3-{1-[(3-{2-[L-alpha-aspartyl(methyl)amino]ethoxy}-5,7-dimethyltricyclo[3.3.1.1$^{3,7}$]dec-1-yl)methyl]-5-methyl-1H-pyrazol-4-yl}-6-[8-(1,3-benzothiazol-2-ylcarbamoyl)-3,4-dihydroisoquinolin-2(1H)-yl]pyridine-2-carboxylic acid A solution of Example 1.17.1 (0.049 g) in dichloromethane (1 mL) was treated with trifluoroacetic acid (0.5 mL), and the reaction was stirred overnight. The reaction was concentrated, dissolved in N,N-dimethylformamide (2 mL) and water (0.5 mL) then purified by reverse phase HPLC using a Gilson system, eluting with 20-80% acetonitrile in water containing 0.1% v/v trifluoroacetic acid. The desired fractions were combined and freeze-dried to provide the title compound. $^1$H NMR (400 MHz, dimethyl sulfoxide-d$_6$) δ ppm 12.85 (s, 1H), 8.15 (d, 3H), 8.03 (d, 1H), 7.79 (d, 1H), 7.62 (d, 1H), 7.55-7.41 (m, 3H), 7.36 (td, 2H), 7.29 (d, 1H), 6.95 (d, 1H), 4.96 (s, 2H), 4.55 (s, 1H), 3.92-3.86 (m, 2H), 3.60-3.47 (m, 2H), 3.47-3.37 (m, 2H), 3.32-3.21 (m, 1H), 3.09-2.97 (m, 4H), 2.92-2.72 (m, 3H), 2.67-2.53 (m, 1H), 2.10 (s, 3H), 1.46-0.94 (m, 12H), 0.85 (s, 6H). MS (ESI) m/e 875.2 (M+H)$^+$.

1.18 Synthesis of 6-{4-[({2-[2-(2-aminoethoxy)ethoxy]ethyl}[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl]amino)methyl]benzyl}-2,6-anhydro-L-gulonic acid (Compound W2.18)

1.18.1 (2S,3S,4R,5S)-3,4,5-Triacetoxy-6-(4-bromomethyl-benzyl)-tetrahydro-pyran-2-carboxylic acid methyl ester The title compound was prepared as described in J. R. Walker et al., *Bioorg. Med. Chem.* 2006, 14, 3038-3048. MS (ESI) m/e 518, 520 (M+NH$_4$)$^+$.

1.18.2 (2S,3S,4R,5S)-3,4,5-Triacetoxy-6-(4-formyl-benzyl)-tetrahydro-pyran-2-carboxylic acid methyl ester Example 1.18.1 (75 mg) and pyridine N-oxide (14 mg) were added to acetonitrile (0.75 mL). Silver (I) oxide (24 mg) was added to the solution, and the solution was stirred at room temperature for 16 hours. Anhydrous sodium sulfate (5 mg) was added, and the solution was stirred for five minutes. The solution was filtered and concentrated. The crude material was purified by flash column chromatography on silica gel, eluting with 50-70% ethyl acetate in heptanes. The solvent was evaporated under reduced pressure to provide the title compound.

1.18.3 (3R,4S,5R,6R)-2-(4-(((2-((3-((4-(6-(8-(benzo[d]thiazol-2-ylcarbamoyl)-3,4-dihydroisoquinolin-2(1H)-yl)-2-(tert-butoxycarbonyl)pyridin-3-yl)-5-methyl-1H-pyrazol-1-yl)methyl)-5,7-dimethyladamantan-1-yl)oxy)ethyl)amino)methyl)benzyl)-6-(methoxycarbonyl)tetrahydro-2H-pyran-3,4,5-triyl triacetate The title compound was prepared by substituting Example 1.18.2 for Example 1.5.3 in Example 1.5.4. MS (ESI) m/e 1222 (M+H)$^+$.

1.18.4 {2-[2-(2-Oxo-ethoxy)-ethoxy]-ethyl}-carbamic acid tert-butyl ester

The title compound was prepared by substituting {2-[2-(2-hydroxy-ethoxy)-ethoxy]-ethyl}-carbamic acid tert-butyl ester for Example 1.5.1 in Example 1.5.2.

1.18.5 (3R,4S,5R,6R)-2-(4-(2-(2-(((3-((4-(6-(8-(benzo[d]thiazol-2-ylcarbamoyl)-3,4-dihydroisoquinolin-2(1H)-yl)-2-(tert-butoxycarbonyl)pyridin-3-yl)-5-methyl-1H-pyrazol-1-yl)methyl)-5,7-dimethyladamantan-1-yl)oxy)ethyl)-14,14-dimethyl-12-oxo-5,8,13-trioxa-2,11-diazapentadecyl)benzyl)-6-(methoxycarbonyl)tetrahydro-2H-pyran-3,4,5-triyl triacetate The title compound was prepared by substituting Example 1.18.3 for Example 1.2.7 and Example 1.18.4 for Example 1.5.3 in Example 1.5.4. MS (ESI) m/e 1453 (M+H)$^+$.

1.18.6 6-{4-[({2-[2-(2-aminoethoxy)ethoxy]ethyl}[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl]amino)methyl]benzyl}-2,6-anhydro-L-gulonic acid The title compound was prepared by substituting Example 1.18.5 for Example 1.5.4 in Example 1.5.5. $^1$H NMR (400 MHz, dimethyl sulfoxide-d$_6$) δ ppm 9.38 (bs, 1H), 8.05 (dd, 1H), 7.90-7.68 (m, 6H), 7.62 (m, 2H), 7.53-7.27 (m, 8H), 6.94 (d, 1H), 4.96 (bs, 1H), 4.38 (bs, 4H), 3.91-3.57 (m, 11H), 3.37-3.11 (m, 14H), 2.98 (m, 6H), 2.61 (m, 1H), 2.10 (s, 3H), 1.44 (bs, 2H), 1.26 (m, 4H), 1.18-0.90 (m, 6H), 0.87 (bs, 6H). MS (ESI) m/e 1157 (M+H)$^+$.

1.19 Synthesis of 4-({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl]amino}methyl)phenyl hexopyranosiduronic acid (Compound W2.19)

1.19.1 (2R,3S,4R,5R,6R)-2-(4-formylphenoxy)-6-(methoxycarbonyl)tetrahydro-2H-pyran-3,4,5-triyl triacetate To a solution of (2R,3R,4S,5S,6S)-2-bromo-6-(methoxycarbonyl)tetrahydro-2H-pyran-3,4,5-triyl triacetate (2.42 g) in acetonitrile (30 mL) was added silver(I) oxide (1.4 g) and 4-hydroxybenzaldehyde (620 mg). The reaction mixture was stirred for 4 hours and filtered. The filtrate was concentrated, and the residue was purified by silica gel chromatography, eluting with 5-50% ethyl acetate in heptanes, to provide the title compound. MS (ESI) m/e 439.2 (M+H)$^+$.

1.19.2 4-({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl]amino}methyl)phenyl hexopyranosiduronic acid To a solution of Example 1.2.7 (36 mg) in tetrahydrofuran (2 mL) and acetic acid (0.2 mL) was added Example 1.19.1 (21 mg) followed by MgSO$_4$ (60 mg). The mixture was stirred for 1 hour before the addition of NaBH$_3$CN on resin (153 mg). The mixture was then stirred for 3 hours. The mixture was filtered and lithium hydroxide monohydrate (20 mg) was added to the filtrate. The mixture was stirred for 2 hours and was acidified with trifluoroacetic acid and purified by reverse phase HPLC (Gilson system), eluting with 10-85% acetonitrile in 0.1% trifluoroacetic acid in water, to give the title compound. $^1$H NMR (400 MHz, dimethyl sulfoxide-$d_6$) δ ppm 12.86 (s, 1H), 8.57-8.72 (m, 2H), 8.03 (d, 1H), 7.79 (d, 1H), 7.62 (d, 1H), 7.34-7.53 (m, 6H), 7.08 (t, 2H), 6.95 (d, 1H), 5.10 (d, 1H), 4.96 (s, 2H), 4.06-4.15 (m, 4H), 3.83-3.97 (m, 6H), 3.26-3.42 (m, 8H), 2.93-3.10 (m, 6H), 2.10 (s, 3H), 1.43 (s, 2H), 1.24-1.38 (m, 6H), 0.97-1.16 (m, 4H), 0.86 (s, 6H). MS (ESI) m/e 1028.3 (M+H)$^+$.

1.20 Synthesis of 6-[1-(1,3-benzothiazol-2-ylcarbamoyl)-1,2,3,4-tetrahydroquinolin-7-yl]-3-{1-[(3,5-dimethyl-7-{2-[(2-phosphonoethyl)amino]ethoxy}tricyclo[3.3.1.1$^{3,7}$]dec-1-yl)methyl]-5-methyl-1H-pyrazol-4-yl}pyridine-2-carboxylic acid (Compound W2.20)

1.20.1 2-((3,5-dimethyl-7-((5-methyl-4-(4,4,5,5-tetramethyl-1,3,2-dioxaborolan-2-yl)-1H-pyrazol-1-yl)methyl)adamantan-1-yl)oxy)ethanol To a solution of Example 1.1.6 (9 g) and [1,1'-bis(diphenylphosphino)ferrocene]dichloropalladium(II) dichloromethane (827 mg) in acetonitrile (60 mL) was added triethylamine (10 mL) and pinacolborane (6 mL). The mixture was stirred at reflux overnight, cooled and used directly in the next step. MS (ESI) m/e 445.4 (M+H)$^+$.

1.20.2 tert-butyl 6-chloro-3-(1-((3-(2-hydroxyethoxy)-5,7-dimethyladamantan-1-yl)methyl)-5-methyl-1H-pyrazol-4-yl)picolinate To a solution of tert-butyl 3-bromo-6-chloropicolinate (5.92 g) in tetrahydrofuran (60 mL) and water (30 mL) was added the crude Example 1.20.1 (4.44 g), 1,3,5,7-tetramethyl-6-phenyl-2,4,8-trioxa-6-phosphaadamante (1.5 g), tris(dibenzylideneacetone)dipalladium(0) (927 mg) and $K_3PO_4$ (22 g). The mixture was stirred at reflux overnight, cooled, diluted with ethyl acetate (800 mL) and washed with water and brine. The organic layer was dried over sodium sulfate, filtered, and concentrated. The residue was purified by flash chromatography, eluting with 20% ethyl acetate in heptane followed by 5% methanol in dichloromethane, to give the title compound. MS (ESI) m/e 531.1 (M+H)$^+$.

1.20.3 tert-butyl 3-(1-((3-(2-((tert-butyldimethylsilyl)oxy)ethoxy)-5,7-dimethyladamantan-1-yl)methyl)-5-methyl-1H-pyrazol-4-yl)-6-chloropicolinate To a solution of Example 1.20.2 (3.2 g) in N,N-dimethylformamide (20 mL) was added imidazole (0.62 g) and chloro t-buytldimethylsilane (1.37 g). The mixture was stirred overnight, diluted with ethyl acetate (300 mL), and washed with water and brine. The organic layer was dried over sodium sulfate, filtered, and concentrated. The residue was purified by flash chromatography, eluting with 20% ethyl acetate in heptanes, to provide the title compound. MS (ESI) m/e 645.4 (M+H)$^+$.

1.20.4 tert-butyl 3-(1-((3-(2-((tert-butyldimethylsilyl)oxy)ethoxy)-5,7-dimethyladamantan-1-yl)methyl)-5-methyl-1H-pyrazol-4-yl)-6-(1,2,3,4-tetrahydroquinolin-7-yl)picolinate To a solution of 7-(4,4,5,5-tetramethyl-1,3,2-dioxaborolan-2-yl)-1,2,3,4-tetrahydroquinoline (507 mg) in 1,4-dioxane (10 mL) and water (5 mL) was added Example 1.20.3 (1.25 g), bis(triphenylphosphine)palladium(II)dichloride (136 mg), and cesium fluoride (884 mg). The mixture was heated at 120° C. in a microwave synthesizer (Biotage, Initiator) for 20 minutes. The mixture was diluted with ethyl acetate (500 mL), and washed with water and brine. The organic layer was dried over sodium sulfate, filtered, concentrated and purified by flash chromatography, eluting with 20% ethyl acetate in heptanes and then with 5% methanol in dichloromethane, to provide the title compound. MS (ESI) m/e 741.5 (M+H)$^+$.

1.20.5 tert-butyl 6-(1-(benzo[d]thiazol-2-ylcarbamoyl)-1,2,3,4-tetrahydroquinolin-7-yl)-3-(1-(3-(2-((tert-butyldimethylsilyl)oxy)ethoxy)-5,7-dimethyladamantan-1-yl)methyl)-5-methyl-1H-pyrazol-4-yl)picolinate To a suspension of bis(2,5-dioxopyrrolidin-1-yl) carbonate (295 mg) in acetonitrile (10 mL) was added benzo[d]thiazol-2-amine (173 mg), and the mixture was stirred for 1 hour. A solution of Example 1.20.4 (710 mg) in acetonitrile (10 mL) was added, and the suspension was stirred overnight. The mixture was diluted with ethyl acetate (300 mL), washed with water and brine and dried over sodium sulfate. After filtration, the organic layer was concentrated and purified by silica gel chromatography, eluting with 20% ethyl acetate in heptanes, to provide the title compound. MS (ESI) m/e 917.2 (M+H)$^+$.

1.20.6 tert-butyl 6-(1-(benzo[d]thiazol-2-ylcarbamoyl)-1,2,3,4-tetrahydroquinolin-7-yl)-3-(1-((3-(2-hydroxyethoxy)-5,7-dimethyladamantan-1-yl)methyl)-5-methyl-1H-pyrazol-4-yl)picolinate To a solution of Example 1.20.5 (1.4 g) in tetrahydrofuran (10 mL) was added tetrabutyl ammonium fluoride (1.0 M in tetrahydrofuran, 6 mL). The mixture was stirred for 3 hours, diluted with ethyl acetate (300 mL) and washed with water and brine. The organic layer was dried over sodium sulfate, filtered, and concentrated to provide the title compound. MS (ESI) m/e 803.4 (M+H)$^+$.

1.20.7 tert-butyl 6-(1-(benzo[d]thiazol-2-ylcarbamoyl)-1,2,3,4-tetrahydroquinolin-7-yl)-3-(1-((3,5-dimethyl-7-(2-((methylsulfonyl)oxy)ethoxy)adamantan-1-yl)methyl)-5-methyl-1H-pyrazol-4-yl)picolinate To a cooled (0° C.) solution of Example 1.20.6 (1.2 g) in dichloromethane (20 mL) and triethylamine (2 mL) was added methanesulfonyl chloride (300 mg). The mixture was stirred for 4 hours, diluted with ethyl acetate (200 mL) and washed with water and brine. The organic layer was dried over sodium sulfate, filtered, and concentrated to provide the title compound. MS (ESI) m/e 881.3 (M+H)$^+$.

1.20.8 tert-butyl 3-(1-((3-(2-azidoethoxy)-5,7-dimethyladamantan-1-yl)methyl)-5-methyl-1H-pyrazol-4-yl)-6-(1-(benzo[d]thiazol-2-ylcarbamoyl)-1,2,3,4-tetrahydroquinolin-7-yl)picolinate To a solution of Example 1.20.7 (1.5 g) in N,N-dimethylformamide (20 mL) was added sodium azide (331 mg). The mixture was stirred for 48 hours, diluted with ethyl acetate (20.0 mL) and washed with water and brine. The organic layer was dried over sodium sulfate, filtered, concentrated and purified by silica gel chromatography, eluting with 20% ethyl acetate in dichloromethane, to provide the title compound. MS (ESI) m/e 828.4 (M+H)+.

1.20.9 tert-butyl 3-(1-((3-(2-aminoethoxy)-5,7-dimethyladamantan-1-yl)methyl)-5-methyl-1H-pyrazol-4-yl)-6-(1-(benzo[d]thiazol-2-ylcarbamoyl)-1,2,3,4-tetrahydroquinolin-7-yl)picolinate To a solution of Example 1.20.8 (1.5 g) in tetrahydrofuran (30 mL) was added Pd/C (10%, 200 mg). The mixture was stirred under a hydrogen atmosphere overnight. The reaction was filtered, and the filtrate was concentrated to provide the title compound. MS (ESI) m/e 802.4 (M+H)+.

1.20.10 tert-butyl 6-(1-(benzo[d]thiazol-2-ylcarbamoyl)-1,2,3,4-tetrahydroquinolin-7-yl)-3-(1-((3-(2-((2-(diethoxyphosphoryl)ethyl)amino)ethoxy)-5,7-dimethyladamantan-1-yl)methyl)-5-methyl-1H-pyrazol-4-yl)picolinate The title compound was prepared as described in Example 1.12.1, replacing Example 1.2.7 with Example 1.20.9.

1.20.11 6-[1-(1,3-benzothiazol-2-ylcarbamoyl)-1,2,3,4-tetrahydroquinolin-7-yl]-3-{1-[(3,5-dimethyl-7-{2-[(2-phosphonoethyl)amino]ethoxy}tricyclo[3.3.1.1$^{3,7}$]dec-1-yl)methyl]-5-methyl-1H-pyrazol-4-yl}pyridine-2-carboxylic acid The title compound was prepared as described in Example 1.12.2, replacing Example 1.12.1 with Example 1.20.10. $^1$H NMR (500 MHz, dimethyl sulfoxide-d$_6$) δ ppm 8.40 (s, 2H), 8.02 (d, 1H), 7.74-7.89 (m, 3H), 7.47 (s, 2H), 7.38 (t, 1H), 7.30 (d, 1H), 7.23 (t, 1H), 3.96 (s, 2H), 3.90 (s, 2H), 3.53-3.64 (m, 2H), 3.03-3.18 (m, 2H), 2.84 (t, 2H), 2.23 (s, 3H), 1.87-2.02 (m, 4H), 1.46 (s, 2H), 1.26-1.38 (m, 4H), 1.12-1.23 (m, 4H), 0.99-1.11 (m, 2H), 0.89 (s, 6H). MS (ESI) m/e 854.1 (M+H)+.

1.21 Synthesis of 6-[1-(1,3-benzothiazol-2-ylcarbamoyl)-1,2,3,4-tetrahydroquinolin-7-yl]-3-{1-[(3,5-dimethyl-7-{2-[methyl(3-sulfo-L-alanyl)amino]ethoxy}tricyclo[3.3.1.1$^{3,7}$]dec-1-yl)methyl]-5-methyl-1H-pyrazol-4-yl}pyridine-2-carboxylic acid (Compound W2.21)

1.21.1 tert-butyl (2-((3,5-dimethyl-7-((5-methyl-4-(4,4,5,5-tetramethyl-1,3,2-dioxaborolan-2-yl)-1H-pyrazol-1-yl)methyl)adamantan-1-yl)oxy)ethyl)(methyl)carbamate To a solution of Example 1.13.3 (1.2 g) in 1,4-dioxane was added bis(benzonitrile)palladium(II) chloride (0.04 g), 4,4,5,5-tetramethyl-1,3,2-dioxaborolane (0.937 mL) and triethylamine (0.9 mL). The mixture was heated at reflux overnight, diluted with ethyl acetate and washed with water (60 mL) and brine (60 mL). The organic layer was dried over sodium sulfate, filtered and concentrated to provide the title compound.

1.21.2 tert-butyl 3-(1-((3-(2-((tert-butoxycarbonyl)(methyl)amino)ethoxy)-5,7-dimethyladamantan-1-yl)methyl)-5-methyl-1H-pyrazol-4-yl)-6-chloropicolinate The title compound was prepared as described in Example 1.1.12, replacing Example 1.1.11 and Example 1.1.8 with tert-butyl 3-bromo-6-chloropicolinate and Example 1.21.1, respectively. MS (APCI) m/e 643.9 (M+H)+.

1.21.3 tert-butyl 3-(1-((3-(2-((tert-butoxycarbonyl)(methyl)amino)ethoxy)-5,7-dimethyladamantan-1-yl)methyl)-5-methyl-1H-pyrazol-4-yl)-6-(1,2,3,4-tetrahydroquinolin-7-yl)picolinate A mixture of Example 1.21.2 (480 mg), 7-(4,4,5,5-tetramethyl-1,3,2-dioxaborolan-2-yl)-1,2,3,4-tetrahydroquinoline (387 mg), dichlorobis(triphenylphosphine)-palladium(II) (78 mg) and cesium fluoride (340 mg) in 1,4-dioxane (12 mL) and water (5 mL) was heated at 100° C. for 5 hours. The reaction was cooled and diluted with ethyl acetate. The resulting mixture was washed with water and brine, and the organic layer was dried over sodium sulfate, filtered, and concentrated. The residue was purified by flash chromatography, eluting with 50% ethyl acetate in heptanes, to provide the title compound. MS (APCI) m/e 740.4 (M+H)+.

1.21.4 tert-butyl 6-(1-(benzo[d]thiazol-2-ylcarbamoyl)-1,2,3,4-tetrahydroquinolin-7-yl)-3-(1-((3-(2-((tert-butoxycarbonyl)(methyl)amino)ethoxy)-5,7-dimethyladamantan-1-yl)methyl)-5-methyl-1H-pyrazol-4-yl)picolinate To a solution of benzo[d]thiazol-2-amine (114 mg) in acetonitrile (5 mL) was added bis(2,5-dioxopyrrolidin-1-yl) carbonate (194 mg). The mixture was stirred for 1 hour, and Example 1.21.3 (432 mg) in acetonitrile (5 mL) was added. The mixture was stirred overnight, diluted with ethyl acetate, washed with water and brine. The organic layer was dried over sodium sulfate, filtered, and concentrated. The residue was purified by silica gel chromatography, eluting with 50% ethyl acetate in heptanes, to provide the title compound.

1.21.5 6-(1-(benzo[d]thiazol-2-ylcarbamoyl)-1,2,3,4-tetrahydroquinolin-7-yl)-3-(1-((3,5-dimethyl-7-(2-(methylamino)ethoxy)adamantan-1-yl)methyl)-5-methyl-1H-pyrazol-4-yl)picolinic acid Example 1.2.4 (200 mg) in dichloromethane (5 mL) was treated with trifluoroacetic acid (2.5 mL) overnight. The mixture was concentrated to provide the title compound. $^1$H NMR (400 MHz, dimethyl sulfoxide-d$_6$) δ ppm 8.40 (s, 1H), 8.30 (s, 2H), 8.02 (d, 1H), 7.85 (d, 1H), 7.74-7.83 (m, 2H), 7.42-7.53 (m, 2H), 7.38 (t, 1H), 7.30 (d, 1H), 7.23 (t, 1H), 3.93-4.05 (m, 2H), 3.52-3.62 (m, 2H), 2.97-3.10 (m, 2H), 2.84 (t, 2H), 2.56 (t, 2H), 2.23 (s, 3H), 1.88-2.00 (m, 2H), 1.45 (s, 2H), 1.25-1.39 (m, 4H), 1.12-1.22 (m, 4H), 1.00-1.09 (m, 2H), 0.89 (s, 6H). MS (ESI) m/e 760.1 (M+H)+.

1.21.6 6-(1-(benzo[d]thiazol-2-ylcarbamoyl)-1,2,3,4-tetrahydroquinolin-7-yl)-3-(1-((3-(2-((R)-2-((tert-butoxycarbonyl)amino)-N-methyl-3-sulfopropanamido)ethoxy)-5,7-dimethyladamantan-1-yl)methyl)-5-methyl-1H-pyrazol-4-yl)picolinic acid (R)-2-((tert-butoxycarbonyl)amino)-3-sulfopropanoic acid (70.9 mg) and O-(7-azabenzotriazol-1-yl)-N,N,N',N'-tetramethyluronium hexafluorophosphate (HATU, 65 mg) in N,N-dimethylformamide (1.5 ml) was cooled in ice-bath, and N,N-diisopropylethylamine (68.9 µL) was added. The mixture was stirred at 0° C. for 15 minutes and at room temperature for 8 hours. Example 1.21.5 (100 mg) in N,N-dimethylformamide (1 mL) and N,N-diisopropylethylamine (60 µL) were added. The resulting mixture was stirred overnight, concentrated and purified by reverse phase chromatography (C18 column), eluting with 20-60% acetonitrile in water containing 0.1% trifluoroacetic acid, to provide the title compound.

1.21.7 6-[1-(1,3-benzothiazol-2-ylcarbamoyl)-1,2,3,4-tetrahydroquinolin-7-yl]-3-{1-[(3,5-dimethyl-7-{2-[methyl(3-sulfo-L-alanyl)amino]ethoxy}tricyclo[3.3.1.1$^{3,7}$]dec-1-yl)methyl]-5-methyl-1H-pyrazol-4-yl}pyridine-2-carboxylic acid Example 1.21.6 (80 mg) in dichloromethane (3 mL) was treated with trifluoroacetic acid (1.5 mL) for 20 minutes. The reaction mixture was concentrated and purified by reverse phase chromatography (C18 column), eluting with 0-50% acetonitrile in 4 mM aqueous ammonium acetate solution, to provide the title compound. $^1$H NMR (500 MHz, dimethyl sulfoxide-d$_6$) δ ppm 8.57 (s, 1H), 7.59-7.67 (m, 3H), 7.54 (d, 1H), 7.46-7.51 (m, 1H), 7.30 (d, 1H), 7.08-7.17 (m, 2H), 6.90 (t, 1H), 3.91-4.10 (m, 3H), 3.84 (s, 2H), 3.04 (s, 2H), 2.75-2.83 (m, 4H), 2.59-2.70 (m, 2H), 2.27-2.39 (m, 2H), 2.26 (s, 3H), 1.81-1.93 (m, 2H), 1.74 (s, 9H), 1.42 (s, 2H), 0.96-1.33 (m, 10H), 0.86 (s, 3H). MS (ESI) m/e 909.2 (M−H)$^-$.

1.22 Synthesis of 3-{1-[(3,5-dimethyl-7-{2-[(2-sulfoethyl)amino]ethoxy}tricyclo[3.3.1.1$^{3,7}$]dec-1-yl)methyl]-5-methyl-1H-pyrazol-4-yl}-6-[8-([1,3]thiazolo[5,4-b]pyridin-2-ylcarbamoyl)-3,4-dihydroisoquinolin-2(1H)-yl]pyridine-2-carboxylic acid (Compound W2.22)

1.22.1 tert-butyl 3-(1-((3-(2-azidoethoxy)-5,7-dimethyladamantan-1-yl)methyl)-5-methyl-1H-pyrazol-4-yl)-6-(8-(thiazolo[5,4-b]pyridin-2-ylcarbamoyl)-3,4-dihydroisoquinolin-2(1H)-yl)picolinate Example 1.2.5 (560 mg) and thiazolo[5,4-b]pyridin-2-amine (135 mg) were dissolved in dichloromethane (12 mL). N,N-Dimethylpyridin-4-amine (165 mg) and N-ethyl-N'-(3-dimethylaminopropyl)carbodiimide hydrochloride (260 mg) were added, and the reaction stirred at room temperature overnight. The reaction mixture was concentrated, and the crude residue was purified by silica gel chromatography, eluting with 65/35 dichloromethane/ethyl acetate, to provide the title compound. MS (ESI) m/e 829.1 (M+H)$^+$.

1.22.2 tert-butyl 3-(1-((3-(2-aminoethoxy)-5,7-dimethyladamantan-1-yl)methyl)-5-methyl-1H-pyrazol-4-yl)-6-(8-(thiazolo[5,4-b]pyridin-2-ylcarbamoyl)-3,4-dihydroisoquinolin-2(1H)-yl)picolinate The title compound was prepared by substituting Example 1.22.1 for Example 1.2.6 in Example 1.2.7. MS (ESI) m/e 803.2 (M+H)$^+$.

1.22.3 tert-butyl 3-[1-({3,5-dimethyl-7-[(2,2,7,7-tetramethyl-10,10-dioxido-3,3-diphenyl-4,9-dioxa-10λ$^6$-thia-13-aza-3-silapentadecan-15-yl)oxy]tricyclo[3.3.1.1$^{3,7}$]dec-1-yl}methyl)-5-methyl-1H-pyrazol-4-yl]-6-[8-([1,3]thiazolo[5,4-b]pyridin-2-ylcarbamoyl)-3,4-dihydroisoquinolin-2(1H)-yl]pyridine-2-carboxylate To a solution of Example 1.22.2 (70 mg) and 4-((tert-butyldiphenylsilyl)oxy)-2,2-dimethylbutyl ethenesulfonate (48 mg) in dichloromethane (1 mL) was added N,N-diisopropylethylamine (0.06 mL), and the reaction stirred at room temperature overnight. The reaction was concentrated, and the crude residue was purified by silica gel chromatography, eluting with a gradient of 1-4% methanol in dichloromethane, to provide the title compound. MS (ESI) m/e 1249.2 (M+H)$^+$.

1.22.4 2-((2-((3-((4-(2-tert-butoxycarbonyl)-6-(8-(thiazolo[5,4-b]pyridin-2-ylcarbamoyl)-3,4-dihydroisoquinolin-2(1H)-yl)pyridin-3-yl)-5-methyl-1H-pyrazol-1-yl)methyl)-5,7-dimethyladamantan-1-yl)oxy)ethyl)amino)ethanesulfonic acid To a solution of Example 1.22.3 (70 mg) in tetrahydrofuran (0.25 mL) was added tetrabutylammonium fluoride (60 µL, 1.0M solution in tetrahydrofuran), and the reaction was stirred at room temperature for two days. The reaction was concentrated, and the residue was purified by reverse phase chromatography (C18 column), eluting with 10-90% acetonitrile in water containing 0.1% trifluoroacetic acid, to provide the title compound as a trifluoroacetic acid salt. MS (ESI) m/e 911.1 (M+H)$^+$.

1.22.5 3-{1-[(3,5-dimethyl-7-{2-[(2-sulfoethyl)amino]ethoxy}tricyclo[3.3.1.1$^{3,7}$]dec-1-yl)methyl]-5-methyl-1H-pyrazol-4-yl}-6-[8-([1,3]thiazolo[5,4-b]pyridin-2-ylcarbamoyl)-3,4-dihydroisoquinolin-2(1H)-yl]pyridine-2-carboxylic acid The title compound was prepared by substituting Example 1.22.4 for Example 1.2.8 in Example 1.2.9. $^1$H NMR (400 MHz, dimethyl sulfoxide-d$_6$) δ ppm 13.00 (s, 1H), 8.52 (dd, 2H), 8.33 (br s, 2H), 8.16 (dd, 1H), 7.62 (m, 1H), 7.53 (m, 2H), 7.45 (d, 1H), 7.38 (m, 1H), 7.29 (s, 1H), 6.98 (d, 1H), 4.96 (s, 2H), 3.88 (m, 2H), 3.83 (s, 2H), 3.54 (m, 2H), 3.22 (m, 2H), 3.10 (m, 2H), 3.02 (t, 2H), 2.80 (t, 2H), 2.11 (s, 3H), 1.41 (s, 2H), 1.28 (m, 4H), 1.14 (m, 4H), 1.02 (m, 2H), 0.86 (s, 6H). MS (ESI) m/e 855.2 (M+H)$^+$.

1.23 Synthesis of 3-{1-[(3,5-dimethyl-7-{2-[(2-sulfoethyl)amino]ethoxy}tricyclo[3.3.1.1$^{3,7}$]dec-1-yl)methyl]-5-methyl-1H-pyrazol-4-yl}-6-[8-([1,3]thiazolo[4,5-b]pyridin-2-ylcarbamoyl)-3,4-dihydroisoquinolin-2(1H)-yl]pyridine-2-carboxylic acid (Compound W2.23)

1.23.1 tert-butyl 3-(1-((3-(2-azidoethoxy)-5,7-dimethyladamantan-1-yl)methyl)-5-methyl-1H-pyrazol-4-yl)-6-(8-(thiazolo[4,5-b]pyridin-2-ylcarbamoyl)-3,4-dihydroisoquinolin-2(1H)-yl)picolinate The title compound was prepared by substituting thiazolo[4,5-b]pyridin-2-amine for thiazolo[5,4-b]pyridin-2-amine in Example 1.22.1. MS (ESI) m/e 855.2 (M+H)$^+$.

1.23.2 tert-butyl 3-(1-((3-(2-aminoethoxy)-5,7-dimethyladamantan-1-yl)methyl)-5-methyl-1H-pyrazol-4-yl)-6-(8-(thiazolo[4,5-b]pyridin-2-ylcarbamoyl)-3,4-dihydroisoquinolin-2(1H)-yl)picolinate The title compound was prepared by substituting Example 1.23.1 for Example 1.2.6 in Example 1.2.7. MS (ESI) m/e 803.2 (M+H)$^+$.

1.23.3 tert-butyl 3-[1-({3,5-dimethyl-7-[(2,2,7,7-tetramethyl-10,10-dioxido-3,3-diphenyl-4,9-dioxa-10λ⁶-thia-13-aza-3-silapentadecan-15-yl)oxy]tricyclo[3.3.1.1³,⁷]dec-1-yl}methyl)-5-methyl-1H-pyrazol-4-yl]-6-[8-([1,3]thiazolo[4,5-b]pyridin-2-ylcarbamoyl)-3,4-dihydroisoquinolin-2(1H)-yl]pyridine-2-carboxylate The title compound was prepared by substituting Example 1.23.2 for Example 1.22.2 in Example 1.22.3. MS (ESI) m/e 1249.2 (M+H)⁺.

1.23.4 3-{1-[(3,5-dimethyl-7-{2-[(2-sulfoethyl)amino]ethoxy}tricyclo[3.3.1.1³,⁷]dec-1-yl)methyl]-5-methyl-1H-pyrazol-4-yl}-6-[8-([1,3]thiazolo[4,5-b]pyridin-2-ylcarbamoyl)-3,4-dihydroisoquinolin-2(1H)-yl]pyridine-2-carboxylic acid The title compound was prepared by substituting Example 1.23.3 for Example 1.2.8 in Example 1.2.9. ¹H NMR (400 MHz, dimethyl sulfoxide-$d_6$) δ ppm 13.20 (br s, 1H), 8.61 (dd, 1H), 8.56 (dd, 1H), 8.33 (br s, 2H), 7.56 (d, 1H) 7.52 (d, 1H), 7.46 (d, 1H), 7.39 (m, 2H), 7.29 (s, 1H), 6.98 (d, 1H), 4.98 (s, 2H), 3.88 (m, 2H), 3.83 (s, 2H), 3.54 (m, 2H), 3.22 (m, 2H), 3.10 (m, 2H), 3.02 (t, 2H), 2.80 (t, 2H), 2.10 (s, 3H), 1.41 (s, 2H), 1.30 (m, 4H), 1.12 (m, 4H), 1.02 (m, 2H), 0.86 (s, 6H). MS (ESI) m/e 855.1 (M+H)⁺.

1.24 Synthesis of 6-[1-(1,3-benzothiazol-2-ylcarbamoyl)-1,2,3,4-tetrahydroquinolin-7-yl]-3-{1-[(3,5-dimethyl-7-{2-[(2-sulfoethyl)amino]ethoxy}tricyclo[3.3.1.1³,⁷]dec-1-yl)methyl]-5-methyl-1H-pyrazol-4-yl}pyridine-2-carboxylic acid (Compound W2.24)

1.24.1 tert-butyl 6-[1-(1,3-benzothiazol-2-ylcarbamoyl)-1,2,3,4-tetrahydroquinolin-7-yl]-3-[1-({3,5-dimethyl-7-[(2,2,7,7-tetramethyl-10,10-dioxido-3,3-diphenyl-4,9-dioxa-10λ⁶-thia-13-aza-3-silapentadecan-15-yl)oxy]tricyclo[3.3.1.1³,⁷]dec-1-yl}methyl)-5-methyl-1H-pyrazol-4-yl]pyridine-2-carboxylate The title compound was prepared as described in Example 1.2.8, replacing Example 1.2.7 with Example 1.20.9.

1.24.2 6-[1-(1,3-benzothiazol-2-ylcarbamoyl)-1,2,3,4-tetrahydroquinolin-7-yl]-3-{1-[(3,5-dimethyl-7-{2-[(2-sulfoethyl)amino]ethoxy}tricyclo[3.3.1.1³,⁷]dec-1-yl)methyl]-5-methyl-1H-pyrazol-4-yl}pyridine-2-carboxylic acid The title compound was prepared as described in Example 1.2.9, replacing Example 1.2.8 with Example 1.24.1. ¹H NMR (500 MHz, dimethyl sulfoxide-$d_6$) δ ppm 8.26-8.46 (m, 3H), 8.02 (d, 1H), 7.89 (d, 1H), 7.82 (d, 1H), 7.75-7.79 (m, 1H), 7.47 (s, 2H), 7.37 (t, 1H), 7.30 (d, 1H), 7.22 (t, 1H), 3.96 (s, 2H), 3.90 (s, 2H), 3.54-3.61 (m, 2H), 3.18-3.29 (m, 2H), 3.07-3.15 (m, 2H), 2.78-2.92 (m, 4H), 2.23 (s, 3H), 1.87-2.02 (m, 2H), 1.44 (s, 2H), 1.32 (q, 4H), 1.12-1.25 (m, 4H), 1.00-1.11 (m, 2H), 0.88 (s, 6H). MS (ESI) m/e 854.0 (M+H)⁺.

1.25 Synthesis of 6-[8-(1,3-benzothiazol-2-ylcarbamoyl)-3,4-dihydroisoquinolin-2(1H)-yl]-3-{1-[(3-{2-[(2-carboxyethyl)amino]ethoxy}-5,7-dimethyltricyclo[3.3.1.1³,⁷]dec-1-yl)methyl]-5-methyl-1H-pyrazol-4-yl}pyridine-2-carboxylic acid (W2.25)

1.25.1 tert-butyl 6-(8-(benzo[d]thiazol-2-ylcarbamoyl)-3,4-dihydroisoquinolin-2(1H)-yl)-3-(1-((3-(2-((3-(tert-butoxy)-3-oxopropyl)amino)ethoxy)-5,7-dimethyladamantan-1-yl)methyl)-5-methyl-1H-pyrazol-4-yl)picolinate The title compound was prepared as described in Example 1.12.1, replacing diethyl vinylphosphonate with tert-butyl acrylate. MS (APCI) m/e 930.6 (M+H)⁺.

1.25.2 6-[8-(1,3-benzothiazol-2-ylcarbamoyl)-3,4-dihydroisoquinolin-2(1H)-yl]-3-{1-[(3-{2-[(2-carboxyethyl)amino]ethoxy}-5,7-dimethyltricyclo[3.3.1.1³,⁷]dec-1-yl)methyl]-5-methyl-1H-pyrazol-4-yl}pyridine-2-carboxylic acid The title compound was prepared as described in Example 1.6.2, replacing Example 1.6.1 with Example 1.25.1. ¹H NMR (400 MHz, dimethyl sulfoxide-$d_6$) δ ppm 8.03 (d, 1H), 7.78 (d, 1H), 7.61 (d, 1H), 7.39-7.50 (m, 2H), 7.32-7.38 (m, 3H), 7.23 (s, 1H), 6.73 (d, 1H), 4.88 (s, 2H), 3.88 (t, 2H), 3.79 (s, 2H), 2.99 (t, 2H), 2.86-2.93 (m, 2H), 2.50-2.58 (m, 2H), 2.08 (s, 3H), 1.35 (d, 2H), 1.01-1.30 (m, 10H), 0.86 (s, 6H). MS (APCI) m/e 819.0 (M+H)⁺.

1.26 Synthesis of 6-[8-(1,3-benzothiazol-2-ylcarbamoyl)-3,4-dihydroisoquinolin-2(1H)-yl]-3-{1-[(3,5-dimethyl-7-{2-[(3-phosphonopropyl)(piperidin-4-yl)amino]ethoxy}tricyclo[3.3.1.1³,⁷]dec-1-yl)methyl]-5-methyl-1H-pyrazol-4-yl}pyridine-2-carboxylic acid (Compound W2.26)

1.26.1 tert-butyl 6-(8-(benzo[d]thiazol-2-ylcarbamoyl)-3,4-dihydroisoquinolin-2(1H)-yl)-3-(1-(((1r,3r)-3-(2-((1-(tert-butoxycarbonyl)piperidin-4-yl)amino)ethoxy)-5,7-dimethyladamantan-1-yl)methyl)-5-methyl-1H-pyrazol-4-yl)picolinate A solution of Example 1.2.7 (0.020 g), tert-butyl 4-oxopiperidine-1-carboxylate (4.79 mg) and sodium triacetoxyborohydride (7 mg) was stirred in dichloromethane (0.5 mL) at room temperature. The reaction was stirred overnight and purified without workup by silica gel chromatography, eluting with 0 to 10% methanol in dichloromethane, to give the title compound. MS (ELSD) m/e 985.4 (M+H)⁺.

1.26.2 6-[8-(1,3-benzothiazol-2-ylcarbamoyl)-3,4-dihydroisoquinolin-2(1H)-yl]-3-{1-[(3,5-dimethyl-7-{2-[(3-phosphonopropyl)(piperidin-4-yl)amino]ethoxy}tricyclo[3.3.1.1³,⁷]dec-1-yl)methyl]-5-methyl-1H-pyrazol-4-yl}pyridine-2-carboxylic acid A solution of Example 1.26.1 (0.108 g), Example 1.14.2 (0.030 g) and sodium triacetoxyborohydride (0.035 g) in dichloromethane (1 mL) was stirred at room temperature for 1 hour. Trifluoroacetic acid (1 mL) was added to the reaction, and stirring was continued overnight. The reaction was concentrated, dissolved in N,N-dimethylformamide (2 mL) and water (0.5 mL) and purified by reverse phase HPLC using a Gilson system, eluting with 10-75% acetonitrile in water containing 0.1% v/v trifluoroacetic acid. The desired fractions were combined and freeze-dried to provide the title compound. $^1$H NMR (400 MHz, dimethyl sulfoxide-d$_6$) δ ppm 8.83 (s, 1H), 8.50 (s, 1H), 8.04 (d, 2H), 7.80 (d, 2H), 7.63 (d, 2H), 7.56-7.42 (m, 5H), 7.37 (tt, 3H), 7.30 (s, 1H), 6.96 (d, 1H), 4.96 (s, 2H), 3.89 (t, 2H), 3.44 (d, 6H), 3.31-3.16 (m, 6H), 3.09-2.98 (m, 2H), 2.98-2.85 (m, 1H), 2.18 (d, 2H), 2.10 (s, 3H), 2.00-1.74 (m, 4H), 1.71-1.57 (m, 2H), 1.51-0.97 (m, 12H), 0.87 (s, 6H). MS (ESI) m/e 951.2 (M+H)$^+$.

1.27 Synthesis of 3-{1-[(3-{2-[D-alpha-aspartyl (methyl)amino]ethoxy}-5,7-dimethyltricyclo [3.3.1.1$^{3,7}$]dec-1-yl)methyl]-5-methyl-1H-pyrazol-4-yl}-6-[8-(1,3-benzothiazol-2-ylcarbamoyl)-3,4-dihydroisoquinolin-2(1H)-yl]pyridine-2-carboxylic acid (Compound W2.27)

1.27.1 tert-butyl 6-(8-(benzo[d]thiazol-2-ylcarbamoyl)-3,4-dihydroisoquinolin-2(1H)-yl)-3-(1-((3,5-dimethyl-7-(2-(methylamino)ethoxy)adamantan-1-yl)methyl)-5-methyl-1H-pyrazol-4-yl)picolinate The title compound was prepared as described in Example 1.11.1 by substituting Example 1.10.9 with Example 1.13.6.

1.27.2 3-{1-[(3-{2-[D-alpha-aspartyl(methyl)amino] ethoxy}-5,7-dimethyltricyclo[3.3.1.1$^{3,7}$]dec-1-yl) methyl]-5-methyl-1H-pyrazol-4-yl}-6-[8-(1,3-benzothiazol-2-ylcarbamoyl)-3,4-dihydroisoquinolin-2 (1H)-yl]pyridine-2-carboxylic acid A solution of Example 1.27.1 (0.074 g), 2-(3H-[1,2,3] triazolo[4,5-b]pyridin-3-yl)-1,1,3,3-tetramethylisouronium hexafluorophosphate(V) (0.038 g), N,N-diisopropylethylamine (0.048 mL) and (R)-4-(tert-butoxy)-2-((tert-butoxycarbonyl)amino)-4-oxobutanoic acid (0.029 g) in dichloromethane (1 mL) was stirred for 2 hours. Trifluoroacetic acid (0.5 mL) was added, and stirring was continued overnight. The reaction was concentrated, dissolved in N,N-dimethylformamide (1.5 mL) and water (0.5 mL), and purified by reverse phase HPLC using a Gilson system, eluting with 10-75% acetonitrile in water containing 0.1% v/v trifluoroacetic acid. The desired fractions were combined and freeze-dried to provide the title compound. $^1$H NMR (500 MHz, dimethyl sulfoxide-d$_6$) δ ppm 12.88 (s, 1H), 8.16 (s, 3H), 8.04 (d, 1H), 7.80 (d, 1H), 7.62 (d, 1H), 7.55-7.42 (m, 3H), 7.41-7.33 (m, 2H), 7.33-7.27 (m, 1H), 6.96 (d, 1H), 4.96 (s, 2H), 4.63-4.49 (m, 1H), 3.89 (t, 2H), 3.82 (s, 2H), 3.61-3.37 (m, 4H), 3.10-2.97 (m, 4H), 2.89-2.73 (m, 2H), 2.67-2.52 (m, 1H), 2.10 (s, 3H), 1.45-0.95 (m, 12H), 0.85 (s, 6H). MS (ESI) m/e 875.3 (M+H)$^+$.

1.28 Synthesis of 6-[8-(1,3-benzothiazol-2-ylcarbamoyl)-3,4-dihydroisoquinolin-2(1H)-yl]-3-(1-{[3-(2-{[1-(carboxymethyl)piperidin-4-yl] amino}ethoxy)-5,7-dimethyltricyclo[3.3.1.1$^{3,7}$]dec-1-yl]methyl}-5-methyl-1H-pyrazol-4-yl)pyridine-2-carboxylic acid (Compound W2.28)

A solution of Example 1.2.7 (0.055 g), tert-butyl 2-(4-oxopiperidin-1-yl)acetate (0.014 g) and sodium triacetoxyborohydride (0.019 g) was stirred in dichloromethane (0.5 mL) at room temperature. After stirring for 2 hours, trifluoroacetic acid (0.5 mL) was added to the reaction, and stirring was continued overnight. The reaction was concentrated, dissolved in N,N-dimethylformamide (1.5 mL) and water (0.5 mL) and purified by reverse phase HPLC using a Gilson system, eluting with 10-80% acetonitrile in water containing 0.1% v/v trifluoroacetic acid. The desired fractions were combined and freeze-dried to provide the title compound. $^1$H NMR (501 MHz, dimethyl sulfoxide-d$_6$) δ ppm 12.85 (s, 1H), 8.80 (s, 2H), 8.03 (d, 1H), 7.80 (d, 1H), 7.62 (d, 1H), 7.55-7.41 (m, 3H), 7.36 (q, 2H), 7.29 (s, 1H), 6.96 (d, 1H), 4.96 (s, 2H), 4.07 (s, 2H), 3.89 (t, 2H), 3.83 (s, 2H), 3.66-3.55 (m, 4H), 3.30 (s, 1H), 3.08 (s, 4H), 3.02 (t, 2H), 2.22 (d, 2H), 2.10 (s, 3H), 1.97-1.78 (m, 2H), 1.44 (s, 2H), 1.31 (q, 4H), 1.20-0.96 (m, 6H), 0.87 (s, 6H). MS (ESI) m/e 887.3 (M+H)$^+$.

1.29 Synthesis of N-[(5S)-5-amino-6-{[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl] (methyl)amino}-6-oxohexyl]-N,N-dimethylmethanaminium (Compound W2.29)

A solution of Fmoc-N-ϵ-(trimethyl)-L-lysine hydrochloride (0.032 g), 2-(3H-[1,2,3]triazolo[4,5-b]pyridin-3-yl)-1,1,3,3-tetramethylisouronium hexafluorophosphate(V) (0.028 g) and N,N-diisopropylethylamine (0.034 mL) in N,N-dimethylformamide (0.5 mL) was stirred for 5 minutes. The reaction was added to Example 1.13.7 (0.050 g), and stirring was continued at room temperature overnight. Diethylamine (0.069 mL) was added to the reaction, and stirring was continued for an additional 2 hours. The reaction was diluted with N,N-dimethylformamide (1 mL), water (0.5 mL), and trifluoroacetic acid (0.101 mL). The mixture was purified by reverse phase HPLC using a Gilson system, eluting with 10-90% acetonitrile in water containing 0.1% v/v trifluoroacetic acid. The desired fractions were combined and freeze-dried to provide the title compound. $^1$H NMR (500 MHz, dimethyl sulfoxide-d$_6$) δ ppm 12.87 (s, 1H), 8.13 (s, 3H), 8.04 (d, 1H), 7.80 (d, 1H), 7.62 (d, 1H), 7.54-7.42 (m, 3H), 7.42-7.34 (m, 2H), 7.29 (s, 1H), 6.96 (d, 1H), 4.96 (s, 2H), 4.42-4.24 (m, 1H), 3.89 (t, 2H), 3.82 (s, 2H), 3.29-3.16 (m, 2H), 3.08-3.00 (m, 15H), 2.87 (s, 2H), 2.10 (s, 3H), 1.84-1.60 (m, 4H), 1.42-0.97 (m, 15H), 0.85 (s, 6H). MS (ESI) m/e 930.3 (M+H)$^+$.

1.30 Synthesis of 6-[8-(1,3-benzothiazol-2-ylcarbamoyl)-3,4-dihydroisoquinolin-2(1H)-yl]-3-{1-[(3,5-dimethyl-7-{2-[piperidin-4-yl(2-sulfoethyl)amino] ethoxy}tricyclo[3.3.1.1$^{3,7}$]dec-1-yl)methyl]-5-methyl-1H-pyrazol-4-yl}pyridine-2-carboxylic acid (Compound W2.30)

1.30.1 tert-butyl 6-(8-(1,3-benzothiazol-2-ylcarbamoyl)-3,4-dihydroisoquinolin-2(1H)-yl]-3-(1-{[3-({13-[1-(tert-butoxycarbonyl)piperidin-4-yl]-2,2,7,7-tetramethyl-10,10-dioxido-3,3-diphenyl-4,9-dioxa-10λ$^6$-thia-13-aza-3-silapentadecan-15-yl}oxy)-5,7-dimethyltricyclo[3.3.1.1$^{3,7}$]dec-1-yl]methyl}-5-methyl-1H-pyrazol-4-yl)pyridine-2-carboxylate A solution of Example 1.2.8 (0.111 g), tert-butyl 4-oxopiperidine-1-carboxylate (0.021 g) and sodium triacetoxyborohydride (0.028 g) in dichloromethane (1 mL) was stirred at room temperature for 1 hour. Acetic acid (7.63 µL) was added, and stirring was continued overnight. Additional tert-butyl 4-oxopiperidine-1-carboxylate (0.021 g), sodium triacetoxyborohydride (0.028 g) and acetic acid (8 µL) were added to the reaction, and stirring was continued for an additional 4 hours. The reaction was loaded directly onto

1.30.2 6-[8-(1,3-benzothiazol-2-ylcarbamoyl)-3,4-dihydroisoquinolin-2(1H)-yl]-3-{1-[(3,5-dimethyl-7-{2-[piperidin-4-yl(2-sulfoethyl)amino]ethoxy}tricyclo[3.3.1.1³,⁷]dec-1-yl)methyl]-5-methyl-1H-pyrazol-4-yl}pyridine-2-carboxylic acid To a solution of Example 1.30.1 (0.078 g) in dichloromethane (1 mL) was added trifluoroacetic acid (0.5 mL), and the reaction was stirred at room temperature overnight. The reaction was concentrated and dissolved in N,N-dimethylformamide (1.5 mL) and water (0.5 mL). The mixture was purified by reverse phase HPLC using a Gilson system, eluting with 10-75% acetonitrile in water containing 0.1% v/v trifluoroacetic acid. The desired fractions were combined and freeze-dried to provide the title compound. $^1$H NMR (400 MHz, dimethyl sulfoxide-$d_6$) δ ppm 12.89 (s, 1H), 9.31 (s, 1H), 8.75 (d, 1H), 8.36-8.19 (m, 1H), 8.08 (d, 1H), 7.84 (d, 1H), 7.66 (d, 1H), 7.58 (d, 1H), 7.55-7.45 (m, 2H), 7.40 (td, 2H), 7.34 (s, 1H), 6.99 (d, 1H), 5.00 (s, 2H), 3.93 (t, 2H), 3.87 (s, 2H), 3.49 (d, 6H), 3.39-3.31 (m, 2H), 3.01 (m, 6H), 2.15 (s, 6H), 1.94 (s, 2H), 1.58-0.99 (m, 12H), 0.91 (s, 6H). MS (ESI) m/e 937.3 (M+H)⁺.

1.31 Synthesis of 6-[8-(1,3-benzothiazol-2-ylcarbamoyl)-5-(3-phosphonopropoxy)-3,4-dihydroisoquinolin-2(1H)-yl]-3-[1-({3,5-dimethyl-7-[2-(methylamino)ethoxy]tricyclo[3.3.1.1³,⁷]dec-1-yl}methyl)-5-methyl-1H-pyrazol-4-yl]pyridine-2-carboxylic acid (Compound W2.31)

1.31.1 tert-butyl 8-bromo-5-hydroxy-3,4-dihydroisoquinoline-2(1H)-carboxylate To a solution of tert-butyl 5-hydroxy-3,4-dihydroisoquinoline-2(1H)-carboxylate (9 g) in N,N-dimethylformamide (150 mL) was added N-bromosuccinimide (6.43 g). The mixture was stirred overnight and quenched with water (200 mL). The mixture was diluted with ethyl acetate (500 mL), washed with water and brine, and dried over sodium sulfate. Evaporation of the solvent gave the title compound, which was used in the next reaction without further purification. MS(ESI) m/e 329.2 (M+H)⁺.

1.31.2 tert-butyl 5-(benzyloxy)-8-bromo-3,4-dihydroisoquinoline-2(1H)-carboxylate To a solution of Example 1.31.1 (11.8 g) in acetone (200 mL) was added benzyl bromide (7.42 g) and $K_2CO_3$ (5 g), and the mixture was stirred at reflux overnight. The mixture was concentrated, and the residue was partitioned between ethyl acetate (600 mL) and water (200 mL). The organic layer was washed with water and brine, dried over sodium sulfate, filtered and concentrated. The residue was purified by silica gel chromatography, eluting with 10% ethyl acetate in heptane, to provide the title compound. MS (ESI) m/e 418.1 (M+H)⁺.

1.31.3 2-tert-butyl 8-methyl 5-(benzyloxy)-3,4-dihydroisoquinoline-2,8(1H)-dicarboxylate Methanol (100 mL) and triethylamine (9.15 mL) were added to Example 1.31.2 (10.8 g) and [1,1'-bis(diphenylphosphino)ferrocene]dichloropalladium(II) (0.48 g) in a 500 mL stainless steel pressure reactor. The vessel was sparged with argon several times. The reactor was pressurized with carbon monoxide and stirred for 2 hours at 100° C. under 60 psi of carbon monoxide. After cooling, the crude reaction mixture was concentrated under vacuum. The residue was added to ethyl acetate (500 mL) and water (200 mL). The organic layer was further washed with water and brine, dried over sodium sulfate, filtered and concentrated. The residue was purified by silica gel chromatography, eluting with 10-20% ethyl acetate in heptane, to provide the title compound. MS (ESI) m/e 398.1 (M+H)⁺.

1.31.4 methyl 5-(benzyloxy)-1,2,3,4-tetrahydroisoquinoline-8-carboxylate hydrochloride To a solution of Example 1.31.3 (3.78 g) in tetrahydrofuran (20 mL) was added 4N HCl in 1,4-dioxane (20 mL), and the mixture was stirred overnight. The mixture was concentrated under vacuum to give the title compound, which was used in the next reaction without further purification. MS(ESI) m/e 298.1 (M+H)⁺.

1.31.5 methyl 5-(benzyloxy)-2-(5-bromo-6-(tert-butoxycarbonyl)pyridin-2-yl)-1,2,3,4-tetrahydroisoquinoline-8-carboxylate To a solution of Example 1.31.4 (3.03 g) in dimethyl sulfoxide (50 mL) was added Example 1.1.10 (2.52 g) and triethylamine (3.8 mL), and the mixture was stirred at 60° C. overnight under nitrogen. The reaction mixture was diluted with ethyl acetate (500 mL), washed with water and brine, dried over sodium sulfate, filtered and concentrated. The residue was purified by silica gel chromatography, eluting with 20% ethyl acetate in heptane, to give the title compound. MS (ESI) m/e 553.1 (M+H)⁺.

1.31.6 tert-butyl (2-((3,5-dimethyl-7-((5-methyl-4-(4,4,5,5-tetramethyl-1,3,2-dioxaborolan-2-yl)-1H-pyrazol-1-yl)methyl)adamantan-1-yl)oxy)ethyl)(methyl)carbamate To a solution of Example 1.13.3 (2.6 g) and [1,1'-bis(diphenylphosphino)ferrocene]dichloropalladium(II) dichloromethane (190 mg) in acetonitrile (30 mL) was added triethylamine (2.0 mL) and pinacolborane (1.4 mL), and the mixture was stirred at reflux overnight. The mixture was used directly in the next reaction without work up. MS (ESI) m/e 558.4 (M+H)⁺.

1.31.7 methyl 5-(benzyloxy)-2-(6-(tert-butoxycarbonyl)-5-(1-((3-(2-((tert-butoxycarbonyl)(methyl)amino)ethoxy)-5,7-dimethyladamantan-1-yl)methyl)-5-methyl-1H-pyrazol-4-yl)pyridin-2-yl)-1,2,3,4-tetrahydroisoquinoline-8-carboxylate To a solution of Example 1.31.5 (2.58 g) in tetrahydrofuran (40 mL) and water (20 mL) was added Example 1.31.6 (2.66 g), 1,3,5,7-tetramethyl-6-phenyl-2,4,8-trioxa-6-phosphaadamante (341 mg), tris(dibenzylideneacetone)dipalladium(0) (214 mg), and $K_3PO_4$ (4.95 g), and the mixture was stirred at reflux for 4 hours. The mixture was diluted with ethyl acetate (500 mL), washed with water and brine, dried over sodium sulfate, filtered and concentrated. The residue was purified by silica gel chromatography, eluting with 20% ethyl acetate in dichloromethane, to provide the title compound. MS (ESI) m/e 904.5 (M+H)⁺.

1.31.8 methyl 2-(6-(tert-butoxycarbonyl)-5-(1-((3-(2-((tert-butoxycarbonyl)(methyl)amino)ethoxy)-5,7-dimethyladamantan-1-yl)methyl)-5-methyl-1H-pyrazol-4-yl)pyridin-2-yl)-5-hydroxy-1,2,3,4-tetrahydroisoquinoline-8-carboxylate Example 1.31.7 (3.0 g) in tetrahydrofuran (60 mL) was added to Pd(OH)$_2$ (0.6 g, Degussa #E101NE/W, 20% on carbon, 49% water content) in a 250 mL stainless steel pressure bottle. The mixture was shaken for 16 hours under 30 psi of hydrogen gas at 50° C. The mixture was filtered through a nylon membrane, and the solvent was evaporated under vacuum to provide the title compound. MS (ESI) m/e 815.1 (M+H)$^+$.

1.31.9 methyl 2-(6-(tert-butoxycarbonyl)-5-(1-((3-(2-((tert-butoxycarbonyl)(methyl)amino)ethoxy)-5,7-dimethyladamantan-1-yl)methyl)-5-methyl-1H-pyrazol-4-yl)pyridin-2-yl)-5-(3-(di-tert-butoxyphosphoryl)propoxy)-1,2,3,4-tetrahydroisoquinoline-8-carboxylate To a solution of Example 1.31.8 (163 mg) in tetrahydrofuran (10 mL) was added Example 1.14.1 (50.5 mg), triphenylphosphine (52.5 mg) and di-tert-butylazodicarboxylate (46.2 mg), and the mixture was stirred for 3 hours. The mixture was diluted with ethyl acetate (200 mL), washed with water and brine, dried over sodium sulfate, filtered and concentrated. The residue was purified by silica gel chromatography, eluting with 20% ethyl acetate in heptanes followed by 5% methanol in dichloromethane, to provide the title compound. MS (ESI) m/e 1049.2 (M+H)$^+$.

1.31.10 2-(6-(tert-butoxycarbonyl)-5-(1-((3-(2-((tert-butoxycarbonyl)(methyl)amino)ethoxy)-5,7-dimethyladamantan-1-yl)methyl)-5-methyl-1H-pyrazol-4-yl)pyridin-2-yl)-5-(3-(di-tert-butoxyphosphoryl)propoxy)-1,2,3,4-tetrahydroisoquinoline-8-carboxylic acid To a solution of Example 1.31.9 (3 g) in tetrahydrofuran (20 mL), methanol (10 mL) and water (10 mL) was added lithium hydroxide monohydrate (30 mg), and the mixture was stirred at room temperature for 24 hours. The reaction mixture was neutralized with 2% aqueous HCl and concentrated under vacuum. The residue was diluted with ethyl acetate (800 mL), washed with water and brine, and dried over sodium sulfate. Filtration and evaporation of solvent provided the title compound. MS (ESI) m/e 1034.5 (M+H)$^+$.

1.31.11 6-[8-(1,3-benzothiazol-2-ylcarbamoyl)-5-(3-phosphonopropoxy)-3,4-dihydroisoquinolin-2(1H)-yl]-3-[1-({3,5-dimethyl-7-[2-(methylamino)ethoxy]tricyclo[3.3.1.1$^{3,7}$]dec-1-yl}methyl)-5-methyl-1H-pyrazol-4-yl]pyridine-2-carboxylic acid To a solution of Example 1.31.10 (207 mg) in N,N-dimethylformamide (4 mL) was added benzo[d]thiazol-2-amine (45.1 mg, 0.3 mmol), fluoro-N,N,N',N'-tetramethylformamidinium hexafluorophosphate (79 mg) and N,N-diisopropylethylamine (150 mg), and the mixture was stirred at 60° C. for 3 hours. The reaction mixture was diluted with ethyl acetate (200 mL) washed with water and brine, dried over sodium sulfate, filtered and concentrated. The residue was purified by silica gel chromatography, eluting with 20% ethyl acetate in heptane followed by 5% methanol in dichloromethane. After concentration, the material was dissolved in a mixture of dichloromethane and trifluoroacetic acid (1:1, 6 mL) and was allowed to sit at room temperature overnight. The solvent was evaporated, and the residue was dissolved in dimethyl sulfoxide/methanol (1:1, 9 mL). The mixture was purified by reverse phase HPLC using a Gilson system, eluting with 10-85% acetonitrile in water containing 0.1% v/v trifluoroacetic acid, to give the title compound. $^1$H NMR (501 MHz, dimethyl sulfoxide-d$_6$) δ ppm 8.27 (s, 2H), 8.02 (d, 1H), 7.76 (dd, 2H), 7.43-7.56 (m, 2H), 7.32-7.37 (m, 1H), 7.29 (s, 1H), 7.00 (dd, 2H), 5.02 (s, 2H), 4.15 (t, 2H), 3.88-3.93 (m, 2H), 3.83 (s, 3H), 3.50-3.59 (m, 4H), 2.95-3.08 (m, 2H), 2.78-2.87 (m, 2H), 2.51-2.55 (m, 3H), 2.11 (s, 3H), 1.90-2.01 (m, 2H), 1.65-1.75 (m, 2H), 1.41 (s, 2H), 1.22-1.36 (m, 6H), 0.98-1.18 (m, 6H), 0.87 (s, 6H). MS (ESI) m/e 898.2 (M+H)$^+$.

1.32 Synthesis of 6-[8-(1,3-benzothiazol-2-ylcarbamoyl)-3,4-dihydroisoquinolin-2(1H)-yl]-3-(1-{[3-(2-{[N-(2-carboxyethyl)-L-alpha-aspartyl]amino}ethoxy)-5,7-dimethyltricyclo[3.3.1.1$^{3,7}$]dec-1-yl]methyl}-5-methyl-1H-pyrazol-4-yl)pyridine-2-carboxylic acid (Compound W2.32)

1.32.1 tert-butyl 6-(8-(benzo[d]thiazol-2-ylcarbamoyl)-3,4-dihydroisoquinolin-2(1H)-yl)-3-(1-((3-(2-((S)-4-(tert-butoxy)-2-((tert-butoxycarbonyl)amino)-4-oxobutanamido)ethoxy)-5,7-dimethyladamantan-1-yl)methyl)-5-methyl-1H-pyrazol-4-yl)picolinate To a cold (0° C.) solution of (S)-4-(tert-butoxy)-2-((tert-butoxycarbonyl)amino)-4-oxobutanoic acid (136 mg) and O-(7-azabenzotriazol-1-yl)-N,N,N',N'-tetramethyluronium hexafluorophosphate (HATU, 179 mg) in N,N-dimethylformamide (3 mL) was added N,N-diisopropylethylamine (165 µL). The reaction mixture was stirred for 10 minutes, and Example 1.2.7 (252 mg) in N,N-dimethylformamide (1 mL) was added. The mixture was stirred at room temperature for 1.5 hours and was purified by reverse phase chromatography (C18 column), eluting with 50-100% acetonitrile in water containing 0.1% v/v trifluoroacetic acid, to provide the title compound.

1.32.2 3-(1-((3-(2-((S)-2-amino-3-carboxypropanamido)ethoxy)-5,7-dimethyladamantan-1-yl)methyl)-5-methyl-1H-pyrazol-4-yl)-6-(8-(benzo[d]thiazol-2-ylcarbamoyl)-3,4-dihydroisoquinolin-2(1H)-yl)picolinic acid Example 1.32.1 (100 mg) in dichloromethane (3 mL) was treated with trifluoroacetic acid (2.5 mL) overnight. The reaction mixture was concentrated to provide the title compound.

1.32.3 6-(8-(benzo[d]thiazol-2-ylcarbamoyl)-3,4-dihydroisoquinolin-2(1H)-yl)-3-(1-((3-(2-((S)-2-((3-(tert-butoxy)-3-oxopropyl)amino)-3-carboxypropanamido)ethoxy)-5,7-dimethyladamantan-1-yl)methyl)-5-methyl-1H-pyrazol-4-yl)picolinic acid To a mixture of Example 1.32.2 (102 mg) and N,N-diisopropylethylamine (0.21 mL) in N,N-dimethylformamide (1.5 mL) was added tert-butyl acrylate (80 mg) and water (1.5 mL). The mixture was heated at 50° C. for 24 hours and purified by reverse phase chromatography (C18 column), eluting with 20-60% acetonitrile in water contain- 1.32.4 6-[8-(1,3-benzothiazol-2-ylcarbamoyl)-3,4-dihydroisoquinolin-2(1H)-yl]-3-(1-{[3-(2-{[N-(2-carboxyethyl)-L-alpha-aspartyl]amino}ethoxy)-5,7-dimethyltricyclo[3.3.1.1³,⁷]dec-1-yl]methyl}-5-methyl-1H-pyrazol-4-yl)pyridine-2-carboxylic acid The title compound was prepared as described in Example 1.6.2, replacing Example 1.6.1 with Example 1.32.3. $^1$H NMR (400 MHz, dimethyl sulfoxide-$d_6$) δ ppm 12.86 (s, 3H), 8.62-9.21 (m, 2H), 8.52 (t, 1H), 8.03 (d, 1H), 7.79 (d, 1H), 7.62 (d, 1H), 7.42-7.53 (m, 3H), 7.33-7.41 (m, 2H), 7.29 (s, 1H), 6.95 (d, 1H), 4.96 (s, 2H), 4.04-4.19 (m, 1H), 3.89 (t, 2H), 3.81 (s, 2H), 3.32-3.41 (m, 2H), 3.16-3.27 (m, 2H), 3.10 (t, 2H), 3.01 (t, 2H), 2.83 (d, 2H), 2.66 (t, 2H), 2.10 (s, 3H), 1.39 (s, 2H), 1.20-1.32 (m, 4H), 0.94-1.16 (m, 6H), 0.85 (s, 6H). MS (ESI) m/e 933.2 (M+H)$^+$.

1.33 Synthesis of 3-{1-[(3-{2-[(2-aminoethyl)(2-sulfoethyl)amino]ethoxy}-5,7-dimethyltricyclo[3.3.1.1³,⁷]dec-1-yl)methyl]-5-methyl-1H-pyrazol-4-yl}-6-[8-(1,3-benzothiazol-2-ylcarbamoyl)-3,4-dihydroisoquinolin-2(1H)-yl]pyridine-2-carboxylic acid (Compound W2.33)

1.33.1 6-(8-(benzo[d]thiazol-2-ylcarbamoyl)-3,4-dihydroisoquinolin-2(1H)-yl)-3-(1-((3-(2-((2-((tert-butoxycarbonyl)amino)ethyl)(2-sulfoethyl)amino)ethoxy)-5,7-dimethyladamantan-1-yl)methyl)-5-methyl-1H-pyrazol-4-yl)picolinic acid To a solution of Example 1.2.9 (188 mg), tert-butyl (2-oxoethyl)carbamate (70.1 mg) and N,N-diisopropylethylamine (384 μL) was added sodium triacetoxyborohydride (140 mg), and the mixture was stirred overnight. NaCNBH$_3$ (13.83 mg) was added. The resulting mixture was stirred for 1 hour, and methanol (1 mL) was added. The mixture was stirred for 10 minutes, diluted with ethyl acetate, and washed with brine. The organic layer was dried over sodium sulfate, filtered and concentrated. The residue was purified by reverse phase chromatography (C18 column), eluting with 20-80% acetonitrile in water containing 0.1% v/v trifluoroacetic acid, to provide the title compound.

1.33.2 3-{1-[(3-{2-[(2-aminoethyl)(2-sulfoethyl)amino]ethoxy}-5,7-dimethyltricyclo[3.3.1.1³,⁷]dec-1-yl)methyl]-5-methyl-1H-pyrazol-4-yl}-6-[8-(1,3-benzothiazol-2-ylcarbamoyl)-3,4-dihydroisoquinolin-2(1H)-yl]pyridine-2-carboxylic acid The title compound was prepared as described in Example 1.6.2, replacing Example 1.6.1 with Example 1.33.1. $^1$H NMR (400 MHz, dimethyl sulfoxide-$d_6$) δ ppm 12.85 (s, 1H), 8.03 (d, 1H), 7.87 (s, 2H), 7.79 (d, 1H), 7.62 (d, 1H), 7.41-7.56 (m, 3H), 7.33-7.40 (m, 2H), 7.29 (s, 1H), 6.96 (d, 1H), 4.96 (s, 2H), 3.89 (t, 2H), 3.50 (s, 2H), 3.29-3.40 (m, 4H), 3.19 (s, 2H), 3.01 (t, 2H), 2.94 (t, 2H), 2.11 (s, 3H), 1.43 (s, 2H), 1.25-1.37 (m, 4H), 0.98-1.19 (m, 6H), 0.87 (s, 6H). MS (ESI) m/e 897.2 (M+H)$^+$.

1.34 Synthesis of 6-[5-(2-aminoethoxy)-8-(1,3-benzothiazol-2-ylcarbamoyl)-3,4-dihydroisoquinolin-2(1H)-yl]-3-[1-({3,5-dimethyl-7-[2-(methylamino)ethoxy]tricyclo[3.3.1.1³,⁷]dec-1-yl}methyl)-5-methyl-1H-pyrazol-4-yl]pyridine-2-carboxylic acid (Compound W2.34)

1.34.1 methyl 5-(2-(((benzyloxy)carbonyl)amino)ethoxy)-2-(6-(tert-butoxycarbonyl)-5-(1-((3-(2-((tert-butoxycarbonyl)(methyl)amino)ethoxy)-5,7-dimethyladamantan-1-yl)methyl)-5-methyl-1H-pyrazol-4-yl)pyridin-2-yl)-1,2,3,4-tetrahydroisoquinoline-8-carboxylate To a mixture of Example 1.31.8 (500 mg), benzyl (2-hydroxyethyl)carbamate (180 mg) and triphenyl phosphine (242 mg) in tetrahydrofuran (9 mL) was added (E)-di-tert-butyl diazene-1,2-dicarboxylate (212 mg). The mixture was stirred for 2 hours, diluted with ethyl acetate and washed with water and brine. The organic layer was dried over sodium sulfate, filtered, and concentrated. The residue was purified by silica gel chromatography, eluting with 50-100% ethyl acetate in heptanes, to provide the title compound. MS (APCI) m/e 991.1 (M+H)$^+$.

1.34.2 5-(2-(((benzyloxy)carbonyl)amino)ethoxy)-2-(6-(tert-butoxycarbonyl)-5-(1-((3-(2-((tert-butoxycarbonyl)(methyl)amino)ethoxy)-5,7-dimethyladamantan-1-yl)methyl)-5-methyl-1H-pyrazol-4-yl)pyridin-2-yl)-1,2,3,4-tetrahydroisoquinoline-8-carboxylic acid To a solution of Example 1.34.1 (480 mg) in tetrahydrofuran (10 mL) and methanol (5 mL) was added 1 M lithium hydroxide (1.94 mL). The mixture was heated at 50° C. overnight, cooled, acidified with 10% aqueous HCl to pH 3 and concentrated. The residue was purified by reverse phase chromatography (C18 column), eluting with 40-99% acetonitrile in water containing 0.1% v/v trifluoroacetic acid, to provide the title compound. MS (ESI) m/e 977.4 (M+H)$^+$.

1.34.3 tert-butyl 6-(8-(benzo[d]thiazol-2-ylcarbamoyl)-5-(2-(((benzyloxy)carbonyl)amino)ethoxy)-3,4-dihydroisoquinolin-2(1H)-yl)-3-(1-((3-(2-((tert-butoxycarbonyl)(methyl)amino)ethoxy)-5,7-dimethyladamantan-1-yl)methyl)-5-methyl-1H-pyrazol-4-yl)picolinate To a mixture of Example 1.34.2 (245 mg), benzo[d]thiazol-2-amine (151 mg) and fluoro-N,N,N',N'-tetramethylformamidinium hexafluorophosphate (TFFH) (132 mg) in N,N-dimethylformamide (3 mL) was added N,N-diisopropylethylamine (876 μL). The reaction mixture was heated at 65° C. for 24 hours, cooled, diluted with ethyl acetate and washed with water and brine. The organic layer was dried over sodium sulfate, filtered and concentrated. The residue was purified by silica gel chromatography, eluting with 0-80% ethyl acetate in heptanes, to provide the title compound. MS (APCI) m/e 1109.5 (M+H)$^+$.

1.34.4 6-[5-(2-aminoethoxy)-8-(1,3-benzothiazol-2-ylcarbamoyl)-3,4-dihydroisoquinolin-2(1H)-yl]-3-[1-({3,5-dimethyl-7-[2-(methylamino)ethoxy]tricyclo[3.3.1.1³,⁷]dec-1-yl}methyl)-5-methyl-1H-pyrazol-4-yl]pyridine-2-carboxylic acid Example 1.34.3 (100 mg) in dichloromethane (0.5 mL) was treated with trifluoroacetic acid (10 mL) overnight. The reaction mixture was concentrated and purified by reverse phase chromatography (C18 column), eluting with 20-60% acetonitrile in water containing 0.1% v/v trifluoroacetic acid, to provide the title compound. $^1$H NMR (400 MHz, dimethyl sulfoxide-d$_6$) δ ppm 12.75 (s, 2H), 8.27 (s, 2H), 7.89-8.09 (m, 4H), 7.77 (s, 2H), 7.44-7.53 (m, 2H), 7.35 (t, 1H), 7.29 (s, 1H), 7.02 (dd, 2H), 5.02 (s, 2H), 4.27 (t, 2H), 3.87-3.97 (m, 2H), 3.83 (s, 2H), 3.50-3.58 (m, 2H), 3.00 (s, 2H), 2.88-2.96 (m, 2H), 2.52-2.60 (m, 2H), 2.10 (s, 3H), 1.42 (s, 2H), 1.23-1.36 (m, 4H), 0.98-1.19 (m, 6H), 0.87 (s, 6H). MS (ESI) m/e 819.3 (M+H)$^+$.

1.35 Synthesis of 6-[8-(1,3-benzothiazol-2-ylcarbamoyl)naphthalen-2-yl]-3-{1-[(3,5-dimethyl-7-{2-[(3-sulfopropyl)amino]ethoxy}tricyclo[3.3.1.1$^{3,7}$]dec-1-yl)methyl]-5-methyl-1H-pyrazol-4-yl}pyridine-2-carboxylic acid (Compound W2.35)

1.35.1 tert-butyl 6-chloro-3-(1-((3,5-dimethyl-7-(2-oxoethoxy)adamantan-1-yl)methyl)-5-methyl-1H-pyrazol-4-yl)picolinate To a solution of oxalyl chloride (8 mL, 2.0 M in dichloromethane) in dichloromethane (20 mL) at −78° C., was added dropwise dimethyl sulfoxide (1 mL) in dichloromethane (10 mL) over 20 minutes. The solution was stirred for 30 minutes under argon, and Example 1.20.2 (3.8 g) as a solution in dichloromethane (30 mL) was added over 10 minutes. The reaction mixture was stirred at −78° C. for an additional 60 minutes. Triethylamine (2 mL) was added at −78° C., and the reaction mixture was stirred for 60 minutes. The cooling bath was removed, and the reaction allowed to warm to room temperature overnight. Water (60 mL) was added. The aqueous layer was acidified with 1% aqueous HCl solution and extracted with dichloromethane. The combined organic layers were washed with 1% aqueous HCl solution, aqueous NaHCO$_3$ solution, and brine. The organic layer was dried over sodium sulfate and concentrated to provide the title compound. MS (ESI) m/e 527.9 (M+H)$^+$.

1.35.2 2,2,2-trifluoro-1-(p-tolyl)ethyl 3-iodopropane-1-sulfonate

The title compound was prepared according to a procedure reported in J. Org. Chem., 2013, 78, 711-716.

1.35.3 2,2,2-trifluoro-1-(p-tolyl)ethyl 3-aminopropane-1-sulfonate

A solution of Example 1.35.2 (2.0 g) in 7 N ammonia in methanol (20 mL) was heated to 80° C. under microwave conditions (Biotage Initiator) for 45 minutes. The mixture was concentrated, and the residue was dissolved in ethyl acetate (300 mL). The organic layer was washed with water and brine, dried over sodium sulfate, filtered, and concentrated to provide the title compound. MS (ESI) m/e 312.23 (M+H)$^+$.

1.35.4 tert-butyl 6-chloro-3-(1-(((3,5-dimethyl-7-(2-((3-((2,2,2-trifluoro-1-(p-tolyl)ethoxy)sulfonyl)propyl)amino)ethoxy)adamantan-1-yl)methyl)-5-methyl-1H-pyrazol-4-yl)picolinate To a solution of Example 1.35.3 (1.96 g) in dichloroethane (30 mL) was added Example 1.35.1 (3.33 g). The reaction mixture was stirred at room temperature for 1 hour, and a suspension of NaBH$_4$ (1.2 g) in methanol (8 mL) was added. The mixture was stirred at room temperature for 3 hours and diluted with ethyl acetate (300 mL). The organic layer was washed with 2N aqueous NaOH, water, and brine, dried over sodium sulfate, filtered and concentrated. The residue was dissolved in tetrahydrofuran (30 mL), and di-tert-butyl dicarbonate (2 g) was added followed by the addition of catalytic amount of 4-dimethylaminopyridine. The mixture was stirred at room temperature overnight. The mixture was diluted with ethyl acetate (300 mL) and washed with water and brine. The organic layer was dried over sodium sulfate, filtered, and concentrated to provide the title compound. MS (ESI) m/e 924.42 (M+H)$^+$.

1.35.5 7-(6-(tert-butoxycarbonyl)-5-(1-((3-(2-((tert-butoxycarbonyl)(3-((2,2,2-trifluoro-1-(p-tolyl) ethoxy)sulfonyl)propyl)amino)ethoxy)-5,7-dimethyladamantan-1-yl)methyl)-5-methyl-1H-pyrazol-4-yl) pyridin-2-yl)-1-naphthoic acid To a solution of methyl 7-(4,4,5,5-tetramethyl-1,3,2-dioxaborolan-2-yl)-1-naphthoate (203 mg) in a mixture of 1,4-dioxane (10 mL) and water (5 mL) was added Example 1.35.4 (600 mg), bis(triphenylphosphine)palladium(II)dichloride (45.6 mg), and cesium fluoride (296 mg). The mixture was heated at 120° C. under microwave conditions (Biotage Initiator) for 30 minutes, diluted with ethyl acetate (200 mL), and washed with water and brine. The organic layer was dried over sodium sulfate, filtered, and concentrated. The residue was purified by silica gel chromatography, eluting with 20% ethyl acetate in heptane, to provide an ester intermediate. The residue was dissolved in a mixture of tetrahydrofuran (8 mL), methanol (4 mL) and water (4 mL), and was treated with lithium hydroxide monohydrate (200 mg) for 3 hours. The reaction was acidified with 1N aqueous HCl to pH 4 and was diluted with ethyl acetate (400 mL). The resulting mixture was washed with water and brine. The organic layer was dried over sodium sulfate, filtered, and concentrated to provide the title compound. MS (ESI) m/e 1060.24 (M+H)$^+$.

1.35.6 6-[8-(1,3-benzothiazol-2-ylcarbamoyl)naphthalen-2-yl]-3-{1-[(3,5-dimethyl-7-{2-[(3-sulfopropyl)amino]ethoxy}tricyclo[3.3.1.1$^{3,7}$]dec-1-yl) methyl]-5-methyl-1H-pyrazol-4-yl}pyridine-2-carboxylic acid To a solution of Example 1.35.5 (405 mg) in dichloromethane (10 mL) was added benzo[d]thiazol-2-amine (57.4 mg), 1-ethyl-3-[3-(dimethylamino)propyl]-carbodiimide hydrochloride (146 mg) and 4-(dimethylamino)pyridine (93 mg). The mixture was stirred at room temperature overnight, diluted with ethyl acetate (200 mL), and washed with water and brine. The organic layer was dried over sodium sulfate, filtered, and concentrated. The residue was dissolved in dichloromethane (3 mL) and treated with trifluoroacetic acid (3 mL) overnight. The reaction mixture was concentrated, and the residue was purified by reverse phase HPLC (Gilson system), eluting with a gradient of 10-85% acetonitrile in water containing 0.1% v/v trifluoroacetic acid, to provide the title compound. $^1$H NMR (400 MHz, dimethyl sulfoxide-d$_6$) δ ppm 13.08 (s, 1H), 9.00 (s, 1H), 8.53 (s, 2H), 8.36 (dd, 1H), 8.26-8.13 (m, 3H), 8.06 (dd, 1H), 8.04-7.97 (m, 1H), 7.94 (d, 1H), 7.80 (d, 1H), 7.69 (dd, 1H), 7.51-7.43 (m, 2H), 7.40-7.31 (m, 1H), 7.19 (d, OH), 3.88 (s, 2H), 3.54 (t, 2H), 3.16-2.91 (m, 4H), 2.68-2.55 (m, 2H), 2.29 (s, OH), 2.22 (s, 3H), 1.93 (p, 2H), 1.43 (s, 2H), 1.38-1.23 (m, 4H), 1.10 (dq, 6H), 0.87 (s, 6H). MS (ESI) m/e 863.2 (M+H)$^+$.

1.36 Synthesis of 6-[8-(1,3-benzothiazol-2-ylcarbamoyl)-3,4-dihydroisoquinolin-2(1H)-yl]-3-{1-[(3-{2-[(2-carboxyethyl)(piperidin-4-yl)amino]ethoxy}-5,7-dimethyltricyclo[3.3.1.1$^{3,7}$]dec-1-yl)methyl]-5-methyl-1H-pyrazol-4-yl}pyridine-2-carboxylic acid (Compound W2.36)

1.36.1 tert-butyl 6-(8-(benzo[d]thiazol-2-ylcarbamoyl)-3,4-dihydroisoquinolin-2(1H)-yl)-3-(1-(((1r,3r)-3-(2-((3-(tert-butoxy)-3-oxopropyl)(1-(tert-butoxycarbonyl)piperidin-4-yl)amino)ethoxy)-5,7-dimethyladamantan-1-yl)methyl)-5-methyl-1H-pyrazol-4-yl)picolinate A solution of Example 1.25.1 (0.086 g), tert-butyl 4-oxopiperidine-1-carboxylate (0.037 g), sodium triacetoxyborohydride (0.039 g) and acetic acid (11 µL) in dichloromethane (1 mL) was stirred at room temperature. After stirring overnight, the reaction was loaded onto silica gel and eluted using a gradient of 0.5 to 5% methanol in dichloromethane to give the title compound. MS (ELSD) m/e 1113.5 (M+H)$^+$.

1.36.2 6-[8-(1,3-benzothiazol-2-ylcarbamoyl)-3,4-dihydroisoquinolin-2(1H)-yl]-3-{1-[(3-{2-[(2-carboxyethyl)(piperidin-4-yl)amino]ethoxy}-5,7-dimethyltricyclo[3.3.1.1$^3$]dec-1-yl)methyl]-5-methyl-1H-pyrazol-4-yl}pyridine-2-carboxylic acid A solution of Example 1.36.1 (0.050) in dichloromethane (0.5 mL) was treated with trifluoroacetic acid (0.5 mL), and the reaction was stirred overnight. The reaction was concentrated and dissolved in dimethyl sulfoxide and methanol (1:1). The mixture was purified by reverse phase HPLC using a Gilson system, eluting with 10-75% acetonitrile in water containing 0.1% v/v trifluoroacetic acid. The desired fractions were combined and freeze-dried to provide the title compound. $^1$H NMR (400 MHz, dimethyl sulfoxide-d$_6$) δ ppm 12.84 (s, 1H), 9.38 (s, 1H), 8.78 (s, 1H), 8.42 (s, 1H), 8.03 (d, 1H), 7.80 (d, 1H), 7.63 (d, 1H), 7.55-7.42 (m, 3H), 7.41-7.33 (m, 2H), 7.30 (s, 1H), 6.96 (d, 1H), 4.96 (s, 2H), 3.89 (t, 2H), 3.83 (s, 2H), 3.73-3.54 (m, 3H), 3.53-3.34 (m, 4H), 3.34-3.25 (m, 2H), 3.02 (t, 2H), 2.99-2.85 (m, 2H), 2.78 (t, 2H), 2.23-2.04 (m, 5H), 1.92-1.76 (m, 2H), 1.43 (s, 2H), 1.39-1.23 (m, 4H), 1.23-0.96 (m, 6H), 0.87 (s, 6H). MS (ESI) m/e 901.3 (M+H)$^+$.

1.37 Synthesis of 6-[8-(1,3-benzothiazol-2-ylcarbamoyl)-3,4-dihydroisoquinolin-2(1H)-yl]-3-{1-[(3,5-dimethyl-7-{2-[(3-sulfo-L-alanyl)(2-sulfoethyl)amino]ethoxy}tricyclo[3.3.1.1$^{3,7}$]dec-1-yl)methyl]-5-methyl-1H-pyrazol-4-yl}pyridine-2-carboxylic acid (Compound W2.37)

A solution of (R)-2-(((((9H-fluoren-9-yl)methoxy)carbonyl)amino)-3-sulfopropanoic acid (0.011 g) and 2-(3H-[1,2,3]triazolo[4,5-b]pyridin-3-yl)-1,1,3,3-tetramethylisouronium hexafluorophosphate(V) (10.80 mg) in N,N-dimethylformamide (0.5 mL) was stirred for 5 minutes. This solution was added to Example 1.2.9 (0.025 g) and N,N-diisopropylethylamine (0.014 mL). After stirring for 2 hours, diethylamine (0.013 mL) was added to the reaction, and stirring was continued for an additional 1 hour. The reaction was diluted with N,N-dimethylformamide and water and quenched with trifluoroacetic acid. The mixture was purified by reverse phase HPLC using a Gilson system, eluting with 10-75% acetonitrile in water containing 0.1% v/v trifluoroacetic acid. The desired fractions were combined and freeze-dried to provide the title compound. $^1$H NMR (400 MHz, dimethyl sulfoxide-d$_6$) δ ppm 12.84 (s, 1H), 8.03 (dd, 4H), 7.79 (d, 1H), 7.62 (d, 1H), 7.54 (dd, 1H), 7.51-7.41 (m, 2H), 7.36 (td, 2H), 7.33 (s, 1H), 6.98 (dd, 1H), 4.96 (s, 2H), 4.42 (dd, 2H), 3.89 (t, 2H), 3.83 (s, 2H), 3.73 (ddd, 2H), 3.57-3.38 (m, 2H), 3.31 (dt, 1H), 3.08 (dd, 1H), 3.02 (t, 2H), 2.87 (tt, 1H), 2.81-2.54 (m, 2H), 2.10 (d, 3H), 1.51-0.91 (m, 12H), 0.85 (s, 6H). MS (ESI) m/e 1005.2 (M+H)$^+$.

1.38 Synthesis of 6-[8-(1,3-benzothiazol-2-ylcarbamoyl)-3,4-dihydroisoquinolin-2(1H)-yl]-3-{1-[(3-{2-[{2-[(2-carboxyethyl)amino]ethyl}(2-sulfoethyl)amino]ethoxy}-5,7-dimethyltricyclo[3.3.1.1$^{3,7}$]dec-1-yl)methyl]-5-methyl-1H-pyrazol-4-yl}pyridine-2-carboxylic acid (Compound W2.38)

1.38.1 6-(8-(benzo[d]thiazol-2-ylcarbamoyl)-3,4-dihydroisoquinolin-2(1H)-yl)-3-(1-((3-(2-((2-((3-(tert-butoxy)-3-oxopropyl)amino)ethyl)(2-sulfoethyl)amino)ethoxy)-5,7-dimethyladamantan-1-yl)methyl)-5-methyl-1H-pyrazol-4-yl)picolinic acid The title compound was prepared as described in Example 1.32.3, replacing Example 1.32.2 with Example 1.33.2.

1.38.2 6-[8-(1,3-benzothiazol-2-ylcarbamoyl)-3,4-dihydroisoquinolin-2(1H)-yl]-3-{1-[(3-{2-[{2-[(2-carboxyethyl)amino]ethyl}(2-sulfoethyl)amino]ethoxy}-5,7-dimethyltricyclo[3.3.1.1$^{3,7}$]dec-1-yl)methyl]-5-methyl-1H-pyrazol-4-yl}pyridine-2-carboxylic acid The title compound was prepared as described in Example 1.6.2, replacing Example 1.6.1 with Example 1.38.1. $^1$H NMR (501 MHz, dimethyl sulfoxide-d$_6$) δ ppm 12.87 (s, 1H), 8.68 (s, 2H), 8.04 (d, 1H), 7.79 (d, 1H), 7.62 (d, 1H), 7.53 (d, 1H), 7.42-7.50 (m, 2H), 7.33-7.40 (m, 2H), 7.29 (s, 1H), 6.96 (d, 1H), 4.96 (s, 3H), 3.89 (t, 2H), 3.83 (s, 2H), 3.66 (t, 2H), 3.31-3.53 (m, 8H), 3.18 (t, 2H), 3.02 (t, 2H), 2.95 (t, 2H), 2.67 (t, 2H), 2.11 (s, 3H), 1.43 (s, 2H), 1.22-1.37 (m, 6H), 0.98-1.19 (m, 6H), 0.87 (s, 6H). MS (APCI) m/e 971.0 (M+H)$^+$.

1.39 Synthesis of 3-{1-[(3,5-dimethyl-7-{2-[(3-phosphonopropyl)amino]ethoxy}tricyclo[3.3.1.1$^{3,7}$]dec-1-yl)methyl]-5-methyl-1H-pyrazol-4-yl}-6-[8-([1,3]thiazolo[4,5-b]pyridin-2-ylcarbamoyl)-3,4-dihydroisoquinolin-2(1H)-yl]pyridine-2-carboxylic acid (Compound W2.39)

1.39.1 tert-butyl 3-(1-((3-(2-((3-(di-tert-butoxyphosphoryl)propyl)amino)ethoxy)-5,7-dimethyladamantan-1-yl)methyl)-5-methyl-1H-pyrazol-4-yl)-6-(8-(thiazolo[4,5-b]pyridin-2-ylcarbamoyl)-3,4-dihydroisoquinolin-2(1H)-yl)picolinate Example 1.23.2 (520 mg) and Example 1.14.2 (175 mg) were dissolved in dichloromethane (6 mL) and stirred at room temperature for two hours. A suspension of sodium borohydride (32 mg) in methanol (1 mL) was added, and the mixture was stirred for 30 minutes. The reaction was added to saturated aqueous NaHCO$_3$ solution and extracted with ethyl acetate. The organic layer was washed with brine and dried over sodium sulfate. After filtration and concentration, purification by silica gel chromatography, eluting with a gradient of 0.5-5.0% methanol in dichloromethane, gave the title compound. MS (ESI) m/e 1037.3 (M+H)+.

1.39.2 3-{1-[(3,5-dimethyl-7-{2-[(3-phosphonopropyl)amino]ethoxy}tricyclo[3.3.1.1$^{3,7}$]dec-1-yl) methyl]-5-methyl-1H-pyrazol-4-yl}-6-[8-([1,3]thiazolo[4,5-b]pyridin-2-ylcarbamoyl)-3,4-dihydroisoquinolin-2(1H)-yl]pyridine-2-carboxylic acid The title compound was prepared by substituting Example 1.39.1 for Example 1.2.8 in Example 1.2.9. $^1$H NMR (400 MHz, dimethyl sulfoxide-d$_6$) δ ppm 8.60 (dd, 1H), 8.52 (dd, 1H), 8.41 (br s, 2H), 7.65 (d, 1H) 7.48 (d, 1H), 7.46 (d, 1H), 7.38 (m, 2H), 7.29 (s, 1H), 6.97 (d, 1H), 4.97 (s, 2H), 3.89 (m, 2H), 3.83 (s, 2H), 3.56 (m, 2H), 3.02 (m, 6H), 2.11 (s, 3H), 1.81 (m, 2H), 1.61 (m, 2H), 2.11 (s, 3H), 1.43 (s, 2H), 1.30 (m, 4H), 1.14 (m, 4H), 1.04 (m, 2H), 0.87 (s, 6H). MS (ESI) m/e 869.2 (M+H)+.

1.40 Synthesis of 3-{1-[(3,5-dimethyl-7-{2-[(3-phosphonopropyl)amino]ethoxy}tricyclo[3.3.1.1$^{3,7}$] dec-1-yl)methyl]-5-methyl-1H-pyrazol-4-yl}-6-[8-([1,3]thiazolo[5,4-b]pyridin-2-ylcarbamoyl)-3,4-dihydroisoquinolin-2(1H)-yl]pyridine-2-carboxylic acid (Compound W2.40)

1.40.1 tert-butyl 3-(1-((3-(2-((3-(di-tert-butoxyphosphoryl)propyl)amino)ethoxy)-5,7-dimethyladamantan-1-yl)methyl)-5-methyl-1H-pyrazol-4-yl)-6-(8-(thiazolo[5,4-b]pyridin-2-ylcarbamoyl)-3,4-dihydroisoquinolin-2(1H)-yl)picolinate The title compound was prepared by substituting Example 1.22.2 for Example 1.23.2 in Example 1.39.1. MS (ESI) m/e 1037.3 (M+H)+.

1.40.2 3-{1-[(3,5-dimethyl-7-{2-[(3-phosphonopropyl)amino]ethoxy}tricyclo[3.3.1.1$^{3,7}$]dec-1-yl) methyl]-5-methyl-1H-pyrazol-4-yl}-6-[8-([1,3]thiazolo[5,4-b]pyridin-2-ylcarbamoyl)-3,4-dihydroisoquinolin-2(1H)-yl]pyridine-2-carboxylic acid The title compound was prepared by substituting Example 1.40.1 for Example 1.2.8 in Example 1.2.9. $^1$H NMR (500 MHz, dimethyl sulfoxide-d$_6$) δ ppm 8.52 (dd, 2H), 8.41 (br s, 2H), 8.17 (dd, 1H), 7.63 (m, 1H), 7.53 (m, 2H), 7.46 (d, 1H), 7.38 (t, 1H), 7.30 (s, 1H), 6.98 (d, 1H), 4.96 (s, 2H), 3.88 (m, 2H), 3.83 (s, 2H), 3.56 (t, 2H), 3.00 (m, 6H), 2.11 (s, 3H), 1.81 (m, 2H), 1.60 (m, 2H), 1.43 (s, 2H), 1.31 (m, 4H), 1.14 (m, 4H), 1.04 (m, 2H), 0.87 (s, 6H). MS (ESI) m/e 869.2 (M+H)+.

1.41 Synthesis of 6-[8-(1,3-benzothiazol-2-ylcarbamoyl)-5-(carboxymethoxy)-3,4-dihydroisoquinolin-2(1H)-yl]-3-[1-({3,5-dimethyl-7-[2-(methylamino)ethoxy]tricyclo[3.3.1.1$^{3,7}$]dec-1-yl}methyl)-5-methyl-1H-pyrazol-4-yl]pyridine-2-carboxylic acid (Compound W2.41)

1.41.1 methyl 5-(2-(tert-butoxy)-2-oxoethoxy)-2-(6-(tert-butoxycarbonyl)-5-(1-((3-(2-((tert-butoxycarbonyl)(methyl)amino)ethoxy)-5,7-dimethyladamantan-1-yl)methyl)-5-methyl-1H-pyrazol-4-yl)pyridin-2-yl)-1,2,3,4-tetrahydroisoquinoline-8-carboxylate To a solution of Example 1.31.8 (163 mg) in N,N-dimethylformamide (10 mL) was added tert-butyl 2-bromoacetate (58.6 mg), and K$_2$CO$_3$ (83 mg), and the reaction was stirred overnight. The mixture was diluted with ethyl acetate (200 mL), washed with water and brine, and dried over sodium sulfate. Filtration and evaporation of the solvent gave a residue that was purified by silica gel chromatography, eluting with 20% ethyl acetate in heptane, to provide the title compound. MS (ESI) m/e 929.2 (M+H)+.

1.41.2 5-(2-(tert-butoxy)-2-oxoethoxy)-2-(6-(tert-butoxycarbonyl)-5-(1-((3-(2-((tert-butoxycarbonyl)(methyl)amino)ethoxy)-5,7-dimethyladamantan-1-yl)methyl)-5-methyl-1H-pyrazol-4-yl)pyridin-2-yl)-1,2,3,4-tetrahydroisoquinoline-8-carboxylic acid To a solution of Example 1.41.1 (3 g) in tetrahydrofuran (20 mL), methanol (10 mL) and water (10 mL) was added lithium hydroxide monohydrate (300 mg). The mixture was stirred at room temperature for 24 hours. The reaction mixture was neutralized with 2% aqueous HCl solution and concentrated under vacuum. The residue was diluted with ethyl acetate (800 mL), washed with water and brine, and dried over sodium sulfate. Filtration and evaporation of the solvent provided the title compound. MS (ESI) m/e 914.5 (M+H)+.

1.41.3 6-[8-(1,3-benzothiazol-2-ylcarbamoyl)-5-(carboxymethoxy)-3,4-dihydroisoquinolin-2(1H)-yl]-3-[1-({3,5-dimethyl-7-[2-(methylamino)ethoxy] tricyclo[3.3.1.1$^{3,7}$]dec-1-yl}methyl)-5-methyl-1H-pyrazol-4-yl]pyridine-2-carboxylic acid To a solution of Example 1.41.2 (183 mg) in N,N-dimethylformamide (4 mL) was added benzo[d]thiazol-2-amine (45.1 mg), fluoro-N,N,N',N'-tetramethylformamidinium hexafluorophosphate (79 mg) and N,N-diisopropylethylamine (0.203 mL). The mixture was stirred at 60° C. overnight. The mixture was diluted with ethyl acetate (300 mL), washed with water and brine, and dried over sodium sulfate. Filtration and evaporation of the solvent gave a residue that was dissolved in dichloromethane/trifluoroacetic acid (1:1, 10 mL) and stirred overnight. The mixture was concentrated, and the residue was purified by reverse phase HPLC using a Gilson system, eluting with 10-85% acetonitrile in in water containing 0.1% v/v trifluoroacetic acid, to provide the title compound. $^1$H NMR (400 MHz, dimethyl sulfoxide-d$_6$) δ ppm 12.73 (s, 1H), 8.30 (s, 2H), 7.99-8.07 (m, 1H), 7.75-7.79 (m, 1H), 7.70 (d, 1H), 7.44-7.56 (m, 2H), 7.30-7.39 (m, 2H), 7.30 (s, 1H), 7.03 (t, 1H), 6.87-6.93 (m, 1H), 4.98-5.18 (m, 4H), 4.84 (s, 3H), 3.78-4.01 (m, 4H), 3.55 (t, 2H). 2.77-3.07 (m, 4H), 2.53-2.61 (m, 3H), 2.04-2.16 (m, 3H), 1.41 (s, 2H), 1.02-1.34 (m, 6H), 0.83-0.91 (m, 6H). MS (ESI) m/e 834.2 (M+H)+.

1.42 Synthesis of 6-[8-(1,3-benzothiazol-2-ylcarbamoyl)-3,4-dihydroisoquinolin-2(1H)-yl]-3-{1-[(3-{2-[(3-carboxypropyl)(piperidin-4-yl)amino] ethoxy}-5,7-dimethyltricyclo[3.3.1.1$^{3,7}$]dec-1-yl) methyl]-5-methyl-1H-pyrazol-4-yl}pyridine-2-carboxylic acid (Compound W2.42)

1.42.1 tert-butyl 6-(8-(benzo[d]thiazol-2-ylcarbamoyl)-3,4-dihydroisoquinolin-2(1H)-yl)-3-(1-(((1r,3r)-3-(2-((1-(tert-butoxycarbonyl)piperidin-4-yl)(4-methoxy-4-oxobutyl)amino)ethoxy)-5,7-dimethyladamantan-1-yl)methyl)-5-methyl-1H-pyrazol-4-yl)picolinate A solution of Example 1.26.1 (0.169 g), methyl 4-oxobutanoate (0.024 g) and sodium triacetoxyborohydride (0.055 g) was stirred in dichloromethane (2 mL) at room temperature. After 2 hours, the reaction was diluted with dichloromethane (50 mL) and washed with saturated aqueous sodium bicarbonate (10 mL). The organic layer was separated, dried over magnesium sulfate, filtered and concentrated. Silica gel chromatography, eluting with a gradient of 0.5-5% methanol/dichloromethane containing ammonia, provided the title compound. MS (ELSD) m/e 1085.5 (M+H)$^+$.

1.42.2 6-[8-(1,3-benzothiazol-2-ylcarbamoyl)-3,4-dihydroisoquinolin-2(1H)-yl]-3-{1-[(3-{2-[(3-carboxypropyl)(piperidin-4-yl)amino]ethoxy}-5,7-dimethyltricyclo[3.3.1.1$^{3,7}$]dec-1-yl)methyl]-5-methyl-1H-pyrazol-4-yl}pyridine-2-carboxylic acid A solution of Example 1.42.1 (0.161 g) in dichloromethane (0.5 mL) was treated with trifluoroacetic acid (0.5 mL), and the reaction was stirred overnight. The reaction was concentrated, dissolved in methanol (0.6 mL) and treated with lithium hydroxide monohydrate (0.124 g) as a solution in water (0.5 mL). After stirring for 1.5 hours, the reaction was quenched with trifluoroacetic acid (0.229 mL) and diluted with N,N-dimethylformamide (0.5 mL). The mixture was purified by reverse phase HPLC using a Gilson system, eluting with 10-60% acetonitrile in water containing 0.1% v/v trifluoroacetic acid. The desired fractions were combined and freeze-dried to provide the title compound. $^1$H NMR (400 MHz, dimethyl sulfoxide-d$_6$) δ ppm 12.84 (s, 1H), 9.40 (s, 1H), 8.89-8.79 (m, 1H), 8.57-8.41 (m, 1H), 8.03 (d, 1H), 7.80 (d, 1H), 7.62 (d, 1H), 7.55-7.41 (m, 3H), 7.41-7.32 (m, 2H), 7.30 (s, 1H), 6.96 (d, 1H), 4.96 (s, 2H), 3.89 (t, 2H), 3.83 (s, 2H), 3.44 (d, 2H), 3.26 (s, 2H), 3.22-3.11 (m, 2H), 3.09-2.85 (m, 6H), 2.34 (t, 2H), 2.19 (d, 2H), 2.10 (s, 3H), 1.95-1.71 (m, 5H), 1.44 (s, 2H), 1.39-1.27 (m, 4H), 1.22-0.96 (m, 6H), 0.87 (s, 6H). MS (ESI) m/e 915.3 (M+H)$^+$.

1.43 Synthesis of 6-[8-(1,3-benzothiazol-2-ylcarbamoyl)naphthalen-2-yl]-3-{1-[(3,5-dimethyl-7-{2-[(2-sulfoethyl)amino]ethoxy}tricyclo[3.3.1.1$^{3,7}$]dec-1-yl)methyl]-5-methyl-1H-pyrazol-4-yl}pyridine-2-carboxylic acid (Compound W2.43)

1.43.1 tert-butyl 3-(1-((3-(2-hydroxyethoxy)-5,7-dimethyladamantan-1-yl)methyl)-5-methyl-1H-pyrazol-4-yl)-6-(8-(methoxycarbonyl)naphthalen-2-yl)picolinate To a solution of methyl 7-(4,4,5,5-tetramethyl-1,3,2-dioxaborolan-2-yl)-1-naphthoate (2.47 g) in 1,4-dioxane (40 mL) and water (20 mL) was added Example 1.20.2 (4.2 g), bis(triphenylphosphine)palladium(II)dichloride (556 mg), and cesium fluoride (3.61 g), and the reaction was stirred at reflux overnight. The mixture was diluted with ethyl acetate (400 mL) and washed with water and brine, and dried over sodium sulfate. Filtration and evaporation of the solvent gave a residue that was purified by silica gel chromatography, eluting with 20% ethyl acetate in heptane followed by 5% methanol in dichloromethane, to provide the title compound. MS (ESI) m/e 680.7 (M+H)$^+$.

1.43.2 tert-butyl 3-(1-((3,5-dimethyl-7-(2-((methylsulfonyl)oxy)ethoxy)adamantan-1-yl)methyl)-5-methyl-1H-pyrazol-4-yl)-6-(8-(methoxycarbonyl)naphthalen-2-yl)picolinate To a cooled (0° C.) solution of Example 1.43.1 (725 mg) in dichloromethane (10 mL) and triethylamine (0.5 mL) was added methanesulfonyl chloride (0.249 mL), and the mixture was stirred for 4 hours. The reaction mixture was diluted with ethyl acetate (200 mL) and washed with water and brine, and dried over sodium sulfate. Filtration and evaporation of the solvent gave the title product, which was used in the next reaction without further purification. MS (ESI) m/e 759.9 (M+H)$^+$.

1.43.3 tert-butyl 3-(1-(((3-(2-azidoethoxy)-5,7-dimethyladamantan-1-yl)methyl)-5-methyl-1H-pyrazol-4-yl)-6-(8-(methoxycarbonyl)naphthalen-2-yl)picolinate To a solution of Example 1.43.2 (4.2 g) in N,N-dimethylformamide (30 mL) was added sodium azide (1.22 g), and the mixture was stirred for 96 hours. The reaction mixture was diluted with ethyl acetate (600 mL), washed with water and brine, and dried over sodium sulfate. Filtration and evaporation of the solvent provided the title compound. MS (ESI) m/e 705.8 (M+H)$^+$.

1.43.4 7-(5-(1-((3-(2-azidoethoxy)-5,7-dimethyladamantan-1-yl)methyl)-5-methyl-1H-pyrazol-4-yl)-6-(tert-butoxycarbonyl)pyridin-2-yl)-1-naphthoic acid To a solution of Example 1.43.3 (3.5 g) in tetrahydrofuran/methanol/water (2:1:1, 30 mL) was added lithium hydroxide monohydrate (1.2 g), and the mixture was stirred overnight. The reaction mixture was acidified with 1N aqueous HCl and was diluted with ethyl acetate (600 mL), washed with water and brine, and dried over sodium sulfate. Filtration and evaporation of the solvent provided the title compound. MS (ESI) m/e 691.8 (M+H)$^+$.

1.43.5 tert-butyl 3-(1-((3-(2-azidoethoxy)-5,7-dimethyladamantan-1-yl)methyl)-5-methyl-1H-pyrazol-4-yl)-6-(8-(benzo[d]thiazol-2-ylcarbamoyl)naphthalen-2-yl)picolinate To a solution of Example 1.43.4 (870 mg) in N,N-dimethylformamide (10 mL) was added benzo[d]thiazol-2-amine (284 mg), fluoro-N,N,N',N'-tetramethylformamidinium hexafluorophosphate (499 mg) and N,N-diisopropylethylamine (488 mg). The mixture was stirred at 60° C. for 3 hours. The reaction mixture was diluted with ethyl acetate (200 mL) and washed with water and brine, and dried over sodium sulfate. Filtration and evaporation of the solvent provided the title compound. MS (ESI) m/e 824.1 (M+H)$^+$.

1.43.6 tert-butyl 3-(1-((3-(2-aminoethoxy)-5,7-dimethyladamantan-1-yl)methyl)-5-methyl-1H-pyrazol-4-yl)-6-(8-(benzo[d]thiazol-2-ylcarbamoyl)naphthalen-2-yl)picolinate To a solution of Example 1.43.5 (890 mg) in tetrahydrofuran (30 mL) was added Pd/C (90 mg). The mixture was stirred under 1 atmosphere of hydrogen overnight. The reaction mixture was filtered, and the catalyst was washed with ethyl acetate. The solvent was evaporated to provide the title compound. MS (ESI) m/e 798.1 (M+H)$^+$.

1.43.7 6-[8-(1,3-benzothiazol-2-ylcarbamoyl)naphthalen-2-yl]-3-{1-[(3,5-dimethyl-7-{2-[(2-sulfoethyl)amino]ethoxy}tricyclo[3.3.1.1$^{3,7}$]dec-1-yl)methyl]-5-methyl-1H-pyrazol-4-yl}pyridine-2-carboxylic acid To a solution of Example 1.43.6 (189 mg) in N,N-dimethylformamide (6 mL) was added 4-((tert-butyldiphenylsilyl)oxy)-2,2-dimethylbutyl ethenesulfonate (106 mg). The mixture was stirred for 4 days. The mixture was diluted with ethyl acetate (300 mL) and washed with water and brine and dried over sodium sulfate. After filtration and evaporation of the solvent, the residue was dissolved in trifluoroacetic acid (10 mL) and sat overnight. The trifluoroacetic acid was evaporated under vacuum, and the residue was dissolved in dimethyl sulfoxide/methanol (1:1, 6 mL). The mixture was purified by reverse phase HPLC (Gilson system), eluting with 10-85% acetonitrile in water containing 0.1% v/v trifluoroacetic acid, to give the title compound. $^1$H NMR (400 MHz, dimethyl sulfoxide-$d_6$) δ ppm 13.09 (s, 1H), 9.02 (s, 1H), 8.31-8.43 (m, 3H), 8.16-8.26 (m, 3H), 7.93-8.08 (m, 3H), 7.82 (d, 1H), 7.66-7.75 (m, 1H), 7.46-7.55 (m, 2H), 7.37 (t, 1H), 3.90 (s, 3H), 3.17-3.28 (m, 2H), 3.07-3.16 (m, 2H), 2.82 (t, 2H), 2.24 (s, 3H), 1.44 (s, 2H), 0.99-1.37 (m, 12H), 0.87 (s, 6H). MS (ESI) m/e 849.1 (M+H)$^+$.

1.44 Synthesis of 3-{1-[(3-{2-[L-alpha-aspartyl(2-sulfoethyl)amino]ethoxy}-5,7-dimethyltricyclo[3.3.1.1$^{3,7}$]dec-1-yl)methyl]-5-methyl-1H-pyrazol-4-yl}-6-[8-(1,3-benzothiazol-2-ylcarbamoyl)-3,4-dihydroisoquinolin-2(1H)-yl]pyridine-2-carboxylic acid (Compound W2.44)

1.44.1 6-(8-(benzo[d]thiazol-2-ylcarbamoyl)-3,4-dihydroisoquinolin-2(1H)-yl)-3-(1-((3-(2-((S)-4-(tert-butoxy)-2-((tert-butoxycarbonyl)amino)-4-oxo-N-(2-sulfoethyl)butanamido)ethoxy)-5,7-dimethyladamantan-1-yl)methyl)-5-methyl-1H-pyrazol-4-yl)picolinic acid To a cold (0° C.) solution of (S)-4-(tert-butoxy)-2-((tert-butoxycarbonyl)amino)-4-oxobutanoic acid (40.7 mg) and O-(7-azabenzotriazol-1-yl)-N,N,N',N'-tetramethyluronium hexafluorophosphate (HATU, 40.1 mg) in N,N-dimethylformamide (3 mL) was added N,N-diisopropylethylamine (98 μL). The reaction mixture was stirred at room temperature for 1 hour, and Example 1.2.9 (60 mg) in N,N-dimethylformamide (1 mL) was added. The mixture was stirred for 1.5 hours and was purified by reverse phase chromatography (C18 column), eluting with 20-90% acetonitrile in water containing 0.1% v/v trifluoroacetic acid, to provide the title compound. MS (ESI) m/e 1123.4 (M−H)$^-$.

1.44.2 3-{1-[(3-{2-[L-alpha-aspartyl(2-sulfoethyl)amino]ethoxy}-5,7-dimethyltricyclo[3.3.1.1$^{3,7}$]dec-1-yl)methyl]-5-methyl-1H-pyrazol-4-yl}-6-[8-(1,3-benzothiazol-2-ylcarbamoyl)-3,4-dihydroisoquinolin-2(1H)-yl]pyridine-2-carboxylic acid Example 1.44.1 (100 mg) in dichloromethane (5 mL) was treated with trifluoroacetic acid (1.5 mL) overnight. The reaction mixture was concentrated and purified by reverse phase chromatography (C18 column), eluting with 20-60% acetonitrile in water containing 0.1% v/v trifluoroacetic acid, to provide the title compound. $^1$H NMR (500 MHz, dimethyl sulfoxide-$d_6$) δ ppm 12.85 (s, 2H), 8.11-8.22 (m, 3H), 8.04 (d, 1H), 7.79 (d, 1H), 7.62 (d, 1H), 7.41-7.54 (m, 3H), 7.32-7.39 (m, 2H), 7.29 (s, 1H), 6.95 (d, 1H), 4.95 (s, 2H), 4.80 (s, 1H), 3.89 (t, 2H), 3.81 (s, 2H), 3.55-3.71 (m, 2H), 3.01 (t, 4H), 2.74-2.86 (m, 1H), 2.57-2.73 (m, 2H), 2.09 (s, 3H), 0.91-1.46 (m, 13H), 0.84 (s, 6H). MS (ESI) m/e 969.2 (M+H)$^+$.

1.45 Synthesis of 6-[8-(1,3-benzothiazol-2-ylcarbamoyl)-3,4-dihydroisoquinolin-2(1H)-yl]-3-{1-[(3-{2-[(1,3-dihydroxypropan-2-yl)amino]ethoxy}-5,7-dimethyltricyclo[3.3.1.1$^{3,7}$]dec-1-yl)methyl]-5-methyl-1H-pyrazol-4-yl}pyridine-2-carboxylic acid (Compound W2.45)

1.45.1 tert-butyl 6-(8-(benzo[d]thiazol-2-ylcarbamoyl)-3,4-dihydroisoquinolin-2(1H)-yl)-3-(1-((3,5-dimethyl-7-(2-(oxetan-3-ylamino)ethoxy)adamantan-1-yl)methyl)-5-methyl-1H-pyrazol-4-yl)picolinate A solution of Example 1.2.7 (0.095 g), oxetan-3-one (10 mg) and sodium triacetoxyborohydride (0.038 g) was stirred in dichloromethane (1 mL) at room temperature. After stirring overnight, the reaction mixture was loaded directly onto silica gel and eluted using a gradient of 0.5-5% methanol in dichloromethane containing ammonia to give the title compound. MS (ELSD) m/e 858.4 (M+H)$^+$.

1.45.2 6-[8-(1,3-benzothiazol-2-ylcarbamoyl)-3,4-dihydroisoquinolin-2(1H)-yl]-3-{1-[(3-{2-[(1,3-dihydroxypropan-2-yl)amino]ethoxy}-5,7-dimethyltricyclo[3.3.1.1$^{3,7}$]dec-1-yl)methyl]-5-methyl-1H-pyrazol-4-yl}pyridine-2-carboxylic acid Example 1.45.1 was dissolved in dichloromethane (0.5 mL) and was treated with trifluoroacetic acid (0.5 mL) and stirred overnight. The reaction was purified by reverse phase HPLC using a Gilson system, eluting with 10-60% acetonitrile in water containing 0.1% v/v trifluoroacetic acid. The desired fractions were combined and freeze-dried to provide the title compound. $^1$H NMR (400 MHz, dimethyl sulfoxide-$d_6$) δ ppm 12.84 (s, 1H), 8.19 (s, 2H), 8.02 (d, 1H), 7.78 (d, 1H), 7.61 (d, 1H), 7.53-7.40 (m, 3H), 7.40-7.31 (m, 2H), 7.28 (s, 1H), 6.94 (d, 1H), 4.95 (s, 2H), 3.87 (t, 2H), 3.82 (s, 2H), 3.67-3.62 (m, 4H), 3.22-3.14 (m, 1H), 3.14-3.06 (m, 2H), 3.00 (t, 4H), 2.09 (s, 3H), 1.41 (s, 2H), 1.37-1.20 (m, 4H), 1.20-0.95 (m, 6H), 0.85 (s, 6H). MS (ESI) m/e 820.2 (M+H)$^+$.

1.46 Synthesis of 6-[5-(2-aminoethoxy)-8-(1,3-benzothiazol-2-ylcarbamoyl)-3,4-dihydroisoquinolin-2(1H)-yl]-3-{1-[(3,5-dimethyl-7-{2-[methyl(2-sulfoethyl)amino]ethoxy}tricyclo[3.3.1.1$^{3,7}$]dec-1-yl)methyl]-5-methyl-1H-pyrazol-4-yl}pyridine-2-carboxylic acid (Compound W2.46)

1.46.1 6-[8-(1,3-benzothiazol-2-ylcarbamoyl)-5-(2-{[(benzyloxy)carbonyl]amino}ethoxy)-3,4-dihydroisoquinolin-2(1H)-yl]-3-[1-({3,5-dimethyl-7-[(2,2,7,13-pentamethyl-10,10-dioxido-3,3-diphenyl-4,9-dioxa-10λ$^6$-thia-13-aza-3-silapentadecan-15-yl)oxy]tricyclo[3.3.1.1$^{3,7}$]dec-1-yl}methyl)-5-methyl-1H-pyrazol-4-yl]pyridine-2-carboxylic acid The title compound was prepared as described in Example 1.2.8, replacing Example 1.2.7 with Example 1.35.

1.46.2 6-[5-(2-aminoethoxy)-8-(1,3-benzothiazol-2-ylcarbamoyl)-3,4-dihydroisoquinolin-2(1H)-yl]-3-{1-[(3,5-dimethyl-7-{2-[methyl(2-sulfoethyl)amino]ethoxy}tricyclo[3.3.1.1$^{3,7}$]dec-1-yl)methyl]-5-methyl-1H-pyrazol-4-yl}pyridine-2-carboxylic acid The title compound was prepared as described in Example 1.34.4, replacing Example 1.34.3 with Example 1.46.1. $^1$H NMR (500 MHz, dimethyl sulfoxide-$d_6$) δ ppm 12.74 (s, 2H), 8.96 (s, 1H), 8.03 (d, 1H), 7.94 (s, 3H), 7.72-7.81 (m, 2H), 7.53 (d, 1H), 7.47 (t, 1H), 7.35 (t, 1H), 7.28 (s, 1H), 7.02 (t, 2H), 5.03 (s, 2H), 4.26 (t, 2H), 3.92 (t, 2H), 3.83 (s, 2H), 3.23-3.38 (m, 4H), 3.13-3.25 (m, 1H), 2.82-3.00 (m, 4H), 2.78 (d, 3H), 2.11 (s, 3H), 1.23-1.50 (m, 6H), 0.95-1.21 (m, 6H), 0.86 (s, 6H). MS (ESI) m/e 927.2 (M+H)$^+$.

1.47 Synthesis of 6-[8-(1,3-benzothiazol-2-ylcarbamoyl)-5-{2-[(2-sulfoethyl)amino]ethoxy}-3,4-dihydroisoquinolin-2(1H)-yl]-3-{1-[(3,5-dimethyl-7-{2-[methyl(2-sulfoethyl)amino]ethoxy}tricyclo[3.3.1.1$^{3,7}$]dec-1-yl)methyl]-5-methyl-1H-pyrazol-4-yl}pyridine-2-carboxylic acid (Compound W2.47)

1.47.1 6-[8-(1,3-benzothiazol-2-ylcarbamoyl)-5-[(2,2,7,7-tetramethyl-10,10-dioxido-3,3-diphenyl-4,9-dioxa-10λ$^6$-thia-13-aza-3-silapentadecan-15-yl)oxy]-3,4-dihydroisoquinolin-2(1H)-yl]-3-{1-[(3,5-dimethyl-7-{2-[methyl(2-sulfoethyl)amino]ethoxy}tricyclo[3.3.1.1$^{3,7}$]dec-1-yl)methyl]-5-methyl-1H-pyrazol-4-yl}pyridine-2-carboxylic acid The title compound was prepared as described in Example 1.2.8, replacing Example 1.2.7 with Example 1.46.2.

1.47.2 6-[8-(1,3-benzothiazol-2-ylcarbamoyl)-5-{2-[(2-sulfoethyl)amino]ethoxy}-3,4-dihydroisoquinolin-2(1H)-yl]-3-{1-[(3,5-dimethyl-7-{2-[methyl(2-sulfoethyl)amino]ethoxy}tricyclo[3.3.1.1$^{3,7}$]dec-1-yl)methyl]-5-methyl-1H-pyrazol-4-yl}pyridine-2-carboxylic acid Example 1.47.1 (100 mg) in dichloromethane (5 mL) was treated with trifluoroacetic acid (5 mL) overnight. The reaction mixture was concentrated and purified by reverse phase chromatography (C18 column), eluting with 20-60% acetonitrile in water containing 0.1% v/v trifluoroacetic acid, to provide the title compound. $^1$H NMR (400 MHz, dimethyl sulfoxide-$d_6$) δ ppm m 12.74 (s, 1H), 8.96 (d, 1H), 8.64 (s, 2H), 8.02 (d, 1H), 7.76 (dd, 2H), 7.41-7.57 (m, 2H), 7.24-7.40 (m, 2H), 7.02 (t, 2H), 5.03 (s, 2H), 4.23-4.42 (m, 2H), 3.90 (t, 2H), 3.83 (s, 2H), 3.25-3.40 (m, 6H), 3.12-3.24 (m, 2H), 2.81-3.01 (m, 6H), 2.78 (d, 3H), 2.10 (s, 3H), 1.22-1.47 (m, 6H), 0.97-1.21 (m, 6H), 0.86 (s, 6H). MS (ESI) m/e 1035.3 (M+H)$^+$.

1.48 Synthesis of 6-[8-(1,3-benzothiazol-2-ylcarbamoyl)-3,4-dihydroisoquinolin-2(1H)-yl]-3-{1-[(3,5-dimethyl-7-{2-[(2-sulfoethyl){2-[(2-sulfoethyl)amino]ethyl}amino]ethoxy}tricyclo[3.3.1.1$^{3,7}$]dec-1-yl)methyl]-5-methyl-1H-pyrazol-4-yl}pyridine-2-carboxylic acid (Compound W2.48)

1.48.1 6-[8-(1,3-benzothiazol-2-ylcarbamoyl)-3,4-dihydroisoquinolin-2(1H)-yl]-3-{1-[(3,5-dimethyl-7-{[2,2,7,7-tetramethyl-10,10-dioxido-3,3-diphenyl-16-(2-sulfoethyl)-4,9-dioxa-10λ$^6$-thia-13,16-diaza-3-silaoctadecan-18-yl]oxy}tricyclo[3.3.1.1$^{3,7}$]dec-1-yl)methyl]-5-methyl-1H-pyrazol-4-yl}pyridine-2-carboxylic acid The title compound was prepared as described in Example 1.2.8, replacing Example 1.2.7 with Example 1.33.2.

1.48.2 6-[8-(1,3-benzothiazol-2-ylcarbamoyl)-3,4-dihydroisoquinolin-2(1H)-yl]-3-{1-[(3,5-dimethyl-7-{2-[(2-sulfoethyl){2-[(2-sulfoethyl)amino]ethyl}amino]ethoxy}tricyclo[3.3.1.1$^{3,7}$]dec-1-yl)methyl]-5-methyl-1H-pyrazol-4-yl}pyridine-2-carboxylic acid The title compound was prepared as described in Example 1.47.2, replacing Example 1.47.1 with Example 1.48.1. $^1$H NMR (400 MHz, dimethyl sulfoxide-$d_6$) δ ppm 12.87 (s, 3H), 8.55 (s, 4H), 8.04 (d, 2H), 7.79 (d, 2H), 7.62 (d, 1H), 7.40-7.56 (m, 3H), 7.32-7.40 (m, 2H), 7.29 (s, 1H), 6.96 (d, 2H), 4.96 (s, 3H), 3.89 (t, 2H), 3.83 (s, 2H), 3.47 (d, 2H), 3.36 (s, 2H), 3.18-3.30 (m, 2H), 3.01 (t, 2H), 2.94 (t, 2H), 2.82 (t, 2H), 2.11 (s, 3H), 1.26-1.49 (m, 6H), 0.96-1.20 (m, 6H), 0.87 (s, 6H). MS (ESI) m/e 1005.2 (M+H)$^+$.

1.49 Synthesis of 6-[8-(1,3-benzothiazol-2-ylcarbamoyl)-5-{2-[(2-carboxyethyl)amino]ethoxy}-3,4-dihydroisoquinolin-2(1H)-yl]-3-{1-[(3,5-dimethyl-7-{2-[methyl(2-sulfoethyl)amino]ethoxy}tricyclo[3.3.1.1$^{3,7}$]dec-1-yl)methyl]-5-methyl-1H-pyrazol-4-yl}pyridine-2-carboxylic acid (Compound W2.49)

1.49.1 6-(8-(benzo[d]thiazol-2-ylcarbamoyl)-5-(2-((3-(tert-butoxy)-3-oxopropyl)amino)ethoxy)-3,4-dihydroisoquinolin-2(1H)-yl)-3-(1-((3,5-dimethyl-7-(2-(methyl(2-sulfoethyl)amino)ethoxy)adamantan-1-yl)methyl)-5-methyl-1H-pyrazol-4-yl)picolinic acid The title compound was prepared as described in Example 1.32.3, replacing Example 1.32.2 with Example 1.46.2.

1.49.2 6-[8-(1,3-benzothiazol-2-ylcarbamoyl)-5-{2-[(2-carboxyethyl)amino]ethoxy}-3,4-dihydroisoquinolin-2(1H)-yl]-3-{1-[(3,5-dimethyl-7-{2-[methyl(2-sulfoethyl)amino]ethoxy}tricyclo[3.3.1.1$^{3,7}$]dec-1-yl)methyl]-5-methyl-1H-pyrazol-4-yl}pyridine-2-carboxylic acid The title compound was prepared as described in Example 1.6.2, replacing Example 1.6.1 with Example 1.49.1. $^1$H NMR (400 MHz, dimethyl sulfoxide-$d_6$) δ ppm 12.75 (s, 1H), 8.96 (s, 1H), 8.59 (s, 2H), 8.03 (d, 1H), 7.72-7.82 (m, 2H), 7.54 (d, 1H), 7.43-7.51 (m, 2H), 7.35 (t, 1H), 7.28 (s, 1H), 7.02 (dd, 2H), 5.02 (s, 2H), 4.34 (s, 2H), 3.93 (s, 2H), 3.83 (s, 2H), 3.62 (s, 2H), 2.84-3.01 (m, 4H), 2.78 (d, 3H), 2.65-2.75 (m, 2H), 2.11 (s, 3H), 1.20-1.45 (m, 7H), 0.95-1.21 (m, 6H), 0.86 (s, 6H). MS (ESI) m/e 999.2 (M+H)$^+$.

1.50 Synthesis of 3-{1-[(3,5-dimethyl-7-{2-[(3-phosphonopropyl)(piperidin-4-yl)amino]ethoxy}tricyclo[3.3.1.1$^{3,7}$]dec-1-yl)methyl]-5-methyl-1H-pyrazol-4-yl}-6-[8-([1,3]thiazolo[4,5-b]pyridin-2-ylcarbamoyl)-3,4-dihydroisoquinolin-2(1H)-yl]pyridine-2-carboxylic acid (Compound W2.50)

1.50.1 tert-butyl 3-(1-((3-(2-((1-(tert-butoxycarbonyl)piperidin-4-yl)amino)ethoxy)-5,7-dimethyladamantan-1-yl)methyl)-5-methyl-1H-pyrazol-4-yl)-6-(8-(thiazolo[4,5-b]pyridin-2-ylcarbamoyl)-3,4-dihydroisoquinolin-2(1H)-yl)picolinate Example 1.23.2 (205 mg) was dissolved in dichloromethane (2.4 mL), and tert-butyl 4-oxopiperidine-1-carboxylate (51 mg) and sodium triacetoxyborohydride (75 mg) were added. The reaction was stirred at room temperature for two hours. More dichloromethane was added, and the reaction was poured into to saturated aqueous NaHCO₃ solution. The organic layer was washed with brine and dried over sodium sulfate. After filtration and concentration, the reside was purified by silica gel chromatography on a Grace Reveleris® Amino cartridge, eluting with a gradient of 0.5 to 5.0% methanol in dichloromethane, to give the title compound. MS (ESI) m/e 986.3 (M+H)$^+$.

1.50.2 3-{1-[(3,5-dimethyl-7-{2-[(3-phosphonopropyl)(piperidin-4-yl)amino]ethoxy}tricyclo[3.3.1.1$^{3,7}$]dec-1-yl)methyl]-5-methyl-1H-pyrazol-4-yl}-6-[8-([1,3]thiazolo[4,5-b]pyridin-2-ylcarbamoyl)-3,4-dihydroisoquinolin-2(1H)-yl]pyridine-2-carboxylic acid Example 1.50.1 (94 mg) was dissolved in dichloromethane (1 mL), then Example 1.14.2 (25 mg) and sodium triacetoxyborohydride (30 mg) were added. The reaction was stirred at room temperature for four hours. Trifluoroacetic acid (1.5 mL) was added, and the reaction stirred at room temperature overnight. The reaction mixture was concentrated and purified by reverse phase chromatography (C18 column), eluting with 10-90% acetonitrile in water containing 0.1% v/v trifluoroacetic acid, to provide the title compound as a trifluoroacetic acid salt. $^1$H NMR (400 MHz, dimethyl sulfoxide-d$_6$) δ ppm 8.82 (br s, 1H) 8.60 (dd, 1H), 8.52 (dd, 1H), 8.50 (br s, 1H), 7.66 (d, 1H), 7.50 (d, 1H), 7.46 (d, 1H), 7.38 (m, 2H), 7.30 (s, 1H), 6.97 (d, 1H), 4.98 (s, 2H), 3.89 (t, 2H), 3.83 (s, 2H) 3.69 (m, 2H), 3.61 (m, 1H), 3.44 (m, 2H) 3.23 (m, 4H), 3.02 (t, 2H), 2.93 (m, 2H), 2.18 (m, 2H), 2.10 (s, 3H), 1.92 (m, 2H), 1.83 (m, 2H), 1.64 (m, 2H), 1.44 (s, 2H), 1.31 (m, 4H), 1.14 (m, 4H), 1.04 (m, 2H), 0.87 (s, 6H). MS (ESI) m/e 952.3 (M+H)$^+$.

1.51 Synthesis of 6-[4-(1,3-benzothiazol-2-ylcarbamoyl)-3,4-dihydro-2H-1,4-benzoxazin-6-yl]-3-{1-[(3,5-dimethyl-7-{2-[(2-sulfoethyl)amino]ethoxy}tricyclo[3.3.1.1$^{3,7}$]dec-1-yl)methyl]-5-methyl-1H-pyrazol-4-yl}pyridine-2-carboxylic acid (Compound W2.51)

1.51.1 tert-butyl 3-(1-((3-(2-((tert-butyldimethylsilyl)oxy)ethoxy)-5,7-dimethyladamantan-1-yl)methyl)-5-methyl-1H-pyrazol-4-yl)-6-chloropicolinate To a solution of Example 1.20.2 (3.2 g) in N,N-dimethylformamide (20 mL) was added imidazole (0.616 g) and chloro t-butyldimethylsilane (1.37 g). The mixture was stirred overnight. The reaction mixture was diluted with ethyl acetate (300 mL), washed with water and brine, and dried over sodium sulfate. Filtration and evaporation of the solvent gave the crude product that was purified by silica gel chromatography, eluting with 20% ethyl acetate in heptane, to provide the title compound. MS (ESI) m/e 645.4 (M+H)$^+$.

1.51.2 tert-butyl 3-(1-((3-(2-((tert-butyldimethylsilyl)oxy)ethoxy)-5,7-dimethyladamantan-1-yl)methyl)-5-methyl-1H-pyrazol-4-yl)-6-(3,4-dihydro-2H-benzo[b][1,4]oxazin-6-yl)picolinate To a solution of 6-(4,4,5,5-tetramethyl-1,3,2-dioxaborolan-2-yl)-3,4-dihydro-2H-benzo[b][1,4]oxazine (507 mg) in 1,4-dioxane (10 mL) and water (5 mL) was added Example 1.51.1 (1.25 g), bis(triphenylphosphine)palladium(II)dichloride (136 mg), and cesium fluoride (884 mg). The mixture was stirred at 120° C. under microwave conditions (Biotage, Initiator) for 20 minutes. The mixture was diluted with ethyl acetate (500 mL), washed with water and brine, and dried over sodium sulfate. Filtration and evaporation of the solvent gave a residue that was purified by silica gel chromatography, eluting with 20% ethyl acetate in heptane followed by 5% methanol in dichloromethane, to provide the title compound. MS (ESI) m/e 744.1 (M+H)$^+$.

1.51.3 tert-butyl 6-(4-(benzo[d]thiazol-2-ylcarbamoyl)-3,4-dihydro-2H-benzo[b][1,4]oxazin-6-yl)-3-(1-((3-(2-((tert-butyldimethylsilyl)oxy)ethoxy)-5,7-dimethyladamantan-1-yl)methyl)-5-methyl-1H-pyrazol-4-yl)picolinate To an ambient suspension of bis(2,5-dioxopyrrolidin-1-yl) carbonate (295 mg) in acetonitrile (10 mL) was added benzo[d]thiazol-2-amine (173 mg), and the mixture was stirred for 1 hour. A solution of Example 1.51.2 (710 mg) in acetonitrile (10 mL) was added, and the suspension was vigorously stirred overnight. The mixture was diluted with ethyl acetate (300 mL), washed with water and brine, and dried over sodium sulfate. Filtration and evaporation of the solvent gave a residue that was purified by silica gel chromatography, eluting with 20% ethyl acetate in heptane, to give the title compound. MS (ESI) m/e 920.2 (M+H)$^+$.

1.51.4 tert-butyl 6-(4-(benzo[d]thiazol-2-ylcarbamoyl)-3,4-dihydro-2H-benzo[b][1,4]oxazin-6-yl)-3-(1-((3-(2-hydroxyethoxy)-5,7-dimethyladamantan-1-yl)methyl)-5-methyl-1H-pyrazol-4-yl)picolinate To a solution of Example 1.51.3 (1.4 g) in tetrahydrofuran (10 mL) was added tetrabutyl ammonium fluoride (1.0M in tetrahydrofuran, 6 mL). The mixture was stirred for 3 hours. The mixture was diluted with ethyl acetate (300 mL), washed with water and brine, and dried over sodium sulfate. Filtration and evaporation of the solvent gave title product, which was used in the next reaction without further purification. MS (ESI) m/e 806.0 (M+H)$^+$.

1.51.5 tert-butyl 6-(4-(benzo[d]thiazol-2-ylcarbamoyl)-3,4-dihydro-2H-benzo[b][1,4]oxazin-6-yl)-3-(1-((3,5-dimethyl-7-(2-((methylsulfonyl)oxy)ethoxy)adamantan-1-yl)methyl)-5-methyl-1H-pyrazol-4-yl)picolinate To a cooled (0° C.) solution of Example 1.51.4 (1.2 g) in dichloromethane (20 mL) and triethylamine (2 mL) was added methanesulfonyl chloride (300 mg). The mixture was stirred for 4 hours. The reaction mixture was diluted with ethyl acetate (200 mL), washed with water and brine, and dried over sodium sulfate. Filtration and evaporation of the solvent gave title product, which was used in the next reaction without further purification. MS (ESI) m/e 884.1 (M+H)$^+$.

1.51.6 tert-butyl 3-(1-((3-(2-azidoethoxy)-5,7-dimethyladamantan-1-yl)methyl)-5-methyl-1H-pyrazol-4-yl)-6-(4-(benzo[d]thiazol-2-ylcarbamoyl)-3,4-dihydro-2H-benzo[b][1,4]oxazin-6-yl)picolinate To a solution of Example 1.51.5 (1.5 g) in N,N-dimethylformamide (20 mL) was added sodium azide (331 mg). The mixture was stirred for 48 hours. The reaction mixture was diluted with ethyl acetate (200 mL), washed with water and brine, and dried over sodium sulfate. Filtration and evaporation of the solvent gave a residue that was purified by silica gel chromatography, eluting with 20% ethyl acetate in dichloromethane, to provide the title compound. MS (ESI) m/e 831.1 (M+H)⁺.

1.51.7 tert-butyl 3-(1-((3-(2-aminoethoxy)-5,7-dimethyladamantan-1-yl)methyl)-5-methyl-1H-pyrazol-4-yl)-6-(4-(benzo[d]thiazol-2-ylcarbamoyl)-3,4-dihydro-2H-benzo[b][1,4]oxazin-6-yl)picolinate To a solution of Example 1.51.6 (1.5 g) in tetrahydrofuran (30 mL) was added Pd/C (10%, 200 mg). The mixture was stirred under 1 atmosphere of hydrogen overnight. The reaction mixture was filtered, and the filtrate was concentrated under vacuum to give crude product. MS (ESI) m/e 805.1 (M+H)⁺.

1.51.8 6-[4-(1,3-benzothiazol-2-ylcarbamoyl)-3,4-dihydro-2H-1,4-benzoxazin-6-yl]-3-{1-[(3,5-dimethyl-7-{2-[(2-sulfoethyl)amino]ethoxy}tricyclo[3.3.1.1$^{3,7}$]dec-1-yl)methyl]-5-methyl-1H-pyrazol-4-yl}pyridine-2-carboxylic acid To a solution of Example 1.51.7 (164 mg) in N,N-dimethylformamide (10 mL) and N,N-diisopropylethylamine (0.5 mL) was added 4-((tert-butyldiphenylsilyl)oxy)-2,2-dimethylbutyl ethenesulfonate (91 mg). The mixture was stirred overnight. The reaction mixture was diluted with ethyl acetate (200 mL), washed with water and brine, and dried over sodium sulfate. Filtration and evaporation of the solvent gave a residue that was dissolved in tetrahydrofuran (2 mL). Tetrabutyl ammonium fluoride (1 mL, 1M in tetrahydrofuran) was added, and the mixture was stirred overnight. The mixture was concentrated under vacuum, and the residue was dissolved in dichloromethane/trifluoroacetic acid (1:1, 6 mL), which was allowed to sit overnight. After evaporation of the solvent, the residue was purified by reverse phase HPLC (Gilson system), eluting with 10-85% acetonitrile in water containing 0.1% v/v trifluoroacetic acid, to provide the title compound. ¹H NMR (400 MHz, dimethyl sulfoxide-d₆) δ ppm 8.74 (s, 1H), 8.35 (s, 2H), 7.94-8.00 (m, 1H), 7.86 (s, 1H), 7.71-7.82 (m, 2H), 7.46 (s, 1H), 7.34-7.44 (m, 2H), 7.24 (t, 1H), 7.02 (d, 1H), 4.28-4.39 (m, 2H), 4.10-4.19 (m, 2H), 3.90 (s, 3H), 3.55-3.61 (m, 4H), 3.21-3.30 (m, 3H), 3.07-3.16 (m, 3H), 2.23 (s, 3H), 1.44 (s, 2H), 0.98-1.37 (m, 9H), 0.89 (s, 6H). MS (ESI) m/e 856.1 (M+H)⁺.

1.52 Synthesis of 6-[8-(1,3-benzothiazol-2-ylcarbamoyl)-5-(3-sulfopropoxy)-3,4-dihydroisoquinolin-2(1H)-yl]-3-[1-({3,5-dimethyl-7-[2-(methylamino)ethoxy]tricyclo[3.3.1.1$^{3,7}$]dec-1-yl}methyl)-5-methyl-1H-pyrazol-4-yl]pyridine-2-carboxylic acid (Compound W2.52)

1.52.1 methyl 2-(6-(tert-butoxycarbonyl)-5-(1-((3-(2-((tert-butoxycarbonyl)(methyl)amino)ethoxy)-5,7-dimethyladamantan-1-yl)methyl)-5-methyl-1H-pyrazol-4-yl)pyridin-2-yl)-5-(3-((2,2,2-trifluoro-1-(p-tolyl)ethoxy)sulfonyl)propoxy)-1,2,3,4-tetrahydroisoquinoline-8-carboxylate To a solution of Example 1.31.8 (460 mg) in N,N-dimethylformamide (10 mL) was added 2,2,2-trifluoro-1-(p-tolyl)ethyl 3-iodopropane-1-sulfonate (239 mg, prepared according to J. Org. Chem., 2013, 78, 711-716) and K₂CO₃ (234 mg), and the mixture was stirred overnight. The mixture was diluted with ethyl acetate (200 mL), washed with water and brine, and dried over sodium sulfate. Filtration and evaporation of the solvent gave a residue that was purified by silica gel chromatography, eluting with 20% ethyl acetate in heptane, to provide the title compound. MS (ESI) m/e 1018.5 (M+H)⁺.

1.52.2 2-(6-(tert-butoxycarbonyl)-5-(1-((3-(2-((tert-butoxycarbonyl)(methyl)amino)ethoxy)-5,7-dimethyladamantan-1-yl)methyl)-5-methyl-1H-pyrazol-4-yl)pyridin-2-yl)-5-(3-((2,2,2-trifluoro-1-(p-tolyl)ethoxy)sulfonyl)propoxy)-1,2,3,4-tetrahydroisoquinoline-8-carboxylic acid To a solution of Example 1.52.1 (176 mg) in tetrahydrofuran (4 mL), methanol (3 mL) and water (3 mL) was added lithium hydroxide monohydrate (60 mg), and the mixture was stirred overnight. The mixture was then diluted with ethyl acetate (200 mL), washed with 1N aqueous HCl, water and brine, and dried over sodium sulfate. Filtration and evaporation of the solvent gave the title product, which was used in the next reaction without further purification. MS (ESI) m/e 1095.2 (M+H)⁺.

1.52.3 tert-butyl 6-(8-(benzo[d]thiazol-2-ylcarbamoyl)-5-(3-((2,2,2-trifluoro-1-(p-tolyl)ethoxy)sulfonyl)propoxy)-3,4-dihydroisoquinolin-2(1H)-yl)-3-(1-(((-(2-((tert-butoxycarbonyl)(methyl)amino)ethoxy)-5,7-dimethyladamantan-1-yl)methyl)-5-methyl-1H-pyrazol-4-yl)picolinate To a solution of Example 1.52.2 (117 mg) in dichloromethane (6 mL) was added benzo[d]thiazol-2-amine (19.27 mg), 1-ethyl-3-[3-(dimethylamino)propyl]-carbodiimide hydrochloride (37 mg) and 4-(dimethylamino)pyridine (23.5 mg), and the mixture was stirred overnight. The reaction mixture was diluted with ethyl acetate (200 mL), washed with water and brine, and dried over sodium sulfate. Filtration and evaporation of the solvent gave the title product. MS (ESI) m/e 1226.1 (M+H)⁺.

1.52.4 6-[8-(1,3-benzothiazol-2-ylcarbamoyl)-5-(3-sulfopropoxy)-3,4-dihydroisoquinolin-2(1H)-yl]-3-[1-({3,5-dimethyl-7-[2-(methylamino)ethoxy]tricyclo[3.3.1.1$^{3,7}$]dec-1-yl}methyl)-5-methyl-1H-pyrazol-4-yl]pyridine-2-carboxylic acid Example 1.52.3 (130 mg) was dissolved in dichloromethane/trifluoroacetic acid (1:1, 6 mL) and stirred overnight. After evaporation of the solvent, the residue was dissolved in N,N-dimethylformamide/water (1:1, 12 mL) and purified by reverse phase HPLC (Gilson), eluting with 10 to 85% acetonitrile in water containing 0.1% v/v trifluoroacetic acid, to give the title compound. ¹H NMR (400 MHz, dimethyl sulfoxide-d₆) δ ppm 12.68 (s, 1H), 8.13-8.32 (m, 2H), 8.01 (d, 1H), 7.75 (dd, 2H), 7.42-7.56 (m, 2H), 7.29 (s, 1H), 7.28-7.34 (m, 1H), 7.00 (dd, 2H), 5.03 (s, 2H), 4.19 (t, 2H), 3.83 (s, 3H), 3.50-3.57 (m, 4H), 2.95-3.05 (m, 2H), 2.81 (t, 2H), 2.52-2.65 (m, 4H), 1.39 (s, 2H), 0.96-1.32 (m, 12H), 0.87 (s, 6H). MS (ESI) m/e 898.3 (M+H)⁺.

1.53 Synthesis of 3-{1-[(3,5-dimethyl-7-{2-[(2-sulfoethyl)amino]ethoxy}tricyclo[3.3.1.1$^{3,7}$]dec-1-yl)methyl]-5-methyl-1H-pyrazol-4-yl}-6-[1-([1,3]thiazolo[4,5-b]pyridin-2-ylcarbamoyl)-1,2,3,4-tetrahydroquinolin-7-yl]pyridine-2-carboxylic acid (Compound W2.53)

1.53.1 tert-butyl 6-chloro-3-(1-((3-(2-hydroxyethoxy)-5,7-dimethyladamantan-1-yl)methyl)-5-methyl-1H-pyrazol-4-yl)picolinate The title compound was prepared as described in Example 1.51.4, replacing Example 1.51.3 with Example 1.51.1.

1.53.2 tert-butyl 6-chloro-3-(1-((3,5-dimethyl-7-(2-((methylsulfonyl)oxy)ethoxy)adamantan-1-yl)methyl)-5-methyl-1H-pyrazol-4-yl)picolinate To a cooled (0° C.) solution of Example 1.53.1 (1.89 g) in dichloromethane (30 mL) and triethylamine (3 mL) was added methanesulfonyl chloride (1.03 g), and the mixture was stirred for 4 hours. The reaction mixture was diluted with ethyl acetate (200 mL), washed with water and brine, and dried over sodium sulfate. Filtration and evaporation of the solvent gave the title product, which was used in the next reaction without further purification.

1.53.4 tert-butyl 3-(1-((3-(2-aminoethoxy)-5,7-dimethyladamantan-1-yl)methyl)-5-methyl-1H-pyrazol-4-yl)-6-chloropicolinate Example 1.53.2 (2.2 g) was dissolved in 7N ammonia in methanol (40 mL), and the mixture was stirred at 80° C. under microwave conditions (Biotage Initiator) for 2 hours. The mixture was concentrated under vacuum and, and the residue was dissolved in ethyl acetate, washed with water and brine, and dried over sodium sulfate. Filtration and evaporation of the solvent provided the title compound.

1.53.5 tert-butyl 6-chloro-3-[1-({3,5-dimethyl-7-[(2,2,7,7-tetramethyl-10,10-dioxido-3,3-diphenyl-4,9-dioxa-10λ$^6$-thia-13-aza-3-silapentadecan-15-yl)oxy]tricyclo[3.3.1.1$^{3,7}$]dec-1-yl}methyl)-5-methyl-1H-pyrazol-4-yl]pyridine-2-carboxylate To a solution of Example 1.53.3 (1.59 g) in N,N-dimethylformamide (30 mL) was added 4-((tert-butyldiphenylsilyl)oxy)-2,2-dimethylbutyl ethenesulfonate (1.6 g) and N,N-diisopropylethylamine (1 mL), and the mixture was stirred for 4 days. The reaction mixture was dissolved in ethyl acetate (400 mL), washed with water and brine, and dried over sodium sulfate. Filtration and evaporation of the solvent gave the title product, which was used in the next reaction without further purification. MS (ESI) m/e 976.8 (M+H)$^+$.

1.53.6 tert-butyl 3-{1-[(3-{[13-(tert-butoxycarbonyl)-2,2,7,7-tetramethyl-10,10-dioxido-3,3-diphenyl-4,9-dioxa-10λ$^6$-thia-13-aza-3-silapentadecan-15-yl]oxy}-5,7-dimethyltricyclo[3.3.1.1$^{3,7}$]dec-1-yl)methyl]-5-methyl-1H-pyrazol-4-yl}-6-chloropyridine-2-carboxylate To a solution of Example 1.53.4 (2.93 g) in tetrahydrofuran (50 mL) was added di-t-butyldicarbonate (0.786 g) and 4-(dimethylamino)pyridine (100 mg), and the mixture was stirred overnight. The mixture was concentrated under vacuum, and the residue was dissolved in ethyl acetate (300 mL), washed with 1N aqueous HCl solution, water and brine, and dried over sodium sulfate. Filtration and evaporation of the solvent gave a residue that was purified by silica gel chromatography, eluting with 20% ethyl acetate in heptane, to provide the title compound. MS (ESI) m/e 1076.9 (M+H)$^+$.

1.53.7 tert-butyl 3-{1-[(3-{[13-(tert-butoxycarbonyl)-2,2,7,7-tetramethyl-10,10-dioxido-3,3-diphenyl-4,9-dioxa-10λ$^6$-thia-13-aza-3-silapentadecan-15-yl]oxy}-5,7-dimethyltricyclo[3.3.1.1$^{3,7}$]dec-1-yl)methyl]-5-methyl-1H-pyrazol-4-yl}-6-(1,2,3,4-tetrahydroquinolin-7-yl)pyridine-2-carboxylate To a solution of 7-(4,4,5,5-tetramethyl-1,3,2-dioxaborolan-2-yl)-1,2,3,4-tetrahydroquinoline (65 mg) in 1,4-dioxane (10 mL) and water (5 mL) was added Example 1.53.5 (220 mg), bis(triphenylphosphine)palladium(II)dichloride (7 mg), and cesium fluoride (45.6 mg). The mixture was stirred at 120° C. for 30 minutes under microwave conditions (Biotage Initiator). The mixture was diluted with ethyl acetate (200 mL), washed with water and brine, and dried over sodium sulfate. Filtration and evaporation of the solvent gave a residue that was purified by silica gel chromatography, eluting with 20% ethyl acetate in heptane, to give the title compound. MS (ESI) m/e 1173.9 (M+H)$^+$.

1.53.8 3-{1-[(3,5-dimethyl-7-{2-[(2-sulfoethyl)amino]ethoxy}tricyclo[3.3.1.1$^{3,7}$]dec-1-yl)methyl]-5-methyl-1H-pyrazol-4-yl}-6-[1-([1,3]thiazolo[4,5-b]pyridin-2-ylcarbamoyl)-1,2,3,4-tetrahydroquinolin-7-yl]pyridine-2-carboxylic acid To an ambient suspension of bis(2,5-dioxopyrrolidin-1-yl) carbonate (48.2 mg) in acetonitrile (10 mL) was added thiazolo[4,5-b]pyridin-2-amine (34 mg), and the mixture was stirred for 1 hour. A solution of Example 1.53.6 (220 mg) in acetonitrile (5 mL) was added, and the suspension was vigorously stirred overnight. The mixture was diluted with ethyl acetate (200 mL), washed with water and brine, and dried over sodium sulfate. Filtration and evaporation of the solvent gave a residue, which was dissolved in trifluoroacetic acid (10 mL) and stirred overnight. After evaporation of the solvent, the residue was purified by reverse phase HPLC (Gilson system), eluting with 10-85% acetonitrile in water containing 0.1% v/v trifluoroacetic acid, to provide the title compound. $^1$H NMR (500 MHz, dimethyl sulfoxide-d$_6$) δ ppm 8.42-8.48 (m, 1H), 8.31-8.40 (m, 4H), 8.03 (d, 1H), 7.89 (d, 1H), 7.80 (d, 1H), 7.47 (s, 1H), 7.26-7.37 (m, 2H), 3.93-4.02 (m, 3H), 3.90 (s, 3H), 3.52-3.60 (m, 3H), 3.17-3.26 (m, 2H), 3.05-3.14 (m, 2H), 2.76-2.89 (m, 5H), 2.23 (s, 3H), 1.90-2.01 (m, 2H), 1.44 (s, 2H), 1.27-1.37 (m, 4H), 0.99-1.22 (m, 5H), 0.88 (s, 6H). MS (ESI) m/e 855.1 (M+H)$^+$.

1.54 Synthesis of 3-{1-[(3,5-dimethyl-7-{2-[(2-sulfoethyl)amino]ethoxy}tricyclo[3.3.1.1$^{3,7}$]dec-1-yl)methyl]-5-methyl-1H-pyrazol-4-yl}-6-[8-([1,3]thiazolo[4,5-b]pyridin-2-ylcarbamoyl)naphthalen-2-yl]pyridine-2-carboxylic acid (Compound W2.54)

1.54.1 tert-butyl 3-{1-[(3-{[13-(tert-butoxycarbonyl)-2,2,7,7-tetramethyl-10,10-dioxido-3,3-diphenyl-4,9-dioxa-10λ$^6$-thia-13-aza-3-silapentadecan-15-yl]oxy}-5,7-dimethyltricyclo[3.3.1.1$^{3,7}$]dec-1-yl)methyl]-5-methyl-1H-pyrazol-4-yl}-6-[8-(methoxycarbonyl)naphthalen-2-yl]pyridine-2-carboxylate The title compound was prepared by substituting methyl 7-(4,4,5,5-tetramethyl-1,3,2-dioxaborolan-2-yl)-1-naphthoate for 7-(4,4,5,5-tetramethyl-1,3,2-dioxaborolan-2-yl)-1,2,3,4-tetrahydroquinoline in Example 1.53.6. MS (ESI) m/e 1226.6 (M+H)$^+$.

1.54.2 7-[6-(tert-butoxycarbonyl)-5-{1-[(3-{[13-(tert-butoxycarbonyl)-2,2,7,7-tetramethyl-10,10-dioxido-3,3-diphenyl-4,9-dioxa-10$\lambda^6$-thia-13-aza-3-silapentadecan-15-yl]oxy}-5,7-dimethyltricyclo[3.3.1.1$^{3,7}$]dec-1-yl)methyl]-5-methyl-1H-pyrazol-4-yl}pyridin-2-yl]naphthalene-1-carboxylic acid To a solution of Example 1.54.1 (79 mg) in tetrahydrofuran (4 mL), methanol (3 mL) and water (3 mL) was added lithium hydroxide monohydrate (60 mg), and the mixture was stirred overnight. The reaction was diluted with ethyl acetate (200 mL), washed with 1N aqueous HCl, water and brine, and dried over sodium sulfate. Filtration and evaporation of the solvent gave the title product, which was used in the next step without further purification. MS (ESI) m/e 1211.6 (M+H)$^+$.

1.54.3 3-{1-[(3,5-dimethyl-7-{2-[(2-sulfoethyl)amino]ethoxy}tricyclo[3.3.1.1$^{3,7}$]dec-1-yl)methyl]-5-methyl-1H-pyrazol-4-yl}-6-[8-([1,3]thiazolo[4,5-b]pyridin-2-ylcarbamoyl)naphthalen-2-yl]pyridine-2-carboxylic acid To a solution of Example 1.54.2 (60 mg) in dichloromethane (4 mL) was added thiazolo[4,5-b]pyridin-2-amine (7.56 mg), 1-ethyl-3-[3-(dimethylamino)propyl]-carbodiimide hydrochloride (19 mg) and 4-(dimethylamino)pyridine (12.2 mg), and the mixture was stirred overnight. The reaction mixture was diluted with ethyl acetate (200 mL), washed with water and brine, and dried over sodium sulfate. Filtration and evaporation of the solvent gave the title product, which was dissolved in dichloromethane/trifluoroacetic acid (1:1, 6 mL) and stirred overnight. After evaporation of solvent, the residue was dissolved in N,N-dimethylformamide/water (1:1, 12 mL) and purified by reverse phase HPLC (Gilson system), eluting with 10-85% acetonitrile in water containing 0.1% trifluoroacetic acid, to give the title compound. $^1$H NMR (400 MHz, dimethyl sulfoxide-d$_6$) δ ppm 13.42 (s, 1H), 9.05 (s, 1H), 8.51-8.69 (m, 2H), 8.31-8.41 (m, 2H), 8.18-8.26 (m, 4H), 8.06 (d, 1H), 7.97 (d, 1H), 7.68-7.79 (m, 1H), 7.49 (s, 1H), 7.40 (dd, 1H), 3.90 (s, 3H), 3.18-3.29 (m, 3H), 3.07-3.15 (m, 2H), 2.82 (t, 3H), 2.24 (s, 3H), 1.44 (s, 2H), 0.97-1.37 (m, 10H), 0.88 (s, 6H). MS (ESI) m/e 850.1 (M+H)$^+$.

1.55 Synthesis of (1ξ)-1-({2-[5-(1-{[3-(2-aminoethoxy)-5,7-dimethyltricyclo[3.3.1.1$^{3,7}$]dec-1-yl]methyl}-5-methyl-1H-pyrazol-4-yl)-6-carboxypyridin-2-yl]-8-(1,3-benzothiazol-2-ylcarbamoyl)-1,2,3,4-tetrahydroisoquinolin-5-yl}methyl)-1,5-anhydro-D-glucitol (Compound W2.55)

1.55.1 (2R,3R,4S,5R)-3,4,5-tris(methoxymethoxy)-2-((methoxymethoxy)methyl)-6-methylenetetrahydro-2H-pyran The title compound was prepared according to J. R. Walker et al., *Bioorg. Med. Chem.* 2006, 14, 3038-3048. MS (ESI) m/e 370 (M+NH$_4$)$^+$.

1.55.2 4-Bromo-3-cyanomethyl-benzoic acid methyl ester

To a solution of trimethylsilanecarbonitrile (3.59 mL) in tetrahydrofuran (6 mL) was added 1M tetrabutylammonium fluoride (26.8 mL, 1 M in tetrahydrofuran) dropwise over 30 minutes. The solution was stirred at room temperature for 30 minutes. Methyl 4-bromo-3-(bromomethyl)benzoate (7.50 g) was dissolved in acetonitrile (30 mL) and was added to the first solution dropwise over 30 minutes. The solution was heated to 80° C. for 30 minutes and cooled. The solution was concentrated under reduced pressure, and the residue was purified by silica gel chromatography, eluting with 20-30% ethyl acetate in heptanes, to provide the title compound.

1.55.3 3-(2-Aminoethyl)-4-bromobenzoic acid methyl ester

Example 1.55.2 (5.69 g) was dissolved in tetrahydrofuran (135 mL), and 1 M borane (in tetrahydrofuran, 24.6 mL) was added. The solution was stirred at room temperature for 16 hours and was slowly quenched with methanol and 1 M aqueous hydrochloric acid. 4 M Aqueous hydrochloric acid (150 mL) was added, and the solution was stirred at room temperature for 16 hours. The mixture was concentrated under reduced pressure, and the pH was adjusted to between 11 and 12 using solid potassium carbonate. The solution was then extracted with dichloromethane (3×100 mL). The organic extracts were combined and dried over anhydrous sodium sulfate. The solution was filtered and concentrated under reduced pressure, and the residue was purified by silica gel chromatography, eluting with 10-20% methanol in dichloromethane, to provide the title compound. MS (ESI) m/e 258, 260 (M+H)$^+$.

1.55.4 4-Bromo-3-[2-(2,2,2-trifluoroacetylamino)-ethyl]-benzoic acid methyl ester Example 1.55.2 (3.21 g) was dissolved in dichloromethane (60 mL). The solution was cooled to 0° C., and triethylamine (2.1 mL) was added. Trifluoroacetic anhydride (2.6 mL) was added dropwise. The solution was stirred at 0° C. for ten minutes, and the cooling bath was removed. After 1 hour, water (50 mL) was added, and the solution was diluted with ethyl acetate (100 mL). 1 M Aqueous hydrochloric acid was added (50 mL), and the organic layer was separated, washed with 1 M aqueous hydrochloric acid, and washed with brine. The solution was dried with anhydrous sodium sulfate, filtered and concentrated under reduced pressure to provide the title compound. MS (ESI) m/e 371, 373 (M+H)$^+$.

1.55.5 5-Bromo-2-(2,2,2-trifluoroacetyl)-1,2,3,4-tetrahydroisoquinoline-8-carboxylic acid methyl ester Example 1.55.4 (4.40 g) and paraformaldehyde (1.865 g) were placed in a flask and concentrated sulfuric acid (32 mL) was added. The solution was stirred at room temperature for one hour. Cold water (120 mL) was added, and the solution was extracted with ethyl acetate (3×100 mL). The extracts were combined, washed with saturated aqueous sodium bicarbonate (100 mL) and water (100 mL), and dried over anhydrous sodium sulfate. The mixture was filtered and concentrated under reduced pressure. The residue was purified by silica gel chromatography, eluting with 20-30% ethyl acetate in heptanes, to provide the title compound. MS (ESI) m/e 366, 368 (M+H)$^+$.

1.55.6 Methyl 2-(2,2,2-trifluoroacetyl)-5-(((3S,4R,5R,6R)-3,4,5-tris(methoxymethoxy)-6-((methoxymethoxy)methyl)tetrahydro-2H-pyran-2-yl)methyl)-1,2,3,4-tetrahydroisoquinoline-8-carboxylate Example 1.55.1 (242 mg) was dissolved in tetrahydrofuran (7 mL) and 9-borabicyclo[3.3.1]nonane (3.0 mL) was added dropwise. The solution was refluxed for 4.5 hours and allowed to cool to room temperature. Potassium phosphate (3M, 0.6 mL) was added, and the solution was stirred for 10 minutes. The solution was then degassed and flushed with nitrogen three times. Separately, Example 1.55.5 (239 mg) and dichloro[1,1'-bis(diphenylphosphino)ferrocene]palladium (II) dichloromethane adduct (39 mg) were dissolved in N,N-dimethylformamide (7 mL), and the solution was degassed and flushed with nitrogen three times. The N,N-dimethylformamide solution was added dropwise to the tetrahydrofuran solution, and the mixture was stirred for 18 hours. HCl solution (0.1 M aqueous, 25 mL) was added, and the solution was extracted with ethyl acetate (30 mL) three times. The organic extracts were combined, washed with brine, dried over anhydrous sodium sulfate, filtered and concentrated. The residue was purified by silica gel chromatography, eluting with 30-50% ethyl acetate in heptanes, to yield the title compound. MS (ESI) m/e 710 (M+NH$_4$)$^+$.

1.55.7 Methyl 5-(((3S,4R,5R,6R)-3,4,5-tris (methoxymethoxy)-6-((methoxymethoxy)methyl) tetrahydro-2H-pyran-2-yl)methyl)-1,2,3,4-tetrahydroisoquinoline-8-carboxylate Example 1.55.6 (247 mg) was dissolved in methanol (1 mL), tetrahydrofuran (1 mL), and water (0.5 mL). Potassium carbonate (59 mg) was added, and the solution was stirred at room temperature for 16 hours. The solution was diluted with ethyl acetate (10 mL) and washed with saturated aqueous sodium bicarbonate (1 mL). The organic layer was dried over anhydrous sodium sulfate, filtered and concentrated under reduced pressure to yield the title compound. MS (ESI) m/e 600 (M+H)$^+$.

1.55.8 Methyl 2-(5-bromo-6-(tert-butoxycarbonyl) pyridin-2-yl)-5-(((3S,4R,5R,6R)-3,4,5-tris (methoxymethoxy)-6-((methoxymethoxy)methyl) tetrahydro-2H-pyran-2-yl)methyl)-1,2,3,4-tetrahydroisoquinoline-8-carboxylate The title compound was prepared by substituting Example 1.55.7 for methyl 1,2,3,4-tetrahydroisoquinoline-8-carboylate in Example 1.1.11. MS (ESI) m/e 799, 801 (M-tert-butyl)$^+$.

1.55.9 Methyl 2-(6-(tert-butoxycarbonyl)-5-(4,4,5,5-tetramethyl-1,3,2-dioxaborolan-2-yl)pyridin-2-yl)-5-(((3S,4R,5R,6R)-3,4,5-tris(methoxymethoxy)-6-((methoxymethoxy)methyl)tetrahydro-2H-pyran-2-yl)methyl)-1,2,3,4-tetrahydroisoquinoline-8-carboxylate The title compound was prepared by substituting Example 1.55.8 for Example 1.1.11 in Example 1.2.1. MS (ESI) m/e 903 (M+H)$^+$, 933 (M+MeOH-H)$^-$.

1.55.10 2-((3-((4-iodo-5-methyl-1H-pyrazol-1-yl) methyl)-5,7-dimethyladamantan-1-yl)oxy)ethanamine The title compound was prepared by substituting Example 1.13.1 for Example 1.10.4 in Example 1.10.5. MS (ESI) m/e 444 (M+H)$^+$.

1.55.11 tert-butyl (2-((3-((4-iodo-5-methyl-1H-pyrazol-1-yl)methyl)-5,7-dimethyladamantan-1-yl)oxy) ethyl)carbamate The title compound was prepared by substituting Example 1.55.10 for Example 1.10.5 in Example 1.10.6. MS (ESI) m/e 544 (M+H)$^+$, 488 (M-tert-butyl)$^+$, 542 (M-H)$^-$.

1.55.12 Methyl 2-(6-(tert-butoxycarbonyl)-5-(1-((3-(2-((tert-butoxycarbonyl)amino)ethoxy)-5,7-dimethyladamantan-1-yl)methyl)-5-methyl-1H-pyrazol-4-yl)pyridin-2-yl)-5-(((3R,4S,5S,6S)-3,4,5-tris (methoxymethoxy)-6-((methoxymethoxy)methyl) tetrahydro-2H-pyran-2-yl)methyl)-1,2,3,4-tetrahydroisoquinoline-8-carboxylate The title compound was prepared by substituting Example 1.55.9 for Example 1.2.1 and Example 1.55.11 for Example 1.13.3 in Example 1.13.4. MS (ESI) m/e 1192 (M+H)$^+$.

1.55.13 2-(6-(tert-butoxycarbonyl)-5-(1-((3-(2-((tert-butoxycarbonyl)amino)ethoxy)-5,7-dimethyladamantan-1-yl)methyl)-5-methyl-1H-pyrazol-4-yl) pyridin-2-yl)-5-(((3R,4S,5S,6S)-3,4,5-tris (methoxymethoxy)-6-((methoxymethoxy)methyl) tetrahydro-2H-pyran-2-yl)methyl)-1,2,3,4-tetrahydroisoquinoline-8-carboxylic acid The title compound was prepared by substituting Example 1.55.12 for Example 1.2.4 in Example 1.2.5. MS (ESI) m/e 1178 (M+H)$^+$, 1176 (M-H)$^-$.

1.55.14 Tert-butyl 6-(8-(benzo[d]thiazol-2-ylcarbamoyl)-5-(((3R,4S,5S,6S)-3,4,5-tris (methoxymethoxy)-6-((methoxymethoxy)methyl) tetrahydro-2H-pyran-2-yl)methyl)-3,4-dihydroisoquinolin-2(1H)-yl)-3-(1-((3-(2-((tert-butoxycarbonyl)amino)ethoxy)-5,7-dimethyladamantan-1-yl)methyl)-5-methyl-1H-pyrazol-4-yl)picolinate The title compound was prepared by substituting Example 1.55.13 for Example 1.52.2 in Example 1.52.3. MS (ESI) m/e 1310 (M+H)$^+$, 1308 (M-H)$^-$.

1.55.15 (1ξ)-1-({2-[5-(1-{[3-(2-aminoethoxy)-5,7-dimethyltricyclo[3.3.1.1$^{3,7}$]dec-1-yl]methyl}-5-methyl-1H-pyrazol-4-yl)-6-carboxypyridin-2-yl]-8-(1,3-benzothiazol-2-ylcarbamoyl)-1,2,3,4-tetrahydroisoquinolin-5-yl}methyl)-1,5-anhydro-D-glucitol The title compound was prepared by substituting Example 1.55.14 for Example 1.52.3 and 4M aqueous hydrochloric acid for trifluoroacetic acid in Example 1.52.4. $^1$H NMR (400 MHz, dimethyl sulfoxide-d$_6$) δ ppm 7.96 (d, 1H), 7.73 (d, 1H), 7.58 (bs, 3H), 7.46 (d, 1H), 7.43-7.39 (m, 2H), 7.30 (d, 1H), 7.27-7.25 (m, 2H), 6.88 (d, 1H), 4.90 (q, 2H), 3.76 (m, 4H), 3.51 (m, 1H), 3.21 (d, 2H), 3.18 (d, 1H), 3.12 (m, 2H), 3.02 (m, 4H), 2.93 (m, 4H), 2.83 (m, 2H), 2.59 (m, 2H), 2.03 (s, 3H), 1.44 (s, 1H), 1.34 (s, 2H), 1.23 (q, 4H), 1.07 (m, 4H), 0.97 (q, 2H), 0.80 (s, 6H). MS (ESI) m/e 922 (M+H)$^+$, 920 (M-H)$^-$.

1.56 Synthesis of 6-[8-(1,3-benzothiazol-2-ylcarbamoyl)-3,4-dihydroisoquinolin-2(1H)-yl]-3-{1-[(3-{2-[(3-carboxypropyl)amino]ethoxy}-5,7-dimethyltricyclo[3.3.1.1$^{3,7}$]dec-1-yl)methyl]-5-methyl-1H-pyrazol-4-yl}pyridine-2-carboxylic acid (Compound W2.56)

1.56.1 tert-butyl 6-(8-(benzo[d]thiazol-2-ylcarbamoyl)-3,4-dihydroisoquinolin-2(1H)-yl)-3-(1-((3-(2-((4-(tert-butoxy)-4-oxobutyl)amino)ethoxy)-5,7-dimethyladamantan-1-yl)methyl)-5-methyl-1H-pyrazol-4-yl)picolinate To a solution of Example 1.2.7 (0.103 g) and tert-butyl 4-bromobutanoate (0.032 g) in dichloromethane (0.5 mL) was added N,N-diisopropylethylamine (0.034 mL) at 50° C. in a sealed amber vial overnight. The reaction was concentrated, dissolved in dimethyl sulfoxide/methanol (1:1, 2 mL) and purified by reverse phase HPLC using a Gilson system, eluting with 5-75% acetonitrile in water containing 0.1% v/v trifluoroacetic acid. The desired fractions were combined and freeze-dried to provide the title compound. MS (ESI) m/e 944.6 (M+1).

1.56.1 6-[8-(1,3-benzothiazol-2-ylcarbamoyl)-3,4-dihydroisoquinolin-2(1H)-yl]-3-{1-[(3-{2-[(3-carboxypropyl)amino]ethoxy}-5,7-dimethyltricyclo[3.3.1.1$^{3,7}$]dec-1-yl)methyl]-5-methyl-1H-pyrazol-4-yl}pyridine-2-carboxylic acid A solution of Example 1.56.1 (0.049 g) was dissolved in dichloromethane (1 mL) and treated with trifluoroacetic acid (0.5 mL) and the mixture was stirred overnight. The reaction was concentrated, dissolved in a (1:1) N,N-dimethylformamide/water mixture (2 mL), and purified by reverse phase HPLC using a Gilson system, eluting with 5-75% acetonitrile in water containing 0.1% v/v trifluoroacetic acid. The desired fractions were combined and freeze-dried to provide the title compound. $^1$H NMR (400 MHz, dimethyl sulfoxide-d$_6$) δ ppm 13.09-12.32 (m, 2H), 8.31 (s, 2H), 8.03 (d, 1H), 7.79 (d, 1H), 7.62 (d, 1H), 7.54-7.40 (m, 3H), 7.40-7.32 (m, 2H), 7.29 (s, 1H), 6.96 (d, 1H), 4.96 (s, 2H), 3.89 (t, 2H), 3.83 (s, 2H), 3.55 (d, 2H), 3.02 (q, 4H), 2.92 (q, 2H), 2.33 (t, 2H), 2.10 (s, 3H), 1.80 (p, 2H), 1.43 (s, 2H), 1.30 (q, 4H), 1.21-0.95 (m, 6H), 0.87 (s, 6H). MS (ESI) m/e 832.3 (M+H)$^+$.

1.57 Synthesis of 6-[8-(1,3-benzothiazol-2-ylcarbamoyl)naphthalen-2-yl]-3-{1-[(3,5-dimethyl-7-{2-[(3-phosphonopropyl)amino]ethoxy}tricyclo[3.3.1.1$^{3,7}$]dec-1-yl)methyl]-5-methyl-1H-pyrazol-4-yl}pyridine-2-carboxylic acid (Compound W2.57)

1.57.1 tert-butyl 3-(1-((3-(2-hydroxyethoxy)-5,7-dimethyladamantan-1-yl)methyl)-5-methyl-1H-pyrazol-4-yl)-6-(8-(methoxycarbonyl)naphthalen-2-yl)picolinate To a solution of methyl 7-(4,4,5,5-tetramethyl-1,3,2-dioxaborolan-2-yl)-1-naphthoate (2.47 g) in 1,4-dioxane (40 mL) and water (20 mL) was added Example 1.20.2 (4.2 g), bis(triphenylphosphine)palladium(II)dichloride (556 mg), and cesium fluoride (3.61 g). The mixture was refluxed overnight, diluted with ethyl acetate (400 mL) and washed with water and brine. The organic layer was dried over sodium sulfate, filtered, and concentrated. The residue was purified by silica gel chromatography, eluting with 20% ethyl acetate in dichloromethane and then with 5% methanol in dichloromethane, to provide the title compound. MS (ESI) m/e 680.84 (M+H)$^+$.

1.57.2 tert-butyl 3-(1-((3,5-dimethyl-7-(2-((methylsulfonyl)oxy)ethoxy)adamantan-1-yl)methyl)-5-methyl-1H-pyrazol-4-yl)-6-(8-(methoxycarbonyl)naphthalen-2-yl)picolinate To a cooled (0° C.) solution of Example 1.57.1 (725 mg) in dichloromethane (10 mL) and triethylamine (0.5 mL) was added methanesulfonyl chloride (0.249 mL). The mixture was stirred at room temperature for 4 hours, diluted with ethyl acetate, and washed with water and brine. The organic layer was dried over sodium sulfate, filtered, and concentrated to provide the title compound. MS (ESI) m/e 758.93 (M+H)$^+$.

1.57.3 tert-butyl 3-(1-((3-(2-azidoethoxy)-5,7-dimethyladamantan-1-yl)methyl)-5-methyl-1H-pyrazol-4-yl)-6-(8-(methoxycarbonyl)naphthalen-2-yl)picolinate To a solution of Example 1.57.2 (4.2 g) in N,N-dimethylformamide (30 mL) was added sodium azide (1.22 g). The mixture was stirred at room temperature for 96 hours, diluted with ethyl acetate (600 mL) and washed with water and brine. The organic layer was dried over sodium sulfate, filtered, and concentrated to provide the title compound. MS (ESI) m/e 704.86 (M+H)$^+$.

1.57.4 7-(5-(1-((3-(2-azidoethoxy)-5,7-dimethyladamantan-1-yl)methyl)-5-methyl-1H-pyrazol-4-yl)-6-(tert-butoxycarbonyl)pyridin-2-yl)-1-naphthoic acid To a solution of Example 1.57.3 (3.5 g) in tetrahydrofuran/methanol/H$_2$O (2:1:1, 30 mL) was added lithium hydroxide monohydrate (1.2 g), and the mixture was stirred at room temperature overnight. The reaction mixture was acidified with 1N aqueous HCl solution, diluted with ethyl acetate (600 mL) and washed with water and brine. The organic layer was dried over sodium sulfate, filtered, and concentrated to provide the title compound. MS (ESI) m/e 691.82 (M+H)$^+$.

1.57.5 tert-butyl 3-(1-((3-(2-azidoethoxy)-5,7-dimethyladamantan-1-yl)methyl)-5-methyl-1H-pyrazol-4-yl)-6-(8-(benzo[d]thiazol-2-ylcarbamoyl)naphthalen-2-yl)picolinate To a solution of Example 1.57.4 (870 mg) in N,N-dimethylformamide (10 mL) was added benzo[d]thiazol-2-amine (284 mg), fluoro-N,N,N'N'-tetramethylformamidium hexafluorophosphate (499 mg) and N,N-diisopropylethylamine (488 mg). The mixture was stirred at 60° C. for 3 hours, diluted with ethyl acetate (200 mL), and washed with water and brine. The organic layer was dried over sodium sulfate, filtered, and concentrated to provide the title compound. MS (ESI) m/e 824.02 (M+H)$^+$.

1.57.6 tert-butyl 3-(1-((3-(2-aminoethoxy)-5,7-dimethyladamantan-1-yl)methyl)-5-methyl-1H-pyrazol-4-yl)-6-(8-(benzo[d]thiazol-2-ylcarbamoyl)naphthalen-2-yl)picolinate To a solution of Example 1.57.5 (890 mg) in tetrahydrofuran (30 mL) was added Pd/C (90 mg, 5%). The mixture was stirred under a hydrogen atmosphere at room temperature overnight, and filtered. The filtrate was concentrated to provide the title compound. MS (ESI) m/e 798.2 (M+H)$^+$.

1.57.7 6-[8-(1,3-benzothiazol-2-ylcarbamoyl)naphthalen-2-yl]-3-{1-[(3,5-dimethyl-7-{2-[(3-phosphonopropyl)amino]ethoxy}tricyclo[3.3.1.1$^{3,7}$]dec-1-yl)methyl]-5-methyl-1H-pyrazol-4-yl}pyridine-2-carboxylic acid To a solution of Example 1.57.6 (137 mg) in dichloromethane (6 mL) was added Example 1.14.2 (43 mg). The mixture was stirred at room temperature for 1.5 hours, and a solution of NaBH$_4$ (26 mg) in methanol (2 mL) was added. The mixture was stirred at room temperature for 2 hours, diluted with ethyl acetate (200 mL) and washed with 2N aqueous NaOH solution, water and brine. The organic layer was dried over sodium sulfate, filtered, and concentrated. The residue was dissolved in dichloromethane (5 mL) and treated with trifluoroacetic acid (5 mL) overnight. The reaction mixture was concentrated. The residue was purified by reverse phase HPLC (Gilson system), eluting with a gradient of 10-85% acetonitrile in water containing 0.1% v/v trifluoroacetic acid solution, to provide the title compound. $^1$H NMR (500 MHz, dimethyl sulfoxide-d$_6$) δ 9.03 (s, 1H), 8.48-8.35 (m, 3H), 8.29-8.16 (m, 3H), 8.08 (dd, 1H), 8.03 (dd, 1H), 7.94 (d, 1H), 7.82 (d, 1H), 7.71 (dd, 1H), 7.53-7.47 (m, 2H), 7.38 (td, 1H), 4.81-0.53 (m, 89H). MS (ESI) m/e 863.2 (M+H)$^+$.

1.58 Synthesis of 6-[8-(1,3-benzothiazol-2-ylcarbamoyl)-3,4-dihydroisoquinolin-2(1H)-yl]-3-(1-{[3-(2-{[4-(beta-D-glucopyranosyloxy)benzyl]amino}ethoxy)-5,7-dimethyltricyclo[3.3.1.1$^{3,7}$]dec-1-yl]methyl}-5-methyl-1H-pyrazol-4-yl)pyridine-2-carboxylic acid (Compound W2.58)

To a solution of Example 1.3.1 (44.5 mg) in tetrahydrofuran (2 mL) and acetic acid (0.2 mL) was added 4-(((2S,3R,4R,5S,6R)-3,4,5-trihydroxy-6-(hydroxymethyl)tetrahydro-2H-pyran-2-yl)oxy)benzaldehyde (17 mg) and MgSO$_4$ (300 mg). The mixture was stirred at room temperature for 1 hour before the addition of sodium cyanoborohydride on resin (300 mg). The mixture was stirred at room temperature overnight and filtered. The filtrate was concentrated, and the residue was purified by reverse phase HPLC (Gilson system), eluting with a gradient of 10-85% acetonitrile in water containing 0.1% v/v trifluoroacetic acid solution, to provide the title compound. MS (ESI) m/e 1015.20 (M+H)$^+$.

1.59 Synthesis of 3-(1-{[3-(2-{[4-(beta-D-allopyranosyloxy)benzyl]amino}ethoxy)-5,7-dimethyltricyclo[3.3.1.1$^{3,7}$]dec-1-yl]methyl}-5-methyl-1H-pyrazol-4-yl)-6-[8-(1,3-benzothiazol-2-ylcarbamoyl)-3,4-dihydroisoquinolin-2(1H)-yl]pyridine-2-carboxylic acid (Compound W2.59)

To a solution of Example 1.3.1 (44.5 mg) in tetrahydrofuran (2 mL) and acetic acid (0.2 mL) was added 4-(((2S,3R,4S,5S,6R)-3,4,5-trihydroxy-6-(hydroxymethyl)tetrahydro-2H-pyran-2-yl)oxy)benzaldehyde (17 mg) and MgSO$_4$ (300 mg), and the mixture was stirred at room temperature for 1 hour before the addition of sodium cyanoborohydride on resin (300 mg). The mixture was stirred at room temperature overnight and filtered. The filtrate was concentrated, and the residue was purified by reverse phase HPLC (Gilson system), eluting with a gradient of 10-85% acetonitrile in water containing 0.1% v/v trifluoroacetic acid, to provide the title compound. MS (ESI) m/e 1015.20 (M+H)$^+$.

1.60 Synthesis of 3-{1-[(3-{2-[azetidin-3-yl(2-sulfoethyl)amino]ethoxy}-5,7-dimethyltricyclo[3.3.1.1$^{3,7}$]dec-1-yl)methyl]-5-methyl-1H-pyrazol-4-yl}-6-[8-(1,3-benzothiazol-2-ylcarbamoyl)-3,4-dihydroisoquinolin-2(1H)-yl]pyridine-2-carboxylic acid (Compound W2.60)

1.60.1 tert-butyl 6-(8-(benzo[d]thiazol-2-ylcarbamoyl)-3,4-dihydroisoquinolin-2(1H)-yl)-3-(1-((3-(2-((1-(tert-butoxycarbonyl)azetidin-3-yl)(2-((4-(tert-butyldiphenylsilyl)hydroxy-2,2-dimethylbutoxy)sulfonyl)ethyl)amino)ethoxy)-5,7-dimethyladamantan-1-yl)methyl)-5-methyl-1H-pyrazol-4-yl)picolinate A solution of Example 1.2.8 (0.075 g), tert-butyl 3-oxoazetidine-1-carboxylate (0.021 g) and sodium triacetoxyborohydride (0.025 g) in dichloromethane (0.5 mL) was stirred at room temperature overnight. The reaction was loaded onto silica gel and eluted with 0-10% methanol in dichloromethane to give the title compound. MS (ESI) m/e 1403.9 (M+1).

1.60.2 3-{1-[(3-{2-[azetidin-3-yl(2-sulfoethyl)amino]ethoxy}-5,7-dimethyltricyclo[3.3.1.1$^{3,7}$]dec-1-yl)methyl]-5-methyl-1H-pyrazol-4-yl}-6-[8-(1,3-benzothiazol-2-ylcarbamoyl)-3,4-dihydroisoquinolin-2(1H)-yl]pyridine-2-carboxylic acid A solution of Example 1.60.1 (0.029 g) in dichloromethane (1 mL) was treated with trifluoroacetic acid (1 mL) and stirred overnight. The reaction was concentrated, dissolved in 1:1 dimethyl sulfoxide/methanol (2 mL), and the mixture was purified by reverse phase HPLC using a Gilson system, eluting with 10-80% acetonitrile in water containing 0.1% v/v trifluoroacetic acid. The desired fractions were combined and freeze-dried to provide the title compound. $^1$H NMR (400 MHz, dimethyl sulfoxide-d$_6$) δ ppm 12.86 (s, 1H), 8.81 (s, 2H), 8.04 (d, 1H), 7.79 (d, 1H), 7.62 (d, 1H), 7.52 (d, 1H), 7.50-7.46 (m, 1H), 7.44 (d, 1H), 7.40-7.33 (m, 2H), 7.30 (s, 1H), 6.96 (d, 1H), 4.96 (s, 2H), 4.37 (q, 1H), 4.27 (s, 2H), 4.11 (s, 2H), 3.89 (t, 2H), 3.83 (s, 2H), 3.58-3.54 (m, 2H), 3.32 (t, 2H), 3.24 (s, 2H), 3.01 (t, 2H), 2.85 (t, 2H), 2.10 (s, 3H), 1.48-0.97 (m, 12H), 0.87 (s, 6H). MS (ESI) m/e 909.2 (M+H)$^+$.

1.61 Synthesis of 3-{1-[(3-{2-[(3-aminopropyl)(2-sulfoethyl)amino]ethoxy}-5,7-dimethyltricyclo[3.3.1.1³,⁷]dec-1-yl)methyl]-5-methyl-1H-pyrazol-4-yl}-6-[8-(1,3-benzothiazol-2-ylcarbamoyl)-3,4-dihydroisoquinolin-2(1H)-yl]pyridine-2-carboxylic acid (Compound W2.61)

1.61.1 6-(8-(benzo[d]thiazol-2-ylcarbamoyl)-3,4-dihydroisoquinolin-2(1H)-yl)-3-(1-((3-(2-((3-(((tert-butoxycarbonyl)amino)propyl)(2-sulfoethyl)amino)ethoxy)-5,7-dimethyladamantan-1-yl)methyl)-5-methyl-1H-pyrazol-4-yl)picolinic acid The title compound was prepared using the procedure for Example 1.33.1, replacing tert-butyl (2-oxoethyl)carbamate with tert-butyl (3-oxopropyl)carbamate. MS (ESI) m/e 1011.5 (M+H).

1.61.2 3-{1-[(3-{2-[(3-aminopropyl)(2-sulfoethyl)amino]ethoxy}-5,7-dimethyltricyclo[3.3.1.1³,⁷]dec-1-yl)methyl]-5-methyl-1H-pyrazol-4-yl}-6-[8-(1,3-benzothiazol-2-ylcarbamoyl)-3,4-dihydroisoquinolin-2(1H)-yl]pyridine-2-carboxylic acid The title compound was prepared as described in Example 1.6.2, replacing Example 1.6.1 with Example 1.61.1. $^1$H NMR (400 MHz, dimethyl sulfoxide-$d_6$) δ ppm 12.87 (s, 1H), 9.10 (s, 1H), 8.04 (d, 1H), 7.88-7.67 (m, 4H), 7.62 (d, 1H), 7.57-7.40 (m, 3H), 7.36 (td, 2H), 6.96 (d, 1H), 4.96 (s, 2H), 4.05-3.78 (m, 4H), 3.41-3.08 (m, 3H), 2.94 (tt, 6H), 2.11 (s, 3H), 1.92 (t, 2H), 1.53-0.95 (m, 11H), 0.87 (s, 6H). MS (ESI) m/e 911.3 (M+H).

1.62 Synthesis of 6-[1-(1,3-benzothiazol-2-ylcarbamoyl)-1,2,3,4-tetrahydroquinolin-7-yl]-3-{1-[(3-{2-[(2-carboxyethyl)amino]ethoxy}-5,7-dimethyltricyclo[3.3.1.1³,⁷]dec-1-yl)methyl]-5-methyl-1H-pyrazol-4-yl}pyridine-2-carboxylic acid (Compound W2.62)

1.62.1 tert-butyl 3-(1-((3-(2-((3-(tert-butoxy)-3-oxopropyl)amino)ethoxy)-5,7-dimethyladamantan-1-yl)methyl)-5-methyl-1H-pyrazol-4-yl)-6-chloropicolinate To an ambient solution of Example 1.53.3 (521 mg) in ethanol (10 mL) was added triethylamine (3 mL) followed by tert-butyl acrylate (2 mL). The mixture was stirred at room temperature for 3 hours and then concentrated to dryness. The residue was dissolved in ethyl acetate (200 mL), and the solution was washed with water and brine. The organic layer was dried over sodium sulfate, filtered and concentrated under reduced pressure to give the title compound, which was used in the next reaction without further purification. MS (ESI) m/e 657.21 (M+H)$^+$.

1.62.2 tert-butyl 3-(1-((3-(2-((3-(tert-butoxy)-3-oxopropyl)(tert-butoxycarbonyl)amino)ethoxy)-5,7-dimethyladamantan-1-yl)methyl)-5-methyl-1H-pyrazol-4-yl)-6-chloropicolinate To a solution of Example 1.62.1 (780 mg) in tetrahydrofuran (10 mL) was added di-tert-butyl dicarbonate (259 mg) followed by a catalytic amount of 4-dimethylaminopyridine. The reaction was stirred at room temperature for 3 hours and then concentrated to dryness. The residue was dissolved in ethyl acetate (200 mL), and the solution was washed with saturated aqueous NaHCO$_3$ solution, water and brine. The organic layer was dried over sodium sulfate, filtered and concentrated under reduced pressure. The residue was purified by chromatography on silica gel, eluting with 20% ethyl acetate in heptane, to give the title compound. MS (ESI) m/e 757.13 (M+H)$^+$.

1.62.3 tert-butyl 3-(1-((3-(2-((3-(tert-butoxy)-3-oxopropyl)(tert-butoxycarbonyl)amino)ethoxy)-5,7-dimethyladamantan-1-yl)methyl)-5-methyl-1H-pyrazol-4-yl)-6-(1,2,3,4-tetrahydroquinolin-7-yl)picolinate To a solution of 7-(4,4,5,5-tetramethyl-1,3,2-dioxaborolan-2-yl)-1,2,3,4-tetrahydroquinoline (234 mg) in 1,4-dioxane (10 mL) and water (5 mL) was added Example 1.62.2 (685 mg), bis(triphenylphosphine)palladium(II)dichloride (63.2 mg), and cesium fluoride (410 mg). The mixture was heated to 120° C. for 30 minutes by microwave irradiation (Biotage Initiator). The reaction was quenched by the addition of ethyl acetate and water. The layers were separated, and the organic layer was washed with brine, dried over sodium sulfate, filtered and concentrated under reduced pressure. The residue was purified by chromatography on silica gel, eluting with 20% ethyl acetate in heptane, to give the title compound. MS (ESI) m/e 854.82 (M+H)$^+$.

1.62.4 tert-butyl 6-(1-(benzo[d]thiazol-2-ylcarbamoyl)-1,2,3,4-tetrahydroquinolin-7-yl)-3-(1-((3-(2-((3-(tert-butoxy)-3-oxopropyl)(tert-butoxycarbonyl)amino)ethoxy)-5,7-dimethyladamantan-1-yl)methyl)-5-methyl-1H-pyrazol-4-yl)picolinate To an ambient suspension of bis(2,5-dioxopyrrolidin-1-yl) carbonate (150 mg) in acetonitrile (10 mL) was added benzo[d]thiazol-2-amine (88 mg), and the mixture was stirred for 1 hour. A solution of Example 1.62.3 (500 mg) in acetonitrile (2 mL) was added, and the suspension was vigorously stirred overnight. The reaction was quenched by the addition of ethyl acetate and water. The layers were separated, and the organic layer was washed with brine, dried over sodium sulfate, filtered and concentrated under reduced pressure. The residue was purified by chromatography on silica gel, eluting with 20% ethyl acetate in dichloromethane, to give the title compound. MS (ESI) m/e 1030.5 (M+H)$^+$.

1.62.5 6-[1-(1,3-benzothiazol-2-ylcarbamoyl)-1,2,3,4-tetrahydroquinolin-7-yl]-3-{1-[(3-{2-[(2-carboxyethyl)amino]ethoxy}-5,7-dimethyltricyclo[3.3.1.1³,⁷]dec-1-yl)methyl]-5-methyl-1H-pyrazol-4-yl}pyridine-2-carboxylic acid To an ambient solution of Example 1.62.4 (110 mg) in dichloromethane (0.53 mL) was added trifluoroacetic acid (0.53 mL). The reaction was stirred overnight and was concentrated to a viscous oil. The residue was dissolved in dimethyl sulfoxide/methanol (1:1, 2 mL) and purified by reverse phase HPLC (Gilson system), eluting with 10-55% acetonitrile in 0.1% trifluoroacetic acid in water, to give the title compound. $^1$H NMR (400 MHz, dimethyl sulfoxide-$d_6$) δ ppm 13.10 (s, 3H), 8.37 (s, 1H), 8.26 (s, 2H), 7.98 (d, 1H), 7.86-7.71 (m, 3H), 7.44 (s, 1H), 7.39-7.31 (m, 1H), 7.26 (d, 1H), 7.19 (t, 1H), 3.92 (d, 2H), 3.87 (s, 2H), 3.55 (t, 2H), 3.17-3.00 (m, 4H), 2.80 (t, 2H), 2.62 (t, 2H), 2.19 (s, 3H), 1.95-1.88 (m, 2H), 1.43 (s, 2H), 1.33-1.25 (m, 4H), 1.18-1.11 (m, 4H), 1.09-0.97 (m, 2H), 0.85 (s, 6H). MS (ESI) m/e 818.0 (M+H)$^+$.

1.63 Synthesis of 6-[8-(1,3-benzothiazol-2-ylcarbamoyl)-3,4-dihydroisoquinolin-2(1H)-yl]-3-{1-[(3-{2-[(N6,N6-dimethyl-L-lysyl)(methyl)amino]ethoxy}-5,7-dimethyltricyclo[3.3.1.1$^{3,7}$]dec-1-yl)methyl]-5-methyl-1H-pyrazol-4-yl}pyridine-2-carboxylic acid (W2.63)

A solution of (S)-2-((((9H-fluoren-9-yl)methoxy)carbonyl)amino)-6-(dimethylamino)hexanoic acid (0.029 g) and 1-[bis(dimethylamino)methylene]-1H-1,2,3-triazolo[4,5-b]pyridinium 3-oxid hexafluorophosphate (0.028 g) was stirred together in N,N-dimethylformamide (0.5 mL) with N,N-diisopropylamine (0.035 mL). After stirring for 5 minutes, the solution was added to Example 1.13.7 (0.051 g) and stirring was continued at room temperature overnight. To the reaction was added diethylamine (0.070 mL), and the reaction was stirred for 2 hours. The reaction was diluted with N,N-dimethylformamide (1 mL), water (0.5 ml), and 2,2,2-trifluoroacetic acid (0.103 ml) then purified via reverse-phase HPLC using a gradient of 10% to 90% acetonitrile/water. The product containing fractions were collected and lyophilized to give the title compound. $^1$H NMR (500 MHz, dimethyl sulfoxide-d$_6$) δ 9.59 (s, 1H), 8.41 (s, 1H), 8.12 (t, 3H), 8.01 (d, 1H), 7.85 (dd, 1H), 7.81 (d, 1H), 7.77 (dd, 1H), 7.47 (s, 1H), 7.38 (t, 1H), 7.30 (d, 1H), 7.22 (t, 1H), 3.97 (t, 2H), 3.89 (s, 2H), 3.49 (dt, 4H), 3.06 (s, 2H), 2.99 (q, 2H), 2.88 (s, 2H), 2.84 (t, 2H), 2.75 (d, 6H), 2.22 (s, 3H), 2.00-1.90 (m, 2H), 1.84-1.52 (m, 4H), 1.48-0.95 (m, 14H), 0.87 (d, 6H). MS (ESI) m/e 916.2 (M+H)$^+$.

1.64 Synthesis of 3-{1-[(3-{2-[(3-aminopropyl)(methyl)amino]ethoxy}-5,7-dimethyltricyclo[3.3.1.1$^{3,7}$]dec-1-yl)methyl]-5-methyl-1H-pyrazol-4-yl}-6-[1-(1,3-benzothiazol-2-ylcarbamoyl)-1,2,3,4-tetrahydroquinolin-7-yl]pyridine-2-carboxylic acid (W2.64)

1.64.1 6-(1-(benzo[d]thiazol-2-ylcarbamoyl)-1,2,3,4-tetrahydroquinolin-7-yl)-3-(1-((3-(2-((3-((tert-butoxycarbonyl)amino)propyl)(methyl)amino)ethoxy)-5,7-dimethyladamantan-1-yl)methyl)-5-methyl-1H-pyrazol-4-yl)picolinic acid A solution of Example 1.21.5 (100 mg), N,N-diisopropylethylamine (68.9 µL) and tert-butyl (3-oxopropyl)carbamate (68.4 mg) in dichloromethane (3 mL) was stirred at ambient temperature for 2 hours, and NaCNBH$_4$ (8.27 mg) was added. The reaction was stirred at ambient temperature overnight. Methanol (1 mL) and water (0.2 mL) were added. The resulting mixture was stirred for 10 minutes and concentrated. The residue was dissolved in dimethyl sulfoxide and purified by reverse-phase HPLC on a Gilson system (C18 column), eluting with 30-80% acetonitrile in 0.1% trifluoroacetic acid water solution, to provide the title compound as a trifluoroacetic acid salt. MS (ESI) m/e 459.4 (M+2H)$^{2+}$.

1.64.2 3-{1-[(3-{2-[(3-aminopropyl)(methyl)amino]ethoxy}-5,7-dimethyltricyclo[3.3.1.1$^{3,7}$]dec-1-yl)methyl]-5-methyl-1H-pyrazol-4-yl}-6-[1-(1,3-benzothiazol-2-ylcarbamoyl)-1,2,3,4-tetrahydroquinolin-7-yl]pyridine-2-carboxylic acid Example 1.64.1 (100 mg) in dichloromethane (4 mL) at 0° C. was treated with trifluoroacetic acid (1 mL) for 1 hour, and the mixture was concentrated. The residue was purified by reverse phase HPLC (C18 column), eluting with a gradient of 10-60% acetonitrile in 0.1% trifluoroacetic acid water solution, to provide the title compound as a trifluoroacetic acid salt. $^1$H NMR (400 MHz, dimethyl sulfoxide-d$_6$) δ 9.38 (s, 1H), 8.37 (s, 1H), 7.98 (d, 1H), 7.90-7.69 (m, 6H), 7.44 (s, 2H), 7.35 (td, 1H), 7.27 (d, 1H), 7.22-7.16 (m, 1H), 3.94 (d, 2H), 3.87 (s, 2H), 3.64 (t, 2H), 3.28-2.98 (m, 4H), 2.87-2.70 (m, 8H), 2.19 (s, 3H), 1.90 (dp, 4H), 1.43 (s, 2H), 1.36-1.22 (m, 4H), 1.15 (s, 4H), 1.08-0.95 (m, 2H), 0.86 (s, 6H). MS (ESI) m/e 817.6 (M+H)$^+$.

1.65 Synthesis of 3-{1-[(3-{2-[azetidin-3-yl(methyl)amino]ethoxy}-5,7-dimethyltricyclo[3.3.1.1$^{3,7}$]dec-1-yl)methyl]-5-methyl-1H-pyrazol-4-yl}-6-[1-(1,3-benzothiazol-2-ylcarbamoyl)-1,2,3,4-tetrahydroquinolin-7-yl]pyridine-2-carboxylic acid (W2.65)

1.65.1 6-(1-(benzo[d]thiazol-2-ylcarbamoyl)-1,2,3,4-tetrahydroquinolin-7-yl)-3-(1-((3-(2-((1-(tert-butoxycarbonyl)azetidin-3-yl)(methyl)amino)ethoxy)-5,7-dimethyladamantan-1-yl)methyl)-5-methyl-1H-pyrazol-4-yl)picolinic acid The title compound was prepared using the procedure described in Example 1.64.1, substituting tert-butyl (3-oxopropyl)carbamate with tert-butyl 3-oxoazetidine-1-carboxylate. MS (ESI) m/e 915.3 (M+H)$^+$.

1.65.2 3-{1-[(3-{2-[azetidin-3-yl(methyl)amino]ethoxy}-5,7-dimethyltricyclo[3.3.1.1$^{3,7}$]dec-1-yl)methyl]-5-methyl-1H-pyrazol-4-yl}-6-[1-(1,3-benzothiazol-2-ylcarbamoyl)-1,2,3,4-tetrahydroquinolin-7-yl]pyridine-2-carboxylic acid The title compound was prepared using the procedure in Example 1.64.2, substituting Example 1.64.1 with Example 1.65.1. $^1$H NMR (400 MHz, dimethyl sulfoxide-d$_6$) δ 9.01 (s, 2H), 8.37 (s, 1H), 7.98 (d, 1H), 7.86-7.70 (m, 3H), 7.44 (s, 2H), 7.34 (td, 1H), 7.27 (d, 1H), 7.23-7.15 (m, 1H), 4.22 (s, 4H), 4.07 (s, 2H), 3.93 (t, 2H), 3.58 (t, 2H), 3.11 (s, 2H), 2.80 (t, 2H), 2.68 (s, 3H), 2.19 (s, 3H), 1.92 (p, 2H), 1.42 (s, 2H), 1.30 (s, 4H), 1.15 (s, 4H), 1.09-0.96 (m, 2H), 0.85 (s, 6H). MS (ESI) m/e 815.5 (M+H)$^+$.

1.66 Synthesis of N6-(37-oxo-2,5,8,11,14,17,20,23,26,29,32,35-dodecaoxaheptatriacontan-37-yl)-L-lysyl-N-[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl]-L-alaninamide (W2.66)

1.66.1 (S)-6-((((9H-fluoren-9-yl)methoxy)carbonyl)amino)-2-((tert-butoxycarbonyl)amino)hexanoic acid To a solution of (S)-6-amino-2-((tert-butoxycarbonyl)amino)hexanoic acid (8.5 g) in a mixture of 5% aqueous NaHCO$_3$ solution (300 mL) and dioxane (40 mL), chilled in an ice bath, was added dropwise a solution of (9H-fluoren-9-yl)methyl pyrrolidin-1-yl carbonate (11.7 g) in dioxane (40 mL). The reaction mixture was allowed to warm to room temperature and was stirred for 24 hours. Three additional vials were set up as described above. After the reaction was completed, all four reaction mixtures were combined, and the organic solvent was removed under vacuum. The aqueous residue was acidified to pH 3 with aqueous hydrochloric acid solution (1N) and then extracted with ethyl acetate (3×500 mL). The combined organic layers were washed with brine, dried over magnesium sulfate, filtered, and concentrated under vacuum to give a crude compound which was recrystallized from methyl tert-butyl ether to afford the title compound. $^1$H NMR (400 MHz, chloroform-d) δ 11.05 (br. s., 1H), 7.76 (d, 2H), 7.59 (d, 2H), 7.45-7.27 (m, 4H), 6.52-6.17 (m, 1H), 5.16-4.87 (m, 1H), 4.54-4.17 (m, 4H), 3.26-2.98 (m, 2H), 1.76-1.64 (m, 1H), 1.62-1.31 (m, 14H).

1.66.2 tert-butyl 17-hydroxy-3,6,9,12,15-pentaoxaheptadecan-1-oate

To a solution of 3,6,9,12-tetraoxatetradecane-1,14-diol (40 g) in toluene (800 mL) was added portion-wise potassium tert-butoxide (20.7 g). The mixture was stirred at room temperature for 30 minutes. Tert-butyl 2-bromoacetate (36 g) was added dropwise to the mixture. The reaction was stirred at room temperature for 16 hours. Two additional vials were set up as described above. After the reactions were completed, all three reaction mixtures were combined. Water (500 mL) was added to the combined mixture, and the mixture was concentrated to 1 L. The mixture was extracted with dichloromethane and was washed with aqueous 1N potassium tert-butoxide solution (1 L). The organic layer was dried over $Na_2SO_4$, filtered and concentrated to obtain crude product, which was purified by silica gel column chromatography, eluting with dichloromethane:methanol 50:1, to obtain the title compound. $^1$H NMR (400 MHz, chloroform-d) δ 4.01 (s, 2H), 3.75-3.58 (m, 21H), 1.46 (s, 9H).

1.66.3 tert-butyl 17-(tosyloxy)-3,6,9,12,15-pentaoxaheptadecan-1-oate

To a solution of Example 1.66.2 (30 g) in dichloromethane (500 mL) was added dropwise a solution of 4-methylbenzene-1-sulfonyl chloride (19.5 g) and triethylamine (10.3 g) in dichloromethane (500 mL) at 0° C. under a nitrogen atmosphere. The mixture was stirred at room temperature for 18 hours and was poured into water (100 mL). The solution was extracted with dichloromethane (3×150 mL), and the organic layer was washed with hydrochloric acid (6N, 15 mL) then $NaHCO_3$ (5% aqueous solution, 15 mL) followed by water (20 mL). The organic layer was dried over $Na_2SO_4$, filtered and concentrated to obtain a residue, which was purified by silica gel column chromatography, eluting with petroleum ether: ethyl acetate 10:1 to dichloromethane: methanol 5:1, to obtain the title compound. $^1$H NMR (400 MHz, chloroform-d) δ 7.79 (d, 2H), 7.34 (d, 2H), 4.18-4.13 (m, 2H), 4.01 (s, 2H), 3.72-3.56 (m, 18H), 2.44 (s, 3H), 1.47 (s, 9H).

1.66.4 2,5,8,11,14,17,20,23,26,29,32,35-dodecaoxaheptatriacontan-37-oic acid To a solution of 2,5,8,11,14,17-hexaoxanonadecan-19-ol (32.8 g) in tetrahydrofuran (300 mL) was added sodium hydride (1.6 g) at 0° C. The mixture was stirred at room temperature for 4 hours. A solution of Example 1.66.3 (16 g) in tetrahydrofuran (300 mL) was added dropwise at room temperature to the reaction mixture. The resulting reaction mixture was stirred at room temperature for 16 hours and then water (20 mL) was added. The mixture was stirred at room temperature for another 3 hours to complete the tert-butyl ester hydrolysis. The final reaction mixture was concentrated under vacuum to remove the organic solvent. The aqueous residue was extracted with dichloromethane (2×150 mL). The aqueous layer was acidified to pH 3 and then extracted with ethyl acetate (2×150 mL). The aqueous layer was concentrated to obtain crude product, which was purified by silica gel column chromatography, eluting with a gradient of petroleum ether:ethyl acetate 1:1 to dichloromethane:methanol 5:1, to obtain the title compound. $^1$H NMR (400 MHz, chloroform-d) δ 4.19 (s, 2H), 3.80-3.75 (m, 2H), 3.73-3.62 (m, 40H), 3.57 (dd, 2H), 3.40 (s, 3H).

1.66.5 (43S,46S)-43-((tert-butoxycarbonyl)amino)-46-methyl-37,44-dioxo-2,5,8,11,14,17,20,23,26,29,32,35-dodecaoxa-38,45-diazaheptatetracontan-47-oic acid Example 1.66.5 was synthesized using standard Fmoc solid phase peptide synthesis procedures and a 2-chlorotrytil resin. 2-Chlorotrytil resin (12 g, 100 mmol), (S)-2-((((9H-fluoren-9-yl)methoxy)carbonyl)amino)propanoic acid (10 g, 32.1 mmol) and N,N-diisopropylethylamine (44.9 mL, 257 mmol) in anhydrous, sieve-dried dichloromethane (100 mL) was shaken at 14° C. for 24 hours. The mixture was filtered and the cake was washed with dichloromethane (3×500 mL), dimethylformamide (2×250 mL) and methanol (2×250 mL) (for 5 minutes for each step). To the above resin was added 20% piperidine/dimethylformamide (100 mL) to remove the Fmoc group. The mixture was bubbled with nitrogen for 15 minutes and then filtered. The resin was washed with 20% piperidine/dimethylformamide (100 mL) another five times (5 minutes each step), and washed with dimethylformamide (5×100 mL) to give the deprotected, L-Ala loaded resin.

To a solution of Example 1.66.1 (9.0 g) in N,N-dimethylformamide (50 mL) was added hydroxybenzotriazole (3.5 g), 2-(6-chloro-1H-benzotriazole-1-yl)-1,1,3,3-tetramethylaminium hexafluorophosphate (9.3 g) and N,N-diisopropylethylamine (8.4 mL). The mixture was stirred at 20° C. for 30 minutes. The above mixture was added to the D-Ala loaded resin and mixed by bubbling with nitrogen at room temperature for 90 minutes. The mixture was filtered and the resin was washed with dimethylformamide (5 minutes each step). To the above resin was added approximately 20% piperidine/N,N-dimethylformamide (100 mL) to remove the Fmoc group. The mixture was bubbled with nitrogen for 15 minutes and filtered. The resin was washed with 20% piperidine/dimethylformamide (100 mL) for another five times (5 minutes for each step), and finally washed with dimethylformamide (5×100 mL).

To a solution of Example 1.66.4 (11.0 g) in N,N-dimethylformamide (50 mL) was added hydroxybenzotriazole (3.5 g), 2-(6-chloro-1H-benzotriazole-1-yl)-1,1,3,3-tetramethylaminium hexafluorophosphate (9.3 g) and N,N-diisopropylethylamine (8.4 mL), and the mixture was added to the resin and mixed by bubbling with nitrogen at room temperature for 3 hours. The mixture was filtered and the residue was washed with dimethylformamide (5×100 mL), dichloromethane (8×100 mL) (5 minutes for each step).

To the final resin was added 1% trifluoroacetic acid/dichloromethane (100 mL) and nitrogen was bubbled through for 5 minutes. The mixture was filtrated and the filtrate was collected. The cleavage operation was repeated for four times. The combined filtrate was brought to pH 7 by $NaHCO_3$ and washed with water. The organic layer was dried over $Na_2SO_4$, filtered and concentrated to obtain the title compound. $^1$H NMR (400 MHz, methanol-$d_4$) δ 4.44-4.33 (m, 1H), 4.08-4.00 (m, 1H), 3.98 (s, 2H), 3.77-3.57 (m, 42H), 3.57-3.51 (m, 2H), 3.36 (s, 3H), 3.25 (t, 2H), 1.77 (br. s., 1H), 1.70-1.51 (m, 4H), 1.44 (s, 9H), 1.42-1.39 (m, 3H).

1.66.6 tert-butyl 6-(8-(benzo[d]thiazol-2-ylcarbamoyl)-3,4-dihydroisoquinolin-2(1H)-yl)-3-(1-((3-((((43S,46S)-43-((tert-butoxycarbonyl)amino)-46-methyl-37,44,47-trioxo-2,5,8,11,14,17,20,23,26,29,32,35-dodecaoxa-38,45,48-triazapentacontan-50-yl)oxy)-5,7-dimethyladamantan-1-yl)methyl)-5-methyl-1H-pyrazol-4-yl)picolinate Example 1.66.5 (123 mg, 0.141 mmol), was mixed with 1-[bis(dimethylamino)methylene]-1H-1,2,3-triazolo[4,5-b]pyridinium 3-oxid hexafluorophosphate (58.9 mg) and N,N-diisopropylethylamine (0.049 mL) in N-methyl-2-pyrrolidone (1 mL) for 10 minutes and then added to a solution of Example 1.2.7 (142 mg) and N,N-diisopropylethylamine (0.049 mL) in N-methyl-2-pyrrolidone (1.5 mL). The reaction mixture was stirred at room temperature for two hours. The crude reaction mixture was purified by reverse phase HPLC using a Gilson system and a C18 25×100 mm column, eluting with 5-85% acetonitrile in water containing 0.1% v/v trifluoroacetic acid. The product fractions were lyophilized to give the title compound. MS (LC/MS) m/e 1695.5 (M+H)$^+$.

1.66.7 3-(1-((3-(((43S,46S)-43-amino-46-methyl-37,44,47-trioxo-2,5,8,11,14,17,20,23,26,29,32,35-dodecaoxa-38,45,48-triazapentacontan-50-yl)oxy)-5,7-dimethyladamantan-1-yl)methyl)-5-methyl-1H-pyrazol-4-yl)-6-(8-(benzo[d]thiazol-2-ylcarbamoyl)-3,4-dihydroisoquinolin-2(1H)-yl)picolinic acid Example 1.66.6 (82 mg) was treated with 1 mL of trifluoroacetic acid at room temperature for 30 minutes. The solvent was evaporated under a gentle stream of nitrogen, and the residue was purified by reverse phase HPLC using a Gilson system and a C18 25×100 mm column, eluting with 5-85% acetonitrile in water containing 0.1% v/v trifluoroacetic acid. The product fractions were lyophilized to give the title compound as the trifluoroacetic acid salt. $^1$H NMR (400 MHz, dimethyl sulfoxide-d$_6$) δ ppm 12.86 (s, 1H), 8.04 (dd, 4H), 7.64 (dt, 2H), 7.55-7.41 (m, 3H), 7.36 (q, 2H), 6.95 (d, 1H), 4.96 (s, 2H), 4.40-4.27 (m, 1H), 3.93-3.72 (m, 7H), 3.59-3.47 (m, 42H), 3.33-3.27 (m, 3H), 3.23 (s, 5H), 3.05 (dt, 5H), 2.10 (s, 3H), 1.72-1.64 (m, 2H), 1.48-1.36 (m, 4H), 1.35-1.16 (m, 10H), 1.16-0.94 (m, 6H), 0.84 (d, 6H). MS (ESI) m/e 751.8 (2M+H)$^{2+}$.

1.67 Synthesis of methyl 6-[4-(3-{[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl]amino}propyl)-1H-1,2,3-triazol-1-yl]-6-deoxy-beta-L-glucopyranoside (W2.67)

1.67.1 6-(8-(benzo[d]thiazol-2-ylcarbamoyl)-3,4-dihydroisoquinolin-2(1H)-yl)-3-(1-((3,5-dimethyl-7-(2-(pent-4-yn-1-ylamino)ethoxy)adamantan-1-yl)methyl)-5-methyl-1H-pyrazol-4-yl)picolinic acid To a solution of tert-butyl 3-(1-((3-(2-aminoethoxy)-5,7-dimethyladamantan-1-yl)methyl)-5-methyl-1H-pyrazol-4-yl)-6-(8-(benzo[d]thiazol-2-ylcarbamoyl)-3,4-dihydroisoquinolin-2(1H)-yl)picolinate (85 mg) in tetrahydrofuran (2 mL) was added pent-4-ynal (8.7 mg), acetic acid (20 mg, 0.318) and anhydrous sodium sulfate (300 mg). The mixture was stirred at room temperature for 1 hour. Sodium triacetoxyborohydride (45 mg) was added to the reaction mixture. The mixture was stirred at room temperature overnight. The reaction mixture was diluted with ethyl acetate (200 mL), washed with water and brine, and dried over anhydrous sodium sulfate. Filtration and evaporation of the solvent gave crude product, which was dissolved in dichloromethane (5 mL) and trifluoroacetic acid (3 mL). The mixture was stirred at room temperature overnight. After evaporation of the solvent, the residue was dissolved in dimethyl sulfoxide/methanol (1:1, 3 mL) and purified by reverse-phase HPLC on a Gilson system (C18 column), eluting with 20-80% acetonitrile in water containing 0.1% trifluoroacetic acid, to give the title compound. MS (APCI) m/e 812.2 (M+H)$^+$.

1.67.2 methyl 6-[4-(3-{[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl]amino}propyl)-1H-1,2,3-triazol-1-yl]-6-deoxy-beta-L-glucopyranoside To a solution of (2R,3R,4S,5S,6S)-2-azido-6-(methoxycarbonyl)tetrahydro-2H-pyran-3,4,5-triyl triacetate (8.63 mg) in t-BuOH (2 mL) and water (1 mL) was added Example 1.67.1 (20 mg), copper (II) sulfate pentahydrate (2.0 mg) and sodium ascorbate (5 mg). The mixture was heated for 20 minutes at 100° C. under microwave conditions (Biotage Initiator). LiOH H$_2$O (50 mg) was added to the mixture, which was stirred at room temperature overnight. The mixture was neutralized with trifluoroacetic acid and purified by reverse-phase HPLC on a Gilson system (C18 column), eluting with 20-80% acetonitrile in water containing 0.1% trifluoroacetic acid, to give the title compound. MS (APCI) m/e 1032.2 (M+H)$^+$.

1.68 Synthesis of 6-[8-(1,3-benzothiazol-2-ylcarbamoyl)naphthalen-2-yl]-3-{1-[(3-{2-[(2-carboxyethyl)amino]ethoxy}-5,7-dimethyltricyclo[3.3.1.1$^{3,7}$]dec-1-yl)methyl]-5-methyl-1H-pyrazol-4-yl}pyridine-2-carboxylic acid 1.68.1 2-((3,5-dimethyl-7-((5-methyl-4-(4,4,5,5-tetramethyl-1,3,2-dioxaborolan-2-yl)-1H-pyrazol-1-yl)methyl)adamantan-1-yl)oxy)ethanol (W2.68)

To a solution of 2-((3-((4-iodo-5-methyl-1H-pyrazol-1-yl)methyl)-5,7-dimethyladamantan-1-yl)oxy)ethanol (8.9 g) and PdCl$_2$(dppf)-CH$_2$Cl$_2$ adduct (([1,1'-bis(diphenylphosphino)ferrocene]dichloropalladium(II) (1:1), 818 mg) in acetonitrile (120 mL) was added trimethylamine (10 mL) and 4,4,5,5-tetramethyl-1,3,2-dioxaborolane (12.8 mL). The mixture was stirred at reflux overnight. The mixture was cooled to room temperature and used in the next reaction without further work up. MS (ESI) m/e 467.3 (M+Na)$^+$.

1.68.2 tert-butyl 6-chloro-3-(1-((3-(2-hydroxyethoxy)-5,7-dimethyladamantan-1-yl)methyl)-5-methyl-1H-pyrazol-4-yl)picolinate To a solution of tert-butyl 3-bromo-6-chloropicolinate (6.52 g) in tetrahydrofuran (100 mL) and water (20 mL) was added Example 1.68.1 (9.90 g), (1S,3R,5R,7S)-1,3,5,7-tetramethyl-8-tetradecyl-2,4,6-trioxa-8-phosphaadamantane (0.732 g), tris(dibenzylideneacetone)dipalladium(0) (Pd$_2$(dba)$_3$, 1.02 g), and K$_3$PO$_4$ (23.64 g). The mixture was stirred at reflux overnight. The mixture was concentrated under reduced pressure, the residue was dissolved in ethyl acetate (500 mL), washed with water and brine, and dried over anhydrous sodium sulfate. Filtration and evaporation of the solvent gave crude product, which was purified by silica gel chromatography eluting with 20 to 40% ethyl acetate in dichloromethane to give the title compound. MS (ESI) m/e 530.3 (M+H)$^+$.

1.68.3 tert-butyl 6-chloro-3-(1-((3,5-dimethyl-7-(2-((methylsulfonyl)oxy)ethoxy)adamantan-1-yl) methyl)-5-methyl-1H-pyrazol-4-yl)picolinate To a cooled (0° C.) solution of Example 1.68.2 (3.88 g) in dichloromethane (30 mL) and triethylamine (6 mL) was added methanesulfonyl chloride (2.52 g). The mixture was stirred at room temperature for 4 hours. The reaction mixture was diluted with ethyl acetate (400 mL), washed with water and brine, and dried over anhydrous sodium sulfate. Filtration and evaporation of the solvent gave the crude product (4.6 g), which was used in the next reaction without further purification. MS (ESI) m/e 608.1 (M+H)$^+$.

1.68.4 tert-butyl 3-{1-[(3-{2-[bis(tert-butoxycarbonyl)amino]ethoxy}-5,7-dimethyltricyclo[3.3.1.1$^{3,7}$]dec-1-yl)methyl]-5-methyl-1H-pyrazol-4-yl}-6-chloropyridine-2-carboxylate To a solution of Example 1.68.3 (151 mg) in N,N-dimethylformamide (3 mL) was added di-tert-butyl iminodicarboxylate (54 mg). The mixture was stirred at room temperature overnight. The reaction mixture was diluted with ethyl acetate (200 mL), washed with water and brine, and dried over anhydrous sodium sulfate. Filtration and evaporation of the solvent gave the title compound, which was used in the next step without further purification. MS (ESI) m/e 729.4 (M+H)$^+$.

1.68.5 7-(6-(tert-butoxycarbonyl)-5-(1-((3-(2-((tert-butoxycarbonyl)amino)ethoxy)-5,7-dimethyladamantan-1-yl)methyl)-5-methyl-1H-pyrazol-4-yl) pyridin-2-yl)-1-naphthoic acid To a solution of methyl 7-(4,4,5,5-tetramethyl-1,3,2-dioxaborolan-2-yl)-1-naphthoate (257 mg) in 1,4-dioxane (10 mL) and water (5 mL) was added Example 1.68.4 (600 mg), bis(triphenylphosphine)palladium(II) dichloride (57.8 mg), and CsF (375 mg). The mixture was stirred at 120° C. for 30 minutes under microwave conditions (Biotage Initiator). The mixture was diluted with ethyl acetate (200 mL), washed with water and brine, and dried over anhydrous sodium sulfate. Filtration and evaporation of the solvent gave crude product, which was purified by silica gel chromatography, eluting with 20% ethyl acetate in heptane to give a di-ester intermediate. The residue was dissolved in tetrahydrofuran (10 mL), methanol (5 mL) and water (5 mL) and LiOH H$_2$O (500 mg) was added, and the mixture was stirred at room temperature overnight. The mixture was acidified with 2N aqueous HCl, dissolved in 400 mL of ethyl acetate, washed with water and brine, and dried over anhydrous sodium sulfate. Filtration and evaporation of the solvent gave the title compound. MS (APCI) m/e 765.3 (M+H)$^+$.

1.68.6 3-(1-((3-(2-aminoethoxy)-5,7-dimethyladamantan-1-yl)methyl)-5-methyl-1H-pyrazol-4-yl)-6-(8-(benzo[d]thiazol-2-ylcarbamoyl)naphthalen-2-yl) picolinic acid To a solution of Example 1.68.5 (500 mg) in dichloromethane (10 mL) was added benzo[d]thiazol-2-amine (98 mg), 1-ethyl-3-(3-dimethylaminopropyl)carbodiimide (251 mg) and 4-dimethylaminopyridine (160 mg). The mixture was stirred at room temperature overnight. The reaction mixture was diluted with ethyl acetate (400 mL), washed with water and brine, and dried over anhydrous sodium sulfate. Filtration and evaporation of the solvent gave a residue that was dissolved in dichloromethane and trifluoroacetic acid (10 mL, 1:1). After stirring overnight, the solution was concentrated under reduced pressure. The residue was dissolved in N,N-dimethylformamide (12 mL) and purified by reverse-phase HPLC (using a Gilson system and a C18 column, eluting with 20-80% acetonitrile in water containing 0.1% trifluoroacetic acid) to give the title compound. MS (ESI) m/e 741.2 (M+H)$^+$.

1.68.7 6-[8-(1,3-benzothiazol-2-ylcarbamoyl)naphthalen-2-yl]-3-{1-[(3-{2-[(2-carboxyethyl)amino] ethoxy}-5,7-dimethyltricyclo[3.3.1.1$^{3,7}$]dec-1-yl) methyl]-5-methyl-1H-pyrazol-4-yl}pyridine-2-carboxylic acid To a solution of Example 1.68.6 (35 mg) in N,N-dimethylformamide (4 mL) was added tert-butyl acrylate (120 mg) and H$_2$O (138 mg). The mixture was stirred at room temperature overnight. The reaction mixture was diluted with ethyl acetate (400 mL), washed with water and brine, and dried over anhydrous sodium sulfate. Filtration and evaporation of the solvent gave a residue that was dissolved in dichloromethane and trifluoroacetic acid (10 mL, 1:1). After 16 hours, the mixture was concentrated under reduced pressure. The residue was dissolved in N,N-dimethylformamide (2 mL) and purified by reverse-phase HPLC on a Gilson system (C18 column), eluting with 20-80% acetonitrile in water containing 0.1% trifluoroacetic acid, to give the title compound. $^1$H NMR (400 MHz, dimethyl sulfoxide-d$_6$) δ ppm 13.08 (s, 1H), 8.99 (d, 1H), 8.43-8.24 (m, 4H), 8.24-8.11 (m, 3H), 8.04 (d, 1H), 7.99 (d, 1H), 7.90 (d, 1H), 7.78 (d, 1H), 7.74-7.62 (m, 1H), 7.53-7.43 (m, 2H), 7.35 (q, 1H), 3.87 (s, 2H), 3.08 (dp, 4H), 2.62 (t, 2H), 2.20 (s, 3H), 1.43 (s, 2H), 1.29 (q, 4H), 1.14 (s, 4H), 1.03 (q, 2H), 0.85 (s, 6H).

1.69 Synthesis of 6-[5-(1,3-benzothiazol-2-ylcarbamoyl)quinolin-3-yl]-3-{1-[(3,5-dimethyl-7-{2-[(2-sulfoethyl)amino]ethoxy}tricyclo[3.3.1.1$^{3,7}$]dec-1-yl)methyl]-5-methyl-1H-pyrazol-4-yl}pyridine-2-carboxylic acid 1.69.1 methyl 3-bromoquinoline-5-carboxylate (W2.69)

To a solution of 3-bromoquinoline-5-carboxylic acid (2 g) in methanol (30 mL) was added concentrated H$_2$SO$_4$ (5 mL). The solution was stirred at reflux overnight. The mixture was concentrated under reduced pressure. The residue was dissolved in ethyl acetate (300 mL) and washed with aqueous Na$_2$CO$_3$ solution, water and brine. After drying over anhydrous sodium sulfate, filtration and evaporation of the solvent gave the title compound. MS (ESI) m/e 266 (M+H)$^+$.

1.69.2 methyl 3-(4,4,5,5-tetramethyl-1,3,2-dioxaborolan-2-yl)quinoline-5-carboxylate To a solution of Example 1.69.1 (356 mg) in N,N-dimethylformamide (5 mL) was added PdCl$_2$(dppf)-CH$_2$Cl$_2$ adduct ([1,1'-bis(diphenylphosphino)ferrocene]dichloropalladium(II) (1:1), 55 mg) potassium acetate (197 mg) and bis(pinacolato)diboron (510 mg). The mixture was stirred at 60° C. overnight. The mixture was cooled to room temperature and used in the next reaction without further work up. MS (ESI) m/e 339.2 (M+Na)$^+$.

1.69.3 methyl 3-[5-{1-[(3-{2-[bis(tert-butoxycarbonyl)amino]ethoxy}-5,7-dimethyltricyclo[3.3.1.1$^{3,7}$]dec-1-yl)methyl]-5-methyl-1H-pyrazol-4-yl}-6-(tert-butoxycarbonyl)pyridin-2-yl]quinoline-5-carboxylate To a solution of Example 1.69.2 (626 mg) in 1,4-dioxane (10 mL) and water (5 mL) was added Example 1.68.4 (1.46 g), bis(triphenylphosphine)palladium(II) dichloride (140 mg), and CsF (911 mg). The mixture was stirred at 120° C. for 30 minutes under microwave conditions (Biotage Initiator). The mixture was diluted with ethyl acetate (200 mL), washed with water and brine, dried over anhydrous sodium sulfate, filtered and concentrated. The residue was purified by silica gel chromatography, eluting with 20% ethyl acetate in heptane (1 L) to give the title compound. MS (ESI) m/e 880.3 (M+H)$^+$.

1.69.4 3-(6-(tert-butoxycarbonyl)-5-(1-((3-(2-((tert-butoxycarbonyl)amino)ethoxy)-5,7-dimethyladamantan-1-yl)methyl)-5-methyl-1H-pyrazol-4-yl)pyridin-2-yl)quinoline-5-carboxylic acid To a solution of Example 1.69.3 (1.34 g) in tetrahydrofuran (10 mL), methanol (5 mL) and water (5 mL) was added LiOH H$_2$O (120 mg), and the mixture was stirred at room temperature overnight. The mixture was acidified with 2N aqueous HCl, diluted with ethyl acetate (400 mL), washed with water and brine, and dried over anhydrous sodium sulfate. Filtration and evaporation of the solvent gave the title compound. MS (APCI) m/e 766.3 (M+H)$^+$.

1.69.5 3-(1-((3-(2-aminoethoxy)-5,7-dimethyladamantan-1-yl)methyl)-5-methyl-1H-pyrazol-4-yl)-6-(5-(benzo[d]thiazol-2-ylcarbamoyl)quinolin-3-yl)picolinic acid To a solution of Example 1.69.4 (200 mg) in dichloromethane (10 mL) was added benzo[d]thiazol-2-amine (39.2 mg), 1-ethyl-3-(3-dimethylaminopropyl)carbodiimide (50 mg) and 4-dimethylaminopyridine (32 mg). The mixture was stirred at room temperature overnight. The reaction mixture was diluted with ethyl acetate (200 mL), washed with water and brine, dried over anhydrous sodium sulfate, filtered, and concentrated. The residue was dissolved in dichloromethane and trifluoroacetic acid (10 mL, 1:1), and the reaction was stirred overnight. The mixture was concentrated, and the residue was dissolved in N,N-dimethylformamide (12 mL) and purified by reverse-phase HPLC on a Gilson system (C18 column), eluting with 20-80% acetonitrile in water containing 0.1% trifluoroacetic acid, to give the title compound. MS (ESI) m/e 742.1 (M+H)$^+$.

1.69.6 6-[5-(1,3-benzothiazol-2-ylcarbamoyl)quinolin-3-yl]-3-{1-[(3,5-dimethyl-7-{2-[(2-sulfoethyl)amino]ethoxy}tricyclo[3.3.1.1$^{3,7}$]dec-1-yl)methyl]-5-methyl-1H-pyrazol-4-yl}pyridine-2-carboxylic acid To a solution of Example 1.69.5 (36 mg) in N,N-dimethylformamide (2 mL) was added 4-((tert-butyldiphenylsilyl)oxy)-2,2-dimethylbutyl ethenesulfonate (22 mg) and H$_2$O (0.3 mL)). The mixture was stirred at room temperature for 3 hours. The reaction mixture was diluted with dichloromethane and trifluoroacetic acid (10 mL, 1:1) and stirred overnight. The mixture was concentrated, and the residue was dissolved in N,N-dimethylformamide (4 mL) and purified by reverse-phase HPLC on a Gilson system (C18 column), eluting with 20-80% acetonitrile in water containing 0.1% trifluoroacetic acid, to give the title compound. $^1$H NMR (400 MHz, dimethyl sulfoxide-d$_6$) δ ppm 13.19 (s, 2H), 9.70 (d, 1H), 9.40 (s, 1H), 8.31 (d, 2H), 8.16 (d, 1H), 8.06 (d, 1H), 8.01 (d, 1H), 7.98-7.88 (m, 1H), 7.80 (d, 1H), 7.52-7.43 (m, 2H), 7.37 (q, 1H), 3.89 (s, 2H), 3.22 (p, 2H), 3.10 (q, 2H), 2.80 (t, 2H), 2.23 (s, 3H), 1.43 (s, 2H), 1.30 (q, 4H), 1.23-1.10 (m, 4H), 1.04 (q, 2H), 0.87 (s, 6H). MS (ESI) m/e 850.2 (M+H)$^+$.

1.70 Synthesis of 6-[4-(1,3-benzothiazol-2-ylcarbamoyl)quinolin-6-yl]-3-{1-[(3,5-dimethyl-7-{2-[(2-sulfoethyl)amino]ethoxy}tricyclo[3.3.1.1$^{3,7}$]dec-1-yl)methyl]-5-methyl-1H-pyrazol-4-yl}pyridine-2-carboxylic acid (W2.70)

1.70.1 ethyl 6-(4,4,5,5-tetramethyl-1,3,2-dioxaborolan-2-yl)quinoline-4-carboxylate To a solution of ethyl 6-bromoquinoline-4-carboxylate (140 mg) in N,N-dimethylformamide (2 mL) was added PdCl$_2$(dppf)-CH$_2$Cl$_2$ adduct (([1,1'-bis(diphenylphosphino)ferrocene]dichloropalladium(II) (1:1), 20.42 mg), potassium acetate (147 mg) and bis(pinacolato)diboron (190 mg). The mixture was stirred at 60° C. overnight. The mixture was cooled to room temperature and used in the next reaction without further work up. MS (ESI) m/e 328.1 (M+H)$^+$.

1.70.2 ethyl 6-[5-{1-[(3-{2-[bis(tert-butoxycarbonyl)amino]ethoxy}-5,7-dimethyltricyclo[3.3.1.1$^{3,7}$]dec-1-yl)methyl]-5-methyl-1H-pyrazol-4-yl}-6-(tert-butoxycarbonyl)pyridin-2-yl]quinoline-4-carboxylate To a solution of Example 1.70.1 (164 mg) in 1,4-dioxane (10 mL) and water (5 mL) was added Example 1.68.4 (365 mg), bis(triphenylphosphine)palladium(II) dichloride (35 mg), and CsF (228 mg). The mixture was stirred at 120° C. for 30 minutes under microwave conditions (Biotage Initiator). The mixture was diluted with ethyl acetate (200 mL), washed with water and brine, dried over anhydrous sodium sulfate, filtered and concentrated. The residue was purified by silica gel chromatography, eluting with 20% ethyl acetate in heptane (1 L) to give the title compound. MS (ESI) m/e 894.3 (M+H)$^+$.

1.70.3 6-(6-(tert-butoxycarbonyl)-5-(1-((3-(2-((tert-butoxycarbonyl)amino)ethoxy)-5,7-dimethyladamantan-1-yl)methyl)-5-methyl-1H-pyrazol-4-yl)pyridin-2-yl)quinoline-4-carboxylic acid To a solution of Example 1.70.2 (3.1 g) in tetrahydrofuran (20 mL), methanol (10 mL) and water (10 mL) was added LiOH H$_2$O (240 mg). The mixture was stirred at room temperature overnight. The mixture was acidified with 2N aqueous HCl and diluted with ethyl acetate (400 mL). The organic layer was washed with water and brine and dried over anhydrous sodium sulfate. Filtration and evaporation of the solvent gave the title compound. MS (ESI) m/e 766.3 (M+H)$^+$.

1.70.4 3-(1-((3-(2-aminoethoxy)-5,7-dimethyladamantan-1-yl)methyl)-5-methyl-1H-pyrazol-4-yl)-6-(4-(benzo[d]thiazol-2-ylcarbamoyl)quinolin-6-yl)picolinic acid To a solution of Example 1.70.3 (4.2 g) in dichloromethane (30 mL) was added benzo[d]thiazol-2-amine (728 mg), 1-ethyl-3-(3-dimethylaminopropyl)carbodiimide (1.40 g) and 4-dimethylaminopyridine (890 mg), and the mixture was stirred at room temperature overnight. The reaction mixture was diluted with ethyl acetate (500 mL), washed with water and brine, and dried over anhydrous sodium sulfate. Filtration and evaporation of the solvent gave a residue that was dissolved in dichloromethane and trifluoroacetic acid (10 mL, 1:1) and stirred overnight. The mixture was concentrated, and the residue was dissolved in N,N-dimethylformamide (4 mL) and purified by reverse-phase HPLC on a Gilson system (C18 column), eluting with 20-80% acetonitrile in water containing 0.1% trifluoroacetic acid, to give the title compound. MS (ESI) m/e 742.2 $(M+H)^+$.

1.70.5 6-[4-(1,3-benzothiazol-2-ylcarbamoyl)quinolin-6-yl]-3-{1-[(3,5-dimethyl-7-{2-[(2-sulfoethyl)amino]ethoxy}tricyclo[3.3.1.1$^{3,7}$]dec-1-yl)methyl]-5-methyl-1H-pyrazol-4-yl}pyridine-2-carboxylic acid To a solution of Example 1.70.4 (111 mg) in N,N-dimethylformamide (4 mL) was added 4-((tert-butyldiphenylsilyl)oxy)-2,2-dimethylbutylethenesulfonate (67 mg), N,N-diisopropylethylamine (0.2 mL) and H$_2$O (0.3 mL). The mixture was stirred at room temperature for 3 hours. The reaction mixture was diluted with dichloromethane and trifluoroacetic acid (10 mL, 1:1) and stirred overnight. The mixture was concentrated, and the residue was dissolved in N,N-dimethylformamide (4 mL) and purified by reverse-phase HPLC on a Gilson system (C18 column), eluting with 20-80% acetonitrile in water containing 0.1% trifluoroacetic acid, to give the title compound. $^1$H NMR (400 MHz, dimethyl sulfoxide-d$_6$) δ ppm 13.31 (s, 1H), 9.10 (d, 1H), 8.91 (s, 1H), 8.58 (dd, 1H), 8.47-8.16 (m, 4H), 8.06 (dd, 1H), 7.99-7.89 (m, 2H), 7.79 (d, 1H), 7.53-7.43 (m, 2H), 7.42-7.31 (m, 1H), 3.87 (s, 2H), 3.53 (d, 1H), 3.20 (p, 2H), 3.07 (p, 2H), 2.78 (t, 2H), 2.20 (s, 3H), 1.40 (s, 2H), 1.28 (q, 4H), 1.21-1.07 (m, 4H), 1.02 (q, 2H), 0.84 (s, 6H). MS (ESI) m/e 850.1 $(M+H)^+$.

1.71 Synthesis of 6-[5-(1,3-benzothiazol-2-ylcarbamoyl)quinolin-3-yl]-3-{1-[(3-{2-[(2-carboxyethyl)amino]ethoxy}-5,7-dimethyltricyclo[3.3.1.1$^{3,7}$]dec-1-yl)methyl]-5-methyl-1H-pyrazol-4-yl}pyridine-2-carboxylic acid (W2.71)

To a solution of Example 1.69.5 (140 mg) in N,N-dimethylformamide (10 mL) was added tert-butyl acrylate (242 mg), and H$_2$O (0.3 mL), and the mixture was stirred at room temperature over the weekend. The reaction mixture was diluted with dichloromethane and trifluoroacetic acid (10 mL, 1:1) and stirred overnight. The mixture was concentrated, and the residue was dissolved in N,N-dimethylformamide (4 mL) and purified by reverse-phase HPLC on a Gilson system (C18 column), eluting with 20-80% acetonitrile in water containing 0.1% trifluoroacetic acid, to give the title compound. $^1$H NMR (400 MHz, dimethyl sulfoxide-d$_6$) δ ppm 13.17 (s, 2H), 9.69 (d, 1H), 9.37 (d, 1H), 8.30 (dd, 3H), 8.15 (dd, 1H), 8.04 (dd, 1H), 7.99-7.88 (m, 2H), 7.79 (d, 1H), 7.53-7.40 (m, 2H), 7.34 (td, 1H), 3.88 (s, 2H), 3.55 (t, 2H), 3.08 (dt, 4H), 2.62 (t, 2H), 2.21 (s, 3H), 1.43 (s, 2H), 1.29 (q, 4H), 1.14 (s, 4H), 1.03 (q, 2H), 0.85 (s, 6H). MS (ESI) m/e 814.2 $(M+H)^+$.

1.72 Synthesis of 6-[1-(1,3-benzothiazol-2-ylcarbamoyl)-5,6-dihydroimidazo[1,5-a]pyrazin-7(8H)-yl]-3-{1-[(3,5-dimethyl-7-{2-[(2-sulfoethyl)amino]ethoxy}tricyclo[3.3.1.1$^{3,7}$]dec-1-yl)methyl]-5-methyl-1H-pyrazol-4-yl}pyridine-2-carboxylic acid (W2.72)

1.72.1 ethyl 7-(5-bromo-6-(tert-butoxycarbonyl)pyridin-2-yl)-5,6,7,8-tetrahydroimidazo[1,5-a]pyrazine-1-carboxylate The title compound was prepared by substituting ethyl 5,6,7,8-tetrahydroimidazo[1,5-a]pyrazine-1-carboxylate hydrochloride for 1,2,3,4-tetrahydroisoquinoline-8-carboxylate hydrochloride in Example 1.1.11. MS (ESI) m/e 451, 453 $(M+H)^+$, 395, 397 (M-tert-butyl)$^+$.

1.72.2 ethyl 7-(6-(tert-butoxycarbonyl)-5-(4,4,5,5-tetramethyl-1,3,2-dioxaborolan-2-yl)pyridin-2-yl)-5,6,7,8-tetrahydroimidazo[1,5-a]pyrazine-1-carboxylate The title compound was prepared by substituting Example 1.72.1 for Example 1.1.11 in Example 1.2.1. MS (ESI) m/e 499 $(M+H)^+$, 443 (M-tert-butyl)$^+$, 529 $(M+CH_3OH-H)^-$.

1.72.3 ethyl 7-(6-(tert-butoxycarbonyl)-5-(1-((3-(2-((tert-butoxycarbonyl)amino)ethoxy)-5,7-dimethyladamantan-1-yl)methyl)-5-methyl-1H-pyrazol-4-yl)pyridin-2-yl)-5,6,7,8-tetrahydroimidazo[1,5-a]pyrazine-1-carboxylate The title compound was prepared by substituting Example 1.72.2 for Example 1.2.1 and Example 1.55.11 for Example 1.13.3 in Example 1.13.4. MS (ESI) m/e 760 $(M+H)^+$, 758 $(M-H)^-$.

1.72.4 7-(6-(tert-butoxycarbonyl)-5-(1-((3-(2-((tert-butoxycarbonyl)amino)ethoxy)-5,7-dimethyladamantan-1-yl)methyl)-5-methyl-1H-pyrazol-4-yl)pyridin-2-yl)-5,6,7,8-tetrahydroimidazo[1,5-a]pyrazine-1-carboxylic acid The title compound was prepared by substituting Example 1.72.3 for Example 1.1.12 in Example 1.1.13. MS (ESI) m/e 760 $(M+H)^+$, 758 $(M-H)^-$.

1.72.5 tert-butyl 6-(1-(benzo[d]thiazol-2-ylcarbamoyl)-5,6-dihydroimidazo[1,5-a]pyrazin-7(8H)-yl)-3-(1-((3-(2-((tert-butoxycarbonyl)amino)ethoxy)-5,7-dimethyladamantan-1-yl)methyl)-5-methyl-1H-pyrazol-4-yl)picolinate The title compound was prepared by substituting Example 1.72.4 for Example 1.52.2 in Example 1.52.3. MS (ESI) m/e 892 $(M+H)^+$, 890 $(M-H)^-$.

1.72.6 3-(1-{[3-(2-aminoethoxy)-5,7-dimethyltricyclo[3.3.1.1³,⁷]dec-1-yl]methyl}-5-methyl-1H-pyrazol-4-yl)-6-[1-(1,3-benzothiazol-2-ylcarbamoyl)-5,6-dihydroimidazo[1,5-a]pyrazin-7(8H)-yl]pyridine-2-carboxylic acid The title compound was prepared by substituting Example 1.72.5 for Example 1.1.16 in Example 1.1.17. MS (ESI) m/e 736 (M+H)⁺, 734 (M−H)⁻.

1.72.7 6-(1-(benzo[d]thiazol-2-ylcarbamoyl)-5,6-dihydroimidazo[1,5-a]pyrazin-7(8H)-yl)-3-(1-((3-(2-((2-(((4-((tert-butyldiphenylsilyl)oxy)-2-methylbutan-2-yl)oxy)sulfonyl)ethyl)amino)ethoxy)-5,7-dimethyladamantan-1-yl)methyl)-5-methyl-1H-pyrazol-4-yl)picolinic acid The title compound was prepared by substituting Example 1.72.6 for Example 1.2.7 in Example 1.2.8.

1.72.8 6-[1-(1,3-benzothiazol-2-ylcarbamoyl)-5,6-dihydroimidazo[1,5-a]pyrazin-7(8H)-yl]-3-{1-[(3,5-dimethyl-7-{2-[(2-sulfoethyl)amino]ethoxy}tricyclo[3.3.1.1³,⁷]dec-1-yl)methyl]-5-methyl-1H-pyrazol-4-yl}pyridine-2-carboxylic acid The title compound was prepared by substituting Example 1.72.7 for Example 1.2.8 in Example 1.2.9. ¹H NMR (400 MHz, dimethyl sulfoxide-d₆) δ ppm 8.36 (bs, 2H), 8.03 (bs, 1H), 7.99 (d, 1H), 7.76 (d, 1H), 7.64 (d, 1H), 7.46 (t, 1H), 7.34 (s, 1H), 7.33 (t, 1H), 7.17 (d, 1H), 5.12 (s, 2H), 4.28 (t, 2H), 4.11 (t, 2H), 3.86 (s, 2H), 3.56 (t, 2H), 3.24 (m, 2H), 3.11 (m, 2H), 2.82 (t, 2H), 2.15 (s, 3H), 1.42 (s, 2H), 1.32 (q, 4H), 1.17 (q, 4, H), 1.03 (m, 2H), 0.88 (s, 6H). MS (ESI) m/e 844 (M+H)⁺, 842 (M−H)⁻.

1.73 Synthesis of 8-(1,3-benzothiazol-2-ylcarbamoyl)-2-{6-carboxy-5-[1-({3-[2-({3-[1-(beta-D-glucopyranuronosyl)-1H-1,2,3-triazol-4-yl]propyl}amino)ethoxy]-5,7-dimethyltricyclo[3.3.1.1³,⁷]dec-1-yl}methyl)-5-methyl-1H-pyrazol-4-yl]pyridin-2-yl}-1,2,3,4-tetrahydroisoquinoline (W2.73)

To a solution of (2R,3R,4S,5S,6S)-2-azido-6-(methoxycarbonyl)tetrahydro-2H-pyran-3,4,5-triyl triacetate (8.63 mg) in t-CH₃OH (2 mL) and water (1 mL) was added Example 1.67.1 (20 mg), copper(II) sulfate pentahydrate (2.0 mg) and sodium ascorbate (5 mg). The mixture was stirred for 20 minutes at 100° C. under microwave conditions (Biotage Initiator). LiOH H₂O (50 mg) was added to the mixture, and stirring was continued overnight. The mixture was neutralized with trifluoroacetic acid and purified by reverse-phase HPLC on a Gilson system (C18 column), eluting with 20-80% acetonitrile in water containing 0.1% trifluoroacetic acid, to give the title compound. MS (APCI) m/e 987.3 (M+H)⁺.

1.74 Synthesis of 6-[7-(1,3-benzothiazol-2-ylcarbamoyl)-1H-indol-2-yl]-3-{1-[(3,5-dimethyl-7-{2-[(2-sulfoethyl)amino]ethoxy}tricyclo[3.3.1.1³,⁷]dec-1-yl)methyl]-5-methyl-1H-pyrazol-4-yl}pyridine-2-carboxylic acid (W2.74)

1.74.1 methyl 2-[5-{1-[(3-{2-[bis(tert-butoxycarbonyl)amino]ethoxy}-5,7-dimethyltricyclo[3.3.1.1³,⁷]dec-1-yl)methyl]-5-methyl-1H-pyrazol-4-yl}-6-(tert-butoxycarbonyl)pyridin-2-yl]-1H-indole-7-carboxylate Example 1.74.1 was prepared by substituting methyl 2-(4,4,5,5-tetramethyl-1,3,2-dioxaborolan-2-yl)-1H-indole-7-carboxylate for Example 1.2.1 and substituting Example 1.68.4 for Example 1.1.6 in Example 1.1.12. MS (ESI) m/e 866.3 (M−H)⁻.

1.74.2 2-(6-(tert-butoxycarbonyl)-5-(1-((3-(2-((tert-butoxycarbonyl)amino)ethoxy)-5,7-dimethyladamantan-1-yl)methyl)-5-methyl-1H-pyrazol-4-yl)pyridin-2-yl)-1H-indole-7-carboxylic acid Example 1.74.2 was prepared by substituting Example 1.74.1 for Example 1.1.12 in Example 1.1.13. MS (ESI) m/e 754.4 (M+H)⁺.

1.74.3 tert-butyl 6-(7-(benzo[d]thiazol-2-ylcarbamoyl)-1H-indol-2-yl)-3-(1-((3-(2-((tert-butoxycarbonyl)amino)ethoxy)-5,7-dimethyladamantan-1-yl)methyl)-5-methyl-1H-pyrazol-4-yl)picolinate Example 1.74.3 was prepared by substituting Example 1.74.2 for Example 1.1.13 in Example 1.1.14. MS (ESI) m/e 886.5 (M+H)⁺.

1.74.4 3-(1-((3-(2-aminoethoxy)-5,7-dimethyladamantan-1-yl)methyl)-5-methyl-1H-pyrazol-4-yl)-6-(7-(benzo[d]thiazol-2-ylcarbamoyl)-1H-indol-2-yl)picolinic acid Example 1.74.4 was prepared by substituting Example 1.74.3 for Example 1.1.16 in Example 1.1.17. MS (ESI) m/e 730.2 (M+H)⁺.

1.74.5 6-[7-(1,3-benzothiazol-2-ylcarbamoyl)-1H-indol-2-yl]-3-[1-({3,5-dimethyl-7-[(2,2,7,7-tetramethyl-10,10-dioxido-3,3-diphenyl-4,9-dioxa-1016-thia-13-aza-3-silapentadecan-15-yl)oxy]tricyclo[3.3.1.1³,⁷]dec-1-yl}methyl)-5-methyl-1H-pyrazol-4-yl]pyridine-2-carboxylic acid Example 1.74.5 was prepared by substituting Example 1.74.4 for Example 1.2.7 in Example 1.2.8. MS (ESI) m/e 1176.7 (M+H)⁺.

1.74.6 6-[7-(1,3-benzothiazol-2-ylcarbamoyl)-1H-indol-2-yl]-3-{1-[(3,5-dimethyl-7-{2-[(2-sulfoethyl)amino]ethoxy}tricyclo[3.3.1.1³,⁷]dec-1-yl)methyl]-5-methyl-1H-pyrazol-4-yl}pyridine-2-carboxylic acid Example 1.74.6 was prepared by substituting Example 1.74.5 for Example 1.2.8 in Example 1.2.9. ¹H NMR (400 MHz, dimethyl sulfoxide-d₆) δ ppm 11.32 (d, 1H), 8.23 (dd, 1H), 8.18 (d, 1H), 7.93-7.82 (m, 3H), 7.71 (d, 1H), 7.62 (s, 3H), 7.57-7.51 (m, 1H), 7.47 (s, 1H), 7.40 (d, 1H), 7.35 (t, 1H), 7.22 (t, 1H), 4.86 (t, 2H), 3.85 (s, 2H), 3.47 (t, 2H), 3.08 (t, 2H), 2.88 (p, 2H), 2.21 (s, 3H), 1.37 (s, 2H), 1.32-1.20 (m, 4H), 1.14 (q, 4H), 1.07-0.94 (m, 2H), 0.84 (s, 6H). MS (ESI) m/e 838.2 (M+H)⁺.

1.75 Synthesis of 6-[8-(1,3-benzothiazol-2-ylcarbamoyl)-6-[3-(methylamino)propyl]-3,4-dihydroisoquinolin-2(1H)-yl]-3-{1-[(3,5-dimethyl-7-{2-[(2-sulfoethyl)amino]ethoxy}tricyclo[3.3.1.1³,⁷]dec-1-yl)methyl]-5-methyl-1H-pyrazol-4-yl}pyridine-2-carboxylic acid (W2.75)

1.75.1 methyl 3-bromo-5-(bromomethyl)benzoate

Azobisisobutyronitrile (1.79 g) was added to methyl 3-bromo-5-methylbenzoate (50 g) and N-bromosuccinimide (44.7 g) in 350 mL acetonitrile, and the mixture was refluxed overnight. An additional 11 g of N-bromosuccinimide and 0.5 g of azobisisobutyronitrile was added, and the refluxing was continued for 3 hours. The mixture was concentrated, taken up in 500 mL diethyl ether, and stirred for 30 minutes. The mixture was filtered, and the resulting solution was concentrated. The crude product was chromatographed on silica gel using 10% ethyl acetate in heptanes to give the title compound.

1.75.2 methyl 3-bromo-5-(cyanomethyl)benzoate

Tetrabutylammonium cyanide (50 g) was added to Example 1.75.1 (67.1 g) in 300 mL acetonitrile, and the mixture was heated to 70° C. overnight. The mixture was cooled, poured into diethyl ether, and rinsed with water and brine. The mixture was then concentrated and chromatographed on silica gel using 2-20% ethyl acetate in heptanes to give the title compound.

1.75.3 methyl 3-(2-aminoethyl)-5-bromobenzoate

Borane-THF complex (126 mL, 1M solution) was added to a solution of Example 1.75.2 (16 g) in 200 mL tetrahydrofuran, and the mixture was stirred overnight. The reaction was carefully quenched with methanol (50 mL), and then concentrated to 50 mL volume. The mixture was taken up in 120 mL methanol/120 mL 4M HCl/120 mL dioxane, and stirred overnight. The organics were removed under reduced pressure, and the residue was extracted twice with diethyl ether. The extracts were discarded. The organic layer was basified with solid $K_2CO_3$, and then extracted with ethyl acetate, and dichloromethane (2×). The extracts were combined, dried over $Na_2SO_4$, filtered and concentrated to give the title compound.

1.75.4 methyl 3-bromo-5-(2-(2,2,2-trifluoroacetamido)ethyl)benzoate

Trifluoroacetic anhydride (9.52 mL) was added dropwise to a mixture of Example 1.75.3 (14.5 g) and trimethylamine (11.74 mL) in 200 mL dichloromethane at 0° C. Upon addition the mixture was allowed to warm to room temperature and was stirred for three days. The mixture was poured into diethyl ether, and washed with $NaHCO_3$ solution and brine. The mixture was concentrated and chromatographed on silica gel using 5-30% ethyl acetate in heptanes to give the title compound.

1.75.5 methyl 6-bromo-2-(2,2,2-trifluoroacetyl)-1,2,3,4-tetrahydroisoquinoline-8-carboxylate Sulfuric acid was added to Example 1.75.4 (10 g) until it went into solution (40 mL), at which time paraformaldehyde (4.24 g) was added and the mixture was stirred for 2 hours. The solution was then poured onto 400 mL ice, and stirred 10 minutes. The mixture was extracted with ethyl acetate (3×), and the combined extracts were washed with $NaHCO_3$ solution and brine, and then concentrated The crude product was chromatographed on silica gel using 2-15% ethyl acetate in heptanes to give the title compound.

1.75.6 methyl 6-(3-((tert-butoxycarbonyl)(methyl)amino)prop-1-yn-1-yl)-2-(2,2,2-trifluoroacetyl)-1,2,3,4-tetrahydroisoquinoline-8-carboxylate A solution of Example 1.75.5 (5.1 g), tert-butyl methyl (prop-2-yn-1-yl)carbamate (2.71 g), bis(triphenylphosphine)palladium(II) dichloride ($PdCl_2(PPh_3)_2$, 0.49 g), CuI (0.106 g), and triethylamine (5.82 mL) was stirred in 50 mL dioxane at 50° C. overnight. The mixture was concentrated and chromatographed on silica gel using 10-50% ethyl acetate in heptanes to give the title compound.

1.75.7 methyl 6-(3-((tert-butoxycarbonyl)(methyl)amino)propyl)-2-(2,2,2-trifluoroacetyl)-1,2,3,4-tetrahydroisoquinoline-8-carboxylate Example 1.75.6 (4.2 g), tetrahydrofuran (20 mL) and methanol (20.00 mL) were added to wet 20% $Pd(OH)_2/C$ (3 g) in a 250 mL pressure bottle and shaken under a pressure of 50 psi and 50° C. for 12 hours. The solution was filtered and concentrated to give the title compound.

1.75.8 methyl 2-(5-bromo-6-(tert-butoxycarbonyl)pyridin-2-yl)-6-(3-((tert-butoxycarbonyl)(methyl)amino)propyl)-1,2,3,4-tetrahydroisoquinoline-8-carboxylate Example 1.75.7 (4.22 g), and potassium carbonate (1.53 g) were stirred in 60 mL tetrahydrofuran, 25 mL methanol, and 10 mL water overnight. The mixture was concentrated and 60 mL N,N-dimethylformamide was added. To this was then added Example 1.1.9 (3.05 g) and triethylamine (5 mL), and the reaction was stirred at 60° C. overnight. The mixture was cooled to room temperature, poured into ethyl acetate (600 mL), washed with water (3×) and brine, dried over $Na_2SO_4$, filtered, and concentrated. The residue was chromatographed on silica gel using 5-50% ethyl acetate in heptanes to give the title compound. MS (ESI) m/e 618.2 $(M+H)^+$.

1.75.9 methyl 6-(3-((tert-butoxycarbonyl)(methyl)amino)propyl)-2-(6-(tert-butoxycarbonyl)-5-(4,4,5,5-tetramethyl-1,3,2-dioxaborolan-2-yl)pyridin-2-yl)-1,2,3,4-tetrahydroisoquinoline-8-carboxylate To a solution of Example 1.75.8 (3.7 g), triethylamine (2.50 mL) and $PdCl_2(dppf)$ (([1,1'-bis(diphenylphosphino)ferrocene]dichloropalladium(II) (1:1), 0.29 g) in 25 mL acetonitrile was added 4,4,5,5-tetramethyl-1,3,2-dioxaborolane (1.74 mL), and the reaction mixture was heated to 75° C. for 5 hours, then stirred at 60° C. overnight. The mixture was concentrated and chromatographed on silica gel using 5-50% ethyl acetate in heptanes to give the title compound. MS (ESI) m/e 666.4 $(M+H)^+$.

1.75.10 4-((tert-butyldiphenylsilyl)oxy)-2,2-dimethylbutyl 2-((2-((3-((4-iodo-5-methyl-1H-pyrazol-1-yl)methyl)-5,7-dimethyladamantan-1-yl)oxy)ethyl)amino)ethanesulfonate Example 1.55.10 (2.39 g), 4-((tert-butyldiphenylsilyl)oxy)-2,2-dimethylbutyl ethenesulfonate (2.41 g), and triethylamine (1.51 mL) were stirred in 30 mL N,N-dimethylformamide at 45° C. for 3 hours. The mixture was cooled and poured into diethyl ether (400 mL), and the diethyl ether solution was washed with water (3×) and brine, and concentrated. The crude product was chromatographed on silica gel using 2-50% ethyl acetate in heptanes, with 1% added triethylamine to give the title compound. MS (ESI) m/e 890.6 $(M+H)^+$.

1.75.11 6-(6-(3-((tert-butoxycarbonyl)(methyl) amino)propyl)-8-(methoxycarbonyl)-3,4-dihydroisoquinolin-2(1H)-yl)-3-(1-((3-(2-((2-((4-((tert-butyldiphenylsilyl)oxy)-2,2-dimethylbutoxy)sulfonyl)ethyl) amino)ethoxy)-5,7-dimethyladamantan-1-yl) methyl)-5-methyl-1H-pyrazol-4-yl)picolinic acid Example 1.75.9 (1.777 g), Example 1.75.10 (1.98 g), tris(dibenzylideneacetone)dipalladium(0) (0.102 g), 1,3,5,7-tetramethyl-8-tetradecyl-2,4,6-trioxa-8-phosphaadamantane (0.918 g), and potassium phosphate (1.889 g) were added to 25 mL dioxane/10 mL water, and the solution was evacuated/filled with nitrogen several times. The reaction was clear, and was stirred at 70° C. overnight. The mixture was cooled and poured into ethyl acetate (200 mL), and washed with water and brine. The mixture was concentrated and chromatographed on silica gel using 5-50% ethyl acetate in heptanes, followed by 10% methanol in ethyl acetate with 1% triethylamine to give the title compound. MS (ESI) m/e 1301.4 (M+H)$^+$.

1.75.12 6-(3-((tert-butoxycarbonyl)(methyl)amino) propyl)-2-(5-(1-((3-(2-((2-((4-((tert-butyldiphenylsilyl)oxy)-2,2-dimethylbutoxy)sulfonyl)ethyl)amino) ethoxy)-5,7-dimethyladamantan-1-yl)methyl)-5-methyl-1H-pyrazol-4-yl)-6-carboxypyridin-2-yl)-1,2,3,4-tetrahydroisoquinoline-8-carboxylic acid Example 1.75.11 (1.5 g) and LiOH—H$_2$O (0.096 g) were stirred in 15 mL tetrahydrofuran and 3 mL water at 45° C. for 10 days. The mixture was poured into 200 mL ethyl acetate/20 mL NaH$_2$PO$_4$ solution, and concentrated HCl solution was added until the pH reached 3. The layers were separated, and the aqueous layer was extracted twice with ethyl acetate. The combined organic layers were washed with brine and concentrated. The residue was chromatographed on silica gel using 0-5% methanol in ethyl acetate to give the title compound. MS (ESI) m/e 1287.3 (M+H)$^+$.

1.75.13 6-(8-(benzo[d]thiazol-2-ylcarbamoyl)-6-(3-((tert-butoxycarbonyl)(methyl)amino)propyl)-3,4-dihydroisoquinolin-2(1H)-yl)-3-(1-((3-(2-((2-((4-((tert-butyldiphenylsilyl)oxy)-2,2-dimethylbutoxy) sulfonyl)ethyl)amino)ethoxy)-5,7-dimethyladamantan-1-yl)methyl)-5-methyl-1H-pyrazol-4-yl)picolinic acid The title compound was prepared as described in Example 1.2.6, substituting Example 1.2.5 with Example 1.75.12. MS (ESI) m/e 1419.5 (M+H)$^+$.

1.75.14 6-[8-(1,3-benzothiazol-2-ylcarbamoyl)-6-[3-(methylamino)propyl]-3,4-dihydroisoquinolin-2 (1H)-yl]-3-{1-[(3,5-dimethyl-7-{2-[(2-sulfoethyl) amino]ethoxy}tricyclo[3.3.1.1$^{3,7}$]dec-1-yl)methyl]-5-methyl-1H-pyrazol-4-yl}pyridine-2-carboxylic acid The title compound was prepared as described in Example 1.2.9, substituting Example 1.2.8 with Example 1.75.13. $^1$H NMR (400 MHz, dimethyl sulfoxide-d$_6$) δ ppm 12.90 (bs, 1H), 8.33 (m, 2H), 8.02 (d, 1H), 7.78 (d, 1H), 7.66 (m, 1H), 7.47 (m, 3H), 7.35 (m, 3H), 7.25 (s, 2H), 6.95 (d, 1H), 4.95 (s, 2H), 4.28 (t, 2H), 4.11 (t, 2H), 3.95 (m, 2H), 3.20 (m, 2H), 3.08 (m, 2H), 2.96 (m, 2H), 2.89 (m, 2H), 2.78 (m, 2H), 2.65 (m, 2H), 2.55 (t, 2H), 2.12 (s, 3H), 1.95 (m, 2H), 1.39 (s, 2H), 1.25 (m, 6H), 1.12 (m, 6H), 0.93 (s, 3H), 0.85 (s, 6H). MS (ESI) m/e 926.8 (M+H)$^+$.

1.76 Synthesis of 5-{[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl]amino}-5-deoxy-D-arabinitol (W2.76)

1.76.1 tert-butyl 6-(8-(benzo[d]thiazol-2-ylcarbamoyl)-3,4-dihydroisoquinolin-2(1H)-yl)-3-(1-((3,5-dimethyl-7-(2-((((4R,4'R,5R)-2,2,2',2'-tetramethyl-[4,4'-bi(1,3-dioxolan)]-5-yl)methyl)amino)ethoxy) adamantan-1-yl)methyl)-5-methyl-1H-pyrazol-4-yl) picolinate Example 1.2.7 (75 mg) and (4R,4'R,5S)-2,2,2',2'-tetramethyl-[4,4'-bi(1,3-dioxolane)]-5-carbaldehyde (22 mg) were dissolved in dichloromethane (1 mL). Sodium triacetoxyborohydride (40 mg) was added, and the solution was stirred for 16 hours at room temperature. The solution was concentrated under reduced pressure, and the material was purified by flash column chromatography on silica gel, eluting with 5-10% methanol in dichloromethane. The solvent was evaporated under reduced pressure to provide the title compound. MS (ESI) m/e 1016 (M+H)$^+$, 1014 (M−H)$^-$.

1.76.2 5-{[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl) methyl]-5,7-dimethyltricyclo[3.3.1.1$^{37}$]dec-1-yl}oxy)ethyl]amino}-5-deoxy-D-arabinitol Example 1.76.1 (45 mg) was dissolved in trifluoroacetic acid (1 mL) and water (0.2 mL). The solution was mixed at room temperature for five days. The solvents were removed under reduced pressure, and the material was taken up in methanol (2 mL). The material was purified by reverse-phase HPLC using 25-75% acetonitrile in water (w/0.1% TFA) over 30 minutes on a Grace Reveleris equipped with a Luna column: C18(2), 100 A, 250×30 mm. Product fractions were pooled, frozen, and lyophilized to yield the title compound as the bis trifluoroacetic acid salt. $^1$H NMR (400 MHz, dimethyl sulfoxide-d$_6$) δ ppm 12.85 (bs, 2H), 8.31 (m, 1H), 8.16 (m, 1H), 8.04 (d, 1H), 7.80 (d, 1H), 7.62 (d, 1H), 7.51-7.43 (m, 3H), 7.37 (q, 2H), 7.29 (s, 1H), 6.69 (d, 1H), 4.96 (s, 2H), 4.04 (t, 2H), 3.89 (m, 2H), 3.59 (m, 3H), 3.49 (m, 4H), 3.42 (dd, 2H), 3.22 (dd, 2H), 3.06 (m, 2H), 3.02 (m, 4H), 2.10 (s, 3H), 1.43 (s, 2H), 1.30 (q, 4H), 1.14 (t, 4H), 1.04 (q, 2H), 0.87 (s, 6H). MS (ESI) m/e 880 (M+H)$^+$, 878 (M−H)$^-$.

1.77 Synthesis of 1-{[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl]amino}-1,2-dideoxy-D-arabino-hexitol (W2.77)

1.77.1 tert-butyl 6-(8-(benzo[d]thiazol-2-ylcarbamoyl)-3,4-dihydroisoquinolin-2(1H)-yl)-3-(1-((3,5-dimethyl-7-(2-(((3R,4S,5R)-3,4,5,6-tetrahydroxyhexyl)amino)ethoxy)adamantan-1-yl)methyl)-5-methyl-1H-pyrazol-4-yl)picolinate (4R,5S,6R)-6-(Hydroxymethyl)tetrahydro-2H-pyran-2,4,5-triol (15 mg) was dissolved in dimethyl sulfoxide (0.5 mL). Example 1.2.7 (88 mg) was added, followed by sodium cyanoborohydride (27 mg). Acetic acid (82 mg) was added dropwise, and the solution was heated at 60° C. for 16 hours. The reaction was cooled, diluted with 1 mL of methanol, and purified by reverse-phase HPLC using 20-75% acetonitrile in water (w/0.1% TFA) over 60 minutes on a Grace Reveleris equipped with a Luna column: C18(2), 100 A, 150×30 mm. Product fractions were pooled, frozen, and lyophilized to yield the title compound as the bis trifluoroacetic acid salt. MS (ESI) m/e 950 (M+H)$^+$, 948 (M−H)$^−$.

1.77.2 1-{[2-({3-[(4-{6-[8-(1,3-benzothiazol-2-yl-carbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl]amino}-1,2-dideoxy-D-arabino-hexitol Example 1.77.1 (39 mg) was dissolved in dichloromethane (0.5 mL). Trifluoroacetic acid (740 mg) was added, and the solution was stirred at room temperature for 16 hours. The solvents were removed under reduced pressure. The residue was dissolved in N,N-dimethylformamide (0.5 mL) and 1 M aqueous sodium hydroxide (0.5 mL) was added. The solution was stirred at room temperature for one hour. Trifluoroacetic acid (0.25 mL) was added, and the material was purified by reverse-phase HPLC using 20-75% acetonitrile in water (w/0.1% TFA) over 60 minutes on a Grace Reveleris equipped with a Luna column: C18(2), 100 A, 150×30 mm. Product fractions were pooled, frozen, and lyophilized to yield the title compound as the bis trifluoroacetic acid salt. $^1$H NMR (400 MHz, dimethyl sulfoxide-d$_6$) δ ppm 12.86 (s, 1H), 12.74 (bs, 1H), 8.28 (bs, 1H), 8.20 (bs, 1H), 8.04 (d, 1H), 7.80 (d, 1H), 7.62 (d, 1H), 7.51-7.43 (m, 3H), 7.37 (q, 2H), 7.29 (s, 1H), 6.96 (d, 1H), 4.96 (s, 2H), 4.53 (bs, 3H), 3.89 (t, 2H), 3.83 (s, 2H), 3.77 (d, 1H), 3.60 (dd, 2H), 3.56 (t, 2H), 3.48 (m, 2H), 3.15 (d, 1H), 3.02 (m, 6H), 2.10 (s, 3H), 1.84 (m, 1H), 1.69 (m, 1H), 1.43 (s, 2H), 1.31 (q, 4H), 1.14 (t, 4H), 1.05 (q, 2H), 0.87 (s, 6H). MS (ESI) m/e 894 (M+H)$^+$, 892 (M−H)$^−$.

1.78 Synthesis of 6-[4-(1,3-benzothiazol-2-ylcarbamoyl)isoquinolin-6-yl]-3-{1-[(3,5-dimethyl-7-{2-[(2-sulfoethyl)amino]ethoxy}tricyclo[3.3.1.1$^{3,7}$]dec-1-yl)methyl]-5-methyl-1H-pyrazol-4-yl}pyridine-2-carboxylic acid (W2.78)

1.78.1 methyl 6-(4,4,5,5-tetramethyl-1,3,2-dioxaborolan-2-yl)isoquinoline-4-carboxylate To a solution of methyl 6-bromoisoquinoline-4-carboxylate (1.33 g) in N,N-dimethylformamide (30 mL) was added PdCl$_2$(dppf)-CH$_2$Cl$_2$ adduct (([1,1'-bis(diphenylphosphino)ferrocene]dichloropalladium(II) (1:1), 204 mg), potassium acetate (1.48 g) and bis(pinacolato)diboron (1.92 g). The mixture was stirred at 60° C. overnight. The mixture was cooled to room temperature and used in the next reaction without further work up. MS (APCI) m/e 313.3 (M+H)$^+$.

1.78.2 methyl 6-[5-{1-[(3-{2-[bis(tert-butoxycarbonyl)amino]ethoxy}-5,7-dimethyltricyclo[3.3.1.1$^{3,7}$]dec-1-yl)methyl]-5-methyl-1H-pyrazol-4-yl}-6-(tert-butoxycarbonyl)pyridin-2-yl]isoquinoline-4-carboxylate To a solution of the Example 1.68.4 (1.2 g) in 1,4-dioxane (20 mL) and water (10 mL) was added Example 1.78.1 (517 mg), bis(triphenylphosphine)palladium(II) dichloride (58 mg), and CsF (752 mg). The mixture was stirred at reflux overnight. LC/MS showed the expected product as a major peak. The mixture was diluted with ethyl acetate (200 mL), washed with water and brine, dried over anhydrous sodium sulfate, filtered and concentrated. The residue was purified by silica gel chromatography, eluting with 20% ethyl acetate in dichloromethane to give the title compound. MS (ESI) m/e 880.8 (M+H)$^+$.

1.78.3 6-(6-(tert-butoxycarbonyl)-5-(1-((3-(2-((tert-butoxycarbonyl)amino)ethoxy)-5,7-dimethyladamantan-1-yl)methyl)-5-methyl-1H-pyrazol-4-yl)pyridin-2-yl)isoquinoline-4-carboxylic acid To a solution of Example 1.78.2 (3.1 g) in tetrahydrofuran (20 mL), methanol (10 mL) and water (10 mL) was added LiOH H$_2$O (240 mg). The mixture was stirred at room temperature overnight. The mixture was acidified with aqueous 2N HCl and diluted with ethyl acetate (400 mL). The organic layer was washed with water and brine and dried over anhydrous sodium sulfate. Filtration and evaporation of the solvent gave the title compound. MS (ESI) m/e 766.4 (M+H)$^+$.

1.78.4 3-(1-((3-(2-aminoethoxy)-5,7-dimethyladamantan-1-yl)methyl)-5-methyl-1H-pyrazol-4-yl)-6-(4-(benzo[d]thiazol-2-ylcarbamoyl)isoquinolin-6-yl)picolinic acid To a solution of Example 1.78.3 (1.2 g) in dichloromethane (20 mL) was added benzo[d]thiazol-2-amine (0.236 g), 1-ethyl-3-(3-dimethylaminopropyl)carbodiimide (451 mg), and 4-dimethylaminopyridine (288 mg), and the mixture was stirred at room temperature overnight. The reaction mixture was diluted with ethyl acetate (500 mL), washed with water and brine, and dried over anhydrous sodium sulfate. Filtration and evaporation of the solvent gave a residue that was dissolved in dichloromethane and trifluoroacetic acid (10 mL, 1:1) and stirred overnight. The mixture was concentrated, and the residue was dissolved in N,N-dimethylformamide (4 mL) and purified by reverse-phase HPLC on a Gilson system (C18 column), eluting with 20-80% acetonitrile in water containing 0.1% trifluoroacetic acid, to give the title compound. MS (ESI) m/e 742.1 (M+H)$^+$.

1.78.5 6-[4-(1,3-benzothiazol-2-ylcarbamoyl)isoquinolin-6-yl]-3-{1-[(3,5-dimethyl-7-{2-[(2-sulfoethyl)amino]ethoxy}tricyclo[3.3.1.1$^{3,7}$]dec-1-yl)methyl]-5-methyl-1H-pyrazol-4-yl}pyridine-2-carboxylic acid To a solution of Example 1.78.4 (55 mg) in N,N-dimethylformamide (6 mL) was added 4-((tert-butyldiphenylsilyl)oxy)-2,2-dimethylbutyl ethenesulfonate (34 mg), ANN-diisopropylethylamine (0.6 mL) and H$_2$O (0.6 mL). The mixture was stirred at room temperature overnight. The reaction mixture was diluted with dichloromethane and trifluoroacetic acid (10 mL, 1:1) and stirred overnight. The mixture was concentrated, and the residue was dissolved in N,N-dimethylformamide (4 mL) and purified by reverse-phase HPLC on a Gilson system (C18 column), eluting with 20-80% acetonitrile in water containing 0.1% trifluoroacetic acid, to give the title compound. $^1$H NMR (400 MHz, dimethyl sulfoxide-d$_6$) δ ppm 13.25 (s, 2H), 9.58 (s, 1H), 9.06 (s, 1H), 9.00 (s, 1H), 8.52 (dd, 1H), 8.42 (d, 1H), 8.35 (d, 2H), 8.26 (d, 1H), 8.11-8.03 (m, 1H), 8.01 (d, 1H), 7.80

(d, 1H), 7.52-7.44 (m, 2H), 7.41-7.28 (m, 1H), 3.89 (s, 2H), 3.55 (t, 2H), 3.22 (t, 2H), 3.09 (s, 2H), 2.80 (t, 2H), 2.23 (s, 3H), 1.43 (s, 2H), 1.30 (q, 4H), 1.23-1.11 (m, 4H), 1.04 (q, 2H), 0.86 (s, 6H). MS (ESI+) m/e 850.1 (M+H)$^+$.

1.79 Synthesis of 6-[8-(1,3-benzothiazol-2-ylcarbamoyl)-3,4-dihydroisoquinolin-2(1H)-yl]-3-(1-{[3-(2-{[3-hydroxy-2-(hydroxymethyl)propyl]amino}ethoxy)-5,7-dimethyltricyclo[3.3.1.1$^{3,7}$]dec-1-yl]methyl}-5-methyl-1H-pyrazol-4-yl)pyridine-2-carboxylic acid (W2.79)

1.79.1 2,2-dimethyl-1,3-dioxane-5-carbaldehyde

To a stirred suspension of pyridinium chlorochromate (1.1 g) and diatomaceous earth (10 g) in dichloromethane (10 mL) was added (2,2-dimethyl-1,3-dioxan-5-yl)methanol (0.5 g) as a solution in dichloromethane (3 mL) dropwise. The mixture was stirred at room temperature for 2 hours. The suspension was filtered through diatomaceous earth and washed with ethyl acetate. The crude product was filtered through silica gel and concentrated to give the title compound. $^1$H NMR (501 MHz, chloroform-d) δ 9.89 (s, 1H), 4.28-4.17 (m, 4H), 2.42-2.32 (m, 1H), 1.49 (s, 3H), 1.39 (s, 3H). MS (ESI) m/e 305.9 (2M+NH4)$^+$.

1.79.2 tert-butyl 6-(8-(benzo[d]thiazol-2-ylcarbamoyl)-3,4-dihydroisoquinolin-2(1H)-yl)-3-(1-((3-(2-(((2,2-dimethyl-1,3-dioxan-5-yl)methyl)amino)ethoxy)-5,7-dimethyladamantan-1-yl)methyl)-5-methyl-1H-pyrazol-4-yl)picolinate To a solution of Example 1.2.7 (100 mg) and Example 1.79.1 (20 mg) in dichloromethane (1 mL) was added sodium triacetoxyborohydride (40 mg), and the mixture was stirred at room temperature for 2 hours. The reaction was diluted with dichloromethane and washed with saturated sodium bicarbonate solution. The aqueous layer was back extracted with dichloromethane. The combined organic layers were dried over sodium sulfate, filtered and concentrated. Purification of the residue by silica gel chromatography, eluting with 20%-100% ethyl acetate/ethanol (3:1) in heptane, provided the title compound. MS (ESI) m/e 930.3 (M+H)$^+$.

1.79.3 6-[8-(1,3-benzothiazol-2-ylcarbamoyl)-3,4-dihydroisoquinolin-2(1H)-yl]-3-(1-{[3-(2-{[3-hydroxy-2-(hydroxymethyl)propyl]amino}ethoxy)-5,7-dimethyltricyclo[3.3.1.1$^{3,7}$]dec-1-yl]methyl}-5-methyl-1H-pyrazol-4-yl)pyridine-2-carboxylic acid Example 1.79.3 was prepared by substituting Example 1.79.2 for Example 1.2.8 in Example 1.2.9. $^1$H NMR (400 MHz, dimethyl sulfoxide-d$_6$) δ ppm 12.82 (s, 1H), 8.13 (s, 2H), 8.00 (dd, 1H), 7.76 (d, 1H), 7.59 (d, 1H), 7.49-7.38 (m, 3H), 7.37-7.29 (m, 2H), 7.25 (s, 1H), 6.92 (d, 1H), 4.92 (s, 4H), 3.85 (t, 2H), 3.79 (s, 2H), 3.53 (t, 2H), 3.47 (dd, 2H), 3.00 (dt, 7H), 2.07 (s, 3H), 1.93 (p, 1H), 1.38 (s, 2H), 1.32-1.19 (m, 4H), 1.16-0.91 (m, 6H), 0.83 (s, 7H). MS (ESI) m/e 834.3 (M+H)$^+$.

1.80 Synthesis of 1-{[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl]amino}-1,2-dideoxy-D-erythro-pentitol (W2.80)

The title compound was prepared by substituting (4S,5R)-tetrahydro-2H-pyran-2,4,5-triol for (4R,5S,6R)-6-(hydroxymethyl)tetrahydro-2H-pyran-2,4,5-triol and Example 1.3.1 for Example 1.2.7 in Example 1.77.1. $^1$H NMR (400 MHz, dimethyl sulfoxide-d$_6$) δ ppm 12.85 (bs, 1H), 12.72 (bs, 1H), 8.21 (bs, 2H), 8.04 (d, 1H), 7.79 (d, 1H), 7.62 (d, 1H), 7.52-7.42 (m, 3H), 7.37 (q, 2H), 7.29 (s, 1H), 6.95 (d, 1H), 4.96 (s, 2H), 3.89 (t, 2H), 3.83 (s, 2H), 3.65 (m, 2H), 3.56 (m, 2H), 3.38 (m, 2H), 3.32 (m, 2H), 3.24 (m, 2H), 3.03 (m, 5H), 2.10 (s, 3H), 1.89 (m, 1H), 1.67 (m, 1H), 1.44 (s, 2H), 1.31 (q, 4H), 1.14 (t, 4H), 1.05 (q, 2H), 0.86 (s, 6H). MS (ESI) m/e 864 (M+H)$^+$, 862 (M−H)$^−$.

1.81 Synthesis of 6-[8-(1,3-benzothiazol-2-ylcarbamoyl)-3,4-dihydroisoquinolin-2(1H)-yl]-3-(1-{[3,5-dimethyl-7-(2-{[(2S,3S)-2,3,4-trihydroxybutyl]amino}ethoxy)tricyclo[3.3.1.1$^{3,7}$]dec-1-yl]methyl}-5-methyl-1H-pyrazol-4-yl)pyridine-2-carboxylic acid (W2.81)

1.81.1 carbonic acid tert-butyl ester (4S,5S)-5-hydroxymethyl-2,2-dimethyl-[1,3]dioxolan-4-ylmethyl ester ((4S,5S)-2,2-Dimethyl-1,3-dioxolane-4,5-diyl)dimethanol (1000 mg) was dissolved in N,N-dimethylformamide (50 mL). Sodium hydride (60% in mineral oil, 259 mg) was added. The solution was mixed at room temperature for 15 minutes. Di-tert-butyl dicarbonate (1413 mg) was added slowly. The solution was mixed for 30 minutes, and the reaction was quenched with saturated aqueous ammonium chloride solution. The solution was diluted with water (150 mL) and extracted twice using 70% ethyl acetate in heptanes. The organic portions were combined and extracted with water (100 mL), extracted with brine (50 mL), and dried on anhydrous sodium sulfate. The solution was concentrated under reduced pressure, and the material was purified by flash column chromatography on silica gel, eluting with 30% ethyl acetate in heptanes. The solvent was evaporated under reduced pressure to provide the title compound. MS (ESI) m/e 284 (M+Na)$^+$.

1.81.2 carbonic acid tert-butyl ester (4S,5R)-5-formyl-2,2-dimethyl-[1,3]dioxolan-4-ylmethyl ester Example 1.81.1 (528 mg) was dissolved in dichloromethane (20 mL). Dess-Martin periodinane (896 mg) was added, and the solution was stirred at room temperature for four hours. The solution was concentrated under reduced pressure, and the material was purified by flash column chromatography on silica gel, eluting with 20%-50% ethyl acetate in heptanes. The solvent was evaporated under reduced pressure to provide the title compound.

1.81.3 tert-butyl 6-(8-(benzo[d]thiazol-2-ylcarbamoyl)-3,4-dihydroisoquinolin-2(1H)-yl)-3-(1-(((1S,3s,5R,7S)-3-(2-((((4S,5S)-5-(((tert-butoxycarbonyl)oxy)methyl)-2,2-dimethyl-1,3-dioxolan-4-yl)methyl)amino)ethoxy)-5,7-dimethyladamantan-1-yl)methyl)-5-methyl-1H-pyrazol-4-yl)picolinate The title compound was prepared by substituting Example 1.81.2 for (4R,4'R,5S)-2,2,2',2'-tetramethyl-[4,4'-bi(1,3-dioxolane)]-5-carbaldehyde in Example 1.76.1.

1.81.4 6-[8-(1,3-benzothiazol-2-ylcarbamoyl)-3,4-dihydroisoquinolin-2(1H)-yl]-3-(1-{[3,5-dimethyl-7-(2-{[(2S,3S)-2,3,4-trihydroxybutyl]amino}ethoxy)tricyclo[3.3.1.1$^{3,7}$]dec-1-yl]methyl}-5-methyl-1H-pyrazol-4-yl)pyridine-2-carboxylic acid The title compound was prepared by substituting Example 1.81.3 for Example 1.76.1 in Example 1.76.2. $^1$H NMR (400

MHz, dimethyl sulfoxide-d$_6$) δ ppm 12.86 (bs, 2H), 8.28 (bs, 1H), 8.18 (bs, 1H), 8.04 (d, 1H), 7.80 (d, 1H), 7.63 (d, 1H), 7.51-7.43 (m, 3H), 7.36 (q, 2H), 7.29 (s, 1H), 6.96 (d, 1H), 4.96 (s, 2H), 3.89 (t, 2H), 3.83 (m, 3H), 3.46 (m, 4H), 3.40 (m, 4H), 3.08-2.96 (m, 6H), 2.10 (s, 3H), 1.43 (s, 2H), 1.30 (q, 4H), 1.14 (t, 4H), 1.04 (q, 2H), 0.87 (s, 6H). MS (ESI) m/e 850 (M+H)$^+$, 848 (M−H)$^−$.

1.82 Synthesis of 6-[8-(1,3-benzothiazol-2-ylcarbamoyl)-3,4-dihydroisoquinolin-2(1H)-yl]-3-(1-{[3-(2-{[(2S,3S,4R,5R,6R)-2,3,4,5,6,7-hexahydroxyheptyl]amino}ethoxy)-5,7-dimethyltricyclo[3.3.1.1$^{3,7}$]dec-1-yl]methyl}-5-methyl-1H-pyrazol-4-yl)pyridine-2-carboxylic acid (W2.82)

The title compound was prepared by substituting (2R,3R,4S,5R,6R)-2,3,4,5,6,7-hexahydroxyheptanal for (4R,5S,6R)-6-(hydroxymethyl)tetrahydro-2H-pyran-2,4,5-triol and Example 1.3.1 for Example 1.2.7 in Example 1.77.1. $^1$H NMR (400 MHz, dimethyl sulfoxide-d$_6$) 86 ppm 12.86 (bs, 1H), 8.34-8.08 (m, 2H), 8.05 (d, 1H), 7.79 (d, 1H), 7.54-7.43 (m, 3H), 7.37 (m, 2H), 7.30 (s, 1H), 6.95 (d, 1H), 4.96 (s, 2H), 3.93 (m, 2H), 3.90 (m, 4H), 3.83 (s, 2H), 3.47 (m, 4H), 3.41 (m, 4H), 3.18-3.08 (m, 7H), 3.03 (t, 2H), 2.12 (s, 3H), 1.46 (s, 2H), 1.28 (q, 4H), 1.15 (t, 4H), 1.05 (q, 2H), 0.89 (s, 6H). MS (ESI) m/e 940 (M+H)$^+$.

1.83 Synthesis of 6-[8-(1,3-benzothiazol-2-ylcarbamoyl)-3,4-dihydroisoquinolin-2(1H)-yl]-3-{1-[(3-{2-[({3-[(1,3-dihydroxypropan-2-yl)amino]propyl}sulfonyl)amino]ethoxy}-5,7-dimethyltricyclo[3.3.1.1$^{3,7}$]dec-1-yl)methyl]-5-methyl-1H-pyrazol-4-yl}pyridine-2-carboxylic acid (W2.83)

1.83.1 tert-butyl 6-(8-(benzo[d]thiazol-2-ylcarbamoyl)-3,4-dihydroisoquinolin-2(1H)-yl)-3-(1-((3-(2-(3-((1,3-dihydroxypropan-2-yl)amino)propylsulfonamido)ethoxy)-5,7-dimethyladamantan-1-yl)methyl)-5-methyl-1H-pyrazol-4-yl)picolinate To a cooled (ice bath) solution of Example 1.2.7 (31 mg) and N,N-diisopropylethylamine (60 μL) in dichloromethane (1 mL) was added 3-chloropropane-1-sulfonyl chloride (5 μL). The mixture was stirred at room temperature for 2 hours. The reaction was concentrated, dissolved in N,N-dimethylformamide (1 mL), transferred to a 2 mL microwave tube and 2-aminopropane-1,3-diol (70 mg) was added. The mixture was heated at 130° C. under microwave conditions (Biotage Initiator) for 90 minutes. The reaction mixture was concentrated, and the residue was purified by reverse-phase HPLC using a Gilson system, eluting with 20-100% acetonitrile in water containing 0.1% v/v trifluoroacetic acid. The desired fractions were combined and freeze-dried to provide the title compound. MS (ESI) m/e 997.2 (M+H)$^+$.

1.83.2 6-[8-(1,3-benzothiazol-2-ylcarbamoyl)-3,4-dihydroisoquinolin-2(1H)-yl]-3-{1-[(3-{2-[({3-[(1,3-dihydroxypropan-2-yl)amino]propyl}sulfonyl)amino]ethoxy}-5,7-dimethyltricyclo[3.3.1.1$^{3,7}$]dec-1-yl)methyl]-5-methyl-1H-pyrazol-4-yl}pyridine-2-carboxylic acid Example 1.83.2 was prepared by substituting Example 1.83.1 for Example 1.2.8 in Example 1.2.9. $^1$H NMR (400 MHz, dimethyl sulfoxide-d$_6$) δ ppm 12.84 (s, 1H), 8.40 (s, 2H), 8.05-7.98 (m, 1H), 7.77 (d, 1H), 7.60 (d, 1H), 7.51-7.39 (m, 3H), 7.38-7.30 (m, 2H), 7.27 (s, 1H), 7.13 (t, 1H), 6.93 (d, 1H), 4.94 (s, 2H), 3.61 (qd, 4H), 3.36 (t, 2H), 3.16-2.93 (m, 10H), 2.08 (s, 3H), 2.00 (p, 2H), 1.38 (s, 2H), 1.25 (q, 4H), 1.15-0.92 (m, 6H), 0.84 (s, 6H). MS (ESI) m/e 941.2 (M+H)$^+$.

1.84 Synthesis of 6-[8-(1,3-benzothiazol-2-ylcarbamoyl)-3,4-dihydroisoquinolin-2(1H)-yl]-3-{1-[(3-{2-[(3-{[1,3-dihydroxy-2-(hydroxymethyl)propan-2-yl]amino}-3-oxopropyl)amino]ethoxy}-5,7-dimethyltricyclo[3.3.1.1$^{3,7}$]dec-1-yl)methyl]-5-methyl-1H-pyrazol-4-yl}pyridine-2-carboxylic acid (W2.84)

To a solution of tert-butyl 3-(1-((3-(2-aminoethoxy)-5,7-dimethyladamantan-1-yl)methyl)-5-methyl-1H-pyrazol-4-yl)-6-(8-(benzo[d]thiazol-2-ylcarbamoyl)-3,4-dihydroisoquinolin-2(1H)-yl)picolinate (55 mg) in N,N-dimethylformamide (6 mL) was added N-(1,3-dihydroxy-2-(hydroxymethyl)propan-2-yl)acrylamide (73.4 mg), N,N-diisopropylethylamine (0.2 mL) and H$_2$O (0.2 mL). The mixture was stirred at room temperature 4 days. LC/MS showed the expected product as a major peak. The reaction mixture was diluted with ethyl acetate (500 mL), washed with water and brine, and dried over anhydrous sodium sulfate. Filtration and evaporation of the solvent gave a residue that was dissolved in dichloromethane and trifluoroacetic acid (10 mL, 1:1) and stirred overnight. The mixture was concentrated, and the residue was dissolved in N,N-dimethylformamide (8 mL) and purified by reverse-phase HPLC on a Gilson system (C18 column), eluting with 20-80% acetonitrile in water containing 0.1% trifluoroacetic acid, to give the title compound. $^1$H NMR (400 MHz, dimethylsulfonxide-d$_6$) δ ppm 12.84 (s, 1H), 8.45 (s, 2H), 8.01 (d, 4H), 7.78 (d, 1H), 7.60 (d, 1H), 7.53-7.39 (m, 3H), 7.39-7.30 (m, 2H), 7.27 (s, 1H), 6.94 (d, 1H), 4.94 (s, 2H), 4.14 (s, 2H), 3.87 (t, 2H), 3.81 (s, 2H), 3.52 (d, 4H), 3.19 (s, 3H), 3.13-2.97 (m, 5H), 2.75 (t, 2H), 2.08 (s, 3H), 1.42 (s, 2H), 1.29 (q, 4H), 1.12 (s, 4H), 1.09-0.99 (m, 2H), 0.85 (s, 7H). MS (ESI) m/e 921.2 (M+H)$^+$.

1.85 Synthesis of 6-[8-(1,3-benzothiazol-2-ylcarbamoyl)-3,4-dihydroisoquinolin-2(1H)-yl]-3-(1-{[3-(2-{[(3S)-3,4-dihydroxybutyl]amino}ethoxy)-5,7-dimethyltricyclo[3.3.1.1$^{3'}$]dec-1-yl]methyl}-5-methyl-1H-pyrazol-4-yl)pyridine-2-carboxylic acid (W2.85)

To a solution of Example 1.2.7 (213 mg) in dichloromethane (2 mL) was added (S)-2-(2,2-dimethyl-1,3-dioxolan-4-yl)acetaldehyde (42 mg). After stirring at room temperature for 30 minutes, sodium triacetoxyborohydride (144 mg) was added. The reaction mixture was stirred at room temperature overnight. Trifluoroacetic acid (2 mL) was added and stirring was continued overnight. The reaction mixture was concentrated, and the residue was purified by reverse-phase HPLC using a Gilson system, eluting with 5-85% acetonitrile in water containing 0.1% v/v trifluoroacetic acid. The desired fractions were combined and freeze-dried to provide the title compound. $^1$H NMR (400 MHz, dimethyl sulfoxide-d$_6$) δ ppm 12.86 (s, 1H), 8.22 (d, 2H), 8.05-8.01 (m, 1H), 7.79 (d, 1H), 7.61 (d, 1H), 7.53-7.41 (m, 3H), 7.36 (td, 2H), 7.28 (s, 1H), 6.95 (d, 1H), 4.95 (s, 2H), 3.88 (t, 2H), 3.82 (s, 2H), 3.26-2.94 (m, 7H), 2.10 (s, 3H), 1.84-1.75 (m, 1H), 1.52-1.63 (m, 1H), 1.45-1.23 (m, 6H), 1.19-0.96 (m, 7H), 0.86 (s, 6H). MS (ESI) m/e 834.3 (M+H)$^+$.

1.86 Synthesis of 4-({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl]amino}methyl)phenyl beta-D-glucopyranosiduronic acid (W2.86)

To a solution of 3-(1-((3-(2-aminoethoxy)-5,7-dimethyladamantan-1-yl)methyl)-5-methyl-1H-pyrazol-4-yl)-6-(8-(benzo[d]thiazol-2-ylcarbamoyl)-3,4-dihydroisoquinolin-2(1H)-yl)picolinic acid (36 mg) in tetrahydrofuran (2 mL) and acetic acid (0.2 mL) was added (2S,3R,4S,5S,6S)-2-(4-formylphenoxy)-6-(methoxycarbonyl)tetrahydro-2H-pyran-3,4,5-triyl triacetate (21 mg) followed by MgSO$_4$ (60 mg). The mixture was stirred at room temperature for 1 hour before the addition of MP-cyanoborohydride (Biotage, 153 mg, 2.49 mmol/g). The mixture was then stirred at room temperature for 3 hours. The mixture was filtered, and LiOH H$_2$O (20 mg) was added to the filtrate. The mixture was stirred at room temperature for 2 hours and then acidified with trifluoroacetic acid. The solution was purified by reverse-phase HPLC on a Gilson system (C18 column), eluting with 20-80% acetonitrile in water containing 0.1% trifluoroacetic acid, to give the title compound. MS (ESI) m/e 1028.3 (M+H)$^+$.

1.87 Synthesis of 3-{[2-({3-[(4-{6-[8-(1,3-benzothiazol-2-ylcarbamoyl)naphthalen-2-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl]amino}propyl beta-D-glucopyranosiduronic acid (W2.87)

1.87.1 (2R,3R,5S,6S)-2-(3-hydroxypropoxy)-6-(methoxycarbonyl)tetrahydro-2H-pyran-3,4,5-triyl triacetate To a stirred solution of (2R,3R,5S,6S)-2-bromo-6-(methoxycarbonyl)tetrahydro-2H-pyran-3,4,5-triyl triacetate (3.98 g) in toluene (60 mL) was added propane-1,3-diol (15.22 g). The mixture was stirred at 75° C., and Ag$_2$CO$_3$ (5.52 g) was added in three portions over a period of 3 hours. The mixture was stirred at room temperature overnight, after which the suspension was filtered. The filtrate was concentrated, and the residue was purified by silica gel chromatography eluting with 50% ethyl acetate in heptane to give the title compound. MS (ESI) m/e 409.9 (M+NH$_4$)$^+$.

1.87.2 (2S,3S,5R,6R)-2-(methoxycarbonyl)-6-(3-oxopropoxy)tetrahydro-2H-pyran-3,4,5-triyl triacetate To a solution of dimethyl sulfoxide (0.5 mL) in dichloromethane (10 mL) at −78° C. was added oxalyl chloride (0.2 mL). The mixture was stirred 20 minutes at −78° C., and a solution of Example 1.87.1 (393 mg) in dichloromethane (10 mL) was added through a syringe. After 20 minutes, triethylamine (1 mL) was added. The mixture was stirred for 30 minutes, and the temperature was allowed to rise to room temperature. The reaction mixture was diluted with ethyl acetate (300 mL), washed with water and brine, and dried over anhydrous sodium sulfate. Filtration and evaporation of the solvent gave the title compound, which was used without further purification. MS (DCI) m/e 408.1 (M+NH$_4$)$^+$.

1.87.3 3-{[2-({3-[(4-{6-[8-(1,3-benzothiazol-2-ylcarbamoyl)naphthalen-2-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl]amino}propyl beta-D-glucopyranosiduronic acid To a solution of Example 1.68.6 (171 mg) in dichloromethane (10 mL) was added Example 1.87.2 (90 mg), and NaBH(OAc)$_3$ (147 mg). The mixture was stirred at room temperature overnight. The reaction mixture was diluted with ethyl acetate (200 mL), washed with 2% aqueous HCl solution, water, and brine, dried over anhydrous sodium sulfate, filtered and concentrated. The residue was dissolved in tetrahydrofuran (6 mL), methanol (3 mL) and water (3 mL) and LiOH H$_2$O (100 mg) was added. The mixture was stirred at room temperature for 2 hours, acidified with trifluoroacetic acid and concentrated under reduced pressure. The residue was dissolved in dimethyl sulfoxide/methanol (1:1, 12 mL) and purified by reverse-phase HPLC on a Gilson system (C18 column), eluting with 20-80% acetonitrile in water containing 0.1% trifluoroacetic acid) to give the title compound. $^1$H NMR (400 MHz, dimethylsulfonxide-d$_6$) δ ppm 13.07 (s, 2H), 8.99 (s, 1H), 8.34 (dd, 1H), 8.29-8.11 (m, 5H), 8.06-8.02 (m, 1H), 7.99 (d, 1H), 7.90 (d, 1H), 7.78 (d, 1H), 7.68 (dd, 1H), 7.55-7.40 (m, 2H), 7.34 (td, 1H), 4.23 (d, 1H), 3.87 (s, 2H), 3.76 (dt, 1H), 3.60 (d, 1H), 3.53 (dt, 3H), 3.29 (t, 1H), 3.15 (t, 1H), 3.06-2.91 (m, 6H), 2.20 (s, 3H), 1.83 (p, 2H), 1.44 (s, 2H), 1.30 (q, 4H), 1.14 (s, 4H), 1.03 (q, 2H), 0.85 (s, 7H). MS (ESI) m/e 975.2 (M+H)$^+$.

1.88 Synthesis of 6-[4-(1,3-benzothiazol-2-ylcarbamoyl)-2-oxidoisoquinolin-6-yl]-3-[1-({3,5-dimethyl-7-[2-(methylamino)ethoxy]tricyclo[3.3.1.1$^{3,7}$]dec-1-yl}methyl)-5-methyl-1H-pyrazol-4-yl]pyridine-2-carboxylic acid (W2.88)

1.88.1 methyl 6-(6-(tert-butoxycarbonyl)-5-(1-((3-(2-((tert-butoxycarbonyl)(methyl)amino)ethoxy)-5,7-dimethyladamantan-1-yl)methyl)-5-methyl-1H-pyrazol-4-yl)pyridin-2-yl)isoquinoline-4-carboxylate To a solution of Example 1.78.1 (0.73 g) in 1,4-dioxane (20 mL) and water (10 mL) was added tert-butyl 3-(1-((3-(2-((tert-butoxycarbonyl)(methyl)amino)ethoxy)-5,7-dimethyladamantan-1-yl)methyl)-5-methyl-1H-pyrazol-4-yl)-6-chloropicolinate (1.5 g), bis(triphenylphosphine)palladium (II) dichloride (82 mg), and CsF (1.06 g), and the reaction was stirred at reflux overnight. The mixture was diluted with ethyl acetate (200 mL), washed with water and brine, dried over anhydrous sodium sulfate, filtered, and concentrated. The residue was purified by silica gel chromatography, eluting with 20% ethyl acetate in heptane (1 L) to give the title compound. MS (ESI) m/e 794.8 (M+H)$^+$.

1.88.2 6-(6-(tert-butoxycarbonyl)-5-(1-((3-(2-((tert-butoxycarbonyl)(methyl)amino)ethoxy)-5,7-dimethyladamantan-1-yl)methyl)-5-methyl-1H-pyrazol-4-yl)pyridin-2-yl)isoquinoline-4-carboxylic acid To a solution of Example 1.88.1 (300 mg) in tetrahydrofuran (6 mL), methanol (3 mL) and water (3 mL) was added LiOH H$_2$O (100 mg). The mixture was stirred at room temperature for 2 hours. The mixture was acidified with aqueous 2N HCl solution, diluted with ethyl acetate (300 mL), washed with water and brine, dried over anhydrous sodium sulfate, filtered and concentrated to give the title compound, which was used without further purification. MS (ESI) m/e 781.2 (M+H)$^+$.

1.88.3 tert-butyl 6-(4-(benzo[d]thiazol-2-ylcarbamoyl)isoquinolin-6-yl)-3-(1-((3-(2-((tert-butoxycarbonyl)(methyl)amino)ethoxy)-5,7-dimethyladamantan-1-yl)methyl)-5-methyl-1H-pyrazol-4-yl)picolinate To a solution of Example 1.88.2 (350 mg) in dichloromethane (10 mL) was added benzo[d]thiazol-2-amine (67.5 mg), 1-ethyl-3-(3-dimethylaminopropyl)carbodiimide (129 mg), and 4-dimethylaminopyridine (82 mg). The mixture was stirred at room temperature overnight. The mixture was diluted with ethyl acetate (300 mL), washed with water and brine, and dried over anhydrous sodium sulfate. Filtration and evaporation of the solvent gave a residue, which was purified by silica gel chromatography, eluting with 5% methanol in dichloromethane, to give the title compound. MS (APCI) m/e 912.3 (M+H)$^+$.

1.88.4 4-(benzo[d]thiazol-2-ylcarbamoyl)-6-(6-carboxy-5-(1-((3,5-dimethyl-7-(2-(methylamino)ethoxy)adamantan-1-yl)methyl)-5-methyl-1H-pyrazol-4-yl)pyridin-2-yl)isoquinoline 2-oxide To a solution of Example 1.88.3 (100 mg) in dichloromethane (6 mL) was added nm-chloroperoxybenzoic acid (19 mg). The mixture was stirred at room temperature for 4 hours. The mixture was diluted with ethyl acetate (200 mL), washed with saturated aqueous NaHCO$_3$ solution, water, and brine, and dried over anhydrous sodium sulfate. Filtration and evaporation of the solvent gave a residue that was dissolved in dichloromethane/trifluoroacetic acid (10 mL, 1:1) and stirred at room temperature overnight. The solvents were evaporated, and the residue was purified by reverse-phase HPLC on a Gilson system (C18 column), eluting with 20-80% acetonitrile in water containing 0.1% trifluoroacetic acid, to give the title compound. $^1$H NMR (501 MHz, dimethyl sulfoxide-d$_6$) δ ppm 13.32 (s, 2H), 9.21 (d, 1H), 8.71 (d, 1H), 8.49 (dd, 1H), 8.36-8.19 (m, 4H), 8.12 (dd, 1H), 8.07 (d, 1H), 7.96 (dd, 1H), 7.82 (d, 1H), 7.56-7.46 (m, 3H), 7.42-7.35 (m, 1H), 3.90 (d, 3H), 3.56 (td, 3H), 3.02 (p, 3H), 2.55 (t, 4H), 2.29-2.19 (m, 4H), 1.45 (d, 3H), 1.37-1.26 (m, 5H), 1.16 (d, 6H), 1.10-1.01 (m, 3H), 0.88 (d, 8H). MS (ESI) m/e 772.1 (M+H)$^+$.

1.89 Synthesis of 6-{8-[(1,3-benzothiazol-2-yl)carbamoyl]-3,4-dihydroisoquinolin-2(1H)-yl}-3-{1-[(3,5-dimethyl-7-{2-[(2-sulfoethyl)amino]acetamido}tricyclo[3.3.1.1$^{3,7}$]decan-1-yl)methyl]-5-methyl-1H-pyrazol-4-yl}pyridine-2-carboxylic acid (W2.89)

1.89.1 1-((3-bromo-5,7-dimethyladamantan-1-yl)methyl)-5-methyl-1H-pyrazole

To a cooled (−30° C.) solution of Example 1.1.3 (500 mg) in tetrahydrofuran (30 mL) was added n-butyllithium (9.67 mL), and the mixture was stirred at −30° C. for 2 hours. Methyl iodide (1.934 mL) was added dropwise at −30° C. After completion of the addition, the mixture was stirred at −30° C. for additional 2 hours. 1N aqueous HCl in ice water was added slowly, such that the temperature was maintained below 0° C., until the pH reached 6. The mixture was stirred at room temperature for 10 minutes, and diluted with ice-water (10 mL) and ethyl acetate (20 mL). The layers were separated, and the aqueous layer was extracted twice with ethyl acetate. The combined organic phases were washed with brine, dried over MgSO$_4$, filtered and concentrated. The residue was purified by flash silica gel chromatography, eluting with 15/1 to 10/1 petroleumeum/ethyl acetate, to give the title compound. MS (LC-MS) m/e 337, 339 (M+H)$^+$.

1.89.2 1-(3,5-dimethyl-7-((5-methyl-1H-pyrazol-1-yl)methyl)adamantan-1-yl)urea

Example 1.89.1 (2.7 g) and urea (4.81 g) was mixed and stirred at 140° C. for 16 hours.
The mixture was cooled to room temperature and suspended in methanol (200 mL×2). The insoluble material was removed by filtration. The filtrate was concentrated to give the title compound. MS (LC-MS) m/e 317.3 (M+H)$^+$.

1.89.3 3,5-dimethyl-7-((5-methyl-1H-pyrazol-1-yl)methyl)adamantan-1-amine

To a solution of Example 1.40.2 (2.53 g) in 20% ethanol in water (20 mL) was added sodium hydroxide (12.79 g). The mixture was stirred at 120° C. for 16 hours and at 140° C. for another 16 hours. 6N Aqueous HCl was added until pH 6. The mixture was concentrated, and the residue was suspended in methanol (200 mL). The insoluble material was filtered off. The filtrate was concentrated to give the title compound as an HCl salt. MS (LC-MS) m/e 273.9 (M+H)$^+$.

1.89.4 tert-butyl (2-((3,5-dimethyl-7-((5-methyl-1H-pyrazol-1-yl)methyl)adamantan-1-yl)amino)-2-oxoethyl)carbamate To a solution of Example 1.89.3 (2.16 g) in N,N-dimethylformamide (100 mL) was added triethylamine (3.30 mL), 2-((tert-butoxycarbonyl)amino)acetic acid (1.799 g) and 1-[bis(dimethylamino)methylene]-H-1,2,3-triazolo[4,5-b]pyridinium 3-oxid hexafluorophosphate (3.90 g). The mixture was stirred at room temperature for 2 hours. Water (40 mL) was added, and the mixture was extracted with ethyl acetate (70 mL×2). The combined organic phases were washed with brine, dried over sodium sulfate, filtered and concentrated. The residue was purified by silica gel chromatography, eluting with 3/1 to 2/1 petroleum/ethyl acetate, to give the title compound. MS (LC-MS) m/e 430.8 (M+H)$^+$.

1.89.5 tert-butyl (2-((3-((4-iodo-5-methyl-1H-pyrazol-1-yl)methyl)-5,7-dimethyladamantan-1-yl)amino)-2-oxoethyl)carbamate To an ambient solution of Example 1.89.4 (1.7 g) in N,N-dimethylformamide (20 mL) was added NIS (N-iodosuccinimide, 1.066 g) in portions, and the mixture was stirred at room temperature for 16 hours. Ice-water (10 mL) and saturated aqueous Na$_2$S$_2$O$_3$ solution (10 mL) were added. The mixture was extracted with ethyl acetate (30 mL×2). The combined organic phases were washed with brine, dried over sodium sulfate, filtered and concentrated. The residue was purified by silica gel chromatography, eluting with 3/1 to 2/1 petroleum/ethyl acetate, to give the title compound. MS (LC-MS) m/e 556.6 (M+H)$^+$.

1.89.6 methyl 2-(5-bromo-6-(tert-butoxycarbonyl)pyridin-2-yl)-1,2,3,4-tetrahydroisoquinoline-8-carboxylate To a solution of methyl 1,2,3,4-tetrahydroisoquinoline-8-carboxylate hydrochloride (12.37 g) and Example 1.1.10 (15 g) in dimethyl sulfoxide (100 mL) was added N,N-diisopropylethylamine (12 mL), and the mixture was stirred at 50° C. for 24 hours. The mixture was then diluted with ethyl acetate (500 mL) and washed with water and brine. The organic layer was dried over sodium sulfate, filtered and concentrated under reduced pressure. The residue was purified by silica gel chromatography, eluting with 20% ethyl acetate in hexane, to give the title compound. MS (ESI) m/e 448.4 (M+H)+.

1.89.7 methyl 2-(6-(tert-butoxycarbonyl)-5-(4,4,5,5-tetramethyl-1,3,2-dioxaborolan-2-yl)pyridin-2-yl)-1,2,3,4-tetrahydroisoquinoline-8-carboxylate To a solution of Example 1.89.6 (2.25 g) and [1,1'-bis(diphenylphosphino)ferrocene]dichloropalladium(II) (205 mg) in acetonitrile (30 mL) was added triethylamine (3 mL) and pinacolborane (2 mL), and the mixture was stirred at reflux for 3 hours. The mixture was diluted with ethyl acetate (200 mL) and washed with water and brine. The organic layer was dried over sodium sulfate, filtered and concentrated under reduced pressure. Purification of the residue by flash chromatography, eluting with 20% ethyl acetate in hexane, provided the title compound.

1.89.8 methyl 2-(6-(tert-butoxycarbonyl)-5-(1-((3-(2-((tert-butoxycarbonyl)amino)acetamido)-5,7-dimethyladamantan-1-yl)methyl)-5-methyl-1H-pyrazol-4-yl)pyridin-2-yl)-1,2,3,4-tetrahydroisoquinoline-8-carboxylate The title compound was prepared using the procedure in Example 1.2.2, substituting Example 1.1.6 with Example 1.89.5. MS (ESI) m/e 797.4 (M+H)+.

1.89.9 2-(6-(tert-butoxycarbonyl)-5-(1-((3-(2-((tert-butoxycarbonyl)amino)acetamido)-5,7-dimethyladamantan-1-yl)methyl)-5-methyl-1H-pyrazol-4-yl)pyridin-2-yl)-1,2,3,4-tetrahydroisoquinoline-8-carboxylic acid The title compound was prepared using the procedure in Example 1.2.5, substituting Example 1.2.4 with Example 1.89.8. MS (ESI) m/e 783.4 (M+H)+.

1.89.10 tert-butyl 6-(8-(benzo[d]thiazol-2-ylcarbamoyl)-3,4-dihydroisoquinolin-2(1H)-yl)-3-(1-((3-(2-((tert-butoxycarbonyl)amino)acetamido)-5,7-dimethyladamantan-1-yl)methyl)-5-methyl-1H-pyrazol-4-yl)picolinate The title compound was prepared using the procedure in Example 1.2.6, substituting Example 1.2.5 with Example 1.89.9. MS (ESI) m/e 915.3 (M+H)+.

1.89.11 3-(1-{[3-(2-aminoacetamido)-5,7-dimethyltricyclo[3.3.1.1$^{3,7}$]decan-1-yl]methyl}-5-methyl-1H-pyrazol-4-yl)-6-{8-[(1,3-benzothiazol-2-yl)carbamoyl]-3,4-dihydroisoquinolin-2(1H)-yl}pyridine-2-carboxylic acid The title compound was prepared using the procedure in Example 1.2.9, substituting Example 1.2.8 with Example 1.89.10. $^1$H NMR (400 MHz, dimethyl sulfoxide-d) δ 12.82 (s, 1H), 8.00 (dd, 1H), 7.90-7.79 (m, 4H), 7.76 (d, 1H), 7.59 (dd, 1H), 7.49-7.38 (m, 3H), 7.37-7.29 (m, 2H), 7.25 (s, 1H), 6.92 (d, 1H), 4.92 (s, 2H), 3.85 (t, 2H), 3.77 (s, 2H), 3.40 (q, 2H), 2.98 (t, 2H), 2.07 (s, 3H), 1.63 (s, 2H), 1.57-1.38 (m, 4H), 1.15-0.93 (m, 6H), 0.80 (s, 6H). MS (ESI) m/e 759.2 (M+H)+.

1.89.12 6-{8-[(1,3-benzothiazol-2-yl)carbamoyl]-3,4-dihydroisoquinolin-2(1H)-yl}-3-{1-[(3,5-dimethyl-7-{2-[(2-sulfoethyl)amino]acetamido}tricyclo[3.3.1.1$^{3,7}$]decan-1-yl)methyl]-5-methyl-1H-pyrazol-4-yl}pyridine-2-carboxylic acid To a solution of Example 1.89.11 (102 mg) in N,N-dimethylformamide (6 mL) was added 4-((tert-butyldiphenylsilyl)oxy)-2,2-dimethylbutyl ethenesulfonate (60 mg), and the mixture was stirred at room temperature over a weekend. The mixture was diluted with ethyl acetate (300 mL), washed with water and brine, and dried over anhydrous sodium sulfate. Filtration and evaporation of the solvent gave a residue that was dissolved in dichloromethane/trifluoroacetic acid (10 mL, 1:1) and stirred at room temperature overnight. The solvents were evaporated, and the residue was purified by reverse-phase HPLC on a Gilson system (C18 column), eluting with 20-80% acetonitrile in water containing 0.1% trifluoroacetic acid, to give the title compound. $^1$H NMR (501 MHz, dimethyl sulfoxide-d$_6$) δ 12.83 (s, 1H), 8.57 (s, 2H), 8.02 (d, 1H), 7.95 (s, 1H), 7.77 (d, 1H), 7.60 (d, 1H), 7.52-7.37 (m, 3H), 7.39-7.29 (m, 2H), 7.26 (s, 1H), 6.94 (d, 1H), 4.94 (s, 2H), 3.87 (t, 2H), 3.79 (s, 2H), 3.16 (q, 2H), 2.99 (t, 2H), 2.77 (t, 2H), 2.08 (s, 3H), 1.64 (s, 2H), 1.55 (d, 2H), 1.45 (d, 2H), 1.21-0.95 (m, 6H), 0.82 (s, 6H). MS (ESI) m/e 867.2 (M+H)+.

1.90 Synthesis of 6-[8-(1,3-benzothiazol-2-ylcarbamoyl)-3,4-dihydroisoquinolin-2(1H)-yl]-3-(1-{[3,5-dimethyl-7-({2-[(2-sulfoethyl)amino]ethyl}sulfanyl)tricyclo[3.3.1.1$^{3,7}$]dec-1-yl]methyl}-5-methyl-1H-pyrazol-4-yl)pyridine-2-carboxylic acid (W2.90)

1.90.1 3-((1H-pyrazol-1-yl)methyl)-5,7-dimethyladamantane-1-thiol

A mixture of Example 1.1.3 (2.8 g) and thiourea (15.82 g) in 33% (w/w) HBr in acetic acid (50 mL) was stirred at 110° C. for 16 hours and was concentrated under reduced pressure to give a residue. The residue was dissolved in 20% ethanol in water (v/v: 200 mL), and sodium hydroxide (19.06 g) was added. The resulting solution was stirred at room temperature for 16 hours and was concentrated. The residue was dissolved in water (60 mL), and acidified with 6 N aqueous HCl to pH 5-pH 6. The mixture was extracted with ethyl acetate (200 mL×2). The combined organic layers were washed with brine, dried over MgSO$_4$, filtered and concentrated to give the title compound. MS (ESI) m/e 319.1 (M+H)+.

1.90.2 2-((-3-((1H-pyrazol-1-yl)methyl)-5,7-dimethyladamantan-1-yl)thio)ethanol

To a solution of Example 1.90.1 (3.3 g) in ethanol (120 mL) was added sodium ethoxide (2.437 g). The mixture was stirred for 10 minutes, and 2-chloroethanol (1.80 mL) was added dropwise. The mixture was stirred at room temperature for 6 hours and was neutralized with 1 N aqueous HCl to pH 7. The mixture was concentrated, and the residue was extracted with ethyl acetate (200 mL×2). The combined organic layers were washed with brine, dried over MgSO$_4$, filtered and concentrated. The residue was purified by column chromatography on silica gel, eluting with petroleum ether/ethyl acetate from 6/1 to 2/1, to give the title compound. MS (ESI) m/e 321.2 (M+H)$^+$.

1.90.3 2-((-3,5-dimethyl-7-((5-methyl-1H-pyrazol-1-yl)methyl)adamantan-1-yl)thio)ethanol To a solution of Example 1.90.2 (2.3 g) in tetrahydrofuran (60 mL) was added n-butyllithium (14.35 mL, 2M in hexane) at −20° C. dropwise under nitrogen. The mixture was stirred at this temperature for 2 hours. Methyl iodide (4.49 mL) was added to the resulting mixture at −20° C., and the mixture was stirred at −20° C. for 2 hours. The reaction was quenched by the dropwise addition of saturated aqueous NH$_4$Cl solution at −20° C. The resulting mixture was stirred for 10 minutes and acidified with 1 N aqueous HCl to pH 5. The mixture was extracted with ethyl acetate twice. The combined organic layers were washed with brine, dried over MgSO$_4$, filtered and concentrated to give the title compound. MS (ESI) m/e 335.3 (M+H)$^+$.

1.90.4 2-((-3-((4-iodo-5-methyl-1H-pyrazol-1-yl)methyl)-5,7-dimethyladamantan-1-yl)thio)ethanol To a solution of Example 1.90.3 (3.65 g) in N,N-dimethylformamide (90 mL) was added N-iodosuccinimide (3.68 g). The mixture was stirred at room temperature for 16 hours. The reaction was quenched by the addition of ice-water (8 mL) and saturated aqueous NaS$_2$O3 solution (8 mL). The mixture was stirred for an additional 10 minutes and was extracted with ethyl acetate (30 mL×2). The combined organic layers were washed with brine, dried over MgSO$_4$, filtered and concentrated under reduced pressure. The residue was purified by silica gel chromatography, eluting with petroleum ether/ethyl acetate (6/1 to 3/1), to give the title compound. MS (ESI) m/e 461.2 (M+H)$^+$.

1.90.5 di-tert-butyl[2-({3-[(4-iodo-5-methyl-1H-pyrazol-1-yl)methyl]-5,7-dimethyltricyclo[3.3.1.1$^{3,7}$]decan-1-yl}sulfanyl)ethyl]-2-imidodicarbonate To a cold solution (0° C. bath) of Example 1.90.4 (3 g) in dichloromethane (100 mL) was added triethylamine (1.181 mL) and mesyl chloride (0.559 mL). The mixture was stirred at room temperature for 4 hours, and the reaction was quenched by the addition of ice-water (30 mL). The mixture was stirred for an additional 10 minutes and was extracted with dichloromethane (50 mL×2). The combined organic layers were washed with brine, dried over MgSO$_4$, filtered and concentrated under reduced pressure. The residue was dissolved in acetonitrile (100 mL) and NH(Boc)$_2$ (1.695 g) and Cs$_2$CO$_3$ (4.24 g) were added. The mixture was stirred at 85° C. for 16 hours, and the reaction was quenched by the addition of water (20 mL). The mixture was stirred for 10 minutes and was extracted with ethyl acetate (40 mL×2). The combined organic layers were washed with brine, dried over MgSO$_4$, filtered and concentrated. The residue was purified by silica gel chromatography, eluting with petroleum ether/ethyl acetate from 10/1 to 6/1, to give the title compound. MS (ESI) m/e 660.1 (M+H)$^+$.

1.90.6 methyl 2-[5-(1-{[3-({2-[bis(tert-butoxycarbonyl)amino]ethyl}sulfanyl)-5,7-dimethyltricyclo [3.3.1.1$^{3,7}$]decan-1-yl]methyl}-5-methyl-1H-pyrazol-4-yl)-6-(tert-butoxycarbonyl)pyridin-2-yl]-1,2,3,4-tetrahydroisoquinoline-8-carboxylate The title compound was prepared using the procedure in Example 1.2.2, replacing Example 1.1.6 with Example 1.90.5. MS (ESI) m/e 900.2 (M+H)$^+$.

190.7A 2-(6-(tert-butoxycarbonyl)-5-(1-((3-((2-((tert-butoxycarbonyl)amino)ethyl)thio)-5,7-dimethyladamantan-1-yl)methyl)-5-methyl-1H-pyrazol-4-yl)pyridin-2-yl)-1,2,3,4-tetrahydroisoquinoline-8-carboxylic acid The title compound was prepared as described in Example 1.2.5, replacing Example 1.2.4 with Example 1.90.6. MS (ESI) m/e 786.2 (M+H)$^+$.

190.7B tert-butyl 6-(8-(benzo[d]thiazol-2-ylcarbamoyl)-3,4-dihydroisoquinolin-2(1H)-yl)-3-(1-((3-((2-((tert-butoxycarbonyl)amino)ethyl)thio)-5,7-dimethyladamantan-1-yl)methyl)-5-methyl-1H-pyrazol-4-yl)picolinate The title compound was prepared as described in Example 1.2.6, replacing Example 1.2.5 with Example 1.90.7A. MS (ESI) m/e 918.8 (M+H)$^+$.

1.90.8 tert-butyl 3-(1-((3-((2-aminoethyl)thio)-5,7-dimethyladamantan-1-yl)methyl)-5-methyl-1H-pyrazol-4-yl)-6-(8-(benzo[d]thiazol-2-ylcarbamoyl)-3,4-dihydroisoquinolin-2(1H)-yl)picolinate To a solution of Example 1.90.7B (510 mg) in dichloromethane (5 mL) was added trifluoroacetic acid (5 mL) and the reaction was stirred at room temperature for 30 minutes. The reaction was quenched by the addition of saturated aqueous sodium bicarbonate solution and extracted with dichloromethane thrice. The combined organics were dried with anhydrous sodium sulfate, filtered and concentrated under reduced pressure. The residue was purified by reverse-phase HPLC on a Gilson system (C18 column), eluting with 20-80% acetonitrile in water containing 0.1% trifluoroacetic acid, to give the title product. MS (ESI) m/e 818.1 (M+H)$^+$.

1.90.9 3-(1-((3-((2-aminoethyl)thio)-5,7-dimethyladamantan-1-yl)methyl)-5-methyl-1H-pyrazol-4-yl)-6-(8-(benzo[d]thiazol-2-ylcarbamoyl)-3,4-dihydroisoquinolin-2(1H)-yl)picolinic acid Example 1.90.9 was isolated during the preparation of Example 1.90.8. MS (ESI) 762.2 (M+H)$^+$.

1.90.10 tert-butyl 6-(8-(benzo[d]thiazol-2-ylcarbamoyl)-3,4-dihydroisoquinolin-2(1H)-yl)-3-(1-((3-((2-((2-((4-((tert-butyldiphenylsilyl)oxy)-2,2-dimethylbutoxy)sulfonyl)ethyl)amino)ethyl)thio)-5,7-dimethyladamantan-1-yl)methyl)-5-methyl-1H-pyrazol-4-yl)picolinate Example 1.90.8 (235 mg) and 4-((tert-butyldiphenylsilyl)oxy)-2,2-dimethylbutyl ethenesulfonate (150 mg) were dissolved in dichloromethane (1 mL), N,N-diisopropylethylamine (140 μL) was added, and the mixture was stirred at room temperature for six days. The reaction was directly purified by silica gel chromatography, eluting with a gradient of 0.5-3.0% methanol in dichloromethane, to give the title compound.

1.90.11 6-(8-(benzo[d]thiazol-2-ylcarbamoyl)-3,4-dihydroisoquinolin-2(1H)-yl)-3-(1-((3,5-dimethyl-7-((2-((2-sulfoethyl)amino)ethyl)thio)adamantan-1-yl)methyl)-5-methyl-1H-pyrazol-4-yl)picolinic acid The title compound was prepared by substituting Example 1.90.10 for Example 1.2.8 in Example 1.2.9. $^1$H NMR (500 MHz, dimethyl sulfoxide-$d_6$) δ ppm 8.39 (br s, 2H), 8.03 (d, 1H), 7.79 (d, 1H), 7.62 (d, 1H), 7.51 (d, 1H), 7.47 (ddd, 1H), 7.43 (d, 1H), 7.37 (d, 1H), 7.35 (ddd, 1H), 7.30 (s, 1H), 6.96 (d, 1H), 4.96 (s, 2H), 3.89 (t, 2H), 3.81 (s, 2H), 3.22 (m, 2H), 3.06 (br m, 2H), 3.01 (t, 2H), 2.79 (t, 2H), 2.74 (m, 2H), 2.10 (s, 3H), 1.51 (s, 2H), 1.37 (m, 4H), 1.15 (m, 4H), 1.05 (m, 2H), 0.83 (s, 6H). MS (ESI) m/e 870.1 (M+H)$^+$.

1.91 Synthesis of 6-{8-[(1,3-benzothiazol-2-yl)carbamoyl]-3,4-dihydroisoquinolin-2(1H)-yl}-3-{1-[(3,5-dimethyl-7-{3-[(2-sulfoethyl)amino]propyl}tricyclo[3.3.1.1$^{3,7}$]decan-1-yl)methyl]-5-methyl-1H-pyrazol-4-yl}pyridine-2-carboxylic acid (W2.91)

1.91.1 1-((3-allyl-5,7-dimethyladamantan-1-yl)methyl)-1H-pyrazole

To a solution of Example 1.1.3 (0.825 g, 2.55 mmol) in toluene (5 mL) was added N, N'-azoisobutyronitrile (AIBN, 0.419 g, 2.55 mmol) and allyltributylstannane (2.039 ml, 6.38 mmol). The mixture was purged with $N_2$ stream for 15 minutes, heated at 80° C. for 8 hours and concentrated. The residue was purified by flash chromatography, eluting with 5% ethyl acetate in petroleum ether to provide the title compound. MS (ESI) m/e 285.2 (M+H)$^+$.

1.91.2 1-((3-allyl-5,7-dimethyladamantan-1-yl)methyl)-5-methyl-1H-pyrazole

To a solution of Example 1.91.1 (200 mg, 0.703 mmol) in tetrahydrofuran (5 ml) at −78° C. under $N_2$ was added n-butyllithium (2.81 mL, 7.03 mmol). The mixture was stirred for 2 hours while the temperature increased to −20° C. and then it was stirred at −20° C. for 1 hour. Iodomethane (0.659 ml, 10.55 mmol) was added and the resulting mixture was stirred for 0.5 hours at −20° C. The reaction was quenched with saturated $NH_4Cl$ and extracted with ethyl acetate twice. The combined organic layer was washed with brine and concentrated to give the title compound. MS (ESI) m/e 299.2 (M+H)$^+$.

1.91.3 3-(3,5-dimethyl-7-((5-methyl-1H-pyrazol-1-yl)methyl)adamantan-1-yl)propan-1-ol Under nitrogen atmosphere, a solution of Example 1.91.2 (2.175 g, 7.29 mmol) in anhydrous tetrahydrofuran (42.5 mL) was cooled to 0° C. $BH_3$.THF (15.30 mL, 15.30 mmol) was added dropwise. The reaction mixture was stirred at room temperature for 2 hours and cooled to 0° C. To the reaction mixture was added 10 N aqueous NaOH (5.03 mL, 50.3 mmol) dropwise, followed by 30 percent $H_2O_2$(16.52 mL, 146 mmol) water solution. The resulting mixture was warmed to room temperature and stirred for 90 minutes. The reaction was quenched with 10 percent hydrochloric acid (35 mL). The organic layer was separated and the aqueous layer was extracted with ethyl acetate (2×60 mL). The combined organic layers were washed with brine (3×60 mL) and cooled in an ice bath. A saturated aqueous solution of sodium sulfite (15 mL) was carefully added and the mixture was stirred for a few minutes. The organic layer was dried over sodium sulfate, filtered, and concentrated in vacuo. The residue was purified by flash chromatography, eluting with petroleum ether/ethyl acetate (3:1 to 1:1) to provide the title compound. MS (ESI) m/e 317.3 (M+H)$^+$.

1.91.4 3-(3-((4-iodo-5-methyl-1H-pyrazol-1-yl)methyl)-5,7-dimethyladamantan-1-yl)propan-1-ol A mixture of Example 1.91.3 (1.19 g, 3.76 mmol) and 1-iodopyrrolidine-2,5-dione (1.015 g, 4.51 mmol) in N,N-dimethylformamide (7.5 mL) was stirred for 16 hours at room temperature. The reaction was quenched with saturated $Na_2SO_3$. The mixture was diluted with ethyl acetate and washed with saturated $Na_2SO_3$, saturated $Na_2CO_3$, water and brine. The organic layer was dried over anhydrous $Na_2SO_4$, filtered, and concentrated. The residue was purified by flash chromatography, eluting with petroleum ether/ethyl acetate (3:1 to 1:1) to provide the title compound. MS (ESI) m/e 443.1 (M+H)$^+$.

1.91.5 3-(3-((4-iodo-5-methyl-1H-pyrazol-1-yl)methyl)-5,7-dimethyladamantan-1-yl)propyl methanesulfonate To a solution of Example 1.91.4 (1.55 g, 3.50 mmol) in $CH_2Cl_2$ (20 mL) at 0° C. were added $(CH_3CH_2)_3N$ (0.693 mL, 4.98 mmol) and mesyl chloride (0.374 mL, 4.80 mmol) slowly. The mixture was stirred for 3.5 hours at 20° C. and diluted with $CH_2Cl_2$, washed with saturated $NH_4Cl$, $NaHCO_3$ and brine. The organic layer was dried over $Na_2SO_4$, filtered, and concentrated to provide the title compound. MS (ESI) m/e 521.1 (M+H)$^+$.

1.91.6 di-tert-butyl (3-{3-[(4-iodo-5-methyl-1H-pyrazol-1-yl)methyl]-5,7-dimethyltricyclo[3.3.1.1$^{3,7}$]decan-1-yl}propyl)-2-imidodicarbonate To a solution of Example 1.91.5 (1.92 g, 3.69 mmol) in $CH_3CN$ (40 ml) at 20° C. was added di-tert-butyl iminodicarbonate (0.962 g, 4.43 mmol) and $Cs_2CO_3$ (2.404 g, 7.38 mmol). The mixture was stirred for 16 hours at 80° C. and was diluted with ethyl acetate, and was washed with water and brine. The organic layer was dried over $Na_2SO_4$, filtered, and concentrated. The residue was purified by flash chromatography, eluting with petroleum ether/ethyl acetate (10:1) to provide the title compound. MS (ESI) m/e 642.3 (M+H)$^+$.

1.91.7 methyl 2-[5-{1-[(3-{3-[bis(tert-butoxycarbonyl)amino]propyl}-5,7-dimethyltricyclo[3.3.1.1$^{3,7}$]decan-1-yl)methyl]-5-methyl-1H-pyrazol-4-yl}-6-(tert-butoxycarbonyl)pyridin-2-yl]-1,2,3,4-tetrahydroisoquinoline-8-carboxylate The title compound was prepared using the procedure in Example 1.2.2, replacing Example 1.1.6 with Example 1.91.6. MS (ESI) m/e 882.2 (M+H)$^+$.

1.91.8 2-[6-(tert-butoxycarbonyl)-5-{1-[(3-{3-[(tert-butoxycarbonyl)amino]propyl}-5,7-dimethyltricyclo[3.3.1.1³,⁷]decan-1-yl)methyl]-5-methyl-1H-pyrazol-4-yl}pyridin-2-yl]-1,2,3,4-tetrahydroisoquinoline-8-carboxylic acid The title compound was prepared using the procedure in Example 1.2.5, replacing Example 1.2.4 with Example 1.91.7. MS (ESI) m/e 768.4 (M+H)⁺.

1.91.9 tert-butyl 6-(8-(benzo[d]thiazol-2-ylcarbamoyl)-3,4-dihydroisoquinolin-2(1H)-yl)-3-(1-((3-(3-((tert-butoxycarbonyl)amino)propyl)-5,7-dimethyladamantan-1-yl)methyl)-5-methyl-1H-pyrazol-4-yl)picolinate The title compound was prepared using the procedure in Example 1.2.6, replacing Example 1.2.5 with Example 1.91.8. MS (ESI) m/e 901.1 (M+H)⁺.

1.91.10 tert-butyl 3-(1-((3-(3-aminopropyl)-5,7-dimethyladamantan-1-yl)methyl)-5-methyl-1H-pyrazol-4-yl)-6-(8-(benzo[d]thiazol-2-ylcarbamoyl)-3,4-dihydroisoquinolin-2(1H)-yl)picolinate To a solution of Example 1.91.9 (500 mg) in dichloromethane (5 mL) was added trifluoroacetic acid (5 mL) and the reaction was stirred at room temperature for 30 minutes. The reaction was quenched by the addition of saturated aqueous sodium bicarbonate solution and extracted with dichloromethane thrice. The combined organics were dried with anhydrous sodium sulfate, filtered and concentrated under reduced pressure. The residue was purified by reverse-phase HPLC on a Gilson system (C18 column), eluting with 20-80% acetonitrile in water containing 0.1% trifluoroacetic acid, to give the title product.

1.91.11 3-(1-((3-(3-aminopropyl)-5,7-dimethyladamantan-1-yl)methyl)-5-methyl-1H-pyrazol-4-yl)-6-(8-(benzo[d]thiazol-2-ylcarbamoyl)-3,4-dihydroisoquinolin-2(1H)-yl)picolinic acid To a solution of Example 1.91.9 (350 mg) in dichloromethane (5 mL) was added trifluoroacetic acid (5 mL). The mixture was stirred overnight. The mixture was concentrated and the residue was purified by reverse phase HPLC using a Gilson system, eluting with 20-80% acetonitrile in water containing 0.1% v/v trifluoroacetic acid, to provide the title compound. ¹H NMR (500 MHz, DMSO-d₆) δ ppm 12.86 (s, 1H), 8.03 (d, 1H), 7.79 (d, 1H), 7.62 (d, 4H), 7.47 (dt, 3H), 7.36 (q, 2H), 7.27 (s, 1H), 6.95 (d, 1H), 4.95 (s, 2H), 3.77 (s, 2H), 3.01 (t, 2H), 2.72 (q, 2H), 2.09 (s, 3H), 1.45 (t, 2H), 1.18-1.05 (m, 9H), 1.00 (d, 6H), 0.80 (s, 6H). MS (ESI) m/e 744.2 (M+H)⁺.

1.91.12 tert-butyl 6-(8-(benzo[d]thiazol-2-ylcarbamoyl)-3,4-dihydroisoquinolin-2(1H)-yl)-3-(1-((3-(3-((2-((4-((tert-butyldiphenylsilyl)oxy)-2,2-dimethylbutoxy)sulfonyl)ethyl)amino)propyl)-5,7-dimethyladamantan-1-yl)methyl)-5-methyl-1H-pyrazol-4-yl)picolinate The title compound was prepared using the procedure in Example 1.2.8, replacing Example 1.2.7 with Example 1.91.10.

1.91.13 6-{8-[(1,3-benzothiazol-2-yl)carbamoyl]-3,4-dihydroisoquinolin-2(1H)-yl}-3-{1-[(3,5-dimethyl-7-{3-[(2-sulfoethyl)amino]propyl}tricyclo[3.3.1.1³,⁷]decan-1-yl)methyl]-5-methyl-1H-pyrazol-4-yl}pyridine-2-carboxylic acid The title compound was prepared using the procedure in Example 1.2.9, replacing Example 1.2.8 with Example 1.91.12. ¹H NMR (501 MHz, DMSO-d₆) δ 12.85 (s, 1H), 8.02 (dd, 1H), 7.77 (d, 1H), 7.60 (d, 1H), 7.54-7.39 (m, 3H), 7.38-7.31 (m, 2H), 7.26 (s, 1H), 6.94 (d, 1H), 4.94 (s, 2H), 3.87 (t, 2H), 3.15 (p, 2H), 3.00 (t, 2H), 2.86 (dq, 2H), 2.76 (t, 2H), 2.08 (s, 3H), 1.47 (td, 2H), 1.08 (d, 9H), 0.99 (d, 7H), 0.79 (s, 7H). MS (ESI) m/e 852.2 (M+H)⁺.

Example 2: Synthesis of Exemplary Synthons

This example provides synthetic methods for exemplary synthons useful to make ADCs.

2.1 Synthesis of N-[6-(2,5-dioxo-2,5-dihydro-1H-pyrrol-1-yl)hexanoyl]-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1³,⁷]dec-1-yl}oxy)ethyl](2-sulfoethyl)carbamoyl}oxy)methyl]phenyl}-N⁵-carbamoyl-L-ornithinamide (Synthon CZ)

Example 1.2.9 (100 mg) and 4-((S)-2-((S)-2-(6-(2,5-dioxo-2,5-dihydro-1H-pyrrol-1-yl)hexanamido)-3-methylbutanamido)-5-ureidopentanamido)benzyl (4-nitrophenyl) carbonate (purchased from Synchem, 114 mg) in N,N-dimethylformamide (7 mL) was cooled in an water-ice bath, and N,N-diisopropylethylamine (0.15 mL) was added. The mixture was stirred at 0° C. for 30 minutes and then at room temperature overnight. The reaction was purified by a reverse phase HPLC using a Gilson system, eluting with 20-60% acetonitrile in water containing 0.1% v/v trifluoroacetic acid, to provide the title compound. ¹H NMR (400 MHz, dimethyl sulfoxide-d₆) δ ppm 12.85 (s, 1H), 9.99 (s, 1H), 8.04 (t, 2H), 7.75-7.82 (m, 2H), 7.40-7.63 (m, 6H), 7.32-7.39 (m, 2H), 7.24-7.29 (m, 3H), 6.99 (s, 2H), 6.95 (d, 1H), 6.01 (s, 1H), 4.83-5.08 (m, 4H), 4.29-4.48 (m, 1H), 4.19 (t, 1H), 3.84-3.94 (m, 2H), 3.80 (d, 2H), 3.14-3.29 (m, 2H), 2.87-3.06 (m, 4H), 2.57-2.69 (m, 2H), 2.03-2.24 (m, 5H), 1.89-2.02 (m, 1H), 1.53-1.78 (m, 2H), 1.26-1.53 (m, 8H), 0.89-1.27 (m, 12H), 0.75-0.88 (m, 12H). MS (ESI) m/e 1452.2 (M+H)⁺.

2.2 Synthesis of N-[6-(2,5-dioxo-2,5-dihydro-1H-pyrrol-1-yl)hexanoyl]-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1³,⁷]dec-1-yl}oxy)ethyl](3-sulfopropyl)carbamoyl}oxy)methyl]phenyl}-N-carbamoyl-L-ornithinamide (Synthon DH)

The title compound was prepared as described in Example 2.1, replacing Example 1.2.9 with Example 1.6.2. ¹H NMR (400 MHz, dimethyl sulfoxide-d₆) δ ppm 12.83 (s, 1H), 9.98 (s, 1H), 8.04 (t, 2H), 7.75-7.81 (m, 2H), 7.54-7.64 (m, 3H), 7.40-7.54 (m, 3H), 7.32-7.39 (m, 2H), 7.24-7.31 (m, 3H), 6.93-7.01 (m, 3H), 4.86-5.03 (m, 4H), 4.32-4.48 (m, 2H), 4.13-4.26 (m, 2H), 3.31-3.45 (m, 4H), 3.24 (d, 4H), 2.88-

3.07 (m, 4H), 2.30-2.39 (m, 2H), 2.04-2.24 (m, 5H), 1.86-2.03 (m, 1H), 0.89-1.82 (m, 27H), 0.74-0.88 (m, 13H). MS (ESI) m/e 1466.3 (M+H)+.

2.3 This paragraph was intentionally left blank 2.4 Synthesis of N-[6-(2,5-dioxo-2,5-dihydro-1H-pyrrol-1-yl)hexanoyl]-L-valyl-N-[4-({[{2-[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethoxy]ethyl}(2-sulfoethyl)carbamoyl]oxy}methyl)phenyl]-N$^5$-carbamoyl-L-ornithinamide (Synthon EP)

The title compound was prepared as described in Example 2.1, replacing Example 1.2.9 with Example 1.11.4. $^1$H NMR (500 MHz, dimethyl sulfoxide-d$_6$) δ ppm 12.85 (s, 1H), 10.00 (s, 1H), 8.01-8.10 (m, 2H), 7.79 (dd, 2H), 7.55-7.65 (m, 3H), 7.41-7.53 (m, 3H), 7.32-7.38 (m, 2H), 7.25-7.30 (m, 3H), 6.97-7.02 (m, 2H), 6.96 (d, 1H), 6.03 (s, 1H), 4.90-5.03 (m, 4H), 4.31-4.46 (m, 1H), 4.20 (s, 1H), 3.88 (t, 2H), 3.82 (s, 2H), 2.97-3.06 (m, 2H), 2.88-2.98 (m, 1H), 2.58-2.68 (m, 2H), 2.05-2.22 (m, 5H), 1.92-2.02 (m, 1H), 0.89-1.75 (m, 23H), 0.77-0.87 (m, 12H). MS (ESI) m/e 1496.3 (M+H)+.

2.5 Synthesis of methyl 6-[4-(3-{[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl]({[4-({N-[6-(2,5-dioxo-2,5-dihydro-1H-pyrrol-1-yl)hexanoyl]-L-valyl-N$^5$-carbamoyl-L-ornithyl}amino)benzyl]oxy}carbonyl)amino}propyl)-1H-1,2,3-triazol-1-yl]-6-deoxy-beta-L-glucopyranoside (Synthon EF)

2.5.1 pent-4-ynal

To a solution of oxalyl chloride (9.12 mL) dissolved in dichloromethane (200 mL) at −78° C. was added dimethyl sulfoxide (14.8 mL) dissolved in dichloromethane (40 mL) over 20 minutes. After the solution was stirred for an additional 30 minutes, 4-pentynol (8.0 g) dissolved in dichloromethane (80 mL) was added over 10 minutes. The reaction mixture was stirred at −78° C. for an additional 60 minutes. Triethylamine (66.2 mL) was added at −78° C., and the reaction mixture was stirred for 60 minutes and then allowed to warm to 10° C. over an additional hour. Water (200 mL) was added, and the two layers were separated. The aqueous layer was acidified with 1% aqueous HCl and then back-extracted with dichloromethane (3×100 mL). The combined organic layers were washed with 1% aqueous HCl, and aqueous NaHCO$_3$. The aqueous extracts were back-extracted with dichloromethane (2×100 mL), and the combined organic extracts were washed with brine and dried over sodium sulfate. After filtration, the solvent was removed by rotary evaporation (30° C. water bath) to provide the title compound.

2.5.2 6-(8-(benzo[d]thiazol-2-ylcarbamoyl)-3,4-dihydroisoquinolin-2(1H)-yl)-3-(1-((3,5-dimethyl-7-(2-(pent-4-yn-1-ylamino)ethoxy)adamantan-1-yl)methyl)-5-methyl-1H-pyrazol-4-yl)picolinic acid To a solution of Example 1.2.7 (85 mg) in tetrahydrofuran (2 mL) was added pent-4-ynal (8.7 mg), acetic acid (20 mg) and sodium sulfate (300 mg). The mixture was stirred for 1 hour, and sodium triacetoxyborohydride (45 mg) was added to the reaction mixture. The mixture was stirred overnight, then diluted with ethyl acetate (200 mL), washed with water and brine, and dried over sodium sulfate. Filtration and evaporation of the solvent gave a residue, which was dissolved in dimethyl sulfoxide/methanol (1:1, 3 mL). The mixture was purified by reverse phase HPLC on a Gilson system, eluting with 10-85% acetonitrile in 0.1% trifluoroacetic acid in water, to give the title compound. MS (ESI) m/e 812.1 (M+H)+.

2.5.3 6-(8-(benzo[d]thiazol-2-ylcarbamoyl)-3,4-dihydroisoquinolin-2(1H)-yl)-3-(1-((3,5-dimethyl-7-(2-((3-(1-(((2S,3R,4R,5S,6S)-3,4,5-trihydroxy-6-methoxytetrahydro-2H-pyran-2-yl)methyl)-1H-1,2,3-triazol-4-yl)propyl)amino)ethoxy)adamantan-1-yl)methyl)-5-methyl-1H-pyrazol-4-yl)picolinic acid To a solution of (2S,3S,4R,5S,6S)-2-(azidomethyl)-6-methoxytetrahydro-2H-pyran-3,4,5-triyl triacetate (8.63 mg) in t-butanol (2 mL) and water (1 mL) was added Example 2.5.2 (20 mg), copper(II) sulfate pentahydrate (2.0 mg) and sodium ascorbate (5 mg). The mixture was stirred 20 minutes at 100° C. under microwave conditions (Biotage Initiator). Lithium hydroxide monohydrate (50 mg) was added to the mixture, and it was stirred overnight. The mixture was neutralized with trifluoroacetic acid and purified by reverse phase HPLC (Gilson system), eluting with 10-85% acetonitrile in 0.1% trifluoroacetic acid in water, to provide the title compound. MS (ESI) m/e 1032.2 (M+H)+.

2.5.4 methyl 6-[4-(3-{[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl]({[4-({N-[6-(2,5-dioxo-2,5-dihydro-1H-pyrrol-1-yl)hexanoyl]-L-valyl-N$^5$-carbamoyl-L-ornithyl}amino)benzyl]oxy}carbonyl)amino}propyl)-1H-1,2,3-triazol-1-yl]-6-deoxy-beta-L-glucopyranoside To a solution of 4-((S)-2-((S)-2-(6-(2,5-dioxo-2,5-dihydro-1H-pyrrol-1-yl)hexanamido)-3-methylbutanamido)-5-ureidopentanamido)benzyl 4-nitrophenyl carbonate (7.16 mg) and Example 2.5.3 (10 mg) in N,N-dimethylformamide (2 mL) was added N,N-diisopropylethylamine (0.1 mL). The mixture was stirred overnight, then acidified with trifluoroacetic acid and purified by reverse phase HPLC (Gilson system), eluting with 10-85% acetonitrile in 0.1% trifluoroacetic acid in water, to provide the title compound. $^1$H NMR (400 MHz, dimethyl sulfoxide-d$_6$) δ ppm 9.65 (s, 1H), 7.97 (d, 1H), 7.76 (d, 1H), 7.64-7.72 (m, 2H), 7.53-7.63 (m, 3H), 7.38-7.51 (m, 4H), 7.30-7.37 (m, 2H), 7.22-7.27 (m, 3H), 6.84-6.98 (m, 3H), 4.97 (d, 4H), 4.65 (dd, 1H), 4.50 (d, 1H), 4.36-4.46 (m, 1H), 4.25-4.32 (m, 1H), 4.10-4.20 (m, 1H), 3.85-3.95 (m, 2H), 3.79 (s, 2H), 3.66-3.73 (m, 2H), 2.99-3.03 (m, 7H), 2.57 (t, 3H), 2.12-2.22 (m, 3H), 2.08 (s, 3H), 1.99-2.05 (m, 2H), 1.70-1.88 (m, 4H), 1.39-1.67 (m, 8H), 1.35 (s, 3H), 0.92-1.28 (m, 14H), 0.80-0.88 (m, 16H). MS (ESI) m/e 1629.5 (M+H)+.

2.6 Synthesis of N-[6-(2,5-dioxo-2,5-dihydro-1H-pyrrol-1-yl)hexanoyl]-L-valyl-N-(4-{[((2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl]{3-[1-(beta-D-glucopyranuronosyl)-1H-1,2,3-triazol-4-yl]propyl}carbamoyl)oxy]methyl}phenyl)-N$^5$-carbamoyl-L-ornithinamide (Synthon EG)

2.6.1 6-(8-(benzo[d]thiazol-2-ylcarbamoyl)-3,4-dihydroisoquinolin-2(1H)-yl)-3-(1-((3-(2-((3-(1-((2R,3R,4S,5S,6S)-6-carboxy-3,4,5-trihydroxytetrahydro-2H-pyran-2-yl)-1H-1,2,3-triazol-4-yl)propyl)amino)ethoxy)-5,7-dimethyladamantan-1-yl)methyl)-5-methyl-1H-pyrazol-4-yl)picolinic acid To a solution of (2R,3R,4S,5S,6S)-2-azido-6-(methoxycarbonyl)tetrahydro-2H-pyran-3,4,5-triyl triacetate (8.63 mg) in t-butanol (2 mL) and water (1 mL) was added Example 2.5.2 (20 mg), copper(II) sulfate pentahydrate (2.0 mg) and sodium ascorbate (5 mg). The mixture was stirred 20 minutes at 100° C. under microwave conditions (Biotage Initiator). Lithium hydroxide monohydrate (50 mg) was added to the mixture, and it was stirred overnight. The mixture was neutralized with trifluoroacetic acid and purified by reverse phase HPLC (Gilson system) eluting with 10-85% acetonitrile in 0.1% trifluoroacetic acid in water, to provide the title compound. MS (ESI) m/e 1032.1 (M+H)$^+$.

2.6.2 N-[6-(2,5-dioxo-2,5-dihydro-1H-pyrrol-1-yl)hexanoyl]-L-valyl-N-(4-{[((2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl]{3-[1-(beta-D-glucopyranuronosyl)-1H-1,2,3-triazol-4-yl]propyl}carbamoyl)oxy]methyl}phenyl)-N$^5$-carbamoyl-L-ornithinamide The title compound was prepared by substituting Example 2.6.1 for Example 2.5.3 in Example 2.5.4. $^1$H NMR (400 MHz, dimethyl sulfoxide-d$_6$) δ ppm 9.64 (s, 1H), 7.98 (d, 1H), 7.90 (s, 1H), 7.76 (d, 1H), 7.68 (s, 1H), 7.52-7.62 (m, 3H), 7.20-7.50 (m, 9H), 6.84-6.98 (m, 3H), 5.56 (d, 1H), 4.98 (d, 4H), 4.36-4.49 (m, 4H), 4.11-4.23 (m, 2H), 3.96 (d, 2H), 3.74-3.91 (m, 7H), 3.51-3.58 (m, 5H), 3.35-3.49 (m, 10H), 2.97-3.02 (m, 6H), 2.57-2.66 (m, 3H), 2.12-2.24 (m, 2H), 2.08 (s, 3H), 1.69-2.01 (m, 3H), 1.35-1.65 (m, 9H), 0.93-1.28 (m, 10H), 0.81-0.89 (m, 10H). MS (ESI) m/e 1629.4 (M+H)$^+$.

2.7 Synthesis of N-[6-(2,5-dioxo-2,5-dihydro-1H-pyrrol-1-yl)hexanoyl]-L-valyl-N-{4-[({[(2R)-1-{[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](methyl)amino}-1-oxo-3-sulfopropan-2-yl]carbamoyl}oxy)methyl]phenyl}-L-alaninamide (Synthon EH)

To a solution of Example 1.13.8 (0.018 g) and 4-((S)-2-((S)-2-(6-(2,5-dioxo-2,5-dihydro-1H-pyrrol-1-yl)hexanamido)-3-methylbutanamido)propanamido)benzyl (4-nitrophenyl) carbonate (0.015 g, 0.023 mmol) in N,N-dimethylformamide (0.75 mL) was added N,N-diisopropylethylamine (0.015 mL). After stirring overnight, the reaction was diluted with N,N-dimethylformamide (0.75 mL) and water (0.5 mL). The mixture was purified by reverse phase HPLC using a Gilson system, eluting with 10-70% acetonitrile in water containing 0.1% v/v trifluoroacetic acid. The desired fractions were combined and freeze-dried to provide the title compound. $^1$H NMR (500 MHz, dimethyl sulfoxide-d$_6$) δ ppm 12.86 (s, 1H), 9.93 (s, 1H), 8.14 (d, 1H), 8.04 (d, 1H), 7.84-7.76 (m, 2H), 7.61 (d, 1H), 7.57 (d, 2H), 7.53 (dd, 1H), 7.47 (t, 1H), 7.43 (d, 1H), 7.39-7.30 (m, 4H), 7.26 (d, 2H), 6.99 (s, 2H), 6.97 (dd, 1H), 4.96 (s, 2H), 4.90 (t, 2H), 4.75-4.65 (m, 1H), 4.46-4.33 (m, 2H), 4.17 (dd, 2H), 3.66-3.47 (m, 4H), 3.36 (t, 4H), 3.12 (s, 2H), 3.01 (t, 2H), 2.85-2.60 (m, 4H), 2.25-2.05 (m, 5H), 2.05-1.90 (m, 1H), 1.58-0.76 (m, 32H). MS (ESI) m/e 1423.2 (M+H)$^+$.

2.8 Synthesis of N-[6-(2,5-dioxo-2,5-dihydro-1H-pyrrol-1-yl)hexanoyl]-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl][4-(beta-D-glucopyranosyloxy)benzyl]carbamoyl}oxy)methyl]phenyl}-N$^5$-carbamoyl-L-ornithinamide (Synthon ER)

2.8.1 6-(8-(benzo[d]thiazol-2-ylcarbamoyl)-3,4-dihydroisoquinolin-2(1H)-yl)-3-(1-((3,5-dimethyl-7-(2-((4-(((2S,3R,4S,5S,6R)-3,4,5-trihydroxy-6-(hydroxymethyl)tetrahydro-2H-pyran-2-yl)oxy)benzyl)amino)ethoxy)adamantan-1-yl)methyl)-5-methyl-1H-pyrazol-4-yl)picolinic acid To a solution of Example 1.2.7 (44.5 mg) in tetrahydrofuran (2 mL) and acetic acid (0.2 mL) was added 4-(((2S,3R,4S,5S,6R)-3,4,5-trihydroxy-6-(hydroxymethyl)tetrahydro-2H-pyran-2-yl)oxy)benzaldehyde (17 mg) and MgSO$_4$ (300 mg). The mixture was stirred for 1 hour before the addition of sodium cyanoborohydride on resin (300 mg). The mixture was stirred overnight. The mixture was filtered, and the solvent was evaporated. The residue was dissolved in dimethyl sulfoxide/methanol (1:1, 4 mL) and purified by reverse phase HPLC (Gilson system), eluting with 10-85% acetonitrile in 0.1% trifluoroacetic acid in water, to give the title compound. MS (ESI) m/e 1015.2 (M+H)$^+$.

2.8.2 N-[6-(2,5-dioxo-2,5-dihydro-1H-pyrrol-1-yl)hexanoyl]-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl][4-(beta-D-glucopyranosyloxy)benzyl]carbamoyl}oxy)methyl]phenyl}-N$^5$-carbamoyl-L-ornithinamide The title compound was prepared by substituting Example 2.8.1 for Example 2.5.3 in Example 2.5.4. $^1$H NMR (400 MHz, dimethyl sulfoxide-d$_6$) δ ppm 12.87 (s, 1H), 10.00 (s, 1H), 7.96-8.14 (m, 2H), 7.79 (d, 2H), 7.55-7.68 (m, 3H), 7.09-7.52 (m, 11H), 6.91-7.01 (m, 5H), 5.09 (d, 1H), 4.95 (dd, 4H), 4.35-4.47 (m, 4H), 4.14-4.23 (m, 3H), 3.86-3.94 (m, 6H), 3.31-3.46 (m, 8H), 3.16-3.25 (m, 3H), 2.90-3.04 (m, 4H), 2.59 (s, 1H), 1.88-2.24 (m, 6H), 0.88-1.75 (m, 24H), 0.76-0.90 (m, 12H). MS (ESI) m/e 1613.7 (M+H)$^+$.

2.9 Synthesis of N-[6-(2,5-dioxo-2,5-dihydro-1H-pyrrol-1-yl)hexanoyl]-L-valyl-N-{4-[({[4-(beta-D-allopyranosyloxy)benzyl][2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl]carbamoyl}oxy)methyl]phenyl}-N$^5$-carbamoyl-L-ornithinamide (Synthon ES)

2.9.1 6-(8-(benzo[d]thiazol-2-ylcarbamoyl)-3,4-dihydroisoquinolin-2(1H)-yl)-3-(1-(((3,5-dimethyl-7-(2-((4-(((2S,3R,4R,5S,6R)-3,4,5-trihydroxy-6-(hydroxymethyl)tetrahydro-2H-pyran-2-yl)oxy)benzyl)amino)ethoxy)adamantan-1-yl)methyl)-5-methyl-1H-pyrazol-4-yl)picolinic acid To a solution of Example 1.2.7 (44.5 mg) in tetrahydrofuran (2 mL) and acetic acid (0.2 mL) was added 4-(((2S,3R,4R,5S,6R)-3,4,5-trihydroxy-6-(hydroxymethyl)tetrahydro-2H-pyran-2-yl)oxy)benzaldehyde (17 mg) and MgSO$_4$ (300 mg). The mixture was stirred for 1 hour before the addition of sodium cyanoborohydride on resin (300 mg). The mixture was stirred overnight. The mixture was filtered, and the solvent was evaporated. The residue was dissolved in dimethyl sulfoxide/methanol (1:1, 4 mL) and purified by reverse phase HPLC (Gilson system), eluting with 10-85% acetonitrile in 0.1% trifluoroacetic acid in water, to give the title compound. MS (ESI) m/e 1015.2 (M+H)$^+$.

2.9.2 N-[6-(2,5-dioxo-2,5-dihydro-1H-pyrrol-1-yl)hexanoyl]-L-valyl-N-{4-[({[4-(beta-D-allopyranosyloxy)benzyl][2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl]carbamoyl}oxy)methyl]phenyl}-N$^5$-carbamoyl-L-ornithinamide The title compound was prepared by substituting Example 2.9.1 for Example 2.5.3 in Example 2.5.4. $^1$H NMR (500 MHz, dimethyl sulfoxide-d$_6$) δ ppm 12.86 (s, 1H), 10.00 (s, 1H), 7.96-8.11 (m, 2H), 7.79 (d, 2H), 7.53-7.65 (m, 3H), 7.08-7.52 (m, 10H), 6.91-7.00 (m, 5H), 5.09 (d, 1H), 4.99 (d, 4H), 4.35-4.48 (m, 3H), 4.13-4.23 (m, 2H), 3.82-3.96 (m, 8H), 3.32-3.50 (m, 10H), 3.12-3.25 (m, 3H), 2.90-3.06 (m, 5H), 1.89-2.19 (m, 6H), 0.88-1.75 (m, 22H), 0.76-0.88 (m, 11H). MS (ESI) m/e 1612.5 (M+H)$^+$.

2.10 Synthesis of N-[6-(2,5-dioxo-2,5-dihydro-1H-pyrrol-1-yl)hexanoyl]-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-phosphonoethyl)carbamoyl}oxy)methyl]phenyl}-N$^5$-carbamoyl-L-ornithinamide (Synthon EQ)

The title compound was prepared as described in Example 2.1, replacing Example 1.2.9 with Example 1.12.2. $^1$H NMR (500 MHz, dimethyl sulfoxide-d$_6$) δ ppm 9.99 (s, 1H), 8.01-8.09 (m, 2H), 7.76-7.81 (m, 2H), 7.56-7.64 (m, 3H), 7.41-7.53 (m, 3H), 7.36 (q, 2H), 7.25-7.30 (m, 3H), 6.99 (s, 2H), 6.94 (d, 1H), 5.98 (s, 1H), 4.89-5.07 (m, 4H), 4.38 (s, 1H), 4.19 (t, 1H), 3.88 (t, 2H), 3.80 (d, 2H), 2.89-3.08 (m, 5H), 2.04-2.24 (m, 5H), 1.89-2.02 (m, 1H), 1.76-1.87 (m, 2H), 0.89-1.72 (m, 23H), 0.78-0.88 (m, 12H). MS (ESI) m/e 1452.2 (M+H)$^+$.

2.11 Synthesis of N-[6-(2,5-dioxo-2,5-dihydro-1H-pyrrol-1-yl)hexanoyl]-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-phosphonoethyl)carbamoyl}oxy)methyl]phenyl}-L-alaninamide (Synthon EU)

The title compound was prepared as described in Example 2.1, replacing Example 1.2.9 and 4-((S)-2-((S)-2-(6-(2,5-dioxo-2,5-dihydro-1H-pyrrol-1-yl)hexanamido)-3-methylbutanamido)-5-ureidopentanamido)benzyl (4-nitrophenyl) carbonate with Example 1.12.2 and 4-((S)-2-((S)-2-(6-(2,5-dioxo-2,5-dihydro-1H-pyrrol-1-yl)hexanamido)-3-methylbutanamido)propanamido)benzyl (4-nitrophenyl) carbonate, respectively. $^1$H NMR (400 MHz, dimethyl sulfoxide-d$_6$) δ ppm 9.93 (s, 1H), 8.12 (d, 1H), 8.03 (d, 1H), 7.72-7.83 (m, 2H), 7.54-7.65 (m, 3H), 7.41-7.54 (m, 3H), 7.31-7.40 (m, 2H), 7.24-7.30 (m, 3H), 6.99 (s, 2H), 6.94 (d, 1H), 4.87-5.11 (m, 3H), 4.11-4.45 (m, 1H), 3.88 (t, 2H), 3.79 (d, 2H), 2.97-3.05 (m, 2H), 2.63-2.70 (m, 1H), 2.29-2.37 (m, 1H), 2.03-2.20 (m, 5H), 1.73-2.00 (m, 5H), 1.39-1.55 (m, 4H), 0.88-1.38 (m, 19H), 0.72-0.89 (m, 12H). MS (ESI) m/e 1364.5 (M−H)$^−$.

2.12 Synthesis of N-[6-(2,5-dioxo-2,5-dihydro-1H-pyrrol-1-yl)hexanoyl]-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](3-phosphonopropyl)carbamoyl}oxy)methyl]phenyl}-N-carbamoyl-L-ornithinamide (Synthon EV)

The title compound was prepared as described in Example 2.1, replacing Example 1.2.9 with Example 1.14.4. $^1$H NMR (400 MHz, dimethyl sulfoxide-d$_6$) δ ppm 9.98 (s, 1H), 8.04 (t, 2H), 7.78 (t, 2H), 7.61 (t, 3H), 7.39-7.54 (m, 3H), 7.32-7.39 (m, 2H), 7.25-7.30 (m, 3H), 6.99 (s, 2H), 6.95 (d, 1H), 6.01 (s, 1H), 4.97 (d, 4H), 4.29-4.47 (m, 2H), 4.14-4.23 (m, 2H), 3.85-3.93 (m, 2H), 3.32-3.42 (m, 2H), 3.24 (s, 2H), 2.88-3.09 (m, 3H), 1.87-2.23 (m, 6H), 0.91-1.74 (m, 27H), 0.72-0.89 (m, 12H). MS (ESI) m/e 1466.3 (M+H)$^+$.

2.13 Synthesis of N-[6-(2,5-dioxo-2,5-dihydro-1H-pyrrol-1-yl)hexanoyl]-L-valyl-N-{4-[({[(2R)-1-{[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl]amino}-1-oxo-3-sulfopropan-2-yl]carbamoyl}oxy)methyl]phenyl}-L-alaninamide (Synthon EW)

To a solution of Example 1.15 (0.020 g) and 4-((S)-2-((S)-2-(6-(2,5-dioxo-2,5-dihydro-1H-pyrrol-1-yl)hexanamido)-3-methylbutanamido)propanamido)benzyl (4-nitrophenyl) carbonate (0.017 g) in N,N-dimethylformamide (0.5 mL) was added N,N-diisopropylethylamine (0.017 mL). The reaction was stirred overnight and was diluted with N,N-dimethylformamide (1 mL), water (0.5 mL). The mixture was purified by reverse phase HPLC using a Gilson system, eluting with 10-70% acetonitrile in water containing 0.1% v/v trifluoroacetic acid. The desired fractions were combined and freeze-dried to provide the title compound. $^1$H NMR (400 MHz, dimethyl sulfoxide-d$_6$) δ ppm 12.85 (s, 1H), 9.93 (s, 1H), 8.12 (d, 1H), 8.04 (d, 1H), 7.86-7.76 (m, 3H), 7.63-7.41 (m, 7H), 7.39-7.32 (m, 2H), 7.30 (s, 1H), 7.30-7.21 (m, 2H), 6.99 (s, 2H), 6.97 (d, 1H), 4.96 (s, 2H), 4.93 (s, 2H), 4.49-4.33 (m, 2H), 4.18 (dd, 2H), 4.15-4.08 (m, 2H), 3.90-3.86 (m, 2H), 3.36 (t, 2H), 3.34-3.27 (m, 1H), 3.18-3.04 (m, 2H), 3.04-2.96 (m, 2H), 2.89-2.61 (m, 2H), 2.27-2.05 (m, 5H), 2.03-1.87 (m, 1H), 1.59-1.42 (m, 4H), 1.42-0.91 (m, 18H), 0.91-0.76 (m, 11H). MS (-ESI) m/e 1407.5 (M−H)−.

2.14 Synthesis of N-[6-(2,5-dioxo-2,5-dihydro-1H-pyrrol-1-yl)hexanoyl]-L-valyl-N-[4-({[{2-[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethoxy]ethyl}(3-phosphonopropyl)carbamoyl]oxy}methyl)phenyl]-N$^5$-carbamoyl-L-ornithinamide (Synthon EX)

A mixture of Example 1.16.2 (59 mg), 4-((S)-2-((S)-2-(6-(2,5-dioxo-2,5-dihydro-1H-pyrrol-1-yl)hexanamido)-3-methylbutanamido)-5-ureidopentanamido)benzyl (4-nitrophenyl) carbonate (48 mg), and N,N-diisopropylethylamine (0.056 mL) in 2 mL N,N-dimethylformamide was stirred for 24 hours. The mixture was purified via reverse phase chromatography on a Biotage Isolera One system using a 40 g C18 column, eluting with 10-90% acetonitrile in 0.1% trifluoroacetic acid/water. The desired fractions were concentrated and the product was lyophilized from water and 1,4-dioxane to give the title compound as a trifluoroacetic acid salt. $^1$H NMR (400 MHz, dimethyl sulfoxide-d$_6$) δ ppm 9.97 (bs, 1H), 8.04 (m, 2H), 7.79 (d, 2H), 7.59 (m, 3H), 7.46 (m, 3H), 7.36 (m, 2H), 7.27 (m, 2H), 6.99 (s, 2H), 6.94 (d, 1H), 4.97 (m, 4H), 4.40 (m, 2H), 4.17 (dd, 2H), 3.50-4.10 (m, 6H), 3.45 (m, 2H), 3.40 (m, 2H), 3.26 (m, 2H), 3.01 (m, 2H), 2.95 (s, 2H), 2.79 (s, 2H), 2.15 (m, 2H), 2.09 (s, 2H), 1.68 (m, 2H), 1.60 (m, 1-2H), 1.35-1.50 (m, 6H), 1.25 (m, 4H), 1.17 (m, 2H), 1.10 (m, 2H), 0.97 (m, 1-2H), 0.84 (m, 12H). MS (ESI) m/e 1510.4 (M+H)+.

2.15 Synthesis of N-[6-(2,5-dioxo-2,5-dihydro-1H-pyrrol-1-yl)hexanoyl]-L-valyl-N-[4-({[{2-[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethoxy]ethyl}(3-phosphonopropyl)carbamoyl]oxy}methyl)phenyl]-L-alaninamide (Synthon EY)

A mixture of Example 1.16.2 (59 mg), 4-((S)-2-((S)-2-(6-(2,5-dioxo-2,5-dihydro-1H-pyrrol-1-yl)hexanamido)-3-methylbutanamido)propanamido)benzyl (4-nitrophenyl) carbonate (42 mg), and N,N-diisopropylethylamine (0.042 mg) in 2 mL N,N-dimethylformamide was stirred for 24 hours. The mixture was purified via reverse phase chromatography on a Biotage Isolera One system using a 40 g C18 column, eluting with 10-90% acetonitrile in 0.1% trifluoroacetic acid/water. Fractions were concentrated and the product was lyophilized from water and 1,4-dioxane to give the title compound as a trifluoroacetic acid salt. MS (ESI) m/e 1422.6 (M−H)+.

2.16 Synthesis of N-[6-(2,5-dioxo-2,5-dihydro-1H-pyrrol-1-yl)hexanoyl]-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](3-phosphonopropyl)carbamoyl}oxy)methyl]phenyl}-L-alaninamide (Synthon EZ)

A mixture of Example 1.14.4 (50 mg), 4-((S)-2-((S)-2-(6-(2,5-dioxo-2,5-dihydro-1H-pyrrol-1-yl)hexanamido)-3-methylbutanamido)propanamido)benzyl (4-nitrophenyl) carbonate (38 mg), and N,N-diisopropylethylamine (0.050 mL) in 2 mL N,N-dimethylformamide was stirred for 24 hours. The mixture was purified via reverse phase chromatography on a Biotage Isolera One system using a 40 g C18 column, eluting with 10-90% acetonitrile in 0.1% trifluoroacetic acid/water. The desired fractions were concentrated and the product was lyophilized from water and 1,4-dioxane to give the title compound as a trifluoroacetic acid salt. $^1$H NMR (400 MHz, dimethyl sulfoxide-d$_6$) δ ppm 9.94 (bs, 1H), 8.12 (d, 1H), 8.04 (d, 1H), 7.80 (d, 2H), 7.61 (m, 3H), 7.47 (m, 3H), 7.36 (m, 2H), 7.29 (m, 2H), 6.99 (s, 2H), 6.95 (d, 1H), 4.97 (m, 4H), 4.40 (m, 2H), 4.16 (dd, 2H), 3.50-4.10 (m, 6H), 3.68 (m, 2H), 3.55 (m, 2H), 3.25 (m, 4H), 3.02 (m, 2H), 2.94 (s, 2H), 2.79 (s, 2H), 2.15 (m, 1H), 2.08 (s, 2H), 1.65 (m, 2H), 1.40-1.50 (m, 6H), 1.20-1.30 (m, 6H), 1.08-1.19 (m, 4H), 0.97 (m, 1-2H), 0.76-0.89 (m, 12H). MS (ESI) m/e 1380.3 (M+H)+.

2.17 Synthesis of 6-[8-(1,3-benzothiazol-2-ylcarbamoyl)-3,4-dihydroisoquinolin-2(1H)-yl]-3-(1-{[3-(2-{[(2)-2-({[(4-{(2S)-2-{[(2S)-2-{[6-(2,5-dioxo-2,5-dihydro-1H-pyrrol-1-yl)hexanoyl]amino}-3-methylbutanoyl]amino}propanoyl]amino}benzyl)oxy]carbonyl}amino)propanoyl](methyl)amino}ethoxy)-5,7-dimethyltricyclo[3.3.1.1$^{3,7}$]dec-1-yl]methyl}-5-methyl-1H-pyrazol-4-yl)pyridine-2-carboxylic acid (Synthon FD)

To a solution of Example 1.17 (0.040 g) and 4-((S)-2-((S)-2-(6-(2,5-dioxo-2,5-dihydro-1H-pyrrol-1-yl)hexanamido)-3-methylbutanamido)propanamido)benzyl (4-nitrophenyl) carbonate (0.034 g) in N,N-dimethylformamide (1 mL) was added N,N-diisopropylethylamine (0.035 mL). The reaction was stirred overnight and diluted with N,N-dimethylformamide (1 mL) and water (0.5 mL). The mixture was purified by reverse phase HPLC using a Gilson system, eluting with 10-70% acetonitrile in water containing 0.1% v/v trifluoroacetic acid. The desired fractions were combined and freeze-dried to provide the title compound. $^1$H NMR (400 MHz, dimethyl sulfoxide-d$_6$) δ ppm 12.84 (s, 1H), 9.92 (s, 1H), 8.13 (d, 1H), 8.03 (d, 1H), 7.79 (d, 2H), 7.62 (d, 1H), 7.57 (d, 2H), 7.54-7.41 (m, 3H), 7.40-7.32 (m, 2H), 7.31-7.23 (m, 4H), 6.99 (s, 2H), 6.95 (dd, 1H), 5.01-4.89 (m, 4H), 4.78 (dq, 1H), 4.45-4.30 (m, 1H), 4.23-4.11 (m, 1H), 3.88 (t, 2H), 3.80 (s, 2H), 3.42-3.26 (m, 6H), 3.06 (s, 1H), 3.01 (t, 2H), 2.80 (s, 2H), 2.76-2.62 (m, 1H), 2.46-2.36 (m, 1H), 2.25-2.05 (m, 5H), 2.05-1.92 (m, 1H), 1.58-1.42 (m, 4H), 1.42-0.91 (m, 20H), 0.91-0.78 (m, 9H). MS (ESI) m/e 1387.4 (M+H)+.

2.18 Synthesis of N-[6-(2,5-dioxo-2,5-dihydro-1H-pyrrol-1-yl)hexanoyl]-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl][4-(beta-D-glucopyranuronosyloxy)benzyl]carbamoyl}oxy)methyl]phenyl}-N$^5$-carbamoyl-L-ornithinamide (Synthon FS)

The title compound was prepared by substituting Example 1.19.2 for Example 2.5.3 in Example 2.5.4. $^1$H NMR (500 MHz, dimethyl sulfoxide-d$_6$) δ ppm 12.86 (s, 1H), 10.00 (s, 1H), 7.97-8.14 (m, 2H), 7.79 (d, 2H), 7.07-7.65 (m, 13H), 6.87-7.01 (m, 4H), 5.92-6.08 (m, 1H), 4.87-5.07 (m, 4H), 4.33-4.48 (m, 3H), 4.13-4.26 (m, 1H), 3.74-3.94 (m, 6H), 3.14-3.34 (m, 8H), 2.84-3.05 (m, 6H), 1.87-2.25 (m, 6H), 0.89-1.73 (m, 21H), 0.76-0.87 (m, 12H). MS (ESI) m/e 1626.4 (M+H)$^+$.

2.19 Synthesis of N-[6-(2,5-dioxo-2,5-dihydro-1H-pyrrol-1-yl)hexanoyl]-L-valyl-N-{4-[({[2-({3-[(4-{6-[1-(1,3-benzothiazol-2-ylcarbamoyl)-1,2,3,4-tetrahydroquinolin-7-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-phosphonoethyl)carbamoyl}oxy)methyl]phenyl}-N-carbamoyl-L-ornithinamide (Synthon FI)

The title compound was prepared as described in Example 2.1, replacing Example 1.2.9 with Example 1.20.11. $^1$H NMR (500 MHz, dimethyl sulfoxide-d$_6$) δ ppm 10.00 (s, 1H), 8.40 (s, 1H), 8.07 (d, 1H), 8.00 (d, 1H), 7.84-7.90 (m, 1H), 7.79 (dd, 3H), 7.55-7.66 (m, 2H), 7.46 (s, 2H), 7.37 (t, 1H), 7.29 (t, 3H), 7.18-7.25 (m, 1H), 6.99 (s, 2H), 5.99 (s, 1H), 5.00 (d, 1H), 4.38 (s, 1H), 4.13-4.24 (m, 1H), 3.96 (s, 2H), 3.87 (d, 2H), 2.88-3.08 (m, 4H), 2.84 (q, 2H), 2.04-2.26 (m, 5H), 1.89-2.01 (m, 3H), 1.75-1.88 (m, 2H), 1.63-1.74 (m, 1H), 0.91-1.63 (m, 21H), 0.76-0.89 (m, 12H). MS (ESI) m/e 1450.5 (M−H)$^-$.

2.20 Synthesis of N-[6-(2,5-dioxo-2,5-dihydro-1H-pyrrol-1-yl)hexanoyl]-L-valyl-N$^5$-carbamoyl-N-{4-[({[2-({3-[(4-{2-carboxy-6-[8-([1,3]thiazolo[5,4-b]pyridin-2-ylcarbamoyl)-3,4-dihydroisoquinolin-2(1H)-yl]pyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]phenyl}-L-ornithinamide (Synthon FV)

The title compound was prepared by substituting Example 1.22.5 for Example 1.2.9 in Example 2.1. $^1$H NMR (500 MHz, dimethyl sulfoxide-d$_6$) δ ppm 13.00 (v br s, 1H), 10.00 (s, 1H), 8.52 (dd, 1H), 8.16 (dd, 1H), 8.06 (d, 1H), 7.78 (d, 1H), 7.62 (d, 1H), 7.59 (br m, 2H), 7.53 (m, 2H), 7.45 (d, 1H), 7.37 (t, 1H), 7.30 (s, 1H) 7.27 (d, 2H), 6.99 (s, 2H), 6.97 (d, 1H), 4.98 (m, 4H), 4.39 (m, 1H), 4.19 (br m, 1H), 3.88 (t, 2H), 3.80 (br d, 2H), 3.44, 3.36 (br m, m, total 6H), 3.24 (m, 2H), 2.94-3.01 (m, 4H), 2.63 (br m, 2H), 2.14 (m, 2H), 2.10 (s, 3H), 1.97 (br m, 1H), 1.68 (br m, 1H), 1.58 (br m, 1H), 1.34-1.47 (m, 8H), 1.08-1.23 (m 10H), 0.95 (br m, 2H), 0.85-0.80 (m, 12H). MS (ESI) m/e 1451.4 (M−H)$^-$.

2.21 Synthesis of N-[6-(2,5-dioxo-2,5-dihydro-1H-pyrrol-1-yl)hexanoyl]-L-valyl-N-{4-[({[(2R)-1-{[2-({3-[(4-{6-[1-(1,3-benzothiazol-2-ylcarbamoyl)-1,2,3,4-tetrahydroquinolin-7-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](methyl)amino}-1-oxo-3-sulfopropan-2-yl]carbamoyl}oxy)methyl]phenyl}-N$^5$-carbamoyl-L-ornithinamide (Synthon GC)

The title compound was prepared as described in Example 2.1, replacing Example 1.2.9 with Example 1.21.7. $^1$H NMR (500 MHz, dimethyl sulfoxide-d$_6$) δ ppm 9.98 (s, 1H), 8.40 (s, 1H), 8.07 (d, 1H), 8.01 (dd, 1H), 7.89 (t, 1H), 7.74-7.84 (m, 3H), 7.58 (d, 2H), 7.47 (s, 2H), 7.37 (t, 1H), 7.19-7.33 (m, 5H), 7.00 (s, 2H), 4.91 (q, 2H), 4.64-4.76 (m, 2H), 4.33-4.43 (m, 2H), 4.15-4.24 (m, 2H), 3.92-4.03 (m, 2H), 3.88 (s, 2H), 3.32-3.50 (m, 6H), 3.10-3.22 (m, 2H), 2.89-3.07 (m, 2H), 2.70-2.89 (m, 4H), 2.60-2.70 (m, 1H), 2.05-2.28 (m, 5H), 1.90-2.03 (m, 3H), 1.64-1.77 (m, 1H), 1.53-1.65 (m, 1H), 0.92-1.53 (m, 21H), 0.77-0.92 (m, 12H). MS (ESI) m/e 1507.3 (M−H)$^-$.

2.22 Synthesis of N-[6-(2,5-dioxo-2,5-dihydro-1H-pyrrol-1-yl)hexanoyl]-L-valyl-N-{4-[({[(2R)-1-{[2-({3-[(4-{6-[1-(1,3-benzothiazol-2-ylcarbamoyl)-1,2,3,4-tetrahydroquinolin-7-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](methyl)amino}-1-oxo-3-sulfopropan-2-yl]carbamoyl}oxy)methyl]phenyl}-L-alaninamide (Synthon GB)

The title compound was prepared as described in Example 2.1, replacing Example 1.2.9 and 4-((S)-2-((S)-2-(6-(2,5-dioxo-2,5-dihydro-1H-pyrrol-1-yl)hexanamido)-3-methylbutanamido)-5-ureidopentanamido)benzyl (4-nitrophenyl) carbonate with Example 1.21.7 and 4-((S)-2-((S)-2-(6-(2,5-dioxo-2,5-dihydro-1H-pyrrol-1-yl)hexanamido)-3-methylbutanamido)propanamido)benzyl (4-nitrophenyl) carbonate, respectively. $^1$H NMR (500 MHz, dimethyl sulfoxide-d$_6$) δ ppm 9.93 (s, 1H), 8.39 (s, 1H), 8.13 (d, 1H), 8.01 (dd, 1H), 7.88 (t, 1H), 7.74-7.84 (m, 3H), 7.57 (d, 2H), 7.46 (s, 2H), 7.37 (t, 1H), 7.17-7.33 (m, 5H), 6.99 (s, 2H), 4.91 (d, 2H), 4.65-4.76 (m, 1H), 4.30-4.51 (m, 1H), 4.13-4.21 (m, 1H), 3.92-4.00 (m, 2H), 3.88 (s, 2H), 3.29-3.46 (m, 4H), 2.93-3.21 (m, 3H), 2.68-2.88 (m, 4H), 2.58-2.68 (m, 1H), 2.04-2.26 (m, 5H), 1.89-2.02 (m, 3H), 1.37-1.54 (m, 6H), 0.92-1.34 (m, 15H), 0.75-0.91 (m, 12H). MS (ESI) m/e (M+H)$^+$.

2.23 Synthesis of N-[6-(2,5-dioxo-2,5-dihydro-1H-pyrrol-1-yl)hexanoyl]-L-valyl-N$^5$-carbamoyl-N-{4-[({[2-({3-[(4-{2-carboxy-6-[8-([1,3]thiazolo[4,5-b]pyridin-2-ylcarbamoyl)-3,4-dihydroisoquinolin-2(1H)-yl]pyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]phenyl}-L-ornithinamide (Synthon FW)

The title compound was prepared by substituting Example 1.23.4 for Example 1.2.9 in Example 2.1. $^1$H NMR (500 MHz, dimethyl sulfoxide-d$_6$) δ ppm 13.38 (v br s, 1H), 10.00 (s, 1H), 8.66 (m, 2H), 8.06 (d, 1H), 7.78 (d, 1H), 7.65 (d, 1H), 7.59 (br m, 2H), 7.53 (m, 1H), 7.47 (m 2H), 7.37 (t, 1H), 7.30 (s, 1H) 7.27 (d, 2H), 6.99 (s, 2H), 6.97 (d, 1H), 4.98 (m, 4H), 4.39 (m, 1H), 4.19 (br m, 1H), 3.88 (t, 2H), 3.80 (br d, 2H), 3.40 (br m, 6H), 3.24 (m, 2H), 2.98 (m, 4H), 2.63 (m, 2H), 2.16 (m, 2H), 2.10 (s, 3H), 1.97 (br m, 1H), 1.68 (br m, 1H), 1.58 (br m, 1H), 1.34-1.47 (m, 8H), 1.08-1.23 (m, 10H), 0.95 (br m, 2H), 0.85-0.80 (m, 12H). MS (ESI) m/e 1451.5 (M−H)⁻.

2.24 Synthesis of N-[6-(2,5-dioxo-2,5-dihydro-1H-pyrrol-1-yl)hexanoyl]-L-valyl-N-{4-[({[2-({3-[(4-{6-[1-(1,3-benzothiazol-2-ylcarbamoyl)-1,2,3,4-tetrahydroquinolin-7-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]phenyl}-N$^5$-carbamoyl-L-ornithinamide (Synthon GD)

The title compound was prepared as described in Example 2.1, replacing Example 1.2.9 with Example 1.24.2. ¹H NMR (500 MHz, dimethyl sulfoxide-d₆) δ ppm 10.00 (s, 1H), 8.38 (s, 1H), 8.07 (d, 1H), 8.00 (d, 1H), 7.85-7.92 (m, 1H), 7.73-7.85 (m, 3H), 7.55-7.65 (m, 2H), 7.46 (s, 2H), 7.37 (t, 1H), 7.28 (t, 3H), 7.22 (t, 1H), 6.99 (s, 2H), 6.00 (s, 1H), 4.99 (d, 1H), 4.28-4.50 (m, 1H), 4.19 (s, 1H), 3.77-4.03 (m, 4H), 3.31-3.41 (m, 2H), 3.20-3.29 (m, 2H), 2.87-3.08 (m, 3H), 2.83 (t, 2H), 2.63 (d, 2H), 2.05-2.25 (m, 5H), 1.88-2.01 (m, 3H), 1.69 (t, 1H), 1.53-1.63 (m, 1H), 1.31-1.53 (m, 8H), 1.04-1.29 (m, 11H), 0.89-1.02 (m, 2H), 0.77-0.88 (m, 12H). MS (ESI) m/e 1450.4 (M−H)⁻.

2.25 Synthesis of N-[6-(2,5-dioxo-2,5-dihydro-1H-pyrrol-1-yl)hexanoyl]-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-carboxyethyl)carbamoyl}oxy)methyl]phenyl}-N$^5$-carbamoyl-L-ornithinamide (Synthon GK)

The title compound was prepared as described in Example 2.1, replacing Example 1.2.9 with Example 1.25.2. ¹H NMR (400 MHz, dimethyl sulfoxide-d₆) δ ppm 12.85 (s, 1H), 9.98 (s, 1H), 8.04 (t, 2H), 7.75-7.82 (m, 2H), 7.60 (t, 3H), 7.41-7.53 (m, 3H), 7.32-7.39 (m, 2H), 7.24-7.29 (m, 3H), 6.99 (s, 2H), 6.94 (d, 3H), 5.97 (s, 1H), 4.88-5.04 (m, 4H), 4.38 (d, 1H), 4.12-4.24 (m, 1H), 3.88 (t, 2H), 3.75-3.84 (m, 2H), 3.32-3.40 (m, 2H), 3.28 (d, 2H), 2.90-3.05 (m, 4H), 2.42-2.49 (m, 2H), 2.05-2.22 (m, 5H), 1.87-2.01 (m, 1H), 0.90-1.76 (m, 22H), 0.74-0.88 (m, 12H). MS (ESI) m/e 1414.5 (M−H)⁻.

2.26 Synthesis of N-[6-(2,5-dioxo-2,5-dihydro-1H-pyrrol-1-yl)hexanoyl]-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-carboxyethyl)carbamoyl}oxy)methyl]phenyl}-L-alaninamide (Synthon GJ)

The title compound was prepared as described in Example 2.1, replacing Example 1.2.9 and 4-((S)-2-((S)-2-(6-(2,5-dioxo-2,5-dihydro-1H-pyrrol-1-yl)hexanamido)-3-methylbutanamido)-5-ureidopentanamido)benzyl (4-nitrophenyl) carbonate with Example 1.25.2 and 4-((S)-2-((S)-2-(6-(2,5-dioxo-2,5-dihydro-1H-pyrrol-1-yl)hexanamido)-3-methylbutanamido)propanamido)benzyl (4-nitrophenyl) carbonate, respectively. ¹H NMR (400 MHz, dimethyl sulfoxide-d₆) δ ppm 12.78 (s, 1H), 9.93 (s, 1H), 8.12 (d, 1H), 8.03 (d, 1H), 7.75-7.83 (m, 2H), 7.54-7.65 (m, 3H), 7.41-7.52 (m, 3H), 7.32-7.40 (m, 2H), 7.24-7.29 (m, 3H), 6.98 (s, 2H), 6.94 (d, 1H), 4.90-5.04 (m, 4H), 4.32-4.45 (m, 2H), 4.12-4.21 (m, 2H), 3.88 (t, 2H), 3.79 (d, 2H), 3.31-3.46 (m, 4H), 3.23-3.31 (m, 2H), 3.01 (t, 2H), 2.46 (t, 2H), 2.04-2.22 (m, 5H), 1.87-2.02 (m, 1H), 1.40-1.60 (m, 4H), 0.91-1.37 (m, 17H), 0.76-0.88 (m, 12H). MS (ESI) m/e 1328.4 (M−H)⁻.

2.27 Synthesis of 6-[8-(1,3-benzothiazol-2-ylcarbamoyl)-3,4-dihydroisoquinolin-2(1H)-yl]-3-(1-{[3-(2-{[(2R)-3-carboxy-2-({[(4-{[(2S)-2-{[(2S)-2-{[6-(2,5-dioxo-2,5-dihydro-1H-pyrrol-1-yl)hexanoyl]amino}-3-methylbutanoyl]amino}propanoyl]amino}benzyl)oxy]carbonyl}amino)propanoyl](methyl)amino}ethoxy)-5,7-dimethyltricyclo[3.3.1.1$^{3,7}$]dec-1-yl]methyl}-5-methyl-1H-pyrazol-4-yl)pyridine-2-carboxylic acid (Synthon GW)

A solution of Example 1.27 (0.043 g) in N,N-dimethylformamide (0.5 mL) was added 4-((S)-2-((S)-2-(6-(2,5-dioxo-2,5-dihydro-1H-pyrrol-1-yl)hexanamido)-3-methylbutanamido)propanamido)benzyl (4-nitrophenyl) carbonate (0.042 g) followed by N,N-diisopropylethylamine (0.038 mL), and the reaction was stirred at room temperature. After stirring for 16 hours, the reaction was diluted with water (0.5 mL) and N,N-dimethylformamide (1 mL). The mixture was purified by reverse phase HPLC using a Gilson system, eluting with 10-70% acetonitrile in water containing 0.1% v/v trifluoroacetic acid. The desired fractions were combined and freeze-dried to provide the title compound. ¹H NMR (400 MHz, dimethyl sulfoxide-d₆) δ ppm 13.05 (s, 1H), 10.15 (s, 1H), 8.36 (d, 1H), 8.26 (d, 1H), 8.02 (d, 2H), 7.95-7.77 (m, 4H), 7.77-7.63 (m, 3H), 7.63-7.54 (m, 2H), 7.54-7.46 (m, 3H), 7.22 (s, 2H), 7.18 (dd, 1H), 5.17 (d, 4H), 5.01 (dq, 1H), 4.61 (p, 1H), 4.39 (t, 1H), 4.11 (t, 2H), 4.03 (s, 2H), 3.64-3.49 (m, 2H), 3.29 (s, 1H), 3.24 (t, 2H), 3.03 (s, 2H), 2.92 (dt, 1H), 2.73-2.61 (m, 4H), 2.35 (d, 4H), 2.18 (dt, 1H), 1.71 (h, 4H), 1.65-1.13 (m, 18H), 1.13-1.01 (m, 13H). MS (ESI) m/e 1387.3 (M+H)⁺.

2.28 Synthesis of N-[6-(2,5-dioxo-2,5-dihydro-1H-pyrrol-1-yl)hexanoyl]-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl][1-(carboxymethyl)piperidin-4-yl]carbamoyl}oxy)methyl]phenyl}-N$^5$-carbamoyl-L-ornithinamide (Synthon HF)

A solution of Example 1.28 (0.0449 g), 4-((S)-2-((S)-2-(6-(2,5-dioxo-2,5-dihydro-1H-pyrrol-1-yl)hexanamido)-3-methylbutanamido)-5-ureidopentanamido)benzyl (4-nitrophenyl) carbonate (0.049 g) and N,N-diisopropylethylamine (0.044 mL) were stirred together in N,N-dimethylformamide (0.5 mL) at room temperature. The reaction mixture was stirred overnight and diluted with N,N-dimethylformamide (1 mL) and water (0.5 mL). The mixture was purified by reverse phase HPLC using a Gilson system, eluting with 10-90% acetonitrile in water containing 0.1% v/v trifluoroacetic acid. The desired fractions were combined and freeze-dried to provide the title compound. ¹H NMR (400 MHz, dimethyl sulfoxide-d₆) δ ppm 12.85 (s, 1H), 9.99 (s, 1H), 8.04 (t, 2H), 7.78 (t, 2H), 7.65-7.58 (m, 3H), 7.54-7.41 (m, 3H), 7.38 (d, 1H), 7.34 (d, 1H), 7.32-7.24 (m, 3H), 6.99 (s, 2H), 6.95 (d, 1H), 5.97 (s, 1H), 5.01 (s, 2H), 4.96 (s, 2H), 4.38 (q, 1H), 4.23-4.14 (m, 1H), 4.05 (s, 2H), 3.88 (t, 2H), 3.80 (s, 2H), 3.36 (t, 2H), 3.26-2.86 (m, 8H), 2.27-2.02 (m, 6H), 2.02-1.86 (m, 2H), 1.86-1.75 (m, 2H), 1.75-1.54 (m, 2H), 1.54-0.90 (m, 24H), 0.89-0.72 (m, 14H). MS (ESI) m/e 1485.2 (M+H)$^+$.

2.29 Synthesis of (S)-6-((2-((3-((4-(6-(8-(benzo[d] thiazol-2-ylcarbamoyl)-3,4-dihydroisoquinolin-2 (1H)-yl)-2-carboxypyridin-3-yl)-5-methyl-1H-pyrazol-1-yl)methyl)-5,7-dimethyladamantan-1-yl)oxy) ethyl)(methyl)amino)-5-(((((4-((S)-2-((S)-2-(6-(2,5-dioxo-2,5-dihydro-1H-pyrrol-1-yl)hexanamido)-3-methylbutanamido)-5-ureidopentanamido)benzyl) oxy)carbonyl)amino)-N,N,N-trimethyl-6-oxohexan-1-aminium salt (Synthon HG)

A solution of Example 1.29 (8 mg), 4-((S)-2-((S)-2-(6-(2,5-dioxo-2,5-dihydro-1H-pyrrol-1-yl)hexanamido)-3-methylbutanamido)-5-ureidopentanamido)benzyl (4-nitrophenyl) carbonate (8.24 mg) and N,N-diisopropylethylamine (7.50 µl, 0.043 mmol) in N,N-dimethylformamide (0.250 mL) was stirred at room temperature. After 3 hours, the reaction was diluted with N,N-dimethylformamide (1.25 mL) and water (0.5 mL). The mixture was purified by reverse phase HPLC using a Gilson system, eluting with 10-90% acetonitrile in water containing 0.1% v/v trifluoroacetic acid. The desired fractions were combined and freeze-dried to provide the title compound. $^1$H NMR (400 MHz, dimethyl sulfoxide-d$_6$) δ ppm 12.85 (s, 1H), 9.96 (s, 1H), 8.04 (t, 2H), 7.83-7.76 (m, 2H), 7.66-7.56 (m, 3H), 7.53-7.42 (m, 4H), 7.41-7.32 (m, 2H), 7.31-7.23 (m, 3H), 6.99 (s, 2H), 6.95 (d, 1H), 5.99 (s, 1H), 5.04-4.87 (m, 4H), 4.44-4.33 (m, 2H), 4.24-4.12 (m, 2H), 3.88 (t, 2H), 3.81 (s, 2H), 3.50-3.13 (m, 9H), 3.11-2.92 (m, 14H), 2.80 (s, 1H), 2.25-2.04 (m, 5H), 2.03-1.89 (m, 1H), 1.75-0.91 (m, 28H), 0.91-0.77 (m, 12H). MS (ESI) m/e 1528.5 (M+H)$^+$.

2.30 Synthesis of N-[6-(2,5-dioxo-2,5-dihydro-1H-pyrrol-1-yl)hexanoyl]-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]phenyl}-L-alaninamide (Synthon HP)

The title compound was prepared as described in Example 2.1, replacing 4-((S)-2-((S)-2-(6-(2,5-dioxo-2,5-dihydro-1H-pyrrol-1-yl)hexanamido)-3-methylbutanamido)-5-ureidopentanamido)benzyl (4-nitrophenyl) carbonate with 4-((S)-2-((S)-2-(6-(2,5-dioxo-2,5-dihydro-1H-pyrrol-1-yl) hexanamido)-3-methylbutanamido)propanamido)benzyl (4-nitrophenyl) carbonate. $^1$H NMR (400 MHz, dimethyl sulfoxide-d$_6$) δ ppm 12.83 (s, 1H), 9.94 (s, 1H), 8.12 (d, 1H), 8.04 (d, 1H), 7.79 (d, 2H), 7.40-7.63 (m, 6H), 7.32-7.39 (m, 2H), 7.24-7.30 (m, 3H), 6.99 (s, 2H), 6.95 (d, 1H), 4.90-5.03 (m, 4H), 4.31-4.47 (m, 1H), 4.09-4.24 (m, 1H), 3.84-3.93 (m, 2H), 3.81 (s, 2H), 3.30-3.39 (m, 2H), 3.20-3.28 (m, 2H), 3.01 (t, 2H), 2.57-2.65 (m, 2H), 2.05-2.22 (m, 5H), 1.87-2.02 (m, 2H), 1.41-1.58 (m, 4H), 1.22 (d, 18H), 0.74-0.89 (m, 12H). MS (ESI) m/e 1364.5 (M−H)$^−$.

2.31 Synthesis of N-[6-(2,5-dioxo-2,5-dihydro-1H-pyrrol-1-yl)hexanoyl]-L-valyl-N-[4-({[(4-{[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)amino}piperidin-1-yl)carbonyl] oxy}methyl)phenyl]-N-carbamoyl-L-ornithinamide (Synthon HR)

A solution of Example 1.30.2 (0.038 g), 4-((S)-2-((S)-2-(6-(2,5-dioxo-2,5-dihydro-1H-pyrrol-1-yl)hexanamido)-3-methylbutanamido)-5-ureidopentanamido)benzyl (4-nitrophenyl) carbonate (0.035 g) and N,N-diisopropylethylamine (0.032 mL) in N,N-dimethylformamide (0.5 mL) was stirred at room temperature. After stirring for 3 hours, the reaction was diluted with N,N-dimethylformamide (1.25 mL) and water (0.5 mL). The mixture was purified by reverse phase HPLC using a Gilson system, eluting with 10-90% acetonitrile in water containing 0.1% v/v trifluoroacetic acid. The desired fractions were combined and freeze-dried to provide the title compound. $^1$H NMR (400 MHz, dimethyl sulfoxide-d$_6$) δ ppm 9.98 (s, 1H), 9.02 (s, 1H), 8.10-8.00 (m, 2H), 7.79 (d, 2H), 7.64-7.56 (m, 3H), 7.53 (d, 1H), 7.47 (t, 1H), 7.43 (d, 1H), 7.39-7.32 (m, 2H), 7.29 (d, 3H), 6.99 (s, 2H), 6.95 (d, 1H), 6.00 (s, 1H), 4.99 (s, 2H), 4.96 (s, 2H), 4.48-4.32 (m, 2H), 4.27-4.15 (m, 2H), 4.11 (d, 2H), 3.88 (t, 2H), 3.82 (s, 2H), 3.40-3.33 (m, 4H), 3.24-3.11 (m, 2H), 3.11-2.72 (m, 8H), 2.26-2.04 (m, 4H), 2.04-1.80 (m, 3H), 1.80-0.92 (m, 26H), 0.92-0.77 (m, 12H). MS (ESI) m/e 1535.4 (M+H)$^+$.

2.32 Synthesis of N-[6-(2,5-dioxo-2,5-dihydro-1H-pyrrol-1-yl)hexanoyl]-L-valyl-N-{4-[({[2-({3-[(4-{6-[8-(1,3-benzothiazol-2-ylcarbamoyl)-5-(3-phosphonopropoxy)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](methyl)carbamoyl}oxy)methyl] phenyl}-N$^5$-carbamoyl-L-ornithinamide (Synthon HU)

The title compound was prepared by substituting Example 1.31.11 for Example 2.5.3 in Example 2.5.4. $^1$H NMR (400 MHz, dimethyl sulfoxide-d$_6$) δ ppm 9.98 (s, 1H), 8.03 (dd, 2H), 7.70-7.84 (m, 3H), 7.59 (d, 2H), 7.48 (dd, 2H), 7.23-7.37 (m, 4H), 6.93-7.02 (m, 4H), 4.99 (d, 4H), 4.12-4.21 (m, 8H), 3.88-3.96 (m, 4H), 3.75-3.84 (m, 4H), 3.23-3.49 (m, 7H), 2.73-3.07 (m, 8H), 1.89-2.21 (m, 9H), 0.91-1.77 (m, 25H), 0.77-0.91 (m, 12H). MS (ESI) m/e 1496.3 (M+H)$^+$.

2.33 Synthesis of N-[6-(2,5-dioxo-2,5-dihydro-1H-pyrrol-1-yl)hexanoyl]-L-valyl-N-[4-({[(4-{[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](3-phosphonopropyl)amino}piperidin-1-yl)carbonyl] oxy}methyl)phenyl]-N$^5$-carbamoyl-L-ornithinamide (Synthon HT)

A solution of Example 1.26.2 (0.040 g), 4-((S)-2-((S)-2-(6-(2,5-dioxo-2,5-dihydro-1H-pyrrol-1-yl)hexanamido)-3-methylbutanamido)-5-ureidopentanamido)benzyl (4-nitrophenyl) carbonate (0.030 g) and N,N-diisopropylethylamine (0.020 mL) in N,N-dimethylformamide (0.5 mL) was stirred at room temperature. After 3 hours, the reaction was diluted with N,N-dimethylformamide (1.25 mL) and water (0.5 mL). The mixture was purified by reverse phase HPLC using a Gilson system, eluting with 10-90% acetonitrile in water containing 0.1% v/v trifluoroacetic acid. The desired fractions were combined and freeze-dried to provide the title compound. $^1$H NMR (500 MHz, dimethyl sulfoxide-d$_6$) δ ppm 9.98 (s, 1H), 9.26 (s, 1H), 8.06 (d, 1H), 8.05-8.01 (m, 1H), 7.79 (d, 2H), 7.62 (d, 1H), 7.61-7.57 (m, 2H), 7.52-7.42 (m, 3H), 7.38 (d, 1H), 7.35 (d, 1H), 7.32-7.26 (m, 3H), 6.99 (s, 2H), 6.95 (d, 1H), 6.01 (s, 1H), 4.99 (s, 2H), 4.96 (s, 3H), 4.44-4.33 (m, 2H), 4.18 (dd, 2H), 3.88 (t, 2H), 3.83 (s, 2H), 3.71-3.61 (m, 2H), 3.53 (t, 2H), 3.36 (t, 2H), 3.07-2.66 (m, 8H), 2.28-2.06 (m, 6H), 2.05-1.92 (m, 2H), 1.92-1.80 (m, 2H), 1.78-0.95 (m, 32H), 0.92-0.77 (m, 14H). MS (ESI) m/e 1549.5 (M+H)$^+$.

2.34 Synthesis of N-[6-(2,5-dioxo-2,5-dihydro-1H-pyrrol-1-yl)hexanoyl]-L-valyl-N-{4-[({[2-({3-[(4-{6-[8-(1,3-benzothiazol-2-ylcarbamoyl)naphthalen-2-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](3-phosphonopropyl)carbamoyl}oxy)methyl]phenyl}-N-carbamoyl-L-ornithinamide (Synthon HV)

The title compound was prepared by substituting Example 1.14.4 for Example 2.5.3 in Example 2.5.4. $^1$H NMR (400 MHz, dimethyl sulfoxide-d$_6$) δ ppm 9.98 (s, 1H), 9.02 (s, 1H), 8.32-8.45 (m, 1H), 8.12-8.27 (m, 3H), 7.98-8.09 (m, 3H), 7.93 (d, 1H), 7.66-7.83 (m, 4H), 7.54-7.64 (m, 2H), 7.46-7.50 (m, 2H), 7.24-7.40 (m, 3H), 6.99 (s, 2H), 5.93-6.09 (m, 1H), 4.99 (s, 3H), 4.33-4.49 (m, 3H), 4.15-4.20 (m, 3H), 3.19-3.50 (m, 10H), 2.86-3.07 (m, 3H), 1.87-2.27 (m, 7H), 0.91-1.77 (m, 26H), 0.76-0.89 (m, 10H). MS (ESI) m/e 1461.1 (M+H)$^+$.

2.35 Synthesis of N-[6-(2,5-dioxo-2,5-dihydro-1H-pyrrol-1-yl)hexanoyl]-L-valyl-N-[4-({[(4-{[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-carboxyethyl)amino}piperidin-1-yl)carbonyl]oxy}methyl)phenyl]-N-carbamoyl-L-ornithinamide (Synthon HZ)

A solution of Example 1.36.2 (0.031 g), 4-((S)-2-((S)-2-(6-(2,5-dioxo-2,5-dihydro-1H-pyrrol-1-yl)hexanamido)-3-methylbutanamido)-5-ureidopentanamido)benzyl (4-nitrophenyl) carbonate (0.025 g) and N,N-diisopropylethylamine (0.016 mL) in N,N-dimethylformamide (0.5 mL) was stirred at room temperature. After stirring for 3 hours, the reaction was diluted with N,N-dimethylformamide (1.25 mL) and water (0.5 mL). The mixture was purified by reverse phase HPLC using a Gilson system, eluting with 10-90% acetonitrile in water containing 0.1% v/v trifluoroacetic acid. The desired fractions were combined and freeze-dried to provide the title compound. $^1$H NMR (400 MHz, dimethyl sulfoxide-d$_6$) δ ppm 12.84 (s, 1H), 9.98 (s, 1H), 8.82 (s, 1H), 8.05 (dd, 2H), 7.79 (d, 2H), 7.70-7.53 (m, 2H), 7.53-7.24 (m, 6H), 6.99 (s, 2H), 6.95 (d, 1H), 6.00 (s, 1H), 4.99 (s, 2H), 4.96 (s, 2H), 4.37 (q, 2H), 4.25-4.15 (m, 2H), 3.88 (t, 2H), 3.83 (s, 2H), 3.69-3.61 (m, 2H), 3.44-3.30 (m, 4H), 3.08-2.90 (m, 4H), 2.90-2.72 (m, 4H), 2.27-2.04 (m, 5H), 2.04-1.89 (m, 2H), 1.77-0.94 (m, 28H), 0.91-0.78 (m, 14H). MS (ESI) m/e 1499.5 (M+H)$^+$.

2.36 Synthesis of N-[6-(2,5-dioxo-2,5-dihydro-1H-pyrrol-1-yl)hexanoyl]-L-valyl-N$^5$-carbamoyl-N-{4-[({[2-({3-[(4-{2-carboxy-6-[8-([1,3]thiazolo[4,5-b]pyridin-2-ylcarbamoyl)-3,4-dihydroisoquinolin-2(1H)-yl]pyridin-3-yl}-5-methyl-1H-pyrazol-1-yl)methyl]-5,7-dimethyltricyclo[3.3.1.1$^{3,7}$]dec-1-yl}oxy)ethyl](3-phosphonopropyl)carbamoyl}oxy)methyl]phenyl}-L-ornithinamide (Synthon IA)

The title compound was prepared by substituting Example 1.39.2 for Example 1.2.9 in Example 2.1. $^1$H NMR (400 MHz, dimethyl sulfoxide-d$_6$) δ ppm 9.98 (s, 1H), 8.60 (dd, 1H), 8.52 (dd, 1H), 8.06 (d, 1H), 7.78 (d, 1H), 7.65 (d, 1H), 7.59 (br m, 2H), 7.50 (m, 1H), 7.45 (d, 1H), 7.38 (m, 2H), 7.28 (s, 1H), 7.27 (d, 2H), 6.99 (s, 2H), 6.97 (d, 1H), 5.98 (br s, 1H), 4.98 (s, 4H), 4.39 (m, 1H), 4.19 (br m, 1H), 3.88 (t, 2H), 3.80 (br d, 2H), 3.36 (br m, 3H), 3.24 br (m, 4H), 2.98 (m, 4H), 2.16 (m, 2H), 2.12 (s, 3H), 1.95 (br m, 1H), 1.67 (br m, 3H), 1.34-1.47 (m, 9H), 1.08-1.23 (m, 11H), 0.95 (br m, 2H), 0.85-0.80 (m, 12H). MS (ESI) m/e 1465.5 (M−H)$^−$.

2.37 Synthesis of N-[6-(2,5-dioxo-2,5-dihydro-1H-pyrrol-1-yl)hexanoyl]-L-valyl-N$^5$-carbamoyl-N-{4-[({[2-({3-[(4-{2-carboxy-6-[8-([1,3]thiazolo[5,4-b]pyridin-2-ylcarbamoyl)-3,4-dihydroisoquinolin-2(1H)-yl]pyridin-3-yl}-5-methyl-1H-pyrazol-1-yl)methyl]-5,7-dimethyltricyclo[3.3.1.1$^{3,7}$]dec-1-yl}oxy)ethyl](3-phosphonopropyl)carbamoyl}oxy)methyl]phenyl}-L-ornithinamide (Synthon IF)

The title compound was prepared by substituting Example 1.40.2 for Example 1.2.9 in Example 2.1. $^1$H NMR (400 MHz, dimethyl sulfoxide-d$_6$) δ ppm 9.98 (s, 1H), 8.52 (dd, 1H), 8.16 (dd, 1H), 8.05 (br d, 1H), 7.78 (br d, 1H), 7.62 (m, 1H), 7.58 (br m, 2H), 7.52 (m, 2H), 7.44 (d, 1H), 7.38 (t, 1H), 7.29 (s, 1H) 7.27 (d, 2H), 6.99 (s, 2H), 6.97 (d, 1H), 4.98 (s, 2H), 4.96 (s, 2H), 4.39 (m, 1H), 4.19 (br m, 1H), 3.88 (t, 2H), 3.80 (br d, 2H), 3.36 (br m, 3H), 3.24 br (m, 4H), 2.98 (m, 4H), 2.16 (m, 2H), 2.12 (s, 3H), 1.95 (br m, 1H), 1.67 (br m, 3H), 1.47-1.34 (m, 9H), 1.08-1.23 (m, 11H), 0.95 (br m, 2H), 0.85-0.80 (m, 12H). MS (ESI) m/e 1451.5 (M−H)$^−$.

2.38 Synthesis of N-{6-[(chloroacetyl)amino]hexanoyl}-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]phenyl}-L-alaninamide (Synthon IG)

2.38.1 3-(1-((3-(2-(((((4-((S)-2-((S)-2-amino-3-methylbutanamido)propanamido)benzyl)oxy)carbonyl)(2-sulfoethyl)amino)ethoxy)-5,7-dimethyladamantan-1-yl)methyl)-5-methyl-1H-pyrazol-4-yl)-6-(8-(benzo[d]thiazol-2-ylcarbamoyl)-3,4-dihydroisoquinolin-2(1H)-yl)picolinic acid A solution of Example 1.2.9 (0.050 g), (9H-fluoren-9-yl)methyl ((S)-3-methyl-1-(((S)-1-((4-((((4-nitrophenoxy)carbonyl)oxy)methyl)phenyl)amino)-1-oxopropan-2-yl)amino)-1-oxobutan-2-yl)carbamate (0.039 g) and N,N-diisopropylethylamine (0.027 mL) in N,N-dimethylformamide (1 mL) was stirred at room temperature. After stirring overnight, diethylamine (0.027 mL) was added to the reaction, and stirring was continued for 2 hours. The reaction was quenched with trifluoroacetic acid, and the mixture was purified by reverse phase HPLC using a Gilson system, eluting with 5-75% acetonitrile in water containing 0.1% v/v trifluoroacetic acid. The desired fractions were combined and freeze-dried to provide the title compound. MS (ESI) m/e 1499.5 (M+H)$^+$.

2.38.2 N-{6-[(chloroacetyl)amino]hexanoyl}-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]phenyl}-L-alaninamide To a solution of 6-(2-chloroacetamido)hexanoic acid (6 mg) and 2-(3H-[1,2,3]triazolo[4,5-b]pyridin-3-yl)-1,1,3,3-tetramethylisouronium hexafluorophosphate(V) (0.011 g) in N,N-dimethylformamide (1 mL) was added N,N-diisopropylethylamine (0.015 mL), and the reaction stirred for 5 minutes. This solution was added to Example 2.38.1 (0.022 g) and was stirred for 1 hour. The reaction was diluted with N,N-dimethylformamide (1 mL) and water (0.5 mL). The mixture was purified by reverse phase HPLC using a Gilson system, eluting with 10-90% acetonitrile in water containing 0.1% v/v trifluoroacetic acid. The desired fractions were combined and freeze-dried to provide the title compound. $^1$H NMR (400 MHz, dimethyl sulfoxide-d$_6$) δ ppm 12.83 (s, 1H), 9.93 (s, 1H), 8.20-8.10 (m, 2H), 8.04 (d, 1H), 7.83-7.76 (m, 2H), 7.64-7.55 (m, 3H), 7.55-7.50 (m, 1H), 7.50-7.41 (m, 2H), 7.40-7.32 (m, 2H), 7.32-7.24 (m, 3H), 6.96 (d, 1H), 5.07-4.92 (m, 3H), 4.39 (p, 1H), 4.18 (dd, 2H), 4.01 (s, 2H), 3.92-3.76 (m, 6H), 3.54-3.32 (m, 4H), 3.25 (t, 2H), 3.13-2.93 (m, 4H), 2.72-2.58 (m, 2H), 2.29-2.12 (m, 2H), 2.09 (s, 3H), 2.05-1.92 (m, 1H), 1.58-0.89 (m, 18H), 0.89-0.77 (m, 12H). MS (ESI) m/e 1362.2 (M+H)$^+$.

2.39 Synthesis of N-[6-(2,5-dioxo-2,5-dihydro-1H-pyrrol-1-yl)hexanoyl]-L-valyl-N-{4-[({[2-({3-[(4-{6-[8-(1,3-benzothiazol-2-ylcarbamoyl)-5-(carboxymethoxy)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](methyl)carbamoyl}oxy)methyl]phenyl}-N$^5$-carbamoyl-L-ornithinamide (Synthon IJ)

The title compound was prepared by substituting Example 1.41.3 for Example 2.5.3 in Example 2.5.4. $^1$H NMR (400 MHz, dimethyl sulfoxide-d$_6$) δ ppm 10.03 (s, 1H), 9.96 (s, 1H), 8.26-8.34 (m, 1H), 7.95-8.11 (m, 2H), 7.73-7.82 (m, 2H), 7.22-7.70 (m, 11H), 6.95-7.05 (m, 3H), 6.89 (d, 1H), 5.23 (s, 1H), 4.98 (d, 3H), 4.83 (s, 1H), 4.33-4.43 (m, 1H), 4.11-4.23 (m, 1H), 3.74-3.95 (m, 3H), 3.22-3.39 (m, 10H), 2.78-3.06 (m, 12H), 1.91-2.22 (m, 8H), 0.93-1.68 (m, 20H), 0.77-0.88 (m, 10H). MS (ESI) m/e 1432.2 (M+H)$^+$.

2.40 Synthesis of N-[6-(2,5-dioxo-2,5-dihydro-1H-pyrrol-1-yl)hexanoyl]-L-valyl-N-[4-({[2-{[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)amino}ethyl)(2-carboxyethyl)carbamoyl]oxy}methyl)phenyl]-N$^5$-carbamoyl-L-ornithinamide (Synthon IJ)

The title compound was prepared as described in Example 2.1, replacing Example 1.2.9 with Example 1.38.2. $^1$H NMR (400 MHz, dimethyl sulfoxide-d$_6$) δ ppm 12.86 (s, 1H), 9.99 (s, 1H), 9.10 (s, 1H), 8.04 (t, 2H), 7.73-7.85 (m, 2H), 7.61 (t, 3H), 7.41-7.55 (m, 3H), 7.26-7.39 (m, 5H), 6.99 (s, 2H), 6.95 (d, 1H), 6.00 (s, 1H), 4.99 (d, 4H), 4.34-4.45 (m, 2H), 4.19 (dd, 2H), 3.88 (t, 2H), 3.82 (s, 2H), 3.36 (t, 4H), 2.85-3.09 (m, 5H), 2.06-2.22 (m, 4H), 1.89-2.02 (m, 1H), 0.94-1.77 (m, 20H), 0.77-0.90 (m, 11H). MS (ESI) m/e 1567.4 (M+H)$^+$.

2.41 Synthesis of 6-[8-(1,3-benzothiazol-2-ylcarbamoyl)-3,4-dihydroisoquinolin-2(1H)-yl]-3-[1-({3-[2-({[(2S)-2-[{[(4-{[(2S)-5-(carbamoylamino)-2-{[(2S)-2-{[6-(2,5-dioxo-2,5-dihydro-1H-pyrrol-1-yl)hexanoyl]amino}-3-methylbutanoyl]amino}pentanoyl]amino}benzyl)oxy]carbonyl}(2-carboxyethyl)amino]-3-carboxypropanoyl}amino)ethoxy]-5,7-dimethyltricyclo[3.3.1.1$^{3,7}$]dec-1-yl}methyl)-5-methyl-1H-pyrazol-4-yl]pyridine-2-carboxylic acid (Synthon IK)

The title compound was prepared as described in Example 2.1, replacing Example 1.2.9 with Example 1.32.4. MS (ESI) m/e 1592.4 (M−H)$^-$.

2.42 Synthesis of 6-[8-(1,3-benzothiazol-2-ylcarbamoyl)-3,4-dihydroisoquinolin-2(1H)-yl]-3-(1-{[3-(2-{[(2S)-2-({[(4-{[(2S)-5-(carbamoylamino)-2-{[(2S)-2-{[6-(2,5-dioxo-2,5-dihydro-1H-pyrrol-1-yl)hexanoyl]amino}-3-methylbutanoyl]amino}pentanoyl]amino}benzyl)oxy]carbonyl}amino)-3-carboxypropanoyl](2-sulfoethyl)amino}ethoxy)-5,7-dimethyltricyclo[3.3.1.1$^{3,7}$]dec-1-yl]methyl}-5-methyl-1H-pyrazol-4-yl)pyridine-2-carboxylic acid (Synthon IL)

The title compound was prepared as described in Example 2.1, replacing Example 1.2.9 with Example 1.44.2. $^1$H NMR (400 MHz, dimethyl sulfoxide-d$_6$) δ ppm 12.82 (s, 1H), 9.96 (s, 1H), 8.03 (t, 2H), 7.77 (d, 2H), 7.39-7.62 (m, 7H), 7.30-7.39 (m, 2H), 7.22-7.29 (m, 3H), 6.98 (s, 2H), 6.92-6.96 (m, 1H), 5.97 (s, 1H), 4.83-5.05 (m, 3H), 3.83-3.92 (m, 1H), 3.79 (s, 1H), 3.00 (s, 2H), 2.03-2.22 (m, 8H), 1.94 (s, 2H), 1.34 (d, 30H), 0.69-0.90 (m, 13H). MS (ESI) m/e 1565.5 (M−H)$^-$.

2.43 Synthesis of N-[6-(2,5-dioxo-2,5-dihydro-1H-pyrrol-1-yl)hexanoyl]-L-valyl-N-[4-({[(4-{[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](3-carboxypropyl)amino}piperidin-1-yl)carbonyl]oxy}methyl)phenyl]-N-carbamoyl-L-ornithinamide (Synthon IM)

A solution of Example 1.42.2 (0.045 g), 4-((S)-2-((S)-2-(6-(2,5-dioxo-2,5-dihydro-1H-pyrrol-1-yl)hexanamido)-3-methylbutanamido)-5-ureidopentanamido)benzyl (4-nitrophenyl) carbonate (0.035 g) and N,N-diisopropylethylamine (0.038 mL) in N,N-dimethylformamide (0.5 mL) was stirred at room temperature. After stirring for 3 hours, the reaction was diluted with N,N-dimethylformamide (1.25 mL) and water (0.5 mL). The mixture was purified by reverse phase HPLC using a Gilson system, eluting with 10-90% acetonitrile in water containing 0.1% v/v trifluoroacetic acid. The desired fractions were combined and freeze-dried to provide the title compound. $^1$H NMR (400 MHz, dimethyl sulfoxide-d₆) δ ppm 12.76 (s, 1H), 9.91 (s, 1H), 8.79 (s, 1H), 7.98 (dd, 2H), 7.72 (d, 2H), 7.68-7.47 (m, 3H), 7.47-7.00 (m, 7H), 6.96-6.83 (m, 3H), 5.93 (s, 1H), 4.91 (d, 3H), 4.30 (q, 1H), 4.17-3.97 (m, 4H), 3.96-3.53 (m, 4H), 3.34-2.65 (m, 12H), 2.25 (t, 2H), 2.16-1.67 (m, 12H), 1.67-0.88 (m, 26H), 0.84-0.70 (m, 12H). MS (ESI) m/e 1513.6 (M+H)⁺.

2.44 Synthesis of 4-[(1E)-3-({[2-({3-[(4-{6-[8-(1,3-benzothiazol-2-ylcarbamoyl)-5-(carboxymethoxy)-3,4-dihydroisoquinolin-2(1H)-yl]-2-carboxypyridin-3-yl}-5-methyl-1H-pyrazol-1-yl)methyl]-5,7-dimethyltricyclo[3.3.1.1³,⁷]dec-1-yl}oxy)ethyl](methyl)carbamoyl}oxy)prop-1-en-1-yl]-2-({N-[6-(2,5-dioxo-2,5-dihydro-1H-pyrrol-1-yl)hexanoyl]-beta-alanyl}amino)phenyl beta-D-glucopyranosiduronic acid (Synthon IO)

2.44.1 (E)-tert-butyldimethyl((3-(4,4,5,5-tetramethyl-1,3,2-dioxaborolan-2-yl)allyl)oxy)silane To a flask charged with tert-butyldimethyl(prop-2-yn-1-yloxy)silane (5 g) and dichloromethane (14.7 mL) under nitrogen atmosphere was added dropwise 4,4,5,5-tetramethyl-1,3,2-dioxaborolane (3.94 g). The mixture was stirred at room temperature for one minute then transferred via cannula to a nitrogen-sparged flask containing Cp₂ZrClH (chloridobis(η5-cyclopentadienyl)hydridozirconium, Schwartz's Reagent) (379 mg). The resulting reaction mixture was stirred at room temperature for 16 hours. The mixture was carefully quenched with water (15 mL), and then extracted with diethyl ether (3×30 mL). The combined organic phases were washed with water (15 mL), dried over MgSO₄, filtered, and purified by silica gel chromatography, eluting with a gradient from 0-8% ethyl acetate/heptanes to give the title compound. MS (ESI) m/z 316.0 (M+NH₄)⁺.

2.44.2 (2S,3R,4S,5S,6S)-2-(4-bromo-2-nitrophenoxy)-6-(methoxycarbonyl)tetrahydro-2H-pyran-3,4,5-triyl triacetate (2R,3R,4S,5S,6S)-2-Bromo-6-(methoxycarbonyl)tetrahydro-2H-pyran-3,4,5-triyl triacetate (5 g) was dissolved in acetonitrile (100 mL). Ag₂O (2.92 g) was added to the solution, and the reaction was stirred for 5 minutes at room temperature. 4-Bromo-2-nitrophenol (2.74 g) was added, and the reaction mixture was stirred at room temperature for 4 hours. The silver salt residue was filtered through diatomaceous earth, and the filtrate was concentrated under reduced pressure. The residue was purified by silica gel chromatography, eluting with a gradient of 10-70% ethyl acetate in heptanes, to give the title compound. MS (ESI+) m/z 550.9 (M+NH₄)⁺.

2.44.3 (2S,3R,4S,5S,6S)-2-(4-((E)-3-((tert-butyldimethylsilyl)oxy)prop-1-en-1-yl)-2-nitrophenoxy)-6-(methoxycarbonyl)tetrahydro-2H-pyran-3,4,5-triyl triacetate Example 2.44.2 (1 g), sodium carbonate (0.595 g), tris(dibenzylideneacetone)dipalladium (Pd₂(dba)₃) (0.086 g), and 1,3,5,7-tetramethyl-6-phenyl-2,4,8-trioxa-6-phosphaadamantane (0.055 g) were combined in a 3-neck 50-mL round bottom flask equipped with a reflux condenser and the system was degassed with nitrogen. Separately, a solution of Example 2.44.1 (0.726 g) in tetrahydrofuran (15 mL) was degassed with nitrogen for 30 minutes. The latter solution was transferred via cannula into the flask containing the solid reagents, followed by addition of degassed water (3 mL) via syringe. The reaction was heated to 60° C. for two hours. The reaction mixture was partitioned between ethyl acetate (3×30 mL) and water (30 mL). The combined organic phases were dried (Na₂SO₄), filtered, and concentrated. The residue was purified by silica gel chromatography, eluting with a gradient from 0-35% ethyl acetate in heptanes, to provide the title compound. MS (ESI+) m/z 643.1 (M+NH₄)⁺.

2.44.4 (2S,3R,4S,5S,6S)-2-(2-amino-4-((E)-3-hydroxyprop-1-en-1-yl)phenoxy)-6-(methoxycarbonyl)tetrahydro-2H-pyran-3,4,5-triyl triacetate A 500-mL three-neck, nitrogen-flushed flask equipped with a pressure-equalizing addition funnel was charged with zinc dust (8.77 g). A degassed solution of Example 2.44.3 (8.39 g) in tetrahydrofuran (67 mL) was added via cannula. The resulting suspension was chilled in an ice bath, and 6N HCl (22.3 mL) was added dropwise via the addition funnel at such a rate that the internal temperature of the reaction did not exceed 35° C. After the addition was complete, the reaction was stirred for two hours at room temperature, and filtered through a pad of diatomaceous earth, rinsing with water and ethyl acetate. The filtrate was treated with saturated aqueous NaHCO₃ solution until the water layer was no longer acidic, and the mixture was filtered to remove the resulting solids. The filtrate was transferred to a separatory funnel, and the layers were separated. The aqueous layer was extracted with ethyl acetate (3×75 mL), and the combined organic layers were washed with water (100 mL), dried over Na₂SO₄, filtered, and concentrated. The residue was triturated with diethyl ether and the solid collected by filtration to provide the title compound. MS (ESI+) m/z 482.0 (M+H)⁺.

2.44.5 (9H-fluoren-9-yl)methyl (3-chloro-3-oxopropyl)carbamate

To a solution of 3-((((9H-fluoren-9-yl)methoxy)carbonyl)amino)propanoic acid (5.0 g) in dichloromethane (53.5 mL) was added sulfurous dichloride (0.703 mL). The mixture was stirred at 60° C. for one hour. The mixture was cooled and concentrated to give the title compound, which was used in the next step without further purification.

2.44.6 (2S,3R,4S,5S,6S)-2-(2-(3-((((9H-fluoren-9-yl)methoxy)carbonyl)amino)propanamido)-4-((E)-3-hydroxyprop-1-en-1-yl)phenoxy)-6-(methoxycarbonyl)tetrahydro-2H-pyran-3,4,5-triyl triacetate Example 2.44.4 (6.78 g) was dissolved in dichloromethane (50 mL), and the solution was chilled to 0° C. in an ice bath. N,N-Diisopropylethylamine (3.64 g) was added, followed by dropwise addition of a solution of Example 2.44.5 (4.88 g) in dichloromethane (50 mL). The reaction was stirred for 16 hours allowing the ice bath to come to room temperature. Saturated aqueous NaHCO₃ solution (100 mL) was added, and the layers were separated. The aqueous layer was further extracted with dichloromethane (2×50 mL). The extracts were dried over Na₂SO₄, filtered, concentrated and purified by silica gel chromatography, eluting with a gradient of 5-95% ethyl acetate/heptane, to give an inseparable mixture of starting aniline and desired product. The mixture was partitioned between 1N aqueous HCl (40 mL) and a 1:1 mixture of diethyl ether and ethyl acetate (40 mL), and then the aqueous phase was further extracted with ethyl acetate (2×25 mL). The organic phases were combined, washed with water (2×25 mL), dried over $Na_2SO_4$, filtered, and concentrated to give the title compound. MS (ESI+) m/z 774.9 (M+H)$^+$.

2.44.7 (2S,3R,4S,5S,6S)-2-(2-(3-((((9H-fluoren-9-yl)methoxy)carbonyl)amino)propanamido)-4-((E)-3-(((4-nitrophenoxy)carbonyl)oxy)prop-1-en-1-yl)phenoxy)-6-(methoxycarbonyl)tetrahydro-2H-pyran-3,4,5-triyl triacetate Example 2.44.6 (3.57 g) was dissolved in dichloromethane (45 mL) and bis(4-nitrophenyl)carbonate (2.80 g) was added, followed by dropwise addition of N,N-diisopropylethylamine (0.896 g). The reaction mixture was stirred at room temperature for two hours. Silica gel (20 g) was added to the reaction solution, and the mixture was concentrated to dryness under reduced pressure, keeping the bath temperature at or below 25° C. The silica residue was loaded atop a column, and the product was purified by silica gel chromatography, eluting with a gradient from 0-100% ethyl acetate-heptane, providing partially purified product which was contaminated with nitrophenol. The material was triturated with methyl tert-butyl ether (250 mL), and the resulting slurry was allowed to sit for 1 hour. The product was collected by filtration. Three successive crops were collected in a similar fashion to give the title compound. MS (ESI+) m/z 939.8 (M+H)$^+$.

2.44.8 3-(1-((3-(2-(((((E)-3-(3-(3-aminopropanamido)-4-(((2S,3R,4S,5S,6S)-6-carboxy-3,4,5-trihydroxytetrahydro-2H-pyran-2-yl)oxy)phenyl)allyl)oxy)carbonyl)(methyl)amino)ethoxy)-5,7-dimethyladamantan-1-yl)methyl)-5-methyl-1H-pyrazol-4-yl)-6-(8-(benzo[d]thiazol-2-ylcarbamoyl)-5-(carboxymethoxy)-3,4-dihydroisoquinolin-2(1H)-yl)picolinic acid To a cold (0° C.) solution of Example 2.44.7 (19.7 mg) and Example 1.41.3 (18.5 mg) in N,N-dimethylformamide (2 mL) was added N,N-diisopropylethylamine (0.054 mL). The reaction was slowly warmed to room temperature and stirred overnight. To the reaction mixture was added water (2 mL) and lithium hydroxide monohydrate (50 mg), and the mixture was stirred overnight. The mixture was acidified with trifluoroacetic acid and filtered. The mixture was purified by reverse phase HPLC (Gilson system), eluting with 10-85% acetonitrile in 0.1% trifluoroacetic acid in water, to provide the title compound. MS (ESI) m/e 1273.2 (M+H)$^+$.

2.44.9 4-[(1E)-3-({[2-({3-[(4-{6-[8-(1,3-benzothiazol-2-ylcarbamoyl)-5-(carboxymethoxy)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](methyl)carbamoyl}oxy)prop-1-en-1-yl]-2-({N-[6-(2,5-dioxo-2,5-dihydro-1H-pyrrol-1-yl)hexanoyl]-beta-alanyl}amino)phenyl beta-D-glucopyranosiduronic acid To a solution of Example 2.44.8 (10 mg) and 2,5-dioxopyrrolidin-1-yl 6-(2,5-dioxo-2,5-dihydro-1H-pyrrol-1-yl)hexanoate (2.3 mg) in N,N-dimethylformamide (2 mL) was added N,N-diisopropylethylamine (0.054 mL). The reaction was stirred overnight. The reaction mixture was diluted with methanol (2 mL) and acidified with trifluoroacetic acid. The mixture was purified by reverse phase HPLC (Gilson system), eluting with 10-85% acetonitrile in 0.1% trifluoroacetic acid in water, to give the title compound. $^1$H NMR (400 MHz, dimethyl sulfoxide-d$_6$) δ ppm 12.70 (s, 1H), 9.03 (s, 1H), 8.25 (s, 1H), 8.01 (d, 1H), 7.87 (t, 1H), 7.77 (d, 1H), 7.69 (d, 1H), 7.41-7.55 (m, 2H), 7.23-7.38 (m, 2H), 6.79-7.16 (m, 7H), 6.56 (d, 1H), 6.09-6.25 (m, 1H), 4.96-5.07 (m, 3H), 4.84 (s, 3H), 4.64 (d, 3H), 3.87-3.97 (m, 5H), 3.24-3.47 (m, 12H), 2.77-2.95 (m, 6H), 1.94-2.08 (m, 6H), 0.92-1.56 (m, 20H), 0.74-0.86 (m, 6H). MS (ESI) m/e 1487.3 (M+Na)$^+$.

2.45 Synthesis of N-[6-(2,5-dioxo-2,5-dihydro-1H-pyrrol-1-yl)hexanoyl]-L-valyl-N-{4-[({[2-({3-[(4-{6-[8-(1,3-benzothiazol-2-ylcarbamoyl)naphthalen-2-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]phenyl}-N$^5$-carbamoyl-L-ornithinamide (Synthon IP)

The title compound was prepared by substituting Example 1.43.7 for Example 2.5.3 in Example 2.5.4. $^1$H NMR (400 MHz, dimethyl sulfoxide-d$_6$) δ ppm 13.09 (s, 1H), 9.99 (s, 1H), 9.02 (s, 1H), 8.30-8.40 (m, 3H), 7.93-8.25 (m, 6H), 7.23-7.86 (m, 10H), 6.92-7.05 (m, 2H), 4.99 (d, 2H), 4.36-4.44 (m, 2H), 4.14-4.23 (m, 2H), 2.87-3.35 (m, 12H), 2.81 (t, 2H), 2.59-2.70 (m, 2H), 1.84-2.28 (m, 8H), 0.97-1.77 (m, 20H), 0.77-0.88 (m, 10H). MS (ESI) m/e 1448.3 (M+Na)$^+$.

2.46 Synthesis of N-[6-(2,5-dioxo-2,5-dihydro-1H-pyrrol-1-yl)hexanoyl]-L-valyl-N-[4-({[(2-{[8-(1,3-benzothiazol-2-ylcarbamoyl)-2-(6-carboxy-5-{1-[(3,5-dimethyl-7-{2-[methyl(2-sulfoethyl)amino]ethoxy}tricyclo[3.3.1.1$^{3,7}$]dec-1-yl)methyl]-5-methyl-1H-pyrazol-4-yl}pyridin-2-yl)-1,2,3,4-tetrahydroisoquinolin-5-yl]oxy}ethyl)carbamoyl]oxy}methyl)phenyl]-N$^5$-carbamoyl-L-ornithinamide (Synthon IS)

The title compound was prepared as described in Example 2.1, replacing Example 1.2.9 with Example 1.46.2. $^1$H NMR (400 MHz, dimethyl sulfoxide-d$_6$) δ ppm 12.69 (s, 1H), 9.97 (s, 1H), 8.97 (s, 1H), 8.04 (dd, 2H), 7.78 (d, 2H), 7.71 (d, 1H), 7.59 (d, 2H), 7.44-7.54 (m, 3H), 7.26-7.37 (m, 4H), 6.96-7.03 (m, 4H), 5.97 (s, 1H), 4.99 (d, 4H), 4.31-4.45 (m, 1H), 4.18 (dd, 1H), 4.09 (s, 2H), 3.85-3.93 (m, 2H), 3.83 (s, 2H), 3.39-3.47 (m, 2H), 3.24-3.39 (m, 4H), 3.12-3.24 (m, 2H), 2.75-3.07 (m, 9H), 2.06-2.23 (m, 5H), 1.90-2.01 (m, 1H), 1.54-1.75 (m, 2H), 1.24-1.52 (m, 12H), 0.91-1.24 (m, 8H), 0.77-0.88 (m, 12H). MS (ESI) m/e 1525.4 (M+H)$^+$.

2.47 Synthesis of N-[6-(2,5-dioxo-2,5-dihydro-1H-pyrrol-1-yl)hexanoyl]-L-valyl-N-[4-({[(2-{[8-(1,3-benzothiazol-2-ylcarbamoyl)-2-(6-carboxy-5-{1-[(3,5-dimethyl-7-{2-[methyl(2-sulfoethyl)amino]ethoxy}tricyclo[3.3.1.1$^{3,7}$]dec-1-yl)methyl]-5-methyl-1H-pyrazol-4-yl}pyridin-2-yl)-1,2,3,4-tetrahydroisoquinolin-5-yl]oxy}ethyl)(2-sulfoethyl)carbamoyl]oxy}methyl)phenyl]-N$^5$-carbamoyl-L-ornithinamide (Synthon IU)

The title compound was prepared as described in Example 2.1, replacing Example 1.2.9 with Example 1.47.2. $^1$H NMR (400 MHz, dimethyl sulfoxide-d$_6$) δ ppm 12.70 (s, 1H), 9.99 (s, 1H), 8.97 (s, 1H), 8.04 (dd, 2H), 7.78 (d, 2H), 7.71 (d, 1H), 7.59 (d, 2H), 7.43-7.55 (m, 2H), 7.28-7.37 (m, 4H), 6.94-7.07 (m, 4H), 6.05 (s, 1H), 4.93-5.11 (m, 4H), 4.31-

4.46 (m, 2H), 4.12-4.26 (m, 4H), 3.80-3.95 (m, 4H), 3.40-3.50 (m, 2H), 3.24-3.40 (m, 6H), 3.13-3.24 (m, 2H), 2.74-3.08 (m, 9H), 2.63-2.73 (m, 2H), 2.05-2.23 (m, 5H), 1.96 (s, 1H), 1.52-1.77 (m, 2H), 1.23-1.53 (m, 12H), 0.97-1.22 (m, 8H), 0.77-0.89 (m, 12H). MS (ESI) m/e 1631.5 (M−H)$^-$.

2.48 Synthesis of N-[6-(2,5-dioxo-2,5-dihydro-1H-pyrrol-1-yl)hexanoyl]-L-valyl-N-[4-({[(2-{[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)amino}ethyl)(2-sulfoethyl)carbamoyl]oxy}methyl)phenyl]-N$^5$-carbamoyl-L-ornithinamide (Synthon IV)

The title compound was prepared as described in Example 2.1, replacing Example 1.2.9 with Example 1.48.2. $^1$H NMR (400 MHz, dimethyl sulfoxide-d$_6$) δ ppm 12.82 (s, 1H), 10.00 (s, 1H), 9.29-9.57 (m, 1H), 8.05 (t, 2H), 7.79 (d, 2H), 7.51-7.63 (m, 4H), 7.40-7.50 (m, 2H), 7.27-7.39 (m, 5H), 6.93-7.02 (m, 3H), 4.99 (d, 3H), 4.30-4.47 (m, 1H), 4.19 (t, 1H), 3.79-3.92 (m, 3H), 3.60-3.74 (m, 2H), 3.01 (s, 9H), 2.70 (d, 4H), 2.05-2.23 (m, 6H), 1.96 (d, 2H), 1.53-1.78 (m, 3H), 1.22-1.54 (m, 13H), 0.89-1.22 (m, 9H), 0.75-0.89 (m, 13H). MS (ESI) m/e 1603.3 (M+H)$^+$.

2.49 Synthesis of N-{6-[(chloroacetyl)amino]hexanoyl}-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]phenyl}-N$^5$-carbamoyl-L-ornithinamide (Synthon IZ)

2.49.1 3-(1-(((1r,3r)-3-(2-((((4-((S)-2-((S)-2-amino-3-methylbutanamido)-5-ureidopentanamido)benzyl)oxy)carbonyl)(2-sulfoethyl)amino)ethoxy)-5,7-dimethyladamantan-1-yl)methyl)-5-methyl-1H-pyrazol-4-yl)-6-(8-(benzo[d]thiazol-2-ylcarbamoyl)-3,4-dihydroisoquinolin-2(1H)-yl)picolinic acid A solution of Example 1.2.9 (0.045 g) (9H-fluoren-9-yl)methyl ((S)-3-methyl-1-(((S)-1-((4-((((4-nitrophenoxy)carbonyl)oxy)methyl)phenyl)amino)-1-oxo-5-ureidopentan-2-yl)amino)-1-oxobutan-2-yl)carbamate (0.043 g) and N,N-diisopropylethylamine (0.041 mL) were stirred together in N,N-dimethylformamide (1 mL) at room temperature. After stirring overnight, diethylamine (0.024 mL) was added to the reaction, and stirring was continued for 2 hours. The reaction was quenched with trifluoroacetic acid then purified by reverse phase HPLC using a Gilson system, eluting with 10-75% acetonitrile in water containing 0.1% v/v trifluoroacetic acid. The desired fractions were combined and freeze-dried to provide the title compound.

2.49.2 N-{6-[(chloroacetyl)amino]hexanoyl}-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]phenyl}-N$^5$-carbamoyl-L-ornithinamide A solution of 6-(2-chloroacetamido)hexanoic acid (6.43 mg) and 2-(3H-[1,2,3]triazolo[4,5-b]pyridin-3-yl)-1,1,3,3-tetramethylisouronium hexafluorophosphate(V) (0.012 g) in N,N-dimethylformamide (0.5 mL) was added N,N-diisopropylethylamine (0.019 mL), and the reaction stirred for 5 minutes. This solution was added to Example 2.49.1 (0.026 g) and was stirred for 1 hour. The reaction was diluted with N,N-dimethylformamide (1 mL) and water (0.5 mL). The mixture was purified by reverse phase HPLC using a Gilson system, eluting with 10-60% acetonitrile in water containing 0.1% v/v trifluoroacetic acid. The desired fractions were combined and freeze-dried to provide the title compound. $^1$H NMR (500 MHz, dimethyl sulfoxide-d$_6$) δ ppm 12.85 (s, 1H), 9.99 (s, 1H), 8.18 (q, 1H), 8.08 (d, 1H), 8.04 (d, 1H), 7.84-7.76 (m, 2H), 7.64-7.56 (m, 3H), 7.56-7.50 (m, 1H), 7.47 (t, 1H), 7.43 (d, 1H), 7.37 (d, 1H), 7.35 (d, 1H), 7.29 (s, 1H), 7.27 (d, 2H), 6.95 (d, 1H), 6.05 (s, 1H), 5.05-4.91 (m, 4H), 4.48-4.33 (m, 1H), 4.26-4.14 (m, 1H), 4.02 (s, 2H), 3.88 (t, 2H), 3.81 (d, 2H), 3.25 (t, 2H), 3.14-2.98 (m, 6H), 2.98-2.87 (m, 2H), 2.74-2.59 (m, 2H), 2.27-2.05 (m, 6H), 2.04-1.92 (m, 1H), 1.78-1.65 (m, 1H), 1.65-1.53 (m, 1H), 1.53-0.90 (m, 22H), 0.90-0.73 (m, 12H). MS (ESI) m/e 1448.2 (M+H)$^+$.

2.50 Synthesis of N-[6-(2,5-dioxo-2,5-dihydro-1H-pyrrol-1-yl)hexanoyl]-L-valyl-N-{4-[({[2-({3-[(4-{6-[4-(1,3-benzothiazol-2-ylcarbamoyl)-3,4-dihydro-2H-1,4-benzoxazin-6-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]phenyl}-N$^5$-carbamoyl-L-ornithinamide (Synthon JD)

The title compound was prepared by substituting Example 1.51.8 for Example 2.5.3 in Example 2.5.4. $^1$H NMR (400 MHz, dimethyl sulfoxide-d$_6$) δ ppm 9.56 (s, 1H), 8.51-8.59 (m, 1H), 7.89 (d, 1H), 7.82 (d, 1H), 7.69-7.77 (m, 2H), 7.34-7.62 (m, 7H), 7.16-7.34 (m, 4H), 6.95 (dd, 1H), 5.95-6.05 (m, 1H), 4.95 (s, 2H), 4.06-4.44 (m, 6H), 3.85 (s, 3H), 3.39-3.59 (m, 7H), 2.61-2.74 (m, 3H), 2.19 (s, 3H), 1.88-2.16 (m, 3H), 0.96-1.75 (m, 22H), 0.71-0.89 (m, 13H). MS (ESI) m/e 1454.2 (M+Na)$^+$.

2.51 Synthesis of N-[6-(2,5-dioxo-2,5-dihydro-1H-pyrrol-1-yl)hexanoyl]-L-valyl-N-[4-({[(2-{[8-(1,3-benzothiazol-2-ylcarbamoyl)-2-(6-carboxy-5-{1-[(3,5-dimethyl-7-{2-[methyl(2-sulfoethyl)amino]ethoxy}tricyclo[3.3.1.1$^{3,7}$]dec-1-yl)methyl]-5-methyl-1H-pyrazol-4-yl}pyridin-2-yl)-1,2,3,4-tetrahydroisoquinolin-5-yl]oxy}ethyl)(2-carboxyethyl)carbamoyl]oxy}methyl)phenyl]-N5-carbamoyl-L-ornithinamide (Synthon JF)

The title compound was prepared as described in Example 2.1, replacing Example 1.2.9 with Example 1.49.2. $^1$H NMR (500 MHz, dimethyl sulfoxide-d$_6$) δ ppm 12.71 (s, 1H), 10.00 (s, 1H), 8.97 (s, 1H), 8.08 (d, 1H), 8.02 (d, 1H), 7.78 (d, 2H), 7.72 (d, 1H), 7.60 (d, 2H), 7.52 (d, 1H), 7.44-7.50 (m, 1H), 7.27-7.39 (m, 4H), 6.96-7.06 (m, 3H), 5.98 (s, 1H), 5.01 (d, 4H), 4.31-4.46 (m, 1H), 4.18 (s, 3H), 3.79-3.95 (m, 4H), 3.67-3.76 (m, 2H), 3.12-3.39 (m, 6H), 2.73-3.07 (m, 8H), 2.04-2.24 (m, 4H), 1.87-2.02 (m, 1H), 1.22-1.75 (m, 12H), 0.96-1.20 (m, 7H), 0.76-0.90 (m, 10H). MS (ESI) m/e 1597.4 (M+H)$^+$.

2.52 Synthesis of N-[6-(2,5-dioxo-2,5-dihydro-1H-pyrrol-1-yl)hexanoyl]-L-valyl-N-{4-[({[2-({3-[(4-{6-[8-(1,3-benzothiazol-2-ylcarbamoyl)-5-(3-sulfopropoxy)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](methyl)carbamoyl}oxy)methyl]phenyl}-N$^5$-carbamoyl-L-ornithinamide (Synthon JK)

The title compound was prepared by substituting Example 1.52.4 for Example 2.5.3 in Example 2.5.4. $^1$H NMR (400 MHz, dimethyl sulfoxide-d$_6$) δ ppm 9.97 (s, 1H), 7.96-8.11 (m, 2H), 7.67-7.82 (m, 3H), 7.59 (d, 2H), 7.42-7.52 (m, 2H), 7.23-7.36 (m, 4H), 6.91-7.08 (m, 4H), 4.99 (d, 4H), 4.33-4.47 (m, 1H), 4.14-4.23 (m, 4H), 3.86-3.95 (m, 6H), 3.21-3.45 (m, 15H), 2.75-3.07 (m, 9H), 2.56-2.69 (m, 2H), 1.93-2.20 (m, 8H), 0.88-1.72 (m, 20H), 0.74-0.89 (m, 11H). MS (ESI) m/e 1496.3 (M+Na)$^+$.

2.53 Synthesis of N-[3-(2,5-dioxo-2,5-dihydro-1H-pyrrol-1-yl)propanoyl]-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]phenyl}-N$^5$-carbamoyl-L-ornithinamide (Synthon JJ)

A solution of Example 2.49.1 (0.030 g), 2,5-dioxopyrrolidin-1-yl 3-(2,5-dioxo-2,5-dihydro-1H-pyrrol-1-yl)propanoate (6.34 mg) and N,N-diisopropylethylamine (0.012 mL) in N,N-dimethylformamide (0.5 mL) was stirred at room temperature. After 1 hour the reaction was quenched with a 3:1 mixture of N,N-dimethylformamide:water (1.5 mL). The mixture was purified by reverse phase HPLC using a Gilson system, eluting with 10-85% acetonitrile in water containing 0.1% v/v trifluoroacetic acid. The desired fractions were combined and freeze-dried to provide the title compound. $^1$H NMR (500 MHz, dimethyl sulfoxide-d$_6$) δ ppm 12.85 (s, 1H), 9.99 (s, 1H), 8.18 (q, 1H), 8.12-8.00 (m, 2H), 7.86-7.75 (m, 2H), 7.65-7.55 (m, 3H), 7.53 (dd, 1H), 7.47 (t, 1H), 7.43 (d, 1H), 7.36 (q, 2H), 7.33-7.23 (m, 3H), 6.95 (d, 1H), 6.05 (s, 1H), 5.03-4.92 (m, 4H), 4.39 (q, 1H), 4.24-4.14 (m, 1H), 4.02 (s, 2H), 3.88 (t, 2H), 3.81 (d, 2H), 3.39-3.16 (m, 2H), 3.14-2.86 (m, 10H), 2.68-2.60 (m, 2H), 2.25-2.04 (m, 6H), 2.03-1.90 (m, 1H), 1.78-1.65 (m, 1H), 1.64-1.54 (m, 1H), 1.54-0.90 (m, 20H), 0.89-0.75 (m, 12H). MS (ESI) m/e 1410.1 (M+H)$^+$.

2.54 Synthesis of N-[(2,5-dioxo-2,5-dihydro-1H-pyrrol-1-yl)acetyl]-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]phenyl}-N$^5$-carbamoyl-L-ornithinamide (Synthon JL)

A solution of Example 2.49.1 (0.039 g), 2,5-dioxopyrrolidin-1-yl 2-(2,5-dioxo-2,5-dihydro-1H-pyrrol-1-yl)acetate (7.81 mg) and N,N-diisopropylethylamine (0.016 mL) in N,N-dimethylformamide (0.5 mL) was stirred at room temperature. After 1 hour, the reaction was quenched with a 3:1 mixture of N,N-dimethylformamide:water (1.5 mL). The mixture was purified by reverse phase HPLC using a Gilson system, eluting with 10-85% acetonitrile in water containing 0.1% v/v trifluoroacetic acid. The desired fractions were combined and freeze-dried to provide the title compound. $^1$H NMR (400 MHz, dimethyl sulfoxide-d$_6$) δ ppm 12.85 (s, 1H), 10.00 (d, 1H), 8.24 (d, 2H), 8.04 (d, 1H), 7.79 (d, 1H), 7.59 (q, 3H), 7.53 (dd, 1H), 7.47 (t, 1H), 7.43 (d, 1H), 7.36 (td, 2H), 7.30 (s, 1H), 7.27 (d, 2H), 7.07 (s, 2H), 6.96 (d, 1H), 5.04-4.85 (m, 4H), 4.39 (q, 2H), 4.26 (dd, 2H), 4.13 (s, 2H), 3.86-3.17 (m, 8H), 3.07-2.81 (m, 4H), 2.63 (t, 2H), 2.09 (s, 3H), 2.03-1.79 (m, 1H), 1.75-1.51 (m, 2H), 1.51-1.03 (m, 12H), 1.01-0.76 (m, 16H). MS (ESI) m/e 1394.4 (M−H)$^−$.

2.55 Synthesis of 6-[8-(1,3-benzothiazol-2-ylcarbamoyl)-3,4-dihydroisoquinolin-2(1H)-yl]-3-(1-{[3-(2-{[(2S)-2-({[(4-{[(2S,3R,4S,5S,6S)-6-carboxy-3,4,5-trihydroxytetrahydro-2H-pyran-2-yl]oxy}-3-[(3-{[6-(2,5-dioxo-2,5-dihydro-1H-pyrrol-1-yl)hexanoyl]amino}propanoyl)amino]benzyl)oxy]carbonyl}amino)-3-sulfopropanoyl](methyl)amino}ethoxy)-5,7-dimethyltricyclo[3.3.1.1$^{3,7}$]dec-1-yl]methyl}-5-methyl-1H-pyrazol-4-yl)pyridine-2-carboxylic acid (Synthon FE)

2.55.1 (2S,3R,4S,5S,6S)-2-(4-formyl-2-nitrophenoxy)-6-(methoxycarbonyl)tetrahydro-2H-pyran-3,4,5-triyl triacetate To a solution of (2R,3R,4S,5S,6S)-2-bromo-6-(methoxycarbonyl)tetrahydro-2H-pyran-3,4,5-triyl triacetate (4 g) in acetonitrile (100 mL)) was added silver(I) oxide (10.04 g) and 4-hydroxy-3-nitrobenzaldehyde (1.683 g). The reaction mixture was stirred for 4 hours at room temperature and filtered. The filtrate was concentrated, and the residue was purified by silica gel chromatography, eluting with 5-50% ethyl acetate in heptanes, to provide the title compound. MS (ESI) m/e (M+18)$^+$.

2.55.2 (2S,3R,4S,5S,6S)-2-(4-(hydroxymethyl)-2-nitrophenoxy)-6-(methoxycarbonyl)tetrahydro-2H-pyran-3,4,5-triyl triacetate To a solution of Example 2.55.1 (6 g) in a mixture of chloroform (75 mL) and isopropanol (18.75 mL) was added 0.87 g of silica gel. The resulting mixture was cooled to 0° C., NaBH$_4$ (0.470 g) was added, and the resulting suspension was stirred at 0° C. for 45 minutes. The reaction mixture was diluted with dichloromethane (100 mL) and filtered through diatomaceous earth. The filtrate was washed with water and brine and concentrated to give the crude product, which was used without further purification. MS (ESI) m/e (M+NH$_4$)+:

2.55.3 (2S,3R,4S,5S,6S)-2-(2-amino-4-(hydroxymethyl)phenoxy)-6-(methoxycarbonyl)tetrahydro-2H-pyran-3,4,5-triyl triacetate A stirred solution of Example 2.55.2 (7 g) in ethyl acetate (81 mL) was hydrogenated at 20° C. under 1 atmosphere H$_2$, using 10% Pd/C (1.535 g) as a catalyst for 12 hours. The reaction mixture was filtered through diatomaceous earth, and the solvent was evaporated under reduced pressure. The residue was purified by silica gel chromatography, eluting with 95/5 dichloromethane/methanol, to give the title compound.

2.55.4 3-(((((9H-fluoren-9-yl)methoxy)carbonyl)amino)propanoic acid

3-Aminopropanoic acid (4.99 g) was dissolved in 10% aqueous Na$_2$CO$_3$ solution (120 mL) in a 500 mL flask and cooled with an ice bath. To the resulting solution, (9H-fluoren-9-yl)methyl carbonochloridate (14.5 g) in 1,4-dioxane (100 mL) was gradually added. The reaction mixture was stirred at room temperature for 4 hours, and water (800 mL) was then added. The aqueous phase layer was separated from the reaction mixture and washed with diethyl ether (3×750 mL). The aqueous layer was acidified with 2N HCl aqueous solution to a pH value of 2 and extracted with ethyl acetate (3×750 mL). The organic layers were combined and concentrated to obtain crude product. The crude product was recrystallized in a mixed solvent of ethyl acetate: hexane 1:2 (300 mL) to give the title compound.

2.55.5 (9H-fluoren-9-yl)methyl (3-chloro-3-oxopropyl)carbamate

To a solution of Example 2.55.4 in dichloromethane (160 mL) was added sulfurous dichloride (50 mL). The mixture was stirred at 60° C. for 1 hour. The mixture was cooled and concentrated to give the title compound.

2.55.6 (2S,3R,4S,5S,6S)-2-(2-(3-((((9H-fluoren-9-yl)methoxy)carbonyl)amino)propanamido)-4-(hydroxymethyl)phenoxy)-6-(methoxycarbonyl)tetrahydro-2H-pyran-3,4,5-triyl triacetate To a solution of Example 2.55.3 (6 g) in dichloromethane (480 mL) was added N,N-diisopropylethylamine (4.60 mL). Example 2.55.5 (5.34 g) was added, and the mixture was stirred at room temperature for 30 minutes. The mixture was poured into saturated aqueous sodium bicarbonate and was extracted with ethyl acetate. The combined extracts were washed with water and brine and were dried over sodium sulfate. Filtration and concentration gave a residue that was purified via radial chromatography, using 0-100% ethyl acetate in petroleum ether as mobile phase, to give the title compound.

2.55.7 (2S,3R,4S,5S,6S)-2-(2-(3-((((9H-fluoren-9-yl)methoxy)carbonyl)amino)propanamido)-4-((((4-nitrophenoxy)carbonyl)oxy)methyl)phenoxy)-6-(methoxycarbonyl)tetrahydro-2H-pyran-3,4,5-triyl triacetate To a mixture of Example 2.55.6 (5.1 g) in N,N-dimethylformamide (200 mL) was added bis(4-nitrophenyl) carbonate (4.14 g) and N,N-diisopropylethylamine (1.784 mL). The mixture was stirred for 16 hours at room temperature and concentrated under reduced pressure. The crude material was dissolved in dichloromethane and aspirated directly onto a 1 mm radial Chromatotron plate and eluted with 50-100% ethyl acetate in hexanes to give the title compound. MS (ESI) m/e (M+H)$^+$.

2.55.8 3-(1-((3-(2-((R)-2-((((3-(3-aminopropanamido)-4-(((2S,3R,4S,5S,6S)-6-carboxy-3,4,5-trihydroxytetrahydro-2H-pyran-2-yl)oxy)benzyl)oxy)carbonyl)amino)-N-methyl-3-sulfopropanamido)ethoxy)-5,7-dimethyladamantan-1-yl)methyl)-5-methyl-1H-pyrazol-4-yl)-6-(8-(benzo[d]thiazol-2-ylcarbamoyl)-3,4-dihydroisoquinolin-2(1H)-yl) picolinic acid A solution of Example 1.13.7 (0.055 g) and Example 2.55.7 (0.055 g) were stirred together in N,N-dimethylformamide (1.5 mL) and N,N-diisopropylethylamine (0.053 mL) was added. After stirring for 3 hours, the reaction was diluted with ethyl acetate (75 mL) and washed with water (20 mL) and brine (25 mL), dried over magnesium sulfate, filtered, and concentrated. The residue was dissolved in methanol (1 mL) and treated with lithium hydroxide hydrate (0.025 g) in water (0.6 mL). After stirring for 2 hours, the reaction was quenched with trifluoroacetic acid (0.047 ml) and diluted with N,N-dimethylformamide (1 mL). The mixture was purified by reverse phase HPLC using a Gilson system, eluting with 10-80% acetonitrile in water containing 0.1% v/v trifluoroacetic acid. The desired fractions were combined and freeze-dried to provide the title compound as a trifluoroacetic acid salt.

2.55.9 6-[8-(1,3-benzothiazol-2-ylcarbamoyl)-3,4-dihydroisoquinolin-2(1H)-yl]-3-(1-{[3-(2-{[(2S)-2-({[(4-{[(2S,3R,4S,5S,6S)-6-carboxy-3,4,5-trihydroxytetrahydro-2H-pyran-2-yl]oxy}-3-[(3-{[6-(2,5-dioxo-2,5-dihydro-1H-pyrrol-1-yl)hexanoyl]amino}propanoyl)amino]benzyl)oxy]carbonyl}amino)-3-sulfopropanoyl](methyl)amino}ethoxy)-5,7-dimethyltricyclo[3.3.1.1$^{3,7}$]dec-1-yl]methyl}-5-methyl-1H-pyrazol-4-yl)pyridine-2-carboxylic acid A solution of Example 2.55.8 (0.013 g) and 2,5-dioxopyrrolidin-1-yl 6-(2,5-dioxo-2,5-dihydro-1H-pyrrol-1-yl)hexanoate (3.07 mg) were stirred in N,N-dimethylformamide (1 mL) and N,N-diisopropylethylamine (7.90 μL) was added. The reaction was stirred for 1 hour and diluted with N,N-dimethylformamide and water. The mixture was purified by reverse phase HPLC using a Gilson system, eluting with 10-75% acetonitrile in water containing 0.1% v/v trifluoroacetic acid. The desired fractions were combined and freeze-dried to provide the title compound. $^1$H NMR (400 MHz, dimethyl sulfoxide-d$_6$) δ ppm 12.84 (s, 1H), 9.07 (s, 1H), 8.15 (s, 1H), 8.04 (d, 1H), 7.89 (t, 1H), 7.79 (d, 1H), 7.61 (d, 1H), 7.56-7.50 (m, 1H), 7.47 (t, 1H), 7.43 (d, 1H), 7.39-7.32 (m, 2H), 7.31 (s, 1H), 7.28 (d, 1H), 7.06 (d, 1H), 7.04-6.92 (m, 4H), 5.00-4.79 (m, 5H), 4.73-4.64 (m, 1H), 3.94-3.78 (m, 4H), 3.57-2.84 (m, 12H), 2.84-2.56 (m, 6H), 2.14-1.73 (m, 5H), 1.57-0.89 (m, 22H), 0.84 (s, 6H). MS (ESI) m/e 1516.2 (M–H)$^-$.

2.56 Synthesis of 4-[(1E)-3-({[2-({3-[(4-{2-carboxy-6-[8-([1,3]thiazolo[5,4-b]pyridin-2-ylcarbamoyl)-3,4-dihydroisoquinolin-2(1H)-yl]pyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)prop-1-en-1-yl]-2-({N-[6-(2,5-dioxo-2,5-dihydro-1H-pyrrol-1-yl)hexanoyl]-beta-alanyl}amino)phenyl beta-D-glucopyranosiduronic acid (Synthon GG)

2.56.1 3-(1-((3-(2-(((((E)-3-(3-(3-aminopropanamido)-4-(((2S,3R,4S,5S,6S)-6-carboxy-3,4,5-trihydroxytetrahydro-2H-pyran-2-yl)oxy)phenyl)allyl)oxy)carbonyl)(2-sulfoethyl)amino)ethoxy)-5,7-dimethyladamantan-1-yl)methyl)-5-methyl-1H-pyrazol-4-yl)-6-(8-(thiazolo[5,4-b]pyridin-2-ylcarbamoyl)-3,4-dihydroisoquinolin-2(1H)-yl) picolinic acid Example 1.22.5 (48 mg) was dissolved in dimethylformamide (0.5 mL), and Example 2.44.7 (55 mg) and N,N-diisopropylethylamine (90 μL) were added. The reaction mixture was stirred at room temperature overnight. The reaction was concentrated, and the residue was dissolved in methanol (1 mL) and 1.94N aqueous LiOH (0.27 mL) was added. The mixture was stirred at room temperature for one hour. Purification of the mixture by reverse phase chromatography (C18 column), eluting with 10-90% acetonitrile in water containing 0.1% v/v trifluoroacetic acid, provided the title compound as a trifluoroacetic acid salt. MS (ESI–) m/e 1291.4 (M–H)⁻.

2.56.2 4-[(1E)-3-({[2-({3-[(4-{2-carboxy-6-[8-([1,3]thiazolo[5,4-b]pyridin-2-ylcarbamoyl)-3,4-dihydroisoquinolin-2(1H)-yl]pyridin-3-yl}-5-methyl-1H-pyrazol-1-yl)methyl]-5,7-dimethyltricyclo[3.3.1.1³,⁷]dec-1-yl}oxy)ethyl](2-sulfoethyl)carbamoyl}oxy)prop-1-en-1-yl]-2-({N-[6-(2,5-dioxo-2,5-dihydro-1H-pyrrol-1-yl)hexanoyl]-beta-alanyl}amino)phenyl beta-D-glucopyranosiduronic acid The title compound was prepared by substituting Example 1.56.1 for Example 1.2.9 in Example 2.1. ¹H NMR (400 MHz, dimethyl sulfoxide-d₆) δ ppm 13.00 (v br s, 1H), 9.03 (s, 1H), 8.53 (dd, 1H), 8.24 (s, 1H), 8.16 (dd, 1H), 7.90 (br s, 1H), 7.61 (d, 1H), 7.54 (d, 1H) 7.52 (d, 1H), 7.44 (d, 1H), 7.37 (t, 1H), 7.30 (s, 1H), 7.11 (br d, 1H), 7.03 (d, 1H), 6.98 (s, 2H), 6.97 (d, 1H), 6.58 (m, 1H), 6.15 (m, 1H), 4.96 (s, 2H), 4.88 (br m, 1H), 4.64 (br m, 2H), 3.88 (m, 3H), 3.79 (br m, 2H), 3.27-3.48 (m, 14H), 3.01 (m, 2H), 2.67 (br m, 2H), 2.54 (m, 2H), 2.09 (s, 3H), 2.03 (t, 2H), 1.45 (m, 6H), 1.37 (br m, 2H), 1.28-0.90 (m, 10H), 0.77-0.82 (m, 6H). MS (ESI) m/e 1484.4 (M–H)⁻.

2.57 Synthesis of 4-[(1E)-3-({[2-({3-[(4-{2-carboxy-6-[8-([1,3]thiazolo[4,5-b]pyridin-2-ylcarbamoyl)-3,4-dihydroisoquinolin-2(1H)-yl]pyridin-3-yl}-5-methyl-1H-pyrazol-1-yl)methyl]-5,7-dimethyltricyclo[3.3.1.1³,⁷]dec-1-yl}oxy)ethyl](2-sulfoethyl)carbamoyl}oxy)prop-1-en-1-yl]-2-({N-[6-(2,5-dioxo-2,5-dihydro-1H-pyrrol-1-yl)hexanoyl]-beta-alanyl}amino)phenyl beta-D-glucopyranosiduronic acid (Synthon GM)

2.57.1 3-(1-((3-(2-(((((E)-3-(3-(3-aminopropanamido)-4-(((2S,3R,4S,5S,6S)-6-carboxy-3,4,5-trihydroxytetrahydro-2H-pyran-2-yl)oxy)phenyl)allyl)oxy)carbonyl)(2-sulfoethyl)amino)ethoxy)-5,7-dimethyladamantan-1-yl)methyl)-5-methyl-1H-pyrazol-4-yl)-6-(8-(thiazolo[4,5-b]pyridin-2-ylcarbamoyl)-3,4-dihydroisoquinolin-2(1H)-yl)picolinic acid The title compound was prepared by substituting Example 1.23.4 for Example 1.22.5 in Example 2.56.1. MS (ESI) m/e 1291.4 (M–H)⁻.

2.57.2 4-[(1E)-3-({[2-({3-[(4-{2-carboxy-6-[8-([1,3]thiazolo[4,5-b]pyridin-2-ylcarbamoyl)-3,4-dihydroisoquinolin-2(1H)-yl]pyridin-3-yl}-5-methyl-1H-pyrazol-1-yl)methyl]-5,7-dimethyltricyclo[3.3.1.1³,⁷]dec-1-yl}oxy)ethyl](2-sulfoethyl)carbamoyl}oxy)prop-1-en-1-yl]-2-({N-[6-(2,5-dioxo-2,5-dihydro-1H-pyrrol-1-yl)hexanoyl]-beta-alanyl}amino)phenyl beta-D-glucopyranosiduronic acid The title compound was prepared by substituting Example 1.57.1 for Example 1.2.9 in Example 2.1. ¹H NMR (500 MHz, dimethyl sulfoxide-d₆) δ ppm 9.03 (s, 1H), 8.72 (d, 1H), 8.66 (d, 1H), 8.25 (s, 1H), 7.89 (br m, 1H), 7.65 (d, 1H), 7.52 (br m, 2H), 7.46 (d, 1H), 7.39 (t, 1H), 7.30 (s, 1H), 7.11 (br d, 1H), 7.03 (d, 1H), 6.98 (s, 2H), 6.97 (d, 1H), 6.58 (m, 1H), 6.15 (m, 1H), 4.96 (s, 2H), 4.88 (br m, 1H), 4.64 (br m, 2H), 3.88 (m, 3H), 3.79 (br m, 2H), 3.27-3.48 (m, 14H), 3.01 (m, 2H), 2.67 (br m, 2H), 2.54 (m, 2H), 2.09 (s, 3H), 2.03 (t, 2H), 1.45 (m, 6H), 1.37 (br m, 2H), 1.28-0.90 (m, 10H), 0.77-0.82 (m, 6H). MS (ESI) m/e 1484.4 (M–H)⁻.

2.58 Synthesis of 4-[(1E)-3-({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1³,⁷]dec-1-yl}oxy)ethyl](2-sulfoethyl)carbamoyl}oxy)prop-1-en-1-yl]-2-({N-[6-(2,5-dioxo-2,5-dihydro-1H-pyrrol-1-yl)hexanoyl]-beta-alanyl}amino)phenyl beta-D-glucopyranosiduronic acid (Synthon HD)

2.58.1 3-(1-((3-(2-(((((E)-3-(3-(3-aminopropanamido)-4-(((2S,3R,4S,5S,6S)-6-carboxy-3,4,5-trihydroxytetrahydro-2H-pyran-2-yl)oxy)phenyl)allyl)oxy)carbonyl)(2-sulfoethyl)amino)ethoxy)-5,7-dimethyladamantan-1-yl)methyl)-5-methyl-1H-pyrazol-4-yl)-6-(8-(benzo[d]thiazol-2-ylcarbamoyl)-3,4-dihydroisoquinolin-2(1H)-yl)picolinic acid The title compound was prepared by substituting Example 1.2.9 for Example 1.22.5 in Example 2.56.1. MS (ESI–) m/e 1290.2 (M–H)⁻.

2.58.2 4-[(1E)-3-({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1³,⁷]dec-1-yl}oxy)ethyl](2-sulfoethyl)carbamoyl}oxy)prop-1-en-1-yl]-2-({N-[6-(2,5-dioxo-2,5-dihydro-1H-pyrrol-1-yl)hexanoyl]-beta-alanyl}amino)phenyl beta-D-glucopyranosiduronic acid The title compound was prepared by substituting Example 1.58.1 for Example 1.56.1 in Example 2.56.2. ¹H NMR (400 MHz, dimethyl sulfoxide-d₆) δ ppm 9.03 (s, 1H), 8.25 (s, 1H), 8.03 (d, 1H), 7.89 (br m, 1H), 7.79 (d, 1H), 7.61 (d, 1H), 7.53 (br m, 1H), 7.46 (m, 2H), 7.37 (m, 2H), 7.32 (s, 1H), 7.11 (br d, 1H), 7.03 (d, 1H), 6.98 (s, 2H), 6.97 (d, 1H), 6.58 (m, 1H), 6.15 (m, 1H), 4.96 (s, 2H), 4.88 (br m, 1H), 4.64 (br m, 2H), 3.88 (m, 3H), 3.79 (br m, 2H), 3.27-3.48 (m, 14H), 3.01 (m, 2H), 2.67 (br m, 2H), 2.54 (m, 2H), 2.09 (s, 3H), 2.03 (t, 2H), 1.45 (m, 6H), 1.37 (br m, 2H), 1.28-0.90 (m, 10H), 0.77-0.82 (m, 6H). MS (ESI–) m/e 1483.3 (M–H)⁻.

2.59 Synthesis of 4-[(1E)-3-({[2-({3-[(4-{2-carboxy-6-[8-([1,3]thiazolo[5,4-b]pyridin-2-ylcarbamoyl)-3,4-dihydroisoquinolin-2(1H)-yl]pyridin-3-yl}-5-methyl-1H-pyrazol-1-yl)methyl]-5,7-dimethyltricyclo[3.3.1.1$^{3,7}$]dec-1-yl}oxy)ethyl](3-phosphonopropyl)carbamoyl}oxy)prop-1-en-1-yl]-2-({N-[6-(2,5-dioxo-2,5-dihydro-1H-pyrrol-1-yl)hexanoyl]-beta-alanyl}amino)phenyl beta-D-glucopyranosiduronic acid (Synthon HS)

2.59.1 3-(1-((3-(2-(((((E)-3-(3-(3-aminopropanamido)-4-(((2S,3R,4S,5S,6S)-6-carboxy-3,4,5-trihydroxytetrahydro-2H-pyran-2-yl)oxy)phenyl)allyl)oxy)carbonyl)(3-phosphonopropyl)amino)ethoxy)-5,7-dimethyladamantan-1-yl)methyl)-5-methyl-1H-pyrazol-4-yl)-6-(8-(thiazolo[5,4-b]pyridin-2-ylcarbamoyl)-3,4-dihydroisoquinolin-2(1H)-yl) picolinic acid The title compound was prepared by substituting Example 1.40.2 for Example 1.22.5 in Example 2.56.1. MS (ESI–) m/e 1305.4 (M–H)⁻.

2.59.2 4-[(1E)-3-({[2-({3-[(4-{2-carboxy-6-[8-([1,3]thiazolo[5,4-b]pyridin-2-ylcarbamoyl)-3,4-dihydroisoquinolin-2(1H)-yl]pyridin-3-yl}-5-methyl-1H-pyrazol-1-yl)methyl]-5,7-dimethyltricyclo[3.3.1.1$^{3,7}$]dec-1-yl}oxy)ethyl](3-phosphonopropyl)carbamoyl}oxy)prop-1-en-1-yl]-2-({N-[6-(2,5-dioxo-2,5-dihydro-1H-pyrrol-1-yl)hexanoyl]-beta-alanyl}amino)phenyl beta-D-glucopyranosiduronic acid The title compound was prepared by substituting Example 1.59.1 for Example 1.56.1 in Example 2.56.2. $^1$H NMR (400 MHz, dimethyl sulfoxide-d$_6$) δ ppm 9.03 (s, 1H), 8.53 (dd, 1H), 8.24 (s, 1H), 8.16 (dd, 1H), 7.90 (br s, 1H), 7.61 (d, 1H), 7.54 (d, 1H) 7.52 (d, 1H), 7.44 (d, 1H), 7.37 (t, 1H), 7.28 (s, 1H), 7.11 (br d, 1H), 7.03 (d, 1H), 6.98 (s, 2H), 6.97 (d, 1H), 6.56 (m, 1H), 6.16 (m, 1H), 4.96 (s, 2H), 4.86 (br m, 1H), 4.64 (br d, 2H), 3.88 (m, 3H), 3.79 (br m, 2H), 3.27-3.44 (m, 14H), 3.01 (m, 2H), 2.54 (m, 2H), 2.08 (s, 3H), 2.03 (t, 2H), 1.46 (m, 6H), 1.37 (br m, 2H), 1.28-0.90 (m, 10H), 0.77-0.82 (m, 6H). MS (ESI) m/e 1498.4 (M–H)⁻.

2.60 Synthesis of 4-[(1E)-3-({[2-({3-[(4-{6-[8-(1,3-benzothiazol-2-ylcarbamoyl)-5-(3-phosphonopropoxy)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](methyl)carbamoyl}oxy)prop-1-en-1-yl]-2-({N-[6-(2,5-dioxo-2,5-dihydro-1H-pyrrol-1-yl)hexanoyl]-beta-alanyl}amino)phenyl beta-D-glucopyranosiduronic acid (Synthon HW)

2.60.1 3-(1-(((3-(2-(((((E)-3-(3-(3-aminopropanamido)-4-(((2S,3R,4S,5S,6S)-6-carboxy-3,4,5-trihydroxytetrahydro-2H-pyran-2-yl)oxy)phenyl)allyl)oxy)carbonyl)(methyl)amino)ethoxy)-5,7-dimethyladamantan-1-yl)methyl)-5-methyl-1H-pyrazol-4-yl)-6-(8-(benzo[d]thiazol-2-ylcarbamoyl)-5-(3-phosphonopropoxy)-3,4-dihydroisoquinolin-2(1H)-yl)picolinic acid The title compound was prepared by substituting Example 1.31.11 for Example 1.22.5 in Example 2.56.1. MS (ESI) m/e 1336.2 (M+Na)⁺.

2.60.2 4-[(1E)-3-({[2-({3-[(4-{6-[8-(1,3-benzothiazol-2-ylcarbamoyl)-5-(3-phosphonopropoxy)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](methyl)carbamoyl}oxy)prop-1-en-1-yl]-2-({N-[6-(2,5-dioxo-2,5-dihydro-1H-pyrrol-1-yl)hexanoyl]-beta-alanyl}amino)phenyl beta-D-glucopyranosiduronic acid The title compound was prepared by substituting Example 1.60.1 for Example 1.56.1 in Example 2.56.2. $^1$H NMR (400 MHz, dimethyl sulfoxide-d$_6$) δ ppm 9.03 (s, 1H) 8.25 (s, 1H), 8.01 (d, 1H), 7.83-7.91 (m, 1H), 7.75 (dd, 2H), 7.42-7.58 (m, 2H), 7.34 (t, 1H), 7.28 (s, 1H), 6.93-7.15 (m, 6H), 6.56 (d, 1H), 6.09-6.24 (m, 1H), 5.01 (s, 3H), 4.80-4.92 (m, 2H), 4.57-4.69 (m, 3H), 4.12-4.21 (m, 6H), 3.86-3.94 (m, 7H), 3.28-3.47 (m, 12H), 2.77-2.96 (m, 6H), 2.52-2.58 (m, 2H), 2.09 (s, 3H), 1.90-2.05 (m, 4H), 1.65-1.78 (m, 2H), 0.90-1.53 (m, 16H), 0.80 (m, 6H). MS (ESI) m/e 1529.5 (M+H)⁺.

2.61 Synthesis of 4-[(1E)-3-({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](3-phosphonopropyl)carbamoyl}oxy)prop-1-en-1-yl]-2-({N-[6-(2,5-dioxo-2,5-dihydro-1H-pyrrol-1-yl)hexanoyl]-beta-alanyl}amino)phenyl beta-D-glucopyranosiduronic acid (Synthon HX)

2.61.1 3-(1-((3-(2-(((((E)-3-(3-(3-aminopropanamido)-4-(((2S,3R,4S,5S,6S)-6-carboxy-3,4,5-trihydroxytetrahydro-2H-pyran-2-yl)oxy)phenyl)allyl)oxy)carbonyl)(3-phosphonopropyl)amino)ethoxy)-5,7-dimethyladamantan-1-yl)methyl)-5-methyl-1H-pyrazol-4-yl)-6-(8-(benzo[d]thiazol-2-ylcarbamoyl)-3,4-dihydroisoquinolin-2(1H)-yl)picolinic acid The title compound was prepared by substituting Example 1.14.4 for Example 1.22.5 in Example 2.56.1. MS (ESI) m/e 1304.3 (M–H)⁻.

2.61.2 4-[(1E)-3-({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](3-phosphonopropyl)carbamoyl}oxy)prop-1-en-1-yl]-2-({N-[6-(2,5-dioxo-2,5-dihydro-1H-pyrrol-1-yl)hexanoyl]-beta-alanyl}amino)phenyl beta-D-glucopyranosiduronic acid The title compound was prepared by substituting Example 1.61.1 for Example 1.56.1 in Example 2.56.2. $^1$H NMR (400 MHz, dimethyl sulfoxide-d$_6$) δ ppm 9.03 (s, 1H), 8.25 (br s, 1H), 8.03 (d, 1H), 7.89 (br m, 1H), 7.79 (d, 1H), 7.61 (d, 1H), 7.53 (br m, 1H), 7.46 (m, 2H), 7.37 (m, 2H), 7.28 (s, 1H), 7.11 (br d, 1H), 7.03 (d, 1H), 6.98 (s, 2H), 6.97 (d, 1H), 6.56 (m, 1H), 6.17 (m, 1H), 4.96 (s, 2H), 4.86 (br m, 1H), 4.64 (br d, 2H), 3.88 (m, 3H), 3.79 (br m, 2H), 3.27-3.44 (m, 14H), 3.01 (m, 2H), 2.54 (m, 2H), 2.08 (s, 3H), 2.03 (t, 2H), 1.46 (m, 6H), 1.37 (br m, 2H), 1.28-0.90 (m, 10H), 0.77-0.82 (m, 6H). MS (ESI–) m/e 1497.4 (M–H)⁻.

2.62 Synthesis of 4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1³,⁷]dec-1-yl}oxy)ethyl](2-sulfoethyl)carbamoyl}oxy)methyl]-3-[2-(2-{[3-(2,5-dioxo-2,5-dihydro-1H-pyrrol-1-yl)propanoyl]amino}ethoxy)ethoxy]phenyl beta-D-glucopyranosiduronic acid (Synthon HY)

2.62.1 (2S,3R,4S,5S,6S)-2-(4-formyl-3-hydroxyphenoxy)-6-(methoxycarbonyl)tetrahydro-2H-pyran-3,4,5-triyl triacetate 2,4-Dihydroxybenzaldehyde (15 g) and (2S,3R,4S,5S,6S)-2-bromo-6-(methoxycarbonyl)tetrahydro-2H-pyran-3,4,5-triyl triacetate (10 g) were dissolved in acetonitrile followed by the addition of silver carbonate (10 g) and the reaction was heated to 49° C. After stirring for 4 hours, the reaction was cooled, filtered and concentrated. The crude title compound was suspended in dichloromethane and was filtered through diatomaceous earth and concentrated. The residue was purified by silica gel chromatography eluting with 1-100% ethyl acetate/heptane to provide the title compound.

2.62.2 (2S,3R,4S,5S,6S)-2-(3-hydroxy-4-(hydroxymethyl)phenoxy)-6-(methoxycarbonyl)tetrahydro-2H-pyran-3,4,5-triyl triacetate A solution of Example 2.62.1 (16.12 g) in tetrahydrofuran (200 mL) and methanol (200 mL) was cooled to 0° C. and sodium borohydride (1.476 g) was added portionwise. The reaction was stirred for 20 minutes and was quenched with a 1:1 mixture of water:aqueous saturated sodium bicarbonate solution (400 mL). The resulting solids were filtered off and rinsed with ethyl acetate. The phases were separated and the aqueous layer was extracted four times with ethyl acetate. The combined organic layers were dried over magnesium sulfate, filtered, and concentrated. The crude title compound was purified via silica gel chromatography eluting with 1-100% ethyl acetate/heptanes to provide the title compound. MS (ESI) m/e 473.9 (M+NH₄)⁺.

2.62.3 (2S,3R,4S,5S,6S)-2-(4-(((tert-butyldimethylsilyl)oxy)methyl)-3-hydroxyphenoxy)-6-(methoxycarbonyl)tetrahydro-2H-pyran-3,4,5-triyl triacetate Example 2.62.2 (7.66 g) and tert-butyldimethylsilyl chloride (2.78 g) in dichloromethane (168 mL) at −5° C. was added imidazole (2.63 g) and the reaction was stirred overnight allowing the internal temperature of the reaction to warm to 12° C. The reaction mixture was poured into saturated aqueous ammonium chloride and extracted four times with dichloromethane. The combined organics were washed with brine, dried over magnesium sulfate, filtered and concentrated. The crude title compound was purified via silica gel chromatography eluting with 1-50% ethyl acetate/heptanes to provide the title compound. MS (ESI) m/e 593.0 (M+Na)⁺.

2.62.4 (2S,3R,4S,5S,6S)-2-(3-(2-(2-((((9H-fluoren-9-yl)methoxy)carbonyl)amino)ethoxy)ethoxy)-4-(((tert-butyldimethylsilyl)oxy)methyl)phenoxy)-6-(methoxycarbonyl)tetrahydro-2H-pyran-3,4,5-triyl triacetate To Example 2.62.3 (5.03 g) and triphenylphosphine (4.62 g) in toluene (88 mL) was added di-tert-butyl-azodicarboxylate (4.06 g) and the reaction was stirred for 30 minutes. (9H-Fluoren-9-yl)methyl (2-(2-hydroxyethoxy)ethyl)carbamate was added and the reaction was stirred for an addition 1.5 hours. The reaction was loaded directly onto silica gel and was eluted with 1-50% ethyl acetate/heptanes to provide the title compound.

2.62.5 (2S,3R,4S,5S,6S)-2-(3-(2-(2-((((9H-fluoren-9-yl)methoxy)carbonyl)amino)ethoxy)ethoxy)-4-(hydroxymethyl)phenoxy)-6-(methoxycarbonyl)tetrahydro-2H-pyran-3,4,5-triyl triacetate Example 2.62.4 (4.29 g) was stirred in a 3:1:1 solution of acetic acid:water:tetrahydrofuran (100 mL) overnight. The reaction was poured into saturated aqueous sodium bicarbonate and extracted with ethyl acetate. The organic layer was dried over magnesium sulfate, filtered and concentrated. The crude title compound was purified via silica gel chromatography, eluting with 1-50% ethyl acetate/heptanes to provide the title compound.

2.62.6 (2S,3R,4S,5S,6S)-2-(3-(2-(2-((((9H-fluoren-9-yl)methoxy)carbonyl)amino)ethoxy)ethoxy)-4-((((4-nitrophenoxy)carbonyl)oxy)methyl)phenoxy)-6-(methoxycarbonyl)tetrahydro-2H-pyran-3,4,5-triyl triacetate To a solution of Example 2.62.5 (0.595 g) and bis(4-nitrophenyl) carbonate (0.492 g) in N,N-dimethylformamide (4 mL) was added N-ethyl-N-isopropylpropan-2-amine (0.212 mL). After 1.5 hours, the reaction was concentrated under high vacuum. The reaction was loaded directly onto silica gel and eluted using 1-50% ethyl acetate/heptanes to provide the title compound. MS (ESI) m/e 922.9 (M+Na)⁺.

2.62.7 3-(1-((3-(2-((((2-(2-(2-aminoethoxy)ethoxy)-4-(((2S,3R,4S,5S,6S)-6-carboxy-3,4,5-trihydroxytetrahydro-2H-pyran-2-yl)oxy)benzyl)oxy)carbonyl)(2-sulfoethyl)amino)ethoxy)-5,7-dimethyladamantan-1-yl)methyl)-5-methyl-1H-pyrazol-4-yl)-6-(8-(benzo[d]thiazol-2-ylcarbamoyl)-3,4-dihydroisoquinolin-2(1H)-yl)picolinic acid To a solution of Example 1.2.9 (0.073 g) and Example 2.62.6 (0.077 g) in N,N-dimethylformamide (0.5 mL) was added N,N-diisopropylethylamine (0.066 mL), and the reaction was stirred overnight. The reaction was concentrated, and the residue was dissolved in tetrahydrofuran (0.5 mL) and methanol (0.5 mL) and treated with lithium hydroxide monohydrate (0.047 g) as a solution in water (0.5 mL). After 1 hour, the reaction was diluted with N,N-dimethylformamide and water and was quenched by the addition of trifluoroacetic acid (0.116 mL). The mixture was purified by reverse phase HPLC using a Gilson system, eluting with 10-75% acetonitrile in water containing 0.1% v/v trifluoroacetic acid. The desired fractions were combined and freeze-dried to provide the title compound.

2.62.8 4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1³,⁷]dec-1-yl}oxy)ethyl](2-sulfoethyl)carbamoyl}oxy)methyl]-3-[2-(2-{[3-(2,5-dioxo-2,5-dihydro-1H-pyrrol-1-yl)propanoyl]amino}ethoxy)ethoxy]phenyl beta-D-glucopyranosiduronic acid A solution of Example 2.62.7 (0.053 g), 2,5-dioxopyrrolidin-1-yl 3-(2,5-dioxo-2,5-dihydro-1H-pyrrol-1-yl)propanoate (0.012 g) and N,N-diisopropylethylamine (0.033 mL) in N,N-dimethylformamide (0.75 mL) was stirred at room temperature. After stirring for 1 hour, the reaction was diluted with N,N-dimethylformamide and water. The mixture was purified by reverse phase HPLC using a Gilson system, eluting with 10-75% acetonitrile in water containing 0.1% v/v trifluoroacetic acid. The desired fractions were combined and freeze-dried to provide the title compound. $^1$H NMR (400 MHz, dimethyl sulfoxide-$d_6$) δ ppm 12.85 (s, 1H), 8.04 (d, 2H), 7.79 (d, 1H), 7.61 (d, 1H), 7.54 (d, 1H), 7.51-7.40 (m, 2H), 7.40-7.31 (m, 3H), 7.20 (d, 1H), 7.00-6.94 (m, 3H), 6.73-6.57 (m, 2H), 5.06 (t, 1H), 5.01-4.91 (m, 4H), 3.96-3.85 (m, 2H), 3.85-3.78 (m, 2H), 3.78-3.69 (m, 2H), 3.59 (t, 2H), 3.53-3.34 (m, 6H), 3.34-3.21 (m, 4H), 3.17 (q, 2H), 3.02 (t, 2H), 2.66 (t, 2H), 2.33 (t, 2H), 2.10 (s, 3H), 1.44-0.90 (m, 16H), 0.83 (d, 6H). MS (-ESI) m/e 1432.4 (M−H)$^-$.

2.63 Synthesis of 4-[(1E)-3-({[2-({3-[(4-{2-carboxy-6-[8-([1,3]thiazolo[4,5-b]pyridin-2-ylcarbamoyl)-3,4-dihydroisoquinolin-2(1H)-yl]pyridin-3-yl}-5-methyl-1H-pyrazol-1-yl)methyl]-5,7-dimethyltricyclo[3.3.1.1$^{3,7}$]dec-1-yl}oxy)ethyl](3-phosphonopropyl)carbamoyl}oxy)prop-1-en-1-yl]-2-({N-[6-(2,5-dioxo-2,5-dihydro-1H-pyrrol-1-yl)hexanoyl]-beta-alanyl}amino)phenyl beta-D-glucopyranosiduronic acid (Synthon IB)

2.63.1 3-(1-((3-(2-(((((E)-3-(3-(3-aminopropanamido)-4-(((2S,3R,4S,5S,6S)-6-carboxy-3,4,5-trihydroxytetrahydro-2H-pyran-2-yl)oxy)phenyl)allyl)oxy)carbonyl)(3-phosphonopropyl)amino)ethoxy)-5,7-dimethyladamantan-1-yl)methyl)-5-methyl-1H-pyrazol-4-yl)-6-(8-(thiazolo[4,5-b]pyridin-2-ylcarbamoyl)-3,4-dihydroisoquinolin-2(1H)-yl)picolinic acid The title compound was prepared by substituting Example 1.39.2 for Example 1.22.5 in Example 2.56.1.

2.63.2 4-[(1E)-3-({[2-({3-[(4-{2-carboxy-6-[8-([1,3]thiazolo[4,5-b]pyridin-2-ylcarbamoyl)-3,4-dihydroisoquinolin-2(1H)-yl]pyridin-3-yl}-5-methyl-1H-pyrazol-1-yl)methyl]-5,7-dimethyltricyclo[3.3.1.1$^{3,7}$]dec-1-yl}oxy)ethyl](3-phosphonopropyl)carbamoyl}oxy)prop-1-en-1-yl]-2-({N-[6-(2,5-dioxo-2,5-dihydro-1H-pyrrol-1-yl)hexanoyl]-beta-alanyl}amino)phenyl beta-D-glucopyranosiduronic acid The title compound was prepared by substituting Example 2.63.1 for Example 1.56.1 in Example 2.56.2. $^1$H NMR (400 MHz, dimethyl sulfoxide-$d_6$) δ ppm 9.03 (s, 1H), 8.61 (d, 1H), 8.55 (d, 1H), 8.25 (br s, 1H), 7.89 (br m, 1H), 7.65 (d, 1H), 7.50 (br d, 1H), 7.46 (d, 1H), 7.39 (m, 2H), 7.28 (s, 1H), 7.11 (br d, 1H), 7.03 (d, 1H), 6.98 (s, 2H), 6.97 (d, 1H), 6.56 (m, 1H), 6.17 (m, 1H), 4.97 (s, 2H), 4.86 (br m, 1H), 4.64 (br d, 2H), 3.88 (m, 3H), 3.79 (br m, 2H), 3.27-3.44 (m, 14H), 3.01 (m, 2H), 2.54 (m, 2H), 2.08 (s, 3H), 2.03 (t, 2H), 1.46 (m, 6H), 1.37 (br m, 2H), 1.28-0.90 (m, 10H), 0.77-0.82 (m, 6H). MS (ESI) m/e 1498.3 (M−H)$^-$.

2.64 Synthesis of 6-[8-(1,3-benzothiazol-2-ylcarbamoyl)-3,4-dihydroisoquinolin-2(1H)-yl]-3-{1-[(3-{2-[(2-carboxyethyl)({[(2E)-3-(4-{[(2S,3R,4S,5S,6S)-6-carboxy-3,4,5-trihydroxytetrahydro-2H-pyran-2-yl]oxy}-3-[(3-{[6-(2,5-dioxo-2,5-dihydro-1H-pyrrol-1-yl)hexanoyl]amino}propanoyl)amino]phenyl)prop-2-en-1-yl]oxy}carbonyl)amino]ethoxy}-5,7-dimethyltricyclo[3.3.1.1$^{3,7}$]dec-1-yl)methyl]-5-methyl-1H-pyrazol-4-yl}pyridine-2-carboxylic acid (Synthon IE)

2.64.1 3-(1-((3-(2-(((((E)-3-(3-(3-aminopropanamido)-4-(((2S,3R,4S,5S,6S)-6-carboxy-3,4,5-trihydroxytetrahydro-2H-pyran-2-yl)oxy)phenyl)allyl)oxy)carbonyl)(2-carboxyethyl)amino)ethoxy)-5,7-dimethyladamantan-1-yl)methyl)-5-methyl-1H-pyrazol-4-yl)-6-(8-(benzo[d]thiazol-2-ylcarbamoyl)-3,4-dihydroisoquinolin-2(1H)-yl)picolinic acid, trifluoroacetic acid salt To a solution of Example 1.25.2 (0.050 g) and Example 2.44.7 (0.061 g) in N,N-dimethylformamide (1 mL) was added N,N-diisopropylethylamine (0.047 mL), and the reaction was stirred at room temperature overnight. The reaction was concentrated, and the residue was dissolved in methanol (0.5 mL) and tetrahydrofuran (0.5 mL) and treated with a solution of lithium hydroxide hydrate (0.034 g) in water (0.5 mL). The reaction was stirred at room temperature for 1 hour. The reaction was quenched with trifluoroacetic acid (0.083 mL) and diluted with N,N-dimethylformamide (1 mL). The mixture was purified by reverse phase HPLC using a Gilson system, eluting with 10-75% acetonitrile in water containing 0.1% v/v trifluoroacetic acid. The desired fractions were combined and freeze-dried to provide the title compound 2.64.2 6-[8-(1,3-benzothiazol-2-ylcarbamoyl)-3,4-dihydroisoquinolin-2(1H)-yl]-3-{1-[(3-{2-[(2-carboxyethyl)({[(2E)-3-(4-{[(2S,3R,4S,5S,6S)-6-carboxy-3,4,5-trihydroxytetrahydro-2H-pyran-2-yl]oxy}-3-[(3-{[6-(2,5-dioxo-2,5-dihydro-1H-pyrrol-1-yl)hexanoyl]amino}propanoyl)amino]phenyl)prop-2-en-1-yl]oxy}carbonyl)amino]ethoxy}-5,7-dimethyltricyclo[3.3.1.1$^{3,7}$]dec-1-yl)methyl]-5-methyl-1H-pyrazol-4-yl}pyridine-2-carboxylic acid To a solution of Example 2.64.1 (0.042 g) and 2,5-dioxopyrrolidin-1-yl 6-(2,5-dioxo-2,5-dihydro-1H-pyrrol-1-yl)hexanoate (10 mg) in N,N-dimethylformamide (0.5 mL) was added N,N-diisopropylethylamine (0.027 mL), and the reaction was stirred at room temperature for 2 hours. The reaction was diluted with N,N-dimethylformamide (1 mL) and water (0.5 mL). The mixture was purified by reverse phase HPLC using a Gilson system, eluting with 10-75% acetonitrile in water containing 0.1% v/v trifluoroacetic acid. The desired fractions were combined and freeze-dried to provide the title compound. $^1$H NMR (400 MHz, dimethyl sulfoxide-$d_6$) δ ppm 12.85 (s, 1H), 9.04 (s, 1H), 8.25 (s, 1H), 8.03 (d, 1H), 7.87 (t, 1H), 7.79 (d, 1H), 7.61 (d, 1H), 7.54-7.40 (m, 3H), 7.40-7.31 (m, 2H), 7.28 (s, 1H), 7.10 (d, 1H), 7.04 (d, 1H), 6.98 (s, 2H), 6.95 (d, 1H), 6.57 (d, 1H), 6.24-6.11 (m, 1H), 4.96 (s, 2H), 4.86 (t, 1H), 4.65 (d, 2H), 3.95-3.84 (m, 2H), 3.84-3.75 (m, 4H), 3.44-3.24 (m, 10H), 3.01 (t, 2H), 2.62-2.52 (m, 4H), 2.09 (s, 3H), 2.03 (t, 2H), 1.46 (h, 4H), 1.40-1.31 (m, 2H), 1.30-0.88 (m, 14H), 0.87-0.75 (m, 6H). MS (ESI) m/e 1447.5 (M−H)−.

2.65 Synthesis of 6-[8-(1,3-benzothiazol-2-ylcarbamoyl)-3,4-dihydroisoquinolin-2(1H)-yl]-3-{1-[(3-{2-[(2-carboxyethyl){[(4-{[(2S,3R,4S,5S,6S)-6-carboxy-3,4,5-trihydroxytetrahydro-2H-pyran-2-yl]oxy}-2-[2-(2-{[3-(2,5-dioxo-2,5-dihydro-1H-pyrrol-1-yl)propanoyl]amino}ethoxy)ethoxy]benzyl)oxy]carbonyl}amino]ethoxy}-5,7-dimethyltricyclo[3.3.1.1$^{3,7}$]dec-1-yl)methyl]-5-methyl-1H-pyrazol-4-yl}pyridine-2-carboxylic acid (Synthon II)

2.65.1 3-(1-((3-(2-((((2-(2-(2-aminoethoxy)ethoxy)-4-(((2S,3R,4S,5S,6S)-6-carboxy-3,4,5-trihydroxytetrahydro-2H-pyran-2-yl)oxy)benzyl)oxy)carbonyl)(2-carboxyethyl)amino)ethoxy)-5,7-dimethyladamantan-1-yl)methyl)-5-methyl-1H-pyrazol-4-yl)-6-(8-(benzo[d]thiazol-2-ylcarbamoyl)-3,4-dihydroisoquinolin-2(1H)-yl)picolinic acid A solution of Example 1.25.2 (0.055 g), Example 2.62.6 (0.060 g) and N,N-diisopropylethylamine (0.052 mL) in N,N-dimethylformamide (0.4 mL) as stirred overnight. The reaction was concentrated, and the residue was dissolved in tetrahydrofuan (0.5 mL), methanol (0.5 mL) then treated with lithium hydroxide hydrate (0.037 g) as a solution in water (0.5 mL). After stirring for 1 hour, the reaction was quenched with trifluoroacetic acid (0.091 mL) and diluted with N,N-dimethylformamide (1 mL). The mixture was purified by reverse phase HPLC using a Gilson system, eluting with 10-75% acetonitrile in water containing 0.1% v/v trifluoroacetic acid. The desired fractions were combined and freeze-dried to provide the title compound as the trifluoroacetic acid salt.

2.65.2 6-[8-(1,3-benzothiazol-2-ylcarbamoyl)-3,4-dihydroisoquinolin-2(1H)-yl]-3-{1-[(3-{2-[(2-carboxyethyl){[(4-{[(2S,3R,4S,5S,6S)-6-carboxy-3,4,5-trihydroxytetrahydro-2H-pyran-2-yl]oxy}-2-[2-(2-{[3-(2,5-dioxo-2,5-dihydro-1H-pyrrol-1-yl)propanoyl]amino}ethoxy)ethoxy]benzyl)oxy]carbonyl}amino]ethoxy}-5,7-dimethyltricyclo[3.3.1.1$^{3,7}$]dec-1-yl)methyl]-5-methyl-1H-pyrazol-4-yl}pyridine-2-carboxylic acid A solution of the trifluoroacetic acid salt of Example 2.65.1 (0.043), 2,5-dioxopyrrolidin-1-yl 3-(2,5-dioxo-2,5-dihydro-1H-pyrrol-1-yl)propanoate (10 mg) and N,N-diisopropylethylamine (0.028 mL) were stirred together in N,N-dimethylformamide (1 mL) at room temperature. After stirring for 1 hour, the reaction was diluted with N,N-dimethylformamide (0.5 mL) and water (0.5 mL). The mixture was purified by reverse phase HPLC using a Gilson system, eluting with 5-75% acetonitrile in water containing 0.1% v/v trifluoroacetic acid. The desired fractions were combined and freeze-dried to provide the title compound. $^1$H NMR (400 MHz, dimethyl sulfoxide-d$_6$) δ ppm 12.84 (s, 1H), 8.03 (d, 1H), 8.00 (t, 1H), 7.79 (d, 1H), 7.62 (d, 1H), 7.54-7.41 (m, 3H), 7.36 (td, 2H), 7.29 (s, 1H), 7.19 (d, 1H), 6.97 (s, 2H), 6.95 (d, 1H), 6.67 (d, 1H), 6.60 (dd, 1H), 5.14-5.03 (m, 1H), 4.96 (d, 4H), 4.08 (tt, 4H), 3.89 (q, 4H), 3.84-3.77 (m, 2H), 3.71 (t, 2H), 3.59 (t, 2H), 3.52-3.35 (m, 6H), 3.28 (q, 4H), 3.17 (q, 4H), 3.01 (t, 2H), 2.46 (d, 1H), 2.33 (t, 2H), 2.09 (s, 3H), 1.45-0.90 (m, 12H), 0.82 (d, 6H). MS (ESI) m/e 1396.4 (M−H)−.

2.66 Synthesis of N-[6-(ethenylsulfonyl)hexanoyl]-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]phenyl}-N$^5$-carbamoyl-L-ornithinamide (Synthon KY)

2.66.1 3-(1-((3-(2-((((4-((S)-2-((S)-2-amino-3-methylbutanamido)-5-ureidopentanamido)benzyl)oxy)carbonyl)(2-sulfoethyl)amino)ethoxy)-5,7-dimethyladamantan-1-yl)methyl)-5-methyl-1H-pyrazol-4-yl)-6-(8-(benzo[d]thiazol-2-ylcarbamoyl)-3,4-dihydroisoquinolin-2(1H)-yl)picolinic acid To a mixture of Example 1.2.9 (57 mg) and (9H-fluoren-9-yl)methyl ((S)-3-methyl-1-(((S)-1-((4-((((4-nitrophenoxy)carbonyl)oxy)methyl)phenyl)amino)-1-oxo-5-ureidopentan-2-yl)amino)-1-oxobutan-2-yl)carbamate (54 mg) in N,N-dimethylformamide (2 mL) was added N,N-diisopropylethylamine (103 µL). The mixture was stirred overnight, and diethylamine (61.5 µL) was added. The resulting mixture was stirred for 4 hours and purified by reverse phase HPLC using a Gilson system and C18 column, eluting with 10-70% acetonitrile in water containing 0.1% v/v trifluoroacetic acid, to provide the title compound. MS (ESI) m/e 1257.4 (M−H).

2.66.2 N-[6-(ethenylsulfonyl)hexanoyl]-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]phenyl}-N$^5$-carbamoyl-L-ornithinamide The title compound was prepared using the procedure in Example 2.83, replacing Example 1.2.9 and 2,5-dioxopyrrolidin-1-yl 6-(2-chloroacetamido)hexanoate with Example 2.66.1 and Example 2.82.5, respectively. $^1$H NMR (400 MHz, dimethyl sulfoxide-d$_6$) δ ppm 12.88 (s, OH), 9.99 (s, 1H), 8.05 (t, 2H), 7.80 (t, 2H), 7.60 (q, 3H), 7.36 (td, 2H), 7.28 (d, 3H), 7.01-6.89 (m, 2H), 6.29-6.15 (m, 2H), 6.02 (s, 1H), 4.97 (d, 4H), 4.40 (td, 1H), 4.20 (t, 1H), 4.00-3.77 (m, 4H), 3.55-3.33 (m, 4H), 3.25 (d, 2H), 3.14-2.88 (m, 6H), 2.62 (t, 2H), 2.09 (s, 4H), 1.82-0.90 (m, 10H), 0.84 (dd, 13H). MS (ESI) m/e 1447.2 (M+H).

2.67 Synthesis of 4-[(1E)-3-{[(4-{[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](3-phosphonopropyl)amino}piperidin-1-yl)carbonyl]oxy}prop-1-en-1-yl]-2-({N-[6-(2,5-dioxo-2,5-dihydro-1H-pyrrol-1-yl)hexanoyl]-beta-alanyl}amino)phenyl beta-D-glucopyranosiduronic acid (Synthon IW)

2.67.1 3-(1-((3-(2-((1-(((((E)-3-(3-(3-aminopropanamido)-4-(((2S,3R,4S,5S,6S)-6-carboxy-3,4,5-trihydroxytetrahydro-2H-pyran-2-yl)oxy)phenyl)allyl)oxy)carbonyl)piperidin-4-yl)(3-phosphonopropyl)amino)ethoxy)-5,7-dimethyladamantan-1-yl)methyl)-5-methyl-1H-pyrazol-4-yl)-6-(8-(benzo[d]thiazol-2-ylcarbamoyl)-3,4-dihydroisoquinolin-2(1H)-yl)picolinic acid To a solution of Example 1.26.2 (0.045 g) and Example 2.44.7 (0.053 g) in N,N-dimethylformamide (1 mL) was added N,N-diisopropylethylamine (0.041 mL), and the reaction was stirred at room temperature overnight. The reaction was concentrated, and the residue was dissolved in methanol (0.5 mL) and tetrahydrofuran (0.5 mL) and treated with a solution of lithium hydroxide monohydrate (0.030 g) in water (0.5 mL) at room temperature. After stirring for 1 hour, the reaction was quenched with trifluoroacetic acid (0.073 mL) and diluted with N,N-dimethylformamide (1 mL). The mixture was purified by reverse phase HPLC using a Gilson system, eluting with 10-60% acetonitrile in water containing 0.1% v/v trifluoroacetic acid. The desired fractions were combined and freeze-dried to provide the title compound.

2.67.2 4-[(1E)-3-{[(4-{[2-({3-[(4-{6-[8-(1,3-benzo-thiazol-2-ylcarbamoyl)-3,4-dihydroisoquinolin-2 (1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](3-phosphonopropyl) amino}piperidin-1-yl)carbonyl]oxy}prop-1-en-1-yl]-2-({N-[6-(2,5-dioxo-2,5-dihydro-1H-pyrrol-1-yl) hexanoyl]-beta-alanyl}amino)phenyl beta-D-glucopyranosiduronic acid To a solution of Example 2.67.1 (0.040 g) and 2,5-dioxopyrrolidin-1-yl 6-(2,5-dioxo-2,5-dihydro-1H-pyrrol-1-yl)hexanoate (9.84 mg) in N,N-dimethylformamide (1 mL) was added N,N-diisopropylethylamine (0.023 mL), and the reaction was stirred at room temperature for 2 hours. The reaction was diluted with N,N-dimethylformamide (1 mL) and water (1 mL). The mixture was purified by reverse phase HPLC using a Gilson system, eluting with 10-60% acetonitrile in water containing 0.1% v/v trifluoroacetic acid. The desired fractions were combined and freeze-dried to provide the title compound. $^1$H NMR (400 MHz, dimethyl sulfoxide-$d_6$) δ ppm 9.28 (s, 1H), 9.04 (s, 1H), 8.25 (s, 1H), 8.03 (d, 1H), 7.87 (t, 1H), 7.79 (d, 1H), 7.62 (dd, 1H), 7.55-7.40 (m, 3H), 7.36 (td, 2H), 7.29 (s, 1H), 7.11 (dd, 1H), 7.05 (d, 1H), 6.98 (s, 2H), 6.95 (d, 1H), 6.59 (d, 1H), 6.20 (t, 1H), 6.16 (t, OH), 4.96 (s, 2H), 4.88 (d, 1H), 4.66 (d, 2H), 4.14 (d, 2H), 3.96-3.86 (m, 2H), 3.83 (s, 2H), 3.54 (t, 7H), 3.48-3.28 (m, 12H), 3.01 (t, 2H), 2.84 (s, 2H), 2.55 (t, 2H), 2.10 (s, 3H), 2.07-1.95 (m, 4H), 1.88 (s, 2H), 1.73-1.54 (m, 4H), 1.54-1.38 (m, 6H), 1.39-1.26 (m, 4H), 1.26-0.93 (m, 8H), 0.86 (s, 6H). MS (ESI) m/e 1582.4 (M+H)$^+$.

2.68 Synthesis of 4-[(1E)-3-{[(4-{[2-({3-[(4-{2-carboxy-6-[8-([1,3]thiazolo[4,5-b]pyridin-2-ylcarbamoyl)-3,4-dihydroisoquinolin-2(1H)-yl]pyridin-3-yl}-5-methyl-1H-pyrazol-1-yl)methyl]-5,7-dimethyltricyclo[3.3.1.1$^{3,7}$]dec-1-yl}oxy)ethyl](3-phosphonopropyl)amino}piperidin-1-yl)carbonyl] oxy}prop-1-en-1-yl]-2-({N-[6-(2,5-dioxo-2,5-dihydro-1H-pyrrol-1-yl)hexanoyl]-beta-alanyl}amino)phenyl beta-D-glucopyranosiduronic acid (Synthon IY)

2.68.1 3-(1-((3-(2-(((1-((((E)-3-(3-(3-aminopropana-mido)-4-(((2S,3R,4S,5S,6S)-6-carboxy-3,4,5-trihydroxytetrahydro-2H-pyran-2-yl)oxy)phenyl)allyl)oxy)carbonyl)piperidin-4-yl)(3-phosphonopropyl) amino)ethoxy)-5,7-dimethyladamantan-1-yl) methyl)-5-methyl-1H-pyrazol-4-yl)-6-(8-(thiazolo[4,5-b]pyridin-2-ylcarbamoyl)-3,4-dihydroisoquinolin-2(1H)-yl)picolinic acid The title compound was prepared by substituting Example 1.50.2 for Example 1.44.7 in Example 2.56.1. MS (ESI) m/e 1388.5 (M–H)$^-$.

2.68.2 4-[(1E)-3-{[(4-{[2-({3-[(4-{2-carboxy-6-[8-([1,3]thiazolo[4,5-b]pyridin-2-ylcarbamoyl)-3,4-dihydroisoquinolin-2(1H)-yl]pyridin-3-yl}-5-methyl-1H-pyrazol-1-yl)methyl]-5,7-dimethyltricyclo[3.3.1.1$^{3,7}$]dec-1-yl}oxy)ethyl](3-phosphonopropyl)amino}piperidin-1-yl)carbonyl] oxy}prop-1-en-1-yl]-2-({N-[6-(2,5-dioxo-2,5-dihydro-1H-pyrrol-1-yl)hexanoyl]-beta-alanyl}amino)phenyl beta-D-glucopyranosiduronic acid The title compound was prepared by substituting Example 1.68.1 for Example 1.56.1 in Example 2.56.2. $^1$H NMR (400 MHz, dimethyl sulfoxide-$d_6$) δ ppm 9.03 (s, 1H), 8.61 (d, 1H), 8.50 (d, 1H), 8.25 (br s, 1H), 7.89 (t, 1H), 7.65 (d, 1H), 7.49 (d, 1H), 7.46 (d, 1H), 7.36 (m, 2H), 7.29 (s, 1H), 7.11 (br d, 1H), 7.03 (d, 1H), 6.98 (s, 2H), 6.97 (d, 1H), 6.58 (m, 1H), 6.17 (m, 1H), 4.97 (s, 2H), 4.88 (d, 1H), 4.65 (br d, 2H), 3.88 (m, 3H), 3.79 (br m, 2H), 3.66 (br m, 2H), 3.27-3.44, (m, 14H), 3.01 (m, 2H), 2.85 (br m, 2H), 2.54 (m, 2H), 2.10 (s, 3H), 2.03 (t, 2H), 1.98 (br m, 2H), 1.89 (m, 1H), 1.62 (m, 4H), 1.46 (m, 6H), 1.31 (m, 4H), 1.15 (m, 6H), 1.04 (m, 2H), 0.86 (s, 6H). MS (ESI) m/e 1581.4 (M–H)$^-$.

2.69 Synthesis of 4-[(1E)-3-({[2-({3-[(4-{6-[8-(1,3-benzothiazol-2-ylcarbamoyl)naphthalen-2-yl]-2-carboxypyridin-3-yl}-5-methyl-1H-pyrazol-1-yl) methyl]-5,7-dimethyltricyclo[3.3.1.1$^{3,7}$]dec-1-yl}oxy)ethyl](2-sulfoethyl)carbamoyl}oxy)prop-1-en-1-yl]-2-({N-[6-(2,5-dioxo-2,5-dihydro-1H-pyrrol-1-yl)hexanoyl]-beta-alanyl}amino)phenyl beta-D-glucopyranosiduronic acid (Synthon JA)

2.69.1 3-(1-((3-(2-(((((E)-3-(3-(3-aminopropana-mido)-4-(((2S,3R,4S,5S,6S)-6-carboxy-3,4,5-trihydroxytetrahydro-2H-pyran-2-yl)oxy)phenyl)allyl) oxy)carbonyl)(2-sulfoethyl)amino)ethoxy)-5,7-dimethyladamantan-1-yl)methyl)-5-methyl-1H-pyrazol-4-yl)-6-(8-(benzo[d]thiazol-2-ylcarbamoyl) naphthalen-2-yl)picolinic acid The title compound was prepared by substituting Example 1.43.7 for Example 2.44.7 in Example 2.56.1. MS (ESI) m/e 1309.1 (M+Na)$^+$.

2.69.2 4-[(1E)-3-({[2-({3-[(4-{6-[8-(1,3-benzothiazol-2-ylcarbamoyl)naphthalen-2-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)prop-1-en-1-yl]-2-({N-[6-(2,5-dioxo-2,5-dihydro-1H-pyrrol-1-yl)hexanoyl]-beta-alanyl}amino)phenyl beta-D-glucopyranosiduronic acid The title compound was prepared by substituting Example 2.69.1 for Example 2.56.1 in Example 2.56.2. $^1$H NMR (400 MHz, dimethyl sulfoxide-$d_6$) δ ppm 13.09 (s, 1H), 9.02 (s, 2H), 8.35 (d, 1H), 8.13-8.29 (m, 4H), 7.86-8.09 (m, 5H), 7.81 (d, 1H), 7.66-7.75 (m, 1H), 7.44-7.55 (m, 1H), 7.37 (t, 1H), 7.09-7.18 (m, 1H), 7.03 (d, 1H), 6.98 (s, 1H), 6.48-6.62 (m, 1H), 6.07-6.22 (m, 1H), 4.81-4.92 (m, 1H), 4.58-4.74 (m, 5H), 3.80-3.93 (m, 3H), 3.27-3.37 (m, 5H), 2.53-2.68 (m, 4H), 2.15-2.23 (m, 3H), 2.03 (t, 2H), 1.36-1.53 (m, 6H), 0.97-1.33 (m, 24H), 0.81 (d, 6H). MS (ESI) m/e 1478.3 (M–H)$^-$.

2.70 This paragraph was intentionally left blank 2.71 This paragraph was intentionally left blank 2.72 This paragraph was intentionally left blank 2.73 This paragraph was intentionally left blank 2.74 This paragraph was intentionally left blank 2.75 This paragraph was intentionally left blank 2.76 This paragraph was intentionally left blank 2.77 Synthesis of 6-[8-(1,3-benzothiazol-2-ylcarbamoyl)-3,4-dihydroisoquinolin-2(1H)-yl]-3-[1-({3-[2-({N-[6-(2,5-dioxo-2,5-dihydro-1H-pyrrol-1-yl)hexanoyl]-3-sulfo-L-alanyl}amino)ethoxy]-5,7-dimethyltricyclo[3.3.1.1$^{3,7}$]dec-1-yl}methyl)-5-methyl-1H-pyrazol-4-yl]pyridine-2-carboxylic acid (Synthon FA)

To a solution of Example 1.15 (0.023 g) and 2,5-dioxopyrrolidin-1-yl 6-(2,5-dioxo-2,5-dihydro-1H-pyrrol-1-yl)hexanoate (9.12 mg) in N,N-dimethylformamide (0.5 mL) was added N,N-diisopropylethylamine (0.012 mL), and the reaction was stirred overnight. The reaction was diluted with N,N-dimethylformamide (1 mL) and water (0.5 mL). The mixture was purified by reverse phase HPLC using a Gilson system, eluting with 10-85% acetonitrile in water containing 0.1% v/v trifluoroacetic acid. The desired fractions were combined and freeze-dried to provide the title compound. $^1$H NMR (400 MHz, dimethyl sulfoxide-d$_6$) δ ppm 12.84 (s, 1H), 8.04 (d, 1H), 7.90 (d, 1H), 7.79 (d, 1H), 7.65-7.57 (m, 2H), 7.54 (d, 1H), 7.51-7.41 (m, 2H), 7.40-7.31 (m, 3H), 7.01-6.96 (m, 3H), 4.96 (s, 2H), 4.34-4.28 (m, 3H), 3.89 (t, 2H), 3.83 (s, 2H), 3.37 (t, 2H), 3.29 (t, 2H), 3.16-2.95 (m, 4H), 2.80 (dd, 1H), 2.70 (dd, 1H), 2.11 (s, 3H), 2.06 (t, 2H), 1.47 (tt, 4H), 1.40-0.92 (m, 12H), 0.84 (s, 6H). MS (ESI) m/e 1090.3 (M+H)$^+$.

2.78 Synthesis of 6-[8-(1,3-benzothiazol-2-ylcarbamoyl)-3,4-dihydroisoquinolin-2(1H)-yl]-3-[1-({3-[2-(2-{[6-(2,5-dioxo-2,5-dihydro-1H-pyrrol-1-yl)hexanoyl](2-sulfoethyl)amino}ethoxy)ethoxy]-5,7-dimethyltricyclo[3.3.1.1$^{3,7}$]dec-1-yl}methyl)-5-methyl-1H-pyrazol-4-yl]pyridine-2-carboxylic acid (Synthon FJ)

The title compound was prepared as described in Example 2.1, replacing Example 1.2.9 and 4-((S)-2-((S)-2-(6-(2,5-dioxo-2,5-dihydro-1H-pyrrol-1-yl)hexanamido)-3-methylbutanamido)-5-ureidopentanamido)benzyl (4-nitrophenyl) carbonate with Example 1.11.4 and perfluorophenyl 6-(2,5-dioxo-2,5-dihydro-1H-pyrrol-1-yl)hexanoate, respectively. $^1$H NMR (400 MHz, dimethyl sulfoxide-d$_6$) δ ppm 12.84 (s, 1H), 8.04 (d, 1H), 7.79 (d, 1H), 7.61 (d, 1H), 7.52 (dd, 1H), 7.42-7.49 (m, 2H), 7.33-7.39 (m, 2H), 7.30 (s, 1H), 6.98 (s, 2H), 6.96 (d, 1H), 4.95 (s, 2H), 3.89 (t, 2H), 3.82 (s, 2H), 3.46-3.56 (m, 4H), 3.31-3.46 (m, 10H), 3.01 (t, 2H), 2.61-2.68 (m, 2H), 2.55-2.60 (m, 1H), 2.21-2.32 (m, 2H), 2.10 (s, 3H), 1.40-1.51 (m, 4H), 1.37 (d, 2H), 0.91-1.30 (m, 12H), 0.83 (s, 6H). MS (ESI) m/e 1091.2 (M+H)$^+$.

2.79 Synthesis of 6-[8-(1,3-benzothiazol-2-ylcarbamoyl)-3,4-dihydroisoquinolin-2(1H)-yl]-3-(1-{[3-(2-{[6-(2,5-dioxo-2,5-dihydro-1H-pyrrol-1-yl)hexanoyl](2-sulfoethyl)amino}ethoxy)-5,7-dimethyltricyclo[3.3.1.1$^{3,7}$]dec-1-yl]methyl}-5-methyl-1H-pyrazol-4-yl)pyridine-2-carboxylic acid (Synthon FK)

The title compound was prepared as described in Example 2.1, replacing 4-((S)-2-((S)-2-(6-(2,5-dioxo-2,5-dihydro-1H-pyrrol-1-yl)hexanamido)-3-methylbutanamido)-5-ureidopentanamido)benzyl (4-nitrophenyl) carbonate with perfluorophenyl 6-(2,5-dioxo-2,5-dihydro-1H-pyrrol-1-yl)hexanoate. $^1$H NMR (400 MHz, dimethyl sulfoxide-d$_6$) δ ppm 12.85 (s, 1H), 8.04 (d, 1H), 7.79 (d, 1H), 7.61 (d, 1H), 7.52 (dd, 1H), 7.41-7.49 (m, 2H), 7.32-7.39 (m, 2H), 7.28 (s, 1H), 6.93-6.98 (m, 3H), 4.95 (s, 2H), 3.89 (t, 2H), 3.81 (s, 2H), 3.32-3.38 (m, 2H), 3.21-3.27 (m, 2H), 3.01 (t, 2H), 2.61-2.67 (m, 2H), 2.53-2.58 (m, 2H), 2.33-2.39 (m, 1H), 2.20-2.29 (m, 2H), 2.09 (s, 3H), 1.40-1.51 (m, 4H), 1.34 (s, 2H), 0.93-1.27 (m, 13H), 0.83 (s, 6H). MS (ESI) m/e 1047.2 (M+H)$^+$.

2.80 Synthesis of 6-[8-(1,3-benzothiazol-2-ylcarbamoyl)-3,4-dihydroisoquinolin-2(1H)-yl]-3-{1-[(3-{[1-(2,5-dioxo-2,5-dihydro-1H-pyrrol-1-yl)-21-oxo-22-(2-sulfoethyl)-3,6,9,12,15,18-hexaoxa-22-azatetracosan-24-yl]oxy}-5,7-dimethyltricyclo[3.3.1.1$^{3,7}$]dec-1-yl)methyl]-5-methyl-1H-pyrazol-4-yl}pyridine-2-carboxylic acid (Synthon FQ)

The title compound was prepared as described in Example 2.1, replacing 4-((S)-2-((S)-2-(6-(2,5-dioxo-2,5-dihydro-1H-pyrrol-1-yl)hexanamido)-3-methylbutanamido)-5-ureidopentanamido)benzyl (4-nitrophenyl) carbonate with perfluorophenyl 1-(2,5-dioxo-2,5-dihydro-1H-pyrrol-1-yl)-3,9,12,15,18-pentaoxahenicosan-21-oate. $^1$H NMR (400 MHz, dimethyl sulfoxide-d$_6$) δ ppm 12.84 (s, 1H), 8.04 (d, 1H), 7.79 (d, 1H), 7.61 (d, 1H), 7.42-7.54 (m, 3H), 7.33-7.38 (m, 2H), 7.28 (s, 1H), 6.95 (dd, 1H), 4.95 (s, 2H), 3.89 (t, 2H), 3.81 (s, 2H), 3.07-3.53 (m, 24H), 3.01 (t, 2H), 2.61-2.69 (m, 1H), 2.54-2.60 (m, 1H), 2.09 (s, 3H), 1.96 (d, 2H), 0.92-1.39 (m, 13H), 0.84 (s, 6H). MS (ESI) m/e 1269.4 (M+H)$^+$.

2.81 Synthesis of 6-[8-(1,3-benzothiazol-2-ylcarbamoyl)-3,4-dihydroisoquinolin-2(1H)-yl]-3-{1-[(3-{[1-(2,5-dioxo-2,5-dihydro-1H-pyrrol-1-yl)-21-oxo-22-(2-sulfoethyl)-3,6,9,12,15,18,25-heptaoxa-22-azaheptacosan-27-yl]oxy}-5,7-dimethyltricyclo[3.3.1.1$^{3,7}$]dec-1-yl)methyl]-5-methyl-1H-pyrazol-4-yl}pyridine-2-carboxylic acid (Synthon FR)

The title compound was prepared as described in Example 2.1, replacing Example 1.2.9 and 4-((S)-2-((S)-2-(6-(2,5-dioxo-2,5-dihydro-1H-pyrrol-1-yl)hexanamido)-3-methylbutanamido)-5-ureidopentanamido)benzyl (4-nitrophenyl) carbonate with Example 1.11.4 and perfluorophenyl 1-(2,5-dioxo-2,5-dihydro-1H-pyrrol-1-yl)-3,6,9,12,15,18-hexaoxahenicosan-21-oate, respectively. $^1$H NMR (500 MHz, dimethyl sulfoxide-d$_6$) δ ppm 12.84 (s, 1H), 8.04 (d, 1H), 7.79 (d, 1H), 7.61 (d, 1H), 7.52 (d, 1H), 7.41-7.50 (m, 2H), 7.33-7.39 (m, 2H), 7.31 (s, 1H), 7.01 (d, 2H), 6.97 (d, 1H), 4.96 (s, 2H), 3.89 (t, 2H), 3.83 (s, 2H), 3.31-3.60 (m, 30H), 3.01 (t, 2H), 2.64-2.71 (m, 1H), 2.53-2.61 (m, 3H), 2.10 (s, 3H), 1.38 (s, 2H), 1.20-1.31 (m, 4H), 1.12-1.18 (m, 2H), 0.91-1.12 (m, 4H), 0.84 (s, 6H).

2.82 Synthesis of 6-[8-(1,3-benzothiazol-2-ylcarbamoyl)-3,4-dihydroisoquinolin-2(1H)-yl]-3-(1-{[3-(2-{[6-(ethenylsulfonyl)hexanoyl](2-sulfoethyl)amino}ethoxy)-5,7-dimethyltricyclo[3.3.1.1$^{3,7}$]dec-1-yl]methyl}-5-methyl-1H-pyrazol-4-yl)pyridine-2-carboxylic acid (Synthon JE)

2.82.1 ethyl 6-((2-hydroxyethyl)thio)hexanoate

A mixture of ethyl 6-bromohexanoate (3 g), 2-mercaptoethanol (0.947 mL) and K$_2$CO$_3$ (12 g) in ethanol (100 mL) was stirred overnight and filtered. The filtrate was concentrated. The residue was dissolved in dichloromethane (100 mL) and washed with water and brine. The organic layer was dried over sodium sulfate, filtered, and concentrated to provide the title compound.

2.82.2 6-((2-hydroxyethyl)thio)hexanoic acid

A mixture of Example 2.82.1 (12 g) and 3 M aqueous NaOH solution (30 mL) in ethanol (30 mL) was stirred overnight. The organics were removed under reduced pressure. The residual aqueous phase was washed with ethyl acetate, acidified with HCl to pH 5 and extracted with dichloromethane. The extracts were combined, dried over sodium sulfate, filtered and concentrated to provide the title compound.

2.82.3 6-((2-hydroxyethyl)sulfonyl)hexanoic acid

To a stirred solution of Example 2.82.2 (4 g) in a mixture of water (40 mL) and 1,4-dioxane (160 mL) was added Oxone® (38.4 g), and the mixture was stirred overnight. The mixture was filtered, and the filtrate was concentrated. The residual aqueous layer was extracted with dichloromethane. The extracts were combined and dried over sodium sulfate, filtered, and concentrated to provide the title compound.

2.82.4 6-(vinylsulfonyl)hexanoic acid

To a cold (0° C.) solution of Example 2.82.3 (1 g) in dichloromethane (10 mL) was added triethylamine (2.8 mL), followed by the addition of methanesulfonyl chloride (1.1 mL) under argon. The mixture was stirred overnight and washed with water and brine. The organic layer was dried over sodium sulfate, filtered, and concentrated to provide the title compound.

2.82.5 2,5-dioxopyrrolidin-1-yl 6-(vinylsulfonyl)hexanoate

To a stirred solution of Example 2.82.4 (0.88 g) in dichloromethane (10 ml) was added 1-hydroxypyrrolidine-2,5-dione (0.54 g) and N,N'-methanediylidenedicyclohexanamine (0.92 g). The mixture was stirred overnight and filtered. The filtrate was concentrated and purified by flash chromatography, eluting with 10-25% ethyl acetate in petroleum, to provide the title compound. MS (ESI) m/e 304.1 (M+1).

2.82.6 6-[8-(1,3-benzothiazol-2-ylcarbamoyl)-3,4-dihydroisoquinolin-2(1H)-yl]-3-(1-{[3-(2-{[6-(ethenylsulfonyl)hexanoyl](2-sulfoethyl)amino}ethoxy)-5,7-dimethyltricyclo[3.3.1.1$^{3,7}$]dec-1-yl]methyl}-5-methyl-1H-pyrazol-4-yl)pyridine-2-carboxylic acid The title compound was prepared as described in Example 2.83, replacing 2,5-dioxopyrrolidin-1-yl 6-(2-chloroacetamido)hexanoate with Example 2.82.5. $^1$H NMR (400 MHz, dimethyl sulfoxide-d$_6$) δ ppm 12.86 (s, 1H), 8.04 (d, 1H), 7.79 (d, 1H), 7.61 (d, 1H), 7.53 (dd, 1H), 7.42-7.49 (m, 2H), 7.33-7.40 (m, 2H), 7.28 (s, 1H), 6.88-7.00 (m, 2H), 6.17-6.25 (m, 2H), 4.95 (s, 2H), 3.89 (t, 2H), 3.81 (s, 2H), 3.38 (dd, 2H), 3.25 (t, 2H), 3.04-3.12 (m, 2H), 3.01 (t, 2H), 2.62-2.69 (m, 1H), 2.56 (dd, 1H), 2.27 (q, 2H), 2.09 (s, 3H), 1.53-1.62 (m, 2H), 1.43-1.51 (m, 2H), 1.28-1.38 (m, 4H), 1.20-1.27 (m, 4H), 0.92-1.19 (m, 6H), 0.84 (s, 6H). MS (ESI) m/e 1042.2 (M+H)$^+$.

2.83 Synthesis of 6-[8-(1,3-benzothiazol-2-ylcarbamoyl)-3,4-dihydroisoquinolin-2(1H)-yl]-3-{1-[(3-{2-[{6-[(chloroacetyl)amino]hexanoyl}(2-sulfoethyl)amino]ethoxy}-5,7-dimethyltricyclo[3.3.1.1$^{3,7}$]dec-1-yl)methyl]-5-methyl-1H-pyrazol-4-yl}pyridine-2-carboxylic acid (Synthon JM)

To a mixture of Example 1.2.9 (12.5 mg) and 2,5-dioxopyrrolidin-1-yl 6-(2-chloroacetamido)hexanoate (6.7 mg) in N,N-dimethylformamide (1.5 mL) was added N,N-diisopropylethylamine (26 μL). The mixture was stirred for 10 days and purified by reverse phase HPLC using a Gilson system and C18 column, eluting with 20-60% acetonitrile in water containing 0.1% v/v trifluoroacetic acid, to provide the title compound. $^1$H NMR (500 MHz, dimethyl sulfoxide-d$_6$) δ ppm 12.83 (s, 1H), 8.15-8.21 (m, 1H), 8.04 (d, 1H), 7.79 (d, 1H), 7.61 (d, 1H), 7.52 (dd, 1H), 7.41-7.49 (m, 2H), 7.32-7.39 (m, 2H), 7.28 (s, 1H), 6.96 (dd, 1H), 4.95 (s, 2H), 4.01 (d, 2H), 3.89 (t, 2H), 3.81 (s, 2H), 3.39 (d, 2H), 3.25 (t, 2H), 2.98-3.10 (m, 5H), 2.62-2.70 (m, 1H), 2.56-2.61 (m, 1H), 2.23-2.30 (m, 2H), 2.09 (s, 3H), 1.33-1.52 (m, 5H), 1.19-1.30 (m, 6H), 0.91-1.18 (m, 6H), 0.84 (s, 6H). MS (ESI) m/e 1043.2 (M+H)$^+$.

2.84 Synthesis of N-[6-(2,5-dioxo-2,5-dihydro-1H-pyrrol-1-yl)hexanoyl]-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](3-carboxypropyl)carbamoyl}oxy)methyl]phenyl}-N-carbamoyl-L-ornithinamide (Synthon LE)

A mixture of Example 1.56 (0.020 g), 4-((S)-2-((S)-2-(6-(2,5-dioxo-2,5-dihydro-1H-pyrrol-1-yl)hexanamido)-3-methylbutanamido)-5-ureidopentanamido)benzyl (4-nitrophenyl) carbonate (0.022 g) and N,N-diisopropylethylamine (0.018 mL) were stirred together in N,N-dimethylformamide (0.4 mL) at room temperature. After stirring for 5 hours, the reaction was diluted with a 1:1 mixture of N,N-dimethylformamide and water (2 mL). The mixture was purified by reverse phase HPLC using a Gilson system, eluting with 10-85% acetonitrile in water containing 0.1% v/v trifluoroacetic acid. The desired fractions were combined and freeze-dried to provide the title compound. $^1$H NMR (400 MHz, dimethyl sulfoxide-d$_6$) δ ppm 12.82 (s, 1H), 9.97 (s, 1H), 8.10-7.98 (m, 2H), 7.84-7.72 (m, 2H), 7.67-7.54 (m, 3H), 7.54-7.41 (m, 3H), 7.40-7.32 (m, 2H), 7.30-7.23 (m, 3H), 6.99 (s, 2H), 6.94 (d, 1H), 5.99 (s, 1H), 4.98 (s, 2H), 4.95 (s, 2H), 4.45-4.35 (m, 2H), 4.19 (dd, 2H), 3.88 (t, 2H), 3.82-3.76 (m, 2H), 3.47-3.31 (m, 4H), 3.28-3.19 (m, 4H), 3.07-2.89 (m, 4H), 2.21-2.11 (m, 4H), 2.09 (s, 2H), 2.02-1.89 (m, 1H), 1.77-1.63 (m, 2H), 1.62-1.27 (m, 10H), 1.27-0.90 (m, 13H), 0.88-0.78 (m, 12H); MS (ESI) m/e 1430.3 (M+1)$^+$.

2.85 Synthesis of N-{6-[(bromoacetyl)amino]hexanoyl}-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]phenyl}-N$^5$-carbamoyl-L-ornithinamide (Synthon LH)

2.85.1 1H-benzo[d][1,2,3]triazol-1-yl 6-(2-bromoacetamido)hexanoate

To a solution of 6-(2-bromoacetamido)hexanoic acid (105 mg) and benzotriazol-1-yloxy)tripyrrolidinophosphonium hexafluorophosphate (PyBOP, 325 mg) in N,N-dimethylformamide (3 mL) was added triethylamine (87 µL). The mixture was stirred for 1 hour and purified by a Gilson HPLC system (C18 column), eluting with 20-60% acetonitrile in 0.1% TFA water to provide the title compound. MS (ESI) m/e 368.7 (M+H).

2.85.2 N-{6-[(bromoacetyl)amino]hexanoyl}-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]phenyl}-N$^5$-carbamoyl-L-ornithinamide To a mixture of Example 2.66.1 (6.6 mg) and Example 2.85.2 (3.6 mg) in N,N-dimethylformamide (0.3 mL) was added N,N-diisopropylethylamine (2.52 µL). The mixture was stirred for 5 minutes, diluted with dimethyl sulfoxide and purified by reverse phase HPLC using a Gilson system and C18 column, eluting with 20-60% acetonitrile in water containing 0.1% v/v trifluoroacetic acid, to provide the title compound. $^1$H NMR (500 MHz, dimethyl sulfoxide-d$_6$) δ 9.99 (s, 1H), 8.24 (s, 1H), 8.08 (d, 1H), 8.04 (d, 1H), 7.80 (dd, 2H), 7.60 (q, 3H), 7.56-7.50 (m, 1H), 7.50-7.41 (m, 2H), 7.36 (q, 2H), 7.32-7.25 (m, 3H), 6.96 (d, 1H), 4.98 (d, 4H), 4.39 (q, 1H), 4.20 (dd, 1H), 3.92-3.68 (m, 6H), 3.42 (dd, 1H), 3.25 (t, 2H), 3.09-2.87 (m, 6H), 2.64 (s, 2H), 2.25-1.87 (m, 5H), 1.79-0.89 (m, 17H), 0.88-0.67 (m, 12H). MS (ESI) m/e 1492.5 (M−H).

2.86 Synthesis of 4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](3-carboxypropyl)carbamoyl}oxy)methyl]-3-[2-(2-{[3-(2,5-dioxo-2,5-dihydro-1H-pyrrol-1-yl)propanoyl]amino}ethoxy)ethoxy]phenyl beta-D-glucopyranosiduronic acid (Synthon LJ)

2.86.1 3-(1-((3-(2-((((2-(2-(2-aminoethoxy)ethoxy)-4-(((2S,3R,4S,5S,6S)-6-carboxy-3,4,5-trihydroxytetrahydro-2H-pyran-2-yl)oxy)benzyl)oxy)carbonyl)(3-carboxypropyl)amino)ethoxy)-5,7-dimethyladamantan-1-yl)methyl)-5-methyl-1H-pyrazol-4-yl)-6-(8-(benzo[d]thiazol-2-ylcarbamoyl)-3,4-dihydroisoquinolin-2(1H)-yl)picolinic acid To a solution of Example 1.56 (0.024 g) and Example 2.62.6 (0.030 g) in N,N-dimethylformamide (0.4 mL) was added N,N-diisopropylethylamine (0.025 mL), and the reaction was stirred overnight. The reaction was concentrated, and the residue dissolved in tetrahydrofuran (0.5 mL) and methanol (0.5 mL) and treated with lithium hydroxide hydrate (0.018 g) as a solution in water (0.5 mL). After stirring for 1 hour, the reaction was diluted with N,N-dimethylformamide (1 mL) and purified by reverse phase HPLC using a Gilson system, eluting with 10-75% acetonitrile in water containing 0.1% v/v trifluoroacetic acid. The desired fractions were combined and freeze-dried to provide the title compound. MS (ESI) m/e 1262.7 (M+H)$^+$.

2.86.2 4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](3-carboxypropyl)carbamoyl}oxy)methyl]-3-[2-(2-{[3-(2,5-dioxo-2,5-dihydro-1H-pyrrol-1-yl)propanoyl]amino}ethoxy)ethoxy]phenyl beta-D-glucopyranosiduronic acid To a solution of Example 2.86.1 (0.0173 g) and 2,5-dioxopyrrolidin-1-yl 3-(2,5-dioxo-2,5-dihydro-1H-pyrrol-1-yl)propanoate (4.38 mg) in N,N-dimethylformamide (0.8 mL) was added 2,5-dioxopyrrolidin-1-yl 3-(2,5-dioxo-2,5-dihydro-1H-pyrrol-1-yl)propanoate (4.38 mg), and the reaction was stirred for 2 hours. The reaction was diluted with a 1:1 mixture of N,N-dimethylformamide:water (1 mL), and the mixture was purified by reverse phase HPLC using a Gilson system, eluting with 10-80% acetonitrile in water containing 0.1% v/v trifluoroacetic acid. The desired fractions were combined and freeze-dried to provide the title compound. $^1$H NMR (400 MHz, dimethyl sulfoxide-d$_6$) δ ppm 12.77 (s, 1H), 8.03 (d, 1H), 7.99 (t, 1H), 7.77 (d, 1H), 7.62 (d, 1H), 7.55-7.41 (m, 3H), 7.40-7.32 (m, 2H), 8.28 (s, 1H), 7.23-7.17 (m, 1H), 6.97 (s, 2H), 6.94 (d, 1H), 6.66 (s, 1H), 6.60 (dd, 1H), 5.07 (m, 1H), 5.00-4.91 (m, 4H), 4.17-4.02 (m, 2H), 3.96-3.85 (m, 2H), 3.85-3.76 (m, 2H), 3.71 (t, 2H), 3.64-3.56 (m, 4H), 3.34-3.12 (m, 10H), 3.01 (2H), 2.33 (t, 2H), 2.24-2.12 (m, 2H), 2.09 (s, 3H), 1.70 (p, 2H), 1.45-0.88 (m, 12H), 0.88-0.77 (m, 6H); MS (ESI) m/e 1434.2 (M+Na)$^+$.

2.87 Synthesis of 4-({[(4-{[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](3-carboxypropyl)amino]piperidin-1-yl)carbonyl]oxy}methyl)-3-[2-(2-{[3-(2,5-dioxo-2,5-dihydro-1H-pyrrol-1-yl)propanoyl]amino}ethoxy)ethoxy]phenyl beta-D-glucopyranosiduronic acid (Synthon MA)

2.87.1 3-(1-((3-(2-((1-(((2-(2-(2-aminoethoxy)ethoxy)-4-(((2S,3R,4S,5S,6S)-6-carboxy-3,4,5-trihydroxytetrahydro-2H-pyran-2-yl)oxy)benzyl)oxy)carbonyl)piperidin-4-yl)(3-carboxypropyl)amino)ethoxy)-5,7-dimethyladamantan-1-yl)methyl)-5-methyl-1H-pyrazol-4-yl)-6-(8-(benzo[d]thiazol-2-ylcarbamoyl)-3,4-dihydroisoquinolin-2(1H)-yl) picolinic acid A solution of Example 1.42 (0.050 g) and Example 2.62.6 (0.050 g) in N,N-dimethylformamide (0.5 mL) was treated with N,N-diisopropylethylamine (0.042 mL), and the reaction was stirred at room temperature for 2 hours. The reaction was concentrated, and the residue was dissolved in methanol (0.5 mL) and tetrahydrofuan (0.5 mL) and treated with lithium hydroxide hydrate (0.031 g) as a solution in water (0.5 mL). The reaction was stirred for 1.5 hours and diluted with N,N-dimethylformamide (1 mL). The mixture was purified by reverse phase HPLC using a Gilson system, eluting with 10-80% acetonitrile in water containing 0.1% v/v trifluoroacetic acid. The desired fractions were combined and freeze-dried to provide the title compound. MS (ESI) m/e 1345.7 (M+H)$^+$.

2.87.2 4-({[(4-{[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](3-carboxypropyl)amino}piperidin-1-yl)carbonyl]oxy}methyl)-3-[2-(2-{[3-(2,5-dioxo-2,5-dihydro-1H-pyrrol-1-yl)propanoyl]amino}ethoxy)ethoxy]phenyl beta-D-glucopyranosiduronic acid A solution of Example 2.87.1 (0.047 g) and 2,5-dioxopyrrolidin-1-yl 3-(2,5-dioxo-2,5-dihydro-1H-pyrrol-1-yl)propanoate (0.011 g) in N,N-dimethylformamide (0.5 mL) was treated with N,N-diisopropylethylamine (0.031 mL), and the reaction was stirred at room temperature for 2 hours. The reaction was diluted with a 1:1 mixture of N,N-dimethylformamide:water (2 mL). The mixture was purified by reverse phase HPLC using a Gilson system, eluting with 10-85% acetonitrile in water containing 0.1% v/v trifluoroacetic acid. The desired fractions were combined and freeze-dried to provide the title compound. $^1$H NMR (400 MHz, dimethyl sulfoxide-d$_6$) δ ppm 12.87 (s, 1H), 8.96 (s, 1H), 8.15-8.07 (m, 2H), 7.88 (d, J=8.1 Hz, 1H), 7.71 (d, J=7.5 Hz, 1H), 7.62-7.50 (m, 3H), 7.50-7.45 (m, 1H), 7.45-7.42 (m, 1H), 7.37 (s, 1H), 7.33-7.27 (m, 1H), 7.07 (s, 2H), 7.07-7.02 (m, 1H), 6.80-6.74 (m, 1H), 6.72-6.66 (m, 1H), 5.23-5.14 (m, 1H), 5.13-5.00 (m, 4H), 4.27-4.12 (m, 4H), 4.06-3.95 (m, 4H), 3.92 (s, 2H), 3.83-3.78 (m, 2H), 3.57-3.32 (m, 10H), 3.32-3.14 (m, 4H), 3.14-3.06 (m, 2H), 2.90 (s, 2H), 2.49-2.37 (m, 4H), 2.19 (s, 3H), 2.12-2.01 (m, 2H), 2.02-1.88 (m, 2H), 1.74-1.57 (m, 2H), 1.52 (s, 2H), 1.45-1.30 (m, 4H), 1.30-1.05 (m, 6H), 0.95 (s, 6H); MS (ESI) m/e 1495.4 (M+H)$^+$.

2.88 Synthesis of 4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](3-sulfopropyl)carbamoyl}oxy)methyl]-3-[2-(2-{[3-(2,5-dioxo-2,5-dihydro-1H-pyrrol-1-yl)propanoyl]amino}ethoxy)ethoxy]phenyl beta-D-glucopyranosiduronic acid (Synthon MD)

2.88.1 3-(1-((3-(2-((((2-(2-(2-aminoethoxy)ethoxy)-4-(((2S,3R,4S,5S,6S)-6-carboxy-3,4,5-trihydroxytetrahydro-2H-pyran-2-yl)oxy)benzyl)oxy)carbonyl)(3-sulfopropyl)amino)ethoxy)-5,7-dimethyladamantan-1-yl)methyl)-5-methyl-1H-pyrazol-4-yl)-6-(8-(benzo[d]thiazol-2-ylcarbamoyl)-3,4-dihydroisoquinolin-2(1H)-yl)picolinic acid A solution of Example 1.6 (0.039 g) and Example 2.62.6 (0.041 g) in N,N-dimethylformamide (0.5 mL) was treated with N,N-diisopropylethylamine (0.035 mL), and the reaction was stirred at room temperature for 2 hours. The reaction was concentrated, and the residue was dissolved in methanol (0.5 mL) and tetrahydrofuan (0.5 mL) and treated with lithium hydroxide hydrate (0.025 g) as a solution in water (0.5 mL). The reaction was stirred for 1.5 hours and diluted with N,N-dimethylformamide (1 mL). The mixture was purified by reverse phase HPLC using a Gilson system, eluting with 10-80% acetonitrile in water containing 0.1% v/v trifluoroacetic acid. The desired fractions were combined and freeze-dried to provide the title compound. MS (ESI) m/e 1297.8 (M+H)$^+$.

2.88.2 4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](3-sulfopropyl)carbamoyl}oxy)methyl]-3-[2-(2-{[3-(2,5-dioxo-2,5-dihydro-1H-pyrrol-1-yl)propanoyl]amino}ethoxy)ethoxy]phenyl beta-D-glucopyranosiduronic acid To a solution of Example 2.88.1 (0.024 g) and 2,5-dioxopyrrolidin-1-yl 3-(2,5-dioxo-2,5-dihydro-1H-pyrrol-1-yl)propanoate (6.40 mg) in N,N-dimethylformamide (0.5 mL) was added N,N-diisopropylethylamine (0.016 mL), and the reaction was stirred at room temperature for 1 hour. The reaction was diluted with a 1:1 mixture of N,N-dimethylformamide:water (2 mL). The mixture was purified by reverse phase HPLC using a Gilson system, eluting with 10-80% acetonitrile in water containing 0.1% v/v trifluoroacetic acid. The desired fractions were combined and freeze-dried to provide the title compound. $^1$H NMR (500 MHz, dimethyl sulfoxide-d$_6$) δ ppm 12.87 (s, 1H), 8.09-8.02 (m, 2H), 7.79 (d, 1H), 7.61 (d, 1H), 7.52 (dd, 1H), 7.50-7.42 (m, 2H), 7.40-7.33 (m, 2H), 7.31 (s, 1H), 7.20 (t, 1H), 6.98 (s, 3H), 6.66 (s, 1H), 6.60 (dd, 1H), 5.06 (t, 1H), 4.96 (s, 4H), 4.10 (dq, 4H), 3.81 (d, 4H), 3.71 (t, 2H), 3.59 (t, 2H), 3.51-3.35 (m, 4H), 3.26 (td, 6H), 3.17 (q, 2H), 3.01 (t, 2H), 2.35 (dt, 4H), 2.10 (d, 3H), 1.75 (d, 2H), 1.44-0.88 (m, 12H), 0.82 (d, 6H); MS (ESI) m/e 1446.4 (M−H)$^-$.

2.89 Synthesis of N-[6-(2,5-dioxo-2,5-dihydro-1H-pyrrol-1-yl)hexanoyl]-L-valyl-N-[4-({[(3-{[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)amino}azetidin-1-yl)carbonyl]oxy}methyl)phenyl]-N5-carbamoyl-L-ornithinamide (Synthon MG)

A solution of Example 1.60 (0.026 g), 4-((S)-2-((S)-2-(6-(2,5-dioxo-2,5-dihydro-1H-pyrrol-1-yl)hexanamido)-3-methylbutanamido)-5-ureidopentanamido)benzyl (4-nitrophenyl) carbonate (0.024 g) and N,N-diisopropylethylamine (0.022 mL) were stirred together in N,N-dimethylformamide (0.8 mL) at room temperature for 3 hours. The reaction was diluted with a 1:1 mixture of N,N-dimethylformamide:water (2 mL). The mixture was purified by reverse phase HPLC using a Gilson system, eluting with 10-80% acetonitrile in water containing 0.1% v/v trifluoroacetic acid. The desired fractions were combined and freeze-dried to provide the title compound. $^1$H NMR (400 MHz, dimethyl sulfoxide-d$_6$) δ ppm 12.85 (s, 1H), 9.99 (s, 1H), 8.06 (d, 1H), 8.03 (d, 1H), 7.79 (dd, 2H), 7.60 (dd, 3H), 7.55-7.41 (m, 3H), 7.36 (td, 2H), 7.29 (t, 3H), 6.99 (s, 2H), 6.95 (d, 1H), 5.99 (s, 1H), 5.04-4.92 (m, 4H), 4.37 (q, 1H), 4.34-4.24 (m, 1H), 4.24-4.10 (m, 4H), 3.88 (t, 2H), 3.82 (s, 2H), 3.40-3.29 (m, 4H), 3.01 (t, 2H), 2.99-2.91 (m, 1H), 2.87 (t, 2H), 2.25-2.06 (m, 5H), 1.95 (dt, 1H), 1.68 (s, 1H), 1.60 (s, 1H), 1.54-1.24 (m, 12H), 1.24-0.94 (m, 9H), 0.90-0.78 (m, 12H); MS (ESI) m/e 1507.4 (M+H)$^+$.

2.90 Synthesis of 6-[8-(1,3-benzothiazol-2-ylcarbamoyl)-3,4-dihydroisoquinolin-2(1H)-yl]-3-{1-[(3-{[26-(2,5-dioxo-2,5-dihydro-1H-pyrrol-1-yl)-8,24-dioxo-3-(2-sulfoethyl)-11,14,17,20-tetraoxa-3,7,23-triazahexacos-1-yl]oxy}-5,7-dimethyltricyclo[3.3.1.1$^{3,7}$]dec-1-yl)methyl]-5-methyl-1H-pyrazol-4-yl}pyridine-2-carboxylic acid (Synthon MS)

To a mixture of Example 1.61.2 (15 mg) and 2,5-dioxopyrrolidin-1-yl 1-(2,5-dioxo-2,5-dihydro-1H-pyrrol-1-yl)-3-oxo-7,10,13,16-tetraoxa-4-azanonadecan-19-oate (16.91 mg) in N,N-dimethylformamide (0.8 mL) was added N,N-diisopropylethylamine (28.8 µL) at 0° C. The mixture was stirred for 3 hours and purified by reverse phase HPLC, using a Gilson system and C18 column, eluting with 20-60% acetonitrile in water containing 0.1% trifluoroacetic acid, to provide the title compound. $^1$H NMR (400 MHz, dimethyl sulfoxide-d$_6$) δ ppm 12.87 (s, 1H), 8.98 (s, 1H), 8.08-7.92 (m, 3H), 7.79 (d, 1H), 7.62 (d, 1H), 7.57-7.41 (m, 3H), 7.36 (td, 2H), 7.29 (s, 1H), 7.04-6.92 (m, 3H), 4.96 (s, 2H), 3.89 (t, 2H), 3.83 (s, 2H), 3.48 (d, 4H), 3.44-3.17 (m, 3H), 3.18-2.83 (m, 10H), 2.38-2.24 (m, 4H), 2.11 (s, 3H), 1.78 (m, 2H), 1.50-0.94 (m, 12H), 0.86 (s, 6H). MS (ESI) m/e 1309.3 (M−H).

2.91 Synthesis of N-[6-(2,5-dioxo-2,5-dihydro-1H-pyrrol-1-yl)hexanoyl]-L-valyl-N-[4-({[(3-{[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)amino}propyl)carbamoyl]oxy}methyl)phenyl]-N$^5$-carbamoyl-L-ornithinamide (Synthon MR)

To a mixture of Example 1.61.2 (12.8 mg) and 4-((S)-2-((S)-2-(6-(2,5-dioxo-2,5-dihydro-1H-pyrrol-1-yl)hexanamido)-3-methylbutanamido)-5-ureidopentanamido)benzyl (4-nitrophenyl) carbonate (10.4 mg) in N,N-dimethylformamide (0.5 mL) at 0° C. was added N,N-diisopropylethylamine (24.54 µL). The mixture was stirred for 3 hours and purified by reverse phase HPLC using a Gilson system and a C18 column, eluting with 20-60% acetonitrile in water containing 0.1% trifluoroacetic acid, to provide the title compound. $^1$H NMR (400 MHz, dimethyl sulfoxide-d$_6$) δ ppm 12.85 (s, 1H), 9.97 (s, 1H), 8.97 (s, 1H), 8.04 (t, 2H), 7.79 (dd, 2H), 7.65-7.40 (m, 7H), 7.36 (td, 3H), 7.28 (d, 3H), 6.99 (s, 2H), 6.95 (d, 1H), 5.98 (s, 1H), 4.95 (d, 4H), 4.49-4.30 (m, 1H), 4.24-4.11 (m, 1H), 3.88 (t, 2H), 3.82 (s, 2H), 3.36 (t, 3H), 3.18-2.84 (m, 9H), 2.25-1.88 (m, 5H), 1.85-0.90 (m, 14H), 0.91-0.75 (m, 13H). MS (ESI) m/e (M+H).

2.92 Synthesis of N-{6-[(iodoacetyl)amino]hexanoyl}-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]phenyl}-N$^5$-carbamoyl-L-ornithinamide (Synthon MQ)

To a mixture of Example 1.2.9 (8.2 mg) and 2,5-dioxopyrrolidin-1-yl 6-(2-iodoacetamido)hexanoate (4.7 mg) in N,N-dimethylformamide (0.3 mL) in an ice-bath was added N,N-diisopropylethylamine (3 µL). The mixture was stirred at 0° C. for 1.5 hours. The reaction was diluted with dimethyl sulfoxide, and the mixture purified by reverse phase HPLC using a Gilson system and a C18 column, eluting with 20-60% acetonitrile in water containing 0.1% trifluoroacetic acid, to provide the title compound. $^1$H NMR (400 MHz, dimethyl sulfoxide-d$_6$) δ ppm 12.87 (s, 1H), 10.00 (s, 1H), 8.21 (d, 1H), 8.06 (dd, 2H), 7.81 (dd, 2H), 7.60 (t, 3H), 7.48 (ddd, 3H), 7.36 (td, 2H), 7.28 (d, 3H), 6.95 (d, 1H), 4.97 (d, 4H), 4.39 (q, 1H), 4.19 (t, 1H), 3.88 (t, 2H), 3.80 (d, 2H), 3.25 (d, 2H), 2.97 (dq, 6H), 2.63 (s, 2H), 2.25-1.88 (m, 5H), 1.78-0.70 (m, 29H). MS (ESI) m/e 1538.4 (M−H).

2.93 Synthesis of N-{6-[(ethenylsulfonyl)amino]hexanoyl}-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]phenyl}-N$^5$-carbamoyl-L-ornithinamide (Synthon MZ)

2.93.1 methyl 6-(vinylsulfonamido)hexanoate

To a solution of 6-methoxy-6-oxohexan-1-aminium chloride (0.3 g) and triethylamine (1.15 mL) in dichloromethane at 0° C. was added ethenesulfonyl chloride (0.209 g) dropwise. The reaction mixture was warmed to room temperature and stirred for 1 hour. The mixture was diluted with dichloromethane and washed with brine. The organic layer was dried over sodium sulfate, filtered, and concentrated to provide the title compound. MS (ESI) m/e 471.0 (2M+H)$^+$.

2.93.2 6-(vinylsulfonamido)hexanoic acid

A solution of Example 2.93.1 (80 mg) and lithium hydroxide monohydrate (81 mg) in a mixture of tetrahydrofuran (1 mL) and water (1 mL) was stirred for 2 hours, then diluted with water (20 mL), and washed with diethyl ether (10 mL). The aqueous layer was acidified to pH 4 with 1N aqueous HCl and extracted with dichloromethane (3×10 mL). The organic layer was washed with brine (5 mL), dried over sodium sulfate, filtered and concentrated to provide the title compound.

2.93.3 2,5-dioxopyrrolidin-1-yl 6-(vinylsulfonamido)hexanoate

A mixture of Example 2.93.2 (25 mg), 1-ethyl-3-[3-(dimethylamino)propyl]-carbodiimide hydrochloride (43.3 mg) and 1-hydroxypyrrolidine-2,5-dione (15.6 mg) in dichloromethane (8 mL) was stirred overnight, washed with saturated aqueous ammonium chloride solution and brine, and concentrated to provide the title compound.

2.93.4 N-{6-[(ethenylsulfonyl)amino]hexanoyl}-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.13,7]dec-1-yl}oxy)ethyl](2-sulfoethyl)carbamoyl}oxy)methyl]phenyl}-N5-carbamoyl-L-ornithinamide The title compound was prepared as described in Example 2.83, replacing Example 1.2.9 and 2,5-dioxopyrrolidin-1-yl 6-(2-chloroacetamido)hexanoate with Example 2.66.1 and Example 2.93.3, respectively. $^1$H NMR (400 MHz, dimethyl sulfoxide-d$_6$) δ ppm 12.85 (s, 1H), 9.98 (s, 1H), 8.05 (dd, 2H), 7.79 (d, 2H), 7.60 (t, 3H), 7.55-7.40 (m, 3H), 7.36 (td, 2H), 7.27 (d, 3H), 7.19 (t, 1H), 6.95 (d, 1H), 6.66 (dd, 1H), 6.09-5.90 (m, 2H), 4.97 (d, 4H), 4.39 (q, 1H), 4.20 (t, 1H), 3.88 (t, 2H), 3.80 (d, 2H), 3.25 (d, 2H), 2.97 (dt, 4H), 2.78 (q, 2H), 2.64 (q, 2H), 2.22-1.86 (m, 6H), 1.77-0.89 (m, 16H), 0.89-0.72 (m, 12H). MS (ESI) m/e 1460.6 (M−H).

2.94 Synthesis of 6-[8-(1,3-benzothiazol-2-ylcarbamoyl)-3,4-dihydroisoquinolin-2(1H)-yl]-3-(1-{[3-(2-{[3-({6-[(iodoacetyl)amino]hexanoyl}amino)propyl](2-sulfoethyl)amino}ethoxy)-5,7-dimethyltricyclo[3.3.1.1$^{3,7}$]dec-1-yl]methyl}-5-methyl-1H-pyrazol-4-yl)pyridine-2-carboxylic acid (Synthon NA)

The title compound was prepared using the procedure in Example 2.83, replacing Example 1.2.9 and 2,5-dioxopyrrolidin-1-yl 6-(2-chloroacetamido)hexanoate with Example 2.61.2 and 2,5-dioxopyrrolidin-1-yl 6-(2-iodoacetamido)hexanoate, respectively. $^1$H NMR (400 MHz, dimethyl sulfoxide-d$_6$) δ ppm 12.87 (s, 1H), 8.98 (s, 1H), 8.20 (t, 1H), 8.04 (d, 1H), 7.91 (t, 1H), 7.79 (d, 1H), 7.62 (d, 1H), 7.53 (d, 1H), 7.50-7.41 (m, 2H), 7.36 (td, 2H), 7.29 (s, 1H), 6.96 (d, 1H), 4.96 (s, 2H), 3.89 (t, 2H), 3.83 (s, 2H), 3.06 (dt, 8H), 2.89 (t, 2H), 2.17-1.99 (m, 5H), 1.76 (s, 2H), 1.56-0.93 (m, 14H), 0.86 (s, 6H). MS (ESI) m/e 1190.3 (M−H).

2.95 Synthesis of 6-[8-(1,3-benzothiazol-2-ylcarbamoyl)-3,4-dihydroisoquinolin-2(1H)-yl]-3-{1-[(3-{2-[(3-{[6-(ethenylsulfonyl)hexanoyl]amino}propyl)(2-sulfoethyl)amino]ethoxy}-5,7-dimethyltricyclo[3.3.1.1$^{3,7}$]dec-1-yl)methyl]-5-methyl-1H-pyrazol-4-yl}pyridine-2-carboxylic acid (Synthon NB)

The title compound was prepared using the procedure in Example 2.83, replacing Example 1.2.9 and 2,5-dioxopyrrolidin-1-yl 6-(2-chloroacetamido)hexanoate with Example 1.61.2 and Example 2.82.5, respectively. $^1$H NMR (400 MHz, dimethyl sulfoxide-d$_6$) δ ppm 12.87 (s, 1H), 8.98 (s, 1H), 8.04 (d, 1H), 7.92 (t, 1H), 7.79 (d, 1H), 7.62 (d, 1H), 7.53 (d, 1H), 7.51-7.41 (m, 2H), 7.36 (td, 2H), 7.29 (s, 1H), 7.01-6.90 (m, 2H), 6.29-6.16 (m, 2H), 4.96 (s, 2H), 3.89 (t, 2H), 3.83 (s, 2H), 3.45-3.19 (m, 2H), 3.19-2.95 (m, 8H), 2.89 (t, 2H), 2.16-1.98 (m, 5H), 1.84-1.66 (m, 2H), 1.64-1.21 (m, 13H), 1.08 (dq, 6H), 0.86 (s, 6H). MS (ESI) m/e 1199.3 (M+H).

2.96 Synthesis of N-[3-(2,5-dioxo-2,5-dihydro-1H-pyrrol-1-yl)propanoyl]-L-valyl-N-{4-[({[2-({3-[(4-{6-[1-(1,3-benzothiazol-2-ylcarbamoyl)-1,2,3,4-tetrahydroquinolin-7-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]phenyl}-N$^5$-carbamoyl-L-ornithinamide (Synthon NP)

2.96.1 (S)-(9H-fluoren-9-yl)methyl (1-((4-(hydroxymethyl)phenyl)amino)-1-oxo-5-ureidopentan-2-yl)carbamate (S)-2-((((9H-Fluoren-9-yl)methoxy)carbonyl)amino)-5-ureidopentanoic acid (40 g) was dissolved in dichloromethane (1.3 L). (4-Aminophenyl)methanol (13.01 g), 2-(3H-[1,2,3]triazolo[4,5-b]pyridin-3-yl)-1,1,3,3-tetramethylisouronium hexafluorophosphate(V) (42.1 g) and N,N-diisopropylethylamine (0.035 L) were added to the solution, and the resulting mixture was stirred at room temperature for 16 hours. The product was collected by filtration and rinsed with dichloromethane. The combined solids were dried under vacuum to yield the title compound, which was used in the next step without further purification. MS (ESI) m/e 503.3 (M+H)$^+$.

2.96.2 (S)-2-amino-N-(4-(hydroxymethyl)phenyl)-5-ureidopentanamide

Example 2.96.1 (44 g) was dissolved in N,N-dimethylformamide (300 mL). The solution was treated with diethylamine (37.2 mL) and stirred for one hour at room temperature. The reaction mixture was filtered, and the solvent was concentrated under reduced pressure. The crude product was purified by basic alumina chromatography eluting with a gradient of 0-30% methanol in ethyl acetate to give the title compound. MS (ESI) m/e 281.2 (M+H)$^+$.

2.96.3 tert-butyl ((S)-1-(((S)-1-((4-(hydroxymethyl)phenyl)amino)-1-oxo-5-ureidopentan-2-yl)amino)-3-methyl-1-oxobutan-2-yl)carbamate (S)-2-(Tert-butoxycarbonylamino)-3-methylbutanoic acid (9.69 g) was dissolved in N,N-dimethylformamide (200 mL). To the solution was added 2-(3H-[1,2,3]triazolo[4,5-b]pyridin-3-yl)-1,1,3,3-tetramethylisouronium hexafluorophosphate(V) (18.65 g), and the reaction was stirred for one hour at room temperature. Example 2.96.2 (12.5 g) and N,N-diisopropylethylamine (15.58 mL) were added and the reaction mixture was stirred for 16 hours at room temperature. The solvent was concentrated under reduced pressure and the residue was purified by silica gel chromatography, eluting with 10% methanol in dichloromethane, to give the title compound. MS (ESI) m/e 480.2 (M+H)$^+$.

2.96.4 (S)-2-((S)-2-amino-3-methylbutanamido)-N-(4-(hydroxymethyl)phenyl)-5-ureidopentanamide Example 2.96.3 (31.8 g) was dissolved in dichloromethane (650 mL) and trifluoroacetic acid (4.85 mL) was added to the solution. The reaction mixture was stirred for three hours at room temperature. The solvent was concentrated under reduced pressure to yield a mixture of the crude title compound and 4-((S)-2-((S)-2-amino-3-methylbutanamido)-5-ureidopentanamido)benzyl 2,2,2-trifluoroacetate. The crude material was dissolved in a 1:1 dioxane/water solution (300 mL) and to the solution was added sodium hydroxide (5.55 g). The mixture was stirred for three hours at room temperature. The solvent was concentrated under vacuum, and the crude product was purified by reverse phase HPLC using a CombiFlash system, eluting with a gradient of 5-60% acetonitrile in water containing 0.05% v/v ammonium hydroxide, to give the title compound. MS (ESI) m/e 380.2 (M+H)$^+$.

2.96.5 (S)-2-((S)-2-(3-(2,5-dioxo-2,5-dihydro-1H-pyrrol-1-yl)propanamido)-3-methylbutanamido)-N-(4-(hydroxymethyl)phenyl)-5-ureidopentanamide To a solution of Example 2.96.4 (38 mg) in N,N-dimethylformamide (1 mL) was added 2,5-dioxopyrrolidin-1-yl 3-(2,5-dioxo-2,5-dihydro-1H-pyrrol-1-yl)propanoate (26.7 mg). The reaction mixture was stirred at room temperature overnight and purified by reverse phase HPLC using a Gilson system, eluting with a gradient of 10-85% acetonitrile in water containing 0.1% v/v trifluoroacetic acid, to give the title compound. MS (ESI) m/e 531.06 (M+H)+.

2.96.6 4-((S)-2-((S)-2-(3-(2,5-dioxo-2,5-dihydro-1H-pyrrol-1-yl)propanamido)-3-methylbutanamido)-5-ureidopentanamido)benzyl (4-nitrophenyl) carbonate To a solution of Example 2.96.5 (53.1 mg) in N,N-dimethylformamide (3 mL) was added bis(4-nitrophenyl) carbonate (60.8 mg). The reaction mixture was stirred at room temperature overnight and purified by reverse phase HPLC using a Gilson system, eluting with a gradient of 10-85% acetonitrile in water containing 0.1% v/v trifluoroacetic acid, to give the title compound. MS (ESI) m/e 696.2 (M+H)+.

2.96.7 N-[3-(2,5-dioxo-2,5-dihydro-1H-pyrrol-1-yl)propanoyl]-L-valyl-N-{4-[({[2-({3-[(4-{6-[1-(1,3-benzothiazol-2-ylcarbamoyl)-1,2,3,4-tetrahydroquinolin-7-yl]-2-carboxypyridin-3-yl}-5-methyl-1H-pyrazol-1-yl)methyl]-5,7-dimethyltricyclo[3.3.1.1³,⁷]dec-1-yl}oxy)ethyl](2-sulfoethyl)carbamoyl}oxy)methyl]phenyl}-N5-carbamoyl-L-ornithinamide The title compound was prepared as described in Example 2.1, replacing Example 1.2.9 and 4-((S)-2-((S)-2-(6-(2,5-dioxo-2,5-dihydro-1H-pyrrol-1-yl)hexanamido)-3-methylbutanamido)-5-ureidopentanamido)benzyl (4-nitrophenyl) carbonate with Example 1.24.2 and Example 2.96.6, respectively. ¹H NMR (400 MHz, dimethyl sulfoxide-d₆) δ ppm 9.91 (s, 1H), 9.80 (s, 2H), 8.33 (s, 2H), 7.96 (s, 2H), 7.81 (d, 4H), 7.61 (s, 2H), 7.43 (d, 10H), 7.34-7.02 (m, 14H), 5.92 (s, 8H), 4.94-4.70 (m, 6H), 4.18 (d, 11H), 3.85 (s, 8H), 3.05-2.66 (m, 8H), 2.30-2.13 (m, 14H), 2.03-1.49 (m, 2H), 0.92-0.63 (m, 40H). MS (ESI) m/e 1408.3 (M−H)+.

2.97 Synthesis of 6-[8-(1,3-benzothiazol-2-ylcarbamoyl)-3,4-dihydroisoquinolin-2(1H)-yl]-3-{1-[(3-{2-[(2-carboxyethyl){[(2-{[(2S,3R,4S,5S,6S)-6-carboxy-3,4,5-trihydroxytetrahydro-2H-pyran-2-yl]oxy}-4-[2-(2-{[3-(2,5-dioxo-2,5-dihydro-1H-pyrrol-1-yl)propanoyl]amino}ethoxy)ethoxy]benzyl)oxy]carbonyl}amino]ethoxy}-5,7-dimethyltricyclo[3.3.1.1³,⁷]dec-1-yl)methyl]-5-methyl-1H-pyrazol-4-yl}pyridine-2-carboxylic acid (Synthon NN)

2.97.1 4-(2-(2-bromoethoxy)ethoxy)-2-hydroxybenzaldehyde

A solution of 2,4-dihydroxybenzaldehyde (1.0 g), 1-bromo-2-(2-bromoethoxy)ethane (3.4 g) and potassium carbonate (1.0 g) in acetonitrile (30 mL) was heated to 75° C. for 2 days. The reaction was cooled, diluted with ethyl acetate (100 mL), washed with water (50 mL) and brine (50 mL), dried over magnesium sulfate, filtered and concentrated. Purification of the residue by silica gel chromatography, eluting with a gradient of 5-30% ethyl acetate in heptane, provided the title compound. MS (ELSD) m/e 290.4 (M+H)+.

2.97.2 4-(2-(2-azidoethoxy)ethoxy)-2-hydroxybenzaldehyde

To a solution of Example 2.97.1 (1.26 g) in N,N-dimethylformamide (10 mL) was added sodium azide (0.43 g), and the reaction was stirred at room temperature overnight. The reaction was diluted with diethyl ether (100 mL), washed with water (50 mL) and brine (50 mL), dried over magnesium sulfate, filtered, and concentrated. Purification of the residue by silica gel chromatography, eluting with a gradient of 5-30% ethyl acetate in heptane, gave the title compound. MS (ELSD) m/e 251.4 (M+H)+.

2.97.3 (2S,3R,4S,5S,6S)-2-(5-(2-(2-azidoethoxy)ethoxy)-2-formylphenoxy)-6-(methoxycarbonyl)tetrahydro-2H-pyran-3,4,5-triyl triacetate A solution of Example 2.97.2 (0.84 g), (3R,4S,5S,6S)-2-bromo-6-(methoxycarbonyl)tetrahydro-2H-pyran-3,4,5-triyl triacetate (1.99 g) and silver (I) oxide (1.16 g) were stirred together in acetonitrile (15 mL). After stirring overnight, the reaction was diluted with dichloromethane (20 mL). Diatomaceous earth was added, and the reaction filtered and concentrated. Purification of the residue by silica gel chromatography, eluting with a gradient of 5-75% ethyl acetate in heptane, gave the title compound.

2.97.4 (2S,3R,4S,5S,6S)-2-(5-(2-(2-azidoethoxy)ethoxy)-2-(hydroxymethyl)phenoxy)-6-(methoxycarbonyl)tetrahydro-2H-pyran-3,4,5-triyl triacetate A solution of Example 2.97.3 (0.695 g) in methanol (5 mL) and tetrahydrofuran (2 mL) was cooled to 0° C. Sodium borohydride (0.023 g) was added, and the reaction was warmed to room temperature. After stirring for a total of 1 hour, the reaction was poured into a mixture of ethyl acetate (75 mL) and water (25 mL), and saturated aqueous sodium bicarbonate (10 mL) was added. The organic layer was separated, washed with brine (50 mL), dried over magnesium sulfate, filtered, and concentrated. Purification of the residue by silica gel chromatography, eluting with a gradient of 5-85% ethyl acetate in heptane, gave the title compound. MS (ELSD) m/e 551.8 (M−H₂O)−.

2.97.5 (2S,3R,4S,5S,6S)-2-(5-(2-(2-aminoethoxy)ethoxy)-2-(hydroxymethyl)phenoxy)-6-(methoxycarbonyl)tetrahydro-2H-pyran-3,4,5-triyl triacetate To Example 2.97.4 (0.465 g) in tetrahydrofuran (20 mL) was added 5% Pd/C (0.1 g) in a 50 mL pressure bottle, and the mixture was shaken for 16 hours under 30 psi hydrogen. The reaction was filtered and concentrated to give the title compound, which was used without further purification. MS (ELSD) m/e 544.1 (M+H)+.

2.97.6 (2S,3R,4S,5S,6S)-2-(5-(2-(2-((((9H-fluoren-9-yl)methoxy)carbonyl)amino)ethoxy)ethoxy)-2-(hydroxymethyl)phenoxy)-6-(methoxycarbonyl)tetrahydro-2H-pyran-3,4,5-triyl triacetate A solution of Example 2.97.5 (0.443 g) in dichloromethane (8 mL) was cooled to 0° C., then N,N-diisopropylethylamine (0.214 mL) and (9H-fluoren-9-yl)methyl carbonochloridate (0.190 g) were added. After 1 hour, the reaction was concentrated. Purification of the residue by silica gel chromatography, eluting with a gradient of 5-95% ethyl acetate in heptane, gave the title compound. MS (ELSD) m/e 748.15 (M−OH)−.

2.97.7 (2S,3R,4S,5S,6S)-2-(5-(2-(2-((((9H-fluoren-9-yl)methoxy)carbonyl)amino)ethoxy)ethoxy)-2-((((4-nitrophenoxy)carbonyl)oxy)methyl)phenoxy)-6-(methoxycarbonyl)tetrahydro-2H-pyran-3,4,5-triyl triacetate To a solution of Example 2.97.6 (0.444 g) in N,N-dimethylformamide (5 mL) was added N,N-diisopropylethylamine (0.152 mL) and bis(4-nitrophenyl) carbonate (0.353 g), and the reaction was stirred at room temperature. After 5 hours, the reaction was concentrated. Purification of the residue by silica gel chromatography, eluting with a gradient of 5-90% ethyl acetate in heptane, gave the title compound.

2.97.8 3-(1-((3-(2-((((4-(2-(2-aminoethoxy)ethoxy)-2-(((2S,3R,4S,5S,6S)-6-carboxy-3,4,5-trihydroxytetrahydro-2H-pyran-2-yl)oxy)benzyl)oxy)carbonyl)(2-carboxyethyl)amino)ethoxy)-5,7-dimethyladamantan-1-yl)methyl)-5-methyl-1H-pyrazol-4-yl)-6-(8-(benzo[d]thiazol-2-ylcarbamoyl)-3,4-dihydroisoquinolin-2(1H)-yl)picolinic acid, trifluoroacetic acid salt To a solution of Example 1.25 (0.070 g) and Example 2.97.7 (0.070 g) in N,N-dimethylformamide (0.4 mL) was added N,N-diisopropylethylamine (0.066 mL). After stirring overnight, the reaction was concentrated. The residue was dissolved in tetrahydrofuran (0.75 mL) and methanol (0.75 mL), and lithium hydroxide monohydrate (0.047 g) was added as a solution in water (0.75 mL). After 3 hours, the reaction was diluted with N,N-dimethylformamide (1 mL) and quenched with trifluoroacetic acid (0.116 mL). The mixture was purified by reverse phase HPLC using a Gilson system, eluting with 10-75% acetonitrile in water containing 0.1% v/v trifluoroacetic acid. The desired fractions were combined and freeze-dried to provide the title compound.

2.97.9 6-(8-(benzo[d]thiazol-2-ylcarbamoyl)-3,4-dihydroisoquinolin-2(1H)-yl)-3-(1-((3-(2-((((2-(((2S,3R,4S,5S,6S)-6-carboxy-3,4,5-trihydroxytetrahydro-2H-pyran-2-yl)oxy)-4-(2-(2-(3-(2,5-dioxo-2,5-dihydro-1H-pyrrol-1-yl)propanamido)ethoxy)ethoxy)benzyl)oxy)carbonyl)(2-carboxyethyl)amino)ethoxy)-5,7-dimethyladamantan-1-yl)methyl)-5-methyl-1H-pyrazol-4-yl)picolinic acid A solution of Example 2.97.8 (0.027 g), 2,5-dioxopyrrolidin-1-yl 3-(2,5-dioxo-2,5-dihydro-1H-pyrrol-1-yl)propanoate (7.92 mg) and N,N-diisopropylethylamine (0.017 mL) were stirred together in N,N-dimethylformamide (0.4 mL) for 1 hour. The reaction was quenched with a 1:1 mixture of water and N,N-dimethylformamide (2 mL). The mixture was purified by reverse phase HPLC using a Gilson system, eluting with 10-75% acetonitrile in water containing 0.1% v/v trifluoroacetic acid. The desired fractions were combined and freeze-dried to provide the title compound. $^1$H NMR (400 MHz, dimethyl sulfoxide-d$_6$) δ ppm 12.81 (s, 1H), 8.03 (d, 2H), 7.79 (d, 1H), 7.62 (d, 1H), 7.54-7.40 (m, 3H), 7.36 (td, 2H), 7.28 (s, 1H), 7.18 (d, 1H), 6.98 (s, 2H), 6.95 (d, 1H), 6.69 (d, 1H), 6.60 (d, 1H), 5.03 (d, 3H), 4.96 (s, 2H), 4.05 (s, 2H), 3.93 (d, 2H), 3.88 (t, 2H), 3.80 (d, 2H), 3.75-3.67 (m, 2H), 3.59 (t, 6H), 3.29 (q, 6H), 3.17 (q, 2H), 3.01 (t, 2H), 2.47 (d, 2H), 2.33 (t, 2H), 2.09 (s, 3H), 1.44-0.88 (m, 12H), 0.82 (d, 6H); MS (ESI) m/e 1396.5 (M−H)$^−$.

2.98 Synthesis of N-[6-(2,5-dioxo-2,5-dihydro-1H-pyrrol-1-yl)hexanoyl]-3-sulfo-L-alanyl-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-carboxyethyl)carbamoyl}oxy)methyl]phenyl}-N$^5$-carbamoyl-L-ornithinamide (Synthon NO)

2.98.1 3-(1-((3-(2-((((4-((S)-2-((S)-2-amino-3-methylbutanamido)-5-ureidopentanamido)benzyl)oxy)carbonyl)(2-carboxyethyl)amino)ethoxy)-5,7-dimethyladamantan-1-yl)methyl)-5-methyl-1H-pyrazol-4-yl)-6-(8-(benzo[d]thiazol-2-ylcarbamoyl)-3,4-dihydroisoquinolin-2(1H)-yl)picolinic acid A solution of Example 1.25.2 (0.059 g), (9H-fluoren-9-yl)methyl ((S)-3-methyl-1-(((S)-1-((4-((((4-nitrophenoxy)carbonyl)oxy)methyl)phenyl)amino)-1-oxo-5-ureidopentan-2-yl)amino)-1-oxobutan-2-yl)carbamate (0.053 g) and N,N-diisopropylethylamine (0.055 mL) in N,N-dimethylformamide (0.5 mL) was stirred at room temperature overnight. Diethylamine (0.066 mL) was added to the reaction, and stirring was continued for 30 minutes. The reaction was diluted with a 1:1 mixture of N,N-dimethylformamide and water (2 mL) and quenched by the addition of trifluoroacetic acid (0.073 mL). The mixture was purified by reverse phase HPLC using a Gilson system, eluting with 10-75% acetonitrile in water containing 0.1% v/v trifluoroacetic acid. The desired fractions were combined and freeze-dried to provide the title compound. MS (ESI) m/e 1223.8 (M+H)$^+$.

2.98.2 3-(1-((3-(2-((((4-((S)-2-((S)-2-((R)-2-amino-3-sulfopropanamido)-3-methylbutanamido)-5-ureidopentanamido)benzyl)oxy)carbonyl)(2-carboxyethyl)amino)ethoxy)-5,7-dimethyladamantan-1-yl)methyl)-5-methyl-1H-pyrazol-4-yl)-6-(8-(benzo[d]thiazol-2-ylcarbamoyl)-3,4-dihydroisoquinolin-2(1H)-yl)picolinic acid, trifluoroacetic acid salt A solution of (R)-2-((((9H-fluoren-9-yl)methoxy)carbonyl)amino)-3-sulfopropanoic acid (0.021 g), O-(7-azabenzotriazol-1-yl)-N,N,N',N'-tetramethyluronium hexafluorophosphate (0.020 g) and N,N-diisopropylethylamine (0.031 mL) in N,N-dimethylformamide (0.4 mL) was stirred for 3 minutes. The solution was added to Example 2.98.1 (0.043 g) as a solution in N,N-dimethylformamide (0.4 mL). After stirring for 30 minutes, a solution of lithium hydroxide monohydrate (0.022 g) in water (0.5 mL) was added, and the reaction was stirred for 1 hour. The reaction was diluted with a 1:1 mixture of N,N-dimethylformamide and water (2 mL) and quenched by the addition of trifluoroacetic acid (0.054 mL). The mixture was purified by reverse phase HPLC using a Gilson system, eluting with 10-75% acetonitrile in water containing 0.1% v/v trifluoroacetic acid. The desired fractions were combined and freeze-dried to provide the title compound. MS (ESI) m/e 1376.5 (M+1).

2.98.3 6-(8-(benzo[d]thiazol-2-ylcarbamoyl)-3,4-dihydroisoquinolin-2(1H)-yl)-3-(1-((3-(2-((2-carboxyethyl)(((4-((S)-2-((S)-2-((R)-2-(6-(2,5-dioxo-2,5-dihydro-1H-pyrrol-1-yl)hexanamido)-3-sulfopropanamido)-3-methylbutanamido)-5-ureidopentanamido)benzyl)oxy)carbonyl)amino)ethoxy)-5,7-dimethyladamantan-1-yl)methyl)-5-methyl-1H-pyrazol-4-yl)picolinic acid A solution of Example 2.98.2 (0.025 g), 2,5-dioxopyrrolidin-1-yl 6-(2,5-dioxo-2,5-dihydro-1H-pyrrol-1-yl)hexanoate (7.77 mg) and N,N-diisopropylethylamine (0.015 mL) in N,N-dimethylformamide (0.4 mL) was stirred for 1 hour. The reaction was diluted with a 1:1 mixture of water and N,N-dimethylformamide (2 mL). The mixture was purified by reverse phase HPLC using a Gilson system, eluting with 10-75% acetonitrile in water containing 0.1% v/v trifluoroacetic acid. The desired fractions were combined and freeze-dried to provide the title compound. $^1$H NMR (400 MHz, dimethyl sulfoxide-$d_6$) δ ppm 12.85 (s, 1H), 9.46 (s, 1H), 8.20 (d, 1H), 8.07 (d, 1H), 8.03 (d, 1H), 8.00 (d, 1H), 7.79 (d, 1H), 7.69 (d, 2H), 7.61 (d, 1H), 7.51 (d, 1H), 7.49-7.45 (m, 1H), 7.43 (d, 1H), 7.36 (td, 2H), 7.29 (s, 1H), 7.25 (d, 2H), 6.97 (s, 2H), 6.95 (d, 1H), 4.98 (s, 2H), 4.96 (s, 2H), 4.73 (s, 2H), 4.16 (s, 2H), 4.03 (dd, 2H), 3.88 (t, 2H), 3.81 (s, 2H), 3.51-3.32 (m, 6H), 3.28 (t, 2H), 3.09 (dd, 1H), 3.06-2.94 (m, 4H), 2.89 (dd, 1H), 2.46 (d, 2H), 2.16 (dd, 1H), 2.09 (d, 4H), 1.74 (s, 2H), 1.62-1.29 (m, 8H), 1.29-0.92 (m, 12H), 0.92-0.78 (m, 12H). MS (ESI) m/e 1566.6 (M−H)$^−$.

2.99 Synthesis of Control Synthon 4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](methyl)carbamoyl}oxy)methyl]-2-({N-[6-(2,5-dioxo-2,5-dihydro-1H-pyrrol-1-yl)hexanoyl]-beta-alanyl}amino)phenyl beta-D-glucopyranosiduronic acid (Synthon H)

2.99.1 (2S,3R,4S,5S,6S)-2-(4-formyl-2-nitrophenoxy)-6-(methoxycarbonyl)tetrahydro-2H-pyran-3,4,5-triyl triacetate To a solution of (2R,3R,4S,5S,6S)-2-bromo-6-(methoxycarbonyl)tetrahydro-2H-pyran-3,4,5-triyl triacetate (4 g) in acetonitrile (100 mL)) was added silver(I) oxide (10.04 g) and 4-hydroxy-3-nitrobenzaldehyde (1.683 g). The reaction mixture was stirred for 4 hours at room temperature and filtered. The filtrate was concentrated, and the residue was purified by silica gel chromatography, eluting with 5-50% ethyl acetate in heptanes, to provide the title compound. MS (ESI) m/e (M+18)$^+$.

2.99.2 (2S,3R,4S,5S,6S)-2-(4-(hydroxymethyl)-2-nitrophenoxy)-6-(methoxycarbonyl)tetrahydro-2H-pyran-3,4,5-triyl triacetate To a solution of Example 2.99.1 (6 g) in a mixture of chloroform (75 mL) and isopropanol (18.75 mL) was added 0.87 g of silica gel. The resulting mixture was cooled to 0° C., NaBH$_4$ (0.470 g) was added, and the resulting suspension was stirred at 0° C. for 45 minutes. The reaction mixture was diluted with dichloromethane (100 mL) and filtered through diatomaceous earth. The filtrate was washed with water and brine and concentrated to give the crude product, which was used without further purification. MS (ESI) m/e (M+NH$_4$)+:

2.99.3 (2S,3R,4S,5S,6S)-2-(2-amino-4-(hydroxymethyl)phenoxy)-6-(methoxycarbonyl)tetrahydro-2H-pyran-3,4,5-triyl triacetate A stirred solution of Example 2.99.2 (7 g) in ethyl acetate (81 mL) was hydrogenated at 20° C. under 1 atmosphere H$_2$, using 10% Pd/C (1.535 g) as a catalyst for 12 hours. The reaction mixture was filtered through diatomaceous earth, and the solvent was evaporated under reduced pressure. The residue was purified by silica gel chromatography, eluting with 95/5 dichloromethane/methanol, to give the title compound.

2.99.4 3-((((9H-fluoren-9-yl)methoxy)carbonyl)amino)propanoic acid

3-Aminopropanoic acid (4.99 g) was dissolved in 10% aqueous Na$_2$CO$_3$ solution (120 mL) in a 500 mL flask and cooled with an ice bath. To the resulting solution, (9H-fluoren-9-yl)methyl carbonochloridate (14.5 g) in 1,4-dioxane (100 mL) was gradually added. The reaction mixture was stirred at room temperature for 4 hours, and water (800 mL) was then added. The aqueous phase layer was separated from the reaction mixture and washed with diethyl ether (3×750 mL). The aqueous layer was acidified with 2N HCl aqueous solution to a pH value of 2 and extracted with ethyl acetate (3×750 mL). The organic layers were combined and concentrated to obtain crude product. The crude product was recrystallized in a mixed solvent of ethyl acetate: hexane 1:2 (300 mL) to give the title compound.

2.99.5 (9H-fluoren-9-yl)methyl (3-chloro-3-oxopropyl)carbamate

To a solution of Example 2.99.4 in dichloromethane (160 mL) was added sulfurous dichloride (50 mL). The mixture was stirred at 60° C. for 1 hour. The mixture was cooled and concentrated to give the title compound.

2.99.6 (2S,3R,4S,5S,6S)-2-(2-(3-((((9H-fluoren-9-yl)methoxy)carbonyl)amino)propanamido)-4-(hydroxymethyl)phenoxy)-6-(methoxycarbonyl)tetrahydro-2H-pyran-3,4,5-triyl triacetate To a solution of Example 2.99.3 (6 g) in dichloromethane (480 mL) was added N,N-diisopropylethylamine (4.60 mL). Example 2.99.5 (5.34 g) was added, and the mixture was stirred at room temperature for 30 minutes. The mixture was poured into saturated aqueous sodium bicarbonate and was extracted with ethyl acetate. The combined extracts were washed with water and brine and were dried over sodium sulfate. Filtration and concentration gave a residue that was purified via radial chromatography, using 0-100% ethyl acetate in petroleum ether as mobile phase, to give the title compound.

2.99.7 (2S,3R,4S,5S,6S)-2-(2-(3-((((9H-fluoren-9-yl)methoxy)carbonyl)amino)propanamido)-4-((((4-nitrophenoxy)carbonyl)oxy)methyl)phenoxy)-6-(methoxycarbonyl)tetrahydro-2H-pyran-3,4,5-triyl triacetate To a mixture of Example 2.99.6 (5.1 g) in N,N-dimethylformamide (200 mL) was added bis(4-nitrophenyl) carbonate (4.14 g) and N,N-diisopropylethylamine (1.784 mL). The mixture was stirred for 16 hours at room temperature and concentrated under reduced pressure. The crude material was dissolved in dichloromethane and aspirated directly onto a 1 mm radial Chromatotron plate and eluted with 50-100% ethyl acetate in hexanes to give the title compound. MS (ESI) m/e (M+H)$^+$.

2.99.8 3-(1-((3-(2-((((2S,3R,4S,5S,6S)-6-carboxy-3,4,5-trihydroxytetrahydro-2H-pyran-2-yl)oxy)benzyl)oxy)carbonyl)(methyl)amino)ethoxy)-5,7-dimethyladamantan-1-yl)methyl)-5-methyl-1H-pyrazol-4-yl)-6-(8-(benzo[d]thiazol-2-ylcarbamoyl)-3,4-dihydroisoquinolin-2(1H)-yl)picolinic acid To a solution of Example 1.13.7 (325 mg) and Example 2.99.7 (382 mg) in N,N-dimethylformamide (9 mL) at 0° C. was added N,N-diisopropylamine (49.1 mg). The reaction mixture was stirred at 0° C. for 5 hours, and acetic acid (22.8 mg) was added. The resulting mixture was diluted with ethyl acetate and washed with water and brine. The organic layer was dried over $Na_2SO_4$, filtered and concentrated. The residue was dissolved in a mixture of tetrahydrofuran (10 mL) and methanol (5 mL). To this solution at 0° C. was added 1 M aqueous lithium hydroxide solution (3.8 mL). The resulting mixture was stirred at 0° C. for 1 hour, acidified with acetic acid and concentrated. The concentrate was lyophilized to provide a powder. The powder was dissolved in N,N-dimethylformamide (10 mL), cooled in an ice-bath, and piperidine (1 mL) at 0° C. was added. The mixture was stirred at 0° C. for 15 minutes and 1.5 mL of acetic acid was added. The solution was purified by reverse-phase HPLC using a Gilson system, eluting with 30-80% acetonitrile in water containing 0.1% v/v trifluoroacetic acid, to provide the title compound. MS (ESI) m/e 1172.2 $(M+H)^+$.

2.99.9 4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1 3,7]dec-1-yl}oxy)ethyl](methyl)carbamoyl}oxy)methyl]-2-({N-[6-(2,5-dioxo-2,5-dihydro-1H-pyrrol-1-yl)hexanoyl]-beta-alanyl}amino)phenyl beta-D-glucopyranosiduronic acid To Example 2.99.8 (200 mg) in N,N-dimethylformamide (5 mL) at 0° C. was added 2,5-dioxopyrrolidin-1-yl 6-(2,5-dioxo-2,5-dihydro-1H-pyrrol-1-yl)hexanoate (105 mg) and N,N-diisopropylethylamine (0.12 mL). The mixture was stirred at 0° C. for 15 minutes, warmed to room temperature and purified by reverse-phase HPLC on a Gilson system using a 100 g C18 column, eluting with 30-80% acetonitrile in water containing 0.1% v/v trifluoroacetic acid, to provide the title compound. $^1$H NMR (500 MHz, dimethyl sulfoxide-$d_6$) δ ppm 12.85 (s, 2H) 9.07 (s, 1H) 8.18 (s, 1H) 8.03 (d, 1H) 7.87 (t, 1H) 7.79 (d, 1H) 7.61 (d, 1H) 7.41-7.53 (m, 3H) 7.36 (q, 2H) 7.28 (s, 1H) 7.03-7.09 (m, 1H) 6.96-7.03 (m, 3H) 6.94 (d, 1H) 4.95 (s, 4H) 4.82 (t, 1H) 3.88 (t, 3H) 3.80 (d, 2H) 3.01 (t, 2H) 2.86 (d, 3H) 2.54 (t, 2H) 2.08 (s, 3H) 2.03 (t, 2H) 1.40-1.53 (m, 4H) 1.34 (d, 2H) 0.90-1.28 (m, 12H) 0.82 (d, 6H). MS (ESI) m/e 1365.3 $(M+H)^+$.

2.100 Synthesis of Control Synthon 4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1 3,7]dec-1-yl}oxy)ethyl](methyl)carbamoyl}oxy)methyl]-2-({N-[19-(2,5-dioxo-2,5-dihydro-1H-pyrrol-1-yl)-17-oxo-4,7,10,13-tetraoxa-16-azanonadec-1-oyl]-beta-alanyl}amino)phenyl beta-D-glucopyranosiduronic acid (Synthon I)

The title compound was prepared using the procedure in Example 2.99.9, replacing 2,5-dioxopyrrolidin-1-yl 6-(2,5-dioxo-2,5-dihydro-1H-pyrrol-1-yl)hexanoate with 2,5-dioxopyrrolidin-1-yl 1-(2,5-dioxo-2,5-dihydro-H-pyrrol-1-yl)-3-ox-7,10,13-tetraoxa-4-azanonadecan-19-oate. $^1$H NMR (500 MHz, dimethyl sulfoxide-$d_6$) δ ppm 8.95 (s, 1H) 8.16 (s, 1H) 7.99 (d, 1H) 7.57-7.81 (m, 4H) 7.38-7.50 (m, 3H) 7.34 (q, 2H) 7.27 (s, 1H) 7.10 (d, 1H) 7.00 (d, 1H) 6.88-6.95 (m, 2H) 4.97 (d, 4H) 4.76 (d, 2H) 3.89 (t, 2H) 3.84 (d, 2H) 3.80 (s, 2H) 3.57-3.63 (m, 4H) 3.44-3.50 (m, 4H) 3.32-3.43 (m, 6H) 3.29 (t, 2H) 3.16 (q, 2H) 3.02 (t, 2H) 2.87 (s, 3H) 2.52-2.60 (m, 2H) 2.29-2.39 (m, 3H) 2.09 (s, 3H) 1.37 (s, 2H) 1.20-1.29 (m, 4H) 1.06-1.18 (m, 4H) 0.92-1.05 (m, 2H) 0.83 (s, 6H). MS (ESI) m/e 1568.6 (M−H)⁻.

2.101 Synthesis of 6-[8-(1,3-benzothiazol-2-ylcarbamoyl)-3,4-dihydroisoquinolin-2(1H)-yl]-3-{1-[(3-{[(43S,46S)-43-({[(4-{[(2S)-2-{[(2S)-2-{[6-(2,5-dioxo-2,5-dihydro-1H-pyrrol-1-yl)hexanoyl]amino}-3-methylbutanoyl]amino}propanoyl]amino}benzyl)oxy]carbonyl}amino)-46-methyl-37,44,47-trioxo-2,5,8,11,14,17,20,23,26,29,32,35-dodecaoxa-38,45,48-triazapentacontan-50-yl]oxy}-5,7-dimethyltricyclo[3.3.1.1 3,7]dec-1-yl)methyl]-5-methyl-1H-pyrazol-4-yl}pyridine-2-carboxylic acid (Synthon OK)

The title compound was prepared as described in Example 2.7, replacing Example 1.13.8 with Example 1.66.7. $^1$H NMR (400 MHz, dimethyl sulfoxide-$d_6$) δ ppm 12.85 (s, 1H), 8.21-7.97 (m, 4H), 7.79 (d, 4H), 7.71-7.32 (m, 15H), 7.28 (t, 4H), 7.02-6.91 (m, 3H), 4.95 (d, 5H), 4.33-4.12 (m, 3H), 3.98-3.76 (m, 11H), 3.41-3.21 (m, 22H), 3.21-2.90 (m, 12H), 2.24-2.05 (m, 7H), 1.81-0.90 (m, 46H), 0.90-0.78 (m, 17H). MS (ESI) m/e 2014.0 $(M+H)^+$, 1007.5 $(M+2H)^{2+}$, 672.0 $(M+3H)^{3+}$.

2.102 Synthesis of N-[6-(2,5-dioxo-2,5-dihydro-1H-pyrrol-1-yl)hexanoyl]-L-valyl-N-{4-[({[2-({3-[(4-{6-[1-(1,3-benzothiazol-2-ylcarbamoyl)-1,2,3,4-tetrahydroquinolin-7-yl]-2-carboxypyridin-3-yl}-5-methyl-1H-pyrazol-1-yl)methyl]-5,7-dimethyltricyclo[3.3.1.1 3,7]dec-1-yl}oxy)ethyl](2-carboxyethyl)carbamoyl}oxy)methyl]phenyl}-N⁵-carbamoyl-L-ornithinamide (Synthon OW)

The title compound was prepared as described in Example 2.1, replacing Example 1.2.9 with Example 1.62.5 $^1$H NMR (400 MHz, dimethyl sulfoxide-$d_6$) δ ppm 9.95 (s, 1H), 8.36 (s, 1H), 8.02 (d, 1H), 7.96 (d, 1H), 7.88-7.68 (m, 4H), 7.57 (d, 2H), 7.42 (s, 2H), 7.34 (t, 1H), 7.25 (dd, 3H), 7.19 (t, 1H), 6.95 (s, 2H), 5.96 (s, 1H), 4.96 (s, 2H), 4.35 (q, 1H), 4.15 (dd, 1H), 3.93 (t, 2H), 3.83 (d, 2H), 3.32 (t, 2H), 3.27 (d, 1H), 2.93 (dtd, 1H), 2.80 (t, 2H), 2.47 (p, 19H), 2.24-2.02 (m, 5H), 1.91 (p, 3H), 1.74-1.25 (m, 8H), 1.27-0.89 (m, 10H), 0.79 (dd, 13H). MS (ESI) m/e 1414.4 $(M+H)^+$.

2.103 Synthesis of N-[6-(2,5-dioxo-2,5-dihydro-1H-pyrrol-1-yl)hexanoyl]-L-valyl-N-{4-[({[2-({3-[(4-{6-[8-(1,3-benzothiazol-2-ylcarbamoyl)naphthalen-2-yl]-2-carboxypyridin-3-yl}-5-methyl-1H-pyrazol-1-yl)methyl]-5,7-dimethyltricyclo[3.3.1.1 3,7]dec-1-yl}oxy)ethyl](2-carboxyethyl)carbamoyl}oxy)methyl]phenyl}-N⁵-carbamoyl-L-ornithinamide (Synthon PC)

The title compound was prepared as described in Example 2.1, replacing Example 1.2.9 with Example 1.68.7. $^1$H NMR (400 MHz, dimethyl sulfoxide-$d_6$) δ ppm 13.07 (s, 1H), 9.95 (s, 1H), 8.99 (s, 1H), 8.33 (dd, 1H), 8.25-8.09 (m, 3H), 8.12-7.95 (m, 3H), 7.90 (d, 1H), 7.76 (dd, 2H), 7.73-7.63 (m, 1H), 7.56 (s, 3H), 7.41-7.29 (m, 1H), 6.95 (s, 2H), 5.97 (s, 1H), 4.96 (s, 2H), 4.35 (d, 2H), 4.15 (dd, 1H), 3.50-3.22 (m, 10H), 2.92 (dtd, 3H), 2.29-2.00 (m, 6H), 1.92 (q, 1H), 1.75-0.88 (m, 24H), 0.79 (dd, 15H). MS (ESI) m/e 1409.5 (M+H)+.

2.104 Synthesis of 6-[8-(1,3-benzothiazol-2-ylcarbamoyl)naphthalen-2-yl]-3-{1-[(3-{2-[(2-carboxyethyl){[(2-{[(2R,3S,4R,5R,6R)-6-carboxy-3,4,5-trihydroxytetrahydro-2H-pyran-2-yl]oxy}-4-[2-(2-{[6-(2,5-dioxo-2,5-dihydro-1H-pyrrol-1-yl)hexanoyl]amino}ethoxy)ethoxy]benzyl)oxy]carbonyl}amino]ethoxy}-5,7-dimethyltricyclo[3.3.1.1$^{3,7}$]dec-1-yl)methyl]-5-methyl-1H-pyrazol-4-yl}pyridine-2-carboxylic acid (Synthon PI)

2.104.1 3-(1-((3-(2-((((4-(2-(2-aminoethoxy)ethoxy)-2-(((2R,3S,4R,5R,6R)-6-carboxy-3,4,5-trihydroxytetrahydro-2H-pyran-2-yl)oxy)benzyl)oxy)carbonyl)(2-carboxyethyl)amino)ethoxy)-5,7-dimethyladamantan-1-yl)methyl)-5-methyl-1H-pyrazol-4-yl)-6-(8-(benzo[d]thiazol-2-ylcarbamoyl)naphthalen-2-yl)picolinic acid To a cold (0° C.) mixture of Example 2.97.7 (26.9 mg) and Example 1.68.7 (23.5 mg) in N,N-dimethylformamide (2 mL) was added N-ethyl-N-isopropylpropan-2-amine (0.043 mL). The reaction was slowly warmed to room temperature and stirred overnight. LC/MS showed the expected product as the major peak. To the reaction mixture was added water (1 mL) and LiOH H$_2$O (20 mg). The mixture was stirred at room temperature for 3 hours. The mixture was diluted with N,N-dimethylformamide (2 mL), filtered and purified by reverse-phase HPLC on a Gilson system (C18 column), eluting with 20-80% acetonitrile in water containing 0.1% trifluoroacetic acid, to give the title compound. MS (ESI) m/e 1242.2 (M−H)−.

2.104.2 6-[8-(1,3-benzothiazol-2-ylcarbamoyl)naphthalen-2-yl]-3-{1-[(3-{2-[(2-carboxyethyl){[(2-{[(2R,3S,4R,5R,6R)-6-carboxy-3,4,5-trihydroxytetrahydro-2H-pyran-2-yl]oxy}-4-[2-(2-{[6-(2,5-dioxo-2,5-dihydro-1H-pyrrol-1-yl)hexanoyl]amino}ethoxy)ethoxy]benzyl)oxy]carbonyl}amino]ethoxy}-5,7-dimethyltricyclo[3.3.1.13,7]dec-1-yl)methyl]-5-methyl-1H-pyrazol-4-yl}pyridine-2-carboxylic acid The title compound was prepared as described in Example 2.97.9 by replacing Example 2.97.8 with Example 2.104.1 and replacing 2,5-dioxopyrrolidin-1-yl 3-(2,5-dioxo-2,5-dihydro-1H-pyrrol-1-yl)propanoate with 2,5-dioxopyrrolidin-1-yl 6-(2,5-dioxo-2,5-dihydro-1H-pyrrol-1-yl)hexanoate. $^1$H NMR (400 MHz, dimethyl sulfoxide-d$_6$) δ ppm 13.06 (s, 2H), 8.99 (s, 1H), 8.34 (dd, 1H), 8.25-8.10 (m, 3H), 8.04 (d, 1H), 7.98 (d, 1H), 7.90 (d, 1H), 7.78 (d, 2H), 7.72-7.63 (m, 1H), 7.50-7.42 (m, 2H), 7.34 (t, 1H), 7.16 (d, 1H), 6.94 (s, 2H), 6.65 (d, 1H), 6.56 (dd, 1H), 4.02 (t, 2H), 3.90 (d, 1H), 3.83 (s, 2H), 3.66 (t, 3H), 3.28 (q, 4H), 3.15 (q, 2H), 2.19 (s, 3H), 1.99 (t, 2H), 1.51-1.30 (m, 6H), 1.28-0.88 (m, 11H), 0.81 (d, 6H). MS (ESI) m/e 1433.4 (M+H)+.

2.105 Synthesis of N-[6-(2,5-dioxo-2,5-dihydro-1H-pyrrol-1-yl)hexanoyl]-L-valyl-N-{4-[({[2-({3-[(4-{6-[5-(1,3-benzothiazol-2-ylcarbamoyl)quinolin-3-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]phenyl}-N$^5$-carbamoyl-L-ornithinamide (Synthon PJ)

The title compound was prepared as described in Example 2.1, replacing Example 1.2.9 with Example 1.69.6. $^1$H NMR (500 MHz, dimethyl sulfoxide-d$_6$) δ ppm 13.23 (s, 1H), 9.99 (s, 1H), 9.73 (d, 1H), 9.45 (s, 1H), 8.33 (t, 2H), 8.18 (d, 1H), 8.07 (dd, 2H), 8.02 (dd, 1H), 7.97 (dd, 1H), 7.80 (t, 2H), 7.65-7.55 (m, 2H), 7.53-7.44 (m, 2H), 7.37 (t, 1H), 7.27 (d, 2H), 6.98 (s, 2H), 4.98 (d, 2H), 4.38 (d, 1H), 4.18 (d, 1H), 3.56-3.31 (m, 3H), 3.26 (d, 2H), 3.08-2.89 (m, 2H), 2.64 (t, 2H), 2.23 (d, 3H), 2.12 (dp, 2H), 1.95 (s, 1H), 1.68 (s, 1H), 1.62-1.29 (m, 7H), 1.29-0.90 (m, 9H), 0.90-0.74 (m, 12H). MS (ESI) m/e 1446.3 (M−H)−.

2.106 Synthesis of N-[6-(2,5-dioxo-2,5-dihydro-1H-pyrrol-1-yl)hexanoyl]-L-valyl-N-{4-[({[2-({3-[(4-{6-[4-(1,3-benzothiazol-2-ylcarbamoyl)quinolin-6-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-carboxyethyl)carbamoyl}oxy)methyl]phenyl}-N$^5$-carbamoyl-L-ornithinamide (Synthon PU)

The title compound was prepared as described in Example 2.1, replacing Example 1.2.9 with Example 1.70. $^1$H NMR (400 MHz, dimethyl sulfoxide-d$_6$) δ ppm 9.97 (s, 1H), 9.12 (d, 1H), 8.93 (s, 1H), 8.60 (dd, 1H), 8.24 (dd, 2H), 8.05 (dd, 2H), 7.99-7.87 (m, 2H), 7.78 (dd, 2H), 7.67-7.51 (m, 3H), 7.43-7.31 (m, 1H), 7.26 (d, 2H), 6.97 (s, 2H), 5.98 (s, 1H), 4.97 (s, 2H), 4.37 (d, 2H), 4.17 (dd, 1H), 3.49-3.22 (m, 11H), 2.95 (ddd, 3H), 2.20 (s, 4H), 2.19-1.86 (m, 3H), 1.74-0.89 (m, 22H), 0.81 (dd, 15H). MS (ESI) m/e 1410.4 (M−H)−.

2.107 Synthesis of N-[6-(2,5-dioxo-2,5-dihydro-1H-pyrrol-1-yl)hexanoyl]-L-valyl-N-{4-[({[2-({3-[(4-{6-[4-(1,3-benzothiazol-2-ylcarbamoyl)quinolin-6-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]phenyl}-N$^5$-carbamoyl-L-ornithinamide (Synthon PV)

The title compound was prepared as described in Example 2.1, replacing Example 1.2.9 with Example 1.70.5. $^1$H NMR (400 MHz, dimethyl sulfoxide-d$_6$) δ ppm 9.96 (s, 1H), 9.11 (d, 1H), 8.92 (s, 1H), 8.60 (dd, 1H), 8.23 (dd, 2H), 8.12-7.97 (m, 2H), 7.98-7.92 (m, 2H), 7.77 (dd, 2H), 7.56 (t, 2H), 7.51-7.42 (m, 2H), 7.42-7.31 (m, 1H), 7.24 (d, 2H), 6.95 (s, 2H), 4.95 (d, 2H), 4.36 (q, 1H), 3.90-3.80 (m, 3H), 3.52-3.27 (m, 3H), 3.23 (t, 2H), 3.06-2.83 (m, 2H), 2.67-2.58 (m, 2H), 2.19 (s, 3H), 2.09 (dp, 2H), 1.93 (d, 1H), 1.72-1.25 (m, 7H), 1.27-0.88 (m, 10H), 0.88-0.70 (m, 13H). MS (ESI) m/e 1446.3 (M−H)−.

2.108 Synthesis of N-[6-(2,5-dioxo-2,5-dihydro-1H-pyrrol-1-yl)hexanoyl]-L-valyl-N-{4-[({[2-({3-[(4-{6-[5-(1,3-benzothiazol-2-ylcarbamoyl)quinolin-3-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-carboxyethyl)carbamoyl}oxy)methyl]phenyl}-N$^5$-carbamoyl-L-ornithinamide (Synthon PW)

The title compound was prepared as described in Example 2.1, replacing Example 1.2.9 with Example 1.71. $^1$H NMR (400 MHz, dimethyl sulfoxide-$d_6$) δ ppm 9.97 (s, 1H), 9.70 (d, 1H), 9.40 (d, 1H), 8.31 (dd, 2H), 8.16 (d, 1H), 8.05 (t, 2H), 8.01-7.91 (m, 2H), 7.78 (dd, 2H), 7.59 (d, 3H), 7.52-7.44 (m, 2H), 7.36 (t, 1H), 7.26 (d, 2H), 6.96 (s, 2H), 5.99 (s, 1H), 4.97 (s, 2H), 4.37 (d, 2H), 4.16 (dd, 1H), 3.53-3.20 (m, 9H), 2.94 (dtd, 2H), 2.21 (s, 3H), 2.17-1.85 (m, 3H), 1.71-0.89 (m, 22H), 0.81 (dd, 14H). MS (ESI) m/e 1410.4 (M–H)⁻.

2.109 Synthesis of N-[6-(2,5-dioxo-2,5-dihydro-1H-pyrrol-1-yl)hexanoyl]-L-valyl-N-{4-[({[2-({3-[(4-{6-[1-(1,3-benzothiazol-2-ylcarbamoyl)-5,6-dihydroimidazo[1,5-a]pyrazin-7(8H)-yl]-2-carboxypyridin-3-yl}-5-methyl-1H-pyrazol-1-yl)methyl]-5,7-dimethyltricyclo[3.3.1.1³,⁷]dec-1-yl}oxy)ethyl](2-sulfoethyl)carbamoyl}oxy)methyl]phenyl}-N⁵-carbamoyl-L-ornithinamide (Synthon QW)

The title compound was prepared by substituting Example 1.72.8 for Example 1.2.9 in Example 2.1. ¹H NMR (400 MHz, dimethyl sulfoxide $d_6$) δ ppm 11.07 (bs, 1H), 10.00 (bs, 1H), 8.27 (bs, 1H), 8.12 (m, 2H), 8.07 (d, 1H), 7.99 (d, 1H), 7.84-7.74 (m, 2H), 7.65 (d, 1H), 7.59 (m, 2H), 7.54-7.44 (m, 1H), 7.42-7.31 (m, 2H), 7.28 (m, 2H), 7.21 (q, 1H), 7.00 (m, 1H) 6.94-6.92 (m, 2H), 6.04 (bs, 1H), 5.14 (s, 2H), 4.99 (m, 3H), 4.39 (m, 2H), 4.30 (bs, 2H), 4.20 (m, 2H), 4.12 (bs, 2H), 3.70-3.64 (m, 3H), 3.50 (m, 2H), 3.44-3.35 (m, 2H), 3.27 (m, 2H), 3.02 (m, 2H), 2.95 (m, 2H), 2.68 (t, 2H), 2.14 (m, 4H), 1.96 (m, 1H), 1.69 (m, 1H), 1.58 (m, 1H), 1.47 (m, 4H), 1.36 (m, 2H), 1.30-1.02 (m, 8H), 0.98 (m, 2H), 0.85-0.80 (m, 16H).

2.110 Synthesis of N-[6-(2,5-dioxo-2,5-dihydro-1H-pyrrol-1-yl)hexanoyl]-L-valyl-N-{4-[({[2-({3-[(4-{6-[7-(1,3-benzothiazol-2-ylcarbamoyl)-1H-indol-2-yl]-2-carboxypyridin-3-yl}-5-methyl-1H-pyrazol-1-yl)methyl]-5,7-dimethyltricyclo[3.3.1.1³,⁷]dec-1-yl}oxy)ethyl](2-sulfoethyl)carbamoyl}oxy)methyl]phenyl}-N⁵-carbamoyl-L-ornithinamide (Synthon RM)

Example 2.110 was prepared by substituting Example 1.74.6 for Example 1.2.9 in Example 2.1. ¹H NMR (400 MHz, dimethyl sulfoxide-$d_6$) δ ppm 11.30 (s, 1H), 9.93 (s, 1H), 8.26 (d, 1H), 8.17 (d, 1H), 8.02 (d, 1H), 7.92-7.84 (m, 3H), 7.76 (d, 1H), 7.69 (d, 1H), 7.54 (d, 3H), 7.47 (s, 1H), 7.35 (dd, 2H), 7.22 (t, 3H), 7.08 (t, 1H), 6.93 (s, 2H), 4.90 (s, 2H), 4.84 (t, 2H), 4.33 (q, 1H), 4.16-4.09 (m, 1H), 3.32 (t, 4H), 2.99 (m, 6H), 2.21 (s, 3H), 2.09 (m, 2H), 1.91 (m, 1H), 1.71-0.71 (m, 25H). MS (ESI) m/e 1434.4 (M–H)⁻.

2.111 Synthesis of N-[6-(2,5-dioxo-2,5-dihydro-1H-pyrrol-1-yl)hexanoyl]-L-valyl-N-[4-({[[{3-[8-(1,3-benzothiazol-2-ylcarbamoyl)-2-(6-carboxy-5-{1-[(3,5-dimethyl-7-{2-[(2-sulfoethyl)amino]ethoxy}tricyclo[3.3.1.1³,⁷]dec-1-yl)methyl]-5-methyl-1H-pyrazol-4-yl}pyridin-2-yl)-1,2,3,4-tetrahydroisoquinolin-6-yl]propyl}(methyl)carbamoyl]oxy}methyl)phenyl]-N⁵-carbamoyl-L-ornithinamide (Synthon RR)

The title compound was prepared as described in Example 2.1, replacing Example 1.2.9 with Example 1.75.14. ¹H NMR (400 MHz, dimethyl sulfoxide-$d_6$) δ ppm 12.60 (bs, 1H), 9.98 (s, 1H), 8.33 (m, 2H), 8.02 (d, 2H), 7.75 (d, 2H), 7.55 (d, 2H), 7.49 (m, 3H), 7.29 (m, 1H), 7.25 (s, 4H), 6.99 (d, 2H), 6.95 (d, 1H), 5.90 (m, 1H), 5.42 (m, 2H), 4.95 (s, 2H), 4.90 (m, 2H), 4.35 (t, 1H), 4.18 (t, 1H), 3.85 (m, 2H), 3.80 (s, 3H), 3.55 (s, 3H), 3.52 (m, 2H), 3.35 (m, 4H), 3.22 (m, 4H), 3.08 (m, 2H), 2.99 (m, 2H), 2.92 (m, 2H), 2.85 (m, 2H), 2.79 (t, 2H), 2.52 (m, 1H), 2.15 (m, 1H), 2.09 (s, 3H), 1.94 (m, 1H), 1.88 (m, 1H), 1.68 (m, 1H), 1.54 (m, 1H), 1.42 (m, 4H), 1.38 (m, 4H), 1.27 (m, 4H), 1.13 (m, 4H), 1.02 (m, 2H), 0.85 (s, 6H), 0.78 (m, 6H). MS (ESI) m/e 1523.3 (M+H)⁺, 1521.6 (M–H)

2.112 Synthesis of N-(6-{[(2,5-dioxo-2,5-dihydro-1H-pyrrol-1-yl)acetyl]amino}hexanoyl)-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1³,⁷]dec-1-yl}oxy)ethyl](2-sulfoethyl)carbamoyl}oxy)methyl]phenyl}-N⁵-carbamoyl-L-ornithinamide (Synthon SJ)

2.112.1 6-(8-(benzo[d]thiazol-2-ylcarbamoyl)-3,4-dihydroisoquinolin-2(1H)-yl)-3-(1-(((3-(2-(((((4-((S)-2-((S)-2-((tert-butoxycarbonyl)amino)-3-methylbutanamido)-5-ureidopentanamido)benzyl)oxy)carbonyl)(2-sulfoethyl)amino)ethoxy)-5,7-dimethyladamantan-1-yl)methyl)-5-methyl-1H-pyrazol-4-yl)picolinic acid Example 1.2.9, trifluoroacetic acid salt (390 mg), tert-butyl ((S)-3-methyl-1-(((S)-1-((4-(((((4-nitrophenoxy)carbonyl)oxy)methyl)phenyl)amino)-1-oxo-5-ureidopentan-2-yl)amino)-1-oxobutan-2-yl)carbamate (286 mg) and 1-hydroxybenzotriazole hydrate (185 mg) in N,N-dimethylformamide (5 mL) was cooled in an ice-bath and N,N-diisopropylethylamine (0.35 mL) was added. The mixture was stirred at 0° C. for 30 minutes and at room temperature overnight. The reaction mixture was diluted with dimethyl sulfoxide to 10 mL and purified by reverse-phase HPLC on a Gilson system (C18 column), eluting with 20-80% acetonitrile in water containing 0.1% trifluoroacetic acid, to give the title compound. MS (ESI) m/e 680.1 (M+2H)²⁺.

2.112.2 3-(1-((3-(2-(((((4-((S)-2-((S)-2-amino-3-methylbutanamido)-5-ureidopentanamido)benzyl)oxy)carbonyl)(2-sulfoethyl)amino)ethoxy)-5,7-dimethyladamantan-1-yl)methyl)-5-methyl-1H-pyrazol-4-yl)-6-(8-(benzo[d]thiazol-2-ylcarbamoyl)-3,4-dihydroisoquinolin-2(1H)-yl)picolinic acid Example 2.112.1 (300 mg) in 10 mL of dichloromethane at 0° C. was treated with trifluoroacetic acid (4 mL) for 30 minutes and the mixture was concentrated. The residue was dissolved in a mixture of acetonitrile and water and lyophilized to provide the desired product as a TFA salt. MS (ESI) m/e 1257.4 (M–H)⁻.

2.112.3 6-(8-(benzo[d]thiazol-2-ylcarbamoyl)-3,4-dihydroisoquinolin-2(1H)-yl)-3-(1-(((3-(2-(((((4-(((13S,16S)-13-isopropyl-2,2-dimethyl-4,11,14-trioxo-16-(3-ureidopropyl)-3-oxa-5,12,15-triazaheptadecanamido)benzyl)oxy)carbonyl)(2-sulfoethyl)amino)ethoxy)-5,7-dimethyladamantan-1-yl)methyl)-5-methyl-1H-pyrazol-4-yl)picolinic acid Example 2.112.2 (trifluoroacetic acid salt, 385 mg) and 1-hydroxybenzotriazole hydrate (140 mg) in N,N-dimethylformamide (3 mL) was cooled in an ice-water bath. N,N-

Diisopropylethylamine (226 µL) was added dropwise, followed by the addition of 2,5-dioxopyrrolidin-1-yl 6-((tert-butoxycarbonyl)amino)hexanoate (127 mg), and the mixture was stirred overnight. The mixture was purified by reverse-phase HPLC on a Gilson system (C18 column), eluting with 20-75% acetonitrile in water containing 0.1% trifluoroacetic acid, to give the title compound. MS (ESI) m/e 1470.2 (M−H)⁻.

2.112.4 3-(1-((3-(2-(((((4-((S)-2-((S)-2-(6-amino-hexanamido)-3-methylbutanamido)-5-ureidopentanamido)benzyl)oxy)carbonyl)(2-sulfoethyl)amino)ethoxy)-5,7-dimethyladamantan-1-yl)methyl)-5-methyl-1H-pyrazol-4-yl)-6-(8-(benzo[d]thiazol-2-ylcarbamoyl)-3,4-dihydroisoquinolin-2(1H)-yl)picolinic acid The title compound was prepared using the procedure in Example 2.112.2, replacing Example 2.112.1 with Example 2.112.3. MS (ESI) m/e 1370.5 (M−H)⁻.

2.112.5 N-(6-{[(2,5-dioxo-2,5-dihydro-1H-pyrrol-1-yl)acetyl]amino}hexanoyl)-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1 3,7]dec-1-yl}oxy)ethyl](2-sulfoethyl)carbamoyl}oxy)methyl]phenyl}-N5-carbamoyl-L-ornithinamide Example 2.112.4 (25 mg) and 2,5-dioxopyrrolidin-1-yl 2-(2,5-dioxo-2,5-dihydro-1H-pyrrol-1-yl)acetate (9.19 mg) in N,N-dimethylformamide (0.3 mL) was treated with N,N-diisopropylethylamine (25.4 µL) for 30 minutes at 0° C. The reaction mixture was purified by reverse-phase HPLC on a Gilson system (C18 column), eluting with 35-65% acetonitrile in 4 mM ammonium acetate water mixture, to provide the title compound as an ammonium salt. ¹H NMR (400 MHz, dimethyl sulfoxide-d₆) δ 12.81 (s, 1H), 9.94 (s, 1H), 8.01 (dd, 2H), 7.75 (d, 2H), 7.56 (s, 3H), 7.51-7.45 (m, 1H), 7.45-7.37 (m, 2H), 7.36-7.28 (m, 2H), 7.24 (t, 3H), 7.17 (s, 2H), 7.05 (s, 3H), 7.04 (s, 2H), 6.92 (s, 3H), 5.93 (s, 1H), 5.36 (s, 2H), 5.05-4.85 (m, 4H), 4.36 (q, 1H), 4.16 (dd, 1H), 3.95 (s, 2H), 3.85 (t, 2H), 3.76 (d, 2H), 3.22 (d, 1H), 3.05-2.81 (m, 6H), 2.68-2.53 (m, 2H), 2.09 (d, 4H), 1.76-0.86 (m, 14H), 0.86-0.71 (m, 12H). MS (ESI) m/e 1507.5 (M−H)⁻.

2.113 Synthesis of N-[6-(2,5-dioxo-2,5-dihydro-1H-pyrrol-1-yl)hexanoyl]-L-valyl-N-{4-[({[2-({3-[(4-{6-[8-(1,3-benzothiazol-2-ylcarbamoyl)naphthalen-2-yl]-2-carboxypyridin-3-yl}-5-methyl-1H-pyrazol-1-yl)methyl]-5,7-dimethyltricyclo[3.3.1.1 3,7]dec-1-yl}oxy)ethyl][3-(beta-L-glucopyranuronosyloxy)propyl]carbamoyl}oxy)methyl]phenyl}-N⁵-carbamoyl-L-ornithinamide (Synthon SM)

The title compound was prepared as described in Example 2.1, replacing Example 1.2.9 with Example 1.87.3. ¹H NMR (501 MHz, dimethyl sulfoxide-d₆) δ ppm 13.08 (s, 1H), 9.96 (s, 1H), 9.00 (s, 1H), 8.35 (dd, 1H), 8.24-8.13 (m, 3H), 8.09-8.02 (m, 2H), 8.00 (d, 1H), 7.91 (d, 1H), 7.77 (dd, 2H), 7.71-7.64 (m, 1H), 7.58 (t, 2H), 7.49-7.44 (m, 2H), 7.39-7.32 (m, 1H), 7.26 (d, 2H), 6.96 (s, 2H), 5.97 (s, 1H), 4.96 (s, 2H), 4.37 (d, 1H), 4.22-4.12 (m, 2H), 3.84 (s, 1H), 3.37-3.20 (m, 6H), 3.15 (t, 1H), 3.04-2.81 (m, 2H), 2.20 (s, 3H), 2.11 (dp, 2H), 1.99-1.88 (m, 1H), 1.71 (q, 2H), 1.62-1.26 (m, 8H), 1.29-0.88 (m, 11H), 0.80 (dd, 14H). MS (ESI) m/e 1571.4 (M−H)⁻.

2.114 Synthesis of N-[6-(2,5-dioxo-2,5-dihydro-1H-pyrrol-1-yl)hexanoyl]-L-valyl-N-{4-[({[2-({3-[(4-{6-[4-(1,3-benzothiazol-2-ylcarbamoyl)isoquinolin-6-yl]-2-carboxypyridin-3-yl}-5-methyl-1H-pyrazol-1-yl)methyl]-5,7-dimethyltricyclo[3.3.1.1 3,7]dec-1-yl}oxy)ethyl](2-sulfoethyl)carbamoyl}oxy)methyl]phenyl}-N⁵-carbamoyl-L-ornithinamide (Synthon SN)

The title compound was prepared as described in Example 2.1, replacing Example 1.2.9 with Example 1.78.5. ¹H NMR (400 MHz, dimethyl sulfoxide-d₆) δ ppm 9.95 (s, 1H), 9.61 (s, 1H), 9.08 (s, 1H), 9.00 (s, 1H), 8.54 (dd, 1H), 8.43 (d, 1H), 8.24 (d, 1H), 8.08-7.95 (m, 3H), 7.77 (dd, 2H), 7.63-7.51 (m, 2H), 7.50-7.42 (m, 2H), 7.40-7.31 (m, 1H), 7.24 (d, 2H), 6.95 (s, 2H), 6.00 (s, 1H), 4.95 (d, 2H), 4.36 (q, 1H), 4.15 (t, 1H), 3.27 (dt, 4H), 3.10-2.79 (m, 2H), 2.68-2.56 (m, 2H), 2.20 (s, 3H), 1.98-1.84 (m, 1H), 1.72-0.87 (m, 19H), 0.79 (dd, 13H). MS (ESI) m/e 1446.4 (M−H)

2.115 Synthesis of N-[6-(2,5-dioxo-2,5-dihydro-1H-pyrrol-1-yl)hexanoyl]-L-alpha-glutamyl-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1 3,7]dec-1-yl}oxy)ethyl](2-sulfoethyl)carbamoyl}oxy)methyl]phenyl}-N⁵-carbamoyl-L-ornithinamide (Synthon SS)

2.115.1 6-(8-(benzo[d]thiazol-2-ylcarbamoyl)-3,4-dihydroisoquinolin-2(1H)-yl)-3-(1-((3-(2-(((((4-((6S,9S,12S)-6-(3-(tert-butoxy)-3-oxopropyl)-9-isopropyl-2,2-dimethyl-4,7,10-trioxo-12-(3-ureidopropyl)-3-oxa-5,8,11-triazatridecanamido)benzyl)oxy)carbonyl)(2-sulfoethyl)amino)ethoxy)-5,7-dimethyladamantan-1-yl)methyl)-5-methyl-1H-pyrazol-4-yl)picolinic acid To a mixture of Example 2.112.2 (85 mg), 1-hydroxybenzotriazole hydrate (41.3 mg), and (S)-5-tert-butyl 1-(2,5-dioxopyrrolidin-1-yl) 2-((tert-butoxycarbonyl)amino)pentanedioate (54.0 mg) in N,N-dimethylformamide (3 mL) at 0° C. was added N,N-diisopropylethylamine (118 µL) dropwise, and the mixture was stirred at 0° C. for 1 hour. The mixture was purified by reverse-phase HPLC on a Gilson system (C18 column), eluting with 35-100% acetonitrile in water containing 0.1% trifluoroacetic acid, to give the title compound. MS (ESI) m/e 773.4 (M+2H)²⁺.

2.115.2 3-(1-((3-(2-(((((4-((S)-2-((S)-2-(S)-2-amino-4-carboxybutanamido)-3-methylbutanamido)-5-ureidopentanamido)benzyl)oxy)carbonyl)(2-sulfoethyl)amino)ethoxy)-5,7-dimethyladamantan-1-yl)methyl)-5-methyl-1H-pyrazol-4-yl)-6-(8-(benzo[d]thiazol-2-ylcarbamoyl)-3,4-dihydroisoquinolin-2(1H)-yl)picolinic acid Example 2.115.1 (100 mg) in dichloromethane (11 mL) at 0° C. was treated with trifluoroacetic acid (4 mL). The mixture was stirred at 0° C. for 3.5 hours and concentrated. The residue was purified by reverse phase HPLC, eluting with 5-60% acetonitrile in 0.1% trifluoroacetic acid water mixture to provide the title compound.

2.115.3 N-[6-(2,5-dioxo-2,5-dihydro-1H-pyrrol-1-yl)hexanoyl]-L-alpha-glutamyl-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]phenyl}-N5-carbamoyl-L-ornithinamide To a mixture of 1-hydroxybenzotriazole hydrate (2.87 mg), 2,5-dioxopyrrolidin-1-yl 6-(2,5-dioxo-2,5-dihydro-1H-pyrrol-1-yl)hexanoate (5.77 mg) and Example 2.115.2 (13 mg) at 0° C. was added N,N-diisopropylethylamine (13.08 μL), and the mixture was stirred at 0° C. for 1 hour. The reaction was purified by reverse-phase HPLC on a Gilson system (C18 column), eluting with 20-75% acetonitrile in water containing 0.1% trifluoroacetic acid, to give the title compound. $^1$H NMR (501 MHz, dimethyl sulfoxide-$d_6$) δ 12.83 (s, 1H), 9.99 (s, 1H), 8.13 (d, 1H), 8.02 (dd, 1H), 7.97 (d, 1H), 7.80-7.74 (m, 1H), 7.64 (t, 1H), 7.61-7.48 (m, 4H), 7.47-7.38 (m, 2H), 7.38-7.30 (m, 2H), 7.29-7.23 (m, 3H), 6.96 (s, 2H), 6.93 (d, 1H), 5.99 (s, 1H), 5.06-4.88 (m, 5H), 4.37 (q, 1H), 4.28 (q, 1H), 4.18 (dd, 1H), 3.86 (t, 2H), 3.78 (d, 2H), 3.34 (t, 3H), 3.23 (d, 2H), 2.99 (t, 3H), 2.97-2.85 (m, 1H), 2.62 (dt, 1H), 2.26-2.15 (m, 2H), 2.16-2.00 (m, 5H), 2.01-1.79 (m, 1H), 1.75-1.50 (m, 3H), 1.50-0.87 (m, 17H), 0.81 (dd, 14H). MS (ESI) m/e 1579.6 (M–H)⁻.

2.116 Synthesis of N-[(2,5-dioxo-2,5-dihydro-1H-pyrrol-1-yl)acetyl]-L-alpha-glutamyl-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]phenyl}-N⁵-carbamoyl-L-ornithinamide (Synthon TA)

The title compound was prepared using the procedure in Example 2.115.3, replacing 2,5-dioxopyrrolidin-1-yl 6-(2,5-dioxo-2,5-dihydro-1H-pyrrol-1-yl)hexanoate with 2,5-dioxopyrrolidin-1-yl 2-(2,5-dioxo-2,5-dihydro-1H-pyrrol-1-yl)acetate. $^1$H NMR (400 MHz, dimethyl sulfoxide-$d_6$) δ 10.02 (s, 1H), 8.38 (d, 1H), 8.14 (d, 1H), 8.03 (d, 1H), 7.82 (dd, 2H), 7.60 (t, 3H), 7.55-7.40 (m, 3H), 7.35 (td, 2H), 7.31-7.24 (m, 3H), 7.07 (s, 2H), 6.95 (d, 1H), 4.97 (d, 4H), 4.37 (ddd, 2H), 4.23-4.05 (m, 3H), 3.88 (t, 6H), 3.80 (d, 2H), 3.25 (d, 2H), 3.09-2.88 (m, 4H), 2.64 (s, 2H), 2.22 (dd, 2H), 2.09 (s, 3H), 2.02-1.49 (m, 5H), 1.47-0.89 (m, 12H), 0.83 (dd, 12H). MS (ESI) m/e 1523.5 (M–H)⁻.

2.117 Synthesis of 1-{[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl]({[4-({N-[6-(2,5-dioxo-2,5-dihydro-1H-pyrrol-1-yl)hexanoyl]-D-valyl-N⁵-carbamoyl-D-ornithyl}amino)benzyl]oxy}carbonyl)amino}-1,2-dideoxy-D-arabino-hexitol (Synthon TW)

The title compound was prepared by substituting Example 1.77.2 for Example 1.2.9 in Example 2.1. $^1$H NMR (400 MHz, dimethyl sulfoxide-$d_6$) δ ppm 12.85 (bs, 1H), 9.98 (s, 1H), 8.06 (d, 1H), 8.03 (d, 1H), 7.78 (t, 2H), 7.60 (m, 3H), 7.52-7.42 (m, 4H), 7.36 (q, 2H), 7.28 (s, 1H), 7.27 (d, 2H), 6.99 (s, 1H), 6.95 (d, 1H), 5.97 (bs, 1H), 5.00 (m, 2H), 4.95 (s, 2H), 4.39 (m, 1H), 4.19 (m, 2H), 3.88 (t, 2H), 3.79 (m, 4H), 3.58 (m, 4H), 3.46-3.33 (m, 10H), 3.26 (m, 4H), 3.01 (m, 2H), 2.94 (m, 1H), 2.14 (m, 2H), 2.09 (s, 3H), 1.96 (m, 1H), 1.69 (m, 2H), 1.59 (m, 1H), 1.47 (m, 4H), 1.35 (m, 4H), 1.28-1.03 (m, 10H), 0.95 (m, 2H), 0.82 (m, 12H). MS (ESI) m/e 1493 (M+H)⁺, 1491 (M–H)⁻.

2.118 Synthesis of N-[6-(2,5-dioxo-2,5-dihydro-1H-pyrrol-1-yl)hexanoyl]-L-valyl-N-{4-[({[2-({3-[(4-{6-[4-(1,3-benzothiazol-2-ylcarbamoyl)-2-oxoisoquinolin-6-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](methyl)carbamoyl}oxy)methyl]phenyl}-N⁵-carbamoyl-L-ornithinamide (Synthon ST)

The title compound was prepared as described in Example 2.1, replacing Example 1.2.9 with Example 1.88.4. $^1$H NMR (400 MHz, dimethyl sulfoxide-$d_6$) δ ppm 13.29 (s, 2H), 9.95 (s, 1H), 9.18 (s, 1H), 8.67 (s, 1H), 8.57-8.36 (m, 1H), 8.29-7.87 (m, 4H), 7.77 (dd, 2H), 7.56 (d, 2H), 7.53-7.41 (m, 2H), 7.24 (d, 2H), 6.95 (s, 2H), 5.95 (s, 1H), 4.94 (s, 2H), 4.35 (q, 1H), 4.15 (dd, 1H), 3.84 (s, 3H), 3.28 (dt, 4H), 3.06-2.77 (m, 3H), 2.19 (d, 3H), 2.17-1.80 (m, 3H), 1.74-0.88 (m, 22H), 0.79 (dd, 13H). MS (ESI) m/e 1368.4 (M–H)⁻.

2.119 Synthesis of N-({(3S,5S)-3-(2,5-dioxo-2,5-dihydro-1H-pyrrol-1-yl)-2-oxo-5-[(2-sulfoethoxy)methyl]pyrrolidin-1-yl}acetyl)-L-valyl-N-{4-[({[2-({3-[(4-{6-[8-(1,3-benzothiazol-2-ylcarbamoyl)naphthalen-2-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]phenyl}-N⁵-carbamoyl-L-ornithinamide (Synthon ZL)

2.119.1 (3R,7aS)-3-phenyltetrahydropyrrolo[1,2-c]oxazol-5(3H)-one

A mixture of (S)-5-(hydroxymethyl)pyrrolidin-2-one (25 g), benzaldehyde (25.5 g) and para-toluenesulfonic acid monohydrate (0.50 g) in toluene (300 mL) was heated to reflux using a Dean-Stark trap under a drying tube for 16 hours. The reaction was cooled to room temperature, and the solvent was decanted from the insoluble materials. The organic layer was washed with saturated aqueous sodium bicarbonate mixture (2×) and brine (1x). The organic layer was dried over sodium sulfate, filtered and concentrated under reduced pressure. The residue was purified by flash chromatography on silica gel, eluting with 35/65 heptane/ethyl acetate, to give the title compound. MS (DCI) m/e 204.0 (M+H)⁺.

2.119.2 (3R,6R,7aS)-6-bromo-3-phenyltetrahydropyrrolo[1,2-c]oxazol-5(3H)-one To a cold (–77° C.) mixture of Example 2.119.1 (44.6 g) in tetrahydrofuran (670 mL) was added lithium bis(trimethylsilyl)amide (1.0M in hexanes, 250 mL) dropwise over 40 minutes, keeping $T_{rxn}$<–73° C. The reaction was stirred at –77° C. for 2 hours, and bromine (12.5 mL) was added dropwise over 20 minutes, keeping $T_{rxn}$<–64° C. The reaction was stirred at –77° C. for 75 minutes and was quenched by the addition of 150 mL cold 10% aqueous sodium thiosulfate mixture to the −77° C. reaction. The reaction was warmed to room temperature and partitioned between half-saturated aqueous ammonium chloride mixture and ethyl acetate. The layers were separated, and the organic layer was washed with water and brine, dried over sodium sulfate, filtered and concentrated under reduced pressure. The residue was purified by silica gel chromatography, eluting with a gradient of 80/20, 75/25, and 70/30 heptane/ethyl acetate to give the title compound. MS (DCI) m/e 299.0 and 301.0 $(M+NH_3+H)^+$.

2.119.3 (3R,6S,7aS)-6-bromo-3-phenyltetrahydropyrrolo[1,2-c]oxazol-5(3H)-one

The title compound was isolated as a by-product from Example 2.119.2. MS (DCI) m/e 299.0 and 301.0 $(M+NH_3+H)^+$.

2.119.4 (3R,6S,7aS)-6-azido-3-phenyltetrahydropyrrolo[1,2-c]oxazol-5(3H)-one

To a mixture of Example 2.119.2 (19.3 g) in N,N-dimethylformamide (100 mL) was added sodium azide (13.5 g). The reaction was heated to 60° C. for 2.5 hours. The reaction was cooled to room temperature and quenched by the addition of water (500 mL) and ethyl acetate (200 mL). The layers were separated, and the organic layer was washed brine. The combined aqueous layers were back-extracted with ethyl acetate (50 mL). The combined organic layers were dried with sodium sulfate, filtered and concentrated under reduced pressure. The residue was purified by silica gel chromatography, eluting with 78/22 heptane/ethyl acetate, to give the title compound. MS (DCI) m/e 262.0 $(M+NH_3+H)^+$.

2.119.5 (3R,6S,7aS)-6-amino-3-phenyltetrahydropyrrolo[1,2-c]oxazol-5(3H)-one

To a mixture of Example 2.119.4 (13.5 g) in tetrahydrofuran (500 mL) and water (50 mL) was added polymer-supported triphenylphosphine (55 g). The reaction was mechanically stirred overnight at room temperature. The reaction was filtered through diatomaceous earth, eluting with ethyl acetate and toluene. The mixture was concentrated under reduced pressure, dissolved in dichloromethane (100 mL), dried with sodium sulfate, then filtered and concentrated to give the title compound, which was used in the subsequent step without further purification. MS (DCI) m/e 219.0 $(M+H)^+$.

2.119.6 (3R,6S,7aS)-6-(dibenzylamino)-3-phenyltetrahydropyrrolo[1,2-c]oxazol-5(3H)-one To a mixture of Example 2.119.5 (11.3 g) in N,N-dimethylformamide (100 mL) was added potassium carbonate (7.0 g), potassium iodide (4.2 g), and benzyl bromide (14.5 mL). The reaction was stirred at room temperature overnight and quenched by the addition of water and ethyl acetate. The layers were separated, and the organic layer was washed brine. The combined aqueous layers were back-extracted with ethyl acetate. The combined organic layers were dried with sodium sulfate, filtered and concentrated under reduced pressure. The residue was purified by silica gel chromatography, eluting with a gradient of 10 to 15% ethyl acetate in heptane to give a solid that was triturated with heptane to give the title compound. MS (DCI) m/e 399.1 $(M+H)^+$.

2.119.7 (3S,5S)-3-(dibenzylamino)-5-(hydroxymethyl)pyrrolidin-2-one

To a mixture of Example 2.119.6 (13 g) in tetrahydrofuran (130 mL) was added para-toluene sulfonic acid monohydrate (12.4 g) and water (50 mL), and the reaction was heated to 65° C. for 6 days. The reaction was cooled to room temperature and quenched by the addition of saturated aqueous sodium bicarbonate and ethyl acetate. The layers were separated, and the organic layer was washed with brine. The combined aqueous layers were back-extracted with ethyl acetate. The combined organic layers were dried with sodium sulfate, filtered and concentrated under reduced pressure. The waxy solids were triturated with heptane (150 mL) to give the title compound. MS (DCI) m/e 311.1 $(M+H)^+$.

2.119.8 (3S,5S)-5-(((tert-butyldimethylsilyl)oxy)methyl)-3-(dibenzylamino)pyrrolidin-2-one To a mixture of Example 2.119.7 (9.3 g) and 1H-imidazole (2.2 g) in N,N-dimethylformamide was added tert-butylchlorodimethylsilane (11.2 mL, 50 weight % in toluene), and the reaction mixture was stirred overnight. The reaction mixture was quenched by the addition of water and ethyl ether. The layers were separated, and the organic layer was washed with brine. The combined aqueous layers were back-extracted with diethyl ether. The combined organic layers were dried with sodium sulfate, filtered and concentrated under reduced pressure. The residue was purified by silica gel chromatography, eluting with 35% ethyl acetate in heptane, to give the title compound. MS (DCI) m/e 425.1 $(M+H)^+$.

2.119.9 tert-butyl 2-((3S,5S)-5-(((tert-butyldimethylsilyl)oxy)methyl)-3-(dibenzylamino)-2-oxopyrrolidin-1-yl)acetate To a cold (0° C.) mixture of Example 2.119.8 (4.5 g) in tetrahydrofuran (45 mL) was added 95% sodium hydride (320 mg) in two portions. The cold mixture was stirred for 40 minutes, and tert-butyl 2-bromoacetate (3.2 mL) was added. The reaction was warmed to room temperature and stirred overnight. The reaction was quenched by the addition of water and ethyl acetate. The layers were separated, and the organic layer was washed with brine. The combined aqueous layers were back-extracted with ethyl acetate. The combined organic layers were dried with sodium sulfate, filtered and concentrated under reduced pressure. The residue was purified by silica gel chromatography, eluting with a gradient of 5-12% ethyl acetate in heptane, to give the title compound. MS (DCI) m/e 539.2 $(M+H)^+$.

2.119.10 tert-butyl 2-((3S,5S)-3-(dibenzylamino)-5-(hydroxymethyl)-2-oxopyrrolidin-1-yl)acetate To a mixture of Example 2.119.9 (5.3 g) in tetrahydrofuran (25 mL) was added tetrabutylammonium fluoride (11 mL, 1.0M in 95/5 tetrahydrofuran/water). The reaction was stirred at room temperature for one hour and then quenched by the addition of saturated aqueous ammonium chloride mixture, water and ethyl acetate. The layers were separated, and the organic layer was washed with brine. The combined aqueous layers were back-extracted with ethyl acetate. The combined organic layers were dried with sodium sulfate, filtered and concentrated under reduced pressure. The residue was purified by silica gel chromatography, eluting with 35% ethyl acetate in heptane, to give the title compound. MS (DCI) m/e 425.1 (M+H)$^+$.

2.119.11 tert-butyl 2-((3S,5S)-5-((2-((4-((tert-butyldimethylsilyl)oxy)-2,2-dimethylbutoxy)sulfonyl) ethoxy)methyl)-3-(dibenzylamino)-2-oxopyrrolidin-1-yl)acetate To a mixture of Example 2.119.10 (4.7 g) in dimethyl sulfoxide (14 mL) was added a mixture of 4-((tert-butyldiphenylsilyl)oxy)-2,2-dimethylbutyl ethenesulfonate (14.5 g) in dimethyl sulfoxide (14 mL). Potassium carbonate (2.6 g) and water (28 µL) were added, and the reaction was heated at 60° C. under nitrogen for one day. The reaction was cooled to room temperature, and then quenched by the addition of brine mixture, water and diethyl ether. The layers were separated, and the organic layer was washed with brine. The combined aqueous layers were back-extracted with diethyl ether. The combined organic layers were dried with sodium sulfate, filtered and concentrated under reduced pressure. The residue was purified by silica gel chromatography, eluting with a gradient of 15-25% ethyl acetate in heptane, to give the title compound. MS (ESI+) m/e 871.2 (M+H)$^+$.

2.119.12 tert-butyl 2-((3S,5S)-3-amino-5-((2-((4-((tert-butyldimethylsilyl)oxy)-2,2-dimethylbutoxy) sulfonyl)ethoxy)methyl)-2-oxopyrrolidin-1-yl)acetate Example 2.119.11 (873 mg) was dissolved in ethyl acetate (5 mL) and methanol (15 mL), and palladium hydroxide on carbon, 20% by wt (180 mg) was added. The reaction mixture was stirred under a hydrogen atmosphere (30 psi) at room temperature for 30 hours, then at 50° C. for one hour. The reaction was cooled to room temperature, filtered, and concentrated to give the desired product. MS (ESI+) m/e 691.0 (M+H)$^+$.

2.119.13 4-(((3S,5S)-1-(2-(tert-butoxy)-2-oxoethyl)-5-((2-((4-((tert-butyldimethylsilyl)oxy)-2,2-dimethylbutoxy)sulfonyl)ethoxy)methyl)-2-oxopyrrolidin-3-yl)amino)-4-oxobut-2-enoic acid Maleic anhydride (100 mg) was dissolved in dichloromethane (0.90 mL), and a mixture of Example 2.119.12 (650 mg) in dichloromethane (0.90 mL) was added dropwise, then heated at 40° C. for 2 hours. The reaction mixture was directly purified by silica gel chromatography, eluting with a gradient of 1.0-2.5% methanol in dichloromethane containing 0.2% acetic acid. After concentrating the product-bearing fractions, toluene (10 mL) was added, and the mixture was concentrated again to give the title compound. MS (ESI−) m/e 787.3 (M−H)$^-$.

2.119.14 tert-butyl 2-((3S,5S)-5-((2-((4-((tert-butyldimethylsilyl)oxy)-2,2-dimethylbutoxy)sulfonyl) ethoxy)methyl)-3-(2,5-dioxo-2,5-dihydro-1H-pyrrol-1-yl)-2-oxopyrrolidin-1-yl)acetate Example 2.119.13 (560 mg) was slurried in toluene (7 mL), and triethylamine (220 µL) and sodium sulfate (525 mg) were added. The reaction was heated at reflux under a nitrogen atmosphere for 6 hours, and the reaction mixture was stirred at room temperature overnight. The reaction was filtered, and the solids were rinsed with ethyl acetate. The eluent was concentrated under reduced pressure, and the residue was purified by silica gel chromatography, eluting with 45/55 heptane/ethyl acetate to give the title compound.

2.119.15 2-((3S,5S)-3-(2,5-dioxo-2,5-dihydro-1H-pyrrol-1-yl)-2-oxo-5-((2-sulfoethoxy)methyl)pyrrolidin-1-yl)acetic acid Example 2.119.14 (1.2 g) was dissolved in trifluoroacetic acid (15 mL) and heated to 65-70° C. under nitrogen overnight. The trifluoroacetic acid was removed under reduced pressure. The residue was dissolved in acetonitrile (2.5 mL) and purified by preparative reverse-phase liquid chromatography on a Luna C18(2) AXIA column (250×50 mm, 10 µm particle size) using a gradient of 5-75% acetonitrile containing 0.1% trifluoroacetic acid in water over 30 minutes, to give the title compound. MS (ESI−) m/e 375.2 (M−H)$^-$.

2.119.16 3-(1-((3-(2-((((4-((S)-2-((S)-2-amino-3-methylbutanamido)-5-ureidopentanamido)benzyl) oxy)carbonyl)(2-sulfoethyl)amino)ethoxy)-5,7-dimethyladamantan-1-yl)methyl)-5-methyl-1H-pyrazol-4-yl)-6-(8-(benzo[d]thiazol-2-ylcarbamoyl) naphthalen-2-yl)picolinic acid The title compound was prepared by substituting Example 1.43.7 for Example 1.2.9 in Example 2.49.1. MS (ESI−) m/e 1252.4 (M−H)$^-$.

2.119.17 N-({(3S,5S)-3-(2,5-dioxo-2,5-dihydro-1H-pyrrol-1-yl)-2-oxo-5-[(2-sulfoethoxy)methyl]pyrrolidin-1-yl}acetyl)-L-valyl-N-{4-[({[2-({3-[(4-{6-[8-(1,3-benzothiazol-2-ylcarbamoyl)naphthalen-2-yl]-2-carboxypyridin-3-yl}-5-methyl-1H-pyrazol-1-yl) methyl]-5,7-dimethyltricyclo[3.3.1.13,7]dec-1-yl}oxy)ethyl](2-sulfoethyl)carbamoyl}oxy)methyl] phenyl}-N5-carbamoyl-L-ornithinamide Example 2.119.15 (7 mg) was dissolved in N,N-dimethylformamide (0.15 mL), and O-(7-azabenzotriazol-1-yl)-N,N,N',N'-tetramethyluronium hexafluorophosphate (9 mg) and N,N-diisopropylethylamine (7 µL) were added. The mixture was stirred for 3 minutes at room temperature and added to a mixture of Example 2.119.16 (28 mg) and N,N-diisopropylethylamine (15 µL) in N,N-dimethylformamide (0.15 mL). After 1 hour, the reaction was diluted with N,N-dimethylformamide/water 1/1 (1.0 mL) and purified by reverse-phase chromatography (C18 column), eluting with 5-75% acetonitrile in 0.1% TFA water, to provide the title compound. $^1$H NMR (500 MHz, dimethyl sulfoxide-d$_6$) δ ppm 9.95 (s, 1H), 9.02 (s, 1H), 8.37 (d, 1H), 8.22 (m, 2H), 8.18 (m, 2H), 8.08 (m, 2H), 8.03 (m, 1H), 7.96 (br d, 1H), 7.81 (d, 1H), 7.70 (t, 1H), 7.61 (br m, 3H), 7.48 (m, 2H), 7.37 (t, 1H), 7.27 (br m, 2H), 7.08 (s, 2H), 4.99 (br d, 3H), 4.68 (t, 1H), 4.39 (m, 1H), 4.20 (m, 2H), 4.04 (m, 1H), 3.87 (br d, 2H), 3.74 (br m, 1H) 3.65 (br t, 2H), 3.48 (br m, 4H), 3.43 (br m, 2H), 3.26 (br m, 2H), 3.00 (br m, 2H), 2.80 (m, 1H), 2.76 (m, 1H), 2.66 (br m, 2H), 2.36 (br m, 1H), 2.22 (s, 3H), 2.00 (m, 1H), 1.87 (m, 1H), 1.69 (br m, 1H), 1.62 (br m, 1H), 1.40 (br m, 4H), 1.31-1.02 (m, 10H), 0.96 (m, 2H), 0.85 (m, 12H). MS (ESI−) m/e 1610.3 (M−H)$^-$.

2.120 Synthesis of N-{(2S)-2-(2,5-dioxo-2,5-dihydro-1H-pyrrol-1-yl)-3-[4-(2,5,8,11,14,17,20,23,26,29,32-undecaoxatetratriacontan-34-yloxy)phenyl]propanoyl}-L-valyl-N-{4-[({[2-({3-[(4-{6-[8-(1,3-benzothiazol-2-ylcarbamoyl)naphthalen-2-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]phenyl}-N-carbamoyl-L-ornithinamide (Synthon SX)

2.120.1 (S)-methyl 3-(4-(2,5,8,11,14,17,20,23,26,29,32-undecaoxatetratriacontan-34-yloxy)phenyl)-2-((tert-butoxycarbonyl)amino)propanoate To a mixture of 2,5,8,11,14,17,20,23,26,29,32-undecaoxatetratriacontan-34-yl 4-methylbenzenesulfonate (82.48 g) and potassium carbonate (84.97 g) in acetonitrile (1.5 L) was added (S)-methyl 2-((tert-butoxycarbonyl)amino)-3-(4-hydroxyphenyl)propanoate (72.63 g), and the reaction mixture was stirred at 30° C. for 12 hours. After LC/MS indicated the starting material was consumed and the major product was the desired product, the reaction was filtered, and the filtrate was concentrated to afford the crude product which was purified by prep-HPLC to provide the title compound. MS (ESI): m/e 811 (M+H$_2$O)$^+$.

2.120.2 3-(4-(2,5,8,11,14,17,20,23,26,29,32-undecaoxatetratriacontan-34-yloxy)phenyl)-2-((tert-butoxycarbonyl)amino)propanoic acid To a mixture of Example 2.120.1 (90.00 g) in tetrahydrofuran (1.5 L) and water (500 mL) was added lithium hydroxide monohydrate (14.27 g). The reaction mixture was stirred at 30° C. for 12 hours, and LC/MS indicated the starting material was consumed and the major product was the desired product. The reaction mixture was adjusted using aqueous HCl to pH=6, and the mixture was concentrated to provide the crude title compound. MS (ESI): m/e 778.3 (M−H)$^−$.

2.120.3 3-(4-(2,5,8,11,14,17,20,23,26,29,32-undecaoxatetratriacontan-34-yloxy)phenyl)-2-aminopropanoic acid To a mixture of Example 2.120.2 (88.41 g) in dichloromethane (1.5 L) was added trifluoroacetic acid (100 mL) at 25° C. under N$_2$, and the reaction mixture was stirred at 40° C. for 12 hours. LC/MS indicated the starting material was consumed, and the major product was the desired product. The mixture was concentrated to afford the crude product which was purified by prep-HPLC provide the title compound as a trifluoroacetic acid salt. $^1$H NMR (400 MHz, CDCl$_3$) δ ppm 7.20 (d, J=8.6 Hz, 2H), 6.93 (d, J=8.2 Hz, 2H), 4.22 (dd, J=5.5, 7.4 Hz, 1H), 4.14-4.06 (m, 2H), 3.84-3.79 (m, 2H), 3.68-3.50 (m, 40H), 3.33 (s, 3H), 3.21 (d, J=5.5 Hz, 1H), 3.12-3.05 (m, 1H). MS (ESI) m/e 680.1 (M+H)$^+$.

2.120.4 4-((2-(4-(2,5,8,11,14,17,20,23,26,29,32-undecaoxatetratriacontan-34-yloxy)phenyl)-1-carboxyethyl)amino)-4-oxobut-2-enoic acid To a mixture of Example 2.120.3 (80.00 g) in dioxane (1 L) was added furan-2,5-dione (35 g), and the reaction mixture was stirred at 120° C. for 4 hours. LC/MS indicated the starting material was consumed, and the major product was the desired product. The mixture was concentrated to afford crude title compound which was used without purification in the next step. MS (ESI) m/e 795.4 (M+H)$^+$.

2.120.5 (S)-3-(4-(2,5,8,11,14,17,20,23,26,29,32-undecaoxatetratriacontan-34-yloxy)phenyl)-2-(2,5-dioxo-2,5-dihydro-1H-pyrrol-1-yl)propanoic acid To a mixture of Example 2.120.4 (96 g, crude) in toluene (1.5 L) and was added triethylamine (35.13 g), and the reaction mixture was stirred at 120° C. for 4 hours. LC/MS indicated the starting material was consumed, and the major product was the desired product. The reaction was filtered to isolate the organic phase, and the organics were concentrated to afford the crude product which was purified by prep-HPLC (Instrument: Shimadzu LC-20AP preparative HPLC, Column: Phenomenex® Luna® (2) C18 250*50 mm i.d. 10u, Mobile phase: A for H$_2$O (0.09% trifluoroacetic acid) and B for CH$_3$CN, Gradient: B from 15% to 43% in 20 minutes, Flow rate: 80 ml/minute, Wavelength: 220 & 254 nm, Injection amount: 1 gram per injection), followed by SFC-HPLC to provide the title compound. $^1$H NMR (400 MHz, CDCl$_3$) δ ppm 6.98 (d, 2H), 6.74 (d, 2H), 6.56 (s, 2H), 4.85 (dd, 1H), 4.03 (t, 2H), 3.84-3.76 (m, 2H), 3.71-3.66 (m, 2H), 3.65-3.58 (m, 39H), 3.55-3.50 (m, 2H), 3.41-3.30 (m, 4H). MS (ESI) m/e 760.3 (M+H)$^+$.

2.120.6 N-{(2S)-2-(2,5-dioxo-2,5-dihydro-1H-pyrrol-1-yl)-3-[4-(2,5,8,11,14,17,20,23,26,29,32-undecaoxatetratriacontan-34-yloxy)phenyl]propanoyl}-L-valyl-N-{4-[({[2-({3-[(4-{6-[8-(1,3-benzothiazol-2-ylcarbamoyl)naphthalen-2-yl]-2-carboxypyridin-3-yl}-5-methyl-1H-pyrazol-1-yl)methyl]-5,7-dimethyltricyclo[3.3.1.13,7]dec-1-yl}oxy)ethyl](2-sulfoethyl)carbamoyl}oxy)methyl]phenyl}-N5-carbamoyl-L-ornithinamide The title compound was prepared by substituting Example 2.120.5 for Example 2.119.15 in Example 2.119.17. $^1$H NMR (400 MHz, dimethyl sulfoxide-d$_6$) δ ppm 10.03 (s, 1H), 9.02 (s, 1H), 8.37 (d, 1H), 8.22 (m, 3H), 8.16 (d, 1H), 8.12 (br m, 1H), 8.07 (d, 1H), 8.01 (d, 1H), 7.96 (br d, 1H), 7.81 (d, 1H), 7.70 (t, 1H), 7.59 (br m, 2H), 7.48 (m, 2H), 7.37 (t, 1H), 7.28 (d, 2H), 7.02 (d, 2H), 6.89 (s, 2H), 6.77 (d, 2H), 4.98 (br d, 2H), 4.79 (dd, 1H), 4.39 (br m, 1H), 4.23 (br m, 2H), 3.99 (br m, 2H), 3.88 (br m, 2H), 3.69 (br m, 4H), 3.55 (m, 4H), 3.50 (s, 32H), 3.42 (m, 4H), 3.27 (m, 4H), 3.23 (s, 3H), 3.20 (m, 1H), 3.03 (br m, 1H), 2.98 (m, 1H), 2.65 (br t, 2H), 2.22 (s, 3H), 1.97 (br m, 1H), 1.69 (br m, 1H), 1.61 (br m, 1H), 1.39 (m, 4H), 1.31-0.91 (m, 12H), 0.85 (m, 9H), 0.77 (d, 3H). MS (ESI) m/e 1993.7 (M−H)$^−$.

2.121 Synthesis of N-({(3S,5S)-3-(2,5-dioxo-2,5-dihydro-1H-pyrrol-1-yl)-2-oxo-5-[(2-sulfoethoxy)methyl]pyrrolidin-1-yl}acetyl)-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]phenyl}-N$^5$-carbamoyl-L-ornithinamide (Synthon SW)

The title compound was prepared by substituting Example 2.49.1 for Example 2.119.16 in Example 2.119.17. $^1$H NMR (400 MHz, dimethyl sulfoxide-d$_6$) δ ppm 9.96 (s, 1H), 8.17 (br d, 1H), 8.03 (d, 2H), 7.79 (d, 1H), 7.61 (m, 3H), 7.55 (d, 1H), 7.45 (m, 2H), 7.37 (m, 3H), 7.27 (d, 2H), 7.08 (s, 2H), 6.98 (d, 1H), 4.97 (m, 4H), 4.68 (t, 1H), 4.37 (br m, 1H), 4.22 (br s, 1H), 4.17 (d, 1H), 4.03 (d, 1H), 3.89 (br t, 2H), 3.83 (br d, 2H), 3.74 (br m, 1H), 3.65 (t, 2H), 3.49 (m, 3H), 3.40 (br m, 4H), 3.25 (br m, 2H), 3.02 (br m, 4H), 2.80 (m, 2H), 2.67 (br m, 2H), 2.37 (br m, 1H), 2.10 (s, 3H), 1.99 (m, 1H), 1.86 (m, 1H), 1.69 (br m, 1H), 1.61 (br m, 1H), 1.52-0.91 (m, 16H), 0.85 (m, 12H). MS (ESI) m/e 1615.4 (M−H)$^-$.

2.122 Synthesis of N-{(2S)-2-(2,5-dioxo-2,5-dihydro-1H-pyrrol-1-yl)-3-[4-(2,5,8,11,14,17,20,23,26,29,32-undecaoxatetratriacontan-34-yloxy)phenyl]propanoyl}-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]phenyl}-N$^5$-carbamoyl-L-ornithinamide (Synthon TV)

To a mixture of Example 2.120.5 (19.61 mg), and O-(7-azabenzotriazol-1-yl)-N,N,N',N'-tetramethyluronium hexafluorophosphate (9.81 mg) in N,N-dimethylformamide (0.8 mL) was added N,N-diisopropylethylamine (27.7 µL). The mixture was stirred for 5 minutes and added to a cold mixture of Example 2.112.2 in N,N-dimethylformamide (0.5 mL) at 0° C. The reaction mixture was stirred at 0° C. for 40 minutes, and purified by reverse-phase HPLC on a Gilson system (C18 column), eluting with 20-80% acetonitrile in water containing 0.1% trifluoroacetic acid, to give the title compound. $^1$H NMR (400 MHz, dimethyl sulfoxide-d$_6$) δ 9.99 (s, 1H), 8.19 (d, 1H), 8.14-8.04 (m, 1H), 8.00 (dd, 1H), 7.75 (d, 1H), 7.62-7.52 (m, 3H), 7.49 (d, 1H), 7.46-7.37 (m, 2H), 7.36-7.29 (m, 2H), 7.28-7.21 (m, 3H), 6.99 (d, 2H), 6.92 (d, 1H), 6.85 (s, 2H), 6.79-6.71 (m, 2H), 4.94 (d, 3H), 4.76 (dd, 1H), 4.35 (d, 1H), 4.20 (t, 1H), 3.96 (dd, 2H), 3.85 (t, 2H), 3.77 (d, 2H), 3.66 (dd, 2H), 3.52 (dd, 2H), 3.50-3.47 (m, 2H), 3.39 (dd, 2H), 3.20 (s, 4H), 2.97 (t, 3H), 2.60 (t, 2H), 2.13-2.01 (m, 3H), 1.93 (s, 1H), 1.61 (d, 2H), 1.49-0.88 (m, 10H), 0.87-0.59 (m, 12H). MS (ESI) m/e 1998.7 (M−H)$^-$.

2.123 Synthesis of (6S)-2,6-anhydro-6-(2-{2-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]-5-({N-[(2,5-dioxo-2,5-dihydro-1H-pyrrol-1-yl)acetyl]-L-valyl-L-alanyl}amino)phenyl}ethyl)-L-gulonic acid (Synthon SZ)

2.123.1 (3R,4S,5R,6R)-3,4,5-tris(benzyloxy)-6-(benzyloxymethyl)-tetrahydropyran-2-one To a mixture of (3R,4S,5R,6R)-3,4,5-tris(benzyloxy)-6-((benzyloxy)methyl)tetrahydro-2H-pyran-2-ol (75 g) in dimethyl sulfoxide (400 mL) at 0° C. was added acetic anhydride (225 mL). The mixture was stirred for 16 hours at room temperature before it was cooled to 0° C. A large volume of water was added, and stirring was stopped so that the reaction mixture was allowed to settle for 3 hours (the crude lactone migrated to the bottom of the flask). The supernatant was removed, and the crude mixture was diluted with ethyl acetate and was washed 3 times with water, neutralized with saturated aqueous mixture of NaHCO$_3$, and washed again twice with water. The organic layer was then dried over magnesium sulfate, filtered and concentrated to give the title compound. MS (ESI) m/e 561 (M+Na)$^+$.

2.123.2 (3R,4S,5R,6R)-3,4,5-tris(benzyloxy)-6-(benzyloxymethyl)-2-ethynyl-tetrahydro-2H-pyran-2-ol To a mixture of ethynyltrimethylsilane (18.23 g) in tetrahydrofuran (400 mL) under nitrogen and chilled in a dry ice/acetone bath (internal temp −65° C.) was added 2.5M BuLi in hexane (55.7 mL) dropwise, keeping the temperature below −60° C. The mixture was stirred in a cold bath for 40 minutes, followed by an ice-water bath (internal temp rose to 0.4° C.) for 40 minutes, and finally cooled to −75° C. again. A mixture of Example 2.123.1 (50 g) in tetrahydrofuran (50 mL) was added dropwise, keeping the internal temperature below −70° C. The mixture was stirred in a dry ice/acetone bath for additional 3 hours. The reaction was quenched with saturated aqueous NaHCO$_3$ mixture (250 mL). The mixture was allowed to warm to room temperature, extracted with ethyl acetate (3×300 mL), dried over MgSO$_4$, filtered, and concentrated in vacuo to give the title compound. MS (ESI) m/e 659 (M+Na)$^+$.

2.123.3 trimethyl(((3S,4R,5R,6R)-3,4,5-tris(benzyloxy)-6-(benzyloxymethyl)-tetrahydro-2H-pyran-2-yl)ethynyl)silane To a mixed mixture of Example 2.123.2 (60 g) in acetonitrile (450 mL) and dichloromethane (150 mL) at −15° C. in an ice-salt bath was added triethylsilane (81 mL) dropwise, followed by addition of boron trifluoride diethyl ether complex (40.6 mL) at such a rate that the internal temperature did not exceed −10° C. The mixture was then stirred at −15° C. to −10° C. for 2 hours. The reaction was quenched with saturated aqueous NaHCO$_3$ mixture (275 mL) and stirred for 1 hour at room temperature. The mixture was then extracted with ethyl acetate (3×550 mL). The extracts were dried over MgSO$_4$, filtered, and concentrated. The residue was purified by flash chromatography eluting with a gradient of 0% to 7% ethyl acetate/petroleum ether to give the title compound. MS (ESI) m/e 643 (M+Na)$^+$.

2.123.4 (2R,3R,4R,5S)-3,4,5-tris(benzyloxy)-2-(benzyloxymethyl)-6-ethynyl-tetrahydro-2H-pyran To a mixed mixture of Example 2.123.3 (80 g) in dichloromethane (200 mL) and methanol (1000 mL) was added 1N aqueous NaOH mixture (258 mL). The mixture was stirred at room temperature for 2 hours. The solvent was removed. The residue was then partitioned between water and dichloromethane. The extracts were washed with brine, dried over Na$_2$SO$_4$, filtered, and concentrated to give the title compound. MS (ESI) m/e 571 (M+Na)$^+$.

2.123.5 (2R,3R,4R,5S)-2-(acetoxymethyl)-6-ethynyl-tetrahydro-2H-pyran-3,4,5-triyl triacetate To a mixture of Example 2.123.4 (66 g) in acetic anhydride (500 mL) cooled by an ice/water bath was added boron trifluoride diethyl ether complex (152 mL) dropwise. The mixture was stirred at room temperature for 16 hours, cooled with an ice/water bath and neutralized with saturated aqueous NaHCO$_3$ mixture. The mixture was extracted with ethyl acetate (3×500 mL), dried over Na$_2$SO$_4$, filtered, and concentrated in vacuo. The residue was purified by flash chromatography eluting with a gradient of 0% to 30% ethyl acetate/petroleum ether to give the title compound. MS (ESI) m/e 357 (M+H)$^+$.

2.123.6 (3R,4R,5S,6R)-2-ethynyl-6-(hydroxymethyl)-tetrahydro-2H-pyran-3,4,5-triol To a mixture of Example 2.123.5 (25 g) in methanol (440 mL) was added sodium methanolate (2.1 g). The mixture was stirred at room temperature for 2 hours, and then neutralized with 4 M HCl in dioxane. The solvent was removed, and the residue was adsorbed onto silica gel and loaded onto a silica gel column. The column was eluted with a gradient of 0 to 100% ethyl acetate/petroleum ether then 0% to 12% methanol/ethyl acetate to give the title compound. MS (ESI) m/e 211 (M+Na)$^+$.

2.123.7 (2S,3S,4R,5R)-6-ethynyl-3,4,5-trihydroxy-tetrahydro-2H-pyran-2-carboxylic acid A three-necked round bottom flask was charged with Example 2.123.6 (6.00 g), KBr (0.30 g), tetrabutylammonium bromide (0.41 g) and 60 mL of saturated aqueous NaHCO$_3$ mixture. TEMPO ((2,2,6,6-tetramethylpiperidin-1-yl)oxyl, 0.15 g) in 60 mL dichloromethane was added. The mixture was stirred vigorously and cooled in an ice-salt bath to −2° C. internal temperature. A mixture of brine (12 mL), aqueous NaHCO$_3$ mixture (24 mL) and NaOCl (154 mL) was added dropwise such that the internal temperature was maintained below 2° C. The pH of the reaction mixture was maintained in the 8.2-8.4 range with the addition of solid Na$_2$CO$_3$. After a total of 6 hours, the reaction mixture was cooled to 3° C. internal temperature and ethanol (~20 mL) was added dropwise. The mixture was stirred for ~30 minutes. The mixture was transferred to a separatory funnel, and the dichloromethane layer was discarded. The pH of the aqueous layer was adjusted to 2-3 using 1 M aqueous HCl. The aqueous layer was then concentrated to dryness to afford a solid. Methanol (100 mL was) added to the dry solid, and the slurry was stirred for ~30 minutes. The mixture was filtered over a pad of diatomaceous earth, and the residue in the funnel was washed with ~100 mL of methanol. The filtrate was concentrated under reduced pressure to obtain the title compound.

2.123.8 (2S,3S,4R,5R)-methyl 6-ethynyl-3,4,5-trihydroxytetrahydro-2H-pyran-2-carboxylate A 500 mL three-necked round bottom flask was charged with a suspension of Example 2.123.7 (6.45 g) in methanol (96 mL) and was cooled in an ice-salt-bath with internal temperature of −1° C. Neat thionyl chloride (2.79 mL) was carefully added. The internal temperature kept rising throughout the addition but did not exceed 10° C. The reaction was allowed to slowly warm up to 15-20° C. over 2.5 hours. After 2.5 hours, the reaction was concentrated to give the title compound.

2.123.9 (3S,4R,5S,6S)-2-ethynyl-6-(methoxycarbonyl)tetrahydro-2H-pyran-3,4,5-triyl triacetate To Example 2.123.8 (6.9 g) as a mixture in N,N-dimethylformamide (75 mL) was added 4-(dimethylamino)pyridine (0.17 g) and acetic anhydride (36.1 mL). The suspension was cooled in an ice-bath and pyridine (18.04 mL) was added via syringe over 15 minutes. The reaction was allowed to warm to room temperature overnight. Additional acetic anhydride (12 mL) and pyridine (6 mL) were added and stirring was continued for an additional 6 hours. The reaction was cooled in an ice-bath and 250 mL of saturated aqueous NaHCO$_3$ mixture was added and stirred for 1 hour. Water (100 mL) was added, and the mixture was extracted with ethyl acetate. The organic extract was washed twice with saturated CuSO$_4$ mixture, dried, filtered, and concentrated. The residue was purified by flash chromatography, eluting with 50% ethyl acetate/petroleum ether to give the title compound. $^1$H NMR (500 MHz, methanol-d$_4$) δ ppm 5.29 (t, 1H), 5.08 (td, 2H), 4.48 (dd, 1H), 4.23 (d, 1H), 3.71 (s, 3H), 3.04 (d, 1H), 2.03 (s, 3H), 1.99 (s, 3H), 1.98 (s, 4H).

2.123.10 2-iodo-4-nitrobenzoic acid

A 3 L fully jacketed flask equipped with a mechanical stirrer, temperature probe and an addition funnel under a nitrogen atmosphere, was charged with 2-amino-4-nitrobenzoic acid (69.1 g, Combi-Blocks) and sulfuric acid, 1.5 M aqueous (696 mL). The resulting suspension was cooled to 0° C. internal temperature, and a mixture of sodium nitrite (28.8 g) in water (250 mL) was added dropwise over 43 minutes with the temperature kept below 1° C. The reaction was stirred at ca. 0° C. for 1 hour. A mixture of potassium iodide (107 g) in water (250 mL) was added dropwise over 44 minutes with the internal temperature kept below 1° C. (Initially addition was exothermic and there was gas evolution). The reaction was stirred 1 hour at 0° C. The temperature was raised to 20° C. and then stirred at ambient temperature overnight. The reaction mixture became a suspension. The reaction mixture was filtered, and the collected solid was washed with water. The wet solid (~108 g) was stirred in 10% sodium sulfite (350 ml, with ~200 mL water used to wash in the solid) for 30 minutes. The suspension was acidified with concentrated hydrochloric acid (35 mL), and the solid was collected by filtration and washed with water. The solid was slurried in water (1L) and re-filtered, and the solid was left to dry in the funnel overnight. The solid was then dried in a vacuum oven for 2 hours at 60° C. The resulting solid was triturated with dichloromethane (500 mL), and the suspension was filtered and washed with additional dichloromethane. The solid was air-dried to give the title compound

2.123.11 (2-iodo-4-nitrophenyl)methanol

A flame-dried 3 L 3-necked flask was charged with Example 2.123.10 (51.9 g) and tetrahydrofuran (700 mL). The mixture was cooled in an ice bath to 0.5° C., and borane-tetrahydrofuran complex (443 mL, 1M in THF) was added dropwise (gas evolution) over 50 minutes, reaching a final internal temperature of 1.3° C. The reaction mixture was stirred for 15 minutes, and the ice bath was removed. The reaction was left to come to ambient temperature over 30 minutes. A heating mantle was installed, and the reaction was heated to an internal temperature of 65.5° C. for 3 hours, and then allowed to cool to room temperature while stirring overnight. The reaction mixture was cooled in an ice bath to 0° C. and quenched by dropwise addition of methanol (400 mL). After a brief incubation period, the temperature rose quickly to 2.5° C. with gas evolution. After the first 100 mL are added over ~30 minutes, the addition was no longer exothermic, and the gas evolution ceased. The ice bath was removed, and the mixture was stirred at ambient temperature under nitrogen overnight. The mixture was concentrated to a solid, dissolved in dichloromethane/methanol and adsorbed on to silica gel (~150 g). The residue was loaded on a plug of silica gel (3000 mL) and eluted with dichloromethane to give the title compound.

2.123.12 (4-amino-2-iodophenyl)methanol

A 5 L flask equipped with a mechanical stirrer, heating mantle controlled by a JKEM temperature probe and a condenser was charged with Example 2.123.11 (98.83 g) and ethanol (2 L). The reaction was stirred rapidly, and iron (99 g) was added, followed by a mixture of ammonium chloride (20.84 g) in water (500 mL). The reaction was heated over the course of 20 minutes to an internal temperature of 80.3° C., where it began to reflux vigorously. The mantle was dropped until the reflux calmed. Thereafter, the mixture was heated to 80° C. for 1.5 hour. The reaction was filtered hot through a membrane filter, and the iron residue was washed with hot 50% ethyl acetate/methanol (800 mL). The eluent was passed through a diatomaceous earth pad, and the filtrate was concentrated. The residue was partitioned between 50% brine (1500 mL) and ethyl acetate (1500 mL). The layers were separated, and the aqueous layer was extracted with ethyl acetate (400 mL×3). The combined organic layers were dried over sodium sulfate, filtered and concentrated to give the title compound, which was used without further purification.

2.123.13 4-(((tert-butyldimethylsilyl)oxy)methyl)-3-iodoaniline

A 5 L flask with a mechanical stirrer was charged with Example 2.123.12 (88 g) and dichloromethane (2 L). The suspension was cooled in an ice bath to an internal temperature of 2.5° C., and tert-butylchlorodimethylsilane (53.3 g) was added portion-wise over 8 minutes. After 10 minutes, 1H-imidazole (33.7 g) was added portionwise to the cold reaction. The reaction was stirred 90 minutes while the internal temperature rose to 15° C. The reaction mixture was diluted with water (3 L) and dichloromethane (1 L). The layers were separated, and the organic layer was dried over sodium sulfate, filtered, and concentrated to an oil. The residue was purified by silica gel chromatography (1600 g silica gel), eluting a gradient of 0-25% ethyl acetate in heptane, to give the title compound as an oil.

2.123.14 (S)-2-((S)-2-((((9H-fluoren-9-yl)methoxy)carbonyl)amino)-3-methylbutanamido)propanoic acid To a mixture of (S)-2-((((9H-fluoren-9-yl)methoxy)carbonyl)amino)-3-methylbutanoic acid (6.5 g) in dimethoxyethane (40 mL) was added (S)-2-aminopropanoic acid (1.393 g) and sodium bicarbonate (1.314 g) in water (40 mL). Tetrahydrofuran (20 mL) was added to aid solubility. The resulting mixture was stirred at room temperature for 16 hours. Aqueous citric acid (15%, 75 mL) was added, and the mixture was extracted with 10% 2-propanol in ethyl acetate (2×100 mL). A precipitate formed in the organic layer. The combined organic layers were washed with water (2×150 mL). The organic layer was concentrated under reduced pressure and then triturated with diethyl ether (80 mL). After brief sonication, the title compound was collected by filtration. MS (ESI) m/e 411 (M+H)$^+$.

2.123.15 (9H-fluoren-9-yl)methyl ((S)-1-(((S)-1-((4-(((tert-butyldimethylsilyl)oxy)methyl)-3-iodophenyl)amino)-1-oxopropan-2-yl)amino)-3-methyl-1-oxobutan-2-yl)carbamate A mixture of Example 2.123.13 (5.44 g) and Example 2.123.14 (6.15 g) in a mixture of dichloromethane (70 mL) and methanol (35.0 mL) was added ethyl 2-ethoxyquinoline-1(2H)-carboxylate (4.08 g), and the reaction was stirred overnight. The reaction mixture was concentrated and loaded onto silica gel, eluting with a gradient of 10% to 95% heptane in ethyl acetate followed by 5% methanol in dichloromethane. The product-containing fractions were concentrated, dissolved in 0.2% methanol in dichloromethane (50 mL), loaded onto silica gel and eluted with a gradient of 0.2% to 2% methanol in dichloromethane. The product containing fractions were collected to give the title compound. MS (ESI) m/e 756.0 (M+H)$^+$.

2.123.16 (2S,3S,4R,5S,6S)-2-((5-((S)-2-((S)-2-((((9H-fluoren-9-yl)methoxy)carbonyl)amino)-3-methylbutanamido)propanamido)-2-(((tert-butyldimethylsilyl)oxy)methyl)phenyl)ethynyl)-6-(methoxycarbonyl)tetrahydro-2H-pyran-3,4,5-triyl triacetate A mixture of Example 2.123.9 (4.500 g), Example 2.123.15 (6.62 g), copper(I) iodide (0.083 g) and bis(triphenylphosphine)palladium(II) dichloride (0.308 g) were combined in vial and degassed. N,N-dimethylformamide (45 mL) and N-ethyl-N-isopropylpropan-2-amine (4.55 mL) were added, and the reaction vessel was flushed with nitrogen and stirred at room temperature overnight. The reaction was partitioned between water (100 mL) and ethyl acetate (250 mL). The layers were separated, and the organic layer was dried over magnesium sulfate, filtered, and concentrated. The residue was purified by silica gel chromatography, eluting with a gradient of 5% to 95% ethyl acetate in heptane. The product containing fractions were collected, concentrated and purified by silica gel chromatography, eluting with a gradient of 0.25% to 2.5% methanol in dichloromethane to give the title compound. MS (ESI) m/e 970.4 (M+H)$^+$.

2.123.17 (2S,3S,4R,5S,6S)-2-(5-((S)-2-((S)-2-((((9H-fluoren-9-yl)methoxy)carbonyl)amino)-3-methylbutanamido)propanamido)-2-(((tert-butyldimethylsilyl)oxy)methyl)phenethyl)-6-(methoxycarbonyl)tetrahydro-2H-pyran-3,4,5-triyl triacetate Example 2.123.16 (4.7 g) and tetrahydrofuran (95 mL) were added to 5% Pt/C (2.42 g, wet) in a 50 mL pressure bottle and shaken for 90 minutes at room temperature under 50 psi of hydrogen. The reaction was filtered and concentrated to give the title compound. MS (ESI) m/e 974.6 (M+H)$^+$.

2.123.18 (2S,3S,4R,5S,6S)-2-(5-((S)-2-((S)-2-((((9H-fluoren-9-yl)methoxy)carbonyl)amino)-3-methylbutanamido)propanamido)-2-(hydroxymethyl)phenethyl)-6-(methoxycarbonyl)tetrahydro-2H-pyran-3,4,5-triyl triacetate A mixture of Example 2.123.17 (5.4 g) in tetrahydrofuran (7 mL), water (7 mL) and glacial acetic acid (21 mL) was stirred overnight at room temperature. The reaction was diluted with ethyl acetate (200 mL) and washed with water (100 mL), saturated aqueous NaHCO$_3$ mixture (100 mL), brine (100 mL), dried over magnesium sulfate, filtered, and concentrated. The residue was purified by silica gel chromatography, eluting with a gradient of 0.5% to 5% methanol in dichloromethane, to give the title compound. MS (ESI) m/e 860.4 (M+H)$^+$.

2.123.19 (2S,3S,4R,5S,6S)-2-(5-((S)-2-((S)-2-((((9H-fluoren-9-yl)methoxy)carbonyl)amino)-3-methylbutanamido)propanamido)-2-((((4-nitrophenoxy)carbonyl)oxy)methyl)phenethyl)-6-(methoxycarbonyl)tetrahydro-2H-pyran-3,4,5-triyl triacetate To a mixture of Example 2.123.18 (4.00 g) and bis(4-nitrophenyl) carbonate (2.83 g) in acetonitrile (80 mL) was added N-ethyl-N-isopropylpropan-2-amine (1.22 mL) at room temperature. After stirring overnight, the reaction was concentrated, dissolved in dichloromethane (250 mL) and washed with saturated aqueous NaHCO₃ mixture (4×150 mL). The organic layer was dried over magnesium sulfate, filtered, and concentrated. The resulting foam was purified by silica gel chromatography, eluting with a gradient of 5% to 75% ethyl acetate in hexanes to give the title compound. MS (ESI) m/e 1025.5 (M+H)⁺.

2.123.20 3-(1-((3-(2-(((((4-((R)-2-((R)-2-amino-3-methylbutanamido)propanamido)-2-(2-((2S,3R,4R,5S,6S)-6-carboxy-3,4,5-trihydroxytetrahydro-2H-pyran-2-yl)ethyl)benzyl)oxy)carbonyl)(2-sulfoethyl)amino)ethoxy)-5,7-dimethyladamantan-1-yl)methyl)-5-methyl-1H-pyrazol-4-yl)-6-(8-(benzo[d]thiazol-2-ylcarbamoyl)-3,4-dihydroisoquinolin-2(1H)-yl)picolinic acid To a cold (0° C.) mixture of Example 2.123.19 (70 mg) and Example 1.2.9 (58.1 mg) in N,N-dimethylformamide (4 mL) was added N-ethyl-N-isopropylpropan-2-amine (0.026 mL). The reaction was slowly warmed to room temperature and stirred overnight. To the reaction mixture was added water (1 mL) and LiOH H₂O (20 mg). The mixture was stirred at room temperature for 3 hours. The mixture was acidified with trifluoroacetic acid, filtered and purified by reverse-phase HPLC on a Gilson system (C18 column), eluting with 20-80% acetonitrile in water containing 0.1% trifluoroacetic acid, to give the title compound. MS (ESI) m/e 1564.4 (M−H)⁻.

2.123.21 (6S)-2,6-anhydro-6-(2-{2-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.13,7]dec-1-yl}oxy)ethyl](2-sulfoethyl)carbamoyl}oxy)methyl]-5-({N-[(2,5-dioxo-2,5-dihydro-1H-pyrrol-1-yl)acetyl]-L-valyl-L-alanyl}amino)phenyl}ethyl)-L-gulonic acid The title compound was prepared as described in Example 2.54, replacing Example 2.49.1 with Example 2.123.20. ¹H NMR (500 MHz, dimethyl sulfoxide-d₆) δ ppm 12.86 (s, 1H), 9.92 (d, 1H), 8.35-8.19 (m, 2H), 8.04 (d, 1H), 7.80 (d, 1H), 7.61 (d, 1H), 7.57-7.32 (m, 8H), 7.28 (s, 1H), 7.22 (d, 1H), 7.08 (s, 2H), 6.95 (d, 1H), 5.12-4.91 (m, 5H), 4.39 (t, 1H), 4.32-4.19 (m, 1H), 4.12 (s, 2H), 3.89 (t, 2H), 3.80 (d, 2H), 3.14 (t, 1H), 3.06-2.87 (m, 4H), 2.69-2.58 (m, 4H), 2.37 (p, 1H), 2.09 (d, 4H), 2.04-1.91 (m, 4H), 1.54 (d, 1H), 1.40-0.99 (m, 20H), 0.99-0.74 (m, 16H). MS (ESI) m/e 1513.5 (M−H)⁻.

2.124 Synthesis of 3-{[2-({3-[(4-{6-[8-(1,3-benzothiazol-2-ylcarbamoyl)naphthalen-2-yl]-2-carboxypyridin-3-yl}-5-methyl-1H-pyrazol-1-yl)methyl]-5,7-dimethyltricyclo[3.3.1.1³,⁷]dec-1-yl}oxy)ethyl]({[4-(4-{[6-(2,5-dioxo-2,5-dihydro-1H-pyrrol-1-yl)hexanoyl]amino}butyl)-2-(beta-D-glucopyranuronosyloxy)benzyl]oxy}carbonyl)amino}propyl beta-D-glucopyranosiduronic acid (Synthon ZM)

2.124.1A (9H-fluoren-9-yl)methyl but-3-yn-1-ylcarbamate

A mixture of but-3-yn-1-amine hydrochloride (9 g) and N,N-diisopropylethylamine (44.7 mL) was stirred in dichloromethane (70 mL) and cooled to 0° C. A mixture of (9H-fluoren-9-yl)methyl carbonochloridate (22.06 g) in dichloromethane (35 mL) was added, and the reaction stirred for 2 hours. The reaction was concentrated, and the residue purified by silica gel chromatography, eluting with petroleum ether in ethyl acetate (10%-25%) to give the title compound. MS (ESI) m/e 314 (M+Na)⁺.

2.124.1B (3R,4S,5S,6S)-2-(2-formyl-5-iodophenoxy)-6-(methoxycarbonyl)tetrahydro-2H-pyran-3,4,5-triyl triacetate To a stirred solution of 2-hydroxy-4-iodobenzaldehyde (0.95 g) in acetonitrile (10 ml) was added (3R,4S,5S,6S)-2-bromo-6-(methoxycarbonyl)tetrahydro-2H-pyran-3,4,5-triyl triacetate (2.5 g) and silver oxide (2 g). The mixture was covered with aluminum foil and was stirred at room temperature overnight. After filtration through diatomaceous earth, the filtrate was washed with ethyl acetate, the solution was concentrated. The reaction mixture was purified by flash chromatography using an ISCO CombiFlash system, SF40-80 g column, eluted with 15-30% ethyl acetate/heptane (flow rate: 60 ml/min), to provide the title compound. MS (ESI) m/e 586.9 (M+Na)⁺.

2.124.2 (2S,3S,4S,5R,6S)-methyl 6-(5-(4-(((9H-fluoren-9-yl)methoxy)carbonylamino)but-1-ynyl)-2-formylphenoxy)-3,4,5-triacetoxy-tetrahydro-2H-pyran-2-carboxylate Example 2.124.1B (2.7 g), Example 2.124.1A (2.091 g), bis(triphenylphosphine)palladium(II) chloride (0.336 g) and copper(I) iodide (0.091 g) were weighed into a vial and flushed with a stream of nitrogen. Triethylamine (2.001 mL) and tetrahydrofuran (45 mL) were added, and the reaction stirred at room temperature. After stirring for 16 hours, the reaction was diluted with ethyl acetate (200 mL) and washed with water (100 mL) and brine (100 mL). The organic layer was dried over magnesium sulfate, filtered, and concentrated. The residue was purified by silica gel chromatography, eluting with petroleum ether in ethyl acetate (10%-50%), to give the title compound. MS (ESI) m/e 750 (M+Na)⁺.

2.124.3 (2S,3S,4S,5R,6S)-methyl 6-(5-(4-(((9H-fluoren-9-yl)methoxy)carbonylamino)butyl)-2-formylphenoxy)-3,4,5-triacetoxy-tetrahydro-2H-pyran-2-carboxylate Example 2.124.2 (1.5 g) and tetrahydrofuran (45 mL) were added to 10% Pd—C (0.483 g) in a 100 mL pressure bottle and stirred for 16 hours under 1 atm H₂ at room

2.124.4 (2S,3S,4S,5R,6S)-methyl 6-(5-(4-(((9H-fluoren-9-yl)methoxy)carbonylamino)butyl)-2-(hydroxymethyl)phenoxy)-3,4,5-triacetoxy-tetrahydro-2H-pyran-2-carboxylate A mixture of Example 2.124.3 (2.0 g) in tetrahydrofuran (7.00 mL) and methanol (7 mL) was cooled to 0° C. and NaBH$_4$ (0.052 g) was added in one portion. After 30 minutes, the reaction was diluted with ethyl acetate (150 mL) and water (100 mL). The organic layer was separated, washed with brine (100 mL), dried over magnesium sulfate, filtered, and concentrated. The residue was purified by silica gel chromatography, eluting with petroleum ether in ethyl acetate (10%-40%), to give the title compound. MS (ESI) m/e 756 (M+Na)$^+$.

2.124.5 (2S,3S,4S,5R,6S)-methyl 6-(5-(4-(((9H-fluoren-9-yl)methoxy)carbonylamino)butyl)-2-(((4-nitrophenoxy)carbonyloxy)methyl)phenoxy)-3,4,5-triacetoxy-tetrahydro-2H-pyran-2-carboxylate To a mixture of Example 2.124.4 (3.0 g) and bis(4-nitrophenyl) carbonate (2.488 g) in dry acetonitrile (70 mL) at 0° C. was added N,N-diisopropylethylamine (1.07 mL). After stirring at room temperature for 16 hours, the reaction was concentrated to give the residue, which was purified by silica gel chromatography, eluting with petroleum ether in ethyl acetate (10%-50%), to give the title compound. MS (ESI) m/e 921 (M+Na)$^+$.

2.124.6 3-(1-((3-(2-((((4-(4-aminobutyl)-2-(((2R,3S,4R,5R,6R)-6-carboxy-3,4,5-trihydroxytetrahydro-2H-pyran-2-yl)oxy)benzyl)oxy)carbonyl)(3-(((2S,3S,4R,5R,6R)-6-carboxy-3,4,5-trihydroxytetrahydro-2H-pyran-2-yl)oxy)propyl)amino)ethoxy)-5,7-dimethyladamantan-1-yl)methyl)-5-methyl-1H-pyrazol-4-yl)-6-(8-(benzo[d]thiazol-2-ylcarbamoyl)naphthalen-2-yl)picolinic acid To a cold (0° C.) mixture of Example 2.124.5 (44 mg) and Example 1.87.3 (47.4 mg) in N,N-dimethylformamide (4 mL) was added N-ethyl-N-isopropylpropan-2-amine (0.026 mL). The reaction was slowly warmed to room temperature and stirred overnight. To the reaction mixture was added water (1 mL) and LiOH H$_2$O (20 mg). The mixture was stirred at room temperature for 3 hours. The mixture was acidified with trifluoroacetic acid, filtered and purified by reverse-phase HPLC on a Gilson system (C18 column), eluting with 20-80% acetonitrile in water containing 0.1% trifluoroacetic acid, to give the title compound. MS (ESI) m/e 1564.4 (M–H)$^-$.

2.124.7 3-{[2-({3-[(4-{6-[8-(1,3-benzothiazol-2-ylcarbamoyl)naphthalen-2-yl]-2-carboxypyridin-3-yl}-5-methyl-1H-pyrazol-1-yl)methyl]-5,7-dimethyltricyclo[3.3.1.13,7]dec-1-yl}oxy)ethyl]({[4-(4-{[6-(2,5-dioxo-2,5-dihydro-1H-pyrrol-1-yl)hexanoyl]amino}butyl)-2-(beta-D-glucopyranuronosyloxy)benzyl]oxy}carbonyl)amino}propyl beta-D-glucopyranosiduronic acid The title compound was prepared as described in Example 2.5.4, replacing Example 2.5.3 with Example 2.124.6. $^1$H NMR (400 MHz, dimethyl sulfoxide-d$_6$) δ ppm 13.06 (s, 2H), 8.99 (s, 1H), 8.34 (dd, 1H), 8.25-8.09 (m, 3H), 8.08-8.02 (m, 1H), 7.98 (d, 1H), 7.89 (d, 1H), 7.78 (d, 1H), 7.66 (q, 2H), 7.50-7.41 (m, 2H), 7.37-7.31 (m, 1H), 7.14 (t, 1H), 6.94 (s, 2H), 6.90 (s, 1H), 6.82 (d, 1H), 5.14-5.02 (m, 2H), 4.97 (d, 1H), 4.19 (d, 1H), 3.85 (dd, 3H), 3.37-3.23 (m, 9H), 3.14 (t, 1H), 3.04-2.92 (m, 4H), 2.19 (s, 3H), 1.96 (t, 2H), 1.73 (s, 2H), 1.55-0.87 (m, 21H), 0.81 (d, 6H). MS (ESI) m/e 1564.4 (M–H)$^-$.

2.125 Synthesis of N-{[(3S,5S)-3-(2,5-dioxo-2,5-dihydro-1H-pyrrol-1-yl)-5-(methoxymethyl)-2-oxopyrrolidin-1-yl]acetyl}-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]phenyl}-N$^5$-carbamoyl-L-ornithinamide (Synthon SV)

2.125.1 tert-butyl 2-((3S,5S)-3-(dibenzylamino)-5-(methoxymethyl)-2-oxopyrrolidin-1-yl)acetate To a mixture of Example 2.119.10 (1.4 g) in N,N-dimethylformamide (5 mL) was added iodomethane (0.8 mL). The reaction was cooled to 0° C., and 95% sodium hydride (80 mg) was added. After five minutes the cooling bath was removed, and the reaction stirred at room temperature for 2.5 hours. The reaction was quenched by the addition of water (20 mL) and ethyl acetate (40 mL). The layers were separated, and the organic layer was washed with brine. The combined aqueous layers were back-extracted with ethyl acetate (10 mL). The combined organic layers were dried with sodium sulfate, filtered and concentrated under reduced pressure. The residue was purified by silica gel chromatography, eluting with 80/20 heptane/ethyl acetate, to give the title compound. MS (DCI) m/e 439.2 (M+H)$^+$.

2.125.2 tert-butyl 2-((3S,5S)-3-amino-5-(methoxymethyl)-2-oxopyrrolidin-1-yl)acetate To a mixture of Example 2.125.1 (726 mg) in 2,2,2-trifluoroethanol (10 mL) was added palladium hydroxide on carbon (20% by wt, 150 mg). The reaction was stirred under a hydrogen atmosphere (50 psi) at room temperature for two hours. The reaction was filtered and concentrated to give the title compound. MS (DCI) m/e 259.0 (M+H)$^+$.

2.125.3 4-(((3S,5S)-1-(2-(tert-butoxy)-2-oxoethyl)-5-(methoxymethyl)-2-oxopyrrolidin-3-yl)amino)-4-oxobut-2-enoic acid The title compound was prepared by substituting Example 2.125.2 for Example 2.119.12 in Example 2.119.13. MS (DCI) m/e 374.0 (M+NH$_3$+H)$^+$.

2.125.4 tert-butyl 2-((3S,5S)-3-(2,5-dioxo-2,5-dihydro-1H-pyrrol-1-yl)-5-(methoxymethyl)-2-oxopyrrolidin-1-yl)acetate The title compound was prepared by substituting Example 2.125.3 for Example 2.119.13 in Example 2.119.14. MS (DCI) m/e 356.0 (M+NH$_3$+H)$^+$.

2.125.5 2-((3S,5S)-3-(2,5-dioxo-2,5-dihydro-1H-pyrrol-1-yl)-5-(methoxymethyl)-2-oxopyrrolidin-1-yl)acetic acid To a mixture of Example 2.125.4 (120 mg) in dichloromethane (8 mL) was added trifluoroacetic acid (4 mL). The reaction was stirred at room temperature for 90 minutes and then concentrated under reduced pressure. The residue was dissolved in acetonitrile (4 mL) and purified by preparative reverse-phase HPLC with a Luna C18(2) AXIA column, 250×50 mm, 10 g particle size, using a gradient of 5-75% acetonitrile in 0.1% trifluoroacetic acid in water over 30 minutes, to give the title compound. MS (DCI) m/e 300.0 $(M+NH_3+H)^+$.

2.125.6 N-{[(3S,5S)-3-(2,5-dioxo-2,5-dihydro-1H-pyrrol-1-yl)-5-(methoxymethyl)-2-oxopyrrolidin-1-yl]acetyl}-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1³,⁷]dec-1-yl}oxy)ethyl](2-sulfoethyl)carbamoyl}oxy)methyl]phenyl}-N5-carbamoyl-L-ornithinamide The title compound was prepared by substituting Example 2.125.5 for Example 2.119.15 and Example 2.49.1 for Example 2.119.16 in Example 2.119.17. $^1$H NMR (400 MHz, dimethyl sulfoxide-$d_6$) δ ppm 9.98 (s, 1H), 8.19 (br d, 1H), 8.03 (d, 1H), 7.96 (d, 1H), 7.79 (d, 1H), 7.61 (m, 3H), 7.55 (d, 1H), 7.45 (m, 2H), 7.37 (m, 2H), 7.32 (s, 1H), 7.27 (d, 2H), 7.08 (s, 2H), 6.96 (d, 1H), 5.00 (m, 2H), 4.96 (s, 2H), 4.69 (t, 1H), 4.39 (br m, 1H), 4.28 (m, 1H), 4.20 (d, 1H), 3.88 (t, 3H), 3.81 (br m, 3H), 3.46 (m, 3H), 3.40 (m, 2H), 3.26 (br m, 2H), 3.25 (s, 3H), 3.01 (m, 3H), 2.96 (m, 1H), 2.65 (t, 2H), 2.36 (br m, 1H), 2.10 (s, 3H), 2.00 (m, 1H), 1.94 (m, 1H), 1.69 (br m, 1H), 1.59 (br m, 1H), 1.49-0.92 (m, 16H), 0.88 (d, 3H), 0.83 (m, 9H). MS (ESI) m/e 1521.5 (M−H)⁻.

2.126 Synthesis of (6S)-2,6-anhydro-6-(2-{2-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1³,⁷]dec-1-yl}oxy)ethyl](2-sulfoethyl)carbamoyl}oxy)methyl]-5-({N-[6-(2,5-dioxo-2,5-dihydro-1H-pyrrol-1-yl)hexanoyl]-L-valyl-L-alanyl}amino)phenyl}ethyl)-L-gulonic acid (Synthon SY)

The title compound was prepared as described in Example 2.123.21, replacing 2,5-dioxopyrrolidin-1-yl 2-(2,5-dioxo-2,5-dihydro-1H-pyrrol-1-yl)acetate with 2,5-dioxopyrrolidin-1-yl 6-(2,5-dioxo-2,5-dihydro-1H-pyrrol-1-yl)hexanoate. $^1$H NMR (501 MHz, dimethyl sulfoxide-$d_6$) δ ppm 12.83 (s, 1H), 9.87 (s, 1H), 8.09 (d, 1H), 8.05-7.95 (m, 1H), 7.77 (d, 2H), 7.59 (d, 1H), 7.55-7.31 (m, 7H), 7.28 (s, 1H), 7.20 (d, 1H), 6.97 (s, 2H), 6.94 (d, 1H), 5.08-4.84 (m, 5H), 4.36 (p, 1H), 3.78 (d, 2H), 3.54 (t, 1H), 3.48-3.28 (m, 9H), 3.21 (s, 2H), 3.12 (t, 2H), 3.02-2.84 (m, 4H), 2.81-2.54 (m, 6H), 2.19-1.84 (m, 9H), 1.63-1.39 (m, 6H), 1.35 (s, 1H), 1.29-0.86 (m, 18H), 0.80 (td, 15H). MS (ESI) m/e 1568.4 (M−H)⁻.

2.127 Synthesis of 2-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1³,⁷]dec-1-yl}oxy)ethyl](2-sulfoethyl)carbamoyl}oxy)methyl]-5-(4-{[3-(2,5-dioxo-2,5-dihydro-1H-pyrrol-1-yl)propanoyl]amino}butyl)phenyl beta-D-glucopyranosiduronic acid (Synthon TK)

2.127.1 3-(1-(((3-(2-(((((4-(4-aminobutyl)-2-(((2S,3R,4S,5S,6S)-6-carboxy-3,4,5-trihydroxytetrahydro-2H-pyran-2-yl)oxy)benzyl)oxy)carbonyl)(2-sulfoethyl)amino)ethoxy)-5,7-dimethyladamantan-1-yl)methyl)-5-methyl-1H-pyrazol-4-yl)-6-(8-(benzo[d]thiazol-2-ylcarbamoyl)-3,4-dihydroisoquinolin-2(1H)-yl)picolinic acid To a mixture of Example 1.2.9 (0.030 g), Example 2.124.5 (0.031 g) and 1H-benzo[d][1,2,3]triazol-1-ol hydrate (5 mg) in N,N-dimethylformamide (0.5 mL) was added N-ethyl-N-isopropylpropan-2-amine (0.017 mL), and the reaction mixture was stirred for 3 hours. The reaction mixture was concentrated, dissolved in tetrahydrofuran (0.4 mL) and methanol (0.4 mL) and treated with lithium hydroxide hydrate (0.020 g) as a mixture in water (0.5 mL). After 1 hour, the reaction was quenched with 2,2,2-trifluoroacetic acid (0.072 mL), diluted with N,N-dimethylformamide:water (1:1) (1 mL) and purified by preparatory reverse-phase HPLC using a Gilson PLC 2020 system, eluting with a gradient of 5% to 75% acetonitrile/water. Product-containing fractions were combined and lyophilized to give to title compound. MS (ESI) m/e 1251.7 (M+H)⁺.

2.127.2 2-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.13,7]dec-1-yl}oxy)ethyl](2-sulfoethyl)carbamoyl}oxy)methyl]-5-(4-{[3-(2,5-dioxo-2,5-dihydro-1H-pyrrol-1-yl)propanoyl]amino}butyl)phenyl beta-D-glucopyranosiduronic acid To a mixture of Example 2.127.1 (0.027 g) and 2,5-dioxopyrrolidin-1-yl 3-(2,5-dioxo-2,5-dihydro-1H-pyrrol-1-yl)propanoate (6.32 mg) in N,N-dimethylformamide (0.4 mL) was added N-ethyl-N-isopropylpropan-2-amine (0.017 mL), and the reaction was stirred for 1 hour at room temperature. The reaction was quenched with a mixture of 2,2,2-trifluoroacetic acid (0.038 mL), water (1.5 mL) and N,N-dimethylformamide (0.5 mL) and purified by preparatory reverse-phase HPLC on a Gilson 2020 system, using a gradient of 5% to 75% acetonitrile/water. The product-containing fractions were lyophilized to give the title compound. $^1$H NMR (501 MHz, dimethyl sulfoxide-$d_6$) δ 12.84 (s, 1H), 8.03 (dd, 1H), 7.91-7.85 (m, 1H), 7.78 (d, 1H), 7.61 (dd, 1H), 7.52 (dd, 1H), 7.50-7.40 (m, 2H), 7.39-7.31 (m, 2H), 7.31 (s, 1H), 7.17 (dd, 1H), 6.99-6.90 (m, 4H), 6.83 (d, 1H), 5.15-5.04 (m, 2H), 5.05-4.96 (m, 1H), 4.95 (s, 2H), 3.91-3.83 (m, 4H), 3.81 (d, 3H), 3.58 (t, 2H), 3.42 (td, 3H), 3.33-3.24 (m, 5H), 3.00 (q, 4H), 2.68 (dt, 2H), 2.29 (t, 2H), 2.09 (d, 3H), 1.49 (d, 3H), 1.34 (td, 5H), 1.21 (dd, 5H), 1.15-1.07 (m, 2H), 1.07 (s, 4H), 0.95 (q, 1H), 0.82 (d, 6H). MS (ESI) m/e 1402.1 (M+H)⁺.

2.128 Synthesis of 2-[({[2-({3-[(4-{6-[8-(1,3-benzo-thiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1³,⁷]dec-1-yl}oxy)ethyl](2-sulfoethyl)carbamoyl}oxy)methyl]-5-[4-({(2S)-2-(2,5-dioxo-2,5-dihydro-1H-pyrrol-1-yl)-3-[4-(2,5,8,11,14,17,20,23,26,29,32-undecaoxatetratriacontan-34-yloxy)phenyl]propanoyl}amino)butyl]phenyl beta-D-glucopyranosiduronic acid (Synthon TR)

A mixture of Example 2.120.5 (0.035 g), O-(7-azabenzotriazol-1-yl)-N,N,N',N'-tetramethyluronium hexafluorophosphate (0.015 g) and N-ethyl-N-isopropylpropan-2-amine (0.015 mL) was stirred in N,N-dimethylformamide (0.4 mL) for 5 minutes. The mixture was added to a mixture of Example 2.127.1 (0.030 g) and N-ethyl-N-isopropylpropan-2-amine (0.015 mL) in N,N-dimethylformamide (0.4 mL) and stirred at room temperature for 3 hours. The reaction was diluted with a mixture of water (1.5 mL), N,N-dimethylformamide (0.5 mL) and 2,2,2-trifluoroacetic acid (0.034 mL) and purified by preparatory reverse-phase HPLC on a Gilson 2020 system, using a gradient of 5% to 85% acetonitrile/water. The product-containing fractions were lyophilized to give the title compound. $^1$H NMR (400 MHz, dimethyl sulfoxide-$d_6$) δ 12.83 (s, 1H), 8.04-7.93 (m, 2H), 7.76 (d, 1H), 7.58 (dd, 1H), 7.53-7.36 (m, 3H), 7.37-7.25 (m, 3H), 7.15 (d, 1H), 6.97-6.88 (m, 4H), 6.87 (d, 2H), 6.85-6.77 (m, 1H), 6.76-6.69 (m, 2H), 5.13-4.96 (m, 3H), 4.92 (s, 2H), 3.95 (dd, 2H), 3.84 (d, 2H), 3.78 (s, 8H), 3.69-3.60 (m, 2H), 3.47 (d, 38H), 3.48-3.35 (m, 6H), 3.20 (s, 8H), 3.10 (dd, 2H), 2.98 (t, 2H), 2.69-2.60 (m, 2H), 2.50 (d, 1H), 2.06 (s, 3H), 1.49 (t, 2H), 1.35 (s, 4H), 1.21 (d, 4H), 1.05 (s, 6H), 0.79 (d, 6H). MS (ESI) m/e 1991.6 (M−H)⁻.

2.129 Synthesis of (6S)-2,6-anhydro-6-(2-{2-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1³,⁷]dec-1-yl}oxy)ethyl](2-sulfoethyl)carbamoyl}oxy)methyl]-5-[(N-{(2S)-2-(2,5-dioxo-2,5-dihydro-1H-pyrrol-1-yl)-3-[4-(2,5,8,11,14,17,20,23,26,29,32-undecaoxatetratriacontan-34-yloxy)phenyl]propanoyl}-L-valyl-L-alanyl]amino]phenyl}ethyl)-L-gulonic acid (Synthon TY)

A mixture of Example 2.120.5 (0.033 g), O-(7-azabenzotriazol-1-yl)-N,N,N',N'-tetramethyluronium hexafluorophosphate (0.014 g) and N-ethyl-N-isopropylpropan-2-amine (0.015 mL) was stirred in N,N-dimethylformamide (0.4 mL) for 5 minutes. This mixture was added to a mixture of Example 2.123.20 (0.032 g) and N-ethyl-N-isopropylpropan-2-amine (0.015 mL) in N,N-dimethylformamide (0.4 mL) and stirred at room temperature for 3 hours. The reaction was diluted with a mixture of water (1.5 mL), N,N-dimethylformamide (0.5 mL) and 2,2,2-trifluoroacetic acid (0.033 mL) and purified by preparatory reverse-phase HPLC on a Gilson 2020 system, using a gradient of 5% to 85% acetonitrile/water. The product-containing fractions were lyophilized to give the title compound. $^1$H NMR (501 MHz, dimethyl sulfoxide-$d_6$) δ 9.90 (d, 1H), 8.25 (d, 1H), 8.12 (m, 1), 8.01 (m, 1H), 1.78 (m, 1H), 7.59 (d, 1H), 7.53-7.40 (m, 4H), 7.43-7.30 (m, 4H), 7.27 (s, 1H), 7.18 (d, 2H), 7.06 (s, 1H), 7.00 (d, 2H), 6.97-6.91 (m, 2H), 6.87 (s, 2H), 6.76 (d, 2H), 5.02-4.92 (m, 4H), 4.77 (dd, 1H), 4.20 (t, 1H), 3.98 (dd, 2H), 3.86 (t, 2H), 3.78 (d, 2H), 3.70-3.65 (m, 2H), 3.54 (s, 2H), 3.55-3.45 (m, 38H), 3.45-3.37 (m, 2H), 3.35-3.25 (m, 2H), 3.21 (s, 4H), 3.17-3.06 (m, 2H), 2.99 (t, 2H), 2.73 (s, 2H), 2.61 (s, 4H), 2.07 (d, 4H), 2.01 (s, 2H), 1.94 (s, 2H), 1.54 (s, 2H), 1.27 (d, 4H), 1.22 (s, 2H), 1.11 (s, 6H), 1.08-0.99 (m, 2H), 0.90-0.79 (m, 6H), 0.76 (d, 6H). MS (ESI) m/e 705.6 (M−3H)³⁻.

2.130 Synthesis of 6-(8-(benzo[d]thiazol-2-ylcarbamoyl)-3,4-dihydroisoquinolin-2(1H)-yl)-3-(1-((3-(2-((((2-(2-((2S,3R,4R,5S,6S)-6-carboxy-3,4,5-trihydroxytetrahydro-2H-pyran-2-yl)ethyl)-4-((S)-2-((S)-2-(2-((3S,5S)-3-(2,5-dioxo-2,5-dihydro-1H-pyrrol-1-yl)-2-oxo-5-((2-sulfoethoxy)methyl)pyrrolidin-1-yl)acetamido)-3-methylbutanamido)propanamido)benzyl)oxy)carbonyl)(2-sulfoethyl)amino)ethoxy)-5,7-dimethyladamantan-1-yl)methyl)-5-methyl-1H-pyrazol-4-yl)picolinic acid (Synthon TX)

The title compound was prepared by substituting Example 2.123.20 for Example 2.119.16 in Example 2.119.17. $^1$H NMR (400 MHz, dimethyl sulfoxide-$d_6$) δ ppm 9.85 (s, 1H), 8.17 (br d, 1H), 8.01 (d, 2H), 7.77 (d, 1H), 7.59 (d, 1H), 7.53 (d, 1H), 7.43 (m, 4H), 7.34 (m, 3H), 7.19 (d, 1H), 7.06 (s, 2H), 6.96 (d, 1H), 4.99 (m, 2H), 4.95 (s, 2H), 4.63 (t, 1H), 4.36 (t, 1H), 4.19 (br m, 1H), 4.16 (d, 1H), 3.98 (d, 1H), 3.87 (br t, 2H), 3.81 (br d, 2H), 3.73 (brm, 1H), 3.63 (t, 2H), 3.53 (m, 2H), 3.44 (m, 4H), 3.31 (t, 2H), 3.21 (br m, 2H), 3.17 (m, 2H), 3.00 (m, 2H), 2.92 (br m, 1H), 2.75 (m, 3H), 2.65 (br m, 3H), 2.35 (br m, 1H), 2.07 (s, 3H), 1.98 (br m, 2H), 1.85 (m, 1H), 1.55 (br m, 1H), 1.34 (br m, 1H), 1.26 (br m, 6H), 1.09 (br m, 7H), 0.93 (br m, 1H), 0.87, 0.83, 0.79 (all d, total 12H). MS (ESI) m/e 1733.4 (M−H)⁻.

2.131 Synthesis of 6-(8-(benzo[d]thiazol-2-ylcarbamoyl)-3,4-dihydroisoquinolin-2(1H)-yl)-3-(1-((3-(2-((((2-(((2S,3R,4S,5S,6S)-6-carboxy-3,4,5-trihydroxytetrahydro-2H-pyran-2-yl)oxy)-4-(4-(2-((3S,5S)-3-(2,5-dioxo-2,5-dihydro-1H-pyrrol-1-yl)-2-oxo-5-((2-sulfoethoxy)methyl)pyrrolidin-1-yl)acetamido)butyl)benzyl)oxy)carbonyl)(2-sulfoethyl)amino)ethoxy)-5,7-dimethyladamantan-1-yl)methyl)-5-methyl-1H-pyrazol-4-yl)picolinic acid (Synthon TZ)

The title compound was prepared by substituting Example 2.127.1 for Example 2.119.16 in Example 2.119.17. $^1$H NMR (500 MHz, dimethyl sulfoxide-$d_6$) δ ppm 8.02 (d, 1H), 7.82 (br t, 1H), 7.77 (d, 1H), 7.60 (d, 1H), 7.53 (br d, 1H), 7.45 (d, 1H), 7.42 (d, 1H), 7.36 (d, 1H), 7.35 (s, 1H), 7.33 (m, 1H), 7.15 (d, 1H), 7.05 (s, 2H), 6.97 (d, 1H), 6.94 (s, 1H), 6.83 (d, 1H), 5.07 (br m, 2H), 5.00 (d, 1H), 4.95 (s, 2H), 4.69 (t, 1H), 4.04 (d, 2H), 3.87 (m, 3H), 3.82 (m, 3H), 3.73 (br m, 1H), 3.61 (m, 2H), 3.47 (br m, 3H), 3.40 (m, 4H), 3.29 (m, 4H), 3.06 (br m, 2H), 3.00 (t, 2H), 2.73 (br m, 2H) 2.69 (br m, 2H), 2.52 (br t, 2H), 2.35 (br m, 1H), 2.08 (s, 3H), 1.81 (m, 1H), 1.53 (br m, 2H), 1.40 (m, 2H), 1.35 (br m, 2H), 1.29-0.88 (br m, 10H), 0.82, 0.80 (both s, total 6H). MS (ESI−) m/e 1607.5 (M−H)⁻.

2.132 Synthesis of 2-[({[2-({3-[(4-{6-[8-(1,3-benzo-thiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1³,⁷]dec-1-yl}oxy)ethyl](2-sulfoethyl)carbamoyl}oxy)methyl]-5-(4-{[(2,5-dioxo-2,5-dihydro-1H-pyrrol-1-yl)acetyl]amino}butyl)phenyl beta-D-glucopyranosiduronic acid (Synthon UA)

To a mixture of Example 2.127.1 (0.032 g) in N,N-dimethylformamide (0.4 mL) was added N-ethyl-N-isopropylpropan-2-amine (0.025 mL), and the mixture cooled to 0° C. 2,5-Dioxopyrrolidin-1-yl 2-(2,5-dioxo-2,5-dihydro-1H-pyrrol-1-yl)acetate (8.86 mg) was added in one portion and stirred at 0° C. for 45 minutes. The reaction was diluted with a mixture of water (1.5 mL), N,N-dimethylformamide (0.5 mL) and 2,2,2-trifluoroacetic acid (0.036 mL) and was purified by preparatory reverse-phase HPLC on a Gilson 2020 system, using a gradient of 5% to 75% acetonitrile/water. The product-containing fractions were lyophilized to give the title compound. $^1$H NMR (501 MHz, dimethyl sulfoxide-$d_6$) δ 12.86 (s, 1H), 8.06 (s, 1H), 8.02 (dd, 1H), 7.77 (d, 1H), 7.60 (dd, 1H), 7.51 (dd, 1H), 7.49-7.39 (m, 2H), 7.38-7.28 (m, 3H), 7.17 (dd, 1H), 7.06 (d, 2H), 6.98-6.89 (m, 2H), 6.83 (d, 1H), 5.13-5.03 (m, 2H), 5.04-4.96 (m, 1H), 4.94 (s, 2H), 3.97 (s, 2H), 3.90-3.77 (m, 6H), 3.50 (s, 1H), 3.50-3.41 (m, 2H), 3.41 (dt, 3H), 3.28 (dt, 4H), 3.06-2.96 (m, 4H), 2.66 (dt, 2H), 2.51 (s, 2H), 2.08 (d, 3H), 1.52 (s, 2H), 1.42-1.32 (m, 4H), 1.23 (d, 4H), 1.11 (q, 2H), 1.06 (s, 4H), 0.81 (d, 6H). MS (ESI) m/e 1388.0 (M+H)$^+$.

2.133 Synthesis of 2-[({[2-({3-[(4-{6-[8-(1,3-benzothiazol-2-ylcarbamoyl)naphthalen-2-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]-5-(4-{[(2,5-dioxo-2,5-dihydro-1H-pyrrol-1-yl)acetyl]amino}butyl)phenyl beta-D-glucopyranosiduronic acid (Synthon UZ)

2.133.1 3-(1-((3-(2-((((4-(4-aminobutyl)-2-(((2S,3R,4S,5S,6S)-6-carboxy-3,4,5-trihydroxytetrahydro-2H-pyran-2-yl)oxy)benzyl)oxy)carbonyl)(2-sulfoethyl)amino)ethoxy)-5,7-dimethyladamantan-1-yl)methyl)-5-methyl-1H-pyrazol-4-yl)-6-(8-(benzo[d]thiazol-2-ylcarbamoyl)naphthalen-2-yl)picolinic acid To a mixture of Example 2.124.5 (0.060 g), Example 1.43.7 (0.056 g) and 1H-benzo[d][1,2,3]triazol-1-ol (8 mg) in dimethyl sulfoxide (0.5 mL) was added N-ethyl-N-isopropylpropan-2-amine (0.056 mL), and the reaction was stirred at room temperature for 3 hours. The reaction was treated with a mixture of lithium hydroxide hydrate (0.026 g) in water (1 mL) and stirred for 30 minutes. Methanol (0.5 mL) was added to the reaction and stirring was continued for 30 minutes. Diethylamine (0.033 mL) was added to the reaction and stirring was continued overnight. The reaction was quenched with 2,2,2-trifluoroacetic acid (0.120 mL) and purified by preparatory reverse-phase HPLC on a Gilson 2020 system, using a gradient of 5% to 75% acetonitrile/water. The product-containing fractions were lyophilized to give the title compound. MS (ESI) m/e 1247.7 (M+H)$^+$.

2.133.2 2-[({[2-({3-[(4-{6-[8-(1,3-benzothiazol-2-ylcarbamoyl)naphthalen-2-yl]-2-carboxypyridin-3-yl}-5-methyl-1H-pyrazol-1-yl)methyl]-5,7-dimethyltricyclo[3.3.1.13,7]dec-1-yl}oxy)ethyl](2-sulfoethyl)carbamoyl}oxy)methyl]-5-(4-{[(2,5-dioxo-2,5-dihydro-1H-pyrrol-1-yl)acetyl]amino}butyl)phenyl beta-D-glucopyranosiduronic acid To a mixture of Example 2.133.1 (0.030 g) in N,N-dimethylformamide (0.400 mL) was added N-ethyl-N-isopropylpropan-2-amine (0.023 mL) and the mixture was cooled to 0° C. 2,5-Dioxopyrrolidin-1-yl 2-(2,5-dioxo-2,5-dihydro-1H-pyrrol-1-yl)acetate (8.34 mg) was added in one portion and he mixture was stirred at 0° C. for 30 minutes. The reaction was diluted with a mixture of water (1.5 mL), N,N-dimethylformamide (0.5 mL) and 2,2,2-trifluoroacetic acid (0.034 mL) and was purified by preparatory reverse-phase HPLC on a Gilson 2020 system, using a gradient of 5% to 75% acetonitrile/water. The product-containing fractions were lyophilized to give the title compound. $^1$H NMR (400 MHz, dimethyl sulfoxide-$d_6$) δ 13.08 (s, 1H), 9.01 (s, 1H), 8.39-8.31 (m, 1H), 8.25-8.11 (m, 3H), 8.06 (d, 2H), 7.99 (d, 1H), 7.94 (d, 1H), 7.79 (d, 1H), 7.68 (t, 1H), 7.51-7.42 (m, 1H), 7.46 (s, 1H), 7.35 (t, 1H), 7.22-7.13 (m, 1H), 7.06 (d, 2H), 6.93 (d, 1H), 6.83 (d, 1H), 5.15-5.00 (m, 2H), 4.99 (d, 1H), 3.97 (s, 2H), 3.86 (d, 3H), 3.42 (d, 4H), 3.29 (d, 5H), 3.03 (p, 2H), 2.72-2.62 (m, 2H), 2.51 (d, 3H), 2.21 (s, 3H), 1.51 (q, 2H), 1.37 (q, 4H), 1.24 (d, 4H), 1.10 (s, 5H), 0.83 (d, 6H), 0.61 (s, 2H). MS (ESI) m/e 1383.0 (M+H)$^+$.

2.134 Synthesis of 2-[({[2-({3-[(4-{6-[8-(1,3-benzothiazol-2-ylcarbamoyl)naphthalen-2-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]-5-[4-({(2S)-2-(2,5-dioxo-2,5-dihydro-1H-pyrrol-1-yl)-3-[4-(2,5,8,11,14,17,20,23,26,29,32-undecaoxatetratriacontan-34-yloxy)phenyl]propanoyl}amino)butyl]phenyl beta-D-glucopyranosiduronic acid (Synthon UK)

A mixture of Example 2.120.5 (0.028 g), O-(7-azabenzotriazol-1-yl)-N,N,N',N'-tetramethyluronium hexafluorophosphate (0.013 g) and N-ethyl-N-isopropylpropan-2-amine (0.015 mL) were stirred in N,N-dimethylformamide (0.4 mL) for 5 minutes. The mixture was added to a mixture of Example 2.133.1 (0.030 g) and N-ethyl-N-isopropylpropan-2-amine (0.015 mL) in N,N-dimethylformamide (0.4 mL) and was stirred at room temperature for 1 hour. The reaction was diluted with a mixture of water (1.5 mL), N,N-dimethylformamide (0.5 mL) and 2,2,2-trifluoroacetic acid (0.042 mL) and was purified by preparatory reverse-phase HPLC on a Gilson 2020 system, using a gradient of 5% to 75% acetonitrile/water. The product-containing fractions were lyophilized to give the title compound. $^1$H NMR (400 MHz, dimethyl sulfoxide-$d_6$) δ 9.01 (s, 1H), 8.35 (dd, 1H), 8.27-8.13 (m, 3H), 8.06 (d, 1H), 8.00 (d, 1H), 7.94 (d, 1H), 7.79 (d, 1H), 7.73-7.64 (m, 1H), 7.53-7.43 (m, 2H), 7.42-7.32 (m, 1H), 7.17 (d, 1H), 7.06 (s, 1H), 7.04-6.91 (m, 3H), 6.89 (d, 2H), 6.83 (d, 1H), 6.74 (d, 1H), 5.16-4.93 (m, 4H), 4.63 (dd, 2H), 3.96 (t, 2H), 3.86 (d, 4H), 3.66 (s, 4H), 3.55-3.46 (m, 36H), 3.45-3.35 (m, 8H), 3.35-3.24 (m, 6H), 3.21 (s, 2H), 3.11 (s, 2H), 2.99 (d, 2H), 2.83-2.59 (m, 3H), 2.52 (d, 2H), 2.21 (s, 3H), 1.57-0.86 (m, 14H), 0.83 (d, 4H). MS (ESI) m/e 1986.6 (M−H)$^−$.

2.135 Synthesis of N-[(2,5-dioxo-2,5-dihydro-1H-pyrrol-1-yl)acetyl]-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]-3-(4-carboxybutyl)phenyl}-L-alaninamide (Synthon UU)

2.135.1 methyl 4-((tert-butoxycarbonyl)amino)-2-iodobenzoate

3-Iodo-4-(methoxycarbonyl)benzoic acid (9 g) was dissolved in tert-butanol (100 mL), and diphenyl phosphorazidate (7.6 mL) and triethylamine (4.9 mL) were added. The mixture was heated to 83° C. (internal temperature) overnight. The mixture was concentrated to dryness and purified by flash chromatography, eluting with a gradient of 0% to 20% ethyl acetate in heptane to give the title compound. MS (ESI) m/e 377.9 (M+H)+.

2.135.2 methyl 4-amino-2-iodobenzoate

Example 2.135.1 (3 g) was stirred in dichloromethane (30 mL) and trifluoroacetic acid (10 mL) at room temperature for 1.5 hours. The reaction was concentrated to dryness and partitioned between water (adjusted to pH 1 with hydrochloric acid) and diethyl ether. The layers were separated, and the aqueous layer was washed with aqueous sodium bicarbonate mixture, dried over sodium sulfate, filtered and concentrated to dryness. The resulting solid was triturated with toluene to give the title compound. MS (ESI) m/e 278.0 (M+H)+.

2.135.3 methyl 4-((S)-2-((S)-2-((((9H-fluoren-9-yl)methoxy)carbonyl)amino)-3-methylbutanamido)propanamido)-2-iodobenzoate A flask was charged with Example 2.135.2 (337 mg) and Example 2.123.14 (500 mg). Ethyl acetate (18 mL) was added followed by pyridine (0.296 mL). The resulting suspension was chilled in an ice bath, and 2,4,6-tripropyl-1,3,5,2,4,6-trioxatriphosphinane 2,4,6-trioxide (50% mixture in ethyl acetate, 1.4 mL) was added dropwise. Stirring was continued at 0° C. for 45 minutes, and the reaction was placed in a −20° C. freezer overnight. The reaction was allowed to warm to room temperature and was quenched with water. The layers were separated, and the aqueous layer was extracted twice more with ethyl acetate. The combined extracts were dried with anhydrous sodium sulfate, filtered and concentrated. The residue was dissolved in dichloromethane and diluted with diethyl ether to precipitate the title compound, which was collected by filtration. MS (ESI) m/e 669.7 (M+H)+.

2.135.4 (9H-fluoren-9-yl)methyl ((S)-1-(((S)-1-((4-(hydroxymethyl)-3-iodophenyl)amino)-1-oxopropan-2-yl)amino)-3-methyl-1-oxobutan-2-yl)carbamate Example 2.54.3 (1 g) was dissolved in tetrahydrofuran (15 mL), and the mixture was chilled to −15° C. in an ice-acetone bath. Lithium aluminum hydride (1N in tetrahydrofuran, 3 mL) was then added dropwise, keeping the temperature below −10° C. The reaction was stirred for 1 hour and carefully quenched with 10% citric acid (25 mL). The layers were separated, and the aqueous layer was extracted thrice with ethyl acetate. The combined organic layers were washed with water and brine, dried over anhydrous sodium sulfate, filtered and concentrated. The residue was adsorbed onto silica gel and purified by flash chromatography, eluting with a gradient of 5% to 6% methanol in dichloromethane, to give the title compound. MS (ESI) m/e 664.1 (M+H)+.

2.135.5 methyl 5-(5-((S)-2-((S)-2-((((9H-fluoren-9-yl)methoxy)carbonyl)amino)-3-methylbutanamido)propanamido)-2-(hydroxymethyl)phenyl)pent-4-ynoate To a stirred mixture of methyl pent-4-ynoate (50 mg), Example 2.135.4 (180 mg) and N,N-diisopropylethylamine (0.15 mL) in N,N-dimethylformamide (2 mL) was added bis(triphenylphosphine)palladium(II) dichloride (20 mg) and copper iodide (5 mg). The mixture was purged with nitrogen three times and stirred at room temperature overnight. The reaction was diluted with ethyl acetate and washed with water and brine. The aqueous layers were back extracted with ethyl acetate. The combined organic layers were dried over sodium sulfate, filtered and concentrated. The residue was purified by reverse-phase HPLC on a Gilson system, eluting with 20-90% acetonitrile in water containing 0.1% v/v trifluoroacetic acid. The desired fractions were combined and freeze-dried to provide the title compound. MS (ESI) m/e 608.0 (M−H$_2$O)+.

2.135.6 methyl 5-(5-((S)-2-((S)-2-((((9H-fluoren-9-yl)methoxy)carbonyl)amino)-3-methylbutanamido)propanamido)-2-(hydroxymethyl)phenyl)pentanoate A mixture of Example 2.135.5 (0.084 g) and 10% Pd/C (0.02 g) in tetrahydrofuran (5 mL) was stirred at 20° C. under an atmosphere of 50 psi H$_2$ for 1 hour. The reaction mixture was filtered through diatomaceous earth, and the solvent was evaporated under reduced pressure to provide the title compound. MS (ESI) m/e 612.0 (M−H$_2$O)+.

2.135.7 methyl 5-(5-((S)-2-((S)-2-((((9H-fluoren-9-yl)methoxy)carbonyl)amino)-3-methylbutanamido)propanamido)-2-((((4-nitrophenoxy)carbonyl)oxy)methyl)phenyl)pentanoate Example 2.135.7 was prepared by substituting Example 2.135.7 for Example 2.55.6 in Example 2.55.7. MS (ESI) m/e 795.4 (M+H)+.

2.135.8 3-(1-((3-(2-((((4-((S)-2-((S)-2-amino-3-methylbutanamido)propanamido)-2-(4-carboxybutyl)benzyl)oxy)carbonyl)(2-sulfoethyl)amino)ethoxy)-5,7-dimethyladamantan-1-yl)methyl)-5-methyl-1H-pyrazol-4-yl)-6-(8-(benzo[d]thiazol-2-ylcarbamoyl)-3,4-dihydroisoquinolin-2(1H)-yl)picolinic acid Example 2.135.8 was prepared by substituting 2.135.7 for (9H-fluoren-9-yl)methyl ((S)-3-methyl-1-(((S)-1-((4-((((4-nitrophenoxy)carbonyl)oxy)methyl)phenyl)amino)-1-oxo-5-ureidopentan-2-yl)amino)-1-oxobutan-2-yl)carbamate in Example 2.49.1. MS (ESI) m/e 1271.4 (M−H)−.

2.135.9 N-[(2,5-dioxo-2,5-dihydro-1H-pyrrol-1-yl)acetyl]-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.13,7]dec-1-yl}oxy)ethyl](2-sulfoethyl)carbamoyl}oxy)methyl]-3-(4-carboxybutyl)phenyl}-L-alaninamide Example 2.135.9 was prepared by substituting 2.135.8 for Example 2.49.1 in Example 2.54. $^1$H NMR (400 MHz, dimethyl sulfoxide-d$_6$) δ ppm 9.88 (d, 1H), 8.3-8.2 (m, 2H), 8.01 (dd, 1H), 7.77 (d, 1H), 7.59 (dd, 1H), 7.52 (dd, 1H), 7.47-7.29 (m, 8H), 7.23-7.18 (m, 1H), 7.05 (s, 2H), 6.95 (d, 1H), 5.00 (d, 2H), 4.94 (s, 2H), 4.37 (p, 1H), 3.51-3.28 (m, 5H), 3.26-3.14 (m, 2H), 2.99 (t, 2H), 2.65 (t, 2H), 2.57 (s, 2H), 2.26-2.17 (m, 3H), 2.07 (d, 3H), 1.94 (dd, 1H), 1.61-0.69 (m, 35H). MS (ESI) m/e 1408.5 (M−H)+.

2.136 Synthesis of 2-[({[2-({3-[(4-{6-[8-(1,3-benzo-thiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]-5-(3-{[(2,5-dioxo-2,5-dihydro-1H-pyrrol-1-yl)acetyl]amino}propyl)phenyl beta-D-glucopyranosiduronic acid (Synthon UV)

2.136.1 (3R,4S,5S,6S)-2-(5-(3-((((9H-fluoren-9-yl)methoxy)carbonyl)amino)prop-1-yn-1-yl)-2-formylphenoxy)-6-(methoxycarbonyl)tetrahydro-2H-pyran-3,4,5-triyl triacetate Example 2.136.1 was prepared by substituting (9H-fluoren-9-yl)methyl prop-2-yn-1-ylcarbamate for 2.124.1A in Example 2.124.2. MS (ESI) m/e 714.1 (M+H)$^+$.

2.136.2 (2S,3R,4S,5S,6S)-2-(5-(3-((((9H-fluoren-9-yl)methoxy)carbonyl)amino)propyl)-2-formylphenoxy)-6-(methoxycarbonyl)tetrahydro-2H-pyran-3,4,5-triyl triacetate Example 2.136.2 was prepared by substituting 2.136.1 for 2.124.2 in Example 2.124.3. MS (ESI) m/e 718.5 (M+H)$^+$.

2.136.3 (2S,3R,4S,5S,6S)-2-(5-(3-((((9H-fluoren-9-yl)methoxy)carbonyl)amino)propyl)-2-(hydroxymethyl)phenoxy)-6-(methoxycarbonyl)tetrahydro-2H-pyran-3,4,5-triyl triacetate Example 2.136.3 was prepared by substituting 2.136.2 for 2.124.3 in Example 2.124.4. MS (ESI) m/e 742.2 (M+Na)$^+$.

2.136.4 (2S,3R,4S,5S,6S)-2-(5-(3-((((9H-fluoren-9-yl)methoxy)carbonyl)amino)propyl)-2-((((4-nitrophenoxy)carbonyl)oxy)methyl)phenoxy)-6-(methoxycarbonyl)tetrahydro-2H-pyran-3,4,5-triyl triacetate Example 2.136.4 was prepared by substituting 2.136.3 for 2.124.4 in Example 2.124.5. MS (ESI) m/e 885.2 (M+Na)$^+$.

2.136.5 3-(1-((3-(2-((((4-(3-aminopropyl)-2-(((3R,4S,5S,6S)-6-carboxy-3,4,5-trihydroxytetrahydro-2H-pyran-2-yl)oxy)benzyl)oxy)carbonyl)(2-sulfoethyl)amino)ethoxy)-5,7-dimethyladamantan-1-yl)methyl)-5-methyl-1H-pyrazol-4-yl)-6-(8-(benzo[d]thiazol-2-ylcarbamoyl)-3,4-dihydroisoquinolin-2(1H)-yl)picolinic acid Example 2.136.5 was prepared by substituting Example 2.136.4 for (9H-fluoren-9-yl)methyl ((S)-3-methyl-1-(((S)-1-((4-(((((4-nitrophenoxy)carbonyl)oxy)methyl)phenyl)amino)-1-oxo-5-ureidopentan-2-yl)amino)-1-oxobutan-2-yl)carbamate in Example 2.49.1. MS (ESI) m/e 1237.7 (M+H)$^+$.

2.136.6 2-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.13,7]dec-1-yl}oxy)ethyl](2-sulfoethyl)carbamoyl}oxy)methyl]-5-(3-{[(2,5-dioxo-2,5-dihydro-1H-pyrrol-1-yl)acetyl]amino}propyl)phenyl beta-D-glucopyranosiduronic acid Example 2.136.6 was prepared by substituting Example 2.136.5 for Example 2.49.1 in Example 2.54. $^1$H NMR (400 MHz, dimethyl sulfoxide-d$_6$) δ ppm 8.14 (d, 1H), 8.01 (d, 1H), 7.59 (d, 1H), 7.53-7.39 (m, 4H), 7.38-7.28 (m, 3H), 7.22-7.15 (m, 2H), 7.13-6.91 (m, 5H), 6.84 (d, 1H), 5.17-4.91 (m, 5H), 3.35-3.2 (m, 4H), 3.10-2.90 (m, 4H), 2.75-2.65 (m, 2H), 2.08 (s, 3H), 1.65 (s, 2H), 1.39-0.71 (m, 21H). MS (ESI) m/e 1372.3 (M−H)$^-$.

2.137 Synthesis of 6-[8-(1,3-benzothiazol-2-ylcarbamoyl)-3,4-dihydroisoquinolin-2(1H)-yl]-3-{1-[(3-{2-[({[2-{[(2S,3R,4S,5S,6S)-6-carboxy-3,4,5-trihydroxytetrahydro-2H-pyran-2-yl]oxy}-4-(4-{[(2,5-dioxo-2,5-dihydro-1H-pyrrol-1-yl)acetyl]amino}butyl)benzyl]oxy}carbonyl)(3-{[1,3-dihydroxy-2-(hydroxymethyl)propan-2-yl]amino}-3-oxopropyl)amino]ethoxy}-5,7-dimethyltricyclo[3.3.1.1$^{3,7}$]dec-1-yl)methyl]-5-methyl-1H-pyrazol-4-yl}pyridine-2-carboxylic acid (Synthon UZ)

2.137.1 3-(1-((3-(2-((((4-(4-aminobutyl)-2-(((2R,3S,4R,5R,6R)-6-carboxy-3,4,5-trihydroxytetrahydro-2H-pyran-2-yl)oxy)benzyl)oxy)carbonyl)(3-((1,3-dihydroxy-2-(hydroxymethyl)propan-2-yl)amino)-3-oxopropyl)amino)ethoxy)-5,7-dimethyladamantan-1-yl)methyl)-5-methyl-1H-pyrazol-4-yl)-6-(8-(benzo[d]thiazol-2-ylcarbamoyl)-3,4-dihydroisoquinolin-2(1H)-yl)picolinic acid The title compound was prepared as described in Example 2.124.6, replacing Example 1.87.3 with Example 1.84. MS (ESI) m/e 1319.4 (M−H)$^-$.

2.137.2 6-[8-(1,3-benzothiazol-2-ylcarbamoyl)-3,4-dihydroisoquinolin-2(1H)-yl]-3-{1-[(3-{2-[({[2-{[(2S,3R,4S,5S,6S)-6-carboxy-3,4,5-trihydroxytetrahydro-2H-pyran-2-yl]oxy}-4-(4-{[(2,5-dioxo-2,5-dihydro-1H-pyrrol-1-yl)acetyl]amino}butyl)benzyl]oxy}carbonyl)(3-{[1,3-dihydroxy-2-(hydroxymethyl)propan-2-yl]amino}-3-oxopropyl)amino]ethoxy}-5,7-dimethyltricyclo[3.3.1.13,7]dec-1-yl)methyl]-5-methyl-1H-pyrazol-4-yl}pyridine-2-carboxylic acid The title compound was prepared as described in Example 2.54, replacing Example 2.49.1 with Example 2.137.1. $^1$H NMR (501 MHz, dimethyl sulfoxide-d$_6$) δ ppm 12.83 (s, 2H), 8.12 (s, OH), 8.06 (s, 1H), 8.03-7.99 (m, 1H), 7.77 (d, 1H), 7.72 (s, OH), 7.60 (d, 1H), 7.52-7.39 (m, 3H), 7.34 (td, 2H), 7.26 (s, 1H), 7.21-7.11 (m, 2H), 7.05 (s, 2H), 6.93 (d, 2H), 6.83 (d, 1H), 5.09 (d, 2H), 5.00 (d, 1H), 4.94 (s, 2H), 4.12 (t, 1H), 3.97 (s, 2H), 3.87 (q, 4H), 3.79 (d, 2H), 3.29 (q, 2H), 3.12-2.93 (m, 5H), 2.47-2.23 (m, 1H), 2.07 (d, 3H), 1.50 (d, 3H), 1.36 (d, 5H), 1.31-0.85 (m, 9H), 0.81 (d, 7H). MS (ESI) m/e 1568.4 (M−H)$^-$.

2.138 Synthesis of 6-(8-(benzo[d]thiazol-2-ylcarbamoyl)naphthalen-2-yl)-3-(1-((3-(2-((((2-(((2S,3R,4S,5S,6S)-6-carboxy-3,4,5-trihydroxytetrahydro-2H-pyran-2-yl)oxy)-4-(2-((3S,5S)-3-(2,5-dioxo-2,5-dihydro-1H-pyrrol-1-yl)-2-oxo-5-((2-sulfoethoxy)methyl)pyrrolidin-1-yl)acetamido)butyl)benzyl)oxy)carbonyl)(2-sulfoethyl)amino)ethoxy)-5,7-dimethyladamantan-1-yl)methyl)-5-methyl-1H-pyrazol-4-yl)picolinic acid (Synthon VB)

The title compound was prepared by substituting Example 2.133.1 for Example 2.119.16 in Example 2.119.17. $^1$H NMR (400 MHz, dimethyl sulfoxide-d$_6$) δ ppm 8.99 (s, 1H), 8.34 (dd, 1H), 8.19 (d, 1H), 8.17 (d, 1H), 8.13 (d, 1H), 8.04 (d, 1H), 7.97 (d, 1H), 7.93 (d, 1H), 7.80 (br t, 1H), 7.77 (d, 1H), 7.67 (dd, 1H), 7.45 (s, 1H), 7.45 (dd, 1H), 7.34 (dd, 1H), 7.14 (d, 1H), 7.03 (s, 2H), 6.93 (s, 1H), 6.82 (br d, 1H), 5.06 (br m, 2H), 4.98 (d, 1H), 4.67 (t, 1H), 4.02 (d, 2H), 3.85 (m, 3H), 3.71 (br m, 1H), 3.59 (t, 2H), 3.45 (br m, 3H), 3.41 (m, 4H), 3.27 (m, 4H), 3.03 (m, 2H), 2.70 (m, 2H) 2.65 (br m, 2H), 2.50 (br t, 2H), 2.31 (br m, 1H), 2.19 (s, 3H), 1.80 (m, 1H), 1.52 (br m, 2H), 1.38 (m, 2H), 1.35 (br m, 2H), 1.29-0.88 (br m, 10H), 0.82 (s, 3H), 0.80 (s, 3H). MS (ESI) m/e 1602.4 (M−H)⁻.

2.139 Synthesis of 2-[({2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl][3-hydroxy-2-(hydroxymethyl)propyl]carbamoyl}oxy)methyl]-5-(3-{[(2,5-dioxo-2,5-dihydro-1H-pyrrol-1-yl)acetyl]amino}propyl)phenyl beta-D-glucopyranosiduronic acid (Synthon VC)

2.139.1 3-(1-((3-(2-(((((4-(3-aminopropyl)-2-(((2S,3R,4S,5S,6S)-6-carboxy-3,4,5-trihydroxytetrahydro-2H-pyran-2-yl)oxy)benzyl)oxy)carbonyl)(3-hydroxy-2-(hydroxymethyl)propyl)amino)ethoxy)-5,7-dimethyladamantan-1-yl)methyl)-5-methyl-1H-pyrazol-4-yl)-6-(8-(benzo[d]thiazol-2-ylcarbamoyl)-3,4-dihydroisoquinolin-2(1H)-yl)picolinic acid Example 2.139.1 was prepared by substituting Example 2.136.4 for (9H-fluoren-9-yl)methyl ((S)-3-methyl-1-(((S)-1-((4-(((((4-nitrophenoxy)carbonyl)oxy)methyl)phenyl)amino)-1-oxo-5-ureidopentan-2-yl)amino)-1-oxobutan-2-yl)carbamate and substituting Example 1.79.3 for Example 1.2.9 in Example 2.49.1. MS (ESI) m/e 1217.7 (M+H)⁺.

2.139.2 2-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.13,7]dec-1-yl}oxy)ethyl][3-hydroxy-2-(hydroxymethyl)propyl]carbamoyl}oxy)methyl]-5-(3-{[(2,5-dioxo-2,5-dihydro-1H-pyrrol-1-yl)acetyl]amino}propyl)phenyl beta-D-glucopyranosiduronic acid Example 2.139.1 was prepared by substituting Example 2.139.1 for Example 2.49.1 in Example 2.54. ¹H NMR (400 MHz, dimethyl sulfoxide-d₆) δ ppm 12.84 (s, 2H), 8.11 (t, 1H), 8.00 (dd, 1H), 7.76 (d, 1H), 7.62-7.56 (m, 1H), 7.50-7.37 (m, 3H), 7.37-7.29 (m, 2H), 7.25 (s, 1H), 7.16 (d, 1H), 7.04 (s, 2H), 6.96-6.88 (m, 2H), 6.82 (d, 1H), 5.06 (s, 2H), 4.98 (d, 1H), 4.92 (s, 2H), 3.97 (s, 2H), 3.44-3.18 (m, 11H), 3.07-2.90 (m, 4H), 2.05 (s, 3H), 1.80 (s, 1H), 1.64 (p, 2H), 1.38-0.67 (m, 19H). (m, 21H). MS (ESI) m/e 1352.5 (M−H)⁻.

2.140 Synthesis of N-({(3S,5S)-3-(2,5-dioxo-2,5-dihydro-1H-pyrrol-1-yl)-2-oxo-5-[(2-sulfoethoxy)methyl]pyrrolidin-1-yl}acetyl)-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]-3-(2,5,8,11,14,17,20,23,26,29,32,35,38,41,44,47,50-heptadecaoxatripentacont-52-yn-53-yl)phenyl}-L-alaninamide (Synthon VS)

2.140.1 2-iodo-4-nitrobenzoic acid

2-Amino-4-nitrobenzoic acid (50 g) was added to a mixture of concentrated H₂SO₄ (75 mL) and water (750 mL) at 0° C., and the mixture was stirred for 1 hour. To the mixture was added a mixture of sodium nitrite (24.62 g) in water (300 mL) dropwise at 0° C. The resulting mixture was stirred at 0° C. for 3 hours. A mixture of sodium iodide (65.8 g) in water (300 mL) was added to above mixture slowly. After the completion of the addition, the resulting mixture was stirred at 0° C. for 2 hours, then at room temperature for 16 hours and at 60° C. for 2 hours. The resulting mixture was cooled to room temperature and diluted with ice-water (300 mL). The solid was collected by filtration, washed by water (100 mL×5), and dried in air for 16 hours to give the title compound. MS (LC-MS) m/e 291.9 (M−H)⁻.

2.140.2 methyl 2-iodo-4-nitrobenzoate

A mixture of Example 2.140.1 (130 g) in a mixture of methanol (1000 mL) and sulfuric acid (23.65 mL) was stirred at 85° C. for 16 hours and concentrated to dryness. The residue was triturated with methanol (100 mL) and the suspension was stirred for 10 minutes. The solid was collected by filtration, washed with water (200 mL×3) and methanol (20 mL), and air-dried for 16 hours to give the title compound. MS (LC-MS) m/e 308.0 (M+H)⁺.

2.140.3 methyl 4-amino-2-iodobenzoate

To a mixture of ammonium chloride (122 g) and iron (38.2 g) in ethanol (1000 mL) and water (100 mL) was added Example 2.140.2 (70 g) at room temperature. The mixture was stirred at 80° C. for 4 hours and filtered to remove insoluble material. The filtrate was concentrated under reduced pressure. The residue was dissolved in ethyl acetate (1000 mL) and washed with water (500 mL). The aqueous phase was extracted with ethyl acetate (1000 mL×2). The combined organic phase was washed with brine, dried over MgSO₄, filtered and concentrated to give the title compound. MS (LC-MS) m/e 278.0 (M+H)⁺.

2.140.4 (4-amino-2-iodophenyl)methanol

To a mixture of Example 2.140.3 (40 g) in tetrahydrofuran (800 mL) was added 1M diisobutylaluminum hydride (505 mL) dropwise at −50° C. The mixture was stirred at −50° C. for 3 hours and cooled to −20° C. Ice-water (180 mL) was added dropwise (keeping temperature below 0° C.) to the mixture. After the addition of ice-water, the mixture was stirred for 10 minutes and filtered. The filtrate was concentrated, and the residue was dissolved in ethyl acetate (800 mL) and water (200 mL). The aqueous phase was extracted with ethyl acetate (300 mL×2). The combined organic phases were washed with brine, dried over MgSO$_4$, filtered and concentrated to give the title compound. MS (LC-MS) m/e 250.0 (M+H)$^+$.

2.140.5 4-(((tert-butyldimethylsilyl)oxy)methyl)-3-iodoaniline

To a mixture of Example 2.140.4 (40 g) and imidazole (21.87 g) in dichloromethane (600 mL) and tetrahydrofuran (150 mL) was added tert-butyldimethylchlorosilane (29.0 g). The mixture was stirred at room temperature for 16 hours and filtered to remove the solid. To the filtrate was added ice-water (50 mL). The mixture was stirred for 10 minutes and water (100 mL) was added. The mixture was extracted with dichloromethane (500 mL×2). The combined organic phases were washed with brine, dried over MgSO$_4$, filtered and concentrated. The residue was purified by silica gel chromatography, eluting with 15/1 to 10/1 petroleum ether/ethyl acetate, to give the title compound. MS (LC-MS) m/e 364.0 (M+H)$^+$.

2.140.6 (S)-tert-butyl (1-((4-(((tert-butyldimethylsilyl)oxy)methyl)-3-iodophenyl)amino)-1-oxopropan-2-yl)carbamate To a mixed mixture of (S)-2-((tert-butoxycarbonyl)amino)propanoic acid (15.62 g) and Example 2.140.5 (30 g) in dichloromethane (600 mL) at 0° C. was added POCl$_3$ (15.39 mL) dropwise. The mixture was stirred at 0° C. for 2 hours. Ice-water (60 mL) was carefully added to the mixture dropwise (keeping temperature below 5° C.). The mixture was stirred for 30 minutes and concentrated to remove dichloromethane. The residue was suspended in ethyl acetate (500 mL) and water (100 mL). The suspension was filtered. The organic phase was washed by water (200 mL×2) and brine, dried over MgSO$_4$, filtered and concentrated to give the title compound. MS (LC-MS) m/e 533.0 (M–H)$^+$.

2.140.7 (S)-tert-butyl (1-((4-(hydroxymethyl)-3-iodophenyl)amino)-1-oxopropan-2-yl)carbamate To a mixture of Example 2.140.6 (60 g) in tetrahydrofuran (600 mL) was added tetrabutyl ammonium fluoride (28.2 g) in tetrahydrofuran (120 mL) at 0° C. The mixture was stirred at room temperature for 16 hours and filtered. To the filtrate was added water (100 mL). The mixture was stirred for 10 minutes and then concentrated. The residue was diluted with ethyl acetate (800 mL) and water (300 mL). The aqueous phase was extracted with ethyl acetate (200 mL×3). The combined organic phases were washed with brine, dried over MgSO$_4$, filtered and concentrated. The residue was purified by silica gel chromatography, eluting with 3/1 to 1/1 petroleum ether/ethyl acetate, to give the title compound. MS (LC-MS) m/e 443.0 (M+Na)$^+$.

2.140.8 (S)-2-amino-N-(4-(hydroxymethyl)-3-iodophenyl)propanamide

A mixture of Example 2.140.7 (20 g) in a mixture of dichloromethane (80 mL) and trifluoroacetic acid (40 mL) was stirred at room temperature for 2 hours and concentrated. The residue was dissolved in dichloromethane (80 mL) and triethylamine (16.95 mL) was added to adjust the pH to 8. The title compound was obtained as free base in dichloromethane, which was used in next step without further purification. MS (LC-MS) m/e 321.1 (M+H)$^+$.

2.140.9 tert-butyl ((S)-1-(((S)-1-((4-(hydroxymethyl)-3-iodophenyl)amino)-1-oxopropan-2-yl)amino)-3-methyl-1-oxobutan-2-yl)carbamate A mixture of (S)-2-((tert-butoxycarbonyl)amino)-3-methylbutanoic acid (6.79 g), triethylamine (9.58 mL) and 1-hydroxybenzotriazole hydrate (5.26 g) in dichloromethane (250 mL) was stirred for 20 minutes. The resulting mixture was added to a mixture of Example 2.140.8 (10 g) and 1-ethyl-3-[3-(dimethylamino)propyl]-carbodiimide hydrochloride (6.59 g) in dichloromethane (100 mL) at 0° C., dropwise. After the completion of addition, the mixture was stirred at 0° C. for 2 hours. Ice-water (200 mL) was added, and the resulting mixture was stirred for 20 minutes. The organic phase was washed with saturated aqueous sodium bicarbonate mixture (100 mL×2), water (100 mL×2) and brine (100 mL), dried over MgSO$_4$, filtered and concentrated. The residue was purified by silica gel chromatography, eluting with 3/1 to 1/1 petroleum ether/ethyl acetate, to give the title compound. LC-MS m/e 542.1 (M+Na)$^+$.

2.140.10 tert-butyl ((S)-1-(((S)-1-((4-(hydroxymethyl)-3-(2,5,8,11,14,17,20,23,26,29,32,35,38,41,44,47,50-heptadecaoxatripentacont-52-yn-53-yl)phenyl)amino)-1-oxopropan-2-yl)amino)-3-methyl-1-oxobutan-2-yl)carbamate To a mixture of Example 2.140.9 (50 mg), 2,5,8,11,14,17,20,23,26,29,32,35,38,41,44,47,50-heptadecaoxatripentacont-52-yne (149 mg), bis(triphenylphosphine)palladium (II) dichloride (27.0 mg) and N,N-diisopropylethylamine (0.05 mL) in N,N-dimethylformamide (1 mL) was added copper(I) iodide (3.67 mg). The reaction was purged with a stream of nitrogen gas for 10 minutes and stirred overnight. The reaction was diluted with dimethyl sulfoxide purified by reverse-phase HPLC on a Gilson system (C18 column), eluting with 20-70% acetonitrile in water containing 0.1% trifluoroacetic acid, to give the title compound. MS (LC-MS) m/e 1164.2 (M–H)$^-$.

2.140.11 tert-butyl ((S)-3-methyl-1-(((S)-1-((4-((((4-nitrophenoxy)carbonyl)oxy)methyl)-3-(2,5,8,11,14,17,20,23,26,29,32,35,38,41,44,47,50-heptadecaoxatripentacont-52-yn-53-yl)phenyl)amino)-1-oxopropan-2-yl)amino)-1-oxobutan-2-yl)carbamate To a mixture of Example 2.140.10 (80 mg) and bis(4-nitrophenyl) carbonate (31.3 mg) in N,N-dimethylformamide (0.2 mL) was added N,N-diisopropylethylamine (0.06 mL). The mixture was stirred 3 hours and was purified by reverse-phase HPLC on a Gilson system (C18 column), eluting with 35-75% acetonitrile in water containing 0.1% trifluoroacetic acid, to give the title compound.

2.140.12 6-(8-(benzo[d]thiazol-2-ylcarbamoyl)-3,4-dihydroisoquinolin-2(1H)-yl)-3-(1-((3-(2-((((4-((S)-2-((S)-2-((tert-butoxycarbonyl)amino)-3-methylbutanamido)propanamido)-2-(2,5,8,11,14,17,20,23,26,29,32,35,38,41,44,47,50-heptadecaoxatripentacont-52-yn-53-yl)benzyl)oxy)carbonyl)(2-sulfoethyl)amino)ethoxy)-5,7-dimethyladamantan-1-yl)methyl)-5-methyl-1H-pyrazol-4-yl)picolinic acid To a mixture of Example 1.2.9 (95 mg), Example 2.140.11 (148 mg) and 1-hydroxybenzotriazole hydrate (68.1 mg) in N,N-dimethylformamide (2.5 mL) was added N,N-diisopropylethylamine (97 µL). The mixture was stirred for 3.5 hours and purified by reverse-phase HPLC on a Gilson system (C18 column), eluting with 35-80% acetonitrile in water containing 0.1% trifluoroacetic acid, to give the title compound.

2.140.13 3-(1-((3-(2-(((4-((S)-2-((S)-2-amino-3-methylbutanamido)propanamido)-2-(2,5,8,11,14,17,20,23,26,29,32,35,38,41,44,47,50-heptadecaoxatripentacont-52-yn-53-yl)benzyl)oxy)carbonyl)(2-sulfoethyl)amino)ethoxy)-5,7-dimethyladamantan-1-yl)methyl)-5-methyl-1H-pyrazol-4-yl)-6-(8-(benzo[d]thiazol-2-ylcarbamoyl)-3,4-dihydroisoquinolin-2(1H)-yl)picolinic acid A cold (0° C.) mixture of Example 2.140.12 (135 mg) in dichloromethane (4 mL) was treated with trifluoroacetic acid (1 mL) for 5 hours. The mixture was concentrated and purified by reverse-phase HPLC on a Gilson system (C18 column), eluting with 20-60% acetonitrile in water containing 0.1% trifluoroacetic acid, to give the title compound. MS (ESI) m/e 973.4 (M+2H)$^{2+}$.

2.140.14 N-({(3S,5S)-3-(2,5-dioxo-2,5-dihydro-1H-pyrrol-1-yl)-2-oxo-5-[(2-sulfoethoxy)methyl]pyrrolidin-1-yl}acetyl)-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.13,7]dec-1-yl}oxy)ethyl](2-sulfoethyl)carbamoyl}oxy)methyl]-3-(2,5,8,11,14,17,20,23,26,29,32,35,38,41,44,47,50-heptadecaoxatripentacont-52-yn-53-yl)phenyl}-L-alaninamide A mixture of Example 2.119.15 (20.88 mg) and O-(7-azabenzotriazol-1-yl)-N,N,N',N'-tetramethyluronium hexafluorophosphate (21.1 mg) in N,N-dimethylformamide (0.4 mL) was treated with N,N-diisopropylethylamine (16.2 µL) for 7 minutes, and a mixture of Example 2.140.13 (60 mg) and N,N-diisopropylethylamine (32.3 µL) in N,N-dimethylformamide (0.6 mL) was slowly added. The reaction mixture was stirred for 10 minutes and was purified by reverse-phase HPLC on a Gilson system (C18 column), eluting with 20-70% acetonitrile in water containing 0.1% trifluoroacetic acid, to give the title compound. 1H NMR (500 MHz, dimethyl sulfoxide-d6) δ 10.01 (d, 1H), 8.22 (d, 1H), 8.02 (t, 2H), 7.90-7.75 (m, 2H), 7.66-7.50 (m, 3H), 7.50-7.39 (m, 3H), 7.35 (q, 3H), 7.05 (s, 2H), 7.00 (d, 1H), 5.08 (d, 2H), 4.97 (s, 2H), 4.65 (t, 1H), 4.47-4.31 (m, 4H), 4.23-4.14 (m, 2H), 3.90-3.69 (m, 5H), 3.68-3.58 (m, 4H), 3.57-3.53 (m, 2H), 3.52-3.43 (m, 57H), 3.42-3.33 (m, 4H), 3.22 (s, 5H), 3.01 (t, 2H), 2.49 (p, 3H), 2.09 (d, 3H), 2.04-1.77 (m, 1H), 1.40-1.17 (m, 6H), 1.06 (dd, 6H), 0.97-0.63 (m, 11H). MS (ESI) m/e 1153.3 (M+2H)$^{2+}$.

2.141 Synthesis of N-({(3S,5S)-3-(2,5-dioxo-2,5-dihydro-1H-pyrrol-1-yl)-2-oxo-5-[(2-sulfoethoxy)methyl]pyrrolidin-1-yl}acetyl)-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]-3-(2,5,8,11,14,17,20,23,26,29,32,35,38,41,44,47,50-heptadecaoxatripentacontan-53-yl)phenyl}-L-alaninamide (Synthon VT)

2.141.1 tert-butyl ((S)-1-(((S)-1-((3-(2,5,8,11,14,17,20,23,26,29,32,35,38,41,44,47,50-heptadecaoxadopentacontan-52-yl)-4-(hydroxymethyl)phenyl)amino)-1-oxopropan-2-yl)amino)-3-methyl-1-oxobutan-2-yl)carbamate A mixture of Example 2.140.10 (304 mg) and 10% Pd/C (90 mg, dry) in tetrahydrofuran (20 mL) was shaken in a pressure bottle for 2 hours under 50 psi of hydrogen gas. The insoluble material was filtered off, and the filtrate was concentrated to provide the title compound. MS (ESI) m/e 1168.3 (M−H)$^-$.

2.141.2 tert-butyl ((S)-1-(((S)-1-((3-(2,5,8,11,14,17,20,23,26,29,32,35,38,41,44,47,50-heptadecaoxadopentacontan-52-yl)-4-((((4-nitrophenoxy)carbonyl)oxy)methyl)phenyl)amino)-1-oxopropan-2-yl)amino)-3-methyl-1-oxobutan-2-yl)carbamate The title compound was prepared using the procedure in Example 2.140.11, replacing Example 2.140.10 with Example 2.141.1.

2.141.3 6-(8-(benzo[d]thiazol-2-ylcarbamoyl)-3,4-dihydroisoquinolin-2(1H)-yl)-3-(1-((3-(2-((((4-((S)-2-((S)-2-((tert-butoxycarbonyl)amino)-3-methylbutanamido)propanamido)-2-(2,5,8,11,14,17,20,23,26,29,32,35,38,41,44,47,50-heptadecaoxatripentacontan-53-yl)benzyl)oxy)carbonyl)(2-sulfoethyl)amino)ethoxy)-5,7-dimethyladamantan-1-yl)methyl)-5-methyl-1H-pyrazol-4-yl)picolinic acid The title compound was prepared using the procedure in Example 2.140.12, replacing Example 2.140.11 with Example 2.141.2.

2.141.4 3-(1-((3-(2-(((4-((S)-2-((S)-2-amino-3-methylbutanamido)propanamido)-2-(2,5,8,11,14,17,20,23,26,29,32,35,38,41,44,47,50-heptadecaoxatripentacontan-53-yl)benzyl)oxy)carbonyl)(2-sulfoethyl)amino)ethoxy)-5,7-dimethyladamantan-1-yl)methyl)-5-methyl-1H-pyrazol-4-yl)-6-(8-(benzo[d]thiazol-2-ylcarbamoyl)-3,4-dihydroisoquinolin-2(1H)-yl)picolinic acid The title compound was prepared using the procedure in Example 2.140.13, replacing Example 2.140.12 with Example 2.141.3. MS (ESI) m/e 1948.8 (M−H)$^-$.

2.141.5 N-({(3S,5S)-3-(2,5-dioxo-2,5-dihydro-1H-pyrrol-1-yl)-2-oxo-5-[(2-sulfoethoxy)methyl]pyrrolidin-1-yl}acetyl)-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1³,⁷]dec-1-yl}oxy)ethyl](2-sulfoethyl)carbamoyl}oxy)methyl]-3-(2,5,8,11,14,17,20,23,26,29,32,35,38,41,44,47,50-heptadecaoxatripentacontan-53-yl)phenyl}-L-alaninamide The title compound was prepared using the procedure in Example 2.140.14, replacing Example 2.140.13 with Example 2.141.4. $^1$H NMR (501 MHz, dimethyl sulfoxide-d$_6$) δ 12.87 (s, 1H), 9.84 (s, 1H), 8.18 (d, 1H), 8.03 (dd, 2H), 7.78 (d, 1H), 7.61 (d, 1H), 7.52 (d, 1H), 7.45 (ddd, 4H), 7.40-7.32 (m, 2H), 7.30 (s, 1H), 7.22 (d, 1H), 7.07 (s, 2H), 6.96 (d, 1H), 5.01 (d, 2H), 4.95 (s, 2H), 4.64 (t, 1H), 4.38 (t, 1H), 4.24-4.12 (m, 2H), 4.00 (d, 1H), 3.88 (t, 2H), 3.78 (t, 3H), 3.64 (ddt, 2H), 3.49 (dd, 62H), 3.43-3.37 (m, 6H), 3.23 (s, 3H), 3.01 (t, 2H), 2.84-2.68 (m, 1.5H), 2.63 (dd, 4H), 2.36 (d, 0.5H), 2.08 (d, 3H), 1.74 (t, 2H), 1.25 (dt, 6H), 1.17-1.00 (m, 6H), 0.99-0.72 (m, 11H). MS (ESI) m/e 1153.0 (M−2H)$^{2-}$.

2.142 Synthesis of 2-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1³,⁷]dec-1-yl}oxy)ethyl][(3S)-3,4-dihydroxybutyl]carbamoyl}oxy)methyl]-5-(3-{[(2,5-dioxo-2,5-dihydro-1H-pyrrol-1-yl)acetyl]amino}propyl)phenyl beta-D-glucopyranosiduronic acid (Synthon VY)

2.142.1 3-(1-((3-(2-((((4-(3-aminopropyl)-2-(((2S,3R,4S,5S,6S)-6-carboxy-3,4,5-trihydroxytetrahydro-2H-pyran-2-yl)oxy)benzyl)oxy)carbonyl)((S)-3,4-dihydroxybutyl)amino)ethoxy)-5,7-dimethyladamantan-1-yl)methyl)-5-methyl-1H-pyrazol-4-yl)-6-(8-(benzo[d]thiazol-2-ylcarbamoyl)-3,4-dihydroisoquinolin-2(1H)-yl)picolinic acid Example 2.142.1 was prepared by substituting Example 2.136.4 for (9H-fluoren-9-yl)methyl ((S)-3-methyl-1-(((S)-1-((4-((((4-nitrophenoxy)carbonyl)oxy)methyl)phenyl)amino)-1-oxo-5-ureidopentan-2-yl)amino)-1-oxobutan-2-yl)carbamate and substituting Example 1.85 for Example 1.2.9 in Example 2.49.1. MS (ESI) m/e 1217.3 (M+H)$^+$.

2.142.2 2-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.13,7]dec-1-yl}oxy)ethyl][(3S)-3,4-dihydroxybutyl]carbamoyl}oxy)methyl]-5-(3-{[(2,5-dioxo-2,5-dihydro-1H-pyrrol-1-yl)acetyl]amino}propyl)phenyl beta-D-glucopyranosiduronic acid Example 2.142.2 was prepared by substituting Example 2.142.1 for Example 2.49.1 in Example 2.54. 1H NMR (400 MHz, dimethyl sulfoxide-d6) 6 ppm 8.14 (d, 1H), 8.03 (dt, 1H), 7.81-7.76 (m, 1H), 7.61 (dd, 1H), 7.53-7.41 (m, 3H), 7.38-7.32 (m, 2H), 7.28 (s, 1H), 7.18 (d, 1H), 7.06 (d, 2H), 6.97-6.92 (m, 2H), 6.85 (dd, 1H), 5.10 (q, 2H), 5.01 (d, 1H), 4.96 (s, 2H), 3.48-3.18 (m, 12H), 3.06 (q, 2H), 3.00 (t, 2H), 2.08 (s, 3H), 1.77-0.66 (m, 16H). MS (ESI) m/e 1352.5 (M−H)$^-$.

2.143 Synthesis of 1-{[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1³,⁷]dec-1-yl}oxy)ethyl]({[4-(4-{[(2,5-dioxo-2,5-dihydro-1H-pyrrol-1-yl)acetyl]amino}butyl)-2-(beta-D-glucopyranuronosyloxy)benzyl]oxy}carbonyl)amino}-1,2-dideoxy-D-arabino-hexitol (Synthon WI)

2.143.1 3-(1-((3-(2-((((4-(4-aminobutyl)-2-(((2S,3R,4S,5S,6S)-6-carboxy-3,4,5-trihydroxytetrahydro-2H-pyran-2-yl)oxy)benzyl)oxy)carbonyl)((3R,4S,5R)-3,4,5,6-tetrahydroxyhexyl)amino)ethoxy)-5,7-dimethyladamantan-1-yl)methyl)-5-methyl-1H-pyrazol-4-yl)-6-(8-(benzo[d]thiazol-2-ylcarbamoyl)-3,4-dihydroisoquinolin-2(1H)-yl)picolinic acid The title compound was prepared by substituting Example 1.77.2 for Example 1.25 and Example 2.124.5 for Example 2.97.7 in Example 2.97.8. MS (ESI) m/e 1291 (M+H)$^+$, 1289 (M−H)$^-$.

2.143.2 1-{[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.13,7]dec-1-yl}oxy)ethyl]({[4-(4-{[(2,5-dioxo-2,5-dihydro-1H-pyrrol-1-yl)acetyl]amino}butyl)-2-(beta-D-glucopyranuronosyloxy)benzyl]oxy}carbonyl)amino}-1,2-dideoxy-D-arabino-hexitol The title compound was prepared by substituting Example 2.143.1 for Example 2.49.1 in Example 2.54. $^1$H NMR (400 MHz, dimethyl sulfoxide-d$_6$) δ ppm 8.04 (d, 1H), 7.81 (d, 1H), 7.61 (d, 1H), 7.54-7.43 (m, 3H), 7.41-7.35 (m, 2H), 7.29 (s, 1H), 7.18 (m, 1H), 7.03 (s, 2H), 6.97 (d, 1H), 6.93 (s, 1H), 6.86 (d, 1H), 5.18-5.05 (m, 3H), 5.03 (d, 1H), 4.97 (s, 2H), 4.01 (s, 2H), 3.91 (d, 1H), 3.87 (t, 2H), 3.83 (m, 2H), 3.72 (s, 2H), 3.67 (m, 2H), 3.59 (dd, 2H), 3.50-3.27 (m, 16H), 3.14 (d, 2H), 3.04 (m, 4H), 2.09 (s, 3H), 1.68 (m, 2H), 1.52 (m, 2H), 1.44-1.31 (m, 4H), 1.26-1.14 (m, 4H), 1.10 (m, 4H), 0.98 (q, 2H), 0.85 (m, 6H). MS (ESI) m/e 1428 (M+H)$^+$, 1426 (M−H)$^-$.

2.144 Synthesis of 1-{[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl]({[4-(4-{[(2,5-dioxo-2,5-dihydro-1H-pyrrol-1-yl)acetyl]amino}butyl)-2-(beta-D-glucopyranuronosyloxy)benzyl]oxy}carbonyl)amino}-1,2-dideoxy-D-erythro-pentitol (Synthon WK)

2.144.1 3-(1-((3-(2-(((((4-(4-aminobutyl)-2-(((2S,3R, 4S,5S,6S)-6-carboxy-3,4,5-trihydroxytetrahydro-2H-pyran-2-yl)oxy)benzyl)oxy)carbonyl)((3S,4R)-3,4,5-trihydroxypentyl)amino)ethoxy)-5,7-dimethyladamantan-1-yl)methyl)-5-methyl-1H-pyrazol-4-yl)-6-(8-(benzo[d]thiazol-2-ylcarbamoyl)-3,4-dihydroisoquinolin-2(1H)-yl)picolinic acid The title compound was prepared by substituting Example 1.80 for Example 1.25 and Example 2.124.5 for Example 2.97.7 in Example 2.97.8. MS (ESI) m/e 1261 (M+H)$^+$, 1259 (M−H)$^-$.

2.144.2 1-{[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.13,7]dec-1-yl}oxy)ethyl]({[4-(4-{[(2,5-dioxo-2,5-dihydro-1H-pyrrol-1-yl)acetyl]amino}butyl)-2-(beta-D-glucopyranuronosyloxy)benzyl]oxy}carbonyl)amino}-1,2-dideoxy-D-erythro-pentitol The title compound was prepared by substituting Example 2.144.1 for Example 2.49.1 in Example 2.54. $^1$H NMR (400 MHz, dimethyl sulfoxide-d$_6$) δ ppm 8.08 (t, 1H), 8.03 (d, 1H), 7.79 (d, 1H), 7.62 (d, 1H), 7.53-7.42 (m, 3H), 7.38-7.33 (m, 2H), 7.20 (s, 1H), 7.17 (m, 1H), 7.07 (s, 2H), 6.97-6.93 (m, 2H), 6.85 (d, 1H), 5.17-5.05 (m, 3H), 5.02 (d, 1H), 4.96 (s, 2H), 3.98 (s, 2H), 3.88 (m, 4H), 3.80 (m, 4H), 3.67 (m, 2H), 3.42 (m, 4H), 3.36-3.23 (m, 13H), 3.08-2.99 (m, 5H), 2.09 (s, 3H), 1.86 (m, 1H), 1.53 (m, 2H), 1.38 (m, 4H), 1.25 (m, 4H), 1.11 (m, 4H), 0.96 (m, 2H), 0.83 (m, 6H). MS (ESI) m/e 1398 (M+H)$^+$, 1396 (M−H)$^-$.

2.145 Synthesis of N-[(2,5-dioxo-2,5-dihydro-1H-pyrrol-1-yl)acetyl]-L-valyl-N-{4-[({[2-({3-[(4-{6-[8-(1,3-benzothiazol-2-ylcarbamoyl)naphthalen-2-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]-3-[27-(2,5,8,11,14,17,20,23-octaoxahexacosan-26-yl)-2,5,8,11,14,17,20,23-octaoxa-27-azatriacontan-30-yl]phenyl}-L-alaninamide (Synthon WP)

2.145.1 tert-butyl ((S)-1-(((S)-1-((3-(3-(((benzyloxy)carbonyl)amino)prop-1-yn-1-yl)-4-(hydroxymethyl)phenyl)amino)-1-oxopropan-2-yl)amino)-3-methyl-1-oxobutan-2-yl)carbamate To a mixture of tert-butyl ((S)-1-(((S)-1-((4-(hydroxymethyl)-3-iodophenyl)amino)-1-oxopropan-2-yl)amino)-3-methyl-1-oxobutan-2-yl)carbamate (0.5 g) in N,N-dimethylformamide (6 mL) was added benzyl prop-2-yn-1-ylcarbamate (0.182 g), CuI (9.2 mg), bis(triphenylphosphine)palladium(II) dichloride (35 mg) and N,N-diisopropylethylamine (1.0 mL). The mixture was stirred at room temperature overnight. The mixture was concentrated under vacuum. The residue was dissolved in ethyl acetate (300 mL), washed with water, brine, dried over anhydrous sodium sulfate, filtered and concentrated. Evaporation of the solvent, and purification of the residue by silica gel chromatography, eluting with 30% ethyl acetate in dichloromethane, gave the title compound. MS (APCI) m/e 581.2 (M−H)$^-$.

2.145.2 tert-butyl ((S)-1-(((S)-1-((3-(3-aminopropyl)-4-(hydroxymethyl)phenyl)amino)-1-oxopropan-2-yl)amino)-3-methyl-1-oxobutan-2-yl)carbamate To a mixture of Example 2.145.1 (1.7 g) in ethanol (30 mL) was added 5% Pd/C (0.3 g) and cyclohexene (large excess). The reaction was stirred at 100° C. for 45 minutes. The reaction was filtered and concentrated under reduced pressure. The residue was dissolved in N,N-dimethylformamide and purified by reverse-phase HPLC on a Gilson system (C18 column), eluting with 20-80% acetonitrile in water containing 0.1% trifluoroacetic acid, to give the title compound. MS (ESI) m/e 451.1 (M−H)$^-$.

2.145.3 tert-butyl ((S)-1-(((S)-1-((3-(27-(2,5,8,11,14,17,20,23-octaoxahexacosan-26-yl)-2,5,8,11,14,17,20,23-octaoxa-27-azatriacontan-30-yl)-4-(hydroxymethyl)phenyl)amino)-1-oxopropan-2-yl)amino)-3-methyl-1-oxobutan-2-yl)carbamate To a mixture of Example 2.145.2 (45 mg) in dichloromethane (4 mL) was added 2,5,8,11,14,17,20,23-octaoxahexacosan-26-al (79 mg) followed by NaH(OAc)$_3$ (63.5 mg). The mixture was stirred at room temperature for 3 hours and then concentrated under reduced pressure. The residue was dissolved in N,N-dimethylformamide and purified by reverse-phase HPLC on a Gilson system (C18 column), eluting with 20-80% acetonitrile in water containing 0.1% trifluoroacetic acid, to give the title compound. MS (ESI) m/e 1212.1 (M−H)$^-$.

2.145.4 tert-butyl ((S)-1-(((S)-1-((3-(27-(2,5,8,11,14,17,20,23-octaoxahexacosan-26-yl)-2,5,8,11,14,17,20,23-octaoxa-27-azatriacontan-30-yl)-4-(((((4-nitrophenoxy)carbonyl)oxy)methyl)phenyl)amino)-1-oxopropan-2-yl)amino)-3-methyl-1-oxobutan-2-yl)carbamate To a mixture of Example 2.145.3 (80 mg) in N,N-dimethylformamide (2 mL) was added bis(4-nitrophenyl)carbonate (26 mg) followed by N,N-diisopropylamine (0.012 mL). The mixture was stirred at room temperature overnight and purified directly by reverse phase HPLC on a Gilson system (C18 column), eluting with 20-80% acetonitrile in water containing 0.1% trifluoroacetic acid, to give the title compound. MS (ESI) m/e 1376.97 (M−H)$^-$.

2.145.5 3-(1-((3-(2-(((((2-(27-(2,5,8,11,14,17,20,23-octaoxahexacosan-26-yl)-2,5,8,11,14,17,20,23-octaoxa-27-azatriacontan-30-yl)-4-((S)-2-((S)-2-amino-3-methylbutanamido)propanamido)benzyl)oxy)carbonyl)(2-sulfoethyl)amino)ethoxy)-5,7-dimethyladamantan-1-yl)methyl)-5-methyl-1H-pyrazol-4-yl)-6-(8-(benzo[d]thiazol-2-ylcarbamoyl)naphthalen-2-yl)picolinic acid To a mixture of Example 2.145.4 (30 mg) in N,N-dimethylformamide (4 mL) was added Example 1.43 (18.68 mg) followed by 1-hydroxybenzotriazole hydrate (3.4 mg)

and N,N-diisopropylamine (3.84 uL). The mixture was stirred at room temperature overnight. Trifluoroacetic acid (0.55 mL) was added to the mixture and stirred at room temperature for 3 hours. The mixture was purified by reverse-phase HPLC on a Gilson system (C18 column), eluting with 20-80% acetonitrile in water containing 0.1% trifluoroacetic acid, to give the title compound. MS (ESI) m/e 1986.6 (M−H)⁻.

2.145.6 N-[(2,5-dioxo-2,5-dihydro-1H-pyrrol-1-yl) acetyl]-L-valyl-N-{4-[({[2-({3-[(4-{6-[8-(1,3-benzo-thiazol-2-ylcarbamoyl)naphthalen-2-yl]-2-carboxy-pyridin-3-yl}-5-methyl-1H-pyrazol-1-yl)methyl]-5,7-dimethyltricyclo[3.3.1.13,7]dec-1-yl}oxy)ethyl](2-sulfoethyl)carbamoyl}oxy)methyl]-3-[27-(2,5,8,11,14,17,20,23-octaoxahexacosan-26-yl)-2,5,8,11,14,17,20,23-octaoxa-27-azatriacontan-30-yl]phenyl}-L-alaninamide The title compound was prepared as described in Example 2.123.21, replacing Example 2.123.20 with Example 2.145.5. ¹H NMR (400 MHz, dimethyl sulfoxide-d₆) δ ppm 13.10 (s, 1H), 9.92 (s, 1H), 9.43 (s, 1H), 9.02 (s, 1H), 8.37 (dd, 1H), 8.30-8.14 (m, 5H), 8.07 (d, 1H), 8.02 (d, 1H), 7.96 (d, 1H), 7.81 (d, 1H), 7.74-7.68 (m, 1H), 7.57 (s, 1H), 7.52-7.45 (m, 2H), 7.42-7.34 (m, 2H), 7.28 (d, 1H), 7.08 (s, 2H), 5.05 (d, 2H), 4.39 (t, 1H), 4.21 (dd, 1H), 4.12 (s, 2H), 3.88 (s, 2H), 3.49 (d, 55H), 3.34 (s, 200H), 3.23 (s, 5H), 3.13 (d, 4H), 2.79-2.65 (m, 5H), 2.23 (s, 3H), 1.94 (d, 8H), 1.47-0.94 (m, 15H), 0.92-0.76 (m, 12H).

2.146 Synthesis of (6S)-2,6-anhydro-6-(2-{2-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.13,7]dec-1-yl}oxy)ethyl](2-sulfoethyl)carbamoyl}oxy)methyl]-5-({N-[(2S)-3-[3,4-bis(2,5,8,11,14,17,20,23,26,29,32-undecaoxatetratriacontan-34-yloxy)phenyl]-2-(2,5-dioxo-2,5-dihydro-1H-pyrrol-1-yl)propanoyl]-L-valyl-L-alanyl}amino)phenyl}ethyl)-L-gulonic acid (Synthon XD)

2.146.1 (S)-2-(((benzyloxy)carbonyl)amino)-3-(3,4-dihydroxyphenyl)propanoic acid To a mixture of (S)-2-amino-3-(3,4-dihydroxyphenyl)propanoic acid (1.00 kg) and NaHCO₃ (1.28 kg) in dioxane (5.00 L) and water (5.00 L) was added benzyl carbonochloridate (1.04 k) dropwise. The reaction mixture was stirred at 25° C. for 12 hours. The reaction mixture was adjusted to pH=3.0-4.0 by addition of 6 N aqueous HCl and extracted with ethyl acetate (25 L). The organic layer was dried over Na₂SO₄, filtered, and concentrated in vacuo to afford the title compound. ¹H NMR (400 MHz, dimethyl sulfoxide-d₆) δ ppm 8.73 (s, 1H), 7.54-7.26 (m, 8H), 6.64-6.45 (m, 3H), 4.98 (s, 2H), 4.49 (s, 1H), 2.87 (d, J=9.60 Hz, 1H), 2.68-2.62 (m, 1H).

2.146.2 (S)-benzyl 2-(((benzyloxy)carbonyl)amino)-3-(3,4-dihydroxyphenyl)propanoate To a mixture of Example 2.146.1 (800.00 g) and Cs₂CO₃ (1.18 kg) was added bromomethylbenzene (259.67 g) at 20° C. The reaction mixture was stirred for 1 hour, and TLC showed the reaction was complete. The residue was diluted with H₂O (5 L) and extracted with ethyl acetate (three times 5 L). The combined organic layers were washed with brine (5 L), dried over Na₂SO₄ (150 g), filtered, and concentrated under reduce pressure. The residue was purified by column chromatography (SiO₂, petroleum ether/ethyl acetate=100:1 to 1:1) twice to provide the title compound. ¹H NMR (400 MHz, CDCl₃) δ ppm 2.77-3.02 (m, 2H), 4.47 (br. s., 1H), 4.61 (d, J=7.94 Hz, 1H), 5.01-5.17 (m, 4H), 5.35-5.47 (m, 1H), 6.32 (br. s., 1H), 6.38 (d, J=7.94 Hz, 1H), 6.51 (s, 1H), 6.65 (d, J=7.94 Hz, 1H), 7.17-7.42 (m, 9H).

2.146.3 (S)-benzyl 2-(((benzyloxy)carbonyl)amino)-3-(3,4-bis(2,5,8,11,14,17,20,23,26,29,32-undecaoxa-tetratriacontan-34-yloxy)phenyl)propanoate To a mixture of K₂CO₃ (27.04 g) and KI (5.95 g) in N,N-dimethylformamide (150 mL) was added Example 2.146.2 (8.12 g) and 2,5,8,11,14,17,20,23,26,29,32-undecaoxatetratriacontan-34-yl 4-methylbenzenesulfonate (27.00 g) in dimethylformamide (150 mL). The mixture was stirred at 75° C. for 12 hours under N₂. Two additional vials were set up as described above. All three reaction mixtures were combined for purification. The mixture was poured into NH₄Cl aqueous mixture (9 L), and extracted with ethyl acetate (five times with 900 mL). The combined organic layers were washed with brine (1500 mL), dried over Na₂SO₄ (150 g), filtered, and concentrated under reduce pressure to afford the crude residue. The residue was purified by column chromatography (SiO₂, dichloromethane/methanol=100/1 to 20:1) to provide the title compound. ¹H NMR (400 MHz, CDCl₃) δ ppm 2.95-3.08 (m, 2H), 3.38 (s, 6H), 3.57-3.68 (m, 80H), 3.78 (t, J=4.85 Hz, 2H), 3.83 (t, J=5.29 Hz, 2H), 4.01 (t, J=5.07 Hz, 2H), 4.10 (t, J=5.07 Hz, 2H), 4.58-4.70 (m, 1H), 5.09 (s, 2H), 5.14 (d, J=3.53 Hz, 2H), 6.55 (d, J=8.38 Hz, 1H), 6.62 (d, J=1.76 Hz, 1H), 6.74 (d, J=7.94 Hz, 1H), 7.27-7.49 (m, 10H).

2.146.4 (S)-2-amino-3-(3,4-bis(2,5,8,11,14,17,20,23,26,29,32-undecaoxatetratriacontan-34-yloxy)phenyl) propanoic acid To a mixture of Example 2.146.3 (16.50 g) in methanol (200 mL) was added Pd/C (9.00 g), and the mixture was stirred at 50° C. under H₂ (50 psi) for 16 hours. An additional reaction was set up as described above. LC/MS showed the reaction was complete, and both reaction mixtures were combined for purification. The mixture was filtered and concentrated. The crude title compound was used in the next step without further purification.

2.146.5 (S)-3-(3,4-bis(2,5,8,11,14,17,20,23,26,29,32-undecaoxatetratriacontan-34-yloxy)phenyl)-2-(2,5-dioxo-2,5-dihydro-1H-pyrrol-1-yl)propanoic acid To a mixture of Example 2.146.4 (5.94 g) in H₂O (60.00 mL) was added Na₂CO₃ (790.67 mg) and methyl 2,5-dioxopyrrole-1-carboxylate (1.19 g). The mixture was stirred at 25° C. for 3 hours. Four additional reactions were set up as described above. All five reaction mixtures were combined for purification. Aqueous 4M HCl was added to adjust the pH to 2. The combined mixture was purified by preparatory reverse-phase HPLC (trifluoroacetic acid conditions) to provide the title compound. ¹H NMR (400 MHz, CDCl₃) δ ppm 3.35-3.40 (m, 6H), 3.51-3.58 (m, 4H), 3.58-3.75 (m, 78H), 3.81 (q, J=4.70 Hz, 4H), 4.11 (dt, J=10.14, 5.07 Hz, 4H), 4.91 (dd, J=11.47, 5.29 Hz, 1H), 6.53-6.69 (m, 3H), 6.71-6.89 (m, 2H). MS (ESI) m/e 638.0 (M+H)⁺.

2.146.6 (6S)-2,6-anhydro-6-(2-{2-[({[2-({3-[(4-{6-[8-(1,3-benzothiazol-2-ylcarbamoyl)-3,4-dihydroiso-quinolin-2(1H)-yl]-2-carboxypyridin-3-yl}-5-methyl-1H-pyrazol-1-yl)methyl]-5,7-dimethyltricyclo[3.3.1.1³,⁷]dec-1-yl}oxy)ethyl](2-sulfoethyl)carbamoyl}oxy)methyl]-5-({N-[(2S)-3-[3,4-bis(2,5,8,11,14,17,20,23,26,29,32-undecaoxatetratriacontan-34-yloxy)phenyl]-2-(2,5-dioxo-2,5-dihydro-1H-pyrrol-1-yl)propanoyl]-L-valyl-L-alanyl}amino)phenyl}ethyl)-L-gulonic acid A mixture of Example 2.146.5 (0.020 mL), O-(7-azabenzotriazol-1-yl)-N,N,N',N'-tetramethyluronium hexafluorophosphate (0.014 g) and N-ethyl-N-isopropylpropan-2-amine (0.020 mL) was stirred in N,N-dimethylformamide (0.4 mL) for 5 minutes. The mixture was added to a mixture of Example 2.123.20 (0.042 g) and N-ethyl-N-isopropylpropan-2-amine (0.020 mL) in N,N-dimethylformamide (0.4 mL) and it was stirred at room temperature for 3 hours. The reaction was diluted with a mixture of water (1.5 mL), N,N-dimethylformamide (0.5 mL) and 2,2,2-trifluoroacetic acid (0.054 mL) and purified by preparatory reverse-phase HPLC on a Gilson 2020 system, using a gradient of 5% to 85% acetonitrile/water. The product-containing fractions were lyophilized to give the title compound. $^1$H NMR (501 MHz, dimethyl sulfoxide-$d_6$) δ 12.86 (s, 4H), 9.92 (s, 2H), 8.26 (d, 1H), 8.10 (s, 1H), 8.02 (dd, 1H), 7.77 (d, 1H), 7.64 (s, 1H), 7.54-7.49 (m, 1H), 7.49-7.39 (m, 2H), 7.39-7.31 (m, 2H), 7.28 (s, 1H), 7.20 (d, 1H), 6.94 (d, 1H), 6.87 (s, 2H), 6.77 (d, 1H), 6.60-6.53 (m, 1H), 5.05-4.91 (m, 5H), 4.80 (dd, 2H), 4.37 (t, 2H), 4.21 (t, 2H), 3.97 (dt, 3H), 3.86 (t, 3H), 3.78 (d, 3H), 3.68 (dt, 4H), 3.65-3.28 (m, 102H), 3.20-3.08 (m, 2H), 2.99 (t, 2H), 2.92 (d, 2H), 2.68 (dd, 2H), 2.07 (d, 4H), 1.54 (s, 2H), 1.37-0.71 (m, 16H). MS (ESI) m/e 2631.2 (M−H)⁻.

2.147 Synthesis of N-[(2,5-dioxo-2,5-dihydro-1H-pyrrol-1-yl)acetyl]-N-(2,5,8,11,14,17,20,23,26,29,32-undecaoxatetratriacontan-34-yl)-beta-alanyl-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1³,⁷]dec-1-yl}oxy)ethyl](2-sulfoethyl)carbamoyl}oxy)methyl]-3-(2,5,8,11,14,17,20,23,26,29,32,35,38,41,44,47,50-heptadecaoxatripentacontan-53-yl)phenyl}-L-alaninamide (Synthon XK)

2.147.1 benzyl 2,5,8,11,14,17,20,23,26,29,32-undecaoxa-35-azaoctatriacontan-38-oate To a mixture of 2,5,8,11,14,17,20,23,26,29,32-undecaoxatetratriacontan-34-amine (1 g) in N,N-dimethylformamide (4 mL) and water (3 mL) was added benzyl acrylate (0.377 g), dropwise. The reaction mixture was stirred overnight purified by reverse-phase HPLC on a Gilson system (C18 column), eluting with 20-70% acetonitrile in water containing 0.1% trifluoroacetic acid, to give the title compound. MS (ESI) m/e 678.4 (M+H)⁺.

2.147.2 2,5,8,11,14,17,20,23,26,29,32-undecaoxa-35-azaoctatriacontan-38-oic acid Example 2.147.1 (220 mg) and 10% Pd/C (44 mg, dry) in tetrahydrofuran (10 mL) was shaken in a pressure bottle for 1 hour under 50 psi of hydrogen gas. The reaction was filtered, and the filtrate was concentrated. The residue was dried under high vacuum to provide the title compound. MS (ESI) m/e 588.3 (M+H)⁺.

2.147.3 2,5-dioxopyrrolidin-1-yl 35-(2-(2,5-dioxo-2,5-dihydro-1H-pyrrol-1-yl)acetyl)-2,5,8,11,14,17,20,23,26,29,32-undecaoxa-35-azaoctatriacontan-38-oate A cold (0° C.) mixture of 2,5-dioxopyrrolidin-1-yl 2-(2,5-dioxo-2,5-dihydro-1H-pyrrol-1-yl)acetate (566 mg), 1-hydroxybenzotriazole hydrate (229 mg), 1-hydroxypyrrolidine-2,5-dione (86 mg) and Example 2.147.2 (440 mg) in N,N-dimethylformamide (3 mL) was treated with N,N-diisopropylethylamine (785 µL) for 25 minutes. The reaction was diluted with dimethyl sulfoxide and purified by reverse-phase HPLC on a Gilson system (C18 column), eluting with 5-55% acetonitrile in water containing 0.1% trifluoroacetic acid, to give the title compound. MS (ESI) m/e 822.3 (M+H)⁺.

2.147.4 N-[(2,5-dioxo-2,5-dihydro-1H-pyrrol-1-yl)acetyl]-N-(2,5,8,11,14,17,20,23,26,29,32-undecaoxatetratriacontan-34-yl)-beta-alanyl-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1³,⁷]dec-1-yl}oxy)ethyl](2-sulfoethyl)carbamoyl}oxy)methyl]-3-(2,5,8,11,14,17,20,23,26,29,32,35,38,41,44,47,50-heptadecaoxatripentacontan-53-yl)phenyl}-L-alaninamide To a cold (0° C.) mixture of Example 2.141.4 (28 mg), Example 2.147.3 (27.1 mg) and 1-hydroxybenzotriazole hydrate (6.6 mg) in N,N-dimethylformamide (0.8 mL) was added N,N-diisopropylethylamine-2 (20.1 µL). The mixture was stirred for 10 minutes and was purified by reverse-phase HPLC on a Gilson system (C18 column), eluting with 30-70% acetonitrile in water containing 0.1% trifluoroacetic acid, to give the title compound. $^1$H NMR (400 MHz, dimethyl sulfoxide-$d_6$) δ 12.81 (s, 1H), 9.84 (s, 1H), 8.21-7.86 (m, 2H), 7.75 (d, 1H), 7.57 (d, 1H), 7.52-7.28 (m, 7H), 7.27-7.15 (m, 2H), 7.04 (d, 2H), 6.91 (d, 1H), 4.94 (d, 4H), 4.36 (dt, 3H), 4.19 (dt, 1H), 3.84 (t, 2H), 3.75 (d, 2H), 3.63 (d, 1H), 3.46 (dd, 104H), 3.36 (s, 2H), 3.19 (s, 5H), 2.97 (t, 2H), 2.57 (t, 5H), 2.42-2.26 (m, 1H), 2.03 (s, 7H), 2.00-1.83 (m, 1H), 1.70 (t, 2H), 1.38-0.96 (m, 13H), 0.96-0.69 (m, 13H). MS (ESI) m/e 1327.7 (M−2H)²⁻.

2.148 Synthesis of N-[(2,5-dioxo-2,5-dihydro-1H-pyrrol-1-yl)acetyl]-N-(2,5,8,11,14,17,20,23,26,29,32-undecaoxatetratriacontan-34-yl)-beta-alanyl-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1³,⁷]dec-1-yl}oxy)ethyl](2-sulfoethyl)carbamoyl}oxy)methyl]phenyl}-N⁵-carbamoyl-L-ornithinamide (Synthon XL)

The title compound was prepared using the procedure in Example 2.147.4, replacing Example 2.141.4 with Example 2.112.2. $^1$H NMR (400 MHz, dimethyl sulfoxide-$d_6$) δ 12.83 (s, 1H), 9.96 (d, 1H), 8.18-7.85 (m, 3H), 7.75 (d, 1H), 7.64-7.37 (m, 7H), 7.32 (td, 2H), 7.28-7.20 (m, 3H), 7.04 (s, 2H), 6.92 (d, 1H), 5.17-4.79 (m, 4H), 4.59-4.31 (m, 3H), 4.21 (dt, 1H), 3.84 (t, 2H), 3.77 (d, 2H), 3.52 (s, 4H), 3.39 (d, 2H), 3.19 (s, 5H), 2.94 (dt, 4H), 2.60 (t, 3H), 2.43-2.27 (m, 1H), 2.05 (s, 4H), 1.60 (d, 2H), 1.44-0.57 (m, 22H). MS (ESI) m/e 1964.8 (M−H)⁻.

2.149 Synthesis of N-[(2,5-dioxo-2,5-dihydro-1H-pyrrol-1-yl)acetyl]-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1³,⁷]dec-1-yl}oxy)ethyl](2-sulfoethyl)carbamoyl}oxy)methyl]-3-[27-(2,5,8,11,14,17,20,23-octaoxahexacosan-26-yl)-2,5,8,11,14,17,20,23-octaoxa-27-azatriacontan-30-yl]phenyl}-L-alaninamide (Synthon YJ)

2.149.1 3-(1-((3-(2-((((2-(27-(2,5,8,11,14,17,20,23-octaoxahexacosan-26-yl)-2,5,8,11,14,17,20,23-octaoxa-27-azatriacontan-30-yl)-4-((S)-2-((S)-2-amino-3-methylbutanamido)propanamido)benzyl)oxy)carbonyl)(2-sulfoethyl)amino)ethoxy)-5,7-dimethyladamantan-1-yl)methyl)-5-methyl-1H-pyrazol-4-yl)-6-(8-(benzo[d]thiazol-2-ylcarbamoyl)-3,4-dihydroisoquinolin-2(1H)-yl)picolinic acid The title compound was prepared as described in Example 2.145.5, replacing Example 1.43 with Example 1.2.9. MS (ESI) m/e 1991.4 (M−H)⁻.

2.149.2 N-[(2,5-dioxo-2,5-dihydro-1H-pyrrol-1-yl)acetyl]-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.13,7]dec-1-yl}oxy)ethyl](2-sulfoethyl)carbamoyl}oxy)methyl]-3-[27-(2,5,8,11,14,17,20,23-octaoxahexacosan-26-yl)-2,5,8,11,14,17,20,23-octaoxa-27-azatriacontan-30-yl]phenyl}-L-alaninamide The title compound was prepared as described in Example 2.145, replacing Example 2.145.5 with Example 2.149.1. ¹H NMR (400 MHz, dimethyl sulfoxide-d₆) δ ppm 12.83 (s, 1H), 9.90 (s, 1H), 9.41 (s, 1H), 8.24 (d, 2H), 8.01 (d, 1H), 7.77 (d, 1H), 7.67-7.29 (m, 8H), 7.26 (s, 2H), 7.06 (s, 2H), 6.93 (d, 1H), 5.03 (d, 2H), 4.93 (s, 2H), 4.37 (t, 1H), 4.19 (dd, 1H), 4.11 (s, 2H), 3.86 (t, 2H), 3.79 (s, 2H), 3.70-3.26 (m, 226H), 3.21 (s, 6H), 3.11 (s, 5H), 2.99 (t, 2H), 2.66 (d, 4H), 2.08 (s, 3H), 1.89 (s, 8H), 1.44-0.90 (m, 14H), 0.89-0.68 (m, 11H).

2.150 Synthesis of N-{(3S)-3-(2,5-dioxo-2,5-dihydro-1H-pyrrol-1-yl)-3-[1-(2,5,8,11,14,17,20,23,26,29,32,35-dodecaoxaheptatriacontan-37-yl)-1H-1,2,3-triazol-4-yl]propanoyl}-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1³,⁷]dec-1-yl}oxy)ethyl](2-sulfoethyl)carbamoyl}oxy)methyl]phenyl}-N⁵-carbamoyl-L-ornithinamide (Synthon YQ)

2.150.1 3-(2,5-dioxo-2,5-dihydro-1H-pyrrol-1-yl)pent-4-ynoic acid

To a mixture of 3-aminopent-4-ynoic acid trifluoroacetic acid salt (1.9 g) in tetrahydrofuran (30 mL) was added methyl 2,5-dioxo-2,5-dihydro-1H-pyrrole-1-carboxylate (1.946 g), followed by the rapid addition of N,N-diisopropylethylamine (8.04 mL). The resulting mixture was stirred at 60° C. for 16 hours. The mixture was concentrated to dryness. The residue was purified by reverse-phase HPLC on a Gilson system (C18 column), eluting with 20-80% acetonitrile in water containing 0.1% trifluoroacetic acid, to give the title compound. MS (LC-MS) m/e 194 (M+H). ¹H-NMR (dimethyl sulfoxide-d₆, 400 MHz) δ 2.92-3.07 (m, 2H), 3.38 (d, 1H), 5.07-5.12 (m, 1H), 7.08 (s, 2H), 12.27 (bs, 0.6H).

2.150.2 3-(1-(2,5,8,11,14,17,20,23,26,29,32,35-dodecaoxaheptatriacontan-37-yl)-1H-1,2,3-triazol-4-yl)-3-(2,5-dioxo-2,5-dihydro-1H-pyrrol-1-yl)propanoic acid To Example 2.150.1 (700 mg) in a mixture of t-butanol/H₂O, (2:1, 15 mL) was added 37-azido-2,5,8,11,14,17,20,23,26,29,32,35-dodecaoxaheptatriacontane (2123 mg). Sodium (R)-2-((S)-1,2-dihydroxyethyl)-4-hydroxy-5-oxo-2,5-dihydrofuran-3-olate (71.8 mg) and copper(II) sulfate (28.9 mg) were sequentially added to the mixture. The resulting mixture was stirred at room temperature for 16 hours and concentrated. The residue was purified by reverse-phase HPLC on a Gilson system (C18 column), eluting with 20-80% acetonitrile in water containing 0.1% trifluoroacetic acid, to give the title compound. ¹H NMR (400 MHz, dimethyl sulfoxide-d₆) δ 3.24 (s, 3H), 3.15-3.28 (m, 2H), 3.41-3.52 (m, 44H), 3.79 (t, 2H), 4.48 (t, 2H), 5.56-5.60 (m, 1H), 7.05 (s, 2H), 8.03 (s, 1H). MS (LC-MS) m/e 779 (M+H)⁺.

2.150.3 N-{(3S)-3-(2,5-dioxo-2,5-dihydro-1H-pyrrol-1-yl)-3-[1-(2,5,8,11,14,17,20,23,26,29,32,35-dodecaoxaheptatriacontan-37-yl)-1H-1,2,3-triazol-4-yl]propanoyl}-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.13,7]dec-1-yl}oxy)ethyl](2-sulfoethyl)carbamoyl}oxy)methyl]phenyl}-N5-carbamoyl-L-ornithinamide To a mixture of O-(7-azabenzotriazol-1-yl)-N,N,N',N'-tetramethyluronium hexafluorophosphate (8.45 mg), and Example 2.150.2 (20 mg) in N,N-dimethylformamide (0.3 mL) at 0° C. was slowly added N,N-diisopropylethylamine (22.19 µL), and the reaction mixture was stirred for 1 minute. A cold (0° C.) mixture of Example 2.112.2 (20 mg) and N,N-diisopropylethylamine (22 µL) in N,N-dimethylformamide (0.4 mL) was added. The resulting mixture was stirred for 10 minutes and was purified by reverse-phase HPLC on a Gilson system (C18 column), eluting with 20-80% acetonitrile in water containing 0.1% trifluoroacetic acid, to give the title compound. (The absolute configuration of the 3-position was arbitrarily assigned.) ¹H NMR (501 MHz, dimethyl sulfoxide-d₆) δ 9.95 (s, 1H), 8.07 (d, 3H), 8.04-7.96 (m, 2H), 7.77 (d, 1H), 7.64-7.53 (m, 3H), 7.50 (s, 1H), 7.48-7.39 (m, 2H), 7.34 (q, 2H), 7.30-7.23 (m, 3H), 6.98 (s, 2H), 6.93 (d, 1H), 5.61 (t, 1H), 4.96 (d, 4H), 4.54-4.27 (m, 3H), 4.14 (t, 1H), 3.86 (t, 2H), 3.77 (q, 4H), 3.43 (d, 71H), 3.21 (s, 6H), 3.00 (d, 5H), 2.61 (s, 2H), 2.07 (d, 3H), 1.92 (s, 1H), 1.60 (d, 2H), 1.47-0.86 (m, 10H), 0.85-0.67 (m, 12H). MS (ESI) m/e 1010.6 (M−2H)²⁻.

2.151 Synthesis of N-{(3R)-3-(2,5-dioxo-2,5-dihydro-1H-pyrrol-1-yl)-3-[1-(2,5,8,11,14,17,20,23,26,29,32,35-dodecaoxaheptatriacontan-37-yl)-1H-1,2,3-triazol-4-yl]propanoyl}-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]phenyl}-N$^5$-carbamoyl-L-ornithinamide (Synthon YR)

Example 2.151 was isolated during the preparation of 2.150.3. (The absolute configuration of the 3-position was arbitrarily assigned.) $^1$H NMR (501 MHz, dimethyl sulfoxide-d$_6$) δ 9.91 (s, 1H), 8.11 (dd, 2H), 8.04-7.99 (m, 1H), 7.96 (s, 1H), 7.77 (d, 1H), 7.58 (t, 3H), 7.54-7.39 (m, 2H), 7.39-7.31 (m, 2H), 7.31-7.24 (m, 3H), 7.00 (s, 2H), 6.94 (d, 1H), 5.61 (dd, 1H), 5.08-4.79 (m, 4H), 4.40 (dt, 3H), 4.16 (s, 1H), 3.86 (t, 2H), 3.82-3.73 (m, 4H), 3.51-3.30 (m, 46H), 3.21 (s, 7H), 3.05-2.87 (m, 3H), 2.62 (t, 2H), 2.07 (d, 3H), 1.95 (s, 2H), 1.69 (s, 1H), 1.51-0.86 (m, 10H), 0.88-0.70 (m, 13H). MS (ESI) m/e 1010.6 (M−2H)$^{2-}$.

2.152 Synthesis of 6-[8-(1,3-benzothiazol-2-ylcarbamoyl)-3,4-dihydroisoquinolin-2(1H)-yl]-3-[1-({3-[2-({[(2-{2-[(2S,3R,4R,5S,6S)-6-carboxy-3,4,5-trihydroxytetrahydro-2H-pyran-2-yl]ethyl}-4-{[(2S)-2-{[(2S)-2-{[(2,5-dioxo-2,5-dihydro-1H-pyrrol-1-yl)acetyl]amino}-3-methylbutanoyl]amino}propanoyl]amino}benzyl)oxy]carbonyl}[(3R,4S,5R)-3,4,5,6-tetrahydroxyhexyl]amino)ethoxy]-5,7-dimethyltricyclo[3.3.1.1$^{3,7}$]dec-1-yl}methyl)-5-methyl-1H-pyrazol-4-yl]pyridine-2-carboxylic acid (Synthon YS)

2.152.1 3-(1-((3-(2-(((((4-((S)-2-((S)-2-amino-3-methylbutanamido)propanamido)-2-(2-((2S,3R,4R,5S,6S)-6-carboxy-3,4,5-trihydroxytetrahydro-2H-pyran-2-yl)ethyl)benzyl)oxy)carbonyl)((3R,4S,5R)-3,4,5,6-tetrahydroxyhexyl)amino)ethoxy)-5,7-dimethyladamantan-1-yl)methyl)-5-methyl-1H-pyrazol-4-yl)-6-(8-(benzo[d]thiazol-2-ylcarbamoyl)-3,4-dihydroisoquinolin-2(1H)-yl)picolinic acid The title compound was prepared by substituting Example 1.77.2 for Example 1.25 and Example 2.123.19 for Example 2.97.7 in Example 2.97.8. MS (ESI) m/e 1417 (M+H)$^+$, 1415 (M−H)$^+$.

2.152.2 6-[8-(1,3-benzothiazol-2-ylcarbamoyl)-3,4-dihydroisoquinolin-2(1H)-yl]-3-[1-({3-[2-({[(2-{2-[(2S,3R,4R,5S,6S)-6-carboxy-3,4,5-trihydroxytetrahydro-2H-pyran-2-yl]ethyl}-4-{[(2S)-2-{[(2S)-2-{[(2,5-dioxo-2,5-dihydro-1H-pyrrol-1-yl)acetyl]amino}-3-methylbutanoyl]amino}propanoyl]amino}benzyl)oxy]carbonyl}[(3R,4S,5R)-3,4,5,6-tetrahydroxyhexyl]amino)ethoxy]-5,7-dimethyltricyclo[3.3.1.13,7]dec-1-yl}methyl)-5-methyl-1H-pyrazol-4-yl]pyridine-2-carboxylic acid The title compound was prepared by substituting Example 2.152.1 for Example 2.49.1 in Example 2.54. $^1$H NMR (400 MHz, dimethyl sulfoxide-d$_6$) δ ppm 9.85 (m, 1H), 8.18 (t, 2H), 7.96 (d, 1H), 7.73 (d, 1H), 7.55 (d, 1H), 7.46-7.25 (m, 8H), 7.21 (m, 1H), 7.15 (d, 1H), 7.00 (s, 1H), 6.99 (d, 1H), 6.88 (d, 1H), 4.95 (bs, 2H), 4.88 (s, 2H), 4.32 (m, 1H), 4.15 (t, 1H), 4.05 (s, 2H), 3.82 (t, 2H), 3.72 (m, 4H), 3.58-3.29 (m, 6H), 3.19 (m, 4H), 3.11-3.00 (m, 6H), 2.97 (t, 2H), 2.91 (t, 2H), 2.72 (m, 2H), 2.55 (m, 2H), 2.04 (s, 3H), 2.02-1.85 (m, 3H), 1.54 (m, 4H), 1.44 (s, 1H), 1.33 (bs, 1H), 1.22 (m, 6H), 1.04 (m, 6H), 0.86 (m, 2H), 0.77 (m, 12H). MS (ESI) m/e 1554 (M+H)$^+$, 1552 (M−H)$^-$.

2.153 Synthesis of 6-[8-(1,3-benzothiazol-2-ylcarbamoyl)-3,4-dihydroisoquinolin-2(1H)-yl]-3-[1-({3-[2-({[(2-{2-[(2S,3R,4R,5S,6S)-6-carboxy-3,4,5-trihydroxytetrahydro-2H-pyran-2-yl]ethyl}-4-{[(2S)-2-({(2S)-2-[({(3S,5S)-3-(2,5-dioxo-2,5-dihydro-1H-pyrrol-1-yl)-2-oxo-5-[(2-sulfoethoxy)methyl]pyrrolidin-1-yl}acetyl)amino]-3-methylbutanoyl}amino)propanoyl]amino}benzyl)oxy]carbonyl}[(3R,4S,5R)-3,4,5,6-tetrahydroxyhexyl]amino)ethoxy]-5,7-dimethyltricyclo[3.3.1.1$^{3,7}$]dec-1-yl}methyl)-5-methyl-1H-pyrazol-4-yl]pyridine-2-carboxylic acid (Synthon YY)

Example 2.119.15 (11 mg) was dissolved in N,N-dimethylformamide (0.1 mL). 2-(3H-[1,2,3]triazolo[4,5-b]pyridin-3-yl)-1,1,3,3-tetramethylisouronium hexafluorophosphate (V) (11 mg) and N,N-diisopropylethylamine (7.4 mg) were added. The mixture was stirred at room temperature for five minutes. The mixture was then added to another mixture of Example 2.152.1 (34 mg) and N,N-diisopropylethylamine (16.3 mg) in N,N-dimethylformamide (0.2 mL). The reaction was stirred for 60 minutes at room temperature and quenched with trifluoroacetic acid (36 mg). The mixture was diluted with water (0.75 mL) and dimethyl sulfoxide (0.75 mL) and purified by reverse-phase HPLC using 10-75% acetonitrile in water (w/0.1% TFA) over 30 minutes on a Grace Reveleris equipped with a Luna column: C18(2), 100 A, 150×30 mm. Product fractions were pooled, frozen, and lyophilized to yield the title compound as the trifluoroacetic acid salt. $^1$H NMR (400 MHz, dimethyl sulfoxide-d$_6$) δ ppm 9.85 (m, 1H), 8.18 (d, 1H), 8.05 (d, 1H), 8.04 (d, 1H), 7.79 (d, 1H), 7.53-7.39 (m, 8H), 7.36 (q, 2H), 7.29 (s, 1H), 7.22 (d, 1H), 7.07 (s, 1H), 6.96 (d, 1H), 5.18 (bs, 2H), 4.96 (s, 2H), 4.65 (t, 1H), 4.37 (t, 1H), 4.19 (t, 1H), 4.16 (s, 1H), 4.01 (d, 2H), 3.89 (t, 2H), 3.78 (m, 4H), 3.73 (m, 2H), 3.49-3.44 (m, 4H), 3.40-3.20 (m, 8H), 3.24 (m, 4H), 3.17-3.07 (m, 4H), 3.02 (t, 2H), 2.95 (t, 2H), 2.76 (m, 4H), 2.62 (m, 1H), 2.37 (m, 1H), 2.09 (s, 3H), 1.99 (m, 2H), 1.86 (q, 1H), 1.62 (m, 4H), 1.38 (bs, 2H), 1.28 (m, 6H), 1.18-1.02 (m, 6H), 0.96 (m, 2H), 0.91-0.79 (m, 12H). MS (ESI) m/e 1773 (M−H)$^-$.

2.154 Synthesis of (6S)-2,6-anhydro-6-(2-{2-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]-5-({N-[(2,5-dioxo-2,5-dihydro-1H-pyrrol-1-yl)acetyl]-N-(2,5,8,11,14,17,20,23,26,29,32-undecaoxatetratriacontan-34-yl)-beta-alanyl-L-valyl-L-alanyl}amino)phenyl}ethyl)-L-gulonic acid (Synthon YT)

2.154.1 3-(1-((3-(2-(((((4-((S)-2-((S)-2-amino-3-methylbutanamido)propanamido)-2-(2-((2S,3R,4R,5S,6S)-6-carboxy-3,4,5-trihydroxytetrahydro-2H-pyran-2-yl)ethyl)benzyl)oxy)carbonyl)(2-sulfoethyl)amino)ethoxy)-5,7-dimethyladamantan-1-yl)methyl)-5-methyl-1H-pyrazol-4-yl)-6-(8-(benzo[d]thiazol-2-ylcarbamoyl)-3,4-dihydroisoquinolin-2(1H)-yl)picolinic acid A mixture of Example 1.2.9 (200 mg), Example 2.123.19 (288 mg), and 1-hydroxybenzotriazole hydrate (50.2 mg) in N,N-dimethylformamide (2 mL) was cooled in an ice-bath, and N,N-diisopropylethylamine (143 µL) was added. The reaction mixture was stirred at room temperature for 2.5 hours and concentrated. Tetrahydrofuran (0.5 mL) and methanol (0.5 mL) were added into the residue. The resulting mixture was cooled in ice-bath and lithium hydroxide hydrate (147 mg) in water (2.5 mL) was slowly added. The mixture was stirred at room temperature for 1.5 hours, and cooled in ice bath. Trifluoroacetic acid (361 µL) was added dropwise until the pH reached 6. The mixture was purified by reverse-phase HPLC on a Gilson system (C18 column), eluting with 35-45% acetonitrile in water containing 0.1% trifluoroacetic acid, to give the title compound. MS (ESI) m/e 1375.5 (M−H)−.

2.154.2 (6S)-2,6-anhydro-6-(2-{2-[({[2-({3-[(4-{6-[8-(1,3-benzothiazol-2-ylcarbamoyl)-3,4-dihydroiso-quinolin-2(1H)-yl]-2-carboxypyridin-3-yl}-5-methyl-1H-pyrazol-1-yl)methyl]-5,7-dimethyltricyclo[3.3.1.1.3,7]dec-1-yl}oxy)ethyl](2-sulfoethyl)carbamoyl}oxy)methyl]-5-({N-[(2,5-dioxo-2,5-dihydro-1H-pyrrol-1-yl)acetyl]-N-(2,5,8,11,14,17,20,23,26,29,32-undecaoxatetriacontan-34-yl)-beta-alanyl-L-valyl-L-alanyl}amino)phenyl}ethyl)-L-gulonic acid To a mixture of 1-hydroxybenzotriazole hydrate (5.22 mg), Example 2.154.1 (23.5 mg) and Example 2.147.3 (24 mg) in N,N-dimethylformamide (1 mL) at 0° C. was slowly added N,N-diisopropylethylamine (23.84 µL). The reaction mixture was stirred at room temperature for 15 minutes and purified by reverse-phase HPLC on a Gilson system (C18 column), eluting with 35-50% acetonitrile in water containing 0.1% trifluoroacetic acid, to give the title compound. $^1$H NMR (501 MHz, dimethyl sulfoxide-$d_6$) δ 12.83 (s, 1H), 9.88 (s, 1H), 8.23-8.04 (m, 2H), 8.02 (dd, 1H), 7.92 (s, 1H), 7.77 (d, 1H), 7.59 (d, 1H), 7.55-7.30 (m, 7H), 7.27 (s, 1H), 7.20 (d, 1H), 7.07 (d, 2H), 6.93 (d, 1H), 5.07-4.88 (m, 4H), 4.47-4.32 (m, 3H), 4.22 (dt, 1H), 3.97-3.73 (m, 4H), 3.62-3.45 (m, 35H), 3.31 (t, 3H), 3.21 (s, 3H), 3.06 (d, 2H), 2.83-2.54 (m, 5H), 2.47-2.29 (m, 1H), 2.13-1.84 (m, 5H), 1.52 (d, 1H), 1.43-0.69 (m, 26H). MS (ESI) m/e 1043.0 (M−2H)$^{2-}$.

2.155 Synthesis of (6S)-2,6-anhydro-6-(2-{2-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]-5-[(N-{2-(2,5-dioxo-2,5-dihydro-1H-pyrrol-1-yl)-3-[1-(2,5,8,11,14,17,20,23,26,29,32,35-dodecaoxaheptatriacontan-37-yl)-1H-1,2,3-triazol-4-yl]propanoyl}-L-valyl-L-alanyl)amino]phenyl}ethyl)-L-gulonic acid (Synthon YU)

2.155.1 3-(1-(2,5,8,11,14,17,20,23,26,29,32,35-dodecaoxaheptatriacontan-37-yl)-1H-1,2,3-triazol-4-yl)-2-(2,5-dioxo-2,5-dihydro-1H-pyrrol-1-yl)propanoic acid The title compound was prepared using the procedure in Example 2.150.2, replacing Example 2.150.1 with 2-(2,5-dioxo-2,5-dihydro-1H-pyrrol-1-yl)pent-4-ynoic acid.

2.155.2 (6S)-2,6-anhydro-6-(2-{2-[({[2-({3-[(4-{6-[8-(1,3-benzothiazol-2-ylcarbamoyl)-3,4-dihydroiso-quinolin-2(1H)-yl]-2-carboxypyridin-3-yl}-5-methyl-1H-pyrazol-1-yl)methyl]-5,7-dimethyltricyclo[3.3.1.13,7]dec-1-yl}oxy)ethyl](2-sulfoethyl)carbamoyl}oxy)methyl]-5-[(N-{2-(2,5-dioxo-2,5-dihydro-1H-pyrrol-1-yl)-3-[1-(2,5,8,11,14,17,20,23,26,29,32,35-dodecaoxaheptatriacontan-37-yl)-1H-1,2,3-triazol-4-yl]propanoyl}-L-valyl-L-alanyl)amino]phenyl}ethyl)-L-gulonic acid The title compound was prepared using the procedure in Example 2.150.3, replacing Example 2.150.2 and Example 2.112.2 with Example 2.155.1 and Example 2.154.1, respectively. $^1$H NMR (400 MHz, dimethyl sulfoxide-$d_6$) δ 12.83 (s, 1H), 9.87 (d, 1H), 8.25-8.06 (m, 2H), 8.00 (d, 1H), 7.75 (d, 1H), 7.71 (s, 1H), 7.57 (d, 1H), 7.54-7.28 (m, 6H), 7.25 (s, 1H), 7.18 (d, 1H), 6.98-6.85 (m, 3H), 5.09-4.89 (m, 4H), 4.76 (ddd, 1H), 4.36 (ddd, 3H), 4.17 (q, 1H), 3.84 (t, 2H), 3.76 (d, 2H), 3.72-3.66 (m, 2H), 3.49-3.44 (m, 37H), 3.20 (s, 5H), 3.01-2.82 (m, 3H), 2.13-1.81 (m, 5H), 1.52 (s, 1H), 1.39-0.50 (m, 23H). MS (ESI) m/e 1069.7 (M+2H)$^{2+}$.

2.156 Synthesis of (6S)-2,6-anhydro-6-(2-{2-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]-5-[(N-{(3S)-3-(2,5-dioxo-2,5-dihydro-1H-pyrrol-1-yl)-3-[1-(2,5,8,11,14,17,20,23,26,29,32,35-dodecaoxaheptatriacontan-37-yl)-1H-1,2,3-triazol-4-yl]propanoyl}-L-valyl-L-alanyl)amino]phenyl}ethyl)-L-gulonic acid (Synthon YV)

Example 2.156 was isolated as a pure diastereomer during the preparation of Example 2.155.2. (The assignment of absolute configuration at the 3-position is arbitrary.) $^1$H NMR (400 MHz, dimethyl sulfoxide-$d_6$) δ 12.82 (s, 1H), 9.85 (s, 1H), 8.08 (d, 2H), 8.03-7.95 (m, 2H), 7.75 (d, 1H), 7.57 (d, 1H), 7.51-7.29 (m, 6H), 7.24 (s, 1H), 7.18 (d, 1H), 6.95 (s, 2H), 6.91 (d, 1H), 5.59 (dd, 1H), 5.06-4.86 (m, 4H), 4.43 (dt, 2H), 4.32 (t, 1H), 4.11 (t, 1H), 3.84 (t, 2H), 3.75 (t, 3H), 3.55-3.41 (m, 43H), 3.41-3.36 (m, 2H), 3.19 (s, 5H), 3.10 (t, 1H), 3.03-2.86 (m, 3H), 2.59 (s, 3H), 2.13-1.82 (m, 6H), 1.52 (s, 1H), 1.37-0.65 (m, 26H). MS (ESI) m/e 1067.8 (M−2H)$^{2-}$.

2.157 Synthesis of (6S)-2,6-anhydro-6-(2-{2-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]-5-[(N-{(3R)-3-(2,5-dioxo-2,5-dihydro-1H-pyrrol-1-yl)-3-[1-(2,5,8,11,14,17,20,23,26,29,32,35-dodecaoxaheptatriacontan-37-yl)-1H-1,2,3-triazol-4-yl]propanoyl}-L-valyl-L-alanyl)amino]phenyl}ethyl)-L-gulonic acid (Synthon YW)

Example 2.157 was isolated as a pure diastereomer during the preparation of Example 2.155.2. (The assignment of absolute configuration at the 3-position is arbitrary.) $^1$H NMR (400 MHz, dimethyl sulfoxide-$d_6$) δ 12.81 (s, 1H), 9.81 (s, 1H), 8.10 (d, 2H), 8.00 (d, 1H), 7.94 (s, 1H), 7.75 (d, 1H), 7.57 (d, 1H), 7.51-7.28 (m, 6H), 7.24 (s, 1H), 7.18 (d, 1H), 6.98 (s, 2H), 6.91 (d, 1H), 5.59 (t, 1H), 5.06-4.87

(m, 4H), 4.46-4.26 (m, 2H), 4.12 (d, 1H), 3.84 (t, 2H), 3.75 (d, 3H), 3.46 (d, 27H), 3.40-3.36 (m, 2H), 3.19 (s, 5H), 3.01-2.85 (m, 3H), 2.60 (s, 3H), 1.99 (d, 4H), 1.52 (s, 1H), 1.35-0.65 (m, 23H). MS (ESI) m/e 1067.8 (M−2H)$^{2-}$.

2.158 Synthesis of (6S)-2,6-anhydro-6-(2-{2-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]-5-[(N-{(3S)-3-(2,5-dioxo-2,5-dihydro-1H-pyrrol-1-yl)-3-[1-(3-sulfopropyl)-1H-1,2,3-triazol-4-yl]propanoyl}-L-valyl-L-alanyl)amino]phenyl}ethyl)-L-gulonic acid
(Synthon ZB)

2.158.1 sodium 3-azidopropane-1-sulfonate

To a mixture of sodium azide (3.25 g) in water (25 mL) was added 1, 2-oxathiolane 2,2-dioxide (6.1 g) in acetone (25 mL). The resulting mixture was stirred at room temperature for 24 hours and concentrated to dryness. The solid was suspended in diethyl ether (100 mL) and stirred at reflux for 1 hour. The suspension was cooled to room temperature, and the solid was collected by filtration, washed with acetone and diethyl ether, and dried under vacuum to afford the title compound. MS (LC-MS) m/e 164 (M−H)$^-$.

2.158.2 isopropyl 3-azidopropane-1-sulfonate

A mixture of Example 2.158.1 (6.8 g) in concentrated HCl (90 mL) was stirred at room temperature for 1 hour. The mixture was concentrated to dryness. The residue was dissolved in dichloromethane (350 mL), and triisopropoxymethane (42.0 mL) was added in one portion to the mixture. The resulting mixture was stirred at 50° C. for 2 hours and concentrated to dryness. The crude residue was purified by silica gel chromatography, eluting with 10/1 petroleum ether/ethyl acetate, to give the title compound. $^1$H-NMR (CDCl$_3$, 400 MHz): 1.42 (s, 3H), 1.44 (s, 3H), 2.08-2.15 (m, 2H), 3.17 (t, 2H), 3.51 (t, 2H), 4.95-5.01 (m, 1H).

2.158.3 3-(2,5-dioxo-2,5-dihydro-1H-pyrrol-1-yl)-3-(1-(3-sulfopropyl)-1H-1,2,3-triazol-4-yl)propanoic acid To a mixture of Example 2.150.1 (450 mg) in t-butanol/H$_2$O (2:1, 9 mL) was added Example 2.158.2 (483 mg) followed by copper(II) sulfate (18.59 mg) and sodium (R)-2-((S)-1,2-dihydroxyethyl)-4-hydroxy-5-oxo-2,5-dihydrofuran-3-olate (46.2 mg). The resulting mixture was stirred at room temperature for 16 hours, and the mixture was concentrated to dryness. The residue was purified by reverse-phase HPLC on a Gilson system (C18 column), eluting with 20-80% acetonitrile in water containing 0.1% trifluoroacetic acid, to give the title compound. $^1$H-NMR (dimethyl sulfoxide-d$_6$, 400 MHz): 2.06-2.10 (m, 2H), 2.45-2.48 (m, 2H), 3.21-3.23 (m, 2H), 4.40-4.44 (m, 2H), 5.55-5.59 (m, 1H), 7.05 (s, 2H), 8.10 (s, 1H). MS (LCMS) m/e 359 (M+H)$^+$.

2.158.4 (6S)-2,6-anhydro-6-(2-{2-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.13,7]dec-1-yl}oxy)ethyl](2-sulfoethyl)carbamoyl}oxy)methyl]-5-[(N-{(3S)-3-(2,5-dioxo-2,5-dihydro-1H-pyrrol-1-yl)-3-[1-(3-sulfopropyl)-1H-1,2,3-triazol-4-yl]propanoyl}-L-valyl-L-alanyl)amino]phenyl}ethyl)-L-gulonic acid The title compound was prepared using the procedure in Example 2.150.3, replacing Example 2.150.2 and Example 2.112.2 with Example 2.158.3 and Example 2.154.1, respectively. The compound was isolated as a pure diastereomer. (The absolute configuration of the 3-position was arbitrarily assigned.) $^1$H NMR (400 MHz, dimethyl sulfoxide-d$_6$) δ 10.14-9.66 (m, 1H), 8.07 (d, 2H), 8.04-7.96 (m, 2H), 7.75 (d, 1H), 7.57 (d, 1H), 7.52-7.29 (m, 7H), 7.26 (s, 1H), 7.18 (d, 1H), 6.92 (d, 3H), 5.58 (t, 1H), 5.09-4.84 (m, 4H), 4.35 (dt, 3H), 4.15-4.02 (m, 1H), 3.89-3.65 (m, 4H), 3.28 (d, 1H), 3.21 (dd, 2H), 3.14-3.02 (m, 2H), 3.01-2.86 (m, 4H), 2.62 (d, 3H), 2.37 (t, 2H), 2.29 (s, OH), 2.02 (dt, 5H), 1.52 (s, 1H), 1.40-0.59 (m, 24H). MS (ESI) m/e 1715.3 (M−H)$^-$.

2.159 Synthesis of (6S)-2,6-anhydro-6-(2-{2-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]-5-[(N-{(3R)-3-(2,5-dioxo-2,5-dihydro-1H-pyrrol-1-yl)-3-[1-(3-sulfopropyl)-1H-1,2,3-triazol-4-yl]propanoyl}-L-valyl-L-alanyl)amino]phenyl}ethyl)-L-gulonic acid
(Synthon ZC)

Example 2.159 was isolated as a pure diastereomer during the preparation of Example 2.158. (The absolute configuration of the 3-position was arbitrarily assigned.) $^1$H NMR (400 MHz, dimethyl sulfoxide-d$_6$) δ 9.97 (d, 1H), 8.21 (d, 1H), 8.13 (d, 1H), 8.04-7.96 (m, 2H), 7.75 (d, 1H), 7.57 (d, 1H), 7.55-7.37 (m, 4H), 7.36-7.25 (m, 3H), 7.17 (d, 1H), 6.98 (s, 2H), 6.93 (d, 1H), 5.58 (t, 1H), 4.94 (d, 4H), 4.50-4.26 (m, 3H), 4.10 (s, 1H), 3.98-3.73 (m, 3H), 3.51 (d, 1H), 3.42 (s, 3H), 3.34-3.01 (m, 6H), 3.01-2.83 (m, 4H), 2.63 (d, 4H), 2.42 (d, 1H), 2.18-1.80 (m, 8H), 1.53 (s, 1H), 1.39-0.68 (m, 27H). MS (ESI) m/e 1715.4 (M−H)$^-$.

2.160 Synthesis of (6S)-2,6-anhydro-6-(2-{2-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl](2-sulfoethyl)carbamoyl}oxy)methyl]-5-({N-[(2,5-dioxo-2,5-dihydro-1H-pyrrol-1-yl)acetyl]-N-[2-(2-sulfoethoxy)ethyl]-beta-alanyl-L-valyl-L-alanyl}amino)phenyl}ethyl)-L-gulonic acid
(Synthon ZJ)

2.160.1 4-((tert-butyldiphenylsilyl)oxy)-2,2-dimethylbutyl 2-(2-((tert-butoxycarbonyl)amino)ethoxy)ethanesulfonate To a mixture of tert-butyl (2-hydroxyethyl)carbamate (433 mg) in dimethyl sulfoxide (0.9 mL) at 20° C. were added 4-((tert-butyldiphenylsilyl)oxy)-2,2-dimethylbutyl ethenesulfonate (500 mg) and K$_2$CO$_3$ (210 mg). The mixture was warmed to 60° C. and stirred for 16 hours in a capped bottle. The mixture was diluted with ethyl acetate, washed with water and brine. The organic layer was dried over anhydrous sodium sulfate, filtered, and concentrated. The residue was purified by silica gel flash chromatography, eluting with petrol ether/ethyl acetate (10:1-2:1), to give the title compound. MS (LC-MS) m/e 630.3 (M+Na)+.

2.160.2 4-((tert-butyldiphenylsilyl)oxy)-2,2-dimethylbutyl 2-(2-aminoethoxy)ethanesulfonate To a mixture of Example 2.160.1 (1.5 g) in anhydrous dichloromethane (100 mL) at 20° C. was added zinc(II) bromide (0.445 g). The mixture was stirred at room temperature for 16 hours. Additional zinc(II) bromide (278 mg) was added to above mixture, and the reaction was stirred for additional 16 hours. The reaction was quenched with 1 M aqueous $Na_2CO_3$ mixture (5 mL), and the aqueous layer was extracted with ethyl acetate three times. The combined organic layers were dried over sodium sulfate, filtered, and concentrated. The residue was purified by silica gel column chromatography, eluting with dichloromethane/methanol (10:1), to give the title compound. MS (LC-MS) m/e 508.2 (M+H)+.

2.160.3 tert-butyl 3-((2-(2-((4-((tert-butyldiphenylsilyl)oxy)-2,2-dimethylbutoxy)sulfonyl)ethoxy)ethyl)amino)propanoate To a mixture of Example 2.160.2 (0.365 g) in N, N-dimethylformamide (5.5 mL) and water (0.55 mL) were added tert-butyl acrylate (0.105 mL) and triethylamine (10.02 μL). The mixture was stirred at 60° C. for 30 hours. The mixture was concentrated. The residue was mixed with 1 M aqueous $Na_2CO_3$ mixture (5 mL). The aqueous layer was extracted with ethyl acetate three times. The combined organic layers were dried over sodium sulfate, filtered and concentrated. The residue was purified by silica gel column chromatography, eluting with dichloromethane/ethyl acetate (3:1) and dichloromethane/methanol (10:1), to give the title compound. MS (LC-MS) m/e 636.3 (M+H)+.

2.160.4 tert-butyl 3-(N-(2-(2-((4-((tert-butyldiphenylsilyl)oxy)-2,2-dimethylbutoxy)sulfonyl)ethoxy)ethyl)-2-(2,5-dioxo-2,5-dihydro-1H-pyrrol-1-yl)acetamido)propanoate To a mixture of Example 2.160.3 (557.5 mg), 2-(2,5-dioxo-2,5-dihydro-1H-pyrrol-1-yl)acetic acid (272 mg) and O-(7-azabenzotriazol-1-yl)-N,N,N',N'-tetramethyluronium hexafluorophosphate (667 mg) in N, N-dimethylformamide (1.75 mL) at 0° C. was added N,N-diisopropylethylamine (0.459 mL). The resulting mixture was stirred at 0° C. for 1 hour. The reaction mixture was mixed with saturated aqueous $NH_4Cl$ mixture, extracted with ethyl acetate and washed with brine. The organic layer was dried over sodium sulfate, filtered and concentrated. The residue was purified by silica gel column chromatography, eluting with petroleum ether/ethyl acetate (2/1), to provide the title compound. MS (LC-MS) m/e 795.3 (M+Na)+.

2.160.5 3-(2-(2,5-dioxo-2,5-dihydro-1H-pyrrol-1-yl)-N-(2-(2-sulfoethoxy)ethyl)acetamido)propanoic acid To a mixture of Example 2.160.4 (230 mg) in dichloromethane (4 mL) was added trifluoroacetic acid (3 mL). The mixture was stirred at 20° C. for 16 hours and was concentrated. The residue was purified by reverse-phase HPLC on a Gilson system (C18 column), eluting with 20-80% acetonitrile in water containing 0.1% trifluoroacetic acid, to give the title compound. MS (LC-MS) m/e 379.0 (M+Na)+.

2.160.6 2-(2-(2-(2,5-dioxo-2,5-dihydro-1H-pyrrol-1-yl)-N-(3-((2,5-dioxopyrrolidin-1-yl)oxy)-3-oxopropyl)acetamido)ethoxy)ethane-1-sulfonic acid A mixture of 1-hydroxypyrrolidine-2,5-dione (16.43 mg), Example 2.160.5 (30 mg), 1-ethyl-3-[3-(dimethylamino)propyl]-carbodiimide hydrochloride (45.6 mg) in N,N-dimethylformamide were stirred overnight. The reaction mixture was purified by reverse-phase HPLC on a Gilson system (C18 column), eluting with 2-30% acetonitrile in water containing 0.1% trifluoroacetic acid, to give the title compound. MS (ESI) m/e 475.9 (M+H)+.

2.160.7 (6S)-2,6-anhydro-6-(2-{2-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.13,7]dec-1-yl}oxy)ethyl](2-sulfoethyl)carbamoyl}oxy)methyl]-5-({N-[(2,5-dioxo-2,5-dihydro-1H-pyrrol-1-yl)acetyl]-N-[2-(2-sulfoethoxy)ethyl]-beta-alanyl-L-valyl-L-alanyl}amino)phenyl}ethyl)-L-gulonic acid To a mixture of 1-hydroxybenzotriazole hydrate (4.45 mg), Example 2.160.6 (8.97 mg) and Example 2.154.1 (20 mg) in N,N-dimethylformamide (0.8 mL) at 0° C. was added N,N-diisopropylethylamine (20 μL dropwise). The reaction mixture was stirred at room temperature for 1 hour and purified by reverse-phase HPLC on a Gilson system (C18 column), eluting with 30-55% acetonitrile in water containing 0.1% trifluoroacetic acid, to give the title compound. $^1$H NMR (500 MHz, dimethyl sulfoxide-$d_6$) δ 12.87 (s, 1H), 9.88 (d, 1H), 8.28-8.10 (m, 1H), 8.03 (d, 1H), 7.95 (d, 1H), 7.78 (d, 1H), 7.60 (d, 1H), 7.56-7.31 (m, 7H), 7.28 (s, 1H), 7.21 (d, 1H), 7.06 (d, 2H), 6.95 (d, 1H), 5.06-4.90 (m, 4H), 4.38 (q, 3H), 4.28-4.11 (m, 1H), 3.87 (t, 2H), 3.79 (d, 2H), 3.71-3.49 (m, 5H), 3.21 (d, 2H), 3.12 (q, 2H), 2.97 (dt, 3H), 2.84-2.57 (m, 6H), 2.38 (dd, 1H), 2.13-1.86 (m, 5H), 1.55 (s, 1H), 1.39-0.64 (m, 25H). MS (ESI) m/e 867.6 (M−2H)$^2$.

2.161 Synthesis of 6-{8-[(1,3-benzothiazol-2-yl)carbamoyl]-3,4-dihydroisoquinolin-2(1H)-yl}-3-[1-({3-[2-({[(2-{2-[(2S,3R,4R,5S,6S)-6-carboxy-3,4,5-trihydroxyoxan-2-yl]ethyl}-4-{[(2S)-2-{[(2S)-2-{[(2S)-2-(2,5-dioxo-2,5-dihydro-1H-pyrrol-1-yl)-3-{4-[(2,5,8,11,14,17,20,23,26,29,32-undecaoxatetratriacontan-34-yl)oxy]phenyl}propanoyl]amino}-3-methylbutanoyl]amino}propanoyl]amino}phenyl)methoxy]carbonyl}[(3R,4S,5R)-3,4,5,6-tetrahydroxyhexyl]amino)ethoxy]-5,7-dimethyltricyclo[3.3.1.1$^{3,7}$]decan-1-yl}methyl)-5-methyl-1H-pyrazol-4-yl]pyridine-2-carboxylic acid (Synthon ZE)

The title compound was prepared by substituting Example 2.120.5 for Example 2.119.15 in Example 2.153. $^1$H NMR (400 MHz, dimethyl sulfoxide-$d_6$) δ ppm 12.84 (bs, 2H), 9.92 (m, 1H), 8.26 (d, 1H), 8.13 (d, 1H), 8.03 (d, 1H), 7.79 (d, 1H), 7.61 (d, 1H), 7.52-7.41 (m, 4H), 7.36 (m, 3H), 7.27 (s, 1H), 7.21 (d, 1H), 7.02 (d, 2H), 6.95 (d, 1H), 6.89 (s, 2H), 6.78 (d, 2H), 5.02 (bs, 4H), 4.96 (s, 2H), 4.59 (dd, 1H), 4.38

(m, 2H), 4.21 (t, 1H), 3.99 (t, 2H), 3.88 (t, 2H), 3.79 (m, 2H), 3.69 (t, 2H), 3.64 (m, 1H), 3.57 (m, 4H), 3.53 (m, 4H), 3.50 (s, 40H), 3.42 (m, 2H), 3.38 (m, 1H), 3.30 (m, 2H), 3.23 (s, 6H), 3.20-3.08 (m, 6H), 3.01 (t, 2H), 2.94 (t, 1H), 2.76 (m, 1H), 2.61 (m, 1H), 2.08 (s, 3H), 2.06-1.92 (m, 2H), 1.67-1.52 (m, 3H), 1.38 (m, 1H), 1.32-1.22 (m, 6H), 1.18-1.01 (m, 6H), 0.92 (min, 2H), 0.84 (m, 6H), 0.78 (m, 6H). MS (ESI) m/e 1078 (M−2H)⁻.

2.162 Synthesis of 4-{[({2-[(3-{[4-(6-{8-[(1,3-benzothiazol-2-yl)carbamoyl]-3,4-dihydroisoquinolin-2(1H)-yl}-2-carboxypyridin-3-yl)-5-methyl-1H-pyrazol-1-yl]methyl}-5,7-dimethyltricyclo[3.3.1.1$^{3,7}$]decan-1-yl)oxy]ethyl}[(3S)-3,4-dihydroxybutyl]carbamoyl)oxy]methyl}-3-(2-{2-[2-(2,5-dioxo-2,5-dihydro-1H-pyrrol-1-yl)acetamido]ethoxy}ethoxy)phenyl beta-D-glucopyranosiduronic acid (Synthon ZS)

2.162.1 3-(1-((3-(2-(((((2-(2-(2-aminoethoxy)ethoxy)-4-(((2S,3R,4S,5S,6S)-6-carboxy-3,4,5-trihydroxytetrahydro-2H-pyran-2-yl)oxy)benzyl)oxy)carbonyl)((S)-3,4-dihydroxybutyl)amino)ethoxy)-5,7-dimethyladamantan-1-yl)methyl)-5-methyl-1H-pyrazol-4-yl)-6-(8-(benzo[d]thiazol-2-ylcarbamoyl)-3,4-dihydroisoquinolin-2(1H)-yl)picolinic acid Example 2.162.1 was prepared by substituting Example 2.62.6 for (9H-fluoren-9-yl)methyl ((S)-3-methyl-1-(((S)-1-((4-(((((4-nitrophenoxy)carbonyl)oxy)methyl)phenyl)amino)-1-oxo-5-ureidopentan-2-yl)amino)-1-oxobutan-2-yl)carbamate and substituting Example 1.85 for Example 1.2.9 in Example 2.49.1. MS (ESI) m/e 1261.4 (M−H)⁻.

2.162.2 4-{[({2-[(3-{[4-(6-{8-[(1,3-benzothiazol-2-yl)carbamoyl]-3,4-dihydroisoquinolin-2(1H)-yl}-2-carboxypyridin-3-yl)-5-methyl-1H-pyrazol-1-yl]methyl}-5,7-dimethyltricyclo[3.3.1.13,7]decan-1-yl)oxy]ethyl}[(3S)-3,4-dihydroxybutyl]carbamoyl)oxy]methyl}-3-(2-{2-[2-(2,5-dioxo-2,5-dihydro-1H-pyrrol-1-yl)acetamido]ethoxy}ethoxy)phenyl beta-D-glucopyranosiduronic acid Example 2.162.2 was prepared by substituting Example 2.162.1 for Example 2.49.1 in Example 2.54. ¹H NMR (400 MHz, dimethyl sulfoxide-d₆) δ 8.18 (t, 1H), 8.00 (dd, 1H), 7.76 (d, 1H), 7.58 (dd, 1H), 7.50-7.29 (m, 6H), 7.26 (s, 1H), 7.17 (d, 1H), 7.03 (s, 2H), 6.92 (d, 1H), 6.64 (d, 1H), 6.57 (dd, 1H), 4.94 (d, 4H), 4.08 (hept, 2H), 4.00 (s, 2H), 3.92-3.68 (m, 8H), 3.51-3.13 (m, 12H), 2.98 (t, 2H), 2.06 (s, 3H), 1.65 (s, 1H), 1.43-0.66 (m, 18H). MS (ESI) m/e 1398.5 (M−H)⁻.

2.163 Synthesis of 2,6-anhydro-8-[2-({[{2-[(3-{[4-(6-{8-[(1,3-benzothiazol-2-yl)carbamoyl]-3,4-dihydroisoquinolin-2(1H)-yl}-2-carboxypyridin-3-yl)-5-methyl-1H-pyrazol-1-yl]methyl}-5,7-dimethyltricyclo[3.3.1.1$^{3,7}$]decan-1-yl)oxy]ethyl}(2-sulfoethyl)carbamoyl]oxy}methyl)-5-{[(79S,82S)-74-[(2,5-dioxo-2,5-dihydro-1H-pyrrol-1-yl)acetyl]-82-methyl-77,80,83-trioxo-79-(propan-2-yl)-2,5,8,11,14,17,20,23,26,29,32,35,38,41,44,47,50,53,56,59,62,65,68,71-tetracosaoxa-74,78,81-triazatrioctacontan-83-yl]amino}phenyl]-7,8-dideoxy-L-glycero-L-gulo-octonic acid (Synthon ZW)

2.163.1 benzyl 2,5,8,11,14,17,20,23,26,29,32,35,38,41,44,47,50,53, 56,59,62, 65,68,71-tetracosaoxa-74-azaheptaheptacontan-77-oate The title compound was prepared using the procedure in Example 2.147.1, replacing 2,5,8,11,14,17,20,23,26,29,32-undecaoxatetratriacontan-34-amine with 2,5,8,11,14,17,20,23,26,29,32,35,38,41,44,47,50,53,56,59,62,65,68,71-tetracosaoxatriheptacontan-73-amine. MS (ESI) m/e 625.9 (M+2H)²⁺.

2.163.2 2,5,8,11,14,17,20,23,26,29,32,35,38,41,44,47,50,53,56,59, 62,65,68,71-tetracosaoxa-74-azaheptaheptacontan-77-oic acid The title compound was prepared using the procedure in Example 2.147.2, replacing Example 2.147.1 with Example 2.163.1. MS (ESI) m/e 1160.7 (M+H)⁺.

2.163.3 2,5-dioxopyrrolidin-1-yl 74-(2-(2,5-dioxo-2,5-dihydro-1H-pyrrol-1-yl)acetyl)-2,5,8,11,14,17,20,23,26,29,32,35,38,41,44, 47,50,53, 56,59,62,65,68, 71-tetracosaoxa-74-azaheptaheptacontan-77-oate The title compound was prepared using the procedure in Example 2.147.3, replacing Example 2.147.2 with Example 2.163.2. MS (ESI) m/e 698.1 (M+2H)²⁺.

2.163.4 2,6-anhydro-8-[2-({[{2-[(3-{[4-(6-{8-[(1,3-benzothiazol-2-yl)carbamoyl]-3,4-dihydroisoquinolin-2(1H)-yl}-2-carboxypyridin-3-yl)-5-methyl-1H-pyrazol-1-yl]methyl}-5,7-dimethyltricyclo[3.3.1.13,7]decan-1-yl)oxy]ethyl}(2-sulfoethyl)carbamoyl]oxy}methyl)-5-{[(79S,82S)-74-[(2,5-dioxo-2,5-dihydro-1H-pyrrol-1-yl)acetyl]-82-methyl-77,80,83-trioxo-79-(propan-2-yl)-2,5,8,11,14,17,20,23,26,29,32,35,38, 41,44,47,50,53,56, 59,62,65,68,71-tetracosaoxa-74,78,81-triazatrioctacontan-83-yl]amino}phenyl]-7,8-dideoxy-L-glycero-L-gulo-octonic acid The title compound was prepared using the procedure in Example 2.147.4, replacing Example 2.147.3 and Example 2.141.4 with Example 2.163.3 and Example 2.154.1, respectively. ¹H NMR (400 MHz, dimethyl sulfoxide-d₆) δ 9.86 (s, 1H), 8.23-7.87 (m, 3H), 7.76 (d, 1H), 7.58 (dd, 1H), 7.53-7.25 (m, 7H), 7.19 (d, 1H), 7.05 (d, 2H), 6.92 (d, 1H), 5.07-4.85 (m, 4H), 4.49-4.30 (m, 3H), 4.20 (dt, 1H), 3.52 (d, 8H), 3.46-3.26 (m, 7H), 3.20 (s, 4H), 3.15-2.82 (m, 4H), 2.61 (s, 3H), 2.38 (dq, 1H), 2.11-1.82 (m, 5H), 1.53 (s, 1H), 1.39-0.66 (m, 24H). MS (ESI) m/e 1326.9 (M−2H)²⁻.

2.164 Synthesis of 6-{8-[(1,3-benzothiazol-2-yl)carbamoyl]-3,4-dihydroisoquinolin-2(1H)-yl}-3-{1-[(3-{2-[{[(4-{[(2S,5S)-2-[3-(carbamoylamino)propyl]-10-[(2,5-dioxo-2,5-dihydro-1H-pyrrol-1-yl)acetyl]-4,7-dioxo-5-(propan-2-yl)-15-sulfo-13-oxa-3,6,10-triazapentadecanan-1-oyl]amino}phenyl)methoxy]carbonyl}(2-sulfoethyl)amino]ethoxy}-5,7-dimethyltricyclo[3.3.1.13,7]decan-1-yl)methyl]-5-methyl-1H-pyrazol-4-yl}pyridine-2-carboxylic acid (Synthon ZX)

A mixture of 1-hydroxypyrrolidine-2,5-dione (2.74 mg), 1-ethyl-3-[3-(dimethylamino)propyl]-carbodiimide hydrochloride (4.26 mg) and Example 2.160.5 (9.01 mg) in N,N-dimethylformamide (0.3 mL) were stirred at room temperature overnight. The mixture was cooled in ice bath. 1-Hydroxybenzotriazole hydrate (3.65 mg) and a mixture of Example 2.112.2 (20 mg) and N,N-diisopropylethylamine (22.19 µL) were added. The resulting mixture was stirred at 0° C. for 10 minutes and purified by reverse phase HPLC, eluting with 30%-55% acetonitrile in 0.1% trifluoroacetic acid water, to provide the title compound. $^1$H NMR (400 MHz, dimethyl sulfoxide-$d_6$) δ 9.95 (d, 1H), 8.18-7.89 (m, 3H), 7.76 (d, 1H), 7.57 (d, 3H), 7.52-7.21 (m, 8H), 7.04 (d, 2H), 6.92 (d, 1H), 4.94 (d, 4H), 4.37 (d, 2H), 4.19 (d, 1H), 3.85 (t, 2H), 3.77 (d, 2H), 3.22 (d, 2H), 2.96 (dt, 4H), 2.73 (dt, 2H), 2.66-2.55 (m, 2H), 2.36 (s, 1H), 2.06 (s, 3H), 1.91 (s, 1H), 1.61 (d, 3H), 1.47-0.86 (m, 11H), 0.80 (ddd, 12H). MS (ESI) m/e 1617.5 (M−H)$^-$.

2.165 This paragraph was intentionally left blank

2.166 Synthesis of 6-(8-(benzo[d]thiazol-2-ylcarbamoyl)-3,4-dihydroisoquinolin-2(1H)-yl)-3-(1-((3-(2-((((2-(2-((2S,3R,4R,5S,6S)-6-carboxy-3,4,5-trihydroxytetrahydro-2H-pyran-2-yl)ethyl)-4-((S)-2-((S)-2-(2-((3S,5S)-3-(2,5-dioxo-2,5-dihydro-1H-pyrrol-1-yl)-2-oxo-5-((2-sulfoethoxy)methyl)pyrrolidin-1-yl)acetamido)-3-methylbutanamido)propanamido)benzyl)oxy)carbonyl)((S)-3,4-dihydroxybutyl)amino)ethoxy)-5,7-dimethyladamantan-1-yl)methyl)-5-methyl-1H-pyrazol-4-yl)picolinic acid (Synthon AAA)

The title compound was prepared by substituting Example 2.167.1 for Example 2.119.16 in Example 2.119.17. $^1$H NMR (500 MHz, dimethyl sulfoxide-$d_6$) δ ppm 9.86 (br d, 1H), 8.17 (br d, 1H), 8.04 (m, 2H), 7.78 (d, 1H), 7.61 (d, 1H), 7.51 (br d, 1H), 7.49-7.39 (m, 4H), 7.36 (m, 2H), 7.29 (s, 1H), 7.21 (d, 1H), 7.07 (s, 2H), 6.95 (d, 1H), 5.00 (s, 2H), 4.96 (s, 2H), 4.64 (t, 1H), 4.36 (m, 1H), 4.19 (m, 1H), 4.16 (d, 1H), 4.01 (d, 1H), 3.88 (br t, 2H), 3.82 (br m, 3H), 3.75 (br m, 1H), 3.64 (t, 2H), 3.54 (d, 2H), 3.47 (m, 4H), 3.43 (br m, 4H), 3.23 (br m, 5H), 3.13 (t, 1H), 3.10 (br m, 1H), 3.01 (br m, 2H), 2.93 (m, 2H), 2.83-2.68 (m, 3H), 2.37 (m, 1H), 2.08 (s, 3H), 1.99 (br m, 2H), 1.85 (m, 1H), 1.55 (br m, 1H), 1.37 (br m, 1H), 1.28 (br m, 6H), 1.10 (br m, 7H), 0.93 (br m, 1H), 0.88-0.69 (m, 12H). MS (ESI) m/e 1713.6 (M−H)$^-$.

Alternative Synthesis of 6-(8-(benzo[d]thiazol-2-ylcarbamoyl)-3,4-dihydroisoquinolin-2(1H)-yl)-3-(1-((3-(2-((((2-(2-((2S,3R,4R,5S,6S)-6-carboxy-3,4,5-trihydroxytetrahydro-2H-pyran-2-yl)ethyl)-4-((S)-2-((S)-2-(2-((3S,5S)-3-(2,5-dioxo-2,5-dihydro-1H-pyrrol-1-yl)-2-oxo-5-((2-sulfoethoxy)methyl)pyrrolidin-1-yl)acetamido)-3-methylbutanamido)propanamido)benzyl)oxy)carbonyl)((S)-3,4-dihydroxybutyl)amino)ethoxy)-5,7-dimethyladamantan-1-yl)methyl)-5-methyl-1H-pyrazol-4-yl)picolinic acid (Synthon AAA)

2.166.1 3-(1-((3-(2-((((4-((S)-2-((S)-2-amino-3-methylbutanamido)propanamido)-2-(2-((2S,3R,4R,5S,6S)-6-carboxy-3,4,5-trihydroxytetrahydro-2H-pyran-2-yl)ethyl)benzyl)oxy)carbonyl)((S)-3,4-dihydroxybutyl)amino)ethoxy)-5,7-dimethyladamantan-1-yl)methyl)-5-methyl-1H-pyrazol-4-yl)-6-(8-(benzo[d]thiazol-2-ylcarbamoyl)-3,4-dihydroisoquinolin-2(1H)-yl)picolinic acid To a stirred solution of Example 1.85 (0.065 g), 1-hydroxybenzotriazole (0.013 g) and N,N-diisopropylethylamine (0.06 mL) in N,N-dimethylformamide (0.5 mL) was added Example 2.123.19 (0.085 g), and the mixture was stirred at room temperature for 2 hours. The reaction was concentrated under reduced pressure. The residue was dissolved in a solvent mixture of methanol (0.5 mL) and tetrahydrofuran (0.5 mL), and lithium hydroxide monohydrate (30 mg) was added. The reaction was stirred for 1 hour at ambient temperature, after which the reaction was concentrated under reduced pressure. The residue was dissolved in methanol/water (1:1, 1 mL) containing 0.1 mL trifluoroacetic acid. The sample was purified by reverse-phase HPLC (Phenomenex® Luna® C18 250×50 mm column, 100 mL/min), eluting with 20-100% acetonitrile in water containing 0.01% trifluoroacetic acid over 40 minutes. The fractions containing product were lyophilized to give the title compound. MS (ESI) m/z 1357.5 (M+H)$^+$.

2.166.2 6-(8-(benzo[d]thiazol-2-ylcarbamoyl)-3,4-dihydroisoquinolin-2(1H)-yl)-3-(1-((3-(2-((((2-(2-((2S,3R,4R,5S,6S)-6-carboxy-3,4,5-trihydroxytetrahydro-2H-pyran-2-yl)ethyl)-4-((S)-2-((S)-2-(2-((3S,5S)-3-(2,5-dioxo-2,5-dihydro-1H-pyrrol-1-yl)-2-oxo-5-((2-sulfoethoxy)methyl)pyrrolidin-1-yl)acetamido)-3-methylbutanamido)propanamido)benzyl)oxy)carbonyl)((S)-3,4-dihydroxybutyl)amino)ethoxy)-5,7-dimethyladamantan-1-yl)methyl)-5-methyl-1H-pyrazol-4-yl)picolinic acid (Synthon AAA)

To a solution of Example 2.119.15 (16 mg) in N,N-dimethylformamide (200 µL) was added 1-[bis(dimethylamino)methylene]-1H-1,2,3-triazolo[4,5-b]pyridinium 3-oxid hexafluorophosphate (16 mg, HATU) and N,N-diisopropylethylamine (17 µL). The reaction was stirred for 5 minutes, and a solution of Example 2.166.1 (48 mg) and N,N-diisopropylethylamine (20 µL) in N,N-dimethylformamide (200 µL) was added. The reaction was stirred for one hour and diluted with a mixture of N,N-dimethylformamide/water (1/1, 1.5 mL). The sample was purified by reverse-phase HPLC (Phenomenex® Luna® C18 250×50 mm column, 100 mL/min), eluting with 20-70% acetonitrile in water containing 0.01% trifluoroacetic acid over 40 minutes. The fractions containing the product were lyophilized to give the title compound. $^1$H NMR (500 MHz, dimethyl sulfoxide-d$_6$) δ ppm 9.86 (br d, 1H), 8.17 (br d, 1H), 8.04 (m, 2H), 7.78 (d, 1H), 7.61 (d, 1H), 7.51 (br d, 1H), 7.49-7.39 (m, 4H), 7.36 (m, 2H), 7.29 (s, 1H), 7.21 (d, 1H), 7.07 (s, 2H), 6.95 (d, 1H), 5.00 (s, 2H), 4.96 (s, 2H), 4.64 (t, 1H), 4.36 (m, 1H), 4.19 (m, 1H), 4.16 (d, 1H), 4.01 (d, 1H), 3.88 (br t, 2H), 3.82 (br m, 3H), 3.75 (br m, 1H), 3.64 (t, 2H), 3.54 (d, 2H), 3.47 (m, 4H), 3.43 (br m, 4H), 3.23 (br m, 5H), 3.13 (t, 1H), 3.10 (br m, 1H), 3.01 (br m, 2H), 2.93 (t, 1H), 2.83-2.68 (m, 3H), 2.37 (m, 1H), 2.08 (s, 3H), 1.99 (br m, 2H), 1.85 (m, 1H), 1.55 (br m, 1H), 1.37 (br m, 1H), 1.28 (br m, 6H), 1.10 (br m, 7H), 0.93 (br m, 1H), 0.88-0.69 (m, 12H). MS (ESI) m/z 1713.6 (M−H)⁻.

2.167 Synthesis of 2,6-anhydro-8-(2-{[({2-[(3-{[4-(6-{8-[(1,3-benzothiazol-2-yl)carbamoyl]-3,4-dihydroisoquinolin-2(1H)-yl}-2-carboxypyridin-3-yl)-5-methyl-1H-pyrazol-1-yl]methyl}-5,7-dimethyltricyclo[3.3.1.1³,⁷]decan-1-yl)oxy]ethyl}[(3S)-3,4-dihydroxybutyl]carbamoyl)oxy]methyl}-5-{[(2S)-2-({(2S)-2-[2-(2,5-dioxo-2,5-dihydro-1H-pyrrol-1-yl)acetamido]-3-methylbutanoyl}amino)propanoyl]amino}phenyl)-7,8-dideoxy-L-glycero-L-gulo-octonic acid (Synthon AAD)

2.167.1 3-(1-((3-(2-(((((4-((S)-2-((S)-2-amino-3-methylbutanamido)propanamido)-2-(2-((2S,3R,4R,5S,6S)-6-carboxy-3,4,5-trihydroxytetrahydro-2H-pyran-2-yl)ethyl)benzyl)oxy)carbonyl)((S)-3,4-dihydroxybutyl)amino)ethoxy)-5,7-dimethyladamantan-1-yl)methyl)-5-methyl-1H-pyrazol-4-yl)-6-(8-(benzo[d]thiazol-2-ylcarbamoyl)-3,4-dihydroisoquinolin-2(1H)-yl)picolinic acid Example 2.167.1 was prepared by substituting Example 2.123.19 for (9H-fluoren-9-yl)methyl ((S)-3-methyl-1-(((S)-1-((4-(((((4-nitrophenoxy)carbonyl)oxy)methyl)phenyl)amino)-1-oxo-5-ureidopentan-2-yl)amino)-1-oxobutan-2-yl)carbamate and substituting Example 1.85 for Example 1.2.9 in Example 2.49.1. MS (ESI) m/e 1355.5 (M−H)⁻.

2.167.2 2,6-anhydro-8-(2-{[({2-[(3-{[4-(6-{8-[(1,3-benzothiazol-2-yl)carbamoyl]-3,4-dihydroisoquinolin-2(1H)-yl}-2-carboxypyridin-3-yl)-5-methyl-1H-pyrazol-1-yl]methyl}-5,7-dimethyltricyclo[3.3.1.1³,⁷]decan-1-yl)oxy]ethyl}[(3S)-3,4-dihydroxybutyl]carbamoyl)oxy]methyl}-5-{[(2S)-2-({(2S)-2-[2-(2,5-dioxo-2,5-dihydro-1H-pyrrol-1-yl)acetamido]-3-methylbutanoyl}amino)propanoyl]amino}phenyl)-7,8-dideoxy-L-glycero-L-gulo-octonic acid Example 2.167.2 was prepared by substituting Example 2.167.1 for Example 2.49.1 in Example 2.54. ¹H NMR (501 MHz, dimethyl sulfoxide-d$_6$) δ 9.90 (d, 1H), 8.25 (m, 2H), 8.01 (d, 1H), 7.77 (d, 1H), 7.59 (d, 1H), 7.51-7.40 (m, 4H), 7.40-7.31 (m, 3H), 7.26 (s, 1H), 7.20 (d, 1H), 7.05 (s, 2H), 6.93 (d, 1H), 4.96 (d, 4H), 4.36 (t, 1H), 4.22-4.06 (m, 3H), 3.85 (t, 2H), 3.26-3.17 (m, 4H), 3.14-2.88 (m, 5H), 2.78-2.55 (m, 2H), 2.10-1.88 (m, 5H), 1.69-1.49 (m, 2H), 1.39-0.73 (m, 28H). MS (ESI) m/e 1492.5 (M−H)⁻.

2.168 Synthesis of 2-{[({2-[(3-{[4-(6-{8-[(1,3-benzothiazol-2-yl)carbamoyl]-3,4-dihydroisoquinolin-2(1H)-yl}-2-carboxypyridin-3-yl)-5-methyl-1H-pyrazol-1-yl]methyl}-5,7-dimethyltricyclo[3.3.1.1³,⁷]decan-1-yl)oxy]ethyl}[(3S)-3,4-dihydroxybutyl]carbamoyl)oxy]methyl}-5-{4-[2-(2,5-dioxo-2,5-dihydro-1H-pyrrol-1-yl)acetamido]butyl}phenyl beta-D-glucopyranosiduronic acid (Synthon AAE)

2.168.1 3-(1-((3-(2-((((4-(4-aminobutyl)-2-(((2S,3R,4S,5S,6S)-6-carboxy-3,4,5-trihydroxytetrahydro-2H-pyran-2-yl)oxy)benzyl)oxy)carbonyl)((S)-3,4-dihydroxybutyl)amino)ethoxy)-5,7-dimethyladamantan-1-yl)methyl)-5-methyl-1H-pyrazol-4-yl)-6-(8-(benzo[d]thiazol-2-ylcarbamoyl)-3,4-dihydroisoquinolin-2(1H)-yl)picolinic acid Example 2.168.1 was prepared by substituting Example 2.124.5 for (9H-fluoren-9-yl)methyl ((S)-3-methyl-1-(((S)-1-((4-(((((4-nitrophenoxy)carbonyl)oxy)methyl)phenyl)amino)-1-oxo-5-ureidopentan-2-yl)amino)-1-oxobutan-2-yl)carbamate and substituting Example 1.85 for Example 1.2.9 in Example 2.49.1. MS (ESI) m/e 1229.5 (M−H)⁻.

2.168.2 2-{[({2-[(3-{[4-(6-{8-[(1,3-benzothiazol-2-yl)carbamoyl]-3,4-dihydroisoquinolin-2(1H)-yl}-2-carboxypyridin-3-yl)-5-methyl-1H-pyrazol-1-yl]methyl}-5,7-dimethyltricyclo[3.3.1.1³,⁷]decan-1-yl)oxy]ethyl}[(3S)-3,4-dihydroxybutyl]carbamoyl)oxy]methyl}-5-{4-[2-(2,5-dioxo-2,5-dihydro-1H-pyrrol-1-yl)acetamido]butyl}phenyl beta-D-glucopyranosiduronic acid Example 2.168.2 was prepared by substituting Example 2.168.1 for Example 2.49.1 in Example 2.54. ¹H NMR (501 MHz, dimethyl sulfoxide-d$_6$) δ 8.07 (s, 1H), 8.01 (dt, 1H), 7.77 (dt, 1H), 7.63-7.57 (m, 1H), 7.51-7.39 (m, 3H), 7.38-7.31 (m, 2H), 7.26 (s, 1H), 7.16 (d, 1H), 7.05 (s, 2H), 6.93 (d, 2H), 6.84-6.80 (m, 1H), 5.14-4.98 (m, 3H), 4.94 (s, 2H), 3.79 (d, 2H), 3.48-3.19 (m, 10H), 3.08-2.96 (m, 4H), 2.52 (s, 4H), 2.07 (s, 2H), 1.77-0.72 (m, 14H). MS (ESI) m/e 1366.5 (M−H)⁻.

2.169 Synthesis of 6-{8-[(1,3-benzothiazol-2-yl)carbamoyl]-3,4-dihydroisoquinolin-2(1H)-yl}-3-{1-[(3-{2-[{[(4-{[(2S)-5-(carbamoylamino)-2-{[(2S)-2-{[6-(2,5-dioxo-2,5-dihydro-1H-pyrrol-1-yl)hexanoyl]amino}-3-methylbutanoyl]amino}pentanoyl]amino}phenyl)methoxy]carbonyl}(2-sulfoethyl)amino]acetamido}-5,7-dimethyltricyclo[3.3.1.1³,⁷]decan-1-yl)methyl]-5-methyl-1H-pyrazol-4-yl}pyridine-2-carboxylic acid (Synthon ABG)

The title compound was prepared as described in Example 2.54, replacing Example 2.49.1 with Example 1.89.12. ¹H NMR (501 MHz, dimethyl sulfoxide-d$_6$) δ ppm 9.95 (d, 1H), 8.10-7.96 (m, 1H), 7.75 (t, 2H), 7.57 (dd, 3H), 7.51-7.18 (m, 8H), 6.95 (d, 3H), 6.92 (s, OH), 5.03-4.86 (m, 4H), 4.36 (d, 1H), 3.85 (t, 2H), 3.78-3.67 (m, 4H), 3.42 (s, 2H), 3.33 (t, 2H), 3.04-2.86 (m, 4H), 2.63 (d, 2H), 2.13 (dd, 2H), 2.07 (s, 3H), 1.98-1.87 (m, OH), 1.71-1.23 (m, 10H), 1.24-0.85 (m, 6H), 0.78 (t, 11H). MS (ESI) m/e 1463.5 (M−H)⁻.

2.170 Synthesis of N-[6-(2,5-dioxo-2,5-dihydro-1H-pyrrol-1-yl)hexanoyl]-L-valyl-N-{4-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.13,7]dec-1-yl}sulfanyl)ethyl](2-sulfoethyl)carbamoyl}oxy)methyl]phenyl}-N5-carbamoyl-L-ornithinamide (Synthon ABL)

The title compound was prepared by substituting Example 1.90.11 for Example 1.2.9 in Example 2.1. $^1$H NMR (500 MHz, dimethyl sulfoxide-$d_6$) δ ppm 10.0 (s, 1H), 8.08 (br s, 1H), 8.03 (d, 1H), 7.81 (br s, 1H) 7.78 (d, 1H), 7.60 (m, 3H) 7.52 (t, 1H), 7.47 (t, 1H), 7.43 (d, 1H), 7.37 (d, 1H), 7.34 (d, 1H) 7.32 (s, 1H), 7.28 (d, 2H), 6.99 (s, 1H), 6.96 (d, 2H), 5.00 (s, 2H), 4.96 (s, 2H), 4.39 (m, 1H), 4.18 (m, 2H), 3.88 (m, 2H), 3.82 (s, 1H), 3.77 (s, 1H), 3.46 (br m, 2H), 3.58 (t, 2H), 3.29 (v br m, 2H), 3.01 (br m, 3H), 2.95 (br m, 1H), 2.47 (m, 2H), 2.61 (br m, 2H) 2.16 (m, 1H), 2.10 (m, 4H), 1.96 (br m, 1H), 1.69 (v br m, 1H), 1.59 (v br m, 1H), 1.53-1.40 (m, 7H), 1.39-1.22 (m, 5H), 1.17 (m, 3H), 1.13-0.88 (m, 6H), 0.87-0.77 (m, 9H), 0.75 (s, 3H). MS (ESI) m/e 1466.5 (M−H)$^-$.

2.171 Synthesis of N-[6-(2,5-dioxo-2,5-dihydro-1H-pyrrol-1-yl)hexanoyl]-L-valyl-N-[4-({[(3-{3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.13,7]dec-1-yl}propyl)(2-sulfoethyl)carbamoyl]oxy}methyl)phenyl]-N5-carbamoyl-L-ornithinamide (Synthon ABN)

The title compound was prepared as described in Example 2.1, replacing Example 1.2.9 with Example 1.91.13. $^1$H NMR (501 MHz, DMSO-$d_6$) δ ppm 12.83 (s, 1H), 9.96 (s, 1H), 8.03 (t, 2H), 7.77 (d, 2H), 7.64-7.52 (m, 3H), 7.45 (ddd, 3H), 7.34 (td, 2H), 7.29-7.21 (m, 3H), 7.03-6.91 (m, 3H), 4.95 (d, 4H), 4.37 (q, 1H), 4.17 (s, 1H), 3.86 (t, 2H), 3.45-3.29 (m, 4H), 3.10 (t, 2H), 2.95 (dt, 4H), 2.61 (q, 2H), 2.15 (td, 2H), 2.07 (s, 3H), 2.00-1.89 (m, 1H), 1.74-1.24 (m, 10H), 1.25-0.87 (m, 13H), 0.88-0.70 (m, 12H). MS (ESI) m/e 1450.2 (M+H)$^+$.

2.172 Synthesis of 2-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.13,7]dec-1-yl}oxy)ethyl][(3S)-3,4-dihydroxybutyl]carbamoyl}oxy)methyl]-5-{4-[({(3S,5S)-3-(2,5-dioxo-2,5-dihydro-1H-pyrrol-1-yl)-2-oxo-5-[(2-sulfoethoxy)methyl]pyrrolidin-1-yl}acetyl)amino]butyl}phenyl beta-D-glucopyranosiduronic acid (Synthon AAF)

The title compound was prepared as described in Example 2.119.17, replacing Example 2.168.1 for Example 2.119.16. $^1$H NMR (400 MHz, dimethyl sulfoxide-$d_6$) δ ppm 8.03 (d, 1H), 7.84 (br t, 1H), 7.78 (d, 1H), 7.61 (d, 1H), 7.50 (br d, 1H), 7.45 (dd, 1H), 7.43 (d, 1H), 7.36 (m, 2H), 7.29 (s, 1H), 7.17 (br m, 1H), 7.06 (s, 2H), 6.95 (m, 2H), 6.85 (d, 1H), 5.08 (s, 2H), 5.02 (d, 1H), 4.96 (s, 2H), 4.70 (t, 1H), 4.06 (d, 2H), 3.88 (m, 4H), 3.81 (m, 2H), 3.73 (br m, 1H), 3.62 (m, 2H), 3.47 (br m, 4H), 3.40 (m, 4H), 3.35 (m, 2H), 3.29 (m, 4H), 3.07 (m, 2H), 3.00 (t, 2H), 2.73 (m, 2H), 2.54 (m, 2H), 2.36 (br m, 1H), 2.09 (s, 3H), 1.83 (m, 1H), 1.71 (br m, 1H), 1.55 (br m, 2H), 1.40 (br m, 5H), 1.24 (br m, 4H), 1.10 (br m, 5H), 0.94 (br m, 1H), 0.83, 0.81 (both s, total 6H). MS (ESI) m/e 1587.5 (M−H)$^-$.

2.173 Synthesis of 2,6-anhydro-8-[2-({[{2-[(3-{[4-(6-{8-[(1,3-benzothiazol-2-yl)carbamoyl]-3,4-dihydroisoquinolin-2(1H)-yl}-2-carboxypyridin-3-yl)-5-methyl-1H-pyrazol-1-yl]methyl}-5,7-dimethyltricyclo[3.3.1.13,7]decan-1-yl)oxy]ethyl}(2-sulfoethyl)carbamoyl]oxy}methyl)-5-{[N-({(3R,5S)-3-(2,5-dioxo-2,5-dihydro-1H-pyrrol-1-yl)-2-oxo-5-[(2-sulfoethoxy)methyl]pyrrolidin-1-yl}acetyl)-L-valyl-L-alanyl]amino}phenyl]-7,8-dideoxy-L-glycero-L-gulo-octonic acid (Synthon ABO)

2.173.1 (3R,6R,7aS)-6-azido-3-phenyltetrahydropyrrolo[1,2-c]oxazol-5(3H)-one The title compound was prepared by substituting Example 2.119.3 for Example 2.119.2 in Example 2.119.4. MS (DCI) m/e 262.0 (M+NH$_4$)$^+$.

2.173.2 (3R,6R,7aS)-6-amino-3-phenyltetrahydropyrrolo[1,2-c]oxazol-5(3H)-one The title compound was prepared by substituting Example 2.173.1 for Example 2.119.4 in Example 2.119.5. MS (DCI) m/e 219.0 (M+H)$^+$.

2173.3 (3R,6R,7aS)-6-(dibenzylamino)-3-phenyltetrahydropyrrolo[1,2-c]oxazol-5(3H)-one The title compound was prepared by substituting Example 2.173.2 for Example 2.119.5 in Example 2.119.6. MS (DCI) m/e 399.1 (M+H)$^+$.

2.173.4 (3R,5S)-3-(dibenzylamino)-5-(hydroxymethyl)pyrrolidin-2-one

The title compound was prepared by substituting Example 2.173.3 for Example 2.119.6 in Example 2.119.7, with the exception that the reaction was heated to 65° C. for one day rather than 6 days. MS (DCI) m/e 311.1 (M+H)+.

2.173.5 (3R,5S)-5-(((tert-butyldimethylsilyl)oxy)methyl)-3-(dibenzylamino)pyrrolidin-2-one The title compound was prepared by substituting Example 2.173.4 for Example 2.119.7 in Example 2.119.8. The title compound was carried on to the next step without purification. MS (DCI) m/e 425.2 (M+H)$^+$.

2.173.6 tert-butyl 2-((3R,5S)-5-(((tert-butyldimethylsilyl)oxy)methyl)-3-(dibenzylamino)-2-oxopyrrolidin-1-yl)acetate The title compound was prepared by substituting Example 2.173.5 for Example 2.119.8 in Example 2.119.9. The title compound was carried on to the next step without purification. MS (DCI) m/e 539.3 (M+H)$^+$.

2.173.7 tert-butyl 2-((3R,5S)-3-(dibenzylamino)-5-(hydroxymethyl)-2-oxopyrrolidin-1-yl)acetate The title compound was prepared by substituting Example 2.173.6 for Example 2.119.9 in Example 2.119.10. MS (DCI) m/e 425.2 (M+H)$^+$.

2.173.8 tert-butyl 2-((3R,5S)-5-((2-((4-((tert-butyl-diphenylsilyl)oxy)-2,2-dimethylbutoxy)sulfonyl)ethoxy)methyl)-3-(dibenzylamino)-2-oxopyrrolidin-1-yl)acetate The title compound was prepared by substituting Example 2.173.7 for Example 2.119.10 in Example 2.119.11.

2.173.9 tert-butyl (S)-2-(2-((2-((4-((tert-butyldiphenylsilyl)oxy)-2,2-dimethylbutoxy)sulfonyl)ethoxy)methyl)-5-oxopyrrolidin-1-yl)acetate The title compound was prepared by substituting Example 2.173.8 for Example 2.119.11 in Example 2.119.12. MS (ESI) m/e 691.1 (M+H)+.

2.173.10 4-(((3R,5S)-1-(2-(tert-butoxy)-2-oxoethyl)-5-((2-((4-((tert-butyldiphenylsilyl)oxy)-2,2-dimethylbutoxy)sulfonyl)ethoxy)methyl)-2-oxopyrrolidin-3-yl)amino)-4-oxobut-2-enoic acid The title compound was prepared by substituting Example 2.173.9 for Example 2.119.12 in Example 2.119.13. MS (ESI) m/e 789.0 (M+H)+.

2.173.11 tert-butyl 2-((3R,5S)-5-((2-((4-((tert-butyl-diphenylsilyl)oxy)-2,2-dimethylbutoxy)sulfonyl)ethoxy)methyl)-3-(2,5-dioxo-2,5-dihydro-1H-pyrrol-1-yl)-2-oxopyrrolidin-1-yl)acetate The title compound was prepared by substituting Example 2173.10 for Example 2.119.13 in Example 2.119.14.

2.173.12 2-((3R,5S)-3-(2,5-dioxo-2,5-dihydro-1H-pyrrol-1-yl)-2-oxo-5-((2-sulfoethoxy)methyl)pyrrolidin-1-yl)acetic acid The title compound was prepared by substituting Example 2.173.11 for Example 2.119.14 in Example 2.119.15. MS (ESI) m/e 377.0 (M+H)+.

2.173.13 2,6-anhydro-8-[2-({[{2-[(3-{[4-(6-{8-[(1,3-benzothiazol-2-yl)carbamoyl]-3,4-dihydroisoquinolin-2(1H)-yl}-2-carboxypyridin-3-yl)-5-methyl-1H-pyrazol-1-yl]methyl}-5,7-dimethyltricyclo[3.3.1.13,7]decan-1-yl)oxy]ethyl}(2-sulfoethyl)carbamoyl]oxy}methyl)-5-{N-({(3R,5S)-3-(2,5-dioxo-2,5-dihydro-1H-pyrrol-1-yl)-2-oxo-5-[(2-sulfoethoxy)methyl]pyrrolidin-1-yl}acetyl)-L-valyl-L-alanyl]amino}phenyl]-7,8-dideoxy-L-glycero-L-gulo-octonic acid The title compound was prepared by substituting Example 2.123.20 for Example 2.119.16 and Example 2.173.12 for Example 2.119.15 in Example 2.119.17. 1H NMR (400 MHz, dimethyl sulfoxide-d6) δ ppm 9.94 (d, 1H), 8.28 (br d, 1H), 8.01 (d, 2H), 7.77 (d, 1H), 7.59 (d, 1H), 7.53 (d, 1H), 7.43 (m, 4H), 7.34 (m, 3H), 7.19 (d, 1H), 7.06 (s, 2H), 6.96 (d, 1H), 4.99 (m, 2H), 4.95 (s, 2H), 4.78 (t, 1H), 4.36 (t, 1H), 4.19 (br m, 1H), 4.16 (d, 1H), 3.98 (d, 1H), 3.87 (br t, 2H), 3.81 (br d, 2H), 3.73 (brm, 1H), 3.63 (t, 2H), 3.53 (m, 2H), 3.44 (m, 4H), 3.31 (t, 2H), 3.21 (br m, 2H), 3.17 (m, 2H), 3.00 (m, 2H), 2.92 (br m, 1H), 2.75 (m, 3H), 2.65 (br m, 3H), 2.35 (br m, 1H), 2.16 (m, 1H), 2.07 (s, 3H), 1.98 (br m, 2H), 1.55 (br m, 1H), 1.34 (br m, 1H), 1.26 (br m, 6H), 1.09 (br m, 7H), 0.93 (br m, 1H), 0.87, 0.83, 0.79 (all d, total 12H). MS (ESI) m/e 1733.3 (M−H)−.

2.174 Synthesis of 2,6-anhydro-8-{2-({[{2-[(3-{[4-(6-{8-[(1,3-benzothiazol-2-yl)carbamoyl]-3,4-dihydroisoquinolin-2(1H)-yl}-2-carboxypyridin-3-yl)-5-methyl-1H-pyrazol-1-yl]methyl}-5,7-dimethyltricyclo[3.3.1.13,7]decan-1-yl)oxy]ethyl}(2-sulfoethyl)carbamoyl]oxy}methyl)-5-[(N-{[(3R,5S)-3-(2,5-dioxo-2,5-dihydro-1H-pyrrol-1-yl)-2-oxo-5-(41-oxo-2,5,8,11,14,17,20,23,26,29,32,35,38-tridecaoxa-42-azatritetracontan-43-yl)pyrrolidin-1-yl]acetyl}-L-valyl-L-alanyl)amino]phenyl}-7,8-dideoxy-L-glycero-L-gulo-octonic acid (Synthon ABM)

2.174.1 tert-butyl[(3R,5S)-5-{[bis(tert-butoxycarbonyl)amino]methyl}-3-(dibenzylamino)-2-oxopyrrolidin-1-yl]acetate To a cold (0° C.) solution of Example 2.173.7 (1.6 g) in dichloromethane (15 mL) was added triethylamine (0.70 mL) and methanesulfonyl chloride (0.39 mL) dropwise. The ice-bath was removed, and the reaction was stirred at room temperature for two hours. The reaction was quenched by the addition of saturated aqueous sodium bicarbonate solution. The layers were separated, and the organic layer was washed with brine. The combined aqueous layers were back-extracted with dichloromethane. The combined organic layers were dried with anhydrous sodium sulfate, filtered and concentrated under reduced pressure to give the intermediate mesylate (1.9 g). The residue was dissolved in acetonitrile (15 mL), and di-tert-butyl-iminodicarboxylate (1.0 g) and cesium carbonate (2.4 g) were added. The reaction was heated to reflux under nitrogen for one day. The reaction was cooled and quenched by the addition of water and diethyl ether. The layers were separated, and the organic was washed with brine. The combined aqueous layers were back-extracted with diethyl ether. The combined organic layers were dried with anhydrous sodium sulfate, filtered and concentrated under reduced pressure. The residue was purified by silica gel chromatography, eluting with 20% ethyl acetate in heptanes, to give the title compound. MS (DCI) m/e 624.3 (M+H)+.

2.174.2 tert-butyl[(3R,5S)-3-amino-5-{[bis(tert-butoxycarbonyl)amino]methyl}-2-oxopyrrolidin-1-yl]acetate To a solution of Example 2.174.1 (1.0 g) in ethyl acetate (6 mL) and methanol (18 mL) was added palladium hydroxide on carbon (100 mg, 20% by weight). The reaction was stirred at room temperature under a hydrogen balloon for one day. The reaction was filtered through diatomaceous earth, eluting with ethyl acetate. The filtrate was concentrated under reduced pressure, dissolved in dichloromethane (10 mL) and filtered through a syringe-tip Teflon 40 micron filter. The filtrate was concentrated under reduced pressure to give the title compound. MS (DCI) m/e 444.1 (M+H)+.

2.174.3 4-{[(3R,5S)-5-{[bis(tert-butoxycarbonyl)amino]methyl}-1-(2-tert-butoxy-2-oxoethyl)-2-oxopyrrolidin-3-yl]amino}-4-oxobut-2-enoic acid The title compound was prepared by substituting Example 2.174.2 for Example 2.119.12 in Example 2.119.13. MS (ESI) m/e 540.2 (M−H)−.

2.174.4 tert-butyl[(3R,5S)-5-{[bis(tert-butoxycarbonyl)amino]methyl}-3-(2,5-dioxo-2,5-dihydro-1H-pyrrol-1-yl)-2-oxopyrrolidin-1-yl]acetate The title compound was prepared by substituting Example 2.174.3 for Example 2.119.13 in Example 2.119.14. MS (DCI) m/e 541.1 (M+NH$_4$)$^+$.

2.174.5 2-((3R,5S)-5-(aminomethyl)-3-(2,5-dioxo-2,5-dihydro-1H-pyrrol-1-yl)-2-oxopyrrolidin-1-yl)acetic acid To a solution of Example 2.174.4 (284 mg) in dichloromethane (10 mL) was added trifluoroacetic acid (5 mL). The reaction was stirred at room temperature for two hours and was concentrated under reduced pressure. The residue was dissolved in water/acetonitrile 7/3 (5 mL), frozen and lyophilized to provide the title compound, which was used in the subsequent step without further purification. MS (ESI) m/e 266.1 (M–H)$^-$.

2.174.6 2-((3R,5S)-3-(2,5-dioxo-2,5-dihydro-1H-pyrrol-1-yl)-2-oxo-5-(41-oxo-2,5,8,11,14,17,20,23,26,29,32,35,38-tridecaoxa-42-azatritetracontan-43-yl)pyrrolidin-1-yl)acetic acid To a solution of 2,5,8,11,14,17,20,23,26,29,32,35,38-tridecaoxahentetracontan-41-oic acid (160 mg) in N,N-dimethylformamide (1.0 mL) was added O-(7-azabenzotriazol-1-yl)-N,N,N',N'-tetramethyluronium hexafluorophosphate (85 mg) and N,N-diisopropylethylamine (130 μL). The reaction mixture was stirred for three minutes at room temperature, and a solution of Example 2.174.5 (70 mg) and N,N-diisopropylethylamine (130 μL) in N,N-dimethylformamide (1.0 mL) was added. The reaction was stirred at room temperature for one hour and diluted with N,N-dimethylformamide/water 1/1 (3.5 mL). The solution was purified by reverse phase HPLC on a Gilson system (C18 column), eluting with 20-70% acetonitrile in 0.1% TFA water, to provide the title compound. MS (ESI) m/e 880.4 (M–H)$^-$.

2.174.7 2,6-anhydro-8-{(2-{[(3-{[4-(6-{8-[(1,3-benzothiazol-2-yl)carbamoyl]-3,4-dihydroisoquinolin-2(1H)-yl}-2-carboxypyridin-3-yl)-5-methyl-1H-pyrazol-1-yl]methyl}-5,7-dimethyltricyclo[3.3.1.1$^{3,7}$]decan-1-yl)oxy]ethyl}(2-sulfoethyl)carbamoyl]oxy}methyl)-5-[(N-{[(3R,5S)-3-(2,5-dioxo-2,5-dihydro-1H-pyrrol-1-yl)-2-oxo-5-(41-oxo-2,5,8,11,14,17,20,23,26,29,32,35,38-tridecaoxa-42-azatritetracontan-43-yl)pyrrolidin-1-yl]acetyl}-L-valyl-L-alanyl)amino]phenyl}-7,8-dideoxy-L-glycero-L-gulo-octonic acid The title compound was prepared by substituting Example 2.174.6 for Example 2.119.15 and Example 2.123.20 for Example 2.119.16 in Example 2.119.17 $^1$H NMR (500 MHz, dimethyl sulfoxide-d$_6$) δ ppm 9.93 (br d, 1H), 8.28 (d, 1H), 8.03 (d, 1H), 8.02 (br s, 1H), 7.91 (br d, 1H), 7.79 (d, 1H), 7.61 (d, 1H), 7.51 (br d, 1H), 7.49-7.42 (m, 3H), 7.40 (br d, 1H), 7.36 (m, 2H), 7.28 (s, 1H), 7.22 (d, 1H), 7.06 (s, 2H), 6.95 (d, 1H), 5.00 (br d, 2H), 4.95 (s, 2H), 4.70 (t, 1H), 4.39 (m, 1H), 4.28 (m, 1H), 4.00 (dd, 2H), 3.88 (br m, 2H), 3.85 (br m, 1H), 3.80 (br m, 2H), 3.62 (t, 2H), 3.50 (s, 44H), 3.48 (d, 4H), 3.43 (br m, 2H), 3.34 (br m, 2H), 3.23 (s, 3H), 3.21 (v br m, 2H), 3.14 (t, 2H), 3.10 (v br m, 1H), 3.00 (t, 2H), 2.94 (br m, 1H), 2.76 (v br m, 1H), 2.64 (v br m, 3H), 2.34 (br t, 2H), 2.32 (m, 1H), 2.17 (m, 1H), 2.09 (br d, 3H), 2.00 (br m, 1H), 1.56 (br m, 1H), 1.39-1.19 (br m, 8H), 1.19-0.92 (br m, 8H), 0.88 (br d, 3H), 0.87 (br m, 1H), 0.82 (br d, 6H), 0.79 (br s, 3H). MS (ESI) m/e 1119.2 [(M–2H)/2]$^-$.

2.175 Synthesis of (6S)-2,6-anhydro-6-(2-{2-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.1$^{3,7}$]dec-1-yl}oxy)ethyl][(3S)-3,4-dihydroxybutyl]carbamoyl}oxy)methyl]-5-({N-[(2,5-dioxo-2,5-dihydro-1H-pyrrol-1-yl)acetyl]-N-(2,5,8,11,14,17,20,23,26,29,32-undecaoxatetratriacontan-34-yl)-b-alanyl-L-valyl-L-alanyl}amino)phenyl}ethyl)-L-gulonic acid (Synthon ABU)

The title compound was prepared using the procedure in Example 2.147.4, replacing Example 2.141.4 with Example 2.167.1. MS (ESI) m/e 1033.4 (M+2H)$^{2+}$.

2.176 Synthesis of (6S)-2,6-anhydro-6-(2-{2-[({[2-({3-[(4-{6-[8-(1,3-benzothiazol-2-ylcarbamoyl)-3,4-dihydroisoquinolin-2(1H)-yl]-2-carboxypyridin-3-yl}-5-methyl-1H-pyrazol-1-yl)methyl]-5,7-dimethyltricyclo[3.3.1.13,7]dec-1-yl}oxy)ethyl][(3S)-3,4-dihydroxybutyl]carbamoyl}oxy)methyl]-5-({N-[(2,5-dioxo-2,5-dihydro-1H-pyrrol-1-yl)acetyl]-N-[2-(2-sulfoethoxy)ethyl]-b-alanyl-L-valyl-L-alanyl}amino)phenyl}ethyl)-L-gulonic acid (Synthon ABV)

The title compound was prepared using the procedure in Example 2.160.7, replacing Example 2.154.1 with Example 2.167.1. MS (ESI) m/e 859.4 (M+2H)$^{2+}$.

Example 3: Generation of Mouse Anti-B7-H3 Monoclonal Antibodies by Mouse Hybridoma Technology B7-H3 specific antibodies were raised using mouse hybridomas technology. Specifically, a mouse fibroblast cell line (3T12) expressing full length human B7-H3 as well as recombinant human or mouse B7-H3-ECD-human Fc fusion proteins were used as immunogens, the sequences of which are provided in Table 1. Human HCT116 cell lines expressing human B7-H3 were used for determining anti-sera titer and for screening antigen-specific antibodies. Cell lines were exposed to approximately 3000 mREM of gamma source radiation prior to immunization. Two different strains of mice were immunized in the hock with dosages containing 5×10$^6$ cells/mouse/injection or 10 ug of protein/mouse/injection in the presence of Gerbu MM adjuvant (Cooper-Casey Corporation, Valley Center, Calif., US) for both primary and boost immunizations. To increase immune response to mouse B7-H3, the mice were further boosted with a mixture of human and mouse B7-H3-ECD-human Fc proteins for the final boosts. Briefly, the antigens were prepared in PBS as follows: 200×10$^6$ cells/mL or 400 ug/mL protein. The calculated volume of antigen was transferred to a sterile microcentrifuge tube and equal volume of Gerbu MM was then added. The solution was mixed by gently vortexing for 1 minute. The adjuvant-antigen solution was then drawn into a proper syringe for animal injection. A total of 25 μL of the mixture was injected into the hock of each leg of the mouse. Each animal was boosted 3 times before serum titer was determined for the groups. All animals were given 2 additional boosts with an equal mixture of mouse B7-H3-ECD-human Fc and human B7-H3-ECD-human Fc proteins in adjuvant before fusion.

TABLE 1

Amino acid sequences of recombinant proteins used for immunization or screening

| Protein | Amino Acid Sequence |
|---|---|
| Human full length B7-H3 | <u>MLRRRGSPGMGVHVGAALGALWF</u>CLTGALEVQVPEDPVVALVGTDATLCCSFSPEPG<br>FSLAQLNLIWQLTDTKQLVHSFAEGQDQGSAYANRTALFPDLLAQGNASLRLQRVRV<br>ADEGSFTCFVSIRDFGSAAVSLQVAAPYSKPSMTLEPNKDLRPGDTVTITCSSYQGY<br>PEAEVFWQDGQGVPLTGNVTTSQMANEQGLFDVHSILRVVLGANGTYSCLVRNPVLQ<br>QDAHSSVTITPQRSPTGAVEVQVPEDPVVALVGTDATLRCSFSPEPGFSLAQLNLIW<br>QLTDTKQLVHSFTEGRDQGSAYANRTALFPDLLAQGNASLRLQRVRVADEGSFTCFV<br>SIRDFGSAAVSLQVAAPYSKPSMTLEPNKDLRPGDTVTITCSSYRGYPEAEVFWQDG<br>QGVPLIGNVITSQMANEQGLFDVHSVLRVVLGANGTYSCLVRNPVLQQDAHGSVTIT<br>GQPMTFPPEALWVTVGLSVCLIALLVALAFVCWRKIKQSCEEENAGAEDQDGEGEGS<br>KTALQPLKHSDSKEDDGQEIA (SEQ ID NO: 149) |
| Human B7-H3-ECD (fc fusion) | <u>MLRRRGSPGMGVHVGAALGALWF</u>CLTGALEVQVPEDPVVALVGTDATLCCSFSPEPG<br>FSLAQLNLIWQLTDTKQLVHSFAEGQDQGSAYANRTALFPDLLAQGNASLRLQRVRV<br>ADEGSFTCFVSIRDFGSAAVSLQVAAPYSKPSMTLEPNKDLRPGDTVTITCSSYQGY<br>PEAEVFWQDGQGVPLTGNVTTSQMANEQGLFDVHSILRVVLGANGTYSCLVRNPVLQ<br>QDAHSSVTITPQRSPTGAVEVQVPEDPVVALVGTDATLRCSFSPEPGFSLAQLNLIW<br>QLTDTKQLVHSFTEGRDQGSAYANRTALFPDLLAQGNASLRLQRVRVADEGSFTCFV<br>SIRDFGSAAVSLQVAAPYSKPSMTLEPNKDLRPGDTVTITCSSYRGYPEAEVFWQDG<br>QGVPLIGNVITSQMANEQGLFDVHSVLRVVLGANGTYSCLVRNPVLQQDAHGSVTIT<br>GQPMTFAAA<u>DKTHTCPPCPAPEAEGAPSVFLFPPKPKDTLMISRTPEVICVVVDVSH</u><br><u>EDPEVKFNWYVDGVEVHNAKTKPREEQYNSTYRVVSVLTVLHQDWLNGKEYKCKVSN</u><br><u>KALPAPIEKTISKAKGQPREPQVYTLPPSREEMTKNQVSLTCLVKGFYPSDIAVEWE</u><br><u>SNGQPENNYKTTPPVLDSDGSFFLYSKLTVDKSRWQQGNVFSCSVMHEALHNHYTQK</u><br><u>SLSLSPGK</u> (SEQ ID NO: 150) |
| Mouse B7-H3-ECD (fc fusion) | <u>MLRGWGGPSVGVCVRTALGVLCLLT</u>GAVEVQVSEDPVVALVDTDATLRCSFSPEPG<br>FSLAQLNLIWQLTDTKQLVHSFTEGRDQGSAYSNRTALFPDLLVQGNASLRLQRVRV<br>TDEGSYTCFVSIQDFDSAAVSLQVAAPYSKPSMTLEPNKDLRPGNMVTITCSSYQGY<br>PEAEVFWKDGQGVPLTGNVTTSQMANERGLFDVHSVLRVVLGANGTYSCLVRNPVLQ<br>QDAHGSVTITGQPLTFAAA<u>DKTHTCPPCPAPEAEGAPSVFLFPPKPKDTLMISRTPE</u><br><u>VICVVVDVSHEDPEVKFNWYVDGVEVHNAKTKPREEQYNSTYRVVSVLTVLHQDWLN</u><br><u>GKEYKCKVSNKALPAPIEKTISKAKGQPREPQVYTLPPSREEMTKNQVSLTCLVKGF</u><br><u>YPSDIAVEWESNGQPENNYKTTPPVLDSDGSFFLYSKLTVDKSRWQQGNVFSCSVMH</u><br><u>EALHNHYTQKSLSLSPGK</u> (SEQ ID NO: 151) |
| Human B7-H3-ECD (His tag) | <u>MEFGLSWLFL</u>VAILKGVQCGALEVQVPEDPVVALVGTDATLCCSFSPEPGFSLAQLN<br>LIWQLTDTKQLVHSFAEGQDQGSAYANRTALFPDLLAQGNASLRLQRVRVADEGSFT<br>CFVSIRDFGSAAVSLQVAAPYSKPSMTLEPNKDLRPGDTVTITCSSYQGYPEAEVFW<br>QDGQGVPLTGNVTTSQMANEQGLFDVHSILRVVLGANGTYSCLVRNPVLQQDAHSSV<br>TITPQRSPTGAVEVQVPEDPVVALVGTDATLRCSFSPEPGFSLAQLNLIWQLTDTKQ<br>LVHSFTEGRDQGSAYANRTALFPDLLAQGNASLRLQRVRVADEGSFTCFVSIRDFGS<br>AAVSLQVAAPYSKPSMTLEPNKDLRPGDTVTITCSSYRGYPEAEVFWQDGQGVPLTG<br>NVTTSQMANEQGLFDVHSVLRVVLGANGTYSCLVRNPVLQQDAHGSVTITGQPMT<u>HH</u><br><u>HHHH</u> (SEQ ID NO: 152) |
| Mouse B7-H3-ECD (His tag) | <u>MEFGLSWLFL</u>VAILKGVQCVEVQVSEDPVVALVDTDATLRCSFSPEPGFSLAQLNLI<br>WQLTDTKQLVHSFTEGRDQGSAYSNRTALFPDLLVQGNASLRLQRVRVTDEGSYTCF<br>VSIQDFDSAAVSLQVAAPYSKPSMTLEPNKDLRPGNMVTITCSSYQGYPEAEVFWKD<br>GQGVPLIGNVITSQMANERGLFDVHSVLRVVLGANGTYSCLVRNPVLQQDAHGSVTI<br>TGQPLTF<u>HHHHHH</u> (SEQ ID NO: 153) |
| Cyno B7-H3-ECD (his tag) | <u>MLHRRGSPGMGVHVGAALGALWF</u>CLTGALEVQVPEDPVVALVGTDATLRCSFSPEPG<br>FSLAQLNLIWQLTDTKQLVHSFTEGRDQGSAYANRTALFLDLLAQGNASLRLQRVRV<br>ADEGSFTCFVSIRDFGSAAVSLQVAAPYSKPSMTLEPNKDLRPGDTVTITCSSYRGY<br>PEAEVFWQDGQGAPLTGNVTTSQMANEQGLFDVHSVLRVVLGANGTYSCLVRNPVLQ<br>QDAHGSITITPQRSPTGAVEVQVPEDPVVALVGTDATLRCSFSPEPGFSLAQLNLIW<br>QLTDTKQLVHSFTEGRDQGSAYANRTALFLDLLAQGNASLRLQRVRVADEGSFTCFV<br>SIRDFGSAAVSLQVAAPYSKPSMTLEPNKDLRPGDTVTITCSSYRGYPEAEVFWQDG<br>QGAPLIGNVITSQMANEQGLFDVHSVLRVVLGANGTYSCLVRNPVLQQDAHGSVTIT<br>GQPMTFAAAHH<u>HHHHHH</u> (SEQ ID NO: 154) |

Note:
leader sequence, Fc, and His sequences are underlined

Hybridoma Fusion and Screening

Cells of murine myeloma cell line (NS-0, ECACC No. 85110503) were cultured to reach the log phase stage right before fusion. Popliteal and inguinal lymph nodes were removed from each mouse and single cell suspensions were prepared sterilely. Lymphocytes were fused with myeloma cells (E. Harlow, D. Lane, *Antibody: A Laboratory Manual*, Cold Spring Harbor Laboratory Press, Cold Spring Harbor, N.Y., 1998); Kohler G. and Milstein C., "Continuous cultures of fused cell secreting antibody of predefined specificity," *Nature*, 256:495-497 (1975); BTX Harvard Apparatus (Holliston, Mass., US) ECM 2001 technical manual). Fused hybrid cells were dispensed into 96-well plates in DMEM/10% FBS/HAT media. Supernatants from surviving hybridoma colonies were subjected to cell-based screening using human cell lines expressing the recombinant human B7-H3. Briefly, a human cell line expressing the human B7-H3 was thawed and directly dispensed into 96 well (black with clear bottom for imaging) plates at 50,000 cells/well in growth media and incubated for 2 days at 37° C. to reach 50% confluency. Hybridoma supernatants (50 µL/well) were transferred to respective plates and incubated at room temperature for 30 minutes. Media was removed from each well and goat anti-mouse IgG-AF488 (Invitrogen, No. A11029, Grand Island, N.Y., US) was used for detection using the InCell Analyzer 2000 (GE). Hits were expanded and binding was confirmed by FACS using a different human cell line or a mouse cell line expressing the human B7-H3 and goat anti-mouse IgG-PE for detection. Species specificity was determined using the ELISA format according to the following procedure. ELISA plates were coated with human B7-H3-ECD-human Fc, cynomolgous B7-H3-ECD-his, or mouse B7-H3-ECD-human Fc proteins overnight at room temperature. Plates were washed and hybridoma supes (100 µL) was added to each well, and incubated at room temperature for 1 hour. Plates were washed, donkey anti-mouse IgG-HRP (Jackson Immunochemicals, No. 115-035-071, West Grove, Pa., US) was used for detection, and binding ODs were observed at 650 nm.

A selection of hits were subcloned using the MoFlo (Beckman, Indianapolis, Ind., US) by depositing a single cell per well into 96 well cell culture plates to ensure clonality of the cell line. Resulting colonies were screened for specificity by FACS using mouse 3T12 fibroblast cell lines expressing the human B7-H3, cynomolgous B7-H3 or mouse B7-H3. Isotype of each monoclonal antibody was determined using the Mouse Monoclonal Isotyping Kit (Roche, No. 11-493-027-001, Indianapolis, Ind., USA). Hybridoma clones producing antibodies that showed high specific binding activity against human and cynomolgus B7-H3 antigen were subcloned and purified (Table 2).

TABLE 2

List of Anti-B7-H3 antibodies generated using mouse hybridoma technology

| Clone Name | Species/Isotype | FACS Binding ($EC_{50}$ nM) | | |
|---|---|---|---|---|
| | | Human B7-H3 | Cynomolgous B7-H3 | Mouse B7-H3 |
| Ab1 | mouse IgG1/k | 2.10 | 1.79 | 299.0 |
| Ab2 | mouse IgG1/k | 1.70 | 1.50 | 1.00 |
| Ab3 | mouse IgG1/k | 1.66 | 1.42 | 0.94 |
| Ab4 | mouse IgG2b/k | 4.06 | 3.10 | 1.75 |
| Ab5 | mouse IgG1/k | 2.71 | 1.91 | 6.01 |
| Ab6 | mouse IgG1/k | 1.59 | 1.53 | No binding |
| Ab7 | mouse IgG1/k | 3.22 | 2.67 | 67.13 |
| Ab8 | mouse IgG1/k | 3.83 | 8.63 | 193.0 |
| Ab9 | mouse IgG1/k | 4.49 | 259.0 | 0.72 |
| Ab10 | mouse IgG2b/k | 3.97 | 4.46 | 3.80 |
| Ab11 | mouse IgG1/k | 23.40 | 2.03 | 568.60 |
| Ab12 | mouse IgG1/k | 3.88 | 6.71 | 8.72 |
| Ab13 | mouse IgG1/k | 1.94 | 4.12 | 25.80 |
| Ab14 | mouse IgG1/k | 3.03 | 2.97 | 102.2 |
| Ab15 | mouse IgG1/k | 5.37 | 6.52 | 4.61 |
| Ab16 | mouse IgG1/k | 3.94 | 4.28 | 318.7 |
| Ab17 | mouse IgG2b/k | 2.75 | 2.60 | 2.39 |
| Ab18 | mouse IgG1/k | 5.98 | 6.49 | No binding |

Example 4: In Vitro Characterization of Anti-B7-H3 Mouse Monoclonal Antibodies

The binding affinity of the purified anti-B7-H3 monoclonal antibodies was determined by surface plasma resonance. Table 3 shows the association rate constants ($k_a$) dissociation rate constants ($k_d$) and equilibrium dissociation constants ($K_D$) for a series of mouse hybridoma derived anti-B7-H3 monoclonal antibodies (mAbs) binding to the soluble ECDs of human B7-H3 and cyno B7-H3. The binding kinetics were derived from SPR measurements using a Biacore T200 instrument and a mAb capture approach (as described in the materials and methods below).

TABLE 3

Biacore kinetics of anti-B7-H3 mouse hybridoma antibodies binding to human and cynomolgus monkey B7-H3.

| Murine Antibody Name | huB7-H3 | | | cynoB7-H3 | | |
|---|---|---|---|---|---|---|
| | $k_a$ (1/Ms) | $k_d$ (1/s) | $K_D$ (M) | $k_a$ (1/Ms) | $k_d$ (1/s) | $K_D$ (M) |
| Ab17 | 5.4E+05 | 1.9E−05 | 3.4E−11 | 5.1E+05 | 1.0E−05 | 1.9E−11 |
| Ab18 | 2.1E+05 | 3.6E−05 | 1.7E−10 | 2.4E+05 | 2.9E−05 | 1.2E−10 |
| Ab15 | 8.0E+04 | 3.4E−05 | 4.3E−10 | 7.7E+04 | 7.0E−05 | 9.1E−10 |
| Ab4 | 6.9E+05 | 1.1E−03 | 1.6E−09 | 5.4E+05 | 9.6E−04 | 1.8E−09 |
| Ab8 | 5.8E+04 | 9.9E−05 | 1.7E−09 | 1.6E+05 | 2.6E−04 | 1.7E−09 |
| Ab10 | 4.1E+04 | 1.9E−04 | 4.6E−09 | 2.0E+05 | 4.2E−03 | 2.0E−08 |
| Ab12 | 3.8E+04 | 2.5E−04 | 6.7E−09 | 5.5E+04 | 1.0E−05 | 1.8E−10 |
| Ab5 | 1.3E+06 | 1.2E−02 | 9.2E−09 | 1.4E+06 | 2.8E−01 | 2.0E−07 |
| Ab14 | 1.1E+05 | 1.4E−03 | 1.3E−08 | 6.9E+05 | 3.0E−03 | 4.3E−09 |
| Ab9 | 6.6E+04 | 1.1E−03 | 1.7E−08 | poor kinetic fit | | |
| Ab13 | 3.3E+05 | 5.8E−03 | 1.7E−08 | 4.4E+05 | 3.7E−03 | 8.4E−09 |
| Ab3 | 5.2E+05 | 1.0E−02 | 1.9E−08 | 3.8E+05 | 1.0E−02 | 2.6E−08 |
| Ab16 | 1.4E+05 | 3.2E−03 | 2.4E−08 | 7.5E+05 | 5.6E−03 | 7.5E−09 |
| Ab2 | 1.2E+05 | 2.9E−03 | 2.4E−08 | 2.3E+05 | 1.1E−02 | 5.0E−08 |
| Ab11 | 2.0E+04 | 8.9E−04 | 4.5E−08 | 2.7E+04 | 7.2E−05 | 2.6E−09 |
| Ab6 | 1.2E+04 | 1.0E−02 | 8.4E−07 | 2.8E+04 | 1.2E−02 | 4.1E−07 |

TABLE 3-continued

Biacore kinetics of anti-B7-H3 mouse hybridoma antibodies binding to human and cynomolgus monkey B7-H3.

| Murine Antibody | huB7-H3 | | | cynoB7-H3 | | |
|---|---|---|---|---|---|---|
| Name | $k_a$ (1/Ms) | $k_d$ (1/s) | $K_D$ (M) | $k_a$ (1/Ms) | $k_d$ (1/s) | $K_D$ (M) |
| Ab1 | | no observable binding | | | no observable binding | |
| Ab7 | | little observable binding | | | little observable binding | |

Pair-wise binding assays performed on Biacore T200 SPR instruments were used to determine the relative epitope grouping for the murine anti-B7-H3 mAbs as described in the methods below. FIG. 1 shows an epitope grouping depiction, which describes the relative human B7-H3 epitope diversity and overlap for a series of anti-B7-H3 mAbs identified herein. Epitope groups are represented as individual ovals, some of which overlap with each other. Antibodies in different epitope groups can bind to B7-H3 simultaneously and likely bind to different epitopes while antibodies within a given epitope group cannot bind to B7-H3 simultaneously and likely bind to overlapping epitopes. The grouping information was derived from a simultaneous binding assay as described in materials and methods. Ab3, Ab4, Ab5, Ab11, Ab12, and Ab8 groupings were ambiguous.

Materials and Methods: Binding Kinetics

Biacore T200 SPR instruments were used to measure the binding kinetics of human B7-H3 (analyte) binding to various mAbs (ligands). The assay format was Fc-based capture via immobilized anti-mouse (Fc) (Pierce 31170) or immobilized anti-human (Fc) (Pierce 31125). A standard amine coupling protocol was employed to immobilize the capture reagents via primary amines to the carboxy-methyl (CM) dextran surface of CM5 sensorchips (Biacore); capture antibodies were coupled to a level of approximately 5000 RU. For binding kinetic measurements the assay buffer was HBS-EP+ (Biacore): 10 mM Hepes, pH7.4, 150 mM NaCl, 3 mM EDTA, 0.05% polysorbate 20. During the assay, all measurements were referenced against the capture surface alone. Each assay cycle consisted of the following steps: 1) Capture of ligand to approximately 50 RU; 2) Analyte injection over both reference and test surface, 240 µL at 80 µL/min, after which the dissociation was monitored for 900 seconds at 80 µL/min; 3) Regeneration of capture surface with low pH glycine. For kinetic determinations analyte injections were 3-point, 9-fold dilution series of 900 nM, 100 nM and 11.11 nM, buffer only injections were included for secondary referencing. Data were processed and fit to a 1:1 binding model using Biacore T200 Evaluation Software to determine the binding kinetic rate constants, $k_a$ (on-rate) and $k_d$ (off-rate), and the equilibrium dissociation constant (affinity, $K_D$).

Materials and Methods: Epitope Grouping

Pair-wise binding assays performed on Biacore T200 SPR instruments were used to determine the relative epitope grouping for a series of anti-B7-H3 mAbs. The assay format was Fc-based capture via immobilized anti-mouse(Fc) (Pierce 31170) or immobilized anti-human (Fc) (Pierce 31125). A standard amine coupling protocol was employed to immobilize the capture reagents via primary amines to the carboxy-methyl (CM) dextran surface of CM5 sensorchips (Biacore); capture antibodies were coupled to a level of approximately 2000 RU. Epitope grouping measurements were done at 12° C. (low temperature allows for grouping information on fast off-rate mAbs), the assay buffer was HBS-EP+(Biacore): 10 mM Hepes, pH7.4, 150 mM NaCl, 3 mM EDTA, 0.05% polysorbate 20. Each assay cycle consisted of the following steps in a four flowcell system: 1) separate test mAbs were captured in flowcells 2, 3 & 4 (flowcell 1 was reference, no test mAb); 2) all 4 flowcells were then blocked by injection with isotype control mAb or isotype mAb cocktail at 50 µg/mL; 3) all 4 flowcells were then injected with antigen or buffer only (buffer only is for double referencing, done for each mAb pair individually); 4) all 4 flowcells were then injected with 2nd test mAb at 10 µg/mL; 5) all 4 flowcells were then regenerated with glycine, pH1.5. The assay was done for each test mAb pair in reciprocal orientations. Simultaneous binding was evaluated examining the ratio of the 2nd test mAb response to the Ag response ($RU_{mAb2}/RU_{Ag}$); if this ratio was equal to or greater than 0.2 the interaction was scored as a simultaneous binder. From this pair-wise binding assay data a "venn" style diagram was constructed manually to depict relative epitope groupings.

Example 5: Generation of Anti-hB7-H3 Chimeric Antibodies

Following the identification of mouse anti-B7-H3 hybridoma antibodies, heavy and light chain variable regions (VH and VL) corresponding to the secreted antibodies were determined from cells using reverse transcriptase-polymerase chain reaction (RT-PCR). Murine variable regions were expressed in mammalian host cells in the context of a human immunoglobulin constant region to provide chimeric antibodies. Table 4 below provides the variable region amino acid sequences for the mouse chimerized hybridomas.

TABLE 4

Variable region amino acid sequences of anti-B7-H3 antibodies from mouse hybridomas

| SEQ ID NO: | Clone | Protein Region | Residues | Amino Acid Sequence |
|---|---|---|---|---|
| 1 | chAb2 | VH | | QVQLQQPGAELVKPGASVKLSCKASGYTFTSYWMHWVKQRPGQGLEWIGMIHPDSGTTNYNEKFRSKATLTVDKSSSTAYMQLSSLTSEDSAVYYCAVYYGSTYWYFDVWGTGTTVTVSS |
| 2 | chAb2 | CDR-H1 | Residues 26-35 of SEQ ID NO: 1 | GYTFTSYWMH |
| 3 | chAb2 | CDR-H2 | Residues 50-66 of SEQ ID NO: 1 | MIHPDSGTTNYNEKFRS |
| 4 | chAb2 | CDR-H3 | Residues 99-109 of SEQ ID NO: 1 | YYGSTYWYFDV |
| 5 | chAb2 | VL | | DVVMTQTPLSLPVSLGDQAYISCRSSQSLVHINGNTYLHWYRQKPGQSPKLLIYKVSNRFSGVPDRFSGSGSGTDFTLKISRVEAEDLGVYFCSQSTHFPFTFGSGTKLEIK |
| 6 | chAb2 | CDR-L1 | Residues 24-39 of SEQ ID NO: 5 | RSSQSLVHINGNTYLH |
| 7 | chAb2 | CDR-L2 | Residues 55-61 of SEQ ID NO: 5 | KVSNRFS |
| 8 | chAb2 | CDR-L3 | Residues 94-102 of SEQ ID NO: 5 | SQSTHFPFT |
| 9 | chAb3 | VH | | QVQLQQPGAELVKPGASVKLSCKASGYTFSSYWMHWVKQRPGQGLEWIGLIHPDSGSTNYNEMFKNKATLTVDRSSTAYVQLSSLTSEDSAVYFCAGGGRLYFDYWGQGTTLTVSS |
| 10 | chAb3 | CDR-H1 | Residues 26-35 of SEQ ID NO: 9 | GYTFSSYWMH |
| 11 | chAb3 | CDR-H2 | Residues 50-66 of SEQ ID NO: 9 | LIHPDSGSTNYNEMFKN |
| 12 | chAb3 | CDR-H3 | Residues 99-106 of SEQ ID NO: 9 | GGRLYFDY |
| 13 | chAb3 | VL | | DVVMTQTPLSLPVSLGDQASISCRSSQSLVHSNGDTYLRWYLQKPGQSPKLLIYKVSNRFSGVPDRFSGSGSGTDFTLKITRVEAEDLGVYFCSQSTHVPYTFGGGTKLEIK |
| 14 | chAb3 | CDR-L1 | Residues 24-39 of SEQ ID NO: 13 | RSSQSLVHSNGDTYLR |
| 7 | chAb3 | CDR-L2 | Residues 55-61 of SEQ ID NO: 13 | KVSNRFS |
| 15 | chAb3 | CDR-L3 | Residues 94-102 of SEQ ID NO: 13 | SQSTHVPYT |
| 16 | chAb4 | VH | | QVQLQQPGAELVKPGASVKLSCKASGYSFTSYWMHWVKQRPGQGLEWIGMIHPNSGSNNYNEKFKSKATLTVDKSSNTAYMQLSSLTSEDSAVYYCARRLGLHFDYWGQGTTLTVSS |
| 17 | chAb4 | CDR-H1 | Residues 26-35 of SEQ ID NO: 16 | GYSFTSYWMH |
| 18 | chAb4 | CDR-H2 | Residues 50-66 of SEQ ID NO: 16 | MIHPNSGSNNYNEKFKS |
| 19 | chAb4 | CDR-H3 | Residues 99-106 of SEQ ID NO: 16 | RLGLHFDY |

TABLE 4-continued

Variable region amino acid sequences of
anti-B7-H3 antibodies from mouse hybridomas

| SEQ ID NO: | Clone | Protein Region | Residues | Amino Acid Sequence |
|---|---|---|---|---|
| 20 | chAb4 | VL | | DIVMTQSQKFMSTPVGDRVSITCKASQ NVGTAVAWYQQKPGQSPKLLIYSASNR YTGVPDRFTGSGSGTDFTLTISNMQSE DLADYFCQQYSSYPYTFGGGTKLEIK |
| 21 | chAb4 | CDR-L1 | Residues 24-34 of SEQ ID NO: 20 | KASQNVGTAVA |
| 22 | chAb4 | CDR-L2 | Residues 50-56 of SEQ ID NO: 20 | SASNRYT |
| 23 | chAb4 | CDR-L3 | Residues 89-97 of SEQ ID NO: 20 | QQYSSYPYT |
| 24 | chAb18 | VH | | QVQLQQSAAELARPGASVKMSCKASGY SFTSYTIHWVKQRPGQGLEWIGYINPN SRNTDYNQKFKDETTLTADRSSSTAYM QLISLTSEDSAVYYCARYSGSTPYWYF DVWGAGTTVTSS |
| 25 | chAb18 | CDR-H1 | Residues 26-35 of SEQ ID NO: 24 | GYSFTSYTIH |
| 26 | chAb18 | CDR-H2 | Residues 50-66 of SEQ ID NO: 24 | YINPNSRNTDYNQKFKD |
| 27 | chAb18 | CDR-H3 | Residues 99-110 of SEQ ID NO: 24 | YSGSTPYWYFDV |
| 28 | chAb18 | VL | | QIVLTQSPAILSASPGEKVTMTCRASS SVSYMNWYQQKPGSSPKPWIYATSNLA SGVPARFSVSVSGTSHSLTISRVEAED AATYYCQQWSSNPLTFGAGTKLELK |
| 29 | chAb18 | CDR-L1 | Residues 24-33 of SEQ ID NO: 28 | RASSSVSYMN |
| 30 | chAb18 | CDR-L2 | Residues 49-55 of SEQ ID NO: 28 | ATSNLAS |
| 31 | chAb18 | CDR-L3 | Residues 88-96 of SEQ ID NO: 28 | QQWSSNPLT |
| 32 | chAb13 | VH | | DVQLQESGPDLVKPSQSLSLTCTVTGY SITSGYSWHWIRQFPGNKLEWMGYIHS SGSTNYNPSLKSRISINRDTSKNQFFL QLNSVTTEDTATYYCAGYDDYFEYWGQ GTTLTVSS |
| 33 | chAb13 | CDR-H1 | Residues 26-36 of SEQ ID NO: 32 | GYSITSGYSWH |
| 34 | chAb13 | CDR-H2 | Residues 51-66 of SEQ ID NO: 32 | YIHSSGSTNYNPSLKS |
| 35 | chAb13 | CDR-H3 | Residues 99-105 of SEQ ID NO: 32 | YDDYFEY |
| 36 | chAb13 | VL | | DIVMTQSQKFMSTSVGDRVSVTCKASQ NVGFNVAWYQQKPGQSPKALIYSASYR YSGVPDRFTGSGSGTDFTLTISNVQSE DLAEYFCQQYNSYPFTFGSGTKLEIK |
| 37 | chAb13 | CDR-L1 | Residues 24-34 of SEQ ID NO: 36 | KASQNVGFNVA |
| 38 | chAb13 | CDR-L2 | Residues 50-56 of SEQ ID NO: 36 | SASYRYS |
| 182 | enAb13 | CDR-L3 | Residues 89-97 of SEQ ID NO: 36 | QQYNSYPFT |

TABLE 4-continued

Variable region amino acid sequences of anti-B7-H3 antibodies from mouse hybridomas

| SEQ ID NO: | Clone | Protein Region | Residues | Amino Acid Sequence |
|---|---|---|---|---|
| 40 | chAb12 | VH | | EVQLVESGGGLVKPGGSLKLSCAASGFTFSSYAMSWVRQTPEKRLEWVATISSGTNYTYYPDSVKGRFTISRDNAKNTLYLQMTSLRSEDTAMYYCARQGRYSWIAYWGQGTLVTVSA |
| 41 | chAb12 | CDR-H1 | Residues 26-35 of SEQ ID NO: 40 | GFTFSSYAMS |
| 42 | chAb12 | CDR-H2 | Residues 50-66 of SEQ ID NO: 40 | TISSGTNYTYYPDSVKG |
| 43 | chAb12 | CDR-H3 | Residues 99-107 of SEQ ID NO: 40 | QGRYSWIAY |
| 44 | chAb12 | VL | | DIVLTQSPASLAVSLGQRATISCRASKSVSTSDYSYMHWNQQKPGQPPKLLIYLASNLESGVPARFSGSGSGTDFTLNIHPVEEEDAATYYCQHSRELLTFGAGTKLELK |
| 45 | chAb12 | CDR-L1 | Residues 24-38 of SEQ ID NO: 44 | RASKSVSTSDYSYMH |
| 46 | chAb12 | CDR-L2 | Residues 54-60 of SEQ ID NO: 44 | LASNLES |
| 47 | chAb12 | CDR-L3 | Residues 93-100 of SEQ ID NO: 44 | QHSRELLT |
| 48 | chAb14 | VH | | EVKLVESGGGLVKPGGSLKLSCAASGFTFSSYGMSWVRQTPEKRLEWVATISGGGTNTYYPDSVEGRFTISRDNAKNFLYLQMSSLRSEDTALYYCARHYGSQTMDYWGQGTSVTVSS |
| 49 | chAb14 | CDR-H1 | Residues 26-35 of SEQ ID NO: 48 | GFTFSSYGMS |
| 50 | chAb14 | CDR-H2 | Residues 50-66 of SEQ ID NO: 48 | TISGGGTNTYYPDSVEG |
| 51 | chAb14 | CDR-H3 | Residues 99-107 of SEQ ID NO: 48 | HYGSQTMDY |
| 52 | chAb14 | VL | | DIQMTQSPASLSASVGETVTITCRTSGNIHNYLTWYQQKQGKSPQLLVYNAKTLADGVPSRFSGSGSGTQFSLKINSLQPEDFGSYYCQHFWSIMWTFGGGTKLEIK |
| 53 | chAb14 | CDR-L1 | Residues 24-34 of SEQ ID NO: 52 | RTSGNIHNYLT |
| 54 | chAb14 | CDR-L2 | Residues 50-56 of SEQ ID NO: 52 | NAKTLAD |
| 55 | chAb14 | CDR-L3 | Residues 89-97 of SEQ ID NO: 52 | QHFWSIMWT |
| 56 | chAb6 | VH | | QVQLQQSGAELMKPGASVKISCKATGYTFSRYWIEWVKQRPGHGLEWIGEILPGSGSTNYNEKFKGKATFTADTSSNTAYMQVSSLTSEDSAVHYCARRGYGYVPYALDYWGQGTSVTVSS |
| 57 | chAb6 | CDR-H1 | Residues 26-35 of SEQ ID NO: 56 | GYTFSRYWIE |
| 58 | chAb6 | CDR-H2 | Residues 50-66 of SEQ ID NO: 56 | EILPGSGSTNYNEKFKG |
| 59 | chAb6 | CDR-H3 | Residues 99-110 of SEQ ID NO: 56 | RGYGYVPYALDY |

TABLE 4-continued

Variable region amino acid sequences of anti-B7-H3 antibodies from mouse hybridomas

| SEQ ID NO: | Clone | Protein Region | Residues | Amino Acid Sequence |
|---|---|---|---|---|
| 60 | chAb6 | VL | | EIQMTQTTSSLSASLGDRVTISCRASQ DISNSLNWYQQKPDGTVNLLIYYTSRL YSGVPSRFSGSGSGTDYSLTISNLEQE DIATYFCQQGNTLPYTFGGGTKLEIK |
| 61 | chAb6 | CDR-L1 | Residues 24-34 of SEQ ID NO: 60 | RASQDISNSLN |
| 62 | chAb6 | CDR-L2 | Residues 50-56 of SEQ ID NO: 60 | YTSRLYS |
| 63 | chAb6 | CDR-L3 | Residues 89-97 of SEQ ID NO: 60 | QQGNTLPYT |
| 64 | chAb11 | VH | | EVKLVESGGGLVQPGGSLRLSCATSGF TFTNYYMSWVRQPPGKALEWLGFIRNK ANDYTTEYSASVKGRFTISRDNSQSIL YLQMNTLRAEDSATYYCARESPGNPFA YWGQGTLVTVSA |
| 65 | chAb11 | CDR-H1 | Residues 26-35 of SEQ ID NO: 64 | GFTFTNYYMS |
| 66 | chAb11 | CDR-H2 | Residues 50-68 of SEQ ID NO: 64 | FIRNKANDYTTEYSASVKG |
| 67 | chAb11 | CDR-H3 | Residues 101-109 of SEQ ID NO: 64 | ESPGNPFAY |
| 68 | chAb11 | VL | | DIVMTQSPSSLTVTAGEKVTMTCKSSQ SLLNSGTQKNFLTWYQQKPGQPPKLLI YWASTRESGVPDRFTGSGSGTDFTLTI SSVQAEDLAVYFCNDYIYPLTFGAGT KLELK |
| 69 | chAb11 | CDR-L1 | Residues 24-40 of SEQ ID NO: 68 | KSSQSLLNSGTQKNFLT |
| 70 | chAb11 | CDR-L2 | Residues 56-62 of SEQ ID NO: 68 | WASTRES |
| 71 | chAb11 | CDR-L3 | Residues 95-103 of SEQ ID NO: 68 | QNDYIYPLT |
| 72 | chAb16 | VH | | EVKLLESGGGLVQPGGSLKLSCAASGF DFSRYWMSWVRQAPGKGLEWIGEINPD SSTINYTPSLKDKFIISRDNAKNTLYL QMSKVRSEDTALYYCARPGFGNYIYAM DYWGQGTSVTVSS |
| 73 | chAb16 | CDR-H1 | Residues 26-35 of SEQ ID NO: 72 | GFDFSRYWMS |
| 74 | chAb16 | CDR-H2 | Residues 50-66 of SEQ ID NO: 72 | EINPDSSTINYTPSLKD |
| 75 | chAb16 | CDR-H3 | Residues 99-110 of SEQ ID NO: 72 | PGFGNYIYAMDY |
| 76 | chAb16 | VL | | DIQMTQTTSSLSASLGDRVTINCRASQ DISNFLNWYQQKPDGTVKLLIYYTSRL YLGVPSRFSGSGSGTDYSLTISNLEQE DIATYFCQQGNTLPPTFGGGTKLEIK |
| 77 | chAb16 | CDR-L1 | Residues 24-34 of SEQ ID NO: 76 | RASQDISNFLN |
| 78 | chAb16 | CDR-L2 | Residues 50-56 of SEQ ID NO: 76 | YTSRLYL |
| 79 | chAb16 | CDR-L3 | Residues 89-97 of SEQ ID NO: 76 | QQGNTLPPT |

TABLE 4-continued

Variable region amino acid sequences of
anti-B7-H3 antibodies from mouse hybridomas

| SEQ ID NO: | Clone | Protein Region | Residues | Amino Acid Sequence |
|---|---|---|---|---|
| 80 | chAb10 | VH | | DVQLQESGPGLVKPSQSLSLTCTVTGY SITSDYAWNWIRQFPGNRLEWMGHINY SGITNYNPSLKSRISITRDTSKNQFFL QLYSVTTEDTATYFCARRSLFYYYGSS LYAMDYWGQGTSVIVSS |
| 81 | chAb10 | CDR-H1 | Residues 26-36 of SEQ ID NO: 80 | GYSITSDYAWN |
| 82 | chAb10 | CDR-H2 | Residues 51-66 of SEQ ID NO: 80 | HINYSGITNYNPSLKS |
| 83 | chAb10 | CDR-H3 | Residues 99-114 of SEQ ID NO: 80 | RSLFYYYGSSLYAMDY |
| 84 | chAb10 | VL | | DVVMTQSPFSLPVSLGDQASISCRSSQ SLVHSNGNTYLHWYLQKPGQSPKLLIY KVSNRFSGVPDRFSGSGSGTDFTLKIS RVEAEDLGVYFCSQSTHVPWTFGGGTK LEIK |
| 85 | chAb10 | CDR-L1 | Residues 24-39 of SEQ ID NO: 84 | RSSQSLVHSNGNTYLH |
| 7 | chAb10 | CDR-L2 | Residues 55-61 of SEQ ID NO: 84 | KVSNRFS |
| 86 | chAb10 | CDR-L3 | Residues 94-102 of SEQ ID NO: 84 | SQSTHVPWT |
| 87 | chAb7 | VH | | EVQLVESGENLVKPGGSLKLSCAASGF SFRGYGMSWVRQTPDKRLEWVAAISTG GNYTYYPDSVQGRFTISRDNANNTLYL QMSSLKSEDTAMYYCARRGGNYAGFAY WGQGTLVTVSA |
| 88 | chAb7 | CDR-H1 | Residues 26-35 of SEQ ID NO: 87 | GFSFRGYGMS |
| 89 | chAb7 | CDR-H2 | Residues 50-66 of SEQ ID NO: 87 | AISTGGNYTYYPDSVQG |
| 90 | chAb7 | CDR-H3 | Residues 99-108 of SEQ ID NO: 87 | RGGNYAGFAY |
| 91 | chAb7 | VL | | DIQMTQSPASLSVSVGETVTITCRPSE NIYSNLAWYQQKQGKSPQLLVYAATNL ADGVPSRFSGSGSGTQYSLKINSLQSE DFGTYYCQHFWGTPFTFGSGTKLEIK |
| 92 | chAb7 | CDR-L1 | Residues 24-34 of SEQ ID NO: 91 | RPSENIYSNLA |
| 93 | chAb7 | CDR-L2 | Residues 50-56 of SEQ ID NO: 91 | AATNLAD |
| 94 | chAb7 | CDR-L3 | Residues 89-97 of SEQ ID NO: 91 | QHFWGTPFT |
| 95 | chAb8 | VH | | EVKLVESGGGLVKPGGSLKLSCAASGF TFSSYGMSWVRQTPEKRLEWVATISGG GNYTYCPDSVKGRFTISRDNAKNNLYL QMSSLRSEDTALYYCTRQRGYDYHYAM DFWGQGTSVTVSS |
| 49 | chAb8 | CDR-H1 | Residues 26-35 of SEQ ID NO: 95 | GFTFSSYGMS |
| 96 | chAb8 | CDR-H2 | Residues 50-66 of SEQ ID NO: 95 | TISGGGNYTYCPDSVKG |
| 97 | chAb8 | CDR-H3 | Residues 99-110 of SEQ ID NO: 95 | QRGYDYHYAMDF |

TABLE 4-continued

Variable region amino acid sequences of
anti-B7-H3 antibodies from mouse hybridomas

| SEQ ID NO: | Clone | Protein Region | Residues | Amino Acid Sequence |
|---|---|---|---|---|
| 98 | chAb8 | VL | | DIQMTQSPASLSVSVGETVTITCRASE NIYSNLAWHQQKQGKSPQLLVYAATNL ADGVPSRFSGNGSDTQYSLKINSLQSE DFGSYFCQNFWGTSWTFGGGTKLEIK |
| 99 | chAb8 | CDR-L1 | Residues 24-34 of SEQ ID NO: 98 | RASENIYSNLA |
| 93 | chAb8 | CDR-L2 | Residues 50-56 of SEQ ID NO: 98 | AATNLAD |
| 100 | chAb8 | CDR-L3 | Residues 89-97 of SEQ ID NO: 98 | QNFWGTSWT |
| 101 | chAb17 | VH | | EVKLVESGGGLVQPGGSLKLSCAASGF TFSSYIMSWVRQTPEKRLEWVASIVSS NITYYPDSMKGRFTISRDNARNILYLQ MSSLKSEDTAMYYCARSGTRAWFAYWG QGTLVTVSA |
| 102 | chAb17 | CDR-H1 | Residues 26-35 of SEQ ID NO: 101 | GFTFSSYIMS |
| 103 | chAb17 | CDR-H2 | Residues 50-65 of SEQ ID NO: 101 | SIVSSNITYYPDSMKG |
| 104 | chAb17 | CDR-H3 | Residues 98-106 of SEQ ID NO: 101 | SGTRAWFAY |
| 105 | chAb17 | VL | | DIVLTQSPASLAVSLGQRATISCRASK SVSTSAYSYMHWYQQKPGQPPKLLIYL ASNLESGVPARFSGSGSGTDFTLNIHP VEEEDAATYYCQHSRELPYTFGGGTKL EIK |
| 106 | chAb17 | CDR-L1 | Residues 24-38 of SEQ ID NO: 105 | RASKSVSTSAYSYMH |
| 46 | chAb17 | CDR-L2 | Residues 54-60 of SEQ ID NO: 105 | LASNLES |
| 107 | chAb17 | CDR-L3 | Residues 93-101 of SEQ ID NO: 105 | QHSRELPYT |
| 108 | chAb5 | VH | | QVQLQQPGDELVKPGASVKLSCKTSGY TFTTDWMHWVKQRPGQGLEWIGMIHPN SGTTNYNEKFKSKAALTVDKSSSTACM QLSSLTSEDSAVYYCARSYWKWYFDVW GTGTTVTVSS |
| 109 | chAb5 | CDR-H1 | Residues 26-35 of SEQ ID NO: 108 | GYTFTTDWMH |
| 110 | chAb5 | CDR-H2 | Residues 50-66 of SEQ ID NO: 108 | MIHPNSGTTNYNEKFKS |
| 111 | chAb5 | CDR-H3 | Residues 99-107 of SEQ ID NO: 108 | SYWKWYFDV |
| 112 | chAb5 | VL | | QIVLTQSPAIMSASLGEEITLTCSASS SVSYMHWYQQKSGTSPKLLIYSTSNLA SGVPSRFSGSGSGTFYSLTISSVEAED SADYYCHQWTSYMYTFGGGTKLEIK |
| 113 | chAb5 | CDR-L1 | Residues 24-33 of SEQ ID NO: 112 | SASSSVSYMH |
| 114 | chAb5 | CDR-L2 | Residues 49-55 of SEQ ID NO: 112 | STSNLAS |
| 115 | chAb5 | CDR-L3 | Residues 88-96 of SEQ ID NO: 112 | HQWTSYMYT |

Example 6: Binding Characterization of Chimeric Anti-B7-H3 Antibodies

To generate purified chimeric antibodies, expression vectors were transiently transfected into HEK293 6E suspension cell cultures in a ratio of 60% to 40% light to heavy chain construct. 1 mg/ml of polyethylenimine (PEI) or 2.6 µL/mL of Expifectamine was used to transfect the cells. Cell supernatants were harvested after five days in shaking flasks, spun down to pellet cells, and filtered through 0.22 µm filters to separate IgG from culture contaminants. Antibody-containing supernatants were purified on Akta Pure using protein A mAb SelectSure. Columns were equilibrated in PBS pH 7.4, supernatants were then passed through the column and a wash was performed with PBS pH 7.4. IgG were eluted with 0.1 M acetic acid pH 3.5 and collected in several aliquots. Fractions containing IgG were pooled and dialyzed in PBS overnight at 4° C. Anti-B7-H3 chimeric antibodies that were successfully expressed were characterized for the ability to bind the B7-H3 overexpressing human non-small cell lung cancer cell line NCI-H1650 (ATCC® No. CRL-5883) by FACS using the methods described below. Table 5 summarizes the binding properties of the chimeric anti-B7-H3 antibodies.

TABLE 5

In vitro characterization of B7-H3 chimeric antibodies

| Chimeric Ab Name | Isotype | Parental Hybridoma | FACS binding ($EC_{50}$ nM) |
|---|---|---|---|
| chAb2 | huIgG1/k | Ab2 | 0.10 |
| chAb3 | huIgG1/k | Ab3 | 0.61 |
| chAb4 | huIgG1/k | Ab4 | 0.56 |
| chAb18 | huIgG1/k | Ab18 | 1.14 |
| chAb13 | huIgG1/k | Ab13 | 1.53 |
| chAb11 | huIgG1/k | Ab11 | 1.12 |
| chAb6 | huIgG1/k | Ab6 | 0.33 |
| chAb16 | huIgG1/k | Ab16 | 0.27 |
| chAb14 | huIgG1/k | Ab14 | 0.81 |

FACS Binding Methods

Cells were harvested from flasks when approximately 80% confluent using Gibco® Cell Dissociation Buffer. Cells were washed once in PBS/1% FBS (FACS buffer) then resuspended at $2.5 \times 10^6$ cells/mL in FACS buffer. 100 µL of cells/well were added to a round bottom 96-well plate. 10 µL of a 10× concentration of mAb/ADC (final concentrations are indicated in the figures). Wells were washed twice with FACS buffer and resuspended in 50 µL of secondary Ab (AlexaFluor 488) diluted in FACS buffer. The plate was incubated at 4° C. for one hour and washed twice with FACS buffer. Cells were resuspended in 100 µL of PBS/1% formaldehyde and analyzed on a Becton Dickinson LSRII flow cytometer. Data was analyzed using WinList flow cytometry analysis software.

Example 7: Characterization of Chimeric Anti-B7-H3 Antibodies as Bcl-xL Inhibiting Antibody Drug Conjugates Nine anti-B7-H3 chimeric antibodies were conjugated to the Bcl-xL inhibiting (Bcl-xLi) synthon CZ (Example 2.1) using conjugation Method A described below. The resulting ADCs (anti-B7-H3 antibodies conjugated to synthon CZ) were tested for binding to cell surface human B7-H3 by FACS (as described in Example 6) and for cell cytotoxicity in cell lines expressing B7-H3. Of the nine antibodies, three antibodies (chAb2, chAb6, and chAb16) precipitated following conjugation to synthon CZ and showed weak cytotoxicity in cells expressing human B7-H3. Table 6 provides cell surface binding and cytotoxicity activity of anti-B7-H3 chimera ADCs against breast cancer cell HCC38 expressing human B7-H3.

TABLE 6

In vitro characterization of B7-H3 chimeric-CZ conjugates

| ADC Name | Conjugation observation | FACS Binding Human B7-H3 $EC_{50}$ nM | Cytotoxicity (HCC38 cell line $IC_{50}$ nM) | Conjugation Method | DAR by MS | % agg by SEC |
|---|---|---|---|---|---|---|
| chAb2-CZ | Precipitates | 2.60 | 4.77 | A | 1.0 | 5.9 |
| chAb3-CZ | Clear | 0.65 | 0.17 | A | 4.6 | 6.3 |
| chAb4-CZ | Clear | 0.54 | 0.26 | A | 1.4 | 5.7 |
| chAb18-CZ | Clear | 1.78 | 0.28 | A | 2.3 | 4.3 |
| chAb13-CZ | Clear | 1.49 | 0.18 | A | 3.8 | 8.3 |
| chAb11-CZ | Clear | 1.12 | 2.34 | A | 3.2 | 5.6 |
| chAb6-CZ | Precipitates | 0.56 | 80.98 | A | 1.3 | 0.5 |
| chAb16-CZ | Precipitates | 0.62 | 21.89 | A | 0.9 | 2.3 |
| chAb14-CZ | Clear | 0.50 | 2.01 | A | 1.4 | 1.9 |

Materials and Methods: Conjugation of Bcl-xL Inhibitory ADCs

ADCs were synthesized using one of the methods described below. Exemplary ADCs were synthesized using one of nine exemplary methods, described below.

Method A.

A solution of Bond-Breaker™ tris(2-carboxyethyl)phosphine (TCEP) solution (10 mM, 0.017 mL) was added to a solution of antibody (10 mg/mL, 1 mL) preheated to 37° C. The reaction mixture was kept at 37° C. for 1 hour. The solution of reduced antibody was added to a solution of synthon (3.3 mM, 0.160 mL in DMSO) and gently mixed for 30 minutes. The reaction solution was loaded onto a desalting column (PD10, washed with Dulbecco's phosphate-buffered saline [DPBS] 3× before use), followed by DPBS (3 mL). The purified ADC solution was filtered through a 0.2 micron, low protein-binding 13 mm syringe-filter and stored at 4° C.

Method B.

A solution of Bond-Breaker™ tris(2-carboxyethyl)phosphine (TCEP) solution (10 mM, 0.017 mL) was added to the solution of antibody (10 mg/mL, 1 mL) preheated to 37° C. The reaction mixture was kept at 37° C. for 1 hour. The solution of reduced antibody was adjusted to pH=8 by adding boric buffer (0.05 mL, 0.5 M, pH 8), added to a solution of synthon (3.3 mM, 0.160 mL in DMSO) and gently mixed for 4 hours. The reaction solution was loaded onto a desalting column (PD10, washed with DPBS 3× before use), followed by DPBS (1.6 mL) and eluted with additional DPBS (3 mL). The purified ADC solution was filtered through a 0.2 micron, low protein-binding 13 mm syringe-filter and stored at 4° C.

Method C.

Conjugations were performed using a PerkinElmer Janus (part AJL8M01) robotic liquid handling system equipped with an 1235/96 tip ModuLar Dispense Technology (MDT), disposable head (part 70243540) containing a gripper arm (part 7400358), and an 8-tip Varispan pipetting arm (part 7002357) on an expanded deck. The PerkinElmer Janus system was controlled using the WinPREP version 4.8.3.315 Software.

A Pall Filter plate 5052 was pre-wet with 100 µL 1×DPBS using the MDT. Vacuum was applied to the filter plate for 10 seconds and was followed by a 5 second vent to remove DPBS from filter plate. A 50% slurry of Protein A resin (GE MabSelect Sure) in DPBS was poured into an 8 well reservoir equipped with a magnetic ball, and the resin was mixed by passing a traveling magnet underneath the reservoir plate. The 8 tip Varispan arm, equipped with 1 mL conductive tips, was used to aspirate the resin (250 µL) and transfer to a 96-well filter plate. A vacuum was applied for 2 cycles to remove most of the buffer. Using the MDT, 150 µL of 1×PBS was aspirated and dispensed to the 96-well filter plate holding the resin. A vacuum was applied, removing the buffer from the resin. The rinse/vacuum cycle was repeated 3 times. A 2 mL, 96-well collection plate was mounted on the Janus deck, and the MDT transferred 450 µL of 5×DPBS to the collection plate for later use. Reduced antibody (2 mg) as a solution in (200 µL) DPBS was prepared as described above for Conditions A and preloaded into a 96 well plate. The solutions of reduced antibody were transferred to the filter plate wells containing the resin, and the mixture was mixed with the MDT by repeated aspiration/dispensation of a 100 µL volume within the well for 45 seconds per cycle. The aspiration/dispensation cycle was repeated for a total of 5 times over the course of 5 minutes. A vacuum was applied to the filter plate for 2 cycles, thereby removing excess antibody. The MDT tips were rinsed with water for 5 cycles (200 µL, 1 mL total volume). The MDT aspirated and dispensed 150 µL of DPBS to the filter plate wells containing resin-bound antibody, and a vacuum was applied for two cycles. The wash and vacuum sequence was repeated two more times. After the last vacuum cycle, 100 µL of 1×DPBS was dispensed to the wells containing the resin-bound antibody. The MDT then collected 30 µL each of 3.3 mM dimethyl sulfoxide solutions of synthons plated in a 96-well format and dispensed it to the filter plate containing resin-bound antibody in DPBS. The wells containing the conjugation mixture were mixed with the MDT by repeated aspiration/dispensation of a 100 µL volume within the well for 45 seconds per cycle. The aspiration/dispensation sequence was repeated for a total of 5 times over the course of 5 minutes. A vacuum was applied for 2 cycles to remove excess synthon to waste. The MDT tips were rinsed with water for 5 cycles (200 µL, 1 mL total volume). The MDT aspirated and dispensed DPBS (150 µL) to the conjugation mixture, and a vacuum was applied for two cycles. The wash and vacuum sequence was repeated two more times. The MDT gripper then moved the filter plate and collar to a holding station. The MDT placed the 2 mL collection plate containing 450 µL of 10×DPBS inside the vacuum manifold. The MDT reassembled the vacuum manifold by placement of the filter plate and collar. The MDT tips were rinsed with water for 5 cycles (200 µL, 1 mL total volume). The MDT aspirated and dispensed 100 µL of IgG Elution Buffer 3.75 (Pierce) to the conjugation mixture. After one minute, a vacuum was applied for 2 cycles, and the eluent was captured in the receiving plate containing 450 µL of 5×DPBS. The aspiration/dispensation sequence was repeated 3 additional times to deliver ADC samples with concentrations in the range of 1.5-2.5 mg/mL at pH 7.4 in DPBS.

Method D.

Conjugations were performed using a PerkinElmer Janus (part AJL8M01) robotic liquid handling system equipped with an 1235/96 tip ModuLar Dispense Technology (MDT), disposable head (part 70243540) containing a gripper arm (part 7400358), and an 8-tip Varispan pipetting arm (part 7002357) on an expanded deck. The PerkinElmer Janus system was controlled using the WinPREP version 4.8.3.315 Software.

A Pall Filter plate 5052 was prewet with 100 µL 1×DPBS using the MDT. Vacuum was applied to the filter plate for 10 seconds and was followed by a 5 second vent to remove DPBS from filter plate. A 50% slurry of Protein A resin (GE MabSelect Sure) in DPBS was poured into an 8-well reservoir equipped with a magnetic ball, and the resin was mixed by passing a traveling magnet underneath the reservoir plate. The 8 tip Varispan arm, equipped with 1 mL conductive tips, was used to aspirate the resin (250 µL) and transfer to a 96-well filter plate. A vacuum was applied to the filter plate for 2 cycles to remove most of the buffer. The MDT aspirated and dispensed 150 µL of DPBS to the filter plate wells containing the resin. The wash and vacuum sequence was repeated two more times. A 2 mL, 96-well collection plate was mounted on the Janus deck, and the MDT transferred 450 µL of 5×DPBS to the collection plate for later use. Reduced antibody (2 mg) as a solution in (200 µL) DPBS was prepared as described above for Conditions A and dispensed into the 96-well plate. The MDT then collected 30 µL each of 3.3 mM dimethyl sulfoxide solutions of synthons plated in a 96-well format and dispensed it to the plate loaded with reduced antibody in DPBS. The mixture was mixed with the MDT by twice repeated aspiration/dispensation of a 100 µL volume within the well. After five minutes, the conjugation reaction mixture (230 µL) was transferred to the 96-well filter plate containing the resin. The wells containing the conjugation mixture and resin were mixed with the MDT by repeated aspiration/dispensation of a 100 µL volume within the well for 45 seconds per cycle. The aspiration/dispensation sequence was repeated for a total of 5 times over the course of 5 minutes. A vacuum was applied for 2 cycles to remove excess synthon and protein to waste. The MDT tips were rinsed with water for 5 cycles (200 µL, 1 mL total volume). The MDT aspirated and dispensed DPBS (150 µL) to the conjugation mixture, and a vacuum was applied for two cycles. The wash and vacuum sequence was repeated two more times. The MDT gripper then moved the filter plate and collar to a holding station. The MDT placed the 2 mL collection plate containing 450 µL of 10×DPBS inside the vacuum manifold. The MDT reassembled the vacuum manifold by placement of the filter plate and collar. The MDT tips were rinsed with water for 5 cycles (200 µL, 1 mL total volume). The MDT aspirated and dispensed 100 µL of IgG Elution Buffer 3.75 (P) to the conjugation mixture. After one minute, a vacuum was applied for 2 cycles, and the eluent was captured in the receiving plate containing 450 µL of 5×DPBS. The aspiration/dispensation sequence was repeated 3 additional times to deliver ADC samples with concentrations in the range of 1.5-2.5 mg/mL at pH 7.4 in DPBS.

Method E.

A solution of Bond-Breaker™ tris(2-carboxyethyl)phosphine (TCEP) solution (10 mM, 0.017 mL) was added to the solution of antibody (10 mg/mL, 1 mL) at room temperature. The reaction mixture was heated to 37° C. for 75 minutes. The solution of reduced antibody cooled to room temperature and was added to a solution of synthon (10 mM, 0.040 mL in DMSO) followed by addition of boric buffer (0.1 mL, 1M, pH 8). The reaction solution was let to stand for 3 days at room temperature, loaded onto a desalting column (PD10, washed with DPBS 3×5 mL before use), followed by DPBS (1.6 mL) and eluted with additional DPBS (3 mL). The purified ADC solution was filtered through a 0.2 micron, low protein-binding 13 mm syringe-filter and stored at 4° C.

Method F.

Conjugations were performed using a Tecan Freedom Evo robotic liquid handling system. The solution of antibody (10 mg/mL) was preheated to 37° C. and aliquoted to a heated 96 deep-well plate in amounts of 3 mg per well (0.3 mL) and kept at 37° C. A solution of Bond-Breaker™ tris(2-carboxyethyl)phosphine (TCEP) solution (1 mM, 0.051 mL/well) was added to antibodies, and the reaction mixture was kept at 37° C. for 75 minutes. The solution of reduced antibody was transferred to an unheated 96 deep-well plate. Corresponding solutions of synthons (5 mM, 0.024 mL in DMSO) were added to the wells with reduced antibodies and treated for 15 minutes. The reaction solutions were loaded onto a platform (8×12) of desalting columns (NAPS, washed with DPBS 4× before use), followed by DPBS (0.3 mL) and eluted with additional DPBS (0.8 mL). The purified ADC solutions were further aliquoted for analytics and stored at 4° C.

Method G.

Conjugations were performed using a Tecan Freedom Evo robotic liquid handling system. The solution of antibody (10 mg/mL) was preheated to 37° C. and aliquoted onto a heated 96 deep-well plate in amounts of 3 mg per well (0.3 mL) and kept at 37 C. A solution of Bond-Breaker™ tris(2-carboxyethyl)phosphine (TCEP) solution (1 mM, 0.051 mL/well) was added to antibodies, and the reaction mixture was kept at 37° C. for 75 minutes. The solutions of reduced antibody were transferred to an unheated 96 deep-well plate. Corresponding solutions of synthons (5 mM, 0.024 mL/well in DMSO) were added to the wells with reduced antibodies followed by addition of boric buffer (pH=8, 0.03 mL/well) and treated for 3 days. The reaction solutions were loaded onto a platform (8×12) of desalting columns (NAPS, washed with DPBS 4× before use), followed by DPBS (0.3 mL) and eluted with additional DPBS (0.8 mL). The purified ADC solutions were further aliquoted for analytics and stored at 4° C.

Method H.

A solution of Bond-Breaker™ tris(2-carboxyethyl)phosphine (TCEP) solution (10 mM, 0.17 mL) was added to the solution of antibody (10 mg/mL, 10 mL) at room temperature. The reaction mixture was heated to 37° C. for 75 minutes. The solution of synthon (10 mM, 0.40 mL in DMSO) was added to a solution of reduced antibody cooled to room temperature. The reaction solution was let to stand for 30 minutes at room temperature. The solution of ADC was treated with saturated ammonium sulfate solution (~2-2.5 mL) until a slightly cloudy solution formed. This solution was loaded onto butyl sepharose column (5 mL of butyl sepharose) equilibrated with 30% phase B in phase A (phase A: 1.5 M ammonium sulphate, 25 mM phosphate; phase B: 25 mM phosphate, 25% isopropanol v/v). Individual fractions with DAR2 (also referred to as "E2") and DAR4 (also referred to as "E4") eluted upon applying gradient A/B up to 75% phase B. Each ADC solution was concentrated and buffer switched using centrifuge concentrators or TFF for larger scales. The purified ADC solutions were filtered through a 0.2 micron, low protein-binding 13 mm syringe-filter and stored at 4° C.

Method I.

A solution of Bond-Breaker™ tris(2-carboxyethyl)phosphine (TCEP) solution (10 mM, 0.17 mL) was added to the solution of antibody (10 mg/mL, 10 mL) at room temperature. The reaction mixture was heated to 37° C. for 75 minutes. The solution of synthon (10 mM, 0.40 mL in DMSO) was added to a solution of reduced antibody cooled to room temperature. The reaction solution was let to stand for 30 minutes at room temperature. The solution of ADC was treated with saturated ammonium sulfate solution (~2-2.5 mL) until a slightly cloudy solution formed. This solution was loaded onto a butyl sepharose column (5 mL of butyl sepharose) equilibrated with 30% phase B in Phase A (phase A: 1.5 M ammonium sulphate, 25 mM phosphate; phase B: 25 mM phosphate, 25% isopropanol v/v). Individual fractions with DAR2 (also referred to as "E2") and DAR 4 (also referred to as "E4") eluted upon applying a gradient A/B up to 75% phase B. Each ADC solution was concentrated and buffer switched using centrifuge concentrators or TFF for larger scales. The ADC solutions were treated with boric buffer (0.1 mL, 1M, pH8). The reaction solution was let stand for 3 days at room temperature, then loaded onto a desalting column (PD10, washed with DPBS 3×5 mL before use), followed by DPBS (1.6 mL) and eluted with additional DPBS (3 mL). The purified ADC solution was filtered through a 0.2 micron, low protein-binding 13 mm syringe-filter and stored at 4° C.

DAR and Aggregation of ADCs

The DAR and percentage aggregation of ADCs synthesized were determined by LC-MS and size exclusion chromatography (SEC), respectively.

LC-MS General Methodology

LC-MS analysis was performed using an Agilent 1100 HPLC system interfaced to an Agilent LC/MSD TOF 6220 ESI mass spectrometer. The ADC was reduced with 5 mM (final concentration) Bond-Breaker® TCEP solution (Thermo Scientific, Rockford, Ill.), loaded onto a Protein Microtrap (Michrom Bioresorces, Auburn, Calif.) desalting cartridge, and eluted with a gradient of 10% B to 75% B in 0.2 minutes at ambient temperature. Mobile phase A was $H_2O$ with 0.1% formic acid (FA), mobile phase B was acetonitrile with 0.1% FA, and the flow rate was 0.2 mL/min. Electrospray-ionization time-of-flight mass spectra of the co-eluting light and heavy chains were acquired using Agilent MassHunter™ acquisition software. The extracted intensity vs. m/z spectrum was deconvoluted using the Maximum Entropy feature of MassHunter software to determine the mass of each reduced antibody fragment. DAR was calculated from the deconvoluted spectrum by summing intensities of the naked and modified peaks for the light chain and heavy chain, normalized by multiplying intensity by the number of drugs attached. The summed, normalized intensities were divided by the sum of the intensities, and the summing results for two light chains and two heavy chains produced a final average DAR value for the full ADC.

Thiosuccinimide hydrolysis of a bioconjugate can be monitored by electrospray mass spectrometry, since the addition of water to the conjugate results in an increase of 18 Daltons to the observable molecular weight of the conjugate.

Figure 2:
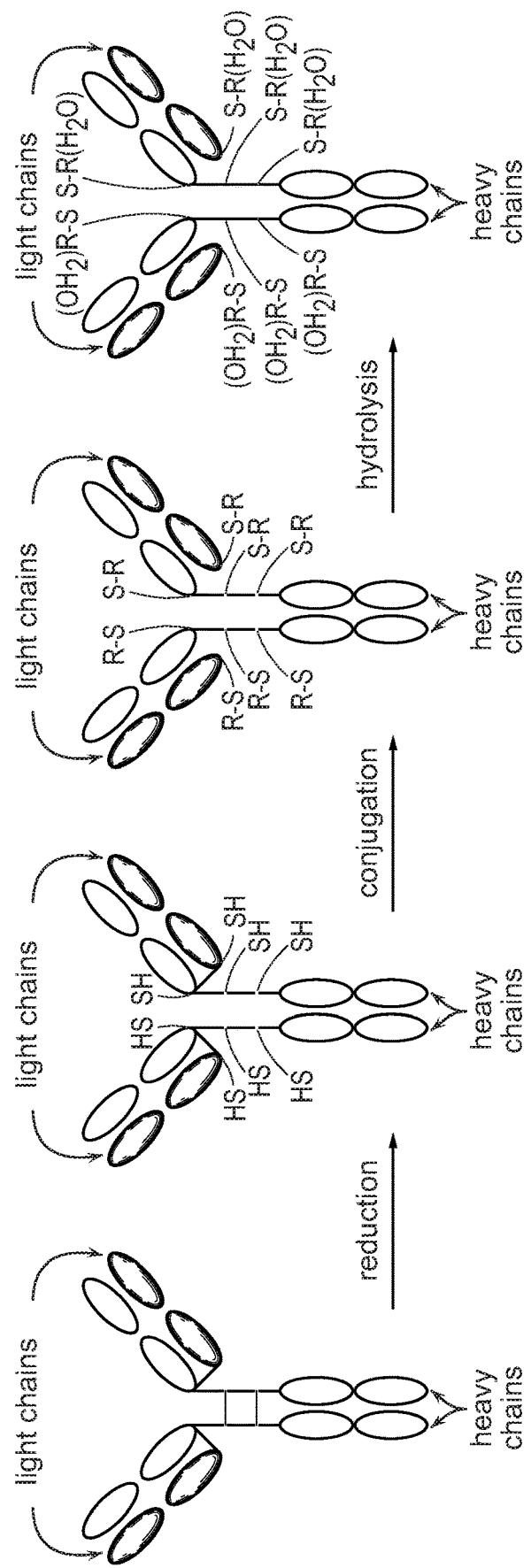
FIG. 2 depicts an antibody reduction, modification with a maleimide derivative to give a thiosuccinimide intermediate, and subsequent hydrolysis of thiosuccinimide moiety
Figure 5:
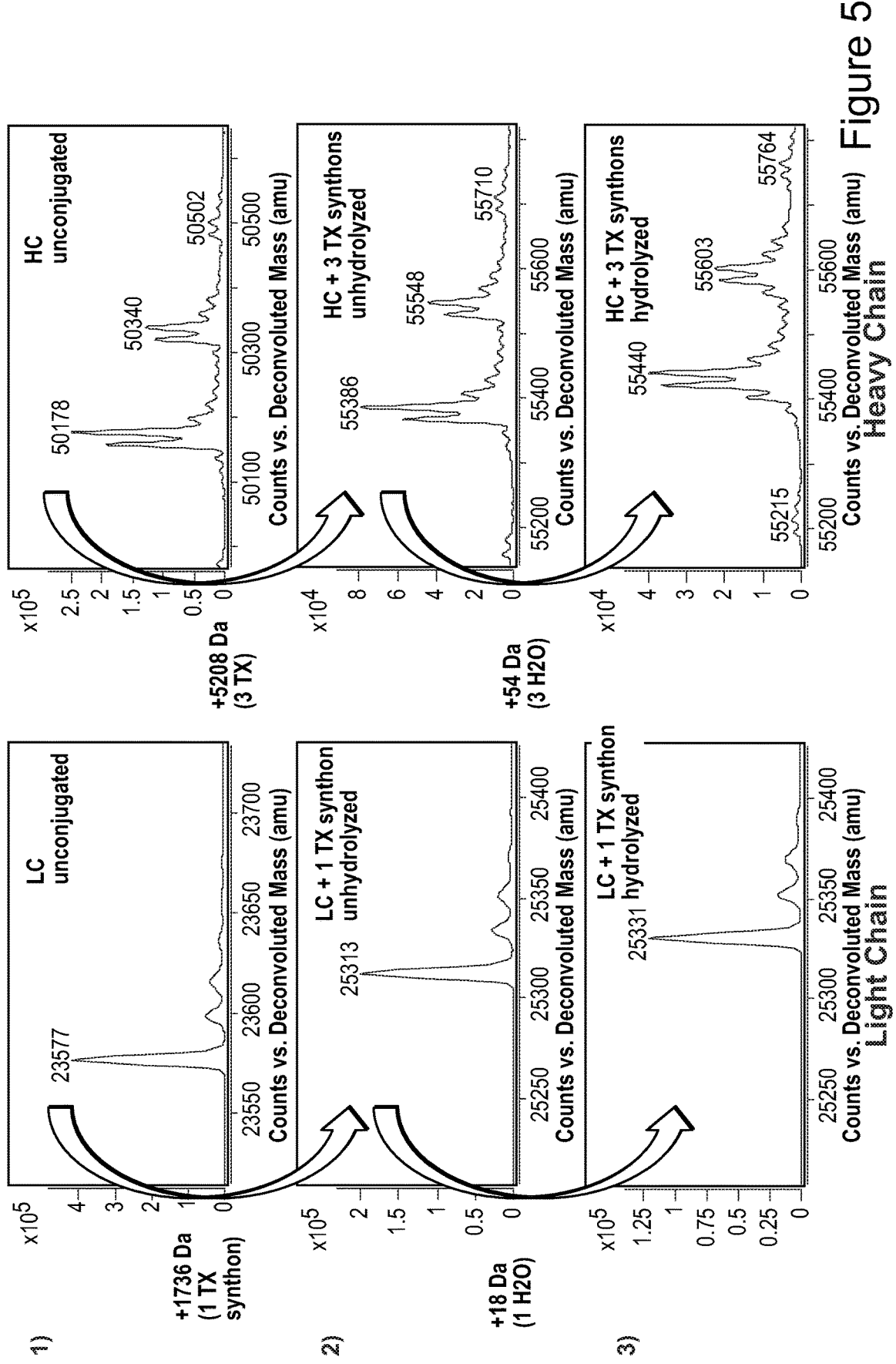
FIG. 5 depicts the MS characterization of light chain and heavy chain of huAb13v1 1) prior to conjugation, 2) after conjugation to a maleimide derivative to give a thiosuccinimide intermediate and 3) post pH 8-mediated hydrolysis of the thiosuccinimide ring.

When a conjugate is prepared by fully reducing the interchain disulfides of a human IgG1 antibody and conjugating the maleimide derivative to each of the resulting cysteines, each light chain of the antibody will contain a single maleimide modification and each heavy chain will contain three maleimide modifications, as described in FIG. 2. Upon complete hydrolysis of the resulting thiosuccinimides, the mass of the light chain will therefore increase by 18 Daltons, while the mass of each heavy chain will increase by 54 Daltons. This is illustrated in FIG. 5 with the conjugation and subsequent hydrolysis of an exemplary maleimide drug-linker (synthon TX, molecular weight 1736 Da) to the fully reduced huAb13v1 antibody.

Size Exclusion Chromatography General Methodology

Size exclusion chromatography was performed using a Shodex KW802.5 column in 0.2 M potassium phosphate pH 6.2 with 0.25 mM potassium chloride and 15% IPA at a flow rate of 0.75 ml/min. The peak area absorbance at 280 nm was determined for each of the high molecular weight and monomeric eluents by integration of the area under the curve. The % aggregate fraction of the conjugate sample was determined by dividing the peak area absorbance at 280 nM for the high molecular weight eluent by the sum of the peak area absorbances at 280 nM of the high molecular weight and monomeric eluents multiplied by 100%.

In Vitro Cell Viability Assay Methods

The tumor cell lines HCC38 (breast cancer), NCI-H1650 (NSCLC) and NCI-H847 (small cell lung cancer cell line) were obtained from American Type Culture Collection (ATCC). Cells were grown in 96-well culture plates using recommended growth media overnight at a density of $5 \times 10^3$ (HCC38) or $20 \times 10^3$ (NCI-H847) or $40 \times 10^3$ (NCI-H1650) per well. The following day, treatments were added in fresh media to triplicate wells. Cellular viability was determined 5 days later using the CellTiter-Glo Luminescent Cell Viability Assay kit (Promega), as directed in the manufacturer's protocol. Cell viability was assessed as percentage of control untreated cells.

Example 8: In vivo Efficacy of Anti-B7-H3 Antibody Drug Conjugates

Of the nine chimeric antibodies tested in vitro conjugtaed to CZ synthons, four showed subnanomolar cytotoxicity (Table 6). chAb3-CZ, chAb18-CZ, and chAb13-CZ achieved DARS ranging from 2.6 to 4.2 (see Table 7) and were assessed for anti-tumor activity in a mouse small cell lung cancer cell line xenograft model NCI-H146, of human origin, using the methods described below. Antibody MSL109 (an IgG1 antibody that binds to cytomegalovirus (CMV) glycoprotein H) was used as a control, both as a naked antibody and as an ADC (conjugated to the same synthon (CZ) as the chAb3, chAb18, and chAb13 antibodies). MSL109 is an isotype matched non-targeting control. The methods of this xenograft assay are described below. The results are presented in Table 7. The results show that each of the anti-B7-H3 Bcl-xL inhibiting ADCs were able to significantly inhibit tumor growth relative to the naked antibody control (MSL109) or non-target specific Bcl-xL ADC control (MSL109-CZ).

TABLE 7

In vivo efficacy of chimeric anti-B7-H3 antibody as Bcl-xL drug conjugates

| ADC | Conjugation Method | DAR | Dose[a]/route/ regimen | Number of mice | $TGI_{max}$ (%) | TGD (%) |
|---|---|---|---|---|---|---|
| MSL109 | — | — | 10 mg/kg/IP/QD×1 | 8 | 0 | 0 |
| MSL109-CZ | A | 4.2 | 10 mg/kg/IP/QD×1 | 8 | 34 | 10 |
| chAb3-CZ | A | 3.5 | 10 mg/kg/IP/QD×1 | 8 | 87 | 109 |
| chAb18-CZ | A | 2.6 | 10 mg/kg/IP/QD×1 | 8 | 90 | 100 |
| chAb13-CZ | A | 3.7 | 10 mg/kg/IP/QD×1 | 8 | 81 | 104 |

[a]dose is given in mg/kg/day

Evaluation of Efficacy in Xenograft Models Methods

NCI-H146 cells, NCI-1650 cells, and EBC-1 cells were obtained from the American Type Culture Collection (ATCC, Manassas, Va.). The cells were cultured as monolayers in RPMI-1640 (NCI-H146, NCI-H1650) or MEM (EBC-1) culture media (Invitrogen, Carlsbad, Calif.) that was supplemented with 10% Fetal Bovine Serum (FBS, Hyclone, Logan, Utah). To generate xenografts, $5 \times 10^6$ viable cells were inoculated subcutaneously into the right flank of immune deficient female SCID/bg mice (Charles River Laboratories, Wilmington, Mass.) respectively. The injection volume was 0.2 mL and composed of a 1:1 mixture of S MEM and Matrigel (BD, Franklin Lakes, N.J.). Tumors were size matched at approximately 200 mm$^3$. Antibodies and conjugates were formulated in 0.9% sodium chloride for injection and injected intraperitoneally. Injection volume did not exceed 200 µL. Therapy began within 24 hours after size matching of the tumors. Mice weighed approximately 22 g at the onset of therapy. Tumor volume was estimated two to three times weekly. Measurements of the length (L) and width (W) of the tumor were taken via electronic caliper and the volume was calculated according to the following equation: $V = L \times W^2/2$. Mice were euthanized when tumor volume reached 3,000 mm3 or skin ulcerations occurred. Eight mice were housed per cage. Food and water were available ad libitum. Mice were acclimated to the animal facilities for a period of at least one week prior to commencement of experiments. Animals were tested in the light phase of a 12-hour light: 12-hour dark schedule (lights on at 06:00 hours). As described above, human IgG control antibody (MSL109) was used as a negative control agent.

To refer to efficacy of therapeutic agents, parameters of amplitude ($TGI_{max}$), durability (TGD) of therapeutic response are used. $TGI_{max}$ is the maximum tumor growth inhibition during the experiment. Tumor growth inhibition is calculated by $100*(1-T_v/C_v)$ where $T_v$ and $C_v$ are the mean tumor volumes of the treated and control groups, respectively. TGD or tumor growth delay is the extended time of a treated tumor needed to reach a volume of 1 cm$^3$ relative to the control group. TGD is calculated by $100*(T_t/C_t-1)$ where $T_t$ and $C_t$ are the median time periods to reach 1 cm$^3$ of the treated and control groups, respectively.

Example 9: Humanization of Anti-B7-H3 Antibody chAb18

Anti-B7-H3 chimeric antibody chAb18 was selected for humanization based on its binding characteristics and favorable properties as an ADC, including its properties when conjugated to a Bcl-xL inhibitor (described above as exemplary conjugate CZ).

Humanized antibodies were generated based on the variable heavy (VH) and variable light (VL) CDR sequences of chAb18. Specifically, human germline sequences were selected for constructing CDR-grafted, humanized chAb18 antibodies, where the CDR domains of the VH and VL chains were grafted onto different human heavy and light chain acceptor sequences. Based on the alignments with the VH and VL sequences of monoclonal antibody chAb18, the following human sequences were selected as acceptors:

IGHV1-69*06 and IGHJ6*01 for constructing heavy chain acceptor sequences

IGKV1-9*01 and IGKJ2*01 for constructing light chain acceptor sequences

IGKV6-21*01 and IGKJ2*01 as backup acceptor for constructing light chain

Thus, the VH and VL CDRs of chAb18 were grafted into said acceptor sequences.

To generate humanized antibodies, framework back-mutations were identified and introduced into the CDR-grafted antibody sequences by de novo synthesis of the variable domain, or mutagenic oligonucleotide primers and polymerase chain reactions, or both by methods well known in the art. Different combinations of back mutations and other mutations were constructed for each of the CDR-grafts as described below. Residue numbers for these mutations are based on the Kabat numbering system.

For heavy chains huAb18VH.1, one or more of the following Vernier and VH/VL interfacing residues were back mutated as follows: L46P, L47W, G64V, F71H. Additional mutations include the following: Q1E, N60A, K64Q, D65G. For light chains huAb18VL.1, one or more of the following Vernier and VH/VL interfacing residues were back mutated as follows: A43S, L46P, L47W, G64V, G66V, F71H. For light chains huAb18VL.2, one or more of the following Vernier and VH/VL interfacing residues were back mutated as follows: L46P, L47W, K49Y, G64V, G66V, F71H.

The variable region and CDR amino acid sequences of the humanized antibodies are described in Table 8 below.

TABLE 8

VH and VL amino acid sequences of humanized versions of chAb18

| SEQ ID NO: | Clone | Protein Region | Residues | Amino Acid Sequence |
|---|---|---|---|---|
| 116 | huAb18VH.1 | VH | | EVQLVQSGAEVKKPGSSVKVSCKAS GYSFTSYTIHWVRQAPGQGLEWMGY INPNSRNTDYNQKFKDRVTITADKS TSTAYMELSSLRSEDTAVYYCARYS GSTPYWYFDVWGQGTTVTVSS |
| 25 | huAb18VH.1 | CDR-H1 | Residues 26-35 of SEQ ID NO: 116 | GYSFTSYTIH |
| 26 | huAb18VH.1 | CDR-H2 | Residues 50-66 of SEQ ID NO: 116 | YINPNSRNTDYNQKFKD |
| 27 | huAb18VH.1 | CDR-H3 | Residues 99-110 of SEQ ID NO: 116 | YSGSTPYWYFDV |
| 117 | huAb18VH.1a | VH | | EVQLVQSGAEVKKPGSSVKVSCKAS GYSFTSYTIHWVRQAPGQGLEWIGY INPNSRNTDYNQKFKDRTTLTADRS TSTAYMELSSLRSEDTAVYYCARYS GSTPYWYFDVWGQGTTVTVSS |
| 25 | huAb18VH.1a | CDR-H1 | Residues 26-35 of SEQ ID NO: 117 | GYSFTSYTIH |
| 26 | huAb18VH.1a | CDR-H2 | Residues 50-66 of SEQ ID NO: 117 | YINPNSRNTDYNQKFKD |
| 27 | huAb18VH.1a | CDR-H3 | Residues 99-110 of SEQ ID NO: 117 | YSGSTPYWYFDV |
| 118 | huAb18VH.1b | VH | | EVQLVQSGAEVKKPGSSVKVSCKAS GYSFTSYTIHWVRQAPGQGLEWMGY INPNSRNTDYAQKFQGRVTLTADKS TSTAYMELSSLRSEDTAVYYCARYS GSTPYWYFDVWGQGTTVTVSS |
| 25 | huAb18VH.1b | CDR-H1 | Residues 26-35 of SEQ ID NO: 118 | GYSFTSYTIH |
| 119 | huAb18VH.1b | CDR-H2 | Residues 50-66 of SEQ ID NO: 118 | YINPNSRNTDYAQKFQG |
| 27 | huAb18VH.1b | CDR-H3 | Residues 99-110 of SEQ ID NO: 118 | YSGSTPYWYFDV |
| 120 | huAb18VL.1 | VL | | DIQLTQSPSFLSASVGDRVTITCRA SSSVSYMNWYQQKPGKAPKLLIYAT |

TABLE 8-continued

VH and VL amino acid sequences of humanized versions of chAb18

| SEQ ID NO: | Clone | Protein Region | Residues | Amino Acid Sequence |
|---|---|---|---|---|
| | | | | SNLASGVPSRFSGSGSGTEFTLTIS SLQPEDFATYYCQQWSSNPLTFGQG TKLEIK |
| 29 | huAb18VL.1 | CDR-L1 | Residues 24-33 of SEQ ID NO: 120 | RASSSVSYMN |
| 30 | huAb18VL.1 | CDR-L2 | Residues 49-55 of SEQ ID NO: 120 | ATSNLAS |
| 31 | huAb18VL.1 | CDR-L3 | Residues 88-96 of SEQ ID NO: 120 | QQWSSNPLT |
| 121 | huAb18VL.1a | VL | | DIQLTQSPSFLSASVGDRVTITCRA SSSVSYMNWYQQKPGKSPKPWIYAT SNLASGVPSRFSVSVSGTEHTLTIS SLQPEDFATYYCQQWSSNPLTFGQG TKLEIK |
| 29 | hu18AbVL.1a | CDR-L1 | Residues 24-33 of SEQ ID NO: 121 | RASSSVSYMN |
| 30 | huAb18VL.1a | CDR-L2 | Residues 49-55 of SEQ ID NO: 121 | ATSNLAS |
| 31 | huAb18VL.1a | CDR-L3 | Residues 88-96 of SEQ ID NO: 121 | QQWSSNPLT |
| 122 | huAb18VL.1b | VL | | DIQLTQSPSFLSASVGDRVTITCRA SSSVSYMNWYQQKPGKAPKPWIYAT SNLASGVPSRFSVSGSGTEHTLTIS SLQPEDFATYYCQQWSSNPLTFGQG TKLEIK |
| 29 | huAb18VL.1b | CDR-L1 | Residues 24-33 of SEQ ID NO: 122 | RASSSVSYMN |
| 30 | huAb18VL.1b | CDR-L2 | Residues 49-55 of SEQ ID NO: 122 | ATSNLAS |
| 31 | huAb18VL.1b | CDR-L3 | Residues 88-96 of SEQ ID NO: 122 | QQWSSNPLT |
| 123 | huAb18VL.2 | VL | | EIVLTQSPDFQSVTPKEKVTITCRA SSSVSYMNWYQQKPDQSPKLLIKAT SNLASGVPSRFSGSGSGTDFTLTIN SLEAEDAATYYCQQWSSNPLTFGQG TKLEIK |
| 29 | huAb18VL.2 | CDR-L1 | Residues 24-33 of SEQ ID NO: 123 | RASSSVSYMN |
| 30 | huAb18VL.2 | CDR-L2 | Residues 49-55 of SEQ ID NO: 123 | ATSNLAS |
| 31 | huAb18VL.2 | CDR-L3 | Residues 88-96 of SEQ ID NO: 123 | QQWSSNPLT |
| 124 | huAb18VL.2a | VL | | EIVLTQSPDFQSVTPKEKVTITCRA SSSVSYMNWYQQKPDQSPKPWIYAT SNLASGVPSRFSVSVSGTDHTLTIN SLEAEDAATYYCQQWSSNPLTFGQG TKLEIK |
| 29 | huAb18VL.2a | CDR-L1 | Residues 24-33 of SEQ ID NO: 124 | RASSSVSYMN |
| 30 | huAb18VL.2a | CDR-L2 | Residues 49-55 of SEQ ID NO: 124 | ATSNLAS |
| 31 | huAb18VL.2a | CDR-L3 | Residues 88-96 of SEQ ID NO: 124 | QQWSSNPLT |

Humanized variable regions of the murine monoclonal Ab18 (described above) were cloned into IgG expression vectors for functional characterization:

Humanized Ab18VH.1 (huAb18VH.1) is a CDR-grafted, humanized Ab18 VH containing IGHV1-69*06 and IGHJ6*01 framework sequences. It also contains a Q1E change to prevent pyroglutamate formation. The variable and CDR sequences of huAb18VH.1 are described in Table 8.

Humanized Ab18VH1.a (huAb18VH.1a) is a humanized design based on huAb18VH.1 and contains 4 proposed framework back-mutations: M48I, V67T, L69I, K73R. The variable and CDR sequences of huAb18VH.1a are described in Table 8.

Humanized Ab18VH1.b (huAb18VH.1b) is a humanized design based on huAb18VH.1 and huAb18VH.1a and contains 1 proposed framework back-mutation L69I and 3 HCDR2 germlining changes N60A, K64Q, D65G. The variable and CDR sequences of huAb18VH.1b are described in Table 8.

Humanized Ab18VL.1 (huAb18VL.1) is a CDR-grafted, humanized Ab18 VL containing IGKV1-9*01 and IGKJ2*01 framework sequences. The variable and CDR sequences of huAb18VL.1 are described in Table 8.

Humanized Ab18VL.1a (huAb18VL.1a) is a humanized design based on huAb18VL.1 and contains 6 proposed framework back-mutations: A43S, L46P, L47W, G64V, G66V, F71H. The variable and CDR sequences of huAb18VL.11 are described in Table 8.

Humanized Ab18VL.1b (huAb18VL.1b) is a humanized design based on huAb18VL.1 and huAb18VL.1a contains 4 proposed framework back-mutations: L46P, L47W, G64V, F71H. The variable and CDR sequences of huAb18VL.1b are described in Table 8.

Humanized Ab18VL.2 (huAb18VL.2) is a CDR-grafted, humanized Ab18 VL containing IGKV6-21*01 and IGKJ2*01 framework sequences. The variable and CDR sequences of huAb18VL.2 are described in Table 8.

Humanized Ab18VL.2a (huAb18VL.2a) is a humanized design based on huAb18VL.2 and contains 6 proposed framework back-mutations: L46P, L47W, K49Y, G64V, G66V, F71H. The variable and CDR sequences of huAb18VL.2a are described in Table 8.

Thus, the humanization of chAb18 resulted in 10 humanized antibodies, including huAb18v1, huAb18v2, huAb18v3, huAb18v4, huAb18v5, huAb18v6, huAb18v7, huAb18v8, huAb18v9, and huAb18v10. The variable and heavy light chains for each of these humanized versions of Ab18 are provided below:

TABLE 9

| Anti-B7-H3 Ab18 humanized antibodies | |
|---|---|
| huAb18v1 | huAb18 VH1/huAb18VL1 |
| huAb18v2 | huAb18 VH1b/huAb18VL1 |
| huAb18v3 | huAb18 VH1a/huAbVL1a |
| huAb18v4 | huAb18 VH1b/huAb18VL1a |
| huAb18v5 | huAn18 VH1/huAb18VL2 |
| huAb18v6 | huAb18 VH1b/huAb18VL2 |
| huAb18v7 | huAb18 VH1b/huAb18 VL2a |
| huAb18v8 | huAb18 VH1a/huAb18 VL1b |
| huAb18v9 | huAb18 VH1a/huAb18 VL2a |
| huAb18v10 | huAb18 VH1b/huAb18 VL1b |

Example 10: In vitro Characterization of Anti-B7-H3 chAb18 Humanized Variants

The humanization of chAb18 generated 10 variants (described above in Table 9) that retained binding to human and cyno B7-H3 as assessed by FACS (the method of which is described above in Example 6). These variants were further characterized for binding by SPR and were successfully conjugated to the Bcl-xL inhibitor synthon CZ using Method A (described above) and assessed for cell cytotoxicity as described in Example 7. Table 10 summarizes the in vitro characteristics of the various humanized Ab18 variants. The parental chAb18 from which the variants were derived was also tested as a comparator. All humanized variants had similar binding properties as assessed by biacore, and retained binding activity to cell surface expressed as conjugates with the CZ synthon. The cytotoxicity of all of the variants as CZ synthons were similar to the chAb18 from which they were derived.

TABLE 10

In vitro characterization of humanized anti-B7-H3 Ab18 variants

| Variant name | Sequence Numbers | DAR by MS | % agg by SEC | FACS Binding to hu B7-H3 | Affinity of naked mAbs (Biacore, $K_D$) | Cytotoxicity (HCC38 Cell line $IC_{50}$) |
|---|---|---|---|---|---|---|
| chAb18-CZ | 24, 28 | 2.3 | | 1.14 | 1.70E−10 | 0.28 |
| huAb18v1-CZ | 116, 120 | 2.6 | 3.3 | 1.27 | 5.20E−10 | 0.39 |
| huAb18v2-CZ | 118, 120 | 1.8 | 3.3 | 2.25 | 6.90E−10 | 1.19 |
| huAb18v3-CZ | 117, 121 | 2.4 | 3.6 | 1.27 | 2.30E−10 | 0.32 |
| huAb18v4-CZ | 118, 121 | 2.5 | 5.5 | 0.90 | 5.70E−10 | 0.29 |
| huAb18v5-CZ | 116, 123 | 3.4 | 4.2 | 2.91 | 2.30E−10 | 0.12 |
| huAb18v6-CZ | 118, 123 | 3.4 | 3.5 | 2.09 | 2.00E−10 | 0.14 |
| huAb18v7-CZ | 118, 124 | 4.3 | 3.6 | 1.92 | 4.00E−10 | 0.03 |
| huAb18v8-CZ | 117, 122 | 2.6 | 3.5 | 1.98 | 2.50E−10 | 1.3 |
| huAb18v9-CZ | 117, 124 | 2.4 | 3.8 | 1.58 | 3.80E−10 | 0.9 |
| huAb18v10-CZ | 118, 122 | 2.7 | 3.2 | 1.19 | 2.50E−10 | 0.57 |

Humanized chAb18 variants were conjugated to the CZ synthon and tested for cytotoxicity in HCC38 cell line. As described in Table 10, most humanized antibodies showed potent cytotoxicity, similar to those observed with control antibody chAb18.

Example 11: In Vivo Efficacy of Humanized Ab18 Variants as Bcl-xL Inhibitor ADCs Six of the humanized chAb18 variants were selected based on in vitro cytotoxicity results described in Example 10. Specifically, antibodies huAb18v1, huAb18v3, huAb18v4, huAb18v6, huAb18v7, and huAb18v9 were each conjugated to the CZ synthon (to form an anti-B7-H3 CZ ADC) for evaluation in an in vivo xenograft model of small cell lung cancer (using NCI-H146 cells), as described in Example 8. Single dose treatment of the tumor bearing mice resulted in tumor growth inhibition and tumor growth delay and the results are summarized in Table 11. Ab095 was used as a negative control for the effect of administering IgG, as it is an isotype matched non-target specific antibody raised against tetanus toxoid. See Larrick et al., 1992, Immunological Reviews 69-85. Mice were administered 6 mg/kg of the ADC intraperitoneally QDx1.

TABLE 11

In vivo efficacy of anti-B7-H3 ADCS (humanized chAb18-CZ variants)

| ADC | Conjugation Method | DAR by MS | Dose[a]//route/ regimen | Number of mice | TGI$_{max}$ (%) | TGD (%) |
|---|---|---|---|---|---|---|
| AB095 | — | n/a | 6 mg/kg/IP/QDx1 | 8 | 0 | 0 |
| huAb18v1-CZ | A | 2.6 | 6 mg/kg/IP/QDx1 | 8 | 79 | 45 |
| huAb18v3-CZ | A | 2.4 | 6 mg/kg/IP/QDx1 | 8 | 81 | 39 |
| huAB18v4-CZ | A | 2.5 | 6 mg/kg/IP/QDx1 | 8 | 85 | 48 |
| huAB18v6-CZ | A | 3.4 | 6 mg/kg/IP/QDx1 | 8 | 86 | 45 |
| huAb18v7-CZ | A | 4.3 | 6 mg/kg/IP/QDx1 | 8 | 87 | 42 |
| huAb18v9-CZ | A | 2.4 | 6 mg/kg/IP/QDx1 | 8 | 83 | 35 |

[a]dose is given in mg/kg/day

As described in Table 11, each of the tested humanized antibodies was able to inhibit tumor growth in the mouse xenograft model.

Example 12: Humanization of Anti-B7-H3 Antibody chAb3

Anti-B7-H3 chimeric antibody chAb3 was selected for humanization based on its favorable properties as a Bcl-xL inhibiting (Bcl-xLi) conjugate. Humanized antibodies were generated based on the variable heavy (VH) and variable light (VL) CDR sequences of chAB3. Specifically, human germline sequences were selected for constructing CDR-grafted, humanized chAb3 antibodies where the CDR domains of the VH and VL chains of chAb3 were grafted onto different human heavy and light chain acceptor sequences. Based on the alignments with the VH and VL sequences of monoclonal antibody chAb3 the following human sequences were selected as acceptors:

IGHV1-69*06 and IGHJ6*01 for constructing heavy chain acceptor sequences

IGKV2-28*01 and IGKJ4*01 for constructing light chain acceptor sequences

IGHV1-69*06 IGHJ6
(SEQ ID NO: 174)
QVQLVQSGAEVKKPGSSVKVSCKASggtfssyaisWVRQAPGQGLEWMGg iipifgtanyaqkfqgRVTITADKSTSTAYMELSSLRSEDTAVYYCARxx xxxxxxWGQGTTVTVSS; where xxxxxxxx represents the CDR-H3 region.

IGKV2-28*01 IGKJ4
(SEQ ID NO: 175)
DIVMTQSPLSLPVTPGEPASISCrssqsllhsngynyldWYLQKPGQSPQ LLIYlgsnrasGVPDRFSGSGSGTDFTLKISRVEAEDVGVYYCxxxxxxx xxFGGGTKVEIK; where xxxxxxxxx represents the CDR-L3 region.

By grafting the corresponding VH and VL CDRs of chAb3 into said acceptor sequences, CDR-grafted, humanized, and modified VH and VL sequences were prepared. To generate humanized antibodies with potential framework back-mutations, the mutations were identified and introduced into the CDR-grafted antibody sequences by de novo synthesis of the variable domain, or mutagenic oligonucleotide primers and polymerase chain reactions, or both. Different combinations of back mutations and other mutations are constructed for each of the CDR-grafts as follows. Residue numbers for these mutations are based on the Kabat numbering system.

The amino acid sequences of the various humanized heavy and light chain variable regions are described below in Table 12.

For heavy chains huAb3VH. 1, one or more of the following Vernier and VH/VL interfacing residues were back mutated as follows: M48I, V67A, I69L, A71V, K73R, M80V, Y91F, R94G. For light chains huAb31 VL. 1, one or more of the following Vernier and VH/VL interfacing residues were back mutated as follows: I2V, Y87F.

The following humanized variable regions of the murine monoclonal chAb3 antibody were cloned into IgG expression vectors for functional characterization:

Humanized Ab3 VH.1 (huAb3VH. 1) is a CDR-grafted, humanized Ab3 VH containing IGHV1-69*06 and IGHJ6*01 framework sequences. It also contains a Q1E change to prevent pyroglutamate formation.

Humanized Ab3 VH.1a (huAb3VH.1a) is a humanized design based on huAb3VH.1 and contains 8 proposed framework back-mutations: M48I, V67A, I69L, A71V, K73R, M80V, Y91F, R94G.

Humanized Ab3 VH.1b (huAb3VH.1b) is a humanized design between huAb3VH.1 and huAb3VH.1a and contains 6 proposed framework back-mutations: M48I, V67A, I69L, A71V, K73R, R94G.

Humanized Ab3 VL.1 (huAb3VL.1) is a CDR-grafted, humanized Ab3 VL containing IGKV2-28*01 and IGKJ4*01 framework sequences.

Humanized Ab3 VL.1a (huAb3VL.1a is a humanized design based on huAb3VL.1 and contains 2 proposed framework back-mutations: I2V, Y87F.

Humanized Ab3 VL.1b (huAb3VL.1b) is a humanized design contains only 1 proposed framework back-mutations: 12V.

The variable region and CDR amino acid sequences of the foregoing humanized antibodies are described in Table 12 below.

TABLE 12

VH and VL sequences of humanized versions of chAb3

| SEQ ID NO: | Clone | Protein Region | Residues | Amino Acid Sequence |
|---|---|---|---|---|
| 125 | huAb3VH.1 | VH | | EVQLVQSGAEVKKPGSSVKVS CKASGYTFSSYWMHWVRQAPG QGLEWMGLIHPDSGSTNYNEM FKNRVTITADKSTSTAYMELS SLRSEDTAVYYCARGGRLYFD YWGQGTTVTVSS |
| 10 | huAb3VH.1 | CDR-H1 | Residues 26-35 of SEQ ID NO: 125 | GYTFSSYWMH |
| 11 | huAb3VH.1 | CDR-H2 | Residues 50-66 of SEQ ID NO: 125 | LIHPDSGSTNYNEMFKR |
| 12 | huAb3VH.1 | CDR-H3 | Residues 99-106 of SEQ ID NO: 125 | GGRLYFDY |
| 126 | huAb3VH.1a | VH | | EVQLVQSGAEVKKPGSSVKVS CKASGYTFSSYWMHWVRQAPG QGLEWIGLIHPDSGSTNYNEM FKNRATLTVDRSTSTAYVELS SLRSEDTAVYFCAGGGRLYFD YWGQGTTVTVSS |
| 10 | huAb3VH.1a | CDR-H1 | Residues 26-35 of SEQ ID NO: 126 | GYTFSSYWMH |
| 11 | huAb3VH.1a | CDR-H2 | Residues 50-66 of SEQ ID NO: 126 | LIHPDSGSTNYNEMFKR |
| 12 | huAb3VH.1a | CDR-H3 | Residues 99-106 of SEQ ID NO: 126 | GGRLYFDY |
| 127 | huAb3VH.1b | VH | | EVQLVQSGAEVKKPGSSVKVS CKASGYTFSSYWMHWVRQAPG QGLEWIGLIHPDSGSTNYNEM FKNRATLTVDRSTSTAYMELS SLRSEDTAVYYCAGGGRLYFD YWGQGTTVTVSS |
| 10 | huAb3VH.1b | CDR-H1 | Residues 26-35 of SEQ ID NO: 127 | GYTFSSYWMH |
| 11 | huAb3VH.1b | CDR-H2 | Residues 50-66 of SEQ ID NO: 127 | LIHPDSGSTNYNEMFKR |
| 12 | huAb3VH.1b | CDR-H3 | Residues 99-106 of SEQ ID NO: 127 | GGRLYFDY |
| 128 | huAb3VL.1 | VL | | DIVMTQSPLSLPVTPGEPASI SCRSSQSLVHSNGDTYLRWYL QKPGQSPQLLIYKVSNRFSGV PDRFSGSGSGTDFTLKISRVE AEDVGVYYCSQSTHVPYTFGG GTKVEIK |
| 14 | huAb3VL.1 | CDR-L1 | Residues 24-39 of SEQ ID NO: 128 | RSSQSLVHSNGDTYLR |
| 7 | huAb3VL.1 | CDR-L2 | Residues 55-61 of SEQ ID NO: 128 | KVSNRFS |
| 15 | huAb3VL.1 | CDR-L3 | Residues 94-102 of SEQ ID NO: 128 | SQSTHVPYT |

TABLE 12-continued

VH and VL sequences of humanized versions of chAb3

| SEQ ID NO: | Clone | Protein Region | Residues | Amino Acid Sequence |
|---|---|---|---|---|
| 129 | huAb3VL.1a | VL | | DVVMTQSPLSLPVTPGEPASI SCRSSQSLVHSNGDTYLRWYL QKPGQSPQLLIYKVSNRFSGV PDRFSGSGSGTDFTLKISRVE AEDVGVYFCSQSTHVPYTFGG GTKVEIK |
| 14 | huAb3VL.1a | CDR-L1 | Residues 24-39 of SEQ ID NO: 129 | RSSQSLVHSNGDTYLR |
| 7 | huAb3VL.1a | CDR-L2 | Residues 55-61 of SEQ ID NO: 129 | KVSNRFS |
| 15 | huAb3VL.1a | CDR-L3 | Residues 94-102 of SEQ ID NO: 129 | SQSTHVPYT |
| 130 | huAb3VL.1b | VL | | DVVMTQSPLSLPVTPGEPASI SCRSSQSLVHSNGDTYLRWYL QKPGQSPQLLIYKVSNRFSGV PDRFSGSGSGTDFTLKISRVE AEDVGVYYCSQSTHVPYTFGG GTKVEIK |
| 14 | huAb3VL.1b | CDR-L1 | Residues 24-39 of SEQ ID NO: 130 | RSSQSLVHSNGDTYLR |
| 7 | huAb3VL.1b | CDR-L2 | Residues 55-61 of SEQ ID NO: 130 | KVSNRFS |
| 15 | huAb3VL.1b | CDR-L3 | Residues 94-102 of SEQ ID NO: 130 | SQSTHVPYT |

The humanization of chAb3 resulted in 6 humanized antibodies, including huAb3v1, huAb3v2, huAb3v3, huAb3v4, huAb18v5, and huAb3v6. The variable and heavy light chains for each of these humanized versions of Ab18 are provided below in Table 13.

TABLE 13

| Humanized Ab3 antibodies | |
|---|---|
| huAb3v1 | huAb3 VH1/huAb3 VL1 |
| huAb3v2 | huAb3 VH1b/huAb3 VL1 |
| huAb3v3 | huAb3 VH1a/huAb3 VL1a |
| huAb3v4 | huAb3 VH1/huAb3 VL1b |
| huAb3v5 | huAb3 VH1b/huAb3 VL1b |
| huAb3v6 | huAb3 VH1a/huAb3 VL1b |

Example 13: In Vitro Characterization of chAb3 Humanized Variants

The humanization of chAb3 generated 6 variants (described in Table 13) that retained binding to human B7-H3 as assessed by FACS (as described in Example 6). These variants were further characterized for binding by SPR and as ADCs conjugated to the Bcl-xL inhibitor synthon (linker warhead) CZ. The humanized Ab3 antibodies were also assessed for cell cytotoxicity (using the assay described above in Example 7). Table 14 summarizes in vitro characteristics of chAb3 humanized variants. An ADC comprising chAb3 conjugated to synthon CZ was used as a control.

TABLE 14

In vitro characterization of humanized variants of chAb3

| ADC | Seq. Id. Number | Conjugation Method | DAR by MS | % agg by SEC | FACS Binding to hu B7-H3) $EC_{50}$ (nM) | Affinity of naked mAbs (Biacore, $K_D$) | Cytotoxicity (HCC38 Cell line $IC_{50}$) (nM) |
|---|---|---|---|---|---|---|---|
| chAb3-CZ | 9, 13 | A | 3.8 | | 0.61 | 1.90E-08 | 0.17 |
| huAb3v1-CZ | 125, 128 | A | 3.6 | 3.3 | 1.45 | 5.20E-10 | 0.53 |
| huAb3v2-CZ | 127, 128 | A | 3.8 | 10.1 | 0.73 | 6.90E-10 | 0.13 |
| huAb3v3-CZ | 126, 129 | A | 3.6 | 2.5 | 1.68 | 2.30E-10 | 9.22 |
| huAb3v4-CZ | 125, 130 | A | 3.1 | 3.1 | n/a | 5.70E-10 | n/a |

TABLE 14-continued

In vitro characterization of humanized variants of chAb3

| ADC | Seq. Id. Number | Conjugation Method | DAR by MS | % agg by SEC | FACS Binding to hu B7-H3) EC$_{50}$ (nM) | Affinity of naked mAbs (Biacore, K$_D$) | Cytotoxicity (HCC38 Cell line IC$_{50}$) (nM) |
|---|---|---|---|---|---|---|---|
| huAb3v5-CZ | 127, 130 | A | 3.1 | 5.9 | 0.85 | 2.30E−10 | 0.17 |
| huAb3v6-CZ | 126, 130 | A | 3.3 | 4.9 | 1.78 | 2.00E−10 | 0.13 |

Example 14: In Vivo Efficacy of chAb3 Humanized Variants as Bcl-xL ADCs

Two of the humanized variants (huAb3v2 and huAb3v6) were selected based on potent in vitro cytotoxicity as CZ conjugates and acceptable aggregation properties for evaluation in an in vivo murine xenograft model of small cell lung cancer cells (NCI-H146 cells) as described in materials and methods in Example 8. Single dose treatment of tumor bearing mice resulted in tumor growth inhibition and tumor growth delay for both humanized antibodies conjugated to an exemplary Bcl-xL inhibitor, and the results are summarized in Table 15.

TABLE 15

In vivo efficacy of humanized chAb3-CZ variants

| ADC | Conjugation Method | DAR | Dose[a]/route/ regimen | Number of mice | TGI$_{max}$ (%) | TGD (%) |
|---|---|---|---|---|---|---|
| AB095 | — | | 6 mg/kg/IP/QDx1 | 8 | 0 | 0 |
| huAb3v2-CZ | A | 3.8 | 6 mg/kg/IP/QDx1 | 8 | 83 | 52 |
| huAb3v6-CZ | A | 3.3 | 6 mg/kg/IP/QDx1 | 8 | 91 | 88 |

[a]dose is given in mg/kg/day

Example 15: Modifications of the CDRs of Humanized Variant Antibody huAb3v2 huAb3v2 showed favorable binding and cell killing properties. An examination of the variable region amino acid sequences of huAb3v2, however, revealed potential deamidation and/or isomerization sites.

The amino acid sequences of huAb3 variable regions are described below, including the light chain (huAb3VL1) and the heavy chain (huAb3VH1b). The potential deamidation and/or isomerization sites in CDRs of the VH (CDR2 at amino acids "ds" and VL (CDR1 at amino acids "ng") are italicized and were thus engineered to improve antibody manufacturing. The CDRs are described in lower case letters in the sequences below.

To make huAb3v2 variants lacking these potential deamidation and/or isomerization sites, each of the amino acids indicated below (x and z; representing the potential sites in the CDR1 of the VL and the CDR2 of the VH) were mutagenized. The resulting 30 VL variants were paired with the original huAb3v2 VH and tested for binding. The resulting 29 VH variants were paired with the original huAb3v2 VL and tested for binding. Successful VH variants were combined and tested with productive VL variants harboring changes in LCDR1 to make the final humanized variants lacking the potential deamidation and/or isomerization sites in CDRs. The amino acid sequences of the variants are provided in Table 16 below. The full length amino acid sequences of the heavy chain and light chain of the huAb3v2 variant, huAb3v2.5 are provided in SEQ ID NOs: 170 and 171, respectively. The full length amino acid sequences of the heavy chain and light chain of the huAb3v2 variant, huAb3v2.6 are provided in SEQ ID NOs: 172 and 173, respectively.

huAb3 VL1

(SEQ ID NO: 128)
DIVMTQSPLSLPVTPGEPASISCrssqslvhs*ng*dtylrWYLQKPGQSPQ

LLIYkvsnrfsGVPDRFSGSGSGTDFTLKISRVEAEDVGVYYCsqsthvp ytFGGGTKVEIK (SEQ ID NO: 178)
*x*g (15 variants)

(SEQ ID NO: 179)
n*z* (15 variants)

huAb3 VH1b (SEQ ID NO: 127)
EVQLVQSGAEVKKPGSSVKVSCKASgytfssywmhWVRQAPGQGLEW<u>I</u>G1 ihp*ds*gstnynemfknR<u>ATL</u>T<u>VDR</u>STSTAYMELSSLRSEDTAVYYCAGgg rlyfdyWGQGTTVTVSS (SEQ ID NO: 180)
(15 variants) *x*s (SEQ ID NO: 181)
(14 variants) d*z* where (for both the VL and VH), x=All amino acids, except: M, C, N, D, or Q.

z=All amino acids, except: M, C, G, S, N, or P.

Proposed framework back mutations are underlined (see Example 12).

TABLE 16

Variable region sequences of huAb3v2 antibody variants

| SEQ ID NO: | Clone Region | Protein | Residues | Amino Acid Sequence |
|---|---|---|---|---|
| 131 | huAb3v2.1 | VH | | EVQLVQSGAEVKKPGSSVKVSCK ASGYTFSSYWMHWVRQAPGQGLE WIGLIHPWSGSTNYNEMFKNRAT LTVDRSTSTAYMELSSLRSEDTA VYYCAGGGRLYFDYWGQGTTVTV SS |
| 10 | huAb3v2.1 | CDR-H1 | Residues 26-35 of SEQ ID NO: 131 | GYTFSSYWMH |
| 132 | huAb3v2.1 | CDR-H2 | Residues 50-66 of SEQ ID NO: 131 | LIHPWSGSTNYNEMFKN |
| 12 | huAb3v2.1 | CDR-H3 | Residues 99-106 of SEQ ID NO: 131 | GGRLYFDY |
| 133 | huAb3v2.1 | VL | | DIVMTQSPLSLPVTPGEPASISC RSSQSLVHSSGDTYLRWYLQKPG QSPQLLIYKVSNRFSGVPDRFSG SGSGTDFTLKISRVEAEDVGVYY CSQSTHVPYTFGGGTKVEIK |
| 134 | huAb3v2.1 | CDR-L1 | Residues 24-39 of SEQ ID NO: 133 | RSSQSLVHSSGDTYLR |
| 7 | huAb3v2.1 | CDR-L2 | Residues 55-61 of SEQ ID NO: 133 | KVSNRFS |
| 15 | huAb3v2.1 | CDR-L3 | Residues 94-102 of SEQ ID NO: 133 | SQSTHVPYT |
| 131 | huAb3v2.2 | VH | | EVQLVQSGAEVKKPGSSVKVSCK ASGYTFSSYWMHWVRQAPGQGLE WIGLIHPWSGSTNYNEMFKNRAT LTVDRSTSTAYMELSSLRSEDTA VYYCAGGGRLYFDYWGQGTTVTV SS |
| 10 | huAb3v2.2 | CDR-H1 | Residues 26-35 of SEQ ID NO: 131 | GYTFSSYWMH |
| 132 | huAb3v2.2 | CDR-H2 | Residues 50-66 of SEQ ID NO: 131 | LIHPWSGSTNYNEMFKN |
| 12 | huAb3v2.2 | CDR-H3 | Residues 99-106 of SEQ ID NO: 131 | GGRLYFDY |
| 135 | huAb3v2.2 | VL | | DIVMTQSPLSLPVTPGEPASISC RSSQSLVHSNRDTYLRWYLQKPG QSPQLLIYKVSNRFSGVPDRFSG SGSGTDFTLKISRVEAEDVGVYY CSQSTHVPYTFGGGTKVEIK |
| 136 | huAb3v2.2 | CDR-L1 | Residues 24-39 of SEQ ID NO: 135 | RSSQSLVHSNRDTYLR |
| 7 | huAb3v2.2 | CDR-L2 | Residues 55-61 of SEQ ID NO: 135 | KVSNRFS |
| 15 | huAb3v2.2 | CDR-L3 | Residues 94-102 of SEQ ID NO: 135 | SQSTHVPYT |
| 131 | huAb3v2.3 | VH | | EVQLVQSGAEVKKPGSSVKVSCK ASGYTFSSYWMHWVRQAPGQGLE WIGLIHPWSGSTNYNEMFKNRAT LTVDRSTSTAYMELSSLRSEDTA VYYCAGGGRLYFDYWGQGTTVTV SS |
| 10 | huAb3v2.3 | CDR-H1 | Residues 26-35 of SEQ ID NO: 131 | GYTFSSYWMH |
| 132 | huAb3v2.3 | CDR-H2 | Residues 50-66 of SEQ ID NO: 131 | LIHPWSGSTNYNEMFKN |

TABLE 16-continued

Variable region sequences of huAb3v2 antibody variants

| SEQ ID NO: | Clone Region | Protein | Residues | Amino Acid Sequence |
|---|---|---|---|---|
| 12 | huAb3v2.3 | CDR-H3 | Residues 99-106 of SEQ ID NO: 131 | GGRLYFDY |
| 137 | huAb3v2.3 | VL | | DIVMTQSPLSLPVTPGEPASISCRSSQSLVHSNQDTYLRWYLQKPGQSPQLLIYKVSNRFSGVPDRFSGSGSGTDFTLKISRVEAEDVGVYYCSQSTHVPYTFGGGTKVEIK |
| 138 | huAb3v2.3 | CDR-L1 | Residues 24-39 of SEQ ID NO: 137 | RSSQSLVHSNQDTYLR |
| 7 | huAb3v2.3 | CDR-L2 | Residues 55-61 of SEQ ID NO: 137 | KVSNRFS |
| 15 | huAb3v2.3 | CDR-L3 | Residues 94-102 of SEQ ID NO: 137 | SQSTHVPYT |
| 139 | huAb3v2.4 | VH | | EVQLVQSGAEVKKPGSSVKVSCKASGYTFSSYWMHWVRQAPGQGLEWIGLIHPESGSTNYNEMFKNRATLTVDRSTSTAYMELSSLRSEDTAVYYCAGGGRLYFDYWGQGTTVTVSS |
| 10 | huAb3v2.4 | CDR-H1 | Residues 26-35 of SEQ ID NO: 139 | GYTFSSYWMH |
| 140 | huAb3v2.4 | CDR-H2 | Residues 50-66 of SEQ ID NO: 139 | LIHPESGSTNYNEMFKN |
| 12 | huAb3v2.4 | CDR-H3 | Residues 99-106 of SEQ ID NO: 139 | GGRLYFDY |
| 133 | huAb3v2.4 | VL | | DIVMTQSPLSLPVTPGEPASISCRSSQSLVHSSGDTYLRWYLQKPGQSPQLLIYKVSNRFSGVPDRFSGSGSGTDFTLKISRVEAEDVGVYYCSQSTHVPYTFGGGTKVEIK |
| 134 | huAb3v2.4 | CDR-L1 | Residues 24-39 of SEQ ID NO: 133 | RSSQSLVHSSGDTYLR |
| 7 | huAb3v2.4 | CDR-L2 | Residues 55-61 of SEQ ID NO: 133 | KVSNRFS |
| 15 | huAb3v2.4 | CDR-L3 | Residues 94-102 of SEQ ID NO: 133 | SQSTHVPYT |
| 139 | huAb3v2.5 | VH | | EVQLVQSGAEVKKPGSSVKVSCKASGYTFSSYWMHWVRQAPGQGLEWIGLIHPESGSTNYNEMFKNRATLTVDRSTSTAYMELSSLRSEDTAVYYCAGGGRLYFDYWGQGTTVTVSS |
| 10 | huAb3v2.5 | CDR-H1 | Residues 26-35 of SEQ ID NO: 139 | GYTFSSYWMH |
| 140 | huAb3v2.5 | CDR-H2 | Residues 50-66 of SEQ ID NO: 139 | LIHPESGSTNYNEMFKN |
| 12 | huAb3v2.5 | CDR-H3 | Residues 99-106 of SEQ ID NO: 139 | GGRLYFDY |
| 135 | huAb3v2.5 | VL | | DIVMTQSPLSLPVTPGEPASISCRSSQSLVHSNRDTYLRWYLQKPGQSPQLLIYKVSNRFSGVPDRFSGSGSGTDFTLKISRVEAEDVGVYYCSQSTHVPYTFGGGTKVEIK |
| 136 | huAb3v2.5 | CDR-L1 | Residues 24-39 of SEQ ID NO: 135 | RSSQSLVHSNRDTYLR |

TABLE 16-continued

Variable region sequences of huAb3v2 antibody variants

| SEQ ID NO: | Clone Region | Protein | Residues | Amino Acid Sequence |
|---|---|---|---|---|
| 7 | huAb3v2.5 | CDR-L2 | Residues 55-61 of SEQ ID NO: 135 | KVSNRFS |
| 15 | huAb3v2.5 | CDR-L3 | Residues 94-102 of SEQ ID NO: 135 | SQSTHVPYT |
| 139 | huAb3v2.6 | VH | | EVQLVQSGAEVKKPGSSVKVSCK ASGGYTFSSYWMHWVRQAPGQGLE WIGLIHPESGSTNYNEMFKNRAT LTVDRSTSTAYMELSSLRSEDTA VYYCAGGGRLYFDYWGQGTTVTV SS |
| 10 | huAb3v2.6 | CDR-H1 | Residues 26-35 of SEQ ID NO: 139 | GYTFSSYWMH |
| 140 | huAb3v2.6 | CDR-H2 | Residues 50-66 of SEQ ID NO: 139 | LIHPESGSTNYNEMFKN |
| 12 | huAb3v2.6 | CDR-H3 | Residues 99-106 of SEQ ID NO: 139 | GGRLYFDY |
| 137 | huAb3v2.6 | VL | | DIVMTQSPLSLPVTPGEPASISC RSSQSLVHSNQDTYLRWYLQKPG QSPQLLIYKVSNRFSGVPDRFSG SGSGTDFTLKISRVEAEDVGVYY CSQSTHVPYTFGGGTKVEIK |
| 138 | huAb3v2.6 | CDR-L1 | Residues 24-39 of SEQ ID NO: 137 | RSSQSLVHSNQDTYLR |
| 7 | huAb3v2.6 | CDR-L2 | Residues 55-61 of SEQ ID NO: 137 | KVSNRFS |
| 15 | huAb3v2.6 | CDR-L3 | Residues 94-102 of SEQ ID NO: 137 | SQSTHVPYT |
| 141 | huAb3v2.7 | | | EVQLVQSGAEVKKPGSSVKVSCK ASGGYTFSSYWMHWVRQAPGQGLE WIGLIHPISGSTNYNEMFKNRAT LTVDRSTSTAYMELSSLRSEDTA VYYCAGGGRLYFDYWGQGTTVTV SS |
| 10 | huAb3v2.7 | CDR-H1 | Residues 26-35 of SEQ ID NO: 141 | GYTFSSYWMH |
| 142 | huAb3v2.7 | CDR-H2 | Residues 50-66 of SEQ ID NO: 141 | LIHPISGSTNYNEMFKN |
| 12 | huAb3v2.7 | CDR-H3 | Residues 99-106 of SEQ ID NO: 141 | GGRLYFDY |
| 133 | huAb3v2.7 | | | DIVMTQSPLSLPVTPGEPASISC RSSQSLVHSSGDTYLRWYLQKPG QSPQLLIYKVSNRFSGVPDRFSG SGSGTDFTLKISRVEAEDVGVYY CSQSTHVPYTFGGGTKVEIK |
| 134 | huAb3v2.7 | CDR-L1 | Residues 24-39 of SEQ ID NO: 133 | RSSQSLVHSSGDTYLR |
| 7 | huAb3v2.7 | CDR-L2 | Residues 55-61 of SEQ ID NO: 133 | KVSNRFS |
| 15 | huAb3v2.7 | CDR-L3 | Residues 94-102 of SEQ ID NO: 133 | SQSTHVPYT |

TABLE 16-continued

Variable region sequences of huAb3v2 antibody variants

| SEQ ID NO: | Clone Region | Protein | Residues | Amino Acid Sequence |
|---|---|---|---|---|
| 141 | huAb3v2.8 | VH | | EVQLVQSGAEVKKPGSSVKVSCK ASGYTFSSYWMHWVRQAPGQGLE WIGLIHPISGSTNYNEMFKNRAT LTVDRSTSTAYMELSSLRSEDTA VYYCAGGGRLYFDYWGQGTTVTV SS |
| 10 | huAb3v2.8 | CDR-H1 | Residues 26-35 of SEQ ID NO: 141 | GYTFSSYWMH |
| 142 | huAb3v2.8 | CDR-H2 | Residues 50-66 of SEQ ID NO: 141 | LIHPISGSTNYNEMFKN |
| 12 | huAb3v2.8 | CDR-H3 | Residues 99-106 of SEQ ID NO: 141 | GGRLYFDY |
| 135 | huAb3v2.8 | VL | | DIVMTQSPLSLPVTPGEPASISC RSSQSLVHSNRDTYLRWYLQKPG QSPQLLIYKVSNRFSGVPDRFSG SGSGTDFTLKISRVEAEDVGVYY CSQSTHVPYTFGGGTKVEIK |
| 136 | huAb3v2.8 | CDR-L1 | Residues 24-39 of SEQ ID NO: 135 | RSSQSLVHSNRDTYLR |
| 7 | huAb3v2.8 | CDR-L2 | Residues 55-61 of SEQ ID NO: 135 | KVSNRFS |
| 15 | huAb3v2.8 | CDR-L3 | Residues 94-102 of SEQ ID NO: 135 | SQSTHVPYT |
| 141 | huAb3v2.9 | VH | | EVQLVQSGAEVKKPGSSVKVSCK ASGYTFSSYWMHWVRQAPGQGLE WIGLIHPISGSTNYNEMFKNRAT LTVDRSTSTAYMELSSLRSEDTA VYYCAGGGRLYFDYWGQGTTVTV SS |
| 10 | huAb3v2.9 | CDR-H1 | Residues 26-35 of SEQ ID NO: 141 | GYTFSSYWMH |
| 142 | huAb3v2.9 | CDR-H2 | Residues 50-66 of SEQ ID NO: 141 | LIHPISGSTNYNEMFKN |
| 12 | huAb3v2.9 | CDR-H3 | Residues 99-106 of SEQ ID NO: 141 | GGRLYFDY |
| 137 | huAb3v2.9 | VL | | DIVMTQSPLSLPVTPGEPASISC RSSQSLVHSNQDTYLRWYLQKPG QSPQLLIYKVSNRFSGVPDRFSG SGSGTDFTLKISRVEAEDVGVYY CSQSTHVPYTFGGGTKVEIK |
| 138 | huAb3v2.9 | CDR-L1 | Residues 24-39 of SEQ ID NO: 137 | RSSQSLVHSNQDTYLR |
| 7 | huAb3v2.9 | CDR-L2 | Residues 55-61 of SEQ ID NO: 137 | KVSNRFS |
| 15 | huAb3v2.9 | CDR-L3 | Residues 94-102 of SEQ ID NO: 137 | SQSTHVPYT |

Example 16: In vitro characterization of huAb3v2 Variants

Removal of potential deamidation and/or isomerization sites (described in Example 15) generated only 6 variants that retained binding to both human and cyno B7-H3 exogenously expressed on mouse 3T12 fibroblasts as assessed by FACS (as described in the methods of Example 6).

These new anti-B7-H3 antibodies were further characterized for binding by SPR and conjugated to the Bcl-xLi synthon CZ and assessed for cell cytotoxicity (using the methods described in Example 7). Table 17 provides in vitro characteristics of six huAb3v2 humanized variants.

surprising given the structural differences between serine and tryptophan as well as the significant role the CDR3 plays in antigen binding.

Humanized antibodies were generated based on the variable heavy (VH) and variable light (VL) CDR sequences of chAb13, including the "NW" light chain CDR3. Specifically, human germline sequences were selected for constructing CDR-grafted, humanized chAb13 antibodies, where the CDR domains of the VH and VL chains were grafted onto different human heavy and light chain acceptor sequences. Based on the alignments with the VH and VL sequences of monoclonal antibody chAb13, the following human sequences were selected as acceptors:

TABLE 17

In vitro characterization of humanized huAb3v2 variants, including naked antibodies and ADCs

| ADC | Sequence number | Conjugation Method | DAR by MS | % agg by SEC | ELISA hB7-H3 EC$_{50}$ nM | FACS (EC$_{50}$ nM) hB7-H3 | FACS (EC$_{50}$ nM) cyB7-H3 | Affinity of naked mAbs (Biacore, K$_D$) | Cytotoxicity (H847 Cell line IC$_{50}$) (nM) |
|---|---|---|---|---|---|---|---|---|---|
| huAb3v2-CZ | 127, 128 | A | 3.5 | | 0.44 | 5.11 | 2.87 | 2.30E−09 | 1.49 |
| huAb3v2.2-CZ | 131, 135 | A | 0.7 | 1.8 | 0.10 | 5.29 | 3.68 | Poor fit | 26.7 |
| huAb3v2.3-CZ | 131, 137 | A | 1.1 | 1.5 | 0.11 | 6.50 | 4.03 | Poor fit | — |
| huAb3v2.5-CZ | 139, 135 | A | 3.4 | 15.6 | 0.13 | 5.14 | 4.86 | 5.30E−09 | 1.57 |
| huAb3v2.6-CZ | 139, 137 | A | 3.3 | 15 | 0.09 | 5.64 | 3.31 | 5.80E−08 | 1.70 |
| huAb3v2.8-CZ | 141, 135 | A | 2.0 | 5.7 | 0.14 | 3.94 | 3.01 | Poor fit | 2.36 |
| huAb3v2.9-CZ | 141, 137 | A | 2.7 | 4.3 | 0.16 | 6.16 | 4.64 | Poor fit | 2.30 |

As described in Table 17, the results showed that all six huAb3v2 variants had similar binding properties to cells expressing human or cynoB7-H3 as compared to the parental huAb3v2. Of the six huAb3v2 variants, four antibodies (huAb3v2.5, huAb3v2.6, huAb3v2.8, huAb3v2.9) showed potent cytotoxicity in H847 cells when conjugated to exemplary Bcl-xLi synthon CZ.

Example 17: Humanization of Anti-B7-H3 Antibody chAb13

The anti-B7-H3 chimeric antibody chAb13 was selected for humanization based on its binding characteristics and favorable properties as an ADC (conjugated to a Bcl-xL inhibitor).

Prior to humanization, chAb13 was modified in order to minimize potential deamidation in the light chain CDR3 (QQYNSYPFT (SEQ ID NO:182); potential deamidation site is indicated as residues "NS" (italicized)). Point mutations in the amino acid position corresponding to "N" and/or "S" within the light chain CDR3 of chAb13 were introduced, resulting in 30 variants. Antibodies containing these CDR3 light chain variants were then screened for their ability to retain the binding characteristics of chAb13. Variants comprising a CDR3 having a tryptophan (W) point mutation instead of the serine "S" in the "NS" motif (i.e., QQYNWYPFT (SEQ ID NO: 39)) retained the binding features of the parent chAb13 antibody. The substitution of the S residue with a W residue within the CDR3 was IGHV4-b*01(0-1) and IGHJ6*01 for constructing heavy chain acceptor sequences IGKV1-39*01 and IGKJ2*01 for constructing light chain acceptor sequences IGHV4-b_IGHJ6
(SEQ ID NO: 176)
QVQLQESGPGLVKPSETLSLTCAVSgysissgyywgWIRQPPGKGLEWIG siyhsgstyynpslksRVTISVDTSKNQFSLKLSSVTAADTAVYYCARxx xxxxxWGQGTTVTVSS;

where xxxxxxx represents the CDR-H3 region.

IGKV1-39_IGKJ2
(SEQ ID NO: 177)
DIQMTQSPSSLSASVGDRVTITCrasqsissylnWYQQKPGKAPKLLIYa asslqsGVPSRFSGSGSGTDFTLTISSLQPEDFATYYCxxxxxxxxxFGQ

GTKLEIK;

where xxxxxxxxx represents the CDR-L3 region.

By grafting the "NW" light chain CDR3 and the remaining five corresponding VH and VL CDRs of chAb13 into said acceptor sequences, CDR-grafted, humanized, and modified VH and VL sequences were prepared. To generate humanized antibodies with potential framework back-mutations, mutations were identified and introduced into the CDR-grafted antibody sequences by de novo synthesis of the variable domain, or mutagenic oligonucleotide primers and polymerase chain reactions, or both by methods well known in the art. Different combinations of back mutations and other mutations were constructed for each of the CDR-grafts as follows. Residue numbers for these mutations are based on the Kabat numbering system.

The following humanized variable regions of the murine monoclonal chAb13 antibodies were cloned into IgG expression vectors for functional characterization:

Humanized Ab13 VH.1 (huAb13VH.1) is a CDR-grafted, humanized Ab13 VH containing IGHV4-b*01(0-1) and IGHJ6*01 framework sequences. It also contains a Q1E change to prevent pyroglutamate formation.

Humanized Ab13 VH.1 (huAb13 VH.1a) is a humanized design based on huAb13VH.1 and contains 9 proposed framework back-mutation(s): S25T, P40F, K43N, I48M, V67I, T68S, V71R, S79F, R94G.

Humanized Ab13 VH.1b (huAb13VH.1b) is an intermediate design between on huAb13VH.1 and huAb13VH.1a and contains 4 proposed framework back-mutation(s): K43N, I48M, V67I, V71R.

Humanized Ab13 VL.1 (huAb13VL.1) is a CDR-grafted, humanized Ab13 VL containing IGKV1-39*01 and IGHJ6*01 framework sequences.

Humanized Ab13 VL.1a (huAb13VL.1a) is a humanized design based on huAb13VL.1 and contains 4 proposed framework back-mutation(s): A43S, L46A, T85E, Y87F.

Humanized Ab13 VL.1b (huAb13VL.1b) is an intermediate design between on huAb13VL.1 and huAb13VL.1a and contains 1 proposed framework back-mutation(s): Y87F.

The variable region and CDR amino acid sequences of the foregoing are described in Table 18 below.

TABLE 18

Amino acid variable region sequences of humanized Ab13

| SEQ ID NO: | Clone | Protein Region | Residues | Amino Acid Sequence |
|---|---|---|---|---|
| 143 | huAb13VL.1 | VL | | DIQMTQSPSSLSASVGDRVTIT CKASQNVGFNVAWYQQKPGKAP KLLIYSASYRYSGVPSRFSGSG SGTDFTLTISSLQPEDFATYYC QQYNWYPFTFGQGTKLEIK |
| 37 | huAb13VL.1 | CDR-L1 | Residues 24-34 of SEQ ID NO: 143 | KASQNVGFNVA |
| 38 | huAb13VL.1 | CDR-L2 | Residues 50-56 of SEQ ID NO: 143 | SASYRYS |
| 39 | huAb13VL.1 | CDR-L3 | Residues 89-97 of SEQ ID NO: 143 | QQYNWYPFT |
| 144 | huAb13VL.1a | VL | | DIQMTQSPSSLSASVGDRVTIT CKASQNVGFNVAWYQQKPGKSP KALIYSASYRYSGVPSRFSGSG SGTDFTLTISSLQPEDFAEYFC QQYNWYPFTFGQGTKLEIK |
| 37 | huAb13VL.1a | CDR-L1 | Residues 24-34 of SEQ ID NO: 144 | KASQNVGFNVA |
| 38 | huAb13VL.1a | CDR-L2 | Residues 50-56 of SEQ ID NO: 144 | SASYRYS |
| 39 | huAb13VL.1a | CDR-L3 | Residues 89-97 of SEQ ID NO: 144 | QQYNWYPFT |
| 146 | huAb13VH.1 | VH | | EVQLQESGPGLVKPSETLSLTC AVSGYSITSGYSWHWIRQPPGK GLEWIGYIHSSGSTNYNPSLKS RVTISVDTSKNQFSLKLSSVTA ADTAVYYCARYDDYFEYWGQGT TVTVSS |
| 33 | huAb13VH.1 | CDR-H1 | Residues 26-36 of SEQ ID NO: 146 | GYSITSGYSWH |
| 34 | huAb13VH.1 | CDR-H2 | Residues 51-66 of SEQ ID NO: 146 | YIHSSGSTNYNPSLKS |
| 35 | huAb13VH.1 | CDR-H3 | Residues 99-105 of SEQ ID NO: 146 | YDDYFEY |
| 145 | huAB13VL.1b | VL | | DIQMTQSPSSLSASVGDRVTIT CKASQNVGFNVAWYQQKPGKAP KLLIYSASYRYSGVPSRFSGSG SGTDFTLTISSLQPEDFATYFC QQYNWYPFTFGQGTKLEIK |

TABLE 18-continued

Amino acid variable region sequences of humanized Ab13

| SEQ ID NO: | Clone | Protein Region | Residues | Amino Acid Sequence |
|---|---|---|---|---|
| 37 | huAb13VL.1b | CDR-L1 | Residues 24-34 of SEQ ID NO: 145 | KASQNVGFNVA |
| 38 | huAb13VL.1b | CDR-L2 | Residues 50-56 of SEQ ID NO: 145 | SASYRYS |
| 39 | huAb13VL.1b | CDR-L3 | Residues 89-97 of SEQ ID NO: 145 | QQYNWYPFT |
| 147 | huAb13VH.1a | VH | | EVQLQESGPGLVKPSETLSLTCAVTGYSITSGYSWHWIRQFPGNGLEWMGYIHSSGSTNYNPSLKSRISISRDTSKNQFFLKLSSVTAADTAVYYCAGYDDYFEYWGQGTTVTVSS |
| 33 | huAb13VH.1a | CDR-H1 | Residues 26-36 of SEQ ID NO: 147 | GYSITSGYSWH |
| 34 | huAb13VH.1a | CDR-H2 | Residues 51-66 of SEQ ID NO: 147 | YIHSSGSTNYNPSLKS |
| 35 | huAb13VH.1a | CDR-H3 | Residues 99-105 of SEQ ID NO: 147 | YDDYFEY |
| 148 | huAb13VH.1b | VH | | EVQLQESGPGLVKPSETLSLTCAVSGYSITSGYSWHWIRQPPGNGLEWMGYIHSSGSTNYNPSLKSRITISRDTSKNQFSLKLSSVTAADTAVYYCARYDDYFEYWGQGTTVTVSS |
| 33 | huAb13VH.1b | CDR-H1 | Residues 26-36 of SEQ ID NO: 148 | GYSITSGYSWH |
| 34 | huAb13VH.1b | CDR-H2 | Residues 51-66 of SEQ ID NO: 148 | YIHSSGSTNYNPSLKS |
| 35 | huAb13VH.1b | CDR-H3 | Residues 99-105 of SEQ ID NO: 148 | YDDYFEY |

Example 18: Generation of huAb13 Variants

The 3 VH and 3 VL region amino acid sequences of humanized Ab13 variants described in Table 18 were paired together to generate 9 huAb13 variants described in Table 19. The full length amino acid sequences of the heavy chain and light chain of the huAb13v1 variant, huAb13v1 are provided in SEQ ID NOs: 168 and 169, respectively.

TABLE 19

Variable region sequences of engineered huAb13 variants

| SEQ ID NO: | Clone | Protein Region | Residues | Amino acid sequence |
|---|---|---|---|---|
| 147 | huAb13v1 | VH | | EVQLQESGPGLVKPSETLSLTCAVTGYSITSGYSWHWIRQFPGNGLEWMGYIHSSGSTNYNPSLKSRISISRDTSKNQFFLKLSSVTAADTAVYYCAGYDDYFEYWGQGTTVIVSS |
| 33 | huAb13v1 | CDR-H1 | Residues 26-36 of SEQ ID NO: 147 | GYSITSGYSWH |
| 34 | huAb13v1 | CDR-H2 | Residues 51-66 of SEQ ID NO: 147 | YIHSSGSTNYNPSLKS |
| 35 | huAb13v1 | CDR-H3 | Residues 99-105 of SEQ ID NO: 147 | YDDYFEY |
| 144 | huAb13v1 | VL | | DIQMTQSPSSLSASVGDRVTITCKASQNVGFNVAWYQQKPGKSPKALI |

TABLE 19-continued

Variable region sequences of engineered huAb13 variants

| SEQ ID NO: | Clone | Protein Region | Residues | Amino acid sequence |
|---|---|---|---|---|
| | | | | YSASYRYSGVPSRFSGSGSGTDFT LTISSLQPEDFAEYFCQQYNWYPF TFGQGTKLEIK |
| 37 | huAb13v1 | CDR-L1 | Residues 24-34 of SEQ ID NO: 144 | KASQNVGFNVA |
| 38 | huAb13v1 | CDR-L2 | Residues 50-56 of SEQ ID NO: 144 | SASYRYS |
| 39 | huAb13v1 | CDR-L3 | Residues 89-97 of SEQ ID NO: 144 | QQYNWYPFT |
| 146 | huAb13v2 | VH | | EVQLQESGPGLVKPSETLSLTCAV SGYSITSGYSWHWIRQPPGKGLEW IGYIHSSGSTNYNPSLKSRVTISV DTSKNQFSLKLSSVTAADTAVYYC ARYDDYFEYWGQGTTVIVSS |
| 33 | huAb13v2 | CDR-H1 | Residues 26-36 of SEQ ID NO: 146 | GYSITSGYSWH |
| 34 | huAb13v2 | CDR-H2 | Residues 51-66 of SEQ ID NO: 146 | YIHSSGSTNYNPSLKS |
| 35 | huAb13v2 | CDR-H3 | Residues 99-105 of SEQ ID NO: 146 | YDDYFEY |
| 143 | huAb13v2 | VL | | DIQMTQSPSSLSASVGDRVTITCK ASQNVGFNVAWYQQKPGKAPKLLI YSASYRYSGVPSRFSGSGSGTDFT LTISSLQPEDFATYYCQQYNWYPF TFGQGTKLEIK |
| 37 | huAb13v2 | CDR-L1 | Residues 24-34 of SEQ ID NO: 143 | KASQNVGFNVA |
| 38 | huAb13v2 | CDR-L2 | Residues 50-56 of SEQ ID NO: 143 | SASYRYS |
| 39 | huAb13v2 | CDR-L3 | Residues 89-97 of SEQ ID NO: 143 | QQYNWYPFT |
| 146 | huAb13v3 | VH | | EVQLQESGPGLVKPSETLSLTCAV SGYSITSGYSWHWIRQPPGKGLEW IGYIHSSGSTNYNPSLKSRVTISV DTSKNQFSLKLSSVTAADTAVYYC ARYDDYFEYWGQGTTVIVSS |
| 33 | huAb13v3 | CDR-H1 | Residues 26-36 of SEQ ID NO: 146 | GYSITSGYSWH |
| 34 | huAb13v3 | CDR-H2 | Residues 51-66 of SEQ ID NO: 146 | YIHSSGSTNYNPSLKS |
| 35 | huAb13v3 | CDR-H3 | Residues 99-105 of SEQ ID NO: 146 | YDDYFEY |
| 144 | huAb13v3 | VL | | DIQMTQSPSSLSASVGDRVTITCK ASQNVGFNVAWYQQKPGKSPKALI YSASYRYSGVPSRFSGSGSGTDFT LTISSLQPEDFAEYFCQQYNWYPF TFGQGTKLEIK |
| 37 | huAb13v3 | CDR-L1 | Residues 24-34 of SEQ ID NO: 144 | KASQNVGFNVA |
| 38 | huAb13v3 | CDR-L2 | Residues 50-56 of SEQ ID NO: 144 | SASYRYS |

TABLE 19-continued

Variable region sequences of engineered huAb13 variants

| SEQ ID NO: | Clone | Protein Region | Residues | Amino acid sequence |
|---|---|---|---|---|
| 39 | huAb13v3 | CDR-L3 | Residues 89-97 of SEQ ID NO: 144 | QQYNWYPFT |
| 146 | huAb13v4 | VH | | EVQLQESGPGLVKPSETLSLTCAVSGYSITSGYSWHWIRQPPGKGLEWIGYIHSSGSTNYNPSLKSRVTISVDTSKNQFSLKLSSVTAADTAVYYCARYDDYFEYWGQGTTVIVSS |
| 33 | huAb13v4 | CDR-H1 | Residues 26-36 of SEQ ID NO: 146 | GYSITSGYSWH |
| 34 | huAb13v4 | CDR-H2 | Residues 51-66 of SEQ ID NO: 146 | YIHSSGSTNYNPSLKS |
| 35 | huAb13v4 | CDR-H3 | Residues 99-105 of SEQ ID NO: 146 | YDDYFEY |
| 145 | huAb13v4 | VL | | DIQMTQSPSSLSASVGDRVTITCKASQNVGFNVAWYQQKPGKAPKLLIYSASYRYSGVPSRFSGSGSGTDFTLTISSLQPEDFATYFCQQYNWYPFTFGQGTKLEIK |
| 37 | huAb13v4 | CDR-L1 | Residues 24-34 of SEQ ID NO: 145 | KASQNVGFNVA |
| 38 | huAb13v4 | CDR-L2 | Residues 50-56 of SEQ ID NO: 145 | SASYRYS |
| 39 | huAb13v4 | CDR-L3 | Residues 89-97 of SEQ ID NO: 145 | QQYNWYPFT |
| 147 | huAb13v5 | VH | | EVQLQESGPGLVKPSETLSLTCAVTGYSITSGYSWHWIRQFPGNGLEWMGYIHSSGSTNYNPSLKSRISISRDTSKNQFFLKLSSVTAADTAVYYCAGYDDYFEYWGQGTTVIVSS |
| 33 | huAb13v5 | CDR-H1 | Residues 26-36 of SEQ ID NO: 147 | GYSITSGYSWH |
| 34 | huAb13v5 | CDR-H2 | Residues 51-66 of SEQ ID NO: 147 | YIHSSGSTNYNPSLKS |
| 35 | huAb13v5 | CDR-H3 | Residues 99-105 of SEQ ID NO: 147 | YDDYFEY |
| 143 | huAb13v5 | VL | | DIQMTQSPSSLSASVGDRVTITCKASQNVGFNVAWYQQKPGKAPKLLIYSASYRYSGVPSRFSGSGSGTDFTLTISSLQPEDFATYYCQQYNWYPFTFGQGTKLEIK |
| 37 | huAb13v5 | CDR-L1 | Residues 24-34 of SEQ ID NO: 143 | KASQNVGFNVA |
| 38 | huAb13v5 | CDR-L2 | Residues 50-56 of SEQ ID NO: 143 | SASYRYS |
| 39 | huAb13v5 | CDR-L3 | Residues 89-97 of SEQ ID NO: 143 | QQYNWYPFT |
| 147 | huAb13v6 | VH | | EVQLQESGPGLVKPSETLSLTCAVTGYSITSGYSWHWIRQFPGNGLEWMGYIHSSGSTNYNPSLKSRISISRDTSKNQFFLKLSSVTAADTAVYYCAGYDDYFEYWGQGTTVIVSS |
| 33 | huAb13v6 | CDR-H1 | Residues 26-36 of SEQ ID NO: 147 | GYSITSGYSWH |
| 34 | huAb13v6 | CDR-H2 | Residues 51-66 of SEQ ID NO: 147 | YIHSSGSTNYNPSLKS |

TABLE 19-continued

Variable region sequences of engineered huAb13 variants

| SEQ ID NO: | Clone | Protein Region | Residues | Amino acid sequence |
|---|---|---|---|---|
| 35 | huAb13v6 | CDR-H3 | Residues 99-105 of SEQ ID NO: 147 | YDDYFEY |
| 145 | huAb13v6 | VL | | DIQMTQSPSSLSASVGDRVTITCKASQNVGFNVAWYQQKPGKAPKLLIYSASYRYSGVPSRFSGSGSGTDFTLTISSLQPEDFATYFCQQYNWYPFTFGQGTKLEIK |
| 37 | huAb13v6 | CDR-L1 | Residues 24-34 of SEQ ID NO: 145 | KASQNVGFNVA |
| 38 | huAb13v6 | CDR-L2 | Residues 50-56 of SEQ ID NO: 145 | SASYRYS |
| 39 | huAb13v6 | CDR-L3 | Residues 89-97 of SEQ ID NO: 145 | QQYNWYPFT |
| 148 | huAb13v7 | VH | | EVQLQESGPGLVKPSETLSLTCAVSGYSITSGYSWHWIRQPPGNGLEWMGYIHSSGSTNYNPSLKSRITISRDTSKNQFSLKLSSVTAADTAVYYCARYDDYFEYWGQGTTVIVSS |
| 33 | huAb13v7 | CDR-H1 | Residues 26-36 of SEQ ID NO: 148 | GYSITSGYSWH |
| 34 | huAb13v7 | CDR-H2 | Residues 51-66 of SEQ ID NO: 148 | YIHSSGSTNYNPSLKS |
| 35 | huAb13v7 | CDR-H3 | Residues 99-105 of SEQ ID NO: 148 | YDDYFEY |
| 143 | huAb13v7 | VL | | DIQMTQSPSSLSASVGDRVTITCKASQNVGFNVAWYQQKPGKAPKLLIYSASYRYSGVPSRFSGSGSGTDFTLTISSLQPEDFATYYCQQYNWYPFTFGQGTKLEIK |
| 37 | huAb13v7 | CDR-L1 | Residues 24-34 of SEQ ID NO: 143 | KASQNVGFNVA |
| 38 | huAb13v7 | CDR-L2 | Residues 50-56 of SEQ ID NO: 143 | SASYRYS |
| 39 | huAb13v7 | CDR-L3 | Residues 89-97 of SEQ ID NO: 143 | QQYNWYPFT |
| 148 | huAb13v8 | VH | | EVQLQESGPGLVKPSETLSLTCAVSGYSITSGYSWHWIRQPPGNGLEWMGYIHSSGSTNYNPSLKSRITISRDTSKNQFSLKLSSVTAADTAVYYCARYDDYFEYWGQGTTVTVSS |
| 33 | huAb13v8 | CDR-H1 | Residues 26-36 of SEQ ID NO: 148 | GYSITSGYSWH |
| 34 | huAb13v8 | CDR-H2 | Residues 51-66 of SEQ ID NO: 148 | YIHSSGSTNYNPSLKS |
| 35 | huAb13v8 | CDR-H3 | Residues 99-105 of SEQ ID NO: 148 | YDDYFEY |
| 144 | huAb13v8 | VL | | DIQMTQSPSSLSASVGDRVTITCKASQNVGFNVAWYQQKPGKSPKALIYSASYRYSGVPSRFSGSGSGTDFTLTISSLQPEDFAEYFCQQYNWYPFTFGQGTKLEIK |
| 37 | huAb13v8 | CDR-L1 | Residues 24-34 of SEQ ID NO: 144 | KASQNVGFNVA |
| 38 | huAb13v8 | CDR-L2 | Residues 50-56 of SEQ ID NO: 144 | SASYRYS |

TABLE 19-continued

Variable region sequences of engineered huAb13 variants

| SEQ ID NO: | Clone | Protein Region | Residues | Amino acid sequence |
|---|---|---|---|---|
| 39 | huAb13v8 | CDR-L3 | Residues 89-97 of SEQ ID NO: 144 | QQYNWYPFT |
| 148 | huAb13v9 | VH | | EVQLQESGPGLVKPSETLSLTCAV SGYSITSGYSWHWIRQPPGNGLEW MGYIHSSGSTNYNPSLKSRITISR DTSKNQFSLKLSSVTAADTAVYYC ARYDDYFEYWGQGTTVTVSS |
| 33 | huAb13v9 | CDR-H1 | Residues 26-36 of SEQ ID NO: 148 | GYSITSGYSWH |
| 34 | huAb13v9 | CDR-H2 | Residues 51-66 of SEQ ID NO: 148 | YIHSSGSTNYNPSLKS |
| 35 | huAb13v9 | CDR-H3 | Residues 99-105 of SEQ ID NO: 148 | YDDYFEY |
| 145 | huAb13v9 | VL | | DIQMTQSPSSLSASVGDRVTITCK ASQNVGFNVAWYQQKPGKAPKLLI YSASYRYSGVPSRFSGSGSGTDFT LTISSLQPEDFATYFCQQYNWYPF TFGQGTKLEIK |
| 37 | huAb13v9 | CDR-L1 | Residues 24-34 of SEQ ID NO: 145 | KASQNVGFNVA |
| 38 | huAb13v9 | CDR-L2 | Residues 50-56 of SEQ ID NO: 145 | SASYRYS |
| 39 | huAb13v9 | CDR-L3 | Residues 89-97 of SEQ ID NO: 145 | QQYNWYPFT |

Example 19: Characterization of huAb13 VL.1a Humanized Variants

Nine huAb13 variants described in Examples 17 and 18 were generated and tested for binding to B7-H3 by FACS (according to methods described in Example 6). Six variants did not bind to human B7-H3. The remaining three variants were further characterized for binding by SPR and conjugated (via Method A) to the Bcl-xL inhibitor (specifically the linker warhead (or synthon) CZ) and assessed for cell cytotoxicity (according to methods described in Example 7). Table 20 provides the in vitro characteristics of these variants.

HuAb13v1 was selected for further study due in part to its potent and superior cytotoxicity against H847 cells and similar binding characteristics as chAb13 from which it was derived. In contrast, huAb13v5 and huAb13v6 showed poor fit kinetics in Biacore experiments suggesting their binding properties are more divergent from the parental chAb13 than huAb13v1 and have reduced activity in the cell killing assay.

Example 20: In Vitro Potency of Selected Humanized B7-H3 Antibodies with Exemplary Bcl-xL Inhibitor Linker Warheads (Synthons)

Humanized antibodies huAb13v1, huAb3v2.5 and huAb3v2.6 were selected to be conjugated with several

TABLE 20

In vitro characterization of huAb13 VL.1a variants conjugated to synthon (or linker payload) CZ

| Variant name | Sequence Number | DAR by MS | % agg by SEC | ELISA hB7-H3 EC$_{50}$ nM | FACS (EC$_{50}$ nM) hB7-H3 | FACS (EC$_{50}$ nM) cyB7-H3 | Affinity of naked mAbs (Biacore, K$_D$) | Cytotoxicity (H847 Cell line IC$_{50}$) (nM) |
|---|---|---|---|---|---|---|---|---|
| chAb13-CZ | 32, 36 | — | — | 0.26 | 6.27 | 18.35 | 5.7E−09 | — |
| huAb13v1-CZ | 147, 144 | 4.0 | 5.1 | 0.12 | 6.01 | 10.0 | 6.2E−09 | 0.09 |
| huAb13v5-CZ | 147, 143 | 3.4 | 2.4 | 0.19 | 5.21 | 10.59 | Poor fit | 1.60 |
| huAb13v6-CZ | 147, 145 | 3.6 | 7.3 | 0.14 | 5.83 | 12.95 | Poor fit | 0.84 |

Bcl-xL inhibitor payloads (or synthons) at a 3 mg scale using Methods A, E or G, as described in Example 7. The anti-tumor activity of these ADCs was tested in cytotoxicity assays using the NCI-H1650 non-small cell lung cancer cell line as described in Example 7. As control, the in vitro anti-tumor activity of ADCs comprising the non-targeting antibody MSL109 (a monoclonal antibody that binds to the CMV glycoprotein H conjugated to Bcl-xL inhibitor payloads (or synthons) was also evaluated. The results are described in Table 21.

TABLE 21

In vitro tumor cell cytotoxicity of selected humanized B7-H3 ADCs with exemplary Bcl-xL inhibitor linker warheads (synthons)

| ADC | Conjugation Method | DAR by MS | % agg by SEC | ADC conc (mg/ml) | $EC_{50}$ nM H1650 |
|---|---|---|---|---|---|
| huAb13v1-CZ | G | 4 | 3.9 | 3 | 0.18 |
| huAb13v1-TX | G | 3.6 | 2.8 | 2.6 | 0.22 |
| huAb13v1-TV | G | 2.4 | 3 | 3.9 | 0.43 |
| huAb13v1-AAA | G | 2 | 20.2 | 2.7 | 0.37 |
| huAb13v1-AAD | G | 3.7 | 3.3 | 2.7 | 0.21 |
| huAb13v1-WD | E | 3 | 5.4 | 5.8 | 0.45 |
| huAb13v1-LB | A | 2.2 | 21.9 | 3.7 | >133 |
| huAb13v1-ZT | G | 2.4 | 10.6 | 1.7 | 0.3 |
| huAb13v1-ZZ | G | 1.4 | 20.3 | 2.5 | 0.42 |
| huAb13v1-XW | G | 4.3 | 6.3 | 2.6 | 0.86 |
| huAb13v1-SE | A | 3.7 | 4 | 5.4 | 0.63 |
| huAb13v1-SR | A | 2.6 | 49.5 | 4.5 | 0.59 |
| huAb13v1-YG | E | 3.3 | 2.1 | 3.8 | 0.33 |
| huAb13v1-KZ | A | 2.8 | 16.8 | 3.5 | 178.8 |
| huAb3v2.5-CZ | G | 3.3 | 15.6 | 3.6 | 0.40 |
| huAb3v2.5-TX | G | 3.3 | 8.9 | 2.9 | 0.62 |
| huAb3v2.5-TV | G | 3.7 | 10.4 | 3.5 | 0.53 |
| huAb3v2.5-YY | G | 2.3 | 16.2 | 3.2 | 0.71 |
| huAb3v2.5-AAA | G | 2 | 14.8 | 3.3 | 0.85 |
| huAb3v2.5-AAD | G | 3.4 | 11.3 | 3.7 | 0.49 |
| huAb3v2.5-WD | E | 2.8 | 11.5 | 5.4 | 0.83 |
| huAb3v2.5-LB | A | 2.2 | 24.4 | 3.9 | 2.59 |
| huAb3v2.5-ZT | G | 1.6 | 70.1 | 3.3 | 0.95 |
| huAb3v2.5-ZZ | G | 1.2 | 19.4 | 3.7 | 1.1 |
| huAb3v2.5-XW | G | 3.9 | 16.4 | 3.4 | 2.18 |
| huAb3v2.5-SE | A | 3.7 | 10.6 | 5.4 | 0.85 |
| huAb3v2.5-SR | A | 1.8 | 48.5 | 5.1 | 0.59 |
| huAb3v2.5-YG | E | 4 | 8.6 | 3.3 | 0.71 |
| huAb3v2.5-KZ | A | 2.6 | 24.5 | 3.4 | 0.87 |
| huAb3v2.6-CZ | G | 3.4 | 15 | 3.6 | 0.40 |
| huAb3v2.6-TX | G | 3.2 | 10.4 | 3.4 | 0.47 |
| huAb3v2.6-TV | G | 3.3 | 10.7 | 3.8 | 0.52 |
| huAb3v2.6-YY | G | 2.2 | 19.9 | 3.4 | 0.72 |
| huAb3v2.6-AAA | G | 1.9 | 20.2 | 3.6 | 1.24 |
| huAb3v2.6-AAD | G | 3.4 | 11.9 | 3.7 | 0.85 |
| huAb3v2.6-WD | E | 3.1 | 12.4 | 5.3 | 0.79 |
| huAb3v2.6-LB | A | 2.4 | 27.2 | 3.9 | 2.07 |
| huAb3v2.6-ZT | G | 1.7 | 21.6 | 3.7 | 1.11 |
| huAb3v2.6-ZZ | G | 1.2 | 70.7 | 3.5 | 1.35 |
| huAb3v2.6-XW | G | 4 | 16.8 | 3.2 | 2.4 |
| huAb3v2.6-SE | A | 3.6 | 11.8 | 5.7 | 1.01 |
| huAb3v2.6-SR | A | 2.5 | 48.2 | 5.2 | 0.71 |
| huAb3v2.6-YG | E | 3.7 | 9.9 | 4.8 | 0.68 |
| huAb3v2.6-KZ | A | 3.5 | 26.1 | 3.6 | 5.52 |
| MSL109-CZ | G | 3.2 | 0.5 | 3.7 | 19.50 |
| MSL109-TX | G | 3.5 | 0.7 | 3 | 20.00 |
| MSL109-TV | G | 3.6 | 0 | 2.6 | 31.13 |
| MSL109-YY | G | 2.9 | 0 | 1.8 | 26.53 |
| MSL109-AAA | G | 1.9 | 13.7 | 3.2 | 23.52 |
| MSL109-AAD | G | 3 | 0.4 | 3.8 | >67 |
| MSL109-WD | E | 2.9 | 0 | 7.06 | 18.22 |
| MSL109-LB | A | 1.8 | 0 | 4.2 | 9.88 |
| MSL109-ZT | G | 2.3 | 7.5 | 2.2 | >67 |
| MSL109-ZZ | G | 1.4 | 15 | 3.5 | >67 |
| MSL109-XW | G | 3.3 | 3.7 | 3.2 | >67 |
| MSL109-SE | A | 3.6 | 33.4 | 6.0 | 29.56 |
| MSL109-SR | A | 1.8 | 2.3 | 3.8 | 53.29 |
| MSL109-YG | E | 3.1 | 13.2 | 4.0 | 19.93 |
| MSL109-KZ | A | 2.5 | 18 | 4.3 | 50.16 |

In contrast to the low anti-tumor activity exhibited by the ADCs comprising the non-targeting antibody MSL109 conjugated to a Bcl-xL inhibitor payload, the B7-H3-targeting ADCs exhibited greater tumor cell killing, which reflects the antigen-dependent delivery of the B7-H3-targeting ADCs to the B7-H3-expressing tumor cells.

The anti-tumor activity of two of these ADCs was tested in cytotoxicity assays using the NCI-H146 small cell lung cancer cell line as described in Example 7. The results are described in Table 22.

TABLE 22

In vitro tumor cell cytotoxicity of selected humanized B7-H3 ADCs with exemplary Bcl-xL inhibitor synthons.

| ADC | Conjugation Method | DAR | % agg by SEC | ADC conc (mg/ml) | $EC_{50}$ nM H146 |
|---|---|---|---|---|---|
| huAb13v1-AAA E2 | I | 2 | 3.3 | 11.6 | 2 |
| huAb13v1-WD E2 | I | 2 | 4.5 | 14.5 | 2 | huAb13v1-AAA E2 and huAb13v1-WD E2 were tested for cytotoxicity using H146 cells. Both conjugates show potent and comparable cytotoxicity.

Example 21: In Vivo Analysis of Anti-B7-H3 ADCs

Humanized anti-B7-H3 antibodies huAb13v1, huAb3v2.5 and huAb3v2.6 were selected to be conjugated with several Bcl-xL inhibitor payloads and were evaluated in xenograft models of small cell lung cancer (H146) as conjugates using a number of Bcl-xL inhibitor warheads (synthons) using the methods described in Example 7 and Example 8. The results are summarized in Table 23 and Table 24.

TABLE 23

In vivo efficacy of humanized anti-B7-H3 ADCs

| ADC | Conjugation Method | DAR | Dose[a]/route/ regimen | Number of mice | TGI$_{max}$ (%) | TGD (%) |
|---|---|---|---|---|---|---|
| AB095 | — | n/a | 6 mg/kg/IP/QDx1 | 8 | 0 | 0 |
| huAb3v2.5-CZ | A | 3.5 | 6 mg/kg/IP/QDx1 | 8 | 92 | 122 |
| huAb3v2.6-CZ | A | 3.4 | 6 mg/kg/IP/QDx1 | 8 | 93 | 130 |
| huAb3v2.9-CZ | A | 2.8 | 6 mg/kg/IP/QDx1 | 8 | 94 | 135 |
| huAb3v2.9-TX | E | 1.7 | 6 mg/kg/IP/QDx1 | 8 | 93 | 109 |
| huAb3v2.6-TX | E | 2.7 | 6 mg/kg/IP/QDx1 | 8 | 92 | 130 |
| huAb3v2.5-TX | E | 2.5 | 6 mg/kg/IP/QDx1 | 8 | 86 | 89 |

[a]dose is given in mg/kg/day

TABLE 24

In vivo efficacy of humanized anti-B7-H3 ADCs

| ADC | Conjugation Method | DAR | Dose[a]/route/ regimen | Number of mice | TGI$_{max}$ (%) |
|---|---|---|---|---|---|
| AB095 | — | n/a | 6 mg/kg/IP/QDx1 | 8 | 0 |
| huAb3v2.5-AAA | E | 2.3 | 6 mg/kg/IP/QDx1 | 8 | 65 |
| huAb3v2.5-XW | E | 3.1 | 6 mg/kg/IP/QDx1 | 8 | 51 |
| huAb3v2.6-AAA | E | 3.5 | 6 mg/kg/IP/QDx1 | 8 | 47 |
| huAb3v2.6-XW | E | 4.0 | 6 mg/kg/IP/QDx1 | 8 | 43 |
| huAb13v1-AAA | E | 3.5 | 6 mg/kg/IP/QDx1 | 8 | 76 |
| huAb13v1-XW | E | 4.2 | 6 mg/kg/IP/QDx1 | 8 | 35 |
| huAb13v1-TX E2 | I | 2 | 6 mg/kg/IP/QDx1 | 8 | 88 |

[a]dose is given in mg/kg/day

Humanized anti-B7-H3 antibody huAb13v1 was conjugated with the Bcl-xL inhibitor synthon WD and evaluated in a xenograft model of the B7-H3-positive small cell lung cancer (H1650) as conjugates using the methods described in Example 7 and Example 8. As control, the in vivo anti-tumor activity of a non-targeting IgG isotype matched antibody (AB095) was also evaluated. The results are summarized in Table 25.

TABLE 25

In vivo efficacy of humanized anti-B7-H3 ADC huAb13v1-WD in H1650

| ADC | DAR/ Conjugation Method | Dose mg/kg/ day | route/ regimen | TGI$_{max}$ (%) | TGD (%) |
|---|---|---|---|---|---|
| AB095[a] | N.A. | 10 | IP/QDx1 | 0 | 0 |
| huAb13v1-WD-E2 | 2/I | 1 | IP/QDx1 | 46* | 47* |
| huAb13v1-WD-E2 | 2/I | 3 | IP/QDx1 | 48* | 47* |
| huAb13v1-WD-E2 | 2/I | 10 | IP/QDx1 | 62* | 77* |

[a]IgG1 mAb
*= p < 0.05 as compared to control treatment (AB095)
¥= p < 0.05 as compared to the most active partner in a drug combination
N.A. = not applicable In contrast to the lack of activity observed using the non-targeting IgG isotype-matched antibody Ab095, the B7-H3-targeting Bcl-xL ADCs exhibited tumor growth inhibition (TGI) and tumor growth delay (TGD), as shown in Tables 24 and 25, reflecting the antigen-dependent delivery of the B7-H3-targeting ADCs which deliver the Bcl-xL inhibitor to the B7-H3-expressing tumor cells in this xenograft mouse model. As an additional control, the in vivo anti-tumor activity of ADCs comprising the non-targeting antibody MSL109 conjugated with Bcl-xL inhibitor synthons was evaluated in the xenograft model of the B7-H3-positive small cell lung cancer (H1650). The activity of these ADCs was compared that of the non-targeting IgG isotype matched antibody, AB095, as control. As shown in Table 26, the ADCs comprising the non-targeting antibody MSL109 conjugated with Bcl-xL inhibitor synthons exhibited very modest tumor growth inhibition and low or no tumor growth delay. In contrast, the B7-H3-targeting Bcl-xL ADCs (as shown in Table 25) exhibited, much greater tumor growth inhibition (TGI) and tumor growth delay (TGD), reflecting the antigen-dependent delivery of these ADCs to B7-H3-expressing cells in this mouse xenograft model.

TABLE 26

In vivo efficacy of non-targeting (MSL109) BCL-xL inhibiting ADCs in NCI-H1650 model of NSCLC

| Treatment | Dose[a]/route/regimen | Growth Inhibition TGI$_{max}$ (%) | TGD (%) |
|---|---|---|---|
| MSL109†-H | 3/IP/Q4Dx6 | 18* | 0 |
| MSL109†-H | 10/IP/Q4Dx6 | 43* | 20* |
| MSL109†-H | 30/IP/Q4Dx6 | 8 | 0 |
| MSL109†-CZ | 3/IP/Q4Dx6 | 29* | 0 |
| MSL109†-CZ | 3/IP/Q7Dx6 | 18* | 0 |
| MSL109†-CZ | 10/IP/Q4Dx6 | 32* | 16 |
| MSL109†-CZ | 30/IP/Q4Dx6 | 32* | 12 |

†Non-targeting antibody
[a]dose is given in mg/kg/day
*= p < 0.05 as compared to control treatment (AB095)
Q4Dx6 indicates one dose every 4 days for a total of 6 doses

Example 22: B7-H3 Combination Therapy

The anti-tumor activity of huAb13v1 as CZ or TX conjugates as purified DAR2 (E2) conjugates were characterized in xenograft models of non-small cell lung cancer (H1650, H1299, H1975, and EBC1) of human origin using the methods described in Example 8. The anti-tumor activity was assessed as monotherapy and in combination with docetaxel (H1650, H1299, H1975, and EBC1). The results are presented in Table 27.

TABLE 27

In vivo efficacy of humanized huAb13v1 anti-B7-H3 conjugates as monotherapy and in combination with docetaxel

| ADC | DAR/Conjugation Method | Dose mg/kg/day | route/regimen | $TGI_{max}$ (%) | TGD (%) |
|---|---|---|---|---|---|
| | | EBC1 | | | |
| AB095 | — | 10 | Q4Dx6/IP | 0 | 0 |
| huAb13v1-TX E2 | 2/I | 10 | Q4Dx6/IP | 58 | 67 |
| Docetaxel | — | 7.5 | QDx1/IV | 85 | 80 |
| huAb13v1-TX E2 + Docetaxel | 2/I | 10 + 7.5 | Q4Dx6/IP + QDx1/IV | 140 | 140 |
| | | NCI-H1299 | | | |
| AB095 | — | 10 | Q4Dx6/IP | 0 | 0 |
| huAb13v1-TX E2 | 2/I | 10 | Q4Dx6/IP | 80 | 24 |
| Docetaxel | — | 7.5 | QDx1/IV | 87 | 48 |
| huAb13v1-TX E2 + Docetaxel | 2/I | 10 + 7.5 | Q4Dx6/IP + QDx1/IV | 97 | 83 |
| | | NCI-H1975 | | | |
| AB095 | — | 10 | Q4Dx6/IP | 0 | 0 |
| huAb13v1-TX E2 | 2/I | 10 | Q4Dx6/IP | 52 | 62 |
| Docetaxel | — | 7.5 | QDx1/IV | 81 | 77 |
| huAb13v1-TX E2 + Docetaxel | 2/I | 10 + 7.5 | Q4Dx6/IP + QDx1/IV | 92 | 108 |
| | | NCI-H1650 | | | |
| AB095 | — | 8 | Q7Dx6/IP | 0 | 0 |
| huAb13v1-CZ | 2/I | 10 | QDx1/IP | 80 | 100 |
| Docetaxel | — | 7.5 | QDx1/IV | 84 | 143 |
| huAb13v1-CZ + Docetaxel | — | 10 + 7.5 | QDx1/IP + QDx1/IV | 99 | >600 |
| AB095[a] | N.A. | 10 | IP/Q14Dx3 | 0 | 0 |
| DTX | N.A. | 7.5 | IV/Q14Dx3 | 80* | 158* |
| huAb13v1-WD E2 | 2/I | 10 | IP/Q14Dx3 | 67* | 83* |
| huAb13v1-WD E2 + DTX) | 2/I + N.A. | 10 + 7.5 | IP/Q14Dx3 + IV/Q14Dx3 | 98*¥ | >717*¥ |
| huAb13v1-WD E2 | 2/. | 3 | IP/Q14Dx3 | 56* | 75* |
| huAb13v1-WD E2 + DTX) | 2/I + N.A. | 3 + 7.5 | IP/Q14Dx3 + IV/Q14Dx3 | 99*¥ | >717*¥ |
| huAb13v1-WD E2 | 2/I | 1 | IP/Q14Dx3 | 60* | 67* |
| huAb13v1-WD E2 + DTX | 2/I + N.A | 1 + 7.5 | IP/Q14Dx3 + IV/Q14Dx3 | 88*¥ | 467*¥ |
| huAb13v1-AAA E2 | 2/I | 10 | IP/Q14Dx3 | 63* | 117* |
| huAb13v1-AAA E2 + DTX | 2/I + N.A | 10 + 7.5 | IP/Q14Dx3 + IV/Q14Dx3 | 99*¥ | >717*¥ |
| huAb13v1-AAA E2 | 2/I | 3 | IP/Q14Dx3 | 60* | 117* |
| huAb13v1-AAA E2 + DTX | 2/I + N.A | 3 + 7.5 | IP/Q14Dx3 + IV/Q14Dx3 | 99*¥ | >717*¥ |
| huAb13v1-AAA E2 | 2/I | 1 | IP/Q14Dx3 | 50* | 67* |
| huAb13v1-AAA E2 + DTX | 2/I + N.A | 1 + 7.5 | IP/Q14Dx3 + IV/Q14Dx3 | 92*¥ | >717*¥ |

[a] IgG1 mAb
* = $p < 0.05$ as compared to control treatment (AB095)
¥ = $p < 0.05$ as compared to the most active partner in a drug combination
N.A. = not applicable The results presented in Table 27 demonstrate that above, huAb13v1 as CZ, TX, WD or AAA purified DAR2 (E2) conjugates inhibited the growth of all four NSCLC xenograft models as monotherapy. In addition, huAb13v1 as CZ, TX, WD or AAA purified DAR2 (E2) conjugates effectively combined with docetaxel to produce more sustained tumor growth inhibition. This is most dramatically illustrated in the H1650 xenograft model where the combination therapy resulted in a TGD of between 467% and >717%, whereas the individual monotherapies resulted in TGD in the range of 67%-158%. These results support the clinical utility of Bcl-xL inhibitor (Bcl-xLi) ADCs to be dosed in combination with chemotherapy.

SEQUENCE SUMMARY

| SEQ ID NO: | Description | Amino Acid Sequence |
|---|---|---|
| 1 | chAb2 VH amino acid sequence | QVQLQQPGAELVKPGASVKLSCKASGYTFTSYWMHWVKQRPGQGLEWIGMIHPDSGTTNYNEKFRSKATLTVDKSSSTAYMQLSSLTSEDSAVYYCAVYYGSTYWYFDVWGTGTTVTVSS |
| 2 | chAb2 VH CDR1 amino acid sequence | GYTFTSYWMH |
| 3 | chAb2 VH CDR2 amino acid sequence | MIHPDSGTTNYNEKFRS |
| 4 | chAb2 VH CDR3 amino acid sequence | YYGSTYWYFDV |
| 5 | chAb2 VL amino acid sequence | DVVMTQTPLSLPVSLGDQAYISCRSSQSLVHINGNTYLHWYRQKPGQSPKLLIYKVSNRFSGVPDRFSGSGSGIDFILKISRVEAEDLGVYFCSQSTHFPFTFGSGTKLEIK |
| 6 | chAb2 VL CDR1 amino acid sequence | RSSQSLVHINGNTYLH |
| 7 | chAb2, chAb3, chAb10, huAb3VL.1, huAb3VL.1a, huAb3VL.1b, huAb3v2.1, huAb3v2.2, huAb3v2.3, huAb3v2.4, huAb3v2.5, huAb3v2.6, huAb3v2.7, huAb3v2.8, and huAb3v2.9 VL CDR2 amino acid sequence | KVSNRFS |
| 8 | chAb2 VL CDR3 amino acid sequence | SQSTHFPFT |
| 9 | chAb3 VH amino acid sequence | QVQLQQPGAELVKPGASVKLSCKASGYTFSSYWMHWVKQRPGQGLEWIGLIHPDSGSTNYNEMFKNKATLTVDRSSSTAYVQLSSLTSEDSAVYFCAGGGRLYFDYWGQGTTLIVSS |
| 10 | chAb3, huAb3VH.1, huAb3VH.1a, huAb3VH.1b, huAb3v2.1, huAb3v2.2, huAb3v2.3, huAb3v2.4, huAb3v2.5, huAb3v2.6, huAb3v2.7, huAb3v2.8, and huAb3v2.9 VH CDR1 amino acid sequence | GYTFSSYWMH |
| 11 | chAb3, huAb3VH.1, huAb3VH.1a, and huAb3VH.1b VH CDR2 amino acid sequence | LIHPDSGSTNYNEMFKN |
| 12 | chAb3, huAb3VH.1, huAb3VH.1a, huAb3VH.1b, huAb3v2.1, huAb3v2.2, huAb3v2.3, huAb3v2.4, huAb3v2.5, huAb3v2.6, huAb3v2.7, huAb3v2.8, and huAb3v2.9 VH CDR3 amino acid sequence | GGRLYFDY |
| 13 | chAb3 VL amino acid sequence | DVVMTQTPLSLPVSLGDQASISCRSSQSLVHSNGDTYLRWYLQKPGQSPKLLIYKVSNRFSGVPDRFSGSGSGTDFTLKITRVEAEDLGVYFCSQSTHVPYTFGGGTKLEIK |
| 14 | chAb3, huAb3VL.1, huAb3VL.1a, and huAb3VL.1b VL CDR1 amino acid sequence | RSSQSLVHSNGDTYLR |
| 15 | chAb3, huAb3VL.1, huAb3VL.1a, huAb3VL.1b, huAb3v2.1, huAb3v2.2, huAb3v2.3, huAb3v2.4, huAb3v2.5, huAb3v2.6, huAb3v2.7, huAb3v2.8, and huAb3v2.9 VL CDR3 amino acid sequence | SQSTHVPYT |

SEQUENCE SUMMARY

| SEQ ID NO: | Description | Amino Acid Sequence |
|---|---|---|
| 16 | chAb4 VH amino acid sequence | QVQLQQPGAELVKPGASVKLSCKA SGYSFTSYWMHWVKQRPGQGLEWI GMIHPNSGSNNYNEKFKSKATLTV DKSSNTAYMQLSSLTSEDSAVYYC ARRLGLHFDYWGQGTTLIVSS |
| 17 | chAb4 VH CDR1 amino acid sequence | GYSFTSYWMH |
| 18 | chAb4 VH CDR2 amino acid sequence | MIHPNSGSNNYNEKFKS |
| 19 | chAb4 VH CDR3 amino acid sequence | RLGLHFDY |
| 20 | chAb4 VL amino acid sequence | DIVMTQSQKFMSTPVGDRVSITCK ASQNVGTAVAWYQQKPGQSPKLLI YSASNRYTGVPDRFTGSGSGTDFT LTISNMQSEDLADYFCQQYSSYPY TFGGGTKLEIK |
| 21 | chAb4 VL CDR1 amino acid sequence | KASQNVGTAVA |
| 22 | chAb4 VL CDR2 amino acid sequence | SASNRYT |
| 23 | chAb4 VL CDR3 amino acid sequence | QQYSSYPYT |
| 24 | chAb18 VH amino acid sequence | QVQLQQSAAELARPGASVKMSCKA SGYSFTSYTIHWVKQRPGQGLEWI GYINPNSRNTDYNQKFKDETTLTA DRSSSTAYMQLISLTSEDSAVYYC ARYSGSTPYWYFDVWGAGTTVTVS S |
| 25 | chAb18, huAb18VH.1, huAb18VH.1a, and huAb18VH.1b VH CDR1 amino acid sequence | GYSFTSYTIH |
| 26 | chAb18, huAb18VH.1, and huAb18VH.1a VH CDR2 amino acid sequence | YINPNSRNTDYNQKFKD |
| 27 | chAb18, huAb18VH.1, huAb18VH.1a, and huAb18VH.1b VH CDR3 amino acid sequence | YSGSTPYWYFDV |
| 28 | chAb18 VL amino acid sequence | QIVLTQSPAILSASPGEKVTMTCR ASSSVSYMNWYQQKPGSSPKPWIY ATSNLASGVPARFSVSVSGTSHSL TISRVEAEDAATYYCQQWSSNPLT FGAGTKLELK |
| 29 | chAb18, huAb18VL.1, huAb18VL.1a, huAb18VL.1b, huAb18VL.2, and huAb18VL.2a, VL CDR1 amino acid sequence | RASSSVSYMN |
| 30 | chAb18, huAb18VL.1, huAb18VL.1a, huAb18VL.1b, huAb18VL.2, and huAb18VL.2a, VL CDR2 amino acid sequence | ATSNLAS |
| 31 | chAb18, huAb18VL.1, huAb18VL.1a, huAb18VL.1b, huAb18VL.2, and huAb18VL.2a, VL CDR3 amino acid sequence | QQWSSNPLT |
| 32 | chAb13 VH amino acid sequence | DVQLQESGPDLVKPSQSLSLTCTV TGYSITSGYSWHWIRQFPGNKLEW MGYIHSSGSTNYNPSLKSRISINR DTSKNQFFLQLNSVTTEDTATYYC AGYDDYFEYWGQGTTLTVSS |
| 33 | chAb13, huAb13Vh.1, huAb13Vh.1a, huAb13Vh.1b, huAb13v1, huAb13v2, huAb13v3, huAb13v4, huAb13v5, huAb13v6, huAb13v7, huAb13v8, and huAb13v9 VH CDR1 amino acid sequence | GYSITSGYSWH |

SEQUENCE SUMMARY

| SEQ ID NO: | Description | Amino Acid Sequence |
|---|---|---|
| 34 | chAb13, huAb13Vh.1, huAb13Vh.1a, huAb13Vh.1b, huAb13v1, huAb13v2, huAb13v3, huAb13v4, huAb13v5, huAb13v6, huAb13v7, huAb13v8, and huAb13v9 VH CDR2 amino acid sequence | YIHSSGSTNYNPSLKS |
| 35 | chAb13, huAb13Vh.1, huAb13Vh.1a, huAb13Vh.1b, huAb13v1, huAb13v2, huAb13v3, huAb13v4, huAb13v5, huAb13v6, huAb13v7, huAb13v8, and huAb13v9 VH CDR3 amino acid sequence | YDDYFEY |
| 36 | chAb13 VL amino acid sequence | DIVMTQSQKFMSTSVGDRVSVTCK ASQNVGFNVAWYQQKPGQSPKALI YSASYRYSGVPDRFTGSGSGTDFT LTISNVQSEDLAEYFCQQYNSYPF TFGSGTKLEIK |
| 37 | chAb13, huAb13VL.1, huAb13VL.1a, huAb13VL.1b, huAb13v1, huAb13v2, huAb13v3, huAb13v4, huAb13v5, huAb13v6, huAb13v7, huAb13v8, and huAb13v9 VL CDR1 amino acid sequence | KASQNVGFNVA |
| 38 | chAb13, huAb13VL.1, huAb13VL.1a, huAb13VL.1b, huAb13v1, huAb13v2, huAb13v3, huAb13v4, huAb13v5, huAb13v6, huAb13v7, huAb13v8, and huAb13v9 VL CDR2 amino acid sequence | SASYRYS |
| 39 | huAb13VL.1, huAb13VL.1a, huAb13VL.1b, huAb13v1, huAb13v2, huAb13v3, huAb13v4, huAb13v5, huAb13v6, huAb13v7, huAb13v8, and huAb13v9 VL CDR3 amino acid sequence | QQYNWYPFT |
| 40 | chAb12 VH amino acid sequence | EVQLVESGGGLVKPGGSLKLSCAA SGFTFSSYAMSWVRQTPEKRLEWV ATISSGTNYTYYPDSVKGRFTISR DNAKNTLYLQMTSLRSEDTAMYYC ARQGRYSWIAYWGQGTLVTVSA |
| 41 | chAb12 VH CDR1 amino acid sequence | GFTFSSYAMS |
| 42 | chAb12 VH CDR2 amino acid sequence | TISSGTNYTYYPDSVKG |
| 43 | chAb12 VH CDR3 amino acid sequence | QGRYSWIAY |
| 44 | chAb12 VL amino acid sequence | DIVLTQSPASLAVSLGQRATISCR ASKSVSTSDYSYMHWNQQKPGQPP KLLIYLASNLESGVPARFSGSGSG TDFTLNIHPVEEEDAATYYCQHSR ELLTFGAGTKLELK |
| 45 | chAb12 VL CDR1 amino acid sequence | RASKSVSTSDYSYMH |
| 46 | chAb12 and chAb17 VL CDR2 amino acid | LASNLES |
| 47 | chAb12 VL CDR3 amino acid sequence | QHSRELLT |
| 48 | chAb14 VH amino acid sequence | EVKLVESGGGLVKPGGSLKLSCAA SGFTFSSYGMSWVRQTPEKRLEWV ATISGGGTNTYYPDSVEGRFTISR DNAKNFLYLQMSSLRSEDTALYYC ARHYGSQTMDYWGQGTSVTVSS |
| 49 | chAb14 and chAb8 VH CDR1 amino acid sequence | GFTFSSYGMS |
| 50 | chAb14 VH CDR2 amino acid sequence | TISGGGTNTYYPDSVEG |

-continued

| SEQUENCE SUMMARY | |
|---|---|
| SEQ ID NO:Description | Amino Acid Sequence |
| 51 chAb14 VH CDR3 amino acid sequence | HYGSQTMDY |
| 52 chAb14 VL amino acid sequence | DIQMTQSPASLSASVGETVTITCRTSGNIHNYLTWYQQKQGKSPQLLV YNAKTLADGVPSRFSGSGSGTQFS LKINSLQPEDFGSYYCQHFWSIMW TFGGGTKLEIK |
| 53 chAb14 VL CDR1 amino acid sequence | RTSGNIHNYLT |
| 54 chAb14 VL CDR2 amino acid sequence | NAKTLAD |
| 55 chAb14 VL CDR3 amino acid sequence | QHFWSIMWT |
| 56 chAb6 VH amino acid sequence | QVQLQQSGAELMKPGASVKISCKA TGYTFSRYWIEWVKQRPGHGLEWI GEILPGSGSTNYNEKFKGKATFTA DTSSNTAYMQVSSLTSEDSAVHYC ARRGYGYVPYALDYWGQGTSVIVS S |
| 57 chAb6 VH CDR1 amino acid sequence | GYTFSRYWIE |
| 58 chAb6 VH CDR2 amino acid sequence | EILPGSGSTNYNEKFKG |
| 59 chAb6 VH CDR3 amino acid sequence | RGYGYVPYALDY |
| 60 chAb6 VL amino acid sequence | EIQMTQTTSSLSASLGDRVTISCR ASQDISNSLNWYQQKPDGTVNLLI YYTSRLYSGVPSRFSGSGSGTDYS LTISNLEQEDIATYFCQQGNTLPY TFGGGTKLEIK |
| 61 chAb6 VL CDR1 amino acid sequence | RASQDISNSLN |
| 62 chAb6 VL CDR2 amino acid sequence | YTSRLYS |
| 63 chAb6 VL CDR3 amino acid sequence | QQGNTLPYT |
| 64 chAb11 VH amino acid sequence | EVKLVESGGGLVQPGGSLRLSCAT SGFTFTNYYMSWVRQPPGKALEWL GFIRNKANDYTTEYSASVKGRFTI SRDNSQSILYLQMNTLRAEDSATY YCARESPGNPFAYWGQGTLVTVSA |
| 65 chAb11 VH CDR1 amino acid sequence | GFTFTNYYMS |
| 66 chAb11 VH CDR2 amino acid sequence | FIRNKANDYTTEYSASVKG |
| 67 chAb11 VH CDR3 amino acid sequence | ESPGNPFAY |
| 68 chAb11 VL amino acid sequence | DIVMTQSPSSLTVTAGEKVTMTCK SSQSLLNSGTQKNFLTWYQQKPGQ PPKLLIYWASTRESGVPDRFTGSG SGTDFTLTISSVQAEDLAVYFCQN DYIYPLTFGAGTKLELK |
| 70 chAb11 VL CDR2 amino acid sequence | WASTRES |
| 71 chAb11 VL CDR3 amino acid sequence | QNDYIYPLT |
| 72 chAb16 VH amino acid sequence | EVKLLESGGGLVQPGGSLKLSCAA SGFDFSRYWMSWVRQAPGKGLEWI GEINPDSSTINYTPSLKDKFIISR DNAKNTLYLQMSKVRSEDTALYYC ARPGFGNYIYAMDYWGQGTSVTVS S |
| 73 chAb16 VH CDR1 amino acid sequence | GFDFSRYWMS |
| 74 chAb16 VH CDR2 amino acid sequence | EINPDSSTINYTPSLKD |
| 75 chAb16 VH CDR3 amino acid sequence | PGFGNYIYAMDY |

SEQUENCE SUMMARY

| SEQ ID NO: Description | Amino Acid Sequence |
|---|---|
| 76 chAb16 VL amino acid sequence | DIQMTQTTSSLSASLGDRVTINCR ASQDISNFLNWYQQKPDGTVKLLI YYTSRLYLGVPSRFSGSGSGTDYS LTISNLEQEDIATYFCQQGNTLPP TFGGGTKLEIK |
| 77 chAb16 VL CDR1 amino acid sequence | RASQDISNFLN |
| 78 chAb16 VL CDR2 amino acid sequence | YTSRLYL |
| 79 chAb16 VL CDR3 amino acid sequence | QQGNTLPPT |
| 80 chAb10 VH amino acid sequence | DVQLQESGPGLVKPSQSLSLTCTV TGYSITSDYAWNWIRQFPGNRLEW MGHINYSGITNYNPSLKSRISITR DTSKNQFFLQLYSVTTEDTATYFC ARRSLFYYYGSSLYAMDYWGQGTS VTVSS |
| 81 chAb10 VH CDR1 amino acid sequence | GYSITSDYAWN |
| 82 chAb10 VH CDR2 amino acid sequence | HINYSGITNYNPSLKS |
| 83 chAb10 VH CDR3 amino acid sequence | RSLFYYYGSSLYAMDY |
| 84 chAb10 VL amino acid sequence | DVVMTQSPFSLPVSLGDQASISCR SSQSLVHSNGNTYLHWYLQKPGQS PKLLIYKVSNRFSGVPDRFSGSGS GTDFTLKISRVEAEDLGVYFCSQS THVPWTFGGGTKLEIK |
| 85 chAb10 VL CDR1 amino acid sequence | RSSQSLVHSNGNTYLH |
| 86 chAb10 VL CDR3 amino acid sequence | SQSTHVPWT |
| 87 chAb7 VH amino acid sequence | EVQLVESGENLVKPGGSLKLSCAA SGFSFRGYGMSWVRQTPDKRLEWV AAISTGGNYTYYPDSVQGRFTISR DNANNTLYLQMSSLKSEDTAMYYC ARRGGNYAGFAYWGQGTLVTVSA |
| 88 chAb7 VH CDR1 amino acid sequence | GFSFRGYGMS |
| 89 chAb7 VH CDR2 amino acid sequence | AISTGGNYTYYPDSVQG |
| 90 chAb7 VH CDR3 amino acid sequence | RGGNYAGFAY |
| 91 chAb7 VL amino acid sequence | DIQMTQSPASLSVSVGETVTITCR PSENIYSNLAWYQQKQGKSPQLLV YAATNLADGVPSRFSGSGSGTQYS LKINSLQSEDFGTYYCQHFWGTPF TFGSGTKLEIK |
| 92 chAb7 VL CDR1 amino acid sequence | RPSENIYSNLA |
| 93 chAb7 and chAb8 VL CDR2 amino acid | AATNLAD |
| 94 chAb7 VL CDR3 amino acid sequence | QHFWGTPFT |
| 95 chAb8 VH amino acid sequence | EVKLVESGGGLVKPGGSLKLSCAA SGFTFSSYGMSWVRQTPEKRLEWV ATISGGGNYTYCPDSVKGRFTISR DNAKNNLYLQMSSLRSEDTALYYC TRQRGYDYHYAMDFWGQGTSVIVS S |
| 96 chAb8 VH CDR2 amino acid sequence | TISGGGNYTYCPDSVKG |
| 97 chAb8 VH CDR3 amino acid sequence | QRGYDYHYAMDF |
| 98 chAb8 VL amino acid sequence | DIQMTQSPASLSVSVGETVTITCR ASENIYSNLAWHQQKQGKSPQLLV |

-continued

| SEQ ID NO: Description | Amino Acid Sequence |
|---|---|
| | YAATNLADGVPSRFSGNGSDTQYS LKINSLQSEDFGSYFCQNFWGTSW TFGGGTKLEIK |
| 99 chAb8 VL CDR1 amino acid sequence | RASENIYSNLA |
| 100 chAb8 VL CDR3 amino acid sequence | QNFWGTSWT |
| 101 chAb17 VH amino acid sequence | EVKLVESGGGLVQPGGSLKLSCAA SGFTFSSYIMSWVRQTPEKRLEWV ASIVSSNITYYPDSMKGRFTISRD NARNILYLQMSSLKSEDTAMYYCA RSGTRAWFAYWGQGTLVTVSA |
| 102 chAb17 VH CDR1 amino acid sequence | GFTFSSYIMS |
| 103 chAb17 VH CDR2 amino acid sequence | SIVSSNITYYPDSMKG |
| 104 chAb17 VH CDR3 amino acid sequence | SGTRAWFAY |
| 105 chAb17 VL amino acid sequence | DIVLTQSPASLAVSLGQRATISCR ASKSVSTSAYSYMHWYQQKPGQPP KLLIYLASNLESGVPARFSGSGSG TDFTLNIHPVEEEDAATYYCQHSR ELPYTFGGGTKLEIK |
| 106 chAb17 VL CDR1 amino acid sequence | RASKSVSTSAYSYMH |
| 107 chAb17 VL CDR3 amino acid sequence | QHSRELPYT |
| 108 chAb5 VH amino acid sequence | QVQLQQPGDELVKPGASVKLSCKT SGYTFTTDWMHWVKQRPGQGLEWI GMIHPNSGTTNYNEKFKSKAALTV DKSSSTACMQLSSLTSEDSAVYYC ARSYWKWYFDVWGIGTTVIVSS |
| 109 chAb5 VH CDR1 amino acid sequence | GYTFTTDWMH |
| 110 chAb5 VH CDR2 amino acid sequence | MIHPNSGTTNYNEKFKS |
| 111 chAb5 VH CDR3 amino acid sequence | SYWKWYFDV |
| 112 chAb5 VL amino acid sequence | QIVLTQSPAIMSASLGEEITLTCS ASSSVSYMHWYQQKSGTSPKLLIY STSNLASGVPSRFSGSGSGTFYSL TISSVEAEDSADYYCHQWTSYMYT FGGGTKLEIK |
| 113 chAb5 VL CDR1 amino acid sequence | SASSSVSYMH |
| 114 chAb5 VL CDR2 amino acid sequence | STSNLAS |
| 115 chAb5 VL CDR3 amino acid sequence | HQWTSYMYT |
| 116 huAb18VH.1, huAb18v1, and huAb18v5 VH amino acid sequence | EVQLVQSGAEVKKPGSSVKVSCKA SGYSFTSYTIHWVRQAPGQGLEWM GYINPNSRNTDYNQKFKDRVTITA DKSTSTAYMELSSLRSEDTAVYYC ARYSGSTPYWYFDVWGQGTIVTVS S |
| 117 huAb18VH.1a, huAb18v3, huAb18v8, and huAb18v9 VH amino acid sequence | EVQLVQSGAEVKKPGSSVKVSCKA SGYSFTSYTIHWVRQAPGQGLEWI GYINPNSRNTDYNQKFKDRTTLTA DRSTSTAYMELSSLRSEDTAVYYC ARYSGSTPYWYFDVWGQGTIVTVS S |

-continued

SEQUENCE SUMMARY

| SEQ ID NO: Description | Amino Acid Sequence |
|---|---|
| 118 huAb18VH.1b, huAb18v2, huAb18v4, huAb18v6, huAb18v7, and huAb18v10 VH amino acid sequence | EVQLVQSGAEVKKPGSSVKVSCKASGYSFTSYTIHWVRQAPGQGLEWMGYINPNSRNTDYAQKFQGRVTLTADKSTSTAYMELSSLRSEDTAVYYCARYSGSTPYWYFDVWGQGTIVTVSS |
| 119 huAb18VH.1b VH CDR2 amino acid sequence | YINPNSRNTDYAQKFQG |
| 120 huAb18VL.1, huAb18v1, and huAb18v2 VL amino acid sequence | DIQLTQSPSFLSASVGDRVTITCRASSSVSYMNWYQQKPGKAPKLLIYATSNLASGVPSRFSGSGSGTEFTLTISSLQPEDFATYYCQQWSSNPLTFGQGTKLEIK |
| 121 huAb18VL.1a, huAb18v3, and huAb18v4 VL amino acid sequence | DIQLTQSPSFLSASVGDRVTITCRASSSVSYMNWYQQKPGKSPKPWIYATSNLASGVPSRFSVSVSGTEHTLTISSLQPEDFATYYCQQWSSNPLTFGQGTKLEIK |
| 122 huAb18VL.1b, huAb18v8, and huAb18v10 VL amino acid sequence | DIQLTQSPSFLSASVGDRVTITCRASSSVSYMNWYQQKPGKAPKPWIYATSNLASGVPSRFSVSGSGTEHTLTISSLQPEDFATYYCQQWSSNPLTFGQGTKLEIK |
| 123 huAb18VL.2, huAb18v5, and huAb18v6 VL amino acid sequence | EIVLTQSPDFQSVTPKEKVTITCRASSSVSYMNWYQQKPDQSPKLLIKATSNLASGVPSRFSGSGSGTDFTLTINSLEAEDAATYYCQQWSSNPLTFGQGTKLEIK |
| 124 huAb18VL.2a, huAb18v7, and huAb18v9 VL amino acid sequence | EIVLTQSPDFQSVTPKEKVTITCRASSSVSYMNWYQQKPDQSPKPWIYATSNLASGVPSRFSVSVSGTDHTLTINSLEAEDAATYYCQQWSSNPLTFGQGTKLEIK |
| 125 huAb3VH.1, huAb3v1, and huAb3v4 VH amino acid sequence | EVQLVQSGAEVKKPGSSVKVSCKASGYTFSSYWMHWVRQAPGQGLEWMGLIHPDSGSTNYNEMFKNRVTITADKSTSTAYMELSSLRSEDTAVYYCARGGRLYFDYWGQGTTVIVSS |
| 126 huAb3VH.1a, huAb3v3, and huAb3v6 VH amino acid sequence | EVQLVQSGAEVKKPGSSVKVSCKASGYTFSSYWMHWVRQAPGQGLEWIGLIHPDSGSTNYNEMFKNRATLTVDRSTSTAYVELSSLRSEDTAVYFCAGGGRLYFDYWGQGTTVIVSS |
| 127 huAb3VH.1b, huAb3v2, and huAb3v5 VH amino acid sequence | EVQLVQSGAEVKKPGSSVKVSCKASGYTFSSYWMHWVRQAPGQGLEWIGLIHPDSGSTNYNEMFKNRATLTVDRSTSTAYMELSSLRSEDTAVYYCAGGGRLYFDYWGQGTTVIVSS |
| 128 huAb3VL.1, huAb3v1, and huAb3v2 VL amino acid sequence | DIVMTQSPLSLPVTPGEPASISCRSSQSLVHSNGDTYLRWYLQKPGQSPQLLIYKVSNRFSGVPDRFSGSGSGTDFTLKISRVEAEDVGVYYCSQSTHVPYTFGGGTKVEIK |
| 129 huAb3VL.1a and huAb3v3 VL amino acid sequence | DVVMTQSPLSLPVTPGEPASISCRSSQSLVHSNGDTYLRWYLQKPGQSPQLLIYKVSNRFSGVPDRFSGSGSGTDFTLKISRVEAEDVGVYFCSQSTHVPYTFGGGTKVEIK |

SEQUENCE SUMMARY

| SEQ ID NO: | Description | Amino Acid Sequence |
|---|---|---|
| 130 | huAb3VL.1b, huAb3v4, huAb3v5, and huAb3v6 VL amino acid sequence | DVVMTQSPLSLPVTPGEPASISCRSSQSLVHSNGDTYLRWYLQKPGQSPQLLIYKVSNRFSGVPDRFSGSGSGTDFTLKISRVEAEDVGVYYCSQSTHVPYTFGGGTKVEIK |
| 131 | huAb3v2.1, huAb3v2.2, and huAb3v2.3 VH amino acid sequence | EVQLVQSGAEVKKPGSSVKVSCKASGYTFSSYWMHWVRQAPGQGLEWIGLIHPWSGSTNYNEMFKNRATLTVDRSTSTAYMELSSLRSEDTAVYYCAGGGRLYFDYWGQGTTVIVSS |
| 132 | huAb3v2.1, huAb3v2.2, and huAb3v2.3 VH CDR2 amino acid sequence | LIHPWSGSTNYNEMFKN |
| 133 | huAb3v2.1, huAb3v2.4, and huAb3v2.7 VL amino acid sequence | DIVMTQSPLSLPVTPGEPASISCRSSQSLVHSSGDTYLRWYLQKPGQSPQLLIYKVSNRFSGVPDRFSGSGSGTDFTLKISRVEAEDVGVYYCSQSTHVPYTFGGGTKVEIK |
| 134 | huAb3v2.1, huAb3v2.4, and huAb3v2.7 VL CDR1 amino acid sequence | RSSQSLVHSSGDTYLR |
| 135 | huAb3v2.2, huAb3v2.5, and huAb3v2.8 VL amino acid sequence | DIVMTQSPLSLPVTPGEPASISCRSSQSLVHSNRDTYLRWYLQKPGQSPQLLIYKVSNRFSGVPDRFSGSGSGTDFTLKISRVEAEDVGVYYCSQSTHVPYTFGGGTKVEIK |
| 136 | huAb3v2.2, huAb3v2.5, and huAb3v2.8 VL CDR1 amino acid sequence | RSSQSLVHSNRDTYLR |
| 137 | huAb3v2.3, huAb3v2.6, and huAb3v2.9 VL amino acid sequence | DIVMTQSPLSLPVTPGEPASISCRSSQSLVHSNQDTYLRWYLQKPGQSPQLLIYKVSNRFSGVPDRFSGSGSGTDFTLKISRVEAEDVGVYYCSQSTHVPYTFGGGTKVEIK |
| 138 | huAb3v2.3, huAb3v2.6, and huAb3v2.9 VL CDR1 amino acid sequence | RSSQSLVHSNQDTYLR |
| 139 | huAb3v2.4, huAb3v2.5, and huAb3v2.6 VH amino acid sequence | EVQLVQSGAEVKKPGSSVKVSCKASGYTFSSYWMHWVRQAPGQGLEWIGLIHPESGSTNYNEMFKNRATLTVDRSTSTAYMELSSLRSEDTAVYYCAGGGRLYFDYWGQGTTVIVSS |
| 140 | huAb3v2.4, huAb3v2.5, and huAb3v2.6 VH CDR2 amino acid sequence | LIHPESGSTNYNEMFKN |
| 141 | huAb3v2.7, huAb3v2.8, and huAb3v2.9 VH amino acid sequence | EVQLVQSGAEVKKPGSSVKVSCKASGYTFSSYWMHWVRQAPGQGLEWIGLIHPISGSTNYNEMFKNRATLTVDRSTSTAYMELSSLRSEDTAVYYCAGGGRLYFDYWGQGTTVIVSS |
| 142 | huAb3v2.7, huAb3v2.8, and huAb3v2.9 VH CDR2 amino acid sequence | LIHPISGSTNYNEMFKN |
| 143 | huAb13VL.1, huAb13v2, huAb13v5, and huAb13v7 VL amino acid sequence | DIQMTQSPSSLSASVGDRVTITCKASQNVGFNVAWYQQKPGKAPKLLIYSASYRYSGVPSRFSGSGSGTDFTLTISSLQPEDFATYYCQQYNWYPFTFGQGTKLEIK |
| 144 | huAb13VL.1a, huAb13v1, huAb13v3, and huAb13v8 VL amino acid sequence | DIQMTQSPSSLSASVGDRVTITCKASQNVGFNVAWYQQKPGKSPKALIYSASYRYSGVPSRFSGSGSGTDFTLTISSLQPEDFAEYFCQQYNWYPFTFGQGTKLEIK |

| SEQ ID NO: Description | Amino Acid Sequence |
|---|---|
| 145 huAB13VL.1b, huAb13v4, huAb13v6, and huAb13v9 VL amino acid sequence | DIQMTQSPSSLSASVGDRVTITCK ASQNVGFNVAWYQQKPGKAPKLLI YSASYRYSGVPSRFSGSGSGTDFT LTISSLQPEDFATYFCQQYNWYPF TFGQGTKLEIK |
| 146 huAb13VH.1, huAb13v2, huAb13v3, and huAb13v4 VH amino acid sequence | EVQLQESGPGLVKPSETLSLTCAV SGYSITSGYSWHWIRQPPGKGLEW IGYIHSSGSTNYNPSLKSRVTISV DTSKNQFSLKLSSVTAADTAVYYC ARYDDYFEYWGQGTTVTSS |
| 147 huAb13VH.1a, huAb13v1, huAb13v5, and huAb13v6 VH amino acid sequence | EVQLQESGPGLVKPSETLSLTCAV TGYSITSGYSWHWIRQFPGNGLEW MGYIHSSGSTNYNPSLKSRISISR DTSKNQFFLKLSSVTAADTAVYYC AGYDDYFEYWGQGTTVTVSS |
| 148 huAb13VH.1b, huAb13v7, huAb13v8, and huAb13v9 VH amino acid sequence | EVQLQESGPGLVKPSETLSLTCAV SGYSITSGYSWHWIRQPPGNGLEW MGYIHSSGSTNYNPSLKSRITISR DTSKNQFSLKLSSVTAADTAVYYC ARYDDYFEYWGQGTTVTVSS |
| 149 B7-H3 amino acid sequence (human) | MLRRRGSPGMGVHVGAALGALWFC LTGALEVQVPEDPVVALVGTDATL CCSFSPEPGFSLAQLNLIWQLTDT KQLVHSFAEGQDQGSAYANRTALF PDLLAQGNASLRLQRVRVADEGSF TCFVSIRDFGSAAVSLQVAAPYSK PSMTLEPNKDLRPGDTVTITCSSY QGYPEAEVFWQDGQGVPLIGNVIT SQMANEQGLFDVHSILRVVLGANG TYSCLVRNPVLQQDAHSSVTITPQ RSPTGAVEVQVPEDPVVALVGTDA TLRCSFSPEPGFSLAQLNLIWQLT DTKQLVHSFTEGRDQGSAYANRTA LFPDLLAQGNASLRLQRVRVADEG SFTCFVSIRDFGSAAVSLQVAAPY SKPSMTLEPNKDLRPGDTVTITCS SYRGYPEAEVFWQDGQGVPLTGNV TTSQMANEQGLFDVHSVLRVVLGA NGTYSCLVRNPVLQQDAHGSVTIT GQPMTFPPEALWVTVGLSVCLIAL LVALAFVCWRKIKQSCEEENAGAE DQDGEGEGSKTALQPLKHSDSKED DGQEIA |
| 150 Human B7-H3-ECD (fc fusion) Note: Fc sequence is underlined | MLRRRGSPGMGVHVGAALGALWFC LTGALEVQVPEDPVVALVGTDATL CCSFSPEPGFSLAQLNLIWQLTDT KQLVHSFAEGQDQGSAYANRTALF PDLLAQGNASLRLQRVRVADEGSF TCFVSIRDFGSAAVSLQVAAPYSK PSMTLEPNKDLRPGDTVTITCSSY QGYPEAEVFWQDGQGVPLTGNVTT SQMANEQGLFDVHSILRVVLGANG TYSCLVRNPVLQQDAHSSVTITPQ RSPTGAVEVQVPEDPVVALVGTDA TLRCSFSPEPGFSLAQLNLIWQLT DTKQLVHSFTEGRDQGSAYANRTA LFPDLLAQGNASLRLQRVRVADEG SFTCFVSIRDFGSAAVSLQVAAPY SKPSMTLEPNKDLRPGDTVTITCS SYRGYPEAEVFWQDGQGVPLTGNV TTSQMANEQGLFDVHSVLRVVLGA NGTYSCLVRNPVLQQDAHGSVTIT GQPMTFAAADK<u>THTCPPCPAPEAE</u> <u>GAPSVFLFPPKPKDTLMISRTPEV</u> <u>TCVVVDVSHEDPEVKFNWYVDGVE</u> <u>VHNAKTKPREEQYNSTYRVVSVLT</u> <u>VLHQDWLNGKEYKCKVSNKALPAP</u> <u>IEKTISKAKGQPREPQVYTLPPSR</u> |

| SEQ ID NO: Description | Amino Acid Sequence |
|---|---|
| | EEMTKNQVSLTCLVKGFYPSDIAV EWESNGQPENNYKTTPPVLDSDGS FFLYSKLTVDKSRWQQGNVFSCSV MHEALHNHYTQKSLSLSPGK |
| 151 Mouse B7-H3-ECD (fc fusion) Note: Fc sequence is underlined | MLRGWGGPSVGVCVRTALGVLCLC LTGAVEVQVSEDPVVALVDTDATL RCSFSPEPGFSLAQLNLIWQLTDT KQLVHSFTEGRDQGSAYSNRTALF PDLLVQGNASLRLQRVRVTDEGSY TCFVSIQDFDSAAVSLQVAAPYSK PSMTLEPNKDLRPGNMVTITCSSY QGYPEAEVFWKDGQGVPLTGNVTT SQMANERGLFDVHSVLRVVLGANG TYSCLVRNPVLQQDAHGSVTITGQ PLTFAAADKTHTCPPCPAPEAEGA PSVFLFPPKPKDTLMISRTPEVTC VVVDVSHEDPEVKFNWYVDGVEVH NAKTKPREEQYNSTYRVVSVLTVL HQDWLNGKEYKCKVSNKALPAPIE KTISKAKGQPREPQVYTLPPSREE MTKNQVSLTCLVKGFYPSDIAVEW ESNGQPENNYKTTPPVLDSDGSFF LYSKLTVDKSRWQQGNVFSCSVMH EALHNHYTQKSLSLSPGK |
| 152 Human B7-H3-ECD (his tag) | MEFGLSWLFLVAILKGVQCGALEV QVPEDPVVALVGTDATLCCSFSPE PGFSLAQLNLIWQLTDTKQLVHSF AEGQDQGSAYANRTALFPDLLAQG NASLRLQRVRVADEGSFTCFVSIR DFGSAAVSLQVAAPYSKPSMTLEP NKDLRPGDTVTITCSSYQGYPEAE VFWQDGQGVPLTGNVTTSQMANEQ GLFDVHSILRVVLGANGTYSCLVR NPVLQQDAHSSVTITPQRSPTGAV EVQVPEDPVVALVGTDATLRCSFS PEPGFSLAQLNLIWQLTDTKQLVH SFTEGRDQGSAYANRTALFPDLLA QGNASLRLQRVRVADEGSFTCFVS IRDFGSAAVSLQVAAPYSKPSMTL EPNKDLRPGDTVTITCSSYRGYPE AEVFWQDGQGVPLTGNVTTSQMAN EQGLFDVHSVLRVVLGANGTYSCL VRNPVLQQDAHGSVTITGQPMTHH HHHH |
| 153 Mouse B7-H3-ECD (his tag) | MEFGLSWLFLVAILKGVQCVEVQV SEDPVVALVDTDATLRCSFSPEPG FSLAQLNLIWQLTDTKQLVHSFTE GRDQGSAYSNRTALFPDLLVQGNA SLRLQRVRVTDEGSYTCFVSIQDF DSAAVSLQVAAPYSKPSMTLEPNK DLRPGNMVTITCSSYQGYPEAEVF WKDGQGVPLTGNVTTSQMANERGL FDVHSVLRVVLGANGTYSCLVRNP VLQQDAHGSVTITGQPLTFHHHHH H |
| 154 Cynomolgus B7-H3-ECD (his tag) | MLHRRGSPGMGVHVGAALGALWFC LTGALEVQVPEDPVVALVGTDATL RCSFSPEPGFSLAQLNLIWQLTDT KQLVHSFTEGRDQGSAYANRTALF LDLLAQGNASLRLQRVRVADEGSF TCFVSIRDFGSAAVSLQVAAPYSK PSMTLEPNKDLRPGDTVTITCSSY RGYPEAEVFWQDGQGAPLTGNVTT SQMANEQGLFDVHSVLRVVLGANG TYSCLVRNPVLQQDAHGSITITPQ RSPTGAVEVQVPEDPVVALVGTDA TLRCSF SPEPGFSLAQLNLIWQLTDTKQLV HSFTEGRDQGSAYANRTALFLDLL |

SEQUENCE SUMMARY

| SEQ ID NO:Description | Amino Acid Sequence |
|---|---|
| | AQGNASLRLQRVRVADEGSFTCFV SIRDFGSAAVSLQVAAPYSKPSMT LEPNKDLRPGDTVTITCSSYRGYP EAEVFWQDGQGAPLTGNVTTSQMA NEQGLFDVHSVLRVVLGANGTYSC LVRNPVLQQDAHGSVTITGQPMTF AAAHHHHHHHH |
| 155 Amino acid sequence of IGHV1-69*06 | QVQLVQSGAEVKKPGSSVKVSCKA SGGTFSSYAISWVRQAPGQGLEWM GGIIPIFGTANYAQKFQGRVTITA DKSTSTAYMELSSLRSEDTAVYYC AR |
| 156 Amino acid sequence of IGHJ6*01 | WGQGTTVTVSS |
| 157 Amino acid sequence of IGKV1-9*01 | DIQLTQSPSFLSASVGDRVTITCR ASQGISSYLAWYQQKPGKAPKLLI YAASTLQSGVPSRFSGSGSGTEFT LTISSLQPEDFATYYCQQLNSYPP |
| 158 Amino acid sequence of IGKJ2*01 | FGQGTKLEIK |
| 159 Ig gamma-1 constant region | ASTKGPSVFPLAPSSKSTSGGTAA LGCLVKDYFPEPVTVSWNSGALTS GVHTFPAVLQSSGLYSLSSVVTVP SSSLGTQTYICNVNHKPSNTKVDK KVEPKSCDKTHTCPPCPAPELLGG PSVFLFPPKPKDTLMISRTPEVTC VVVDVSHEDPEVKFNWYVDGVEVH NAKTKPREEQYNSTYRVVSVLTVL HQDWLNGKEYKCKVSNKALPAPIE KTISKAKGQPREPQVYTLPPSREE MTKNQVSLTCLVKGFYPSDIAVEW ESNGQPENNYKTTPPVLDSDGSFF LYSKLTVDKSRWQQGNVFSCSVMH EALHNHYTQKSLSLSPGK |
| 160 Ig gamma-1 constant region mutant | ASTKGPSVFPLAPSSKSTSGGTAA LGCLVKDYFPEPVTVSWNSGALTS GVHTFPAVLQSSGLYSLSSVVTVP SSSLGTQTYICNVNHKPSNTKVDK KVEPKSCDKTHTCPPCPAPEAAGG PSVFLFPPKPKDTLMISRTPEVTC VVVDVSHEDPEVKFNWYVDGVEVH NAKTKPREEQYNSTYRVVSVLTVL HQDWLNGKEYKCKVSNKALPAPIE KTISKAKGQPREPQVYTLPPSREE MTKNQVSLTCLVKGFYPSDIAVEW ESNGQPENNYKTTPPVLDSDGSFF LYSKLTVDKSRWQQGNVFSCSVMH EALHNHYTQKSLSLSPGK |
| 161 Ig Kappa constant region | RTVAAPSVFIFPPSDEQLKSGTAS VVCLLNNFYPREAKVQWKVDNALQ SGNSQESVTEQDSKDSTYSLSSTL TLSKADYEKHKVYACEVTHQGLSS PVTKSFNRGEC |
| 162 Ig Lambda constant region | QPKAAPSVTLFPPSSEELQANKAT LVCLISDFYPGAVTVAWKADSSPV KAGVETTTPSKQSNNKYAASSYLS LTPEQWKSHRSYSCQVTHEGSTVE KTVAPTECS |
| 163 Amino acid sequence of IGKV6-21*01 | EIVLTQSPDFQSVTPKEKVTITCR ASQSIGSSLHWYQQKPDQSPKLLI KYASQSFSGVPSRFSGSGSGTDFT LTINSLEAEDAATYYCHQSSSLPX |
| 164 Amino acid sequence of IGKV2-28*01 | DIVMTQSPLSLPVTPGEPASISCR SSQSLLHSNGYNYLDWYLQKPGQS PQLLIYLGSNRASGVPDRFSGSGS |

SEQUENCE SUMMARY

| SEQ ID NO: | Description | Amino Acid Sequence |
|---|---|---|
| | | GTDFTLKISRVEAEDVGVYYCMQA LQTPP |
| 165 | Amino acid sequence of IGKJ4*01 | FGGGTKVEIK |
| 166 | Amino acid sequence of IGHV-b*01(0-1) | QVQLQESGPGLVKPSETLSLTCAV SGYSISSGYYWGWIRQPPGKGLEW IGSIYHSGSTYYNPSLKSRVTISV DTSKNQFSLKLSSVTAADTAVYYC AR |
| 167 | Amino acid sequence of IGKv1-39*01 | DIQMTQSPSSLSASVGDRVTITCR ASQSISSYLNWYQQKPGKAPKLLI YAASSLQSGVPSRFSGSGSGTDFT LTISSLQPEDFATYYCQQSYSTPP |
| 168 | Amino acid sequence of huAb13v1 heavy chain<br>Note: Ig gamma-1 constant region mutant sequence is underlined. | EVQLQESGPGLVKPSETLSLTCAV TGYSITSGYSWHWIRQFPGNGLEW MGYIHSSGSTNYNPSLKSRISISR DTSKNQFFLKLSSVTAADTAVYYC AGYDDYFEYWGQGTTVTVSS<u>ASTK GPSVFPLAPSSKSTSGGTAALGCL VKDYFPEPVTVSWNSGALTSGVHT FPAVLQSSGLYSLSSVVTVPSSSL GTQTYICNVNHKPSNTKVDKKVEP KSCDKTHTCPPCPAPEAAGGPSVF LFPPKPKDTLMISRTPEVICVVVD VSHEDPEVKFNWYVDGVEVHNAKT KPREEQYNSTYRVVSVLTVLHQDW LNGKEYKCKVSNKALPAPIEKTIS KAKGQPREPQVYTLPPSREEMTKN QVSLTCLVKGFYPSDIAVEWESNG QPENNYKTTPPVLDSDGSFFLYSK LTVDKSRWQQGNVFSCSVMHEALH NHYTQKSLSLSPGK</u> |
| 169 | Amino acid sequence of huAb13v1 light chain<br>Note: Ig kappa constant region sequence is underlined. | DIQMTQSPSSLSASVGDRVTITCK ASQNVGFNVAWYQQKPGKSPKALI YSASYRYSGVPSRFSGSGSGTDFT LTISSLQPEDFAEYFCQQYNWYPF TFGQGTKLEIK<u>RTVAAPSVFIFPP SDEQLKSGTASVVCLLNNFYPREA KVQWKVDNALQSGNSQESVTEQDS KDSTYSLSSTLTLSKADYEKHKVY ACEVTHQGLSSPVTKSFNRGEC</u> |
| 170 | Amino acid sequence of huAb3v2.5 heavy chain<br>Note: Ig gamma-1 constant region mutant sequence is underlined. | EVQLVQSGAEVKKPGSSVKVSCKA SGYTFSSYWMHWVRQAPGQGLEWI GLIHPESGSTNYNEMFKNRATLTV DRSTSTAYMELSSLRSEDTAVYYC AGGGRLYFDYWGQGTTVTVSS<u>AST KGPSVFPLAPSSKSTSGGTAALGC LVKDYFPEPVTVSWNSGALTSGVH TFPAVLQSSGLYSLSSVVTVPSSS LGTQTYICNVNHKPSNTKVDKKVE PKSCDKTHTCPPCPAPEAAGGPSV FLFPPKPKDTLMISRTPEVTCVVV DVSHEDPEVKFNWYVDGVEVHNAK TKPREEQYNSTYRVVSVLTVLHQD WLNGKEYKCKVSNKALPAPIEKTI SKAKGQPREPQVYTLPPSREEMTK NQVSLTCLVKGFYPSDIAVEWESN GQPENNYKTTPPVLDSDGSFFLYS KLTVDKSRWQQGNVFSCSVMHEAL HNHYTQKSLSLSPGK</u> |
| 171 | Amino acid sequence of huAb3v2.5 light chain<br>Note: Ig kappa constant region sequence is underlined. | DIVMTQSPLSLPVTPGEPASISCR SSQSLVHSNRDTYLRWYLQKPGQS PQLLIYKVSNRFSGVPDRFSGSGS GTDFTLKISRVEAEDVGVYYCSQS THVPYTFGGGTKVEIK<u>RTVAAPSV FIFPPSDEQLKSGTASVVCLLNNF YPREAKVQWKVDNALQSGNSQESV</u> |

SEQUENCE SUMMARY

| SEQ ID NO: | Description | Amino Acid Sequence |
|---|---|---|
| | | TEQDSKDSTYSLSSTLTLSKADYE KHKVYACEVTHQGLSSPVTKSFNR GEC |
| 172 | Amino acid sequence of huAb3v2.6 heavy chain<br>Note: Ig gamma-1 constant region mutant sequence is underlined. | EVQLVQSGAEVKKPGSSVKVSCKA SGYTFSSYWMHWVRQAPGQGLEWI GLIHPESGSTNYNEMFKNRATLTV DRSTSTAYM ELSSLRSEDTAVYYCAGGGRLYFD YWGQGTTVTVSS<u>ASTKGPSVFPLA PSSKSTSGGTAALGCLVKDYFPEP VTVSWNSGALTSGVHTFPAVLQSS GLYSLSSVVTVPSSSLGTQTYICN VNHKPSNTKVDKKVEPKSCDKTHT CPPCPAPEAAGGPSVFLFPPKPKD TLMISRTPEVTCVVVDVSHEDPEV KFNWYVDGVEVHNAKTKPREEQYN STYRVVSVLTVLHQDWLNGKEYKC KVSNKALPAPIEKTISKAKGQPRE PQVYTLPPSREEMTKNQVSLTCLV KGFYPSDIAVEWESNGQPENNYKT TPPVLDSDGSFFLYSKLTVDKSRW QQGNVFSCSVMHEALHNHYTQKSL SLSPGK</u> |
| 173 | Amino acid sequence of huAb3v2.6 light chain<br>Note: Ig kappa constant region sequence is underlined. | DIVMTQSPLSLPVTPGEPASISCR SSQSLVHSNQDTYLRWYLQKPGQS PQLLIYKVSNRFSGVPDRFSGSGS GTDFTLKISRVEAEDVGVYYCSQS THVPYTFGGGTKVEIK<u>RTVAAPSV FIFPPSDEQLKSGTASVVCLLNNF YPREAKVQWKVDNALQSGNSQESV TEQDSKDSTYSLSSTLTLSKADYE KHKVYACEVTHQGLSSPVTKSFNR GEC</u> |
| 174 | Amino acid sequence of IGHV1-69*06 IGHJ6 | QVQLVQSGAEVKKPGSSVKVSCKA SGGTFSSYAISWVRQAPGQGLEWM GGIIPIFGTANYAQKFQGRVTITA DKSTSTAYMELSSLRSEDTAVYYC ARXXXXXXXXWGQGTTVTVSS |
| 175 | Amino acid sequence of IGKV2-28*01 IGKJ4 | DIVMTQSPLSLPVTPGEPASISCR SSQSLLHSNGYNYLDWYLQKPGQS PQLLIYLGSNRASGVPDRFSGSGS GTDFTLKISRVEAEDVGVYYCXXX XXXXXXFGGGTKVEIK |
| 176 | Amino acid sequence of IGHV4-b IGHJ6 | QVQLQESGPGLVKPSETLSLTCAV SGYSISSGYYWGWIRQPPGKGLEW IGSIYHSGSTYYNPSLKSRVTISV DTSKNQFSLKLSSVTAADTAVYYC ARXXXXXXXXWGQGTTVTVSS |
| 177 | Amino acid sequence of IGKV1-39 IGKJ2 | DIQMTQSPSSLSASVGDRVTITCR ASQSISSYLNWYQQKPGKAPKLLI YAASSLQSGVPSRFSGSGSGTDFT LTISSLQPEDFATYYCXXXXXXXX XFGQGTKLEIK |
| 178 | Amino acid sequence of huAb3 VL1 variants<br>Note: X can be any amino acid except: M, C, N, D, or Q | DIVMTQSPLSLPVTPGEPASISCR SSQSLVHSXGDTYLRWYLQKPGQS PQLLIYKVSNRFSGVPDRFSGSGS GTDFTLKISRVEAEDVGVYYCSQS THVPYTFGGGTKVEIK |
| 179 | Amino acid sequence of huAb3 VL1 variants<br>Note: X can be any amino acid except: M, C, G, S, N, or P | DIVMTQSPLSLPVTPGEPASISCR SSQSLVHSNXDTYLRWYLQKPGQS PQLLIYKVSNRFSGVPDRFSGSGS GTDFTLKISRVEAEDVGVYYCSQS THVPYTFGGGTKVEIK |

-continued

SEQUENCE SUMMARY

| SEQ ID NO: | Description | Amino Acid Sequence |
|---|---|---|
| 180 | Amino acid sequence of huAb3 VH1b variants<br>Note: X can be any amino acid except: M, C, N, D, or Q | EVQLVQSGAEVKKPGSSVKVSCKA<br>SGYTFSSYWMHWVRQAPGQGLEWI<br>GLIHPXSGSTNYNEMFKNRATLTV<br>DRSTSTAYMELSSLRSEDTAVYYC<br>AGGGRLYFDYWGQGTTVTVSS |
| 181 | Amino acid sequence of huAb3 VH1b variants<br>Note: X can be any amino acid except: M, C, G, S, N, or P | EVQLVQSGAEVKKPGSSVKVSCKA<br>SGYTFSSYWMHWVRQAPGQGLEWI<br>GLIHPDXGSTNYNEMFKNRATLTV<br>DRSTSTAYMELSSLRSEDTAVYYC<br>AGGGRLYFDYWGQGTTVTVSS |
| 182 | chAb13 VL CDR3 amino acid sequence | QQYNSYPFT |

INCORPORATION BY REFERENCE

The contents of all references, patents, pending patent applications and published patents, cited throughout this application are hereby expressly incorporated by reference.

EQUIVALENTS

Those skilled in the art will recognize, or be able to ascertain using no more than routine experimentation, many equivalents to the specific embodiments of the invention described herein.

Such equivalents are intended to be encompassed by the following claims.

The invention claimed is:

1. An anti-hB7-H3 antibody drug conjugate comprising the following structure:

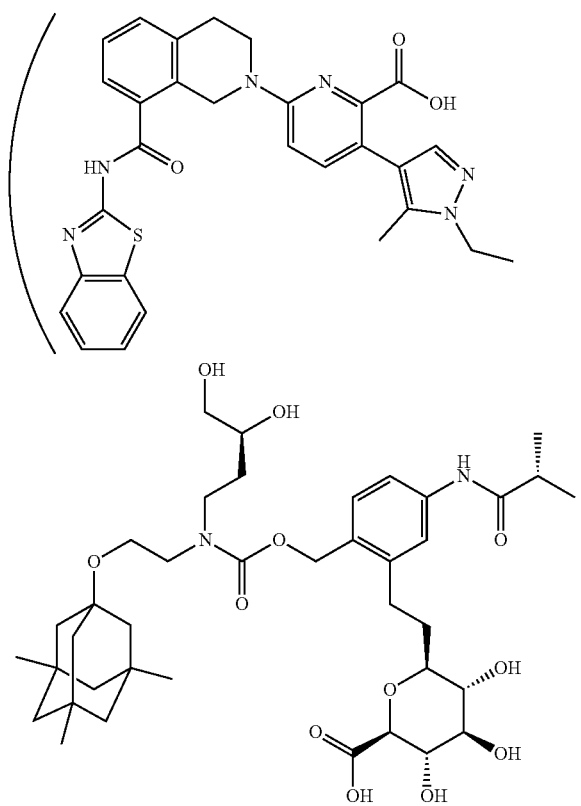

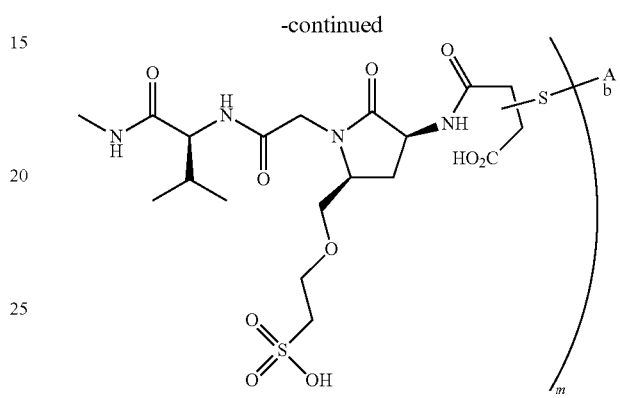

wherein Ab is an IgG1 anti-hB7-H3 antibody comprising
- a heavy chain variable region comprising a heavy chain CDR3 domain comprising the amino acid sequence set forth in SEQ ID NO: 35, a heavy chain CDR2 domain comprising the amino acid sequence set forth in SEQ ID NO: 34, and a heavy chain CDR1 domain comprising the amino acid sequence set forth in SEQ ID NO: 33; and
- a light chain variable region comprising a light chain CDR3 domain comprising the amino acid sequence set forth in SEQ ID NO: 39, a light chain CDR2 domain comprising the amino acid sequence set forth in SEQ ID NO: 38, and a light chain CDR1 domain comprising the amino acid sequence set forth in SEQ ID NO: 37; and wherein m is 2.

2. An anti-hB7-H3 antibody drug conjugate comprising the following structure:

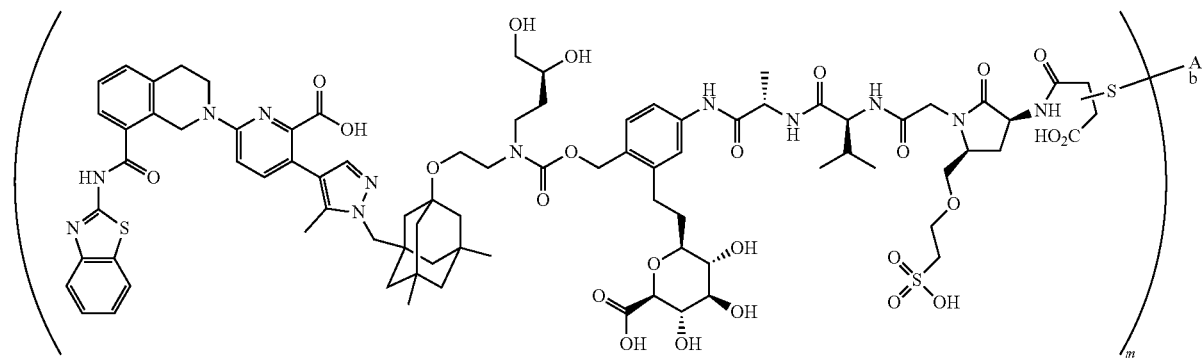

wherein Ab is an IgG1 anti-hB7-H3 antibody comprising a heavy chain variable domain comprising an amino acid sequence set forth in SEQ ID NO: 147 and a light chain variable domain comprising an amino acid sequence set forth in SEQ ID NO: 144; and wherein m is 2.

3. An anti-hB7-H3 antibody drug conjugate comprising the following structure:

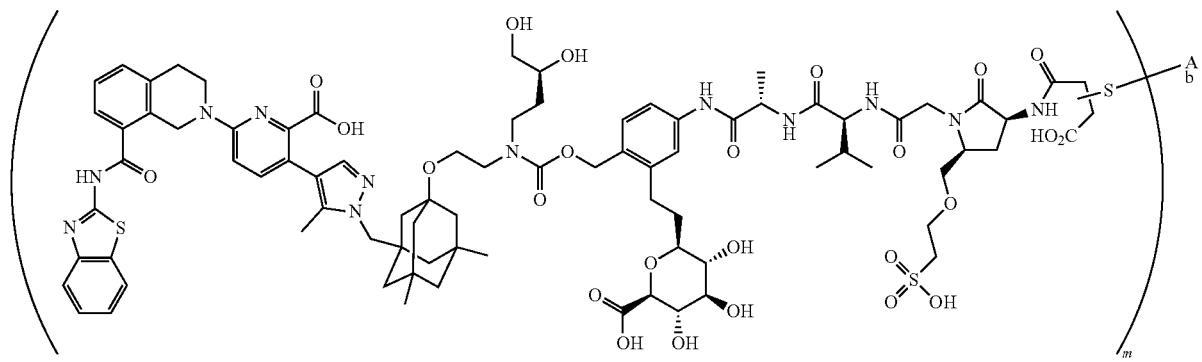

wherein Ab is an IgG1 anti-hB7-H3 antibody comprising a heavy chain comprising the amino acid sequence of SEQ ID NO: 168 and a light chain comprising the amino acid sequence of SEQ ID NO: 169; and wherein m is 2.

* * * * *

SEQUENCE LISTING

```
<160> NUMBER OF SEQ ID NOS: 182

<210> SEQ ID NO 1
<211> LENGTH: 120
<212> TYPE: PRT
<213> ORGANISM: Artificial Sequence
<220> FEATURE:
<223> OTHER INFORMATION: Synthetic: chAb2 VH amino acid sequence

<400> SEQUENCE: 1

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Met Ile His Pro Asp Ser Gly Thr Thr Asn Tyr Asn Glu Lys Phe
    50                  55                  60

Arg Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Val Tyr Tyr Gly Ser Thr Tyr Trp Tyr Phe Asp Val Trp Gly Thr
            100                 105                 110

Gly Thr Thr Val Thr Val Ser Ser
        115                 120
```

```
<210> SEQ ID NO 2
<211> LENGTH: 10
<212> TYPE: PRT
<213> ORGANISM: Artificial Sequence
<220> FEATURE:
<223> OTHER INFORMATION: Synthetic: chAb2 VH CDR1 amino acid sequence

<400> SEQUENCE: 2

Gly Tyr Thr Phe Thr Ser Tyr Trp Met His
1               5                   10

<210> SEQ ID NO 3
<211> LENGTH: 17
<212> TYPE: PRT
<213> ORGANISM: Artificial Sequence
<220> FEATURE:
<223> OTHER INFORMATION: Synthetic: chAb2 VH CDR2 amino acid sequence

<400> SEQUENCE: 3

Met Ile His Pro Asp Ser Gly Thr Thr Asn Tyr Asn Glu Lys Phe Arg
1               5                   10                  15

Ser

<210> SEQ ID NO 4
<211> LENGTH: 11
<212> TYPE: PRT
<213> ORGANISM: Artificial Sequence
<220> FEATURE:
<223> OTHER INFORMATION: Synthetic: chAb2 VH CDR3 amino acid sequence

<400> SEQUENCE: 4

Tyr Tyr Gly Ser Thr Tyr Trp Tyr Phe Asp Val
1               5                   10

<210> SEQ ID NO 5
<211> LENGTH: 112
<212> TYPE: PRT
<213> ORGANISM: Artificial Sequence
<220> FEATURE:
<223> OTHER INFORMATION: Synthetic: chAb2 VL amino acid sequence

<400> SEQUENCE: 5

Asp Val Val Met Thr Gln Thr Pro Leu Ser Leu Pro Val Ser Leu Gly
1               5                   10                  15

Asp Gln Ala Tyr Ile Ser Cys Arg Ser Ser Gln Ser Leu Val His Ile
            20                  25                  30

Asn Gly Asn Thr Tyr Leu His Trp Tyr Arg Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Phe Pro Phe Thr Phe Gly Ser Gly Thr Lys Leu Glu Ile Lys
            100                 105                 110

<210> SEQ ID NO 6
<211> LENGTH: 16
<212> TYPE: PRT
<213> ORGANISM: Artificial Sequence
<220> FEATURE:
<223> OTHER INFORMATION: Synthetic: chAb2 VL CDR1 amino acid sequence
```

```
<400> SEQUENCE: 6

Arg Ser Ser Gln Ser Leu Val His Ile Asn Gly Asn Thr Tyr Leu His
1               5                   10                  15

<210> SEQ ID NO 7
<211> LENGTH: 7
<212> TYPE: PRT
<213> ORGANISM: Artificial Sequence
<220> FEATURE:
<223> OTHER INFORMATION: Synthetic: chAb2, chAb3, chAb10, huAb3VL.1,
      huAb3VL.1a, huAb3VL.1b, huAb3v2.1, huAb3v2.2, huAb3v2.3,
      huAb3v2.4, huAb3v2.5, huAb3v2.6, huAb3v2.7, huAb3v2.8, and
      huAb3v2.9 VL CDR2 amino acid sequence

<400> SEQUENCE: 7

Lys Val Ser Asn Arg Phe Ser
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic: chAb2 VL CDR3 amino acid sequence

<400> SEQUENCE: 8

Ser Gln Ser Thr His Phe Pro Phe Thr
1               5

<210> SEQ ID NO 9
<211> LENGTH: 117
<212> TYPE: PRT
<213> ORGANISM: Artificial Sequence
<220> FEATURE:
<223> OTHER INFORMATION: Synthetic: chAb3 VH amino acid sequence

<400> SEQUENCE: 9

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Ser Ser Tyr
            20                  25                  30

Trp Met His Trp Val Lys Gln Arg Pro Gly Gln Gly Leu Glu Trp Ile
        35                  40                  45

Gly Leu Ile His Pro Asp Ser Gly Ser Thr Asn Tyr Asn Glu Met Phe
    50                  55                  60

Lys Asn Lys Ala Thr Leu Thr Val Asp Arg Ser Ser Ser Thr Ala Tyr
65                  70                  75                  80

Val Gln Leu Ser Ser Leu Thr Ser Glu Asp Ser Ala Val Tyr Phe Cys
                85                  90                  95

Ala Gly Gly Gly Arg Leu Tyr Phe Asp Tyr Trp Gly Gln Gly Thr Thr
            100                 105                 110

Leu Thr Val Ser Ser
        115

<210> SEQ ID NO 10
<211> LENGTH: 10
<212> TYPE: PRT
<213> ORGANISM: Artificial Sequence
<220> FEATURE:
<223> OTHER INFORMATION: Synthetic: chAb3, huAb3VH.1, huAb3VH.1a,
      huAb3VH.1b, huAb3v2.1, huAb3v2.2, huAb3v2.3, huAb3v2.4, huAb3v2.5,
      huAb3v2.6, huAb3v2.7, huAb3v2.8, and huAb3v2.9 VH CDR1 amino acid
      sequence
```

```
<400> SEQUENCE: 10

Gly Tyr Thr Phe Ser Ser Tyr Trp Met His
1               5                   10

<210> SEQ ID NO 11
<211> LENGTH: 17
<212> TYPE: PRT
<213> ORGANISM: Artificial Sequence
<220> FEATURE:
<223> OTHER INFORMATION: Synthetic: chAb3, huAb3VH.1, huAb3VH.1a, and
      huAb3VH.1b VH CDR2 amino acid sequence

<400> SEQUENCE: 11

Leu Ile His Pro Asp Ser Gly Ser Thr Asn Tyr Asn Glu Met Phe Lys
1               5                   10                  15

Asn

<210> SEQ ID NO 12
<211> LENGTH: 8
<212> TYPE: PRT
<213> ORGANISM: Artificial Sequence
<220> FEATURE:
<223> OTHER INFORMATION: Synthetic: chAb3, huAb3VH.1, huAb3VH.1a,
      huAb3VH.1b, huAb3v2.1, huAb3v2.2, huAb3v2.3, huAb3v2.4, huAb3v2.5,
      huAb3v2.6, huAb3v2.7, huAb3v2.8, and huAb3v2.9 VH CDR3 amino acid
      sequence

<400> SEQUENCE: 12

Gly Gly Arg Leu Tyr Phe Asp Tyr
1               5

<210> SEQ ID NO 13
<211> LENGTH: 112
<212> TYPE: PRT
<213> ORGANISM: Artificial Sequence
<220> FEATURE:
<223> OTHER INFORMATION: Synthetic: chAb3 VL amino acid sequence

<400> SEQUENCE: 13

Asp Val Val Met Thr Gln Thr Pro Leu Ser Leu Pro Val Ser Leu Gly
1               5                   10                  15

Asp Gln Ala Ser Ile Ser Cys Arg Ser Gln Ser Leu Val His Ser
            20                  25                  30

Asn Gly Asp Thr Tyr Leu Arg Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Thr Arg Val Glu Ala Glu Asp Leu Gly Val Tyr Phe Cys Ser Gln Ser
                85                  90                  95

Thr His Val Pro Tyr Thr Phe Gly Gly Gly Thr Lys Leu Glu Ile Lys
                100                 105                 110

<210> SEQ ID NO 14
<211> LENGTH: 16
<212> TYPE: PRT
<213> ORGANISM: Artificial Sequence
<220> FEATURE:
<223> OTHER INFORMATION: Synthetic: chAb3, huAb3VL.1, huAb3VL.1a, and
      huAb3VL.1b VL CDR1 amino acid sequence

<400> SEQUENCE: 14
```

```
Arg Ser Ser Gln Ser Leu Val His Ser Asn Gly Asp Thr Tyr Leu Arg
1               5                   10                  15

<210> SEQ ID NO 15
<211> LENGTH: 9
<212> TYPE: PRT
<213> ORGANISM: Artificial Sequence
<220> FEATURE:
<223> OTHER INFORMATION: Synthetic: chAb3, huAb3VL.1, huAb3VL.1a,
      huAb3VL.1b, huAb3v2.1, huAb3v2.2, huAb3v2.3, huAb3v2.4, huAb3v2.5,
      huAb3v2.6, huAb3v2.7, huAb3v2.8, and huAb3v2.9 VL CDR3 amino acid
      sequence

<400> SEQUENCE: 15

Ser Gln Ser Thr His Val Pro Tyr Thr
1               5

<210> SEQ ID NO 16
<211> LENGTH: 117
<212> TYPE: PRT
<213> ORGANISM: Artificial Sequence
<220> FEATURE:
<223> OTHER INFORMATION: Synthetic: chAb4 VH amino acid sequence

<400> SEQUENCE: 16

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Ser Phe Thr Ser Tyr
            20                  25                  30

Trp Met His Trp Val Lys Gln Arg Pro Gly Gln Gly Leu Glu Trp Ile
        35                  40                  45

Gly Met Ile His Pro Asn Ser Gly Ser Asn Asn Tyr Asn Glu Lys Phe
    50                  55                  60

Lys Ser Lys Ala Thr Leu Thr Val Asp Lys Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Arg Arg Leu Gly Leu His Phe Asp Tyr Trp Gly Gln Gly Thr Thr
            100                 105                 110

Leu Thr Val Ser Ser
        115

<210> SEQ ID NO 17
<211> LENGTH: 10
<212> TYPE: PRT
<213> ORGANISM: Artificial Sequence
<220> FEATURE:
<223> OTHER INFORMATION: Synthetic: chAb4 VH CDR1 amino acid sequence

<400> SEQUENCE: 17

Gly Tyr Ser Phe Thr Ser Tyr Trp Met His
1               5                   10

<210> SEQ ID NO 18
<211> LENGTH: 17
<212> TYPE: PRT
<213> ORGANISM: Artificial Sequence
<220> FEATURE:
<223> OTHER INFORMATION: Synthetic: chAb4 VH CDR2 amino acid sequence

<400> SEQUENCE: 18

Met Ile His Pro Asn Ser Gly Ser Asn Asn Tyr Asn Glu Lys Phe Lys
1               5                   10                  15
```

Ser

<210> SEQ ID NO 19
<211> LENGTH: 8
<212> TYPE: PRT
<213> ORGANISM: Artificial Sequence
<220> FEATURE:
<223> OTHER INFORMATION: Synthetic: chAb4 VH CDR3 amino acid sequence

<400> SEQUENCE: 19

Arg Leu Gly Leu His Phe Asp Tyr
1               5

<210> SEQ ID NO 20
<211> LENGTH: 107
<212> TYPE: PRT
<213> ORGANISM: Artificial Sequence
<220> FEATURE:
<223> OTHER INFORMATION: Synthetic: chAb4 VL amino acid sequence

<400> SEQUENCE: 20

Asp Ile Val Met Thr Gln Ser Gln Lys Phe Met Ser Thr Pro Val Gly
1               5                   10                  15

Asp Arg Val Ser Ile Thr Cys Lys Ala Ser Gln Asn Val Gly Thr Ala
            20                  25                  30

Val Ala Trp Tyr Gln Gln Lys Pro Gly Gln Ser Pro Lys Leu Leu Ile
        35                  40                  45

Tyr Ser Ala Ser Asn Arg Tyr Thr Gly Val Pro Asp Arg Phe Thr Gly
    50                  55                  60

Ser Gly Ser Gly Thr Asp Phe Thr Leu Thr Ile Ser Asn Met Gln Ser
65                  70                  75                  80

Glu Asp Leu Ala Asp Tyr Phe Cys Gln Gln Tyr Ser Ser Tyr Pro Tyr
                85                  90                  95

Thr Phe Gly Gly Gly Thr Lys Leu Glu Ile Lys
            100                 105

<210> SEQ ID NO 21
<211> LENGTH: 11
<212> TYPE: PRT
<213> ORGANISM: Artificial Sequence
<220> FEATURE:
<223> OTHER INFORMATION: Synthetic: chAb4 VL CDR1 amino acid sequence

<400> SEQUENCE: 21

Lys Ala Ser Gln Asn Val Gly Thr Ala Val Ala
1               5                   10

<210> SEQ ID NO 22
<211> LENGTH: 7
<212> TYPE: PRT
<213> ORGANISM: Artificial Sequence
<220> FEATURE:
<223> OTHER INFORMATION: Synthetic: chAb4 VL CDR2 amino acid sequence

<400> SEQUENCE: 22

Ser Ala Ser Asn Arg Tyr Thr
1               5

<210> SEQ ID NO 23
<211> LENGTH: 9
<212> TYPE: PRT
<213> ORGANISM: Artificial Sequence
<220> FEATURE:

<223> OTHER INFORMATION: Synthetic: chAb4 VL CDR3 amino acid sequence

<400> SEQUENCE: 23

Gln Gln Tyr Ser Ser Tyr Pro Tyr Thr
1               5

<210> SEQ ID NO 24
<211> LENGTH: 121
<212> TYPE: PRT
<213> ORGANISM: Artificial Sequence
<220> FEATURE:
<223> OTHER INFORMATION: Synthetic: chAb18 VH amino acid sequence

<400> SEQUENCE: 24

Gln Val Gln Leu Gln Gln Ser Ala Ala Glu Leu Ala Arg Pro Gly Ala
1               5                   10                  15

Ser Val Lys Met Ser Cys Lys Ala Ser Gly Tyr Ser Phe Thr Ser Tyr
            20                  25                  30

Thr Ile His Trp Val Lys Gln Arg Pro Gly Gln Gly Leu Glu Trp Ile
        35                  40                  45

Gly Tyr Ile Asn Pro Asn Ser Arg Asn Thr Asp Tyr Asn Gln Lys Phe
    50                  55                  60

Lys Asp Glu Thr Thr Leu Thr Ala Asp Arg Ser Ser Ser Thr Ala Tyr
65                  70                  75                  80

Met Gln Leu Ile Ser Leu Thr Ser Glu Asp Ser Ala Val Tyr Tyr Cys
                85                  90                  95

Ala Arg Tyr Ser Gly Ser Thr Pro Tyr Trp Tyr Phe Asp Val Trp Gly
            100                 105                 110

Ala Gly Thr Thr Val Thr Val Ser Ser
        115                 120

<210> SEQ ID NO 25
<211> LENGTH: 10
<212> TYPE: PRT
<213> ORGANISM: Artificial Sequence
<220> FEATURE:
<223> OTHER INFORMATION: Synthetic: chAb18, huAb18VH.1, huAb18VH.1a, and
      huAb18VH.1b VH CDR1 amino acid sequence

<400> SEQUENCE: 25

Gly Tyr Ser Phe Thr Ser Tyr Thr Ile His
1               5                   10

<210> SEQ ID NO 26
<211> LENGTH: 17
<212> TYPE: PRT
<213> ORGANISM: Artificial Sequence
<220> FEATURE:
<223> OTHER INFORMATION: Synthetic: chAb18, huAb18VH.1, and huAb18VH.1a
      VH CDR2 amino acid sequence

<400> SEQUENCE: 26

Tyr Ile Asn Pro Asn Ser Arg Asn Thr Asp Tyr Asn Gln Lys Phe Lys
1               5                   10                  15

Asp

<210> SEQ ID NO 27
<211> LENGTH: 12
<212> TYPE: PRT
<213> ORGANISM: Artificial Sequence
<220> FEATURE:
<223> OTHER INFORMATION: Synthetic: chAb18, huAb18VH.1, huAb18VH.1a, and
      huAb18VH.1b VH CDR3 amino acid sequence

<400> SEQUENCE: 27

Tyr Ser Gly Ser Thr Pro Tyr Trp Tyr Phe Asp Val
1               5                   10

<210> SEQ ID NO 28
<211> LENGTH: 106
<212> TYPE: PRT
<213> ORGANISM: Artificial Sequence
<220> FEATURE:
<223> OTHER INFORMATION: Synthetic: chAb18 VL amino acid sequence

<400> SEQUENCE: 28

Gln Ile Val Leu Thr Gln Ser Pro Ala Ile Leu Ser Ala Ser Pro Gly
1               5                   10                  15

Glu Lys Val Thr Met Thr Cys Arg Ala Ser Ser Ser Val Ser Tyr Met
            20                  25                  30

Asn Trp Tyr Gln Gln Lys Pro Gly Ser Ser Pro Lys Pro Trp Ile Tyr
        35                  40                  45

Ala Thr Ser Asn Leu Ala Ser Gly Val Pro Ala Arg Phe Ser Val Ser
    50                  55                  60

Val Ser Gly Thr Ser His Ser Leu Thr Ile Ser Arg Val Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys
            100                 105

<210> SEQ ID NO 29
<211> LENGTH: 10
<212> TYPE: PRT
<213> ORGANISM: Artificial Sequence
<220> FEATURE:
<223> OTHER INFORMATION: Synthetic: chAb18, huAb18VL.1, huAb18VL.1a,
      huAb18VL.1b, huAb18VL.2, and huAb18VL.2a, VL CDR1 amino acid
      sequence

<400> SEQUENCE: 29

Arg Ala Ser Ser Ser Val Ser Tyr Met Asn
1               5                   10

<210> SEQ ID NO 30
<211> LENGTH: 7
<212> TYPE: PRT
<213> ORGANISM: Artificial Sequence
<220> FEATURE:
<223> OTHER INFORMATION: Synthetic: chAb18, huAb18VL.1, huAb18VL.1a,
      huAb18VL.1b, huAb18VL.2, and huAb18VL.2a, VL CDR2 amino acid
      sequence

<400> SEQUENCE: 30

Ala Thr Ser Asn Leu Ala Ser
1               5

<210> SEQ ID NO 31
<211> LENGTH: 9
<212> TYPE: PRT
<213> ORGANISM: Artificial Sequence
<220> FEATURE:
<223> OTHER INFORMATION: Synthetic: chAb18, huAb18VL.1, huAb18VL.1a,
      huAb18VL.1b, huAb18VL.2, and huAb18VL.2a, VL CDR3 amino acid
      sequence

<400> SEQUENCE: 31

Gln Gln Trp Ser Ser Asn Pro Leu Thr
1               5

<210> SEQ ID NO 32
<211> LENGTH: 116
<212> TYPE: PRT
<213> ORGANISM: Artificial Sequence
<220> FEATURE:
<223> OTHER INFORMATION: Synthetic: chAb13 VH amino acid sequence

<400> SEQUENCE: 32

Asp Val Gln Leu Gln Glu Ser Gly Pro Asp Leu Val Lys Pro Ser Gln
1               5                   10                  15

Ser Leu Ser Leu Thr Cys Thr Val Thr Gly Tyr Ser Ile Thr Ser Gly
            20                  25                  30

Tyr Ser Trp His Trp Ile Arg Gln Phe Pro Gly Asn Lys Leu Glu Trp
        35                  40                  45

Met Gly Tyr Ile His Ser Ser Gly Ser Thr Asn Tyr Asn Pro Ser Leu
    50                  55                  60

Lys Ser Arg Ile Ser Ile Asn Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Gly Tyr Asp Asp Tyr Phe Glu Tyr Trp Gly Gln Gly Thr Thr Leu
            100                 105                 110

Thr Val Ser Ser
        115

<210> SEQ ID NO 33
<211> LENGTH: 11
<212> TYPE: PRT
<213> ORGANISM: Artificial Sequence
<220> FEATURE:
<223> OTHER INFORMATION: Synthetic: chAb13, huAb13Vh.1, huAb13Vh.1a,
      huAb13Vh.1b, huAb13v1, huAb13v2, huAb13v3, huAb13v4, huAb13v5,
      huAb13v6, huAb13v7, huAb13v8, and huAb13v9 VH CDR1 amino acid
      sequence

<400> SEQUENCE: 33

Gly Tyr Ser Ile Thr Ser Gly Tyr Ser Trp His
1               5                   10

<210> SEQ ID NO 34
<211> LENGTH: 16
<212> TYPE: PRT
<213> ORGANISM: Artificial Sequence
<220> FEATURE:
<223> OTHER INFORMATION: Synthetic: chAb13, huAb13Vh.1, huAb13Vh.1a,
      huAb13Vh.1b, huAb13v1, huAb13v2, huAb13v3, huAb13v4, huAb13v5,
      huAb13v6, huAb13v7, huAb13v8, and huAb13v9VH CDR2 amino acid
      sequence

<400> SEQUENCE: 34

Tyr Ile His Ser Ser Gly Ser Thr Asn Tyr Asn Pro Ser Leu Lys Ser
1               5                   10                  15

<210> SEQ ID NO 35
<211> LENGTH: 7
<212> TYPE: PRT
<213> ORGANISM: Artificial Sequence
<220> FEATURE:
<223> OTHER INFORMATION: Synthetic: chAb13, huAb13Vh.1, huAb13Vh.1a,
      huAb13Vh.1b, huAb13v1, huAb13v2, huAb13v3, huAb13v4, huAb13v5,
      huAb13v6, huAb13v7, huAb13v8, and huAb13v9 VH CDR3 amino acid
      sequence

<400> SEQUENCE: 35

Tyr Asp Asp Tyr Phe Glu Tyr
1               5

<210> SEQ ID NO 36
<211> LENGTH: 107
<212> TYPE: PRT
<213> ORGANISM: Artificial Sequence
<220> FEATURE:
<223> OTHER INFORMATION: Synthetic: chAb13 VL amino acid sequence

<400> SEQUENCE: 36

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Phe Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Phe
                85                  90                  95

Thr Phe Gly Ser Gly Thr Lys Leu Glu Ile Lys
            100                 105

<210> SEQ ID NO 37
<211> LENGTH: 11
<212> TYPE: PRT
<213> ORGANISM: Artificial Sequence
<220> FEATURE:
<223> OTHER INFORMATION: Synthetic: chAb13, huAb13VL.1, huAb13VL.1a,
      huAb13VL.1b, huAb13v1, huAb13v2, huAb13v3, huAb13v4, huAb13v5,
      huAb13v6, huAb13v7, huAb13v8, and huAb13v9 VL CDR1 amino acid
      sequence

<400> SEQUENCE: 37

Lys Ala Ser Gln Asn Val Gly Phe Asn Val Ala
1               5                   10

<210> SEQ ID NO 38
<211> LENGTH: 7
<212> TYPE: PRT
<213> ORGANISM: Artificial Sequence
<220> FEATURE:
<223> OTHER INFORMATION: Synthetic: chAb13, huAb13VL.1, huAb13VL.1a,
      huAb13VL.1b, huAb13v1, huAb13v2, huAb13v3, huAb13v4, huAb13v5,
      huAb13v6, huAb13v7, huAb13v8, and huAb13v9 VL CDR2 amino acid
      sequence

<400> SEQUENCE: 38

Ser Ala Ser Tyr Arg Tyr Ser
1               5

<210> SEQ ID NO 39
<211> LENGTH: 9
<212> TYPE: PRT
<213> ORGANISM: Artificial Sequence
<220> FEATURE:
<223> OTHER INFORMATION: Synthetic: huAb13VL.1, huAb13VL.1a, huAb13VL.
      1b, huAb13v1, huAb13v2, huAb13v3, huAb13v4, huAb13v5, huAb13v6,
      huAb13v7, huAb13v8, and huAb13v9 VL CDR3 amino acid
      sequence -continued

```
<400> SEQUENCE: 39

Gln Gln Tyr Asn Trp Tyr Pro Phe Thr
1               5

<210> SEQ ID NO 40
<211> LENGTH: 118
<212> TYPE: PRT
<213> ORGANISM: Artificial Sequence
<220> FEATURE:
<223> OTHER INFORMATION: Synthetic: chAb12 VH amino acid sequence

<400> SEQUENCE: 40

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Thr Pro Glu Lys Arg Leu Glu Trp Val
        35                  40                  45

Ala Thr Ile Ser Ser Gly Thr Asn Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Thr Ser Leu Arg Ser Glu Asp Thr Ala Met Tyr Tyr Cys
                85                  90                  95

Ala Arg Gln Gly Arg Tyr Ser Trp Ile Ala Tyr Trp Gly Gln Gly Thr
            100                 105                 110

Leu Val Thr Val Ser Ala
        115

<210> SEQ ID NO 41
<211> LENGTH: 10
<212> TYPE: PRT
<213> ORGANISM: Artificial Sequence
<220> FEATURE:
<223> OTHER INFORMATION: Synthetic: chAb12 VH CDR1 amino acid sequence

<400> SEQUENCE: 41

Gly Phe Thr Phe Ser Ser Tyr Ala Met Ser
1               5                   10

<210> SEQ ID NO 42
<211> LENGTH: 17
<212> TYPE: PRT
<213> ORGANISM: Artificial Sequence
<220> FEATURE:
<223> OTHER INFORMATION: Synthetic: chAb12 VH CDR2 amino acid sequence

<400> SEQUENCE: 42

Thr Ile Ser Ser Gly Thr Asn Tyr Thr Tyr Tyr Pro Asp Ser Val Lys
1               5                   10                  15

Gly

<210> SEQ ID NO 43
<211> LENGTH: 9
<212> TYPE: PRT
<213> ORGANISM: Artificial Sequence
<220> FEATURE:
<223> OTHER INFORMATION: Synthetic: chAb12 VH CDR3 amino acid sequence

<400> SEQUENCE: 43

Gln Gly Arg Tyr Ser Trp Ile Ala Tyr
```

<210> SEQ ID NO 44
<211> LENGTH: 110
<212> TYPE: PRT
<213> ORGANISM: Artificial Sequence
<220> FEATURE:
<223> OTHER INFORMATION: Synthetic: chAb12 VL amino acid sequence

<400> SEQUENCE: 44

Asp Ile Val Leu Thr Gln Ser Pro Ala Ser Leu Ala Val Ser Leu Gly
1               5                   10                  15
Gln Arg Ala Thr Ile Ser Cys Arg Ala Ser Lys Ser Val Ser Thr Ser
            20                  25                  30
Asp Tyr Ser Tyr Met His Trp Asn Gln Gln Lys Pro Gly Gln Pro Pro
        35                  40                  45
Lys Leu Leu Ile Tyr Leu Ala Ser Asn Leu Glu Ser Gly Val Pro Ala
    50                  55                  60
Arg Phe Ser Gly Ser Gly Ser Gly Thr Asp Phe Thr Leu Asn Ile His
65                  70                  75                  80
Pro Val Glu Glu Glu Asp Ala Ala Thr Tyr Tyr Cys Gln His Ser Arg
                85                  90                  95
Glu Leu Leu Thr Phe Gly Ala Gly Thr Lys Leu Glu Leu Lys
            100                 105                 110

<210> SEQ ID NO 45
<211> LENGTH: 15
<212> TYPE: PRT
<213> ORGANISM: Artificial Sequence
<220> FEATURE:
<223> OTHER INFORMATION: Synthetic: chAb12 VL CDR1 amino acid sequence

<400> SEQUENCE: 45

Arg Ala Ser Lys Ser Val Ser Thr Ser Asp Tyr Ser Tyr Met His
1               5                   10                  15

<210> SEQ ID NO 46
<211> LENGTH: 7
<212> TYPE: PRT
<213> ORGANISM: Artificial Sequence
<220> FEATURE:
<223> OTHER INFORMATION: Synthetic: chAb12 and chAb17 VL CDR2 amino acid
      sequence

<400> SEQUENCE: 46

Leu Ala Ser Asn Leu Glu Ser
1               5

<210> SEQ ID NO 47
<211> LENGTH: 8
<212> TYPE: PRT
<213> ORGANISM: Artificial Sequence
<220> FEATURE:
<223> OTHER INFORMATION: Synthetic: chAb12 VL CDR3 amino acid sequence

<400> SEQUENCE: 47

Gln His Ser Arg Glu Leu Leu Thr
1               5

<210> SEQ ID NO 48
<211> LENGTH: 118
<212> TYPE: PRT
<213> ORGANISM: Artificial Sequence
<220> FEATURE:

<223> OTHER INFORMATION: Synthetic: chAb14 VH amino acid sequence

<400> SEQUENCE: 48

Glu Val Lys Leu Val Glu Ser Gly Gly Gly Leu Val Lys Pro Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Glu Lys Arg Leu Glu Trp Val
        35                  40                  45

Ala Thr Ile Ser Gly Gly Gly Thr Asn Thr Tyr Tyr Pro Asp Ser Val
    50                  55                  60

Glu Gly Arg Phe Thr Ile Ser Arg Asp Asn Ala Lys Asn Phe Leu Tyr
65                  70                  75                  80

Leu Gln Met Ser Ser Leu Arg Ser Glu Asp Thr Ala Leu Tyr Tyr Cys
                85                  90                  95

Ala Arg His Tyr Gly Ser Gln Thr Met Asp Tyr Trp Gly Gln Gly Thr
            100                 105                 110

Ser Val Thr Val Ser Ser
        115

<210> SEQ ID NO 49
<211> LENGTH: 10
<212> TYPE: PRT
<213> ORGANISM: Artificial Sequence
<220> FEATURE:
<223> OTHER INFORMATION: Synthetic: chAb14 and chAb8 VH CDR1 amino acid
      sequence

<400> SEQUENCE: 49

Gly Phe Thr Phe Ser Ser Tyr Gly Met Ser
1               5                   10

<210> SEQ ID NO 50
<211> LENGTH: 17
<212> TYPE: PRT
<213> ORGANISM: Artificial Sequence
<220> FEATURE:
<223> OTHER INFORMATION: Synthetic: chAb14 VH CDR2 amino acid sequence

<400> SEQUENCE: 50

Thr Ile Ser Gly Gly Gly Thr Asn Thr Tyr Tyr Pro Asp Ser Val Glu
1               5                   10                  15

Gly

<210> SEQ ID NO 51
<211> LENGTH: 9
<212> TYPE: PRT
<213> ORGANISM: Artificial Sequence
<220> FEATURE:
<223> OTHER INFORMATION: Synthetic: chAb14 VH CDR3 amino acid sequence

<400> SEQUENCE: 51

His Tyr Gly Ser Gln Thr Met Asp Tyr
1               5

<210> SEQ ID NO 52
<211> LENGTH: 107
<212> TYPE: PRT
<213> ORGANISM: Artificial Sequence
<220> FEATURE:
<223> OTHER INFORMATION: Synthetic: chAb14 VL amino acid sequence

<400> SEQUENCE: 52

```
Asp Ile Gln Met Thr Gln Ser Pro Ala Ser Leu Ser Ala Ser Val Gly
1               5                   10                  15

Glu Thr Val Thr Ile Thr Cys Arg Thr Ser Gly Asn Ile His Asn Tyr
            20                  25                  30

Leu Thr Trp Tyr Gln Gln Lys Gln Gly Lys Ser Pro Gln Leu Leu Val
        35                  40                  45

Tyr Asn Ala Lys Thr Leu Ala Asp Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His Phe Trp Ser Ile Met Trp
                85                  90                  95

Thr Phe Gly Gly Gly Thr Lys Leu Glu Ile Lys
            100                 105
```

<210> SEQ ID NO 53
<211> LENGTH: 11
<212> TYPE: PRT
<213> ORGANISM: Artificial Sequence
<220> FEATURE:
<223> OTHER INFORMATION: Synthetic: chAb14 VL CDR1 amino acid sequence

<400> SEQUENCE: 53

```
Arg Thr Ser Gly Asn Ile His Asn Tyr Leu Thr
1               5                   10
```

<210> SEQ ID NO 54
<211> LENGTH: 7
<212> TYPE: PRT
<213> ORGANISM: Artificial Sequence
<220> FEATURE:
<223> OTHER INFORMATION: Synthetic: chAb14 VL CDR2 amino acid sequence

<400> SEQUENCE: 54

```
Asn Ala Lys Thr Leu Ala Asp
1               5
```

<210> SEQ ID NO 55
<211> LENGTH: 9
<212> TYPE: PRT
<213> ORGANISM: Artificial Sequence
<220> FEATURE:
<223> OTHER INFORMATION: Synthetic: chAb14 VL CDR3 amino acid sequence

<400> SEQUENCE: 55

```
Gln His Phe Trp Ser Ile Met Trp Thr
1               5
```

<210> SEQ ID NO 56
<211> LENGTH: 121
<212> TYPE: PRT
<213> ORGANISM: Artificial Sequence
<220> FEATURE:
<223> OTHER INFORMATION: Synthetic: chAb6 VH amino acid sequence

<400> SEQUENCE: 56

```
Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Ser Arg Tyr
            20                  25                  30

Trp Ile Glu Trp Val Lys Gln Arg Pro Gly His Gly Leu Glu Trp Ile
        35                  40                  45
```

```
Gly Glu Ile Leu Pro Gly Ser Gly Ser Thr Asn Tyr Asn Glu Lys Phe
        50                  55                  60

Lys Gly Lys Ala Thr Phe Thr Ala Asp Thr Ser Ser Asn Thr Ala Tyr
 65                  70                  75                  80

Met Gln Val Ser Ser Leu Thr Ser Glu Asp Ser Ala Val His Tyr Cys
                 85                  90                  95

Ala Arg Arg Gly Tyr Gly Tyr Val Pro Tyr Ala Leu Asp Tyr Trp Gly
            100                 105                 110

Gln Gly Thr Ser Val Thr Val Ser Ser
            115                 120

<210> SEQ ID NO 57
<211> LENGTH: 10
<212> TYPE: PRT
<213> ORGANISM: Artificial Sequence
<220> FEATURE:
<223> OTHER INFORMATION: Synthetic: chAb6 VH CDR1 amino acid sequence

<400> SEQUENCE: 57

Gly Tyr Thr Phe Ser Arg Tyr Trp Ile Glu
1               5                   10

<210> SEQ ID NO 58
<211> LENGTH: 17
<212> TYPE: PRT
<213> ORGANISM: Artificial Sequence
<220> FEATURE:
<223> OTHER INFORMATION: Synthetic: chAb6 VH CDR2 amino acid sequence

<400> SEQUENCE: 58

Glu Ile Leu Pro Gly Ser Gly Ser Thr Asn Tyr Asn Glu Lys Phe Lys
1               5                   10                  15

Gly

<210> SEQ ID NO 59
<211> LENGTH: 12
<212> TYPE: PRT
<213> ORGANISM: Artificial Sequence
<220> FEATURE:
<223> OTHER INFORMATION: Synthetic: chAb6 VH CDR3 amino acid sequence

<400> SEQUENCE: 59

Arg Gly Tyr Gly Tyr Val Pro Tyr Ala Leu Asp Tyr
1               5                   10

<210> SEQ ID NO 60
<211> LENGTH: 107
<212> TYPE: PRT
<213> ORGANISM: Artificial Sequence
<220> FEATURE:
<223> OTHER INFORMATION: Synthetic: chAb6 VL amino acid sequence

<400> SEQUENCE: 60

Glu Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Ser
            20                  25                  30

Leu Asn Trp Tyr Gln Gln Lys Pro Asp Gly Thr Val Asn Leu Leu Ile
        35                  40                  45

Tyr Tyr Thr Ser Arg Leu Tyr Ser Gly Val Pro Ser Arg Phe Ser Gly
    50                  55                  60
```

```
Ser Gly Ser Gly Thr Asp Tyr Ser Leu Thr Ile Ser Asn Leu Glu Gln
 65                  70                  75                  80

Glu Asp Ile Ala Thr Tyr Phe Cys Gln Gln Gly Asn Thr Leu Pro Tyr
                 85                  90                  95

Thr Phe Gly Gly Gly Thr Lys Leu Glu Ile Lys
            100                 105
```

<210> SEQ ID NO 61
<211> LENGTH: 11
<212> TYPE: PRT
<213> ORGANISM: Artificial Sequence
<220> FEATURE:
<223> OTHER INFORMATION: Synthetic: chAb6 VL CDR1 amino acid sequence

<400> SEQUENCE: 61

```
Arg Ala Ser Gln Asp Ile Ser Asn Ser Leu Asn
1               5                   10
```

<210> SEQ ID NO 62
<211> LENGTH: 7
<212> TYPE: PRT
<213> ORGANISM: Artificial Sequence
<220> FEATURE:
<223> OTHER INFORMATION: Synthetic: chAb6 VL CDR2 amino acid sequence

<400> SEQUENCE: 62

```
Tyr Thr Ser Arg Leu Tyr Ser
1               5
```

<210> SEQ ID NO 63
<211> LENGTH: 9
<212> TYPE: PRT
<213> ORGANISM: Artificial Sequence
<220> FEATURE:
<223> OTHER INFORMATION: Synthetic: chAb6 VL CDR3 amino acid sequence

<400> SEQUENCE: 63

```
Gln Gln Gly Asn Thr Leu Pro Tyr Thr
1               5
```

<210> SEQ ID NO 64
<211> LENGTH: 120
<212> TYPE: PRT
<213> ORGANISM: Artificial Sequence
<220> FEATURE:
<223> OTHER INFORMATION: Synthetic: chAb11 VH amino acid sequence

<400> SEQUENCE: 64

```
Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asn Tyr
                20                  25                  30

Tyr Met Ser Trp Val Arg Gln Pro Pro Gly Lys Ala Leu Glu Trp Leu
            35                  40                  45

Gly Phe Ile Arg Asn Lys Ala Asn Asp Tyr Thr Thr Glu Tyr Ser Ala
        50                  55                  60

Ser Val Lys Gly Arg Phe Thr Ile Ser Arg Asp Asn Ser Gln Ser Ile
 65                  70                  75                  80

Leu Tyr Leu Gln Met Asn Thr Leu Arg Ala Glu Asp Ser Ala Thr Tyr
                 85                  90                  95

Tyr Cys Ala Arg Glu Ser Pro Gly Asn Pro Phe Ala Tyr Trp Gly Gln
            100                 105                 110
```

```
Gly Thr Leu Val Thr Val Ser Ala
        115                 120

<210> SEQ ID NO 65
<211> LENGTH: 10
<212> TYPE: PRT
<213> ORGANISM: Artificial Sequence
<220> FEATURE:
<223> OTHER INFORMATION: Synthetic: chAb11 VH CDR1 amino acid sequence

<400> SEQUENCE: 65

Gly Phe Thr Phe Thr Asn Tyr Tyr Met Ser
1               5                   10

<210> SEQ ID NO 66
<211> LENGTH: 19
<212> TYPE: PRT
<213> ORGANISM: Artificial Sequence
<220> FEATURE:
<223> OTHER INFORMATION: Synthetic: chAb11 VH CDR2 amino acid sequence

<400> SEQUENCE: 66

Phe Ile Arg Asn Lys Ala Asn Asp Tyr Thr Thr Glu Tyr Ser Ala Ser
1               5                   10                  15

Val Lys Gly

<210> SEQ ID NO 67
<211> LENGTH: 9
<212> TYPE: PRT
<213> ORGANISM: Artificial Sequence
<220> FEATURE:
<223> OTHER INFORMATION: Synthetic: chAb11 VH CDR3 amino acid sequence

<400> SEQUENCE: 67

Glu Ser Pro Gly Asn Pro Phe Ala Tyr
1               5

<210> SEQ ID NO 68
<211> LENGTH: 113
<212> TYPE: PRT
<213> ORGANISM: Artificial Sequence
<220> FEATURE:
<223> OTHER INFORMATION: Synthetic: chAb11 VL amino acid sequence

<400> SEQUENCE: 68

Asp Ile Val Met Thr Gln Ser Pro Ser Ser Leu Thr Val Thr Ala Gly
1               5                   10                  15

Glu Lys Val Thr Met Thr Cys Lys Ser Ser Gln Ser Leu Leu Asn Ser
            20                  25                  30

Gly Thr Gln Lys Asn Phe Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Phe Cys Gln Asn
                85                  90                  95

Asp Tyr Ile Tyr Pro Leu Thr Phe Gly Ala Gly Thr Lys Leu Glu Leu
            100                 105                 110

Lys

<210> SEQ ID NO 69
```

```
<211> LENGTH: 17
<212> TYPE: PRT
<213> ORGANISM: Artificial Sequence
<220> FEATURE:
<223> OTHER INFORMATION: Synthetic: chAb11 VL CDR1 amino acid sequence

<400> SEQUENCE: 69

Lys Ser Ser Gln Ser Leu Leu Asn Ser Gly Thr Gln Lys Asn Phe Leu
1               5                   10                  15

Thr

<210> SEQ ID NO 70
<211> LENGTH: 7
<212> TYPE: PRT
<213> ORGANISM: Artificial Sequence
<220> FEATURE:
<223> OTHER INFORMATION: Synthetic: chAb11 VL CDR2 amino acid sequence

<400> SEQUENCE: 70

Trp Ala Ser Thr Arg Glu Ser
1               5

<210> SEQ ID NO 71
<211> LENGTH: 9
<212> TYPE: PRT
<213> ORGANISM: Artificial Sequence
<220> FEATURE:
<223> OTHER INFORMATION: Synthetic: chAb11 VL CDR3 amino acid sequence

<400> SEQUENCE: 71

Gln Asn Asp Tyr Ile Tyr Pro Leu Thr
1               5

<210> SEQ ID NO 72
<211> LENGTH: 121
<212> TYPE: PRT
<213> ORGANISM: Artificial Sequence
<220> FEATURE:
<223> OTHER INFORMATION: Synthetic: chAb16 VH amino acid sequence

<400> SEQUENCE: 72

Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Asp Ser Ser Thr Ile Asn Tyr Thr Pro Ser Leu
    50                  55                  60

Lys Asp Lys Phe Ile Ile Ser Arg Asp Asn Ala Lys Asn Thr Leu Tyr
65                  70                  75                  80

Leu Gln Met Ser Lys Val Arg Ser Glu Asp Thr Ala Leu Tyr Tyr Cys
                85                  90                  95

Ala Arg Pro Gly Phe Gly Asn Tyr Ile Tyr Ala Met Asp Tyr Trp Gly
            100                 105                 110

Gln Gly Thr Ser Val Thr Val Ser Ser
        115                 120

<210> SEQ ID NO 73
<211> LENGTH: 10
<212> TYPE: PRT
<213> ORGANISM: Artificial Sequence
<220> FEATURE:
```

<223> OTHER INFORMATION: Synthetic: chAb16 VH CDR1 amino acid sequence

<400> SEQUENCE: 73

Gly Phe Asp Phe Ser Arg Tyr Trp Met Ser
1               5                   10

<210> SEQ ID NO 74
<211> LENGTH: 17
<212> TYPE: PRT
<213> ORGANISM: Artificial Sequence
<220> FEATURE:
<223> OTHER INFORMATION: Synthetic: chAb16 VH CDR2 amino acid sequence

<400> SEQUENCE: 74

Glu Ile Asn Pro Asp Ser Ser Thr Ile Asn Tyr Thr Pro Ser Leu Lys
1               5                   10                  15

Asp

<210> SEQ ID NO 75
<211> LENGTH: 12
<212> TYPE: PRT
<213> ORGANISM: Artificial Sequence
<220> FEATURE:
<223> OTHER INFORMATION: Synthetic: chAb16 VH CDR3 amino acid sequence

<400> SEQUENCE: 75

Pro Gly Phe Gly Asn Tyr Ile Tyr Ala Met Asp Tyr
1               5                   10

<210> SEQ ID NO 76
<211> LENGTH: 107
<212> TYPE: PRT
<213> ORGANISM: Artificial Sequence
<220> FEATURE:
<223> OTHER INFORMATION: Synthetic: chAb16 VL amino acid sequence

<400> SEQUENCE: 76

Asp Ile Gln Met Thr Gln Thr Thr Ser Ser Leu Ser Ala Ser Leu Gly
1               5                   10                  15

Asp Arg Val Thr Ile Asn Cys Arg Ala Ser Gln Asp Ile Ser Asn Phe
            20                  25                  30

Leu Asn Trp Tyr Gln Gln Lys Pro Asp Gly Thr Val Lys Leu Leu Ile
        35                  40                  45

Tyr Tyr Thr Ser Arg Leu Tyr Leu Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Pro
                85                  90                  95

Thr Phe Gly Gly Gly Thr Lys Leu Glu Ile Lys
            100                 105

<210> SEQ ID NO 77
<211> LENGTH: 11
<212> TYPE: PRT
<213> ORGANISM: Artificial Sequence
<220> FEATURE:
<223> OTHER INFORMATION: Synthetic: chAb16 VL CDR1 amino acid sequence

<400> SEQUENCE: 77

Arg Ala Ser Gln Asp Ile Ser Asn Phe Leu Asn
1               5                   10

```
<210> SEQ ID NO 78
<211> LENGTH: 7
<212> TYPE: PRT
<213> ORGANISM: Artificial Sequence
<220> FEATURE:
<223> OTHER INFORMATION: Synthetic: chAb16 VL CDR2 amino acid sequence

<400> SEQUENCE: 78

Tyr Thr Ser Arg Leu Tyr Leu
1               5

<210> SEQ ID NO 79
<211> LENGTH: 9
<212> TYPE: PRT
<213> ORGANISM: Artificial Sequence
<220> FEATURE:
<223> OTHER INFORMATION: Synthetic: chAb16 VL CDR3 amino acid sequence

<400> SEQUENCE: 79

Gln Gln Gly Asn Thr Leu Pro Pro Thr
1               5

<210> SEQ ID NO 80
<211> LENGTH: 125
<212> TYPE: PRT
<213> ORGANISM: Artificial Sequence
<220> FEATURE:
<223> OTHER INFORMATION: Synthetic: chAb10 VH amino acid sequence

<400> SEQUENCE: 80

Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Arg Leu Glu Trp
        35                  40                  45

Met Gly His Ile Asn Tyr Ser Gly Ile Thr Asn Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Tyr Ser Val Thr Thr Glu Asp Thr Ala Thr Tyr Phe Cys
                85                  90                  95

Ala Arg Arg Ser Leu Phe Tyr Tyr Gly Ser Ser Leu Tyr Ala Met
            100                 105                 110

Asp Tyr Trp Gly Gln Gly Thr Ser Val Thr Val Ser Ser
        115                 120                 125

<210> SEQ ID NO 81
<211> LENGTH: 11
<212> TYPE: PRT
<213> ORGANISM: Artificial Sequence
<220> FEATURE:
<223> OTHER INFORMATION: Synthetic: chAb10 VH CDR1 amino acid sequence

<400> SEQUENCE: 81

Gly Tyr Ser Ile Thr Ser Asp Tyr Ala Trp Asn
1               5                   10

<210> SEQ ID NO 82
<211> LENGTH: 16
<212> TYPE: PRT
<213> ORGANISM: Artificial Sequence
<220> FEATURE:
```

<223> OTHER INFORMATION: Synthetic: chAb10 VH CDR2 amino acid sequence

<400> SEQUENCE: 82

His Ile Asn Tyr Ser Gly Ile Thr Asn Tyr Asn Pro Ser Leu Lys Ser
1               5                   10                  15

<210> SEQ ID NO 83
<211> LENGTH: 16
<212> TYPE: PRT
<213> ORGANISM: Artificial Sequence
<220> FEATURE:
<223> OTHER INFORMATION: Synthetic: chAb10 VH CDR3 amino acid sequence

<400> SEQUENCE: 83

Arg Ser Leu Phe Tyr Tyr Tyr Gly Ser Ser Leu Tyr Ala Met Asp Tyr
1               5                   10                  15

<210> SEQ ID NO 84
<211> LENGTH: 112
<212> TYPE: PRT
<213> ORGANISM: Artificial Sequence
<220> FEATURE:
<223> OTHER INFORMATION: Synthetic: chAb10 VL amino acid sequence

<400> SEQUENCE: 84

Asp Val Val Met Thr Gln Ser Pro Phe Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Trp Thr Phe Gly Gly Gly Thr Lys Leu Glu Ile Lys
            100                 105                 110

<210> SEQ ID NO 85
<211> LENGTH: 16
<212> TYPE: PRT
<213> ORGANISM: Artificial Sequence
<220> FEATURE:
<223> OTHER INFORMATION: Synthetic: chAb10 VL CDR1 amino acid sequence

<400> SEQUENCE: 85

Arg Ser Ser Gln Ser Leu Val His Ser Asn Gly Asn Thr Tyr Leu His
1               5                   10                  15

<210> SEQ ID NO 86
<211> LENGTH: 9
<212> TYPE: PRT
<213> ORGANISM: Artificial Sequence
<220> FEATURE:
<223> OTHER INFORMATION: Synthetic: chAb10 VL CDR3 amino acid sequence

<400> SEQUENCE: 86

Ser Gln Ser Thr His Val Pro Trp Thr
1               5

<210> SEQ ID NO 87

<211> LENGTH: 119
<212> TYPE: PRT
<213> ORGANISM: Artificial Sequence
<220> FEATURE:
<223> OTHER INFORMATION: Synthetic: chAb7 VH amino acid sequence

<400> SEQUENCE: 87

Glu Val Gln Leu Val Glu Ser Gly Glu Asn Leu Val Lys Pro Gly Gly
1               5                   10                  15

Ser Leu Lys Leu Ser Cys Ala Ala Ser Gly Phe Ser Phe Arg Gly Tyr
            20                  25                  30

Gly Met Ser Trp Val Arg Gln Thr Pro Asp Lys Arg Leu Glu Trp Val
        35                  40                  45

Ala Ala Ile Ser Thr Gly Gly Asn Tyr Thr Tyr Tyr Pro Asp Ser Val
    50                  55                  60

Gln Gly Arg Phe Thr Ile Ser Arg Asp Asn Ala Asn Asn Thr Leu Tyr
65                  70                  75                  80

Leu Gln Met Ser Ser Leu Lys Ser Glu Asp Thr Ala Met Tyr Tyr Cys
                85                  90                  95

Ala Arg Arg Gly Gly Asn Tyr Ala Gly Phe Ala Tyr Trp Gly Gln Gly
            100                 105                 110

Thr Leu Val Thr Val Ser Ala
        115

<210> SEQ ID NO 88
<211> LENGTH: 10
<212> TYPE: PRT
<213> ORGANISM: Artificial Sequence
<220> FEATURE:
<223> OTHER INFORMATION: Synthetic: chAb7 VH CDR1 amino acid sequence

<400> SEQUENCE: 88

Gly Phe Ser Phe Arg Gly Tyr Gly Met Ser
1               5                   10

<210> SEQ ID NO 89
<211> LENGTH: 17
<212> TYPE: PRT
<213> ORGANISM: Artificial Sequence
<220> FEATURE:
<223> OTHER INFORMATION: Synthetic: chAb7 VH CDR2 amino acid sequence

<400> SEQUENCE: 89

Ala Ile Ser Thr Gly Gly Asn Tyr Thr Tyr Tyr Pro Asp Ser Val Gln
1               5                   10                  15

Gly

<210> SEQ ID NO 90
<211> LENGTH: 10
<212> TYPE: PRT
<213> ORGANISM: Artificial Sequence
<220> FEATURE:
<223> OTHER INFORMATION: Synthetic: chAb7 VH CDR3 amino acid sequence

<400> SEQUENCE: 90

Arg Gly Gly Asn Tyr Ala Gly Phe Ala Tyr
1               5                   10

<210> SEQ ID NO 91
<211> LENGTH: 107
<212> TYPE: PRT
<213> ORGANISM: Artificial Sequence
<220> FEATURE:

<223> OTHER INFORMATION: Synthetic: chAb7 VL amino acid sequence

<400> SEQUENCE: 91

Asp Ile Gln Met Thr Gln Ser Pro Ala Ser Leu Ser Val Ser Val Gly
1               5                   10                  15

Glu Thr Val Thr Ile Thr Cys Arg Pro Ser Glu Asn Ile Tyr Ser Asn
            20                  25                  30

Leu Ala Trp Tyr Gln Gln Lys Gln Gly Lys Ser Pro Gln Leu Leu Val
        35                  40                  45

Tyr Ala Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Thr Tyr Tyr Cys Gln His Phe Trp Gly Thr Pro Phe
                85                  90                  95

Thr Phe Gly Ser Gly Thr Lys Leu Glu Ile Lys
            100                 105

<210> SEQ ID NO 92
<211> LENGTH: 11
<212> TYPE: PRT
<213> ORGANISM: Artificial Sequence
<220> FEATURE:
<223> OTHER INFORMATION: Synthetic: chAb7 VL CDR1 amino acid sequence

<400> SEQUENCE: 92

Arg Pro Ser Glu Asn Ile Tyr Ser Asn Leu Ala
1               5                   10

<210> SEQ ID NO 93
<211> LENGTH: 7
<212> TYPE: PRT
<213> ORGANISM: Artificial Sequence
<220> FEATURE:
<223> OTHER INFORMATION: Synthetic: chAb7 and chAb8 VL CDR2 amino acid
      sequence

<400> SEQUENCE: 93

Ala Ala Thr Asn Leu Ala Asp
1               5

<210> SEQ ID NO 94
<211> LENGTH: 9
<212> TYPE: PRT
<213> ORGANISM: Artificial Sequence
<220> FEATURE:
<223> OTHER INFORMATION: Synthetic: chAb7 VL CDR3 amino acid sequence

<400> SEQUENCE: 94

Gln His Phe Trp Gly Thr Pro Phe Thr
1               5

<210> SEQ ID NO 95
<211> LENGTH: 121
<212> TYPE: PRT
<213> ORGANISM: Artificial Sequence
<220> FEATURE:
<223> OTHER INFORMATION: Synthetic: chAb8 VH amino acid sequence

<400> SEQUENCE: 95

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr

```
                  20                  25                  30
Gly Met Ser Trp Val Arg Gln Thr Pro Glu Lys Arg Leu Glu Trp Val
            35                  40                  45

Ala Thr Ile Ser Gly Gly Asn Tyr Thr Tyr Cys Pro Asp Ser Val
        50                  55                  60

Lys Gly Arg Phe Thr Ile Ser Arg Asp Asn Ala Lys Asn Asn Leu Tyr
65                  70                  75                  80

Leu Gln Met Ser Ser Leu Arg Ser Glu Asp Thr Ala Leu Tyr Tyr Cys
                85                  90                  95

Thr Arg Gln Arg Gly Tyr Asp Tyr His Tyr Ala Met Asp Phe Trp Gly
            100                 105                 110

Gln Gly Thr Ser Val Thr Val Ser Ser
        115                 120

<210> SEQ ID NO 96
<211> LENGTH: 17
<212> TYPE: PRT
<213> ORGANISM: Artificial Sequence
<220> FEATURE:
<223> OTHER INFORMATION: Synthetic: chAb8 VH CDR2 amino acid sequence

<400> SEQUENCE: 96

Thr Ile Ser Gly Gly Gly Asn Tyr Thr Tyr Cys Pro Asp Ser Val Lys
1               5                   10                  15

Gly

<210> SEQ ID NO 97
<211> LENGTH: 12
<212> TYPE: PRT
<213> ORGANISM: Artificial Sequence
<220> FEATURE:
<223> OTHER INFORMATION: Synthetic: chAb8 VH CDR3 amino acid sequence

<400> SEQUENCE: 97

Gln Arg Gly Tyr Asp Tyr His Tyr Ala Met Asp Phe
1               5                   10

<210> SEQ ID NO 98
<211> LENGTH: 107
<212> TYPE: PRT
<213> ORGANISM: Artificial Sequence
<220> FEATURE:
<223> OTHER INFORMATION: Synthetic: chAb8 VL amino acid sequence

<400> SEQUENCE: 98

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ser Asn
            20                  25                  30

Leu Ala Trp His Gln Gln Lys Gln Gly Lys Ser Pro Gln Leu Leu Val
        35                  40                  45

Tyr Ala Ala Thr Asn Leu Ala Asp Gly Val Pro Ser Arg Phe Ser Gly
    50                  55                  60

Asn Gly Ser Asp Thr Gln Tyr Ser Leu Lys Ile Asn Ser Leu Gln Ser
65                  70                  75                  80

Glu Asp Phe Gly Ser Tyr Phe Cys Gln Asn Phe Trp Gly Thr Ser Trp
                85                  90                  95

Thr Phe Gly Gly Gly Thr Lys Leu Glu Ile Lys
            100                 105
```

<210> SEQ ID NO 99
<211> LENGTH: 11
<212> TYPE: PRT
<213> ORGANISM: Artificial Sequence
<220> FEATURE:
<223> OTHER INFORMATION: Synthetic: chAb8 VL CDR1 amino acid sequence

<400> SEQUENCE: 99

Arg Ala Ser Glu Asn Ile Tyr Ser Asn Leu Ala
1               5                   10

<210> SEQ ID NO 100
<211> LENGTH: 9
<212> TYPE: PRT
<213> ORGANISM: Artificial Sequence
<220> FEATURE:
<223> OTHER INFORMATION: Synthetic: chAb8 VL CDR3 amino acid sequence

<400> SEQUENCE: 100

Gln Asn Phe Trp Gly Thr Ser Trp Thr
1               5

<210> SEQ ID NO 101
<211> LENGTH: 117
<212> TYPE: PRT
<213> ORGANISM: Artificial Sequence
<220> FEATURE:
<223> OTHER INFORMATION: Synthetic: chAb17 VH amino acid sequence

<400> SEQUENCE: 101

Glu Val Lys Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Ser Tyr
            20                  25                  30

Ile Met Ser Trp Val Arg Gln Thr Pro Glu Lys Arg Leu Glu Trp Val
        35                  40                  45

Ala Ser Ile Val Ser Ser Asn Ile Thr Tyr Tyr Pro Asp Ser Met Lys
    50                  55                  60

Gly Arg Phe Thr Ile Ser Arg Asp Asn Ala Arg Asn Ile Leu Tyr Leu
65                  70                  75                  80

Gln Met Ser Ser Leu Lys Ser Glu Asp Thr Ala Met Tyr Tyr Cys Ala
                85                  90                  95

Arg Ser Gly Thr Arg Ala Trp Phe Ala Tyr Trp Gly Gln Gly Thr Leu
            100                 105                 110

Val Thr Val Ser Ala
        115

<210> SEQ ID NO 102
<211> LENGTH: 10
<212> TYPE: PRT
<213> ORGANISM: Artificial Sequence
<220> FEATURE:
<223> OTHER INFORMATION: Synthetic: chAb17 VH CDR1 amino acid sequence

<400> SEQUENCE: 102

Gly Phe Thr Phe Ser Ser Tyr Ile Met Ser
1               5                   10

<210> SEQ ID NO 103
<211> LENGTH: 16
<212> TYPE: PRT
<213> ORGANISM: Artificial Sequence
<220> FEATURE:

<223> OTHER INFORMATION: Synthetic: chAb17 VH CDR2 amino acid sequence

<400> SEQUENCE: 103

Ser Ile Val Ser Ser Asn Ile Thr Tyr Tyr Pro Asp Ser Met Lys Gly
1               5                   10                  15

<210> SEQ ID NO 104
<211> LENGTH: 9
<212> TYPE: PRT
<213> ORGANISM: Artificial Sequence
<220> FEATURE:
<223> OTHER INFORMATION: Synthetic: chAb17 VH CDR3 amino acid sequence

<400> SEQUENCE: 104

Ser Gly Thr Arg Ala Trp Phe Ala Tyr
1               5

<210> SEQ ID NO 105
<211> LENGTH: 111
<212> TYPE: PRT
<213> ORGANISM: Artificial Sequence
<220> FEATURE:
<223> OTHER INFORMATION: Synthetic: chAb17 VL amino acid sequence

<400> SEQUENCE: 105

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
                20                  25                  30

Ala Tyr Ser Tyr Met His Trp Tyr Gln Gln Lys Pro Gly Gln Pro Pro
            35                  40                  45

Lys Leu Leu Ile Tyr Leu Ala Ser Asn Leu Glu Ser Gly Val Pro Ala
        50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro Tyr Thr Phe Gly Gly Gly Thr Lys Leu Glu Ile Lys
            100                 105                 110

<210> SEQ ID NO 106
<211> LENGTH: 15
<212> TYPE: PRT
<213> ORGANISM: Artificial Sequence
<220> FEATURE:
<223> OTHER INFORMATION: Synthetic: chAb17 VL CDR1 amino acid sequence

<400> SEQUENCE: 106

Arg Ala Ser Lys Ser Val Ser Thr Ser Ala Tyr Ser Tyr Met His
1               5                   10                  15

<210> SEQ ID NO 107
<211> LENGTH: 9
<212> TYPE: PRT
<213> ORGANISM: Artificial Sequence
<220> FEATURE:
<223> OTHER INFORMATION: Synthetic: chAb17 VL CDR3 amino acid sequence

<400> SEQUENCE: 107

Gln His Ser Arg Glu Leu Pro Tyr Thr
1               5

<210> SEQ ID NO 108

```
<211> LENGTH: 118
<212> TYPE: PRT
<213> ORGANISM: Artificial Sequence
<220> FEATURE:
<223> OTHER INFORMATION: Synthetic: chAb5 VH amino acid sequence

<400> SEQUENCE: 108
```

Gln Val Gln Leu Gln Gln Pro Gly Asp Glu Leu Val Lys Pro Gly Ala
1               5                   10                  15

Ser Val Lys Leu Ser Cys Lys Thr Ser Gly Tyr Thr Phe Thr Thr Asp
            20                  25                  30

Trp Met His Trp Val Lys Gln Arg Pro Gly Gln Gly Leu Glu Trp Ile
        35                  40                  45

Gly Met Ile His Pro Asn Ser Gly Thr Thr Asn Tyr Asn Glu Lys Phe
    50                  55                  60

Lys Ser Lys Ala Ala Leu Thr Val Asp Lys Ser Ser Thr Ala Cys
65                  70                  75                  80

Met Gln Leu Ser Ser Leu Thr Ser Glu Asp Ser Ala Val Tyr Tyr Cys
                85                  90                  95

Ala Arg Ser Tyr Trp Lys Trp Tyr Phe Asp Val Trp Gly Thr Gly Thr
            100                 105                 110

Thr Val Thr Val Ser Ser
        115

```
<210> SEQ ID NO 109
<211> LENGTH: 10
<212> TYPE: PRT
<213> ORGANISM: Artificial Sequence
<220> FEATURE:
<223> OTHER INFORMATION: Synthetic: chAb5 VH CDR1 amino acid sequence

<400> SEQUENCE: 109
```

Gly Tyr Thr Phe Thr Thr Asp Trp Met His
1               5                   10

```
<210> SEQ ID NO 110
<211> LENGTH: 17
<212> TYPE: PRT
<213> ORGANISM: Artificial Sequence
<220> FEATURE:
<223> OTHER INFORMATION: Synthetic: chAb5 VH CDR2 amino acid sequence

<400> SEQUENCE: 110
```

Met Ile His Pro Asn Ser Gly Thr Thr Asn Tyr Asn Glu Lys Phe Lys
1               5                   10                  15

Ser

```
<210> SEQ ID NO 111
<211> LENGTH: 9
<212> TYPE: PRT
<213> ORGANISM: Artificial Sequence
<220> FEATURE:
<223> OTHER INFORMATION: Synthetic: chAb5 VH CDR3 amino acid sequence

<400> SEQUENCE: 111
```

Ser Tyr Trp Lys Trp Tyr Phe Asp Val
1               5

```
<210> SEQ ID NO 112
<211> LENGTH: 106
<212> TYPE: PRT
<213> ORGANISM: Artificial Sequence
<220> FEATURE:
```

<223> OTHER INFORMATION: Synthetic: chAb5 VL amino acid sequence

<400> SEQUENCE: 112

```
Gln Ile Val Leu Thr Gln Ser Pro Ala Ile Met Ser Ala Ser Leu Gly
1               5                   10                  15
Glu Glu Ile Thr Leu Thr Cys Ser Ala Ser Ser Ser Val Ser Tyr Met
            20                  25                  30
His Trp Tyr Gln Gln Lys Ser Gly Thr Ser Pro Lys Leu Leu Ile Tyr
        35                  40                  45
Ser Thr Ser Asn Leu Ala Ser Gly Val Pro Ser Arg Phe Ser Gly Ser
    50                  55                  60
Gly Ser Gly Thr Phe Tyr Ser Leu Thr Ile Ser Ser Val Glu Ala Glu
65                  70                  75                  80
Asp Ser Ala Asp Tyr Tyr Cys His Gln Trp Thr Ser Tyr Met Tyr Thr
                85                  90                  95
Phe Gly Gly Gly Thr Lys Leu Glu Ile Lys
            100                 105
```

<210> SEQ ID NO 113
<211> LENGTH: 10
<212> TYPE: PRT
<213> ORGANISM: Artificial Sequence
<220> FEATURE:
<223> OTHER INFORMATION: Synthetic: chAb5 VL CDR1 amino acid sequence

<400> SEQUENCE: 113

```
Ser Ala Ser Ser Ser Val Ser Tyr Met His
1               5                   10
```

<210> SEQ ID NO 114
<211> LENGTH: 7
<212> TYPE: PRT
<213> ORGANISM: Artificial Sequence
<220> FEATURE:
<223> OTHER INFORMATION: Synthetic: chAb5 VL CDR2 amino acid sequence

<400> SEQUENCE: 114

```
Ser Thr Ser Asn Leu Ala Ser
1               5
```

<210> SEQ ID NO 115
<211> LENGTH: 9
<212> TYPE: PRT
<213> ORGANISM: Artificial Sequence
<220> FEATURE:
<223> OTHER INFORMATION: Synthetic: chAb5 VL CDR3 amino acid sequence

<400> SEQUENCE: 115

```
His Gln Trp Thr Ser Tyr Met Tyr Thr
1               5
```

<210> SEQ ID NO 116
<211> LENGTH: 121
<212> TYPE: PRT
<213> ORGANISM: Artificial Sequence
<220> FEATURE:
<223> OTHER INFORMATION: Synthetic: huAb18VH.1, huAb18v1, and huAb18v5
      VH amino acid sequence

<400> SEQUENCE: 116

```
Glu Val Gln Leu Val Gln Ser Gly Ala Glu Val Lys Lys Pro Gly Ser
1               5                   10                  15
Ser Val Lys Val Ser Cys Lys Ala Ser Gly Tyr Ser Phe Thr Ser Tyr
```

```
                    20                  25                  30
Thr Ile His Trp Val Arg Gln Ala Pro Gly Gln Gly Leu Glu Trp Met
                35                  40                  45

Gly Tyr Ile Asn Pro Asn Ser Arg Asn Thr Asp Tyr Asn Gln Lys Phe
         50                  55                  60

Lys Asp Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Tyr Ser Gly Ser Thr Pro Tyr Trp Tyr Phe Asp Val Trp Gly
             100                 105                 110

Gln Gly Thr Thr Val Thr Val Ser Ser
             115                 120

<210> SEQ ID NO 117
<211> LENGTH: 121
<212> TYPE: PRT
<213> ORGANISM: Artificial Sequence
<220> FEATURE:
<223> OTHER INFORMATION: Synthetic: huAb18VH.1a, huAb18v3, huAb18v8, and
      huAb18v9 VH amino acid sequence

<400> SEQUENCE: 117

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Ser Tyr
                20                  25                  30

Thr Ile His Trp Val Arg Gln Ala Pro Gly Gln Gly Leu Glu Trp Ile
                35                  40                  45

Gly Tyr Ile Asn Pro Asn Ser Arg Asn Thr Asp Tyr Asn Gln Lys Phe
         50                  55                  60

Lys Asp Arg Thr Thr Leu Thr Ala Asp Arg Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Tyr Ser Gly Ser Thr Pro Tyr Trp Tyr Phe Asp Val Trp Gly
             100                 105                 110

Gln Gly Thr Thr Val Thr Val Ser Ser
             115                 120

<210> SEQ ID NO 118
<211> LENGTH: 121
<212> TYPE: PRT
<213> ORGANISM: Artificial Sequence
<220> FEATURE:
<223> OTHER INFORMATION: Synthetic: huAb18VH.1b, huAb18v2, huAb18v4,
      huAb18v6, huAb18v7, and huAb18v10 VH amino acid sequence

<400> SEQUENCE: 118

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Ser Tyr
                20                  25                  30

Thr Ile His Trp Val Arg Gln Ala Pro Gly Gln Gly Leu Glu Trp Met
                35                  40                  45

Gly Tyr Ile Asn Pro Asn Ser Arg Asn Thr Asp Tyr Ala Gln Lys Phe
         50                  55                  60

Gln Gly Arg Val Thr Leu Thr Ala Asp Lys Ser Thr Ser Thr Ala Tyr
```

```
            65                  70                  75                  80
Met Glu Leu Ser Ser Leu Arg Ser Glu Asp Thr Ala Val Tyr Tyr Cys
                    85                  90                  95

Ala Arg Tyr Ser Gly Ser Thr Pro Tyr Trp Tyr Phe Asp Val Trp Gly
                100                 105                 110

Gln Gly Thr Thr Val Thr Val Ser Ser
            115                 120

<210> SEQ ID NO 119
<211> LENGTH: 17
<212> TYPE: PRT
<213> ORGANISM: Artificial Sequence
<220> FEATURE:
<223> OTHER INFORMATION: Synthetic: huAb18VH.1b VH CDR2 amino acid
      sequence

<400> SEQUENCE: 119

Tyr Ile Asn Pro Asn Ser Arg Asn Thr Asp Tyr Ala Gln Lys Phe Gln
1               5                   10                  15

Gly

<210> SEQ ID NO 120
<211> LENGTH: 106
<212> TYPE: PRT
<213> ORGANISM: Artificial Sequence
<220> FEATURE:
<223> OTHER INFORMATION: Synthetic: huAb18VL.1, huAb18v1, and huAb18v2
      VL amino acid sequence

<400> SEQUENCE: 120

Asp Ile Gln Leu Thr Gln Ser Pro Ser Phe Leu Ser Ala Ser Val Gly
1               5                   10                  15

Asp Arg Val Thr Ile Thr Cys Arg Ala Ser Ser Ser Val Ser Tyr Met
                20                  25                  30

Asn Trp Tyr Gln Gln Lys Pro Gly Lys Ala Pro Lys Leu Leu Ile Tyr
            35                  40                  45

Ala Thr Ser Asn Leu Ala Ser Gly Val Pro Ser Arg Phe Ser Gly Ser
        50                  55                  60

Gly Ser Gly Thr Glu Phe Thr Leu Thr Ile Ser Ser Leu Gln Pro Glu
65                  70                  75                  80

Asp Phe Ala Thr Tyr Tyr Cys Gln Gln Trp Ser Ser Asn Pro Leu Thr
                85                  90                  95

Phe Gly Gln Gly Thr Lys Leu Glu Ile Lys
            100                 105

<210> SEQ ID NO 121
<211> LENGTH: 106
<212> TYPE: PRT
<213> ORGANISM: Artificial Sequence
<220> FEATURE:
<223> OTHER INFORMATION: Synthetic: huAb18VL.1a, huAb18v3, and huAb18v4
      VL amino acid sequence

<400> SEQUENCE: 121

Asp Ile Gln Leu Thr Gln Ser Pro Ser Phe Leu Ser Ala Ser Val Gly
1               5                   10                  15

Asp Arg Val Thr Ile Thr Cys Arg Ala Ser Ser Ser Val Ser Tyr Met
                20                  25                  30

Asn Trp Tyr Gln Gln Lys Pro Gly Lys Ser Pro Lys Pro Trp Ile Tyr
            35                  40                  45
```

```
Ala Thr Ser Asn Leu Ala Ser Gly Val Pro Ser Arg Phe Ser Val Ser
    50                  55                  60
Val Ser Gly Thr Glu His Thr Leu Thr Ile Ser Ser Leu Gln Pro Glu
65                  70                  75                  80
Asp Phe Ala Thr Tyr Tyr Cys Gln Gln Trp Ser Ser Asn Pro Leu Thr
                85                  90                  95
Phe Gly Gln Gly Thr Lys Leu Glu Ile Lys
            100                 105
```

<210> SEQ ID NO 122
<211> LENGTH: 106
<212> TYPE: PRT
<213> ORGANISM: Artificial Sequence
<220> FEATURE:
<223> OTHER INFORMATION: Synthetic: huAb18VL.1b, huAb18v8, and huAb18v10
    VL amino acid sequence

<400> SEQUENCE: 122

```
Asp Ile Gln Leu Thr Gln Ser Pro Ser Phe Leu Ser Ala Ser Val Gly
1               5                   10                  15
Asp Arg Val Thr Ile Thr Cys Arg Ala Ser Ser Ser Val Ser Tyr Met
            20                  25                  30
Asn Trp Tyr Gln Gln Lys Pro Gly Lys Ala Pro Lys Pro Trp Ile Tyr
        35                  40                  45
Ala Thr Ser Asn Leu Ala Ser Gly Val Pro Ser Arg Phe Ser Val Ser
    50                  55                  60
Gly Ser Gly Thr Glu His Thr Leu Thr Ile Ser Ser Leu Gln Pro Glu
65                  70                  75                  80
Asp Phe Ala Thr Tyr Tyr Cys Gln Gln Trp Ser Ser Asn Pro Leu Thr
                85                  90                  95
Phe Gly Gln Gly Thr Lys Leu Glu Ile Lys
            100                 105
```

<210> SEQ ID NO 123
<211> LENGTH: 106
<212> TYPE: PRT
<213> ORGANISM: Artificial Sequence
<220> FEATURE:
<223> OTHER INFORMATION: Synthetic: huAb18VL.2, huAb18v5, and huAb18v6
    VL amino acid sequence

<400> SEQUENCE: 123

```
Glu Ile Val Leu Thr Gln Ser Pro Asp Phe Gln Ser Val Thr Pro Lys
1               5                   10                  15
Glu Lys Val Thr Ile Thr Cys Arg Ala Ser Ser Ser Val Ser Tyr Met
            20                  25                  30
Asn Trp Tyr Gln Gln Lys Pro Asp Gln Ser Pro Lys Leu Leu Ile Lys
        35                  40                  45
Ala Thr Ser Asn Leu Ala Ser Gly Val Pro Ser Arg Phe Ser Gly Ser
    50                  55                  60
Gly Ser Gly Thr Asp Phe Thr Leu Thr Ile Asn Ser Leu Glu Ala Glu
65                  70                  75                  80
Asp Ala Ala Thr Tyr Tyr Cys Gln Gln Trp Ser Ser Asn Pro Leu Thr
                85                  90                  95
Phe Gly Gln Gly Thr Lys Leu Glu Ile Lys
            100                 105
```

<210> SEQ ID NO 124
<211> LENGTH: 106

```
<212> TYPE: PRT
<213> ORGANISM: Artificial Sequence
<220> FEATURE:
<223> OTHER INFORMATION: Synthetic: huAb18VL.2a, huAb18v7, and huAb18v9
      VL amino acid sequence

<400> SEQUENCE: 124

Glu Ile Val Leu Thr Gln Ser Pro Asp Phe Gln Ser Val Thr Pro Lys
1               5                   10                  15

Glu Lys Val Thr Ile Thr Cys Arg Ala Ser Ser Ser Val Ser Tyr Met
            20                  25                  30

Asn Trp Tyr Gln Gln Lys Pro Asp Gln Ser Pro Lys Pro Trp Ile Tyr
        35                  40                  45

Ala Thr Ser Asn Leu Ala Ser Gly Val Pro Ser Arg Phe Ser Val Ser
    50                  55                  60

Val Ser Gly Thr Asp His Thr Leu Thr Ile Asn Ser Leu Glu Ala Glu
65                  70                  75                  80

Asp Ala Ala Thr Tyr Tyr Cys Gln Gln Trp Ser Ser Asn Pro Leu Thr
                85                  90                  95

Phe Gly Gln Gly Thr Lys Leu Glu Ile Lys
            100                 105

<210> SEQ ID NO 125
<211> LENGTH: 117
<212> TYPE: PRT
<213> ORGANISM: Artificial Sequence
<220> FEATURE:
<223> OTHER INFORMATION: Synthetic: huAb3VH.1, huAb3v1, and huAb3v4 VH
      amino acid sequence

<400> SEQUENCE: 125

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser Tyr
            20                  25                  30

Trp Met His Trp Val Arg Gln Ala Pro Gly Gln Gly Leu Glu Trp Met
        35                  40                  45

Gly Leu Ile His Pro Asp Ser Gly Ser Thr Asn Tyr Asn Glu Met Phe
    50                  55                  60

Lys Asn Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Arg Leu Tyr Phe Asp Tyr Trp Gly Gln Gly Thr Thr
            100                 105                 110

Val Thr Val Ser Ser
        115

<210> SEQ ID NO 126
<211> LENGTH: 117
<212> TYPE: PRT
<213> ORGANISM: Artificial Sequence
<220> FEATURE:
<223> OTHER INFORMATION: Synthetic: huAb3VH.1a, huAb3v3, and huAb3v6
      VH amino acid sequence

<400> SEQUENCE: 126

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser Tyr
```

```
                20              25              30
Trp Met His Trp Val Arg Gln Ala Pro Gly Gln Gly Leu Glu Trp Ile
            35                  40                  45
Gly Leu Ile His Pro Asp Ser Gly Ser Thr Asn Tyr Asn Glu Met Phe
        50                  55                  60
Lys Asn Arg Ala Thr Leu Thr Val Asp Arg Ser Thr Ser Thr Ala Tyr
65                  70                  75                  80
Val Glu Leu Ser Ser Leu Arg Ser Glu Asp Thr Ala Val Tyr Phe Cys
                85                  90                  95
Ala Gly Gly Gly Arg Leu Tyr Phe Asp Tyr Trp Gly Gln Gly Thr Thr
            100                 105                 110
Val Thr Val Ser Ser
            115

<210> SEQ ID NO 127
<211> LENGTH: 117
<212> TYPE: PRT
<213> ORGANISM: Artificial Sequence
<220> FEATURE:
<223> OTHER INFORMATION: Synthetic: huAb3VH.1b, huAb3v2, and huAb3v5
      VH amino acid sequence

<400> SEQUENCE: 127

Glu Val Gln Leu Val Gln Ser Gly Ala Glu Val Lys Lys Pro Gly Ser
1               5                   10                  15
Ser Val Lys Val Ser Cys Lys Ala Ser Gly Tyr Thr Phe Ser Ser Tyr
                20                  25                  30
Trp Met His Trp Val Arg Gln Ala Pro Gly Gln Gly Leu Glu Trp Ile
            35                  40                  45
Gly Leu Ile His Pro Asp Ser Gly Ser Thr Asn Tyr Asn Glu Met Phe
        50                  55                  60
Lys Asn Arg Ala Thr Leu Thr Val Asp Arg Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Gly Gly Gly Arg Leu Tyr Phe Asp Tyr Trp Gly Gln Gly Thr Thr
            100                 105                 110
Val Thr Val Ser Ser
            115

<210> SEQ ID NO 128
<211> LENGTH: 112
<212> TYPE: PRT
<213> ORGANISM: Artificial Sequence
<220> FEATURE:
<223> OTHER INFORMATION: Synthetic: huAb3VL.1, huAb3v1, and huAb3v2 VL
      amino acid sequence

<400> SEQUENCE: 128

Asp Ile Val Met Thr Gln Ser Pro Leu Ser Leu Pro Val Thr Pro Gly
1               5                   10                  15
Glu Pro Ala Ser Ile Ser Cys Arg Ser Ser Gln Ser Leu Val His Ser
                20                  25                  30
Asn Gly Asp Thr Tyr Leu Arg Trp Tyr Leu Gln Lys Pro Gly Gln Ser
            35                  40                  45
Pro Gln Leu Leu Ile Tyr Lys Val Ser Asn Arg Phe Ser Gly Val Pro
        50                  55                  60
Asp Arg Phe Ser Gly Ser Gly Ser Gly Thr Asp Phe Thr Leu Lys Ile
```

```
                65                  70                  75                  80
Ser Arg Val Glu Ala Glu Asp Val Gly Val Tyr Tyr Cys Ser Gln Ser
                    85                  90                  95

Thr His Val Pro Tyr Thr Phe Gly Gly Gly Thr Lys Val Glu Ile Lys
                100                 105                 110
```

<210> SEQ ID NO 129
<211> LENGTH: 112
<212> TYPE: PRT
<213> ORGANISM: Artificial Sequence
<220> FEATURE:
<223> OTHER INFORMATION: Synthetic: huAb3VL.1a and huAb3v3 VL amino acid
      sequence

<400> SEQUENCE: 129

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
                20                  25                  30

Asn Gly Asp Thr Tyr Leu Arg Trp Tyr Leu Gln Lys Pro Gly Gln Ser
            35                  40                  45

Pro Gln Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                    85                  90                  95

Thr His Val Pro Tyr Thr Phe Gly Gly Gly Thr Lys Val Glu Ile Lys
                100                 105                 110
```

<210> SEQ ID NO 130
<211> LENGTH: 112
<212> TYPE: PRT
<213> ORGANISM: Artificial Sequence
<220> FEATURE:
<223> OTHER INFORMATION: Synthetic: huAb3VL.1b, huAb3v4, huAb3v5, and
      huAb3v6 VL amino acid sequence

<400> SEQUENCE: 130

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
                20                  25                  30

Asn Gly Asp Thr Tyr Leu Arg Trp Tyr Leu Gln Lys Pro Gly Gln Ser
            35                  40                  45

Pro Gln Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                    85                  90                  95

Thr His Val Pro Tyr Thr Phe Gly Gly Gly Thr Lys Val Glu Ile Lys
                100                 105                 110
```

<210> SEQ ID NO 131
<211> LENGTH: 117
<212> TYPE: PRT
<213> ORGANISM: Artificial Sequence
<220> FEATURE:
<223> OTHER INFORMATION: Synthetic: huAb3v2.1, huAb3v2.2, and huAb3v2.3

VH amino acid sequence

<400> SEQUENCE: 131

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser Tyr
            20                  25                  30

Trp Met His Trp Val Arg Gln Ala Pro Gly Gln Gly Leu Glu Trp Ile
        35                  40                  45

Gly Leu Ile His Pro Trp Ser Gly Ser Thr Asn Tyr Asn Glu Met Phe
    50                  55                  60

Lys Asn Arg Ala Thr Leu Thr Val Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Gly Gly Gly Arg Leu Tyr Phe Asp Tyr Trp Gly Gln Gly Thr Thr
            100                 105                 110

Val Thr Val Ser Ser
            115

<210> SEQ ID NO 132
<211> LENGTH: 17
<212> TYPE: PRT
<213> ORGANISM: Artificial Sequence
<220> FEATURE:
<223> OTHER INFORMATION: Synthetic: huAb3v2.1, huAb3v2.2, and huAb3v2.3
      VH CDR2 amino acid sequence

<400> SEQUENCE: 132

Leu Ile His Pro Trp Ser Gly Ser Thr Asn Tyr Asn Glu Met Phe Lys
1               5                   10                  15

Asn

<210> SEQ ID NO 133
<211> LENGTH: 112
<212> TYPE: PRT
<213> ORGANISM: Artificial Sequence
<220> FEATURE:
<223> OTHER INFORMATION: Synthetic: huAb3v2.1, huAb3v2.4, and huAb3v2.7
      VL amino acid sequence

<400> SEQUENCE: 133

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Ser Gly Asp Thr Tyr Leu Arg Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Tyr Thr Phe Gly Gly Gly Thr Lys Val Glu Ile Lys
            100                 105                 110

<210> SEQ ID NO 134
<211> LENGTH: 16

```
<212> TYPE: PRT
<213> ORGANISM: Artificial Sequence
<220> FEATURE:
<223> OTHER INFORMATION: Synthetic: huAb3v2.1, huAb3v2.4, and huAb3v2.7
      VL CDR1 amino acid sequence

<400> SEQUENCE: 134

Arg Ser Ser Gln Ser Leu Val His Ser Ser Gly Asp Thr Tyr Leu Arg
1               5                   10                  15

<210> SEQ ID NO 135
<211> LENGTH: 112
<212> TYPE: PRT
<213> ORGANISM: Artificial Sequence
<220> FEATURE:
<223> OTHER INFORMATION: Synthetic: huAb3v2.2, huAb3v2.5, and huAb3v2.8
      VL amino acid sequence

<400> SEQUENCE: 135

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Arg Asp Thr Tyr Leu Arg Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Tyr Thr Phe Gly Gly Gly Thr Lys Val Glu Ile Lys
            100                 105                 110

<210> SEQ ID NO 136
<211> LENGTH: 16
<212> TYPE: PRT
<213> ORGANISM: Artificial Sequence
<220> FEATURE:
<223> OTHER INFORMATION: Synthetic: huAb3v2.2, huAb3v2.5, and huAb3v2.8
      VL CDR1 amino acid sequence

<400> SEQUENCE: 136

Arg Ser Ser Gln Ser Leu Val His Ser Asn Arg Asp Thr Tyr Leu Arg
1               5                   10                  15

<210> SEQ ID NO 137
<211> LENGTH: 112
<212> TYPE: PRT
<213> ORGANISM: Artificial Sequence
<220> FEATURE:
<223> OTHER INFORMATION: Synthetic: huAb3v2.3, huAb3v2.6, and huAb3v2.9
      VL amino acid sequence

<400> SEQUENCE: 137

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gln Asp Thr Tyr Leu Arg Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60
```

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Tyr Thr Phe Gly Gly Gly Thr Lys Val Glu Ile Lys
            100                 105                 110

<210> SEQ ID NO 138
<211> LENGTH: 16
<212> TYPE: PRT
<213> ORGANISM: Artificial Sequence
<220> FEATURE:
<223> OTHER INFORMATION: Synthetic: huAb3v2.3, huAb3v2.6, and huAb3v2.9
      VL CDR1 amino acid sequence

<400> SEQUENCE: 138

Arg Ser Ser Gln Ser Leu Val His Ser Asn Gln Asp Thr Tyr Leu Arg
1               5                   10                  15

<210> SEQ ID NO 139
<211> LENGTH: 117
<212> TYPE: PRT
<213> ORGANISM: Artificial Sequence
<220> FEATURE:
<223> OTHER INFORMATION: Synthetic: huAb3v2.4, huAb3v2.5, and huAb3v2.6
      VH amino acid sequence

<400> SEQUENCE: 139

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser Tyr
                20                  25                  30

Trp Met His Trp Val Arg Gln Ala Pro Gly Gln Gly Leu Glu Trp Ile
            35                  40                  45

Gly Leu Ile His Pro Glu Ser Gly Ser Thr Asn Tyr Asn Glu Met Phe
    50                  55                  60

Lys Asn Arg Ala Thr Leu Thr Val Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Gly Gly Gly Arg Leu Tyr Phe Asp Tyr Trp Gly Gln Gly Thr Thr
            100                 105                 110

Val Thr Val Ser Ser
        115

<210> SEQ ID NO 140
<211> LENGTH: 17
<212> TYPE: PRT
<213> ORGANISM: Artificial Sequence
<220> FEATURE:
<223> OTHER INFORMATION: Synthetic: huAb3v2.4, huAb3v2.5, and huAb3v2.;
      VH CDR2 amino acid sequence

<400> SEQUENCE: 140

Leu Ile His Pro Glu Ser Gly Ser Thr Asn Tyr Asn Glu Met Phe Lys
1               5                   10                  15

Asn

<210> SEQ ID NO 141
<211> LENGTH: 117
<212> TYPE: PRT

```
<213> ORGANISM: Artificial Sequence
<220> FEATURE:
<223> OTHER INFORMATION: Synthetic: huAb3v2.7, huAb3v2.8, and huAb3v2.9
      VH amino acid sequence

<400> SEQUENCE: 141

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser Tyr
                20                  25                  30

Trp Met His Trp Val Arg Gln Ala Pro Gly Gln Gly Leu Glu Trp Ile
            35                  40                  45

Gly Leu Ile His Pro Ile Ser Gly Ser Thr Asn Tyr Asn Glu Met Phe
        50                  55                  60

Lys Asn Arg Ala Thr Leu Thr Val Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Gly Gly Gly Arg Leu Tyr Phe Asp Tyr Trp Gly Gln Gly Thr Thr
            100                 105                 110

Val Thr Val Ser Ser
        115

<210> SEQ ID NO 142
<211> LENGTH: 17
<212> TYPE: PRT
<213> ORGANISM: Artificial Sequence
<220> FEATURE:
<223> OTHER INFORMATION: Synthetic: huAb3v2.7, huAb3v2.8, and huAb3v2.9
      VH CDR2 amino acid sequence

<400> SEQUENCE: 142

Leu Ile His Pro Ile Ser Gly Ser Thr Asn Tyr Asn Glu Met Phe Lys
1               5                   10                  15

Asn

<210> SEQ ID NO 143
<211> LENGTH: 107
<212> TYPE: PRT
<213> ORGANISM: Artificial Sequence
<220> FEATURE:
<223> OTHER INFORMATION: Synthetic: huAb13VL.1, huAb13v2, huAb13v5, and
      huAb13v7 VL amino acid sequence

<400> SEQUENCE: 143

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Phe Asn
                20                  25                  30

Val Ala Trp Tyr Gln Gln Lys Pro Gly Lys Ala Pro Lys Leu Leu Ile
            35                  40                  45

Tyr Ser Ala Ser Tyr Arg Tyr Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Trp Tyr Pro Phe
                85                  90                  95

Thr Phe Gly Gln Gly Thr Lys Leu Glu Ile Lys
            100                 105
```

<210> SEQ ID NO 144
<211> LENGTH: 107
<212> TYPE: PRT
<213> ORGANISM: Artificial Sequence
<220> FEATURE:
<223> OTHER INFORMATION: Synthetic: huAb13VL.1a, huAb13v1, huAb13v3, and
      huAb13v8 VL amino acid sequence

<400> SEQUENCE: 144

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Phe Asn
            20                  25                  30

Val Ala Trp Tyr Gln Gln Lys Pro Gly Lys Ser Pro Lys Ala Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Glu Tyr Phe Cys Gln Gln Tyr Asn Trp Tyr Pro Phe
                85                  90                  95

Thr Phe Gly Gln Gly Thr Lys Leu Glu Ile Lys
            100                 105

<210> SEQ ID NO 145
<211> LENGTH: 107
<212> TYPE: PRT
<213> ORGANISM: Artificial Sequence
<220> FEATURE:
<223> OTHER INFORMATION: Synthetic: huAB13VL.1b, huAb13v4, huAb13v6, and
      huAb13v9 VL amino acid sequence

<400> SEQUENCE: 145

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Phe Asn
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Tyr Asn Trp Tyr Pro Phe
                85                  90                  95

Thr Phe Gly Gln Gly Thr Lys Leu Glu Ile Lys
            100                 105

<210> SEQ ID NO 146
<211> LENGTH: 116
<212> TYPE: PRT
<213> ORGANISM: Artificial Sequence
<220> FEATURE:
<223> OTHER INFORMATION: Synthetic: huAb13VH.1, huAb13v2, huAb13v3, and
      huAb13v4 VH amino acid sequence

<400> SEQUENCE: 146

Glu Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Thr Ser Gly

```
                     20                  25                  30

Tyr Ser Trp His Trp Ile Arg Gln Pro Gly Lys Gly Leu Glu Trp
            35                  40                  45

Ile Gly Tyr Ile His Ser Ser Gly Ser Thr Asn Tyr Asn Pro Ser Leu
 50                  55                  60

Lys Ser Arg Val Thr Ile Ser Val Asp Thr Ser Lys Asn Gln Phe Ser
 65                  70                  75                  80

Leu Lys Leu Ser Ser Val Thr Ala Ala Asp Thr Ala Val Tyr Tyr Cys
                85                  90                  95

Ala Arg Tyr Asp Asp Tyr Phe Glu Tyr Trp Gly Gln Gly Thr Thr Val
                100                 105                 110

Thr Val Ser Ser
        115

<210> SEQ ID NO 147
<211> LENGTH: 116
<212> TYPE: PRT
<213> ORGANISM: Artificial Sequence
<220> FEATURE:
<223> OTHER INFORMATION: Synthetic: huAb13VH.1a, huAb13v1, huAb13v5, and
      huAb13v6 VH amino acid sequence

<400> SEQUENCE: 147

Glu Val Gln Leu Gln Glu Ser Gly Pro Gly Leu Val Lys Pro Ser Glu
 1               5                  10                  15

Thr Leu Ser Leu Thr Cys Ala Val Thr Gly Tyr Ser Ile Thr Ser Gly
                20                  25                  30

Tyr Ser Trp His Trp Ile Arg Gln Phe Pro Gly Asn Gly Leu Glu Trp
            35                  40                  45

Met Gly Tyr Ile His Ser Ser Gly Ser Thr Asn Tyr Asn Pro Ser Leu
 50                  55                  60

Lys Ser Arg Ile Ser Ile Ser Arg Asp Thr Ser Lys Asn Gln Phe Phe
 65                  70                  75                  80

Leu Lys Leu Ser Ser Val Thr Ala Ala Asp Thr Ala Val Tyr Tyr Cys
                85                  90                  95

Ala Gly Tyr Asp Asp Tyr Phe Glu Tyr Trp Gly Gln Gly Thr Thr Val
                100                 105                 110

Thr Val Ser Ser
        115

<210> SEQ ID NO 148
<211> LENGTH: 116
<212> TYPE: PRT
<213> ORGANISM: Artificial Sequence
<220> FEATURE:
<223> OTHER INFORMATION: Synthetic: huAb13VH.1b, huAb13v7, huAb13v8, and
      huAb13v9 VH amino acid sequence

<400> SEQUENCE: 148

Glu Val Gln Leu Gln Glu Ser Gly Pro Gly Leu Val Lys Pro Ser Glu
 1               5                  10                  15

Thr Leu Ser Leu Thr Cys Ala Val Ser Gly Tyr Ser Ile Thr Ser Gly
                20                  25                  30

Tyr Ser Trp His Trp Ile Arg Gln Pro Pro Gly Asn Gly Leu Glu Trp
            35                  40                  45

Met Gly Tyr Ile His Ser Ser Gly Ser Thr Asn Tyr Asn Pro Ser Leu
 50                  55                  60

Lys Ser Arg Ile Thr Ile Ser Arg Asp Thr Ser Lys Asn Gln Phe Ser
```

```
                65                  70                  75                  80
Leu Lys Leu Ser Ser Val Thr Ala Ala Asp Thr Ala Val Tyr Tyr Cys
                85                  90                  95

Ala Arg Tyr Asp Asp Tyr Phe Glu Tyr Trp Gly Gln Gly Thr Thr Val
            100                 105                 110

Thr Val Ser Ser
        115

<210> SEQ ID NO 149
<211> LENGTH: 534
<212> TYPE: PRT
<213> ORGANISM: Homo sapiens
<220> FEATURE:
<221> NAME/KEY: misc_feature
<222> LOCATION: (1)..(534)
<223> OTHER INFORMATION: B7-H3 amino acid sequence (human)

<400> SEQUENCE: 149

Met Leu Arg Arg Arg Gly Ser Pro Gly Met Gly Val His Val Gly Ala
1               5                   10                  15

Ala Leu Gly Ala Leu Trp Phe Cys Leu Thr Gly Ala Leu Glu Val Gln
                20                  25                  30

Val Pro Glu Asp Pro Val Val Ala Leu Val Gly Thr Asp Ala Thr Leu
            35                  40                  45

Cys Cys Ser Phe Ser Pro Glu Pro Gly Phe Ser Leu Ala Gln Leu Asn
50                  55                  60

Leu Ile Trp Gln Leu Thr Asp Thr Lys Gln Leu Val His Ser Phe Ala
65                  70                  75                  80

Glu Gly Gln Asp Gln Gly Ser Ala Tyr Ala Asn Arg Thr Ala Leu Phe
                85                  90                  95

Pro Asp Leu Leu Ala Gln Gly Asn Ala Ser Leu Arg Leu Gln Arg Val
            100                 105                 110

Arg Val Ala Asp Glu Gly Ser Phe Thr Cys Phe Val Ser Ile Arg Asp
            115                 120                 125

Phe Gly Ser Ala Ala Val Ser Leu Gln Val Ala Ala Pro Tyr Ser Lys
130                 135                 140

Pro Ser Met Thr Leu Glu Pro Asn Lys Asp Leu Arg Pro Gly Asp Thr
145                 150                 155                 160

Val Thr Ile Thr Cys Ser Ser Tyr Gln Gly Tyr Pro Glu Ala Glu Val
                165                 170                 175

Phe Trp Gln Asp Gly Gln Gly Val Pro Leu Thr Gly Asn Val Thr Thr
            180                 185                 190

Ser Gln Met Ala Asn Glu Gln Gly Leu Phe Asp Val His Ser Ile Leu
            195                 200                 205

Arg Val Val Leu Gly Ala Asn Gly Thr Tyr Ser Cys Leu Val Arg Asn
        210                 215                 220

Pro Val Leu Gln Gln Asp Ala His Ser Ser Val Thr Ile Thr Pro Gln
225                 230                 235                 240

Arg Ser Pro Thr Gly Ala Val Glu Val Gln Val Pro Glu Asp Pro Val
                245                 250                 255

Val Ala Leu Val Gly Thr Asp Ala Thr Leu Arg Cys Ser Phe Ser Pro
            260                 265                 270

Glu Pro Gly Phe Ser Leu Ala Gln Leu Asn Leu Ile Trp Gln Leu Thr
            275                 280                 285

Asp Thr Lys Gln Leu Val His Ser Phe Thr Glu Gly Arg Asp Gln Gly
        290                 295                 300
```

-continued

Ser Ala Tyr Ala Asn Arg Thr Ala Leu Phe Pro Asp Leu Leu Ala Gln
305                 310                 315                 320

Gly Asn Ala Ser Leu Arg Leu Gln Arg Val Arg Val Ala Asp Glu Gly
            325                 330                 335

Ser Phe Thr Cys Phe Val Ser Ile Arg Asp Phe Gly Ser Ala Ala Val
        340                 345                 350

Ser Leu Gln Val Ala Ala Pro Tyr Ser Lys Pro Ser Met Thr Leu Glu
    355                 360                 365

Pro Asn Lys Asp Leu Arg Pro Gly Asp Thr Val Thr Ile Thr Cys Ser
370                 375                 380

Ser Tyr Arg Gly Tyr Pro Glu Ala Glu Val Phe Trp Gln Asp Gly Gln
385                 390                 395                 400

Gly Val Pro Leu Thr Gly Asn Val Thr Thr Ser Gln Met Ala Asn Glu
            405                 410                 415

Gln Gly Leu Phe Asp Val His Ser Val Leu Arg Val Val Leu Gly Ala
        420                 425                 430

Asn Gly Thr Tyr Ser Cys Leu Val Arg Asn Pro Val Leu Gln Gln Asp
    435                 440                 445

Ala His Gly Ser Val Thr Ile Thr Gly Gln Pro Met Thr Phe Pro Pro
450                 455                 460

Glu Ala Leu Trp Val Thr Val Gly Leu Ser Val Cys Leu Ile Ala Leu
465                 470                 475                 480

Leu Val Ala Leu Ala Phe Val Cys Trp Arg Lys Ile Lys Gln Ser Cys
            485                 490                 495

Glu Glu Glu Asn Ala Gly Ala Glu Asp Gln Asp Gly Glu Gly Glu Gly
        500                 505                 510

Ser Lys Thr Ala Leu Gln Pro Leu Lys His Ser Asp Ser Lys Glu Asp
    515                 520                 525

Asp Gly Gln Glu Ile Ala
530

<210> SEQ ID NO 150
<211> LENGTH: 692
<212> TYPE: PRT
<213> ORGANISM: Homo sapiens
<220> FEATURE:
<221> NAME/KEY: misc_feature
<222> LOCATION: (1)..(692)
<223> OTHER INFORMATION: Human B7-H3-ECD (fc fusion)

<400> SEQUENCE: 150

Met Leu Arg Arg Arg Gly Ser Pro Gly Met Gly Val His Val Gly Ala
1               5                   10                  15

Ala Leu Gly Ala Leu Trp Phe Cys Leu Thr Gly Ala Leu Glu Val Gln
            20                  25                  30

Val Pro Glu Asp Pro Val Val Ala Leu Val Gly Thr Asp Ala Thr Leu
        35                  40                  45

Cys Cys Ser Phe Ser Pro Glu Pro Gly Phe Ser Leu Ala Gln Leu Asn
    50                  55                  60

Leu Ile Trp Gln Leu Thr Asp Thr Lys Gln Leu Val His Ser Phe Ala
65                  70                  75                  80

Glu Gly Gln Asp Gln Gly Ser Ala Tyr Ala Asn Arg Thr Ala Leu Phe
            85                  90                  95

Pro Asp Leu Leu Ala Gln Gly Asn Ala Ser Leu Arg Leu Gln Arg Val
        100                 105                 110

```
Arg Val Ala Asp Glu Gly Ser Phe Thr Cys Phe Val Ser Ile Arg Asp
            115                 120                 125

Phe Gly Ser Ala Ala Val Ser Leu Gln Val Ala Pro Tyr Ser Lys
130                 135                 140

Pro Ser Met Thr Leu Glu Pro Asn Lys Asp Leu Arg Pro Gly Asp Thr
145                 150                 155                 160

Val Thr Ile Thr Cys Ser Ser Tyr Gln Gly Tyr Pro Glu Ala Glu Val
                165                 170                 175

Phe Trp Gln Asp Gly Gln Gly Val Pro Leu Thr Gly Asn Val Thr Thr
                180                 185                 190

Ser Gln Met Ala Asn Glu Gln Gly Leu Phe Asp Val His Ser Ile Leu
            195                 200                 205

Arg Val Val Leu Gly Ala Asn Gly Thr Tyr Ser Cys Leu Val Arg Asn
            210                 215                 220

Pro Val Leu Gln Gln Asp Ala His Ser Ser Val Thr Ile Thr Pro Gln
225                 230                 235                 240

Arg Ser Pro Thr Gly Ala Val Glu Val Gln Val Pro Glu Asp Pro Val
                245                 250                 255

Val Ala Leu Val Gly Thr Asp Ala Thr Leu Arg Cys Ser Phe Ser Pro
                260                 265                 270

Glu Pro Gly Phe Ser Leu Ala Gln Leu Asn Leu Ile Trp Gln Leu Thr
            275                 280                 285

Asp Thr Lys Gln Leu Val His Ser Phe Thr Glu Gly Arg Asp Gln Gly
            290                 295                 300

Ser Ala Tyr Ala Asn Arg Thr Ala Leu Phe Pro Asp Leu Leu Ala Gln
305                 310                 315                 320

Gly Asn Ala Ser Leu Arg Leu Gln Arg Val Arg Val Ala Asp Glu Gly
                325                 330                 335

Ser Phe Thr Cys Phe Val Ser Ile Arg Asp Phe Gly Ser Ala Ala Val
                340                 345                 350

Ser Leu Gln Val Ala Ala Pro Tyr Ser Lys Pro Ser Met Thr Leu Glu
            355                 360                 365

Pro Asn Lys Asp Leu Arg Pro Gly Asp Thr Val Thr Ile Thr Cys Ser
370                 375                 380

Ser Tyr Arg Gly Tyr Pro Glu Ala Glu Val Phe Trp Gln Asp Gly Gln
385                 390                 395                 400

Gly Val Pro Leu Thr Gly Asn Val Thr Thr Ser Gln Met Ala Asn Glu
                405                 410                 415

Gln Gly Leu Phe Asp Val His Ser Val Leu Arg Val Val Leu Gly Ala
            420                 425                 430

Asn Gly Thr Tyr Ser Cys Leu Val Arg Asn Pro Val Leu Gln Gln Asp
            435                 440                 445

Ala His Gly Ser Val Thr Ile Thr Gly Gln Pro Met Thr Phe Ala Ala
450                 455                 460

Ala Asp Lys Thr His Thr Cys Pro Pro Cys Pro Ala Pro Glu Ala Glu
465                 470                 475                 480

Gly Ala Pro Ser Val Phe Leu Phe Pro Pro Lys Pro Lys Asp Thr Leu
                485                 490                 495

Met Ile Ser Arg Thr Pro Glu Val Thr Cys Val Val Val Asp Val Ser
                500                 505                 510

His Glu Asp Pro Glu Val Lys Phe Asn Trp Tyr Val Asp Gly Val Glu
            515                 520                 525

Val His Asn Ala Lys Thr Lys Pro Arg Glu Glu Gln Tyr Asn Ser Thr
```

```
                    530                 535                 540
Tyr Arg Val Val Ser Val Leu Thr Val Leu His Gln Asp Trp Leu Asn
545                 550                 555                 560

Gly Lys Glu Tyr Lys Cys Lys Val Ser Asn Lys Ala Leu Pro Ala Pro
                    565                 570                 575

Ile Glu Lys Thr Ile Ser Lys Ala Lys Gly Gln Pro Arg Glu Pro Gln
                580                 585                 590

Val Tyr Thr Leu Pro Pro Ser Arg Glu Glu Met Thr Lys Asn Gln Val
                595                 600                 605

Ser Leu Thr Cys Leu Val Lys Gly Phe Tyr Pro Ser Asp Ile Ala Val
                610                 615                 620

Glu Trp Glu Ser Asn Gly Gln Pro Glu Asn Asn Tyr Lys Thr Thr Pro
625                 630                 635                 640

Pro Val Leu Asp Ser Asp Gly Ser Phe Phe Leu Tyr Ser Lys Leu Thr
                645                 650                 655

Val Asp Lys Ser Arg Trp Gln Gln Gly Asn Val Phe Ser Cys Ser Val
                660                 665                 670

Met His Glu Ala Leu His Asn His Tyr Thr Gln Lys Ser Leu Ser Leu
                675                 680                 685

Ser Pro Gly Lys
690

<210> SEQ ID NO 151
<211> LENGTH: 474
<212> TYPE: PRT
<213> ORGANISM: Mus musculus
<220> FEATURE:
<221> NAME/KEY: misc_feature
<222> LOCATION: (1)..(474)
<223> OTHER INFORMATION: Mouse B7-H3-ECD (fc fusion)

<400> SEQUENCE: 151

Met Leu Arg Gly Trp Gly Gly Pro Ser Val Gly Val Cys Val Arg Thr
1               5                   10                  15

Ala Leu Gly Val Leu Cys Leu Cys Leu Thr Gly Ala Val Glu Val Gln
                20                  25                  30

Val Ser Glu Asp Pro Val Val Ala Leu Val Asp Thr Asp Ala Thr Leu
                35                  40                  45

Arg Cys Ser Phe Ser Pro Glu Pro Gly Phe Ser Leu Ala Gln Leu Asn
            50                  55                  60

Leu Ile Trp Gln Leu Thr Asp Thr Lys Gln Leu Val His Ser Phe Thr
65                  70                  75                  80

Glu Gly Arg Asp Gln Gly Ser Ala Tyr Ser Asn Arg Thr Ala Leu Phe
                85                  90                  95

Pro Asp Leu Leu Val Gln Gly Asn Ala Ser Leu Arg Leu Gln Arg Val
                100                 105                 110

Arg Val Thr Asp Glu Gly Ser Tyr Thr Cys Phe Val Ser Ile Gln Asp
                115                 120                 125

Phe Asp Ser Ala Ala Val Ser Leu Gln Val Ala Ala Pro Tyr Ser Lys
130                 135                 140

Pro Ser Met Thr Leu Glu Pro Asn Lys Asp Leu Arg Pro Gly Asn Met
145                 150                 155                 160

Val Thr Ile Thr Cys Ser Ser Tyr Gln Gly Tyr Pro Glu Ala Glu Val
                165                 170                 175

Phe Trp Lys Asp Gly Gln Gly Val Pro Leu Thr Gly Asn Val Thr Thr
                180                 185                 190
```

```
Ser Gln Met Ala Asn Glu Arg Gly Leu Phe Asp Val His Ser Val Leu
        195                 200                 205

Arg Val Val Leu Gly Ala Asn Gly Thr Tyr Ser Cys Leu Val Arg Asn
210                 215                 220

Pro Val Leu Gln Gln Asp Ala His Gly Ser Val Thr Ile Thr Gly Gln
225                 230                 235                 240

Pro Leu Thr Phe Ala Ala Asp Lys Thr His Thr Cys Pro Pro Cys
                245                 250                 255

Pro Ala Pro Glu Ala Glu Gly Ala Pro Ser Val Phe Leu Phe Pro Pro
                260                 265                 270

Lys Pro Lys Asp Thr Leu Met Ile Ser Arg Thr Pro Glu Val Thr Cys
                275                 280                 285

Val Val Val Asp Val Ser His Glu Asp Pro Glu Val Lys Phe Asn Trp
            290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
                340                 345                 350

Lys Ala Leu Pro Ala Pro Ile Glu Lys Thr Ile Ser Lys Ala Lys Gly
                355                 360                 365

Gln Pro Arg Glu Pro Gln Val Tyr Thr Leu Pro Pro Ser Arg Glu Glu
                370                 375                 380

Met Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
                420                 425                 430

Leu Tyr Ser Lys Leu Thr Val Asp Lys Ser Arg Trp Gln Gln Gly Asn
                435                 440                 445

Val Phe Ser Cys Ser Val Met His Glu Ala Leu His Asn His Tyr Thr
            450                 455                 460

Gln Lys Ser Leu Ser Leu Ser Pro Gly Lys
465                 470

<210> SEQ ID NO 152
<211> LENGTH: 460
<212> TYPE: PRT
<213> ORGANISM: Homo sapiens
<220> FEATURE:
<221> NAME/KEY: misc_feature
<222> LOCATION: (1)..(460)
<223> OTHER INFORMATION: Human B7-H3-ECD (his tag)

<400> SEQUENCE: 152

Met Glu Phe Gly Leu Ser Trp Leu Phe Leu Val Ala Ile Leu Lys Gly
1               5                   10                  15

Val Gln Cys Gly Ala Leu Glu Val Gln Val Pro Glu Asp Pro Val Val
                20                  25                  30

Ala Leu Val Gly Thr Asp Ala Thr Leu Cys Cys Ser Phe Ser Pro Glu
                35                  40                  45

Pro Gly Phe Ser Leu Ala Gln Leu Asn Leu Ile Trp Gln Leu Thr Asp
            50                  55                  60
```

Thr Lys Gln Leu Val His Ser Phe Ala Glu Gly Gln Asp Gln Gly Ser
 65                  70                  75                  80

Ala Tyr Ala Asn Arg Thr Ala Leu Phe Pro Asp Leu Leu Ala Gln Gly
                 85                  90                  95

Asn Ala Ser Leu Arg Leu Gln Arg Val Arg Val Ala Asp Glu Gly Ser
            100                 105                 110

Phe Thr Cys Phe Val Ser Ile Arg Asp Phe Gly Ser Ala Ala Val Ser
        115                 120                 125

Leu Gln Val Ala Ala Pro Tyr Ser Lys Pro Ser Met Thr Leu Glu Pro
130                 135                 140

Asn Lys Asp Leu Arg Pro Gly Asp Thr Val Thr Ile Thr Cys Ser Ser
145                 150                 155                 160

Tyr Gln Gly Tyr Pro Glu Ala Glu Val Phe Trp Gln Asp Gly Gln Gly
                165                 170                 175

Val Pro Leu Thr Gly Asn Val Thr Thr Ser Gln Met Ala Asn Glu Gln
            180                 185                 190

Gly Leu Phe Asp Val His Ser Ile Leu Arg Val Val Leu Gly Ala Asn
        195                 200                 205

Gly Thr Tyr Ser Cys Leu Val Arg Asn Pro Val Leu Gln Gln Asp Ala
210                 215                 220

His Ser Ser Val Thr Ile Thr Pro Gln Arg Ser Pro Thr Gly Ala Val
225                 230                 235                 240

Glu Val Gln Val Pro Glu Asp Pro Val Val Ala Leu Val Gly Thr Asp
                245                 250                 255

Ala Thr Leu Arg Cys Ser Phe Ser Pro Glu Pro Gly Phe Ser Leu Ala
            260                 265                 270

Gln Leu Asn Leu Ile Trp Gln Leu Thr Asp Thr Lys Gln Leu Val His
        275                 280                 285

Ser Phe Thr Glu Gly Arg Asp Gln Gly Ser Ala Tyr Ala Asn Arg Thr
290                 295                 300

Ala Leu Phe Pro Asp Leu Leu Ala Gln Gly Asn Ala Ser Leu Arg Leu
305                 310                 315                 320

Gln Arg Val Arg Val Ala Asp Glu Gly Ser Phe Thr Cys Phe Val Ser
                325                 330                 335

Ile Arg Asp Phe Gly Ser Ala Ala Val Ser Leu Gln Val Ala Ala Pro
            340                 345                 350

Tyr Ser Lys Pro Ser Met Thr Leu Glu Pro Asn Lys Asp Leu Arg Pro
        355                 360                 365

Gly Asp Thr Val Thr Ile Thr Cys Ser Ser Tyr Arg Gly Tyr Pro Glu
370                 375                 380

Ala Glu Val Phe Trp Gln Asp Gly Gln Gly Val Pro Leu Thr Gly Asn
385                 390                 395                 400

Val Thr Thr Ser Gln Met Ala Asn Glu Gln Gly Leu Phe Asp Val His
                405                 410                 415

Ser Val Leu Arg Val Val Leu Gly Ala Asn Gly Thr Tyr Ser Cys Leu
            420                 425                 430

Val Arg Asn Pro Val Leu Gln Gln Asp Ala His Gly Ser Val Thr Ile
        435                 440                 445

Thr Gly Gln Pro Met Thr His His His His His
    450                 455                 460

<210> SEQ ID NO 153
<211> LENGTH: 241
<212> TYPE: PRT

<213> ORGANISM: Mus musculus
<220> FEATURE:
<221> NAME/KEY: misc_feature
<222> LOCATION: (1)..(241)
<223> OTHER INFORMATION: Mouse B7-H3-ECD (his tag)

<400> SEQUENCE: 153

```
Met Glu Phe Gly Leu Ser Trp Leu Phe Leu Val Ala Ile Leu Lys Gly
 1               5                  10                  15

Val Gln Cys Val Glu Val Gln Val Ser Glu Asp Pro Val Ala Leu
             20                  25                  30

Val Asp Thr Asp Ala Thr Leu Arg Cys Ser Phe Ser Pro Glu Pro Gly
             35                  40                  45

Phe Ser Leu Ala Gln Leu Asn Leu Ile Trp Gln Leu Thr Asp Thr Lys
         50                  55                  60

Gln Leu Val His Ser Phe Thr Glu Gly Arg Asp Gln Gly Ser Ala Tyr
 65                  70                  75                  80

Ser Asn Arg Thr Ala Leu Phe Pro Asp Leu Leu Val Gln Gly Asn Ala
                 85                  90                  95

Ser Leu Arg Leu Gln Arg Val Arg Val Thr Asp Glu Gly Ser Tyr Thr
            100                 105                 110

Cys Phe Val Ser Ile Gln Asp Phe Asp Ser Ala Ala Val Ser Leu Gln
            115                 120                 125

Val Ala Ala Pro Tyr Ser Lys Pro Ser Met Thr Leu Glu Pro Asn Lys
        130                 135                 140

Asp Leu Arg Pro Gly Asn Met Val Thr Ile Thr Cys Ser Ser Tyr Gln
145                 150                 155                 160

Gly Tyr Pro Glu Ala Glu Val Phe Trp Lys Asp Gly Gln Gly Val Pro
                165                 170                 175

Leu Thr Gly Asn Val Thr Thr Ser Gln Met Ala Asn Glu Arg Gly Leu
            180                 185                 190

Phe Asp Val His Ser Val Leu Arg Val Val Leu Gly Ala Asn Gly Thr
        195                 200                 205

Tyr Ser Cys Leu Val Arg Asn Pro Val Leu Gln Gln Asp Ala His Gly
    210                 215                 220

Ser Val Thr Ile Thr Gly Gln Pro Leu Thr Phe His His His His
225                 230                 235                 240

His
```

<210> SEQ ID NO 154
<211> LENGTH: 473
<212> TYPE: PRT
<213> ORGANISM: Macaca fascicularis
<220> FEATURE:
<221> NAME/KEY: misc_feature
<222> LOCATION: (1)..(473)
<223> OTHER INFORMATION: Cynomolgus B7-H3-ECD (his tag)

<400> SEQUENCE: 154

```
Met Leu His Arg Arg Gly Ser Pro Gly Met Gly Val His Val Gly Ala
 1               5                  10                  15

Ala Leu Gly Ala Leu Trp Phe Cys Leu Thr Gly Ala Leu Glu Val Gln
             20                  25                  30

Val Pro Glu Asp Pro Val Val Ala Leu Val Gly Thr Asp Ala Thr Leu
             35                  40                  45

Arg Cys Ser Phe Ser Pro Glu Pro Gly Phe Ser Leu Ala Gln Leu Asn
         50                  55                  60
```

```
Leu Ile Trp Gln Leu Thr Asp Thr Lys Gln Leu Val His Ser Phe Thr
 65                  70                  75                  80

Glu Gly Arg Asp Gln Gly Ser Ala Tyr Ala Asn Arg Thr Ala Leu Phe
                 85                  90                  95

Leu Asp Leu Leu Ala Gln Gly Asn Ala Ser Leu Arg Leu Gln Arg Val
            100                 105                 110

Arg Val Ala Asp Glu Gly Ser Phe Thr Cys Phe Val Ser Ile Arg Asp
        115                 120                 125

Phe Gly Ser Ala Ala Val Ser Leu Gln Val Ala Ala Pro Tyr Ser Lys
    130                 135                 140

Pro Ser Met Thr Leu Glu Pro Asn Lys Asp Leu Arg Pro Gly Asp Thr
145                 150                 155                 160

Val Thr Ile Thr Cys Ser Ser Tyr Arg Gly Tyr Pro Glu Ala Glu Val
                165                 170                 175

Phe Trp Gln Asp Gly Gln Gly Ala Pro Leu Thr Gly Asn Val Thr Thr
            180                 185                 190

Ser Gln Met Ala Asn Glu Gln Gly Leu Phe Asp Val His Ser Val Leu
        195                 200                 205

Arg Val Val Leu Gly Ala Asn Gly Thr Tyr Ser Cys Leu Val Arg Asn
    210                 215                 220

Pro Val Leu Gln Gln Asp Ala His Gly Ser Ile Thr Ile Thr Pro Gln
225                 230                 235                 240

Arg Ser Pro Thr Gly Ala Val Glu Val Gln Val Pro Glu Asp Pro Val
                245                 250                 255

Val Ala Leu Val Gly Thr Asp Ala Thr Leu Arg Cys Ser Phe Ser Pro
            260                 265                 270

Glu Pro Gly Phe Ser Leu Ala Gln Leu Asn Leu Ile Trp Gln Leu Thr
        275                 280                 285

Asp Thr Lys Gln Leu Val His Ser Phe Thr Glu Gly Arg Asp Gln Gly
    290                 295                 300

Ser Ala Tyr Ala Asn Arg Thr Ala Leu Phe Leu Asp Leu Leu Ala Gln
305                 310                 315                 320

Gly Asn Ala Ser Leu Arg Leu Gln Arg Val Arg Val Ala Asp Glu Gly
                325                 330                 335

Ser Phe Thr Cys Phe Val Ser Ile Arg Asp Phe Gly Ser Ala Ala Val
            340                 345                 350

Ser Leu Gln Val Ala Ala Pro Tyr Ser Lys Pro Ser Met Thr Leu Glu
        355                 360                 365

Pro Asn Lys Asp Leu Arg Pro Gly Asp Thr Val Thr Ile Thr Cys Ser
    370                 375                 380

Ser Tyr Arg Gly Tyr Pro Glu Ala Glu Val Phe Trp Gln Asp Gly Gln
385                 390                 395                 400

Gly Ala Pro Leu Thr Gly Asn Val Thr Thr Ser Gln Met Ala Asn Glu
                405                 410                 415

Gln Gly Leu Phe Asp Val His Ser Val Leu Arg Val Val Leu Gly Ala
            420                 425                 430

Asn Gly Thr Tyr Ser Cys Leu Val Arg Asn Pro Val Leu Gln Gln Asp
        435                 440                 445

Ala His Gly Ser Val Thr Ile Thr Gly Gln Pro Met Thr Phe Ala Ala
    450                 455                 460

Ala His His His His His His His
465                 470
```

```
<210> SEQ ID NO 155
<211> LENGTH: 98
<212> TYPE: PRT
<213> ORGANISM: Artificial Sequence
<220> FEATURE:
<223> OTHER INFORMATION: Synthetic: Amino acid sequence of IGHV1-69*06

<400> SEQUENCE: 155
```

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

```
<210> SEQ ID NO 156
<211> LENGTH: 11
<212> TYPE: PRT
<213> ORGANISM: Artificial Sequence
<220> FEATURE:
<223> OTHER INFORMATION: Synthetic: Amino acid sequence of IGHJ6*01

<400> SEQUENCE: 156
```

Trp Gly Gln Gly Thr Thr Val Thr Val Ser Ser
1               5                   10

```
<210> SEQ ID NO 157
<211> LENGTH: 96
<212> TYPE: PRT
<213> ORGANISM: Artificial Sequence
<220> FEATURE:
<223> OTHER INFORMATION: Synthetic: Amino acid sequence of IGKV1-9*01

<400> SEQUENCE: 157
```

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Pro
                85                  90                  95

```
<210> SEQ ID NO 158
<211> LENGTH: 10
<212> TYPE: PRT
<213> ORGANISM: Artificial Sequence
<220> FEATURE:
<223> OTHER INFORMATION: Synthetic: Amino acid sequence of IGKJ2*01

<400> SEQUENCE: 158
```

```
Phe Gly Gln Gly Thr Lys Leu Glu Ile Lys
1               5                   10
```

```
<210> SEQ ID NO 159
<211> LENGTH: 330
<212> TYPE: PRT
<213> ORGANISM: Artificial Sequence
<220> FEATURE:
<223> OTHER INFORMATION: Synthetic: Ig gamma-1 constant region

<400> SEQUENCE: 159

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 160
```

```
<211> LENGTH: 330
<212> TYPE: PRT
<213> ORGANISM: Artificial Sequence
<220> FEATURE:
<223> OTHER INFORMATION: Synthetic: Ig gamma-1 constant region mutant

<400> SEQUENCE: 160

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 161
<211> LENGTH: 107
<212> TYPE: PRT
<213> ORGANISM: Artificial Sequence
<220> FEATURE:
<223> OTHER INFORMATION: Synthetic: Ig Kappa constant region
```

```
<400> SEQUENCE: 161

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 162
<211> LENGTH: 105
<212> TYPE: PRT
<213> ORGANISM: Artificial Sequence
<220> FEATURE:
<223> OTHER INFORMATION: Synthetic: Ig Lambda constant region

<400> SEQUENCE: 162

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105

<210> SEQ ID NO 163
<211> LENGTH: 96
<212> TYPE: PRT
<213> ORGANISM: Artificial Sequence
<220> FEATURE:
<223> OTHER INFORMATION: Synthetic: Amino acid sequence of IGKV6-21*01
<220> FEATURE:
<221> NAME/KEY: misc_feature
<222> LOCATION: (96)..(96)
<223> OTHER INFORMATION: Xaa can be any naturally occurring amino acid

<400> SEQUENCE: 163

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Ser
            20                  25                  30

Leu His Trp Tyr Gln Gln Lys Pro Asp Gln Ser Pro Lys Leu Leu Ile
        35                  40                  45

Lys Tyr Ala Ser Gln Ser Phe Ser Gly Val Pro Ser Arg Phe Ser Gly
    50                  55                  60
```

```
Ser Gly Ser Gly Thr Asp Phe Thr Leu Thr Ile Asn Ser Leu Glu Ala
 65                  70                  75                  80

Glu Asp Ala Ala Thr Tyr Tyr Cys His Gln Ser Ser Leu Pro Xaa
                 85                  90                  95

<210> SEQ ID NO 164
<211> LENGTH: 101
<212> TYPE: PRT
<213> ORGANISM: Artificial Sequence
<220> FEATURE:
<223> OTHER INFORMATION: Synthetic: Amino acid sequence of IGKV2-28*01

<400> SEQUENCE: 164

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
                 20                  25                  30

Asn Gly Tyr Asn Tyr Leu Asp Trp Tyr Leu Gln Lys Pro Gly Gln Ser
             35                  40                  45

Pro Gln Leu Leu Ile Tyr Leu Gly Ser Asn Arg Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro Pro
            100

<210> SEQ ID NO 165
<211> LENGTH: 10
<212> TYPE: PRT
<213> ORGANISM: Artificial Sequence
<220> FEATURE:
<223> OTHER INFORMATION: Synthetic: Amino acid sequence of IGKJ4*01

<400> SEQUENCE: 165

Phe Gly Gly Gly Thr Lys Val Glu Ile Lys
 1               5                  10

<210> SEQ ID NO 166
<211> LENGTH: 98
<212> TYPE: PRT
<213> ORGANISM: Artificial Sequence
<220> FEATURE:
<223> OTHER INFORMATION: Synthetic: Amino acid sequence of
      IGHV-b*01(0-1)

<400> SEQUENCE: 166

Gln Val Gln Leu Gln Glu Ser Gly Pro Gly Leu Val Lys Pro Ser Glu
 1               5                  10                  15

Thr Leu Ser Leu Thr Cys Ala Val Ser Gly Tyr Ser Ile Ser Ser Gly
                 20                  25                  30

Tyr Tyr Trp Gly Trp Ile Arg Gln Pro Pro Gly Lys Gly Leu Glu Trp
             35                  40                  45

Ile Gly Ser Ile Tyr His Ser Gly Ser Thr Tyr Tyr Asn Pro Ser Leu
     50                  55                  60

Lys Ser Arg Val Thr Ile Ser Val Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95
```

Ala Arg

<210> SEQ ID NO 167
<211> LENGTH: 96
<212> TYPE: PRT
<213> ORGANISM: Artificial Sequence
<220> FEATURE:
<223> OTHER INFORMATION: Synthetic: Amino acid sequence of IGKv1-39*01

<400> SEQUENCE: 167

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95
```

<210> SEQ ID NO 168
<211> LENGTH: 446
<212> TYPE: PRT
<213> ORGANISM: Artificial Sequence
<220> FEATURE:
<223> OTHER INFORMATION: Synthetic: Amino acid sequence of huAb13v1
    heavy chain

<400> SEQUENCE: 168

```
Glu Val Gln Leu Gln Glu Ser Gly Pro Gly Leu Val Lys Pro Ser Glu
1               5                   10                  15

Thr Leu Ser Leu Thr Cys Ala Val Thr Gly Tyr Ser Ile Thr Ser Gly
            20                  25                  30

Tyr Ser Trp His Trp Ile Arg Gln Phe Pro Gly Asn Gly Leu Glu Trp
        35                  40                  45

Met Gly Tyr Ile His Ser Ser Gly Ser Thr Asn Tyr Asn Pro Ser Leu
50                  55                  60

Lys Ser Arg Ile Ser Ile Ser Arg Asp Thr Ser Lys Asn Gln Phe Phe
65                  70                  75                  80

Leu Lys Leu Ser Ser Val Thr Ala Ala Asp Thr Ala Val Tyr Tyr Cys
                85                  90                  95

Ala Gly Tyr Asp Asp Tyr Phe Glu Tyr Trp Gly Gln Gly Thr Thr Val
                100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
```

```
            195                 200                 205
Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 169
<211> LENGTH: 214
<212> TYPE: PRT
<213> ORGANISM: Artificial Sequence
<220> FEATURE:
<223> OTHER INFORMATION: Synthetic: Amino acid sequence of huAb13v1
      light chain

<400> SEQUENCE: 169

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Phe Asn
            20                  25                  30

Val Ala Trp Tyr Gln Gln Lys Pro Gly Lys Ser Pro Lys Ala Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Glu Tyr Phe Cys Gln Gln Tyr Asn Trp Tyr Pro Phe
                85                  90                  95

Thr Phe Gly Gln Gly Thr Lys Leu Glu Ile Lys Arg Thr Val Ala Ala
            100                 105                 110
```

```
Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 170
<211> LENGTH: 447
<212> TYPE: PRT
<213> ORGANISM: Artificial Sequence
<220> FEATURE:
<223> OTHER INFORMATION: Synthetic: Amino acid sequence of huAb3v2.5
      heavy chain

<400> SEQUENCE: 170

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser Tyr
                20                  25                  30

Trp Met His Trp Val Arg Gln Ala Pro Gly Gln Gly Leu Glu Trp Ile
            35                  40                  45

Gly Leu Ile His Pro Glu Ser Gly Ser Thr Asn Tyr Asn Glu Met Phe
        50                  55                  60

Lys Asn Arg Ala Thr Leu Thr Val Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Gly Gly Gly Arg Leu Tyr Phe Asp Tyr Trp Gly Gln Gly Thr Thr
                100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255
```

```
Pro Glu Val Thr Cys Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 171
<211> LENGTH: 219
<212> TYPE: PRT
<213> ORGANISM: Artificial Sequence
<220> FEATURE:
<223> OTHER INFORMATION: Synthetic: Amino acid sequence of huAb3v2.5
      light chain

<400> SEQUENCE: 171

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Arg Asp Thr Tyr Leu Arg Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
```

-continued

```
                165                 170                 175
Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
        210                 215

<210> SEQ ID NO 172
<211> LENGTH: 447
<212> TYPE: PRT
<213> ORGANISM: Artificial Sequence
<220> FEATURE:
<223> OTHER INFORMATION: Synthetic: Amino acid sequence of huAb3v2.6
      heavy chain

<400> SEQUENCE: 172

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser Tyr
            20                  25                  30

Trp Met His Trp Val Arg Gln Ala Pro Gly Gln Gly Leu Glu Trp Ile
        35                  40                  45

Gly Leu Ile His Pro Glu Ser Gly Ser Thr Asn Tyr Asn Glu Met Phe
    50                  55                  60

Lys Asn Arg Ala Thr Leu Thr Val Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Gly Gly Gly Arg Leu Tyr Phe Asp Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300
```

```
Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 173
<211> LENGTH: 219
<212> TYPE: PRT
<213> ORGANISM: Artificial Sequence
<220> FEATURE:
<223> OTHER INFORMATION: Synthetic: Amino acid sequence of huAb3v2.6
      light chain

<400> SEQUENCE: 173

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gln Asp Thr Tyr Leu Arg Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 174
<211> LENGTH: 117
<212> TYPE: PRT
<213> ORGANISM: Artificial Sequence
<220> FEATURE:
<223> OTHER INFORMATION: Synthetic: IGHV1-69*06_IGHJ6
<220> FEATURE:
<221> NAME/KEY: misc_feature
<222> LOCATION: (99)..(106)
<223> OTHER INFORMATION: Xaa can be any naturally occurring amino acid;
      this section represents the CDR-H3 region

<400> SEQUENCE: 174

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Xaa Xaa Xaa Xaa Xaa Xaa Xaa Xaa Trp Gly Gln Gly Thr Thr
            100                 105                 110

Val Thr Val Ser Ser
        115

<210> SEQ ID NO 175
<211> LENGTH: 112
<212> TYPE: PRT
<213> ORGANISM: Artificial Sequence
<220> FEATURE:
<223> OTHER INFORMATION: Synthetic: IGKV2-28*01_IGKJ4
<220> FEATURE:
<221> NAME/KEY: misc_feature
<222> LOCATION: (94)..(102)
<223> OTHER INFORMATION: Xaa can be any naturally occurring amino acid;
      this section represents the CDR-L3 region

<400> SEQUENCE: 175

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Xaa Xaa Xaa
                85                  90                  95

Xaa Xaa Xaa Xaa Xaa Xaa Phe Gly Gly Gly Thr Lys Val Glu Ile Lys
            100                 105                 110

<210> SEQ ID NO 176
<211> LENGTH: 116

```
<212> TYPE: PRT
<213> ORGANISM: Artificial Sequence
<220> FEATURE:
<223> OTHER INFORMATION: Synthetic: IGHV4-b_IGHJ6
<220> FEATURE:
<221> NAME/KEY: misc_feature
<222> LOCATION: (99)..(105)
<223> OTHER INFORMATION: Xaa can be any naturally occurring amino acid;
      this section represents the CDR-H3 region

<400> SEQUENCE: 176

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Tyr His Ser Gly Ser Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Xaa Xaa Xaa Xaa Xaa Xaa Xaa Trp Gly Gln Gly Thr Thr Val
            100                 105                 110

Thr Val Ser Ser
        115

<210> SEQ ID NO 177
<211> LENGTH: 107
<212> TYPE: PRT
<213> ORGANISM: Artificial Sequence
<220> FEATURE:
<223> OTHER INFORMATION: Synthetic: IGKV1-39_IGKJ2
<220> FEATURE:
<221> NAME/KEY: misc_feature
<222> LOCATION: (89)..(97)
<223> OTHER INFORMATION: Xaa can be any naturally occurring amino acid;
      this section represents the CDR-L3 region

<400> SEQUENCE: 177

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Xaa Xaa Xaa Xaa Xaa Xaa Xaa Xaa
                85                  90                  95

Xaa Phe Gly Gln Gly Thr Lys Leu Glu Ile Lys
            100                 105

<210> SEQ ID NO 178
<211> LENGTH: 112
<212> TYPE: PRT
<213> ORGANISM: Artificial Sequence
<220> FEATURE:
<223> OTHER INFORMATION: Synthetic: Amino acid sequence of huAb3 VL1
``` variants
<220> FEATURE:
<221> NAME/KEY: misc_feature
<222> LOCATION: (33)..(33)
<223> OTHER INFORMATION: X can be any naturally occurring amino acid,
      except M, C, N, D or Q

<400> SEQUENCE: 178

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Xaa Gly Asp Thr Tyr Leu Arg Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Tyr Thr Phe Gly Gly Gly Thr Lys Val Glu Ile Lys
            100                 105                 110

<210> SEQ ID NO 179
<211> LENGTH: 112
<212> TYPE: PRT
<213> ORGANISM: Artificial Sequence
<220> FEATURE:
<223> OTHER INFORMATION: Synthetic: Amino acid sequence of huAb3 VL1
      variants
<220> FEATURE:
<221> NAME/KEY: misc_feature
<222> LOCATION: (34)..(34)
<223> OTHER INFORMATION: X can be any naturally occurring amino acid
      except M, C, G, S, N, or P

<400> SEQUENCE: 179

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Xaa Asp Thr Tyr Leu Arg Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Tyr Thr Phe Gly Gly Gly Thr Lys Val Glu Ile Lys
            100                 105                 110

<210> SEQ ID NO 180
<211> LENGTH: 117
<212> TYPE: PRT
<213> ORGANISM: Artificial Sequence
<220> FEATURE:
<223> OTHER INFORMATION: Synthetic: Amino acid sequence of huAb3 VH1b
      variants
<220> FEATURE:
<221> NAME/KEY: misc_feature
<222> LOCATION: (54)..(54)
<223> OTHER INFORMATION: X can be any naturally occurring amino acid, except M, C, N, D or Q

<400> SEQUENCE: 180

```
Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser Tyr
            20                  25                  30

Trp Met His Trp Val Arg Gln Ala Pro Gly Gln Gly Leu Glu Trp Ile
        35                  40                  45

Gly Leu Ile His Pro Xaa Ser Gly Ser Thr Asn Tyr Asn Glu Met Phe
    50                  55                  60

Lys Asn Arg Ala Thr Leu Thr Val Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Gly Gly Gly Arg Leu Tyr Phe Asp Tyr Trp Gly Gln Gly Thr Thr
            100                 105                 110

Val Thr Val Ser Ser
        115
```

<210> SEQ ID NO 181
<211> LENGTH: 117
<212> TYPE: PRT
<213> ORGANISM: Artificial Sequence
<220> FEATURE:
<223> OTHER INFORMATION: Synthetic: Amino acid sequence of huAb3 VH1b
      variants
<220> FEATURE:
<221> NAME/KEY: misc_feature
<222> LOCATION: (55)..(55)
<223> OTHER INFORMATION: X can be any naturally occurring amino acid
      except M, C, G, S, N, or P

<400> SEQUENCE: 181

```
Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser Tyr
            20                  25                  30

Trp Met His Trp Val Arg Gln Ala Pro Gly Gln Gly Leu Glu Trp Ile
        35                  40                  45

Gly Leu Ile His Pro Asp Xaa Gly Ser Thr Asn Tyr Asn Glu Met Phe
    50                  55                  60

Lys Asn Arg Ala Thr Leu Thr Val Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Gly Gly Gly Arg Leu Tyr Phe Asp Tyr Trp Gly Gln Gly Thr Thr
            100                 105                 110

Val Thr Val Ser Ser
        115
```

```
<210> SEQ ID NO 182
<211> LENGTH: 9
<212> TYPE: PRT
<213> ORGANISM: Artificial Sequence
<220> FEATURE:
<223> OTHER INFORMATION: Synthetic: chAb13 VL CDR3 amino acid sequence

<400> SEQUENCE: 182

Gln Gln Tyr Asn Ser Tyr Pro Phe Thr
1               5
```